(12) United States Patent
Sabbadini et al.

(10) Patent No.: US 8,101,396 B2
(45) Date of Patent: *Jan. 24, 2012

(54) MINICELLS DISPLAYING ANTIBODIES OR DERIVATIVES THEREOF AND COMPRISING BIOLOGICALLY ACTIVE COMPOUNDS

(75) Inventors: Roger A. Sabbadini, Lakeside, CA (US); Neil Berkley, San Diego, CA (US); Mark W. Surber, San Diego, CA (US); Robert Klepper, San Diego, CA (US)

(73) Assignee: Vaxiion Therapeutics, Inc., San Diego, CA (US)

( * ) Notice: Subject to any disclaimer, the term of this patent is extended or adjusted under 35 U.S.C. 154(b) by 731 days.

This patent is subject to a terminal disclaimer.

(21) Appl. No.: 11/725,196

(22) Filed: Mar. 16, 2007

(65) Prior Publication Data
US 2011/0281330 A1 Nov. 17, 2011

Related U.S. Application Data

(62) Division of application No. 11/580,095, filed on Oct. 11, 2006, now Pat. No. 7,871,815, which is a division of application No. 10/156,902, filed on May 28, 2002, now Pat. No. 7,183,105, which is a division of application No. 10/154,951, filed on May 24, 2002, now abandoned.

(60) Provisional application No. 60/359,843, filed on Feb. 25, 2002, provisional application No. 60/293,566, filed on May 24, 2001.

(51) Int. Cl.
C12N 1/12 (2006.01)
C12N 1/20 (2006.01)

(52) U.S. Cl. .................................. 435/252.1; 435/252.3

(58) Field of Classification Search .......................... None
See application file for complete search history.

(56) References Cited

U.S. PATENT DOCUMENTS

| | | |
|---|---|---|
| 4,190,495 A | 2/1980 | Curtiss |
| 4,311,797 A | 1/1982 | Khachatourians |
| 4,431,740 A | 2/1984 | Bell et al. |
| 4,732,852 A | 3/1988 | Cohen et al. |
| 4,782,022 A | 11/1988 | Puhler et al. |
| 4,895,724 A | 1/1990 | Cardinal et al. |
| 4,968,619 A | 11/1990 | Curtiss |
| 5,066,596 A | 11/1991 | Manning et al. |
| 5,338,842 A | 8/1994 | Isberg et al. |
| 5,744,336 A | 4/1998 | Hodges et al. |
| 5,808,032 A | 9/1998 | Kurihara et al. |
| 5,830,710 A | 11/1998 | Progulske-Fox et al. |
| 5,834,591 A | 11/1998 | Normark et al. |
| 5,877,159 A | 3/1999 | Powell et al. |
| 5,888,799 A | 3/1999 | Curtiss |
| 5,922,583 A | 7/1999 | Morsey |
| 5,981,182 A | 11/1999 | Jacobs et al. |
| 6,004,815 A | 12/1999 | Portney |
| 6,030,805 A | 2/2000 | Normark et al. |
| 6,080,849 A | 6/2000 | Bermudes et al. |
| 6,100,066 A | 8/2000 | Potter et al. |
| 6,143,566 A | 11/2000 | Heintz et al. |
| 6,150,170 A | 11/2000 | Powell et al. |
| 6,168,945 B1 | 1/2001 | Sokatch et al. |
| 6,172,189 B1 | 1/2001 | Devare et al. |
| 6,248,543 B1 | 6/2001 | de Boer et al. |
| 6,258,359 B1 | 7/2001 | Labigne et al. |
| 6,270,776 B1 | 8/2001 | Bloom et al. |
| 6,291,649 B1 | 9/2001 | Lindberg et al. |
| 2003/0105310 A1 | 6/2003 | Ashkar |
| 2003/0166099 A1 | 9/2003 | Sabbadini et al. |
| 2003/0166279 A1 | 9/2003 | Sabbadini et al. |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0194714 A1 | 10/2003 | Sabbadini et al. |
| 2003/0194798 A1 | 10/2003 | Surber et al. |
| 2003/0198995 A1 | 10/2003 | Sabbadini et al. |
| 2003/0198996 A1 | 10/2003 | Surber et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |

(Continued)

FOREIGN PATENT DOCUMENTS

| | | |
|---|---|---|
| WO | WO 97/14810 | 4/1997 |
| WO | WO 98/52547 | 11/1998 |
| WO | WO 99/13053 | 3/1999 |
| WO | WO 99/52563 | 4/1999 |
| WO | WO 00/09733 | 2/2000 |
| WO | WO 03/072014 | 5/2002 |
| WO | WO 03/033519 A2 | 4/2003 |

OTHER PUBLICATIONS

Francisco, et al. "Production and Fluorescence-Activated Cell Sorting of *Escherichia coli* Expressing a Functional Antibody Fragment on the External Surface", Proceedings of the National Academy of Sciences, USA, 90(22): 1044-48.*

Ackley, et al., Defensive applications of gene transfer technology in the face of bioterrorism: DNA-based vaccines and immune targeting, *Expert Opin. Biol. Ther.* 3(8):1279-1289 (2003).

Acres et al., Vaccination of Cows with Purified K99 Antigen, K99+ Anucleated Live *E. coli*, and Whole Cell Bacterins Containing Enterotoxigenic *E. coli* for Prevention of Enterotoxigenic Colibacillosis of Calves, *Proceedings of Second International Symposium on Neonatal Diarrhea* pp. 443-456 (1979).

Adler et al., Genetic Control of Cell Division in Bacteria, *National Academy of Sciences*, abstracts of paper presented at the auumn meeting, p. 417 (Oct. 17-19, 1966).

Adler et al., Miniature *Escherichia coli* Cells Deficient in DNA, *Microbiology* 57:321-326 (1966).

(Continued)

*Primary Examiner* — Robert M Kelly
(74) *Attorney, Agent, or Firm* — Knobbe, Martens, Olson & Bear LLP

(57) ABSTRACT

Minicells are used to deliver biologically active compounds including radioisotopes, polypeptides, nucleic acids, small molecules, drug molecules, and chemotherapeutic agents. In some cases, the minicell displays ligands or binding moieties that target the minicell to a desired host cell.

3 Claims, 2 Drawing Sheets

U.S. PATENT DOCUMENTS

| | | |
|---|---|---|
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0005700 A1 | 1/2004 | Surber et al. |
| 2005/0147590 A1 | 7/2005 | Sabbadini et al. |
| 2006/0002956 A1 | 1/2006 | Surber et al. |

OTHER PUBLICATIONS

Barker et al., Isolation by Differential and Zonal Centrifugation of Minicells Segregated by *Escherichia coli*, *Jo. General Microbiology* 111:387-397 (1979).

Bollon, et al. DNA Transformation Efficiency of Various Bacterial and Yeast Host-Vector Systems *Journal of Clinical Hematology and Oncology* 10:39-48 (1980).

Bonner & Curtiss, *Use of Minicells in Vaccination Against Salmonella Infection*, Abstract (1976).

Botstein, et al. Making Mutations In Vitro and Putting Them Back Into Yeast, *Miami Winter Symposia* 19:265-275 (1982).

Bouvier et al., A Gene for a New Lipoprotein in the dapA-purC Interval of the *Escherichia coli* Chromosome, *J. of Bacteriology* 173(17):5523-5531 (1991).

Broach, James R. The Yeast: Plasmid 2u Circle, *The Molecular Biology of the Yeast Saccharomyces : Life Cycle and Inheritance* 445-470 (1981).

Broach James R. The Yeast: Plasmid 2u Circle *Cell* 28:203-204 (1982).

Brunel et al., Cloning and Expression of *Trypanosome brucei* kinetoplast DNA in *Escherichia coli*, *Gene* 12:223-234 (1980).

Clark-Curtiss et al., Analysis of Recombinant DNA Using *Escherichia coli* Minicells, *Methods in Enzymology* 101:347-362 (1983).

Courvalin et al., Gene Transfer from Bacteria to Mammalian Cells, *C.R. Acad. Sci.* 318:1207-12 (1995).

Coyne & Mendelson, Use of *Bacillus subtilis* Minicells to Demonstrate an Antegenic Relationship Between the Poles and Lateral Cylindrical Regions of Rod-Shaped Cells, *Infection and Immunity* 12:1189-1194 (1975).

Curtiss III, Roy, Genetic Manipulation of Microorganisms: Potential Benefits and Biohazards *Ann. Rev. Microbiol.* 30:507-533 (1976).

Curtiss III, Roy, Research on bacterial conjugation with minicells and minicell-producing *E. coli* strains, *Microbial Drug Resistance* p. 169. Baltimore University Park Press (1976).

de Boer et al., A Division Inhibitor and a Topological Specificity Factor Coded for by the Minicell Locus Determine Proper Placement of the Division Septum in *E. coli Cell* 56:641-649 (1989).

Eck et al., Cloning and characterization of a gene coding for the caterchol 1,2-dioxygenase of Arthrobacter sp. mA3 *Gene* 123:87-92 (1993).

Eck, et al., *Gene-Based Therapy*, Goodman & Gilmans The Pharmacological Basis of Therapeutics, McGraw-Hill, New York, NY., 9th Ed., pp. 77-101 (1996).

Edge, et al., Chemical Synthesis of a human interferon-$\alpha_2$ gene and its expression in *Escherichia coli*, *Nucleic Acids Research* 11(18):6419-6435 (1983).

Eick et al., From initiation to elongation: comparison of transcription by prokaryotic and eukaryotic RNA polymerases, *TIG* 10(8):292-296 (1994).

Fox, et al., Fate of the DNA in Plasmid-Containing *Escherichia coli* Minicells Ingested by Human Neutrohils, *Blood* 69(5): 1394-1400 (1987).

Frazer et al., Production, Properties and Utility of Bacterial Minicells, 69 *Curr. Top. Microbiol. Immunol.* 1:3-84 (1975).

Gabel et al., The KdpF Subunit s Part of the $K^+$-translocating Kdp Complex of *Escherichia coli* and Is Responsible for Stabilization of the Complex in Vitro, *J. Biol. Chem.* 274(53):37901-37907 (1999).

Giacalone et al., Immune responses elicited by bacterial minicells capable of simultaneous DNA and protein antigen delivery, *Vaccine* 24 6009-6017 (2006).

Gemski & Griffin, Isolation and Characterization of Minicell-Producing Mutants of *Shigella* spp, *Infection & Immunity* 30:297-302 (1980).

Griillot-Courvalin et al., Bacteria as gene delivery vectors for mammalian cells, *Current Opinion in Biotechnology* 10:477-481 (1999).

Gyongyossy-Issa et al., Tumour Minicells: Single, Large Vesicles Released From Cultured Mastocytoma Cells, *Tissue & Cell* 17(6):801-809 (1985).

Gyuris, et al., High-Efficiency Transformation of *Saccharomyces cerevisiae* Cells by Bacterial Minicell Protoplast Fusion, Mol. Cell. Biol. 6(9) 3295-97 (1986).

Hanson et al., Molecular cloning, partial purification, and characterization of a haemin-binding lipoprotein from *Haemophilus influenzae* type b, *Molecular Microbiology* 5(2):267-278 (1991).

Harlow et al., Cloning and Characterization of the gsk Gene Encoding Guanosine Kinase of *Escherichia coli*, *J. of Bacteriology* 177(8):2236-2240 (1995).

Hollenberg et al., Mapping of Regions on Cloned *Saccharomyces cerevisiae* 2-um DNA Coding for Polypeptides Synthesized in *Escherichia coli* Minicells, *Molec. Gen. Genet.* 162:23-34 (1978).

Isaacson et al., In Vitro Adhesion of *Escherichia coli* to Porcine Small Intestinal Epithelial Cells: Pili as Adhesive Factors, *Infection and Immunity* 21:392-397 (1978).

Jacobs, et al., Expression of Mycobacterium leprae genes from a *Streptococcus* mutans promoter in *Escherichia coli* K-12, *Proc. Natl. Acad. Sci. USA* 83:1926-1930 (1986).

Jannatipour et al., Translocation of Vibrio harveyi N. N'-Diacetylchitobiase to the Outer Membrane of *Escherichia coli*, *J. of Bacteriology* 169(8):3785-3791 (1987).

Kawahara et al., Identification and mappin gof mba regions of the *Salmonella choleraesuis* virulence plasmid of pKDSC50 responsible for mouse bacteremia, *Microbial Pathogenesis* 8:13-21 (1990).

Khachatourians & Berezowsky, Expression of Recombinant DNA Functional Products in *Escherichia coli* Anucleate Minicells, *Biotech. Adv.* 4:75-93 (1986).

Khachatourians et al, A New Method for the Preparation of Minicells for Physiological Studies, *Preparative Biochemistry* 3:291-298 (1973).

Khachatourians et al., Fate of Conjugally Transferred DNA in Minicells of *Escherichia coli* K-12, *Molec. gen. Genet.* 128:23-42 (1974).

Khachatourians G., The Potential Use of Minicell Cultures in *E. coli* Vaccines, *Proceedings of Minisymposium on Neonatal Diarrhea in Calves and Pigs*, 82-91 (1976).

Khachatourians et al., Use of Anucleated Minicells in Vaccination Against Enteropathogenic *E. coli*, Abstract 443-455 (1979).

Khachatourians, G., The Use of Anucleated Minicells in Biotechnology: An Overview, *Biotechnology* pp. 309-319 (1985).

Khachatourians, G., *Minicells as Specialized Vaccines and Vaccine Carriers*, Isaacson, R.E. (Ed.). Recombinant DNA Vaccines: Rationale and Strategy, pp. 323-333, (1992).

Kool et al., Proteins Synthesized by a Non-Induced Bacteriocinogenic Factor in Minicells of *Escherichia coli*, *Mole. Gen. Genetics* 115:314-323 (1972).

Kopylova-Sviridova et al., Synthesis of Proteins Coded by Plasmid Vectors of pCV Series ($Ap^r$, $Tc^r$) and their Recombinant Derivatives (pDm) in *E. coli* Minicells, *Gene* 7:121-139 (1979).

Kozak, Marilyn, Initiation of Translation in Prokaryotes and Eukaryotes *Gene* 234:187-208 (1999).

Leung, et al., The yopM Gene of *Yersinia pestis* Encodes a Released Protein Having Homology with the Human Platelet Surface Protein GPIbα *J. of Bacteriology* 4623-4632 (1989).

Lienard et al., Cloning, sequencing and expression of the genes encoding the sodium translocating $N^5$-methyl-tetrahydromethanopterin: coenzyme M . . . , *FEBS Letters* 425:204-208 (1998).

MacConnell et al., Expression of FBJ-MSV Oncogene (fos) Product in Bacteria, *Virology* 131:367-374 (1983).

Maniatis, Tom Recombinant DNA Procedures in the Study of Eukaryotic Genes *Cell Biology* 3:563-608 (1980).

Martinez-Salas, et al. Functional Interactions in Internal Translation Initiation Directed by Viral and Cellular IRES Elements *Journal of General Virology* 82:973-984 (2001).

Matsumura et al., Synthesis of mot and che gene products of *Escherichia coli* programmed by hybrid ColE1 plasmids in minicells, *J. Bacteriol.* 132(3):996-1002 (Dec. 1977).
Meagher et al., Protein Expression in *E. coli* Minicells by Recombinant Plasmids, *Cell* 10:521-536 (1977).
Miller et al., Translation in *Escherichia Coli* minicells containing Hamster mitochondrial DNA-ColE1 Amp[r] Recombinant Plasmids, *Biochemica et Biophysica Acta* 477:323-333 (1977).
Noegel et al., Plasmid Cistrons Controlling Synthesis and Excretion of the Exotoxin α-Haemolysin of *Escherichia coli, Molec. gen. Genet.* 175:343-350 (1979).
Parkhill, et al. Genome Sequence of *Yersina Pestis*, the Causative Agent of Plaque *Nature Publishing Group* 413:523-527 (2001).
Perry, et al. *Yersinia Pestis*-Etiologic Agent of Plaque *Clinical Microbiology Reviews* 10:35-66 (1997).
Pickett et al., Cloning, Sequencing, and Expression of the *Escherichia coli* Cytolethal Distending Toxin Genes, *Infection and Immunity* 62(3):1046-1051 (1994).
Purcell et al., Molecular Cloning and Characterization of the 15-Kilodalton Major Immunogen of *Treponema pallidum*, *Infection and Immunity* 57(12):3708-3714 (1989).
Reeve et al., Minicells of *Bacillus subtilis* A Unique System for Transport Studies, *Biochimica et Biophysica Acta* 352:298-306 (1974).
Roozen et al., Synthesis of Ribonucleic Acid and Protein in Plasmid-Containing Minicells of *Escherichia coli* K-12, *J. of Bacteriology* 107(1):21-33 (1971).
Rosner et al., Expression of a cloned bovine growth hormone gene in *Escherichia coli* minicells, *Can. J. Biochem.* 60:521-524 (1982).
Schaumberg et al., Genetic Mapping of the minB Locus in *Escherichia coli* K-12, *J. of Bacteriology* 153(2):1063-1065 (1983).
Schlosser et al., Subcloning, Nucleotide Sequence, and Expression of trkG, a Gene That Encodes an Integral Membrane Protein Involved in Potassium Uptake . . . , *J. of Bacteriology* 173(10):3170-3176 (1991).
Sizemore, et al., Attenuated *Shigella* as a DNA Delivery Vehicle for DNA-Mediated Immunization, *Science* 270:299-302 (1995).
Sizemore, et al., Attenuated bacteria as a DNA delivery vehicle for DNA-mediated immunization, *Vaccine* 15(8):804-807 (1997).
Stieglitz, et al., Cloning, Sequencing, and Expression in Ficoll-Generated Minicells of an *Escherichia coli* Heat-Stable Enterotoxin Gene, *Plasmid* 20:42-53 (1988).
Suzuki, et al., Production in *Escherichia coli* of biologically active secretin, a gastrointestinal hormone, *Proc. Natl. Acad. Sci. USA*, vol. 79, pp. 2475-2479 (1982).
Tankersley et al., Induction and Isolation of a Minicell-Producing Strain of *Salmonella typhimurium, Proceedings of the Society for Experimental Biology and Medicine* 145:802-805 (1974).
Zink, Gilbert L. Immunizing Agents and Diagnostic Antigens *Remington's Pharmaceutical Sciences* (73)1324-1340 (1980).
Zubay, Geoffrey, The Isolation and Properties of CAP, the Catabolite Gene Activator, *Methods in Enzymology* 65:856-877 (1980).
Supplementary European Search Report dated Oct. 31, 2006, received in Application No. 02747872.6.
Office Action received in U.S. Appl. No. 10/832,000, mailed Apr. 9, 2007.
Office Action received in U.S. Appl. No. 11/096,646, mailed Oct. 30, 2007.
Hale et al. "Characterization of virulent plasmid and plasmid-associated outer membrane protein in *Shigella flexneri, Shigella sonnei,* and *Escherichia coli*," Infection and Immunity, 40(1):340-350 (1983).
Jaffe et al. "Minicell-forming mutants of *Escherichia coli*: Production of minicells and anucleate rods," J. Bacteriol., 170(7):3094-3101 (1988).
Barrett-Bee, K. et al., "The accumulation of novobiocin by *Escherichia coli* and *Staphylococcal aureus*", Journal of Antimicrobial Chemotherapy, 33; 1165-1171 (1994).
Clark, "The fermentation pathways of *Escherichia coli*", FEMS Microbiology Reviews, 63:223-234 (1989).
Desai et al., "The mechanism of uptake of biodegradable microparticles in Caco-2 cells is size dependent," Pharm. Res., 14(11): 1568-1573 (1997).

Dmitriev et al., "Ectodomain of *coxsackievirus* and adenovirus receptor genetically fused to epidermal growth factor mediates adenovirus targeting to epidermal growth factor receptor-positive cells," J. Virol., 74(15): 6875-6884 (2000).
Eliasson et al., "Direct visualization of plasmid DNA in bacterial cells," Molecular Microbiology, 6(2):165-170 (1992).
Fantappie et al., "The MDR phenotype is associated with the expression of COX-2 and iNOS in a human hepatocellular carcinoma cell line," Hepatology, 35(4): 843-852 (2002).
Giacalone et al., "The use of bacterial minicells to transfer plasmid DNA to eukaryotic cells," Cell. Microbiol. 8(10):1624-1633 (2006).
Giacalone et al., "Immunization with non-replicating *E. coli* minicells delivering both protein antigen and DNA protects mice from lethal challenge with *Lymphocytic choriomeningitis* virus," Vaccine, 25(12):2279-2287 (2007).
Giannakakou et al., "Paclitaxel-resistant human ovarian cancer cells have mutant beta-tubulins that exhibit impaired paclitaxel-driven polymerization," Journal of Biological Chemistry, 272(27):11718-11725 (1997).
Gomez-Eichelmann et al., "Effect of nalidixic acid and novobiocin on pBR322 genetic expression in *Escherichia coli* minicells," Journal of Bacteriology, 148(3):745-752, (Dec. 1981).
Guindulain et al., "Involvement of RNA and DNA in the staining of *Escherichia coli* by SYTO 13," Letters Applied Microbiology, 34(3): 182-188 (2002).
Huda et al., "Molecular Cloning and Characterization of an ABC Multidrug Efflux Pump, VcaM, in Non-O1 Vibrio cholerae", Antimicrobial Agents and Chemotherapy, 47(8):2413-2417 (2003).
Iida, et al., "Cell wall alterations of gram-negative bacteria by aminoglycoside antibiotics," Antimicrobial Agents and Chemotherapy, 5(1): 95-97 (1974).
Ishii et al., "A methylated oligonucleotide induced methylation of GSTP1 promoter and suppressed its expression in A549 lung adenocarcinoma cells," Cancer Letters, 212(2): 211-223 (2004).
Izquierdo, et al., "Broad distribution of the multidrug resistance-related vault lung resistance protein in normal human tissues and tumors," American Journal of Pathology, 148(3): 877-887 (1996).
Katsui et al., "Heat-induced blebbing and vesiculation of the outer membrane of *Escherichia coli*," J. Bacteriol., 151(3):1523-1531 (1982).
Kaneko, et al., "Energetics of tetracycline efflux system encoded by Tn10 in *Escherichia coli*." FEBS, 193(2):194-198 (1985).
Knox et al., "Relation between excreted lipopolysaccharide complexes and surface structures of a lysine-limited culture of *Escherichia coli*," J. Bacteriol., 92(4):1206-1217 (1966).
Kuypers, et al., "Cloning of the replication gene O of *E. coli* bacteriophage lambda and its expression under the control of the lac promoter," Gene, 10(3):195-203 (1980).
Levenson et al., "Pleiotropic resistance to DNA-interactive drugs is associated with increased expression of genes involved in DNA replication, repair, and stress response," Cancer Research, 60(18): 5027-5030 (2000).
Ling, "Multidrug resistance: molecular mechanisms and clinical relevance," Cancer Chemotherapy & Pharmacology, 40 Suppl:S3-8 (1997).
Ma et al., "Molecular cloning and Characterization of acrA and acrE Genes in *Escherichia coli*", Journal of Bacteriology, 175(19):6299-6313 (1993).
Ma et al., "Genes acrA and acrB encode a stress-induced efflux system of *Escherichia coli*", Molecular Microbiology 16(1):45-55 (1995).
Mamot et al., "Epidermal growth factor receptor (EGFR)-targeted immunoliposomes mediate specific and efficient drug delivery to EDFR- and EGFRvIII-overexpressing tumor cells," Cancer Res.; 63: 3154-3161 (2003).
Mobley et al, "Energetics of plasmid-mediated arsenate resistance in *Escherichia coli*", Proceedings of the national Academy of Sciences (USA), 79:6119-6122 (1982).
Monfort et al., "Cell cycle characteristics and changes in membrane potential during the growth of *Escherichia coli* as determined by a cyanine fluorescent dye and flow cytometry", Journal of Microbiological Methods, 25:79-86 (1996).

Murakami et al., "Extramembrane Central Pore of Multidrug Exporter AcrB in *Escherichia coli* Plays an Important Role in Drug Transport", The Journal of Biological Chemistry, 279(5):3743-3748 (2004).

Naito et al., "Mechanisms of drug resistance in chemotherapy for urogenital carcinoma," Int. J. Urol., 6(9):427-439 (1999).

Nieva-Gomez and Gennis, "Affinity of intact *Escherichia coli* for hydrophobic membrane probes is a function of the physiological state of the cells", PNAS USA, 74(5):1811-1815 (1977).

Nikaido, "Antibiotic Resistance Caused by Gram-Negative Multidrug Efflux Pumps", Clinical Infectious Disease, 27 (Suppl 1):S32-41 (1998).

Nishino et al., "Overexpression of the Response Regulator evgA of the Two-Component Signal Transduction System Modulates Multidrug Resistance Conferred by Multidrug Resistance Transporters", Journal of Bacteriology, 183(4):1455-1458 (2001).

Pal, et al., "Plasmid-associated adherence of *Shigella flexneri* in a HeLa cell model," Infection Immun., Aug. 57(8): 2580-2582 (1989).

Paulsen et al., "Proton-Dependent Multidrug Efflux Systems", Microbiological Reviews, 60(4):575-608 (1996).

Perreten et al., "Mdt(A), a New Efflux Protein Conferring Multiple Antibiotic Resistance in *Lactobacillus lactis* and *Escherichia coli*.", Antimicrobial Agents and Chemotherapy, 45(4):1109-1114 (2001).

Peterkofsky et al., "Glucose and the Metabolism of Adenosine 3':5'-Cyclic Monophosphate in *Escherichia coli*", PNAS, USA, 68(11):2794-2798 (1971).

Plesiat, et al., "Outer membranes of Gram-negative bacteria are permeable to steroid probes", Molecular Microbiology, 6(10):1323-1333 (1992).

Scherer, et al., "The viral range in vitro of a malignant human epithelial cell (strain HeLa, Gey). III. Studies with pseudolymphocytic choriomeningitis virus; general discussion." Am. J. Pathol., 31(1):31-39 (1955).

Scherer, et al., "Studies on the propagation in vitro of poliomyelitis viruses. IV. Viral multiplication in a stable strain of human malignant epithelial cells (strain HeLa) derived from an epidermoid carcinoma of the cervix," J. Exp. Med., 97(5):695-710 (1953).

Schindler et al., "Action of polymyxin B on bacterial membranes: morphological changes in the cytoplasm and in the outer membrane of *Salmonella typhimurium* and *Escherichia coli* B," Antimicrobial Agents and Chemotherapy, 8(1):95-104 (1975).

Sheehy et al., "Molecular Studies on Entry Exclusion in *Escherichia coli* Minicells", Journal of Bacteriology, 112(2):861-869 (1972).

Someya et al., "Morphological changes of *Escherichia coli* induced by bicyclomycin," Antimicrobial Agents and Chemotherapy, Jul. vol. 16 (1): 84-88 (1979).

Verfaillie, et al., "Gene therapy for chronic myelogenous leukemia," Molecular Medicine Today, 5(8):359-366 (1999).

Wacheck et al., "Small interfering RNA targeting bcl-2 sensitizes malignant melanoma," Oligonucleotides, 13(5): 393-400 (2003).

Walmsley-Borges et al., "Structure and function of efflux pumps that confer resistance to drugs", Biochemical Journal, 376: 313-388 (2003).

Watarai et al., "Interaction of Ipa proteins of *Shigella flexneri* with alpha5beta1 integrin promotes entry of the bacteria into mammalian cells," J. Exp. Med., 183: 991-999 (1996).

Williams, et al., "Accumulation of Rifampicin by *Escherichia coli* and *Staphylococcus aureus*", Journal of Antimicrobial Chemotherapy, 42:597-603 (1998).

Yang et al., "Synthesis of an R plasmid protein associated with tetracycline resistance is negatively regulated", PNAS USA, 73(5):1509-1512 (1976).

Youn et al., "Oncogenic H-Ras up-regulates expression of ERCC1 to protect cells from platinum-based anticancer agents," Cancer Research, 64(14): 4849-4857 (2004).

Zusman et al. "Cell Division in *Escherichia coil:* analysis of double mutants for filamentation and abnormal septation of deoxyribonucleic acid-less cells," J. Bacteriol., 120(3):1427-1433 (1974).

\* cited by examiner to# MINICELLS DISPLAYING ANTIBODIES OR DERIVATIVES THEREOF AND COMPRISING BIOLOGICALLY ACTIVE COMPOUNDS

RELATED APPLICATIONS

This application is a divisional of U.S. application Ser. No. 11/580,095, filed Oct. 11, 2006 now U.S. Pat. No. 7,871,815, which is a divisional of U.S. application Ser. No. 10/156,902, filed May 28, 2002, now U.S. Pat. No. 7,183,105, which is a divisional of U.S. application Ser. No. 10/154,951, filed May 24, 2002, now abandoned, which claims the benefit of U.S. Provisional Application Nos. 60/359,843, filed Feb. 25, 2002, and 60/293,566, filed May 24, 2001, all of which are incorporated by reference in their entirety.

FIELD OF THE INVENTION

The invention is drawn to compositions and methods for the production of achromosomal archeabacterial, eubacterial and anucleate eukaryotic cells that are used as, e.g., therapeutics and/or diagnostics, reagents in drug discovery and functional proteomics, research tools, and in other applications as well.

BACKGROUND OF THE INVENTION

The following description of the background of the invention is provided to aid in understanding the invention, but is not admitted to describe or constitute prior art to the invention. The contents of the articles, patents, and patent applications, and all other documents and electronically available information mentioned or cited in this application, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Minicells are achromosomal cells that are products of aberrant cell division, and contain RNA and protein, but little or no chromosomal DNA. Clark-Curtiss and Curtiss III, Analysis of Recombinant DNA Using *Escherichia coli* Minicells, 101 Methods in Enzymology 347 (1983); Reeve and Mendelson, Minicells of *Bacillus subtilis*. A new system for transport studies in absence of macromolecular biosynthesis, 352 Biochim. Biophys. Acta 298-305 (1974). Minicells are capable of plasmid-directed synthesis of discrete polypeptides in the absence of synthesis directed by mRNA from the bacterial chromosome. Meagher et al., Protein Expression in *E. coli* Minicells by Recombinant Plasmids, 10 Cell 521, 523 (1977); Roozen et al., Synthesis of Ribonucleic Acid and Protein in Plasmid-Containing Minicells of *Escherichia coli* K-12, 107(1) J. of Bacteriology 21 (1971); and Curtiss III, Research on bacterial conjugation with minicells and minicell-producing *E. coli* strains, In: Microbial Drug Resistance, Editors Susumu Mitsuhashi & Hajime Hashimoto, p. 169 (Baltimore: University Park Press 1976). Early descriptions of minicells include those of Adler et al., Genetic control of cell division in bacteria, 154 Science 417 (1966), and Adler et al. (Miniature *Escherichia coli* cells deficient in DNA, 57 Proc. Nat. Acad. Sci. (Wash.) 321 (1967)). However, discovery of the production of minicells can arguably be traced to the 1930's (Frazer and Curtiss III, Production, Properties and Utility of Bacterial Minicells, 69 Curr. Top. Microbiol. Immunol. 1-3 (1975)).

Prokaryotic (a.k.a. eubacterial) minicells have been used to produce various eubacterial proteins. See, e.g., Michael Gaâel, et al., The kdpF Subunit Is Part of the K+-translocating Kdp Complex of *Escherichia coli* and Is Responsible for Stabilization of the Complex in vitro, 274(53) Jn. of Biological Chemistry 37901 (1999); Harlow, et al., Cloning and Characterization of the gsk Gene Encoding Guanosine Kinase of *Escherichia coli*, 177(8) J. of Bacteriology 2236 (1995); Carol L. Pickett, et al., Cloning, Sequencing, and Expression of the *Escherichia coli* Cytolethal Distinding Toxin Genes, 62(3) Infection & Immunity 1046 (1994); Raimund Eck & Jörn Belter, Cloning and characterization of a gene coding for the catechol 1,2 dioxygenase of *Arthrobacter* sp. mA3, 123 Gene 87 (1993); Andreas Schlössser, et al, Subcloning, Nucleotide Sequence, and Expression of trkG, a Gene That Encodes an Integral Membrane Protein Involved in Potassium Uptake via the Trk System of *Escherichia coli*, 173(10) J. of Bacteriology 3170 (1991); Mehrdad Jannatipour, et al., Translocation of *Vibrio harveyi* N,N'-Diacetylchitobiase to the Outer Membrane of *Escherichia coli* 169(8) J. of Bacteriology 3785 (1987); and Jacobs et al., Expression of *Mycobacterium leprae* genes from a *Streptococcus mutans* promoter in *Escherichia coli* K-12, 83(6) Proc. Natl. Acad. Sci. USA 1926 (1986);

Various bacteria have been used, or proposed to be used, as gene delivery vectors to mammalian cells. For reviews, see Grillot-Courvalin et al., Bacteria as gene delivery vectors for mammalian cells, 10 Current Opinion in Biotechnology 477 (1999); Johnsen et al., Transfer of DNA from Genetically Modified Organisms (GMOs), Biotechnological Institute, 1-70 (2000); Sizemore et al., Attenuated *Shigella* as a DNA delivery vehicle for DNA-mediated immunization, 270(5234) Science 299 (1995); Patrice Courvalin, et al., Gene transfer from bacteria to mammalian cells, 318 C. R. Acad. Sci. 1207 (1995); Sizemore, et al. Attenuated bacteria as a DNA delivery vehicle for DNA-mediated immunization, 15(8) Vaccine 804 (1997).

U.S. Pat. No. 4,190,495, which issued Feb. 26, 1980, to Curtiss is drawn to minicell producing strains of *E. coli* that are stated to be useful for the recombinant expression of proteins.

U.S. Pat. No. 4,311,797, which issued Jan. 19, 1982 to Khachatourians is stated to be drawn to a minicell based vaccine. The vaccine is stated to induce the production of antibodies against enteropathogenic *E. coli* cells in cattle and is stated to be effective against coliform enteritis.

Eubacterial minicells expressing immunogens from other prokaryotes have been described. Purcell et al., Molecular cloning and characterization of the 15-kilodalton major immunogen of *Treponema pallidum*, Infect. Immun. 57:3708, 1989.

In "Biotechnology: Promise . . . and Peril" (IDRC Reports 9:4-7, 1980) authors Fleury and Shirkie aver that George Khachatourians at the University of Saskatchewan, Canada, "is working on a vaccine against cholera using 'minicells.'" The minicells are said to contain "genes from the pathogenic agent," and the "pathogen antigens are carried on the surface of the minicells" (p. 5, paragraph bridging the central and right columns).

Lundstrom et al., Secretion of Semliki Forest virus membrane glycoprotein E1 from *Bacillus subtilis*, Virus Res. 2:69-83, 1985, describe the expression of the E1 protein of the eukaryotic virus, Semliki Forest virus (SFV), in *Bacillus* minicells. The SFV E1 protein used in these studies is not the native E1 protein. Rather, it is a fusion protein in which the N-terminal signal sequence and C-terminal transmembrane domain have been removed and replaced with signal sequences from a gene from *Bacillus amyloliquefaciens*. The authors aver that "E1 is properly translocated through the cell membrane and secreted" (p. 81, 1.1. 19-20), and note that "it has been difficult to express viral membrane proteins in prokaryotes" (p. 81, l. 27).

U.S. Pat. No. 4,237,224, which issued Dec. 2, 1980, to Cohen and Boyer, describes the expression of *X. Laevis* DNA in *E. coli* minicells.

U.S. patent application Ser. No. 60/293,566, is entitled "Minicell Compositions and Methods," and was filed May 24, 2001, by Sabbadini, Roger A., Berkley, Neil L., and Klepper, Robert E., and is hereby incorporated in its entirety by reference.

Jespersen et al. describes the use of "proteoliposomes" to generate antibodies to the AMPA receptor. Jespersen L K, Kuusinen A, Orellana A, Keinanen K, Engberg J. Use of proteoliposomes to generate phage antibodies against native AMPA receptor. Eur J. Biochem. 2000 March; 267(5):1382-9

SUMMARY OF THE INVENTION

The invention is drawn to compositions and methods for the production and use of minicells, including but not limited to eubacterial minicells, in applications such as diagnostics, therapeutics, research, compound screening and drug discovery, as well as agents for the delivery of nucleic acids and other bioactive compounds to cells.

Minicells are derivatives of cells that lack chromosomal DNA and which are sometimes referred to as anucleate cells. Because eubacterial and archeabacterial cells, unlike eukaryotic cells, do not have a nucleus (a distinct organelle that contains chromosomes), these non-eukaryotic minicells are more accurately described as being "without chromosomes" or "achromosomal," as opposed to "anucleate." Nonetheless, those skilled in the art often use the term "anucleate" when referring to bacterial minicells in addition to other minicells. Accordingly, in the present disclosure, the term "minicells" encompasses derivatives of eubacterial cells that lack a chromosome; derivatives of archeabacterial cells that lack their chromosome(s), and anucleate derivatives of eukaryotic cells. It is understood, however, that some of the relevant art may use the terms "anucleate minicells" or anucleate cells" loosely to refer to any of the preceeding types of minicells.

In one aspect, the invention is drawn to a eubacterial minicell comprising a membrane protein that is not naturally found in a prokaryote, i.e., a membrane protein from a eukaryote or an archeabacterium. Such minicells may, but need not, comprise an expression element that encodes and expresses the membrane protein that it comprises. The membrane protein may be one found in any non-eubacterial membrane, including, by way of non-limiting example, a cellular membrane, a nuclear membrane, a nucleolar membrane, a membrane of the endoplasmic reticulum (ER), a membrane of a Golgi body, a membrane of a lysosome a membrane of a peroxisome, a caveolar membrane, an outer membrane of a mitochondrion or a chloroplast, and an inner membrane of a mitochondrion or a chloroplast. By way of non-limiting example, a membrane protein may be a receptor, such as a G-protein coupled receptor; an enzyme, such as ATPase or adenylate cyclase, a cytochrome; a channel; a transporter; or a membrane-bound nucleic acid binding factor, such as a transcription and/or translation factor; signaling components; components of the electron transport chain (ETC); or cellular antigens. A membrane fusion protein, which is generated in vitro using molecular cloning techniques, does not occur in nature and is thus a membrane protein that is not naturally found in a prokaryote, even if the fusion protein is prepared using amino acid sequences derived from eubacterial proteins.

Minicells that have segregated from parent cells lack chromosomal and/or nuclear components, but retain the cytoplasm and its contents, including the cellular machinery required for protein expression. Although chromosomes do not segregate into minicells, extrachromosomal and/or episomal genetic expression elements will segregate, or may be introduced into minicells after segregation from parent cells. Thus, in one aspect, the invention is drawn to minicells comprising an expression element, which may be an inducible expression element, that comprises expression sequences operably linked to an open reading frame (ORF) that encodes the non-eubacterial membrane protein. In a related aspect, the invention is drawn to minicell-producing host cells having an expression element, which may be an inducible expression element, that comprises expression sequences operably linked to an ORF that encodes a non-eubacterial membrane protein. In a related aspect, the invention is drawn to a method of making a eubacterial minicell comprising a membrane protein that is not naturally found in a prokaryote, the method comprising growing minicell-producing host cells, the host cells having an expression element, which may be an inducible expression element, that comprises expression sequences operably linked to an ORF that encodes a non-eubacterial membrane protein; and preparing minicells from the host cells. Optionally, at any point in the method, an inducing agent is provided in order to induce expression of an ORF that encodes a non-eubacterial membrane protein.

In one aspect, the invention is drawn to display produced membrane-associated protein(s) on the surface of the minicell. For purposes of this document, the term "display" is defined as exposure of the structure of interest on the outer surface of the minicell. By way of non-limiting example, this structure may be an internally expressed membrane protein or chimeric construct to be inserted in or associated with the minicell membrane such that the extracellular domain or domain of interest is exposed on the outer surface of the minicell (expressed and displayed on the surface of the minicell or expressed in the parental cell to be displayed on the surface of the segregated minicell). In any scenario, the "displayed" protein or protein domain is available for interaction with extracellular components. A membrane-associated protein may have more than one extracellular domain, and a minicell of the invention may display more than one membrane-associated protein.

A membrane protein displayed by eubacterial minicells may be a receptor. Receptors include, by way of non-limiting example, G-coupled protein receptors, hormone receptors, and growth factor receptors. Minicells displaying a receptor may, but need not, bind ligands of the receptor. In therapeutic applications of this aspect of the invention, the ligand is an undesirable compound that is bound to its receptor and, in some aspects, is internalized or inactivated by the minicells. In drug discovery applications of this aspect of the invention, the ligand for the receptor may be detectably labeled so that its binding to its receptor may be quantified. In the latter circumstance, the minicells may be used to identify and isolate, from a pool of compounds, one or more compounds that inhibit or stimulate the activity of the receptor. That is, these minicells can be used in screening assays, including assays such as those used in high throughput screening (HTS) systems and other drug discovery methods, for the purpose of preparing compounds that influence the activity of a receptor of interest.

The displayed domain of a membrane protein may be an enzymatic domain such as on having oxidoreductase, transferase, hydrolase, lyase, isomerase ligase, lipase, kinase, phosphatase, protease, nuclease and/or synthetase activity. Contacting such minicells with the appropriate substrate of the enzyme allows the substrate to be converted to reactant. When either the substrate or reactant is detectable, the reaction catalyzed by the membrane-bound enzyme may be quantified. In the latter instance, the minicells may be used to identify and isolate, from a pool of compounds, one or more compounds that inhibit or stimulate the activity of the enzyme represented by the displayed enzymatic moiety. That is, these minicells can be used in screening assays, including assays such as those used in high throughput screening (HTS) systems and other drug discovery methods, for the purpose of preparing compounds that influence the activity of an enzyme or enzymatic moiety of interest.

The membrane protein displayed by minicells may be a fusion protein, i.e., a protein that comprises a first polypeptide having a first amino acid sequence and a second polypeptide having a second amino acid sequence, wherein the first and second amino acid sequences are not naturally present in the same polypeptide. At least one polypeptide in a membrane fusion protein is a "transmembrane domain" or "membrane-anchoring domain". The transmembrane and membrane-anchoring domains of a membrane fusion protein may be selected from membrane proteins that naturally occur in a eucaryote, such as a fungus, a unicellular eucaryote, a plant and an animal, such as a mammal including a human. Such domains may be from a viral membrane protein naturally found in a virus such as a bacteriophage or a eucaryotic virus, e.g., an adenovirus or a retrovirus. Such domains may be from a membrane protein naturally found in an archaebacterium such as a thermophile.

The displayed domain of a membrane fusion protein may be an enzymatic domain such as one having oxidoreductase, transferase, hydrolase, lyase, isomerase ligase, lipase, kinase, phosphatase, protease, nuclease and/or synthetase activity. Contacting such minicells with the appropriate substrate of the enzyme allows the substrate to be converted to reactant. When either the substrate or reactant is detectable, the reaction catalyzed by the membrane-bound enzyme may be quantified. In the latter instance, the minicells may be used to identify and isolate, from a pool of compounds, one or more compounds that inhibit or stimulate the activity of the enzyme represented by the displayed enzymatic moiety. That is, these minicells can be used in screening assays, including assays such as those used in high throughput screening (HTS) systems and other drug discovery methods, for the purpose of preparing compounds that influence the activity of an enzyme or enzymatic moiety of interest.

The displayed domain of a membrane fusion protein may be a binding moiety. By way of non-limiting example, binding moieties used for particular purposes may be a binding moiety directed to a compound or moiety displayed by a specific cell type or cells found predominantly in one type of tissue, which may be used to target minicells and their contents to specific cell types or tissues; or a binding moiety that is directed to a compound or moiety displayed by a pathogen, which may be used in diagnostic or therapeutic methods; a binding moiety that is directed to an undesirable compound, such as a toxin, which may be used to bind and preferably internalize and/or neutralize the undesirable compound; a diseased cell; or the binding moiety may be a domain that allows for the minicells to be covalently or non-covalently attached to a support material, which may be used in compositions and methods for compound screening and drug discovery. By "diseased cell" it is meant pathogen-infected cells, malfunctioning cells, and dysfunctional cells, e.g., cancer cells.

In various aspects, the minicells of the invention comprise one or more biologically active compounds. The term "biologically active" (synonymous with "bioactive") indicates that a composition or compound itself has a biological effect, or that it modifies, causes, promotes, enhances, blocks, reduces, limits the production or activity of, or reacts with or binds to an endogenous molecule that has a biological effect. A "biological effect" may be but is not limited to one that stimulates or causes an immunoreactive response; one that impacts a biological process in an animal; one that impacts a biological process in a pathogen or parasite; one that generates or causes to be generated a detectable signal; and the like. Biologically active compositions, complexes or compounds may be used in therapeutic, prophylactic and diagnostic methods and compositions. Biologically active compositions, complexes or compounds act to cause or stimulate a desired effect upon an animal. Non-limiting examples of desired effects include, for example, preventing, treating or curing a disease or condition in an animal suffering therefrom; limiting the growth of or killing a pathogen in an animal infected thereby; augmenting the phenotype or genotype of an animal; stimulating a prophylactic immunoreactive response in an animal; or diagnosing a disease or disorder in an animal.

In the context of therapeutic applications of the invention, the term "biologically active" indicates that the composition, complex or compound has an activity that impacts an animal suffering from a disease or disorder in a positive sense and/or impacts a pathogen or parasite in a negative sense. Thus, a biologically active composition, complex or compound may cause or promote a biological or biochemical activity within an animal that is detrimental to the growth and/or maintenance of a pathogen or parasite; or of cells, tissues or organs of an animal that have abnormal growth or biochemical characteristics, such as cancer cells.

In the context of diagnostic applications of the invention, the term "biologically active" indicates that the composition, complex or compound can be used for in vivo or ex vivo diagnostic methods and in diagnostic compositions and kits. For diagnostic purposes, a preferred biologically active composition or compound is one that can be detected, typically (but not necessarily) by virtue of comprising a detectable polypeptide. Antibodies to an epitope found on composition or compound may also be used for its detection.

In the context of prophylactic applications of the invention, the term "biologically active" indicates that the composition or compound induces or stimulates an immunoreactive response. In some preferred embodiments, the immunoreactive response is designed to be prophylactic, i.e., prevents infection by a pathogen. In other preferred embodiments, the immunoreactive response is designed to cause the immune system of an animal to react to the detriment of cells of an animal, such as cancer cells, that have abnormal growth or biochemical characteristics. In this application of the invention, compositions, complexes or compounds comprising antigens are formulated as a vaccine.

It will be understood by those skilled in the art that a given composition, complex or compound may be biologically active in therapeutic, diagnostic and prophylactic applications. A composition, complex or compound that is described as being "biologically active in a cell" is one that has biological activity in vitro (i.e., in a cell culture) or in vivo (i.e., in the cells of an animal). A "biologically active component" of a composition or compound is a portion thereof that is biologically active once it is liberated from the composition or compound. It should be noted, however, that such a component may also be biologically active in the context of the composition or compound.

In one aspect, the minicells of the invention comprise a therapeutic agent. Such minicells may be used to deliver therapeutic agents. In a preferred embodiment, a minicell comprising a therapeutic agent displays a binding moiety that specifically binds a ligand present on the surface of a cell, so that the minicells may be "targeted" to the cell. The therapeutic agent may be any type of compound or moiety, including without limitation small molecules, polypeptides, antibodies and antibody derivatives and nucleic acids. The therapeutic agent may be a drug; a prodrug, i.e., a compound that becomes biologically active in vivo after being introduced into a subject in need of treatment; or an immunogen.

In one aspect, the minicells of the invention comprise a detectable compound or moiety. As is understood by those of skill in the art, a compound or moiety that is "detectable" produces a signal that can detected by spectroscopic, photochemical, biochemical, immunochemical, electromagnetic, radiochemical, or chemical means such as fluorescence, chemifluoresence, or chemiluminescence, electrochemilumenscence, or any other appropriate means. A detectable compound may be a detectable polypeptide, and such polypeptides may, but need not, be incorporated into fusion membrane proteins of the minicell. Detectable polypeptides or amino acid sequences, includes, by way of non-limiting example, a green fluorescent protein (GFP), a luciferase, a beta-galactosidase, a His tag, an epitope, or a biotin-binding protein such as streptavidin or avidin. The detectable compound or moiety may be a radiolabeled compound or a radioisotope. A detectable compound or moiety may be a small molecule such as, by way of non-limiting example, a fluorescent dye; a radioactive iostope; or a compound that may be detected by x-rays or electromagnetic radiation. Image enhancers as those used for CAT and PET scans (e.g., calcium, gallidium) may be used. In another non-limiting example, detectable labels may also include loss of catalytic substrate or gain of catalytic product following catalysis by a minicell displayed, solule cytoplasmic, or secreted enzyme.

In one aspect, the invention is drawn to a minicell comprising one or more bioactive nucleic acids or templates thereof. By way of non-limiting example, a bioactive nucleic acid may be an antisense oligonucleotide, an aptamer, an antisense transcript, a ribosomal RNA (rRNA), a transfer RNA (tRNA), a molecular decoy, or an enzymatically active nucleic acid, such as a ribozyme. Such minicells can, but need not, comprise a displayed polypeptide or protein on the surface of the minicell. The displayed polypeptide or protein may be a binding moiety directed to a compound or moiety displayed by a particular type of cell, or to a compound or moiety displayed by a pathogen. Such minicells can further, but need not, comprise an expression element having eubacterial, archael, eucaryotic, or viral expression sequences operably linked to a nucleotide sequence that serves as a template for a bioactive nucleic acid.

In one aspect, the invention is drawn to immunogenic minicells, i.e., minicells that display an immunogen, vaccines comprising immunogenic minicells, antibodies and antibody derivatives directed to immunogens displayed on immunogenic minicells, and method of making and using immunogenic minicells and antibodies and antibody derivatives produced therefrom in prophylactic, diagnostic, therapeutic and research applications. A preferred immunogen displayed by a minicell is an immunogenic polypeptide, which is preferably expressed from an expression element contained within the minicell in order to maximize the amount of immunogen displayed by the immunogenic minicells. The immunogenic polypeptide can be derived from any organism, obligate intracelluar parasite, organelle or virus with the provisio that, in prophylactic applications, the immunogenic polypeptide is not derived from a prokaryote, including a eubacterial virus. The source organism for the immunogen may be a pathogen. A minicell displaying an immunogen derived from a pathogen is formulated into a vaccine and, in a prophylactic application, used to treat or prevent diseases and disorders caused by or related to the eukaryotic or archeabacterial pathogen.

In a separate aspect, the invention is drawn to minicells that display an immunogen derived from a nonfunctional, dysfunctional and/or diseased cell. By way of non-limiting example, the minicells display an immunogenic polypeptide derived from a hyperproliferative cell, i.e., a cell that is tumorigenic, or part of a tumor or cancer. As another non-limiting example, a cell that is infected with a virus or an obligate intracellular parasite (e.g., Rickettsiae) displays an immunogenic polypeptide that is encoded by the genome of the infected cell but is aberrenatly expressed in an infected cell. A vaccine comprising a minicell displaying an immunogen derived from a nonfunctional, dysfunctional and/or diseased cell is used in methods of treating or preventing hyperproliferative diseases or disorders, including without limitation a cell comprising an intracellular pathogen.

In one aspect, the invention is drawn to methods of using minicells, and expression systems optimized therefore, to manufacture, on a large scale, proteins using recombinant DNA technology. In a related aspect, the invention is drawn to the production, via recombinant DNA technology, and/or segration of exogenous proteins in minicells. The minicells are enriched for the exogenous protein, which is desirable for increased yield and purity of the protein. In addition to protein purification, the minicells can be used for crystallography, the study of intracellular or extracellular protein-protein interactions, the study of intracellular or extracellular protein-nucleic acid interactions, the study of intracellular or extracellular protein-membrane interactions, and the study of other biological, chemical, or physiological event(s).

In one aspect, the invention is drawn to minicells having a membrane protein that has an intracellular domain. By way of non-limiting example, the intracellular domain is exposed on the inner surface of the minicell membrane oriented towards the cytoplasmic compartment. The intracellular protein domain is available for interaction with intracellular components. Intracellular components may be naturally present in the minicells or their parent cells, or may be introduced into minicells after segregation from parent cells. A membrane-associated protein may have more than one intracellular domain, and a minicell of the invention may display more than one membrane-associated protein.

In one aspect, the invention is drawn to a minicell comprising a membrane protein that is linked to a conjugatable compound (a.k.a. "attachable compound"). The conjugatable compound may be of any chemical nature and have one or more therapeutic or detectable moities. By way of non-limiting example, a protein having a transmembrane or membrane anchoring domain is displayed and has the capacity to be specifically cross-linked on its extracellular domain. Through this approach, any conjugatable compound of interest may be quickly and easily attached to the outer surface of minicells containing this expressed membrane-spanning domain. In aspects of the invention wherein minicells are used for drug delivery in vivo, a preferred conjugatable compound is polyethylene glycol (PEG), which provides for "stealth" minicells that are not taken as well and/or as quickly by the reticuloendothelial system (RES). Other conjugatable compounds include polysaccharides, polynucleotides, lipopolysaccharides, lipoproteins, glycosylated proteins, synthetic chemical compounds, and/or chimeric combinations of these examples listed.

In various aspects of the invention, the minicell displays a polypeptide or other compound or moiety on its surface. By way of non-limiting example, a non-eubacterial membrane protein displayed by eubacterial minicells may be a receptor. Minicells displaying a receptor may, but need not, bind ligands of the receptor. In therapeutic applications of this aspect of the invention, the ligand is an undesirable compound that is bound to its receptor and, in some aspects, is internalized by the minicells. In drug discovery applications of this aspect of the invention, the ligand for the receptor may be detectably labeled so that its binding to its receptor may be quantified. In the latter circumstance, the minicells may be used to identify and isolate, from a pool of compounds, one or more compounds that inhibit or stimulate the activity of the receptor. That is, these minicells can be used in screening assays, including assays such as those used in high throughput screening (HTS) systems and other drug discovery methods, for the purpose of preparing compounds that influence the activity of a receptor of interest.

The non-eubacterial membrane protein displayed by minicells may be a fusion protein, i.e., a protein that comprises a first polypeptide having a first amino acid sequence and a second polypeptide having a second amino acid sequence, wherein the first and second amino acid sequences are not naturally present in the same polypeptide. At least one polypeptide in a membrane fusion protein is a "transmembrane domain" or "membrane-anchoring domain". The transmembrane and membrane-anchoring domains of a membrane fusion protein may be selected from membrane proteins that naturally occur in a eukaryote, such as a fungus, a unicellular eukaryote, a plant and an animal, such as a mammal including a human. Such domains may be from a viral membrane protein naturally found in a virus such as a bacteriophage or a eukaryotic virus, e.g., an adenovirus or a retrovirus. Such domains may be from a membrane protein naturally found in an archaebacterium such as a thermophile.

The displayed domain of a membrane fusion protein may be an enzymatic domain such as one having the activity of a lipase, a kinase, a phosphatase, a reductase, a protease, or a nuclease. Contacting such minicells with the appropriate substrate of the enzyme allows the substrate to be converted to reactant. When either the substrate or reactant is detectable, the reaction catalyzed by the membrane-bound enzyme may be quantified. In the latter instance, the minicells may be used to identify and isolate, from a pool of compounds, one or more compounds that inhibit or stimulate the activity of the enzyme represented by the displayed enzymatic moiety. That is, these minicells can be used in screening assays, including assays such as those used in high throughput screening (HTS) systems and other drug discovery methods, for the purpose of preparing compounds that influence the activity of an enzyme or enzymatic moiety of interest.

The displayed domain of a membrane fusion protein may be a binding moiety. By way of non-limiting example, binding moieties used for particular purposes may be a binding moiety directed to a compound or moiety displayed by a specific cell type or cells found predominantly in one type of tissue, which may be used to target minicells and their contents to specific cell types or tissues; or a binding moiety that is directed to a compound or moiety displayed by a pathogen, which may be used in diagnostic or therapeutic methods; a binding moiety that is directed to an undesirable compound, such as a toxin, which may be used to bind and preferably internalize and/or neutralize the undesirable compound; a diseased cell; or the binding moiety may be a domain that allows for the minicells to be covalently or non-covalently attached to a support material, which may be used in compositions and methods for compound screening and drug discovery.

In one aspect, the invention provides compositions and methods for preparing a soluble and/or secreted protein where the protein remains in the cytoplasm of the minicell or is secreted following native secretory pathways for endogenous screted proteins or is secreted using chimeric fusion to secretory signaling sequences. By way of non-limiting example, secreted or cytoplasmic soluble proteins may be produced for purification, targeted therapeutic applications where the protein produced is a therapeutic agent and is produced at the desired site of, detection for screening or diagnostic purposes where the protein is produced in response to a simulous and/or localization event, or to stimulate targeted minicell-cell fusion or interaction events where the protein produced stimulates cell-cell fusion upon targeted stimulation.

In one aspect, the invention provides compositions and methods for preparing antibodies and/or antibody derivatives that recognize an immunogenic epitope present on the native form of a membrane protein, but which is not immunogenic when the membrane protein is denatured or when prepared as a synthetic oligopeptide. Such antibodies and antibody derivatives are said to be "conformation sensitive." Unlike most antibodies and antibody derivatives prepared by using a denatured membrane protein or an oligopeptide derived from the membrane protein, conformation sensitive antibodies and antibody derivatives specifically bind membrane proteins in their native state (i.e., in a membrane) with high affinity. Conformation sensitive antibodies and antibody derivatives are used to target compounds and compositions, including a minicell of the invention, to a cell displaying the membrane protein of choice. Conformation sensitive antibodies and antibody derivatives are also used to prevent receptors from binding their natural ligands by specifically binding to the receptor with a high affinity and thereby limiting access of the ligand to the receptor. Conformation sensitive antibodies and antibody derivatives can be prepared that are specific for a specific isoform or mutant of a membrane protein, which can be useful in research and medical applications.

In one aspect, the invention provides biosensors comprising minicells including, not limited to, the minicells of the invention. An exemplary biosensor of the invention is a BIAcore chip, i.e., a chip onto which minicells are attached, where the minicells undergo some change upon exposure to a preselected compound, and the change is detected using surface plasmon resonance. A biosensor comprising minicells can be used in methods of detecting the presence of an undesirable compound. Undesirable compounds include but are not limited to, toxins; pollutants; explosives, such as those in landmines or illegally present; illegal narcotics; components of biological or chemical weapons. In a related aspect, the invention provides a device comprising a microchip operatively associated with a biosensor comprising a minicell. The device can further comprise an actuator that performs a responsive function when the sensor detects a preselected level of a marker.

In one aspect, the invention provides minicells, that may be used as research tools and/or kits comprising such research tools. The minicells of the invention may be used as is, or incorporated into research tools useful for scientific research regarding all amino acid comprising compounds including, but not limited to membrane-associated proteins, chimeric membrane fusion proteins, and soluble proteins. Such scientific research includes, by way of non-limiting example, basic research, as well as pharmacological, diagnostic, and pharmacogenetic studies. Such studies may be carried out in vivo or in vitro.

In one aspect, the invention is drawn to archaebacterial minicells. In a related aspect, the invention is drawn to archaebacterial minicells comprising at least one exogenous protein, that is, a protein that is not normally found in the parent cell, including without limitation fusion proteins. The archaebacterial minicells of the invention optionally comprise an expression element that directs the production of the exogenous protein(s).

In other aspects, the invention is drawn to methods of preparing the minicells, protoplasts, and Poroplasts™ of the invention for various applications including but not limited to diagnostic, therapeutic, research and screening applications. In a related aspect, the invention is drawn to pharmaceutical compositions, reagents and kits comprising minicells.

In each aspect and embodiment of the invention, unless stated otherwise, embodiments wherein the minicell is a eubacterial minicell, a poroplast, a spheroplast or a protoplast exist.

In a first aspect, the invention provides a minicell comprising a membrane protein selected from the group consisting of a eukaryotic membrane protein, an archeabacterial membrane protein and an organellar membrane protein. In another embodiment, wherein the minicell comprises a biologically active compound. By way of non-limiting example, the biologically active compound is a radioisotope, a polypeptide, a nucleic acid or a small molecule.

In another embodiment, the minicell comprises a expression construct, wherein the first expression construct comprises expression sequences operably linked to an ORF that encodes a protein. In another embodiment, the ORF encodes the membrane protein. In another embodiment, the expression sequences that are operably linked to an ORF are inducible and/or repressible.

In another aspect, the minicell comprises a second expression construct, wherein the second expression construct comprises expression sequences operably linked to a gene. In another embodiment, the expression sequences that are operably linked to a gene are inducible and/or repressible. In a related embodiment, the gene product of the gene regulates the expression of the ORF that encodes the protein. A factor that "regulates" the expression of a gene or a gene product directly or indirectly initiates, enhances, quickens, slows, terminates, limits or completely blocks expression of a gene. In different embodiments, the gene product of the gene is a nucleic acid or a polypeptide. The polypeptide can be of any type, including but not limited to a membrane protein, a soluble protein or a secreted protein. A membrane protein can be a membrane fusion protein comprising a first polypeptide, which comprises at least one transmembrane domain or at least one membrane anchoring domain; and a second polypeptide.

In one aspect, the invention provides a minicell comprising a membrane fusion protein, the fusion protein comprising a first polypeptide, the first polypeptide comprising at least one transmembrane domain or at least one membrane anchoring domain; and a second polypeptide, wherein the second polypeptide is not derived from a eubacterial protein and is neither a His tag nor a glutathione-S-transferase polypeptide. In various embodiments, the minicell is a eubacterial minicell, a poroplast, a spheroplast or a protoplast. In one embodiment, the minicell comprises a biologically active compound.

In one aspect, the invention provides a minicell comprising a membrane conjugate, wherein the membrane conjugate comprises a membrane protein chemically linked to a conjugated compound. In one embodiment, the conjugated compound is selected from the group consisting of a nucleic acid, a polypeptide, a lipid and a small molecule.

In one aspect, the invention provides a method for making minicells, comprising (a) culturing a minicell-producing parent cell, wherein the parent cell comprises an expression construct, wherein the expression construct comprises a gene operably linked to expression sequences that are inducible and/or repressible, and wherein induction or repression of the gene causes or enhances the production of minicells; and (b) separating the minicells from the parent cell, thereby generating a composition comprising minicells, wherein an inducer or repressor is present within the parent cells during one or more steps and/or between two or more steps of the method. In one embodiment, the method further comprises (c) purifying the minicells from the composition.

Relevant gene products are factors involved in or modulating DNA replication, cellular division, cellular partitioning, septation, transcription, translation, or protein folding. The minicells are separated from parent cells by processes such as centrifugation, ultracentrifugation, density gradation, immunoaffinity, immunoprecipitation and other techniques described herein.

In one embodiment, the minicell is a poroplast, and the method further comprises (d) treating the minicells with an agent, or incubating the minicells under a set of conditions, that degrades the outer membrane of the minicell. The outer membrane is degraded by treatment with an agent selected from the group consisting of EDTA, EGTA, lactic acid, citric acid, gluconic acid, tartaric acid, polyethyleneimine, polycationic peptides, cationic leukocyte peptides, aminoglycosides, aminoglycosides, protamine, insect cecropins, reptilian magainins, polymers of basic amino acids, polymixin B, chloroform, nitrilotriacetic acid and sodium hexametaphosphate; by exposure to conditions selected from the group consisting of osmotic shock and insonation; and by other methods described herein.

In one embodiment, further comprising removing one or more contaminants from the composition. Representative contaminants are LPS and peptidoglycan. In a representative embodiment, LPS is removed by contacting the composition to an agent that binds or degrades LPS. At least about 50%, preferably about 65% to about 75%, more preferably 95%, most preferably 99% or >99% of LPS is removed from an initial preparation of minicells. In a related embodiment, the minicell-producing parent cell comprises a mutation in a gene required for lipopolysaccharide synthesis.

In on embodiment, the minicell is a spheroplast, and the method further comprises (d) treating the minicells with an agent, or incubating the minicells under a set of conditions, that disrupts or degrades the outer membrane; and (e) treating the minicells with an agent, or incubating the minicells under a set of conditions, that disrupts or degrades the cell wall. The agent that disrupts or degrades the cell wall can be. e.g., a lysozyme, and the set of conditions that disrupts or degrades the cell wall can be, e.g., incubation in a hypertonic solution.

In one embodiment, the minicell is a protoplast, and the method further comprises (d treating the minicells with an agent, or incubating the minicells under a set of conditions, that disrupt or degrade the outer membrane; (e) treating the minicells with an agent, or incubating the minicells under a set of conditions, that disrupts or degrades the cell wall, in order to generate a composition that comprises protoplasts; and (f) purifying protoplasts from the composition. In one embodiment, the method further comprises preparing a denuded minicell from the minicell. In one embodiment, the method further comprises covalently or non-covalently linking one or more components of the minicell to a conjugated moiety.

In one aspect, the invention provides a L-form minicell comprising (a) culturing an L-form *eubacterium*, wherein the *eubacterium* comprises one or more of the following: (i) an expression element that comprises a gene operably linked to expression sequences that are inducible and/or repressible, wherein induction or repression of the gene regulates the copy number of an episomal expression construct; (ii) a mutation in an endogenous gene, wherein the mutation regulates the copy number of an episomal expression construct; (iii) an expression element that comprises a gene operably linked to expression sequences that are inducible and/or repressible, wherein induction or repression of the gene causes or enhances the production of minicells; and (iv) a mutation in an endogenous gene, wherein the mutation causes or enhances minicell production; (b) culturing the L-form minicell-producing parent cell in media under conditions wherein minicells are produced; and (c) separating the minicells from the parent cell, thereby generating a composition comprising L-form minicells, wherein an inducer or repressor is present within the minicells during one or more steps and/or between two or more steps of the method. In one embodiment, the method further comprises (d) purifying the L-form minicells from the composition.

In one aspect, the invention provides a method of producing a protein, comprising (a) transforming a minicell-producing parent cell with an expression element that comprises expression sequences operably linked to a nucleic acid having an ORF that encodes the protein; (b) culturing the minicell-producing parent cell under conditions wherein minicells are produced; and (c) purifying minicells from the parent cell, (d) purifying the protein from the minicells, wherein the ORF is expressed during step (b), between steps (b) and (c), and during step (c).

In one embodiment, the expression elements segregate into the minicells, and the ORF is expressed between steps (c) and (d). In one embodiment, the protein is a soluble protein contained within the minicells, and the method further comprises (e) lysing the minicells.

In one embodiment, the protein is a secreted protein, and the method further comprises (e) collecting a composition in which the minicells are suspended or with which the minicells are in contact.

In one embodiment, the expression sequences to which the ORF is operably linked are inducible, wherein the method further comprises adding an inducing agent between steps (a) and (b); during step (b); and between steps (b) and (c).

In one embodiment, the expression sequences to which the ORF is operably linked are inducible, wherein the expression elements segregate into the minicells, the method further comprises adding an inducing agent after step (c).

In one embodiment, the method further comprises (e) preparing poroplasts from the minicells, wherein the ORF is expressed during step (b); between steps (b) and (c); during step (c); between step (c) and step (d) when the expression elements segregate into the minicells; and/or after step (d) when the expression elements segregate into the minicells.

In one embodiment, the method further comprises (f) purifying the protein from the poroplasts.

In one embodiment, the method further comprises (e) preparing spheroplasts from the minicells, wherein the ORF is expressed during step (b), between steps (b) and (c), during step (c), between steps (c) and (d) and/or after step (d).

In one embodiment, the method further comprises (f) purifying the protein from the spheroplasts.

In one embodiment, the method further comprises (e) preparing protoplasts from the minicells, wherein the ORF is expressed during step (b), between steps (b) and (c), during step (c), between steps (c) and (d) and/or after step (d).

In one embodiment, the method further comprises (f) purifying the protein from the protoplasts.

In one embodiment, the method further comprises (e) preparing membrane preparations from the minicells, wherein the ORF is expressed during step (b), between steps (b) and (c), during step (c), between steps (c) and (d) and/or after step (d).

In one embodiment, the method further comprises (f) purifying the protein from the membrane preparations.

In one embodiment, the minicell-producing parent cell is an L-form bacterium.

In one aspect, the invention provides a method of producing a protein, comprising (a) transforming a minicell with an expression element that comprises expression sequences operably linked to a nucleic acid having an ORF that encodes the protein; and (b) incubating the minicells under conditions wherein the ORF is expressed.

In one embodiment, the method further comprises (c) purifying the protein from the minicells.

In one aspect, the invention provides a method of producing a protein, comprising (a) transforming a minicell-producing parent cell with an expression element that comprises expression sequences operably linked to a nucleic acid having an ORF that encodes a fusion protein comprising the protein and a polypeptide, wherein a protease-sensitive amino acid sequence is positioned between the protein and the polypeptide; (b) culturing the minicell-producing parent cell under conditions wherein minicells are produced; (c) purifying minicells from the parent cell, wherein the ORF is expressed during step (b); between steps (b) and (c); and/or after step (c) when the expression elements segregate into the minicells; and (d) treating the minicells with a protease that cleaves the sensitive amino acid sequence, thereby separating the protein from the polypeptide.

In one aspect, the invention provides a poroplast, the poroplast comprising a vesicle, bonded by a membrane, wherein the membrane is an eubacterial inner membrane, wherein the vesicle is surrounded by a eubacterial cell wall, and wherein the eubacterial inner membrane is accessible to a compound in solution with the poroplast. In one embodiment, the poroplast is a cellular poroplast. The compound has a molecular weight of at least 1 kD, preferably at least about 0.1 to about 1 kD, more preferably from about 1, 10 or 25 kD to about 50 kD, and most preferably from about 75 or about 100 kD to about 150 or 300 kD.

In one embodiment, the poroplast comprises an exogenous nucleic acid, which may be an expression construct. In one embodiment, the expression construct comprises an ORF that encodes an exogenous protein, wherein the ORF is operably linked to expression sequences. In one embodiment, the exogenous protein is a fusion protein, a soluble protein or a secreted protein. In one embodiment, the exogenous protein is a membrane protein, and is preferably accessible to compounds in solution with the poroplast. In one embodiment, poroplasts are placed in a hypertonic solution, wherein 90% or more of an equivalent amount of spheroplasts or protoplasts lyse in the solution under the same conditions.

In one embodiment, the membrane protein is selected from the group consisting of a eukaryotic membrane protein, an archeabacterial membrane protein, and an organellar membrane protein. In one embodiment, the membrane protein is a fusion protein, the fusion protein comprising a first polypeptide, the first polypeptide comprising at least one transmembrane domain or at least one membrane anchoring domain; and a second polypeptide, wherein the second polypeptide is displayed by the poroplast. In one embodiment, the second polypeptide is displayed on the external side of the eubacterial inner membrane. The second polypeptide can be an enzyme moiety, a binding moiety, a toxin, a cellular uptake sequence, an epitope, a detectable polypeptide, and a polypeptide comprising a conjugatable moiety. An enzyme moiety is a polypeptide derived from, by way of non-limiting example, a cytochrome P450, an oxidoreductase, a transferase, a hydrolase, a lyase, an isomerase, a ligase or a synthetase.

In one embodiment, the poroplast comprises a membrane component that is chemically linked to a conjugated compound.

In one embodiment, the expression construct comprises one or more DNA fragments from a genome or cDNA. In one embodiment, the exogenous protein has a primary amino acid sequence predicted from a nucleic acid sequence.

In one aspect, the invention provides a solid support comprising a minicell. In various embodiments, the solid support is a dipstick, a bead or a mictrotiter multiwell plate. In one embodiment, the minicell comprises a detectable compound, which may be a colorimetric, fluorescent or radioactive compound.

In one embodiment, the minicell displays a membrane component selected from the group consisting of (i) a eukaryotic membrane protein, (ii) an archeabacterial membrane protein, (iii) an organellar membrane protein, (iv) a fusion protein comprising at least one transmembrane domain or at least one membrane anchoring domain, and (v) a membrane conjugate comprising a membrane component chemically linked to a conjugated compound.

In one embodiment, the membrane component is a receptor. In a related embodiment, the solid support further comprises a co-receptor. In one embodiment, the minicell displays a binding moiety.

In one aspect, the invention provides a solid support comprising a minicell, wherein the minicell displays a fusion protein, the fusion protein comprising a first polypeptide that comprises at least one transmembrane domain or at least one membrane anchoring domain, and a second polypeptide. In various embodiments, the second polypeptide comprises a binding moiety or an enzyme moiety.

In one aspect, the invention provides a solid support comprising a minicell, wherein the minicell comprises a membrane conjugate comprising a membrane component chemically linked to a conjugated compound. In one embodiment, the conjugated compound is a spacer. In one embodiment, the spacer is covalently linked to the solid support. In one embodiment, the conjugated compound is covalently linked to the solid support.

In one aspect, the invention provides a minicell comprising a biologically active compound, wherein the minicell displays a ligand or binding moiety, wherein the ligand or binding moiety is part of a fusion protein comprising a first polypeptide that comprises at least one transmembrane domain or at least one membrane anchoring domain and a second polypeptide that comprises a binding moiety, and the minicell is a poroplast, spheroplast or protoplast.

In one aspect, the invention provides a eubacterial minicell comprising a biologically active compound, wherein the minicell displays a binding moiety, wherein the binding moiety is selected from the group consisting of (a) a eukaryotic membrane protein; (b) an archeabacterial membrane protein; (c) an organellar membrane protein; and (d) a fusion protein, the fusion protein comprising a first polypeptide, the first polypeptide comprising at least one transmembrane domain or at least one membrane anchoring domain; and a second polypeptide, wherein the second polypeptide is not derived from a eubacterial protein and is neither a His tag nor a glutathione-S-transferase polypeptide, and wherein the polypeptide comprises a binding moiety.

In one embodiment, the binding moiety is selected from the group consisting of an antibody, an antibody derivative, a receptor and an active site of a non-catalytic derivative of an enzyme. In a preferred embodiment, the binding moiety is a single-chain antibody. In one embodiment, one of the ORFs encodes a protein that comprises the binding moiety.

In one embodiment, the binding moiety is directed to a ligand selected from the group consisting of an epitope displayed on a pathogen, an epitope displayed on an infected cell and an epitope displayed on a hyperproliferative cell.

In one embodiment, the invention further comprises a first and second nucleic acid, wherein the first nucleic acid comprises eukaryotic expression sequences operably linked to a first ORF, and a second nucleic acid, wherein the second nucleic acid comprises eubacterial expression sequences operably linked to a second ORF.

In one embodiment, the eubacterial expression sequences are induced and/or derepressed when the binding moiety is in contact with a target cell. In a variant embodiment, the eukaryotic expression sequences are induced and/or derepressed when the nucleic acid is in the cytoplasm of a eukaryotic cell. In related embodiments, the protein encoded by the first ORF comprises eukaryotic secretion sequences and/or the protein encoded by the second ORF comprises eubacterial secretion sequences.

In one aspect, the invention provides a method of associating a radioactive compound with a cell, wherein the cell displays a ligand specifically recognized by a binding moiety, comprising contacting the cell with a minicell that comprises the radioactive compound and displays the binding moiety. In a diagnostic embodiment, the amount of radiation emitted by the radioactive isotope is sufficient to be detectable. In a therapeutic embodiment, the amount of radiation emitted by the radioactive isotope is sufficient to be cytotoxic. In one embodiment, the ligand displayed by the cell is selected from the group consisting of an epitope displayed on a pathogen, an epitope displayed on an infected cell and an epitope displayed on a hyperproliferative cell. In one embodiment, the binding moiety is selected from the group consisting of an antibody, an antibody derivative, a channel protein and a receptor, and is preferably a single-chain antibody. In other embodiments, the binding moiety is an aptamer or a small molecule. In one embodiment, the ligand is selected from the group consisting of a cytokine, hormone, and a small molecule.

In one aspect, the invention provides a method of delivering a biologically active compound to a cell, wherein the cell displays a ligand specifically recognized by a binding moiety, comprising contacting the cell with a minicell that displays the binding moiety, wherein the minicell comprises the biologically active compound, and wherein the contents of the minicell are delivered into the cell from a minicell bound to the cell. In one embodiment, the biologically active compound is selected from the group consisting of a nucleic acid, a lipid, a polypeptide, a radioactive compound, an ion and a small molecule.

In one embodiment, the membrane of the minicell comprises a system for transferring a molecule from the interior of a minicell into the cytoplasm of the cell. A representative system for transferring a molecule from the interior of a minicell into the cytoplasm of the cell is a Type III secretion system.

In one embodiment, the minicell further comprises a first and second nucleic acid, wherein the first nucleic acid comprises eukaryotic expression sequences operably linked to a first ORF, and a second nucleic acid, wherein the second nucleic acid comprises eubacterial expression sequences operably linked to a second ORF. In one embodiment, one of the ORFs encodes a protein that comprises the binding moiety. In one embodiment, the eubacterial expression sequences are induced and/or derepressed when the binding moiety is in contact with a target cell. In one embodiment, the eukaryotic expression sequences are induced and/or derepressed when the nucleic acid is in the cytoplasm of a eukaryotic cell. In one embodiment, the protein encoded by the first ORF comprises eukaryotic secretion sequences and/or the protein encoded by the second ORF comprises eubacterial secretion sequences. In one embodiment, the ligand is selected from the group consisting of a cytokine, hormone, and a small molecule.

In one aspect, the invention provides a minicell displaying a synthetic linking moiety,
wherein the synthetic linking moiety is covalenty or non-covalently attached to a membrane component of the minicell.

In one aspect, the invention provides a sterically stabilized minicell comprising a displayed moiety that has a longer half-life in vivo than a wild-type minicell, wherein the displayed moiety is a hydrophilic polymer that comprises a PEG moiety, a carboxylic group of a polyalkylene glycol or PEG stearate.

In one aspect, the invention provides a minicell having a membrane comprising an exogenous lipid, wherein a minicell comprising the exogenous lipid has a longer half-life in vivo than a minicell lacking the exogenous lipid, and wherein the minicell is selected from the group consisting of a eubacterial minicell, a poroplast, a spheroplast and a protoplast. In one embodiment, the exogenous lipid is a derivitized lipid which may, by way of non-limiting example, be phosphatidylethanolamine derivatized with PEG, DSPE-PEG, PEG stearate; PEG-derivatized phospholipids, a PEG ceramide or DSPE-PEG.

In one embodiment, the exogenous lipid is not present in a wild-type membrane, or is present in a different proportion than is found in minicells comprising a wild-type membrane. The exogenous lipid can be a ganglioside, sphingomyelin, monosialoganglioside GM1, galactocerebroside sulfate, 1,2-sn-dimyristoylphosphatidylcholine, phosphatidylinositol and cardiolipin.

In one embodiment, the linking moiety is non-covalently attached to the minicell. In one embodiment, one of the linking moiety and the membrane component comprises biotin, and the other comprises avidin or streptavidin. In one embodiment, the synthetic linking moiety is a cross-linker. In one embodiment, the cross-linker is a bifunctional cross-linker.

In one aspect, the invention provides a method of transferring a membrane protein from a minicell membrane to a biological membrane comprising contacting a minicell to the biological membrane, wherein the minicell membrane comprises the membrane protein, and allowing the minicell and the biological membrane to remain in contact for a period of time sufficient for the transfer to occur.

In one embodiment, the biological membrane is a cytoplasmic membrane or an organellar membrane. In one embodiment, the biological membrane is a membrane selected from the group consisting of a membrane of a pathogen, a membrane of an infected cell and a membrane of a hyperproliferative cell. In one embodiment, the biological membrane is the cytoplasmic membrane of a recipient cell, which may be a cultured cell and a cell within an organism. In one embodiment, the biological membrane is present on a cell that has been removed from an animal, the contacting occurs in vitro, after which the cell is returned to the organism.

In one embodiment, the membrane protein is an enzyme. In this embodiment, the membrane protein having enzymatic activity is selected from the group consisting of a cytochrome P450 and a fusion protein, the fusion protein comprising a first polypeptide, the first polypeptide comprising at least one polypeptide, wherein the second polypeptide has enzymatic activity.

In one embodiment, the membrane protein is a membrane fusion protein, the membrane fusion protein comprising a first polypeptide, the first polypeptide comprising at least one transmembrane domain or at least one membrane anchoring domain; and a second polypeptide.

In one embodiment, the second polypeptide is a biologically active polypeptide. In one embodiment, the minicell displays ligand or a binding moiety.

In one aspect, the invention provides a minicell that comprises an expression construct comprising an ORF encoding a membrane protein operably linked to expression sequences, wherein the expression sequences are induced and/or derepressed when the minicell is in contact with a target cell.

In one embodiment, the biological membrane is a cytoplasmic membrane or an organellar membrane. In one embodiment, the biological membrane is a membrane selected from the group consisting of a membrane of a pathogen, a membrane of an infected cell and a membrane of a hyperproliferative cell. In one embodiment, the minicell displays a ligand or a binding moiety selected from the group consisting of an antibody, an antibody derivative, an aptamer and a small molecule. In one embodiment, the membrane protein is a membrane fusion protein, the membrane fusion protein comprising a first polypeptide, the first polypeptide comprising at least one transmembrane domain or at least one membrane anchoring domain; and a second polypeptide. In one embodiment, the ligand is selected from the group consisting of a cytokine, hormone, and a small molecule.

In one aspect, the invention provides a pharmaceutical composition comprising a minicell, wherein the minicell displays a membrane protein, wherein the membrane protein is selected from the group consisting of a eukaryotic membrane protein, an archeabacterial membrane protein and an organellar membrane protein. In one embodiment, the membrane protein is selected from the group consisting of a receptor, a channel protein, a cellular adhesion factor and an integrin. In one embodiment, the pharmaceutical formulation further comprises an adjuvant. In one embodiment, the membrane protein comprises a polypeptide epitope displayed by a hyperproliferative cell. In one embodiment, the membrane protein comprises an epitope displayed by a eukaryotic pathogen, an archeabacterial pathogen, a virus or an infected cell.

In one aspect, the invention provides a pharmaceutical composition comprising a minicell, wherein the minicell displays a membrane protein that is a fusion protein, the fusion protein comprising (i) a first polypeptide, the first polypeptide comprising at least one transmembrane domain or at least one membrane anchoring domain; and (ii) a second polypeptide, wherein the second polypeptide is not derived from a eubacterial protein. In one embodiment, the pharmaceutical formulation further comprises an adjuvant. In one embodiment, the second polypeptide comprises a polypeptide epitope displayed by a hyperproliferative cell. In one embodiment, the membrane protein comprises an epitope displayed by a eukaryotic pathogen, an archeabacterial pathogen, a virus or an infected cell.

In one aspect, the invention provides a pharmaceutical composition comprising a minicell, wherein the minicell displays a membrane conjugate, wherein the membrane conjugate comprises a membrane component chemically linked to a conjugated compound. In one embodiment, the membrane protein is selected from the group consisting of a receptor, a channel protein, a cellular adhesion factor and an integrin. In one embodiment, the pharmaceutical further comprises an adjuvant. In one embodiment, the membrane component is a polypeptide comprising at least one transmembrane domain or at least one membrane anchoring domain, or a lipid that is part of a membrane. In one embodiment, the conjugated compound is a polypeptide, and the chemical linkage between the membrane compound and the conjugated compound is not a peptide bond. In one embodiment, the conjugated compound is a nucleic acid. In one embodiment, the conjugated compound is an organic compound. In one embodiment, the organic compound is selected from the group consisting of a narcotic, a toxin, a venom, a sphingolipid and a soluble protein.

In one aspect, the invention provides a method of making a pharmaceutical composition comprising a minicell, wherein the minicell displays a membrane protein, wherein the membrane protein is selected from the group consisting of a eukaryotic membrane protein, an archeabacterial membrane protein and an organellar membrane protein. In one embodiment, the method further comprises adding an adjuvant to the pharmaceutical formulation. In one embodiment, the method further comprises desiccating the formulation. In one embodiment, the method further comprises adding a suspension buffer to the formulation. In one embodiment, the method further comprises making a chemical modification of the membrane protein. In one embodiment, the chemical modification is selected from the group consisting of glycosylation, deglycosylation, phosphorylation, dephosphorylation and proteolysis. In one aspect, the invention provides a method of making a pharmaceutical composition comprising a minicell, wherein the minicell displays a membrane protein that is a fusion protein, the fusion protein comprising (i) a first polypeptide, the first polypeptide comprising at least one transmembrane domain or at least one membrane anchoring domain; and (ii) a second polypeptide, wherein the second polypeptide is not derived from a eubacterial protein.

In one aspect, the invention provides a method of making a pharmaceutical formulation comprising a minicell, wherein the minicell displays a membrane conjugate, wherein the membrane conjugate comprises a membrane component chemically linked to a conjugated compound. In one embodiment, the method further comprises adding an adjuvant to the pharmaceutical formulation. In one embodiment, the membrane component is a polypeptide comprising at least one transmembrane domain or at least one membrane anchoring domain, or a lipid that is part of a membrane. In one embodiment, the conjugated compound is a polypeptide, and the chemical linkage between the membrane compound and the conjugated compound is not a peptide bond. In one embodiment, the conjugated compound is a nucleic acid. In one embodiment, the conjugated compound is an organic compound. In one embodiment, the organic compound is selected from the group consisting of a narcotic, a toxin, a venom, and a sphingolipid.

In one aspect, the invention provides a method of detecting an agent that is specifically bound by a binding moiety, comprising contacting a minicell displaying the binding moiety with a composition known or suspected to contain the agent, and detecting a signal that is modulated by the binding of the agent to the binding moiety. In one embodiment, the agent is associated with a disease. In one embodiment, the minicell comprises a detectable compound. In one embodiment, the binding moiety is antibody or antibody derivative. In one embodiment, the composition is an environmental sample. In one embodiment, the composition is a biological sample. In one embodiment, the biological sample is selected from the group consisting of blood, serum, plasma, urine, saliva, a biopsy sample, feces and a skin patch.

In one aspect, the invention provides a method of in situ imaging of a tissue or organ, comprising administering to an organism a minicell comprising an imaging agent and a binding moiety and detecting the imaging agent in the organism.

In one embodiment, the minicell is a eubacterial minicell, a poroplast, a spheroplast or a protoplast. In one embodiment, the binding moiety is an antibody or antibody derivative. In one embodiment, the binding moiety specifically binds a cell surface antigen. In one embodiment, the cell surface antigen is an antigen displayed by a tumorigenic cell, a cancer cell, and an infected cell. In one embodiment, the cell surface antigen is a tissue-specific antigen. In one embodiment, the method of imaging is selected from the group consisting of magnetic resonance imaging, ultrasound imaging; and computer axaial tomography (CAT). In one aspect, the invention provides a device comprising a microchip operatively associated with a biosensor comprising a minicell, wherein the microchip comprises or contacts the minicell, and wherein the minicell displays a binding moiety.

In one embodiment, the invention provides a method of detecting a substance that is specifically bound by a binding moiety, comprising contacting the device of claim 16 with a composition known or suspected to contain the substance, and detecting a signal from the device, wherein the signal changes as a function of the amount of the substance present in the composition. In one embodiment, the composition is a biological sample or an environmental sample.

In one aspect, the invention provides a method of identifying an agent that specifically binds a target compound, comprising contacting a minicell displaying the target compound with a library of compounds, and identifying an agent in the library that binds the target compound. In one embodiment, the library of compounds is a protein library. In one embodiment, the protein library is selected from the group consisting of a phage display library, a phagemid display library, a baculovirus library, a yeast display library, and a ribosomal display library. In one embodiment, the library of compounds is selected from the group consisting of a library of aptamers, a library of synthetic peptides and a library of small molecules.

In one embodiment, the target compound is a target polypeptide. In one embodiment, the minicell comprises an expression construct comprising expression sequences operably linked to an ORF encoding the target polypeptide. In one embodiment, the target polypeptide is a membrane protein. In one embodiment, the membrane protein is a receptor or a channel protein. In one embodiment, the membrane protein is an enzyme. In one embodiment, the target compound is a membrane fusion protein, the membrane fusion protein comprising a first polypeptide, wherein the first polypeptide comprises at least one transmembrane domain or at least one membrane anchoring domain; and a second polypeptide, wherein the second polypeptide comprises amino acid sequences derived from a target polypeptide. In one embodiment, the method further comprises comparing the activity of the target compound in the presence of the agent to the activity of the target compound in the absence of the agent.

In one embodiment, the activity of the target compound is an enzyme activity. In one embodiment, the activity of the target compound is a binding activity. In one embodiment, the invention further comprises comparing the binding of the agent to the target compound to the binding of a known ligand of the target compound. In one embodiment, a competition assay is used for the comparing.

In one aspect, the invention provides a device comprising microchips operatively associated with a biosensor comprising a set of minicells in a prearranged pattern, wherein the each of the microchips comprise or contact a minicell, wherein each of the minicell displays a different target compound, and wherein binding of a ligand to a target compound results in an increased or decreased signal. In one embodiment, the invention provides a method of identifying an agent that specifically binds a target compound, comprising contacting the device with a library of compounds, and detecting a signal from the device, wherein the signal changes as a function of the binding of an agent to the target compound. In one embodiment, the invention provides a method of identifying an agent that specifically blocks the binding of a target compound to its ligand, comprising contacting the device with a library of compounds, and detecting a signal from the device, wherein the signal changes as a function of the binding of an agent to the target compound.

In one aspect, the invention provides a method of making a antibody that specifically binds a protein domain, wherein the domain is in its native conformation, wherein the domain is contained within a protein displayed on a minicell, comprising contacting the minicell with a cell, wherein the cell is competent for producing antibodies to an antigen contacted with the cell, in order to generate an immunogenic response in which the cell produces the antibody.

In one embodiment, the protein displayed on a minicell is a membrane protein. In one embodiment, the membrane protein is a receptor or a channel protein. In one embodiment, the domain is found within the second polypeptide of a membrane fusion protein, wherein the membrane fusion protein comprises a first polypeptide, wherein the first polypeptide comprises at least one transmembrane domain or at least one membrane anchoring domain. In one embodiment, the contacting occurs in vivo. In one embodiment, the antibody is a polyclonal antibody or a monoclonal antibody. In one embodiment, the contacting occurs in an animal that comprises an adjuvant.

In one aspect, the invention provides the method of making an antibody derivative that specifically binds a protein domain, wherein the domain is in its native conformation, wherein the domain is displayed on a minicell, comprising contacting the minicell with a protein library, and identifying an antibody derivative from the protein library that specifically binds the protein domain. In one embodiment, the protein library is selected from the group consisting of a phage display library, a phagemid display library, and a ribosomal display library.

In one aspect, the invention provides a method of making an antibody or antibody derivative that specifically binds an epitope, wherein the epitope is selected from the group consisting of (i) an epitope composed of amino acids found within a membrane protein, (ii) an epitope present in an interface between a membrane protein and a membrane component, (iii) an epitope present in an interface between a membrane protein and one or more other proteins and (iv) an epitope in a fusion protein, the fusion protein comprising a first polypeptide, the first polypeptide comprising at least one transmembrane domain or at least one membrane anchoring domain, and a second polypeptide, the second polypeptide comprising the epitope; comprising contacting a minicell displaying the epitope with a protein library, or to a cell, wherein the cell is competent for producing antibodies to an antigen contacted with the cell, in order to generate an immunogenic response in which the cell produces the antibody.

In one embodiment, the cell is contacted in vivo. In various embodiments, the antibody is a polyclonal antibody or a monoclonal antibody. In one embodiment, the protein library is contacted in vitro. In one embodiment, the protein library is selected from the group consisting of a phage display library, a phagemid display library, and a ribosomal display library.

In one aspect, the invention provides a method of determining the rate of transfer of nucleic acid from a minicell to a cell, comprising (a) contacting the cell to the minicell, wherein the minicell comprises the nucleic acid, for a measured period of time; (b) separating minicells from the cells; (c) measuring the amount of nucleic acid in the cells, wherein the amount of nucleic acid in the cells over the set period of time is the rate of transfer of a nucleic acid from a minicell.

In one aspect, the invention provides a method of determining the amount of a nucleic acid transferred to a cell from a minicell, comprising (a) contacting the cell to the minicell, wherein the minicell comprises an expression element having eukaryotic expression sequences operably linked to an ORF encoding a detectable polypeptide, wherein the minicell displays a binding moiety, and wherein the binding moiety binds an epitope of the cell; and (b) detecting a signal from the detectable polypeptide, wherein a change in the signal corresponds to an increase in the amount of a nucleic acid transferred to a cell.

In one embodiment, the cell is a eukaryotic cell. By way of non-limiting example, a eukaryotic cell can be a plant cell, a fungal cell, a unicellular eukaryote, an animal cell, a mammalian cell, a rat cell, a mouse cell, a primate cell or a human cell.

In one embodiment, the binding moiety is an antibody or antibody derivative. In one embodiment, the binding moiety is a single-chain antibody. In one embodiment, the binding moiety is an aptamer. In one embodiment, the binding moiety is an organic compound. In one embodiment, the detectable polypeptide is a fluorescent polypeptide.

In one aspect, the invention provides a method of detecting the expression of an expression element in a cell, comprising (a) contacting the cell to a minicell, wherein the minicell comprises an expression element having cellular expression sequences operably linked to an ORF encoding a detectable polypeptide, wherein the minicell displays a binding moiety, and wherein the binding moiety binds an epitope of the cell; (b) incubating the cell and the minicell for a period of time effective for transfer of nucleic acid from the minicell to the cell; and (c) detecting a signal from the detectable polypeptide, wherein an increase in the signal corresponds to an increase in the expression of the expression element.

In one embodiment, the cell is a eukaryotic cell and the expression sequences are eukaryotic expression sequences. In one embodiment, the eukaryotic cell is a mammalian cell. In one embodiment, the binding moiety is an antibody or antibody derivative. In one embodiment, the binding moiety is a single-chain antibody. In one embodiment, the binding moiety is an aptamer. In one embodiment, the binding moiety is an organic compound.

In a related aspect, the invention provides methods of detecting the transfer of a fusion protein from the cytosol to an organelle of a eukaryotic cell, comprising (a) contacting the cell to a minicell, wherein (i) the minicell comprises an expression element having eukaryotic expression sequences operably linked to an ORF encoding a fusion protein, wherein the fusion protein comprises a first polypeptide that comprises organellar delivery sequences, and a second polypeptide that comprises a detectable polypeptide; and (ii) the minicell displays a binding moiety that binds an epitope of the cell, or an epitope of an organelle; (b) incubating the cell and the minicell for a period of time effective for transfer of nucleic acid from the minicell to the cell and production of the fusion protein; and (c) detecting a signal from the detectable polypeptide, wherein a change in the signal corresponds to an increase in the amount of the fusion protein transferred to the organelle.

In one aspect, the invention provides a minicell comprising at least one nucleic acid, wherein the minicell displays a binding moiety directed to a target compound, wherein the binding moiety is selected from the group consisting of (i) a eukaryotic membrane protein; (ii) an archeabacterial membrane protein; (iii) an organellar membrane protein; and (iv) a fusion protein, the fusion protein comprising a first polypeptide, the first polypeptide comprising at least one transmembrane domain or at least one membrane anchoring domain; and a second polypeptide, wherein the second polypeptide is not derived from a eubacterial protein and is neither a His tag nor a glutathione-S-transferase polypeptide, and wherein the polypeptide comprises a binding moiety.

In one embodiment, the nucleic acid comprises an expression construct comprising expression sequences operably linked to an ORF encoding a protein selected from the group consisting of (i) the eukaryotic membrane protein, (ii) the archeabacterial membrane protein, (iii) the organellar membrane protein; and (iv) the fusion protein.

In one embodiment, the nucleic acid comprises an expression construct comprising expression sequences operably linked to an ORF, wherein the ORF encodes a therapeutic polypeptide. In one embodiment, the therapeutic polypeptide is a membrane polypeptide. In one embodiment, the therapeutic polypeptide is a soluble polypeptide. In one embodiment, the soluble polypeptide comprises a cellular secretion sequence. In one embodiment, the expression sequences are inducible and/or repressible.

In one embodiment, the expression sequences are induced and/or derepressed when the binding moiety displayed by the minicell binds its target compound. In one embodiment, the nucleic acid comprises an expression construct comprising expression sequences operably linked to an ORF, wherein the ORF encodes a polypeptide having an amino acid sequence that facilitates cellular transfer of a biologically active compound contained within or displayed by the minicell. In one embodiment, the membrane of the minicell comprises a system for transferring a molecule from the interior of a minicell into the cytoplasm of the cell. In one embodiment, the system for transferring a molecule from the interior of a minicell into the cytoplasm of the cell is a Type III secretion system.

In one aspect, the invention provides a method of introducing a nucleic acid into a cell, comprising contacting the cell with a minicell that comprises the nucleic acid, wherein the minicell displays a binding moiety, wherein the binding moiety is selected from the group consisting of (i) a eukaryotic membrane protein; (ii) an archeabacterial membrane protein; (iii) an organellar membrane protein; and (iv) a fusion protein, the fusion protein comprising a first polypeptide, the first polypeptide comprising at least one transmembrane domain or at least one membrane anchoring domain; and a second polypeptide, wherein the second polypeptide is not derived from a eubacterial protein and is neither a His tag nor a glutathione-S-transferase polypeptide, and wherein the polypeptide comprises a binding moiety; and wherein the binding moiety binds an epitope of the cell.

In one embodiment, the nucleic acid comprises an expression construct comprising expression sequences operably linked to an ORF encoding a protein selected from the group consisting of (i) the eukaryotic membrane protein, (ii) the archeabacterial membrane protein, (iii) the organellar membrane protein; and (iv) a fusion protein.

In one embodiment, the nucleic acid comprises an expression construct comprising expression sequences operably linked to an ORF, wherein the ORF encodes a therapeutic polypeptide. In one embodiment, the expression sequences are inducible and/or derepressible. In one embodiment, the expression sequences are induced or derepressed when the binding moiety displayed by the minicell binds its target compound. In one embodiment, the expression sequences are induced or derepressed by a transactivation or transrepression event. In one embodiment, the nucleic acid comprises an expression construct comprising expression sequences operably linked to an ORF, wherein the ORF encodes a polypeptide having an amino acid sequence that facilitates cellular transfer of a biologically active compound contained within or displayed by the minicell.

In one aspect, the invention provides a minicell comprising a nucleic acid, wherein the nucleic acid comprises eukaryotic expression sequences and eubacterial expression sequences, each of which is independently operably linked to an ORF.

In one embodiment, the minicell displays a binding moiety. In one embodiment, the eubacterial expression sequences are induced and/or derepressed when the binding moiety is in contact with a target cell. In one embodiment, the eukaryotic expression sequences are induced and/or derepressed when the nucleic acid is in the cytoplasm of a eukaryotic cell. In one embodiment, the protein encoded by the ORF comprises eubacterial or eukaryotic secretion sequences.

In one aspect, the invention provides a minicell comprising a first and second nucleic acid, wherein the first nucleic acid comprises eukaryotic expression sequences operably linked to a first ORF, and a second nucleic acid, wherein the second nucleic acid comprises eubacterial expression sequences operably linked to a second ORF.

In one embodiment, the minicell displays a binding moiety. In one embodiment, the eubacterial expression sequences are induced and/or derepressed when the binding moiety is in contact with a target cell. In one embodiment, the eukaryotic expression sequences are induced and/or derepressed when the nucleic acid is in the cytoplasm of a eukaryotic cell. In one embodiment, the protein encoded by the first ORF comprises eukaryotic secretion sequences and/or the protein encoded by the second ORF comprises eubacterial secretion sequences.

In one aspect, the invention provides a method of introducing into and expressing a nucleic acid in an organism, comprising contacting a minicell to a cell of the organism, wherein the minicell comprises the nucleic acid.

In one embodiment, the minicell displays a binding moiety. In one embodiment, the nucleic acid comprises a eukaryotic expression construct, wherein the eukaryotic expression construct comprises eukaryotic expression sequences operably linked to an ORF. In one embodiment, the ORF encodes a protein selected from the group consisting of a membrane protein, a soluble protein and a protein comprising eukaryotic secretion signal sequences. In one embodiment, the nucleic acid comprises a eubacterial expression construct, wherein the eubacterial expression construct comprises eubacterial expression sequences operably linked to an ORF. In one embodiment, the minicell displays a binding moiety, wherein the eubacterial expression sequences are induced and/or derepressed when the binding moiety is in contact with a target cell. In one embodiment, the protein encoded by the ORF comprises eubacterial secretion sequences. In one aspect, the invention provides a minicell comprising a crystal of a membrane protein. In one embodiment, the minicell is a eubacterial minicell, a poroplast, a spheroplast or a protoplast. In one embodiment, the membrane protein is a receptor. In one embodiment, the receptor is a G-protein coupled receptor. In one embodiment, the crystal is displayed.

In a related aspect, the invention provides a minicell membrane preparation comprising a crystal of a membrane protein.

In one embodiment, the membrane protein is a fusion protein, the fusion protein comprising a first polypeptide, the first polypeptide comprising at least one transmembrane domain or at least one membrane anchoring domain, and a second polypeptide. In one embodiment, the crystal is a crystal of the second polypeptide. In one embodiment, the crystal is displayed.

In one aspect, the invention provides a method of determining the three-dimensional structure of a membrane protein, comprising preparing a crystal of the membrane protein in a minicell, and determining the three-dimensional structure of the crystal.

In one aspect, the invention provides a method for identifying ligand-interacting atoms in a defined three-dimensional structure of a target protein, comprising (a) preparing one or more variant proteins of a target protein having a known or predicted three-dimensional structure, wherein the target protein binds a preselected ligand; (b) expressing and displaying a variant protein in a minicell; and (c) determining if a minicell displaying the variant protein binds the preselected ligand with increased or decreased affinity as compared to the binding of the preselected ligand to the target protein.

In one embodiment, the ligand is a protein that forms a multimer with the target protein, and the ligand interacting atoms are atoms in the defined three-dimensional structure are atoms that are involved in protein-protein interactions. In one embodiment, the ligand is a compound that induces a conformational change in the target protein, and the defined three-dimensional structure is the site of the conformational change. In one embodiment, the method for identifying ligands of a target protein, further comprising identifying the chemical differences in the variant proteins as compared to the target protein. In one embodiment, the invention further comprises mapping the chemical differences onto the defined three-dimensional structure, and correlating the effect of the chemical differences on the defined three-dimensional structure. In one embodiment, the target protein is a wild-type protein. In one aspect, the invention provides a minicell library, comprising two or more minicells, wherein each minicell comprises a different exogenous protein. In one embodiment, the minicell is a eubacterial minicell, a poroplast, a spheroplast or a protoplast. In one embodiment, the exogenous protein is a displayed protein. In one embodiment, the exogenous protein is a membrane protein. In one embodiment, the membrane protein is a receptor. In one embodiment, the protein is a soluble protein that is contained within or secreted from the minicell. In one embodiment, minicells within the library comprise an expression element that comprises expression sequences operably linked to a nucleic acid having an ORF that encodes the exogenous protein. In one embodiment, the nucleic acid has been mutagenized; the mutagenesis can be site-directed or random. In one embodiment, an active site of the exogenous protein has a known or predicted three-dimensional structure, and the a portion of the ORF encoding the active site has been mutagenized. In one embodiment, each of the minicells comprises an exogenous protein that is a variant of a protein having a known or predicted three-dimensional structure.

In one aspect, the invention provides a minicell library, comprising two or more minicells, wherein each minicell comprises a different fusion protein, each of the fusion protein comprising a first polypeptide that is a constant polypeptide, wherein the constant polypeptide comprises at least one transmembrane domain or at least one membrane anchoring domain, and a second polypeptide, wherein the second polypeptide is a variable amino acid sequence that is different in each fusion proteins. In one embodiment, minicells within the library comprise an expression element that comprises expression sequences operably linked to a nucleic acid having an ORF that encodes the fusion protein. In one embodiment, the second polypeptide of the fusion protein is encoded by a nucleic acid that has been cloned. In one embodiment, each of the second polypeptide of each of the fusion proteins comprises a variant of an amino acid sequence from a protein having a known or predicted three-dimensional structure.

In one aspect, the invention provides a minicell library, comprising two or more minicells, wherein each minicell comprises a constant protein that is present in each minicell and a variable protein that differs from minicell to minicell. In one embodiment, one of the constant and variable proteins is a receptor, and the other of the constant and variable proteins is a co-receptor. In one embodiment, each of the constant and variable proteins is different from each other and is a factor in a signal transduction pathway. In one embodiment, one of the constant and variable proteins is a G-protein, and the other of the constant and variable proteins is a G-protein coupled receptor.

In one embodiment, one of the constant and variable proteins comprises a first transrepression domain, and the other of the constant and variable comprises a second transrepression domain, wherein the transrepression domains limit or block expression of a reporter gene when the constant and variable proteins associate with each other.

In one embodiment, one of the constant and variable proteins comprises a first transactivation domain, and the other of the constant and variable comprises a second transactivation domain, wherein the transactivation domains stimulate expression of a reporter gene when the constant and variable proteins associate with each other.

In one aspect, the invention provides a method of identifying a nucleic acid that encodes a protein that binds to or chemically alters a preselected ligand, comprising (a) separately contacting the ligand with individual members of a minicell library, wherein minicells in the library comprise expression elements, wherein the expression elements comprise DNA inserts, wherein an ORF in the DNA insert is operably linked to expression sequences, in order to generate a series of reaction mixes, each reaction mix comprising a different member of the minicell library; (b) incubating the reaction mixes, thereby allowing a protein that binds to or chemically alters the preselected ligand to bind or chemically alter the preselected ligand; (c) detecting a change in a signal from reaction mixes in which the ligand has been bound or chemically altered; (d) preparing DNA from reaction mixes in which the ligand has been bound or chemically altered; wherein the DNA is a nucleic acid that encodes a protein that binds to or chemically alters the preselected ligand.

In one embodiment, the minicell is a eubacterial minicell, a poroplast, a spheroplast or a protoplast. In one embodiment, the preselected ligand is a biologically active compound. In one embodiment, the preselected ligand is a therapeutic drug. In one embodiment, a protein that binds or chemically alters the preselected ligand is a target protein for compounds that are therapeutic for a disease that is treated by administering the drug to an organism in need thereof. In one embodiment, the preselected ligand is detectably labeled, the minicell comprises a detectable compound, and/or a chemically altered derivative of the protein is detectably labeled.

In one aspect, the invention provides a method of determining the amino acid sequence of a protein that binds or chemically alters a preselected ligand, comprising: (a) contacting the ligand with a minicell library, wherein minicells in the library comprise expression elements, wherein the expression elements comprise DNA inserts, wherein an ORF in the DNA insert is operably linked to expression sequences; (b) incubating the mixture of ligand and minicells, under conditions which allow complexes comprising ligands and minicells to form and/or chemical reactions to occur; (c) isolating or identifying the complexes from the ligand and the mixture of ligand and minicells; (d) preparing DNA from an expression element found in one or more of the complexes, or in a minicell thereof; (e) determining the nucleotide sequence of the ORF in the DNA; and (f) generating an amino sequence by in silico translation, wherein the amino acid sequence is or is derived from a protein that binds or chemically alters a preselected ligand.

In one embodiment, the minicell is a eubacterial minicell, a poroplast, a spheroplast or a protoplast. In one embodiment, the DNA is prepared by isolating DNA from the complexes, or in a minicell thereof. In one embodiment, the DNA is prepared by amplifying DNA from the complexes, or in a minicell thereof. In one embodiment, the protein is a fusion protein. In one embodiment, the protein is a membrane or a soluble protein. In one embodiment, the protein comprises secretion sequences. In one embodiment, the preselected ligand is a biologically active compound. In one embodiment, the preselected ligand is a therapeutic drug. In one embodiment, the preselected ligand is a therapeutic drug, and the protein that binds the preselected ligand is a target protein for compounds that are therapeutic for a disease that is treated by administering the drug to an organism in need thereof.

In one aspect, the invention provides a method of identifying a nucleic acid that encodes a protein that inhibits or blocks an agent from binding to or chemically altering a preselected ligand, comprising: (a) separately contacting the ligand with individual members of a minicell library, wherein minicells in the library comprise expression elements, wherein the expression elements comprise DNA inserts, wherein an ORF in the DNA insert is operably linked to expression sequences, in order to generate a series of reaction mixes, each reaction mix comprising a different member of the minicell library; (b) incubating the reaction mixes, thereby allowing a protein that binds to or chemically alters the preselected ligand to bind or chemically alter the preselected ligand; (c) detecting a change in a signal from reaction mixes in which the ligand has been bound or chemically altered; (d) preparing DNA from reaction mixes in which the change in signal ligand has been bound or chemically altered; wherein the DNA is a nucleic acid that encodes a protein that inhibits or blocks the agent from binding to or chemically altering the preselected ligand In one embodiment, the minicell is a eubacterial minicell, a poroplast, a spheroplast or a protoplast. In one embodiment, the DNA has a nucleotide sequence that encodes the amino acid sequence of the protein that inhibits or blocks the agent from binding to or chemically altering the preselected ligand. In one embodiment, a protein that binds or chemically alters the preselected ligand is a target protein for compounds that are therapeutic for a disease that is treated by administering the drug to an organism in need thereof.

In one aspect, the invention provides a method of identifying an agent that effects the activity of a protein, comprising contacting a library of two or more candidate agents with a minicell comprising the protein or a polypeptide derived from the protein, assaying the effect of candidate agents on the activity of the protein, and identifying agents that effect the activity of the protein.

In one embodiment, the protein or the polypeptide derived from the protein is displayed on the surface of the minicell. In one embodiment, the protein is a membrane protein. In one embodiment, the membrane protein is selected from the group consisting of a receptor, a channel protein and an enzyme. In one embodiment, the activity of a protein is a binding activity or an enzymatic activity. In one embodiment, the library of compounds is a protein library. In one embodiment, the protein library is selected from the group consisting of a phage display library, a phagemid display library, and a ribosomal display library. In one embodiment, the library of compounds is a library of aptamers. In one embodiment, the library of compounds is a library of small molecules.

In one aspect, the invention provides a method of identifying an agent that effects the activity of a protein domain containing a library of two or more candidate agents with a minicell displaying a membrane fusion protein, the fusion protein comprising a first polypeptide, the first polypeptide comprising at least one transmembrane domain or at least one membrane anchoring domain, and a second polypeptide, wherein the second polypeptide comprises the protein domain.

In one aspect, the invention provides a method of identifying undesirable side-effects of a biologically active compound that occur as a result of binding of the compound to a protein, wherein binding a compound to the protein is known to result in undesirable side effects, comprising contacting a minicell that comprises the protein to the biologically active compound. In one embodiment, the invention provides comprises characterizing the binding of the biologically active compound to the protein. In one embodiment, the invention provides comprises characterizing the effect of the biologically active compound on the activity of the protein.

In one aspect, the invention provides a method for identifying an agent that effects the interaction of a first signaling protein with a second signaling protein, comprising (a) contacting a library of compounds with a minicell, wherein the minicell comprises: (i) a first protein comprising the first signaling protein and a first trans-acting regulatory domain; (ii) a second protein comprising the second signaling protein and a second trans-acting regulatory domain; and (iii) a reporter gene, the expression of which is modulated by the interaction between the first trans-acting regulatory domain and the second trans-acting regulatory domain; and (b) detecting the gene product of the reporter gene.

In one embodiment, the trans-acting regulatory domains are transactivation domains. In one embodiment, the trans-acting regulatory domains are transrepression domains.

In one embodiment, the reporter gene is induced by the interaction of the first trans-acting regulatory domain and the second trans-acting regulatory domain. In one embodiment, the agent that effects the interaction of the first signaling protein with the second signaling protein is an agent that causes or promotes the interaction. In one embodiment, the reporter gene is repressed by the interaction of the first trans-acting regulatory domain and the second trans-acting regulatory domain. In one embodiment, the agent that effects the interaction of the first signaling protein with the second signaling protein is an agent that inhibits or blocks the interaction.

In one embodiment, the first signaling protein is a GPCR. In one embodiment, the GPCR is an Edg receptor or a ScAMPER.

In one embodiment, the second signalling protein is a G-protein. In related embodiments, G-protein is selected from the group consisting of G-alpha-i, G-alpha-s, G-alpha-q, G-alpha-12/13 and Go. In one embodiment, the library of compounds is a protein library. In one embodiment, the protein library is selected from the group consisting of a phage display library, a phagemid display library, and a ribosomal display library. In one embodiment, the library of compounds is a library of aptamers. In one embodiment, the library of compounds is a library of small molecules.

In one aspect, the invention provides a method for identifying an agent that effects the interaction of a first signaling protein with a second signaling protein, comprising contacting a library of two or more candidate agents with a minicell, wherein the minicell comprises (a) a first fusion protein comprising the first signaling protein and a first detectable domain; and (b) a second fusion protein comprising the second signaling protein and a second detectable domain, wherein a signal is generated when the first and second signaling proteins are in close proximity to each other, and detecting the signal.

In one embodiment, the signal is fluorescence. In one embodiment, the first detectable domain and the second detectable domain are fluorescent and the signal is generated by FRET. In one embodiment, the first and second detectable domains are independently selected from the group consisting of a green fluorescent protein, a blue-shifted green fluorescent protein, a cyan-shifted green fluorescent protein; a red-shifted green fluorescent protein; a yellow-shifted green fluorescent protein, and a red fluorescent protein, wherein the first fluorescent domain and the second fluorescent domain are not identical.

In one aspect, the invention provides a method of bioremediation, the method comprising contacting a composition that comprises an undesirable substance with a minicell, wherein the minicell alters the chemical structure and/or binds the undesirable substance.

In one aspect, the invention provides a method of bioremediation, the method comprising contacting a composition that comprises an undesirable substance with a minicell, wherein the minicell comprises an agent that alters the chemical structure of the undesirable substance. In one embodiment, the agent that alters the chemical structure of the undesirable substance is an inorganic catalyst. In one embodiment, the agent that alters the chemical structure of the undesirable substance is an enzyme. In one embodiment, the enzyme is a soluble protein contained within the minicell. In one embodiment, the enzyme is a secreted protein. In one embodiment, the enzyme is a membrane protein. In one embodiment, the membrane enzyme is selected from the group consisting of a cytochrome P450, an oxidoreductase, a transferase, a hydrolase, a lyase, an isomerase, a ligase and a synthetase. In one embodiment, the agent that alters the chemical structure of the undesirable substance is a fusion protein comprising a first polypeptide that comprises a transmembrane domain or at least one membrane-anchoring domain, and a second polypeptide, wherein the second polypeptide is an enzyme moiety.

In one aspect, the invention provides a method of bioremediation, the method comprising contacting a composition that comprises an undesirable substance with a minicell, wherein the minicell comprises an agent that binds an undesirable substance. In one embodiment, the undesirable substance binds to and is internalized by the minicell or is otherwise inactivated by selective absorption. In one embodiment, the agent that binds the undesirable substance is a secreted soluble protein. In one embodiment, the secreted protein is a transport accessory protein. In one embodiment, the agent that binds the undesirable substance is a membrane protein. In one embodiment, the undesirable substance is selected from the group consisting of a toxin, a pollutant and a pathogen. In one embodiment, the agent that binds the undesirable substance is a fusion protein comprising a first polypeptide that comprises a transmembrane domain or at least one membrane-anchoring domain, and a second polypeptide, wherein the second polypeptide is a binding moiety. In one embodiment, wherein the binding moiety is selected from the group consisting of an antibody, an antibody derivative, the active site of a non-enzymatically active mutant enzyme, a single-chain antibody and an aptamer.

In one aspect, the invention provides a minicell-producing parent cell, wherein the parent cell comprises one or more of the following (a) an expression element that comprises a gene operably linked to expression sequences that are inducible and/or repressible, wherein induction or repression of the gene regulates the copy number of an episomal expression construct; (b) a mutation in an endogenous gene, wherein the mutation regulates the copy number of an episomal expression construct; (c) an expression element that comprises a gene operably linked to expression sequences that are inducible and/or repressible, wherein induction or repression of the gene causes or enhances the production of minicells; and (d) a mutation in an endogenous gene, wherein the mutation causes or enhances minicell production.

In one embodiment, the invention comprises an episomal expression construct. In one embodiment, the invention further comprises a chromosomal expression construct. In one embodiment, the expression sequences of the expression construct are inducible and/or repressible. In one embodiment, the minicell-producing parent cell comprises a biologically active compound. In one embodiment, the gene that causes or enhances the production of minicells has a gene product that is involved in or regulates DNA replication, cellular division, cellular partitioning, septation, transcription, translation, or protein folding.

In one aspect, the invention provides a minicell-producing parent cell, wherein the parent cell comprises an expression construct, wherein the expression construct comprises expression sequences operably linked to an ORF that encodes a protein, and a regulatory expression element, wherein the regulatory expression element comprises expression sequences operably linked to a regulatory gene that encodes a factor that regulates the expression of the ORF. In one embodiment, the expression sequences of the expression construct are inducible and/or repressible. In one embodiment, the expression sequences of the regulatory expression construct are inducible and/or repressible. In one embodiment, one or more of the expression element or the regulatory expression element is located on a chromosome of the parent cell. In one embodiment, one or more of the expression element or the regulatory expression element is located on an episomal expression construct. In one embodiment, both of the expression element and the regulatory expression element are located on an episomal expression construct, and one or both of the expression element and the regulatory expression element segregates into minicells produced from the parent cell. In one embodiment, the minicell-producing parent cell comprises a biologically active compound. In one embodiment, the biologically active compound segregates into minicells produced from the parent cell. In one embodiment, the ORF encodes a membrane protein or a soluble protein. In one embodiment, the protein comprises secretion sequences. In one embodiment, the gene product of the gene regulates the expression of the ORF. In one embodiment, the gene product is a transcription factor. In one embodiment, the gene product is a RNA polymerase. In one embodiment, the parent cell is MC-T7.

In one aspect, the invention provides a minicell comprising a biologically active compound, wherein the minicell displays a binding moiety, wherein the minicell selectively absorbs and/or internalizes an undesirable compound, and the minicell is a poroplast, spheroplast or protoplast. In one embodiment, the binding moiety is selected from the group consisting of an antibody, an antibody derivative, a receptor and an active site of a non-catalytic derivative of an enzyme. In one embodiment, the binding moiety is a single-chain antibody. In one embodiment, the binding moiety is directed to a ligand selected from the group consisting of an epitope displayed on a pathogen, an epitope displayed on an infected cell and an epitope displayed on a hyperproliferative cell. In one embodiment, the biologically active compound is selected from the group consisting of a radioisotope, a polypeptide, a nucleic acid and a small molecule. In one embodiment, a ligand binds to and is internalized by the minicell or is otherwise inactivated by selective absorption. In one embodiment, the invention provides a pharmaceutical composition comprising the minicell. In one aspect, the invention provides a method of reducing the free concentration of a substance in a composition, wherein the substance displays a ligand specifically recognized by a binding moiety, comprising contacting the composition with a minicell that displays the binding moiety, wherein the binding moiety binds the substance, thereby reducing the free concentration of the substance in the composition. In one embodiment, the substance is selected from the group consisting of a nucleic acid, a lipid, a polypeptide, a radioactive compound, an ion and a small molecule. In one embodiment, the binding moiety is selected from the group consisting of an antibody, an antibody derivative, a channel protein and a receptor.

In one embodiment, the composition is present in an environment including but not limited to water, air or soil. In one embodiment, the composition is a biological sample from an organism, including but not limited to blood, serum, plasma, urine, saliva, a biopsy sample, feces, tissue and a skin patch. In one embodiment, the substance binds to and is internalized by the minicell or is otherwise inactivated by selective absorption. In one embodiment, the biological sample is returned to the organism after being contacting to the minicell.

For a better understanding of the present invention, reference is made to the accompanying detailed description and its scope will be pointed out in the appended claims. All references cited herein are hereby incorporated by reference.

ABBREVIATIONS AND DEFINITIONS

Figure 1:
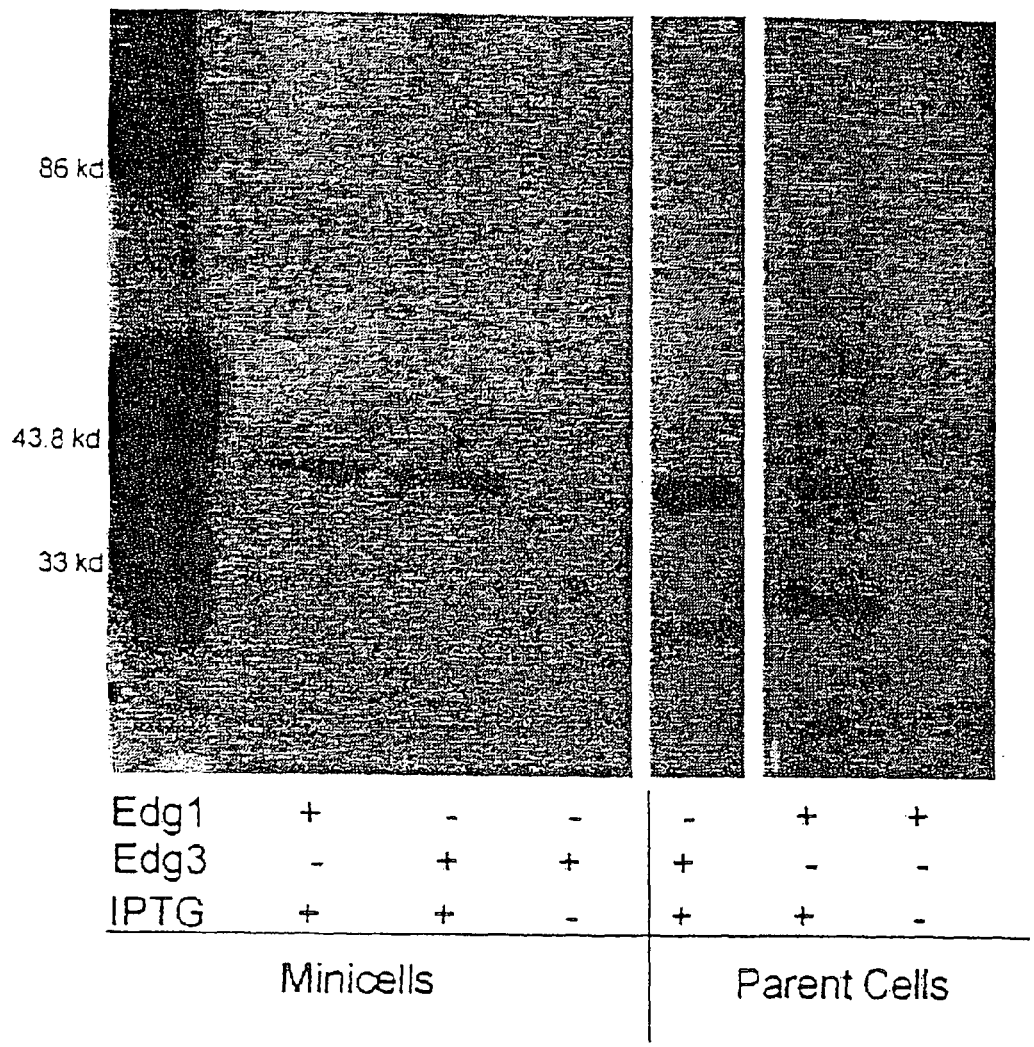
FIG. 1 is a Western blot in which Edg-1-6xHis and Edg-3-6xHis proteins expressed in minicells produced from MC-T7 cells.

For brevity's sake, the single-letter amino acid abbreviations are used in some instances herein. Table 1 describes the correspondence between the 1- and 3-letter amino acid abbreviations.

TABLE 1

THREE- AND ONE- LETTER ABBREVIATIONS FOR AMINO ACIDS

| Amino acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conjugatable compound" or "attachable compound" is capable of being attached to another compound. The terms "conjugated to" and "cross-linked with" indicate that the conjugatable compound is in the state of being attached to another compound. A "conjugate" is the compound formed by the attachment of a conjugatable compound or conjugatable moiety to another compound.

"Culturing" signifies incubating a cell or organism under conditions wherein the cell or organism can carry out some, if not all, biological processes. For example, a cell that is cultured may be growing or reproducing, or it may be non-viable but still capable of carrying out biological and/or biochemical processes such as replication, transcription, translation, etc.

An agent is said to have been "purified" if its concentration is increased, and/or the concentration of one or more undesirable contaminants is decreased, in a composition relative to the composition from which the agent has been purified. Purification thus encompasses enrichment of an agent in a composition and/or isolation of an agent therefrom.

A "solid support" is any solid or semisolid composition to which an agent can be attached or contained within. Common forms of solid support include, but are not limited to, plates, tubes, and beads, all of which could be made of glass or another suitable material, e.g., polystyrene, nylon, cellulose acetate, nitrocellulose, and other polymers. Semisolids and gels that minicells are suspended within are also considered to be solid supports. A solid support can be in the form of a dipstick, flow-through device, or other suitable configuration.

A "mutation" is a change in the nucleotide sequence of a gene relative to the sequence of the "wild-type" gene. Reference wild-type eubacterial strains are those that have been cultured in vitro by scientists for decades; for example, a wild-type strain of Escherichia coli iss E. coli K-12. Mutations include, but are not limited to, point mutations, deletions, insertions and translocations.

A "trans-acting regulatory domain" is a regulatory part of a protein that is expressed from a gene that is not adjacent to the site of regulatory effect. Trans-acting domains can activate or stimulate (transactivate), or limit or block (transrepress) the gene in question.

A "reporter gene" refers to a gene that is operably linked to expression sequences, and which expresses a gene product, typically a detectable polypeptide, the production and detection of which is used as a measure of the robustness and/or control of expression.

A "detectable compound" or "detectable moiety" produces a signal that can be detected by spectroscopic, photochemical, biochemical, immunochemical, electromagnetic, radiochemical, or chemical means such as fluorescence, chemifluoresence, or chemiluminescence, or any other appropriate means. A "radioactive compound" or "radioactive composition" has more than the natural (environmental) amount of one or more radioisotopes.

By "displayed" it is meant that a portion of the membrane protein is present on the surface of a cell or minicell, and is thus in contact with the external environment of the cell or minicell. The external, displayed portion of a membrane protein is an "extracellular domain" or a "displayed domain." A membrane protein may have more than one displayed domain, and a minicell of the invention may display more than one membrane protein.

A "domain" or "protein domain" is a region of a molecule or structure that shares common physical and/or chemical features. Non-limiting examples of protein domains include hydrophobic transmembrane or peripheral membrane binding regions, globular enzymatic or receptor regions, and/or nucleic acid binding domains.

A "transmembrane domain" spans a membrane, a "membrane anchoring domain" is positioned within, but does not traverse, a membrane. An "extracellular" or "displayed" domain is present on the exterior of a cell, or minicell, and is thus in contact with the external environment of the cell or minicell.

A "eukaryote" is as the term is used in the art. A eukaryote may, by way of non-limiting example, be a fungus, a unicellular eukaryote, a plant or an animal. An animal may be a mammal, such as a rat, a mouse, a rabbit, a dog, a cat, a horse, a cow, a pig, a simian or a human.

A "eukaryotic membrane" is a membrane found in a eukaryote. A eukaryotic membrane may, by way of non-limiting example, a cytoplasmic membrane, a nuclear membrane, a nucleolar membrane, a membrane of the endoplasmic reticulum (ER), a membrane of a Golgi body, a membrane of a lysosome a membrane of a peroxisome, a caveolar membrane, or an inner or outer membrane of a mitochondrion, chloroplast or plastid.

The term "endogenous" refers to something that is normally found in a cell as that cell exists in nature.

The term "exogenous" refers to something that is not normally found in a cell as that cell exists in nature.

A "gene" comprises (a) nucleotide sequences that either (i) act as a template for a nucleic acid gene product, or (ii) that encode one or more open reading frames (ORFs); and (b) expression sequences operably linked to (1) or (2). When a gene comprises an ORF, it is a "structural gene."

By "immunogenic," it is meant that a compound elicits production of antibodies or antibody derivatives and, additionally or alternatively, a T-cell mediated response, directed to the compound or a portion thereof. The compound is an "immunogen."

A "ligand" is a compound, composition or moiety that is capable of specifically bound by a binding moiety, including without limitation, a receptor and an antibody or antibody derivative.

A "membrane protein" is a protein found in whole or in part in a membrane. Typically, a membrane protein has (1) at least one membrane anchoring domain, (2) at least one transmembrane domain, or (3) at least one domain that interacts with a protein having (1) or (2).

An "ORF" or "open reading frame" is a nucleotide sequence that encodes an amino acid sequence of a known, predicted or hypothetical polypeptide. An ORF is bounded on its 5' end by a start codon (usually ATG) and on its 3' end by a stop codon (i.e., TAA or TGA). An ORF encoding a 10 amino acid sequence comprises 33 nucleotides (3 for each of 10 amino acids and 3 for a stop codon). ORFs can encode amino acid sequences that comprise from 10, 25, 50, 125, 150, 175, 200, 250, 300, 350, 400, 450, 500, 600, 700, 800, 900 or more amino acids The terms "Eubacteria" and"prokaryote" are used herein as these terms are used by those in the art. The terms "eubacterial" and "prokaryotic" encompasses Eubacteria, including both gram-negative and gram-positive bacteria, prokaryotic viruses (e.g., bacteriophage), and obligate intracellular parasites (e.g., *Rickettsia, Chlamydia*, etc.).

An "active site" is any portion or region of a molecule required for, or that regulates, an activity of the molecule. In the case of a protein, an active site can be a binding site for a ligand or a substrate, an active site of enzyme, a site that directs or undergoes conformational change in response to a signal, or a site of post-translational modification of a protein.

In a poroplast, the eubacterial outer membrane (OM) and LPS have been removed. In a spheroplast, portions of a disrupted eubacterial OM and/or disrupted cell wall either may remain associated with the inner membrane of the minicell, but the membrane is nonetheless porous because the permeability of the disrupted OM has been increased. A membrane is the to be "disrupted" when the membrane's structure has been treated with an agent, or incubated under conditions, that leads to the partial degradation of the membrane, thereby increasing the permeability thereof. In contrast, a membrane that has been "degraded" is essentially, for the applicable intents and purposes, removed. In preferred embodiments, irrespective of the condition of the OM and cell wall, the eubacterial inner membrane is not disrupted, and membrane proteins displayed on the inner membrane are accessible to compounds that are brought into contact with the minicell, poroplast, spheroplast, protoplast or cellular poroplast, as the case may be.

Host cells (and/or minicells) harboring an expression construct are components of expression systems.

An "expression vector" is an artificial nucleic acid molecule into which an exogenous ORF encoding a protein, or a template of a bioactive nucleic acid can be inserted in such a manner so as to be operably linked to appropriate expression sequences that direct the expression of the exogenous gene. Preferred expression vectors are episomal vectors that can replicate independently of chromosomal replication.

By the term "operably linked" it is meant that the gene products encoded by the non-vector nucleic acid sequences are produced from an expression element in vivo.

The term "gene product" refers to either a nucleic acid (the product of transcription, reverse transcription, or replication) or a polypeptide (the product of translation) that is produced using the non-vector nucleic acid sequences as a template.

An "expression construct" is an expression vector into which a nucleotide sequence of interest has been inserted in a manner so as to be positioned to be operably linked to the expression sequences present in the expression vector. Preferred expression constructs are episomal.

An "expression element" is a nucleic acid having nucleotide sequences that are present in an expression construct but not its cognate expression vector. That is, an expression element for a polypeptide is a nucleic acid that comprises an ORF operably linked to appropriate expression sequences.

An expression element can be removed from its expression construct and placed in other expression vectors or into chromosomal DNA.

"Expression sequences" are nucleic acid sequences that bind factors necessary for the expression of genes that have been inserted into an expression vector. An example of an expression sequence is a promoter, a sequence that binds RNA polymerase, which is the enzyme that produces RNA molecules using DNA as a template. An example of an expression sequence that is both inducible and repressible is L-arabinose operon (araC). See Schleif R. Regulation of the L-arabinose operon of *Escherichia coli*. Trends Genet. 2000 December; 16(12):559-65.

In the present disclosure, "a nucleic acid" or "the nucleic acid" refers to a specific nucleic acid molecule. In contrast, the term "nucleic acid" refers to any collection of diverse nucleic acid molecules, and thus signifies that any number of different types of nucleic acids are present.

By way of non-limiting example, a nucleic acid may be a DNA, a dsRNA, a tRNA (including a rare codon usage tRNA), an mRNA, a ribosomal RNA (rRNA), a peptide nucleic acid (PNA), a DNA:RNA hybrid, an antisense oligonucleotide, a ribozyme, or an aptamer.

DETAILED DESCRIPTION OF THE INVENTION

The invention described herein is drawn to compositions and methods for the production of achromosomal archeabacterial, eubacterial and anucleate eukaryotic cells that are used for diagnostic and therapeutic applications, for drug discovery, and as research tools.

The general advantage of minicells over cell-based expression systems (e.g., eucaryotic cells or bacterial expression systems) is that one may express heterologous membrane bound proteins or over express endogenous membrane bound proteins, cytoplasmic or secreted soluble proteins, or small molecules on the cytoplasmic or extracellular surfaces of the minicells that would otherwise be toxic to live cells. Minicells are also advantageous for proteins that require a particular lipid environment for proper functioning because it is very manipulatable in nature. Other advantages include the stability of the minicells due to the lack of toxicity, the high level of expression that can be achieved in the minicell, and the efficient flexible nature of the minicell expression system. Such minicells could be used for in vivo targeting or for selective absorption (i.e., molecular "sponges") and that these molecules can be expressed and "displayed" at high levels. Minicells can also be used to display proteins for low, medium, high, and ultra high throughput screening, crystal formation for structure determination, and for in vitro research use only applications such as transfection. Minicells expressing proteins or small molecules, radioisotopes, image-enhancing reagents can be used for in vivo diagnostics and for in vitro diagnostic and assay platforms. Also, soluble and/or membrane associated signaling cascade elements may be reconstituted in minicells producing encapsulated devices to follow extracellular stimulation events using cytoplasmic reporter events, e.g. transactivation resulting from dimerization of dimerization dependant transcriptional activation or repression of said reporter.

Regarding protein expression, minicells can be engineered to express one or more recombinant proteins in order to produce more protein per surface area of the particle (at least 10× more protein per unit surface area of protein). The proteins or small molecules that are "displayed" on the minicell surfaces can have therapeutic, discovery or diagnostic benefit either when injected into a patient or used in a selective absorption mode during dialysis. In vitro assays include drug screening and discovery, structural proteomics, and other functional proteomics applications. Proteins that are normally soluble can be tethered to membrane anchoring domains or membrane proteins can be expressed for the purpose of displaying these proteins on the surfaces of the minicell particle in therapeutic, discovery, and diagnostic modes. The types of proteins that can be displayed include but are not limited to receptors (e.g., GPCRs, sphingolipid receptors, neurotransmitter receptors, sensory receptors, growth factor receptors, hormone receptors, chemokine receptors, cytokine receptors, immunological receptors, and complement receptors, FC receptors), channels (e.g., potassium channels, sodium channels, calcium channels.), pores (e.g., nuclear pore proteins, water channels), ion and other pumps (e.g., calcium pumps, proton pumps), exchangers (e.g., sodium/potassium exchangers, sodium/hydrogen exchangers, potassium/hydrogen exchangers), electron transport proteins (e.g., cytochrome oxidase), enzymes and kinases (e.g., protein kinases, ATPases, GTPases, phosphatases, proteases.), structural/linker proteins (e.g., Caveolins, clathrin), adapter proteins (e.g., TRAD, TRAP, FAN), chemotactic/adhesion proteins (e.g., ICAM11, selectins, CD34, VCAM-1, LFA-1, VLA-1), and chimeric/fussion proteins (e.g., proteins in which a normally soluble protein is attached to a transmembrane region of another protein). As a non-limiting example, the small molecules that can be tethered and displayed on the surfaces of the minicells can be carbohydrates (e.g., monosaccharides), bioactive lipids (e.g., lysosphingolipids, PAF, lysophospholipids), drugs (e.g., antibiotics, ion channel activators/inhibitors, ligands for receptors and/or enzymes), nucleic acids (e.g., synthetic oligonucleotides), fluorophores, metals, or inorganic and organic small molecules typically found in combinatorial chemistry libraries. Minicells may either contain (encapsulate) or display on their surfaces radionuclides or image-enhancing reagents both of which could be used for therapeutic and/or diagnostic benefit in vivo or for in vitro assays and diagnostic platforms.

For in vivo therapeutic uses, minicells can express proteins and/or display small molecules on their surfaces that would either promote an immune response and passage through the RES system (e.g., to eliminate the minicell and its target quickly), or to evade the RES (e.g., to increase the bioavailability of the minicell). Toxicity is reduced or eliminated because the therapeutic agent is not excreted or processed by the liver and thus does not damage the kidneys or liver, because the minicell-based therapeutic is not activated until entry into the target cell (e.g., in the case of cancer therapeutics or gene therapy). Minicells are of the appropriate size (from about 0.005, 0.1, 0.15 or 0.2 micrometers to about 0.25, 0.3, 0.35, 0.4, 0.45 or 0.5 micrometers) to facilitate deep penetration into the lungs in the cases where administration of the minicell-based therapeutic or diagnostic is via an inhalant (Strong, A. A., et al. 1987. An aerosol generator system for inhalation delivery of pharmacological agents. Med. Instrum. 21:189-194). This is due to the fact that minicells can be aerosolized. Without being limited to the following examples, inhalant therapeutic uses of minicells could be applied to the treatment of anaphylactic shock, viral infection, inflammatory reactions, gene therapy for cystic fibrosis, treatment of lung cancers, and fetal distress syndrome.

Minicells can also display expressed proteins that are enzymes that may have therapeutic and/or diagnostic uses. The enzymes that are displayed may be soluble enzymes that are expressed as fusion proteins with a transmembrane domain of another protein. Display of such enzymes could be used for in vitro assays or for therapeutic benefit.

Gene therapy applications afforded by minicells generally involve the ability of minicells to deliver DNA to target cells (either for replacement therapy, modifation of cell function or to kill cells). Expression plasmids can be delivered to target cells that would encode proteins that could be cytoplasmic or could have intracellular signal sequences that would target the protein to a particular organelle (e.g., mitochondria, nuclei, endoplasmic reticulum, etc.). In the case where minicells are engulfed by the target cell, the minicells themselves could have these intracellular targeting sequences expressed on their surfaces so that the minicells could be 'delivered' to intracellular targets.

Minicells used for the following therapeutic, discovery, and diagnostic applications can be prepared as described in this application and then stored and/or packaged by a variety of ways, including but not limited to lyophilization, freezing, mixing with preservatives (e.g., antioxidants, glycerol), or otherwise stored and packaged in a fashion similar to methods used for liposome and proteoliposome formulations.

The small size of minicells (from about 0.005, 0.1, 0.15 or 0.2 micrometers to about 0.25, 0.3, 0.35, 0.4, 0.45 or 0.5 micrometers) makes them suitable for many in vitro diagnostic platforms, including the non-limiting examples of lateral flow, ELISA, HTS, especially those applications requiring microspheres or nanospheres that display many target proteins or other molecules. The use of protoplast or poroplast minicells may be especially useful in this regard. Assay techniques are dependent on cell or particle size, protein (or molecule to be tested) amount displayed on the surface of the cell or particle, and the sensitivity of the assay being measured. In current whole-cell systems, the expression of the protein of interest is limiting, resulting in the higher cell number requirement to satisfy the sensitivity of most assays. However, the relatively large size of cells prevents the incorporation of large numbers of cells in these assays, e.g. 96, 384, and smaller well formats. In contrast, minicells, protoplasts, and poroplasts are smaller in size and can be manipulated to express high levels of the preselected protein, and can be incorporated into small well assay formats.

I. Types of Minicells

Minicells are derivatives of cells that lack chromosomal DNA and which are sometimes referred to as anucleate cells. Because eubacterial and achreabacterial cells, unlike eukaryotic cells, do not have a nucleus (a distinct organelle that contains chromosomes), these non-eukaryotic minicells are more accurately described as being "without chromosomes" or "achromosomal," as opposed to "anucleate." Nonetheless, those skilled in the art often use the term "anucleate" when referring to bacterial minicells in addition to other minicells. Accordingly, in the present disclosure, the term "minicells" encompasses derivatives of eubacterial cells that lack a chromosome; derivatives of archeabacterial cells that lack their chromosome(s) (Laurence et al., Nucleoid Structure and Partition in *Methanococcus jannaschii*: An Archaeon With Multiple Copies of the Chromosome, Genetics 152:1315-1323, 1999); and anucleate derivatives of eukaryotic cells. It is understood, however, that some of the relevant art may use the terms "anucleate minicells" or anucleate cells" loosely to refer to any of the preceeding types of minicells.

I.A. Eubacterial Minicells

One type of minicell is a eubacterial minicell. For reviews of eubacterial cell cycle and division processes, see Rothfield et al., Bacterial Cell Division, Annu. Rev. Genet., 33:423-48, 1999; Jacobs et al., Bacterial cell division: A moveable feast, Proc. Natl. Acad. Sci. USA, 96:5891-5893, May, 1999; Koch, The Bacterium's Way for Safe Enlargement and Division, Appl. and Envir. Microb., Vol. 66, No. 9, pp. 3657-3663; Bouche and Pichoff, On the birth and fate of bacterial division sites. Mol Microbiol, 1998. 29: 19-26; Khachatourians et al., Cell growth and division in *Escherichia coli*: a common genetic control involved in cell division and minicell formation. J Bacteriol, 1973. 116: 226-229; Cooper, The *Escherichia coli* cell cycle. Res Microbiol, 1990. 141: 17-29; and Danachie and Robinson, "Cell Division: Parameter Values and the Process," in: *Escherichia Coli* and *Salmonella Typhimurium: Cellular and Molecular Biology*, Neidhardt, Frederick C., Editor in Chief, American Society for Microbiology, Washington, D.C., 1987, Volume 2, pages 1578-1592, and references cited therein; and Lutkenhaus et al., "Cell Division," Chapter 101 in: *Escherichia coli* and *Salmonella typhimurium: Cellular and Molecular Biology*, $2^{nd}$ Ed., Neidhardt, Frederick C., Editor in Chief, American Society for Microbiology, Washington, D.C., 1996, Volume 2, pages 1615-1626, and references cited therein. When DNA replication and/or chromosomal partitioning is altered, membrane-bounded vesicles "pinch off" from parent cells before transfer of chromosomal DNA is completed. As a result of this type of dysfunctional division, minicells are produced which contain an intact outer membrane, inner membrane, cell wall, and all of the cytoplasm components but do not contain chromosomal DNA. See Table 2.

I.B. Eukaryotic Minicells

The term "eukaryote" is defined as is used in the art, and includes any organism classified as Eucarya that are usually classified into four kingdoms: plants, animals, fungi and protists. The first three of these correspond to phylogenetically coherent groups. However, the eucaryotic protists do not form a group, but rather are comprised of many phylogenetically disparate groups (including slime molds, multiple groups of algae, and many distinct groups of protozoa). See, e.g., Olsen, G., http://www.bact.wisc.edu/microtextbook/. A type of animal of particular interest is a mammal, including, by way of non-limiting example a rat, a mouse, a rabbit, a dog, a cat, a horse, a cow, a pig, a simian and a human.

Chromosomeless eukaryotic minicells (i.e., anucleate cells) are within the scope of the invention. Platelets are a non-limiting example of eukaryotic minicells. Platelets are anucleate cells with little or no capacity for de novo protein synthesis. The tight regulation of protein synthesis in platelets (Smith et al., Platelets and stroke, Vasc Med 4:165-72, 1999) may allow for the over-production of exogenous proteins and, at the same time, under-production of endogenous proteins. Thrombin-activated expression elements such as those that are associated with Bcl-3 (Weyrich et al., Signal-dependent translation of a regulatory protein, Bcl-3, in activated human platelets, Cel Biology 95:5556-5561, 1998) may be used to modulate the expression of exogenous genes in platelets.

As another non-limiting example, eukaryotic minicells are generated from tumor cell lines (Gyongyossy-Issa and Khachatourians, Tumour minicells: single, large vesicles released from cultured mastocytoma cells (1985) Tissue Cell 17:801-809; Melton, Cell fusion-induced mouse neuroblastomas HPRT revertants with variant enzyme and elevated HPRT protein levels (1981) Somatic Cell Genet 7: 331-344).

Yeast cells are used to generate fungal minicells. See, e.g., Lee et al., Ibd1p, a possible spindle pole body associated protein, regulates nuclear division and bud separation in *Saccharomyces cerevisiae*, Biochim Biophys Acta 3:239-253, 1999; Kopecka et al., A method of isolating anucleated yeast protoplasts unable to synthesize the glucan fibrillar component of the wall J Gen Microbiol 81:111-120, 1974; and Yoo et al., Fission yeast Hrp1, a chromodomain ATPase, is required for proper chromosome segregation and its overexpression interferes with chromatin condensation, Nucl Acids Res 28:2004-2011, 2000. Cell division in yeast is reviewed by Gould and Simanis, The control of septum formation in fission yeast, Genes & Dev 11:2939-51, 1997).

I.C. Archeabacterial Minicells

The term "archeabacterium" is defined as is used in the art and includes extreme thermophiles and other Archaea. Woese, C. R., L. Magrum. G. Fox. 1978. Archeabacteria. Journal of Molecular Evolution. 11:245-252. Three types of Archeabacteria are halophiles, thermophiles and methanogens. By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage (Olsen, G., http://www.bact.wisc.edu/microtextbook/). Non-limiting examples of halophiles include *Halobacterium cutirubrum* and *Halogerax mediterranei*. Non-limiting examples of methanogens include *Methanococcus voltae; Methanococcus vanniela; Methanobacterium thermoautotrophicum; Methanococcus voltae; Methanothermus fervidus*; and *Methanosarcina barkeri*. Non-limiting examples of thermophiles include *Azotobacter vinelandii; Thermoplasma acidophilum; Pyrococcus horikoshii; Pyrococcus furiosus*; and Crenarchaeota (extremely thermophilic archaebacteria) species such as *Sulfolobus solfataricus* and *Sulfolobus acidocaldarius*.

Archeabacterial minicells are within the scope of the invention. Archeabacteria have homologs of eubacterial minicell genes and proteins, such as the MinD polypeptide from *Pyrococcus furiosus* (Hayashi et al., EMBO J 2001 20:1819-28, Structural and functional studies of MinD ATPase: implications for the molecular recognition of the bacterial cell division apparatus). It is thus possible to create Archeabacterial minicells by methods such as, by way of non-limiting example, overexpressing the product of a min gene isolated from a prokaryote or an archeabacterium; or by disrupting expression of a min gene in an archeabacterium of interest by, e.g., the introduction of mutations thereof or antisense molecules thereto. See, e.g., Laurence et al., Nucleoid Structure and Partition in *Methanococcus jannaschii*: An Archaeon With Multiple Copies of the Chromosome, Genetics 152:1315-1323, 1999.

In one aspect, the invention is drawn to archael minicells. By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage (Olsen, G., http://www.bact.wisc.edu/microtextbook/).

I.D. Minicells Produced from Diverse Organisms

There are genes that can be disrupted to cause minicell production that are conserved among the three Kingdoms. For example, SMC (structural maintenance of chormosomes) proteins are conserved among prokaryotes, archeabacteria and eukaryotes (Hirano, SMC-mediated chromosome and mechanics: a conserved scheme from bacteria to vertebrates?, Genes and Dev. 13:11-19, 1999; Holmes et al., Closing the ring: Links between SMC proteins and chromosome partitioning, condensation, and supercoiling, PNAS 97:1322-1324, 2000; Michiko and Hiranol, EMBO J 17:7139-7148, 1998, ATP-dependent aggregation of single-stranded DNA by a bacterial SMC homodimer, 1998). Mutations in *B. subtilis* smc genes result in the production of minicells (Britton et al., Characterization of a eubacterial smc protein involved in chromosome partitioning, Genes and Dev. 12:1254-1259, 1998; Moriya et al., A *Bacillus subtilis* gene-encoding protein homologous to eukaryotic SMC motor protein is necessary for chromosome partition Mol Microbiol 29:179-87, 1998). Disruption of smc genes in various cells is predicted to result in minicell production therefrom.

As another example, mutations in the yeast genes encoding TRF topoisomerases result in the production of minicells, and a human homolog of yeast TRF genes has been stated to exist (Castano et al., A novel family of TRF (DNA topoisomerase I-related function) genes required for proper nuclear segregation, Nucleic Acids Res 24:2404-10, 1996). Mutations in a yeast chromodomain ATPase, Hrp1, result in abnormal chromosomal segregation; (Yoo et al., "Fission yeast Hrp1, a chromogomain ATPase, is required for proper chromosome segregation and its overexpression interferes with chromatin condensation," Nuc. Acids Res. 28:2004-2001). Disruption of TRF and/or Hrp1 function is predicted to cause minicell production in various cells. Genes involved in septum formation in fission yeast (see, e.g., Gould et al., "The control of septum formation in fission yeast," Genes and Dev. 11:2939-2951, 1997) can be used in like fashion.

As another example, mutations in the divIVA gene of *Bacillus subtilis* results in minicell production (Table 2). When expressed in *E. coli* or the yeast *Schizosaccharomyces pombe*, a *B. subtilis* DivIVA-GFP protein is targeted to cell division sites therein, even though clear homologs of DivIVA do not seem to exist in *E. coli* or *S. pombe* (David et al., Promiscuous targeting of *Bacillus subtilis* cell division protein DivIVA to division sites in *Escherichia coli* and fission yeast, EMBO J 19:2719-2727, 2000.) Over- or under-expression of *B. subtilis* DivIVA or a homolog thereof may be used to reduce minicell production in a variety of cells.

II. Production of Minicells

Eubacterial minicells are produced by parent cells having a mutation in, and/or overexpressing, or under expressing a gene involved in cell division and/or chromosomal partitioning, or from parent cells that have been exposed to certain conditions, that result in abberant fission of bacterial cells and/or partitioning in abnormal chromosomal segregation during cellular fission (division). The term "parent cells" or "parental cells" refers to the cells from which minicells are produced. Minicells, most of which lack chromosomal DNA (Mulder et al., The *Escherichia coli* minB mutation resembles gyrB in Defective nucleoid segregation and decreased negative supercoiling of plasmids. Mol Gen Genet, 1990, 221: 87-93), are generally, but need not be, smaller than their parent cells. Typically, minicells produced from *E. coli* cells are generally spherical in shape and are about 0.1 to about 0.3 um in diameter, whereas whole *E. coli* cells are about from about 1 to about 3 um in diameter and from about 2 to about 10 um in length. Micrographs of *E. coli* cells and minicells that have been stained with DAPI (4:6-diamidino-z-phenylindole), a compound that binds to DNA, show that the minicells do not stain while the parent *E. coli* are brightly stained. Such micrographs demonstrate the lack of chromosomal DNA in minicells. (Mulder et al., Mol. Gen. Genet. 221:87-93, 1990).

As shown in Table 2, minicells are produced by several different mechanisms such as, by way of non-limiting example, the over expression of genes involved in chromosomal replication and partitioning, mutations in such genes, and exposure to various environmental conditions. "Overexpression" refers to the expression of a polypeptide or protein encoded by a DNA introduced into a host cell, wherein the polypeptide or protein is either not normally present in the host cell, or wherein the polypeptide or protein is present in the host cell at a higher level than that normally expressed from the endogenous gene encoding the polypeptide or protein. For example, in *E. coli* cells that overexpress the gene product FtsZ (The FtsZ gene encodes a protein that is involved in regulation of divisions; see Cook and Rothfield, Early stages in development of the *Escherichia coli* cell-division site. Mol Microbiol, 1994. 14: p. 485-495; and Lutkenhaus, Regulation of cell division in *E. coli*. Trends Genet, 1990. 6: p. 22-25), there is an increase in the formation of minicells (Begg et al., Roles of FtsA and FtsZ in the activation of division sites. J. Bacteriology, 1997. 180: 881-884). Minicells are also produced by *E. coli* cells having a mutation in one or more genes of the min locus, which is a group of genes that encode proteins that are involved in cell division (de Boer et al., Central role for the *Escherichia coli* minC gene product in two different cell division-inhibition systems. Proc. Natl. Acad. Sci. USA, 1990. 87: 1129-33; Akerlund et al., Cell division in *Escherichia coli* minB mutants. Mol Microbiol, 1992. 6: 2073-2083).

Prokaryotes that have been shown to produce minicells include species of *Escherichia*, *Shigella*, *Bacillus*, *Lactobacillus*, and *Campylobacter*. Bacterial minicell-producing species of particular interest are *E. coli* and *Bacillus subtilis*. *E. coli* is amenable to manipulation by a variety of molecular genetic methods, with a variety of well-characterized expression systems, including many episomal expression systems, factors and elements useful in the present invention. *B. subtilis*, also amenable to genetic manipulation using episomal expression elements, is an important industrial organism involved in the production of many of the world's industrial enzymes (proteases, amylases, etc.), which it efficiently produces and secretes.

In the case of other eubacterial species, homologs of *E. coli* or *B. subilis* genes that cause minicell production therein are known or can be identified and characterized as is known in the art. For example, the min regions of the chromosome of *Strepococcus pneumoniae* and *Neisseria gonorrhoeae* have been characterized (Massidda et al., Unconventional organization of the division and cell wall gene cluster of *Streptococcus pneumoniae*, Microbiology 144:3069-78, 1998; and Ramirez-Arcos et al., Microbiology 147:225-237, 2001 and Szeto et al., Journal of Bacteria 183(21):6253, 2001, respectively). Those skilled in the art are able to isolate minicell producing (min) mutants, or prepare compounds inhibitory to genes that induce a minicell production (e.g., antisense to min transcripts).

TABLE 2

Eubacterial Strains, Mutations and Conditions that Promote Minicell Formation

| Species | Strain | Notes | References |
|---|---|---|---|
| *Campylobacter jejuni* | | may occur naturally late in growth cycle | Brock et al., 1987 |
| *Bacillus subtilis* | | Mutations in divIVB locus (inc. minC, minD) | Barak et al., 1999 |
| | | ripX mutations | Sciochetti et al., 1999; Lemon et al., 2001 |
| | | smc mutations | Moriya et al., 1998; Britton et al., 1998 |
| | | oriC deletions | Moriya et al., 1997; Hassan et al., 1997 |
| | | prfA mutations | Pederson and Setlow, 2001 |
| | | Mutations in divIVA locus | Cha et al., 1997 |
| | B.s. 168 | ts initiation mutation TsB143 | Sargent, 1975 |
| *Bacillus cereus* | WSBC 10030 | Induced by exposure to long-chain polyphosphate | Maier et al., 1999 |
| *Shigella flexneri* (2a) | MC-1 | | Gemski et al., 1980 |
| *S. dysenteriae* (1) | MC-V | | Gemski et al., 1980 |
| *Lactobacillus* spp. | | Variant minicell-producing strains isolated from grains | Pidoux et al., 1990 |
| *Neisseria gonorrhoeae* | | deletion or overepression of min homologues | Ramirez-Arcos et al., 2001; Szeto et al., 2001 |
| *Escherichia coli* | | MinA mutations | Frazer et al., 1975; Cohen et al. 1976 |
| | | MinB mutations and deletions | Adler et al., 1967; Davie et al., 1984; Schaumberg et al.; 1983; Jaffe et al., 1988; Akerlund et al., 1992 |
| | CA8000 | cya, crp mutations | Kumar et al.; 1979 |
| | | MukAI mutation | Hiraga et al., 1996 |
| | | MukE, mukF mutations | Yamanaka et al., 1996 |
| | | hns mutation | Kaidow et al., 1995 |
| | DS410 | | Heighway et al., 1989 |
| | | χ 1972, χ 1776 and χ 2076 | Curtiss, 1980 |
| | P678-54 | Temperature-sensitive cell division mutations | Adler et al. 1967; Allen et al., 1972; Hollenberg et al., 1976 |
| | | Induced by overexpression of minB protein | De Boer et al., 1988 |
| | | Induced by overexpression of minE protein or derivatives | Pichoff et al., 1995 |
| | | Induced by overproduction of ftsZ gene | Ward et al., 1985 |
| | | Induced by overexpression of sdiA gene | Wang et al., 1991 |
| | | Induced by overexpression of min genes from *Neisseria gonorrhoeae* | Ramirez-Arcos et al., 2001; Szeto et al., 2001 |
| | | Induced by exposure to EGTA | Wachi et al., 1999 |
| *Legionella Pneumophila* | | Induced by exposure to ampicillin | Elliot et al., 1985 |

Citations for Table 2
Adler et al., *Proc. Natl. Acad. Sci.* 57:321-326 (1967)
Akerlund et al., *Mol. Microbiol.* 6:2073-2083 (1992)
Allen et al., *Biochem. Biophys. Res. Communi.* 47:1074-1079 (1972)

Barak et al., *J. Bacteriol.* 180:5237-5333 (1998)
Britton et al., *Genes Dev.* 12:1254-9 (1998)
Brock et al., *Can. J. Microbiol.* 33:465-470 (1987)
Cha et al., *J. Bacteria* 179:1671-1683 (1997)
Cohen et al., *Genetics* 56:550-551 (1967)
Curtiss, Roy III, U.S. Pat. No. 4,190,495; Issued Feb. 26, 1980
Davie et al., *J. Bacteria* 170:2106-2112 (1988)
Elliott et al., J. Med. Microbiol, 19:383-390 (1985)
Frazer et al., *Curr. Top. Immunol.* 69:1-84 (1975)
Gemski et al., *Infect. Immun.* 30:297-302 (1980)
Hassan et al., *J. Bacteria* 179:2494-502 (1997)
Heighway et al., *Nucleic Acids Res.* 17:6893-6901 (1989)
Hiraga et al., *J. Bacteriol.* 177:3589-3592 (1995)
Hollenberg et al., Gene 1:33-47 (1976)
Kumar et al., *Mol. Gen. Genet.* 176:449-450 (1979)
Lemon et al., *Proc. Natl. Acad. Sci. USA* 98:212-7 (2001)
Maier et al., *Appl. Environ. Microbiol.* 65:3942-3949 (1999)
Moriya et al., *DNA Res* 4:115-26 (1997)
Moriya et al., *Mol. Microbiol.* 29:179-87 (1998)
Markiewicz et al., *FEMS Microbiol. Lett.* 70:119-123 (1992)
Pederson and Setlow, *J. Bacteriol.* 182:1650-8 (2001)
Pichoff et al., *Mol. Microbiol.* 18:321-329 (1995)
Pidoux et al., *J. App. Bacteria* 69:311-320 (1990)
Ramirez-Arcos et al. *Microbiol.* 147:225-237 (2001)
Sargent M. G., *J. Bacteriol.* 123:1218-1234 (1975)
Sciochetti et al., *J. Bacteriol.* 181:6053-62 (1999)
Schaumberg et al., *J. Bacteria* 153:1063-1065 (1983)
Szeto et al., *Jour. of Bacter.* 183 (21):6253 (2001)
Wachi et al., *Biochimie* 81:909-913 (1999)
Wang et al., *Cell* 42:941-949 (1985)
Yamanaka et al., *Mol. Gen. Genet.* 250:241-251 (1996)

II.A. Optimized Minicell Construction

Minicells are produced by several different eubacterial strains and mechanisms including the overexpression of endogenous or exogenous genes involved in cell division, chromosomal replication and partitioning, mutations in such genes, and exposure to various chemical and/or physical conditions. For example, in *E. coli* cells that overexpress the gene product FtsZ (the ftsZ gene encodes a protein that is involved in regulation of cell division; see Cook and Rothfield, Early stages in development of the *Escherichia coli* cell-division site. Mol Microbiol, 1994. 14: p. 485-495; and Lutkenhaus, Regulation of cell division in *E. coli*. Trends Genet, 1990. 6: p. 22-25), there is an increase in the formation of minicells (Begg et al., Roles of FtsA and FtsZ in the activation of division sites. J. Bacteriology, 1997. 180: 881-884). Minicells are also produced by *E. coli* cells having a mutation in one or more genes of the min locus, which is a group of genes that encode proteins that are involved in cell division (de Boer et al., Central role for the *Escherichia coli* minC gene product in two different cell division-inhibition systems. Proc. Natl. Acad. Sci. USA, 1990. 87: 1129-33; Akerlund et al., Cell division in *Escherichia coli* minB mutants. Mol Microbiol, 1992. 6: 2073-2083).

Eubacterial cells that have been shown to produce minicells include, but are not limited to species of *Escherichia, Shigella, Bacillus, Lactobacillus, Legionella* and *Campylobacter*. Bacterial minicell-producing species of particular interest are *E. coli* and *Bacillus subtilis*. These organisms are amenable to manipulation by a variety of molecular and genetic methods, with a variety of well-characterized expression systems, including many episomal and chromosomal expression systems, as well as other factors and elements useful in the present invention.

The following sections describe genes that may be manipulated so as to stimulate the production of minicells. The invention may include any of these non-limiting examples for the purpose of preparing minicells. Furthermore, these genes and gene products and conditions, may be used in methodologies to identify other gene(s), gene products, biological events, biochemical events, or physiological events that induce or promote the production of minicells. These methodologies include, but are not limited to genetic selection, protein, nucleic acid, or combinatorial chemical library screen, one- or two-hybrid analysis, display selection technologies, e.g. phage or yeast display, hybridization approaches, e.g. array technology, and other high- or low-throughput approaches.

II.A.1. Homologs

Homologs of these genes and gene products from other organisms may also be used. As used herein, a "homolog" is defined is a nucleic acid or protein having a nucleotide sequence or amino acid sequence, respectively, that is "identical," "essentially identical," "substantially identical," "homologous" or "similar" (as described below) to a reference sequence which may, by way of non-limiting example, be the sequence of an isolated nucleic acid or protein, or a consensus sequence derived by comparison of two or more related nucleic acids or proteins, or a group of isoforms of a given nucleic acid or protein. Non-limiting examples of types of isoforms include isoforms of differing molecular weight that result from, e.g., alternate RNA splicing or proteolytic cleavage; and isoforms having different post-translational modifications, such as glycosylation; and the like.

Two sequences are said to be "identical" if the two sequences, when aligned with each other, are exactly the same with no gaps, substitutions, insertions or deletions.

Two sequences are said to be "essentially identical" if the following criteria are met. Two amino acid sequences are "essentially identical" if the two sequences, when aligned with each other, are exactly the same with no gaps, insertions or deletions, and the sequences have only conservative amino acid substitutions. Conservative amino acid substitutions are as described in Table 3.

TABLE 3

CONSERVATIVE AMINO ACID SUBSTITUTIONS

| Type of Amino Acid Side Chain | Groups of Amino Acids that Are Conservative Substitutions Relative to Each Other |
|---|---|
| Short side chain | Glycine, Alanine, Serine, Threonine and Methionine |
| Hydrophobic | Leucine, Isoleucine and Valine |
| Polar | Glutamine and Asparagine |
| Acidic | Glutamic Acid and Aspartic Acid |
| Basic | Arginine, Lysine and Histidine |
| Aromatic | Phenylalanine, Tryptophan and Tyrosine |

Two nucleotide sequences are "essentially identical" if they encode the identical or essentially identical amino acid sequence. As is known in the art, due to the nature of the genetic code, some amino acids are encoded by several different three base codons, and these codons may thus be substituted for each other without altering the amino acid at that position in an amino acid sequence. In the genetic code, TTA, TTG, CTT, CTC, CTA and CTG encode Leu; AGA, AGG, CGT, CGC, CGA and CGG encode Arg; GCT, GCC, GCA and GCG encode Ala; GGT, GGC, GGA and GGG encode Gly; ACT, ACC, ACA and ACG encode Thr; GTT, GTC, GTA and GTG encode Val; TCT, TCC, TCA and TCG encode Ser; CCT, CCC, CCA and CCG encode Pro; ATA, ATC and ATA encode Ile; GAA and GAG encode Glu; CAA and CAG encode Gln; GAT and GAC encode Asp; AAT and AAC encode Asn; AGT and AGC encode Ser; TAT and TAC encode Tyr; TGT and TGC encode Cys; AAA and AAG encode Lys;

CAT and CAC encode His; TTT and TTC encode Phe, TGG encodes Trp; ATG encodes Met; and TGA, TAA and TAG are translation stop codons.

Two amino acid sequences are "substantially identical" if, when aligned, the two sequences are, (i) less than 30%, preferably ≦20%, more preferably ≦15%, most preferably ≦10%, of the identities of the amino acid residues vary between the two sequences; (ii) the number of gaps between or insertions in, deletions of and/or substitutions of, is ≦10%, more preferably ≦5%, more preferably ≦3%, most preferably ≦1%, of the number of amino acid residues that occur over the length of the shortest of two aligned sequences.

Two sequences are said to be "homologous" if any of the following criteria are met. The term "homolog" includes without limitation orthologs (homologs having genetic similarity as the result of sharing a common ancestor and encoding proteins that have the same function in different species) and paralog (similar to orthologs, yet gene and protein similarity is the result of a gene duplication).

One indication that nucleotide sequences are homologous is if two nucleic acid molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 M at pH 7 and the temperature is at least about 60° C.

Another way by which it can be determined if two sequences are homologous is by using an appropriate algorithm to determine if the above-described criteria for substantially identical sequences are met. Sequence comparisons between two (or more) polynucleotides or polypeptides are typically performed by algorithms such as, for example, the local homology algorithm of Smith and Waterman (Adv. Appl. Math. 2:482, 1981); by the homology alignment algorithm of Needleman and Wunsch (J. Mol. Biol. 48:443, 1970); by the search for similarity method of Pearson and Lipman (Proc. Natl. Acad. Sci. U.S.A. 85:2444, 1988); and by computerized implementations of these algorithms (GAP, BESTFIT, FASTA, and TFASTA in the Wisconsin Genetics Software Package, version 10.2 Genetics Computer Group (GCG), 575 Science Dr., Madison, Wis.); BLASTP, BLASTN, and FASTA (Altschul et al., J. Mol. Biol. 215:403-410, 1990); or by visual inspection.

Optimal alignments are found by inserting gaps to maximize the number of matches using the local homology algorithm of Smith and Waterman (1981) Adv. Appl. Math. 2:482-489. "Gap" uses the algorithm of Needleman and Wunsch (1970 J Mol. Biol. 48:443-453) to find the alignment of two complete sequences that maximizes the number of matches and minimizes the number of gaps. In such algorithms, a "penalty" of about 3.0 to about 20 for each gap, and no penalty for end gaps, is used.

Homologous proteins also include members of clusters of orthologous groups of proteins (COGs), which are generated by phylogenetic classification of proteins encoded in complete genomes. To date, COGs have been delineated by comparing protein sequences encoded in 43 complete genomes, representing 30 major phylogenetic lineages. Each COG consists of individual proteins or groups of paralogs from at least 3 lineages and thus corresponds to an ancient conserved domain (see Tatusov et al., A genomic perspective on protein families. Science, 278: 631-637, 1997; Tatusov et al., The COG database: new developments in phylogenetic classification of proteins from complete genomes, Nucleic Acids Res. 29:22-28, 2001; Chervitz et al., Comparisn of the Complete Sets of Worm and Yeast: Orthology and Divergence, Science 282:2022-2028, 1998; and http://www.ncbi.nlm.nih.gov/COG/).

The entirety of two sequences may be identical, essentially identical, substantially identical, or homologous to one another, or portions of such sequences may be identical or substantially identical with sequences of similar length in other sequences. In either case, such sequences are similar to each other. Typically, stretches of identical or essentially within similar sequences have a length of ≧12, preferably ≧24, more preferably ≧48, and most preferably ≧96 residues.

II.A.2. *Escherichia coli* Genes

Exemplary genes and gene products from *E. coli* the expression and/or sequence of which can be manipulated so as to stimulate minicell production in *E. coli* or any other organism, as can homologs thereof from any species, include without limitation, the bolA gene (Aldea, M., et al. 1988. Identification, cloning, and expression of bolA, an ftsZ-dependent morphogene of *Escherichia coli*. J. Bacteriol. 170: 5196-5176; Aldea, M., et al. 1990. Division genes in *Escherichia coli* are expressed coordinately to cell septum requirements by gearbox promoters. EMBO J. 9:3787-3794); the chpA gene (Masuda, Y., et al. 1993. chpA and chpB, *Escherichia coli* chromosomal homologs of the pem locus responsible for stable maintenance of plasmid R100. J. Bacteriol. 175:6850-6856); the chpB gene (Masuda, Y., et al. 1993. chpA and chpB, *Escherichia coli* chromosomal homologs of the pem locus responsible for stable maintenance of plasmid R100. J. Bacteriol. 175:6850-6856); the chpR (chpAI) gene (Masuda, Y., et al. 1993. chpA and chpB, *Escherichia coli* chromosomal homologs of the pem locus responsible for stable maintenance of plasmid R100. J. Bacteriol. 175:6850-6856); the chpS (chpBI) gene (Masuda, Y., et al. 1993. chpA and chpB, *Escherichia coli* chromosomal homologs of the pem locus responsible for stable maintenance of plasmid R100. J. Bacteriol. 175:6850-6856); the crg gene (Redfield, R. J., and A. M. Campbell. 1987. Structurae of cryptic lambda prophages. J. Mol. Biol. 198:393-404); the crp gene (Kumar, S., et al. 1979. Control of minicell producing cell division by cAMP-receptor protein complex in *Escherichia coli*. Mol. Gen. Genet. 176:449-450); the cya gene (Kumar, S., et al. 1979. Control of minicell producing cell division by cAMP-receptor protein complex in *Escherichia coli*. Mol. Gen. Genet. 176:449-450); the dicA gene (Labie, C., et al. 1989. Isolation and mapping of *Escherichia coli* mutations conferring resistance to division inhibition protein DicB. J. Bacteriol. 171:4315-4319); the dicB gene (Labie, C., et al. 1989. Isolation and mapping of *Escherichia coli* mutations conferring resistance to division inhibition protein DicB. J. Bacteriol. 171:4315-4319; Labie, C., et al. 1990. Minicell-forming mutants of *Escherichia coli*: suppression of both DicB- and MinD-dependent division inhibition by inactivation of the minC gene product. J. Bacteriol. 1990. 172:5852-5858); the dicC gene (Bejar, S., et al. 1988. Cell division inhibition gene dicB is regulated by a locus similar to lambdoid bacteriophage immunity loci. Mol. Gen. Genet. 212:11-19); the dicF gene (Tetart, F., and J. P. Bouche. 1992. Regulation of the expression of the cell-cycle gene ftsZ by DicF antisense RNA. Division does not require a fixed number of FtsZ molecules. Mol. Microbiol. 6:615-620); the dif gene (Kuempel, P. L., et al. 1991. dif, a recA-independent recombination site in the terminus region of the chromosome of *Escherichia coli*. New Biol. 3:799-811); the dksA gene (Yamanaka, K., et al. 1994. Cloning, sequencing, and characterization of multicopy suppressors of a mukB mutation in *Escherichia coli*. Mol. Microbiol. 13:301-312); the dnaK gene (Paek, K. H., and G. C. Walker. 1987. *Escherichia coli* dnaK null mutants are inviable at high temperature. J. Bacteriol. 169:283-290); the dnaJ gene (Hoffman, H. J., et al. 1992. Activity of the Hsp70 chaperone complex—DnaK, DnaJ, and GrpE—in initiating phage lambda DNA replication by sequestering and releasing lambda P protein. Proc. Natl. Acad. Sci. 89:12108-12111); the fcsA gene (Kudo, T., et al. 1977. Characteristics of a cold-sensitive cell division mutant *Escherichia coli* K-12. Agric. Biol. Chem. 41:97-107); the fic gene (Utsumi, R., et al. 1982. Involvement of cyclic AMP and its receptor protein in filamentation of an *Escherichia coli* fic mutant. J. Bacteriol. 151:807-812; Komano, T., et al. 1991. Functional analysis of the fic gene involved in regulation of cell division. Res. Microbiol. 142:269-277); the fis gene (Spaeny-Dekking, L. et al. 1995. Effects of N-terminal deletions of the *Escherichia coli* protein Fis on the growth rate, tRNA (2Ser) expression and cell morphology. Mol. Gen. Genet. 246:259-265); the ftsA gene (Bi, E., and J. Lutkenhaus. 1990. Analysis of ftsZ, mutations that confer resistance to the cell division inhibitor SulA (SfiA). J. Bacterial. 172: 5602-5609; Dai, K, and J. Lutkenhaus. 1992. The proper ration of FtsZ to FtsA is required for cell division to occur in *Escherichia coli*. J. Bacteriol. 174:6145-6151); the ftsE gene (Taschner, P. E. et al. 1988. Division behavior and shape changes in isogenic ftsZ, ftsQ, ftsA, pbpB, and ftsE cell division mutants of *Escherichia coli* during temperature shift experiments. J. Bacteriol. 170:1533-1540); the ftsH gene (Ogura, T. et al. 1991. Structure and function of the ftsH gene in *Escherichia coli*. Res. Microbiol. 142:279-282); the ftsI gene (Begg, K. J., and W. D. Donachie. 1985. Cell shape and division in *Escherichia coli*: experiments with shape and division mutants. J. Bacteriol. 163:615-622); the ftsJ gene (Ogura, T. et al. 1991. Structure and function of the ftsH gene in *Escherichia coli*. Res. Microbiol. 142:279-282); the ftsL gene (Guzman, et al. 1992. FtsL, an essential cytoplasmic membrane protein involved in cell division in *Escherichia coli*. J. Bacteriol. 174:7716-7728); the ftsN gene (Dai, K. et al. 1993. Cloning and characterization of ftsN, an essential cell division gene in *Escherichia coli* isolated as a multicopy suppressor of ftsA12(Ts). J. Bacteriol. 175:3790-3797); the ftsQ gene (Wang, X. D. et al. 1991. A factor that positively regulates cell division by activating transcription of the major cluster of essential cell division genes of *Escherichia coli*. EMBO J. 10:3362-3372); the ftsW gene (Khattar, M. M. et al. 1994. Identification of FtsW and characterization of a new ftsW division mutant of *Escherichia coli*. J. Bacteriol. 176: 7140-7147); the ftsX (ftsS) gene (Salmond, G. P. and S. Plakidou. 1984. Genetic analysis of essential genes in the ftsE region of the *Escherichia coli* genetic map and identification of a new cell division gene, ftsS. Mol. Gen. Genet. 197:304-308); the ftsY gene (Gill, D. R. and G. P. Salmond. 1990. The identification of the *Escherichia coli* ftsY gene product: an unusual protein. Mol. Microbiol. 4:575-583); the ftsZ gene (Ward, J. E., and J. Lutkenhaus. 1985. Overproduction of FtsZ induces minicell formation. Cell. 42:941-949; Bi, E., and J. Lutkenhaus. 1993. Cell division inhibitors SulA and MinCD prevent formation of the FtsZ ring. J. Bacteriol. 175: 1118-1125); the gyrB gene (Mulder, E., et al. 1990. The *Escherichia coli* minB mutation resembles gyrB in defective nucleoid segregation and decreased negative supercoiling of plasmids. Mol. Gen. Genet. 221:87-93); the hlfB (ftsH) gene (Herman, C., et al. 1993. Cell growth and lambda phage development controlled by the same essential *Escherichia coli* gene, ftsH/hflB. Proc. Natl. Acad. Sci. 90:10861-10865); the hfq gene (Takada, A., et al. 1999. Negative regulatory role of the *Escherichia coli* hfq gene in cell division. Biochem. Biophys. Res. Commun. 266:579-583; the hipA gene (Scherrer, R., and H. S. Moyed. 1988. Conditional impairment of cell division and altered lethality in hipA mutants of *Escherichia coli* K-12. J. Bacteriol. 170:3321-3326); the hipB gene (Hendricks, E. C., et al. 2000. Cell division, guillotining of dimer chromosomes and SOS induction in resolution mutants (dif, xerC and xerD) of *Escherichia coli*. Mol. Microbiol. 36:973-981); the hns gene (Kaidow, A., et al. 1995. Anucleate cell production by *Escherichia coli* delta hns mutant lacking a histone-like protein, H-NS. J. Bacteriol. 177:3589-3592); the htrB gene (Karow, M., et al. 1991. Complex phenotypes of null mutations in the htr genes, whole products are essential for *Escherichia coli* growth at elevated temperatures. Res. Microbiol. 142:289-294); the 1pxC (envA) gene (Beall, B., and J. Lutkenhaus. 1987. Sequence analysis, transcriptional organization, and insertional mutagenesis of the envA gene of *Escherichia coli*. J. Bacteriol. 169:5408-5415; Young, K., et al. 1995. The envA permeability/cell division gene of *Escherichia coli* encodes the second enzyme of lipid A biosynthesis. UDP-3-O—(R-3-hydroxymyristoyl)-N-acetylglucosamine deacetylase. J. Biol. Chem. 270:30384-30391); the malE gene (Pichoff, S., et al. 1997. MinCD-independent inhibition of cell division by a protein that fuses MalE to the topological specificity factor MinE. J. Bacteriol. 179:4616-4619); the minA gene (Davie, E., et al. 1984. Genetic basis of minicell formation in *Escherichia coli* K-12. J. Bacteriol. 158:1202-1203); the minB gene (Davie, E., et al. 1984. Genetic basis of minicell formation in *Escherichia coli* K-12. J. Bacteriol. 158:1202-1203); the minC gene (de Boer, P. A., et al. 1990. Central role for the *Escherichia coli* minC gene product in two different cell division-inhibition systems. Proc. Natl. Acad. Sci. 87:1129-1133); the minD gene (Labie, C., et al. 1990. Minicell-forming mutants of *Escherichia coli*: suppression of both DicB- and MinD-dependent division inhibition by inactivation of the minC gene product. J. Bacteriol. 172:5852-5855; Hayashi, I., et al. 2001. Structural and functional studies of MinD ATPase: implications for the molecular recognition of the bacterial cell division apparatus. EMBO J. 20:1819-1828); the minE gene (de Boer, P. A., et al. 1989. A division inhibitor and a topological specificity factor coded for by the minicell locus determine proper placement of the division septum in *E. coli*. Cell. 56:641-649); the mreB gene (Doi, M., et al. 1988. Determinations of the DNA sequence of the mreB gene and of the gene products of the mre region that function in formation of the rod shape of *Escherichia coli* cells. J. Bacteriol. 170:4619-4624); the mreC gene (Wachi, M., et al. 1989. New mre genes mreC and mreD, responsible for formation of the rod shape of *Escherichia coli* cells. J. Bacteriol. 171:6511-6516); the mreD gene (Wachi, M., et al. 1989. New mre genes mreC and mreD, responsible for formation of the rod shape of *Escherichia coli* cells. J. Bacteriol. 171:6511-6516); the mukA gene (Hiraga, S., et al. 1989. Chromosome partitioning in *Escherichia coli*: novel mutants producing anucleate cells. J. Bacteriol. 171: 1496-1505); the mukB gene (Hiraga, S., et al. 1991. Mutants defective in chromosome partitioning in *E. coli*. Res. Microbiol. 142:189-194); the mukE gene (Yamanaka, K., et al. 1996. Identification of two new genes, mukE and mukF, involved in chromosome partitioning in *Escherichia coli*. Mol. Gen. Genet. 250:241-251; Yamazoe, M., et al. 1999. Complex formation of MukB, MukE and MukF proteins involved in chromosome partitioning in *Escherichia coli*. EMBO J. 18:5873-5884); the mukF gene (Yamanaka, K., et al. 1996. Identification of two new genes, mukE and mukF, involved in chromosome partitioning in *Escherichia coli*.

Mol. Gen. Genet. 250:241-251; Yamazoe, M., et al. 1999. Complex formation of MukB, MukE and MukF proteins involved in chromosome partitioning in *Escherichia coli*. EMBO J. 18:5873-5884); the parC gene (Kato, J., et al. 1988. Gene organization in the region containing a new gene involved in chromosome partition in *Escherichia coli*. J. Bacteriol. 170:3967-3977); the parE gene (Roberts, R. C., et al. 1994. The parDE operon of the broad-host-range plasmid RK2 specifies growth inhibition associated with plasmid loss. J. Mol. Biol. 237:35-51); the pbpA gene (Rodriguez, M. C., and M. A. de Pedro. 1990. Initiation of growth in pbpAts and rodAts mutants of *Escherichia coli*. FEMS Microbiol. Lett. 60:235-239); the pcnB gene (Makise, M., et al. 1999. Identification of a high-copy-number plasmid suppressor of a lethal phenotype caused by mutant DnaA protein which has decreased intrinsic ATPase activity. Biol. Pharm. Bull. 22:904-909); the parF (plsC in *E. coli*) gene product from *Salmonella* (Luttinger, A. L., et al. 1991. A cluster of genes that affects nucleoid segregation in *Salmonella typhimurium*. New Biol. 3:687-697); the rpoS gene (Cam, K., et al. 1995. Sigma S-dependent overexpression of ftsZ in an *Escherichia coli* K-12 rpoB mutant that is resistant to the division inhibitors DicB and DicF RNA. Mol. Gen. Genet. 248:190-194); the rcsB gene (Gervais, F. G., et al. 1992. The rcsB gene, a positive regulator of colanic acid biosynthesis in *Escherichia coli*, is also an activator of ftsZ expression. J. Bacteriol. 174: 3964-3971); the rcsF gene (Gervais, F. G., and G. R. Drapeau. 1992. Identification, cloning, and characterization of rcsF, a new regulator gene for exopolysaccharide synthesis that suppresses the division mutation ftsZ84 in *Escherichia coli* K-12. J. Bacteriol. 174:8016-8022); the rodA gene (Rodriguez, M. C., and M. A. de Pedro. 1990. Initiation of growth in pbpAts and rodAts mutants of *Escherichia coli*. FEMS Microbiol. Lett. 60:235-239); the sdiA (sulB, sfiB) gene (Wang, X. D., et al. 1991. A factor that positively regulates cell division by activating transcription of the major cluster of essential cell division genes of *Escherichia coli*. EMBO J. 10:3363-3372); the sefA (fabZ) gene (Mohan, S., et al. 1994. An *Escherichia coli* gene (FabZ) encoding (3R)-hydroxymyristoyl acyl carrier protein dehydrase. Relation to fabA and suppression of mutations in lipid A biosynthesis. J. Biol. Chem. 269:32896-32903); the sfiC gene (D'Ari, R., and O. Huisman. 1983. Novel mechanism of cell division inhibition associated with the SOS response in *Escherichia coli*. J. Bacteriol. 156:243-250); the sulA gene (Bi, E., and J. Lutkenhaus. 1990. Interaction between the min locus and ftsZ. J. Bacteriol. 172:5610-5616; Bi, E., and J. Lutkenhaus. 1993. Cell division inhibitors SulA and MinCD prevent formation of the FtsZ ring. J. Bacteriol. 175:1118-1125); the stfZ gene (Dewar, S. J., and W. D. Donachie. 1993. Antisense transcription of the ftsZ-ftsA gene junction inhibits cell division in *Escherichia coli*. J. Bacteriol. 175:7097-7101); the tolC gene (Hiraga, S., et al. 1989. Chromosome partitioning in *Escherichia coli*: novel mutants producing anucleate cells. J. Bacteriol. 171:1496-1505; Hiraga, S., et al. 1991. Mutants defective in chromosome partitioning in *E. coli*. Res. Microbiol. 142:189-194); and the zipA gene (Hale, C. A., and P. A. de Boer. 1997. Direct binding of FtsZ to ZipA, an essential component of the septal ring structure that mediates cell division in *E. coli*. Cell. 88:175-185).

The guanosine 5'-diphosphate 3' diphosphate (ppGpp) or guanosine 5'-triphosphate 3' diphosphate (pppGpp) nucleotides, collectively (p)ppGpp, found in *E. coli* or in other members of the Eubacteria, Eucarya or Archaea may be employed to produce minicells (Vinella, D., et al. 1993. Penicillin-binding protein 2 inactivation in *Escherichia coli* results in cell division inhibition, which is relieved by FtsZ overexpression. J. Bacteriol. 175:6704-6710; Navarro, F., et al. Analysis of the effect of ppGpp on the ftsQAZ operon in *Escherichia coli*. Mol. Microbiol. 29:815-823). The levels, or rate of production of (p)ppGpp may be increased or decreased. By way of non-limiting example, increased (p)ppGpp production results from induction of the stringent response. The stringent response in *E. coli* is a physiological response elicited by a failure of the capacity for tRNA aminoacylation to keep up with the demands of protein synthesis. This response can be provoked either by limiting the availability of amino acids or by limiting the ability to aminoacylate tRNA even in the presence of abundant cognate amino acids. Many features of the stringent response behave as if they are mediated by accumulation of (p)ppGpp. The accumulation of (p)ppGpp can also be provoked by nutritional or other stress conditions in addition to a deficiency of aminoacyl-tRNA. See Cashel et al., "The Stringent Response," Chapter 92 in: *Escherichia coli* and *Salmonella typhimurium: Cellular and Molecular Biology*, 2nd Ed., Neidhardt, Frederick C., Editor in Chief, American Society for Microbiology, Washington, D.C., 1996, Volume 1, pages 1458-1496, and references cited therein.

By way of non-limiting example, factors that may provoke the stringent response include the lyt gene or gene product (Harkness, R. E., et al. 1992. Genetic mapping of the lytA and lytB loci of *Escherichia coli*, which are involved in penicillin tolerance and control of the stringent response. Can J. Microbiol. 38:975-978), the relA gene or gene product (Vinella, D., and R. D'Ari. 1994. Thermoinducible filamentation in *Escherichia coli* due to an altered RNA polymerase beta subunit is suppressed by high levels of ppGpp. J. Bacteriol. 176:96-972), the relB gene or gene product (Christensen, S. K., et al. 2001. RelE, a global inhibitor of translation, is activated during nutritional stress. Proc. Natl. Acad. Sci. 98:14328-14333), the relC (rplK) gene or gene product (Yang, X., and E. E. Ishiguro. 2001. Involvement of the N Terminus of Ribosomal Protein L11 in Regulation of the RelA Protein of *Escherichia coli*. J. Bacteriol. 183:6532-6537), the relX gene or gene product (St. John, A. C., and A. L. Goldberg. 1980. Effects of starvation for potassium and other inorganic ions on protein degradation and ribonucleic acid synthesis in *Escherichia coli*. J. Bacteriol. 143:1223-1233), the spoT gene or gene product (Vinella, D., et al. 1996. Mecillinam resistance in *Escherichia coli* is conferred by loss of a second activity of the AroK protein. J. Bacteriol. 178: 3818-3828), the gpp gene or gene product (Keasling, J. D., et al. 1993. Guanosine pentaphosphate phosphohydrolase of *Escherichia coli* is a long-chain exopolyphosphatase. Proc. Natl. Acad. Sci. 90:7029-7033), the ndk gene or gene product (Kim, H. Y., et al. 1998. Alginate, inorganic polyphosphate, GTP and ppGpp synthesis co-regulated in *Pseudomonas aeruginosa*: implications for stationary phase survival and synthesis of RNA/DNA precursors. Mol. Microbiol. 27:717-725), the rpoB gene or gene product (Vinella, D., and R. D'Ari. 1994. Thermoinducible filamentation in *Escherichia coli* due to an altered RNA polymerase beta subunit is suppressed by high levels of ppGpp. J. Bacteriol. 176:96-972), the rpoC gene or gene product (Bartlett, M. S., et al. 1998. RNA polymerase mutants that destabilize RNA polymerase-promoter complexes alter NTP-sensing by rrn P1 promoters. J. Mol. Biol. 279:331-345), the rpoD gene or gene product (Hernandez, V. J., and M. Cashel. 1995. Changes in conserved region 3 of *Escherichia coli* sigma 70 mediate ppGpp-dependent functions in vivo. 252:536-549), glnF gene or gene product (Powell, B. S., and D. L. Court. 1998. Control of ftsZ expression, cell division, and glutamine metabolism in Luria-Bertani medium by the alarmone ppGpp in *Escherichia coli*. J. Bacteriol. 180:1053-1062), or glnD gene or gene product (Powell, B. S., and D. L. Court. 1998. Control of ftsZ expression, cell division, and glutamine metabolism in Luria-Bertani medium by the alarmone ppGpp in *Escherichia coli*. J. Bacteriol. 180:1053-1062). These genes or gene products, and/or expression thereof, may be manipulated to create minicells.

II.A.3. *Bacillus subtilis* Genes

Exemplary genes and gene products from *B. subtilis*, the expression and/or sequence of which can be manipulated so as to stimulate minicell production in *B. subtilis* or any other organism, as can homologs thereof from any species, include without limitation, the divI (divD) gene (Van Alstyne, D., and M. I. Simon. 1971. Division mutants of *Bacillus subtilis*: isolation of PBS1 transduction of division-specific markers. J. Bacteriol. 108:1366-1379); the divIB (dds, ftsQ) gene (Harry, E. J., et al. 1993. Characterization of mutations in divIB of *Bacillus subtilis* and cellular localization of the DivIB protein. Mol. Microbiol. 7:611-621; Harry E. J., et al. 1994. Expression of divIB of *Bacillus subtilis* during vegetative growth. J. Bacteriol. 176:1172-1179); the divIC gene product from *B. subtilis* or homologues of this gene or gene product found in other members of the Eubacteria, Eucarya or Archaea may be employed to produce minicells (Levin, P. A., and R. Losick. 1994. Characterization of a cell division gene from *Bacillus subtilis* that is required for vegetative and sporulation septum formation. J. Bacteriol. 176:1451-1459; Katis, V. L., et al. 1997. The *Bacillus subtilis* division protein DivIC is a highly abundant membrane-bound protein that localizes to the division site; the divII (divC) gene (Van Alstyne, D., and M. I. Simon. 1971. Division mutations of *Bacillus subtilis*: isolation and PBS1 transduction of division-specific markers. J. Bacteriol. 108:1366-1379); the divIVA (divD) gene (Cha, J.-H., and G. C. Stewart. 1997. The divIVA minicell locus of *Bacillus subtilis*. J. Bacteriol. 179:1671-1683); the divIVC (divA) gene (Van Alstyne, D., and M. I. Simon. 1971. Division mutations of *Bacillus subtilis*: isolation and PBS1 transduction of division-specific markers. J. Bacteriol. 108:1366-1379); the divV (divB) gene (Van Alstyne, D., and M. I. Simon. 1971. Division mutations of *Bacillus subtilis*: isolation and PBS1 transduction of division-specific markers. J. Bacteriol. 108:1366-1379); the erzA (ytwP) gene (Levin, P. A., et al. 1999. Identification and regulation of a negative regulator of FtsZ ring formation in *Bacillus subtilis*. Proc. Natl. Acad. Sci. 96:9642-9647); the ftsA (spoIIN) gene (Feucht, A., et al. 2001. Cytological and biochemical characterization of the FtsA cell division protein of *Bacillus subtilis*. Mol. Microbiol. 40:115-125); the ftsE gene (Yoshida, K., et al. 1994. Cloning and nucleotide sequencing of a 15 kb region of the *Bacillus subtilis* genome containing the iol operon. Microbiology. 140:2289-2298); the ftsH gene (Deuerling. E., et al. 1995. The ftsH gene of *Bacillus subtilis* is transiently induced after osmotic and temperature upshift. J. Bacteriol. 177:4105-4112; Wehrl, W., et al. 2000. The FtsH protein accumulates at the septum of *Bacillus subtilis* during cell division and sporulation. J. Bacteriol. 182:3870-3873); the ftsK gene (Sciochetti, S. A., et al. 2001. Identification and characterization of the dif Site from *Bacillus subtilis*. J. Bacteriol. 183:1058-1068); the ftsL (yIID) gene (Daniel, R. A., et al. 1998. Characterization of the essential cell division gene ftsL (yIID) of *Bacillus subtilis* and its role in the assembly of the division apparatus. Mol. Microbiol. 29:593-604); the ftsW gene (Ikeda, M., et al. 1989. Structural similarity among *Escherichia coli* FtsW and RodA proteins and *Bacillus subtilis* SpoVE protein, which function in cell division, cell elongation, and spore formation, respectively. J. Bacteriol. 171:6375-6378); the ftsX gene (Reizer, J., et al. 1998. A novel protein kinase that controls carbon catabolite repression in bacteria. Mol. Microbiol. 27:1157-1169); the ftsZ gene (Beall, B., and J. Lutkenhaus). FtsZ in *Bacillus subtilis* is required for vegetative septation and for asymmetric septation during sporulation. Genes and Dev. 5:447-45); the gcaD gene (Hove-Jensen, B. 1992. Identification of tms-26 as an allele of the gcaD gene, which encodes N-acetylglucosamine 1-phosphate uridyltransferase in *Bacillus subtilis*. J. Bacteriol. 174:6852-6856); the gid (ylyC) gene (Kunst, F., et al. 1997. The complete genome sequence of the gram-positive bacterium *Bacillus subtilis*. Nature. 390:237-238); the gidA gene (Ogasawara, N., and H. Yoshikawa. 1992. Genes and their organization in the replication origin region of the bacterial chromosome. Mol. Microbiol. 6:629-634; Nakayashiki, T., and H. Inokuchi. 1998. Novel temperature-sensitive mutants of *Escherichia coli* that are unable to grow in the absence of wild-type tRNA6Leu. J. Bacteriol. 180:2931-2935); the gidB gene (Ogasawara, N., and H. Yoshikawa. 1992. Genes and their organization in the replication origin region of the bacterial chromosome. Mol. Microbiol. 6:629-634; Nakayashiki, T., and H. Inokuchi. 1998. Novel temperature-sensitive mutants of *Escherichia coli* that are unable to grow in the absence of wild-type tRNA6Leu. J. Bacteriol. 180:2931-2935); the lytC (cwlB) gene (Blackman, S. A., et al. 1998. The role of autolysins during vegetative growth of *Bacillus subtilis* 168. Microbiology. 144:73-82); the lytD (cwlG) gene (Blackman, S. A., et al. 1998. The role of autolysins during vegetative growth of *Bacillus subtilis* 168. Microbiology. 144:73-82); the lytE (cwlF) gene (Ishikawa, S., et al. 1998. Regulation of a new cell wall hydrolase gene, cwlF, which affects cell separation in *Bacillus subtilis*. J. Bacteriol. 180:23549-2555); the lytF (cwlE, yhdD) gene (Ohnishi, R., et al. 1999. Peptidoglycan hydrolase lytF plays a role in cell separation with CwlF during vegetative growth of *Bacillus subtilis*. J. Bacteriol. 181:3178-1384); the maf gene (Butler, Y. X., et al. 1993. Amplification of the *Bacillus subtilis* maf gene results in arrested septum formation. J. Bacteriol. 175:3139-3145); the minC gene (Varley, A. W., and G. C. Stewart. 1992. The divIVB region of the *Bacillus subtilis* chromosome encodes homologs of *Escherichia coli* septum placement (minCD) and cell shape (mreBCD) determinants. J. Bacteriol. 174:6729-6742; Barak, I., et al. 1998. MinCD proteins control the septation process during sporulation of *Bacillus subtilis*. J. Bacteriol. 180:5327-5333); the minD gene (Varley, A. W., and G. C. Stewart. 1992. The divIVB region of the *Bacillus subtilis* chromosome encodes homologs of *Escherichia coli* septum placement (minCD) and cell shape (mreBCD) determinants. J. Bacteriol. 174:6729-6742; Barak, I., et al. 1998. MinCD proteins control the septation process during sporulation of *Bacillus subtilis*. J. Bacteriol. 180:5327-5333); the pbpB gene (Daniel, R. A., and J. Errington. 2000. Intrinsic instability of the essential cell division protein FtsL of *Bacillus subtilis* and a role for DivIB protinein FtsL turnover. Mol. Microbiol. 35:278-289); the ponA gene (Pederson, L. B., et al. Septal localization of penicillin-binding protein 1 in *Bacillus subtilis*. J. Bacteriol. 181:3201-3211); the prfA gene (Popham, D. L., and P. Setlow. 1995. Cloning, nucleotide sequence, and mutagenesis of the *Bacillus subtilis* ponA operon, which codes for penicillin-binding protein (PBP) 1 and a PBP-related factor. J. Bacteriol. 177:326-335); the rodB gene (Burdett, I. D. 1979. Electron microscope study of the rod-to-coccus shape change in a temperature-sensitive rod-mutant of *Bacillus subtilis*. J. Bacteriol. 137:1395-1405; Burdett, I. D. 1980. Quantitative studies of rod—coccus morphogenesis in a temperature-sensitive rod-mutant of *Bacillus subtilis*. J. Gen. Microbil. 121:93-103); the secA gene (Sadaie, Y., et al. 1991. Sequencing reveals similarity of the wild-type div+ gene of *Bacillus subtilis* to the *Escherichia coli* secA gene. Gene. 98:101-105); the smc gene (Britton, R. A., et al. 1998. Characterization of a prokaryotic SMC protein involved in chromosome partitioning. Genes Dev. 12:1254-1259; Moriya, S., et al. 1998. A *Bacillus subtilis* gene-encoding protein homologous to eukaryotic SMC motor protein is necessary for chromosome partition. Mol. Microbiol. 29:179-187; Hirano, M., and T. Hirano. 1998. ATP-dependent aggregation of single-stranded DNA by a bacterial SMC homodimer. EMBO J. 17:7139-7148); the spoIIE gene (Feucht, a., et al. 1996. Bifunctional protein required for asymmetric cell division and cell-specific transcription in *Bacillus subtilis*. Genes Dev. 10:794-803; Khvorova, A., et al. 1998. The spoIIE locus is involved in the Spo0A-dependent switch in the localization of FtsZ rings in *Bacillus subtilis*. J. Bacteriol. 180:1256-1260; Lucet, I., et al. 2000. Direct interaction between the cell division protein FtsZ and the cell differentiation protein SpoIIE. EMBO J. 19:1467-1475); the spo0A gene (Ireton, K., et al. 1994. spo0J is required for normal chromosome segregation as well as the initiation of sporulation in *Bacillus subtilis*. J. Bacteriol. 176:5320-5329); the spoIVF gene (Lee, S., and C. W. Price. 1993. The minCD locus of *Bacillus subtilis* lacks the minE determinant that provides topological specificity to cell division. Mol. Microbiol. 7:601-610); the spo0J gene (Lin, D. C., et el. 1997. Bipolar localization of a chromosome partition protein in *Bacillus subtilis*. Proc. Natl. Acad. Sci. 94:4721-4726; Yamaichi, Y., and H. Niki. 2000. Active segregation by the *Bacillus subtilis* partitioning system in *Escherichia coli*. Proc. Natl. Acad. Sci. 97:14656-14661); the smc gene (Moriya, S., et al. 1998. A *Bacillus subtilis* gene-encoding protein homologous to eukaryotic SMC motor protein is necessary for chromosome partition. Mol. Microbiol. 29:179-187); the ripX gene (ciochetti, S. A., et al. 1999. The ripX locus of *Bacillus subtilis* encodes a site-specific recombinase involved in proper chromosome partitioning. J. Bacteriol. 181:6053-6062); and the spoIIIE gene (Wu, L. J., and J. Errington. 1994. *Bacillus subtilis* spoIIIE protein required for DNA segregation during asymmetric cell division. Science. 264:572-575); the gene corresponding to the *B. subtilis* mutant alleal ts-31 (Errington, J., and A. D. Richard. Cell division during growth and sporulation. In A. L. Sonenshein, J. A. Hoch., and R. Losick (eds.). *Bacillus subtilis* and its closest relatives: from genes to cells. American Society for Microbiology, Washington D.C.); the gene corresponding to the *B. subtilis* mutant alleal ts-526 (Id.); the yacA gene (Kunst, F., et al. 1997. The complete genome sequence of the gram-positive bacterium *Bacillus subtilis*. Nature. 390:237-238); the yfhF gene (Kunst, F., et al. 1997. The complete genome sequence of the gram-positive bacterium *Bacillus subtilis*: Nature. 390:237-238); the yfhK gene (Kunst, F., et al. 1997. The complete genome sequence of the gram-positive bacterium *Bacillus subtilis*. Nature. 390:237-238); the yjoB gene (Kunst, F., et al. 1997. The complete genome sequence of the gram-positive bacterium *Bacillus subtilis*. Nature. 390: 237-238); and the ywbG gene (Smith, T. J., et al. 2000. Autolysins of *Bacillus subtilis*: multiple enzymes with multiple functions. Microbiology. 146:249-262).

II.A.3. *Saccharomyes cervisiae* Genes

Exemplary genes and gene products from *S. cerevisiae* the expression and/or sequence of which can be manipulated so as to stimulate minicell production in any organism, as can homologs thereof from any species, include without limitation, the trf gene product family (TRF1, TRF2, TRF3, TRF4, and TRF5) from *Saccharomyces cerevisiae* (Sadoff, B. U., et al. 1995. Isolation of mutants of *Saccharomyces cerevisiae* requiring DNA topoisomerase I. Genetics. 141:465-479; Castano, I. B., et al. 1996. A novel family of TRF (DNA topoisomerase I-related function) genes required for proper nuclear segregation. Nucleic Acids Res. 2404-2410); the 1BD1 gene product from *Saccharomyces cerevisiae* (Lee, J., et al. 1999. Ibd1p, a possible spindle pole body associated protein, regulates nuclear division and bud separation in *Saccharomyces cerevisiae*. Biochim. Biophys. Acta. 1449:239-253); the plo1 gene product from *Saccharomyces cerevisiae* (Cullen, C. F., et al. 2000. A new genetic method for isolating functionally interacting genes: high plo1(+)-dependent mutants and their suppressors define genes in mitotic and septation pathways in fission yeast. Genetics. 155:1541-1534); the cdc7 locus product(s) from *Saccharomyces cerevisiae* or homologues of this found in other members of the Eubacteria, Eucarya or Archaea may be employed to produce minicells (Biggins, s. et al. 2001. Genes involved in sister chromatid separation and segregation in the budding yeast *Saccharomyces cerevisiae*. Genetics. 159:453-470); the cdc15 locus product(s) from *Saccharomyces cerevisiae* or homologues of this found in other members of the Eubacteria, Eucarya or Archaea may be employed to produce minicells (Mah, A. S., et al. 2001. Protein kinase Cdc15 activates the Dbf2-Mob1 kinase complex. Proc. Natl. Acad. Sci. 98:7325-7330); the cdc11 locus product(s) from *Saccharomyces cerevisiae* or homologues of this found in other members of the Eubacteria, Eucarya or Archaea may be employed to produce minicells (Fares, H., et al. 1996. Identification of a developmentally regulated septin and involvement of the septins in spore formation in *Saccharomyces cerevisiae*. J. Cell Biol. 132:399-411); the spg1 locus product(s) from *Saccharomyces cerevisiae* or homologues of this found in other members of the Eubacteria, Eucarya or Archaea may be employed to produce minicells (Cullen, C. F., et al. 2000. A new genetic method for isolating functionally interacting genes: high plo1 (+)-dependent mutants and their suppressors define genes in mitotic and septation pathways in fission yeast. Genetics. 155:1521-1534); the sid2 locus product(s) from *Saccharomyces cerevisiae* or homologues of this found in other members of the Eubacteria, Eucarya or Archaea may be employed to produce minicells (Cullen, C. F., et al. 2000. A new genetic method for isolating functionally interacting genes: high plo1 (+)-dependent mutants and their suppressors define genes in mitotic and septation pathways in fission yeast. Genetics. 155:1521-1534); the cdc8 gene product from *Saccharomyces cerevisiae* (Cullen, C. F., et al. 2000. A new genetic method for isolating functionally interacting genes: high plo1(+)-dependent mutants and their suppressors define genes in mitotic and septation pathways in fission yeast. Genetics. 155:1521-1534); the rho1 gene product from *Saccharomyces cerevisiae* (Cullen, C. F., et al. 2000. A new genetic method for isolating functionally interacting genes: high plo1(+)-dependent mutants and their suppressors define genes in mitotic and septation pathways in fission yeast. Genetics. 155:1521-1534); the mpd1 gene product from *Saccharomyces cerevisiae* (Cullen, C. F., et al. 2000. A new genetic method for isolating functionally interacting genes: high plo1 (+)-dependent mutants and their suppressors define genes in mitotic and septation pathways in fission yeast. Genetics. 155:1521-1534); the mpd2 gene product from *Saccharomyces cerevisiae* (Cullen, C. F., et al. 2000. A new genetic method for isolating functionally interacting genes: high plo1 (+)-dependent mutants and their suppressors define genes in mitotic and septation pathways in fission yeast. Genetics. 155:1521-1534); the smy2 gene product from *Saccharomyces cerevisiae* (Cullen, C. F., et al. 2000. A new genetic method for isolating functionally interacting genes: high plo1 (+)-dependent mutants and their suppressors define genes in mitotic and septation pathways in fission yeast. Genetics. 155:1521-1534); the cdc16 gene product from *Saccharomyces cerevisiae* (Heichman, K. A., and J. M. Roberts. 1996. The yeast CDC16 and CDC27 genes restrict DNA replication to once per cell cycle. Cell. 85:39-48); the dma1 gene product from *Saccharomyces cerevisiae* (Murone, M., and V. Simanis. 1996. The fission yeast dma1 gene is a component of the spindle assembly checkpoint, required to prevent septum formation and premature exit from mitosis if spindle function is compromised. EMBO J. 15:6605-6616); the plo1 gene product from *Saccharomyces cerevisiae* (Cullen, C. F., et al. 2000. A new genetic method for isolating functionally interacting genes: high plo1(+)-dependent mutants and their suppressors define genes in mitotic and septation pathways in fission yeast. Genetics. 155:1521-1534); the byr3 gene product from *Saccharomyces cerevisiae* (Cullen, C. F., et al. 2000. A new genetic method for isolating functionally interacting genes: high plo1(+)-dependent mutants and their suppressors define genes in mitotic and septation pathways in fission yeast. Genetics. 155:1521-1534); the byr4 gene product from *Saccharomyces cerevisiae* (Cullen, C. F., et al. 2000. A new genetic method for isolating functionally interacting genes: high plo1(+)-dependent mutants and their suppressors define genes in mitotic and septation pathways in fission yeast. Genetics. 155:1521-1534); the pds1 gene product from *Saccharomyces cerevisiae* (Yamamoto, A., et al. 1996. Pds1p, an inhibitor of anaphase in budding yeast, plays a critical role in the APC and checkpoint pathway(s). J. Cell Biol. 133:99-110); the esp1 gene product from *Saccharomyces cerevisiae* (Rao, H., et al. 2001. Degradation of a cohesin subunit by the N-end rule pathway is essential for chromosome stability. Nature. 410:955-999); the ycs4 gene product from *Saccharomyces cerevisiae* (Biggins, S., et al. 2001. Genes involved in sister chromatid separation and segregation in the budding yeast *Saccharomyces cerevisiae*. Genetics. 159:453-470); the cse4 gene product from *Saccharomyces cerevisiae* (Stoler, S. et al. 1995. A mutation in CSE4, an essential gene encoding a novel chromatin-associated protein in yeast, causes chromosome nondisjunction and cell cycle arrest at mitosis. Genes Dev. 9:573-586); the ipl1 gene product from *Saccharomyces cerevisiae* (Biggins, S., and A. W. Murray. 2001. The budding yeast protein kinase Ipl1/Aurora allows the absence of tension to activate the spindle checkpoint. Genes Dev. 15:3118-3129); the smt3 gene product from *Saccharomyces cerevisiae* (Takahashi, Y., et al. 1999. Smt3, a SUMO-1 homolog, is conjugated to Cdc3, a component of septin rings at the mother-bud neck in budding yeast. Biochem. Biophys. Res. Commun. 259:582-587); the prp16 gene product from *Saccharomyces cerevisiae* (Hotz, H. R., and B. Schwer. 1998. Mutational analysis of the yeast DEAH-box splicing factor Prp16. Genetics. 149:807-815); the prp19 gene product from *Saccharomyces cerevisiae* (Chen, C. H., et al. 2001. Identification and characterization of two novel components of the Prp19p-associated complex, Ntc30p and Ntc20p. J. Biol. Chem. 276:488-494); the wss1 gene product from *Saccharomyces cerevisiae* (Biggins, S., et al. 2001. Genes involved in sister chromatid separation and segregation in the budding yeast *Saccharomyces cerevisiae*. Genetics. 159:453-470); the histone H4 gene product from *Saccharomyces cerevisiae* (Smith, M. M., et al. 1996. A novel histone H4 mutant defective in nuclear division and mitotic chromosome transmission. Mol. Cell Biol. 16:1017-1026); the histone H3 gene product from *Saccharomyces cerevisiae* (Smith, M. M., et al. 1996. A novel histone H4 mutant defective in nuclear division and mitotic chromosome transmission. Mol. Cell Biol. 16:1017-1026); the cse4 gene product from *Saccharomyces cerevisiae* (Stoler, S., et al. 1995. A mutation in CSE4, an essential gene encoding a novel chromatin-associated protein in yeast, causes chromosome nondisjunction and cell cycle arrest at mitosis. Genes Dev. 9:573-586); the spt4 gene product from *Saccharomyces cerevisiae* (Basrai, M. A., et al. 1996. Faithful chromosome transmission requires Spt4p, a putative regulator of chromatin structure in *Saccharomyces cerevisiae*. Mol. Cell Biol. 16:2838-2847); the spt5 gene product from *Saccharomyces cerevisiae* (Yamaguchi, Y., et al. 2001. SPT genes: key players in the regulation of transcription, chromatin structure and other cellular processes. J. Biochem. (Tokyo). 129:185-191); the spt6 gene product from *Saccharomyces cerevisiae* (Clark-Adams, C. D., and F. Winston. 1987. The SPT6 gene is essential for growth and is required for delta-mediated transcription in *Saccharomyces cerevisiae*. Mol. Cell Biol. 7:679-686); the ndc10 gene product from *Saccharomyces cerevisiae* (Chiang, P. W., et al. 1998. Isolation of murine SPT5 homologue: completion of the isolation and characterization of human and murine homologues of yeast chromatin structural protein complex SPT4, SPT5, and SPT6. Genomics. 47:426-428); the ctf13 gene product from *Saccharomyces cerevisiae* (Doheny et al., Identification of essential components of the S. cerevisiae kinetochore, Cell 73:761-774, 1993); the spo1 gene product from *Saccharomyces cerevisiae* (Tavormina et al. 1997. Differential requirements for DNA replication in the activation of mitotic checkpoints in *Saccharomyces cerevisiae*. Mol. Cell Biol. 17:3315-3322); the cwpl gene product from *Saccharomyces cerevisiae* (Tevzadze, G. G., et al. 2000. Spo1, a phospholipase B homolog, is required for spindle pole body duplication during meiosis in *Saccharomyces cerevisiae*. Chromosoma. 109:72-85); the dhp1 gene product from *Schizosaccharomyces pombe* (Shobuike, T., et al. 2001. The dhp1(+) gene, encoding a putative nuclear 5'→3' exoribonuclease, is required for proper chromosome segregation in fission yeast. Nucleic Acids Res. 29:1326-1333); the rat1 gene product from *Saccharomyces cerevisiae* (Shobuike, T., et al. 2001. The dhp1(+) gene, encoding a putative nuclear 5'→3' exoribonuclease, is required for proper chromosome segregation in fission yeast. Nucleic Acids Res. 29:1326-1333); the hsk1 gene product from *Saccharomyces cerevisiae* (Masai, H., et al. 1995. hsk1+, a *Schizosaccharomyces pombe* gene related to *Saccharomyces cerevisiae* CDC7, is required for chromosomal replication. EMBO J. 14:3094-3104); the dfp1 gene product from *Saccharomyces cerevisiae* (Takeda, T., et al. 1999. A fission yeast gene, him1(+)/dfp1(+), encoding a regulatory subunit for Hsk1 kinase, plays essential roles in S-phase initiation as well as in S-phase checkpoint control and recovery from DNA damage. Mol. Cell Biol. 19:5535-5547); the dbf4 gene product from *Saccharomyces cerevisiae* (Weinreich, M., and B. Stillman. 1999. Cdc7p-Dbf4p kinase binds to chromatin during S phase and is regulated by both the APC and the RAD53 checkpoint pathway. EMBO J. 18:5334-5346); the rad53 gene product from *Saccharomyces cerevisiae* (Sun, Z., et al. Spk1/Rad53 is regulated by Mec1-dependent protein phosphorylation in DNA replication and damage checkpoint pathways. Genes Dev. 10:395-406); the ibd1 gene product from *Saccharomyces cerevisiae* (Lee, J., et al. 1999. Ibd1p, a possible spindle pole body associated protein, regulates nuclear division and bud separation in *Saccharomyces cerevisiae*. Biochim. Biophys. Acta. 1449:239-253); and the hrp1 gene product from *Saccharomyces cerevisiae* (Henry, M., et al. 1996. Potential RNA binding proteins in *Saccharomyces cerevisiae* identified as suppressors of temperature-sensitive mutations in NPL3. Genetics. 142:103-115).

II.B. Gene Expression in Minicells
II.B.1. In General

In some aspects of the invention, it may be desirable to alter the expression of a gene and the production of the corresponding gene product. As is known in the art, and is used herein, a "gene product" may be a protein (polypeptide) or nucleic acid. Gene products that are proteins include without limitation enzymes, receptors, transcription factors, termination factors, expression factors, DNA-binding proteins, proteins that effect nucleic acid structure, or subunits of any of the preceding. Gene products that are nucleic acids include, but are not limited to, ribosomal RNAs (rRNAs), transfer RNAs (tRNAs), antisense RNAs, nucleases (including but not limited to catalytic RNAs, ribonucleases, and the like).

Depending on the function of a gene product, and on the type of application of the invention, it may be desirable to increase protein production, decrease protein production, increase protein nucleic acid production and/or increase nucleic acid production. Provided herein are non-limiting examples of genes and gene products that may be manipulated, individually or in combination, in order to modulate the expression of gene products to be included into minicells or parent strains from which minicells are derived. The expression elements so modulated may be chromosomal and/or episomal, and may be expressed constitutively or in a regulated fashion, i.e., repressible and/or inducible. Furthermore, gene products under the regulation may be either monocistronic or polycistronic with other genes or with themselves.

II.B.2. Protein Production

By way of non-limiting example, increased protein production may occur through increased gene dosage (increased copy number of a given gene under the control of the native or artificial promotor where this gene may be on a plasmid or in more than one copy on the chromosome), modification of the native regulatory elements, including, but not limited to the promotor or operator region(s) of DNA, or ribosomal binding sites on RNA, relevant repressors/silencers, relevant activators/enhancers, or relevant antisense nucleic acid or nucleic acid analog, cloning on a plasmid under the control of the native or artificial promotor, and increased or decreased production of native or artificial promotor regulatory element(s) controlling production of the gene or gene product By way of non-limiting example, decreased protein production may occur through modification of the native regulatory elements, including, but not limited to the promotor or operator region(s) of DNA, or ribosomal binding sites on RNA, relevant repressors/silencers, relevant activators/enhancers, or relevant antisense nucleic acid or nucleic acid analog, through cloning on a plasmid under the control of the native regulatory region containing mutations or an artificial promotor, either or both of which resulting in decreased protein production, and through increased or decreased production of native or artificial promotor regulatory element(s) controlling production of the gene or gene product.

As used herein with regards to proteins, "intramolecular activity" refers to the enzymatic function or structure-dependent function. By way of non-limiting example, alteration of intramolecular activity may be accomplished by mutation of the gene, in vivo or in vitro chemical modification of the protein, inhibitor molecules against the function of the protein, e.g. competitive, non-competitive, or uncompetitive enzymatic inhibitors, inhibitors that prevent protein-protein, protein-nucleic acid, or protein-lipid interactions, e.g. expression or introduction of dominant-negative or dominant-positive protein or other protein fragment(s), carbohydrate(s), fatty acid(s), lipid(s), and nucleic acid(s) that may act directly or allosterically upon the protein, and/or modification of protein, carbohydrate, fatty acid, lipid, or nucleic acid moieties that modify the gene or gene product to create the functional protein.

As used herein with regards to proteins, "intermolecular function" refers to the effects resulting from an intermolecular interaction between the protein or nucleic acid and another protein, carbohydrate, fatty acid, lipid, nucleic acid, or other molecule(s) in or on the cell or the action of a product or products resulting from such an interaction. By way of non-limiting example, intermolecular or intramolecular function may be the act or result of intermolecular phosphorylation, biotinylation, methylation, acylation, glycosylation, and/or other signaling event; this function may be the result of a protein-protein, protein-nucleic acid, or protein-lipid complex, and/or carrier function, e.g. the capacity to bind, either covalently or non-covalently small organic or inorganic molecules, protein(s), carbohydrate(s), fatty acid(s), lipid(s), and nucleic acid(s); this function may be to interact with the membrane to recruit other molecules to this compartment of the cell; this function may be to regulate the transcription and/or translation of the gene, other protein, or nucleic acid; and this function may be to stimulate the function of another process that is not yet described or understood.

II.B.3. Nucleic Acid Production

By way of non-limiting example, increased nucleic acid production may occur through increased gene dosage (increased copy number of a given gene under the control of the native or artificial promotor where this gene may be on a plasmid or in more than one copy on the chromosome), modification of the native regulatory elements, including, but not limited to the promotor or operator region(s) of DNA, or ribosomal binding sites on RNA, relevant repressors/silencers, relevant activators/enhancers, or relevant antisense nucleic acid or nucleic acid analog, cloning on a plasmid under the control of the native or artificial promotor, and increased or decreased production of native or artificial promotor regulatory element(s) controlling production of the gene or gene product.

By way of non-limiting example, decreased nucleic acid production may occur through modification of the native regulatory elements, including, but not limited to the promotor or operator region(s) of DNA, or ribosomal binding sites on RNA, relevant repressors/silencers, relevant activators/enhancers, or relevant antisense nucleic acid or nucleic acid analog, through cloning on a plasmid under the control of the native regulatory region containing mutations or an artificial promotor, either or both of which resulting in decreased protein production, and through increased or decreased production of native or artificial promotor regulatory element(s) controlling production of the gene or gene product.

As used herein with regards to nucleic acids, "intramolecular activity" refers to a structure-dependent function. By way of non-limiting example, alteration of intramolecular activity may be accomplished by mutation of the gene, in vivo or in vitro chemical modification of the nucleic acid, inhibitor molecules against the function of the nucleic acid, e.g. competitive, non-competitive, or uncompetitive enzymatic inhibitors, inhibitors that prevent protein-nucleic acid interactions, e.g. expression or introduction of dominant-negative or dominant-positive protein or other nucleic acid fragment(s), or other carbohydrate(s), fatty acid(s), and lipid(s) that may act directly or allosterically upon the nucleic acid or nucleic acid-protein complex, and/or modification of nucleic acid moieties that modify the gene or gene product to create the functional nucleic acid.

As used herein with regards to nucleic acids, "intermolecular function" refers to the effects resulting from an intermolecular interaction between the nucleic acid and another nucleic acid, protein, carbohydrate, fatty acid, lipid, or other molecule(s) in or on the cell or the action of a product or products resulting from such an interaction. By way of non-limiting example, intermolecular function may be the act or result of intermolecular or intramolecular phosphorylation, biotinylation, methylation, acylation, glycosylation, and/or other signaling event; this function may be the result of a protein-nucleic acid, and/or carrier function, e.g. the capacity to bind, either covalently or non-covalently small organic or inorganic molecules, protein(s), carbohydrate(s), fatty acid(s), lipid(s), and other nucleic acid(s); this function may be to interact with the membrane to recruit other molecules to this compartment of the cell; this function may be to regulate the transcription and/or translation of the gene, other nucleic acid, or protein; and this function may be to stimulate the function of another process that is not yet described or understood.

II.C. Genes and Gene Products for Regulation of Expression

As is known in the art, a variety of genes, gene products and expression elements may be manipulated, individually or in combination, in order to modulate the expression of genes and/or production gene products. These include, by way of non-limiting example, RNA polymerases, ribosomes (ribosomal proteins and ribosomal RNAs), transfer RNAs (tRNAs), amino transferases, regulatory elements and promoter regions, transportation of inducible and inhibitory compounds, catabolite repression, general deletions and modifications, cytoplasmic redox state, transcriptional terminators, mechanisms for ribosomal targeting, proteases, chaperones, export apparatus and membrane targeting, and mechanisms for increasing stability and solubility. Each of these is discussed in more detail in the following sections.

II.C.1. RNA Polymerases

Included in the design of the invention are techniques that increase the efficiency of gene expression and protein production in minicells. By way of non-limiting example, these techniques may include modification of an endogenous and/or introduction of an exogenous RNA polymerase. A rpo gene, or any other gene that encodes a RNA polymerase subunit product from *E. coli*, or homologs of this gene or its gene product found in other prokaryotes, eukaryotes, archaebacteria or organelles (mitochondria, chloroplasts, plastids and the like) may be employed to increase the efficiency of gene expression and protein production in parent cells prior to minicell formation and/or in segregated minicells.

The production or activity of a desired gene product may be increased by increasing the level and/or activity of an RNA polymerase that transcribes the gene product's cognate gene. The production or activity of a desired protein gene product may be increased by decreasing the level and/or activity of an RNA polymerase that transcribes a gene product that inhibits the production or function of the desired gene product.

As one example, manipulation of the rpoA (phs, sez) gene or gene product from *E. coli*, or homologs of this gene or gene product found in other members of the Prokaryotes, Eukaryotes, Archaebacteria and/or organelles (e.g., mitochondria, chloroplasts, plastids and the like) may be employed to increase the efficiency of gene expression and protein production in parent cells prior to minicell formation and/or in segregated minicells. In addition to rpoA, *E. coli.* genes that encode RNA polymerase subunits include rpoB (ftsR, groN, nitB, rif, ron, stl, sty, tabD, sdgB, mbrD), rpoC (tabD), rpoD (alt), rpoE, rpoH (fam, hin, htpR), rpoN (glnF, ntrA), rpoS (abrD, dpeB, katF, nur), and rpoZ (spoS). See Berlyn et al., "Linkage Map of *Escherichia coli* K-12, Edition 9," Chapter 109 in: *Escherichia coli and Salmonella typhimurium: Cellular and Molecular Biology,* 2nd Ed., Neidhardt, Frederick C., Editor in Chief, American Society for Microbiology, Washington, D.C., 1996, Volume 2, pages 1715-1902, and references cited therein; and Sanderson et al., "Linkage Map of *Salmonella typhimurium*, Edition VIII" Chapter 110 in: *Escherichia coli and Salmonella typhimurium*: Cellular and Molecular Biology, 2nd Ed., Neidhardt, Frederick C., Editor in Chief, American Society for Microbiology, Washington, D.C., 1996, Volume 2, pages 1903-1999, and references cited therein.

Production of a desired gene product may be preferentially or selectively enhanced by the introduction of an exogenous RNA polymerase that specifically recognizes expression sequences that are operably linked to the corresponding gene. By way of non-limiting example, the use of a T7 RNA polymerase to selectively express genes present on expression elements that segregate into minicells is described herein.

II.C.2. Ribosomes

Included in the design of the invention are techniques that increase the efficiency of gene expression and protein production in minicells. By way of non-limiting example, these techniques may include modification of endogenous, and/or addition of exogenous, ribosomes or ribosomal subunits. The techniques may be employed to increase the efficiency of gene expression and protein production in parent cells prior to minicell formation and/or in segregated minicells.

As is known in the art, a ribosome includes both proteins (polypeptides) and RNA (rRNA). Thus, in the case of a gene that encodes a component of a ribosome, the gene product may be a protein or an RNA. For a review, see Noller et al., "Ribosomes," Chapter 13 in: *Escherichia coli and Salmonella typhimurium: Cellular and Molecular Biology,* 2nd Ed., Neidhardt, Frederick C., Editor in Chief, American Society for Microbiology, Washington, D.C., 1996, Volume 1, pages 167-186, and references cited therein. For the sake of convenience, both ribosomal proteins and rRNAs are encompassed by the term "ribosomal subunits."

The production or activity of a desired protein gene product may be increased by increasing the level and/or activity of a ribosomal subunit that causes or enhances the translation of the desired protein. The production or activity of a desired protein gene product may be increased by decreasing the level and/or activity of a ribosomal subunit that causes or enhances translation of a protein that has a negative impact on the production or activity of the desired protein.

Exemplary ribosomal genes and gene products that may be manipulated include without limitation the *E. coli* genes rimB, rimC, rimD, rimE, rimF (res), rimG, rimH, rimI, rimJ (tcp), rimK, rimL; rplA, rplB, rplC, rplD, rplE, rplF, rplI, rplJ, rplK, rplL, rplM, rplN, rplO, rplP, rplQ, rplR, rplS, rplT, rplU, rplV, rplW, rplX, rplY; rpsA, rpsB, rpsC, rpsE (eps, spc, spcA), rpsF (sdgH), rpsG, rpsH, rpsI, rpsJ (nusE), rpsK, rpsL (strA), rpsM, rpsN, rpsO, rpsP, rpsQ, rpsR, rpsS, rpsT, rpsU, rpsV; rrfA, rrfB, rrfC, rrfD, rrfE, rrfF (rrfDbeta, rrvD), rrfG, rrfH; rrlA, rrlB, rrlC, rrlD, rrlE, rrlG, rrlH; rrnA, rrnB (csqE, rrnB1), rrnC (cqsB), rrnD (cqsD), rrnE (rrnD1), rrnG, rrnH; rrsA, rrsB, rrsC, rrsD, rrsE, rrsG, rrsH, and their cognate gene products.

Homologs of ribosomal genes or gene products found in other members of the Prokaryotes, Eukaryotes, Archaebacteria and organelles (including but not limited to mitochondria, chloroplasts, plastids, and the like) may be employed to increase the efficiency of gene expression and protein production in parent cells prior to minicell formation and/or segregated minicells. See, for example, Barkan, A. and M. Goldschmidt-Clermont, Participation of nuclear genes in chloroplast gene expression, (2000) *Biochimie* 82:559-572; Willhoeft, U., H. Buβ, and E. Tannich, Analysis of cDNA Expressed sequence tags from *Entamoeba histolytica*: Identification of two highly abundant polyadenylated transcripts with no overt open reading frames, (March 1999) *Protist* 150:61-70; Emelyanov, V., Evolutionary relationship of Rickettsiae and mitochondria (February 2001) *FEBS Letters* 501:11-18; and Gray, M., G. Burger and B. Lang, Mitochondrial Evolution (March 1999) *Science* 283:1476-1481. Ribosomal RNA sequences from a multitude of organisms and organelles are available through the Ribosomal Database Project (Maidak et al., A new version of the RDP (Ribosomal Database Project) (1999) *Nucleic Acids Research* 27:171-173). An index of ribosomal proteins classified by families on the basis of sequence similarities is available on-line at http://www.expasy.ch/cgi-bin/lists?ribosomp.txt; see also (Ramakrishnan et al., Ribosomal protein structures: insights into the architecture, machinery and evolution of the ribosome, *TIBS* 23:208-212, 1998.

II.C.3. Transfer RNAs (tRNAs)

Included in the design of the invention are techniques that increase the efficiency of gene expression and protein production in minicells. By way of non-limiting example, these techniques may include utilization and/or modification of endogenous and/or exogenous transfer RNAs (tRNAs). Manipulation of the tRNA genes or gene products from *E. coli*, or homologs of tRNA genes or gene products found in other members of the Prokaryotes, Eukaryotes, Archaebacteria and organelles (including but not limited to mitochondria, chloroplasts, plastids, and the like) may be employed to increase the efficiency of gene expression and protein production in parent cells prior to minicell formation and/or in segregated minicells.

Exemplary *E. coli* tRNA genes include, but are not limited to, the alaT (talA) gene, the alaU (talD) gene, the alaV gene, the alaW (alaWa) gene, the alaX (alaWβ) gene, the argQ (alaVd) gene, the argU (dnaY, pin) gene, the alaU (talD) gene, the argV (argV2) gene, the argW gene, the argX gene, the argY (argVβ) gene, the argZ (argVa) gene, the asnT gene, the asnU gene, the asnV gene, the aspT gene, the aspU gene, the cysT gene, the glnU (supB) gene, the glnV (supE) gene, the glnW (supB) gene, the gltT (tgtB) gene, the gltU (tgtC) gene, the gltV (tgtE) gene, the gltW gene, the glyT (sumA) gene, the glyU (sufD, sumA, sumB, supT) gene, the glyV (ins, mutA) gene, the glyW (ins, mutC) gene, the glyX gene, the glyY gene, the hisR (hisT) gene, the ileT gene, the ileU gene, the ileV gene, the ileX gene, the leuP (leuVβ) gene, the leuQ (leuVd) gene, the leuQ (leuVd) gene, the leuT gene, the leuU gene, the leuV (leuVa) gene, the leuW (feeB) gene, the leuX (supP) gene, the leuZ gene, the lysT gene, the lysV (supN) gene, the lysW gene, the metT (metTa) gene, the metU (metTβ) gene, the metV (metZβ) gene, the metW gene, the metY gene, the pheU (pheR, pheW) gene, the pheV gene, the proK (proV) gene, the proL (proW) gene, the proM (proU) gene, the serT (divE) gene, the serU (ftsM, supD, supH) gene, the serV (supD) gene, the serW gene, the serX (serW) gene, the thrT gene, the thrU gene, the thrV gene, the thrW gene, the trpT (sup U) gene, the tyrT (supC) gene, the tyrU (supM) gene, the atyrV (tyrT, tyrTβ) gene, the valT gene, the valU (valUa) gene, the valV (val) gene, the valW (val) gene, the valX gene, and the valX gene (Komine et al., Genomic Organization and Physical Mapping of the Transfer RNA Genes in *Escherichia coli* K12. J. Mol. Biol. 212:579-598, 1990; Berlyn et al., "Linkage Map of *Escherichia coli* K-12, Edition 9," Chapter 109 in: *Escherichia Coli and Salmonella Typhimurium: Cellular and Molecular Biology*, 2$^{nd}$ Ed., Neidhardt, Frederick C., Editor in Chief, American Society for Microbiology, Washington, D.C., 1996, Volume 2, pages 1715-1902, and references cited therein; Sanderson et al., "Linkage Map of *Salmonella typhimurium*, Edition VIII" Chapter 110, Id., pages 1903-1999, and references cited therein; and Hershey, "Protein Synthesis," Chapter 40 in: *Escherichia Coli and Salmonella Typhimurium: Cellular and Molecular Biology*, Neidhardt, Frederick C., Editor in Chief, American Society for Microbiology, Washington, D.C., 1987, Volume 2, pages 613-647, and references cited therein).

Also included in the modification of transfer RNA molecules are the transfer RNA processing enzymes. Exemplary *E. coli* genes encoding tRNA processing enzymes include, but are not limited to the rnd gene (Blouin R T, Zaniewski R, Deutscher M P. Ribonuclease D is not essential for the normal growth of *Escherichia coli* or bacteriophage T4 or for the biosynthesis of a T4 suppressor tRNA, J Biol Chem. 258: 1423-1426, 1983) and the rnpAB genes (Kirsebom L A, Baer M F, Altman S., Differential effects of mutations in the protein and RNA moieties of RNase P on the efficiency of suppression by various tRNA suppressors, J Mol Biol. 204:879-888, 1988).

Also included in the modification of transfer RNA molecules are modifications in endogenous tmRNAs and/or the introduction of exogenous tmRNAs to minicells and/or their parent cells. The tmRNA (a.k.a. 10S RNA) molecules have properties of tRNAs and mRNAs combined in a single molecule. Examples of tmRNAs are described in Zwieb et al. (Survey and Summary: Comparative Sequence Analysis of tmRNA, Nucl. Acids Res. 27:21063-2071, 1999).

II.C.4. Aminoacyl Synthetases

Included in the design of the invention are techniques that increase the efficiency of gene expression and protein production in minicells. By way of non-limiting example, these techniques may include utilization and/or modification of endogenous and/or exogenous aminoacyl synthetases and proteins that effect their production and/or activity. Aminoacyl synthetases are involved in "charging" a tRNA molecule, i.e., attaching a tRNA to its cognate amino acid. (Martinis et al., Aminoacyl-tRNA Synthetases: General Features and Relationships. Chapter 58 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 1, pages 887-901) and references cited therein; (Grunberg-Manago, Regulation of the Expression of Aminoacyl-tRNA Synthetases and Translation. Chapter 91 in: *Escherichia coli and Salmonella typhimurium*: Cellular and Molecular Biology, 2nd Ed., Neidhardt, Frederick C., Editor in Chief, American Society for Microbiology, Washington, D.C., 1996, Volume 1, pages 1432-1457), and references cited therein; and (Hershey, "Protein Synthesis," Chapter 40 in: *Escherichia Coli and Salmonella Typhimurium: Cellular and Molecular Biology*, Neidhardt, Frederick C., Editor in Chief, American Society for Microbiology, Washington, D.C., 1987, Volume 1, pages 613-647), and references cited therein.

By way of non-limiting example, manipulation of the aat gene or gene product from *E. coli*, or homologs of this gene or gene product found in other members of the Prokaryotes, Eukaryotes, Archaebacteria and/or organelles (e.g., mitochondria, chloroplasts, plastids and the like) may be employed to increase the efficiency of gene expression and protein production in parent cells prior to minicell formation and/or in segregated minicells (Bochner, B. R., and Savageau, M. A. 1979. Inhibition of growth by imidazol(on)e propionic acid: evidence in vivo for coordination of histidine catabolism with the catabolism of other amino acids. Mol. Gen. Genet. 168(1):87-95).

In addition to aat, other exemplary *E. coli* genes encoding aminoacyl synthestases include alaS (act, ala-act, lovB) (Buckel et al., Suppression of temperature-sensitive aminoacyl-tRNA synthetase mutations by ribosomal mutations: a possible mechanism. Mol. Gen. Genet. 149:51-61, 1976); argS (lovB) (Eriani et al., Isolation and characterization of the gene coding for *Escherichia coli* arginyl-tRNA synthetase. Nucleic Acids Res. 17:5725-36, 1989); asnS (lcs, tss) (Yamamoto et al., Identification of a temperature-sensitive asparaginyl-transfer ribonucleic acid synthetase mutant of *Escherichia coli*. J. Bacteriol. 132:127-31, 1977); aspS (tls) (Eriani et al., Aspartyl-tRNA synthetase from *Escherichia coli*: cloning and characterisation of the gene, homologies of its translated amino acid sequence with asparaginyl- and lysl-tRNA syntheases. Nucleic Acids Res. 18:7109-18, 1990); cysS (Eriani et al., Cysteinyl-tRNA synthetase: determination of the last *E. coli* aminoacyl-tRNA synthetase primary structure. Nucleic Acids Res. 19:265-9, 1991); glnS (Yamao et al., *Escherichia coli* glutaminyl-tRNA synthetase. I. Isolation and DNA sequence of the glnS gene. J. Biol. Chem. 257:11639-43, 1982); gltE (Lapointe et al., Thermosensitive mutants of *Escherichia coli* K-12 altered in the catalytic Subunit and in a Regulatory factor of the glutamy-transfer ribonucleic acid synthetase. J. Bacteriol. 122:352-8, 1975); gltM (Lapointe et al., Thermosensitive mutants of *Escherichia coli* K-12 altered in the catalytic Subunit and in a Regulatory factor of the glutamy-transfer ribonucleic acid synthetase. J. Bacteriol. 122:352-8, 1975); gltX (Lapointe et al., Thermosensitive mutants of *Escherichia coli* K-12 altered in the catalytic Subunit and in a Regulatory factor of the glutamy-transfer ribonucleic acid synthetase. J. Bacteriol. 122:352-8, 1975); glyQ (glySa) (Webster et al., Primary structures of both subunits of *Escherichia coli* glycyl-tRNA synthetase, J. Biol. Chem. 252:10637-41, 1983); glyS (act, gly, glySB) (Id.); hisS (Parker et al., Mapping hisS, the structural gene for histidyl-transfer ribonucleic acid synthetase, in *Escherichia coli*. J. Bacteriol. 138:264:7, 1979); ileS (Singer et al., Synthesis of the isoleucyl- and valyl-tRNA synthetases and the isoleucine-valine biosythetic enzymes in a threonine deaminase regulatory mutant of *Escherichia coli* K-12. J. Mol. Biol. 175:39-55, 1984); leuS (Morgan et al., Regulation of biosynthesis of aminoacyl-transfer RNA synthestases and of transfer-RNA in *Escherichia coli*. Arch. Biol. Med. Exp. (Santiago.) 12:415-26, 1979); lysS (herC, asaD) (Clark et al., Roles of the two lysyl-tRNA synthetases of *Escherichia coli*: analysis of nucleotide sequences and mutant behavior. J. Bacteriol. 172: 3237-43, 1990); lysU (Clark et al., Roles of the two lysyl-tRNA synthetases of *Escherichia coli*: analysis of nucleotide sequences and mutant behavior, J. Bacteriol. 172:3237-43, 1990); metG (Dardel et al., Molecular cloning and primary structure of the *Escherichia coli* methionyl-tRNA synthetase gene. J. Bacteriol. 160:1115-22, 1984); pheS (phe-act) (Elseviers et al., Molecular cloning and regulation of expression of the genes for initiation factor 3 and two aminoacyl-tRNA synthetases, J. Bacteriol. 152:357-62, 1982); pheT (Comer et al., Genes for the alpha and beta subunits of the phenylalanyl-transfer ribonucleic acid synthetase of *Escherichia coli*. J. Bacteriol. 127:923-33, 1976); proS (drp) (Bohman et al., A temperature-sensitive mutant in prolinyl-tRNA ligase of *Escherichia coli* K-12 Mo. Gen. Genet. 177:603-5, 1980); serS (Hartlein et al., Cloning and characterization of the gene for *Escherichia coli* seryl-tRNA synthetase. Nucleic Acids Res. 15:1005-17, 1987); thrS (Frohler et al., Genetic analysis of mutations causing borrelidin resistance by overproduction of threonyl-transfer ribonucleic acid synthetase. J. Bacteriol. 143:1135-41, 1980); trpS (Hall et al., Cloning and characterization of the gene for *Escherichia coli* tryptophanyl-transfer ribonucleic acid synthetase. J. Bacteriol. 148: 941-9, 1981); tyrS (Buonocore et al., Properties of tyrosyl transfer ribonucleic acid synthetase from two tyrS mutants of *Escherichia coli* K-12. J. Biol. Chem. 247:4843-9, 1972); and valS (Baer et al., Regulation of the biosynthesis of aminoacyl-transfer ribonucleic acid synthetases and of transfer ribonucleic acid in *Escherichia coli*. V. Mutants with increased levels of valyl-transfer ribonucleic acid synthetase. J. Bacteriol. 139:165-75, 1979).

II.C.5. Regulatory Elements and Promoter Regions

Included in the design of the invention are techniques that increase the efficiency of gene expression and protein production in minicells. By way of non-limiting example, these techniques may include utilization and/or modification of regulatory elements and promoter regions. Such manipulations may result in increased or decreased production, and/or changes in the intramolecular and intermolecular functions, of a protein in a segregated minicell or its parent cell prior to minicell formation; in the latter instance, the protein may be one that is desirably retained in segregated minicells.

The production or activity of a desired gene product may be increased by increasing the level and/or activity of a promoter or other regulatory region that acts to stimulate or enhance the production of the desired gene product. The production or activity of a desired gene product may be increased by decreasing the level and/or activity of a promoter or other regulatory region that acts to stimulate or enhance the production of a gene product that acts to reduce or eliminate the level and/or activity of the desired gene product.

II.C.5.a. *Escherichia coli*

Regulatory elements, promoters and other expression elements and expression factors from *E. coli* include but are not limited to acrR (Ma, D., et al. 1996. The local repressor AcrR plays a modulating role in the regulation of acrAB genes of *Escherichia coli* by global stress signals. Mol. Microbiol. 19:101-112); ampD (Lindquist, S., et al. 1989. Signalling proteins in enterobacterial AmpC beta-lactamase regulation. Mol. Microbiol. 3:1091-1102; Holtje, J. V., et al. 1994. The negative regulator of beta-lactamase induction AmpD is a N-acetyl-anhydromuramyl-L-alanine amidase. FEMS Microbiol. Lett. 122:159-164); appR (Diaz-Guerra, L., et al. 1989. appR gene product activates transcription of microcin C7 plasmid genes. J. Bacteriol. 171:2906-2908; Touati, E., et al. 1991. Are appR and katF the same *Escherichia coli* gene encoding a new sigma transcription initiation factor? Res. Microbiol. 142:29-36); appY (Atlung, T., et al. 1989. Isolation, characterization, and nucleotide sequence of appY, a regulatory gene for growth-phase-dependent gene expression in *Escherichia coli*. J. Bacteriol. 171:1683-1691); araC (Casadaban, M. J., et al. 1976. Regulation of the regulatory gene for the arabinose pathway, araC. J. Mol. Biol. 104:557-566); arcA (Iuchi, S., and E. C. Lin. 1988. arcA (dye), a global regulatory gene in *Escherichia coli* mediating repression of enzymes in aerobic pathways. Proc. Natl. Acad. Sci. 85:1888-1892; Iuchi, S., et al. 1989. Differentiation of arcA, arcB, and cpxA mutant phenotypes of *Escherichia coli* by sex pilus formation and enzyme regulation. J. Bacteriol. 171:2889-2893); argR (xerA, Rarg) (Kelln, R. A., and V. L. Zak. 1978. Arginine regulon control in a *Salmonella typhimurium—Escherichia coli* hybrid merodiploid. Mol. Gen Genet. 161:333-335; Vogel, R. H., et al. 1978. Evidence for translational repression of arginine biosynthetic enzymes in *Escherichia coli*: altered regulation in a streptomycin-resistant mutant. Mol. Gen. Genet. 162:157-162); ascG (Hall, B. G., and L. Xu. Nucleotide sequence, function, activation, and evolution of the cryptic asc operon of *Escherichia coli* K12. Mol. Biol. Evol. 9:688-706); aslB (Bennik, M. H., et al. 2000. Defining a rob regulon in *Escherichia coli* by using transposon mutagenesis. J. Bacteriol. 182:3794-3801); asnC (Kolling, R., and H. Lother. 1985. AsnC: an autogenously regulated activator of asparagine synthetase A transcription in *Escherichia coli*. J. Bacteriol. 164:310-315); atoC (Jenkins, L. S., and W. D. Nunn. 1987. Regulation of the ato operon by the atoC gene in *Escherichia coli*. J. Bacteriol. 169:2096-2102); baeR (Nagasawa, S., et al. 1993. Novel members of the two-component signal transduction genes in *Escherichia coli*. J. Biochem. (Tokyo). 114:350-357); baeS (Id.Id.); barA (Nagasawa, S., et al. 1992. A novel sensor-regulator protein that belongs to the homologous family of signal-transduction proteins involved in adaptive responses in *Escherichia coli*. Mol. Microbiol. 6:799-807; Ishige, K., et al. 1994. A novel device of bacterial signal transducers. EMBO J. 13:5195-5202); basS (Nagasawa, S., et al. 1993. Novel members of the two-component signal transduction genes in *Escherichia coli*. J. Biochem. (Tokyo). 114:350-357); bed (Lamark, T., et al. 1996. The complex bet promoters of *Escherichia coli*: regulation by oxygen (ArcA), choline (BetI), and osmotic stress. J. Bacteriol. 178:1655-1662); bglG (bglC, bglS) (Schnetz, K., and B. Rak. 1988. Regulation of the bgl operon of *Escherichia coli* by transcriptional antitermination. EMBO J. 7:3271-3277; Schnetz, K., and B. Rak. 1990. Beta-glucoside permease represses the bgl operon of *Escherichia coli* by phosphorylation of the antiterminator protein and also interacts with glucose-specific enzyme III, the key element in catabolite control. Proc. Natl. Acad. Sci. 87:5074-5078); birA (bioR, dhbB) (Barker, D. F., and A. M. Campbell. 1981. Genetic and biochemical characterization of the birA gene and its product: evidence for a direct role of biotin holoenzyme synthetase in repression of the biotin operon in *Escherichia coli*. J. Mol. Biol. 146:469-492; Barker, D. F., and A. M. Campbell. 1981. The birA gene of *Escherichia coli* encodes a biotin holoenzyme synthetase. J. Mol. Biol. 146:451-467; Howard, P. K., et al. 1985. Nucleotide sequence of the birA gene encoding the biotin operon repressor and biotin holoenzyme synthetase functions of *Escherichia coli*. Gene. 35:321-331); btuR (Lundrigan, M. D., et al. 1987. Separate regulatory systems for the repression of metE and btuB by vitamin B12 in *Escherichia coli*. Mol. Gen. Genet. 206:401-407; Lundrigan, M. D., and R. J. Kadner. 1989. Altered cobalamin metabolism in *Escherichia coli* btuR mutants affects btuB gene regulation. J. Bacteriol. 171:154-161); cadC (Watson, N., et al. 1992. Identification of elements involved in transcriptional regulation of the *Escherichia coli* cad operon by external pH. J. Bacteriol. 174:530-540); celD (Parker, L. L., and B. G. Hall. 1990. Characterization and nucleotide sequence of the cryptic cel operon of *Escherichia coli* K12. Genetics. 124:455-471); chaB (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); chaC (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); cpxR (Danese, P. N., et al. 1995. The Cpx two-component signal transduction pathway of *Escherichia coli* regulates transcription of the gene specifying the stress-inducible periplasmic protease, DegP. Genes Dev. 9:387-398); crl (Arnqvist, A., et al. 1992. The Crl protein activates cryptic genes for curli formation and fibronectin binding in *Escherichia coli* HB101. Mol. Microbiol. 6:2443-2452); cspA (Bae, W., et al. 1999. Characterization of *Escherichia coli* cspE, whose product negatively regulates transcription of cspA, the gene for the major cold shock protein. Mol. Microbiol. 31:1429-1441); cspE (Id.); csrA (Liu, M. Y., et al. 1995. The product of the pleiotropic *Escherichia coli* gene csrA modulates glycogen biosynthesis via effects on mRNA stability. J. Bacteriol. 177:2663-2672); cynR (Anderson, P. M., et al. 1990. The cyanase operon and cyanate metabolism. FEMS Microbiol. Rev. 7:247-252; Sung, Y. C., and J. A. Fuchs. 1992. The *Escherichia coli* K-12 cyn operon is positively regulated by a member of the lysR family. J. Bacteriol. 174:3645-3650); cysB (Jagura-Burdzy, G., and D. Hulanicka. 1981. Use of gene fusions to study expression of cysB, the regulatory gene of the cysteine regulon. J. Bacteriol. 147:744-751); cytR (Hammer-Jespersen, K., and A. Munch-Ptersen. 1975. Multiple regulation of nucleoside catabolizing enzymes: regulation of the deo operon by the cytR and deoR gene products. Mol. Gen. Genet. 137:327-335); dadQ (alnR) (Wild, J., and B. Obrepalska. 1982. Regulation of expression of the dadA gene encoding D-amino acid dehydrogenase in *Escherichia coli*: analysis of dadA-lac fusions and direction of dadA transcription. Mol. Gen. Genet. 186:405-410); dadR (alnR) (Wild, J., et al. 1985. Identification of the dadX gene coding for the predominant isozyme of alanine racemase in *Escherichia coli* K12. Mol. Gen. Genet. 198:315-322); deoR (nucR, tsc, nupG) (Hammer-Jespersen, K., and A. Munch-Ptersen. 1975. Multiple regulation of nucleoside catabolizing enzymes: regulation of the deo operon by the cytR and deoR gene products. Mol. Gen. Genet. 137:327-335); dgoR (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); dicA (Bejar, S., et al. 1988. Cell division inhibition gene dicB is regulated by a locus similar to lambdoid bacteriophage immunity loci. Mol. Gen. Genet. 212:11-19); dnaK (gro, groP, groPAB, groPC, groPF, grpC, grpF, seg) (Bochner, B. R., et al. 1986. *Escherichia coli* DnaK protein possesses a 5'-nucleotidase activity that is inhibited by ApppA. J. Bacteriol. 168:931-935); dniR (Kajie, S., et al. 1991. Molecular cloning and DNA sequence of dniR, a gene affecting anaerobic expression of the *Escherichia coli* hexaheme nitrite reductase. FEMS Microbiol. Lett. 67:205-211); dsdC (Heincz, M. C., and E. McFall. 1978. Role of the dsdC activator in regulation of D-serine deaminase synthesis. J. Bacteriol. 136:96-103); ebgR (Hall, B. G., and N. D. Clarke. 1977. Regulation of newly evolved enzymes. III Evolution of the ebg repressor during selection for enhanced lactase activity. Genetics. 85:193-201); envY (Lundrigan, M. D., and C. F. Earhart. 1984. Gene envY of *Escherichia coli* K-12 affects thermoregulation of major porin expression. J. Bacteriol. 157:262-268); envZ (ompB, perA, tpo) (Russo, F. D, and T. J. Silhavy. 1991. EnvZ controls the concentration of phosphorylated OmpR to mediate osmoregulation of the porin genes. J. Mol. Biol. 222:567-580); evgA (Nishino, K., and A. Yamaguichi. 2001. Overexpression of the response regulator evgA of the two-component signal transduction system modulates multidrug resistance conferred by multidrug resistance transporters. J. Bacteriol. 183:1455-1458); evgS (Id.); exuR (Portalier, R., et al. 1980. Regulation of *Escherichia coli* K-12 hexuronate system genes: exu regulon. J. Bacteriol. 143:1095-1107); fadR (dec, ole, thdB) (Simons, R. W., et al. 1980. Regulation of fatty acid degradation in *Escherichia* coli: isolation and characterization of strains bearing insertion and temperature-sensitive mutations in gene fadR. J. Bacteriol. 142:621-632); fed (Van Hove, B., et al. 1990. Novel two-component transmembrane transcription control: regulation of iron dicitrate transport in *Escherichia coli* K-12. J. Bacteriol. 172:6749-6758); fecR (Id.); fhlA (Maupin, J. A., and K. T. Shanmugam. 1990. Genetic regulation of formate hydrogenlyase of *Escherichia coli*: role of the fhlA gene product as a transcriptional activator for a new regulatory gene, fhlB. J. Bacteriol. 172:4798-4806; Rossmann, R., et al. 1991. Mechanism of regulation of the formate-hydrogenlyase pathway by oxygen, nitrate, and pH: definition of the formate regulon. Mol. Microbiol. 5:2807-2814); fhlB (Maupin, J. A., and K. T. Shanmugam. 1990. Genetic regulation of formate hydrogenlyase of *Escherichia coli*: role of the fhlA gene product as a transcriptional activator for a new regulatory gene, fhlB. J. Bacteriol. 172:4798-4806); fimB (pil) (Pallesen, L., et al. 1989. Regulation of the phase switch controlling expression of type 1 fimbriae in *Escherichia coli*. Mol. Microbiol. 3:925-931); fimE (pilH) (Id.); flhC (flaI) (Liu, X., and P. Matsumura. 1994. The FlhD/FlhC complex, a transcriptional activator of the *Escherichia coli* flagellar class II operons. J. Bacteriol. 176:7345-7351); flhD (flhB) (Id.); fliA (flaD, rpoF) (Komeda, Y., et al. 1986. Transcriptional control of flagellar genes in *Escherichia coli* K-12. J. Bacteriol. 168:1315-1318); fnr (frdB, nirA, nirR) (Jones, H. M., and R. P. Gunsalus. 1987. Regulation of *Escherichia coli* fumarate reductase (frdABCD) operon expression by respiratory electron acceptors and the fnr gene product. J. Bacteriol. 169:3340-3349); fruR (fruC, shl) (Geerse, R. H., at al. The PEP: fructose phosphotransferase system in *Salmonella typhimurium*: FPr combines enzyme IIIFru and pseudo-HPr activities. Mol. Gen. Genet. 216:517-525); fucR (Zhu, Y., and E. C. Lin. 1986. An evolvant of *Escherichia coli* that employs the L-fucose pathway also for growth on L-galactose and D-arabinose. J. Mol. Evol. 23:259-266); fur (Bagg, A., and J. B. Neilands. 1987. Ferric uptake regulation protein acts as a repressor, employing iron (II) as a cofactor to bind the operator of an iron transport operon in *Escherichia coli*. Biochemistry 26:5471-5477); gadR gene product from *Lactococcus lactis* (Sanders, J. W., et al. 1997. A chloride-inducible gene expression cassette and its use in induced lysis of *Lactococcus lactis*. Appl. Environ. Microbiol. 63:4877-4882); galR (von Wilcken-Bergmann, B., and B. Muller-Hill. 1982. Sequence of galR gene indicates a common evolutionary origin of lac and gal repressor in *Escherichia coli*. Proc. Natl. Acad. Sci. 79:2427-2431); galS (mglD) (Weickert., M. J., and S. Adhya. 1992. Isorepressor of the gal regulon in *Escherichia coli*. J. Mol. Biol. 226:69-83); galU (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli* and *Salmonella typhimurium: cellular and molecular biology*, 2nd ed. American Society for Microbiology, Washington D.C.); gatR (Nobelmann, B., and J. W. Lengeler. 1996. Molecular analysis of the gat genes from *Escherichia coli* and of their roles in galactitol transport and metabolism. J. Bacteriol. 178:6790-6795); gcvA (Wilson, R. L., et al. 1993. Positive regulation of the *Escherichia coli* glycine cleavage enzyme system. J. Bacteriol. 175:902-904); glgS (Hengge-Aronis, R., et al. 1993. Osmotic regulation of rpoS-dependent genes in *Escherichia coli*. J. Bacteriol. 175:259-265; Yang, H., et al. 1996. Coordinate genetic regulation of glycogen catabolism and biosynthesis in *Escherichia coli* via the CsrA gene product. J. Bactgeriol. 178:1012-1017); glnB (Bueno, R., et al. 1985. Role of glnB and glnD gene products in regulation of the glnALG operon of *Escherichia coli*. J. Bacteriol. 164:816-822); glnG (gln, ntrC) (Pahel, G., and B. Tyler. 1979. A new glnA-linked regulatory gene for glutamine synthetase in *Escherichia coli*. Proc. Natl. Acad. Sci. 76:4544-4548); glnL (glnR, ntrB) (MacNeil, T., et al. The products of glnL and glnG are bifunctional regulatory proteins. Mol. Gen. Genet. 188:325-333); glpR (Silhavy, T. J., et al. 1976. Periplasmic protein related to the sn-glycerol-3-phosphate transport system of *Escherichia coli*. J. Bacteriol. 126:951-958); gltF (Castano, I., et al. gltF, a member of the gltBDF operon of *Escherichia coli*, is involved in nitrogen-regulated gene expression. Mol. Microbiol. 6:2733-2741); gntR (Peekhaus, N., and T. Conway. 1998. Positive and negative transcriptional regulation of the *Escherichia coli* gluconate regulon gene gntT by GntR and the cyclic AMP (cAMP)-cAMP receptor protein complex. J. Bacteriol. 180:1777-1785); hha (Neito, J. M., et al. The hha gene modulates haemolysin expression in *Escherichia coli*. Mol. Microbiol. 5:1285-1293); himD (hip) (Goosen, N., et al. 1984. Regulation of Mu transposition. II. The *Escherichia coli* HimD protein positively controls two repressor promoters and the early promoter of bacteriophage Mu. Gene. 32:419-426); hrpB gene product from *Pseudomonas solanacearum* (Van Gijsegem, F., et al. 1995. The hrp gene locus of *Pseudomonas solanacearum*, which controls the production of a type III secretion system, encodes eight proteins related to components of the bacterial flagellar biogenesis complex. Mol. Microbiol. 15:1095-1114); hybF (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli* and *Salmonella typhimurium: cellular and molecular biology*, 2nd ed. American Society for Microbiology, Washington D.C.); hycA (Hopper, S., et al. 1994. Regulated expression in vitro of genes coding for formate hydrogenlyase components of *Escherichia coli*. J. Biol. Chem. 269:19597-19604); hydG (Leonhartsberger, S. et al. 2001. The hydH/G genes from *Escherichia coli* code for a zinc and lead responsive two-component regulatory system. J. Mol. Biol. 307:93-105); hydH (Id.); iciA (Thony, B., et al. 1991. iciA, an *Escherichia coli* gene encoding a specific inhibitor of chromosomal initiation of replication in vitro. Proc. Natl. Acad. Sci. 88:4066-4070); iclR (Maloy, S. R., and W. D. Nunn. 1982. Genetic regulation of the glyoxylate shunt in *Escherichia coli* K-12. J. Bacteriol. 149:173-180); ileR (avr, flrA) (Johnson, D. I., and R. L. Somerville. 1984. New regulatory genes involved in the control of transcription initiation at the thr and ilv promoters of *Escherichia coli* K-12. Mol. Gen. Genet. 195:70-76); ilvR (Id.); ilvU (Fayerman, J. T., et al. 1979. ilvU, a locus in *Escherichia coli* affecting the derepression of isoleucyl-tRNA synthetase and the RPC-5 chromatographic profiles of tRNAIle and tRNAVal. J. Bio. Chem. 254:9429-9440); ilvY (Wek, R. C., and G. W. Hatfield. 1988. Transcriptional activation at adjacent operators in the divergent-overlapping ilvY and ilvC promoters of *Escherichia coli*. J. Mol. Biol. 203:643-663); inaA (White, S., et al. 1992. pH dependence and gene structure of inaA in *Escherichia coli*. J. Bacteriol. 174:1537-1543); inaR (Id.); kdgR (Nemoz, G., et al. 1976. Physiological and genetic regulation of the aldohexuronate transport system in *Escherichia coli*. J. Bacteriol. 127:706-718); lad (Riggs, A. D, and S. Bourgeois. 1968. On the assay, isolation and characterization of the lac repressor. J. Mol. Biol. 34:361-364); leuO (Shi, X., and G. N. Bennett. 1995. Effects of multicopy LeuO on the expression of the acid-inducible lysine decarboxylase gene in *Escherichia coli*. J. Bacteriol. 177:810-814; Klauck, E., et al. 1997. The LysRlike regulator LeuO in *Escherichia coli* is involved in the translational regulation of rpoS by affecting the expression of the small regulatory DsrA-RNA. Mol. Microbiol. 25:559-569); leuR (Theall, G., et al. 1979. Regulation of the biosynthesis of aminoacyl-tRNA synthetases and of tRNA in *Escherichia coli*. IV. Mutants with increased levels of leucyl- or seryl-tRNA synthetase. Mol. Gen. Genet. 169:205-211); leuY (Morgan, S., et al. 1979. Regulation of biosynthesis of aminoacyl-transfer RNA synthetases and of transfer-RNA in *Escherichia coli*. Arch. Biol. Med. Exp. (Santiago) 12:415-426); lexA (Mount, D. W. 1977. A mutant of *Escherichia coli* showing constitutive expression of the lysogenic induction and error-prone DNA repair pathways. Proc. Natl. Acad. Sci. 74:300-304; Little, J. W., et al. 1980. Cleavage of the *Escherichia coli* lexA protein by the recA protease. Proc. Natl. Acad. Sci. 77:3225-3229); lldR (lctR) (Dong, J. M., et al. 1993. Three overlapping lct genes involved in L-lactate utilization by *Escherichia coli*. J. Bacteriol. 175:6671-6678); lpp (Brosius, J. Expression vectors employing lambda-, trp-, lac-, and lpp-derived promoters. 1988. Biotechnology. 10:205-225); lrhA (genR) (Bongaerts, J., et al. 1995. Transcriptional regulation of the proton translocating NADH dehydrogenase genes (nuoA-N) of *Escherichia coli* by electron acceptors, electron donors and gene regulators. Mol. Microbiol. 16:521-534); lrp (ihb, livR, lss, lstR, oppI, rblA, mbf) (Ito, K., et al. Multiple control of *Escherichia coli* lysyl-tRNA synthetase expression involves a transcriptional repressor and a translational enhancer element. Proc. Natl. Acad. Sci. 90:302-306); lysR (Gicquel-Sanzey, B. and P. Cossart. 1982. Homologies between different procaryotic DNA-binding regulatory proteins and between their sites of action. EMBO J. 1:591-595; Stragier, P., et al. 1983. Regulation of diaminopimelate decarboxylase synthesis in *Escherichia coli*. II. Nucleotide sequence of the lysA gene and its regulatory region. J. Mol. Biol. 168:321-331); malI (Reidl, J., et al. 1989. MalI, a novel protein involved in regulation of the maltose system of *Escherichia coli*, is highly homologous to the repressor proteins GalR, CytR, and LacI. J. Bacteriol. 171:4888-4499); malT (malA) (Bebarbouille, M., and M. Schwartz. Mutants which make more malT product, the activator of the maltose regulon in *Escherichia coli*. Mol. Gen. Genet. 178:589-595); marA (cpxB, soxQ) (Ariza, R. R., et al. Repressor mutations in the marRAB operon that activate oxidative stress genes and multiple antibiotic resistance in *Escherichia coli*. J. Bacteriol. 176:143-148); marB (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); marR (Ariza, R. R., et al. Repressor mutations in the marRAB operon that activate oxidative stress genes and multiple antibiotic resistance in *Escherichia coli*. J. Bacteriol. 176:143-148); melR (Williams, J., et al. 1994. Interactions between the *Escherichia coli* MelR transcription activator protein and operator sequences at the melAB promoter. Biochem. J. 300:757-763); metJ (Smith, A. A., et al. 1985. Isolation and characterization of the product of the methionine-regulatory gene metJ of *Escherichia coli* K-12. Proc. Natl. Acad. Sci. 82:6104-6108; Shoeman, R., et al. 1985. Regulation of methionine synthesis in *Escherichia coli*: effect of metJ gene product and S-adenosylmethionine on the in vitro expression of the metB, metL and metJ genes. Biochem. Biophys. Res. Commun. 133:731-739); metR (Maxon, M. E., et al. 1989. Regulation of methionine synthesis in *Escherichia coli*: effect of the MetR protein on the expression of the metE and metR genes. Proc. Natl. Acad. Sci. 86:85-89); mglR (R-MG) (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); mhpR (Ferrandez, A., et al. 1997. Genetic characterization and expression in heterologous hosts of the 3-(3-hydroxyphenyl)propionate catabolic pathway of *Escherichia coli* K-12. J. Bacteriol. 179:2573-2581); mhpS (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); micF (stc) (Aiba, H., et al. 1987. Function of micF as an antisense RNA in osmoregulatory expression of the ompF gene in *Escherichia coli*. J. Bacteriol. 169:3007-3012); mprA (emrR) (del Castillo, I., et al. 1990. mprA, an *Escherichia coli* gene that reduces growth-phase-dependent synthesis of microcins B17 and C7 and blocks osmoinduction of proU when cloned on a high-copy-number plasmid. J. Bacteriol. 172:437-445); mtlR (Figge, R. M., et al. 1994. The mannitol repressor (MtlR) of *Escherichia coli*. J. Bacteriol. 176:840-847); nagC (nagR) (Plumbridge, J. A. 1991. Repression and induction of the nag regulon of *Escherichia coli* K-12: the roles of nagC and nagA in maintenance of the uninduced state. Mol. Microbiol. 5:2053-3062); narL (frdR, narR) (Stewart, V. 1982. Requirement of Fnr and NarL functions for nitrate reductase expression in *Escherichia coli* K-12. J. Bacteriol. 151:1320-1325; Miller, J. B., et al. 1987. Molybdenum-sensitive transcriptional regulation of the chlD locus of *Escherichia coli*. J. Bacteriol. 169:1853-1860; Iuchi, S., and E. C. Lin. 1987. Molybdenum effector of fumarate reductase repression and nitrate reductase induction in *Escherichia coli*. J. Bacteriol. 169:3720-3725); narP (Rabin, R. S., and V. Stewart. 1993. Dual response regulators (NarL and NarP) interact with dual sensors (NarX and NarQ) to control nitrate- and nitrite-regulated gene expression in *Escherichia coli* K-12. J. Bacteriol. 175:3259-3268); nhaR (gene product from *E. coli* (Rahav-Manor, O., et al. 1992. NhaR, a protein homologous to a family of bacterial regulatory proteins (LysR), regulates nhaA, the sodium proton antiporter gene in *Escherichia coli*. J. Biol. Chem. 267:10433-10438); ompR (cry, envZ, ompB) (Taylor, R. K., et al. Identification of OmpR: a positive regulatory protein controlling expression of the major outer membrane matrix porin proteins of *Escherichia coli* K-12. J. Bacteriol. 147:255-258); oxyR (mor, momR) (VanBogelen, R. A, et al. 1987. Differential induction of heat shock, SOS, and oxidation stress regulons and accumulation of nucleotides in *Escherichia coli*. J. Bacteriol. 169:26-32); pdhR (Haydon, D. J., et al. A mutation causing constitutive synthesis of the pyruvate dehydrogenase complex in *Escherichia coli* is located within the pdhR gene. FEBS Lett. 336:43-47); phnF (Wanner, B. L., and W. W. Metcalf. 1992. Molecular genetic studies of a 10.9-kb operon in *Escherichia coli* for phosphonate uptake and biodegradation. FEMS Microbiol. Lett. 79:133-139); phoB (phoRc, phoT) (Pratt, C. 1980. Kinetics and regulation of cell-free alkaline phosphatase synthesis. J. Bacteriol. 143:1265-1274); phoP (Kasahara, M., et al. 1992. Molecular analysis of the *Escherichia coli* phoP-phoQ operon. J. Bacteriol. 174:492-498); phoQ (Id.); phoR (Rlpho, nmpB, phoRl) (Bracha, M., and E. Yagil. 1969. Genetic mapping of the phoR regulator gene of alkaline phosphatase in *Escherichia coli*. J. Gen. Microbiol. 59:77-81); phoU (phoT)

(Nakata, A., et al. 1984. Regulation of the phosphate regulon in *Escherichia coli* K-12: regulation of the negative regulatory gene phoU and identification of the gene product. J. Bacteriol. 159:979-985); poaR (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); poxA (Chang, Y. Y., and J. E. Cronan Jr. 1982. Mapping nonselectable genes of *Escherichia coli* by using transposon Tn10: location of a gene affecting pyruvate oxidase. J. Bacteriol. 151:1279-1289); proQ (Milner, J. L., and J. M. Wood. 1989. Insertion proQ220::Tn5 alters regulation of proline porter II, a transporter of proline and glycine betaine in *Escherichia coli*. J. Bacteriol. 171:947-951); pspA (Weiner, L., et al. 1991. Stress-induced expression of the *Escherichia coli* phage shock protein operon is dependent on sigma 54 and modulated by positive and negative feedback mechanisms. Genes Dev. 5:1912-1923); pspB (Weiner, L., et al. 1991. Stress-induced expression of the *Escherichia coli* phage shock protein operon is dependent on sigma 54 and modulated by positive and negative feedback mechanisms. Genes Dev. 5:1912-1923); pspC (Weiner, L., et al. 1991. Stress-induced expression of the *Escherichia coli* phage shock protein operon is dependent on sigma 54 and modulated by positive and negative feedback mechanisms. Genes Dev. 5:1912-1923); pssR (Sparrow, C. P., and C. R. Raetz. 1983. A trans-acting regulatory mutation that causes overproduction of phosphatidylserine synthase in *Escherichia coli*. J. Biol. Chem. 258:9963-9967); purR (Meng, L. M., et al. 1990. Autoregulation of PurR repressor synthesis and involvement of purR in the regulation of purB, purC, purL, purMN and guaBA expression in *Escherichia coli*. Eur. J. Biochem. 187:373-379); putA (poaA) gene product from *Salmonella enterica* serotype *Typhimurium* (Menzel, R., and J. Roth. 1981. Regulation of the genes for proline utilization in *Salmonella typhimurium*: autogenous repression by the putA gene product. J. Mol. Biol. 148:21-44); pyrI (Cunin, R., et al. 1985. Structure-function relationship in allosteric aspartate carbamoyltransferase from *Escherichia coli*. I. Primary structure of a pyrI gene encoding a modified regulatory subunit. J. Mol. Biol. 186:707-713); rbsR (Lopilato, J. E., et al. 1984. D-ribose metabolism in *Escherichia coli* K-12: genetics, regulation, and transport. J. Bacteriol. 158:665-673); rcsA (Gottesman, S., et al. 1985. Regulation of capsular polysaccharide synthesis in *Escherichia coli* K-12: characterization of three regulatory genes. J. Bacteriol. 162:1111-1119); rcsB (Id.); rcsC (Id.); rcsF (Grevais, F. G., and G. R. Drapeau. 1992. Identification, cloning, and characterization of rcsF, a new regulator gene for exopolysaccharide synthesis that suppresses the division mutation ftsZ84 in *Escherichia coli* K-12. J. Bacteriol. 174:8016-8022); relB (Christensen, S. K., et al. 2001. RelE, a global inhibitor of translation, is activated during nutritional stress. Proc Natl. Acad. Sci. 98:14328-14333); rfaH (sfrB) (Pradel, E., and C. A. Schnaitman. 1991. Effect of rfaH (sfrB) and temperature on expression of rfa genes of *Escherichia coli* K-12. J. Bacteriol. 173:6428-6431); rhaR (Tobin, J. F., and R. F. Schleif. 1987. Positive regulation of the *Escherichia coli* L-rhamnose operon is mediated by the products of tandemly repeated regulatory genes. J. Mol. Biol. 196:789-799); rhaS (Id.); rnk (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); rob (Skarstad, K., et al. A novel binding protein of the origin of the *Escherichia coli* chromosome. J. Biol. Chem. 268:535-5370); rseA (mclA) (Missiakas, D., et al. 1997. Modulation of the *Escherichia coli* sigmaE (RpoE) heat-shock transcription-factor activity by the RseA, RseB and RseC proteins. Mol. Microbiol. 24:355-371; De Las Penas, A. 1997. The sigmaE-mediated response to extracytoplasmic stress in *Escherichia coli* is transduced by RseA and RseB, two negative regulators of sigmaE. Mol. Microbiol. 24:373-385); rseB (Id.); rseC (Id.); rspA (Huisman, G. W., and T. Kolter. 1994. Sensing starvation: a homoserine lactone—dependent signaling pathway in *Escherichia coli*. Science. 265:537-539); rspB (Shafqat, J., et al. An ethanol-inducible MDR ethanol dehydrogenase/acetaldehyde reductase in *Escherichia coli*: structural and enzymatic relationships to the eukaryotic protein forms. Eur. J. Biochem. 263:305-311); rssA (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); rssB (Muffler, A., et al. 1996. The response regulator RssB controls stability of the sigma(S) subunit of RNA polymerase in *Escherichia coli*. EMBO J. 15:1333-1339); sbaA (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); sdaC (Id.); sdiA (Sitnikov, D. M., et al. 1996. Control of cell division in *Escherichia coli*: regulation of transcription of I involves both rpoS and SdiA-mediated autoinduction. Proc. Natl. Acad. Sci. 93:336-341); serR (Theall, G., et al. 1979. Regulation of the biosynthesis of aminoacyl-tRNA synthetases and of tRNA in *Escherichia coli*. IV. Mutants with increased levels of leucyl- or seryl-tRNA synthetase. Mol. Gen. Genet. 169:205-211); sfsA (Takeda, K., et al. 2001. Effects of the *Escherichia coli* sfsA gene on mal genes expression and a DNA binding activity of SfsA. Biosci. Biotechnol. Biochem. 65:213-217); sfsB (nlp, sfsl) (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); soxR (Tsaneva, I. R., and B. Weiss. 1990. soxR, a locus governing a superoxide response regulon in *Escherichia coli* K-12. J. Bacteriol. 172:4197-4205); soxS (Wu, J., and B. Weiss. 1991. Two divergently transcribed genes, soxR and soxS, control a superoxide response regulon of *Escherichia coli*. J. Bacteriol. 173:2864-2871); srlR (gutR) (Csonka, L. N., and A. J. Clark. 1979. Deletions generated by the transposon Tn10 in the srl recA region of the *Escherichia coli* K-12 chromosome. Genetics. 93:321-343); tdcA (Ganduri, Y. L., et al. 1993. TdcA, a transcriptional activator of the tdcABC operon of *Escherichia coli*, is a member of the LysR family of proteins. Mol. Gen. Genet. 240:395-402); tdcR (Hagewood, B. T., et al. 1994. Functional analysis of the tdcABC promoter of *Escherichia coli*: roles of TdcA and TdcR. J. Bacteriol. 176:6241-6220); thrS (Springer, M., et al. 1985. Autogenous control of *Escherichia coli* threonyl-tRNA synthetase expression in vivo. J. Mol. Biol. 185:93-104); torR (Simon, G., et al. 1994. The torR gene of *Escherichia coli* encodes a response regulator protein involved in the expression of the trimethylamine N-oxide reductase genes. J. Bacteriol. 176:5601-5606); treR (Horlacher, R., and W. Boos. 1997. Characterization of TreR, the major regulator of the *Escherichia coli* trehalose system. J. Biol. Chem. 272:13026-13032); trpR (Gunsalus, R. P., and C. Yanofsky. 1980. Nucleotide sequence and expression of *Escherichia coli* trpR, the structural gene for the trp aporepressor. Proc. Natl. Acad. Sci. 77:7117-7121); tyrR (Camakaris, H., and J. Pittard. 1973. Regulation of tyrosine and phenylalanine biosynthesis in *Escherichia coli* K-12: properties of the tyrR gene product. J. Bacteriol. 115:1135-1144); uhpA (Kadner, R. J., and D. M. Shattuck-Eidens. 1983. Genetic control of the hexose phosphate transport system of *Escherichia coli*: mapping of deletion and insertion mutations in the uhp region. J. Bacteriol. 155:1052-1061); uidR (gusR) (Novel, M., and G. Novel. 1976. Regulation of beta-glucuronidase synthesis in *Escherichia coli* K-12: pleiotropic constitutive mutations affecting uxu and uidA expression. J. Bacteriol. 127:418-432); uspA (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology*, 2nd ed. American Society for Microbiology, Washington D.C.); uxuR (Novel, M., and G. Novel. 1976. Regulation of beta-glucuronidase synthesis in *Escherichia coli* K-12: pleiotropic constitutive mutations affecting uxu and uidA expression. J. Bacteriol. 127:418-432); wrbA (Yang, W., et al. 1993. A stationary-phase protein of *Escherichia coli* that affects the mode of association between the trp repressor protein and operator-bearing DNA. Proc. Natl. Acad. Sci. 90:5796-5800); xapR (pndR) (Seeger, C., et al. 1995. Identification and characterization of genes (xapA, xapB, and xapR) involved in xanthosine catabolism in *Escherichia coli*. J. Bacteriol. 177:5506-5516); and xylR (Inouye, S., et al. 1987. Expression of the regulatory gene xylS on the TOL plasmid is positively controlled by the xylR gene product. Proc. Natl. Acad. Sci. 84:5182-5186);

Regulatory elements, promoters and other expression elements and factors from prokaryotes other than *E. coli* and *B. subtilis* include without limitation ahyRI gene product from *Aeromonas hydrophila* and *Aeromonas salmonicida* (Swift, S., et al. 1997. Quorum sensing in *Aeromonas hydrophila* and *Aeromonas salmonicida*: identification of the LuxRI homologs AhyRI and AsaRI and their cognate N-acylhomoserine lactone signal molecules. J. Bacteriol. 179:5271-5281); angR gene product from *Vibrio anguillarum* (Salinas, P. C., et al. 1989. Regulation of the iron uptake system in *Vibrio anguillarum*: evidence for a cooperative effect between two transcriptional activators. Proc. Natl. Acad. Sci. 86:3529-3522); aphA gene product from *Vibrio cholerae* (Kovacikova, G., and K. Skorupski. 2001. Overlapping binding sites for the virulence gene regulators AphA, AphB and cAMP-CRP at the *Vibrio cholerae* tcpPH promoter. Mol. Microbiol. 41:393-407); aphB gene product from *Vibrio cholerae* (Kovachikova, G., and K. Skorupski. 2000. Differential activation of the tcpPH promoter by AphB determines biotype specificity of virulence gene expression in *Vibrio cholerae*. J. Bacteriol. 182:3228-3238); comE gene product from *Streptococcus pneumoniae* (Ween, O., et al. 1999. Identification of DNA binding sites for ComE, a key regulator of natural competence in *Streptococcus pneumoniae*. Mol. Microbiol. 33:817-827); esaI gene product from *Pantoea stewartii* subsp. *stewartii* (von Bodman, S. B., et al. 1998. A negative regulator mediates quorum-sensing control of exopolysaccharide production in *Pantoea stewartii* subsp. *stewartii*. Proc. Natl. Acad. Sci. 95:7687-7692); esaR gene product from *Pantoea stewartii* subsp. *stewartii* (Id.); expI gene product from *Erwinia chrysanthemi* (Nasser, W., et al. 1998. Characterization of the *Erwinia chrysanthemi* expI-expR locus directing the synthesis of two N-acyl-homoserine lactone signal molecules. Mol. Microbiol. 29:1391-1405); expR gene product from *Erwinia chrysanthemi* (Id.); gacA gene product from *Pseudomonas aeruginosa* (Pessi, G., and D. Haas. 2001. Dual control of hydrogen cyanide biosynthesis by the global activator GacA in *Pseudomonas aeruginosa* PAO1. FEMS Microbiol. Lett. 200:73-78); hapR gene product from *Vibrio cholerae* (Jobling, M. G., and R. K. Holmes. Characterization of hapR, a positive regulator of the *Vibrio cholerae* HA/protease gene hap, and its identification as a functional homologue of the *Vibrio harveyi* luxR gene. Mol. Microbiol. 26:1023-1034); hlyR gene product from *Vibrio cholerae* (von Mechow, S., et al. 1985. Mapping of a gene that regulates hemolysin production in *Vibrio cholerae*. J. Bacteriol. 163:799-802); hupR gene product from *Vibrio vulnificus* (Litwin, C. M., and J. Quackenbush. 2001. Characterization of a *Vibrio vulnificus* LysR homologue, HupR, which regulates expression of the haem uptake outer membrane protein, HupA. Microb. Pathog. 31:295-307); lasR gene product from *Pseudomonas aerugenosa* (Gambella, M. J., and B. H. Igleweski. 1991. Cloning and characterization of the *Pseudomonas aeruginosa* lasR gene, a transcriptional activator of elastase expression. J. Bacteriol. 173:3000-3009); leuO gene product from *Salmonella enterica serovar Typhimurium* (Fang, M., and H. Y. Wu. 1998. A promoter relay mechanism for sequential gene activation. J. Bacteriol. 180:626-633); luxI gene product from *Vibrio cholerae* (Engebrecht, J., and M. Silverman. Nucleotide sequence of the regulatory locus controlling expression of bacterial genes for bioluminescence. Nucleic Acids Res. 15:10455-10467); luxO gene product from *Vibrio cholerae* (Bassler, B. L., et al. 1994. Sequence and function of LuxO, a negative regulator of luminescence in *Vibrio harveyi*. Mol. Microbiol. 12:403-412); luxR gene product from *Vibrio cholerae* (Engebrecht, J., and M. Silverman. Nucleotide sequence of the regulatory locus controlling expression of bacterial genes for bioluminescence. Nucleic Acids Res. 15:10455-10467); phzR gene product from *Pseudomonas aureofaciens* (Pierson, L. S., et al. 1994. Phenazine antibiotic biosynthesis in *Pseudomonas aureofaciens* 30-84 is regulated by PhzR in response to cell density. J. Bacteriol. 176:3966-3974); rhlR gene product from *Pseudomonas aeruginosa* (Ochsner, U. A. et al. 1994. Isolation and characterization of a regulatory gene affecting rhamnolipid biosurfactant synthesis in *Pseudomonas aeruginosa*. J. Bacteriol. 176:2044-2054); rsmA gene product from *Erwinia carotovora* subsp. *carotovora* (Cui, Y., et al. 1995. Identification of a global repressor gene, rsmA, of *Erwinia carotovora* subsp. *carotovora* that controls extracellular enzymes, N-(3-oxohexanoyl)-L-homoserine lactone, and pathogenicity in soft-rotting *Erwinia* spp. J. Bacteriol. 177: 5108-5115); rsmB gene product from *Erwinia carotovora* subsp. *carotovora* (Cui, Y., et al. 1999. rsmC of the soft-rotting bacterium *Erwinia carotovora* subsp. *carotovora* negatively controls extracellular enzyme and harpin(Ecc) production and virulence by modulating levels of regulatory RNA (rsmB) and RNA-binding protein (RsmA). J. Bacteriol. 181:6042-6052); sirA gene product from *Salmonella enterica serovar Typhimurium* (Goodier, R. I., and B. M. Ahmer. 2001. SirA orthologs affects both motility and virulence. J. Bacteriol. 183:2249-2258); taf gene product from *Vibrio cholerae* (Salinas, P. C., et al. 1989. Regulation of the iron uptake system in *Vibrio anguillarum*: evidence for a cooperative effect between two transcriptional activators. Proc. Natl. Acad. Sci. 86:3529-3522); tcpP gene product from *Vibrio cholerae* (Hase, C. C., and J. J. Mekalanos. 1998. TcpP protein is a positive regulator of virulence gene expression in *Vibrio cholerae*. Proc. Natl. Acad. Sci. 95:730-734); toxR gene product from *Vibrio cholerae* (Miller, V. L., and J. J. Mekalanos. 1984. Synthesis of cholera toxin is positively regulated at the transcriptional level by toxR. Proc. Natl. Acad. Sci. 81:3471-4375); toxS gene product from *Vibrio cholerae* (Miller, V. L., et al. 1989. Identification of toxS, a regulatory gene whose product enhances toxR-mediated activation of the cholera toxin promoter. J. Bacteriol. 171:1288-1293); toxT from *Vibrio cholerae* (Kaufman, M. R., et al. 1993. Biogenesis and regulation of the *Vibrio cholerae* toxin-coregulated pilus: analogies to other virulence factor secretory systems. Gene. 126:43-49); traM gene product from *Agrobacterium tumefaciens* (Faqua, C., et al. 1995. Activity of the *Agrobacterium* Ti plasmid conjugal transfer regulator TraR is inhibited by the product of the traM gene. J. Bacteriol. 177:1367-1373); traR gene product from *Agrobacterium tumefaciens* (Piper, K. R., et al. 1993. Conjugation factor of *Agrobacterium tumefaciens* regulates Ti plasmid transfer by autoinduction. Nature. 362:448-450); vicH gene product from *Vibrio cholerae* (Tendeng, C., et al. 2000. Isolation and characterization of vicH, encoding a new pleiotropic regulator in *Vibrio cholerae*. J. Bacteriol. 182:2026-2032); vspR gene product from *Vibrio cholerae* (Yildiz, F. H., et al. 2001. VpsR, a Member of the Response Regulators of the Two-Component Regulatory Systems, Is Required for Expression of vps Biosynthesis Genes and EPS(ETr)-Associated Phenotypes in *Vibrio cholerae* O1 El Tor. J. Bacteriol. 183:1716-1726).

II.C.5.b. *Bacillus subtilis*

Regulatory elements, promoters and other expression elements and expression elements from *B subtilis* include but are not limited to abrB (Perego, M., et al. 1988. Structure of the gene for the transition state regulator, abrB: regulator synthesis is controlled by the spo0A sporulation gene in *Bacillus subtilis*. Mol. Microbiol. 2:698-699); acoR (Ali, N. O., et al. 2001. Regulation of the acetoin catabolic pathway is controlled by sigma L in *Bacillus subtilis*. J. Bacteriol. 183:2497-2504); ahrC (Klinger, U., et al. 1995. A binding site for activation by the *Bacillus subtilis* AhrC protein, a repressor/activator of arginine metabolism. Mol. Gen. Genet. 248:329-340); alaR (Sohenshein, A. L., J. A. Hoch, and R. Losick (eds.) 2002. *Bacillus subtilis* and its closest relatives: from genes to cells. American Society for Microbiology, Washington D.C.); alsR (Renna, M. C., et al. 1993. Regulation of the *Bacillus subtilis* alsS, alsD, and alsR genes involved in post-exponential-phase production of acetoin. J. Bacteriol. 175:3863-3875); ansR (Sun, D., and P. Setlow. 1993. Cloning and nucleotide sequence of the *Bacillus subtilis* ansR gene, which encodes a repressor of the ans operon coding for L-asparaginase and L-aspartase. J. Bacteriol. 175:2501-2506); araR (Sa-Nogueira, I., and L. J. Mota. 1997. Negative regulation of L-arabinose metabolism in *Bacillus subtilis*: characterization of the araR (araC) gene. J. Bacteriol. 179:1598-1608); arfM (Marino, M., et al. 2001. Modulation of anaerobic energy metabolism of *Bacillus subtilis* by arfM (ywiD). J. Bacteriol. 183:6815-6821); arsR (Rosenstein, R., et al. 1992. Expression and regulation of the antimonite, arsenite, and arsenate resistance operon of *Staphylococcus xylosus* plasmid pSX267. J. Bacteriol. 174:3676-3683); azlB (Belitsky, B. R., et al. 1997. An lrp-like gene of *Bacillus subtilis* involved in branched-chain amino acid transport. J. Bacteriol. 179:54485457); birA (Bower, S., et al. 1995. Cloning and characterization of the *Bacillus subtilis* birA gene encoding a repressor of the biotin operon. J. Bacteriol. 177:2572-2575); bkdR (Bebarbouille, M., et al. 1999. Role of bkdR, a transcriptional activator of the sigL-dependent isoleucine and valine degradation pathway in *Bacillus subtilis*. J. Bacteriol. 181:2059-2066); bltR (Ahmed, M., et al. 1995. Two highly similar multidrug transporters of *Bacillus subtilis* whose expression is differentially regulated. J. Bacteriol. 177:3904-3910); bmrR (Ahmed, M., et al. 1994. A protein that activates expression of a multidrug efflux transporter upon binding the transporter substrates. J. Biol. Chem. 269:28506-28513); ccpA (Henkin, T. M., et al. 1991. Catabolite repression of alpha-amylase gene expression in *Bacillus subtilis* involves a trans-acting gene product homologous to the *Escherichia coli* lacI and galR repressors. Mol. Microbiol. 5:575-584); ccpB (Chauvaux, S., et al. 1998. CcpB, a novel transcription factor implicated in catabolite repression in *Bacillus subtilis*. J. Bacteriol. 180:491-497); ccpC (Jourlin-Castelli, C., et al. 2000. CcpC, a novel regulator of the LysR family required for glucose repression of the citB gene in *Bacillus subtilis*. J. Mol. Biol. 295:865-878); cggR (Fillinger, S., et al. 2000. Two glyceraldehyde-3-phosphate dehydrogenases with opposite physiological roles in a nonphotosynthetic bacterium. J. Biol. Chem. 275:14031-14037); cheB (Bischoff, D. S., and G. W. Ordal. 1991. Sequence and characterization of *Bacillus subtilis* CheB, a homolog of *Escherichia coli* CheY, and its role in a different mechanism of chemotaxis. J. Biol. Chem. 266:12301-12305); cheY (Bischoff, D. S., et al. 1993. Purification and characterization of *Bacillus subtilis* CheY. Biochemistry 32:9256-9261); citR (Jin, S., and A. L. Sonenshein. 1994. Transcriptional regulation of *Bacillus subtilis* citrate synthase genes. J. Bacteriol. 176:4680-4690); citT (Yamamoto, H., et al. 2000. The CitST two-component system regulates the expression of the Mg-citrate transporter in *Bacillus subtilis*. Mol. Microbiol. 37:898-912); codY (Slack, F. J., et al. 1995. A gene required for nutritional repression of the *Bacillus subtilis* dipeptide permease operon. Mol. Microbiol. 15:689-702); comA (Nakano, M. M., and P. Zuber. 1989. Cloning and characterization of srfB, a regulatory gene involved in surfactin production and competence in *Bacillus subtilis*. J. Bacteriol. 171:5347-5353); comK (Msadek, T., et al. 1994. MecB of *Bacillus subtilis*, a member of the ClpC ATPase family, is a pleiotropic regulator controlling competence gene expression and growth at high temperature. Proc. Natl. Acad. Sci. 91:5788-5792); comQ (Weinrauch, Y., et al. 1991. Sequence and properties of comQ, a new competence regulatory gene of *Bacillus subtilis*. J. Bacteriol. 173:5685-5693); cssR (Hyyrylainen, H. L., et al. 2001. A novel two-component regulatory system in *Bacillus subtilis* for the survival of severe secretion stress. Mol. Microbiol. 41:1159-1172); ctsR (Kruger, E., and M. Hecker. 1998. The first gene of the *Bacillus subtilis* clpC operon, ctsR, encodes a negative regulator of its own operon and other class III heat shock genes. J. Bacteriol. 180:6681-6688); dctR (Sohenshein, A. L., J. A. Hoch, and R. Losick (eds.) 2002. *Bacillus subtilis* and its closest relatives: from genes to cells. American Society for Microbiology, Washington D.C.); degA (Bussey, L. B., and R. L. Switzer. 1993. The degA gene product accelerates degradation of *Bacillus subtilis* phosphoribosylpyrophosphate amidotransferase in *Escherichia coli*. J. Bacteriol. 175:6348-6353); degU (Msadek, T., et al. 1990. Signal transduction pathway controlling synthesis of a class of degradative enzymes in *Bacillus subtilis*: expression of the regulatory genes and analysis of mutations in degS and degU. J. Bacteriol. 172:824-834); deoR (Saxild, H. H., et al. 1996. Dra-nupC-pdp operon of *Bacillus subtilis*: nucleotide sequence, induction by deoxyribonucleosides, and transcriptional regulation by the deoR-encoded DeoR repressor protein. J. Bacteriol. 178:424-434); exuR (Sohenshein, A. L., J. A. Hoch, and R. Losick (eds.) 2002. *Bacillus subtilis* and its closest relatives: from genes to cells. American Society for Microbiology, Washington D.C.); frn (Cruz Ramos, H., et al. 1995. Anaerobic transcription activation in *Bacillus subtilis*: identification of distinct FNR-dependent and -independent regulatory mechanisms. EMBO J. 14:5984-5994); fruR (Saier, M. H. Jr. 1996. Cyclic AMP-independent catabolite repression in bacteria. FEMS Microbiol. Lett. 138:97-103); fur (Chen, L., et al. 1993. Metalloregulation in *Bacillus subtilis*: isolation and characterization of two genes differentially repressed by metal ions. J. Bacteriol. 175:5428-5437); gabR (Sohenshein, A. L., J. A. Hoch, and R. Losick (eds.) 2002. *Bacillus subtilis* and its closest relatives: from genes to cells. American Society for Microbiology, Washington D.C.); gerE (Holand, S. K., et al. 1987. The possible DNA-binding nature of the regulatory proteins, encoded by spoIID and gerE, involved in the sporulation of *Bacillus subtilis*. J. Gen. Microbiol. 133:2381-2391); glcR (Stulke, J., et al. 2001. Characterization of glucose-repression-resistant mutants of *Bacillus subtilis*: identification of the glcR gene. Arch. Microbiol. 175:441-449); glcT (Paulsen, I. T., et al. 1998. Characterization of glucose-specific catabolite repression-resistant mutants of *Bacillus subtilis*: identification of a novel hexose:H+ symporter. J. Bacteriol. 180:498-504); glnR (Schreier, H. J., et al. 1989. Regulation of *Bacillus subtilis* glutamine synthetase gene expression by the product of the glnR gene. J. Mol. Biol. 210:51-63); glpP (Holmberg, C., and B. Rutberg. 1991. Expression of the gene encoding glycerol-3-phosphate dehydrogenase (glpD) in *Bacillus subtilis* is controlled by antitermination. Mol. Microbiol. 5:2891-2900); gltC (Bohannon, D. E. and A. L. Sonenshein. 1989. Positive regulation of glutamate biosynthesis in *Bacillus subtilis*. J. Bacteriol. 171:4718-4727); gltR (Belitsky, B. R., and A. L. Sonenshein. 1997. Altered transcription activation specificity of a mutant form of *Bacillus subtilis* GltR, a LysR family member. J. Bacteriol. 179:1035-1043); gntR (Fujita, Y., and T. Fujita. 1987. The gluconate operon gnt of *Bacillus subtilis* encodes its own transcriptional negative regulator. Proc. Natl. Acad. Sci. 84:4524-4528); gutR (Ye, R., et al. 1994. Glucitol induction in *Bacillus subtilis* is mediated by a regulatory factor, GutR. J. Bacteriol. 176:3321-3327); hpr (Perego, M., and J. A. Hoch. 1988. Sequence analysis and regulation of the hpr locus, a regulatory gene for protease production and sporulation in *Bacillus subtilis*. J. Bacteriol. 170:2560-2567); hrcA (Schulz, A., and W. Schumann. 1996. hrcA, the first gene of the *Bacillus subtilis* dnaK operon encodes a negative regulator of class I heat shock genes. J. Bacteriol. 178:1088-1093); hutP (Oda, M., et al. 1992. Analysis of the transcriptional activity of the but promoter in *Bacillus subtilis* and identification of a cis-acting regulatory region associated with catabolite repression downstream from the site of transcription. Mol. Microbiol. 6:2573-2582); hxlR (Sohenshein, A. L., J. A. Hoch, and R. Losick (eds.) 2002. *Bacillus subtilis* and its closest relatives: from genes to cells. American Society for Microbiology, Washington D.C.); iolR (Yoshida, K. I., et al. 1999. Interaction of a repressor and its binding sites for regulation of the *Bacillus subtilis* iol divergon. J. Mol. Biol. 285:917-929); kdgR (Pujic, P., et al. 1998. The kdgRKAT operon of *Bacillus subtilis*: detection of the transcript and regulation by the kdgR and ccpA genes. Microbiology. 144:3111-3118); kipR (Sohenshein, A. L., J. A. Hoch, and R. Losick (eds.) 2002. *Bacillus subtilis* and its closest relatives: from genes to cells. American Society for Microbiology, Washington D.C.); lacR (Errington, J., and C. H. Vogt. 1990. Isolation and characterization of mutations in the gene encoding an endogenous *Bacillus subtilis* beta-galactosidase and its regulator. J. Bacteriol. 172:488-490); levR (Bebarbouille, M., et al. 1991. The transcriptional regulator LevR of *Bacillus subtilis* has domains homologous to both sigma 54- and phosphotransferase system-dependent regulators. Proc. natl. Acad. Sci. 88:2212-2216); lexA (Lovett, C. M. Jr., and J. W. Roberts. 1985. Purification of a RecA protein analogue from *Bacillus subtilis*. J. Biol. Chem. 260:3305-3313); licR (Tobisch, S., et al. 1997. Identification and characterization of a new beta-glucoside utilization system in *Bacillus subtilis*. J. Bacteriol. 179:496-506); licT (Le Coq, D., et al. 1995. New beta-glucoside (bgl) genes in *Bacillus subtilis*: the bglP gene product has both transport and regulatory functions similar to those of BglF, its *Escherichia coli* homolog. J. Bacteriol. 177:1527-1535); lmrA (Kumano, M., et al. 1997. A 32 kb nucleotide sequence from the region of the lincomycin-resistance gene (22 degrees-25 degrees) of the *Bacillus subtilis* chromosome and identification of the site of the lin-2 mutation. Microbiology. 143:2775-2782); lrpA gene product from *Pyrococcus furiosus* (Brinkman, A. B., et al. 2000. An Lrp-like transcriptional regulator from the archaeon *Pyrococcus furiosus* is negatively autoregulated. J. Biol. Chem. 275:38160-38169); lrpB (Sohenshein, A. L., J. A. Hoch, and R. Losick (eds.) 2002. *Bacillus subtilis* and its closest relatives: from genes to cells. American Society for Microbiology, Washington D.C.); lrpC (Beloin, C., et al. 1997. Characterization of an lrp-like (lrpC) gene from *Bacillus subtilis*. Mol. Gen. Genet. 256:63-71); lytR (Huang, X., and J. D. Heimann. 1998. Identification of target promoters for the *Bacillus subtilis* sigma X factor using a consensus-directed search. J. Mol. Biol. 279:165-173); lytT (Sohenshein, A. L., J. A. Hoch, and R. Losick (eds.) 2002. *Bacillus subtilis* and its closest relatives: from genes to cells. American Society for Microbiology, Washington D.C.); manR gene product from *Listeria monocytogenes* (Dalet, K., et al. 2001. A sigma(54)-dependent PTS permease of the mannose family is responsible for sensitivity of *Listeria monocytogenes* to mesentericin Y105. Microbiology. 147:3263-3269); mntR (Que, Q., and J. D. Helmann. 2000. Manganese homeostasis in *Bacillus subtilis* is regulated by MntR, a bifunctional regulator related to the diphtheria toxin repressor family of proteins. Mol. Microbiol. 35:1454-1468); msmR gene product from *Streptococcus mutans* (Russell, R. R., et al. 1992. A binding protein-dependent transport system in *Streptococcus mutans* responsible for multiple sugar metabolism. J. Biol. Chem. 267:4631-4637); mta (Baranova, N. N., et al. 1999. Mta, a global MerR-type regulator of the *Bacillus subtilis* multidrug-efflux transporters. Mol. Microbiol. 31:1549-1559); mtlR (Henstra, S. A., et al. 1999. The *Bacillus stearothermophilus* mannitol regulator, MtlR, of the phosphotransferase system. A DNA-binding protein, regulated by HPr and iicbmtl-dependent phosphorylation. J. Biol. Chem. 274:4754-4763); mtrB (Gollnick, P., et al. 1990. The mtr locus is a two-gene operon required for transcription attenuation in the trp operon of *Bacillus subtilis*. Proc. Natl. Acad. Sci. 87:8726-8730); nhaX (Sohenshein, A. L., J. A. Hoch, and R. Losick (eds.) 2002. *Bacillus subtilis* and its closest relatives: from genes to cells. American Society for Microbiology, Washington D.C.); toxR gene product from *Vibrio cholerae* (Miller, V. L., and J. J. Mekalanos. 1984. Synthesis of cholera toxin is positively regulated at the transcriptional level by toxR. Proc. Natl. Acad. Sci. 81:3471-3475); padR gene product from *Pediococcus pentosaceus* (Barthelmebs, L., et al. 2000. Inducible metabolism of phenolic acids in *Pediococcus pentosaceus* is encoded by an autoregulated operon which involves a new class of negative transcriptional regulator. J. Bacteriol. 182:6724-6731); paiA (Sohenshein, A. L., J. A. Hoch, and R. Losick (eds.) 2002.

*Bacillus subtilis* and its closest relatives: from genes to cells. American Society for Microbiology, Washington D.C.); paiB (Id.); perA (Id.); phoP (Birkey, S. M., et al. 1994. A pho regulon promoter induced under sporulation conditions. Gene. 147:95-100); pksA (Sohenshein, A. L., J. A. Hoch, and R. Losick (eds.) 2002. *Bacillus subtilis* and its closest relatives: from genes to cells. American Society for Microbiology, Washington D.C.); pucR (Schultz, A. C., et al. 2001. Functional analysis of 14 genes that constitute the purine catabolic pathway in *Bacillus subtilis* and evidence for a novel regulon controlled by the PucR transcription activator. J. Bacteriol. 183:3293-3302); purR (Weng, M., et al. 1995. Identification of the *Bacillus subtilis* pur operon repressor. Proc. Natl. Acad. Sci. 92:7455-7459); pyrR (Martinussen, J., et al. 1995. Two genes encoding uracil phosphoribosyltransferase are present in *Bacillus subtilis*. J. Bacteriol. 177:271-274); rbsR (Rodionov, D. A., et al. 2001. Transcriptional regulation of pentose utilisation systems in the *Bacillus/Clostridium* group of bacteria. FEMS Microbiol. Lett. 205:305-314); resD (Suin, G., et al. 1996. Regulators of aerobic and anaerobic respiration in *Bacillus subtilis*. J. Bacteriol. 178:1374-1385); rocR (Gardan, R., et al. 1997. Role of the transcriptional activator RocR in the arginine-degradation pathway of *Bacillus subtilis*. Mol. Microbiol. 24:825-837); rsiX (Tortosa, P., et al. 2000. Characterization of ylbF, a new gene involved in competence development and sporulation in *Bacillus subtilis*. Mol. Microbiol. 35:1110-1119); sacT (Debarbouille, M., et al. 1990. The sacT gene regulating the sacPA operon in *Bacillus subtilis* shares strong homology with transcriptional antiterminators. J. Bacteriol. 172:3966-3973); sacV (Wong, S. L., et al. 1988. Cloning and nucleotide sequence of senN, a novel '*Bacillus natto*' (*B. subtilis*) gene that regulates expression of extracellular protein genes. J. Gen. Microbiol. 134:3269-3276); sacY (Steinmetz, M., et al 1989. Induction of saccharolytic enzymes by sucrose in *Bacillus subtilis*: evidence for two partially interchangeable regulatory pathways. J. Bacteriol. 171:1519-1523); senS (Wang, L. F., and R. H. Dori. 1990. Complex character of senS, a novel gene regulating expression of extracellular-protein genes of *Bacillus subtilis*. J. Bacteriol. 172:1939-1947); sinR (Bai, U., et al. 1993. SinI modulates the activity of SinR, a developmental switch protein of *Bacillus subtilis*, by protein-protein interaction. Genes Dev. 7:139-148); slr (Asayama, M., et al. 1998. Translational attenuation of the *Bacillus subtilis* spo0B cistron by an RNA structure encompassing the initiation region. Nucleic Acids Res. 26:824-830); splA (Fajardo-Cavazos, P., and W. L. Nicholson. 2000. The TRAP-like SplA protein is a trans-acting negative regulator of spore photoproduct lyase synthesis during *Bacillus subtilis* sporulation. J. Bacteriol. 182:555-560); spo0A (Smith, I., et al. 1991. The role of negative control in sporulation. Res. Microbiol. 142:831-839); spo0F (Lewandoski, M., et al. 1986. Transcriptional regulation of the spo0F gene of *Bacillus subtilis*. J. Bacteriol. 168:870-877); spoIIID (Kunkel, B., et al. 1989. Temporal and spatial control of the mother-cell regulatory gene spoIIID of *Bacillus subtilis*. Genes. Dev. 3:1735-1744); spoVT (Bagyan, I, et al. 1996. A compartmentalized regulator of developmental gene expression in *Bacillus subtilis*. J. Bacteriol. 178:4500-4507); tenA (Pang, A. S., et al. 1991. Cloning and characterization of a pair of novel genes that regulate production of extracellular enzymes in *Bacillus subtilis*. J. Bacteriol. 173:46-54); tenI (Sohenshein, A. L., J. A. Hoch, and R. Losick (eds.) 2002. *Bacillus subtilis* and its closest relatives: from genes to cells. American Society for Microbiology, Washington D.C.); tnrA (Wray, L. V., Jr., et al. 1996. TnrA, a transcription factor required for global nitrogen regulation in *Bacillus subtilis*. Proc. Natl. Acad. Sci. 93:8841-8845); treR (Schock, F., and M. K. Dahl. 1996. Expression of the tre operon of *Bacillus subtilis* 168 is regulated by the repressor TreR. J. Bacteriol. 178:4576-4581); xre (McDonnell, G. E., et al. 1994. Genetic control of bacterial suicide: regulation of the induction of PBSX in *Bacillus subtilis*. J. Bacteriol. 176:5820-5830); xylR gene product from *Bacillus megaterium* (Rygus, T., et al. 1991. Molecular cloning, structure, promoters and regulatory elements for transcription of the *Bacillus megaterium* encoded regulon for xylose utilization. Arch. Microbiol. 155:535:542); yacF (Sohenshein, A. L., J. A. Hoch, and R. Losick (eds.) 2002. *Bacillus subtilis* and its closest relatives: from genes to cells. American Society for Microbiology, Washington D.C.); and zur (Gaballa, A., and J. D. Helmann. 1998. Identification of a zinc-specific metalloregulatory protein, Zur, controlling zinc transport operons in *Bacillus subtilis*. J. Bacteriol. 180:5815-5821).

II.C.5.c. Other Eubacteria

Regulatory elements, promoters and other expression elements and factors from prokaryotes other than *E. coli* and *B. subtilis* include without limitation ahyRI gene product from *Aeromonas hydrophila* and *Aeromonas salmonicida* (Swift, S., et al. 1997. Quorum sensing in *Aeromonas hydrophila* and *Aeromonas salmonicida*: identification of the LuxRI homologs AhyRI and AsaRI and their cognate N-acylhomoserine lactone signal molecules. J. Bacteriol. 179:5271-5281); angR gene product from *Vibrio anguillarum* (Salinas, P. C., et al. 1989. Regulation of the iron uptake system in *Vibrio anguillarum*: evidence for a cooperative effect between two transcriptional activators. Proc. Natl. Acad. Sci. 86:3529-3522); aphA gene product from *Vibrio cholerae* (Kovacikova, G., and K. Skorupski. 2001. Overlapping binding sites for the virulence gene regulators AphA, AphB and cAMP-CRP at the *Vibrio cholerae* tcpPH promoter. Mol. Microbiol. 41:393-407); aphB gene product from *Vibrio cholerae* (Kovachikova, G., and K. Skorupski. 2000. Differential activation of the tcpPH promoter by AphB determines biotype specificity of virulence gene expression in *Vibrio cholerae*. J. Bacteriol. 182:3228-3238); comE gene product from *Streptococcus pneumoniae* (Ween, O., et al. 1999. Identification of DNA binding sites for ComE, a key regulator of natural competence in *Streptococcus pneumoniae*. Mol. Microbiol. 33:817-827); esaI gene product from *Pantoea stewartii* subsp. *stewartii* (von Bodman, S. B., et al. 1998. A negative regulator mediates quorum-sensing control of exopolysaccharide production in *Pantoea stewartii* subsp. *stewartii*. Proc. Natl. Acad. Sci. 95:7687-7692); esaR gene product from *Pantoea stewartii* subsp. *stewartii* (Id.); expI gene product from *Erwinia chrysanthemi* (Nasser, W., et al. 1998. Characterization of the *Erwinia chrysanthemi* expI-expR locus directing the synthesis of two N-acyl-homoserine lactone signal molecules. Mol. Microbiol. 29:1391-1405); expR gene product from *Erwinia chrysanthemi* (Id.); gacA gene product from *Pseudomonas aeruginosa* (Pessi, G., and D. Haas. 2001. Dual control of hydrogen cyanide biosynthesis by the global activator GacA in *Pseudomonas aeruginosa* PAO1. FEMS Microbiol. Lett. 200:73-78); hapR gene product from *Vibrio cholerae* (Jobling, M. G., and R. K. Holmes. Characterization of hapR, a positive regulator of the *Vibrio cholerae* HA/protease gene hap, and its identification as a functional homologue of the *Vibrio harveyi* luxR gene. Mol. Microbiol. 26:1023-1034); hlyR gene product from *Vibrio cholerae* (von Mechow, S., et al. 1985. Mapping of a gene that regulates hemolysin production in *Vibrio cholerae*. J. Bacteriol. 163:799-802); hupR gene product from *Vibrio vulnificus* (Litwin, C. M., and J. Quackenbush. 2001. Characterization of a *Vibrio vulnificus* LysR homologue, HupR, which regulates expression of the haem uptake outer membrane protein, HupA. Microb. Pathog. 31:295-307); lasR gene product from *Pseudomonas aerugenosa* (Gambella, M. J., and B. H. Iglewski. 1991. Cloning and characterization of the *Pseudomonas aeruginosa* lasR gene, a transcriptional activator of elastase expression. J. Bacteriol. 173:3000-3009); leuO gene product from *Salmonella enterica* serovar *Typhimurium* (Fang, M., and H. Y. Wu. 1998. A promoter relay mechanism for sequential gene activation. J. Bacteriol. 180:626-633); luxI gene product from *Vibrio cholerae* (Engebrecht, J., and M. Silverman. Nucleotide sequence of the regulatory locus controlling expression of bacterial genes for bioluminescence. Nucleic Acids Res. 15:10455-10467); luxO gene product from *Vibrio cholerae* (Bassler, B. L., et al. 1994. Sequence and function of LuxO, a negative regulator of luminescence in *Vibrio harveyi*. Mol. Microbiol. 12:403-412); luxR gene product from *Vibrio cholerae* (Engebrecht, J., and M. Silverman. Nucleotide sequence of the regulatory locus controlling expression of bacterial genes for bioluminescence. Nucleic Acids Res. 15:10455-10467); phzR gene product from *Pseudomonas aureofaciens* (Pierson, L. S., et al. 1994. Phenazine antibiotic biosynthesis in *Pseudomonas aureofaciens* 30-84 is regulated by PhzR in response to cell density. J. Bacteriol. 176:3966-3974); rhlR gene product from *Pseudomonas aeruginosa* (Ochsner, U. A. et al. 1994. Isolation and characterization of a regulatory gene affecting rhamnolipid biosurfactant synthesis in *Pseudomonas aeruginosa*. J. Bacteriol. 176:2044-2054); rsmA gene product from *Erwinia carotovora* subsp. *carotovora* (Cui, Y., et al. 1995. Identification of a global repressor gene, rsmA, of *Erwinia carotovora* subsp. *carotovora* that controls extracellular enzymes, N-(3-oxohexanoyl)-L-homoserine lactone, and pathogenicity in soft-rotting *Erwinia* spp. J. Bacteriol. 177: 5108-5115); rsmB gene product from *Erwinia carotovora* subsp. *carotovora* (Cui, Y., et al. 1999. rsmC of the soft-rotting bacterium *Erwinia carotovora* subsp. *carotovora* negatively controls extracellular enzyme and harpin(Ecc) production and virulence by modulating levels of regulatory RNA (rsmB) and RNA-binding protein (RsmA). J. Bacteriol. 181:6042-6052); sirA gene product from *Salmonella enterica* serovar *Typhimurium* (Goodier, R. I., and B. M. Ahmer. 2001. SirA orthologs affects both motility and virulence. J. Bacteriol. 183:2249-2258); taf gene product from *Vibrio cholerae* (Salinas, P. C., et al. 1989. Regulation of the iron uptake system in *Vibrio anguillarum*: evidence for a cooperative effect between two transcriptional activators. Proc. Natl. Acad. Sci. 86:3529-3522); tcpP gene product from *Vibrio cholerae* (Hase, C. C., and J. J. Mekalanos. 1998. TcpP protein is a positive regulator of virulence gene expression in *Vibrio cholerae*. Proc. Natl. Acad. Sci. 95:730-734); toxR gene product from *Vibrio cholerae* (Miller, V. L., and J. J. Mekalanos. 1984. Synthesis of cholera toxin is positively regulated at the transcriptional level by toxR. Proc. Natl. Acad. Sci. 81:3471-4375); toxS gene product from *Vibrio cholerae* (Miller, V. L., et al. 1989. Identification of toxS, a regulatory gene whose product enhances toxR-mediated activation of the cholera toxin promoter. J. Bacteriol. 171:1288-1293); toxT from *Vibrio cholerae* (Kaufman, M. R., et al. 1993. Biogenesis and regulation of the *Vibrio cholerae* toxin-coregulated pilus: analogies to other virulence factor secretory systems. Gene. 126:43-49); traM gene product from *Agrobacterium tumefaciens* (Faqua, C., et al. 1995. Activity of the *Agrobacterium* Ti plasmid conjugal transfer regulator TraR is inhibited by the product of the traM gene. J. Bacteriol. 177:1367-1373); traR gene product from *Agrobacterium tumefaciens* (Piper, K. R., et al. 1993. Conjugation factor of *Agrobacterium tumefaciens* regulates Ti plasmid transfer by autoinduction. Nature. 362:448-450); vicH gene product from *Vibrio cholerae* (Tendeng, C., et al. 2000. Isolation and characterization of vicH, encoding a new pleiotropic regulator in *Vibrio cholerae*. J. Bacteriol. 182:2026-2032); vspR gene product from *Vibrio cholerae* (Yildiz, F. H., et al. 2001. VpsR, a Member of the Response Regulators of the Two-Component Regulatory Systems, Is Required for Expression of vps Biosynthesis Genes and EPS(ETr)-Associated Phenotypes in *Vibrio cholerae* O1 El Tor. J. Bacteriol. 183:1716-1726); gadR gene product from *Lactococcus lactis* (Sanders, J. W., et al. 1997. A chloride-inducible gene expression cassette and its use in induced lysis of *Lactococcus lactis*. Appl. Environ. Microbiol. 63:4877-4882); hrpB gene product from *Pseudomonas solanacearum* (Van Gijsegem, F., et al. 1995. The hrp gene locus of *Pseudomonas solanacearum*, which controls the production of a type III secretion system, encodes eight proteins related to components of the bacterial flagellar biogenesis complex. Mol. Microbiol. 15:1095-1114); *carotovora* subsp. *carotovora* (Cui, Y., et al. 1995. Identification of a global repressor gene, rsmA, of *Erwinia carotovora* subsp. *carotovora* that controls extracellular enzymes, N-(3-oxohexanoyl)-L-homoserine lactone, and pathogenicity in soft-rotting *Erwinia* spp. J. Bacteriol. 177:5108-5115); rsmB gene product from *Erwinia carotovora* subsp. *carotovora* (Cui, Y., et al. 1999. rsmC of the soft-rotting bacterium *Erwinia carotovora* subsp. *carotovora* negatively controls extracellular enzyme and harpin(Ecc) production and virulence by modulating levels of regulatory RNA (rsmB) and RNA-binding protein (RsmA). J. Bacteriol. 181:6042-6052); sirA gene product from *Salmonella enterica* serovar *Typhimurium* (Goodier, R. I., and B. M. Ahmer. 2001. SirA orthologs affects both motility and virulence. J. Bacteriol. 183:2249-2258); taf gene product from *Vibrio cholerae* (Salinas, P. C., et al. 1989. Regulation of the iron uptake system in *Vibrio anguillarum*: evidence for a cooperative effect between two transcriptional activators. Proc. Natl. Acad. Sci. 86:3529-3522); tcpP gene product from *Vibrio cholerae* (Hase, C. C., and J. J. Mekalanos. 1998. TcpP protein is a positive regulator of virulence gene expression in *Vibrio cholerae*. Proc. Natl. Acad. Sci. 95:730-734); toxR gene product from *Vibrio cholerae* (Miller, V. L., and J. J. Mekalanos. 1984. Synthesis of cholera toxin is positively regulated at the transcriptional level by toxR. Proc. Natl. Acad. Sci. 81:3471-4375); toxS gene product from *Vibrio cholerae* (Miller, V. L., et al. 1989. Identification of toxS, a regulatory gene whose product enhances toxR-mediated activation of the cholera toxin promoter. J. Bacteriol. 171:1288-1293); toxT from *Vibrio cholerae* (Kaufman, M. R., et al. 1993. Biogenesis and regulation of the *Vibrio cholerae* toxin-coregulated pilus: analogies to other virulence factor secretory systems. Gene. 126:43-49); traM gene product from *Agrobacterium tumefaciens* (Faqua, C., et al. 1995. Activity of the *Agrobacterium* Ti plasmid conjugal transfer regulator TraR is inhibited by the product of the traM gene. J. Bacteriol. 177:1367-1373); traR gene product from *Agrobacterium tumefaciens* (Piper, K. R., et al. 1993. Conjugation factor of *Agrobacterium tumefaciens* regulates Ti plasmid transfer by autoinduction. Nature. 362:448-450); vicH gene product from *Vibrio cholerae* (Tendeng, C., et al. 2000. Isolation and characterization of vicH, encoding a new pleiotropic regulator in *Vibrio cholerae*. J. Bacteriol. 182:2026-2032); vspR gene product from *Vibrio cholerae* (Yildiz, F. H., et al. 2001. VpsR, a Member of the Response Regulators of the Two-Component Regulatory Systems, Is Required for Expression of vps Biosynthesis Genes and EPS(ETr)-Associated Phenotypes in *Vibrio cholerae* O1 El Tor. J. Bacteriol. 183:1716-1726); lrpA gene product from *Pyrococcus furiosus* (Brinkman, A. B., et al.

2000. An Lrp-like transcriptional regulator from the archaeon *Pyrococcus furiosus* is negatively autoregulated. J. Biol. Chem. 275:38160-38169); manR gene product from *Listeria monocytogenes* (Dalet, K., et al. 2001. A sigma(54)-dependent PTS permease of the mannose family is responsible for sensitivity of *Listeria monocytogenes* to mesentericin Y105. Microbiology. 147:3263-3269); msmR gene product from *Streptococcus mutans* (Russell, R. R., et al. 1992. A binding protein-dependent transport system in *Streptococcus mutans* responsible for multiple sugar metabolism. toxR gene product from *Vibrio cholerae* (Miller, V. L., and J. J. Mekalanos. 1984. Synthesis of cholera toxin is positively regulated at the transcriptional level by toxR. Proc. Natl. Acad. Sci. 81:3471-3475); padR gene product from *Pediococcus pentosaceus* (Barthelmebs, L., et al. 2000. Inducible metabolism of phenolic acids in *Pediococcus pentosaceus* is encoded by an autoregulated operon which involves a new class of negative transcriptional regulator. J. Bacteriol. 182:6724-6731); purR (Weng, M., et al. 1995); and xylR gene product from *Bacillus megaterium* (Rygus, T., et al. 1991. Molecular cloning, structure, promoters and regulatory elements for transcription of the *Bacillus megaterium* encoded regulon for xylose utilization. Arch. Microbiol. 155:535:542).

II.C.5.d. Bacteriophage and Transposable Elements

Regulatory elements, promoters and other expression elements from bacteriophage and transposable elements include without limitation cI gene product from bacteriophage lambda mation and/or segregated minicells (Reichardt, L. F. 1975. Control of bacteriophage lambda repressor synthesis: regulation of the maintenance pathway of the cro and cI products. J. Mol. Biol. 93:289-309); (Love, C. A., et al. 1996. Stable high-copy-number bacteriophage lambda promoter vectors for overproduction of proteins in *Escherichia coli*. Gene. 176:49-53); the c2 gene product from bacteriophage P22 (Gough, M., and S. Tokuno. 1975. Further structural and functional analogies between the repressor regions of phages P22 and lambda. Mol. Gen. Genet. 138:71-79); the cro gene from bacteriophage lambda (Reichardt, L. F. 1975. Control of bacteriophage lambda repressor synthesis: regulation of the maintenance pathway of the cro and cI products. J. Mol. Biol. 93:289-309); the ant gene from bacteriophage P22 (Youderian, P. et al. 1982. Sequence determinants of promotor activity. Cell. 30:843-853); the mnt gene from bacteriophage P22 (Gough, M. 1970. Requirement for a functional int product in temperature inductions of prophage P22 is mnt. J. Virol. 6:320-325; Prell, H. H. 1978. Ant-mediated transactivation of early genes in *Salmonella* prophage P22 by superinfecting virulent P22 mutants. Mol. Gen. Genet. 164:331-334); the tetR gene product from the TetR family of bacterial regulators or homologues of this gene or gene product found in Tn10 and other members of the bacteriophage, animal virus, Eubacteria, Eucarya or Archaea may be employed to increase the efficiency of gene expression and protein production in parent cells prior to minicell formation and/or segregated minicells (Moyed, H. S., and K. P. Bertrand. 1983. Mutations in multicopy Tn10 tet plasmids that confer resistance to inhibitory effects of inducers of tet gene expression. J. Bacteriol. 155: 557-564); the mnt gene product from bacteriophage SP6 mation and/or segregated minicells (Mead, D. A., et al. 1985. Single stranded DNA SP6 promoter plasmids for engineering mutant RNAs and proteins: synthesis of a 'stretched' preproparathyroid hormone. Nucleic Acids Res. 13:1103-1118); and the mnt gene product from bacteriophage T7 mation and/or segregated minicells (Steen, R., et al. 1986. T7 RNA polymerase directed expression of the *Escherichia coli* rrnB operon. EMBO J. 5:1099-1103).

II.C.5.e. Use of Site-Specific Recombination in Expression Systems

Included in the design of the invention are techniques that increase the efficiency of gene expression and protein production in minicells. By way of non-limiting example, these techniques may include modification of endogenous and/or exogenous regulatory elements responsible for activation and/or repression of proteins to be expressed from chromosomal and/or plasmid expression vectors. By way of non-limiting example, this system may be applied to any of the above regulatory elements/systems. Specifically, each of the above mentioned regulatory systems may be constructed such that the promotor regions are oriented in a direction away from the gene to be expressed, or each of the above mentioned gene(s) to be expressed may be constructed such that the gene(s) to be expressed is oriented in a direction away from the regulatory region promotor. Constructed in this system is a methodology dependent upon site-specific genetic recombination for inversion and induction of the gene of interest (Backman, K., et al. 1984. Use of synchronous site-specific recombination in vivo to regulate gene expression. Bio/Technology 2:1045-1049; Balakrishnan, R., et al. 1994. A gene cassette for adapting *Escherichia coli* strains as hosts for att-Int-mediated rearrangement and pL expression vectors. Gene 138:101-104; Hasan, N., and W. Szybalaki. 1987. Control of cloned gene expression by promoter inversion in vivo: construction of improved vectors with a multiple cloning site and the Ptac promotor. Gene 56:145-151; Wulfing, C., and A. Pluckthun. 1993. A versatile and highly repressible *Escherichia coli* expression system based on invertible promoters: expression of a gene encoding a toxic gene product. Gene 136:199-203). These invertible promoters and/or gene regions will allow tight regulation of potentially toxic protein products. By way of non-limiting example, these systems may be derived from bacteriophage lambda, bacteriophage Mu, and/or bacteriophage P22. In any of these potential systems, regulation of the recombinase may be regulated by any of the regulatory systems discussed in section II.C.5 and elsewhere herein.

II.C.5.e. Use of Copy Number Control Switches

A method that can be used to increase the efficiency of gene expression and protein production in minicells involves the modification of endogenous and/or introduction of exogenous genetic expression systems such that the number of copies of a gene encoding a protein to be expressed can be modulated. Copy number control systems comprise elements designed to modulate copy number in a controlled fashion.

In an exemplary mode, copy number is controlled to decrease the effects of "leaky" (uninduced) expression of toxic gene products. This allows one to maintain the integrity of a potentially toxic gene product during processes such as cloning, culture maintenance, and periods of growth prior to minicell-induction. That is, decreasing the copy number of a gene is expected to decrease the opportunity for mutations affecting protein expression and/or function to arise. Immediately prior to, during and/or after minicell formation, the copy number may be increased to optimize the gene dosage in minicells as desired.

The replication of eubacterial plasmids is regulated by a number of factors, some of which are contained within the plasmid, others of which are located on the chromosome. For reviews, see del Solar, G., et al. 2000. Plasmid copy number control: an ever-growing story. Mol Microbiol. 37:492-500; del Solar, G., et al. 1998. Replication and control of circular bacterial plasmids. Microbiol Mol Biol Rev. 62:434-64; and Filutowicz, M., et al. 1987. DNA and protein interactions in the regulation of plasmid replication. J Cell Sci Suppl. 7:15-31.

By way of non-limiting example, the pcnB gene product, the wildtype form of which promotes increased ColE1 plasmid copy number (Soderbom, F., et al. 1997. Regulation of plasmid R1 replication: PcnB and RNase E expedite the decay of the antisense RNA, CopA. Mol. Microbiol. 26:493-504), is modulated; and/or mutant forms of the pcnB gene are introduced into a cell. In an exemplary cell type that may be used in the methods of the invention, the wildtype pcnB chromosomal gene is replaced with a mutant pcnB80 allele (Lopilato, J., et al. 1986. Mutations in a new chromosomal gene of *Escherichia coli* K-12, pcnB, reduce plasmid copy number of pBR322 and its derivatives. Mol. Gen. Genet. 205:285-290). In such cells the copy number of a ColE1-derived plasmid is decreased. The cell may further comprise an expression element comprising an inducible promoter operably linked to an ORF encoding the wild-type pcnB. Because the wild-type pcnB gene is dominant to the mutant pcnB80 gene, and because the wild-type pcnB gene product promotes increased ColE1 plasmid copy number, induction of a wild-type pcnB in the pcnB80 background will increase the plasmid copy number of ColE1-derived plasmids. Such copy number control systems may be expressed from the chromosome and/or plasmid to maintain either low or high plasmid copy number in the absence of induction. Other non-limiting examples of gene and/or gene products that may be employed in copy number control systems for ColE1-based replicons include genes or homologs of genes encoding RNA I, RNA II, rop, RNAse H, enzymes involved in the process of polyadenylation, RNAse E, DNA polymerase I, and DNA polymerase III.

In the case of IncFII-derived replicons, non-limiting examples of gene and/or gene products that may be employed in copy number control systems to control plasmid copy include genes or homologs of the copA, copB, repA, and repB genes. Copy number control systems may additionally or alternatively include manipulation of repC, trfA, dnaA, dnaB, dnaC, seqA, genes protein Pi, genes encoding HU protein subunits (hupA, hupB) and genes encoding IHF subunits.

Other elements may also be included to optimize these plasmid copy number control systems. Such additional elements may include the addition or deletion of iteron nucleic acid sequences (Chattoraj, D. K. 2000. Control of plasmid DNA replication by iterons: no longer paradoxical. Mol. Microbiol. 37:467-476), and modification of chaperone proteins involved in plasmid replication (Konieczny, I., et al. 1997. The replication initiation protein of the broad-host-range plasmid RK2 is activated by the ClpX chaperone. Proc Natl Acad Sci USA 94:14378-14382).

II.C.6. Transportation of Inducible and Inhibitory Compounds

Included in the design of the invention are techniques that increase the efficiency of gene expression and protein production in minicells. By way of non-limiting example, these techniques may include utilization and/or modification of factors and systems that modulate the transport of compounds, including but not limited to inducers and/or inhibitors of expression elements that control expression of a gene in a parent cell prior to minicell formation and/or in segregated minicells. Such manipulations may result in increased or decreased production, and/or changes in the intramolecular and intermolecular functions, of a protein in a minicell or its parent cell. The techniques may be employed to increase the efficiency of gene expression and protein production in parent cells prior to minicell formation and/or in segregated minicells.

II.C.6.a. *Escherichia coli* Genes

By way of non-limiting example, manipulation of the abpS gene or gene product from *E. coli*, or homologs of this gene or gene product found in other members of the Prokaryotes, Eukaryotes, Archaebacteria and/or organelles (e.g., mitochondria, chloroplasts, plastids and the like) may be employed to increase the efficiency of gene expression and protein production in parent cells prior to minicell formation and/or in segregated minicells (Celis, R. T. 1982. Mapping of two loci affecting the synthesis and structure of a periplasmic protein involved in arginine and ornithine transport in *Escherichia coli* K-12. J. Bacteriol. 151(3):1314-9).

In addition to abpS, other exemplary *E. coli* genes encoding factors involved in the transport of inducers, inhibitors and other compounds include, but are not limited to, araE (Khlebnikov, A., et al. 2001. Homogeneous expression of the P(BAD) promoter in *Escherichia coli* by constitutive expression of the low-affinity high-capacity AraE transporter. Microbiology. 147(Pt 12):3241-7); araG (Kehres, D. G., and Hogg, R. W. 1992. *Escherichia coli* K12 arabinose-binding protein mutants with altered transport properties. Protein Sci. 1(12):1652-60); araH (Id.); argP (Celis, R. T. 1999. Repression and activation of arginine transport genes in *Escherichia coli* K 12 by the ArgP protein. J. Mol Biol. 17; 294(5):1087-95); aroT (aroR, trpR) (Edwards, R. M., and Yudkin, M. D. 1982. Location of the gene for the low-affinity tryptophan-specific permease of *Escherichia coli*. Biochem. J. 204(2): 617-9); artI (Wissenbach, U., et al. 1995. A third periplasmic transport system for L-arginine in *Escherichia coli*: molecular characterization of the artPIQMJ genes, arginine binding and transport. Mol. Microbiol. 17(4):675-86); artJ (Id.); artM (Id.); artP (Id.); artQ (Id.); bioP (bir, birB) (Campbell, A., et al. Biotin regulatory (bir) mutations of *Escherichia coli*. 1980. J. Bacteriol. 142(3):1025-8); brnQ (hrbA) (Yamato, I., and Anraku, Y. 1980. Genetic and biochemical studies of transport systems for branched-chain amino acids in *Escherichia coli* K-12: isolation and properties of mutants defective in leucine-repressible transport activities. J. Bacteriol. 144 (1):36-44); brnR (Id.); brnS (Id.); brnT (Id.); btuC (Friedrich, M. J., et al. 1986. Nucleotide sequence of the btuCED genes involved in vitamin B12 transport in *Escherichia coli* and homology with components of periplasmic-binding-protein-dependent transport systems. J. Bacteriol. 167(3):928-34); btuD (Id.) (Friedrich, M. J., et al. 1986. Nucleotide sequence of the btuCED genes involved in vitamin B12 transport in *Escherichia coli* and homology with components of periplasmic-binding-protein-dependent transport systems. J. Bacteriol. 167(3):928-34); caiT (Eichler, K. 1994. Molecular characterization of the cai operon necessary for carnitine metabolism in *Escherichia coli*. Mol. Microbiol. 13(5):775-86); celA (Parker, L. L., and Hall, B. G. 1990. Characterization and nucleotide sequence of the cryptic cel operon of *Escherichia coli* K12. Genetics. 124(3):455-71); celB (Id.); celC (Id.); citA (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein); citB (Id.); codB (Danielsen, S., et al. 1992. Characterization of the *Escherichia coli* codBA operon encoding cytosine permease and cytosine deaminase. Mol. Microbiol. 6(10):1335-44); cysA (Karbonowska, H., et al. 1977. Sulphate permease of *Escherichia coli* K12. Acta. Biochim. Pol. 24(4):329-34);

cysU (cysT) (Sirko, A., et al. 1995. Sulfate and thiosulfate transport in *Escherichia coli* K-12: evidence for a functional overlapping of sulfate- and thiosulfate-binding proteins. J. Bacteriol. 177(14):4134-6); cysW (Id.); dctA (Lo, T. C., and Bewick, M. A. 1978. The molecular mechanisms of dicarboxylic acid transport in *Escherichia coli* K12. The role and orientation of the two membrane-bound dicarboxylate binding proteins. J. Biol. Chem. 10; 253(21):7826-31); dctB (Id.); dcuA (genA) (Six, S., et al. 1994. *Escherichia coli* possesses two homologous anaerobic C4-dicarboxylate membrane transporters (DcuA and DcuB) distinct from the aerobic dicarboxylate transport system (Dct). J. Bacteriol. 176(21): 6470-8); dcuB (genF) (.); dgoT (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein); exuT (Nemoz, G., et al. 1976. Physiological and genetic regulation of the aldohexuronate transport system in *Escherichia coli*. J. Bacteriol. 127(2):706-18); fepD (Ozenberger, B. A., et al. 1987. Genetic organization of multiple fep genes encoding ferric enterobactin transport functions in *Escherichia coli*. J. Bacteriol. 169(8):3638-46); fepG (Chenault, S. S., and Earhart, C. F. 1991. Organization of genes encoding membrane proteins of the *Escherichia coli* ferrienterobactin permease. Mol. Microbiol. 5(6):1405-13); fucP (prd) (Chen, Y. M. 1987. The organization of the fuc regulon specifying L-fucose dissimilation in *Escherichia coli* K12 as determined by gene cloning. Mol. Gen. Genet. 210 (2):331-7); glnP (Masters, P. S., and Hong, J. S. 1981. Genetics of the glutamine transport system in *Escherichia coli*. J. Bacteriol. 147(3):805-19); glnQ (Nohno, T. 1986. Cloning and complete nucleotide sequence of the *Escherichia coli* glutamine permease operon (glnHPQ). Mol. Gen. Genet. 205 (2):260-9); glnR (Masters, P. S., and Hong, J. S. 1981. Genetics of the glutamine transport system in *Escherichia coli*. J. Bacteriol. 147(3):805-19); glpT (Boos, W., et al. 1977. Purification and properties of a periplasmic protein related to sn-glycerol-3-phosphate transport in *Escherichia coli*. Eur. J. Biochem. 72(3):571-81); gltP (Deguchi, Y., et al. 1989. Molecular cloning of gltS and gltP, which encode glutamate carriers of *Escherichia coli*. B. J. Bacteriol. 171(3):1314-9); gltS (Id.); gntR (Bachi, B., and Kornberg, H. L. 1975. Genes involved in the uptake and catabolism of gluconate by *Escherichia coli*. J. Gen. Microbiol. 90(2):321-35); gntS (Id.); gntT (gntM, usgA) (Id.); gntU (Tong, S. 1996. Cloning and molecular genetic characterization of the *Escherichia coli* gntR, gntK, and gntU genes of GntI, the main system for gluconate metabolism. J. Bacteriol. 178(11):3260-9); hisM (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein); hisP (Id.); hisQ (Id.); livG (hrbB, hrbC, hrbD) (Landick, R., et al. 1980. Regulation of high-affinity leucine transport in *Escherichia coli*. J. Supramol. Struct. 14(4):527-37); livH (hrbB, hrbC, hrbD) (Id.); livJ (hrbB, hrbC, hrbD) (Id.); livK (hrbB, hrbC, hrbD) (Id.); livM (Id.); lldP (lctP) (Dong, J. M., et al. 1993. Three overlapping lct genes involved in L-lactate utilization by *Escherichia coli*. J. Bacteriol. 175(20):6671-8); lysP (cadR) (Steffes, C., et al. 1992. The lysP gene encodes the lysine-specific permease. J. Bacteriol. 174(10):3242-9); malF (malB) (Bavoil, P., et al. 1980. Identification of a cytoplasmic membrane-associated component of the maltose transport system of *Escherichia coli*. J. Biol. Chem. 255(18): 8366-9); malG (malB) (Dassa, E., and Hofnung, M. 1985. Sequence of gene malG in *E. coli* K12: homologies between integral membrane components from binding protein-dependent transport systems. EMBO J. 4(9):2287-93); malK (malB) (Id.); mglC (PMG, mglP) (Harayama, S. 1983. Characterization of the mgl operon of *Escherichia coli* by transposon mutagenesis and molecular cloning. J. Bacteriol. 153 (1):408-15); nanT (Vimr, E. R., and Troy, F. A. 1985. Identification of an inducible catabolic system for sialic acids (nan) in *Escherichia coli*. J. Bacteriol. 164(2):845-53); nupC (cru) (Craig, J. E., et al. 1994. Cloning of the nupC gene of *Escherichia coli* encoding a nucleoside transport system, and identification of an adjacent insertion element, IS 186. Mol. Microbiol. 11(6):1159-68); nupG (Westh Hansen, S. E., et al. 1987. Studies on the sequence and structure of the *Escherichia coli* K-12 nupG gene, encoding a nucleoside-transport system. Eur. J. Biochem. 168(2):385-91); panF (Vallari, D. S., and Rock, C. O. 1985. Isolation and characterization of *Escherichia coli* pantothenate permease (panF) mutants. J. Bacteriol. 164(1):136-42); potA (Kashiwagi, K., et al. 1993. Functions of potA and potD proteins in spermidine-preferential uptake system in *Escherichia coli*. J. Biol. Chem. 268 (26):19358-63); potG (Pistocchi, R., et al. 1993. Characteristics of the operon for a putrescine transport system that maps at 19 minutes on the *Escherichia coli* chromosome. J. Biol. Chem. 268(1):146-52); potH (Id.); potI (Id.); prop (Wood, J. M., and Zadworny, D. 1980. Amplification of the put genes and identification of the put gene products in *Escherichia coli* K12. Can. J. Biochem. 58(10):787-96); proT (Id.); proV (proU) (Faatz, E., et al. 1988. Cloned structural genes for the osmotically regulated binding-protein-dependent glycine betaine transport system (ProU) of *Escherichia coli* K-12. Mol. Microbiol. 2(2):265-79); proW (proU) (Id.); proX (pro U) (Id.); pstA (R2pho, phoR2b, phoT) (Amemura, M., et al. 1985. Nucleotide sequence of the genes involved in phosphate transport and regulation of the phosphate regulon in *Escherichia coli*. J. Mol. Biol. 184(2):241-50); pstB (phoT) (Id.); pstC (phoW) (Rao, N. N., and Torriani, A. 1990. Molecular aspects of phosphate transport in *Escherichia coli*. Mol. Microbiol. 4(7):1083-90); pstS (R2pho, nmpA, phoR2a, phoS) (Makino, K., et al. 1988. Regulation of the phosphate regulon of *Escherichia coli*. Activation of pstS transcription by PhoB protein in vitro. J. Mol. Biol. 203(1): 85-95); purP (Burton, K. 1994. Adenine transport in *Escherichia coli*. Proc. R. Soc. Lond. B. Biol. Sci. 255(1343):153-7); putP (Stalmach, M. E., et al. 1983. Two proline porters in *Escherichia coli* K-12. J. Bacteriol. 156(2):481-6); rbsA (rbsP, rbsT) (Iida, A., et al. 1984. Molecular cloning and characterization of genes required for ribose transport and utilization in *Escherichia coli* K-12. J. Bacteriol. 158(2):674-82); rbsC (rbsP, rbsT) (Id.); rbsD (rbsP) (Id.); rhaT (Baldoma, L., et al. 1990. Cloning, mapping and gene product identification of rhaT from *Escherichia coli* K12. FEMS Microbiol. Lett. 60(1-2):103-7); sdaC (Shao, Z., et al. 1994. Sequencing and characterization of the sdaC gene and identification of the sdaCB operon in *Escherichia coli* K12. Eur. J. Biochem. 222(3):901-7); tnaB (trpP) (Sarsero, J. P., et al. 1991. A new family of integral membrane proteins involved in transport of aromatic amino acids in *Escherichia coli*. J. Bacteriol. 173 (10):3231-4); tyrR (Whipp, M. J., and Pittard, A. J. 1977. Regulation of aromatic amino acid transport systems in *Escherichia coli* K-12. J. Bacteriol. 132(2):453-61); ugpC (Schweizer, H., and Boos, W. 1984. Characterization of the ugp region containing the genes for the phoB dependent sn-glycerol-3-phosphate transport system of *Escherichia coli*. Mol. Gen. Genet. 197(1):161-8); uhpT (Weston, L. A., and Kadner, R. J. 1987. Identification of uhp polypeptides and evidence for their role in exogenous induction of the sugar phosphate transport system of *Escherichia coli* K-12. J. Bacteriol. 169(8):3546-55); and xylF (xylT) (Sumiya, M., et al. 1995. Molecular genetics of a receptor protein for D-xylose, encoded by the gene xylF, in *Escherichia coli*. Receptors Channels. 3(2):117-28).

II.C.6.b. *Bacillus subtilis* Genes

By way of non-limiting example, manipulation of the aapA gene or gene product from *B. subtilis*, or homologs of this gene or gene product found in other members of the Prokaryotes, Eukaryotes, Archaebacteria and/or organelles (e.g., mitochondria, chloroplasts, plastids and the like) may be employed to increase the efficiency of gene expression and protein production in parent cells prior to minicell formation and/or in segregated minicells (Sohenshein, A. L., J. A. Hoch, and R. Losick (eds.) 2002. *Bacillus subtilis* and its closest relatives: from genes to cells. American Society for Microbiology, Washington D.C.).

In addition to aapA, other exemplary *B. subtilis* genes encoding factors involved in the transport of inducers, inhibitors and other compounds include, but are not limited to, amyC (Sekiguchi, J., et al. 1975. Genes affecting the productivity of alpha-amylase in *Bacillus subtilis*. J. Bacteriol. 121 (2):688-94); amyD (Id.); araE (Sa-Nogueira, I., and Mota, L. J. 1997. Negative regulation of L-arabinose metabolism in *Bacillus subtilis*: characterization of the araR (araC) gene. J. Bacteriol. 179(5):1598-608); araN (Sa-Nogueira, I., et al. 1997. The *Bacillus subtilis* L-arabinose (ara) operon: nucleotide sequence, genetic organization and expression. Microbiology. 143 (Pt 3):957-69); araP (Id.); araQ (Id.); csbC (Akbar, S., et al. 1999. Two genes from *Bacillus subtilis* under the sole control of the general stress transcription factor sigmaB. Microbiology. 145 (Pt 5):1069-78); cysP (Mansilla, M. C., and de Mendoza, D. 2000. The *Bacillus subtilis* cysP gene encodes a novel sulphate permease related to the inorganic phosphate transporter (Pit) family. Microbiology. 146 (Pt 4):815-21); dctB (Sohenshein, A. L., J. A. Hoch, and R. Losick (eds.) 2002. *Bacillus subtilis* and its closest relatives: from genes to cells. American Society for Microbiology, Washington D.C.); exuT (Rivolta, C., et al. 1998. A 35.7 kb DNA fragment from the *Bacillus subtilis* chromosome containing a putative 12.3 kb operon involved in hexuronate catabolism and a perfectly symmetrical hypothetical catabolite-responsive element. Microbiology. 144 (Pt 4):877-84); gabP (Ferson, A. E., et al. 1996. Expression of the *Bacillus subtilis* gabP gene is regulated independently in response to nitrogen and amino acid availability. Mol. Microbiol. 22(4): 693-701); gamP (Sohenshein, A. L., J. A. Hoch, and R. Losick (eds.) 2002. *Bacillus subtilis* and its closest relatives: from genes to cells. American Society for Microbiology, Washington D.C.); glcP (Paulsen, I. T., et al. 1998. Characterization of glucose-specific catabolite repression-resistant mutants of *Bacillus subtilis*: identification of a novel hexose:H+ symporter. J. Bacteriol. 180(3):498-504); glcU (Sohenshein, A. L., J. A. Hoch, and R. Losick (eds.) 2002. *Bacillus subtilis* and its closest relatives: from genes to cells. American Society for Microbiology, Washington D.C.); glnH (Id.); glnM (Id); glnP (Sohenshein, A. L., J. A. Hoch, and R. Losick (eds.) 2002. *Bacillus subtilis* and its closest relatives: from genes to cells. American Society for Microbiology, Washington D.C.); glnQ (Id.); glpT (Nilsson, R. P., et al. 1994. The glpT and glpQ genes of the glycerol regulon in *Bacillus subtilis*. Microbiology. 140 (Pt 4):723-30); gltP (Tolner, B., et al. 1995. Characterization of the proton/glutamate symport protein of *Bacillus subtilis* and its functional expression in *Escherichia coli*. J. Bacteriol. 177(10):2863-9); gltT (Tolner, B., et al. 1995. Characterization of the proton/glutamate symport protein of *Bacillus subtilis* and its functional expression in *Escherichia coli*. J. Bacteriol. 177(10):2863-9); gntP (Reizer, A., et al. Analysis of the gluconate (gnt) operon of *Bacillus subtilis*. Mol. Microbiol. 5(5):1081-9); gutP (Sohenshein, A. L., J. A. Hoch, and R. Losick (eds.) 2002. *Bacillus subtilis* and its closest relatives: from genes to cells. American Society for Microbiology, Washington D.C.); hutM (Oda, M., et al. 1988. Cloning and nucleotide sequences of histidase and regulatory genes in the *Bacillus subtilis* but operon and positive regulation of the operon. J. Bacteriol. 170(7):3199-205); iolF (Sohenshein, A. L., J. A. Hoch, and R. Losick (eds.) 2002. *Bacillus subtilis* and its closest relatives: from genes to cells. American Society for Microbiology, Washington D.C.); kdgT (Pujic, P., et al. 1998. The kdgRKAT operon of *Bacillus subtilis*: detection of the transcript and regulation by the kdgR and ccpA genes. Microbiology. 144 (Pt 11):3111-8); lctP (Cruz, Ramos H., et al. 2000. Fermentative metabolism of *Bacillus subtilis*: physiology and regulation of gene expression. J. Bacteriol. 182(11):3072-80); maeN (Ito, M., et al. 2000. Effects of nonpolar mutations in each of the seven *Bacillus subtilis* mrp genes suggest complex interactions among the gene products in support of Na(+) and alkali but not cholate resistance. J. Bacteriol. 182(20):5663-70); malP (Sohenshein, A. L., J. A. Hoch, and R. Losick (eds.) 2002. *Bacillus subtilis* and its closest relatives: from genes to cells. American Society for Microbiology, Washington D.C.); manP (Id.); mleN (Id.); nasA (Ogawa, K., et al. 1995. The nasB operon and nasA gene are required for nitrate/nitrite assimilation in *Bacillus subtilis*. J. Bacteriol. 177(5):1409-13); nupC (Sohenshein, A. L., J. A. Hoch, and R. Losick (eds.) 2002. *Bacillus subtilis* and its closest relatives: from genes to cells. American Society for Microbiology, Washington D.C.); opuAB (Kempf, B., et al. 1997. Lipoprotein from the osmoregulated ABC transport system OpuA of *Bacillus subtilis*: purification of the glycine betaine binding protein and characterization of a functional lipidless mutant. J. Bacteriol. 179(20):6213-20); opuBA (Sohenshein, A. L., J. A. Hoch, and R. Losick (eds.) 2002. *Bacillus subtilis* and its closest relatives: from genes to cells. American Society for Microbiology, Washington D.C.); pbuG (Saxild, H. H., et al. 2001. Definition of the *Bacillus subtilis* PurR operator using genetic and bioinformatic tools and expansion of the PurR regulon with glyA, guaC, pbuG, xpt-pbuX, yqhZ-folD, and pbuO. J. Bacteriol. 183(21):6175-83); pbuX (Saxild, H. H., et al. 2001. Definition of the *Bacillus subtilis* PurR operator using genetic and bioinformatic tools and expansion of the PurR regulon with glyA, guaC, pbuG, xpt-pbuX, yqhZ-folD, and pbuO. J. Bacteriol. 183(21):6175-83); pstC (Takemaru, K., et al. 1996. A *Bacillus subtilis* gene cluster similar to the *Escherichia coli* phosphate-specific transport (pst) operon: evidence for a tandemly arranged pstB gene. Microbiology. 142 (Pt 8):2017-20); pstS (Qi, Y., et al. 1997. The pst operon of *Bacillus subtilis* has a phosphate-regulated promoter and is involved in phosphate transport but not in regulation of the pho regulon. J. Bacteriol. 179(8):2534-9); pucJ (Schultz, A. C., et al. 2001. Functional analysis of 14 genes that constitute the purine catabolic pathway in *Bacillus subtilis* and evidence for a novel regulon controlled by the PucR transcription activator. J. Bacteriol. 183(11):3293-302); pucK (Schultz, A. C., et al. 2001. Functional analysis of 14 genes that constitute the purine catabolic pathway in *Bacillus subtilis* and evidence for a novel regulon controlled by the PucR transcription activator. J. Bacteriol. 183(11):3293-302); pyrP (Turner, R. J., et al. 1994. Regulation of the *Bacillus subtilis* pyrimidine biosynthetic (pyr) gene cluster by an autogenous transcriptional attenuation mechanism. J. Bacteriol. 176(12):3708-22); rbsB (Sohenshein, A. L., J. A. Hoch, and R. Losick (eds.) 2002. *Bacillus subtilis* and its closest relatives: from genes to cells. American Society for Microbiology, Washington D.C.); rbsC (Sohenshein, A. L., J. A. Hoch, and R. Losick (eds.) 2002. *Bacillus subtilis* and its closest relatives: from genes to cells. American Society for Microbiology, Washington D.C.); rbsD (Id.); rocC (Gardan, R., et al. 1995. Expression of the rocDEF operon involved in arginine catabolism in *Bacillus subtilis*. J. Mol. Biol. 23; 249(5):843-56); rocE (Gardan, R., et al. 1995. Expression of the rocDEF operon involved in arginine catabolism in *Bacillus subtilis*. J. Mol. Biol. 23; 249(5):843-56); ssuA (Coppee, J. Y., et al. 2001. Sulfur-limitation-regulated proteins in *Bacillus subtilis*: a two-dimensional gel electrophoresis study. Microbiology. 147(Pt 6):1631-40); ssuB (van der Ploeg, J. R., et al. 1998. *Bacillus subtilis* genes for the utilization of sulfur from aliphatic sulfonates. Microbiology. 144 (Pt 9):2555-61); ssuC (van der Ploeg, J. R., et al. 1998. *Bacillus subtilis* genes for the utilization of sulfur from aliphatic sulfonates. Microbiology. 144 (Pt 9):2555-61); treP (Yamamoto, H., et al. 1996. Cloning and sequencing of a 40.6 kb segment in the 73 degrees-76 degrees region of the *Bacillus subtilis* chromosome containing genes for trehalose metabolism and acetoin utilization. Microbiology. 142 (Pt 10:3057-65); xynP (Sohenshein, A. L., J. A. Hoch, and R. Losick (eds.) 2002. *Bacillus subtilis* and its closest relatives: from genes to cells. American Society for Microbiology, Washington D.C.); ybaR (Id.); ybgF (Id.); ybgH (Id.); ycbE (Id.); ycgO (Id.); yckI (Id.); yckJ (Id.); yckK (Id.); ydgF (Id.); yecA (Borriss, R., et al. 1996. The 52 degrees-55 degrees segment of the *Bacillus subtilis* chromosome: a region devoted to purine uptake and metabolism, and containing the genes cotA, gabP and guaA and the pur gene cluster within a 34960 bp nucleotide sequence. Microbiology. 142 (Pt 11): 3027-31); yesP (Sohenshein, A. L., J. A. Hoch, and R. Losick (eds.) 2002. *Bacillus subtilis* and its closest relatives: from genes to cells. American Society for Microbiology, Washington D.C.); yesQ (Id.): yflS (Id.); yhcL (Id.); yhjB (Id.); yjkB (Id.); ykbA (Id.); yoaB (Id.); yocN (Id.); yodF (Id.); yojA (Id.); yqiY (Id.); ytlD (Id.); ytlP (Id.); ytmL (Id.); ytmM (Id.); ytnA (Id.); yurM (Id.); yurN (Id.); yvbW (Id.); yvdH (Id.); yvdl (Id.); yveA (Pereira, Y., et al. 2001. The yveB gene, Encoding endolevanase LevB, is part of the sacB-yveB-yveA levansucrase tricistronic operon in *Bacillus subtilis*. Microbiology. 147(Pt 12):3413-9); yvfH (Sohenshein, A. L., J. A. Hoch, and R. Losick (eds.) 2002. *Bacillus subtilis* and its closest relatives: from genes to cells. American Society for Microbiology, Washington D.C.); yvfL (Id.); yvfM (Id.); yvgM (Id.); yvrO (Id.); yvsH (Id.); ywbF (Id.); ywcJ (Id.); ywoD (Id.); ywoE (Id.); yxeN (Id.); and yxeR (Id.).

II.C.7. Catabolite Repression

Included in the design of the invention are techniques that increase the efficiency of gene expression and protein production in minicells. By way of non-limiting example, these techniques may include utilization and/or modification of factors and systems involved in the synthesis, degradation or transport of catabolites that modulate the genetic expression of a preselected protein. Such manipulations may result in increased or decreased production, and/or changes in the intramolecular and intermolecular functions, of a protein in a minicell or its parent cell; in the latter instance, the protein may be one that is desirably retained in segregated minicells.

By way of non-limiting example, it is known in the art to use promoters from the trp, cst-1, and llp operons of *E. coli*, which are induced by, respectively, reduced tryptophan levels, glucose starvation, and lactose. Manipulation of the catabolites tryptophan, glucose and lactose, respectively, will influence the degree of expression of genes operably linked to these promoters. (Makrides, Savvas C., Strategies for Achieving High-Level Expression of Genes in *Escherichia coli*. Microbiological Reviews. 1996. 60:512-538.)

As another non-limiting example, expression elements from the *E. coli* L-arabinose (ara) operon are used in expression systems. AraC is a protein that acts as a repressor of ara genes in the absence of arabinose, and also as an activator of ara genes when arabinose is present. Induction of ara genes also involves cAMP, which modulates the activity of CRP (cAMP receptor protein), which in turn is required for full induction of ara genes (Schleif, Robert, Regulation of the L-arabinose operon of *Escherichia coli*. 2000. TIG 16:559-564. Thus, maximum expression from an ara-based expression system is achieved by adding cAMP and arabinose to host cells, and optimizing the expression of CRP in hostcells.

As one example, manipulation of the acpS gene or gene product of *E. coli* (Pollacco M. L., and J. E. Cronan Jr. 1981. A mutant of *Escherichia coli* conditionally defective in the synthesis of holo-[acyl carrier protein]. J. Biol. Chem. 256: 5750-5754); or homologs of this gene or its gene product found in other prokaryotes, eukaryotes, archaebacteria or organelles (mitochondria, chloroplasts, plastids and the like) may be employed to increase the efficiency of gene expression and protein production in parent cells prior to minicell formation and/or in segregated minicells.

In addition to acpS, other exemplary *E. coli* genes include the b2383 gene (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein. b2387 gene; the celA gene (Parker L. L., and B. G. Hall. 1990. Characterization and nucleotide sequence of the cryptic cel operon of *Escherichia coli* K12. Genetics. 124:455-471); the celB gene (Cole S. T., and B. Saint-Joanis, and A. P. Pugsley. 1985. Molecular characterisation of the colicin E2 operon and identification of its products. Mol Gen Genet. 198:465-472); the celC gene (Parker L. L., and B. G. Hall. 1990. Characterization and nucleotide sequence of the cryptic cel operon of *Escherichia coli* K12. Genetics. 124:455-471); the cmtB gene (Ezhova N. M., Zaikina, N. A, Shataeva, L. K., Dubinina, N. I., Ovechkina, T. P. and J. V. Kopylova. [Sorption properties of carboxyl cation exchangers with a bacteriostatic effect]. 1980. Prikl Bioikhim Mikrobiol. 16:395-398); the creB gene (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein; the creC gene (Wanner B. L. Gene regulation by phosphate in enteric bacteria. 1993. J Cell Biochem. 51:47-54); the crp gene (Sabourn D., and J. Beckwith. Deletion of the *Escherichia coli* crp gene. 1975. J Bacteriology. 122:338-340); the crr (gsr, iex, tgs, treD) gene (Jones-Mortimer M. C., and H. L. Kornberg, and r. Maltby, and P. D. Watts. Role of the crr-gene in glucose uptake by *Escherichia coli*. 1977. FEBS Lett. 74:17-19); the cya gene (Bachi B., and H. L. Kornberg. Utilization of gluconate by *Escherichia coli*. A role of adenosine 3':5'-cyclic monophosphate in the induction of gluconate catabolism. 1975. Biochem J. 150:123-128); the fruA gene (Prior T. I., and H. L. Kornberg. Nucleotide sequence of fruA, the gene specifying enzyme Iifru of the phosphoenopyruvate-dependent sugar phosphotranssferase system in *Escherichia coli* K12. 1988. J Gen Microbiol. 134:2757-2768); the fruB gene (Bol'shakova T. N. and R. S. Erlagaeva, and Dobrynina Oiu, and V. N. Gershanovich. [Mutation fruB in the fructose regulon affeting beta-galactosidase synthesis and adenylate cyclase activity of *E. coli* K12]. 1988. Mol Gen Mikrobiol virusol. 3:33-39); the fruR gene (Jahreis K., and P. W. Postma, and J. W. Lengeler. Nucleotide sequence of the ilvH-frR gene region of *Escherichia coli* K12 and *Salmonella typhimurium* LT2. 1991. Mol Gen Genet. 226:332-336); the frvA gene (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein); the frwB gene (Id.); the frvD gene (Id.); the gatB gene (Nobelmann B., and J. W. Lengeler. Molecular analysis of the gat genes from *Escherichia coli* and of their roles in galactitol transport and metabolism. 1996. J Bacteriol. 178:6790-6795); the gatC gene (Id.); the malX gene (Reidel J., W. Boos. The malX malY operon of *Escherichia coli* encodes a novel enzyme II of the photophotransferase system recognizing glucose and maltose and an enzyme abolishing the endogenous induction of the maltose system. 1991. J Bacteriol. 173:4862-4876); the manX (gptB, mpt, ptsL, ptsM, ptsX, manIII) gene (Plumbridge J., and A. Kolb. CAP and Nag repressor binding to the regulatory regions of the nagE-B and manX genes of *Escherichia coli*. 1991. J Mol Biol. 217:661-679); the manY (pel, ptsM, ptsP, manPII) gene (Henderson P. J., and R. A. Giddens, and M. C. Jones-Mortimer. Transport of galactose, glucose and their molecular analogues by *Escherichia coli* K12. 1977. Biochem J. 162:309-320); the manZ (gptB, mpt, ptsM, ptsX) gene (Williams N., and D. K. Fox, and C. Shea and S. Roseman. Pel, the protein that permits lambda DNA penetration of *Escherichia coli*, is encoded by a gene in ptsM and is required for mannose utilization by the phosphotransferase system. 1986. Proc Natl Acad Sci USA. 83:8934-8938); the mtlA gene (Lengeler J. Mutations affecting transport of the hexitols D-mannitol, D-glucitol, and galactitol in *Escherichia coli* K-12: isolation and mapping. 1975. J Bacteriol. 124:26-38.); the nagE (pstN) gene (Rogers M. J., and T. Ohgi, and J. Plumbridge, and D. Soll. Nucleotide sequences of the *Escherichia coli* nagE and nagB genes: the structural genes for the N-acetylglucosamine transport protein of the bacterial phosphoenolpyruvate: sugar phosphotransferase system and for glucosamine-6-phosphate deaminase. 1988. Gene. 62:197-207); the pstA gene (Cox G. B., H. Rosenberg, and J. A. Downie, and S. Silver. Genetic analysis of mutants affected in the Pst inorganic phosphate transport system. 1981. J Bacteriol. 148:1-9); the pstB (gutB) gene (Id.); the pstG gene (Cox G. B., H. Rosenberg, and J. A. Downie, and S. Silver. Genetic analysis of mutants affected in the Pst inorganic phosphate transport system. 1981. J Bacteriol. 148:1-9); the pstH gene (Id.); the pstI gene (Id.); the pstN gene (Id.); the pstO gene (Id.); the ptxA (yif U) gene (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein); the sgcA (yjhL) gene (Id.); the sgcC (yjhN) gene (Id.); the treB gene (Boos W., U. Ehmann, H. Forkl, W. Klein, M. Rimmele, and P. Postma. Trehalose transport and metabolism in *Escherichia coli*. 1990. J. Bacteriol. 172:3450-3461); the usg gene (Arps P. J., and M. E. Winkler M E. Structural analysis of the *Escherichia coli* K-12 hisT operon by using a kanamycin resistance cassette. 1987. J Bacteriol. 169:1061-1070); the wcaD gene (Mao Y., and M. P. Doyle, and J. Chen. Insertion mutagenisis of wca reduces acide and heat tolerance of enterohemorrhagic *Escherichia coli*_O157:H7. 2001. J Bacteriol. 183:3811-3815); the yadI gene (Berlyn et al., "Linkage Map of *Escherichia coli* K-12, Edition 9," Chapter 109 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 2, pages 1715-1902, and references cited therein); and the ycgC gene (Gutknecht R., and R. Beutler, and L. F. Garcia-Alles, and U. Baumann, and B. Erni. The dihydroxyacetone kinase of *Escherichia coli* utilizes a phosphoprotein instead of ATP as phosphoryl donor. 2001. EMBO J. 20:2480-2486).

II.C.8. General Deletions and Modifications

Included in the design of the invention are techniques that increase the efficiency of gene expression and protein production in minicells. By way of non-limiting example, these techniques may include modification or deletion of endogenous gene(s) from which their respective gene product decreases the induction and expression efficiency of a desired protein in the parent cell prior to minicell formation and/or the segregated minicell. By way of non-limiting example, these protein components may be the enzymes that degrade chemical inducers of expression, proteins that have a dominant negative affect upon a positive regulatory elements, proteins that have proteolytic activity against the protein to be expressed, proteins that have a negative affect against a chaperone that is required for proper activity of the expressed protein, and/or this protein may have a positive effect upon a protein that either degrades or prevents the proper function of the expressed protein. These gene products that require deletion or modification for optimal protein expression and/or function may also be antisense nucleic acids that have a negative affect upon gene expression.

II.C.9. Cytoplasmic Redox State

Included in the design of the invention are techniques that increase the efficiency of gene expression and functional protein production in minicells. By way of non-limiting example, these techniques may include modification of endogenous and/or exogenous protein components that alter the redox state of the parental cell cytoplasm prior to minicell formation and/or the segregated minicell cytoplasm. By way of non-limiting example, this protein component may be the product of the trxA, grx, dsbA, dsbB, and/or dsbc genes from *E. coli* or homologs of this gene or gene product found in other members of the Eubacteria, Eucarya or Archae (Mark et al., Genetic mapping of trxA, a gene affecting thioredoxin in *Escherichia coli* K12, Mol Gen Genet. 155:145-152, 1977; (Russel et al., Thioredoxin or glutaredoxin in *Escherichia coli* is essential for sulfate reduction but not for deoxyribonucleotide synthesis, J Bacteriol. 172:1923-1929, 1990); Akiyama et al., In vitro catalysis of oxidative folding of disulfide-bonded proteins by the *Escherichia coli* dsbA (ppfA) gene product, J Biol Chem. 267:22440-22445, 1992); (Whitney et al., The DsbA-DsbB system affects the formation of disulfide bonds in periplasmic but not in intramembraneous protein domains, FEBS Lett. 332:49-51, 1993); (Shevchik et al., Characterization of DsbC, a periplasmic protein of *Erwinia chrysanthemi* and *Escherichia coli* with disulfide isomerase activity, EMB J. 13:2007-2012, 1994). These applications may, but are not limited to increased or decreased production, increased or decreased intramolecular TrxA activity, increased or decreased physiological function of the above-mentioned gene products. By way of non-limiting example, increased production of gene product (gene expression) may occur through increased gene dosage (increased copy number of a given gene under the control of the native or artificial promotor where this gene may be on a plasmid or in more than one copy on the chromosome), modification of the native regulatory elements, including, but not limited to the promotor or operator region(s) of DNA, or ribosomal binding sites on RNA, relevant repressors/silencers, relevant activators/inhancers, or relevant antisense nucleic acid or nucleic acid analog, cloning on a plasmid under the control of the native or artificial promotor, and increased or decreased production of native or artificial promotor regulatory elements) controlling production of the gene. By way of non-limiting example, decreased gene expression production may occur through modification of the native regulatory elements, including, but not limited to the promotor or operator region(s) of DNA, or ribosomal binding sites on RNA, relevant repressors/silencers, relevant activators/inhancers, or relevant antisense nucleic acid or nucleic acid analog, through cloning on a plasmid under the control of the native regulatory region containing mutations or an artificial promotor, either or both of which resulting in decrease gene expression, and through increased or decreased production of native or artificial promotor regulatory element(s) controlling gene expression. By definition, intramolecular activity refers to the enzymatic function, structure-dependent function, e.g. the capacity off a gene product to interact in a protein-protein, protein-nucleic acid, or protein-lipid complex, and/or carrier function, e.g. the capacity to bind, either covalently or non-covalently small organic or inorganic molecules, protein(s) carbohydrate(s), fatty acid(s), lipid(s), and nucleic acid(s). By way of non-limiting example, alteration of intramolecular activity may be accomplished by mutation of the gene, in vivo or in vitro chemical modification of the gene product, inhibitor molecules against the function of the gene product, e.g. competitive, non-competitive, or uncompetitive enzymatic inhibitors, inhibitors that prevent protein-protein, protein-nucleic acid, or protein-lipid interactions, e.g. expression or introduction of dominant-negative or dominant-positive or other protein fragment(s), or other carbohydrate(s), fatty acid(s), lipid(s), and nucleic acid(s) that may act directly or allosterically upon the gene product, and/or modification of protein, carbohydrate, fatty acid, lipid, or nucleic acid moieties that modify the gene or gene product to create the functional protein. By definition, physiological function refers to the effects resulting from an intramolecular interaction between the gene product and other protein, carbohydrate, fatty acid, lipid, nucleic acid, or other molecule(s) in or on the cell or the action of a product or products resulting from such an interaction.

By way of non-limiting example, physiological function may be the act or result of intermolecular phosphorylation, biotinylation, methylation, acylation, glycosylation, and/or other signaling event; this function may be the result of protein-protein, protein-nucleic acid, or protein-lipid interaction resulting in a functional moiety; this function may be to interact with the membrane to recruit other molecules to this compartment of the cell; this function may be to regulate the transcription and/or translation of trxA, other protein, or nucleic acid; and this function may be to stimulate the function of another process that is not yet described or understood.

II.C.10. Transcriptional Terminators

Included in the design of the invention are techniques that increase the efficiency of gene expression and protein production in parental cell cytoplasm prior to minicell formation and/or the segregated minicell cytoplasm. By way of non-limiting example, these techniques may include modification of terminator regions of DNA templates or RNA transcripts so that transcription and/or translation of these nucleic acid regions will terminate at greater efficiency. By way of non-limiting example, these techniques may include stem-loop structures, consecutive translational terminators, polyadenylation sequences, or increasing the efficiency of rho-dependent termination. Stem loop structures may include, but are not limited to, inverted repeats containing any combination of deoxyribonucleic acid or ribonucleic acid molecule, more than one such inverted repeat, or variable inverted repeats such that the rate of transcriptional/translational termination may be moderated dependent on nucleic acid and/or amino acid concentration, e.g. the mechanism of regulatory attenuation (Oxdender et al., Attenuation in the *Escherichia coli* tryptophan operon: role of RNA secondary structure involving the tryptophan codon region, Proc. Natl. Acad. Sci. 76:5524-5528, 1979). See also, Yager and von Hippel, "Transcript Elongation and Termination in e. Col. And Landick and Yanofsky, "Transcriptional Attenuation," Chapters 76 and 77, respectively in: *Escherichia Coli and Salmonella Typhimurium: Cellular and Molecular Biology*, Neidhardt, Frederick C., Editor in Chief, American Society for Microbiology, Washington, D.C., 1987, Volume 1, pages 1241-1275 and 1276-1301, respectively, and references cited therein.

II.C.11. Ribosomal Targeting

Included in the design of the invention are techniques that increase the efficiency of gene expression and protein production in parental cell cytoplasm prior to minicell formation and/or the segregated minicell cytoplasm. By way of non-limiting example, these techniques may include modifications of endogenous and/or exogenous ribosomal components such that ribosomes enter the minicell segregates with higher efficiency. By way of non-limiting example, these techniques may include increasing the copy number of ribosomal binding sites on plasmid or like structure to recruit more ribosomal components or increase the synthesis of ribosomal subunits prior to segregation (Mawn et al., Depletion of free 30S ribosomal subunits in *Escherichia coli* by expression of RNA containing Shine-Dalgarno-like sequences, J. Bacteriol. 184:494-502, 2002). This construct may also include the use of plasmid expressed translation initiation factors to assist ribosomal segregation (Celano et al., Interaction of *Escherichia coli* translation-initiation factor IF-1 with ribosomes, Eur. J. Biochem. 178:351-355 1988). See also Hoopes and McClure, "Strategies in Regulation of Transcription Initiation," Chapter 75 in: *Escherichia Coli and Salmonella Typhimurium: Cellular and Molecular Biology*, Neidhardt, Frederick C., Editor in Chief, American Society for Microbiology, Washington, D.C., 1987, Volume 2, pages 1231-1240, and references cited therein.

II.C.12. Proteases

Included in the design of the invention are techniques that increase the efficiency of gene expression and protein production in minicells. By way of non-limiting example, these techniques may include utilization and/or modification of endogenous and/or exogenous proteases. Such manipulations may result in increased or decreased production, and/or changes in the intramolecular and intermolecular functions, of a protein in a minicell or its parent cell; in the latter instance, the protein may be one that is desirably retained in segregated minicells.

The production or activity of a desired protein gene product may be increased by decreasing the level and/or activity of a protease that acts upon the desired protein. The production or activity of a desired protein gene product may be increased by increasing the level and/or activity of a protease that acts upon a protein that inhibits the production or function of the desired protein.

The production or activity of a desired nucleic acid gene product may be increased be increasing the level and/or activity of a protease that acts upon a protein that that inhibits the production or function of the nucleic acid gene product. The production or activity of a desired nucleic acid gene product may be increased by decreasing the level and/or activity of a protease that acts upon a protein that stimulates or enhances the production or function of the desired nucleic acid gene product.

As one example, manipulation of the alpA gene or gene product from *E. coli* (Kirby J. E., and J. E. Trempy, and S. Gottesman. Excision of a P4-like cryptic prophage leads to Alp protease expression in *Escherichia coli*. 1994. J Bacteriol. 176:2068-2081), or homologs of this gene or gene product found in other members of the Prokaryotes, Eukaryotes or Archaebacteria, may be employed to increase the efficiency of gene expression and protein production in parent cells prior to minicell formation and/or segregated minicells postpartum.

In addition to alpA, other exemplary *E. coli* genes and gene products include the clpA gene and gene product from *E. coli* (Katayama Y., and S. Gottesman, and J. Pumphrey, and S. Rudikoff, and W. P. Clark, and M. R. Maurizi. The two-component, ATP-dependent Clp protease of *Escherichia coli*. Purification, cloning, and mutational analysis of the ATP-binding component. 1988, J Biol. Chem. 263-15226-15236); the clpB gene product from *E. coli* (Kitagawa M., and C. Wada, and S. Yoshioka, and T. Yura. Expression of ClpB, an analog of the ATP-dependent proteas regulatory subunit in *Escherichia coli*, is controlled by a heat shock sigma factor (sigma 32). J. Bacteriol. 173:4247-4253); the clpC gene product from *E. coli* (Msadek T., and F. Kunst, and G. Rapoport. MecB of *Bacillus subtilis*, a member of the ClpC ATPase family, is a pleiotropic regulator controlling competence gene expression and growth at high temperature. 1994. Proc Natl Acad Sci USA 91:5788-5792); the clpP gene product from *E. coli* (Maurizi M. R., and W. P. Clark, and Y. Katayama, and S. Rudikoff, and J. Pumphrey, and B. Bowers, and S. Gottesman. Sequence and structure of ClpP, the proteolytic component of the ATP-dependent Clp protease of *Escherichia coli*. 1990. J biol Chem. 265:12536-12545); the clpX gene product from *E. coli* (Gottesman S., and W. P. Clark, and V. de Crecy-Lagard, and M. R. Maurizi. ClpX, an alternative subunit for the ATP-dependent Clp protease of *Escherichia coli*. Sequence and in vivo activities. 1993. J Biol Chem. 268: 22618-22626); the clpY gene product from *E. coli* (Missiakas D., and F. Schwager, J. M. Betton, and C. Georgopoulos, S. Raina. Identification and characterization of HsIV HsIU (ClpQ ClpY) proteins involved in overall proteolysis of misfolded proteins in *Escherichia coli*. 1996. EMBO J. 15:6899-6909); the dcp gene product from *E. coli* (Becker S., and Plapp R. Location of the dcp gene on the physical map of *Escherichia coli*. 1992. J Bacteriol. 174:1698-1699); the degP (htrA) gene product from *E. coli* (Lipinska B., and M. Zylicz, and C. Georgopoulos. The HtrA (DegP) protein, essential for *Escherichia coli* survival at high temperatures, is an endopeptidase. 1990. J Bacteriol. 172:1791-1797); the ggt gene product from *E. coli* (Finidori J., and Y. Laperche, and R. Haguenauer-Tsapis, and R. Barouki, and G. Guellaen, and J. Hanoune. In vitro biosynthesis and membrane insertion of gamma-glutamyl transpeptidase. 1984. J Biol. Chem. 259: 4687-4690); the hfl gene product from *E. coli* (Cheng H. H., and H. Echols. A class of *Escherichia coli* proteins controlled by the hflA locus. 1987. J Mol Biol. 196:737-740); the hflB gene product from *E. coli* (Banuett F., and M. A. Hoyt, and L. McFarlane, and H. Echols, and I. Herskowitz. HflB, a new *Escherichia coli* locus regulating lysogeny and the level of bacteriophage lambda c11 protein. 1986. J Mol Biol. 187: 213-224); the hflC gene product from *E. coli* (Noble J. A., and M. A. Innis, and E. V. Koonin, and K. E. Rudd, and F. Banuett, and I. Herskowitz, The *Escherichia coli* hflA locus encodes a putative GTP-binding protein and two membrane proteins, one of which contains a protease-like domain. 1993. Proc Natl Acad Sci USA. 90:10866-10870); the hflK gene product from *E. coli* (Id.); the hftX gene product from *E. coli* (Noble J. A., and M. A. Innis, and E. V. Koonin, and K. E. Rudd, and F. Banuett, and I. Hertzskowitz. The *Escherichia coli* hflA locus encodes a putative GTP-binding protein and two membrane proteins, one of which contains a protease-like domain. 1993. Proc Natl Acad Sci USA. 90:10866-10870); the hopD gene product from *E. coli* (Whitchurch C. B., and J. S. Mattick *Escherichia coli* contains a set of genes homologous to those involved in protein secretion, DNA uptake and the assembly of type-4 fimbriae in other bacteria. 1994. Gene. 150:9-15); the htrA gene product from *E. coli* (Lipinska B., and S. Sharma, and C. Georgopoulos. Sequence analysis and regulation of the htrA gene of *Escherichia coli*: a sigma 32-independent mechanism of heat-inducible transcription. 1988. Nucleicc Acids Res. 16:10053-10067); the hycI gene product from *E. coli* (Rossmann R., and T. Maier, and F. Lottspeich, and A. Bock. Characterisation of a proteas from *Escherichia coli* involved in hydrogenase maturation. 1995. Eur J Biochem. 227:545-550); the iap gene product from *E. coli* (Nakata A., and M. Yamaguchi, and K. Isutani, and M. Amemura. *Escherichia coli* mutants deficient in the production of alkaline phosphatase isoszymes. 1978. J Bacteriol. 134:287-294); the lep gene product from *E. coli* (Silver P., and W. Wickner. Genetic mapping of the *Escherichia coli* leader (signal) peptidase gene (lep): a new approach for determining the map position of a cloned gene. 1983. J Bacteriol. 54:659-572); the lon gene product from *E. coli* (Donch J., and J. Greenberg. Genetic analysis of lon mutants of strain K-12 of *Escherichia coli*. 1968. Mol Gen Genet. 103:105-115); the lsp gene product from *E. coli* (Regue M., and J. Remenick, and M. tokunaga, and G. A. Mackie, and H. C. Wu. Mapping of the lipoprotein signal peptidase gene (lsp). 1984. J Bacteriol. 1984 158:632-635); the ompT gene product from *E. coli* (Akiyama Y., and K. SecY protein, a membrane-embedded secretion factor of *E. coli*, is cleaved by the ompT proteas in vitro. 1990. Biochem Biophys Res Commun. 167:711-715); the opdA gene product from *E. coli* (Conllin C. A., and C. G. Miller. Location of the prlC (opdA) gene on the physical map of *Escherichia coli*. 1993. J Bacteriiol. 175:5731-5732); the orfX gene product from *E. coli* (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: Cellular and Molecular Biology*, 2$^{nd}$ ed. American Society for Microbiology, Washington D.C.); the pepA gene product from *E. coli* (Stirling C. J., and S. D. Colloms, and J. F. Collins, and G. Szatmari, and D. J. Sherratt. XerB, an *Escherichia coli* gene required for plasmid ColE1 site-specific recombination, is identical to pepA, encoding aminopeptidaseA, a protein with substantial similarity to bovine lens leucine aminopeptidase. 1989. EMBO J. 8:1623-1627); the pepD gene product from *E. coli* (Henrich B., and U. Schroeder, and R. W. Frank, and R. Plapp. Accurate mapping of the *Escherichia coli* pepD gene by sequence analysis of its 5' flanking region. 1989. Mol Gen Genet. 215:369-373); the pepE gene product from *E. coli* (Conlin C. A., and T. M. Knox, and C. G. Miller. Cloning and physical map position of an alpha-aspartyl depeptidase gene, pepE, from *Escherichia coli*. 1994. J Bacteriol. 176:1552-1553); the pepN gene product from *E. coli* (Miller C. G., and G. Schwartz. Peptidase-deficient mutants of *Escherichia coli*. 1978. J Bacteriiol. 135: 603-611); the pepP gene product from *E. coli* (Id.); the pepQ gene product from *E. coli* (Id.); the pepT gene product from *E. coli* (Miller G. G., and G. Schwartz. Peptidase-deficient mutants of *Escherichia coli*. 1978. J Bacteriiol. 135:603-611); the pilD gene product from *E. coli* (Francetic O., and S. Lory, and A. P. Pugsley. A second prepilin peptidase gene in *Escherichia coli* K-12. 1998, Mol Microbiol. 27:763-775); the pinA gene product from *E. coli* (Hilliard J. J., and L. D.

Simon, and L. Van Melderen, and M. R. Maurizi. PinA inhibits ATP hydrolysis and energy-dependent protein degradation by Lon protease. 1998. J Biol Chem. 273:524-527); the prc (tsp) gene product from *E. coli* (Nagasawa H., and Y. Sakagami, and A. Suzuki, and H. Suzuki, and H. Hara, and Y. Hirota. Determination of the cleavage site involved in C-terminal processing of penicillin-binding protein 3 of *Escherichia coli*. 1989. J Bacteriol. 171:5890-5893); the prlC gene product from *E. coli* (Jiang X., and M. Zhang, and Y. Ding, and J. Yao, and H. Chen, and D. Zhu, and M. Muramatu. *Escherichia coli* prlC gene encodes a trypsin-like proteinase regulating the cell cycle. 1998. J Biochem (Tokyo) 128:980-985); the protease V gene product from *E. coli* (Berlyn, M. K. B. et al. 1996. Linkage map of *Escherichia coli* K-12, Edition 9, In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: Cellular and Molecular Biology*, $2^{nd}$ ed. American Society for Microbiology, Washington, D.C.); the protease VI gene product from *E. coli* (Id.); the protease In gene product from *E. coli* (Id.); the protease Fa gene product from *E. coli* or homologues (Id.); the protease Mi gene product from *E. coli* (Id.); the protease So gene product from *E. coli* (Id.); the ptrA gene product from *E. coli* (Id.); the ptrB gene product from *E. coli* (Id.); the sypB gene product from *E. coli* (Barends S., and A. W. Karzai, and R. T. Sauer, and J. Wower, and B. Kraal. Simultaneous an functional binding of SmpB and EF-Tu-TP to the analyl acceptor arm of tmRNA. 2001. J Mol Biol. 314:9-21); the sohB gene product from *E. coli* (Baird L., and B. Lipinska, and S. Raina, and C. Georgopoulos. Identification of the *Escherichia coli* sohB gene, a multicopy suppressor of the HtrA (DegP) null phenotype. 1991. J Bacteriol. 173-5763-5770); the sspA gene product from *E. coli* (Ichihara S., and T. Suzuki, and M. Suzuki, and C. Mizushima. Molecular cloning and sequencing of the sppA gene and characterization of the encoded proteas IV, a signal peptide peptidase of *Escherichia coli*. 1986. J Biol Chem. 261; 9405-9411); the tesA gene product from *E. coli* (Cho H., and J. E. Cronan Jr. *Escherichia coli* thioesterase I, molecular cloning and sequencing of the structural gene and identification as a periplasmic enzyme. 1993 J Biol Chem. 268:9238-9245); the tufA gene product from *E. coli* (Ang., and J. S. Lee, and J. D. Friesen. Evidence for an internal promoter preceding tufA in the str operon of *Escherichia coli*. J Bacteriol. 149:548-553); the tufB gene product from *E. coli* (Mihajima A., and M. Shibuya, and Y. Kaziro. Construction and characterization of the two hybrid ColIE1 plasmids carrying *Escherichia coli* tufB gene. 1979. FEBS Lett. 102:207-210); the ybaU gene product from *E. coli* (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Resnikoff, M. Riley, M. Schaechter, and H. E. Umbarger (eds.). *Escherichia coli and Salmonella typhimurium: Cellular and Molecular Biology*, $2^{nd}$ ed. American Society for Microbiology, Washington, D.C.); the ssrA gene (tmRNA, 10sA RNA) product from *E. coli* (Oh B. K., and A. K. Chauhan, and K. Isono, and D. Apirion. Location of a gene (ssrA) for a small, stable RNA 910Sa RNA) in the *Escherichia coli* chromosome. 1990. J Bacteriol. 172:4708-4709); and the ssrB gene from *E. coli (Berlyn, M. K. B., et al.* 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Ummbarger 9eds.). *Escherichia coli and Salmonella typhimurium: Cellular and Molecular Biology*, $2^{nd}$ ed. American Society for Microbiology, Washington, D.C.).

II.C.13. Chaperones

Included in the design of the invention are techniques that increase the efficiency of gene expression and functional protein production in minicells. By way of non-limiting example, these techniques may include modification of chaperones and chaperonins, i.e., endogenous and/or exogenous protein components that monitor the unfolded state of translated proteins allowing proper folding and/or secretion, membrane insertion, or soluble multimeric assembly of expressed proteins in the parental cell prior to minicell formation and/or the segregated minicell cytoplasm, membrane, periplasm, and/or extracellular environment. See Gottesman et al., Protein folding and unfolding by *Escherichia coli* chaperones and chaperonins, Current Op. Microbiol. 3:197-202, 2000; and Mayhew et al., "Molecular Chaperone Proteins," Chapter 61 in: *Escherichia coli and Salmonella typhimurium: Cellular and Molecular Biology*, 2nd Ed., Neidhardt, Frederick C., Editor in Chief, American Society for Microbiology, Washington, D.C., 1996, Volume 1, pages 922-937, and references cited therein.

These applications may, but are not limited to increased or decreased chaperone production, increased or decreased intramolecular activity of a chaperone, increased or decreased physiological function of a chaperone, or deletion, substitution, inversion, translocation or insertion into, or mutation of, a gene encoding a chaperone. By way of non-limiting example, increased production of a chaperone may occur through increased chaperone gene dosage (increased copy number of a given gene under the control of the native or artificial promotor where this gene may be on a plasmid or in more than one copy on the chromosome), modification of the native regulatory elements, including, but not limited to the promotor or operator region(s) of DNA, or ribosomal binding sites on RNA, relevant repressors/silencers, relevant activators/enhancers, or relevant antisense nucleic acid or nucleic acid analog, cloning on a plasmid under the control of the native or artificial promotor, and increased or decreased production of native or artificial promotor regulatory element(s) controlling production of the chaperone gene or gene product. By way of non-limiting example, decreased production of a chaperone may occur through modification of the native regulatory elements, including, but not limited to the promotor or operator region(s) of DNA, or ribosomal binding sites on RNA, relevant repressors/silencers, relevant activators/enhancers, or relevant antisense nucleic acid or nucleic acid analog, through cloning on a plasmid under the control of the native regulatory region containing mutations or an artificial promotor, either or both of which resulting in decreased chaperone production, and through increased or decreased production of native or artificial promotor regulatory element(s) controlling production of the chaperone gene or gene product. By definition, intramolecular activity refers to the enzymatic function, structure-dependent function, e.g. the capacity of chaperone to interact in a protein-protein, protein-nucleic acid, or protein-lipid complex, and/or carrier function, e.g. the capacity to bind, either covalently or non-covalently small organic or inorganic molecules, protein(s), carbohydrate(s), fatty acid(s), lipid(s), and nucleic acid(s). By way of non-limiting example, alteration of intramolecular activity may be accomplished by mutation of the chaperone gene, in vivo or in vitro chemical modification of Chaperone, inhibitor molecules against the function of chaperone, e.g. competitive, non-competitive, or uncompetitive enzymatic inhibitors, inhibitors that prevent protein-protein, protein-nucleic acid, or protein-lipid interactions, e.g. expression or introduction of dominant-negative or dominant-positive chaperone or other protein fragment(s), or other carbohydrate(s), fatty acid(s), lipid(s), and nucleic acid(s) that may act directly or allosterically upon Chaperone, and/or modification of protein, carbohydrate, fatty acid, lipid, or nucleic acid moieties that modify the chaperone gene or gene product to create the functional protein. By definition, physiological function refers to the effects resulting from an intramolecular interaction between Chaperone and other protein, carbohydrate, fatty acid, lipid, nucleic acid, or other molecule(s) in or on the cell or the action of a product or products resulting from such an interaction. By way of non-limiting example, physiological function may be the act or result of intermolecular phosphorylation, biotinylation, methylation, acylation, glycosylation, and/or other signaling event; this function may be the result of a protein-protein, protein-nucleic acid, or protein-lipid interaction resulting in a functional moiety; this function may be to interact with the membrane to recruit other molecules to this compartment of the cell; this function may be to regulate the transcription and/or translation of chaperone, other protein, or nucleic acid; and this function may be to stimulate the function of another process that is not yet described or understood.

By way of non-limiting example, chaperone genes may be any of the *E. coli* genes listed below, as well as any homologs thereof from prokaryotes, exukariutes, arcahebacteria, or organelles (mitochondria, chloroplasts, plastids, etc.). Exemplary *E. coli* genes encoding chaperones include, by way of non-limiting example, the cbpA gene (Shiozawa T., and C. Ueguchi, and T. Mizuno. The rpoD gene functions as a multicopy suppressor for mutations in the chaperones, CbpA, DnaJ and DnaK, in *Escherichia coli*. 1996 FEMS Microbiol Lett. 138:245-250): the clpB gene (Squires C. L., and S. Pedersen, and B. M. Ross, and C. Squires. ClpB is the *Escherichia coli* heat shock protein F84.1. 1991. J Bacteriol. 173:4254-4262); the dnaK gene (Kroczynska B., and S. Y. Blond. Cloning and characterization of a new soluble murine J-domain protein that stimulates BiP, Hsc70 and DnaK ATPase activity with different efficiencies. 2001. Gene. 273:267-274); the dnaJ gene (Kedzierska S., and E. Matuszewska. The effect of co-overproduction of DnaK/DnaJ/GrpE and ClpB proteins on the removal of heat-aggregated proteins from *Escherichia coli* Delta clpB mutant cells—new insight into the role of Hsp70 in a functional cooperation with Hsp100. 2001. FEMS Microbiol Lett. 204:355-360); the ecpD gene (Raina S., and D. Missiakas, and L. Baird, and S. Kumar, and C. Georgopoulos. Identification and transcriptional analysis of the *Escherichia coli* htrE operon which is homologous to pap and related pilin operons. 1993. J Bacteriol. 175:5009-5021); the ffh gene (Muller, M., et al. 1002. Protein traffic in bacteria: multiple routes from the ribosome to and across the membrane. Prog. Nucleic Acid Res. Mol. Biol. 66:107-157); 4.5S RNA (Muller, M., et al. 1002. Protein traffic in bacteria: multiple routes from the ribosome to and across the membrane. Prog. Nucleic Acid Res. Mol. Biol. 66:107-157); the FtsY gene (Muller, M., et al. 1002. Protein traffic in bacteria: multiple routes from the ribosome to and across the membrane. Prog. Nucleic Acid Res. Mol. Biol. 66:107-157); the fimC gene (Klemm P., and B. J. Jorgensen, and I. van Die, and H. de Ree, and H. Bergmans. The fim genes responsible for synthesis of type 1 fimbriae in *Escherichia coli*, cloning and genetic organization. 1985. Mol Gen Genet. 199:410-414); the groE gene (Burton Z. F., and D. Eisenberg. A procedure for rapid isolation of both groE protein and glutamine synthetase from *E coli*. 1980. Arch Biochem Biophys. 205:478-488); the groL gene (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); the groS gene (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); the hptG gene (Berlyn, M. K. B., et al. 1996. Linkage map of *Escherichia coli* K-12, Edition 9. In F. C. Neidhardt, R. Curtiss, J. L. Ingraham, E. C. C. Lin, K. B. Low, B. Magasanik, W. S. Reznikoff, M. Riley, M. Schaechter, and H. E. Umbarger (eds.). *Escherichia coli and Salmonella typhimurium: cellular and molecular biology,* 2nd ed. American Society for Microbiology, Washington D.C.); the hscA gene (Takahashi Y., and M. Nakamura. Functional assignment of the ORF2-iscS-iscU-iscA-hscB-hscA-fdx-ORF3 gene cluster involved in the assembly of Fe-S clusters in *Escherichia coli*. 1999. J Biochem (Tokyo). 126:917-926); the ibpA gene (Lund P. A. Microbial molecular chaperones. 2001. Adv Microb Physiol. 44:93-140); the papJ gene (Tennent, J. M., et al. 1990. Integrity of *Escherichia coli* P pili during biogenesis: properties and role of PapJ. Mol. Microbiol. 4:747-758); the secB gene (Lecker, S., et al. 1989. Three pure chaperone proteins of *Escherichia coli*—SecB, trigger factor and GroEL—form soluble complexes with precursor proteins in vitro. EMBO J. 8:2703-2709); and the tig gene (Lecker, S., et al. 1989. Three pure chaperone proteins of *Escherichia coli*—SecB, trigger factor and GroEL—form soluble complexes with precursor proteins in vitro. EMBO J. 8:2703-2709); the secE gene (Muller, M., et al. 1002. Protein traffic in bacteria: multiple routes from the ribosome to and across the membrane. Prog. Nucleic Acid Res. Mol. Biol. 66:107-157); and the secY gene (Muller, M., et al. 1002. Protein traffic in bacteria: multiple routes from the ribosome to and across the membrane. Prog. Nucleic Acid Res. Mol. Biol. 66:107-157).

II.C.14. Export Apparatus and Membrane Targeting

Included in the design of the invention are techniques that increase the efficiency of gene expression and protein production in parental cells prior to minicell formation and/or in the segregated minicells. By way of non-limiting example, these techniques may include construction of chimeric proteins including, but not limited to, coupling the expressed protein of interest with native Eubacterial, Eukaryotic, Archeabacterial or organellar leader sequences to drive membrane insertion or secretion of the protein of interest to the periplasm or extracellular environment. In addition to using native leader sequences, these minicell expression constructs may also include proteolytic cleavage sites to remove the leader sequence following insertion into the membrane or secretion. These proteolytic cleavage sites may be native to the organism from which the minicell is derived or non-native. In the latter example, also included in the system are the non-native protease that recognizes the non-native proteolytic cleavage site.

Non-limiting examples of these leader sequences may be the leader from the STII protein (Voss, T., et al. 1994. Periplasmic expression of human interferon-alpha 2c in *Escherichia coli* results in a correctly folded molecule. Biochem. J. 298:719-725), maltose binding protein (malE) (Ito, K. 1982. Purification of the precursor form of maltose-binding protein, a periplasmic protein of *Escherichia coli*. J. Biol. Chem. 257:9895-9897), phoA (Jobling, M. G., et al. 1997. Construction and characterization of versatile cloning vectors for efficient delivery of native foreign proteins to the periplasm of *Escherichia coli*. Plasmid. 38:158-173), lamB (Wong, E. Y., et al. 1988. Expression of secreted insulin-like growth factor-1 in *Escherichia coli*. Gene. 68:193-203), ompA (Loo, T., et al. 2002. Using secretion to solve a solubility problem: high-yield expression in *Escherichia coli* and purification of the bacterial glycoamidase PNGase F. Protein Expr. Purif. 24:90-98), or pelB (Molloy, P. E., et al. 1998. Production of soluble single-chain T-cell receptor fragments in *Escherichia coli* trxB mutants. Mol. Immunol. 35:73-81).

In addition to these leader sequences, mutations in the cellular export machinery may be employed to increase the promiscuity of export to display or export sequences with non-optimized leader sequences. Non-limiting examples of genes that may be altered to increase export promiscuity are mutations in secY (prlA4) (Derman, A. I., et al. 1993. A signal sequence is not required for protein export in prlA mutants of *Escherichia coli*. EMBO J. 12:879-888), and secE (Harris, C. R., and T. J. Silhavy. 1999. Mapping an interface of SecY (PrlA) and SecE (PrlG) by using synthetic phenotypes and in vivo cross-linking. J. Bacteriol. 181:3438-3444).

II.C.15. Increasing Stability and Solubility

Included in the design of the invention are techniques that increase the efficiency of gene expression and protein production in parental cells prior to minicell formation and/or in the segregated minicells. By way of non-limiting example, these techniques may include construction of chimeric/fusion proteins including, but not limited to, coupling the expressed protein of interest with native Eubacterial, Eukaryotic, Archeabacterial or organellar soublizing sequences. As used herein, "soublizing sequences" are complete or truncated amino acid sequences that increase the solubility of the expressed membrane protein of interest. This increased solubility may be used to increase the lifetime of the soluble state until proper membrane insertion may take place. By way of non-limiting example, these soluble chimeric fusion proteins may be ubiquitin (Power, R. F., et al. 1990. High level expression of a truncated chicken progesterone receptor in *Escherichia coli*. J. Biol. Chem. 265:1419-1424), thioredoxin (LaVallie, E. R., et al. 1993. A thioredoxin gene fusion expression system that circumvents inclusion body formation in the *E. coli* cytoplasm. Biotechnology (N.Y.) 11:187-193; Kapust, R. B., and D. S. Waugh. 1999. *Escherichia coli* maltose-binding protein is uncommonly effective at promoting the solubility of polypeptides to which it is fused. Protein Sci. 8:1668-1674), the dsbA gene product (Winter, J., et al. 2001. Increased production of human proinsulin in the periplasmic space of *Escherichia coli* by fusion to DsbA. J. Biotechnol. 84:175-185), the SPG protein (Murphy, J. P., et al. 1992. Amplified expression and large-scale purification of protein G'. Bioseparation 3:63-71), the malE gene product (maltose-binding protein) (Hampe, W., et al. 2000. Engineering of a proteolytically stable human beta 2-adrenergic receptor/maltose-binding protein fusion and production of the chimeric protein in *Escherichia coli* and baculovirus-infected insect cells. J. Biotechnol. 77:219-234; Kapust et al., *Escherichia coli* maltose-binding protein is uncommonly effective at promoting the solubility of polypeptides to which it is fused, Protein Sci. 8:1668-1674, 1999), glutathione-s-transferase (GST); and/or nuclease A (Meeker et al., A fusion protein between serum amyloid A and staphylococcal nuclease—synthesis, purification, and structural studies, Proteins 30:381-387, 1998). In addition to these proteins, Staphylococcal protein A, beta-galactosidase, S-peptide, myosin heavy chain, dihydrofolate reductase, T4 p55, growth hormone N terminus, *E. coli* Hemolysin A, bacteriophage lambda cII protein, TrpE, and TrpLE proteins may also be used as fusion proteins to increase protein expression and/or solubility (Makrides, Stratagies for Achieving High-Level Expression of Genes in *Escherichia coli*, Microbiol. Rev. 60:512-538).

III. Preparation of Minicells

III.A. Parent Cell Mutations

Although it has been reported that relatively few molecules of endogenous RNA polymerase segregate into minicells (Shepherd et al., Cytoplasmic RNA Polymerase in *Escherichia coli*, J Bacteriol 183:2527-34, 2001), other reports and results indicate that many RNA Polymerase molecules follow plasmids into minicells (Funnel) and Gagnier, Partition of P1 plasmids in *Escherichia coli* mukB chromosomal partition mutants, J Bacteriol 177:2381-6, 1995). In any event, applicants have discovered that the introduction of an exogenous RNA polymerase to minicell-producing cells enhances expression of episomal elements in minicells. Such enhanced expression may allow for the successful expression of proteins in minicells, wherein such proteins are expressed poorly or not at all in unmodified minicells. In order to maximize the amount of RNA transcription from episomal elements in minicells, minicell-producing cell lines that express an RNA polymerase specific for certain episomal expression elements may be used. An example of an *E. coli* strain of this type, designated MC-T7, was created and used as is described in the Examples. Those skilled in the art will be able to make and use equivalent strains based on the present disclosure and their knowledge of the art.

Minicell-producing cells may comprise mutations that augment preparative steps. For example, lipopolysaccharide (LPS) synthesis in *E. coli* includes the lipid A biosynthetic pathway. Four of the genes in this pathway have now been identified and sequenced, and three of them are located in a complex operon that also contains genes involved in DNA and phospholipid synthesis. The rfa gene cluster, which contains many of the genes for LPS core synthesis, includes at least 17 genes. The rfb gene cluster encodes protein involved in O-antigen synthesis, and rib genes have been sequenced from a number of serotypes and exhibit the genetic polymorphism anticipated on the basis of the chemical complexity of the O antigens. See Schnaitman and Klena, Genetics of lipopolysaccharide biosynthesis in enteric bacteria, Microbiol. Rev. 57:655-82, 1993. When present, alone, or in combination, the rfb and oms mutations cause alterations in the eubacterial membrane that make it more sensitive to lysozyme and other agents used to process minicells. Similarly, the rfa (Chen, L., and W. G. Coleman Jr. 1993. Cloning and characterization of the *Escherichia coli* K-12 rfa-2 (rfaC) gene, a gene required for lipopolysaccharide inner core synthesis. J. Bacteriol. 175:2534-2540), lpcA (Brooke, J. S., and M. A. Valvano. 1996. Biosynthesis of inner core lipopolysaccharide in enteric bacteria identification and characterization of a conserved phosphoheptose isomerase. J. Biol. Chem. 271:3608-3614), and lpcB (Kadrman, J. L., et al. 1998. Cloning and overexpression of glycosyltransferases that generate the lipopolysaccharide core of *Rhizobium leguminosarum*. J. Biol. Chem. 273:26432-26440) mutations, when present alone or in combination, cause alterations in lipopolysaccharides in the outer membrane causing cells to be more sensitive to lysozyme and agents used to process minicells. In addition, such mutations can be used to reduce the potential antigenicity and/or toxicity of minicells.

III.B. Culturing Conditions

Included in the design of the invention are the conditions to grow parental cells from which minicells will be produced. Non-limiting examples herein are drawn to conditions for growing *E. coli* parental cells to produce minicells derived from *E. coli* parental cells. Non-limiting examples for growth media may include rich media, e.g. Luria broth (LB), defined minimal media, e.g. M63 salts with defined carbon, nitrogen, phosphate, magnesium, and sulfate levels, and complex minimal media, e.g. defined minimal media with casamino acid supplement. This growth may be performed in culture tubes, shake flasks (using a standard air incubator, or modified bioreactor shake flask attachment), or bioreactor. Growth of parental cells may include supplemented additions to assist regulation of expression constructs listed in the sections above. These supplements may include, but are not limited to dextrose, phosphate, inorganic salts, ribonucleic acids, deoxyribonucleic acids, buffering agents, thiamine, or other chemical that stimulates growth, stabilizes growth, serves as an osmo-protectant, regulates gene expression, and/or applies selective pressure to mutation, and/or marker selection. These mutations may include an amino acid or nucleotide auxotrophy, while the selectable marker may include transposable elements, plasmids, bacteriophage, and/or auxotrophic or antibiotic resistance marker. Growth conditions may also require temperature adjustments, carbon alternations, and/or oxygen-level modifications to stimulate temperature sensitive mutations found in designed gene products for a given desired phenotype and optimize culture conditions.

By way of non-limiting example, production of minicells and protein production may occur by using either of two general approaches or any combination of each. First, minicells may be formed, purified, and then contained expression elements may be stimulated to produce their encoded gene products. Second, parental cells, from which the minicells are derived, may be stimulated to express the protein of interest and segregate minicells simultaneously. Finally, any timing variable of minicell formation and protein production may be used to optimize protein and minicell production to best serve the desired application. The two general approaches are shown in the sections below.

III.C. Manipulation of Genetic Expression in Minicell Production

Included in the design of the invention are methods that increase the efficiency, rate and/or level of gene expression and protein production in parent cells and/or minicells. Such methods include, but are not limited to, the following.

By way of non-limiting example, parental cells are grown overnight in the appropriate media. From this culture, the cells are subcultured into the same media and monitored for growth. At the appropriate cell density, the cultures are induced for minicell production using any of the switching mechanisms discussed in section II.B. regulating any construct discussed in section II.A. Non-limiting examples of this minicell-inducing switching mechanism may be the ileR gene product regulating the production of the has minicell-inducing gene product or the melR gene product regulating the production of the minB minicell-inducing gene product. Following minicell induction, the culture is allowed to continue growth until the desired concentration of minicells is obtained. At this point, the minicells are separated from the parental cells as described in section II.E. Purified minicells are induced for protein production by triggering the genetic switching mechanism that segregated into the minicell upon separation from the parental cell. By way of non-limiting example, this genetic switching mechanism may be any of those discussed in section I.B. regulating the production of any protein of interest.

Furthermore, at this point or during the production of minicells the peripheral gene expression, production, and assembly machinery discussed in section II.C. may be triggered to assist in this process. By way of non-limiting example, the groEL complex may be triggered using the temperature sensitive lambda cI inducible system from a co-segregant plasmid to assist in the proper assembly of the expressed protein of interest.

III.D. Separation of Minicells from Parent Cells

A variety of methods are used to separate minicells from parent cells (i.e., the cells from which the minicells are produced) in a mixture of parent cells and minicells. In general, such methods are physical, biochemical and genetic, and can be used in combination.

III.D.1. Physical Separation of Minicells from Parent Cells

By way of non-limiting example, minicells are separated from parent cells glass-fiber filtration (Christen et al., Gene 23:195-198, 1983), and differential and zonal centrifugation (Barker et al., J. Gen. Microbiol. 111:387-396, 1979), size-exclusion chromatography, e.g. gel-filtration, differential sonication (Reeve, J. N., and N. H. Mendelson. 1973. Pronase digestion of amino acid binding components on the surface of *Bacillus subtilis* cells and minicells. Biochem. Biophys. Res. Commun. 53:1325-1330), and UV-irradiation (Tankersley, W. G., and J. M. Woodward. 1973. Induction and isoloation of non-replicative minicells of *Salmonella typhimuium* and their use as immunogens in mice. Bacteriol. Proc. 97).

Some techniques involve different centrifugation techniques, e.g., differential and zonal centrifugation. By way of non-limiting example, minicells may be purified by the double sucrose gradient purification technique described by Frazer and Curtiss, Curr. Topics Microbiol. Immunol. 69:1-84, 1975. The first centrifugation involves differential centrifugation, which separates parent cells from minicells based on differences in size and/or density. The percent of sucrose in the gradient (graduated from about 5 to about 20%), Ficol or glycerol is designed to allow only parent cells to pass through the gradient.

The supernatant, which is enriched for minicells, is then separated from the pellet and is spun at a much higher rate (e.g., $\geq 11,000$ g). This pellets the minicells and any parent cells that did not pellet out in the first spin. The pellet is then resuspended and layered on a sucrose gradient.

The band containing minicells is collected, pelleted by centrifugation, and loaded on another gradient. This procedure is repeated until the minicell preparation is essentially depleted of parent cells, or has a concentration of parent cells that is low enough so as to not interfere with a chosen minicell application or activity. By way of non-limiting example, buffers and media used in these gradient and resuspension steps may be LB, defined minimal media, e.g. M63 salts with defined carbon, nitrogen, phosphate, magnesium, and sulfate levels, complex minimal media, e.g. defined minimal media with casamino acid supplement, and/or other buffer or media that serves as an osmo-protectant, stabilizing agent, and/or energy source, or may contain agents that limit the growth of contaminating parental cells, e.g azide, antibiotic, or lack an auxotrophic supplemental requirement, e.g. thiamine.

Other physical methods may also be used to remove parent cells from minicell preparations. By way of non-limiting example, mixtures of parent cells and minicells are frozen to −20° C. and then thawed slowly (Frazer and Curtiss, Curr. Topics Microbiol. Immunol. 69:1-84, 1975).

III.D.2. Biochemical Separation of Minicells from Parent Cells

Contaminating parental cells may be eliminated from minicell preparations by incubation in the presence of an agent, or under a set of conditions, that selectively kills dividing cells. Because minicells can neither grow nor divide, they are resistant to such treatments.

Examples of biochemical conditions that prevent or kill dividing parental cells is treatment with a antibacterial agent, such as penicillin or derivatives of penicillin. Penicillin has two potential affects. First, penicillin prevent cell wall formation and leads to lysis of dividing cells. Second, prior to lysis dividing cells form filaments that may assist in the physical separation steps described in section III.E.1. In addition to penicillin and its derivatives, other agents may be used to prevent division of parental cells. Such agents may include azide. Azide is a reversible inhibitor of electron transport, and thus prevents cell division. As another example, D-cycloserine or phage MS2 lysis protein may also serve as a biochemical approach to eliminate or inhibit dividing parental cells. (Markiewicz et al., FEMS Microbiol. Lett. 70:119-123, 1992). Khachatourians (U.S. Pat. No. 4,311,797) states that it may be desirable to incubate minicell/parent cell mixtures in brain heart infusion broth at 36° C. to 38° C. prior to the addition of penicillin G and further incubations.

III.D.3. Genetic Separation of Minicells from Parent Cells

Alternatively or additionally, various techniques may be used to selectively kill, preferably lyse, parent cells. For example, although minicells can internally retain M13 phage in the plasmid stage of the M13 life cycle, they are refractory to infection and lysis by M13 phage (Staudenbauer et al., Mol. Gen. Genet. 138:203-212, 1975). In contrast, parent cells are infected and lysed by M13 and are thus are selectively removed from a mixture comprising parent cells and minicells. A mixture comprising parent cells and minicells is treated with M13 phage at an M.O.I.=5 (phage:cells). The infection is allowed to continue to a point where $\geq 50\%$ of the parent cells are lysed, preferably $\geq 75\%$, more preferably $\geq 95\%$ most preferably $\geq 99\%$; and $\leq 25\%$ of the minicells are lysed or killed, preferably $\leq 15\%$, most preferably $\leq 1\%$.

As another non-limiting example of a method by which parent cells can be selectively killed, and preferably lysed, a chromosome of a parent cell may include a conditionally lethal gene. The induction of the chromosomal lethal gene will result in the destruction of parent cells, but will not affect minicells as they lack the chromosome harboring the conditionally lethal gene. As one example, a parent cell may contain a chromosomal integrated bacteriophage comprising a conditionally lethal gene. One example of such a bacteriophage is an integrated lambda phage that has a temperature sensitive repressor gene (e.g., lambda cI857). Induction of this phage, which results in the destruction of the parent cells but not of the achromosomal minicells, is achieved by simply raising the temperature of the growth media. A preferred bacteriophage to be used in this method is one that kills and/or lyses the parent cells but does not produce infective particles. One non-limiting example of this type of phage is one that lyses a cell but which has been engineered to as to not produce capsid proteins that are surround and protect phage DNA in infective particles. That is, capsid proteins are required for the production of infective particles.

As another non-limiting example of a method by which parent cells can be selectively killed or lysed, toxic proteins may be expressed that lead to parental cell lysis. By way of non-limiting example, these inducible constructs may employ a system described in section II.B. to control the expression of a phage holing gene. Holin genes fall with in at least 35 different families with no detectable orthologous relationships (Grundling, A., et al. 2001. Holins kill without warning. Proc. Natl. Acad. Sci. 98:9348-9352) of which each and any may be used to lyse parental cells to improve the purity of minicell preparations.

Gram negative eubacterial cells and minicells are bounded by an inner membrane, which is surrounded by a cell wall, wherein the cell wall is itself enclosed within an outer membrane. That is, proceeding from the external environment to the cytoplasm of a minicell, a molecule first encounters the outer membrane (OM), then the cell wall and finally, the inner membrane (IM). In different aspects of the invention, it is preferred to disrupt or degrade the OM, cell wall or IM of a eubacterial minicell. Such treatments are used, by way of non-limiting example, in order to increase or decrease the immunogenicity, and/or to alter the permeability characteristics, of a minicell.

Eubacterial cells and minicells with altered membranes and/or cell walls are called "Poroplasts™" "spheroplasts," and "protoplasts." Herein, the terms "spheroplast" and "protoplast" refer to spheroplasts and protoplasts prepared from minicells. In contrast, "cellular spheroplasts" and "cellular protoplasts" refer to spheroplasts and protoplasts prepared from cells. Also, as used herein, the term "minicell" encompasses not only minicells per se but also encompasses Poroplasts™, spheroplasts and protoplasts.

In a poroplast, the eubacterial outer membrane (OM) and LPS have been removed. In a spheroplast, portions of a disrupted eubacterial OM and/or disrupted cell wall either may remain associated with the inner membrane of the minicell, but the membrane and cell wall is nonetheless porous because the permeability of the disrupted OM and cell wall has been increased. A membrane is said to be "disrupted" when the membrane's structure has been treated with an agent, or incubated under conditions, that leads to the partial degradation of the membrane, thereby increasing the permeability thereof. In contrast, a membrane that has been "degraded" is essentially, for the applicable intents and purposes, removed. In preferred embodiments, irrespective of the condition of the OM and cell wall, the eubacterial inner membrane is not disrupted, and membrane proteins displayed on the inner membrane are accessible to compounds that are brought into contact with the minicell, poroplast, spheroplast, protoplast or cellular poroplast, as the case may be.

III.E.2. Poroplasts™

For various applications poroplasted minicells are capable of preserving the cytoplasmic integrity while producing increased stability over that of naked protoplasts. Maintenance of the cell wall in poroplasted minicells increases the osmotic resistance, mechanical resistance and storage capacity over protoplasts while permitting passage of small and medium size proteins and molecules through the porous cell wall. A poroplast is a Gram negative bacterium that has its outer membrane only removed. The production of poroplasts involves a modification of the procedure to make protoplasts to remove the outer membrane (Birdsell et al., Production and ultrastructure of lysozyme and ethylenediaminetetraacetate-Lysozyme Spheroplasts of *Escherichia coli*, J. Bacteriology 93: 427-437, 1967; Weiss, Protoplast formation in *Escherichia coli*. J. Bacteriol. 128:668-670, 1976). Like protoplasts, measuring the total LPS that remains in the poroplast preparation may be used to monitor the removal of the outer membrane. Endotoxin kits and antibodies reactive against LPS may be used to measure LPS in solution; increasing amounts of soluble LPS indicates decreased retention of LPS by protoplants. This assay thus makes it possible to quantify the percent removal of total outer membrane from the poroplasted minicells.

Several chemical and physical techniques have been employed to remove the outer membrane of gram negative bacteria. Chemical techniques include the use of EDTA in Tris to make cells susceptible to hydrophobic agents such as actinomycin C. Leive L. The barrier function of the gram-negative envelope. Ann N Y Acad Sci. 1974 May 10; 235(0): 109-29.; Voll M J, Leive L. Actinomycin resistance and actinomycin excretion in a mutant of *Escherichia coli*. J Bacteriol. 1970 May; 102(2):600-2, Lactic Acid disruption of the outer membrane as measured by the uptake of hydrophobic fluorophores; Alakomi H L, Skytta E, Saarela M, Mattila-Sandholm T, Latva-Kala K, Helander I M. Lactic acid permeabilizes gram-negative bacteria by disrupting the outer membrane. Appl Environ Microbiol. 2000 May; 66(5):2001-5; and Polymyxin B disruption as measured by periplasmic constituent release (Teuber M, Cerny G. Release of the periplasmic ribonuclease I into the medium from *Escherichia coli* treated with the membrane-active polypeptide antibiotic polymyxin B. FEBS Lett. 1970 May 11; 8(1):49-51). Physical techniques include the use of osmodifferentiation to facilitate the disruption of the OM. Neu H C, Heppel L A. The release of enzymes from *Escherichia coli* by osmotic shock and during the formation of spheroplasts. J Biol Chem. 1965 September; 240(9):3685-92. See also Voll M J, Leive L. Actinomycin resistance and actinomycin excretion in a mutant of *Escherichia coli*. J Bacteriol. 1970 May; 102(2):600-2; Fiil A, Branton D. Changes in the plasma membrane of *Escherichia coli* during magnesium starvation. J Bacteriol. 1969 June; 98(3):1320-7; and Matsuyama S, Fujita Y, Mizushima S. SecD is involved in the release of translocated secretory proteins from the cytoplasmic membrane of *Escherichia coli*. EMBO J. 1993 January; 12(1):265-70.

III.E.3. Spheroplasts

A spheroplast is a bacterial minicell that has a disrupted cell wall and/or a disrupted OM. Unlike eubacterial minicells and poroplasts, which have a cell well and can thus retain their shape despite changes in osmotic conditions, the absence of an intact cell wall in spheroplasts means that these minicells do not have a rigid form.

III.E.4. Protoplasts

A protoplast is a bacterium that has its outer membrane and cell wall removed. The production of protoplasts involves the use of lysozyme and high salt buffers to remove the outer membrane and cell wall (Birdsell et al., Production and ultrastructure of lysozyme and ethylenediaminetetraacetate-Lysozyme Spheroplasts of *Escherichia coli*, J. Bacteriology 93: 427-437, 1967; Weiss, Protoplast formation in *Escherichia coli*. J. Bacteriol. 128:668-670, 1976). Various commercially available lysozymes can be used in such protocols. Measuring the total LPS that remains in the protoplast preparation is used to monitor the removal of the outer membrane. Endotoxin kits assays can be used to measure LPS in solution; increasing amounts of soluble LPS indicates decreased retention of LPS by protoplasts. This assay thus makes it possible to quantify the percent removal of total outer membrane from the minicells. Endotoxin assays are commerically available from, e.g., BioWhittaker Molecular Applications (Rockland, Me.)

For minicell applications that utilize bacterial-derived minicells, it may be necessary to remove the outer membrane of Gram-negative cells and/or the cell wall of any bacterial-derived minicell. For Gram-positive bacterial cells, removal of the cell wall may be easily accomplished using lysozyme. This enzyme degrades the cell wall allowing easy removal of now soluble cell wall components from the pelletable protoplasted minicells. In a more complex system, the cell wall and outer membrane of Gram-negative cells may be removed by combination treatment with EDTA and lysozyme using a step-wise approach in the presence of an osmoprotecting agent (Birdsell, et al. 1967. Production and ultrastructure of lysozyme and ethylenediaminetetraacetate-lysozyme spheroplasts of *E. coli*, J. Bacteriol. 93:427-437; Weiss, 1976. Protoplast formation in *E. coli*. J. Bacteriol. 128:668-670). By non-limitingBy way of non-limiting example, this osmoprotectant may be sucrose and/or glycerol. It has been found that the concentration of the osmoprotectant sucrose, the cell wall digesting enzyme lysozyme, and chelator EDTA can be optimized to increase the quality of the protoplasts produced. Separation of either prepared Gram-negative spheroplasts prepared in either fashion from removed remaining LPS may occur through exposure of the spheroplast mixture to an anti-LPS antibody. By non-limitingBy way of non-limiting example, the anti-LPS antibody may be covalently or non-covalently attached to magnetic, agarose, sepharose, sepheracyl, polyacrylamide, and/or sephadex beads. Following incubation, LPS is removed from the mixture using a magnet or slow centrifugation resulting in a protoplast-enriched supernatant.

Monitoring loss of LPS may occur through dot-blot analysis of protoplast mixtures or various commercially available endotoxin kit assays can be used to measure LPS in solution; increasing amounts of soluble LPS indicates decreased retention of LPS by protoplasts. This immuno assay may comprise a step of comparing the signal to a standard curve in order to quantify the percent removal of total outer membrane from the minicells. Other endotoxin assays, such as the LAL Systems from BioWhittaker, are commercially available. LPS removal has been measured by gas chromatography of fatty acid methyl esters. Alakomi H L, Skytta E, Saarela M, Mattila-Sandholm T, Latva-Kala K, Helander I M. Lactic acid permeabilizes gram-negative bacteria by disrupting the outer membrane. Appl Environ Microbiol. 2000 May; 66(5):2001-5.

In order to reduce, preferably eliminate, in vivo antigenic potential of minicells or minicell protoplasts, minicell protoplasts may be treated to remove undesirable surface components. Minicell protoplasts so treated are referred to as "denuded minicells" a term that encompasses both spheroplasts and protoplasts. Denuding minicells or minicell protoplasts is accomplished by treatment with one or more enzymes or conditions that selectively or preferentially removes or make less antigenic externally displayed proteins. As one non-limiting example, the protease trypsin is used to digest exposed proteins on the surface of these particles. In this example, the proteolytic activity of trypsin may be modulated or terminated by the additional of a soybean trypsin inhibitor. Non-limiting examples of other proteases that additionally or alternatively may be used include chymotrypsin, papain, elastase, proteinase K and pepsin. For some such proteases, it may be necessary to limit the extent of proteolysis by, e.g., using a suboptimal concentration of protease or by allowing the reaction to proceed for a suboptimal period of time. By the term "suboptimal," it is meant that complete digestion is not achieved under such conditions, even though the reactions could proceed to completion under other (i.e., optimal) conditions.

It is sometimes preferred to use molecular genetic techniques to create mutant derivatives of exogenous proteins that (1) are resistant to the proteases or other enzymes used to prepare minicells and (2) retain the desired biological activity of the receptor that is desired to be retained, i.e., the ability to bind one or more ligands of interest.

It is within the scope of the invention to have two or more exogenous proteins expressed within and preferentially displayed by minicells in order to achieve combined, preferable synergistic, therapeutic compositions. Similarly, two or more therapeutic minicell compositions are formulated into the same composition, or are administered during the same therapeutic minicell compositions (i.e., "cocktail" therapies). In other types of "cocktail" therapy, one or more therapeutic minicell compositions are combined or co-administered with one or more other therapeutic agents that are not minicell compositions such as, e.g., organic compounds, therapeutic proteins, gene therapy constructs, and the like.

III.F. Minicells from L-Form Eubacteria

L-form bacterial strains may be used to prepare minicells and are preferred in some embodiments of the invention. L-form bacterial strains are mutant or variant strains, or eubacteria that have been subject to certain conditions, that lack an outer membrane, a cell wall, a periplasmic space and extracellular proteases. Thus, in L-form Eubacteria, the cytoplasmic membrane is the only barrier between the cytoplasm and its surrounding environment. For reviews, see Grichko, V. P., et al. 1999. The Potential of L-Form Bacteria in Biotechnology, Can. J. Chem. Engineering 77:973-977; and Gumpert J., et al. 1998 Use of cell wall-less bacteria (L-forms) for efficient expression and secretion of heterologous gene products. Curr Opin Biotechnol. 9:506-9.

Segregation of minicells from L-form eubacterial parent cells allows for the generation of minicells that are at least partially deficient in barriers that lie outside of the cytoplasmic membrane, thus providing direct access to components displayed on the minicell membrane. Thus, depending on the strains and methods of preparation used, minicells prepared from L-form eubacterial parent cells will be similar if not identical to various forms of poroplasts, spheroplasts and/or protoplasts. Displayed components that are accessible in L-form minicells include, but are not limited to, lipids, small molecules, proteins, sugars, nucleic acids and/or moieties that are covalently or non-covalently associated with the cytoplasmic membrane or any component thereof.

By way of non-limiting example, L-form Eubacteria that can be used in the methods of the invention include species of *Escherichia, Streptomyces, Proteus, Bacillus, Clostridium, Pseudomonas, Yersinia, Salmonella, Enterococcus* and *Erwinia*. See Onoda, T., et al. 1987. Morphology, growth and reversion in a stable L-form of *Escherichia coli* K12. J. Gen. Microbiol. 133:527-534; Inanova, E. H., et al. 1997. Effect of *Escherichia coli* L-form cytoplasmic membranes on the interaction between macrophages and Lewis lung carcinoma cells: scanning electron microscopy. FEMS Immunol. Med. Microbiol. 17:27-36; Onoda, T., et al. 2000. Effects of calcium and calcium chelators on growth and morphology of *Escherichia coli* L-form NC-7. J Bacteriol. 182:1419-1422; Innes, C. M., et al. 2001. Induction, growth and antibiotic production of *Streptomyces viridifaciens* L-form bacteria. J Appl Microbiol. 90:301-308; Ferguson, C. M., et al. 2000. An ELISA for the detection of *Bacillus subtilis* L-form bacteria confirms their symbiosis in strawberry. Lett Appl Microbiol. 31:390-394; Waterhouse R. N., et al. 1994. An investigation of enumeration and DNA partitioning in *Bacillus subtilis* L-form bacteria. J Appl Bacteriol. 77:497-503; Hoischen, C., et al. 2002. Novel bacterial membrane surface display system using cell wall-less L-forms of *Proteus mirabilis* and *Escherichia coli*. Appl. Environ. Microbiol. 68:525-531; Rippmann, J. F., et al. 1998. Procaryotic expression of single-chain variable-fragment (scFv) antibodies: secretion in L-form cells of *Proteus mirabilis* leads to active product and overcomes the limitations of periplasmic expression in *Escherichia coli*. Appl. Environ. Microbiol. 64:4862-4869; Mahony, D. E., et al. 1988. Transformation of *Clostridium perfringens* L forms with shuttle plasmid DNA. Appl. Environ. Microbiol. 54:264-267); Kurona, M., et al. 1983. Intergenus cell fusions between L-form cells of *Pseudomonas aeruginosa* and *Escherichia coli*. Biken. J. 26:103-111; Ivanova, E., et al. 2000. Studies of the interactions of immunostimulated macrophages and *Yersinia enterocolitica* O:8. Can. J. Microbiol. 46:218-228; Allan, E. J., et al. 1993. Growth and physiological characteristics of *Bacillus subtilis* L-forms. J. Appl. Bacteriol. 74:588-594; Allan, E. J. 1991. Induction and cultivation of a stable L-form of *Bacillus subtilis*. J. Appl. Bacteriol. 70:339-343; Nishikawa, F., et al. 1994. Protective capacity of L-form *Salmonella typhimurium* against murine typhoid in C3H/HeJ mice. Microbiol. Immunol. 38:129-137; Kita, E., et al. 1993. Isolation of a cytotoxin from L-form *Salmonella typhimurium*. FEMS Microbiol. Lett. 109:179-184; Jass, J., et al. Growth and adhesion of *Enterococcus faecium* L-forms. FEMS Microbiol. Lett. 115:157-162; and U.S. Pat. No. 6,376,245.

IV. Assaying Minicells

IV.A. Efficiency of Minicell Production

The level of minicell production will vary and may be evaluated using methods described herein. Relatively high levels of minicell production are generally preferred. Conditions in which about 40% of cells are achromosomal have been reported (see, e.g., Hassan et al., Suppression of initiation defects of chromosome replication in *Bacillus subtilis* dnaA and oriC-deleted mutants by integration of a plasmid replicon into the chromosomes, J Bacteriol 179:2494-502, 1997). Procedures for identifying strains that give high yields of minicells are known in the art; see, e.g., Clark-Curtiss and Curtiss III, Analysis of Recombinant DNA Using *Escherichia coli* Minicells, Meth. Enzol. 101:347-362, 1983.

Minicell production can be assessed by microscopic examination of late log-phase cultures. The ratio of minicells to normal cells and the frequency of cells actively producing minicells are parameters that increase with increasing minicell production.

IV.B. Detecting Protein Synthesis in Minicells

Methods for detecting and assaying protein production are known in the art. See, e.g., Clark-Curtiss and Curtiss III, Meth Enzol 101:347-362, 1983. As an exemplary procedure, transformed *E. coli* minicell-producing cells are grown in LB broth with the appropriate antibiotic overnight. The following day the overnight cultures are diluted 1:50 in fresh media, and grown at 37° C. to mid-log phase. If it is desired to eliminate whole cells, an antibiotic that kills growing (whole) cells but not quiescent cells (minicells) may be used. For example, in the case of cells that are not ampicillin resistant, ampicillin (100 mg per ml is added), and incubation is allowed to continue for about 2 more hrs. Cultures are then centrifuged twice at low speed to pellet most of the large cells. Minicells are pelleted by spinning 10 min at 10,000 rpm, and are then resuspended in M63 minimal media supplemented with 0.5% casamino acids, and 0.5 mM cAMP, or M9 minimal medium supplemented with 1 mM $MgSO_4$, 0.1 mM $CaCl_2$, 0.05% NaCl, 0.2% glucose, and 1 ng per ml thiamine. Labeled ($^{35}S$) methonine is added to the minicells for about 15 to about 90 minutes, and minicells are immediately collected afterwards by centrifugation for 10 min at 4° C. and 14,000 rpm. Cells are resuspended in 50 to 100 µg Laemmeli-buffer, and disrupted by boiling and vortexing (2 min for each step). Incorporation of $^{35}S$-methionine was determined by measuring the amount of radioactivity contained in 1 µl of the lysate after precipitation of proteins with trichloroacetic acid (TCA). Minicell lysates (50,000 to 100,000 cpm per lane) are subjected to PAGE on, e.g., 10% polyacrylamide gels in which proteins of known size are also run as molecular weight standards. Gels are fixed and images there of are generated by, e.g., autoradiography or any other suitable detection systems.

IV.C. Evaluating the Therapeutic Potential of Minicells

Various methods are used at various stages of development of a therapeutic minicell composition to estimate their therapeutic potential. As a non-limiting example, the therapeutic potential of minicells displaying a receptor is examined as follows.

IV.C.1. Receptors

The specificity of, rate of association of, rate of dissociation of, and/or stability of complexes resulting from, receptor binding to its ligand can be measured in vitro using methods known in the art.

In the case of a sphingolipid binding receptor, such as an S1P receptor, the ligand (S1P) is detectably labeled so that the specificity of, rate of formation of, and degree of stability of complexes resulting from the ligand-receptor binding can be examined by measuring the degree and rate at which the labeled ligand is removed from solution due to its binding to minicells displaying the receptor. In order to avoid extraneous factors from influencing these experiments, they are carried out in buffered solutions that are as free of contaminating substances as possible. However, as is understood in the art, stabilizing agents such as BSA (bovine serum albumin) or protease inhibitors may be desirably included in these experiments. In a preferred environment, a sphingolipid binding receptor is the rat EDG-1, rat EDG-3, rat SCaMPER and human SCaMPER, the sequences of which are set forth herein.

Minicell compositions that bind sphingolipids with the desired specificity are identified from the preceding experiments. Typically, studies of ligand-receptor binding then proceed to studies in which the binding capacity of promising minicell compositions is tested under in vitro conditions that are increasingly more representative of in vivo conditions. For example, binding experiments are carried out in the presence of sera or whole blood in order to determine the therapeutic potential of minicell compositions in the presence of compounds that are present within the circulatory system of an animal.

IV.C.2. Molecular Sponge

Minicell compositions can also be tested for their ability to bind and/or interanlize toxic compounds. The therapeutic potential of such capacity is evaluated using experiments in which detectably labeled derivatives of a toxic compound are present in the bloodstream of an anesthetized animal, which may a human. The blood of the animal is shunted out of the body and past a device that incorporates a minicell composition before being returned to the body. The device is constructed so that the blood contacts a semipermeable membrane that is in contact with the minicell composition. By "semipermeable" it is meant that certain agents can be freely exchanged across the membrane, whereas others are retained on one side of the membrane or the other. For example, the toxic compound of interest is able to cross the semipermeable membrane, whereas minicells and blood cells are separately retained in their respective compartments. Detectably labeled derivatives of the toxic compound are present in the bloodstream of the animal. The capacity of the minicells to take up the toxic compound corresponds with a reduction of the levels of detectably labeled material in the blood and an increase in detectably labeled material in the minicell composition.

The above types of minicell-comprising compositions, devices, and procedures may be incorporated into ex vivo modalities such as ex vivo gene therapy and dialysis machines. An "ex vivo modality" is one in which a biological sample, such as a blood sample, is temporarily removed from an animal, altered through in vitro manipulation, and then returned to the body. In "ex vivo gene therapy," cells in the sample from the animal are transformed with DNA in vitro and then returned to the body. A "dialysis machine" is a device in which a fluid such as blood of an animal is temporarily removed therefrom and processed through one or more physical, chemical, biochemical, binding or other processes designed to remove undesirable substances including but are not limited to toxins, venoms, overexpressed or overactive endogenous agents, and pathogens or molecules derived therefrom.

Intraminicellular co-expression of a second molecule that is displayed on the surface of minicells, and which is a ligand for a binding moiety that is immobilized, can optionally be used in order to remove minicells from the sample before it is returned to the body. In the latter aspect, minicells that bind undesirable substances are preferably removed with the undesirable compound remaining bound to the minicells. Minicells that have been used for ex vivo gene therapy, but which have failed to deliver a nucleic acid to any cells in the sample, can be removed in a similar manner.

IV.C.3. Minicell-Solubilized Receptors

It is known in the art to use recombinant DNA technology to prepare soluble (hydrophilic) receptor fragments from receptors that bind a bioactive ligand. Unlike the native, membrane-bound receptor, which is relatively insoluble in water (hydrophobic), soluble receptor fragments can be formulated for therapeutic delivery using techniques that are known to have been used to formulate soluble agents.

Typically, soluble receptor fragments are used to competitively inhibit the binding of the receptor to its ligand. That is, the soluble receptor fragments bind the ligand at the expense of the membrane-bound receptor. Because less of the ligand is bound to its receptor, the cellular response to the ligand is attenuated. Common cellular responses that are desirably attenuated include but are not limited to the uptake of an undesirable agent (e.g., a toxin, a pathogen, etc.) and activation of a signaling pathway having undesirable consequences (e.g., inflammation, apoptosis, unregulated growth, etc.).

Preparing a soluble fragment derived from a receptor is not trivial. Typically, the three dimensional structure of the receptor is not known, and must be predicted based on homology with other receptors or by using software that predicts the tertiary structure of a polypeptide based on its amino acid sequence. Using the hypothetical structure of the receptor, a series of polypeptides are prepared that comprise amino acid sequences from the receptor but lack regions thereof that are thought to be membrane-anchoring or transmembrane domain(s) of the receptor. Some of the polypeptides prepared this way may be soluble, some may retain the binding activity of the receptor, and a few may have both characteristics. Members of the latter class of polypeptides are soluble receptor fragments, some of which may be amenable to development as a therapeutic or diagnostic agent.

For any given receptor, there is always the possibility that none of the soluble fragments derived from the receptor will specifically bind its ligand with sufficient affinity as to be thereapeutically effective. Thus, in some instances, it may not be possible to prepare a receptor fragment that is both soluble and sufficiently biologically active.

The minicells of the invention provide a "universal carrier" for receptors that allows the hydrophobic receptors to be solubilized in the sense that, although they remain associated with a membrane, the minicell is a small, soluble particle. That is, as an alternative to preparing a set of polypeptides to see which, if any of them, are water soluble receptor fragments, one may, using the teachings of the disclosure, prepare soluble minicells that display the receptor.

IV.C.4. Reducing Toxicity

For in vivo use of minicells for the purposes of eliciting an immune response or for therapeutic and diagnostic applications involving delivery of minicells to a human or to an anima, it may be useful to minimize minicell toxicity by using endotoxin-deficient mutants of parent cells. Without being limited to the following example, lipopolysaccharide (LPS) deficient *E. coli* strains could be conjugated with minicell producing cells to make parent cells lacking the endotoxin. LPS synthesis in *E. coli* includes the lipid A biosynthetic pathway. Four of the genes in this pathway have now been identified and sequenced, and three of them are located in a complex operon which also contains genes involved in DNA and phospholipid synthesis. The rfa gene cluster, which contains many of the genes for LPS core synthesis, includes at least 17 genes. The rfb gene cluster encodes protein involved in O-antigen synthesis, and rfb genes have been sequenced from a number of serotypes and exhibit the genetic polymorphism anticipated on the basis of the chemical complexity of the O antigens (Schnaitman and Klena. 1993. Genetics of lipopolysaccharide biosynthesis in enteric bacteria. Microbiol. Rev. 57:655-82). When present alone or in combination the rfb and oms mutations cause alterations in the eubacterial membrane that make it more sensitive to lysozyme and other agents used to process minicells. Similarly, the rfa (Chen, L., and W. G. Coleman Jr. 1993. Cloning and characterization of the *Escherichia coli* K-12 rfa-2 (rfaC) gene, a gene required for lipopolysaccharide inner core synthesis. J. Bacteriol. 175: 2534-2540), lpcA (Brooke, J. S., and M. A. Valvano. 1996. Biosynthesis of inner core lipopolysaccharide in enteric bacteria identification and characterization of a conserved phosphoheptose isomerase. J. Biol. Chem. 271:3608-3614), and lpcB (Kadrman, J. L., et al. 1998. Cloning and overexpression of glycosyltransferases that generate the lipopolysaccharide core of *Rhizobium leguminosarum*. J. Biol. Chem. 273: 26432-26440) mutations, when present alone or in combination, cause alterations in lipopolysaccharides in the outer membrane causing cells to be more sensitive to lysozyme and agents used to process minicells. In addition, such mutations can be used to reduce the potential antigenicity and/or toxicity of minicells.

Minicell-producing cells may comprise mutations that augment preparative steps. For example, lipopolysaccharide (LPS) synthesis in *E. coli* includes the lipid A biosynthetic pathway. Four of the genes in this pathway have now been identified and sequenced, and three of them are located in a complex operon that also contains genes involved in DNA and phospholipid synthesis. The rfa gene cluster, which contains many of the genes for LPS core synthesis, includes at least 17 genes. The rfb gene cluster encodes protein involved in O-antigen synthesis, and rfb genes have been sequenced from a number of serotypes and exhibit the genetic polymorphism anticipated on the basis of the chemical complexity of the O antigens. See Schnaitman and Klena, Genetics of lipopolysaccharide biosynthesis in enteric bacteria, Microbiol. Rev. 57:655-82, 1993. When present, alone, or in combination, the rfb and oms mutations cause alterations in the eubacterial membrane that make it more sensitive to lysozyme and other agents used to process minicells. Similarly, the rfa (Chen, L., and W. G. Coleman Jr. 1993. Cloning and characterization of the *Escherichia coli* K-12 rfa-2 (rfaC) gene, a gene required for lipopolysaccharide inner core synthesis. J. Bacteriol. 175:2534-2540), lpcA (Brooke, J. S., and M. A. Valvano. 1996. Biosynthesis of inner core lipopolysaccharide in enteric bacteria identification and characterization of a conserved phosphoheptose isomerase. J. Biol. Chem. 271:3608-3614), and lpcB (Kadrman, J. L., et al. 1998. Cloning and overexpression of glycosyltransferases that generate the lipopolysaccharide core of *Rhizobium leguminosarum*. J. Biol. Chem. 273:26432-26440) mutations, when present alone or in combination, cause alterations in lipopolysaccharides in the outer membrane causing cells to be more sensitive to lysozyme and agents used to process minicells. In addition, such mutations can be used to reduce the potential antigenicity and/or toxicity of minicells.

V. Genetic Expression in Minicells

Various minicells of the invention use recombinant DNA expression systems to produce a non-eubacterial protein, which may be a membrane protein that is preferably "displayed" on the surface of minicells, a membrane protein that projects portions not associtiated with a membrane towards the interior of a minicell, or a soluble protein present in the exterior of the minicells. By "displayed" it is meant that a protein is present on the surface of a cell (or minicell) and is thus in contact with the external environment of the cell. Non-limiting examples of displayed exogenous proteins of the invention include mammalian receptors and fusion proteins comprising one or more transmembrane domains. In other aspects of the invention, minicells use expression elements to produce bioactive nucleic acids from templates therefor.

V.A. Expression Systems

In vivo and in vitro protein expression systems provide a variety of techniques that allow scientists to transcribe and translate amino acid polypeptides proteins from recombinant DNA templates (Kaufman, Overview of vector design for mammalian gene expression. Mol Biotechnol, 2001. 16: 151-160; and Kozak, Initiation of translation in prokaryotes and eukaryotes. Gene, 1999. 234: 187-208).

Although minicells are virtually depleted of chromosomal DNA (Tudor et al., Presence of nuclear bodies in some minicells of *Escherichia coli*. J Bacteriol, 1969. 98: 298-299), it has been reported that minicells have all the elements required to express nucleotide sequences that are present in episomal expression elements therein (Levy, Very stable prokaryote messenger RNA in chromosomeless *Escherichia coli* minicells. Proc Natl Acad Sci USA, 1975. 72: 2900-2904; Hollenberg et al., Synthesis of high molecular weight polypeptides in *Escherichia coli* minicells directed by cloned *Saccharomyces cerevisiae* 2-micron DNA. Gene, 1976. 1: 33-47; Crooks et al., Transcription of plasmid DNA in *Escherichia coli* minicells. Plasmid, 1983. 10: 66-72; Clark-Curtiss, Analysis of recombinant DNA using *Escherichia coli* minicells. Methods Enzymol, 1983. 101: 347-362).

Preferred expression vectors and constructs according to the invention are episomal genetic elements. By "episomal" it is meant that the expression construct is not always linked to a cell's chromosome but may instead be retained or maintained in host cells as a distinct molecule entity. Minicells can retain, maintain and express episomal expression constructs such as, e.g., plasmids, bacteriophage, viruses and the like (Crooks et al., Plasmin 10:66-72, 1983; Clark-Curtiss, Methods Enzymology 101:347-62, 1983; Witkiewicz et al., Acta. Microbiol. Pol. A 7:21-24, 1975; Ponta et al., Nature 269: 440-2, 1977). By "retained" it is meant that the episomal expression construct is at least temporarily present and expressed in a host parent cell and/or minicell; by "maintained" it is meant that the episomal expression construct is capable of autonomous replication within a host parent cell and/or minicell. In the context of episomal elements, the term "contained" encompasses both "retained" and "maintained." A preferred type of an episomal element according to the invention is one that is always an extrachromocomal element, or which is part of a chromosome but becomes an extrachromosomal element before or during minicell production.

The fact that minicells do not contain chromosomal DNA but do contain episomal expression elements, such as plasmids, that can be used as templates for RNA synthesis means that the only proteins that are actively produced in minicells are those that are encoded by the expression elements that they contain. Minicell-producing *E. coli* cells can be made competent and transformed with expression elements that direct the expression of proteins encoded by the expression elements. An expression element segregates into minicells as they are produced. In isolated minicells that contain expression elements, there is a single DNA template RNA for transcription. Therefore, the only nucleic acids and proteins that are actively produced (expressed) by minicells are those that are encoded by sequences on the expression vector. In the context of the invention, sequences that encode amino acid sequences are designated "open reading frames" or "ORFs." One feature of minicell expression systems of interest as regards the present invention is that endogenous (i.e., chromosomally located) genes are not present and are thus not expressed, whereas genes present on the episomal element are expressed (preferably over-expressed) in the minicells. As a result, the amount of endogenous proteins, including membrane proteins, decreases as the minicells continue to express genes located on episomal expression constructs.

The minicell system can reduce or eliminate undesirable features associated with the transcription and translation of endogenous proteins from the *E. coli* chromosome. For example, expression of proteins in minicell systems results in low background signal ("noise") when radiolabeled proteins produced using recombinant DNA technology (Jannatipour et al., Translocation of *Vibrio Harveyi* N,N'-Dlacetylchitobiase to the outer membrane of *Escherichia coli*. J. Bacteriol, 1987. 169: 3785-3791). A high background signal can make it difficult to detect a protein of interest. In whole cell *E. coli* systems, endogenous proteins (encoded by the bacterial chromosome) are labeled as well as the protein(s) encoded by the expression element; whereas, in minicell systems, only the proteins encoded by the expression element in the minicells are labeled.

There are a variety of proteins, both eubacterial and eukaryotic, that have been expressed from plasmid DNA in minicells (Clark-Curtiss, Methods Enzymal, 101:347-362, 1983). Some examples of proteins and nucleic acids that have been expressed in minicells include the Kdp-ATPase of *E. coli* (Altendorf et al., Structure and function of the Kdp-ATPase of *Escherichia coli*. Acta Physiol Scand, 643: 137-146, 1998); penicillin binding proteins aplha and gamma (Davies et al., Prediction of signal sequence-dependent protein translocation in bacteria: Assessment of the *Escherichia* coli minicell system. Biochem Biophys Res Commun, 150: 371-375, 1988); cell surface antigens of *Polyromaonas gingivalas* (Rigg et al., The molecular cloning, nucleotide sequence and expression of an antigenic determinant from *Porphyromonas gingivalis*. Arch Oral Biol, 45:41-52, 2000); trkG integral membrane protein of *E. coli* (Schlosser et al., Subcloning, Nucleotide sequence, and expression of trkG, a gene that encodes an integral membrane protein involved in potassium uptake via the Trk system of *Escherichia coli*. J. Bacteriol, 173:3170-3176, 1991); the 34 kDa antigen of *Treponema pallidum* (Swancutt et al., Molecular characterization of the pathogen-specific, 34-kilodalton membrane immunogen of *Treponema pallidum*. Infect Immun, 57:3314-23, 1989); late proteins of bacteriophage MB78 (Colla et al., IUBMB Life 48:493-497, 1999); uncharacterisized DNA from *Xenopus laevis* (Cohen and Boyer, U.S. Pat. No. 4,237, 224, which issued Dec. 2, 1980); the one gene v-fos (MacConnell and Verman, Expression of FBJ-MSV oncogene (fos) product in bacteria, 131(2) Virology 367 1983); interferon (Edge et al., Chemical synthesis of a human inteferon-alpha 2 gene and its expression in *Escherichia coli*, Nucleic Acids Res. 11:6419, 1983); bovine growth hormone (Rosner et al., Expression of a cloned bovine growth hormone gene in *Escherichia coli* minicells, Can. J. Biochem. 60:521-4, 1982); gastroitestinal hormone (Suzuki et al., Production in *Escherichia coli* of biologically active secretin, a gastroninstestinal hormone, Proc. Natl. Acad. Sci. USA 79:2475, 1982); and archeabacterial proteins (Lienard and Gottschalk, Cloning, sequencing and expression of the genes encoding the sodium translocating N-methyltetrahydromethanopterin: coenzyme M methyltransferase of the methylotrohic archaeon Methanosarcina mazei Göl, 425 FEBS Letters 204, 1998; and Lemker et al., Overproduction of a functional A1 ATPase from the archaeon Methanosarcina mazei G1 in *Escherichia coli*, European Journal of Biochemistry 268:3744, 2001).

V.B. Modulating Genetic Expression in Minicells

Gene expression in minicells, and/or in minicell-producing (parent) cells, involves the coordinated activity of a variety of expression factors, regulatory elements and expression sequences. Any of these may be modified to alter the extent, timing or regulation of expression of a gene of interest in minicells and/or their parent cells. Often, the goal of the manipulations is to increase the efficiency of protein production in minicells. However, increased expression may, in some instances, desirably include increased or "tight" negative regulation. This may reduce or eliminate selective pressure created by toxic gene products, and allow for functional expression in a controlled fashion by removing the negative regulation and/or inducing expression of the gene product at a preselected time. By way of non-limiting example, these techniques may include modification or deletion of endogenous gene(s) from which their respective gene product decreases the induction and expression efficiency of a desired protein in the parent cell prior to minicell formation and/or the segregated minicell. By way of non-limiting example, these protein components may be the enzymes that degrade chemical inducers of expression, proteins that have a dominant negative affect upon a positive regulatory elements, proteins that have proteolytic activity against the protein to be expressed, proteins that have a negative affect against a chaperone that is required for proper activity of the expressed protein, and/or this protein may have a positive effect upon a protein that either degrades or prevents the proper function of the expressed protein. These gene products that require deletion or modification for optimal protein expression and/or function may also be antisense nucleic acids that have a negative affect upon gene expression.

VI. Fusion (Chimeric) Proteins

In certain aspects of the invention, a fusion protein is expressed and displayed by minicells. One class of fusion proteins of particular interest are those that are displayed on the surface of minicells, e.g., fusion proteins comprising one or more transmembrane domains. Types of displayed fusion proteins of particular interest are, by way of non-limiting example, those that have an extracellular domain that is a binding moiety or an enzymatic moiety. By way of non-limiting example, the fusion protein ToxR-PhoA has been expressed in and displayed on the surface of minicells. The ToxR-PhoA fusion protein comprises a polypeptide corresponding to the normally soluble enzyme, alkaline phosphatase, anchored to the minicell membrane by the single transmembrane domain of ToxR (see the Examples). The fusion protein retains the activity of the enzyme in the context of the minicell membrane in which it is bound. Nearly all of the fusion protein is oriented so that the enzyme's catalytic domain is displayed on the outer surface of the minicell.

VI.A. Generation of Fusion Proteins

Polypeptides, which are polymers of amino acids, are encoded by another class of molecules, known as nucleic acids, which are polymers of structural units known as nucleotides. In particular, proteins are encoded by nucleic acids known as DNA and RNA (deoxyribonucleic acid and ribonucleic acid, respectively).

The nucleotide sequence of a nucleic acid contains the "blueprints" for a protein. Nucleic acids are polymers of nucleotides, four types of which are present in a given nucleic acid. The nucleotides in DNA are adenine, cytosine and guanine and thymine, (represented by A, C, G, and T respectively); in RNA, thymine (T) is replaced by uracil (U). The structures of nucleic acids are represented by the sequence of its nucleotides arranged in a 5' ("5 prime") to 3' ("3 prime") direction, e.g.,

5'-A-T-G-C-C-T-A-A-A-G-C-C-G-C-T-C-C-C-T-C-A-3' (SEQ ID NO. 361)

In biological systems, proteins are typically produced in the following manner. A DNA molecule that has a nucleotide sequence that encodes the amino acid sequence of a protein is used as a template to guide the production of a messenger RNA (mRNA) that also encodes the protein; this process is known as transcription. In a subsequent process called translation, the mRNA is "read" and directs the synthesis of a protein having a particular amino acid sequence.

Each amino acid in a protein is encoded by a series of three contiguous nucleotides, each of which is known as a codon. In the "genetic code," some amino acids are encoded by several codons, each codon having a different sequence; whereas other amino acids are encoded by only one codon sequence. An entire protein (i.e., a complete amino acid sequence) is encoded by a nucleic acid sequence called a reading frame. A reading frame is a continuous nucleotide sequence that encodes the amino acid sequence of a protein; the boundaries of a reading frame are defined by its initiation (start) and termination (stop) codons.

The process by which a protein is produced from a nucleic acid can be diagrammed as follows:

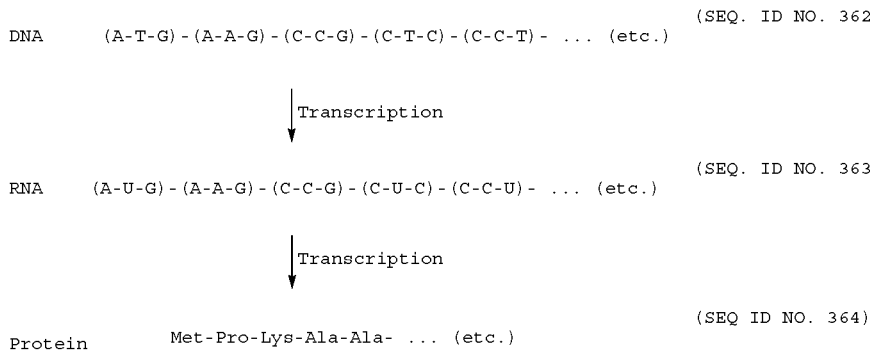

A chimeric reading frame encoding a fusion protein is prepared as follows. A "chimeric reading frame" is a genetically engineered reading frame that results from the fusion of two or more normally distinct reading frames, or fragments thereof, each of which normally encodes a separate polypeptide. Using recombinant DNA techniques, a first reading frame that encodes a first amino acid sequence is linked to a second reading frame that encodes a second amino acid sequence in order to generate a chimeric reading frame. Chimeric reading frames may also include nucleotide sequences that encode optional fusion protein elements (see below).

A hypothetical example of a chimeric reading frame created from two normally separate reading frames is depicted in the following flowchart.

First Open Reading Frame and "Protein-1":

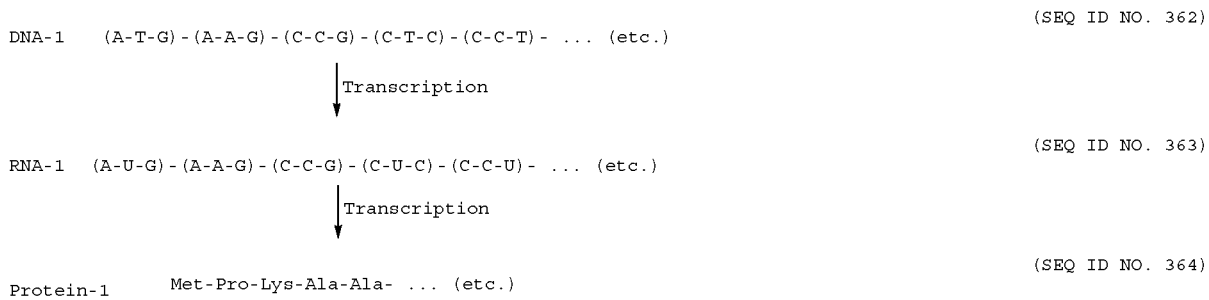

Second Open Reading Frame and "Protein-2":

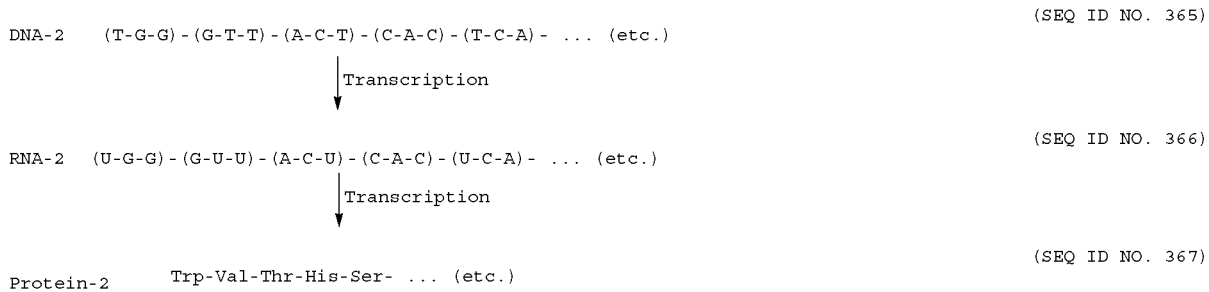

Chimeric Reading Frame that encodes a Fusion Protein having sequences from Protein-1 and Protein-2:

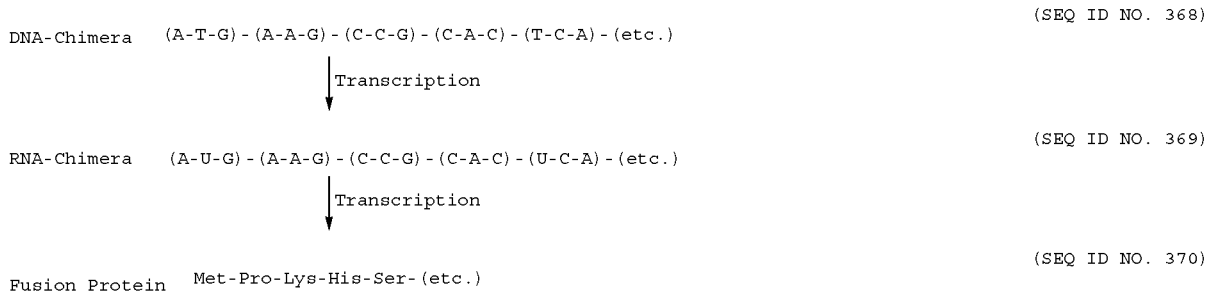

In order for a chimeric reading frame to be functional, each normally distinct reading frame therein must be fused to all of the other normally distinct reading frames in a manner such that all of the reading frames are in frame with each other. By "in frame with each other" it is meant that, in a chimeric reading frame, a first nucleic acid having a first reading frame is covalently linked to a second nucleic acid having a second reading frame in such a manner that the two reading frames are "read" (translated) in register with each other. As a result, the chimeric reading frame encodes one extended amino acid sequence that includes the amino acid sequences encoded by each of the normally separate reading frames. A fusion protein is thus encoded by a chimeric reading frame.

The fusion proteins of the invention are used to display polypeptides on minicells. The fusion proteins comprise (1) at least one polypeptide that is desired to be displayed by minicells (a "displayed polypeptide") and (2) at least one membrane polypeptide, e.g., a transmembrane or a membrane anchoring domain. For various aspects of the invention, optional fusion protein elements, as defined herein, may also be included if required or desired.

VI.B. Optional Fusion Protein Elements

The fusion proteins of the invention may optionally comprise one or more non-biologically active amino acid sequences, i.e., optional fusion protein elements. Such elements include, but are not limited to, the following optional fusion protein elements. It is understood that a chimeric reading frame will include nucleotide sequences that encode such optional fusion protein elements, and that these nucleotide sequences will be positioned so as to be in frame with the reading frame encoding the fusion protein. Optional fusion protein elements may be inserted between the displayed polypeptide and the membrane polypeptide, upstream or downstream (amino proximal and carboxy proximal, respectively) of these and other elements, or within the displayed polypeptide and the membrane polypeptide. A person skilled in the art will be able to determine which optional element(s) should be included in a fusion protein of the invention, and in what order, based on the desired method of production or intended use of the fusion protein.

Detectable polypeptides are optional fusion protein elements that either generate a detectable signal or are specifically recognized by a detectably labeled agent. An example of the former class of detectable polypeptide is green fluorescent protein (GFP). Examples of the latter class include epitopes such as a "His tag" (6 contiguous His residues, a.k.a. 6×His), the "FLAG tag" and the c-myc epitope. These and other epitopes can be detected using labeled antibodies that are specific for the epitope. Several such antibodies are commercially available.

Attachment (support-binding) elements are optionally included in fusion proteins and can be used to attach minicells displaying a fusion protein to a preselected surface or support. Examples of such elements include a "His tag," which binds to surfaces that have been coated with nickel; streptavidin or avidin, which bind to surfaces that have been coated with biotin or "biotinylated" (see U.S. Pat. No. 4,839,293 and Airenne et al., Protein Expr. Purif. 17:139-145, 1999); and glutathione-s-transferase (GST), which binds to surfaces coated with glutathione (Kaplan et al., Protein Sci. 6:399-406, 1997; U.S. Pat. No. 5,654,176). Polypeptides that bind to lead ions have also been described (U.S. Pat. No. 6,111,079).

Spacers (a.k.a. linkers) are amino acid sequences that are optionally included in a fusion protein in between other portions of a fusion protein (e.g., between the membrane polypeptide and the displayed polypeptide, or between an optional fusion protein element and the remainder of the fusion protein). Spacers can be included for a variety of reasons. For example, a spacer can provide some physical separation between two parts of a protein that might otherwise interfere with each other via, e.g., steric hindrance. The ability to manipulate the distance between the membrane polypeptide and the displayed polypeptide allows one to extend the displayed polypeptide to various distances from the surface of minicells.

VI.C. Interactions with Receipient Cells

Many Gram-negative pathogens use a type III secretion machine to translocate protein toxins across the bacterial cell envelope (for a review, see Cheng L W, Schneewind O. Type III machines of Gram-negative bacteria: delivering the goods. Trends Microbiol 2000 May; 8(5):214-20). For example, pathogenic *Yersinia* spp. export over a dozen Yop proteins via a type III mechanism, which recognizes secretion substrates by signals encoded in yop mRNA or chaperones bound to unfolded Yop proteins. A 70-kb virulence plasmid found in pathogenic *Yersinia* spp. to survive and multiply in the lymphoid tissues of the host. The virulence plasmid encodes the Yop virulon, an integrated system allowing extracellular bacteria to inject bacterial proteins into cells. The Yop virulon comprises a variety of Yop proteins and a dedicated type III secretion apparatus, called Ysc (for a review, see Cornelis G R, Boland A, Boyd A P, Geuijen C, Iriarte M, Neyt C, Sory M P, Stainier I. The virulence plasmid of *Yersinia*, an antihost genome. Microbiol Mol Biol Rev 1998 62(4):1315-52).

VII. Minicell Display

Included in the design of the invention is the use of minicells to express and display soluble or membrane-bound protein libraries to identify a soluble or membrane-bound protein that binds a known ligand or to identify proteins (e.g. orphan receptors) for which the known ligand or substrate is not known but for which a reporter could be engineered into the minicell that would signal the presence of the encoded protein. In the preferred embodiment of the invention, this 'minicell display' technique is analogous to phage display for the purpose of identifying genes that encode receptor-like or antibody-like proteins against known ligand. This approach will allow identification of an unknown receptor protein for which a known ligand has affinity. These known ligands may have been identified as having a pharmacological, biological, or other effect without knowledge of the site of effect. In these cases the knowledge of receptor will allow basic research to understand the molecular and/or physiological response and permit directed modification of the ligand for better pharmacological or biological response or modification of the receptor for employment in ligand-binding applications. In another non-limiting embodiment of the invention, the ligand need not be known but some general characteristic of the protein would be.

For purposes of this application, soluble or membrane-bound protein libraries may be constructed by random cloning of DNA fragments or directed cloning using reverse transcriptase polymerase chain reaction (RT-PCR). In either method, DNA fragments may be placed under the regulation of any regulatory element listed in section II.B. on any plasmid or chromosomal construct. In the case of soluble protein receptors, they will be fused to form a chimeric protein with a known transmembrane domain (TMD), e.g. the TMD from the toxR gene product. Upon induction of the soluble or membrane-bound protein library, minicells, minicell protoplasts, or minicell poroplasts (as the experiment requires) will be mixed with the known ligand. Without being limited to the following example, screening could be accomplished by first labeling the known ligand with a molecular fluorophore, e.g. TAMRA, FTC, or in some cases a fluorescent protein, e.g.

GFP. A positive interaction between the minicells displaying the receptor for the labeled ligand will be identified and separated from the library population by fluorescent-activated cell sorting (FACS). Isolated, positive receptor-ligand interactions will be identified by PCR amplification, subcloned into a clean background, and sequenced using plasmid-specific oligonucleotides. Subcloned proteins will be re-screened for interaction with the labeled ligand, and their binding patterns characterized.

Positive interacting receptor proteins may be employed in mutagenesis or other directed evolutionary process to improve or decrease the binding affinity to the ligand. In another application, the receptor-ligand pair may be further employed in a screening process to identify new compounds that may interfere with the interaction. Thus, using a known substance to identify the receptor and the identified receptor-ligand pair to identify other interfering compounds. Chimeric-soluble or membrane-bound protein libraries may be screened versus a protein-array chip that presents a variety of known protein compounds or peptide variations. In this application, the minicell, minicell protoplast, or minicell poroplast will also contain a label, signaling component, and/or antigen recognizable by an antibody for identification of a positive interaction on the protein chip array. Other approaches for identification may include packaged fluorescent molecules or proteins that are constitutively produced, induced by the positive interaction with the ligand, or regulated by a regulatory element described in section II.B.

In a preferred embodiment of the invention, cDNA libraries could be constructed from isolated B-cells, activated B-cell or T-cells for the purpose of identifying receptors or antibodies that are encoded by these cells of the immune system. In a non-limiting example, a small molecule could be used to immunize an experimental animal (e.g., rat, mouse, rabbit), the spleen could be removed, or blood could be drawn and used as a source of mRNA. Reverse transcription reactions could then be used to construct a cDNA library that would eventually be transformed into the minicell parent bacteria, as described above. The minicells would then be isolated, induced and subjected to FACS analysis with subsequent amplification and sequencing of the cDNA fragment of interest (see above). The PCR-amplified plasmid-containing cDNA fragment encoding the "receptor" or "antibody" of interest would be ready for transformation and expression in the minicell context for diagnostic, therapeutic research or screening applications of the invention.

In a related, non-limiting embodiment of the invention, minicells expressing a particular antigen (e.g., protein, carbohydrate, small molecule, lipid) on their surfaces (described elsewhere in this application) are used to generate an immunogenic response. The advantages of presenting an antigen on the surfaces of minicells are that the minicells themselves may be an adjuvant that stimulates the immune response, particularly if administered subcutaneously (SC) or intramuscularly (IM). Moreover, the minicells are not readily eliminated by the renal system and are present in the circulatory system of an immunized animal for a longer time. In addition, small molecules could be tethered to the minicell in a way that presents the desired moiety of the molecule. Animals are presented with minicell-based immunogens, and the antibodies produced in the animals are prepared and used in therapeutic, diagnostic, research and screening applications. Although this aspect of the invention may be used to make antibodies to any molecule displayed on their surface, the extracellular domains of membrane proteins are of particular interest.

Minicell display could be used to identify orphan receptors or other proteins for which a ligand or substrate is not known. As a non-limiting example, orphan G protein coupled receptors (GPCRs) or novel RNA and DNA polymerases could be identified from organisms living in extreme environments. A cDNA library could be is constructed from an organism and expressed in minicells that co-express a reporter system that indicates the presence of the novel protein. In a non-limiting example of GPCRs, the minicells used for minicell display are engineered to express a G-protein in a manner that would signal an interaction with the orphan GPCR.

VIII. Aptamers

Traditionally, techniques for detecting and purifying target molecules have used polypeptides, such as antibodies, that specifically bind such targets. While nucleic acids have long been known to specifically bind other nucleic acids (e.g., ones having complementary sequences), aptamers (i.e., nucleic acids that bind non-nucleic target molecules) have been disclosed. See, e.g., Blackwell et al., Science (1990) 250:1104-1110; Blackwell et al., Science (1990) 250:1149-1152; Tuerk et al., Science (1990) 249:505-510; Joyce, Gene (1989) 82:83-87; and U.S. Pat. No. 5,840,867 entitled "Aptamer analogs specific for biomolecules".

As applied to aptamers, the term "binding" specifically excludes the "Watson-Crick"-type binding interactions (i.e., A:T and G:C base-pairing) traditionally associated with the DNA double helix. The term "aptamer" thus refers to a nucleic acid or a nucleic acid derivative that specifically binds to a target molecule, wherein the target molecule is either (i) not a nucleic acid, or (ii) a nucleic acid or structural element thereof that is bound through mechanisms other than duplex- or triplex-type base pairing. Such a molecule is called a "non-nucleic molecule" herein.

VIII.A. Structures of Nucleic Acids

"Nucleic acids," as used herein, refers to nucleic acids that are isolated a natural source; prepared in vitro, using techniques such as PCR amplification or chemical synthesis; prepared in vivo, e.g., via recombinant DNA technology; or by any appropriate method. Nucleic acids may be of any shape (linear, circular, etc.) or topology (single-stranded, double-stranded, supercoiled, etc.). The term "nucleic acids" also includes without limitation nucleic acid derivatives such as peptide nucleic acids (PNA's) and polypeptide-nucleic acid conjugates; nucleic acids having at least one chemically modified sugar residue, backbone, internucleotide linkage, base, nucleoside, or nucleotide analog; as well as nucleic acids having chemically modified 5' or 3' ends; and nucleic acids having two or more of such modifications. Not all linkages in a nucleic acid need to be identical.

Nucleic acids that are aptamers are often, but need not be, prepared as oligonucleotides. Oligonucleotides include without limitation RNA, DNA and mixed RNA-DNA molecules having sequences of lengths that have minimum lengths of 2, 4, 6, 8, 10, 11, 12, 13, 14, 15, 17, 18, 19, 20, 21, 22, 23, 24 or 25 nucleotides, and maximum lengths of about 100, 75, 50, 40, 25, 20 or 15 or more nucleotides, irrespectively. In general, a minimum of 6 nucleotides, preferably 10 nucleotides, more preferably 14 to 20 nucleotides, is necessary to effect specific binding.

In general, the oligonucleotides may be single-stranded (ss) or double-stranded (ds) DNA or RNA, or conjugates (e.g., RNA molecules having 5' and 3' DNA "clamps") or hybrids (e.g., RNA:DNA paired molecules), or derivatives (chemically modified forms thereof). However, single-stranded DNA is preferred, as DNA is often less labile than RNA. Similarly, chemical modifications that enhance an aptamer's specificity or stability are preferred.

VIII.B. Chemical Modifications of Nucleic Acids

Chemical modifications that may be incorporated into aptamers and other nucleic acids include, with neither limitation nor exclusivity, base modifications, sugar modifications, and backbone modifications.

Base modifications: The base residues in aptamers may be other than naturally occurring bases (e.g., A, G, C, T, U, 5MC, and the like). Derivatives of purines and pyrimidines are known in the art; an exemplary but not exhaustive list includes aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine (5MC), N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. In addition to nucleic acids that incorporate one or more of such base derivatives, nucleic acids having nucleotide residues that are devoid of a purine or a pyrimidine base may also be included in aptamers.

Sugar modifications: The sugar residues in aptamers may be other than conventional ribose and deoxyribose residues. By way of non-limiting example, substitution at the 2'-position of the furanose residue enhances nuclease stability. An exemplary, but not exhaustive list, of modified sugar residues includes 2' substituted sugars such as 2'-O-methyl-, 2'-O-alkyl, 2'-O-allyl, 2'-S-alkyl, 2'-S-allyl, 2'-fluoro-, 2'-halo, or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside, ethyl riboside or propylriboside.

Backbone modifications: Chemically modified backbones include, by way of non-limiting example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Chemically modified backbones that do not contain a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages, including without limitation morpholino linkages; siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; and amide backbones.

VIII.C. Preparation and Identification of Aptamers

In general, techniques for identifying aptamers involve incubating a preselected non-nucleic target molecule with mixtures (2 to 50 members), pools (50 to 5,000 members) or libraries (50 or more members) of different nucleic acids that are potential aptamers under conditions that allow complexes of target molecules and aptamers to form. By "different nucleic acids" it is meant that the nucleotide sequence of each potential aptamer may be different from that of any other member, that is, the sequences of the potential aptamers are random with respect to each other. Randomness can be introduced in a variety of manners such as, e.g., mutagenesis, which can be carried out in vivo by exposing cells harboring a nucleic acid with mutagenic agents, in vitro by chemical treatment of a nucleic acid, or in vitro by biochemical replication (e.g., PCR) that is deliberately allowed to proceed under conditions that reduce fidelity of replication process; randomized chemical synthesis, i.e., by synthesizing a plurality of nucleic acids having a preselected sequence that, with regards to at least one position in the sequence, is random. By "random at a position in a preselected sequence" it is meant that a position in a sequence that is normally synthesized as, e.g., as close to 100% A as possible (e.g., 5'-C-T-T-A-G-T-3') is allowed to be randomly synthesized at that position (C-T-T-N-G-T, wherein N indicates a randomized position where, for example, the synthesizing reaction contains 25% each of A,T,C and G; or x % A, w % T, y % C and z % G, wherein x+w+y+z=100. In later stages of the process, the sequences are increasingly less randomized and consensus sequences may appear; in any event, it is preferred to ultimately obtain an aptamer having a unique nucleotide sequence.

Aptamers and pools of aptamers are prepared, identified, characterized and/or purified by any appropriate technique, including those utilizing in vitro synthesis, recombinant DNA techniques, PCR amplification, and the like. After their formation, target:aptamer complexes are then separated from the uncomplexed members of the nucleic acid mixture, and the nucleic acids that can be prepared from the complexes are candidate aptamers (at early stages of the technique, the aptamers generally being a population of a multiplicity of nucleotide sequences having varying degrees of specificity for the target). The resulting aptamer (mixture or pool) is then substituted for the starting apatamer (library or pool) in repeated iterations of this series of steps. When a limited number (e.g., a pool or mixture, preferably a mixture with less than 100 members, more preferably less than 10 members, most preferably 1, of nucleic acids having satisfactory specificity is obtained, the aptamer is sequenced and characterized. Pure preparations of a given aptamer are generated by any appropriate technique (e.g., PCR amplification, in vitro chemical synthesis, and the like).

For example, Tuerk and Gold (Science (1990) 249:505-510) disclose the use of a procedure termed "systematic evolution of ligands by exponential enrichment" (SELEX). In this method, pools of nucleic acid molecules that are randomized at specific positions are subjected to selection for binding to a nucleic acid-binding protein (see, e.g., PCT International Publication No. WO 91/19813 and U.S. Pat. No. 5,270,163). The oligonucleotides so obtained are sequenced and otherwise characterization. Kinzler, K. W., et al. (Nucleic Acids Res. (1989) 17:3645-3653) used a similar technique to identify synthetic double-stranded DNA molecules that are specifically bound by DNA-binding polypeptides. Ellington, A. D., et al. (Nature (1990) 346: 818-822) disclose the production of a large number of random sequence RNA molecules and the selection and identification of those that bind specifically to specific dyes such as Cibacron blue.

Another technique for identifying nucleic acids that bind non-nucleic target molecules is the oligonucleotide combinatorial technique disclosed by Ecker, D. J. et al. (Nuc. Acids Res. 21, 1853 (1993)) known as "synthetic unrandomization of randomized fragments" (SURF), which is based on repetitive synthesis and screening of increasingly simplified sets of oligonucleotide analogue libraries, pools and mixtures (Tuerk et al., Science 249:505, 1990). The starting library consists of oligonucleotide analogues of defined length with one position in each pool containing a known analogue and the remaining positions containing equimolar mixtures of all other analogues. With each round of synthesis and selection, the identity of at least one position of the oligomer is determined until the sequences of optimized nucleic acid ligand aptamers are discovered.

Once a particular candidate aptamer has been identified through a SURF, SELEX or any other technique, its nucleotide sequence can be determined (as is known in the art), and its three-dimensional molecular structure can be examined by nuclear magnetic resonance (NMR). These techniques are explained in relation to the determination of the three-dimensional structure of a nucleic acid ligand that binds thrombin in Padmanabhan et al., J. Biol. Chem. 24, 17651 (1993); Wang et al., Biochemistry 32, 1899 (1993); and Macaya et al., Proc. Nat'l. Acad. Sci. USA 90, 3745 (1993). Selected aptamers may be resynthesized using one or more modified bases, sugars or backbone linkages. Aptamers consist essentially of the minimum sequence of nucleic acid needed to confer binding specificity, but may be extended on the 5' end, the 3' end, or both, or may be otherwise derivatized or conjugated.

IX. Polypeptidic Binding Moieties

A variety of binding moities can be attached to a minicell of the invention for a variety of purposes. In a preferred embodiment, the binding moiety is directed to a ligand that is displayed by a cell into which it is desired to deliver the therapeutic content of a minicell.

IX.A. Antibodies and Antibody Derivatives

The term "antibody" is meant to encompass an immunoglobulin molecule obtained by in vitro or in vivo generation of an immunogenic response, and includes polyclonal, monospecific and monoclonal antibodies, as well as antibody derivatives, e.g single-chain antibody fragments (scFv). An "immunogenic response" is one that results in the production of antibodies directed to one or more proteins after the appropriate cells have been contacted with such proteins, or polypeptide derivatives thereof, in a manner such that one or more portions of the protein function as epitopes. An epitope is a single antigenic determinant in a molecule. In proteins, particularly denatured proteins, an epitope is typically defined and represented by a contiguous amino acid sequence. However, in the case of nondenatured proteins, epitopes also include structures, such as active sites, that are formed by the three-dimensional folding of a protein in a manner such that amino acids from separate portions of the amino acid sequence of the protein are brought into close physical contact with each other.

Wildtype antibodies have four polypeptide chains, two identical heavy chains and two identical light chains. Both types of polypeptide chains have constant regions, which do not vary or vary minimally among antibodies of the same class (i.e., IgA, IgM, etc.), and variable regions. Variable regions are unique to a particular antibody and comprise an "antigen binding domain" that recognizes a specific epitope. Thus, an antibody's specificity is determined by the variable regions located in the amino terminal regions of the light and heavy chains.

As used herein, the term "antibody" encompasses derivatives of antibodies such as antibody fragments that retain the ability to specifically bind to antigens. Such antibody fragments include Fab fragments (i.e., an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')2 (two Fab' molecules joined by interchain disulfide bonds in the hinge regions of the heavy chains; the Fab' molecules may be directed toward the same or different epitopes); a bispecific Fab (an Fab molecule having two antigen binding domains, each of which may be directed to a different epitope); a single chain Fab chain comprising a variable region, a.k.a., a sFv (the variable, antigen-binding determinative region of a single light and heavy chain of an antibody linked together by a chain of about 10 to about 25 amino acids).

The term "antibody" includes antibodies and antibody derivatives that are produced by recombinant DNA techniques and "humanized" antibodies. Humanized antibodies have been modified, by genetic manipulation and/or in vitro treatment to be more human, in terms of amino acid sequence, glycosylation pattern, etc., in order to reduce the antigenicity of the antibody or antibody fragment in an animal to which the antibody is intended to be administered (Gussow et al., Methods Enz. 203:99-121, 1991).

A single-chain antibody (scFv) is a non-limiting example of a binding moiety that may be displayed on minicells. Single-chain antibodies are produced by recombinant DNA technology and may be incorporated into fusion proteins. The term "single chain" denotes the fact that scFv's are found in a single polypeptide. In contrast, wildtype antibodies have four polypeptide chains, two identical heavy chains and two identical light chains. Both types of polypeptide chains have constant regions, which do not vary or vary minimally among antibodies of the same class (i.e., IgA, IgM, etc.), and variable regions. An antibody's specificity is determined by the variable regions located in the amino terminal regions of the light and heavy chains. The variable regions of a light chain and associated heavy chain form an "antigen binding domain" that recognizes a specific epitope. In a single chain antibody, the amino acid sequences of the variable light and variable heavy regions of an antibody are present in one comtiguous polypeptide. Methods of producing single chain antibodies are known in the art. See, for example, U.S. Pat. Nos. 4,946,778; 5,260,203; 5,455,030; 5,518,889; 5,534,621; 5,869,620; 6,025,165; 6,027,725 and 6,121,424.

Antibody derivatives and other polypeptides that are binding moieties can be isolated from protein display libraries, in which a library of candidate binding agents is displayed on a phage or other agent that comprises a nucleic acid encoding the protein it displays. Thus, an agent that binds to the target compound can be isolated, and nucleic acid prepared therefrom, providing for the rapid isolation of binding moieties and nucleic acids that can be used to produce them. For reviews, see Benhar I. Biotechnological applications of phage and cell display. Biotechnology Adv. 2001 (19):1-33; FitzGerald K. In vitro display technologies—new tools for drug discovery. Drug Discov Today. 2000 5(6):253-258; and Hoogenboom H R, Chames P. Natural and designer binding sites made by phage display technology. Immunol Today. 2000 August; 21(8):371-8.

A variety of protein display systems are known in the art and include various phage display systems such as those described in Jung S, Arndt K, Müller K, Plückthyn A. Selectively infective phage (SIP) technology: scope and limitations. J Immunol Methods. 1999 (231):93-104; Katz B. Structural and mechanistic determinants of affinity and specificity of ligands discovered or engineered by phage display. Annu Rev Biophys Biomol Struct. 1997 (26):27-45; Forrer P, Jung S, Pluckthun A. Beyond binding: using phage display to select for structure, folding and enzymatic activity in proteins. Curr Opin Struct Biol. 1999 August; 9(4):514-20; Rondot S, Koch J, Breitling F, Dubel S. A helper phage to improve single-chain antibody presentation in phage display. Nat Biotechnol. 2001 January; 19(1):75-8. Giebel L B, Cass R T, Milligan D L, Young D C, Arze R, Johnson C R. Screening of cyclic peptide phage libraries identifies ligands that bind streptavidin with high affinities. Biochemistry. 1995 Nov. 28; 34(47):15430-5; de Kruif J, Logtenberg T. Leucine zipper dimerized bivalent and bispecific scFv antibodies from a semi-synthetic antibody phage display library. J Biol Chem. 1996 Mar. 29; 271(13):7630-4; Hoogenboom H R, Henderikx P, de Haard H. Creating and engineering human antibodies for immunotherapy. Adv Drug Deliv Rev. 1998 Apr. 6; 31(1-2):5-31; Helfrich W, Haisma H J, Magdolen V, Luther T, Bom V J, Westra J, van der Hoeven R, Kroesen B J, Molema G, de Leij L. A rapid and versatile method for harnessing scFv antibody fragments with various biological effector functions. J Immunol Methods. 2000 Apr. 3; 237(1-2):131-45; Hoess R H. Bacteriophage lambda as a vehicle for peptide and protein display. Curr Pharm Biotechnol 2002 March; 3(1):23-8; Baek H, Suk K H, Kim Y H, Cha S. An improved helper phage system for efficient isolation of specific antibody molecules in phage display. Nucleic Acids Res. 2002 Mar. 1; 30(5):e18; and Rondot S, Koch J, Breitling F, Dubel S. A helper phage to improve single-chain antibody presentation in phage display. Nat. Biotechnol. 2001 January; 19(1): 75-8.

Other display systems include without limitation "Yeast Display" (Curr Opin Biotechnol 1999 October; 10(5):422-7. Applications of yeast in biotechnology: protein production and genetic analysis. Cereghino G P, Cregg J M.); "Baculovirus Display" (Kost T A, Condreay J P. Recombinant baculoviruses as expression vectors for insect and mammalian cells. Curr Opin Biotechnol. 1999 October; 10(5):428-33; and Liang M, Dubel S, Li D, Queitsch I, Li W, Bautz E K. Baculovirus expression cassette vectors for rapid production of complete human IgG from phage display selected antibody fragments. J Immunol Methods. 2001 Jan. 1; 247(1-2):119-30); "Ribosome Display" (Hanes J, Schaffitzel C, Knappik A, Pluckthun A. Picomolar affinity antibodies from a fully synthetic naive library selected and evolved by ribosome display. Nat. Biotechnol. 2000 December; 18(12):1287-92; Hanes J, Jermutus L, Pluckthun A. Selecting and evolving functional proteins in vitro by ribosome display. Methods Enzymol. 2000; 328:404-30; Schaffitzel C, Hanes J, Jermutus L, Pluckthun A. Ribosome display: an in vitro method for selection and evolution of antibodies from libraries. J Immunol Methods. 1999 Dec. 10; 231(1-2):119-35; Hanes J, Jermutus L, Weber-Bornhauser S, Bosshard H R, Pluckthun A. Ribosome display efficiently selects and evolves high-affinity antibodies in vitro from immune libraries. Proc Natl Acad Sci USA. 1998 Nov. 24; 95(24):14130-5; Hanes J, Pluckthun A. In vitro selection and evolution of functional proteins by using ribosome display. Proc Natl Acad Sci USA. 1997 May 13; 94(10): 4937-42; Coia G, Pontes-Braz L, Nuttall S D, Hudson P J, Irving R A. Panning and selection of proteins using ribosome display. J Immunol Methods. 2001 Aug. 1; 254(1-2):191-7.; Irving R A, Coia G, Roberts A, Nuttall S D, Hudson P J. Ribosome display and affinity maturation: from antibodies to single V-domains and steps towards cancer therapeutics. J Immunol Methods. 2001 Feb. 1; 248(1-2):31-45); and "Bacterial Display" (Hoischen C, Fritsche C, Gumpert J, Westermann M, Gura K, Fahnert B. Novel bacterial membrane surface display system using cell wall-less L-forms of *Proteus mirabilis* and *Escherichia coli*. Appl Environ Microbiol. 2002 February; 68(2):525-31; Etz H, Minh D B, Schellack C, Nagy E, Meinke A. Bacterial phage receptors, versatile tools for display of polypeptides on the cell surface. J Bacteriol. 2001 December; 183(23):6924-35; Patel D, Vitovski S, Senior H J, Edge M D, Hockney R C, Dempsey M J, Sayers J R. Continuous affinity-based selection: rapid screening and simultaneous amplification of bacterial surface-display libraries. Biochem J. 2001 Aug. 1; 357(Pt 3):779-85; Lang H. Outer membrane proteins as surface display systems. Int J Med Microbiol. 2000 December; 290(7):579-85; Earhart C F. Use of an Lpp-OmpA fusion vehicle for bacterial surface display. Methods Enzymol. 2000; 326:506-16; Benhar I, Azriel R, Nahary L, Shaky S, Berdichevsky Y, Tamarkin A, Wels W. Highly efficient selection of phage antibodies mediated by display of antigen as Lpp-OmpA' fusions on live bacteria. J Mol Biol. 2000 Aug. 25; 301(4):893-904; Xu Z, Lee S Y. Display of polyhistidine peptides on the *Escherichia coli* cell surface by using outer membrane protein C as an anchoring motif. Appl Environ Microbiol. 1999 November; 65(11):5142-7; Daugherty P S, Olsen M J, Iverson B L, Georgiou G. Development of an optimized expression system for the screening of antibody libraries displayed on the *Escherichia coli* surface. Protein Eng. 1999 July; 12(7):613-21; Chang H J, Sheu S Y, Lo S J. Expression of foreign antigens on the surface of *Escherichia coli* by fusion to the outer membrane protein traT. J Biomed Sci. 1999 January; 6(1):64-70; Maurer J, Jose J, Meyer T F. Autodisplay: one-component system for efficient surface display and release of soluble recombinant proteins from *Escherichia coli*. J Bacteriol. 1997 February; 179(3):794-804.

Antibodies, particularly single-chain antibodies, directed to surface antigens specific for a particular cell type may also be used as cell- or tissue-specific targeting elements. Single-chain antibody amino acid sequences have been incorporated into a variety of fusion proteins, including those with transmembrane domains and/or membrane-anchoring domains. See, for example, Kuroki et al., "Specific Targeting Strategies of Cancer Gene Therapy Using a Single-Chain Variable Fragment (scFv) with a High Affinity for CEA," Anticancer Res., pp. 4067-71, 2000; U.S. Pat. No. 6,146,885, to Dornburg, entitled "Cell-Type Specific Gene Transfer Using Retroviral Vectors Containing Antibody-Envelope Fusion Proteins"; Jiang et al., "In Vivo Cell Type-Specific Gene Delivery With Retroviral Vectors That Display Single Chain Antibodies," Gene Ther. 1999, 6:1982-7; Engelstadter et al., "Targeting Human T Cells By Retroviral Vectors Displaying Antibody Domains Selected From A Phage Display Library," Hum. Gene Ther. 2000, 11:293-303; Jiang et al., "Cell-Type-Specific Gene Transfer Into Human Cells With Retroviral Vectors That Display Single-Chain Antibodies," J. Virol 1998, 72:10148-56; Chu et al., "Toward Highly Efficient Cell-Type-Specific Gene Transfer With Retroviral Vectors Displaying Single-Chain Antibodies," J. Virol 1997, 71:720-5; Chu et al., "Retroviral Vector Particles Displaying The Antigen-Binding Site Of An Antibody Enable Cell-Type-Specific Gene Transfer," J. Virol 1995, 69:2659-63; Chu et al., "Cell Targeting With Retroviral Vector Particles Containing Antibody-Envelope Fusion Proteins," Gene Ther. 1994, 1:292-9; Esshar et al., "Specific activation and targeting of cytotoxic lymphocytes through chimeric single chains consisting of antibody-binding domains and the ☐ or ☐ subunits of the immunoglobulin and T-cell receptors," Proc. Natl. Acad. Sci. USA, 1993, Vol. 90:720-724; Einfeld et al., "Construction of a Pseudoreceptor That Mediates Transduction by Adenoviruses Expressing a Ligand in Fiber or Penton Base," J. Virol. 1999, 73:9130-9136; Marin et al., "Targeted Infection of Human Cells via Major Histocompatibility Complex Class I Molecules by Moloney Murine Leukemia Virus-Derived Viruses Displaying Single-Chain Antibody Fragment-Envelope Fusion Proteins," J. Virol., 1996, 70:2957-2962; Somia et al., "Generation of targeted retroviral vectors by using single-chain variable fragment: An approach to in vivo gene delivery," Proc. Natl. Acad. Sci. USA, 1995, 92:7570-7574; Liu et al., "Treatment of B-Cell Lymphoma With Chimeric IgG and Single-Chain Fv Antibody-Interleukin-2 Fusion Proteins," Blood, 1998, 92:2103-2112; Martin et al., "Retrovirus Targeting by Tropism Restriction to Melanoma Cells," J. Virol., 1999, 73:6923-6929; Ramjiawan et al., "Noninvasive Localization of Tumors by Immunofluorescence Imaging Using a Single Chain Fv Fragment of a Human Monoclonal Antibody with Broad Cancer Specificity," Amer. Cancer Society, 2000, 89:1134-1144; Snitkovsky et al., "A TVA-Single-Chain Antibody Fusion Protein Mediates Specific Targeting of a Subgroup A Avian Leukosis Virus Vector to Cells Expressing a Tumor-Specific Form of Epidermal Growth Factor Receptor," J. Virol., 2000, 74:9540-9545; Chu et al., "Toward Highly Efficient Cell-Type-Specific Gene Transfer with Retroviral Vectors Displaying Single-Chain Antibodies," J. Virol., 1997, 71:720-725; Kulkarni et al., Programmed cell death signaling via cell-surface expression of a single-chain antibody transgene, Transplantation 2000 Mar. 27; 69(6): 1209-17.

IX.B. Non-Catalytic Derivatives of Active Sites of Enzymes

Enzymes bind their substrates, at least transiently, in regions known as "active sites." It is known in the art that non-catalytic derivatives of enzymes, which bind but do not chemically alter their substrates may be prepared. Non-catalytic enzymes, particularly the mutant active sites thereof, are used to bind substrate molecules.

As a non-limiting example, enzymes from which biologically inactive (non-catalytic) sphingolipid-binding derivatives are obtained. Such derivatives of these enzymes bind their substrate sphingolipid. Sphingosine-1-phosphate (S1P) is bound by non-catalytic derivatives of enzymes having S1P as a substrate, e.g., S1P lyase and S1P phosphatase. Sphingosine (SPH) is bound by non-catalytic derivatives of enzymes having SPH as a substrate, e.g., SPH kinase and ceramide synthase. Ceramide (CER) is bound by non-catalytic derivatives of enzymes having CER as a substrate, such as, by way of non-limiting example, ceramidase, sphingomyelin synthase, ceramide kinase, and glucosylceramide synthase. Sphingomyelin is bound by non-catalytic derivatives of sphingomyelinase, an enzyme having sphingomyelin as a substrate.

IX.C. Nucleic Acid Binding Domains

Nucleic acid binding polypeptide domains may bind nucleic acids in a sequence-dependent or sequence-independent fashion and/or in a manner that is specific for various nucleic acids having different chemical structures (e.g., single- or double-stranded DNA or RNA, RNA:DNA hybrid molecules, etc.). Non-limiting examples of membrane-based transcription factors and DNA-binding protein include Smad proteins (Miyazono et al., TGF-beta signaling by Smad proteins (Review), Adv Immunol 75:115-57, 2000); SREBPs (sterol regulatory element binding proteins) (Ye et al., Asparagine-proline sequence within membrane-spanning segment of SREBP triggers intramembrane cleavage by site-2 protease, Proc Natl Acad Sci USA 97:5123-8, 2000; Shimomura et al., Cholesterol feeding reduces nuclear forms of sterol regulatory element binding proteins in hamster liver, Proc Natl Acad Sci USA 94:12354-9, 1997; Brown and Goldstein, The SREBP pathway: regulation of cholesterol metabolism by proteolysis of a membrane-bound transcription factor (Review), Cell 89:331-40, 1997; Scheek et al., Sphingomyelin depletion in cultured cells blocks proteolysis of sterol regulatory element binding proteins at site 1, Proc Natl Acad Sci USA 94:11179-83, 1997); mitochondrial DNA-binding membrane proteins, e.g., Abf2p and YhmZp (Cho et al., A novel DNA-binding protein bound to the mitochondrial inner membrane restores the null mutation of mitochondrial histone Abf2p in *Saccharomyces cerevisiae*, Mol Cell Biol 18:5712-23, 1998); and bacterial DNA-binding membrane proteins (Smith et al., Transformation in *Bacillus subtilis*: purification and partial characterization of a membrane-bound DNA-binding protein., J Bacteriol 156:101-8, 1983).

IX.D. Attaching Binding Moities, or Other Compounds, to Minicells

Binding compounds or moieties can be chemically attached (conjugated) to minicells via membrane proteins that are displayed on the minicells. The compound to be conjugated to minicells (the "attachable compound") may of any chemical composition, i.e., a small molecule, a nucleic acid, a radioisotope, a lipid or a polypeptide. One type of attachable compound that can be covalently attached to minicells is a binding moitiety, e.g., an antibody or antibody derivative. Another non-limiting example of attachable compounds is polyethylene glycol ("PEG"), which lowers the uptake in vivo of minicells by the reticuloendothelical system (RES). Another non-limiting example of creating stealth minicells to avoid the RES is to express proteins or other molecules on the surfaces of minicells whose lipid compositions have been modified, such as anionic lipid-rich minicells.

By way of non-limiting example, it is possible to prepare minicells that express transmembrane proteins with cysteine moieties on extracellular domains. Linkage of the membrane protein may be achieved through surface cysteinyl groups by, e.g., reduction with cysteinyl residues on other compounds to form disulfide bridges (S=S). If appropriate cysteinyl residues are not present on the membrane protein they may be introduced by genetic manipulation. The substitution of cysteine for another amino acid may be achieved by methods well-known to those skilled in the art, for example, by using methods described in Maniatis, Sambrook, and Fritsch (Molecular Cloning: A Laboratory Manual, Cold Spring Harbor Laboratory Press, 1989). As a non-limiting example, bioactive lysosphingolipids (e.g., sphingosine, sphingosine-1-phosphate, sphingosylphosphoryl choline) are covalently linked to proteins expressed on the surfaces of minicells such that these bioactive lipids are on the surface of the minicells and accessible for therapeutic or diagnostic uses in vivo or in vitro.

When the attachable moiety and the membrane protein both have a reduced sulfhydryl group, a homobifunctional cross-linker that contains maleimide, pyridyl disulfide, or beta-alpha-haloacetyl groups may be used for cross-linking. Examples of such cross-linking reagents include, but are not limited to, bismaleimidohexane (BMH) or 1,4-Di-[3'-(2'-pyridyldithio)propionamido]butane (DPDPB). Alternatively, a heterobifunctional cross-linker that contains a combination of maleimide, pyridyl disulfide, or beta-alpha-haloacetyl groups can be used for cross-linking.

As another non-limiting example, attachable moieties may be chemically conjugated using primary amines. In these instances, a homobifunctional cross-linker that contains succiminide ester, imidoester, acylazide, or isocyanate groups may be used for cross-linking. Examples of such cross-linking reagents include, but are not limited to: Bis[2-(succinimidooxycarbonyloxy)ethyl]sulfone (BSOCOES); Bis[2-(sulfosuccinimidooxycarbonyloxy)ethyl]sulfone (sulfo-BSOCOES); Disuccinimidyl suberate (DSS); Bis-(Sulfosuccinimidyl) Suberate (BS3); Disuccinimidyl glutarate (DSG); Dithiobis(succinimidylpropionate) (DSP); Dithiobois(sulfosuccinimidylpropionate) (DTSSP); Disulfosuccinimidyl tartrate (sulfo-DST); Dithio-bis-maleimidoethane (DTME); Disuccinimidyl tartrate (DST); Ethylene glycolbis(sulfosuccinimidylsuccinate) (sulfo-EGS); Dimethyl malonimidate.2 HCl (DMM); Ethylene glycolbis(succinimidylsuccinate) (EGS); Dimethyl succinimidate.2 HCl (DMSC); Dimethyl adipimidate.2 HCl (DMA); Dimethyl pimelimidate.2 HCl (DMP); and Dimethyl suberimidate.2.HCl (DMS), and Dimethyl 3,3'-dithiobispropionimidate.2 HCl (DTBP). Heterobifunctional cross-linkers that contains a combination of imidoester or succinimide ester groups may also be used for cross-linking.

As another non-limiting example, attachable moieties may be chemically conjugated using sulfhydryl and primary amine groups. In these instances, heterobifunctional cross-linking reagents are preferable used. Examples of such cross-linking reagents include, but are not limited to: N-succinimidyl 3-(2-pyridyldithio)propionate (DPDP); N-succinimidyl 6-[3'-(2-pyridyldithio)-propionamido] hexanoate (sulfo-LC-SPDP); m-maleimidobenzoyl-N-hydroxysuccinimide ester (MBS); m-maleimidobenzoyl-N-hydroxysulfosuccinimide ester (sulfo-MBS); succinimidyl 4-[P-maleimidophenyl] butyrate (SMPB); sulfosuccinimidyl 4-[p-maleimidophenyl] butyrate (sulfo-SMPB); N-[9 -Maleimidobutyryloxy] succinimide ester (GMBS), N-[9 -maleimidobutyryloxy] sulfosuccinimide ester (sulfo-GMBS); N-[9-maleimidocaproyloxy] succinimide ester (EMCS); N-[9-maleimidocaproyloxy]sulfosuccinimide ester (sulfo-EMCS); N-succinimidyl(4-iodoacetyl)aminobenzoate (SIAB); sulfosuccinimidyl(4-iodacetyl)aminobenzoate (sulfo-SIAB); succinimidyl 4-(N-maleimidomethyl)cyclohexane-1-carboxylate (SMCC); sulfosuccinimidyl 4-(N-maleimidomethyl)cyclohexane-1-carboxylate (sulfo-SMCC); succiminidyl-4-(N-maleimidomethyl)cyclohexane-1-carboxy-(6-amido-caproate) (LC-SMCC); 4-succinimidyloxycarbonyl-methyl-(2-pyridyldithio) toluene (SMPT); and sulfo-LC-SMPT.

As an exemplary protocol, a minicell suspension is made 5 mM EDTA/PBS, and a reducing solution of 2-mercaptoethylamine in 5 mM EDTA/PBS is added to the minicells. The mixture is incubated for 90 minutes at 37° C. The minicells are washed with EDTA/PBS to remove excess 2-mercaptoethylamine. The attachable moiety is dissolved in PBS, pH 7.2. A maleimide crosslinker is added to the solution, which is then incubated for 1 hour at room temperature. Excess maleimide is removed by column chromatography.

The minicells with reduced sulfhydryl groups are mixed with the derivatized compounds having an attachable moiety. The mixture is allowed to incubate at 4° C. for 2 hours or overnight to allow maximum coupling. The conjugated minicells are washed to remove unreacted (unattached) compounds having the attachable moiety. Similar protocols are used for expressed membrane proteins with other reactive groups (e.g., carboxyl, amine) that can be conjugated to an attachable moiety.

IX.E. Non-Genetic Methods for Directing Compounds to Membranes

Included within the scope of the invention are compounds that can be inserted into the membrane of segregated minicells. Such compounds include attachable moieties that are chemically conjugated to the surface of a minicell, and compounds that associate with and/or insert into a membrane "spontaneously," i.e., by virtue of their chemical nature. By way of non-limiting example, proteins that "spontaneously" insert into membranes include but are not limited to Thykaloid membrane proteins (Woolhead et al., J. Biol. Chem. 276:14607-14613, 2001), the mitochondrial adenine nucleotide translocator (Jacotot et al., J. Exp. Med. 193:509-519, 2001), and polypeptides obtained using the methods of Hunt et al. (Spontaneous, pH-dependent membrane insertion of a transbilayer alpha-helix, Biochem 36:15177-15192, 1997). Lipids, gangliosides, sphingomyelins, plasmalogens glycosyl diacylglycerols, and sterols can also be incorporated into the membranes of segregated minicells.

X. Membrane Proteins

In certain aspects of the invention, membrane proteins from non-eubacterial organisms are expressed and displayed by minicells. The cellular membrane (a.k.a. the "plasma membrane") is a lipid bilayer that forms the boundary between the interior of a cell and its external environment. The term "membrane proteins" refers to proteins that are found in membranes including without limitation cellular and organellar membranes.

X.A. Types of Membrane Proteins

X.A.1. In General

Membrane proteins consist, in general, of two types, peripheral membrane proteins and integral membrane proteins.

Integral membrane proteins can span both layers (or "leaflets") of a lipid bilayer. Thus, such proteins may have extracellular, transmembrane, and intracellular domains. Extracellular domains are exposed to the external environment of the cell, whereas intracellular domains face the cytosol of the cell. The portion of an integral membrane protein that traverses the membrane is the "transmembrane domain." Transmembrane domains traverse the cell membrane often by one or more regions comprising 15 to 25 hydrophobic amino acids which are predicted to adopt an alpha-helical conformation.

Intergral membrane proteins are classified as bitopic or polytopic (Singer, (1990) Annu. Rev. Cell Biol. 6:247-96). Bitopic proteins span the membrane once while polytopic proteins contain multiple membrane-spanning segments.

A peripheral membrane protein is a membrane protein that is bound to the surface of the membrane and is not integrated into the hydrophobic layer of a membrane region. Peripheral membrane proteins do not span the membrane but instead are bound to the surface of a membrane, one layer of the lipid bilayer that forms a membrane, or the extracellular domain of an integral membrane protein.

X.A.2. In General

The invention can be applied to any membrane protein, including but not limited to the following exemplary receptors and membrane proteins. The proteins include but are not limited to are receptors (e.g., GPCRs, sphingolipid receptors, neurotransmitter receptors, sensory receptors, growth factor receptors, hormone receptors, chemokine receptors, cytokine receptors, immunological receptors, and compliment receptors, FC receptors), channels (e.g., potassium channels, sodium channels, calcium channels.), pores (e.g., nuclear pore proteins, water channels), ion and other pumps (e.g., calcium pumps, proton pumps), exchangers (e.g., sodium/potassium exchangers, sodium/hydrogen exchangers, potassium/hydrogen exchangers), electron transport proteins (e.g., cytochrome oxidase), enzymes and kinases (e.g., protein kinases, ATPases, GTPases, phosphatases, proteases.), structural/linker proteins (e.g., Caveolins, clathrin), adapter proteins (e.g., TRAD, TRAP, FAN), chemotactic/adhesion proteins (e.g., ICAM11, selectins, CD34, VCAM-1, LFA-1, VLA-1), and phospholipases such as PI-specific PLC and other phospholipiases.

X.A.3. Receptors

Within the scope of the invention are any receptor, including without limitation:

The nuclear receptors, e.g the nuclear export receptor;

The peripheral (mitochondrial) benzodiazephine receptor (Gavish et al., "Enigma of the Peripheral Benzodiazephine Receptor," Pharmacological Reviews, Vol. 51, No. 4);

Adrenergic and muscarinic receptors (Brodde et al., "Adrenergic and Muscarinic Receptors in the Human Heart", Pharmacological Review, Vol. 51, No. 4);

Gamma-aminobutyric acid$_A$ receptors (Barnard et al., "International Union of Pharmacology. IV. Subtypes of 命-Aminobutyric Acid$_A$ Receptors: Classification on the Basis of Submit Structure and Receptor Function," Pharmacological Reviews, Vol. 50, No. 2);

Kinin B$_1$ receptors (Marceau et al., "The B$_1$ Receptors for Kinins," Pharmacological Reviews, Vol. 50, No. 3);

Chemokine receptors (Murphy et al., "International Union of Pharmacology. XXII. Nomenclature for Chemokine Receptors" Pharmacological Reviewa, Vol. 52, No. 1);

Glycine and NMDA Receptors (Danysz et al., "Glycine and N-Methyl-D-Aspartate Receptors: Physiological Significance and Possible Therapeutic Applications," Pharmacological Reviews, Vol. 50, No. 4);

Glutamate receptor ion channels (Dingledine et al., "The Glutamate Receptor Ion Channels", Pharmacological Reviews, Vol. 51, No. 1);

Purine and pyrimidine receptors including purinergic (e.g., P2) receptors (Ralevic et al., "Receptors for Purines and Pyrimidines", Pharmacological Reviews, Vol. 50, No. 3);

CNS receptors and membrane transporters (E. Sylvester Vizi, "Role of High-Affinity Receptors and Membrane Transporters in Nonsynaptic Communication and Drug Action in the Central Nervous System," Pharmacological Reviews, Vol. 52, No. 1);

Opoid receptors, including but not limited to the ♭-opioid receptor (Quock et al., "The ♭-Opioid Receptor: Molecular Pharmacology, Signal Transduction and the Determination of Drug Efficacy", Pharmacological Review, Col. 51, No. 3);

Angiotensin II receptors (Gasparo et al., "International Union of Pharmacology. XXIII. The Angiotensin II Receptors" Pharmalogical Review, Vol. 52, No. 3);

Cholecystokinin receptors (Noble et al., "International Union of Pharmacology. XXI. Structure, Distribution, and Functions of Cholecystokinin Receptors", Pharmacological Reviews, Vol. 51, No. 4)

Hormone receptors, including but not limited to, the estrogen receptor; the glucocorticoid receptor; and the insulin receptor;

Receptors found predominantly in the central nervous system, including but not limited to, neuronal nicotinic acetylcholine receptors; the dopamine D2/D3 receptor; GABA receptors; central cannabinoid receptor CB1; opoid receptors, e.g., the kappa opioid receptor, and the methadone-specific opioid receptor; nicotinic acetylcholine receptors; serotonin receptors, e.g., the serotonin 5-HT3 receptor, the serotonin 5-HT4 receptor, and the serotonin-2 receptor; and dopamine receptors, e.g., the dopamine D2/D3 receptor; and the neurotensin receptor;

Receptors for growth factors, including but not limited to, the erythropoietin receptor; the FGF receptor; the EGF receptor; the VEGF receptor; VEGF receptor-2 protein; VEGF-receptor protein (KDR); fibroblast growth factor receptor; the p75 nerve growth factor receptor; epidermal growth factor receptor; IGF-1 receptor; platelet factor-4 receptor; alpha platelet-derived growth factor receptor; hepatocyte growth factor receptor; and human fibroblast growth factor receptor;

Receptors for sphingolipids and lysophospholipids such as the Edg family of GPCRs;

Receptors for interleukins, e.g., receptors for interleukin-1 (IL-1), IL-2, IL-3, IL-4, IL-5, IL-6, IL-7, IL-8, IL-9, IL-10, IL-11, IL-12, IL-13, et seq.; and Various receptors, including by way of non-limiting example, receptors described in U.S. Pat. No. 6,210,967 (DNA encoding a mammalian LPA receptor and uses thereof); U.S. Pat. No. 6,210,921 (CAR: a novel coxsackievirus and adenovirus receptor; U.S. Pat. No. 6,211,343 (Lactoferrin receptor protein; U.S. Pat. No. 6,218,509 (LH/CG receptor, DNA and use thereof; U.S. Pat. No. 6,214,972 (DNA encoding prostaglandin receptor DP); U.S. Pat. No. 6,221,613 (DNA encoding a human melanin concentrating hormone receptor (MCH1) and uses thereof); U.S. Pat. No. 6,221,660 (DNA encoding SNORF25 receptor); U.S. Pat. No. 6,225,080 (Mu-subtype opioid receptor); U.S. Pat. No. 6,222,015 (Estrogen receptor); U.S. Pat. No. 6,228,610 (Human metabotropic glutamate receptor subtypes (hmR4, hmR6, hmR7) and related DNA compounds); U.S. Pat. No. 6,235,496 (Nucleic acid encoding mammalian mu opioid receptor); U.S. Pat. No. 6,258,556 (cDNA and genomic clones encoding human .mu. opiate receptor and the purified gene product); U.S. Pat. No. 6,245,531 (Polynucleotide encoding insect ecdysone receptor); U.S. Pat. No. 6,225,531 Glucan elicitor receptor, DNA molecule coding therefor, fungus-resistant plants transformed with the DNA molecule and method for creating the plants); U.S. Pat. No. 6,245,893 (Receptor that binds anti-convulsant compounds); U.S. Pat. No. 6,248,712 (Urokinase-type plasminogen activator receptor; U.S. Pat. No. 6,248,554 (DNA sequence coding for a BMP receptor); U.S. Pat. No. 6,248,520 (Nucleic acid molecules encoding nuclear hormone receptor coactivators and uses thereof); U.S. Pat. No. 6,242,251 (Rhesus neuropeptide Y5 receptor); U.S. Pat. No. 6,252,056 (Human lysophosphatidic acid receptor and use thereof); U.S. Pat. No. 6,255,472 (Isolated nucleic acid molecule encoding a human skeletal muscle-specific receptor); U.S. Pat. No. 6,291,207 (Herpes virus entry receptor protein); U.S. Pat. No. 6,291,206 (BMP receptor proteins); U.S. Pat. No. 6,291,195 (DNA encoding a human melanin concentrating hormone receptor (MCH1) and uses thereof); U.S. Pat. No. 6,344,200 (Lactoferrin receptor protein); U.S. Pat. No. 6,335,180 (Nucleic acid sequences encoding capsaicin receptor and uses thereof); U.S. Pat. No. 6,265,184 (Polynucleotides encoding chemokine receptor 88C); U.S. Pat. No. 6,207,799 (Neuropeptide Y receptor Y5 and nucleic acid sequences); U.S. Pat. No. 6,290,970 (Transferrin receptor protein of *Moraxella*); U.S. Pat. No. 6,326,350 (Transferrin receptor subunit proteins of *Neisseria meningitidis*); U.S. Pat. No. 6,313,279 (Human glutamate receptor and related DNA compounds); U.S. Pat. No. 6,313,276 (Human endothelin receptor); U.S. Pat. No. 6,307,030 (Androgen receptor proteins, recombinant DNA molecules coding for such, and use of such compositions); U.S. Pat. No. 6,306,622 (cDNA encoding a BMP type II receptor); U.S. Pat. No. 6,300,087 (DNA encoding a human serotonin receptor (5-HT4B) and uses thereof); U.S. Pat. No. 6,297,026 (Nucleic acids encoding the C140 receptor); U.S. Pat. No. 6,277,976 (Or-1, an orphan receptor belonging to the nuclear receptor family); U.S. Pat. No. 6,274,708 (Mouse interleukin-11 receptor); U.S. Pat. No. 6,271,347 (Eosinophil eotaxin receptor); U.S. Pat. No. 6,262,016 (Transferrin receptor genes); U.S. Pat. No. 6,261,838 (Rat melanocortin receptor MC3-R); U.S. Pat. No. 6,258,943 (Human neurokinin-3 receptor); U.S. Pat. No. 6,284,870 (Gamma retinoic acid receptor); U.S. Pat. No. 6,258,944 (OB receptor isoforms and nucleic acids encoding them); U.S. Pat. No. 6,261,801 (Nucleic acids encoding tumor necrosis factor receptor 5); U.S. Pat. No. 6,261,800 (Luteinizing hormone/choriogonadotropin (LH/CG) receptor); U.S. Pat. No. 6,265,563 (Opioid receptor genes); U.S. Pat. No. 6,268,477 (Chemokine receptor 88-C); U.S. Pat. No. 6,316,611 (Human N-methyl-D-aspartate receptor subunits, nucleic acids encoding same and uses therefor); U.S. Pat. No. 6,316,604 (Human C3b/C4b receptor (CR1)); U.S. Pat. No. 6,287,855 (Nucleic acid encoding rat galanin receptor (GALR2)); U.S. Pat. No. 6,268,221 (Melanocyte stimulating hormone receptor and uses); and U.S. Pat. No. 6,268,214 (Vectors encoding a modified low affinity nerve growth factor receptor).

X.A.3. Other Membrane Proteins

Other membrane proteins are within the scope of the invention and include but are not limited to channels (e.g., potassium channels, sodium channels, calcium channels.), pores (e.g., nuclear pore proteins, water channels), ion and other pumps (e.g., calcium pumps, proton pumps), exchangers (e.g., sodium/potassium exchangers, sodium/hydrogen exchangers, potassium/hydrogen exchangers), electron transport proteins (e.g., cytochrome oxidase), enzymes and kinases (e.g., protein kinases, ATPases, GTPases, phosphatases, proteases.), structural/linker proteins (e.g., Caveolins, clathrin), adapter proteins (e.g., TRAD, TRAP, FAN), X.A.3.a. Cellular Adhesion Molecules Cellular adhesion molecules, including but not limited to human rhinovirus receptor (ICAM-1), ICAM-2, ICAM-3, and PECAM-1, and chemotactic/adhesion proteins (e.g., selectins, CD34, VCAM-1, LFA-1, VLA-1) are within the scope of the invention. See also Alpin et al., "Signal Transduction and Signal Modulation by Cell Adhesion Receptors: The Role of Integrins, Cadherins, Immunoglobulin-Cell Adhesion Molecules, and Selectins", Pharmacological Reviews, Vol. 50, No. 2.

X.A.3.b. Cytochrome P450 Enzymes

The family of enzymes known as "cytochrome P450" enzymes (since they absorb light in the 450 nanometer range), or as "cytochrome oxidase" enzymes (since they oxidize a wide range of compounds that do not naturally occur in circulating blood), are included within the scope of the invention. P450 enzymes encompasses a variety of enzymes, many of which are involved in xenobiotic metabolism, including by way of non-limiting example the metabolism of drugs, prodrugs and toxins. Directories and databases of P450s, and information regarding their substrates, are available on-line (Fabian et al., The Directory of P450-containing Systems in 1996, Nucleic Acids Research 25:274-277, 1997). In humans, at least about 200 different P450s are present (for a review, see Hasler et al., Human cytochromes P450, Molecular Aspects of Medicine 20:1-137, 1999). There are multiple forms of these P450s and each of the individual forms exhibit degrees of specificity towards individual compounds or sets of compounds. In some cases, a substrate, whether it is a drug or a carcinogen, is metabolized by more than one cytochrome P450.

Members of the cytochrome P450 family are present in varying levels and their expression and activities are controlled by variables such as chemical environment, sex, developmental stage, nutrition and age. The cytochrome P450s are found at high concentrations in liver cells, and at lower concentrations in other organs and tissues such as the lungs (e.g., Forme-Pfister et al., Xenobiotic and endobiotic inhibitors of cytochrome P-450 db1 function, the target of the debrisoquine/sparteine type polymorphism, Biochem. Pharmacol. 37:3829-35, 1988). By oxidizing lipophilic compounds, which makes them more water-soluble, cytochrome oxidase enzymes help the body eliminate (via urine, or in aerosols exhaled out of the lungs) compounds that might otherwise act as toxins or accumulate to undesired levels.

In humans, several cytochrome P450s have been identified as being involved in xenobiotic metabolism. These include CYP1A1, CYP1A2, CYP2A6, CYP2B6, CYP2C8, CYP2C9, CYP2C18, CYP2C19, CYP2D6, CYP2E1, CYP3A4, and CYP3A5 (Crespi et al., The use of heterologously expressed drug metabolizing enzymes—state of the art and prospects for the future, Pharm Ther 84:121-131, 1999).

X.A.3.c. Miscellaneous Membrane Proteins

In addition to the preceding non-limiting examples, the invention can be applied to the membrane proteins described in U.S. Pat. No. 6,335,018 (High molecular weight major outer membrane protein of *moraxella*); U.S. Pat. No. 6,264,954 (*Haemophilus* outer membrane protein); U.S. Pat. No. 6,197,543 (Human vesicle membrane protein-like proteins); U.S. Pat. No. 6,121,427 (Major outer membrane protein CD of *branhamella*); U.S. Pat. Nos. 6,083,743 and 6,013,514 (*Haemophilus* outer membrane protein); U.S. Pat. No. 6,004,562 (Outer membrane protein B1 of *Moraxella catarrhalis*); U.S. Pat. No. 5,863,764 (DNA encoding a human membrane protein); U.S. Pat. No. 5,861,283 (DNA encoding a limbic system-associated membrane protein); U.S. Pat. No. 5,824,321 (Cloned *leptospira* outer membrane protein); U.S. Pat. No. 5,821,085 (Nucleotide sequences of a *T. pallidum* rare outer membrane protein); U.S. Pat. No. 5,821,055 (*Chlamydia* major outer membrane protein); U.S. Pat. No. 5,808,024 (Nucleic acids encoding high molecular weight major outer membrane protein of *moraxella*); U.S. Pat. No. 5,770,714 (*Chlamydia* major outer membrane protein); U.S. Pat. No. 5,763,589 (Human membrane protein); U.S. Pat. No. 5,753,459 (Nucleotide sequences of *T. pallidum* rare outer membrane protein); U.S. Pat. No. 5,607,920 (Concanavalin a binding proteins and a 76 kD chondrocyte membrane protein (CMP) from chondrocytes and methods for obtaining same); and U.S. Pat. No. 5,503,992 (DNA encoding the kD outer membrane protein of *Haemophilus influenzae*).

X.B. Membrane Anchoring Domains

A membrane-anchoring domain can be incorporated into a fusion protein of the invention. Non-limiting examples of membrane anchoring domains include those derived from Prostaglandin H2 synthases (PGHS-1 and -2) (Nina et al., Anchoring of a monotopic membrane protein: the binding of prostaglandin H2 synthase-1 to the surface of a phospholipid bilayer, Eur. Biophys. J. 29:439-54, 2000; Otto and Smith, Photolabeling of prostaglandin endoperoxide H synthase-1 with 3-trifluoro-3-(m-[125I]iodophenyl)diazirine as a probe of membrane association and the cyclooxygenase active site, J Biol Chem 271:9906-10, 1996; and Otto and Smith, The orientation of prostaglandin endoperoxide synthases-1 and -2 in the endoplasmic reticulum, J Biol Chem 269:19868-75, 1994; those derived from carboxypeptidase E (EC 3.4.17.10) (Fricker et al., Identification of the pH-dependent membrane anchor of carboxypeptidase E (EC 3.4.17.10), J. Biol. Chem., 265, 2476-2482, 1990); and peptide convertase 3 (PC3) (Smeekens et al., Identification of a cDNA encoding a second putative prohormone convertase related to PC2 in AtT20 cells and islets of Langerhans, Proc Natl Acad Sci USA 88, 340-344, 1990).

X.C. Transmembrane Domains

A variety of types and examples of transmembrane domain are known. Proteins with up to 12 transmembrane domains are known (Fujiwara et al., Identification of thyroid hormone transporters in humans: different molecules are involved in a tissue-specific manner, Endocrinology 2001 142:2005-12; Sharina et al., Mutational analysis of the functional role of conserved arginine and lysine residues in transmembrane domains of the murine reduced folate carrier, Mol Pharmacol 2001 59:1022-8). However, the invention is not limited to any particular number of transmembrane domains.

Monotropic ("single pass") domains, which traverse a membrane once, include by way of non-limiting example, those found in receptors for epidermal growth factor (EGF), receptors for tumor necrosis factor (TNF) and the like. Polytropic ("multipass") proteins traverse a membrane two or more times. Non-limiting examples of polytropic proteins are as follows.

Biotropic ("2 passes") membrane proteins include, but are not limited to: EnvZ of *E. coli*; the peroxisomal membrane protein Pex11-1p (Anton et al., ARF- and coatomer-mediated peroxisomal vesiculation, Cell Biochem Biophys 2000; 32 Spring:27-36); pleitropic drug ABC transporters of *S. cervisiae* (Rogers et al., The pleitropic drug ABC transporters from *Saccharomyces cerevisiae*, J Mol Microbiol Biotechnol 2001 3:207-14); and human and rate urate transporters hUAT and rUAT (Lipkowitz et al., Functional reconstitution, membrane targeting, genomic structure, and chromosomal localization of a human urate transporter, J Clin Invest 2001 107:1103-15).

Tritropic ("3 pass") membrane proteins include, but are not limited to: the ethylene receptor ETR1 of *Arabidopsis*; the Cauliflower Card Expression protein CC1 (Palmer et al., A *Brassica oleracea* Gene Expressed in a Variety-Specific Manner May Encode a Novel Plant Transmembrane Receptor, Plant Cell Physiol 2001 42:404-413); and a splice variant of the mitochondrial membrane protein hMRS3/4 (Li et al., Characterization of a novel human putative mitochondrial transporter homologous to the yeast mitochondrial RNA splicing proteins 3 and 4, FEBS Lett 2001 494:79-84).

Tetraspanins or tetraspans are non-limiting examples of membrane proteins with four transmembrane domains. (Levy et al., J. Biol. Chem., 226:14597-14602, 1991; Tomlinson et al., J. Immol. 23:136-40, 1993; and Barclay et al., (In) The Leucocyte antigen factbooks, Academic press, London, 1993). These proteins are collectively known as the 'transmembrane 4 superfamily' (TM4) because they span the plasma membrane four times. The proteins known to belong to this family include, but are not limited to: mammalian antigen CD9 (MIC3), a protein involved in platelet activation and aggregation; mammalian leukocyte antigen CD37, expressed on B lymphocytes; mammalian leukocyte antigen CD53 (OX-44), which may be involved in growth regulation in hematopoietic cells; mammalian lysosomal membrane protein CD63 (Melanoma-associated antigen ME491; antigen AD1); mammalian antigen CD81 (cell surface protein TAPA-1), which may play an important role in the regulation of lymphoma cell growth; mammalian antigen CD82 (Protein R2; Antigen C33; Kangai 1 (KAI1)), which associates with CD4 or CD8 and delivers costimulatory signals for the TCR/CD3 pathway; mammalian antigen CD151 (SFA-1); Platelet-endothelial tetraspan antigen 3 (PETA-3); mammalian TM4SF2 (Cell surface glycoprotein A 15; TALLA-1; MXS1); mammalian TM4SF3 (Tumor-associated antigen CO-029); mammalian TM4SF6 (Tspan-6; TM4-D); mammalian TM4SF7 (Novel antigen 2 (NAG-2); Tspan-4); mammalian Tspan-2; Mammalian Tspan-3 (TM4-A); mammalian Tetraspan NET-5; and *Schistosoma mansoni* and *japonicum* 23 Kd surface antigen (SM23/SJ23).

Non-limiting examples of membrane proteins with six transmembrane domains include the EBV integral membrane protein LMP-1, and a splice variant of the mitochondrial protein hMRS3/4 (Li et al., Characterization of a novel human putative mitochondrial transporter homologous to the yeast mitochondrial RNA splicing proteins 3 and 4, FEBS Lett 2001 Apr. 6; 494(1-2):79-84). Proteins with six transmembrane domains also include STEAP (six transmembrane epithelial antigens of the prostate) proteins (Afar et al., U.S. Pat. No. 6,329,503). The prototype member of the STEAP family, STEAP-1, appears to be a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops.

Literally hundreds of 7-pass membrane proteins are known. G-protein coupled receptors (GPCRs), including without limitation beta-adreno receptors, adrenergic receptors, EDG receptors, adenosine receptors, B receptors for kinins, angiotensin receptors, and opiod receptors are of particular interest. GPCRs are described in more detail elsewhere herein.

A non-limiting example of a protein with 9 transmembrane domains is Lipocalin-1 interacting membrane receptor (Wojnar et al., Molecular cloning of a novel Lipocalin-1 interacting human cell membrane receptor (LIMR) using phage-display, J Biol Chem 2001 3; [epub ahead of print]).

Proteins with both transmembrane and anchoring domains are known. For example, AMPA receptor subunits have transmembrane domains and one membrane-anchoring domain.

A variety of databases that describe known, and software programs that predict, membrane anchoring and transmembrane domains are available to those skilled in the art. See, for example Gcrdb.dba GCRDb [G Protein Coupled Receptor database], Tmbase.dba Tmbase [database of transmembrane domains], Prodom.srv ProDom [Protein domains], Tmap.srv TMAP [Protein transmembrane segments prediction], Tm7.srv TM7 [Retrieval of data on G protein-coupled receptors], and Memsat.sof MEMSAT [transmembrane structure prediction program].

Quentin and Fichant (J Mol Microbiol Biotechnol 2000 2:501-4, ABCdb: an ABC transporter database) have described a database devoted to the ATP-binding cassette (ABC) protein domains (ABCdb), the majority of which energize the transport of compounds across membranes. In bacteria, ABC transporters are involved in the uptake of a wide range of molecules and in mechanisms of virulence and antibiotic resistance. In eukaryotes, most ABC transporters are involved in drug resistance, and many are associated with diseases. ABCdb can be accessed via the World Wide Web (http://ir2lcb.cnrs-mrs.fr/ABCdb/). See also Sanchez-Fernandez et al., The *Arabidopsis thaliana* ABC protein superfamily: a complete inventory, J Biol Chem 2001 May 9; [epub ahead of print], and Rogers et al., The pleitropic drug ABC transporters from *Saccharomyces cerevisiae*, J Mol Microbiol Biotechnol 2001 April; 3(2):207-14.

X.D. Functions and Activites of Membrane Proteins

Non-limiting examples of membrane proteins include membrane-associated enzymes. Membrane-associated enzymes include but not limited to certain enzymes of the electron transport chain (ETC), antigenic proteins such as the major histocompatability (MHC) antigens, transport proteins, channels, hormone receptors, cytokine receptors, glucose permeases, gap junction proteins and bacteriorhodopsins.

A "transport protein" or "transporter" is a type of membrane protein that allows substances to cross plasma membranes at a rate that is faster than what is found by diffusion alone. Some transport proteins expend energy to move substances (active transport). Many active transport proteins are ATPases (e.g., the $Na^+$-$K^+$ ATPase), or at least bind ATP by virtue of comprising an ATP-binding cassette (ABC) (see, e.g., Rogers et al., The pleitropic drug ABC transporters from *Saccharomyces cerevisiae*, J Mol Microbiol Biotechnol 3:207-14, 2001). Nucleobase transporters are reviewed by De Koning and Diallinas (Nucleobase Transporters, Mol Membr Biol 17:75-94, 2000).

A "channel protein" is a protein that facilitates the diffusion of molecules/ions across lipid membranes by forming a hydrophilic pore or "channel" that provides molecules/ions access through lipid membranes, which are generally hydrophobic. Channels are often multimeric, with the pore being formed by subunit-subunit interactions.

A "receptor" is a molecular entity, typically a protein, that is displayed on the surface of a cell. A receptor is characterized by high affinity, often a specific binding of a specific substance, typically resulting in a specific biochemical or physiological effect.

A "hormone" is a naturally occurring substance secreted by specialized cells that affects the metabolism or behavior of other cells having receptors for the hormone. Non-limiting examples of hormones having receptors include but are not limited to insulin, cytokines, steroid hormones, histamines, glucagon, angiotensin, catecholamines, low density lipids (LDLs), tumor necrosis factor alpha, tumor necrosis factor beta, estrogen, and testosterone.

X.E. G-Protein-Coupled Receptors

G protein-coupled receptors (GPCRs) constitute the most prominent family of validated drug targets within biomedical research and are thought to be involved in such diseases and disorders as heart disease, hypertension, cancer, obesity, and depression and other mental illnesses. Over half of approved drugs elicit their therapeutic effects by selectively addressing members of this target family and more than 1000 sequences of the human genome encode for GPCRs containing the classical 7-pass membrane structure characteristic of this family of proteins (Marinissen, M. and J. S. Gutkind, G-protein-coupled receptors and signaling networks: emerging paradigms (Review), Trends. Phamacol. Sci. 22: 368-376, 2001). Many pharmacological drug companies are interested in the study of G-coupled proteins. It is possible to co-express a G-coupled protein receptor and its associated G-protein to study their pharmacological characteristics (Strosberg and Marullo, Functional expression of receptors in microorganisms. TiPS, 1992. 13: 95-98).

G-protein-coupled receptors (GPCRs) are reviewed by Marinissen, M. and J. S. Gutkind, G-protein-coupled receptors and signaling networks: emerging paradigms. Trends. Phamacol. Sci. 22: 368-376, 2001; Sautel and Milligan, Molecular manipulation of G-protein-coupled receptors: a new avenue into drug discovery, Curr Med Chem 2000 889-96; Hibert et al., This is not a G protein-coupled receptor, Trends Pharmacol Sci 1993, 14:7-12; Wilson et al., Orphan G-protein-coupled receptors: the next generation of drug targets?, Br J Pharmacol 1998, 125:1387-92; Roth et al., G protein-coupled receptor (GPCR) trafficking in the central nervous system: relevance for drugs of abuse, Drug Alcohol Depend 1998, 51:73-85; Ferguson and Caron, G protein-coupled receptor adaptation mechanisms, Semin Cell Dev Biol 1998, 9:119-27; Wank, G protein-coupled receptors in gastrointestinal physiology. I. CCK receptors: an exemplary family, Am J Physiol 1998, 274:G607-13; Rohrer and Kobilka, G protein-coupled receptors: functional and mechanistic insights through altered gene expression. (Review), Physiol Rev 1998, 78:35-52; and Larhammar et al., The receptor revolution—multiplicity of G-protein-coupled receptors. (Review), Drug Des Discov 1993, 9:179-88.

GPCR localization and regulation has been studied using GFP-comprising fusion proteins (Kallal and Benovic, Using green fluorescent proteins to study G-protein-coupled receptor localization and trafficking. (Review), Trends Pharmacol Sci 2000 21:175-80; and Ferguson, Using green fluorescent protein to understand the mechanisms of G-protein-coupled receptor regulation. (Review), Braz J Med Biol Res 1998, 31:1471-7); and by using chimeric GPCRs (Milligan and Rees, Chimaeric G alpha proteins: their potential use in drug discovery. (Review), Erratum in: Trends Pharmacol Sci 1999 June; 20(6):252.

GPCRs belong to a superfamily of at least 6 families of receptors, the most important of which is the main family, A. Members of the membrane protein gene superfamily of GPCRs have been characterized as having seven putative transmembrane domains. The transmembrane domains are believed to represent transmembrane alpha-helices connected by extracellular or cytoplasmic loops. A functional G-protein is a trimer which consists of a variable alpha subunit coupled to much more tightly-associated and constant beta and gamma subunits, although G-protein independent actions have been postulated (Marinissen, M. and J. S. Gutkind, G-protein-coupled receptors and signaling networks: emerging paradigms. Trends. Phamacol. Sci. 22: 368-376, 2001 Review). A variety of ligands have been identified which function through GPCRs. In general, binding of an appropriate ligand (e.g., bioactive lipids, ions, bioactive amines, photons, odorants, hormones, neurotransmitters, peptides, nucleosides, etc.) to a GPCR leads to the activation of the receptor. G-protein coupled receptors include a wide range of biologically active receptors, such as hormone, viral, growth factor and neuroreceptors. Typically, activation of a GPCR initiates the regulatory cycle of a corresponding G-protein. This cycle consists of GTP exchange for GDP, dissociation of the alpha and beta/gamma subunits, activation of the second messenger pathway by a complex of GTP and the alpha subunit of the G-protein, and return to the resting state by GTP hydrolysis via the innate GTPase activity of the G-protein alpha subunit A.

GPCRs include, without limitation, dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins and rhodopsins, odorant, cytomegalovirus receptors, and the like.

Most GPCRs have single conserved cysteine residues in each of the first two extracellular loops which form disulfide bonds that are believed to stabilize functional protein structure. The seven transmembrane regions, each comprising conserved hydrophobic stretches of about 20 to 30 amino acids, are designated as TM1, TM2, TM3, TM4, TMS, TM6, and TM7. TM3 is also implicated in signal transduction.

Although not wishing to be bound by any particular theory, it is believed that GPCRs participate in cell signaling through their interactions with heterotrimetric G-proteins composed of alpha, beta and gamma subunits (Marinissen, M. and J. S. Gutkind, G-protein-coupled receptors and signaling networks: emerging paradigms. Trends. Phamacol. Sci. 22:368-376, 2001). In some aspects of the invention, GPCRs and homologs are displayed on the surfaces of minicells.

X.F. EDG Receptors and Other Sphingolipid-Binding Receptors

The Endothelial Differentiation Gene (EDG) receptor family includes but is not limited to eight presently known GPCRs that have a high affinity to lipid ligands (Lynch et al., Life on the edg. Trends Pharmacol. Sci., 1999. 20: 273-5). These transmembrane receptors are found in several different tissues in different species. EDG receptors have been shown to be involved in calcium mobilization, activation of mitogen-activated protein kinase, inhibition of adenylate cyclase activation, and alterations of the cytoskelaton. The EDG family is divided into two different groups based on homology and ligand specificity. The EDG 2, 4, and 7 receptors are specific for the ligand lysophosphatidic acid (LPA) (An et al., Signaling Mechanism and molecular characteristics of G protein-coupled receptors for lysophosphatidic acid and sphingosine 1-phosphate. J. Cell Biochem, 30/31:147-157, 1998; Goetzl et al., Distinctive expression and functions of the type 4 endothelial differentiation gene-encoded G protein-coupled receptor for lysophosphatidic acid in ovarian cancer. Cancer Res., 59:5370-5, 1999). In contrast, EDG 1, 3, and 5 bind sphingosine-1-phosphate (S1P) (Zhang et al., Comparative analysis of three murine G-protein coupled receptors activated by sphingosine-1-phosphate. Gene, 227:89-99, 1999). EDG-6 is believed to interact with S1P (Yamazaki et al., Edg-6 as a putative sphingosine 1-phosphate receptor coupling to $Ca^{2+}$ signaling pathway. Biochem Phys Res Com, 268:583-589, 2000).

Receptors that bind S1P and other sphingolipids are used in one aspect of the invention (for a review of some S1P-binding receptors, see Spiegel et al., Biochim. Biophys. Acta 1484: 107-116, 2000). Such receptors include but are not limited to members of the EDG family of receptors (a.k.a. 1pA receptors, Chun, Crit. Rev. Neuro. 13:151-168, 1999), and isoforms and homologs thereof such as NRG1 and AGR16.

EDG-1 was the first identified member of a class of G protein-coupled endothelial-derived receptors (EDG). Non-limiting examples of other EDG family members that also bind S1P include EDG-3 (a.k.a. ARG16; the rat homolog of EDG-3 is designated H218), EDG-5, EDG-6 and EDG-8. For reviews, see Goetzl et al., Adv. Exp. Med. Biol. 469:259-264, 1999; and Chun et al., Cell. Biochem. Biophys. 30:213-242, 1999).

EDG-1 is described by Lee et al., (Ann. NY Acad. Sci. 845:19-31, 1998). Liu and Hla, The mouse gene for the inducible G-Protein-coupled receptor edg-1. Genomics, 1997, 43: p. 15-24. Human EDG-1c genes and proteins are described in published PCT application WO 99/46277 to Bergsma et al.

EDG-3 is described by Okamoto et al. (Biochem. Biophys. Res. Commun. 260:203-208, 1999) and An et al. (FEBS Letts. 417:279-282, 1997). See also An et al., J. Biol. Chem. 275:288-296, 2000.

EDG-5 human and mammalian genes are described in U.S. Pat. No. 6,057,126 to Munroe et al. and published PCT application WO 99/33972 to Munroe et al. The rat homolog, H218, is described in U.S. Pat. No. 5,585,476 to MacLennan et al. Van Brocklyn et al., J. Biol. Chem. 274:4626-4632, 1999; and Gonda et al., Biochem. J. 337:67-75, 1999. See also An et al., J. Biol. Chem. 275:288-296, 2000.

EDG-6 is described by Graler et al. (Genomics 53:164-169, 1998), Yamazaki et al. (Biochem. Biophys. Res. Commun. 268:583-589, 2000), and Van Brocklyn et al. (Sphingosine-1-phosphate is a ligand for the G protein-coupled receptor EDG-6, Blood 95:2624-9, 2000).

EDG-8 from rat brain is described by Im et al., (J. Biol. Chem. 275:14281-14286, 2000). Homologs of EDG-8 from other species, including humans, may also be used in the present invention.

The Mil receptor (Mil is an abbreviation for "miles apart") binds S1P and regulates cell migration during vertebrate heart development. The Mil receptor of Zebrafish is described by Mohler et al. (J. Immunol. 151:1548-1561, 1993). Another S1P receptor is NRG1 (nerve growth factor regulated gene-1), the rat version of which has been identified (Glickman et al., Mol. Cel. Neurosci. 14:141-152, 1999).

Receptors that bind sphingosylphosphoryl choline (SPC) are also used in this aspect of the invention. Such receptors include but are not limited to members of the SCaMPER family of receptors (Mao et al., Proc. Natl. Acad. Sci. U.S.A. 93:1993-1996, 1996; Betto et al., Biochem. J. 322:327-333, 1997). Some evidence suggests that EDG-3 may bind SPC in addition to S1P (Okamoto et al., Biochem. Biophys. Res. Commun. 260:203-208, 1999). Derivatives of EDG-3 that bind both S1P and SPC are used in one aspect of the invention.

Receptors that bind lysophophatidic acid may be used in the present invention. These include EDG-2 (LPA1), EDG-4 (LPA2), EDG-7 (LPA3). See Moller et al., Expression and function of lysophosphatidic acid receptors in cultured rodent microglial cells, J Biol Chem 2001 May 4 [epub ahead of print]; Fukushima and Chun, The LPA receptors, Prostaglandins 64(1-4):21-32, 2001; Contos and Chun, The mouse lp(A3)/Edg7 lysophosphatidic acid receptor gene: genomic structure, chromosomal localization, and expression pattern, Gene 267:243-53, 2001; Schulte et al., Lysophosphatidic acid, a novel lipid growth factor for human thyroid cells: over-expression of the high-affinity receptor edg4 in differentiated thyroid cancer, Int J Cancer 92249-56, 2001; Kimura et al., Two novel *Xenopus* homologs of mammalian LP(A1)/EDG-2 function as lysophosphatidic acid receptors in *Xenopus* oocytes and mammalian cells, J Biol Chem 276:15208-15, 2001; and Swarthout and Walling, Lysophosphatidic acid: receptors, signaling and survival (Review), Cell Mol Life Sci 57:1978-85, 2000.

Examples of lysophospholipid receptors including, but not limited to EDG proteins, are disclosed in Fukushima et al. (Lysophospholipid receptors. Annu. Rev. Pharmacol. Toxicol. 41:507-534, 2001) Malek and Lee (Nrg-1 Belongs to the Endothelial Differentiation Gene Family of G Protein-coupled Sphingosine-1-phosphate Receptors, J. Biol. Chem. 276:5692-5699, 2001), Hla et al. (Sphingosine-1-phosphate signaling via the EDG-1 family of G-protein-coupled receptors (Review), Ann N Y Acad Sci 905:16-24, 2000; Chun, Lysophospholipid receptors: implications for neural signaling (Review), Crit Rev Neurobiol 13:151-68, 1999); and Chun et al. (A growing family of receptor genes for lysophosphatidic acid (LPA) and other lysophospholipids (LPs) (Review), Cell Biochem Biophys 30:213-42, 1999).

XI. Recombinant DNA Expression

In order to achieve recombinant expression of a fusion protein, an expression cassette or construct capable of expressing a chimeric reading frame is introduced into an appropriate host cell to generate an expression system. The expression cassettes and constructs of the invention may be introduced into a recipient eubacterial or eukaryotic cell either as a nonreplicating DNA or RNA molecule, which may be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

XI.A. Recombinant DNA Expression Systems

A variety of eubacterial recombinant DNA expression systems may be used to produce the fusion proteins of the invention. Host cells that may be used in the expression systems of the present invention are not strictly limited, provided that they are suitable for use in the expression of the fusion protein of interest and can produce minicells. Non-limiting examples of recognized eubacterial hosts that may be used in the present invention include bacteria such as *E. coli, Bacillus, Streptomyces, Pseudomonas, Salmonella, Serratia*, and the like.

Eubacterial expression systems utilize plasmid and viral (bacteriophage) expression vectors that contain replication sites and control sequences derived from a species compatible with the host may be used. Suitable phage or bacteriophage vectors include ⊠gt10, ⊠gt11 and the like. Suitable virus vectors may include pMAM-neo, pKRC and the like. Appropriate eubacterial plasmid vectors include those capable of replication in *E. coli* (such as, by way of non-limiting example, pBR322, pUC118, pUC119, ColE1, pSC101, pACYC 184, ⊙VX. See "Molecular Cloning: A Laboratory Manual" 1989). *Bacillus* plasmids include pC194, pC221, pT127, and the like (Gryczan, In: *The Molecular Biology of the Bacilli*, Academic Press, NY, pp. 307-329, 1982). Suitable *Streptomyces* plasmids include p1J101 (Kendall et al., J. Bacteriol. 169:4177-4183, 1987), and *Streptomyces* bacteriophages such as C31 (Chater et al., In: Sixth International Symposium on Actinomycetales Biology, Akademiai Kaido, Budapest, Hungary, pp. 45-54, 1986). *Pseudomonas* plasmids are reviewed by John et al. (Rev. Infect. Dis. 8:693-704, 1986), and Izaki (Jpn. J. Bacteriol. 33:729-742, 1978). See also Brent et al., "Vectors Derived From Plasmids," Section II, and Lech et al. "Vectors derived from Lambda and Related Bacteriophages" Section III, in Chapter 1 of *Short Protocols in Molecular Biology*, 2nd Ed., Ausubel et al., eds., John Wiley and Sons, New York, 1992, pages 1-13 to 1-27; Lech et al. "Vectors derived from Lambda and Related Bacteriophages" Section III and Id. pages 1-28 to page 1-52.

To express a protein, including but not limited to a fusion protein, in a eubacterial cell, it is necessary to operably link the ORF encoding the protein to a functional eubacterial or viral promoter. Such promoters may be either constitutive or, more preferably, regulatable (i.e., inducible or derepressible). Examples of constitutive promoters include the int promoter of bacteriophage lambda, the bla promoter of the beta-lactamase gene sequence of pBR322, and the cat promoter of the chloramphenicol acetyl transferase gene sequence of pPR325, and the like. Examples of inducible eubacterial promoters include the major right and left promoters of bacteriophage lambda ($P_L$ and $P_R$), the trp, recA, lacZ, lacI, and gal promoters of *E. coli*, the alpha-amylase (Ulmanen et al., J. Bacteriol. 162:176-182, 1985) and the sigma-28-specific promoters of *B. subtilis* (Gilman et al., Gene Sequence 32:11-20, 1984), the promoters of the bacteriophages of *Bacillus* (Gryczan, in: The Molecular Biology of the Bacilli, Academic Press, Inc., NY, 1982), and *Streptomyces* promoters (Ward et al., Mol. Gen. Genet. 203:468-478, 1986). Eubacterial promoters are reviewed by Glick (Ind. Microbiol. 1:277-282, 1987), Cenatiempo (Biochimie 68:505-516, 1986), and Gottesman (Ann. Rev. Genet. 18:415-442, 1984).

Proper expression also requires the presence of a ribosome-binding site upstream of the gene sequence-encoding sequence. Such ribosome-binding sites are disclosed, for example, by Gold et al. (Ann. Rev. Microbiol. 35:365-404, 1981). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Mammalian expression systems utilize host cells such as HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332, which may provide better capacities for correct post-translational processing. Non-limiting examples of mammalian extrachromosomal expression vectors include pCR3.1 and pcDNA3.1, and derivatives thereof including but not limited to those that are described by and are commercially available from Invitrogen (Carlsbad, Calif.).

Several expression vectors are available for the expression of polypeptides in mammalian host cells. A wide variety of transcriptional and translational regulatory sequences may be employed, depending upon the nature of the host. The transcriptional and translational regulatory signals may be derived from viral sources, such as adenovirus, bovine papilloma virus, cytomegalovirus (CMV), simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals that are temperature-sensitive since, by varying the temperature, expression can be repressed or initiated, or are subject to chemical (such as metabolite) regulation.

Preferred eukaryotic plasmids include, for example, BPV, vaccinia, SV40, 2-micron circle, and the like, or their derivatives. Such plasmids are well known in the art (Botstein et al., Miami Wntr. Symp. 19:265-274, 1982; Broach, in: The Molecular Biology of the Yeast *Saccharomyces*: Life Cycle and Inheritance, Cold Spring Harbor Laboratory, Cold Spring Harbor, N.Y., p. 445-470, 1981; Broach, Cell 28:203-204, 1982; Bollon et al., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980).

Expression of polypeptides in eukaryotic hosts generally involves the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-31, 1981); and the yeast gal4 gene sequence promoter (Johnston et al., Proc. Natl. Acad. Sci. (USA) 79:6971-6975, 1982; Silver et al., Proc. Natl. Acad. Sci. (USA) 81:5951-5955, 1984).

Expression sequences and elements are also required for efficient expression. Non-limiting examples include Kozak and IRES elements in eukaryotes, and Shine-Delgarno sequences in prokaryotes, which direct the initiation of translation (Kozak, Initiation of translation in prokaryotes and eukaryotes. Gene, 1999. 234: 187-208; Martinez-Salas et al., Functional interactions in internal translation initiation directed by viral and cellular IRES elements, Jour. of Gen. Virol. 82:973-984, 2001); enhancer sequences; optional sites for repressor and inducers to bind; and recognition sites for enaymes that cleave DNA or RNA in a site-specific manner. Translation of mRNA is generally initiated at the codon which encodes the first methionine; if so, it is preferable to ensure that the linkage between a eukaryotic promoter and a preselected ORF does not contain any intervening codons that encode a methionine (i.e., AUG). The presence of such codons results either in the formation of a fusion protein with an uncharacterized N-terminal extension (if the AUG codon is in the same reading frame as the ORF) or a frame-shift mutation (if the AUG codon is not in the same reading frame as the ORF).

XI.B. Expression of Membrane Proteins Presently, the most commonly used expression systems for the expression of integral membrane proteins are eukaryotic and eubacterial whole cell expression systems. Although minicells have been used to express several eubacterial membrane proteins, the production of non-eubacterial membrane proteins has not been reported. One aspect of the invention is the discovery that the minicell expression system can be made to express and preferably display integral membrane proteins from non-eubacterial organisms.

Some commonly used expression systems include in vitro systems, such as the Rabbit Reticulocyte Lysate System and *E. coli* S30 Extract System (both available from Promega) (Zubay, Methods Enz. 65:856, 1980) and in vivo systems, such as eukaryotic cell culture expression, and bacterial expression systems. Although this is not an exhaustive list, these systems are representative.

The Rabbit Reticulocyte Lysate system utilizes a cell lysate that contains all the enzymes required for transcription and translation to drive protein expression, and is a good in vitro system for producing small amounts of labeled and unlabeled protein. However, this system is not well-suited for the production of large quantities of proteins and is limited to soluble proteins as there are no membranes in which to incorporate membrane proteins.

In eukaryotic cell culture systems, expression vectors suited for expression in host eukaryotic cells are transfected into cultured cells and protein is translated from mRNA produced from the vector DNA template Kaufman, Overview of vector design for mammalian gene expression. Mol Biotechnol, 2001. 16: 151-160; Lee, et al., Heterologous gene expression in avian cells: Potential as a producer of recombinant proteins. J Biomed Sci, 1999. 6: 8-17; Voorma et al., Initiation of protein synthesis in eukaryotes. Mol Biol Rep, 1994. 19: 139-45). Cells can then either be harvested to prepare at least partially purified proteins or proteins produced from the expression element can be studied in the host cell environment.

Regarding membrane proteins, such systems have limitations. Primary cell lines are difficult to maintain and are short lived. Immortalized cell lines divide indefinitely, but have been altered in many ways and can be unpredictable. The transfection efficiency is very low in most eukaryotic cells and some cell types are refractory to transformation. Moreover, other proteins are expressed in these cells along with the protein of interest. This can cause difficulties when performing certain experiments and when attempting to immunoprecipitate the protein. Good experimental data are difficult to obtain from studies such as binding assays (because of high background due to endogenous proteins), and crystal determination of protein structure (because it is difficult to obtain enough purified protein to efficiently form crystals).

Bacterial expression systems are generally similar to that of the eukaryotic expression systems in that they both use the host cell enzymes to drive protein expression from recombinant expression vectors (Cornelis, P., Expressing genes in different *Escherichia coli* compartments. Curr Opin Biotechnol, 2000. 11: p. 450-454; Laage and Langosch, Strategies for prokaryotic expression of eukaryotic membrane proteins. Traffic, 2001. 2: 99-104; Pines, O. and M. Inouye, Expression and secretion in *E. coli*. Mol Biotechnol, 1999. 12: 25-34).

In bacterial expression systems, bacterial cells are transformed with expression elements, and transcription and translation is driven from a bacterial promoter. Bacteria divide very rapidly and are easy to culture; it is relatively easy to produce a large number of bacteria in a short time. Moreover, incorporation of expression elements vector into bacterial cells is efficient. Transformed cells can be isolated that arise from a single bacterium. Cultures of transformed cells are thus genetically identical and all cells in the culture will contain the expression element. However, there are proteins that are not suitable for expression in bacteria because of differences between eukaryotic cells and bacterial cells in transcription, translation, and post-translational modification.

The *E. coli* whole cell expression system has been used to express functional integral membrane proteins. For a review, see Strosberg, Functional expression of receptors in microorganisms. TiPS, 1992. 13: 95-98. Examples of mammalian integral membrane proteins that have been expressed in *Escherichia coli* include rat alpha-2B-adrenoceptors (Xia et al., Functional expression of rat β2B-adrenoceptor in *E. coli*. Euro J. Pharma, 1993. 246: 129-133) and the human beta2-adrenergic receptor (Marullo et al., Human ḃ 2-adrenergic receptors expressed in *Escherichia coli* membranes retain their pharmacological properties. Proc. Natl. Acad. Sci. USA, 1988. 85: 7551-7555). In some of these studies, the integral membrane proteins were not only expressed in *E. coli* expression systems, but also retained their pharmacological properties. This allows for binding studies to be performed with minimal background signal ("noise") from host cell proteins. It has also been shown that signal sequences (the short hydrophobic amino acid sequence at the N-terminus of integral membrane proteins that signals the transport of the protein to the membrane) from mammalian cells may be functional in the *E. coli* system.

As is discussed herein, the expression of membrane proteins such as GPCRs, ion channels, and immuno-receptors in minicells, and their incorporation into the membranes thereof, allows for the study and use of such non-eubacterial membrane proteins. The minicell system of the invention is particularly well-suited for the study and expression of EDG proteins because of the lipid nature of the ligands for these receptors. The identification of ligand binding kinetics and biochemistry of these receptors because of the physiochemical properties of the lipid ligands (LPA and S1P), which results in high non-specific binding (Lee et al., Sphingosine-1-phosphate is a ligand for the G protein-coupled receptor EDG-1. Science, 1998. 279: 1552-1555; Van Brocklyn et al., Sphingosine-1-phosphate is a ligand for the G protein-coupled receptor EDG-6. Blood, 2000. 95: 2624-2629; Liu et al., Edg-1, the G protein-coupled receptor for sphingosine-1-phosphate, is essential for vascular maturation. J. Clin. Investigation, 2000. 106: 951-961).

It is believed, for example, that in the case of the ion channels, the minicell expression system is less cumbersome then procedures that are presently used to study properties of ion channels, such as, e.g., reconstitution studies (Montal, Molecular anatomy and molecular design of channel proteins. FASEB J., 1990. 4: p. 2623-2635). Ionic conditions both inside and outside of minicells can be manipulated in various ways, and the properties of an ion channel that is expressed in a minicell, and factors that activate or modulate the activities of the channel, can be studied. Binding and kinetic studies are performed on ligand mediated ion channels. This type of study is enhanced when the ion channel is able to interact specifically with its ligand and has a low background of non-specific binding from the endogenous proteins. This can be accomplished by making the minicells into protoplasts or poroplasts in which the ligand-activated ion channels in the inner membrane are exposed to the external environment and have better access to their specific ligand.

A "recombinant expression system" (or simply "expression system") is one that directs the production of exogenous gene products in a host cell or minicell of choice. By "expressed" it is meant that a gene product of interest (which can be a protein or nucleic acid) is produced in the expression system of choice.

Host cells (and/or minicells) harboring an expression construct are components of expression systems. An "expression vector" is an artificial nucleic acid molecule into which an exogenous ORF encoding a protein, or a template of a bioactive nucleic acid can be inserted in such a manner so as to be operably linked to appropriate expression sequences that direct the expression of the exogenous gene. By the term "operably linked" it is meant that the part of a gene that is transcribed is correctly aligned and positioned with respect to expression sequences that promote, are needed for and/or regulate this transcription. The term "gene product" refers to either a nucleic acid (the product of transcription, reverse transcription, or replication) or a polypeptide (the product of translation) that is produced using the non-vector nucleic acid sequences as a template.

In some applications, it is preferable to use an expression construct that is an episomal element. If the episomal expression construct expresses (or, preferably in some applications, over-expresses) a an ORF that has been incorporated into the episomal expression construct, the minicells will direct the production of the polypeptide encoded by the ORF. At the same time, any mRNA molecules transcribed from a chromosomal gene prior to minicell formation that have been transferred to the minicell are degraded by endogenous RNases without being replaced by new transcription from the (absent) bacterial chromosome.

Chromosomally-encoded mRNAs will not be produced in minicells and will be "diluted" as increasing amounts of mRNAs transcribed from the episomal element are generated. A similar dilution effect is expected to increase the relative amount of episomally-generated proteins relative to any chromosomally-encoded proteins present in the minicells. It is thus possible to generate minicells that are enriched for proteins encoded by and expressed from episomal expression constructs.

Although by no means exhaustive, a list of episomal expression vectors that have been expressed in eubacterial minicells is presented in Table 4.

It is also possible to transform minicells with exogenous DNA after they have been prepared or separated from their parent cells. For example, phage RNA is produced in minicells after infection by lambda phage (Witkiewicz and Taylor, Ribonucleic acid synthesis after adsorption of the bacteriophage lambda on *Escherichia coli* minicells, Acta Microbiol Pol A 7:21-4, 1975), even though replication of lambda phage may not occur in minicells (Witkiewicz and Taylor, The fate of phage lambda DNA in lambda-infected minicells, Biochim Biophys Acta 564:31-6, 1979).

Because it is the most characterized minicell-producing species, many of these episomal elements have been examined in minicells derived from *E. coli*. It is understood by practitioners of the art, however, that many episomal elements that are expressed in *E. coli* also function in other eubacterial species, and that episomal expression elements for minicell systems in other species are available for use in the invention disclosed herein.

In one aspect of the invention, eukaryotic and archeabacterial minicells are used for expression of membrane proteins, particularly in instances where such desirable proteins have enhanced or altered activity after they undergo post-translational modification processes such as phosphorlyation, proteolysis, mystrilation, GPI anchoring and glycosylation. Expression elements comprising expression sequence operably linked to ORFs encoding the membrane proteins of interest are transformed into eukaryotic cells according to methods and using expression vectors known in the art. By way of non-limiting example, primary cultures of rat cardiomyocytes have been used to produce exogenous proteins after transfection of expression elements therefor by electroporation (Nakajima et al., Expression and characterization of Edg-1 receptors in rat cardiomyocytes: Calcium deregulation in response to sphingosine-1-phosphate, Eur. J. Biochem. 267: 5679-5686, 2000).

Yeast cells that produce minicells are transformed with expression elements comprising an ORF encoding a membrane protein operably linked to yeast expression sequences. Cells that harbor a transferred expression element may be selected using a gene that is part of the expression element that confers resistant to an antibiotic, e.g., neomycin.

Alternatively, in one aspect of the invention, bacterial minicells are prepared that contain expression elements that are prepared from shuttle vectors. A "shuttle vector" has sequences required for its replication and maintenance in cells from two different species of organisms, as well as expression elements, at least one of which is functional in bacterial cells, and at least one of which is functional in yeast cells. For example, *E. coli*-yeast shuttle vectors are known in the art and include, by way of non-limiting example, those derived from Yip, Yrp, Ycp and Yep. Preferred *E. coli*-yeast shuttle vectors are episomal elements that can segregate into yeast minicells (i.e., Yrp, Ycp and Yep. Particularly preferred are expression vectors of the Yep (yeast episomal plasmid) class, and other derivatives of the naturally occurring yeast plasmid known as the 2 μm circle. The latter vectors have relatively high transformation frequencies and are stably maintained through mitosis and meiosis in high copy number.

TABLE 4

Episomal Elements That Segregate Into *Escherichia coli* Minicells

| EPISOMAL ELEMENT | REFERENCES |
| --- | --- |
| Plasmids | |
| R6K, R1DRD19 | Nesvera et al., *Folia Microbiol. (Praha)* 23: 278-285 (1978) |
| PSC101 | Fox et al., *Blood* 69: 1394-1400 (1987) |
| PBR322 | Fox et al., *Blood* 69: 1394-1400 (1987) |
| F element | Cohen et al., *Proc. Natl. Acad. Sci.* 61: 61-68 (1968); Khachatourians G. G., *Biochim. Biophys. Acta.* 561: 294-300 (1979) |
| NR1 | Hochmannova et al., *Folia Microbiol. (Praha)* 26: 270-276 |
| R6δ1 | Hochmannova et al., *Folia Microbiol. (Praha)* 26: 270-276 |
| PTTQ18 | Rigg et al., *Arch. Oral. Biol.* 45: 41-52 (2000) |
| PGPR2.1 | Rigg et al., *Arch. Oral. Biol.* 45: 41-52 (2000); expresses cell surface antigen of *P. gingivalis* |
| "mini-plasmid" derivative of RK2 | Firshein et al., *J. Bacteriol.* 150: 1234-1243 (1982) |
| ColE1 | Rashtchian et al., *J. Bacteriol.* 165: 82-87 (1986); Witkiewicz et al., *Acta. Microbiol. Pol. A* 7: 21-24 (1975) |
| PSC101 | Rashtchian et al., *J. Bacteriol.* 165: 82-87 (1986); Curtiss, Roy, III, U.S. Pat. No. 4,190,495; Issued Feb. 26, 1980 |
| pACYC184 | Chang et al., *J. Bacteriol.* 134: 1141-1156 (1978); Rose, *Nucleic Acids Res* 16: 355 (1988) |
| ColIb, ColIb7 DRD& | Skorupska et al., *Acta. Microbiol. Pol. A* 8: 17-26 (1976) |

TABLE 4-continued

Episomal Elements That Segregate
Into *Escherichia coli* Minicells

| EPISOMAL ELEMENT | REFERENCES |
|---|---|
| pUC19 | Heighway et al., *Nucleic Acids Res. 17*: 6893-6901 (1989) |
| R-plasmid | Hochmannova et al., *Folia Microbiol.* (*Praha*) 25: 11-15 (1980) |
| PCR1 | Hollenberg et al., *Gene 1*: 33-47 (1976); yeast shuttle vector |
| Bacteriophage | |
| Lambda | Witkiewicz et al., *Acta. Microbiol. Pol. A 7*: 21-24 (1975) |
| M13 | Staudenbauer et al., *Mol. Gen. Genet. 138*: 203-212 (1975) |
| T7 | Libby, *Mech Ageing Dev. 27*: 197-206 (1984) |
| P1 | Curtiss, Roy, III, U.S. Pat. No. 4,190,495; Issued Feb. 26, 1980; J Bacteriol 1995; 177: 2381-6, Partition of P1 plasmids in *Escherichia coli* mukB chromosomal partition mutants, Funnell and Gagnier. |

For expression of membrane proteins, and/or other proteins of interest in the recipient cell, ORFs encoding such proteins are operably linked to eukaryotic expression sequences that are appropriate for the recipient cell. For example, in the case of *E. coli*-yeast shuttle vectors, the ORFs are operably linked to expression sequences that function in yeast cells and/or minicells. In order to assess the effectiveness of a gene delivery vehicle, or a gene therapy expression element, an ORF encoding a detectable polypeptide (e.g., GFP, beta-galactosidase) is used. Because the detectable polypeptide is operably linked to eukaryotic expression elements, it is not expressed unless it has been transferred to its recipient (eukaryotic) cell. The signal from the detectable polypeptide thus correlates with the efficiency of gene transfer by a gene delivery agent, or the degree of expression of a eukaryotic expression element.

Gyuris and Duda (High-efficiency transformation of *Saccharoymces* cells by bacterial minicell protoplast fusion, Mol Cel Biol 6:329507, 1986) allegedly demonstrated the transfer of plasmid molecular by fusing minicell protoplasts with yeast protoplasts. Gyuris and Duda state that 10% of *Saccharomyces cerevisiae* cells were found to contain transforming DNA sequences. However, the plasmids did not contain eukaryotic expression elements, were not shuttle vectors, and genetic expression of the plasmids in yeast cells was not examined.

XII. Uses of Minicells in Research

XII.A. In General

The minicells of the invention can be used in research applications such as, by way of non-limiting example, proteomics, physiology, chemistry, molecular biology, physics, genetics, immunology, microbiology, proteomics, virology, pathology, botany, and neurobiology. Research applications include but are not limited to protein-ligand binding studies, competitive inhibition studies, structural studies, protein interaction studies, transfection, signaling studies, viral interaction studies, ELISA, antibody studies, gel electrophoresis, nucleotide acid) applications, peptide production, cell culture applications, cell transport studies, isolation and separation studies, chromatography, labeling studies, synthesis of chemicals, chemical cross linking, flow cytometry, nanotechnology, micro switches, micro-machines, agricultural studies, cell death studies, cell-cell interactions, proliferation studies, and protein-drug interactions. Minicells are applicable to research applications involving, by way of non-limiting example, the elucidation, manipulation, production, replication, structure, modeling, observations, and characterization of proteins.

The types of proteins that can be involved in research applications of minicells can be either soluble proteins or membrane bound proteins, and include but are not limited to receptors (e.g., GPCRs, sphingolipid receptors, neurotransmitter receptors, sensory receptors, growth factor receptors, hormone receptors, chemokine receptors, cytokine receptors, immunological receptors, and compliment receptors, FC receptors), channels (e.g., potassium channels, sodium channels, calcium channels.), pores (e.g., nuclear pore proteins, water channels), ion and other pumps (e.g., calcium pumps, proton pumps), exchangers (e.g., sodium/potassium exchangers, sodium/hydrogen exchangers, potassium/hydrogen exchangers), electron transport proteins (e.g., cytochrome oxidase), enzymes and kinases (e.g., protein kinases, ATPases, GTPases, phosphatases, proteases.), structural/linker proteins (e.g., Caveolins, clathrin), adapter proteins (e.g., TRAD, TRAP, FAN), chemotactic/adhesion proteins (e.g., ICAM11, selectins, CD34, VCAM-1, LFA-1, VLA-1), and chimeric/fusion proteins (e.g., proteins in which a normally soluble protein is attached to a transmembrane region of another protein).

Research products are designed for any specific type of application. These products may be packaged and distributed as, by way of non-limiting example, kits, chemicals, solutions, buffers, powders, solids, filters, columns, gels, matrixes, emulsions, pellets, capsules, and aerosols. Kits and reagents for certain research applications may be required by regulatory agency to be labeled "research use only" in order to indicate that the reagents are not intended for use in humans.

XII.B. Transfection

Transfection is the process of introducing genetic material into eukaryotic and archaebacterial cells using biological, biochemical or physical methods. This process allows researchers to express and study target proteins in cultured cells (research use) as well as to deliver genetic material to cells in vivo or ex vivo systems (gene therapy). There are a variety of techniques which allow for the introduction and expression of proteins into target cells. These include mechanical transfection (Biolistic particles and Electroporation), calcium phosphate, DEAE-dextran/polybrene, viral based techniques and lipid based techniques.

The genetic material and/or nucleic acid to be delivered can be, by way of non-limiting example, nucleic acids that repair damaged or missing genes, nucleic acids for research applications, nucleic acids that kill a dysfunctional cell such as a cancer cell, antisense oligonucleotides to reduce or inhibit expression of a gene product, genetic material that increases expression of another gene, nucleotides and nucleotide analogs, peptide nucleic acids (PNAs), tRNAs, rRNAs, catalytic RNAs, RNA:DNA hybrid molecules, and combinations thereof.

The genetic material may comprise a gene expressing a protein. exemplary proteins include, but are not limited to, receptors (e.g., GPCRs, sphingolipid receptors, neurotransmitter receptors, sensory receptors, growth factor receptors, hormone receptors, chemokine receptors, cytokine receptors, immunological receptors, and compliment receptors, FC receptors), channels (e.g., potassium channels, sodium channels, calcium channels.), pores (e.g., nuclear pore proteins, water channels), ion and other pumps (e.g., calcium pumps, proton pumps), exchangers (e.g., sodium/potassium exchangers, sodium/hydrogen exchangers, potassium/hydrogen exchangers), electron transport proteins (e.g., cytochrome oxidase), enzymes and kinases (e.g., protein kinases, ATPases, GTPases, phosphatases, proteases), structural/linker proteins (e.g., Caveolins, clathrin), adapter proteins (e.g., TRAD, TRAP, FAN), chemotactic/adhesion proteins (e.g., ICAM11, selectins, CD34, VCAM-1, LFA-1, VLA-1), and chimeric/fusion proteins (e.g., proteins in which a normally soluble protein is attached to a transmembrane region of another protein).

A minicell that is used to deliver therapeutic agents may comprise and display a binding moiety. By way of non-limiting example, binding moieties used for particular purposes may be a binding moiety directed to a compound or moiety displayed by a specific cell type or cells found predominantly in one type of tissue, which may be used, among other things, to target minicells and their contents to specific cell types or tissues. A preferred binding moiety is an antibody or antibody derivative. Other binding moieties include, but are not limited to, receptors, enzymes, ligands, binding peptides, fusion proteins, small molecules conjugated to transmembrane proteins, ligands conjugated to transmembrane proteins, viral fusion proteins, and fusion/chimeric proteins.

A minicell containing genetic material may be to a target cell by methods including, but not limited to, receptor mediated endocytosis, cell fusion, or phagocytosis (Aderem et al., Mechanism of Phagocytosis in Macrophages, Annu. Rev. Immunol. 17:593-623, 1999). The minicell gene delivery system is used to deliver genetic material in culture for research applications as well as to cells in vivo as part of gene therapy or other therapeutic applications.

By way of non-limiting example, a minicell may express a protein such as invasin to induce receptor mediated endocytosis (Pepe et al., "*Yersinia enterocolitica* invasin: A primary role in the initiation of infection," Proc. Natl. Acad. Sci. U.S.A. 90:6473-6477, 1993; Alrutz et al., "Involvement of focal adhesion kinase in invasin-mediated uptake," Proc. Natl. Acad. Sci. U.S.A. 95:13658-13663, 1998). Invasin interacts with the Beta2 Integrin protein and causes it to dimerize. Upon dimerization the Beta2 Integrin signals for an endocytotic event. Thus a minicell expressing the invasin protein will be taken up by cells expressing Beta2 Integrin via endocytosis.

Another non-limiting example of the minicell gene delivery and transfection system using invasin involves the expression of invasin following a targeting event. In this example, a minicell expresses a targeting protein that is capable of bringing the minicell in contact with a specific target cell. Upon contact with the target cell, the minicell will be induced to transcribe and translate invasin. The induction is accomplished via signaling events or with a transcription factor dimerization event. The minicells can be engineered to contain targeting proteins that induce protein expression only upon contact with a specific target cell. By way of non-limiting example, the invasin is expressed only at the target cell where it induces endocytosis, thus preventing the minicell from entering any cell but the target cell.

Proteins can be induced and expressed post contact with target cells include but are not limited to antibodies and antibody derivatives, receptors, enzymes, ligands, binding peptides, fusion proteins, small molecules conjugated to transmembrane proteins, ligands conjugated to transmembrane proteins, viral fusion proteins, antibiotics, apoptotic proteins, hormones, toxins, poisons, and fusion/chimeric proteins.

Another non-limiting example of gene delivery or transfection using the minicell involves the use of the type III secretion apparatus of bacteria. The type III secretion apparatus is expressed in the minicell and used to transfer genetic material to a target cell.

Another non-limiting example of gene delivery and transfection using minicells involves minicells that have been engineered to contain anionic lipids or cationic lipids (Axel et al., "Toxicity, Uptake Kinetics and Efficacy of New Transfection Reagents: Increase of Oligonucleotide Uptake," Jour. of Vasc. Res. 040:1-14, 2000). Many types of lipids have been shown to induce or enhance transfection and gene delivery in a variety of cell types. Minicells containing such lipids could be used to transfer genetic material to specific cell types. Minicells can also be engineered to express targeting proteins that would allow the minicell to associate tightly with a target cell, which will facilitate the lipid interactions and gene transfer.

Another non-limiting example of gene delivery or transfection using minicells involves the use of ligands to induce receptor mediated endocytosis. By way of non-limiting example, the ligand is expressed on the surface of the minicell, or is attached to the surface of the minicell. A minicell containing genetic material is then able to associate with a target cell expressing the target receptor for the ligand. The receptor/ligand interaction will result in the endocytosis of the minicell into the target cell where the minicell would release and deliver the genetic material.

Another non-limiting example of gene delivery or transfection using minicells involves the use of fusion proteins, such as but not limited to viral capsid proteins. In this example the fusion protein would be expressed or attached to the outside of the minicell. The fusion protein would then induce fusion of a target cell with the minicell upon contact. The contact could be initiated via random non-targeting events or via the use of specific targeting proteins. In both cases the end result would be the fusion of the minicell with a target cell and the delivery of the genetic material.

XII.C. Non-Limiting Examples of Research Applications of Minicells

XII.C.1. Phage Interactions with Bacterial Membranes

One non-limiting example of a research application for minicells would be the study of phage interactions with a bacterial membrane. The minicells could be used to study how phage associate and enter into a host bacterium. Another non-limiting example is the research application of minicells is to study isolated cell signaling pathways. The proteins of a signaling pathway could be expressed in the minicell and the signal cascade could be monitored. Another non-limiting example of research applications is the use of minicells to determine how recombination events occur. In this example the minicell is used to provide an environment to study the recombination event between two episomal plasmid DNA units.

XII.C.2. Matrices

Another non-limiting example of a research application of minicells is to form chromatography matrices for immunoprecipitation, isolation and separation techniques. The minicell can express and display target proteins with binding activity, including but not limited to antibodies and antibody derivatives. The minicell is then used to generate a matrix and loaded in a column or tube. The solution to be separated is mixed or passed through the column allowing the minicell to bind its target. The minicells are then separated away with the attached substance.

XII.C.3. Mutagenesis

Another non-limiting example of a research application for minicells involves site directed mutagenesis studies of target proteins. In this application minicells are generated to express target proteins with various mutations and deletions to study if function is compromised, enhanced or has an altered specificity for ligand binding.

XII.C.4. Metabolic Pathways

Another non-limiting example of research applications for minicells involves the study of metabolic rates of proteins and metabolites. The minicell can be generated to express metabolic pathways and the kinetics and function of that pathway can be studied.

XII.C.5. Cell Free Production of Proteins

Another non-limiting example of a research application for minicells involves uses in cell free production of functional proteins (Jermutus et al., Recent advances in producing and selecting functional proteins by using cell-free translation, Current Opinion in Biotechnology 9:534-548, 1999). Minicells can be prepared as a reagent used to prepare compositions for in vitro translation. As is described in detail elsewhere herein, the composition of minicells can be manipulated so as to be enriched for particular proteins or nulceic acids, including those involved in protein translation and folding and/or modification of the proteins so produced into functional forms, i.e., forms having the activity of the corresponding protein as it is isolated from natural sources. Non-limiting examples of such proteins and nulceic acids are ribosomal RNAs, ribosomal proteins, tRNAs, and the like.

XII.C.6. Assays

Minicells could also be used in manual, semi-automated, automated and/or robotic assays for the in vitro determinations of the compounds of interest including, by way of non-limiting example, ligands, proteins, small molecules, bioactive lipids, drugs, heavy metals, and the like in environmental samples (e.g., air, water, soil), blood, urine or tissue of humans or samples from non-human organisms (e.g., plants, animals, protists) for the purpose of quantifying one or more compounds in a sample. A non-limiting example of this type of research applications is the expression on the surfaces of the minicells of a receptor such as the receptor that binds a toxin produced by *Baccillus anthracis*. The protein, protective antigen (PA), is a 82.7 kDa protein that binds one of the secreted anthrax toxins, lethal factor (LF) (see Price, B. et al., Infection and Immunity 69: 4509-4515. 2001). Minicells expressing the PA protein could be used to detect LF in an environmental sample or in human blood, urine or tissue for the purposes of determining the presence of anthax. As a non-limiting example, a competitive binding assay or an antibody-based assay could be used to indicate binding of LF in the environmental or tissue sample. Another non-limiting example is the use of PA-expressing minicells in a lateral flow diagnostic where interaction between the minicells and the LF-containing sample is indicated by the presence of a colored reaction product on a test strip.

XIII. Minicell-Based Delivery of Biologically Active Agents

XIII.A. General Considerations

The minicells of the invention are capable of encapsulating and/or loading into a membrane a variety of substances, including but not limited to biologically active agents, including but not limited to diagnostic and therapeutic agents. Biologically active agents include, but are not limited to, nucleic acids, e.g., DNA, RNA, gene therapy constructs, ribozymes, antisense and other synthetic oligonucleotides including those with chemical modifications; peptide nucleic acids (PNAs); proteins; synthetic oligopeptides; peptomimetics; small molecules; radioisotopes; antibiotics; antibodies and antibody derivatives; and combinations and/or prodrugs of any of the preceding.

The surface of a minicell may be chemically altered in order to have certain properties that are desirable for their use as drug delivery agents. By way of non-limiting example, minicells may be chemically conjugated to polyethylene glycol (PEG), which provides for "stealth" minicells that are not taken as well and/or as quickly by the reticuloendothelial system (RES). Other compounds that may be attached to minicells include without limitation polysaccharides, polynucleotides, lipopolysaccharides, lipoproteins, glycosylated proteins, synthetic chemical compounds, and/or combinations of any of the preceding.

A minicell that is used to deliver therapeutic agents may comprise and display a binding moiety. By way of non-limiting example, binding moieties used for particular purposes may be a binding moiety directed to a compound or moiety displayed by a specific cell type or cells found predominantly in one type of tissue, which may be used, among other things, to target minicells and their contents to specific cell types or tissues. A preferred binding moiety is an antibody or antibody derivative, which are described in detail elsewhere herein. Other binding moieties include, but are not limited to, receptors, enzymes, ligands, binding peptides, fusion proteins, small molecules conjugated to transmembrane proteins, ligands conjugated to transmembrane proteins, viral fusion proteins, and fusion/chimeric proteins.

XIII.B. Cellular Uptake

In addition to binding moieties, proteins and other compounds that induce or enhance the uptake or fusion of the minicell with the target gene can be displayed on the surface of a minicell for applications involving the delivery of therapeutic agents, gene therapy, and/or transfection or other research applications. See, generally, *Adhesion Protein Protocols*, Vol. 96, Dejana, E. and Corada, M., eds., Humana Press, 1999.

XIII.B.1. Cellular Uptake Sequences from Eukaryotic Cells

Eukaryotic adhesion receptors, which mediate intercellular adhesion, can be used as agents or targets for cellular uptake. There are at least three distinct classes of adhesive molecules that leukocytes employ during their adhesive interactions (a) integrins, including but not limited to LEC-CAMS/Selectins (ELAM-1, LAM-1/Leu8/TQ1, and GMP140/PADGEM); (b) those belonging to the immunoglobulin superfamily including but not limited to CD2(LFA-2), CD3/TCR, CD4, CD8, CD28, CD44, CD54 (ICAM-1), ICAM-2, CD58 (LFA-3), VCAM-1, B7; and (c) Class I and II Major Histocompatability Antigens (MHC).

The adhesion receptors that belong to the integrin family and control intercellular interactions are of particular interest. At least ten different structurally related cell surface heterodimeric (alpha and beta complexes) molecules have been defined as integrins and further classified into subfamilies (Springer T. A., 1990, Nature 346:425-434; Hynes, R. O., 1987, Cell 48:549-554; Moller, G. Editor, 1990, Immunol. Rev. 114:1-217). Each subfamily has a unique beta subunit, designated integrin beta1 (CD29), integrin beta2 (CD18), and integrin beta3 (CD61), each of which can associate with multiple alpha subunits, each with at least one di-valent cation binding site. The integrin family includes receptors for extracellular matrix components such as fibronectin, laminin, vitronectin, and collagen which recognize Arg-Gly-Asp in their ligands and utilize the beta1 or beta3 subunits (Springer T. A., 1990, Nature 346:425-434; Hynes, R. O., 1987, Cell 48:549-554; Hemler, M. E., 1988, Immunol. Today 9:109-113; Patarroyo, M., and Makgoba, M. W., 1989, Scand. J. Immunol. 30:129-164; Moller, G. Editor, 1990, Immunol. Rev. 11.4:1-217). There are at least six distinct alpha subunits alpha1

(CD49a), alpha2 (CD49b), alpha3 (CD49c), alpha4 (CD49d), alpha5 (CD49e), and alpha6 (CD49f) capable of associating with beta1 (CD29). The beta1 integrins are expressed on many nonhematopoietic and leukocyte cell types and are thought to play an active role in tissue organization by binding to extracellular matrix components found in many tissues and in the basement membranes underlying muscles, nervous system, epithelium and endothelium. While the expression of many beta1 integrins on leukocytes requires consistent activation, their expression on nonhematopoietic cells does not (Hemler, M. E., 1988, Immunol. Today 9:109-113; Patarroyo, M., and Makgoba, M. W., 1989, Scand. J. Immunol. 30:129-164). The complexity of the integrin family has been increased by the discovery of novel beta subunits beta3 (CD61), beta4 and beta5 that can associate with alpha 4, alpha 6, and alpha V subunits (Springer T. A., 1990, Nature 346:425-434; Hemler, M. E., 1988, Immunol. Today 9:109-113). This combinatorial use of alpha and beta subunits confers considerable diversity in ligand recognition and also helps regulate communications between the inside and outside of the cell.

By way of non-limiting example, a minicell display an adhesion receptor, or a fusion protein that has a transmembrane domain linked to a functional portion of an adhesion receptor. Such minicells will bind to cells displaying the ligand for the adhesion receptor.

XIII.B.2. Cellular Uptake Sequences from Prokaryotes

Bacterial adhesion proteins are another source of polypetides that are used to stimulate uptake of minicells. See, generally, *Handbook of Bacterial Adhesion: Priniciples, Methods, and Applications*, Yuehuei H. An; Richard J. Friedman, eds., Humana Press, 2000; and Hultgren et al., "Bacterial Adhesions and Their Assembly," Chapter 150 in: *Eschericia coli and Salmonella typhimurium: Cellular and Molecular Biology*, $2^{nd}$ Ed., Neidhardt, Frederick C., Editor in Chief, American Society for Microbiology, Washington, D.C., 1996, Volume 2, pages 1903-1999, and references cited therein.

By way of non-limiting example, a minicell may express a protein such as invasin to induce receptor mediated endocytosis (Pepe et al., *Yersinia enterocolitica* invasin: A primary role in the initiation of infection, Proc. Natl. Acad. Sci. U.S.A. 90:6473-6477, 1993; Alrutz et al., Involvement of focal adhesion kinase in invasin-mediated uptake, Proc. Natl. Acad. Sci. U.S.A. 95:13658-13663, 1998). Invasin interacts with the Beta2 Integrin protein and causes it to dimerize. Upon dimerization the Beta2 Integrin signals for an endocytotic event. Thus a minicell expressing the invasin protein will be taken up by cells expressing Beta2 Integrin via endocytosis.

As another non-limiting example, the pneumococcal adhesin protein CpbA interacts with the human polyimmunoglobulin receptor (hpIgR) as either a part of the outer surface of a bacterial cell or as a free molecule Zhang et al. (Cell 102:827-837, 2000). The regions of CpbA:hpIgR interaction were mapped using a series of large peptide fragments derived from CpbA. CpbA (Swiss-Prot Accession No. O30874) contains a choline binding domain containing residues 454-663 and two N-terminal repetitive regions called R1 and R2 that are contained in residues 97-203 and 259-365, respectively. Polypeptides containing R1 and R2 interact with hpIgR, whereas polypeptides containing other sequences from CpbA do not bind to hpIgR. The R1 and/or R2 sequences of the CpbA polypeptide, and/or essentially identical, substantially identical, or homologous amino acid sequences, are used to facilitate the uptake of minicells by cells.

Another non-limiting example of gene delivery or transfection using the minicell involves the use of the type III secretion apparatus of bacteria. The type III secretion apparatus is expressed in the minicell and used to transfer genetic material to a target cell.

Other non-limiting examples of a minicell gene delivery and transfection targeting moiety are ETA (detoxified exotoxin a) protein delivery element described in U.S. Pat. No. 6,086,900 to Draper; Interalin and related proteins from *Listeria* species (Galan, Alternative Strategies for Becoming an Insider: Lessons from the Bacterial World, Cell 103:363-366, 2000); Intimin from pathogenic *E. coli* strains (Frankel et al., Intimin and the host cell—is it bound to end in Tir(s)? Trends in Microbiology 9:214-218); and SpeB, streptococcal pyrogenic exotoxin B (Stockbauer et al., A natural variant of the cysteine protease virulence factor of group A *Streptococcus* with an arginine-glycine-aspartic acid (RGD) motif preferentially binds human integrins $a_v\beta_3$ and $a_{11b}\beta_3$ Proc. Natl. Acad. Sci. U.S.A. 96:242-247, 1999).

XIII.B.3. Cellular Uptake Sequences from Viruses

Cellular uptake sequences derived from viruses include, but are not limited to, the VP22 protein delivery element derived from herpes simplex virus-1 and vectors containing sequences encoding the VP22 protein delivery element are commercially available from Invitrogen (Carlsbad, Calif.; see also U.S. Pat. No. 6,017,735 to Ohare et al.); and the Tat protein delivery element derived from the amino acid sequence of the Tat protein of human immunodeficiency virus (HIV). See U.S. Pat. Nos. 5,804,604; 5,747,641; and 5,674,980.

XIII.B.4. Lipids

Another non-limiting example of gene delivery and transfection using minicells involves minicells that have been engineered to contain anionic lipids or cationic lipids (Axel et al., Toxicity, Uptake Kinetics and Efficacy of New Transfection Reagents: Increase of Oligonucleotide Uptake, Jour. of Vasc. Res. 040:1-14, 2000). Many types of lipids have been shown to induce or enhance transfection and gene delivery in a variety of cell types. Minicells containing such lipids could be used to transfer genetic material to specific cell types. Minicells can also be engineered to express targeting proteins that would allow the minicell to associate tightly with a target cell, which will facilitate the lipid interactions and gene transfer.

Another non-limiting example of gene delivery or transfection using minicells involves the use of ligands to induce receptor mediated endocytosis. By way of non-limiting example, the ligand is expressed on the surface of the minicell, or is attached to the surface of the minicell. A minicell containing genetic material is then able to associate with a target cell expressing the target receptor for the ligand. The receptor/ligand interaction will result in the endocytosis of the minicell into the target cell where the minicell would release and deliver the genetic material.

Another non-limiting example of gene delivery or transfection using minicells involves the use of fusion proteins, such as but not limited to viral capsid proteins. In this example the fusion protein would be expressed or attached to the outside of the minicell. The fusion protein would then induce fusion of a target cell with the minicell upon contact. The contact could be initiated via random non-targeting events or via the use of specific targeting proteins. In both cases the end result would be the fusion of the minicell with a target cell and the delivery of the genetic material.

XIII.C. Post-Targeting Expression of Cellular Uptake Sequences

Another non-limiting example of the minicell gene delivery and transfection system using invasin involves the expression of invasin following a targeting event. In this example, a minicell expresses a targeting protein that is capable of bringing the minicell in contact with a specific target cell. Upon contact with the target cell, the minicell will be induced to transcribe and translate invasin. The induction is accomplished via signaling events or with a transcription factor dimerization event. The minicells can be engineered to contain targeting proteins that induce protein expression only upon contact with a specific target cell. By way of non-limiting example, the invasin is expressed only at the target cell where it induces endocytosis, thus preventing the minicell from entering any cell but the target cell.

Proteins can be induced and expressed post contact with target cells include but are not limited to antibodies and antibody derivatives, receptors, enzymes, ligands, binding peptides, fusion proteins, small molecules conjugated to transmembrane proteins, ligands conjugated to transmembrane proteins, viral fusion proteins, antibiotics, apoptotic proteins, hormones, toxins, poisons, and fusion/chimeric proteins.

XIII.D. Intracellular Targeting and Organellar Delivery

After delivery to and entry into a targeted cell, a minicell may be designed so as to be degraded, thereby releasing the therapeutic agent it encapsulates into the cytoplasm of the cell. The minicell and/or therapeutic agent may include one or more organellar delivery elements, which targets a protein into or out of a specific organelle or organelles. For example, the ricin A chain can be included in a fusion protein to mediate its delivery from the endosome into the cytosol. Additionally or alternatively, delivery elements for other organelles or subcellular spaces such as the nucleus, nucleolus, mitochondria, the Golgi apparatus, the endoplasmic reticulum (ER), the cytoplasm, etc. are included Mammalian expression constructs that incorporate organellar delivery elements are commercially available from Invitrogen (Carlsbad, Calif.: pShooter™ vectors). An H/KDEL (i.e., His/Lys-Asp-Glu-Leu sequence) may be incorporated into a fusion protein of the invention, preferably at the carboxy-terminus, in order to direct a fusion protein to the ER (see Andres et al., J. Biol. Chem. 266:14277-142782, 1991; and Pelham, Trends Bio. Sci. 15:483-486, 1990).

Another type of organellar delivery element is one which directs the fusion protein to the cell membrane and which may include a membrane-anchoring element. Depending on the nature of the anchoring element, it can be cleaved on the internal or external leaflet of the membrane, thereby delivering the fusion protein to the intracellular or extracellular compartment, respectively. For example, it has been demonstrated that mammalian proteins can be linked to i) myristic acid by an amide-linkage to an N-terminal glycine residue, to ii) a fatty acid or diacylglycerol through an amide- or thioether-linkage of an N-terminal cysteine, respectively, or covalently to iii) a phophotidylinositol (PI) molecule through a C-terminal amino acid of a protein (for review, see Low, Biochem. J. 244:1-13, 1987). In the latter case, the PI molecule is linked to the C-terminus of the protein through an intervening glycan structure, and the PI then embeds itself into the phopholipid bilayer; hence the term "GPI" anchor. Specific examples of proteins know to have GPI anchors and their C-terminal amino acid sequences have been reported (see Table 1 and FIG. 4 in Low, Biochemica et Biophysica Acta, 988:427-454, 1989; and Table 3 in Ferguson, Ann. Rev. Biochem., 57:285-320, 1988). Incorporation of GPI anchors and other membrane-targeting elements into the amino- or carboxy-terminus of a fusion protein can direct the chimeric molecule to the cell surface.

XIII.E. Minicell-Based Gene Therapy

The delivery of nucleic acids to treat diseases or disorders is known as gene therapy (Kay et al., Gene Therapy, Proc. Natl. Acad. Sci. USA 94:12744-12746, 1997). It has been proposed to use gene therapy to treat genetic disorders as well as pathogenic diseases. For reviews, see Desnick et al., Gene Therapy for Genetic Diseases, Acta Paediatr. Jpn. 40:191-203, 1998; and Bunnell et al., Gene Therapy for Infectious Diseases, Clinical Microbiology Reviews 11:42-56, 1998).

Gene delivery systems use vectors that contain or are attached to therapeutic nucleic acids. These vectors facilitate the uptake of the nucleic acid into the cell and may additionally help direct the nucleic acid to a preferred site of action, e.g., the nucleus or cytoplasm (Wu et al., "Delivery Systems for Gene Therapy," Biotherapy 3:87-95, 1991). Different gene delivery vectors vary with regards to various properties, and different properties are desirable depending on the intended use of such vectors. However, certain properties (for example, safety, ease of preparation, etc.) are generally desirable in most circumstances.

The minicells of the invention may be used as delivery agents for any therapeutic or diagnostic agent, including without limitation gene therapy constructs. Minicells that are used as delivery agents for gene therapy constructs may, but need not be, targeted to specific cells, tissues, organs or systems of an organism, of a pathogen thereof, using binding moieties as described in detail elsewhere herein.

In order to enhance the effectiveness of gene delivery vectors in, by way of non-limiting example, gene therapy and transfection, it is desirable in some applications of the invention to target specific cells or tissues of interest (targeted cells or tissues, respectively). This increases the effective dose (the amount of therapeutic nucleic acid present in the targeted cells or tissues) and minimizes side effects due to distribution of the therapeutic nucleic acid to other cells. For reviews, see Peng et al., "Viral Vector Targeting," Curr. Opin. Biotechnol. 10:454-457, 1999; Gunzburg et al., "Retroviral Vector Targeting for Gene Therapy," Cytokines Mol. Ther. 2:177-184, 1996.; Wickham, "Targeting Adenovirus," Gene Ther. 7:110-114, 2000; Dachs et al., "Targeting Gene Therapy to Cancer: A Review," Oncol. Res. 9:313-325, 1997; Curiel, "Strategies to Adapt Adenoviral Vectors for Targeted Delivery," Ann NY Acad. Sci. 886:158-171, 1999; Findeis et al., "Targeted Delivery of DNA for Gene Therapy via Receptors," Trends Biotechnol. 11:202-205, 1993.

Some targeting strategies make use of cellular receptors and their natural ligands in whole or in part. See, for example, Cristiano et al., "Strategies to Accomplish Gene Delivery Via the Receptor-Mediated Endocytosis Pathway," Cancer Gene Ther., Vol. 3, No. 1, pp. 49-57, January-February 1996.; S. C. Philips, "Receptor-Mediated DNA Delivery Approaches to Human Gene Therapy," Biologicals, Vol. 23, No. 1, pp. 13-6, March 1995; Michael et al., "Strategies to Achieve Targeted Gene Delivery Via the Receptor-Mediated Endocytosis Pathway," Gene Ther., Vol. 1, No. 4, pp. 223-32, July 1994; Lin et al., "Antiangiogenic Gene Therapy Targeting The Endothelium-Specific Receptor Tyrosine Kinase Tie2," Proc. Natl. Acad. Sci., USA, Vol. 95, pp. 8829-8834, 1998. Sudimack et al., "Targeted Drug Delivery Via the Folate Receptor," Adv. Drug Deliv., pp. 147-62, March 2000; Fan et al., "Therapeutic Application of Anti-Growth Factor Receptor Antibodies," Curr. Opin. Oncol., Vol. 10, No. 1, pp. 67-73, January 1998; Wadhwa et al., "Receptor Mediated Glycotargeting," J. Drug Target, Vol. 3, No. 2, pp. 111-27, 1995; Perales et al., "An Evaluation of Receptor-Mediated Gene Transfer Using Synthetic DNA-Ligand Complexes," Eur. J. Biochem, Vol. 1, No 2, pp. 226, 255-66, December 1994; Smith et al., "Hepatocyte-Directed Gene Delivery by Receptor-Mediated Endocytosis," Semin Liver Dis., Vol. 19, No. 1, pp. 83-92, 1999.

Antibodies, particularly single-chain antibodies, to surface antigens specific for a particular cell type may also be used as targeting elements. See, for example, Kuroki et al., "Specific Targeting Strategies of Cancer Gene Therapy Using a Single-Chain Variable Fragment (scFv) with a High Affinity for CEA," Anticancer Res., pp. 4067-71, 2000; U.S. Pat. No. 6,146,885, to Dornburg, entitled "Cell-Type Specific Gene Transfer Using Retroviral Vectors Containing Antibody-Envelope Fusion Proteins"; Jiang et al., "In Vivo Cell Type-Specific Gene Delivery With Retroviral Vectors That Display Single Chain Antibodies," Gene Ther. 1999, 6:1982-7; Engelstadter et al., "Targeting Human T Cells By Retroviral Vectors Displaying Antibody Domains Selected From A Phage Display Library," Hum. Gene Ther. 2000, 11:293-303; Jiang et al., "Cell-Type-Specific Gene Transfer Into Human Cells With Retroviral Vectors That Display Single-Chain Antibodies," J. Virol 1998, 72:10148-56; Chu et al., "Toward Highly Efficient Cell-Type-Specific Gene Transfer With Retroviral Vectors Displaying Single-Chain Antibodies," J. Virol 1997, 71:720-5; Chu et al., "Retroviral Vector Particles Displaying The Antigen-Binding Site Of An Antibody Enable Cell-Type-Specific Gene Transfer," J. Virol 1995, 69:2659-63; and Chu et al., "Cell Targeting With Retroviral Vector Particles Containing Antibody-Envelope Fusion Proteins," Gene Ther. 1994, 1:292-9.

Minicells are used to deliver DNA-based gene therapy to targeted cells and tissues. Double minicell transformants are used not only to target a particular cell/tissue type (e.g. HIV-infected T-cells) but are also engineered to fuse with and enter targeted cells and deliver a protein-based toxin (e.g., antibiotic, or pro-apoptotic gene like Bax), an antisense expression construct (e.g., antisense to a transcription factor), or antisense oligonucleotides (e.g., antisense to an anti-apoptotic gene such as Bcl-2. The doubly-transformed minicells express not only these cell death promoters, but also only target particular cells/tissues, thus minimizing toxicity and lack of specificity of gene therapy vectors. By "doubly-transformed" it is meant that the minicell comprises 2 expression elements, one eubacterial, the other eukaryotic. Alternatively, shuttle vectors, which comprise eubacterial and eukaryotic expression elementsin one vector, may be used.

Minicell-based gene therapy is used to deliver expression plasmids that could correct protein expression deficiencies or abnormalities. As a non-limiting example, minicell inhalants are targeted to pulmonary alveolar cells and are used to deliver chloride transporters that are deficient or otherwise material in cystic fibrosis. Protein hormone deficiencies (e.g., dwarfism) are corrected by minicell expression systems (e.g., growth hormone expression in pituitary cells). Duchene's muscular dystrophy is characterized by a mutation in the dystrophin gene; this condition is corrected by minicell-based gene therapy. Angiogenesis treatment for heart patients is made effective by FGF or VGEF-producing minicells targeted to the heart. In this case, plasmid-driven over-expression of these grown factors is preferred.

XIV. Therapeutic Uses of Minicells

In addition to minicell-based gene therapy, minicells can be used in a variety of therapeutic modalities. Non-limiting examples of these modalities include the following applications.

XIV.A. Diseases and Disorders

Diseases and disorders to which the invention can be applied include, by way of non-limiting example, the following.

Diseases and disorders that involve the respiratory system, such as cystic fibrosis, lung cancer and tumors, asthma, pathogenic infections, allergy-related diseases and disorders, such as asthma; allergic bronchopulmonary aspergillosis; hypersensitivity pneumonia, eosinophilic pneumonia; emphysema; bronchitis; allergic bronchitis bronchiectasis; cystic fibrosis; hypersensitivity pneumotitis; occupational asthma; sarcoid, reactive airway disease syndrome, interstitial lung disease, hyper-eosinophilic syndrome, parasitic lung disease and lung cancer, asthma, adult respiratory distress syndrome, and the like;

Diseases and disorders of the digestive system, such as those of the gastrointestinal tract, including cancers, tumors, pathogenic infections, colitis; ulcerative colitis, diverticulitis, Crohn's disease, gastroenteritis, inflammatory bowel disease, bowel surgery ulceration of the duodenum, a mucosal villous disease including but not limited to coeliac disease, past infective villous atrophy and short gut syndromes, pancreatitis, disorders relating to gastroinstestinal hormones, Crohn's disease, and the like;

Diseases and disorders of the skeletal system, such as spinal muscular atrophy, rheumatoid arthritis, osteoarthritis, osteoporosis, multiple myeloma-related bone disorder, cortical-striatal-spinal degeneration, and the like;

Autoimmune diseases, such as Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis amyotrophic lateral sclerosis, multiple sclerosis, autoimmune gastritis, systemic lupus erythematosus, autoimmune hemolytic anemia, autoimmune neutropenia, systemic lupus erythematosus, graft vs. host disease, bone marrow engraftment, some cases of Type I diabetes, and the like;

Neurological diseases and disorders, such as depression, bipolar disorder, schizophrenia, Alzheimer's disease, Parkinson's disease, familial tremors, Gilles de la Tourette syndrome, eating disorders, Lewy-body dementia, chronic pain and the like;

Pathological diseases and resultant disorders such as bacterial infections such as infection by *Escherichia, Shigella, Salmonella*; sepsis, septic shock, and bacteremia; infections by a virus such as HIV, adenovirus, smallpox virus, hepatovirus, and the like; and AIDS-related encephalitis, HIV-related encephalitis, chronic active hepatitis, and the like;

Proliferative disease and disorders, such as acute lymphoblastic leukemia, acute myelogenous leukemia, chronic myelogenous leukemia, metastatic melanoma, Kaposi's sarcoma, multiple myeloma, breast cancer, anal cancer, vulvar cancer, and the like; and Various diseases, disorders and traumas including, but not limited to, apoptosis mediated diseases, inflammation, cerebral ischemia, myocardial ischemia, aging, sarcoidosis, granulomatous colitis, scleroderma, degenerative diseases, necrotic diseases, alopecia, neurological damage due to stroke, diffuse cerebral cortical atrophy, Pick disease, mesolimbocortical dementia, thalamic degeneration, Huntington chorea, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, glomeralonephritis, chronic thyroiditis, Grave's disease, thrombocytopenia, myasthenia gravis, psoriasis, peroneal muscular atrophy, hypertrophic interstitial polyneuropathy, heredopathia atactica polyneuritiformis, optic neuropathy, and ophthalmoplegia.

A variety of diseases and disorders caused or exacerbated by pathogens may be treated using the invention. For a comprehensive description of pathogens and associated diseases and disorders, see Zinsser Microbiology, 20th Ed., Joklik, ed., Appelton-Century-Crofts, Norwalk, Conn., 1992, and references cited therein.

Minicells could also be used for replacement therapy (via gene therapy) in a variety of conditions known to be caused by protein or proteins that are either absent (e.g. Duchene's Muscular Dystrophy), reduced in level (Dwarfism) or abberant (Sickle-cell anemia).

For a comprehensive description of diseases and disorders that may be treated using the invention, see The Merck Manual of Diagnosis and Therapy, 17th Ed., Beers et al., eds.; published edition, Merck and Co., Rahway, N.J., 1999; on-line edition, Medical Services, Usmedsa, USHH, http://www.merck.com/pubs/mmanual/, and references cited therein.

XIV.B. Removal of Toxins and Pathogens by Selective Absorption

When introduced into the bloodstream of an animal, receptor-displaying minicells bind and absorb toxic compounds, thereby removing such compounds from the general circulation. A therapeutic benefit ensues as the bound toxic compound cannot access the cells upon which it would otherwise exert its toxic effect.

Minicells expressing receptors for toxic substances are introduced IV in order to remove those toxins from the blood. One non-limiting example is in the treatment of sepsis. In one embodiment, a fusion protein is formed from the transmembrane domain of the EGF receptor or toxR and a known soluble receptor for LPS (lipopolysaccharide), such as the LBP (lipopolysaccharide binding protein) or the extracellular domain of CD14 receptor protein, both of which bind the LPS bacterial endotoxin. These minicells inactivate LPS by initially binding to it and preventing LPS binding to naturally occurring CD14 receptors on heart cells and other cells involved in the endotoxic shock response. Eventually, the minicell-LPS complex is cleared from the blood by macrophages and other components of the immune system.

In another embodiment, minicells expressing receptors for toxic drugs (e.g., morphine) are used to treat drug overdoses. In other embodiments, minicells of the invention are used to express receptors to venoms (e.g., snake venom) or poisons (e.g., muscarinic receptor expression for the treatment of muscarine poisoning). In other embodiments, minicells of the invention expressing EDGRs are used to clear the blood of toxins and other undesirable compounds.

As another non-limiting example, minicells that bind pathogens are used to treat disease. Minicells, and pathogens bound thereto, may be ingested by human neutrophils and thus serve as an adjuvant to therapeutic processes mediated by neutrophils (Fox et al., Fate of the DNA in plasmid-containing *Escherichia coli* minicells ingested by human neutrophils, Blood 69:1394-400, 1987). In a related modality, minicells are used to bind compounds required for the growth of a pathogen.

XIV.C. Antiviral Therapy

In one modality, minicells of the invention are used as "sponges" for the selective absorption of any viral particle in the body. Without being limited to the following examples, minicells expression receptors or antibodies selectively directed against viruses such as HIV, Hepatitis B and smallpox are used.

For the treatment of viremia, viruses are cleared from the blood by absorption during dialysis or by IV injection of minicells expressing targets for viral receptors. As the minicells interact with blood-borne virus particles, there is an initial reduction of host cell infection by virtue of the minicell-viral complexes that are formed. Since viral particles attach to and/or enter the minicell, they are not active because of the lack of machinery needed for viral replication in the minicells. The virus infected minicells are then cleared from the system by macrophages and processed by the immune system.

Certain retroviruses that infect particular host cells express viral proteins on the surfaces of the infected cells. HIV infection of T-cells is one non-limiting example of this. The viral protein, GP120, is expressed on the surfaces of infected T-cells (Turner et al., Structural Biology of HIV, J. Mol. Biol. 285:1-32, 1999). Minicells expressing CD4 act as anti-GP120 minicells not only to target virus particles in an infected patient, but also to identify infected T-cells. It may be desirable to also express co-receptors such as CCR5, CXR4 or ARD (Dragic, An overview of the determinants of CCR5 and CXCR4 co-receptor function, J. Gen. Virol. 82:1807-1814, 2001). The minicells are then used to kill the infected T-cells, or to inhibit viral replication and/or virion assembly.

In another non-limiting example of anti-pathogen therapy, minicells can by used to express bacterial surface antigens on their surfaces that facilitate cellular uptake of the minicell by intracellular pathogens such as *Mycobacterium tuberculosis* (the causative agent of tuberculosis), Rickettsiae, or viruses. In this "smart sponge" approach, selective absorption is accompanied by internalization of the pathogen by minicells. Destruction of the pathogen follows as a result of a combination of intraminicell digestion of pathogens and/or by the eventual processing of the virus-containing minicell by the cellular immune system of the patient.

XIV.D. Antibacterial and Antiparasitic Applications

Minicells may be used to kill pathogenic bacteria, protozoans, yeast and other fungi, parasitic worms, viruses and other pathogens by mechanisms that either do or do not rely on selective absorption. Antibiotics can be delivered to pathogenic organisms after first being targeted by the proteins or small molecules on the surfaces of the minicells that promote binding of the minicells to the surfaces of the pathogen. Fusion or injection of minicell contents into the pathogenic cell can result in the death or disablement of the pathogen and thus lower the effective dose of an antibiotic or gene therapeutic agent. Delivery of antibiotics tethered to or encapsulated by the minicells will reduce the effective dose of an antibiotic and will reduce its elimination by the renal system. In the case of delivering encapsulated molecules (e.g., antibiotics), purified/isolated minicells expressing membrane-bound proteins for targeting can be incubated with the molecules in vitro prior to administration. This would be particularly applicable to the use of protoplast minicells or poroplast minicells that have their outer membrane and cell wall or outer membrane only removed, respectively, thus facilitating the diffusion of the small molecule into the intact minicell.

Without being limited by the following example, minicells can be use as antibacterial agents by expressing on the surfaces of the minicells antigens, receptors, antibodies, or other targeting elements that will target the minicell to the pathogenic organism and facilitate the entry of plasmids, proteins, small molecules in order to gain access to or entry into the organism. Antibiotics may be encapsulated by minicells post isolation from the parent strain so that the antibiotic will not be effective against the minicell-producing bacteria itself.

Since minicells are not able to reproduce, the antibiotic will not be lethal to the minicell delivery vehicle, but only to the targeted pathogen. In another non-limiting example, lyosgenic factors e.g., complement may be expressed on the surfaces of the minicells or encapsulated by same as to promote lysis of the pathogen.

Minicells can also be engineered to express toxic proteins or other elements upon binding to the pathogen. Induction of minicell protein expression can be an event that is coincident with targeting or triggered by minicell binding to the target pathogen, thus making minicells toxic only when contact is made with the pathogenic organism. Minicells can be engineered to express fusion/chimeric proteins that are tethered to the membrane by transmembrane domains that have signaling moieties on the cytoplasmic surfaces of the minicells, such as kinases or transcription factors. In one non-limiting example, a minicell fusion membrane-bound protein could be expressed containing an extracellular domain with a receptor, scFv, or other targeting protein that binds to the pathogen. The second segment of the chimera could be a transmembrane domain of a protein such as the EGF receptor or ToxR (that would tether the fusion protein to the membrane). Importantly, the cytoplasmic domain of the fusion protein could be a kinase that phosphorylates a bacterial transcription factor present in the minicell or could be fused to a transcription factor that would be expressed on the cytoplasmic surface of the minicell. The expression plasmid that was previously introduced into the minicells would then be activated by promoters utilizing the activated bacterial transcription factor pre-existing in the minicells or that which may be introduced by the minicell. Without being limited to the following example, the binding event could be signaled by a fusion protein containing elements of a receptor (e.g., EGF) or by an adhesion protein (e.g., an integrin) that require oligomerization. In the example of the use of integrins, bacterial or other transcription factors that also require dimerization could be cloned as fusion proteins such that the binding event would be signaled by a dimerization of two or more identical recombinant chimeric proteins that have association-dependent transcription factors tagged to the C-terminus of the fusion protein. The minicells would only be toxic when contact is made with the pathogen.

The proposed mechanism of induction coincident with targeting is not limited to the antiparasitic uses of minicells but can be used in other therapeutic situations where minicells are used to express proteins of therapeutic benefit when directed against eucaryotic cells of the organism (e.g., kill cancer cells with protein toxins expressed only after binding of the minicell to the cancer cell).

Transfer of DNA-containing plasmids or other expression element, antisense DNA, etc. may be used to express toxic proteins in the target cells or otherwise inhibit transcription and/or translation in the pathogenic organism or would otherwise be toxic to the cell. Without being limited by the following example, minicells can be used to transfer plasmids expressing growth repressors, DNAses, or other proteins or peptides (e.g., pro-apoptotic) that would be toxic to the pathogen.

XIV.E. Cancer Therapy

Fusion proteins expressed in minicells are used for cancer therapy. In a non-limiting example, phage display antibody libraries are used to clone single chain antibodies against tumor-associated (tumor-specific) antigens, such as MUCH-1 or EGFvIII. Fusion proteins expressing these antibodies, and further comprising a single-pass transmembrane domain of an integral membrane protein, are used to "present" the antibody to the surface of the minicells. Injected minicells coated with anti-tumor antibodies target the tumor and deliver pro-apoptotic genes or other toxic substances to the tumor. The minicells are engulfed by the tumor cells by processes such receptor-mediated endocytosis (by, e.g., macrophages). By way of non-limiting example, toxR-invasin could be expressed on the surfaces of the minicells to promote endocytosis through the interaction between invasin and beta2-integrins on the surfaces of the target cells.

Fusion proteins possessing viral fusion-promoting proteins facilitate entry of the minicell to the tumor cell for gene therapy or for delivery of chemotherapy bioactive proteins and nucleic acids. In these and similar applications, the minicell may contain separate eukaryotic and eubacterial expression elements, or the expression elements may be combined into a single "shuttle vector."

XV. Diagnostic Uses of Minicells

Minicells are transformed with plasmids expressing membrane-bound proteins, such as receptors, that bind to specific molecules in a particular biological sample such as blood, urine, feces, sweat, saliva or a tissue such as liver or heart. Minicells can also be used for delivery of therapeutic agents across the blood-brain barrier to the brain. This modality is used, by way of non-limiting example, for imaging purposes, and for the delivery of therapeutic agents, e.g., anti-depressants, and agents for the treatment of cancer, obesity, insomnia, schizophrenia, compulsive disorders and the like. Recombinant expression systems are incorporated into minicells where the plasmid-driven protein expression construct could be the produce a single gene product or a fusion protein, such as a soluble protein for the particular ligand fused with a transmembrane domain of a different gene. The fusion protein then acts as a membrane bound receptor for a particular ligand or molecule in the sample. Conventional cloning techniques (e.g., PCR) are used to identify genes for binding proteins, or phage display is used to identify a gene for a single-stranded variable antibody gene expressing binding protein for a particular ligand. The protein product is preferably a soluble protein. By constructing a plasmid containing this gene plus the transmembrane domain of a known single-pass membrane protein such as that of the EGF receptor, a fusion protein may be expressed on the surfaces of the minicells as an integral membrane protein with an extracellular domain that is preferably capable of binding ligand.

In another type of fusion protein, the transmembrane domain of the EGF receptor is fused to a known soluble receptor for a particular ligand, such as the LBP (lipopolysaccharide binding protein) or the extracellular domain of CD14 receptor protein, both of which bind the bacterial endotoxin, LPS (lipopolysaccharide). The LBP/EGF or CD14/EGF fusion protein is used to measure LPS in the serum of patients suspected of sepsis.

The minicell system is used to express receptors such as those of the EDG (endothelial cell differentiation gene) family (e.g., EDG 1-9) that recognize sphingolipids such as sphingosine-1-phosphate (S1P), sphingosylphosphoryl choline (SPC) and the lysophospholipid, lysophosphatidic acid (LPA). Since these proteins are 7-pass integral membrane proteins, no additional transmembrane domains of another protein are needed, and the receptor protein is thus not a fusion protein.

Truncated or mutant forms of a protein of interest are useful in a diagnostic assay. For example, a protein that is an ligand-binding enzyme can be altered so as to bind its substrate of interest but can no longer convert substrate into product. One example of this application of minicell technology is the expression of a truncated or mutant lactic dehydrogenase which is able to bind lactic acid, but is not able to convert lactic acid to pyruvate. Similarly, hexokinase derivatives are used in minicells for glucose monitoring.

Minicells as diagnostic tools can be used either in vitro or in vivo. In the in vitro context, the minicells are used in an ELISA format or in a lateral flow diagnostic platform to detect the presence and level of a desired analyte. A sample (tissue, cell or body fluid sample) is taken and then tested in vitro. One advantage of the minicell system in detecting substances in tissue, cells or in body fluids is that the minicells can be used in vitro assays where the minicell is labeled with either a radioactive or fluorescent compound to aid in its detection in a an ELISA format or lateral flow platform. Thus, the use of secondary antibody detection systems is obviated.

As an in vivo diagnostic, minicells can be radiolabeled. One method of labeling is to incubate minicells for a short time (about 8 hr) with a $T_{1/2}$ tracer (e.g., Tn99M) that is useful for detecting tumor metastases. The Tn99M accumulates in cells and loads into minicells after isolation or into the parent bacteria during growth phase. As Tn99M is oxidized by either the parent E. coli strain or by the minicells after isolation, the Tn99M is retained by the cell. Iodine-labled proteins may also be used (Krown et al., TNF-alpha receptor expression in rat cardiac myocytes: TNF-alpha inhibition of L-type Ca2+ transiets, FEBS Letters 376:24-30, 1995).

One non-limiting example of in vivo detection of cancer making use of radiolabeled minicells is the use of the minicells to express chimeric membrane-bound single-chain antibodies against tumor-specific antigens (TSA) expressed on malignant melanoma or other transformed cells. Such TSAs include, but are not limited to, the breast cancer associated MUC1 antigen and variant forms of the EGFR (EGFvIII). By way of non-limiting example, minicells expressing antibodies to melanoma cells can be injected (IV) into a patient and then subjected to CAT scan of the lymphatic drainage in order to determine if a metastasis has occurred. This diagnostic technique obviates the need for lymph node dissection.

Another example of an in vivo diagnostic is to use the minicell system to express antibodies against oxidized low-density lipoproteins (LDL). Oxidized LDLs are associated with atherogenic plaques. Radiolabeled minicells (prepared as above) are injected IV into a person prior to nuclear imaging for image enhancement. MRI image contrast enhancement is performed by preparing minicells complexed (loaded) with contrast enhancers such as paramagnetic relaxivity agents and magnetic susceptibility agents.

In diagnostic as well as other applications, minicells preferentially detect a diagnostic marker, i.e., a marker associated with a disease or disorder. A diagnostic marker is statistically more like to occur in individuals sufferening from a disease than in those who are not diseased. Preferably, a diagnostic marker directly causes or is produced during a disease; however, the association may be no more than a correlation.

XVI. Drug Discovery (Screening) with Minicells

XVI.A. Assays

Minicells can be used in assays for screening pharmacological agents. By way of non-limiting example, the minicell system provides an environment for the expression of GPCRs and studies of their ligand binding kinetics. Such GPCR's include any member the Endothelial Differentiation Gene (EDG) receptor family. GPCRs may participate in neoplastic cell proliferation, angiogenesis and cell death. Small molecules that either activate or inhibit the action of these GPCRs can be used in therapeutic interaction.

Assays are performed to determine protein expression and protein function. For example, the production of the protein can be followed using protein $^{35}$S-Met labeling. This is performed by providing the cell only methionine that is labeled with $^{35}$S. The cells are treated with IPTG to induce protein expression, and the $^{35}$S-Met is incorporated into the protein. The cells are then lysed, and the resulting lysates were electrophoresed on an SDS gel and exposed to autoradiography film.

Another technique for assessing protein expression involves the use of western blots. Antibodies directed to various expressed proteins of interest have been generated and many are commercially available. Techniques for generating antibodies to proteins or polypeptides derived therefrom are known in the art (see, e.g., Cooper et al., Section III of Chapter 11 in: Short Protocols in Molecular Biology, 2nd Ed., Ausubel et al., eds., John Wiley and Sons, New York, 1992, pages 11-22 to 11-46). Standard western blot protocols, which may be used to show protein expression from the expression vectors in minicells and other expression systems, are known in the art. (see, e.g., Winston et al., Unit 10.7 of Chapter 10 in: Short Protocols in Molecular Biology, 2nd Ed., Ausubel et al., eds., John Wiley and Sons, New York, 1992, pages 10-32 to 10-35).

The amount of functional protein produced from a minicell expression system is determined through the use of binding studies. Ligands for the proteins of interest are used to show specific binding in the minicell system. Radiolabeled ligand is incubated with cells expressing the protein, in this case, a receptor for TNF-alpha. The cells are then centrifuged and the radioactivity counted in a scintillation counter. The amount of ligand that is bound reflects the amount of functional protein that is present in the sample.

By way of non-limiting example, the minicell system can be made to express EDGRs for the purpose of screening combinatorial chemistry libraries for molecules that enhance EDG activity. EDG activity is assayed in the minicell environment in several ways. One way is to crystallize minicells expressing an EDG protein (or any membrane-bound protein of choice) and then measure changes in the crystal structure to detect novel ligands. Circular dichroism (CD), x-ray diffraction, electron spin resonance (EPR) or other biophysical approaches are used to probe the structure of proteins in the minicell context. Additionally or alternately, minicells are produced that express not only the EDGR, but also express G-proteins (i.e., double transformants). An assay system involving GTP binding and hydrolysis is used to identify and assess which small molecules in the combinatorial chemistry library serve as activating ligands for EDG. The minicell expression system is used in in vitro binding assays and in high throughput drug screenings. The expression of mutant or truncated isoforms of proteins are used for functional analyses in order to discover inactive or overactive proteins for potential use in diagnostics or therapeutics.

XVI.B. High-Throughput Screening (HTS)

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell that causes a disease. High throughput methods enable researchers to try out thousands of different chemicals against each target very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is best to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity determined according to the methods herein. It will be appreciated that modulators can also be combined with the enzyme activators or inhibitors to find modulators which inhibit the enzyme activation or repression that is otherwise caused by the presence of the known enzyme modulator. Similarly, when ligands to a sphingolipid target are sought, known ligands of the target can be present in control/calibration assay wells.

The minicells of the invention are readily adaptable for use in high-throughput screening assays for screening candidate compounds to identify those which have a desired activity, e.g., inhibiting an enzyme that catalyzes a reaction that produces an undesirable compound, inhibiting function of a receptor independent of ligand interference, or blocking the binding of a ligand to a receptor therefor. The compounds thus identified can serve as conventional "lead compounds" or can themselves be used as therapeutic agents.

The methods of screening of the invention comprise using screening assays to identify, from a library of diverse molecules, one or more compounds having a desired activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, agonists and antagonists, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are contained in each well of a multi-well microplate; in the case of enzymes, reactants are also present in the wells. Currently, the most widely established techniques utilize 96-well microtiter plates. In this format, 96 independent tests are performed simultaneously on a single 8 cm×12 cm plastic plate that contains 96 reaction wells. One or more blank wells contains all of the reactants except the candidate compound. Each of the non-standard wells contain at least one candidate compound.

These wells typically require assay volumes that range from 50 to 500 ul. In addition to the plates, many instruments, materials, pipettors, robotics, plate washers and plate readers are commercially available to fit the 96-well format to a wide range of homogeneous and heterogeneous assays. Microtiter plates with more wells, such as 384-well microtiter plates, are also used, as are emerging methods such as the nanowell method described by Schullek et al. (Anal Biochem., 30 246, 20-29, 1997).

In one modality, screening comprises contacting a sphingolipid target with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

Minicells of the invention expressing and/or displaying a protein are used for screening assays designed to identify agents that modulate the activity of the target protein. Such assays include competitive inhibition binding assays for high throughput assays. Competitive inhibition assays include but are not limited to assays that screen agents against a specific target protein to identify agents that inhibit, interfere, block, or compete with protein-ligand interactions, protein-protein interactions, enzymatic activity, or function of a specific protein. Examples of competitive inhibition include but are not limited to the development of neutral inhibitors of the serine protease factor Xa that were discovered using a high throughput screening assay using a compound library (Carr et al, Neutral inhibitors of the serine protease factor Xa, Bioorg Med Chem Lett 11, 2001), the design and characterization of potent inhibitors for the human oxytocin receptor (Seyer et al, Design, synthesis and pharmacological characterization of a potent radio iodinated and photoactivatable peptidic oxytocin antagonist, J Med Chem. 44:3022-30, 2001), and the identification of non-peptide somatostatin antagonists of the sst(3) protein (Thurieau et al, Identification of potent non-peptide somatostatin antagonists with sst(3) selectivity, J Med Chem. 44:2990-3000, 2001).

High throughput competitive inhibition assays are designed to identify agents that inhibit a specific target protein. Such assays include but are not limited to ones that measure enzymatic activity, protein-ligand interactions, protein-protein interactions and other functions of proteins. Minicells that express and/or display a specific protein could be used in all types of competitive inhibition assays.

One non-limiting example of high throughput competitive inhibition screening using minicells for the purpose of this patent involves the competitive inhibition of known ligands. The ligand is attached to but not limited to a fluorophore, fluorescent protein, tags such as 6×His tag or FLAG tag, chromophores, radiolabeled proteins and molecules, binding moieties such as avidin and strepavidin, voltage sensitive dies and proteins, bioluminescent proteins and molecules, or fluorescent peptides. The target protein, which binds the tagged ligand, is expressed and stably displayed by the minicell. When the ligand is added to the minicell solution the ligand binds to the target protein. Following a wash the interaction is detected via the fluorophore, fluorescent protein, tag, or fluorescent peptide. The ligand-bound minicells could either be centrifuged (taking advantage of the sedimentation properties of the minicell particle) or immunoprecipitated with an antibody against an antigen expressed on the minicell membrane or the minicells can be adsorbed/fixed to a substrate such as a standard 96 well plate. The competitive inhibition assay is carried out by adding agents to the minicell mix either before, together or after the ligand is added. Thus if the agent is a competitive inhibitor of the ligand to the target protein the ligand will be washed away from the minicell because it is not associated with the target protein. The agent prevents binding and thus eliminated the detection signal from the minicell.

Minicells of this invention are used in "functional screening HTS assays". Functional screening assays are defined as assays that provide information about the function of a specific target protein. Functional assays screen agents against specific target proteins to identify agents that either act as antagonist or as an agonist against the protein. Functional assays require that the target protein be in an environment that allows it to carry out its natural function. Such functions include but are not limited to G-proteins coupling with a GPCR, enzymatic activity such as phosphorlyation or proteolysis, protein-protein interaction, and transport of molecules and ions.

Functional assays screen agents against proteins which are capable of natural function. Target proteins used in functional studies must carry out a function that is measurable. Examples of protein functions that are measurable include but are not limited to the use of Fluorescent Resonance Energy Transfer (FRET) to measure the G-protein coupling to a GPCR (Ruiz-Velasco et al., Functional expression and FRET analysis of green fluorescent proteins fused to G-protein subunits in rat sympathetic neurons, J Physiol. 537:679-692, 2001; Janetopoulos et al., Receptor-mediated activation of heterotrimeric G-proteins in living cells, Science 291: 2408-2411, 2001); Bioluminescence Resonance Energy Transfer (BRET) to assay for functional ligand induced G-protein coupling to a target GPCR (Menard, L. Bioluminescence Resonance Energy Transfer (BRET): A powerful platform to study G-protein coupled receptors (GPCR) activity in intact cells, Assay Development, Nov. 28-30, 2001), the use of florescent substrates to measure the enzymatic activity of proteases (Grant, Designing biochemical assays for proteases using fluorogenic substrates, Assay Development, Nov. 28-30, 2001); and the determination of ion channel function via the use of voltage sensitive dies (Andrews et al, Correlated measurements of free and total intracellular calcium concentration in central nervous system neurons, Microsc Res Tech. 46:370-379, 1999).

One non-limiting example of high throughput functional screening assay using minicells for the purpose of this patent involves the functional coupling of GPCRs to their respective G-protein. Upon ligand binding, voltage polarization, ion binding, light interaction and other stimulatory events activate GPCRs and cause them to couple to their respective G-protein. In a minicell, both the GPCR and its respective G-proteins can be simultaneously expressed. Upon activation of the GPCR the coupling event will occur in the minicell. Thus by detecting this coupling in the minicell, one could screen for agents that bind GPCRs to identify antagonists and agonists. The antagonists are identified using inhibition assays that detect the inhibition of function of the GPCR. Thus the agent interacts with the GPCR in a way that it inhibits the GPCR from being activated. The agonists are identified by screening for agents that activate the GPCR in the absence of the natural activator.

The detection of GPCR activation and coupling in a minicell is accomplished by using systems that generate a signal upon coupling. One non-limiting example involves the use of BRET or FRET. These systems require that two fluorescent or bioluminescent molecules or proteins be brought into close contact. Thus by attaching one of these molecules or proteins to the GPCR and one to the G-protein, they will be brought together upon coupling and a signal will be generated. This signal can be detected using specific detection equipment and the coupling event can be monitored. Thus the function of the GPCR can be assayed and used in functional assays in minicells.

Another non-limiting functional assay for GPCRs and other proteins in minicells involves the use of transcription factors. Many bacterial transcription factors and eukaryotic transcription factors require dimerization for activation. By attaching one subunit of a transcription factor to a GPCR and the other subunit to a G-protein, the subunits will dimerize upon coupling of the GPCR to the G-protein because they will be brought into close contact. The dimerized transcription factor will then be activated and will act on its target episomal DNA. In the minicell system the episomal DNA target will be a plasmid that encodes for proteins that provide a signal for detection. Such proteins include but are not limited to luciferase; green fluorescent protein (GFP), and derivatives thereof such as YFP, BFP, etc.; alcohol dehydrogenase, and other proteins that can be assayed for expression. The activation of the GPCR will result in coupling and activation of the transcription factor. The transcription factor will then induce transcription and translation of specific detector proteins. Thus the activation of the GPCR will be monitored via the expression of the detector protein.

In another modality, the transcription factor can inhibit expression in the minicell system and thus allowing for the screening of constitutively active GPCRs and proteins. For example if the GPCR were constitutively active then the transcription factor to use would be one that inhibits transcription and translation. Thus agents could be screened against the constitutively active GPCR to identify agents that caused the constitutively active GPCR to uncouple. The uncoupling will result in the inactivation of the transcription factor. The inhibition caused by the transcription factor will be removed and transcription and translation will occur. Thus a detectable protein will be made and a signal will be received.

The transcription dimerization assay can be used for any protein function that involves a protein-protein interaction, protein-ligand interaction and protein-drug interaction. Thus any assay involving such interactions can be carried out in the minicell.

Another non-limiting functional screening assay involves the use of enzymatic function to screen for functionality. In this modality the receptor or other protein performs a specific enzymatic function. This function is then carried out in the minicell and monitored using biochemical and other techniques. For example if the target protein was a protease then fluorescent peptides with the cleavage site of the protease could be used to monitor the activity of the protease. If the protease was functioning then the peptide would be cleaved and the fluorescents would change. Thus agents can be screened against the protease in the minicell system and the fluorescents can be monitored using specific detection systems. In another non-limiting example, a membrane-bound enzyme such as sphingomyelinase could be expressed in minicells and the minicell particles adsorbed to a standard substrate such as a 96 well plate. The enzymatic activity could be assessed by a standard in vitro assay involving the release of product (phosphocholine) (e.g., Amplex™ kit A-12220 sold by Molecular Probes). Sphingomyelinase inhibitors could be screened by measuring the reduction of phosphocholine production in the well when presented with substrate (sphingomyelin) in a coupled fluorescence assay.

Another non-limiting example of minicells used for functional assays involves the screening of agonists/antagonists for ion channels. In this example the calcium channel, SCaMPER, is encoded on a poycistronic episomal plasmid, which also encodes for a luminescent soluble protein, aequorin. In this assay, the minicell will contain aequorin proteins in its cytoplasm and SCaMPER proteins expressed on the minicell membrane. Thus upon activation of SCaMPER by its ligand, SPC, or by an analog thereof, calcium will flow into the minicell and will be bound by the aequorin which will luminescence. Thus a detection signal for the functional activation of the calcium channel is obtained.

Minicell can also be employed for expression of target proteins and the preparation of membrane preparations for use in screening assays. Such proteins include but are not limited to receptors (e.g., GPCRs, sphingolipid receptors, neurotransmitter receptors, sensory receptors, growth factor receptors, hormone receptors, chemokine receptors, cytokine receptors, immunological receptors, and compliment receptors, FC receptors), channels (e.g., potassium channels, sodium channels, calcium channels.), pores (e.g., nuclear pore proteins, water channels), ion and other pumps (e.g., calcium pumps, proton pumps), exchangers (e.g., sodium/potassium exchangers, sodium/hydrogen exchangers, potassium/hydrogen exchangers), electron transport proteins (e.g., cytochrome oxidase), enzymes and kinases (e.g., protein kinases, ATPases, GTPases, phosphatases, proteases.), structural/linker proteins (e.g., Caveolins, clathrin), adapter proteins (e.g., TRAD, TRAP, FAN), chemotactic/adhesion proteins (e.g., ICAM11, selectins, CD34, VCAM-1, LFA-1, VLA-1), and chimeric/fusion proteins (e.g., proteins in which a normally soluble protein is attached to a transmembrane region of another protein). In such assays the membrane preparations are used to screen for agents that are either antagonists or agonists. These assays use various formats including but not limited to competitive inhibition.

The format for the screening of minicells includes but is not limited to the use of test tubes, 6 well plates, 12 well plates, 24 well plates, 96 well plates, 384 well plates, 1536 well plates, and other microtiter well plates. In these systems the minicells can be immobilized, attached, bound, or fused with the above test tubes or plates. The minicells can also be free in solution for use in tubes and plates. The detection systems for the minicell assay include but are not limited to fluorescent plate readers, scintillation counters, spectrophotometers, Viewlux CCD Imager, Luminex, ALPHAQuest, BIAcore, FLIPR and F-MAT. Minicell assays can be carried out with but not limited to techniques such as manual handling, liquid handlers, robotic automated systems and other formats.

XVI.C. Chemical Libraries

Developments in combinatorial chemistry allow the rapid and economical synthesis of hundreds to thousands of discrete compounds. These compounds are typically arrayed in moderate-sized libraries of small organic molecules designed for efficient screening. Combinatorial methods, can be used to generate unbiased libraries suitable for the identification of novel inhibitors. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, Chem Rev 96:555-600, 1996; Kenan et al., Exploring molecular diversity with combinatorial shape libraries, Trends Biochem Sci 19:57-64, 1994; Janda, Tagged versus untagged libraries: methods for the generation and screening of combinatorial chemical libraries, Proc Natl Acad Sci USA. 91:10779-85, 1994; Lebl et al., One-bead-one-structure combinatorial libraries, Biopolymers 37:177-98, 1995; Eichler et al., Peptide, peptidomimetic, and organic synthetic combinatorial libraries, Med Res Rev. 15:481-96, 1995; Chabala, Solid-phase combinatorial chemistry and novel tagging methods for identifying leads, Curr Opin Biotechnol. 6:632-9, 1995; Dolle, Discovery of enzyme inhibitors through combinatorial chemistry, Mol Divers. 2:223-36, 1997; Fauchere et al., Peptide and nonpeptide lead discovery using robotically synthesized soluble libraries, Can J Physiol Pharmacol. 75:683-9, 1997; Eichler et al., Generation and utilization of synthetic combinatorial libraries, Mol Med Today 1:174-80, 1995; and Kay et al., Identification of enzyme inhibitors from phage-displayed combinatorial peptide libraries, Comb Chem High Throughput Screen 4:535-43, 2001.

Such combinatorial chemical libraries include, but are not limited to, peptide libraries (see, e.g., U.S. Pat. No. 5,010,175, Furka, Int. J. Pept. Prot. Res., 37:487-493 (1991) and Houghton, et al., Nature, 354:84-88 1991). Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., Proc. Nat. Acad. Sci. USA, 90:6909-6913 1993); vinylogous polypeptides (Hagihara, et al., J. Amer. Chem. Soc. 114:6568 1992); nonpeptidal peptidomimetics with .beta.-D-glucose scaffolding (Hirschmann, et al., J. Amer. Chem. Soc., 114:9217-9218 1992);

analogous organic syntheses of small compound libraries (Chen, et al., J. Amer. Chem. Soc., 116:2661 1994); oligocarbamates (Cho, et al., Science, 261:1303 1993); and/or peptidyl phosphonates (Campbell, et al., J. Org. Chem. 59:658 1994); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., Nature Biotechnology, 14(3):309-314 (1996) and PCT/US96/10287); carbohydrate libraries (see, e.g., Liang, et al., Science, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

XVI.D. Measuring Enzymatic and Binding Reactions During Screening Assays

Techniques for measuring the progression of enzymatic and binding reactions in multicontainer carriers are known in the art and include, but are not limited to, the following.

Spectrophotometric and spectrofluorometric assays are well known in the art. Examples of such assays include the use of colorimetric assays for the detection of peroxides, as disclosed in Example 1(b) and Gordon, A. J. and Ford, R. A., *The Chemist's Companion: A Handbook Of Practical Data, Techniques, And References*, John Wiley and Sons, N.Y., 1972, Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., *Spectrophotometry and Spectrofluorometry: A Practical Approach*, pp. 91-114, IRL Press Ltd. (1987); and Bell, *Spectroscopy In Biochemistry*, Vol. I, pp. 155-194, CRC Press (1981).

In spectrofluorometric methods, enzymes are exposed to substrates that change their intrinsic fluorescence when processed by the target enzyme. Typically, the substrate is non-fluorescent and converted to a fluorophore through one or more reactions. As a non-limiting example, SMase activity can be detected using the Amplex® Red reagent (Molecular Probes, Eugene, Oreg.). In order to measure sphingomyelinase activity using Amplex Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a eview, see Owickiet al., Application of Fluorescence Polarization Assays in High-Throughput Screening, Genetic Engineering News, 17:27, 1997.

FP is particularly desirable since its readout is independent of the emission intensity (Checovich, W. J., et al., Nature 375:254-256, 1995; Dandliker, W. B., et al., Methods in Enzymology 74:3-28, 1981) and is thus insensitive to the presence of colored compounds that quench fluorescence emission. FP and FRET (see below) are well-suited for identifying compounds that block interactions between receptors and their ligands. See, for example, Parker et al., Development of high throughput screening assays using fluorescence polarization: nuclear receptor-ligand-binding and kinase/phosphatase assays, J Biomol Screen 5:77-88, 2000.

Exemplary normal-and-polarized fluorescence readers include the POLARION fluorescence polarization system (Tecan AG, Hombrechtikon, Switzerland). General multiwell plate readers for other assays are available, such as the VERSAMAX reader and the SPECTRAMAX multiwell plate spectrophotometer (both from Molecular Devices).

Fluorescence resonance energy transfer (FRET) is another useful assay for detecting interaction and has been described previously. See, e.g., Heim et al., Curr. Biol. 6:178-182, 1996; Mitra et al., Gene 173:13-17 1996; and Selvin et al., Meth. Enzymol. 246:300-345, 1995. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., J. Lipid Res. 38:2365-2373 (1997); Kahl et al., Anal. Biochem. 243:282-283 (1996); Undenfriend et al., Anal. Biochem. 161:494-500 (1987)). See also U.S. Pat. Nos. 4,626,513 and 4,568,649, and European Patent No. 0,154,734. An exemplary commercially available system uses FLASHPLATE scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., Anal. Biochem. 257:112-119, 1998).

XVI.E. Screening for Novel Antibiotics

As bacteria and other pathogens acquire resistance to known antibiotics, there is an ongoing interest in identifying novel antibiotics. See, e.g., Powell W A, Catranis C M, Maynard C A. Synthetic antimicrobial peptide design. Mol Plant Microbe Interact 1995 September-October; 8(5):792-4. Minicells can be used to assay, identify and purify novel antibiotics to eubacteria. By way of non-limiting example, a minicell that comprises a detectable compound can be contacted with a candidate antibiotic to see if the minicell is lysed by a candidate compound, which would release the detectable compound from the interior of the minicell into solution, this producing a signal that indicates that the candidate antibiotic is effective at lysing bacteria. In such assays, the detectable compound is such that it produces less or more of the same signal, or a different signal, inside the minicell as compared to in solution post-lysis. By way of non-limiting example, the minicell could comprise a fluorescent compounds that, when contacted with a second fluorescent compound in solution, produces FRET.

XVI. F. Reverse Screening

In one version of minicell display, the invention provides methods for screening libraries of minicells in which each minicell comprises an expression element that encodes a few, preferably one, membrane proteins in order to identify a membrane protein that interacts with a preselected compound. By way of non-limiting example, sequences encoding membrane proteins, fusion proteins, or cytoplasmic proteins are cloned into an expression vector, either by "shotgun" cloning or by directed cloning, e.g., by screening or selecting for cDNA clones, or by PCR amplification of DNA fragments, that encode a protein using one or more oligonucleotides encoding a highly conserved region of a protein family. For a non-limiting example of such techniques, see Krautwurst, D., et al. 1998. Identification of ligands for olfactory receptors by functional expression of a receptor library. Cell 95:917-926. By way of non-limiting example, a minicell expressing a receptor binds a preselected ligand, which may be a drug. Various assays for receptor binding, enzymatic activity, and channeling events are known in the art and may include detectable compounds; in the case of binding assays, competition assays may also be used (Masimirembwa, C. M., et al. 2001. In vitro high throughput screening of compounds for favorable metabolic properties in drug discovery. Comb. Chem. High Throughput Screen. 4:245-263; Mattheakis, L. C., and A. Saychenko. 2001. Assay technologies for screening ion channel targets. Curr. Opin. Drug Discov. Devel. 4:124-134; Numann, R., and P. A. Negulescu. 2001. High-throughput screening strategies for cardiac ion channels. Trends Cardiovasc. Med. 11:54-59; Le Poul, E., et al. 2002. Adaptation of aequorin functional assay to high throughput screening. J. Biomol. Screen. 7:57-65; and Graham, D. L., et al. 2001. Application of beta-galactosidase enzyme complementation technology as a high throughput screening format for antagonists of the epidermal growth factor receptor. J. Biomol. Screen. 6:401-411).

Once a minicell has been identified by an assay and isolated, DNA is prepared from the minicell. The cloned DNA present in the minicell encodes the receptor displayed by the minicell. Having been cloned, the receptor is used as a therapeutic target. For example, the receptor is produced via recombinant DNA expression and used in minicell-based or other assays to identify and characterize known and novel compounds that are ligands, antagonists and/or agonists of the cloned receptor. The ligands, antagonists and agonists may be used as lead compounds and/or drugs to treat diseases in which the receptor plays a role. In particular, when the preselected ligand is a drug, diseases for which that drug is therapeutic are expected to be treated using the novel ligands, antagonists and agonists, or drugs and prodrugs developed therefrom.

Preparations of minicells that express and secrete secretes a soluble protein can be prepared in order to identify ligands, including but not limited to small molecules, that interact with the soluble protein. Soluble proteins include, but are not limited to, known secreted or proteolytically cleaved proteins and peptides, hormones and cytokines. In this format, minicells are placed in, or adhered to, the wells of a microtiter multiwell plate. A different compound or group of compounds is placed in each well, along with any reagents necessary to generate or squelch a signal corresponding to a change in the soluble protein produced by the minicell. Such changes include, by way of non-limiting example, conformational changes in the protein that may occur as a result of binding of a ligand or otherwise. A well that generates the appropriate signal contains a compound that causes a change in the soluble protein.

It is also possible to carry out procedures such as the one described in the immediately preceding paragraph "in reverse." In this format, a known ligand, which may be a drug, is used to identify soluble proteins that bind to the ligand/drug. Libraries of minicells wherein each minicell secretes a different soluble protein are prepared, and each type of minicell is placed into, or adhered to the wall of, a well of a microtiter plate, along with reagents for generating a signal when the ligand/drug binds to a soluble protein. Minicells that generate the appropriate signal comprise a cloned DNA that encodes a soluble protein that interacts with the known ligand/drug. Once cloned, the soluble protein is prepared and used as a therapeutic target in order to identify known or novel compounds that bind thereto. When the preselected ligand is a drug, diseases for which that drug is therapeutic are expected to be treated using the known and novel compounds so identified, or using drugs and prodrugs developed from such compounds.

Minicells expressing known membrane and soluble proteins can also be used to help characterize lead compounds and accelerate the generation of drugs therefrom. In particular, such studies may be used identify potentially detrimental interactions that might occur upon in vivo administration, e.g., ADME/Tox screening (Ekins, S., et al. 2002. In silico ADME/Tox: the state of the art. J. Mol. Graph. Model. 20:305-309; and Li, A., et al. 2002. Early ADME/Tox studies and in silico screening. Drug Discov. Today 7:25-27).

By way of non-limiting example, a human receptor that is known to be important for the normal functioning of a cell may be expressed in minicells, and various chemical derivatives of a lead compound can be tested to ensure that they do not bind to the receptor, as such binding would be expected to have adverse effects in vivo. As another example, an enzyme that degrades a drug, such as a cytochrome P450, is expressed in minicells and used to examine the susceptibility of a candidate drug to such degradation. The cytochrome P450 family of enzymes is primarily responsible for the metabolism of xenobiotics such as drugs, carcinogens and environmental chemicals, as well as several classes of endobiotics such as steroids and prostaglandins. Exemplary P450 cytochromes involved in drug degradation include, but are not limited to, CYP2D6 (cytochrome P4502D6, also known as debrisoquine hydroxylase), CYP1A1, CYP1A2, CYP2A6, CYP2B6, CYP2C9, CYP2C18, CYP2C19, CYP2D6, CYP2E1, CYP3A4 and CYP3A5.

XVI.G. Molecular Variants

In one aspect of the invention, minicells are used in methods of screening to identify agents that improve, enhance, or decrease the interaction of a protein with another compound. These methods include, by way of non-limiting example, modification of protein targets through directed or random mutagenic approaches to identify critical interactions between a wild-type protein target and a specific drug molecule. Information obtained from studies of mutant proteins is used to specifically produce or modify a therapeutic agent to interact more specifically and/or effectively with the wild-type protein target, thus increasing the therapeutic efficacy of the parental drug and/or decreasing non-specific, potentially deleterious interactions. See, for example, Lietha, D., et al. 2001. Crystal structures of NK1-heparin complexes reveal the basis for NK1 activity and enable engineering of potent agonists of the MET receptor. EMBO J. 20:5543-5555; and Chen, Y. Z., et al. Can an optimization/scoring procedure in ligand-protein docking be employed to probe drug-resistant mutations in proteins? J. Mol. Graph. Model. 19:560-570; Zhao, H. and F. H. Arnold. Combinatorial protein design: Strategies for screening protein libraries. Current Opinion in Structural Biology 7:480-485 (1997); and Carrupt P A, el Tayar N, Karlen A, Testa B. Molecular electrostatic potentials for characterizing drug-biosystem interactions. Methods Enzymol. 1991; 203:638-77. Martin Y C. Computer-assisted rational drug design. Methods Enzymol. 1991; 203:587-613.

By way of non-limiting example, information obtained using the methods of the invention may be in conjunction with x-ray crystallographic structural determinations to characterize receptor:ligand interactions (Muller, G. 2000. Towards 3D structures of G protein-coupled receptors: a multidisciplinary approach. Curr. Med. Chem. 7:861-888). By way of non-limiting example, minicells may be used to display the family of molecular variants to characterize the specific mutagenic changes on the functional properties of the protein.

Studies of variant proteins can also be used to modify drugs to fit natural variants of proteins, especially those associated with pathogens. Pathogens such as viruses, including retroviruses such as HIV, may acquire mutations that change a site where a drug acts, thereby rendering the pathogen immune to the drug. Studies of variant proteins can be used to quickly produce derivatives of a drug that are active against a variant protein. See, for example, Varghese J N, Smith P W, Sollis S L, Blick T J, Sahasrabudhe A, McKimm-Breschkin J L, Colman P M. Drug design against a shifting target: a structural basis for resistance to inhibitors in a variant of influenza virus neuraminidase. Structure 1998 Jun. 15; 6(6):735-46; and Baldwin E T, Bhat T N, Liu B, Pattabiraman N, Erickson J W. Structural basis of drug resistance for the V82A mutant of HIV-1 proteinase. 78: Nat Struct Biol 1995 March; 2(3):244-9.

XVI.H. Directed Evolution

The minicells and methods described herein can be used in directed evolution. Unlike natural variation, directed evolution generates new protein variants in vitro (see, e.g., Arnold, F. H. and A. A. Violkov. Directed Evolution of Biocatalysts. Curr Op Chem Biol 1999. 3:54-59). Amino acid substitutions can be introduced into a protein of interest by mutating the gene encoding the protein. Mutations are introduced by, e.g., replicating DNA in mutator strains, by chemical mutagenesis or radiation-induced mutagenesis (Drake, J. W., The Molecular Basis of Mutation, Holden-Day, San Francisco, 1970). Other methods include error-prone PCR and "domain shuffling" (Moore, G. L. and C. D. Maranas. Modeling DNA Mutation and Recombination for Directed Evolution Experiments. J. Ther. Biol. 2000. 205:483-503). In the latter method, different regions of members of the same gene family are recombined so that the inherent variability of members of the family is used to produce novel "isoforms" of genes.

A group of variants is screened to select for those variants which have the desired activity. The activity of the initial variants that are so isolated may be inadequate for a given application, but the process can be repeated using these initial members to generate a second group of variants, or reiterated as many times as is necessary to produce one or more variants having the desired activity or characteristics.

XVI.I. Isolation and Characterization of Components of Signal Tranduction Pathways In one version of minicell display, the invention provides methods for screening libraries of minicells, in which each minicell comprises a preselected component of a signal transduction pathway, in order to identify soluble and membrane proteins that interact with the preselected component. By way of non-limiting example, a plurality of minicells, each of which displays the same G-protein-coupled receptor (GPCR), is used to prepare a minicell library in which a different G-protein encoding sequence is present and expressed in each minicell. Minicells comprising a G-protein that interacts with the GPCR are identified, e.g., via transactivation assays described in Example 18. Once a minicell has been identified by an assay and isolated, DNA is prepared from the minicell. The cloned DNA present in the minicell encodes a G-protein that interacts with the GPCR of the displayed by the minicells of the library. Having been cloned, the G-protein is used as a therapeutic target that can be used in screening assays to identify novel lead compounds and drugs that interfere or alter the activity of the GPCR. In particular, when the GPCR of the minicell library is known to be a therapeutic target for a specific disease, it is expected that compounds that interfere or alter the activity of a G-protein that interacts with the GPCR will be or lead to therapeutics for that specific disease.

In addition to G-protein signal transduction pathways, other non-limiting examples of signal transduction pathways include the MAPK pathway, the SAPK pathway, the p38 pathway and/or the ceramide-mediated stress response pathway. See Zhang, W., and L. E. Samelson. 2000. The role of membrane-associated adaptors in T cell receptor signalling. Semin. Immunol. 12:35-41; Liebmann, C. 2001. Regulation of MAP kinase activity by peptide receptor signalling pathway: paradigms of multiplicity. Cell Signal. 13:777-785; Lee, Jr., J. T., and J. A. McCubrey. 2002. The Raf/MEK/ERK signal transduction cascade as a target for chemotherapeutic intervention in leukemia. Leukemia. 16:486-507; Tibbles, L. A., and J. R. Woodgett. 1999. The stress-activated protein kinase pathways. Cell Mol. Life. Sci. 55:1230-1254; Rao, K. M. 2001. MAP kinase activation of macrophages. J. Leukoc. Biol. 69:3-10; Pelech, S. L., and D. L. Charest. 1995. MAP kinase-dependent pathways in cell cycle control. Prog. Cell Cycle Res. 1:33-52; Lee, S. H., et al. 2001. BetaPix-enhanced p38 activation by Cdc42/Rac/PAK/MKK3/6-mediated pathway. Implication in the regulation of membrane ruffling. J. Biol. Chem. 276:25066-25072; Ono, K., et al. 2000. The p38 signal transduction pathway Activation and function. Cellular Signalling 12:1-13; You, A. 2001. Differentiation, apoptosis, and function of human immature and mature myeloid cells: intracellular signaling mechanism. Int. J. Hematol. 73:438-452; Johnson, D. I. 1999. Cdc42: An essential Rho-type GTPase controlling eukaryotic cell polarity. Microbiol. Mol. Biol. Rev. 63:54-105; Williams, J. A. 2001. Intracellular signaling mechanisms activated by cholecystokinin-regulating synthesis and secretion of digestive enzymes in pancreatic acinar cells. Annu. Rev. Physiol. 63:77-97; Mathias, S., et al. 1998. Signal transduction of stress via ceramide. Biocehm J. 335:465-480; and Hannun, Y. A., et al 2000. Ceramide in the eukaryotic stress response. Trends Cell Biol. 10:73-80.

XVII. Determining the Structures of Membrane Proteins

Three-dimensional (3D) structures of proteins may be used for drug discovery. However, GPCRs and other membrane proteins present challenging problems for 3D structure determination. Muller, Towards 3D structures of G protein-coupled receptors: a multidisciplinary approach. (Review), Curr Med Chem 2000 pp. 861-88; Levy et al., Two-dimensional crystallization on lipid layer: A successful approach for membrane proteins, J Struct Biol 1999 127, 44-52. Although the three-dimensional structures of hundreds of different folds of globular proteins have been determined, fewer than 20 different integral membrane protein structures have been determined. There are many reasons for this. Extracting membrane proteins from the membrane can easily disrupt their native structure, and membrane proteins are notoriously difficult to crystallize.

Some membrane proteins readily form two-dimensional crystals in membranes and can be used for structure determination using electron diffraction spectroscopy (ED) instead of x-ray crystallography. This is the technique that was used to determine the structure of bacteriorhodopsin (see below).

Nuclear magnetic resonance (NMR) is an alternative method for determining membrane protein structure, but most membrane proteins are too large for high-resolution NMR at the present state of the art. Furthermore, membrane proteins require special conditions for NMR, e.g. deuterated lipids must be used to avoid confusing the signal of the protein protons with the noise of membrane lipid protons.

Membrane protein for which structures have been determined include photosynthetic reaction center, porin, porin OmpF, plant light-harvesting complex (chlorophyll a-b binding protein), bacterial light-harvesting complex, cytochrome c oxidase, glycophorin A, the Sec A translocation ATPase of *Bacillus subtilis*, and a bacterial potassium channel. For details, see: Weinkauf et al., (2001): Conformational stabilization and crystallization of the Sec A translocation ATPase from *Bacillus subtilis*. Acta Crystallogr D Biol Crystallogr 57:559-565; Cowan et al., (1992): Crystal structures explain functional properties of two *E. coli* porins. Nature 358:727-33; Deisenhofer et al., (1984): X-ray structure analysis of a membrane protein complex. Electron density map at 3 A resolution and a model of the chromophores of the photosynthetic reaction center from *Rhodopseudomonas viridis*. J Mol Biol 180:385-98; Deisenhofer et al., (1985): Structure of the protein subunits in the photosynthetic reaction centre of *Rhodopseudomonas viridis* at 3 Angstroms resolution. Nature 318:618; Doyle et al., (1998): The structure of the potassium channel: molecular basis of K+ conduction and selectivity. Science 280:69-77; Henderson et al., (1990): Model for the structure of bacteriorhodopsin based on high-resolution electron cryo-microscopy. J Mol Biol 213:899-929; Iwata et al., (1998): Complete structure of the 11-subunit bovine mitochondrial cytochrome bc1 complex. Science 281: 64-71; Koepke et al., (1996): The crystal structure of the light-harvesting complex II (B800-850) from *Rhodospirillum molischianum*. Structure 4:581-97; Kuhlbrandt et al., (1994): Atomic model of plant light-harvesting complex by electron crystallography. Nature 367:614-21; Lemmon et al., (1992): Sequence specificity in the dimerization of transmembrane alpha-helices. Biochemistry 31:12719-25; MacKenzie et al., (1997): A transmembrane helix dimer: structure and implications. Science 276:131-3; McDermott et al., (1995): Crystal structure of an integral membrane light-harvesting complex from photosynthetic bacteria, Nature 374:517-21; Michel (1982): Three-dimensional crystals of a membrane protein complex. The photosynthetic reaction centre from *Rhodopseudomonas viridis*. J Mol Biol 158:567-72; Tsukihara et al., (1996): The whole structure of the 13-subunit oxidized cytochrome c oxidase at 2.8 A. Science 272:1136-44; and Weiss et al., (1991): The structure of porin from *Rhodobacter capsulatus* at 1.8 A resolution. FEBS Lett 280: 379-82. Table 5, which is based upon Preusch et al. (1998) as revised by White & Wimley (1999), lists membrane proteins whose crystallographic structures have been determined.

TABLE 5

Structural Data Regarding Membrane Proteins

| PROTEIN | REFERENCES |
|---|---|
| MONOTOPIC MEMBRANE PROTEINS | |
| Portaglandin H2 synthase-1. Sheep. 3.5 Å | Picot et al. (1994) |
| Cyclooxygenase-2. *Mus Musculus*. 3.0 Å | Kurumbail et al. (1996) |
| Squalene-hopene cyclase. *Alicyclobacillus acidocaldarius*. 2.0 Å | Wendt et al. (1999) |
| TRANSMEMBRANE PROTEINS Bacterial Rhodopsins (*Halobacterium salinarium*) Bacteriorhodopsin (BR) | |
| 2D xtals. EM. 3.5 Å | Grigrorieff et al. (1996) |
| 2D xtals. EM. 3.0 Å | Kimura et al. (1997) |
| 3D xtals. X-ray. 2.5 Å | Pebay-Peyroula et al. (1997) |
| 3D xtals. X-ray. 1.9 Å | Belhrhali et al. (1999) |
| 3D xtals. X-ray 2.1 Å K intermediate | Edman et al. (1999) |
| 3D xtals. X-ray. 2.3 Å | Luecke et al. (1998) |
| 3D xtals. X-ray. 1.55 Å | Luecke et al. (1999) |
| 3D xtals. X-ray. D96N mutant (BR) 1.80 Å. | Luecke et al. (1999) |
| 3D xtals. X-ray. D96N mutant (M) 2.00 Å | |
| 3D xtals. X-ray. 2.9 Å | Essen et al. (1998) |
| Halorhodopsin (HR) | |
| 3D xtals. Xray. 1.8 Å | Kolbe et al. (2000) |
| G PROTEIN-COUPLED RECEPTORS | |
| Rhodopsin. Bovine Rod Outer Segment. 2.8 Å | Palczewski et al. (2000) |
| Photosynthetic Reaction Centers | |
| *Rhodopseudomonas virdis*. 2.3 Å | Deisenhofer et al. (1985) |
| *Rhodobacter sphaeroides*. 3.0 Å | Yeates et al. (1987) |
| *Rhodobacter sphaeroides*. 3.1 Å | Chang et al. (1991) |
| Light Harvesting Complexes | |
| *Rhodopseudomonas acidophila*. 2.5 Å | McDermott et al. (1995) |
| *Rhodospirillum molischianum*. 2.4 Å | Koepke et al. (1996) |
| Photosystems | |
| Photosystem I. *Synechococcus elongates* 4.0 Å | Schubert et al. (1997) |
| Photosystem II. *Synechocoocus elongates* 3.8 Å | Zouni et al. (2001) |
| Beta-Barrel Membrane Proteins-Multimeric (Porins and Relatives) | |
| Porin. *Rhodobacter capsulatus*. 1.8 Å | Weiss & Schulz (1992) |
| Porin. *Rhodopeudomonas blastica* 1.96 Å | Kreutsch et al. (1994) |
| OmpF. *E. coli*. 2.4 Å | Cowan et al. (1992) |
| PhoE. *E. coli*. 3.0 Å | Cowan et al. (1992) |
| Maltoporin. *Salmonella typhimurium*. 2.4 Å | Meyer et al. (1997) |
| Maltoporin. *E. coli* 3.1 Å | Schirmer et al. (1995) |

TABLE 5-continued

Structural Data Regarding Membrane Proteins

| PROTEIN | REFERENCES |
|---|---|
| Beta-Barrel Membrane Proteins-Monomeric/Dimeric | |
| TolC outer membrane protein. E. coli 2.1 Å Protein is a trimer, each contributing 4 strands to a single barrel. | Koronakis et al. (2000) |
| OmpA. E. coli. 2.5 Å | Pautsch & Schulz (1998) |
| OmpA E. coli. By NMR, in DPC micelles | Arora et al. (2001) |
| OmpX. E. coli. 1.9 Å | Vogt & Schulz (1990) |
| OMPLA (outer membrane phospholipase A) E. coli. 2.1 A. monomer (1QD5) and dimer (1QD6) | Snijder et al. (1999) |
| FhuA. E. coli. 2.5 Å | Ferguson et al. (1998); Lambert et al., 1999 |
| FhuA + ferrichrome-iron. E. coli. 2.7 Å | Buchanan et al. (1999) |
| FepA. E. coli. 2.4 Å | Ferguson et al. (1999) |
| Glycophorin A.humanm. | MacKenzie et al. (1997) |
| Non-constitutive Toxins, etc. | |
| Alpha-hemolysin. Staphylococcus aureus. 1.9 Å | Song et al. (1996) |
| LukF. Staphylococcus aureus. 1.9 Å | Olson et al. (1999) |
| Ion Channels | |
| KcsA Potassium, H$^+$ gated. Streptomyces lividans. 3.2 Å | Doyle et al. (1998) |
| MscL Mechanosensitive. Mycobacterium tuberculosis. 3.5 Å | Chang et al. (1998) |
| Other Channels | |
| AQP1 - aquaporin water channel. Red blood cell. Electron crystallography in membrane plane. 3.8 Å | Murata et al. (2000) |
| AQP1 - In vitreous ice by electron microscopy. 3.7 Å | Ren et al. (2000) |
| GipF - glycerol facilitator channel. E. coli. 2.2 Å | Fu et al. (2000) |
| P-type ATPase | |
| Calcium ATPase. Sarcoplasmic reticulum. Rabbit. 2.6 Å | Toyoshima et al. (2000) |
| Respiratory Proteins | |
| Fumerate Reductase Complex. Escherichia coli. 3.3 Å | Iverson et al. (1999) |
| Fumerate Reductase Complex. Wolinella succinogenes 2.2 Å | Lancaster et al. (1999) |
| ATP synthase (F$_1$c$_{10}$). S. cerevisiae. 3.9 Å. X-ray structure is a C alpha model derived from composite of 1BMF, 1A91 & 1AQT | Stock et al. (1999) |
| Cytochrome C Oxidases | |
| aa$_3$bovine heart mitochondria. 2.8 Å | Tsukihara et al. (1996) |
| aa$_3$ Paracoccus denitrificans. 2.8 Å | Iwata et al. (1995) |
| ba$_3$ from T. thermophilus. 2.4 Å | Soulimane et al. (2000) |
| Cytochrome bc$_1$ Complexes | |
| Bovine Heart Mitochondria (5 subunits). 2.9 Å | Xia et al. (1997) |
| Chicken Heart Mitochondria. 3.16 Å | Zhang et al. (1998) |
| Bovine Heart Mitochondria (11 subunits). 2.8-3.0 Å. | Iwata et al. (1998) |
| S. cerevisiae (yeast, 9 subunits). 2.3 Å | Hunte et al. (2000) |

Citations for Table 5

Arora et al., (2001). Structure of outer membrane protein A transmembrane domain by NMR spectroscopy. Nature Structural Biol. 8, 334-338.

Belrhali et al., (1999). Protein, lipid, and water organization in bacteriorhodopsin crystals: A molecular view of the purple membrane at 1.9 Å resolution. Structure 7:909-917.

Buchanan et al., (1999). Crystal Structure of the outer membrane active transporter FepA from Escherichia coli. Nature Struc. Biol. 6:56-63.

Chang et al., (1991). Structure of the membrane-bound protein photosynthetic reaction center from Rhodobacter sphaeroides. Biochemistry 30, 5352-5360.

Chang et al., (1998). Structure of the MscL homolog from Mycobacterium tuberculosis: A gated mechanosensitive ion channel. Science 282, 2220-2226.

Cowan et al., (1992). Crystal structures explain functional properties of two E. coli porins. Nature (London) 358, 727-733.

Deisenhofer et al., (1985). Structure of the protein subunits in the photosynthetic reaction centre of Rhodospeudomonas viridis at 3 Å resolution. Nature (London) 318, 618-624.

Doyle et al., (1998). The structure of the potassium channel: Molecular basis of K+ conduction and selectivity. Science 280, 69-77.

Edman et al., (1999). High-resolution X-ray structure of an early intermediate in the bacteriorhodopsin photocycle. Nature (London) 401, 822-826.

Essen et al., (1998). Lipid patches in membrane protein oligomers: crystal structure of the bacteriorhodopsin-lipid complex. Proc Natl Acad Sci USA 95:11673-11678.

Ferguson et al., (1998). Siderophore-mediated iron transport: Crystal structure of FhuA with bound lipopolysaccharide. Science 282, 2215-2220.

Fu et al., (2000). Structure of a glycerol-conducting channel and the basis for its selectivity. Science 290, 481-486.

Grigorieff et al., (1996). Electron-crystallographic refinement of the structure of bacteriorhodopsin. J. Mol. Biol. 259, 393-421.

Hunte et al., (2000). Structure at 2.3 Å resolution of cytochrome bc1 complex from the yeast Saccharomyces cerevisiae co-crystallized with an antibody Fv fragment. Structure 8:669-684.

Iverson et al., (1999). Structure of the Escherichia coli fumerate reductase respiratory complex. Science 284, 1961-1966.

Iwata et al., (1998). Complete structure of the 11-subunit bovine mitochondrial cytochrome bc1 complex. Science 281, 64-71.

Iwata et al., (1995). Structure at 2.8 Å resolution of cytochrome c oxidase from Paracoccusdenitrificans. Nature (London)376, 660-669.

Kimura et al., (1997). Surface of bacteriorhodopsin revealed by high-resolution electron crystallography. Nature (London) 389, 206-211.

Koepke et al., (1996). The crystal structure of the light-harvesting complex II (B800-850) from Rhodospirillum molischianum. Structure 4, 581-597.

Kolbe et al., (2000). Structure of the light-driven chloride pump halorhodopsin at 1.8 Å. Science 288, 1390-1396.

Koronakis et al., (2000). Crystal structure of the bacterial membrane protein TolC central to multidrug efflux and protein export. Nature (London) 405, 914-919.

Kurumbail et al., (1996). Structural basis for selective inhibition of cyclooxygenase-2 by anti-inflammatory agents. Nature (London) 384, 644-648.

Kreusch et al., (1994). Structure of the membrane channel porin from Rhodopseudomonasblastica at 2.0 Å resolution. Protein Sci. 3, 58-63.

Lambert et al. (1999). An 8-A projected structure of FhuA, A "ligand-gated" channel of the Escherichia coli outer membrane, J Struct Biol 126, 145-55

Lancaster et al., (1999). Structure of fumarate reductase from Wolinella succinogenes at 2.2 Å resolution. Nature 402, 377-385.

Luecke, H., Richter, H. T. & Lanyi, J. K. (1998). Proton transfer pathways in bacteriorhodopsin at 2.3 Angstrom resolution. Science 280, 1934-1937.

Luecke et al., (1999). Structure of bacteriorhodopsin at 1.55 angstrom resolution. J. Mol. Biol. 291, 899-911.

Luecke et al., (1999). Structural changes in bacteriorhodopsin during ion transport at 2 angstrom resolution. Science 286, 255-260.

MacKenzie et al. (1997) A transmembrane helix dimer; structure and implications. Science 276, 131-133.

McDermott et al., (1995). Crystal structure of an integral membrane light-harvesting complex from photosynthetic bacteria. Nature (London) 374, 517-521.

Meyer et al., (1997). Structure of maltoporin from *Salmonella typhimurium* ligated with a nitrophenyl-maltotrioside. J. Mol. Biol. 266, 761-775.

Murata et al., (2000). Structural determinants of water permeation through aquaporin-1. Nature 407, 599-605.

Olson et al., (1999). Crystal structure of Staphylococcal LukF delineates conformational changes accompanying formation of a transmembrane channel. Nature Struc. Biol. 6, 134-140.

Palczewski et al., (2000). Crystal structure of rhodopsin: A G protein-coupled receptor. Science 289, 739-745.

Pautsch and Schulz, (1998). Structure of the outer membrane protein A transmembrane domain. Nature Struct. Biol. 5, 1013-1017.

Pebay-Peyroula et al., (1997). X-ray structure of bacteriorhodopsin at 2.5 Å from microcrystals grown in lipidic cubic phases. Science 277, 1676-1681.

Picot et al., (1994). The x-ray crystal structure of the membrane protein prostaglandin H2 synthase-1. Nature (London) 367, 243-249.

Preusch et al., (1998). Progress away from 'no crystals, no grant' Nature Struct. Biol. 5, 12-14.

Ren et al., (2001). Visualization of a water-selective pore by electron crystallography in vitreous ice. Proc. Natl. Acad. Sci. USA 98, 1398-1403.

Schirmer et al., (1995). Structural basis for sugar translocation through maltoporin channels at 3.1 A resolution. Science 267, 512-4.

Schubert et al., (1997). Photosystem I of *Synechococcus elongatus* at 4 Å resolution: Comprehensive structure analysis. J. Mol. Biol. 272, 741-769.

Snijder et al., (1999). Structural evidence for dimerization-regulated activation of an integral membrane phospholipase. Nature (London) 401, 717-721.

Song et al., (1996). Structure of staphylococcal a-hemolysin, a heptameric transmembrane pore. Science 274, 1859-1866.

Soulimane et al., (2000). Structure and mechanism of the aberrant ba(3)-cytochrome c oxidase from *Thermus thermophilus*. EMBO J. 19, 1766-1776.

Stock et al., (1999). Molecular architecture of rotary motor in ATP synthase. Science 286, 1700-1705.

Toyoshima et al., (2000). Crystal structure of the calcium pump of sarcoplasmic reticulum at 2.6 Å resolution. Nature 405, 647-655.

Tsukihara et al., (1996). The whole structure of the 13-subunit oxidized cytochrome c oxidase at 2.8 Å. Science 272, 1136-1144.

Vogt and Schulz (1999). The structure of the outer membrane protein OmpX from *Escherichia coli* reveals possible mechanisms of virulence. Structure Fold. Des. 7, 1301-1309.

Weiss and Schulz (1992). Structure of porin refined at 1.8 Å resolution. J. Mol. Biol. 227, 493-509.

Wendt et al., (1999). The structure of the membrane protein squalene-hopene cyclase at 2.0 Å resolution. J. Mol. Biol. 286:175-187.

White and Wimley (1999). Membrane protein folding and stability: Physical principles. Annu. Rev. Biophys. Biomol. Struct. 28:319-365.

Xia et al., (1997). Crystal structure of the cytochrome bc1 complex from bovine heart mitochondria. Science 277, 60-66.

Yeates et al., (1987). Structure of the reaction center from *Rhodobacter sphaeroides* R-26: Membrane-protein interactions. Proc. Natl. Acad. Sci. USA 84, 6438-6442.

Zhang et al., (1998). Electron transfer by domain movement in cytochrome bc1. Nature (London) 392, 677-684.

Zouni et al., (2001). Crystal structure of photosystem II from *Synechococcus elongatus* at 3.8 Å resolution. Nature (London) 409:739-743.

XVIII. Biosensors and Environmental Applications

XVIII.A. Minicell-Based Biosensors

The present invention is directed to a device that comprises a sensor adapted to detect one or more specific health and/or nutrition markers in a subject or in the environment. The device may also signal the caretaker, the subject, or an actuator of the occurrence. The sensor comprises a biosensor. As used herein, the term "biosensor" is defined as a component comprising one or more binding moities being adapted to detect a ligand found in one or more target pathogenic microorganisms or related biomolecules.

Generally, biosensors function by providing a means of specifically binding, and therefore detecting, a target biologically active analyte. In this way, the biosensor is highly selective, even when presented with a mixture of many chemical and biological entities. Often the target biological analyte is a minor component of a complex mixture comprising a multiplicity of biological and other components. Thus, in many biosensor applications, detection of target analytes occurs in the parts-per-billion, parts-per-trillion, or even lower ranges levels.

XVIII.A.1. Minicell-Based Biosensor Design

The biosensor of the present invention may comprise a bio-recognition element, or molecular recognition element, that provides the highly specific binding or detection selectivity for a particular analyte. In a biosensor of the invention, the bio-recognition element, or system, is a minicell displaying an enzyme or sequence of enzymes; an antibody or antibody derivative; a membrane receptor protein; or the like, and generally functions to interact specifically with a target biological analyte. The bio-recognition element is responsible for the selective recognition of the analyte and the physicochemical signal that provides the basis for the output signal. The expressed protein or molecule does not need to be a naturally occurring membrane bound protein but could be a soluble protein or small molecule thethered to the minicell by, for example, a transmembrane domain of another protein such as the EGFR or ToxR.

Biosensors may include biocatalytic biosensors, and bioaffinity biosensors. In biocatalytic biosensor embodiments, the bio-recognition element minicell is "biocatalytic," e.g., displays an enzyme. In biocatalytic biosensors, the selective binding sites "turn over" (i.e., can be used again during the detection process), resulting in a significant amplification of the input signal. Biocatalytic sensors such as these are generally useful for real-time, continuous sensing.

Bioaffinity sensors are generally applicable to bacteria, viruses, toxins and other undesirable compounds and include chemoreceptor-based biosensors and/or immunological sensors (i.e., immunosensors). Chemoreceptors are complex biomolecular macroassemblies responsible, in part, for a viable organism's ability to sense chemicals in its environment with high selectivity. Chemoreceptor-based biosensors comprise one or more natural or synthetic chemoreceptors associated with a means to provide a signal (visual, electrical, etc.) of the presence or concentration of a target biological analyte. In certain embodiments, the chemoreceptor may be associated with an electrode (i.e., an electrical transducer) so as to provide a detectable electrical signal. In the biosensors of the invention, minicells displaying a receptor are used in place of chemoreceptors. The minicell has many desired features of a viable cell, and performs similar functions, but is more durable.

On the other hand, the bio-recognition elements of immunosensors are generally antibodies or antibody derivatives. In any case, bioaffinity biosensors are generally irreversible because the receptor sites of the biosensor become saturated when exposed to the target biological analyte. In a biosensor of the invention, an immunosensor may be a minicell displaying an antibody or antibody fragment.

Biocatalytic and bioaffinity biosensor systems are described in more detail in Journal of Chromatography, 510 (1990) 347-354 and in the Kirk-Othmer Encyclopedia of Chemical Technology, 4.sup.th ed. (1992), John Wiley & Sons, NY, the disclosure of which is incorporated by reference herein.

The biosensors of the present invention may detect biologically active analytes related to impending (i.e., future presentation of symptoms is likely) or current human systemic disease states, including, but not limited to, pathogenic bacteria, parasites (e.g., any stage of the life cycle, including eggs or portions thereof, cysts, or mature organisms), viruses, fungi such as *Candida albicans*, antibodies to pathogens, and/or microbially produced toxins. Additionally, the biosensor may target biologically active analytes related to impending or current localized health issues, such as stress proteins (e.g., cytokines) and interleukin 1-alpha that may precede the clinical presentation of skin irritation or inflammation. In preferred embodiments, the biosensor functions as a proactive sensor, detecting and signaling the subject, a caretaker or medical personnel of the impending condition prior to the presentation of clinical symptoms. This allows time to administer prophylactic or remedial treatments to the subject which can significantly reduce, if not prevent, the severity and duration of the symptoms. Further, the sensor, by detecting the presence of a target biological analyte in a sample from the subject, may detect residual contamination on a surface, such as skin or environmental surface, in contact with the biosensor, and provide and appropriate signal.

The physico-chemical signal generated by the bio-recognition element or elements may be communicated visually to the caretaker or medical personnel (i.e., via a color change visible to the human eye). Other embodiments may produce optical signals, which may require other instrumentation to enhance the signal. These include flourescence, bioluminesence, total internal reflectance resonance, surface plasmon resonance, Raman methods and other laser-based methods, such as LED or laser diode sensors. For example, exemplary surface plasmon resonance biosensors are available as IBIS I and IBIS II from XanTec Analysensysteme of Muenster, Germany, which may comprise bioconjugate surfaces as biorecognition elements. Alternatively, the signal may be processed via an associated transducer which, for example, may produce an electrical signal (e.g., current, potential, inductance, or impedance) that may be displayed (e.g., on a readout such as an LED or LCD display) or which triggers an audible or tactile (e.g., vibration) signal or which may trigger an actuator, as described herein. The signal may be qualitative (e.g., indicating the presence of the target biological analyte) or quantitative (i.e., a measurement of the amount or concentration of the target biological analyte). In such embodiments, the transducer may optionally produce an optical, thermal or acoustic signal.

In any case, the signal may also be durable (i.e., stable and readable over a length of time typically at least of the same magnitude as the usage life of the device) or transient (i.e., registering a real-time measurement). Additionally, the signal may be transmitted to a remote indicator site (e.g., via a wire, or transmitter, such as an infrared or rf transmitter) including other locations within or on the device or remote devices. Further, the sensor, or any of its components, may be adapted to detect and/or signal only concentrations of the target biological analyte above a predefined threshold level (e.g., in cases wherein the target biological analyte is normally present in the bodily waste or when the concentration of the analyte is below a known "danger" level).

The target analytes that the biosensors of the present invention are adapted to detect may also be viruses. These may include diarrhea-inducing viruses such as rotavirus, or other viruses such as rhinovirus and human immunodeficiency virus (HIV). An exemplary biosensor adapted to detect HIV is described in U.S. Pat. Nos. 5,830,341 and 5,795,453, referenced above. The disclosure of each of these patents is incorporated by reference herein. Biosensors are adopted to use in different tissues; see, e.g., U.S. Pat. No. 6,342,037; Roe et al. Jan. 29, 2002; Device having fecal component sensor; and using different binding molecules, see, e.g., U.S. Pat. No. 6,329,160; Schneider et al. Dec. 11, 2001; Biosensors.

When minicells are incorporated into a biosensor, they may be immobilized in the biosensor by techniques known in the art such as entrapment, adsorption, crosslinking, encapsulation, covalent attachment, any combination thereof, or the like. Further, the immobilization can be carried out on many different substrates such as known the art. In certain preferred embodiments, the immobilization substrate may be selected from the group of polymer-based materials, hydrogels, tissues, nonwoven materials or woven materials.

In certain embodiments, biosensor embodiments, may comprise, be disposed on, or be operatively associated with a microchip, such as a silicon chip, MEMs (i.e., micro electromechanical system) device, or an integrated circuit. Microchip-based biosensors may be known as "biochips". Regardless of the type of sensor, the microchip may comprise a multiplicity of sensor components having similar or different sensitivities, kinetics, and/or target analytes (i.e., markers) in an array adapted to detect differing levels or combinations of the analyte(s). Further, each sensor in such an array may provide a different type of signal, including those types disclosed herein, and may be associated with different actuators and/or controllers. Also, each sensor in an array may operate independently or in association with (e.g., in parallel, combination, or series) any number of other sensors in the array.

A minicell of a biosensor of the invention may comprise a detectable compound that produces a signal once ligands have bound to the minicell. By way of non-limiting example, a minicell may display a receptor for a ligand and contain a fluorescent compound. The binding and internalization of the ligand into the minicell results in FRET, shifting the wavelength of the signal. See, by way of non-limiting example, Billinton et al., Development of a green fluorescent protein reporter for a yeast genotoxicity biosensor, Biosensors & Bioelectronics 13:831-838, 1998. A biosensor according to the invention may use microbalance sensor systems (Hengerer et al., Determination of phage antibody affinities to antigen by a microbalance sensor system, BioTechniques 26:956-964, 1999).

XVIII.A.2. Surface Plasmon Resonance

Kd is measured using surface plasmon resonance on a chip, for example, with a BIAcore® chip coated with immobilized binding components, or similar systems such as the IAsys from Thermo Labsystems, Affinity Sensors Division (Cambridge, U.K.) or the BIOS-1 system from Artificial Sensing, Inc. (Zurich, Switzerland). See Fitzgerald, Coupling optical biosensor technology with micropreparative HPLC: Part 1, Am Biotech Lab November 2000, p. 10 and 12; Fitzgerald, Coupling optical biosensor technology with micropreparative HPLC: Part 2, Am Biotech Lab February 2001, 14, 16 and 18; and Leatherbarrow et al., Analysis of molecular recognition using optical sensors, Current Opinion in Chem Biol 3:544-547, 1999).

Surface plasmon resonance is used to characterize the microscopic association and dissociation constants of reaction between an antibody or antibody fragment and its ligand. Such methods are generally described in the following references that are incorporated herein by reference. (Vely F. et al., BIAcore analysis to test phosphopeptide-SH2 domain interactions, Methods in Molecular Biology. 121:313-21, 2000; Liparoto et al., Biosensor analysis of the interleukin-2 receptor complex, Journal of Molecular Recognition. 12:316-21, 1999; Lipschultz et al., Experimental design for analysis of complex kinetics using surface plasmon resonance, Methods. 20):310-8, 2000; Malmqvist., BIACORE: an affinity biosensor system for characterization of biomolecular interactions, Biochemical Society Transactions 27:335-40, 1999; Alfthan, Surface plasmon resonance biosensors as a tool in antibody engineering, Biosensors & Bioelectronics. 13:653-63, 1998; Fivash et al., BIAcore for macromolecular interaction, Current Opinion in Biotechnology. 9:97-101, 1998; Price et al.; Summary report on the ISOBM TD-4 Workshop: analysis of 56 monoclonal antibodies against the MUC1 mucin. Tumour Biology 19 Suppl 1:1-20, 1998; Malmqvist et al, Biomolecular interaction analysis: affinity biosensor technologies for functional analysis of proteins, Current Opinion in Chemical Biology. 1:378-83, 1997; O'Shannessy et al., Interpretation of deviations from pseudo-first-order kinetic behavior in the characterization of ligand binding by biosensor technology, Analytical Biochemistry. 236:275-83, 1996; Malmborg et al., BIAcore as a tool in antibody engineering, Journal of Immunological Methods. 183:7-13, 1995; Van Regenmortel, Use of biosensors to characterize recombinant proteins, Developments in Biological Standardization. 83:143-51, 1994; O'Shannessy, Determination of kinetic rate and equilibrium binding constants for macromolecular interactions: a critique of the surface plasmon resonance literature, Current Opinions in Biotechnology. 5:65-71, 1994).

BIAcore® uses the optical properties of surface plasmon resonance (SPR) to detect alterations in protein concentration bound within to a dextran matrix lying on the surface of a gold/glass sensor chip interface, a dextran biosensor matrix. In brief, proteins are covalently bound to the dextran matrix at a known concentration and a ligand for the protein (e.g., antibody) is injected through the dextran matrix. Near infra red light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm2. These changes are displayed with respect to time along the y-axis of a sensorgram, which depicts the association and dissociation of any biological reaction.

Additional details may be found in Jonsson et al., Introducing a biosensor based technology for real-time biospecific interaction analysis, (1993) Ann. Biol. Clin. 51:19-26; Jonsson et al., Real-time biospecific interaction analysis using surface plasmon resonance and a sensor chip technology, (1991) Biotechniques 11:620-627; Johnsson et al., Comparison of methods for immobilization to carboxymethyl dextran sensor surfaces by analysis of the specific activity of monoclonal antibodies, (1995) J. Mol. Recognit. 8:125-131; and Johnsson, Immobilization of proteins to a carboxymethyl-dextran-modified gold surface for biospecific interaction analysis in surface plasmon resonance sensors (1991) Anal. Biochem. 198:268-277, Karlsson et. al., Kinetic analysis of monoclonal antibody-antigen interactions with a new biosensor based analytical system J. Immunol. Meth., 145, 229, 1991; Weinberger et al., Recent trends in protein biochip technology, Pharmacogenomics 2000 November; 1(4):395-416; Lipschultz et al., Experimental design for analysis of complex kinetics using surface plasmon resonance, Methods 2000 March; 20(3):310-8.

XVIII.B. Toxicological Sampling

Minicells are ideally suited for in vitro diagnostic toxicological applications in which toxins, poisons, infectious agents or pathogens, heavy metals, pollutants, caustic agents, allergens, organic molecules, radionuclides, or other environmental contaminants present either in air, water, soil samples and/or fluid and/or tissue samples of organisms can be assessed. An embodiment of this invention, minicells expressing proteins or other molecules could be used in variety of diagnostic detection platforms, including microwell formats, lateral flow devices, molecular switches, biosensors, badges and other sensing devices. Without being limited to the following examples, such devices could be used for early warning of chemical and/or bioweapon attack, illegal drug detection, explosives detection, biohazard detection, pollution assessment, pesticide contamination, allergen detection and detection of toxic or hazardous gasses. In a related application, minicells could be used to eliminate, modify or inactivate the agents.

In one non-limiting example of protein expression on minicells for toxicological detection, olfactory receptors could be expressed by minicells. The olfactory system possesses the ability to recognize and differentiate between a wide range of odorants based on odor molecules interacting with specific receptor proteins in the ciliary membrane of olfactory neurons (Lancet, D., 1986. Vertebrate olfactory reception. Ann. Rev. Neurosci. 9:329-355; Shepherd, G. M., 1994. Discrimination of molecular signals by the olfactory receptor neuron. Neuron 13:771-790). These receptors were found to be 7-transmembrane-domain members of the G protein-coupled receptor family (Buck, L. and R. Alex. 1991. A novel multigene family may encode odorant receptors: A molecular basis for odor recognition. Cell 65:175-187). Using a murine receptor library, olfactory receptors were functionally expressed in HEK-293 cells (Krautwurst, D., et al., 1998. Identification of ligands for olfactory receptors by functional expression of a receptor library. Cell. 95:917-926). By coexpressing the cloned receptors with G□15,16 subunits, the modified receptor system upon activation leads to an increase in intracellular $Ca^{2+}$. Calcium levels were measured employing the dye FURA-2 and ratiofluormetric imaging. This system demonstrated ligand specificity and structure-function relationships for identified olfactory receptors. Employing similar techniques, OR17-40, a human olfactory receptor protein, was expressed in human embryonic kidney 293 cells and *Xenopus Laevis* oocytes (Wetzel, H., et al. 1999. Specificity and sensitivity of a human olfactory receptor functionally expressed in Human Embryonic Kidney 293 Cells and *Xenopus Laevis* Oocytes. J. Neurosciences. 19:7426-7433). The receptor was functionally expressed in a manner designed to assess the specificity of its binding to the ligand, helional.

In one non-limiting example of target protein identification, primers from homologous areas in transmembrane II and transmembrane VII of olfactory GPCRs will be used to identify unique receptor sequences. These sequences are inserted into expression vectors. Minicell producing bacteria are transformed with these vectors and cultured. Minicells are isolated from the culture as previously described and subsequently induced. Using HTS previously described, the functional receptor/minicells which generate signal for binding of an odiferous toxin to the receptor are identified. Large scale-Large-scale production of the minicells is carried out and the minicells are covalently coupled to the surface of a microarraymicro array chip. The chip is supported in an air sampler, which feeds atmosphere over surface of the chip on a continuous basis. If the toxic agent is present in the air, the binding to the receptor activates a series of events ending in the generation of a signal identifying the presence of the agent in the air.

By way of non-limiting example, standard molecular biological techniques can be used as follows: cDNA for GFP is ligated to the 3' end of cDNA sequence for the receptor described above. The resulting sequence is inserted into an expression vector. Minicell producing bacteria are transformed with these vectors and cultured. Minicells are isolated from the culture as previously described and subsequently induced. The minicells now contain the receptor to the ligand on the surface of the minicell with a GFP tag on the C-terminus of the protein in the cytosol. These minicells are packed into filters. Air is passed through the filter. If the ligand is present, it will bind to the receptor. The filter packing is suspended on applied to a diagnostic device. Antibody to the ligand/receptor binding site complex is fixed on the capture zone. When the sample is applied to the device, the receptor/ligand complex is captured. The capture zone is screened for signal resulting from the presence of GFP. This can be extrapolated to have multiple unique receptor/minicell moieties in the same sampling device. Each receptor would have a unique fluorescing protein tag such that different emissions identify specific agents in the air.

Other methods for quantification associated take advantage of the composition of the minicell. Loading of the minicell by transiently permeabilizing the membrane to allow for migration of molecules into to the cytosol. These molecules include but are not limited to radiolabeled molecules (i.e., nucleotides), stains or dyes (DAPI or other DNA staining, heavy metals, fluorophores. The molecules could also be synthesized within the minicell (i.e. GFP). The association of a specific ligand with the minicell could cause a redox shift that induce a color change in the solution or could shift the energy potential in the reaction are generating an electrical current. Each of this examples are associated with well know methods for measuring each of the resulting changes. These include but are not limited to radioactivity or fluorescence generated or the color shift by spectrophotometry.

A multigene family of gustatory G protein-coupled receptors expressed in the lingual epithelia has been identified with structural similarities to olfactory receptors (Abe, K., et al. 1993. Multiple genes for G protein-coupled receptors and their expression in lingual epithelia. FEBS. 316:253-256; Abe, K., et al. 1993. Primary structure and cell-type specific expression of a gustatory G protein-coupled receptor related to olfactory receptors. J. Bio. Chem.). This provides an addition example of receptors which can be isolated, expressed in minicells and then be used for identification of specific substances in various matrices in similar manners as identified for olfactory receptor minicells.

As a non-limiting example of minicell use in toxicological/environmental detection, arrays could be constructed in which each well contains a distinct minicell subtype displaying membrane-bound proteins or other molecules for each of several potential toxins or agents in the environment. For example, minicells in such a format could be used to determine which agents are present in the environment as a consequence of a chemical and/or biological weapons attack. Non-limiting examples of biosensors that have been used toxicological/environmental detection include those described by Sticher et al., Development and characterization of a whole-cell bioluminescent sensor for bioavailable middle-chain alkanes in contaminated groundwater samples, Appl. Envir. Microbiol. 63:4053-4060, 1997; Willardson et al., Development and Testing of a Bacterial Biosensor for Toluene-Based Environmental Contaminants, Appl. Envir. Microbiol. 64:1006-1012, 1998; Lars et al., Detection of Oxytetracycline Production by *Streptomyces rimosus* in Soil Microcosms by Combining Whole-Cell Biosensors and Flow Cytometry, Appl. Envir. Microbiol. 67:239-244, 2001; Højberg et al., Oxygen-Sensing Reporter Strain of *Pseudomonas fluorescens* for Monitoring the Distribution of Low-Oxygen Habitats in Soil, Appl. Envir. Microbiol. 1999 65: 4085-4093, 1999; R. P. Hollis et al., Design and Application of a Biosensor for Monitoring Toxicity of Compounds to Eukaryotes, Appl. Envir. Microbiol. 66: 1676-1679, 2000; Heitzer et al., Optical biosensor for environmental on-line monitoring of naphthalene and salicylate bioavailability with an immobilized bioluminescent catabolic reporter bacterium, Appl. Envir. Microbiol. 60:1487-1494, 1994; Selifonova et al., Bioluminescent sensors for detection of bioavailable Hg(II) in the environment, Appl. Envir. Microbiol. 59: 3083-3090, 1993; Jaeger et al., Mapping of Sugar and Amino Acid Availability in Soil around Roots with Bacterial Sensors of Sucrose and Tryptophan, Appl. Envir. Microbiol. 65: 2685-2690, 1999; and Larsen et al., A Microsensor for Nitrate Based on Immobilized Denitrifying Bacteria, Appl. Envir. Microbiol. 62: 1248-1251, 1996.

XVIII.C. Toxin Elimination

In another embodiment of the invention, minicells displaying a receptor for a particular toxic agent could be used for the elimination of the agent from the environment. In a non-limiting example of this technology, minicells could be placed in a filtering apparatus to eliminate the toxic agent from the environment (e.g., air, water soil). In the example of atmospheric contamination, the air would be circulated through a forced air system containing in-line filters composed of a housing, support matrix and receptor/minicells. As air passes over the minicells, the toxin is bound to the receptor. The purified air passed out of the system and into the atmosphere. A similar method for water purification would follow a similar protocol replacing the receptor for the toxin with the receptor or other protein binding a unique epitope on contaminant wishing to be removed. Examples include but are not limited to removing toxins, parasites or microbes from the matrix such as water or air. This represent non-limiting example of minicell-based technology for expression of functional receptors or binding moieties of receptors on the minicell's surface for the specific purpose of selectively capturing, identifying, quantifying and/or removing molecules of interest for environmental compartments to include but not limited to air water, soil, other gas phases or liquid solutions.

Representative toxins include, but are not limited to, those associated with "red tides"; eubacterial toxins, such as those toxins produced by *Corynebacterium diphtheriae* (diphtheria), *Bordetella pertussis* (whooping cough), *Vibrio cholerae* (cholera), *Bacillus anthracis* (anthrax), *Clostridium botulinum* (botulism), *Clostridium tetani* (tetanus), and enterohemorrhagic *Escherichia coli* (bloody diarrhea and hemolytic uremic syndrome); and fungal toxins (e.g., aflatoxin, gliotoxin, cyclopeptides, orellanine, gyrometrin, coprine, muscarine, ibotenic acid, psilocybin, psilocin and baeocystin).

The treatment of "red tides" with minicells exemplifies this aspect of the invention. A red tide occurs as a result of a higher-than-normal concentration of an algae or dinoflagellate which, when present in dense concentrations as a result of a "bloom," form colored patches on the surface of water. The colored patches are pink, violet, orange, yellow, blue, green, brown, or red, with red being the most common color. The organisms that cause red tides often produce toxins that have negative impacts on other organisms, including humans.

For example, *Karenia brevis* (formerly *Gymnodinium breve*) produces a toxin (domoic acid) that affects the central nervous system of fish, shellfish and other organisms, resulting in a state of paralysis. *Alexandrium* species (e.g., *A. tamarense, A. fundyense*), *Dinophysis* and *Gonyaulax* species; and *Pseudo-nitzschia multiseries*, which cause, respectively, paralytic, diarrhetic and amnesic shellfish poisoning. Because shellfish containing the toxin taste and appear the same as shellfish that do not, and cooking does not destroy the toxin, human ingestion of the former can cause disease in humans and other organisms. For example, one form of paralytic shellfish poisoning, which can be fatal to humans, results from saxitoxin, which is produced by *Gonyaulax tamarenis, Protogonyaulax catanella*, and other species. Other algae that can result in red tides include *Gonyaulax catenella*, and *Ptychdiscus breve*.

Minicells that comprise a binding moiety of an organism that produces a red tide, or of the toxin produced thereby, can be used for remediation. For example, a minicell having a binding moiety directed to a red tide-producing organism can be used to deliver an antibiotic thereto, and a minicell with a binding moiety directed to a toxin can be used to bind and/or internalize the toxin. As is explained in more detail elsewhere herein, a minicell with a binding moiety directed to a toxin can also be used for therapeutic purposes.

XVIII.D. Bioremediation

In another non-limiting example of the potential use of minicells in a toxicological context is their use in bioremediation, the process by which living organisms act to degrade or transform hazardous organic contaminants. As used herein, "bioremediation" is the process of using biological or biologically derived compositions that alter the chemical structure and/or bind, an undesirable substance in order to reduce the effective concentration of the undesirable substance, thereby reducing or eliminating the effect(s) of the undesirable compound on the environment. Undesirable substances include, but are not limited to, pollutants (e.g., heavy metals, pesticides, herbicides, petroleum products); biological toxins (e.g., such as those produced by "red tides", e.g., domoic acid, saxitoxin); pathogens (e.g., viruses, eubacteria); organisms that produce toxins; biological waste products (e.g., sewage, guano), and undesirable organisms therewithin (e.g., pathogenic eubacteria).

The term "bioremediation" encompasess both biodegradation, the breakdown of organic substances by microorganisms, and biotransformation, the alteration of the structure of a compound by a living organism or enzyme. The minicells of the invention may be incorporated into biofilters, i.e., devices in which gases, liquids, powders and the like are passed through media containing biodegrading minicells, including but not limited to devices that biodegrade volatile organic compounds in air by passing the air therethrough.

Bioremediation can be used to process undesirable substances in a composition prior to or after the release of the composition into the environment. For example, bioremediation can be applied in sewage treatment plants to process sewage prior to its release, or to sewage that has been accidentally or otherwise released into the environment.

Environmental microbiologists have sought to identify and use specific bacteria that degrade pollutants and other environmental containments. See, for example, Chakrabarty, Microbial Degradation of Toxic Chemicals: Evolutionary Insights and Practical Considerations, Am. Soc. Micro. Biol. News 62:130-137, 1996; and U.S. Pat. Nos. 4,511,657; 4,493,895; 4,871,673; and 4,535,061. In instances where a live organism is placed into the environment to process undesirable substances, there is a concern that the organism might have undesirable effects that would be made more deleterious due to the ability of the live organism to replicate (Sayler G S, Ripp S. Field applications of genetically engineered microorganisms for bioremediation processes. Curr Opin Biotechnol. 2000 June; 11(3):286-9; and Diaz E, Ferrandez A, Prieto M A, Garcia J L. Biodegradation of aromatic compounds by *Escherichia coli*. Microbiol Mol Biol Rev. 2001 December; 65(4):523-69). For example, when it has been proposed to use genetically altered eubacteria to process oil spills, the concern has been raised that the eubacteria might spread beyond the oil spill and into supplies of petroleum products that are used to produce energy, where they would process and render useless the stored petroleum products. However, because they lack the ability to replicate, such a scenario will not occur when minicells are use for bioremediation.

By way of non-limiting example, octane enhances such as methyl t-butyl ether or aromatic hydrocarbons contaminate the aquifer and soil. These agents negatively impact the many microbes in the effected area thus limiting capability of the microbial community rectify the environmental insult. Bioaugmentation, the addition to the environment of microorganisms that can metabolize and grow on specific organic compounds, to facilitate degradation may prove useful, but concerns exist relative to the regulation of newly introduced bacteria. The minicell provides a vehicle to accomplish biodegradation without bacterial overgrowth.

Diphenyl ethers and cyclic ethers such as dioxane and furan have shown to be metabolized by soil bacteria. Using classic isolation and screening techniques identified above, genes encoding for the oxygenases or hydroylases are isolated. The enzyme sequence is inserted into an expression vector using standard molecular biology techniques. Minicell producing bacteria are transformed with these vectors and cultured. Minicells are isolated from the culture as previously described and subsequently induced. The minicells are applied to the area contaminated with aromatic hydrocarbons. These compounds are transported either actively or passively in to the minicell and subsequently degraded by the oxygenase or hydroylase. One advantage of this focused degradation is the minimizing of feedback inhibition because the only machinery of consequence in the minicell is that related to the degradation of the ether compounds.

Similarly, beginning with genetic material from *Dehalobacter* enzymes responsible for the biodegrading of tetrachloroethane could be isolated as described above. The sequence for the enzyme is inserted into the expression vector and used to transform minicell-producing bacteria. The bacteria are cultured, minicells isolated from the culture and the minicells induced as previously described. Minicell preps are lyophilized using standard lyophilization techniques. The resulting material is transported to the site of tetrachloroethene contamination and reconstituted and applied. As the tetrachloethene was assimilated, it is be degraded by the enzyme system.

These are non-limiting examples scope of bioremediation/biotranformation using minicell technology. The scope of the invention includes taking advantage of metabolic pathways organism in general to include but not limited to eukaryotes, prokaryotes, fungi, animals or plants.

XVIII.E. Fermentation

Delivery of specific enzymes in an untargeted fashion by the minicell allows for packaged delivery without the increased biomass and complex metabolic products associated with processes using live organisms. This aspect can be taken advantage of in fermentation, where the addition of minicells into which unique enzymes have been added are used to modulate the composition of the environment to include but not limited to the alcohol, sugar and acid levels.

XVIII.F. Pesticides

*Bacillus thurigenesis* produces a toxin that kills plant chewing insect larvae as well as mosquito larvae. The toxin, Cry1Ac, binds to aminopeptidase N receptor on the endothelium of the midgut. Minicell technology is allows for delivery of the toxin. The toxin sequence is modified by ligation of a sequence coding for a transmembrane domain as previously described. The sequence for this fusion protein inserted into an expression vector using standard molecular biology techniques. To facilitate the consumption of the toxin/minicell plasmids containing sequences incorporating the sequence for pheromones coupled at the C-terminus to the sequence for a transmembrane domain is generated using standard molecular biological techniques. This fusion protein sequence is inserted into the expression containing coding region for the toxin fusion protein or inserted into a unique expression vector. Minicell producing bacteria are transformed with these vectors and cultured. Minicells are isolated from the culture as previously described and subsequently induced. The minicells are distributed (e.g crop dusting) to the area of infestation. The toxin/minicells are ingested by the larvae and kill the larvae as the minicells passes through the gut.

XIX. Pharmaceutical Compositions

Another aspect of the invention is drawn to compositions, including but not limited to pharmaceutical compositions. According to the invention, a "composition" refers to a mixture comprising at least one carrier, preferably a physiologically acceptable carrier, and one or more minicell compositions. The term "carrier" defines a chemical compound that does not inhibit or prevent the incorporation of the biologically active peptide(s) into cells or tissues. A carrier typically is an inert substance that allows an active ingredient to be formulated or compounded into a suitable dosage form (e.g., a pill, a capsule, a gel, a film, a tablet, a microparticle (e.g., a microsphere), a solution; an ointment; a paste, an aerosol, a droplet, a colloid or an emulsion etc.). A "physiologically acceptable carrier" is a carrier suitable for use under physiological conditions that does not abrogate (reduce, inhibit, or prevent) the biological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically or veterinarily acceptable carrier, in which the minicell composition is disposed.

A "pharmaceutical composition" refers to a composition wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" includes any medium or material that is not biologically or otherwise undesirable, i.e., the carrier may be administered to an organism along with a minicell composition without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application. The terms "therapeutically effective amount" or "pharmaceutically effective amount" mean an amount sufficient to induce or effectuate a measurable response in the target cell, tissue, or body of an organism. What constitutes a therapeutically effective amount will depend on a variety of factors, which the knowledgeable practitioner will take into account in arriving at the desired dosage regimen.

The compositions of the invention can further comprise other chemical components, such as diluents and excipients. A "diluent" is a chemical compound diluted in a solvent, preferably an aqueous solvent, that facilitates dissolution of the composition in the solvent, and it may also serve to stabilize the biologically active form of the composition or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a biologically active peptide.

An "excipient" is any more or less inert substance that can be added to a composition in order to confer a suitable property, for example, a suitable consistency or to form a drug. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropylmethyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The compositions of the invention can be formulated in any suitable manner. Minicell compositions may be uniformly (homogeneously) or non-uniformly (heterogenously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition according to the invention is compressed into tablet or pill form suitable for oral administration or compounded into a sustained release formulation. When the composition is intended for oral administration but is to be delivered to epithelium in the intestines, it is preferred that the formulation be encapsulated with an enteric coating to protect the formulation and prevent premature release of the minicell compositions included therein. As those in the art will appreciate, the compositions of the invention can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some preferred embodiments concern compositions that comprise a bioadhesive, preferably a mucoadhesive, coating. A "bioadhesive coating" is a coating that allows a substance (e.g., a minicellcomposition) to adhere to a biological surface or substance better than occurs absent the coating. A "mucoadhesive coating" is a preferred bioadhesive coating that allows a substance, for example, a composition according to the invention, to adhere better to mucosa occurs absent the coating. For example, micronized particles (e.g., particles having a mean diameter of about 5, 10, 25, 50, or 100 µm) can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the composition interacts with the target cell surface transport moiety.

The compositions of the invention may be administered to any organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (e.g. an enema or suppository) aerosol (e.g., for nasal or pulmonary delivery), parenteral, and topical administration. Preferably, sufficient quantities of the biologically active peptide are delivered to achieve the intended effect. The particular amount of composition to be delivered will depend on many factors, including the effect to be achieved, the type of organism to which the composition is delivered, delivery route, dosage regimen, and the age, health, and sex of the organism. As such, the particular dosage of a composition incorporated into a given formulation is left to the ordinarily skilled artisan's discretion.

Those skilled in the art will appreciate that when the compositions of the present invention are administered as agents to achieve a particular desired biological result, which may include a therapeutic or protective effect(s) (including vaccination), it may be necessary to combine the fusion proteins of the invention with a suitable pharmaceutical carrier. The choice of pharmaceutical carrier and the preparation of the fusion protein as a therapeutic or protective agent will depend on the intended use and mode of administration. Suitable formulations and methods of administration of therapeutic agents include those for oral, pulmonary, nasal, buccal, ocular, dermal, rectal, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, micelle, liposome, and the like, incorporated into a pill, capsule, tablet, suppository, areosol, droplet, or spray. Pills, tablets, suppositories, areosols, powders, droplets, and sprays may have complex, multilayer structures and have a large range of sizes. Aerosols, powders, droplets, and sprays may range from small (1 micron) to large (200 micron) in size.

Pharmaceutical compositions of the present invention can be used in the form of a solid, a lyophilized powder, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Examples of a stabilizing dry agent includes triulose, preferably at concentrations of 0.1% or greater (See, e.g., U.S. Pat. No. 5,314,695). The active compound is included in the pharmaceutical composition in an amount sufficient to produce the desired effect upon the process or condition of diseases.

XX. Small Molecules

The term "small molecule" includes any chemical or other moiety that can act to affect biological processes. Small molecules can include any number of therapeutic agents presently known and used, or can be small molecules synthesized in a library of such molecules for the purpose of screening for biological function(s). Small molecules are distinguished from macromolecules by size. The small molecules of this invention usually have molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than macromolecules such nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocylcic compounds, imidizoles and phenols. An organic compound as used herein also includes nitrated organic compounds and halogenated (e.g., chlorinated) organic compounds. Methods for preparing peptidomimetics are described below. Collections of small molecules, and small molecules identified according to the invention are characterized by techniques such as accelerator mass spectrometry (AMS; see Turteltaub et al., Curr Pharm Des 2000 6(10):991-1007, Bioanalytical applications of accelerator mass spectrometry for pharmaceutical research; and Enjalbal et al., Mass Spectrom Rev 2000 19(3):139-61, Mass spectrometry in combinatorial chemistry.)

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

XXI. Polypeptides and Derivatives

XXI.A. Polypeptides

As used herein, the term "polypeptide" includes proteins, fusion proteins, oligopeptides and polypeptide derivatives, with the exception that peptidomimetics are considered to be small molecules herein. Although they are polypeptides, antibodies and their derivatives are described in a separate section. Antibodies and antibody derivatives are described in a separate section, but antibodies and antibody derivatives are, for purposes of the invention, treated as a subclass of the polypeptides and derivatives.

A "protein" is a molecule having a sequence of amino acids that are linked to each other in a linear molecule by peptide bonds. The term protein refers to a polypeptide that is isolated from a natural source, or produced from an isolated cDNA using recombinant DNA technology; and has a sequence of amino acids having a length of at least about 200 amino acids.

A "fusion protein" is a type of recombinant protein that has an amino acid sequence that results from the linkage of the amino acid sequences of two or more normally separate polypeptides.

A "protein fragment" is a proteolytic fragment of a larger polypeptide, which may be a protein or a fusion protein. A proteolytic fragment may be prepared by in vivo or in vitro proteolytic cleavage of a larger polypeptide, and is generally too large to be prepared by chemical synthesis. Proteolytic fragments have amino acid sequences having a length from about 200 to about 1,000 amino acids.

An "oligopeptide" is a polypeptide having a short amino acid sequence (i.e., 2 to about 200 amino acids). An oligopeptide is generally prepared by chemical synthesis.

Although oligopeptides and protein fragments may be otherwise prepared, it is possible to use recombinant DNA technology and/or in vitro biochemical manipulations. For example, a nucleic acid encoding an amino acid sequence may be prepared and used as a template for in vitro transcription/translation reactions. In such reactions, an exogenous nucleic acid encoding a preselected polypeptide is introduced into a mixture that is essentially depleted of exogenous nucleic acids that contains all of the cellular components required for transcription and translation. One or more radiolabeled amino acids are added before or with the exogenous DNA, and transcription and translation are allowed to proceed. Because the only nucleic acid present in the reaction mix is the exogenous nucleic acid added to the reaction, only polypeptides encoded thereby are produced, and incorporate the radiolabelled amino acid(s). In this manner, polypeptides encoded by a preselected exogenous nucleic acid are radiolabeled. Although other proteins are present in the reaction mix, the preselected polypeptide is the only one that is produced in the presence of the radiolabeled amino acids and is thus uniquely labeled.

As is explained in detail below, "polypeptide derivatives" include without limitation mutant polypeptides, chemically modified polypeptides, and peptidomimetics.

The polypeptides of this invention, including the analogs and other modified variants, may generally be prepared following known techniques. Preferably, synthetic production of the polypeptide of the invention may be according to the solid phase synthetic method. For example, the solid phase synthesis is well understood and is a common method for preparation of polypeptides, as are a variety of modifications of that technique [Merrifield (1964), J. Am. Chem. Soc., 85: 2149; Stewart and Young (1984), Solid Phase polypeptide Synthesis, Pierce Chemical Company, Rockford, Ill.; Bodansky and Bodanszky (1984), The Practice of polypeptide Synthesis, Springer-Verlag, New York; Atherton and Sheppard (1989), Solid Phase polypeptide Synthesis: A Practical Approach, IRL Press, New York]. See, also, the specific method described in Example 1 below.

Alternatively, polypeptides of this invention may be prepared in recombinant systems using polynucleotide sequences encoding the polypeptides. For example, fusion proteins are typically prepared using recombinant DNA technology.

XXI.B. Polypeptide Derivatives

A "derivative" of a polypeptide is a compound that is not, by definition, a polypeptide, i.e., it contains at least one chemical linkage that is not a peptide bond. Thus, polypeptide derivatives include without limitation proteins that naturally undergo post-translational modifications such as, e.g., glycosylation. It is understood that a polypeptide of the invention may contain more than one of the following modifications within the same polypeptide. Preferred polypeptide derivatives retain a desirable attribute, which may be biological activity; more preferably, a polypeptide derivative is enhanced with regard to one or more desirable attributes, or has one or more desirable attributes not found in the parent polypeptide. Although they are described in this section, peptidomimetics are taken as small molecules in the present disclosure.

XXI.C. Mutant Polypeptide Derivatives

A polypeptide having an amino acid sequence identical to that found in a protein prepared from a natural source is a "wildtype" polypeptide. Mutant oligopeptides can be prepared by chemical synthesis, including without limitation combinatorial synthesis.

Mutant polypeptides larger than oligopeptides can be prepared using recombinant DNA technology by altering the nucleotide sequence of a nucleic acid encoding a polypeptide. Although some alterations in the nucleotide sequence will not alter the amino acid sequence of the polypeptide encoded thereby ("silent" mutations), many will result in a polypeptide having an altered amino acid sequence that is altered relative to the parent sequence. Such altered amino acid sequences may comprise substitutions, deletions and additions of amino acids, with the proviso that such amino acids are naturally occurring amino acids.

Thus, subjecting a nucleic acid that encodes a polypeptide to mutagenesis is one technique that can be used to prepare mutant polypeptides, particularly ones having substitutions of amino acids but no deletions or insertions thereof. A variety of mutagenic techniques are known that can be used in vitro or in vivo including without limitation chemical mutagenesis and PCR-mediated mutagenesis. Such mutagenesis may be randomly targeted (i.e., mutations may occur anywhere within the nucleic acid) or directed to a section of the nucleic acid that encodes a stretch of amino acids of particular interest. Using such techniques, it is possible to prepare randomized, combinatorial or focused compound libraries, pools and mixtures.

Polypeptides having deletions or insertions of naturally occurring amino acids may be synthetic oligopeptides that result from the chemical synthesis of amino acid sequences that are based on the amino acid sequence of a parent polypeptide but which have one or more amino acids inserted or deleted relative to the sequence of the parent polypeptide. Insertions and deletions of amino acid residues in polypeptides having longer amino acid sequences may be prepared by directed mutagenesis.

XXI.D. Chemically Modified Polypeptides

As contemplated by this invention, the term "polypeptide" includes those having one or more chemical modification relative to another polypeptide, i.e., chemically modified polypeptides. The polypeptide from which a chemically modified polypeptide is derived may be a wildtype protein, a mutant protein or a mutant polypeptide, or polypeptide fragments thereof; an antibody or other polypeptide ligand according to the invention including without limitation single-chain antibodies, bacterial proteins and polypeptide derivatives thereof; or polypeptide ligands prepared according to the disclosure. Preferably, the chemical modification(s) confer(s) or improve(s) desirable attributes of the polypeptide but does not substantially alter or compromise the biological activity thereof. Desirable attributes include but are limited to increased shelf-life; enhanced serum or other in vivo stability; resistance to proteases; and the like. Such modifications include by way of non-limiting example N-terminal acetylation, glycosylation, and biotinylation.

XXI.D.1. Polypeptides with N-Terminal or C-Terminal Chemical Groups

An effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al. (1993), Pharma. Res. 10: 1268-1273). Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group.

XXI.D.2. Polypeptides with a Terminal D-Amino Acid

The presence of an N-terminal D-amino acid increases the serum stability of a polypeptide that otherwise contains L-amino acids, because exopeptidases acting on the N-terminal residue cannot utilize a D-amino acid as a substrate. Similarly, the presence of a C-terminal D-amino acid also stabilizes a polypeptide, because serum exopeptidases acting on the C-terminal residue cannot utilize a D-amino acid as a substrate. With the exception of these terminal modifications, the amino acid sequences of polypeptides with N-terminal and/or C-terminal D-amino acids are usually identical to the sequences of the parent L-amino acid polypeptide.

XXI.D.3. Polypeptides with Substitution of Natural Amino Acids by Unnatural Amino Acids Substitution of unnatural amino acids for natural amino acids in a subsequence of a polypeptide can confer or enhance desirable attributes including biological activity. Such a substitution can, for example, confer resistance to proteolysis by exopeptidases acting on the N-terminus. The synthesis of polypeptides with unnatural amino acids is routine and known in the art (see, for example, Coller, et al. (1993), cited above).

XXI.D.4. Post-Translational Chemical Modifications

Different host cells will contain different post-translational modification mechanisms that may provide particular types of post-translational modification of a fusion protein if the amino acid sequences required for such modifications is present in the fusion protein. A large number (~100) of post-translational modifications have been described, a few of which are discussed herein. One skilled in the art will be able to choose appropriate host cells, and design chimeric genes that encode protein members comprising the amino acid sequence needed for a particular type of modification.

Glycosylation is one type of post-translational chemical modification that occurs in many eukaryotic systems, and may influence the activity, stability, pharmacogenetics, immunogenicity and/or antigenicity of proteins. However, specific amino acids must be present at such sites to recruit the appropriate glycosylation machinery, and not all host cells have the appropriate molecular machinery. *Saccharomyces cerevisieae* and *Pichia pastoris* provide for the production of glycosylated proteins, as do expression systems that utilize insect cells, although the pattern of glyscoylation may vary depending on which host cells are used to produce the fusion protein.

Another type of post-translation modification is the phosphorylation of a free hydroxyl group of the side chain of one or more Ser, Thr or Tyr residues. Protein kinases catalyze such reactions. Phosphorylation is often reversible due to the action of a protein phosphatase, an enzyme that catalyzes the dephosphorylation of amino acid residues.

Differences in the chemical structure of amino terminal residues result from different host cells, each of which may have a different chemical version of the methionine residue encoded by a start codon, and these will result in amino termini with different chemical modifications.

For example, many or most bacterial proteins are synthesized with an amino terminal amino acid that is a modified form of methionine, i.e, N-formyl-methionine (fMet). Although the statement is often made that all bacterial proteins are synthesized with an fMet initiator amino acid; although this may be true for *E. coli*, recent studies have shown that it is not true in the case of other bacteria such as *Pseudomonas aeruginosa* (Newton et al., J. Biol. Chem. 274: 22143-22146, 1999). In any event, in *E. coli*, the formyl group of fMet is usually enzymatically removed after translation to yield an amino terminal methionine residue, although the entire fMet residue is sometimes removed (see Hershey, Chapter 40, "Protein Synthesis" in: *Escherichia Coli* and *Salmonella Typhimurium*: Cellular and Molecular Biology, Neidhardt, Frederick C., Editor in Chief, American Society for Microbiology, Washington, D.C., 1987, Volume 1, pages 613-647, and references cited therein.) *E. coli* mutants that lack the enzymes (such as, e.g., formylase) that catalyze such post-translational modifications will produce proteins having an amino terminal fMet residue (Guillon et al., J. Bacteriol. 174:4294-4301, 1992).

In eukaryotes, acetylation of the initiator methionine residue, or the penultimate residue if the initiator methionine has been removed, typically occurs co- or post-translationally. The acetylation reactions are catalyzed by N-terminal acetyltransferases (NATs, a.k.a. N-alpha-acetyltransferases), whereas removal of the initiator methionine residue is catalyzed by methionine aminopeptidases (for reviews, see Bradshaw et al., Trends Biochem. Sci. 23:263-267, 1998; and Driessen et al., CRC Crit. Rev. Biochem. 18:281-325, 1985). Amino terminally acetylated proteins are said to be "N-acetylated," "N alpha acetylated" or simply "acetylated."

Another post-translational process that occurs in eukaryotes is the alpha-amidation of the carboxy terminus. For reviews, see Eipper et al. Annu. Rev. Physiol. 50:333-344, 1988, and Bradbury et al. Lung Cancer 14:239-251, 1996. About 50% of known endocrine and neuroendocrine peptide hormones are alpha-amidated (Treston et al., Cell Growth Differ. 4:911-920, 1993). In most cases, carboxy alpha-amidation is required to activate these peptide hormones.

XXI.E. Peptidomimetics

In general, a polypeptide mimetic ("peptidomimetic") is a molecule that mimics the biological activity of a polypeptide but is no longer peptidic in chemical nature. By strict definition, a peptidomimetic is a molecule that contains no peptide bonds (that is, amide bonds between amino acids). However, the term peptidomimetic is sometimes used to describe molecules that are no longer completely peptidic in nature, such as pseudo-peptides, semi-peptides and peptoids. Examples of some peptidomimetics by the broader definition (where part of a polypeptide is replaced by a structure lacking peptide bonds) are described below. Whether completely or partially non-peptide, peptidomimetics according to this invention provide a spatial arrangement of reactive chemical moieties that closely resembles the three-dimensional arrangement of active groups in the polypeptide on which the peptidomimetic is based. As a result of this similar active-site geometry, the peptidomimetic has effects on biological systems that are similar to the biological activity of the polypeptide.

There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that are not experienced with peptidomimetics.

Candidate, lead and other polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference].

Thus, through use of the methods described above, the present invention provides compounds exhibiting enhanced therapeutic activity in comparison to the polypeptides described above. The peptidomimetic compounds obtained by the above methods, having the biological activity of the above named polypeptides and similar three-dimensional structure, are encompassed by this invention. It will be readily apparent to one skilled in the art that a peptidomimetic can be generated from any of the modified polypeptides described in the previous section or from a polypeptide bearing more than one of the modifications described from the previous section. It will furthermore be apparent that the peptidomimetics of this invention can be further used for the development of even more potent non-peptidic compounds, in addition to their utility as therapeutic compounds.

Specific examples of peptidomimetics derived from the polypeptides described in the previous section are presented below. These examples are illustrative and not limiting in terms of the other or additional modifications.

XXI.E.1. Peptides with a Reduced Isostere Pseudopeptide Bond

Proteases act on peptide bonds. It therefore follows that substitution of peptide bonds by pseudopeptide bonds confers resistance to proteolysis. A number of pseudopeptide bonds have been described that in general do not affect polypeptide structure and biological activity. The reduced isostere pseudopeptide bond is a suitable pseudopeptide bond that is known to enhance stability to enzymatic cleavage with no or little loss of biological activity (Couder, et al. (1993), Int. J. Polypeptide Protein Res. 41:181-184, incorporated herein by reference). Thus, the amino acid sequences of these compounds may be identical to the sequences of their parent L-amino acid polypeptides, except that one or more of the peptide bonds are replaced by an isostere pseudopeptide bond. Preferably the most N-terminal peptide bond is substituted, since such a substitution would confer resistance to proteolysis by exopeptidases acting on the N-terminus.

XXI.E.2. Peptides with a Retro-Inverso Pseudopeptide Bond

To confer resistance to proteolysis, peptide bonds may also be substituted by retro-inverso pseudopeptide bonds (Dalpozzo, et al. (1993), Int. J. Polypeptide Protein Res. 41:561-566, incorporated herein by reference). According to this modification, the amino acid sequences of the compounds may be identical to the sequences of their L-amino acid parent polypeptides, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus.

XXI.E.3. Peptoid Derivatives

Peptoid derivatives of polypeptides represent another form of modified polypeptides that retain the important structural determinants for biological activity, yet eliminate the peptide bonds, thereby conferring resistance to proteolysis (Simon, et al., 1992, Proc. Natl. Acad. Sci. USA, 89:9367-9371 and incorporated herein by reference). Peptoids are oligomers of N-substituted glycines. A number of N-alkyl groups have been described, each corresponding to the side chain of a natural amino acid.

XXII. Kits

The invention provides for diagnostic and therapeutic kits related useful for therapeutic, diagnostic, and research applications. Exemplary kits are disclosed in U.S. Pat. Nos. 5,773,024; 6,017,721; and 6,232,127 B1. The kits of the invention incorporate minicells, and/or include methods of using minicells described herein.

XXII.A. Diagnostic and Research Use Kit Components

In one embodiment, the invention relates to kits for determining the diagnosis or prognosis of a patient. These kits preferably comprise devices and reagents for measuring one or more marker levels in a test sample from a patient, and instructions for performing the assay. Optionally, the kits may contain one or more means for converting marker level(s) to a prognosis. Such kits preferably contain sufficient reagents to perform one or more such determinations.

More specifically, a diagnostic kit of the invention comprises any of the following reagents and/or components in any combination.

(1) A detectable or detectably labeled first reagent that binds a ligand of interest. The binding reagent can, but need not, be an antibody or an antibody derivative comprising a detectable moiety. The sphingolipid-binding reagent is stored in an openable container in the kit, or is bound to a surface of a substrate such that it is accessible to other reagents. Examples of the latter include test strips.

(2) If the first reagent in neither detectable nor detectably labeled, the kit may comprise a detectable or detectably labeled second reagent that binds to the first reagent (e.g., a secondary antibody) or which produces a detectable signal when in close proximity to the first reagent (e.g., as results from fluorescent resonance energy transfer FRET). In either case, the signal produced from the second reagent correlates with the amount of ligand in the sample.

(3) One or more positive control reagents. Typically, these reagents comprise a compound that is known to produce a signal in the assay. In one embodiment, the positive control reagents are standards, i.e., comprise a known amount of a detectable or detectably labeled compound, the signal from which may be compared to the signal from a test sample. In addition to serving as positive control reagents, they may be used to develop calibration curves that relate the amount of signal to the known concentration of a detectable or detectably labeled compound. The signal from a test sample is compared to the calibration curve in order to determine what concentration of the detectable or detectably labeled compound corresponds to the signal from the test sample. In this embodiment, the kit provides quantitative measurements of the amount of a ligand in a test sample.

(4) One or more negative control reagents. Typically, these control reagents may comprise buffer or another solution that does not contain any of the detectable or detectably labeled first or second reagents and should thus not produce any detectable signal. Any signal that is detected reflects the background level of "noise" in the assay. Another type of negative control reagent contains most of the components necessary for the signal of the assay to be produced, but lacks at least one such component and therefor should not produce a signal. Yet another type of negative control reagent contains all of the components necessary for the signal of the assay to be produced, but also contains an inhibitor of the process that produced the signal.

(5) One or more auxiliary reagents for use in the diagnostic assays of the kit, e.g., buffers, alcohols, acid solutions, etc. These reagents are generally available in medical facilities and thus are optional components of the kit. However, these reagents preferably are included in the kit to ensure that reagents of sufficient purity and sterility are used, since the resulting protein conjugates are to be administered to mammals, including humans, for medical purposes, and to provide kits that can be used in situations where medical facilities are not readily available, e.g., when hiking in places located far from medical facilities, or in situations where the presence of these auxiliary reagents allows for the immediate treatment of a patient outside of a medical facility as opposed to treatment that arrives at some later time).

(6) Instructions to a person using a kit for its use. The instructions can be present on one or more of the kit components, the kit packaging and/or a kit package insert.

XXII.B. Therapeutic Kit Components

A therapeutic kit of the invention comprises any of the following reagents and/or components in any combination.

(1) One or more therapeutic agents.

(2) If the therapeutic agent(s) are not formulated for delivery via the alimentary canal, which includes but is not limited to sublingual delivery, a device capable of delivering the therapeutic agent through some other routes. One type of device for parenteral delivery is a syringe that is used to inject the therapeutic agent into the body of an animal in need of the therapeutic agent. Inhalation devices may also be used.

(3) Separate containers, each of which comprises one or more reagents of the kit. In a preferred embodiment, the containers are vials contain sterile, lyophilized formulations of a therapeutic composition that are suitable for reconstitution. Other containers include, but are not limited to, a pouch, tray, box, tube, or the like. Kit components may be packaged and maintained sterilely within the containers.

(4) Instructions to a person using a kit for its use. The instructions can be present on one or more of the kit components, the kit packaging and/or a kit package insert. Such instructions include, by way of non-limiting example, instructions for use of the kit and its reagents, for reconstituting lyophilized reagents or otherwise preparing reagents.

A preferred kit of the present invention comprises the elements useful for performing an immunoassay. A kit of the present invention can comprise one or more experimental samples (i.e., formulations of the present invention) and one or more control samples bound to at least one pre-packed dipstick or ELISA plate, and the necessary means for detecting immunocomplex formation (e.g., labelled secondary antibodies or other binding compounds and any necessary solutions needed to resolve such labels, as described in detail above) between antibodies contained in the bodily fluid of the animal being tested and the proteins bound to the dipstick or ELISA plate. It is within the scope of the invention that the kit can comprise simply a formulation of the present invention and that the detecting means can be provided in another way.

An alternative preferred kit of the present invention comprises elements useful for performing a skin test. A kit of the present invention can comprise at least one pre-packed syringe and needle apparatus containing one or more experimental samples and/or one or more control samples. A kit according to the invention may be designed for both diagnostic and therapeutiuc applications. Any combination of the above elements XX.A.(1)-(6) and XX.B.(1)-(4) may be used in a kit, optionally with additional reagents, standards, sample containers, an the like.

XXIII. Immunogenic Minicells

XXIII.A. In General

Minicells are used to immunize subjects. An organism is said to be "immunized" when, after contact with an immunogen, the organism produces antibodies directed to the immunogen, or has increased proliferation or activity of cytotoxic and/or helper T cells, or both. Increased proliferation or activity of T cells may be particularly desirable in the case of parasites that cause a decrease in T cell proliferation.

The use of minicells to present antigens has several potential advantages. An intact membrane protein can be presented in its native form on the surface of an immunogenic minicell, rather than as a denatured protein or as oligopeptides derived from the amino acid sequence of a membrane protein, which allows for antibodies to be developed that are directed to epitopes which, due to protein folding, occur only in the native protein. The minicell surface may naturally be, or may be modified to be, an adjuvant. Moreover, pharmacokinetic properties of minicells, as discussed elsewhere herein, may be improved relative to other forms of administration.

The applications of immunogenic minicells include, but are not limited to, research, prophylactic, diagnostic and therapeutic applications.

In research applications, immunogenic minicells are used to generate antibodies to an antigen displayed on a minicell. Such antibodies are used to detect an antigen, which may be a chemical moiety, molecule, virus, organelle, cell, tissue, organ, or organism that one wishes to study. Classically, such antibodies have been prepared by immunizing an animal, often a rat or a rabbit, and collecting antisera therefrom. Molecular biology techniques can be used to prepare antibodies and antibody fragments, as is described elsewhere herein. Single-chain antibody fragments (scFv) may also be identified, purified, and characterized using minicells displaying a membrane protein or membrane bound chimeric soluble protein.

In prophylactic applications, immunogenic minicells are used to stimulate a subject to produce antibodies and/or activate T cells, so that the subject is "pre-immunized" before contact with a pathogen or hyperproliferative cell. Thus, in the case of a pathogens, the subject is protected by antibodies and/or T cells that are specifically directed to the pathogen before infection.

In therapeutic applications, immunogenic minicells are used in immunotherapy.

Certain aspects of the invention involve active immunotherapy, in which treatment relies on the in vivo stimulation of the endogenous host immune system to react against pathogens or tumors due to the administration of agents that cause, enhance or modulate an immune response. Such agents include, but are not limited to, immunogens, adjuvants, cytokines and chemokines.

Other therapeutic applications involve passive immunotherapy, in which treatment involves the delivery of agents (such as antibodies or effector cells) that are specifically directed to an immunogen of a pathogen or a hyperproliferative cell, and does not necessarily depend on an intact host immune system. Examples of effector cells include T cells; T lymphocytes, such as CD8+ cytotoxic T lymphocytes and CD4+ T-helper tumor-infiltrating lymphocytes; killer cells, such as Natural Killer (NK) cells and lymphokine-activated killer cells.

XXIII.B. Hyperproliferative Disorders

The immunogenic minicells of the invention can be used to treat hyperproliferative disorders by inducing an immune response to an antigen associated therewith. The term "hyperproliferative disorder" refers to disorders characterized by an abnormal or pathological proliferation of cells, for example, cancer, psoriasis, hyperplasia and the like.

For reviews of immunotherapy as applied to hyperproliferative disorders, see Armstrong et al., Cellular immunotherapy for cancer, BMJ 323:1289-1293, 2001; Evans, Vaccine therapy for cancer—fact or fiction?, Proc R Cell Physicians Edinb 31:9-16, 2001; Ravindranath and Morton, "Active Specific Immunotherapy with Vaccines," Chapter 61 in: Holland-Frei Cancer Medicine, Fifth Edition, Bast, Robert C., et al., editors, B.C. Decker, Inc., Hamilton, 2000, pages 800-814.

Types of cancers include without limitation fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, and heavy chain disease.

Tumor specific antigens (TSAs), tumor-associated differentiation antigens (TADAs) and other antigens associated with cancers and other hyperproliferative disorders include, but are not limited to, C1 IAC, a human cancer associated protein (Osther, U.S. Pat. No. 4,132,769); the CA125 antigen, an antigen associated with cystadenocarcinoma of the ovary, (Hanisch et al., Carbohydr. Res. 178:29-47, 1988; O'Brien, U.S. Pat. No. 4,921,790); CEA, an antigen present on many adenocarcinomas (Hong et al., Strategies for cancer therapy using carcinembryonic antigen vaccines, Expert Reviews in Molecular Medicine, http://www-ermm.cbcu.cam.ac.uk: 1, 2000); CORA (carcinoma or orosomucoid-related antigen) described by Toth et al. (U.S. Pat. No. 4,914,021); DF3 antigen from human breast carcinoma (Kufe, in U.S. Pat. Nos. 4,963,484 and 5,053,489); DU-PAN-2, a pancreatic carcinoma antigen (Lan et al., Cancer Res. 45:305-310, 1985); HCA, a human carcinoma antigen (Codington et al., U.S. Pat. No. 5,693,763); Her2, a breast cancer antigen (Fendly et al., The Extracellular Domain of HER2/neu Is a Potential Immunogen for Active Specific Immunotherapy of Breast Cancer, Journal of Biological Response Modifiers 9:449-455, 1990); MSA, a breast carcinoma glycoprotein (Tjandra et al., Br. J. Surg. 75:811-817, 1988); MFGM, a breast carcinoma antigen (Ishida et al., Tumor Biol. 10:12-22, 1989); PSA, prostate specific antigen (Nadji et al., Prostatic-specific-antigen, Cancer 48:1229-1232, 1981); STEAP (six transmembrane epithelial antigens of the prostate) proteins (Afar et al., U.S. Pat. No. 6,329,503); TAG-72, a breast carcinoma glycoprotein (Kjeldsen et al., Cancer Res. 48:2214-2220, 1988); YH206, a lung carcinoma antigen (Hinoda et al., Cancer J. 42:653-658, 1988); the p97 antigen of human melanoma (Estin et al., Recombinant Vaccinia Virus Vaccine Against the Human Melanoma Antigen p97 for Use in Immunotherapy, Proc. Natl. Acad. Sci. USA, 85:1052-1056, 1988); and the melanoma specific antigen described by Pfreundschuh in U.S. Pat. No. 6,025,191);

XXIII.B. Intracellular Pathogens

In certain aspects of the invention, vaccines comprising immunogenic minicells are used to prevent or treat diseases caused by intracellular pathogens. Vaccines may be prepared that stimulate cytotoxic T cell responses against cells infected with viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirous, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II). Vaccines also may be prepared that stimulate cytotoxic T cell responses against cells infected with intracellular obligates, including but not limited to *Chlamydia, Mycobacteria* and *Rickettsia*. Vaccines also may be prepared that stimulate cytotoxic T cell responses against cells infected with intracellular protozoa, including, but not limited to, *leishmania, kokzidioa*, and *trypanosoma*.

The causative agent of Lyme disease, the spirochete *Borrelia burgdorfei*, is also of interest. The outer surface proteins (Osps) A, B and C of *B. burgdorfei* are known antigens that are lipoproteins that associate with membranes. Amino-terminal cysteine residues in Osp proteins are the sites of triacyl lipid modifications that serve as membrane-anchoring moities. The N-terminal portions of the Osp proteins are highly conserved and are preferred portions for display on immunogenic minicells.

XXIII.C. Eukaryotic Pathogens

In addition to intracellular pathogens, other eukaryotic pathogens exist and may also be treated using immunogenic minicells displayed antigens therefrom. A number of antigens have been used to develop anti-parasitic vaccines, e.g. the recombinant 45w protein of *Taenia ovis*; EG95 oncosphere proteins of *Echinococcus granulosis*; cathepsin L antigen of the liver fluke, *Fasciola hepatica*; and the H11 antigen of *Haemonchus contortus* (Dalton et al., Parasite vaccines—a reality?, Vet Parasitol 98:149-167, 2001). Other eukaryotic pathogens include, but are not limited to:

Protozoans, including but not limited to, *Entamoeba histolytica*, a pathogenic amoeba that causes amoebic dysentery and occasionally digests its way through the intestinal wall to invades other organs, which may cause morbidity; *Balantinium coli*, a ciliate that causes diarrhea in humans; *Giardia lamblia*, a flagellate that causes diarrhea and abdominal pain, along with a chronic fatigue syndrome that is otherwise asymptomatic and difficult to diagnose; *Trypanosoma brucei*, a hemoflagellate causing sleeping sickness; and *Trypanosoma cruzi*, the cause of Chagas disease);

*Plasmodia*, sporozoan obligate intracellular parasites of liver and red blood cells, including but not limited to *P. falciparum*, the causative agent of malaria. Dozens of *P. falciparum* antigens have been identified, e.g., CSP-1, STARP, SALSA, SSP-2, LSA-1, EXP-1, LSA-3, RAP-1, RAP-2, SERA-1, MSP-1, MSP-2, MSP-3, MSP-4, MSP-5, AMA-1, EBA-175, RESA, GLURP, EMP-1, Pfs25, Pfg27, Pf35, Pf55, Pfs230, Pfg27, Pfs16, Pfs28 and Pfs45/48.

Helminthes including but not limited to *Ascaris lumbricoides* (roundworm); *Enterobius vermicularis* (pinworm); *Trichuris trichiuria* (whipworm); and *Fasciola hepatica* (liver fluke);

*Taenia* sp. (tapeworms and cestodes);

*Schistosoma* (trematodes), such as *Schistoma mansoni*, which comprises the Sm32 antigen (asparaginyl endopeptidase), which can induce antibody formation in mice (Chlichlia et al., DNA vaccination with asparaginyl endopeptidase (Sm32) from the parasite *Schistosoma mansoni*: anti-fecundity effect induced in mice, Vaccine 20:439-447, 2001); and acetylcholinesterase (Amon et al., Acetylcholinesterase of *Schistoma mansoni*-Functional correlates, Protein Science 8:2553-2561, 1999); and Ticks and other invertebrates, including but not limited to insects, arachnids, etc. For example, a description of a vaccine against the cattle tick *Boophilus microplus* has been described (Valle et al., The evaluation of yeast derivatives as adjuvants for the immune response to the Bm86 antigen in cattle, BMC Biotechnol. 1:2, 2001)

XXIII.D. Formulation and Administration of Immunogenic Minicells

Vaccine formulations of immunogenic minicells include a suitable carrier. Because minicells may be destroyed by digestion, or prevented from acting due to antibody secretion in the gvut, they are preferably administered parenterally, including, for example, administration that is subcutaneous, intramuscular, intravenous, or intradermal. Formulations suitable for parenteral administration include aqueous and non-aqueous sterile injection solutions which may contain antioxidanits, buffers, and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation. Adjuvants are substances that can be used to augment a specific immune response. Normally, the adjuvant and the composition are mixed prior to presentation to the immune system, or presented separately, but into the same site of the mammal being immunized. Examples of materials suitable for use in vaccine compositions are provided in Osol, A., ed., Remington's Pharmaceutical Sciences, Mack Publishing Co, Easton, Pa. (1980), pp. 1324-1341, which reference is entirely incorporated herein by reference.

Compositions comprising immunogenic minicells are injected into a human or animal at a dosage of 1-1000 ug per kg body weight. Antibody titers against growth factor are determined by ELISA, using the recombinant protein and horseradish peroxidase-conjugated goat anti-human or animal immunoglobulins or other serologic techniques (e.g., sandwich ELISA). Booster injections are administered as needed to achieve the desired levels of protective antibodies and/or T cells.

Routes and frequency of administration, as well as dosage, will vary from individual to individual. Between 1 and 10 doses may be administered for a 52-week period. Preferably, 6 doses are administered, at intervals of 1 month, and booster vaccinations may be given periodically thereafter. Alternate protocols may be appropriate for individual patients. In immunotherapy of hyperproliferative disorders, a suitable dose is an amount of a compound that, when administered as described above, is capable of promoting an anti-tumor immune response. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients.

The vaccine according to the invention may contain a single species of immunogenic minicells according to the invention or a variety of immunogenic minicells, each of which displays a different immunogen. Additionally or alternatively, immunogenic minicells may each display and/or express more than one iummunogen.

The summary of the invention described above is non-limiting and other features and advantages of the invention will be apparent from the following detailed description of the invention, and from the claims.

EXAMPLES

Example 1

Creation of a Minicell-Producing Bacterial Cell Line (MC-T7) that Expresses an Exogenous RNA Polymerase In order to maximize the amount of RNA transcription from episomal elements in minicells, a minicell-producing cell line that expresses an RNA polymerase specific for certain episomal expression elements was created. This *E. coli* strain, designated MC-T7, was created as follows.

The P678-54 *E. coli* strain contains mutations that influence cell division and induce the production of minicells (Adler et al., Proc. Natl. Acad. Sci. 57:321-326 (1967), Allen et al., Biochem. Biophys. Res. Communi. 47:1074-1079 (1972), Hollenberg et al., Gene 1:33-47 (1976)). The P678-54 strain is resistant to Lambda phage due to a mutation in the malT gene (Gottesman, Bacteriophage Lambda: The Untold Story. J. Mol. Biol. 293:177-180, 1999; Friedman, Interactions Between Bacteriophage Lambda and its *Escherichia Coli* Host. Curr. Opin. Genet. Dev. 2:727-738, 1992). Thus, as an initial step, the P678-54 strain was altered so as to be sensitive to Lambda phage so that it could form lysogens of Lambda-DE3 (see below). Wildtype MalT-encoding sequences were restored via a HFR (high frequency recombination) conjugation protocol using the G43 *E. coli* strain (CGSC stain 4928).

Recipient (P678-54) and donor (G43:BW6169) strains were grown overnight in 10 mL of LB media (10 g NaCl, 10 g select peptone 140, and 5 g yeast extract in one liter ddH$_2$0). The samples were centrifuged and then concentrated in about 0.2 mL of LB media. The concentrated samples were combined and incubated with slow rotation for 30 minutes at 30° C., and were then plated on LB agar plates that contained streptomycin (50 µg/mL) and tetracycline (50 µg/mL). (Ampicillin, streptomycin, tetracycline; and all other chemicals were purchased from Sigma Chemical (St. Louis, Mo.) unless otherwise indicated.) Recipient cells were resistant to streptomycin and donor cells were resistant to tetracycline; only conjugates, which contained both resistance genes, were able to grow on the LB agar plates that contained streptomycin (50 µg/mL) and tetracycline (50 µg/mL).

Putative conjugates were screened for Lambda phage sensitivity using a cross streak technique, in which putative colonies were cross-streaked on an LB agarose plate (streptomycin, 50 µg/mL, and tetracycline, 50 µg/mL) that had been streaked with live Lambda phage. The streaked conjugate colonies were streaked perpendicular to the Lambda phage streak; if a conjugate was sensitive to Lambda phage infection then, upon contact with the Lambda phage streak, there was cell lysis and thus less or no bacterial growth. Thus, in the case of conjugates that were sensitive to Lambda phage, there was deceased bacterial growth "downstreak" from the phage streak.

The conjugate *E. coli* that were found to be sensitive to Lambda phage infection were then used to create Lambda lysogens. Lysogenization is a process during which Lambda phage incorporates its genome, including exogenous genes added thereto, into a specific site on the chromosome of its *E. coli* host cell.

The DE3 gene, which is present in the genome of the Lamda phage used to create lysogens, encodes RNA polymerase from bacteriophage T7. Lysogenation was carried out using the DE3-Lysogenation kit (Novagen, Madison, Wis.) essentially according to the manufacturer's instructions. A T7 polymerase dependent tester phage was used to confirm the presence and expression of the DE3 gene on the bacterial chromosome. The T7-dependent tester phage can only form plaques on a baterial known in the presence of T7 polymerase. The phage uses a T7 promoter for expression of its essential genes. Therefore in a plaque-forming assay only cells which express T7 polymerase can be lysed by the tester phage and only these cells will allow for the formation of plaques. As is described in more detail herein, episomal expression elements that are used in minicells may be designed such that transcription and translation of a cloned gene is driven by T7 RNA polymerase by utilizing expression sequences specific for the T7 RNA polymerase.

Example 2

Cloning of Rat Edg-1 into the pCAL-C Expression Vector

Materials

Taq Polymerase, PCR Buffers, and PCR reagents were purchased from Roche Molecular Biochemicals (Indianapolis, Ind.). All restriction enzymes were purchased from Gibco BRL (Grand Island, N.Y.) and Stratagene (La Jolla, Calif.). QIAprep mini and maxi kits, PCR purification Kits, RNeasy miniprep kits, and the One Step RT-PCR Kit were purchased from QIAGEN (Valencia, Calif.). The Geneclean Kit was purchased from BIO 101 (Carlsbad, Calif.). IPTG (isopropyl-beta-D-thiogalactopyranoside), T4 DNA Ligase, LB Media components and agarose were purchased from Gibco BRL. The pCAL-c prokaryote expression vector and competent cells were purchased from Stratagene.

The pCAL-c expression vector has a structure in which an ORF may be operably linked to a high-level (but T7 RNA polymerase dependent) promoter, sequences that bind the *E. coli Lac repressor, and the strong T7* gene 10 ribosome-binding site (RBS). The LacI repressor is also encoded by an expressed from to pCAL-c vector. As long as it is bound to its recognition sequences in the pCAL-c expression element, the lac repressor blocks transcription from the T7 promoter. When an inducing agent, such as IPTG is added, the lac repressor is released from its binding sites and transcription proceeds from the T7 protmoter, provided the T7 RNA polymerase is present. After induction, the cloned and expressed protein may constitute the majority of newley expressed cellular proteins due to the efficient transcription and translation processes of the system.

Amplification

The first step in cloning rat Edg-1 (rEDG-1) into an expression vector was to design primers for amplification via PCR (polymerase chain reaction). PCR primers were designed using the rat Edg-1 sequence (Nakajima et al., Biophy, J. 78:319 A, 2000) in such a manner that they contained either sites for NheI (GCTAGC) or BamHI (GGATCC) on their five prime ends. The upstream primer had the sequence of SEQ ID NO:31. The three prime downstream primer (SEQ ID NO:32) also contained a stop codon, as the pCAL-c vector contains a Calmodulin Binding Protein (CBP) "tag" at its carboxyl terminus which was not intended to be incorporated into the rat Edg-1 polypeptide in this expression construct. The primer and resulting PCR products were designed so that the five prime end of the rat Edg-1 ORF was in frame with the methionine start codon found in the pCAL-c vector.

Oligonucleotide Primer Sequences for Cloning into pCAL-C:

```
Edg1/pCAL-c construct primers:

Upstream primer (SEQ ID NO: 31)
5'-AATTGCTAGCTCCACCAGCATCCCAGTGGTTA-3'
Downstream primer (SEQ ID NO: 32)
5'-AATTGGATCCTTAAGAAGAAGAATTGACGTTT-3'
Edg1/CBP fusion construct primers:

Upstream primer (SEQ ID NO: 31)
5'-AATTGCTAGCTCCACCAGCATCCCAGTGGTTA-3'
Downstream primer (SEQ ID NO: 33)
5'-AATTGGATCCAGAAGAAGAATTGACGTTTCCA-3'
Edg1/His6 construct primers:

Upstream primer (SEQ ID NO: 31)
5'-AATTGCTAGCTCCACCAGCATCCCAGTGGTTA-3'
Downstream primer (SEQ ID NO: 34)
5'-AATTGGATCCTTAATGATGATGATGATGAT
GAGAAGAAGAATTGACGTTTCC-3'
Edg3/rtPCR primers:

Upstream primer (SEQ ID NO: 35)
5'-TTATGGCAACCACGCACGCGCAGG-3'
Downstream primer (SEQ ID NO:36)
5'-AGACCGTCACTTGCAGAGGAC-3'
Edg3/pCAL-c construct primers:

Upstream primer (SEQ ID NO: 37)
5'-AATTGCTAGCACGCACGCGCAGGGGCACCCGC-3'
Downstream primer (SEQ ID NO: 38)
5'-AATTGGTACCTCACTTGCAGAGGACCCCATTCTG-3'
Edg3/His6 construct primers:

Upstream primer (SEQ ID NO: 39)
5'-AATTGCTAGCACGCACGCGCAGGGGCACCCGC-3'
Downstream primer (SEQ ID NO: 16)
5'-AATTGGTACCTCAATGATGATGATGATGAT
GCTTGCAGAGGACCCCATTCTG-3'
GFP/pCAL-c construct primers:

Upstream primer (SEQ ID NO: 40)
5'-GGTCGCCACCATGGTGAGCAA-3'
Downstream primer (SEQ ID NO: 41)
5'-TTAAGGATCCTTACTTGTACAGCTCGTCCAT-3'
GFP/CBP construct primers:

Upstream primer (SEQ ID NO: 42)
5'-GGTCGCCACCATGGTGAGCAA-3'
Downstream primer (SEQ ID NO: 43)
5'-TTAAGGATCCCTTGTACAGCTCGTCCATGCC-3'
```

Notes:
Restriction endonuclease sites are underlined
Stop codons are double underlined The primers were used to amplify the rEdg-1 DNA ORF using the polymerase chain reaction (PCR). The template used for amplification was mRNA isolated from rat muscle tissue using the RNeasy Miniprep Kit (Qiagen) and was carried out essentially according to the manufacturer's protocol. Both the rtPCR and PCR amplification steps were carried out in a single reaction using the One Step RT-PCR Kit (Qiagen). The resulting rat Edg-1 PCR fragment was purified using the PCR Purification Kit (Qiagen). The amplified double stranded rEdg-1 DNA sequence contained the NheI site at the 5-prime end and the BamHI site at the 3-prime end. This amplified rEdg-1 fragment was used for cloning into the pCAL-c expression vector.

The pCAL-c expression vector contains NcoI, NheI, and BamHI restriction sites in its multiple cloning site. In order to insert rEdg-1-encoding sequence into the expression vector, the rEdg-1 PCR fragment and the pCAL-c expression vector were digested with NheI and BamHI restriction enzymes for one hour at 37° C. The reaction mixture for the digestion step consisted of 1 µg of DNA, 1× restriction buffer, and 1 µL of each enzyme. The reaction mixture was brought to a final volume of 20 µL with ddH$_2$O (dd, double distilled). After 45 minutes, 1 µL of Calf Intestine Alkaline Phosphatase (CIAP) was added to the pCAL-c reaction mixture in order to remove the terminal phosphates from the digested plasmid DNA. The reactions were incubated for an additional 15 minutes at 37° C. The digested DNA samples were then run on a 1% TAE (Tris-acetate/EDTA electrophoresis buffer) agarose gel at 130 volts for 45 minutes. The bands were visualized with UV light after the gel was stained with ethidium bromide.

The appropriate bands were cut out of the gel for purification using the Geneclean Kit (BIO101). The Purified DNA fragments were then quantified on a 1% TAE agarose gel. For the ligation reaction, ratios of insert to vector of 6:1 and 3:1 were used. A negative control comprising vector only was also included in the ligation reactions. The reaction mixtures contained insert and vector DNA, 4 µL Ligase buffer, and 2 µL Ligase. The reaction was brought up to a final volume of 20 µL with ddH$_2$O. The ligation was carried out at room temperature for about 2 hours. Ten (10) µL of the ligation reaction mixture was used for subsequent transformation steps.

Ligated DNA was introduced into Epicurian Coli XL1-Blue competent cells using the heat shock transformation technique as follows. The ligation mixture was added to 100 µL of competent cells, placed on ice, and was incubated for about 30 minutes. The cells were then heat shocked at 37° C. for 1 minute and put back on ice for 2 minutes. Following heat shock, 950 µL, of room temperature LB media was added to the cells and the cells were shaken at 37° C. for 1 hour. Following the 1-hour agitation the cells were pelleted for one minute at 12000 rpm in a Eppendorf 5417C microcentrifuge. The supernatant was carefully poured off so that about 200 µL remained. The cells were then resuspended in the remaining LB media and spread on 100×15 mm LB agarose plates containing 50 µg/mL ampicilin. The plates were incubated overnight at 37° C. Colonies were counted the following day, and the ratio of colonies between the negative control and the ligated samples was determined. A high ratio of the number of colonies when the ligation mixture was used to transform cells, as contrasted to the number of negative control colonies indicated that the cloning was successful. Transformed colonies were identified, isolated, and grown overnight in LB media in the presence of ampicillin. The resulting bacterial populations were screened for the presence of the Edg-1-pCAL-c expression construct.

Plasmid DNA was isolated from the cells using the QIAprep Spin Miniprep Kit (Qiagen). Isolated Edg-1-pCAL-c constructs were screened using the restriction enzyme ApaI, which digests the Edg-1-pCAL-c construct at two different sites: one in the Edg-1 coding sequence and one in the pCAL-c vector itself. The plasmid preparations were digested with ApaI electrophoresed on a 1% TAE agarose gel and visualized using uv light and ethidium bromide staining. The predicted sizes of the expected DNA fragments were 2065 bp and 4913 bp. As shown in FIG. 3, bands of the predicted size were present on the gel. The entire Edg-1-pCAL-c construct was sequenced in order to confirm its structure. This expression construct, a pCAL-c derivative that contains the rat Edg-1 ORF operably linked to a T7 promoter and lac repressor binding sites, is designated "prEDG-1" herein.

Example 3

Construction of Rat Edg-1-CBP Fusion Protein

In order to detect rat Edg-1 protein expression, rEdg-1 coding sequences were cloned into the pCAL-c vector in frame with a CBP fusion tag. The cloning strategy for the rEdg-1-CBP construct was performed essentially as described for the Edg-1-pCAL-c construct with the following differences. The PCR primers (SEQ ID NOS:3 and 5) were as described for the Edg-1-pCAL-c cloning except for the omission of the stop codon in the downstream primer (SEQ ID NO:33). The removal of the stop codon is required for the construction of the Edg-1-CBP fusion protein. The pCAL-c vector is designed so that, when the BamHI site is used for insertional cloning, and no stop codon is present in an ORF inserted into the pCAL-c expression vector the cloned ORF will be in-frame with the CBP fusion tag. Because the three prime downstream primer did not contain a stop codon, a CBP fusion tag could be cloned in-frame with the Edg-1 ORF. Other cloning steps were performed essentially as described before. The resulting plasmid, a pCAL-c derivative that comprises an ORF encoding a rat Edg-1-CBP fusion protein operably linked to a T7 promoter and lac repressor binding sites, is designated "prEDG-1-CBP" herein.

Example 4

Cloning of a HIS-Tagged Rat Edg-1 into pCAL-C Expression Vector

The rEdg-1 protein was manipulated to generate a fusion protein having a 6×His tag at its carboxyl terminus. A "6×His tag" or "His tag" is an amino acid sequence consisting of six contiguous histidine residues that can be used as an epitope for the binding of anti-6×His antibodies, or as ligand for binding nickel atoms. The His-tagged rEdg-1 fusion protein is used to detect rEdg-1 protein expression in the minicell expression system environment.

The rEdg-1-6×His construct was cloned using the strategy described above for the construction of the rEdg-1-pCAL-c expression construct (prEDG-1), with the upstream primer having the sequence of SEQ ID NO:3, but with the exception that the three prime downstream primer (SEQ ID NO:34) was designed to contain six histidine codons followed by a stop codon. The 18 base pair 6×His tag was incorporated into the carboxyl terminus of the Edg-1 protein as expressed from the pCAL-c vector. Subsequent cloning procedures (PCR, restriction digest, gel purification, ligation, transformation, etc.) were performed as described previously for the Edg-1-pCAL-c construct (prEDG-1). The resulting plasmid, a pCAL-c derivative that comprises an ORF encoding a carboxy-terminal His-tagged rat Edg-1-CBP fusion protein operably linked to a T7 promoter and lac repressor binding sites, is designated "prEDG-1-6×His" herein.

Example 5

Amplification and Cloning of Rat Edg-3 Sequences

The Edg-3 full length coding sequence was amplified via PCR from rat skeletal muscle mRNA using primers (SEQ ID NOS:35 and 36) designed from the known mouse sequence (Genbank accession NM_010101). The mRNA used as a template for the amplification reaction was isolated using the RNeasy Miniprep Kit (Qiagen). Both the rtPCR and PCR amplification steps were carried out in a single reaction using the One Step RT-PCR Kit (Qiagen). The rEdg-3 PCR products were visualized with UV after electrophoresis in 1% TAE agarose gels and ethidium bromide staining.

The predicted size of the amplified PCR products is 1145 base pairs. An appropriately-sized DNA band was isolated from the TAE gel and purified using the Geneclean Kit (BIO101). The purified band was ligated to the pCR3.1 vector using the TA-cloning kit (Invitrogen). Other cloning steps were carried out as described previously for the cloning of the rEdg-1-pCAL-c construct (prEDG-1) with the exception that the samples were screened using the EcoRI restriction enzyme. The expected sizes of the digested bands were 1145 base pairs and 5060 base pairs. Positive clones were analyzed by automated sequencing. The nucleotide sequences were analyzed using BLAST searches from the NCBI web site (www.ncbi.nlm.nih.gov/). The predicted full length rat Edg-3 amino acid sequence was assembled from the nucleotide sequencing data using in silico translation. The pCR3.1 vector comprising the rat Edg-3 ORF is designated "pCR-rEDG-3" herein.

Example 6

Cloning of Rat Edg-3 Coding Sequences into the pCAL-C Expression Vector

In order to express it in the minicell expression system, the rat Edg-3 ORF was cloned into the pCAL-c expression vector. The cloning strategy used was as described above for the cloning of the rat Edg-1 gene into the pCAL-c vector with the following exceptions. The primers used for PCR amplification were designed from the rat Edg-3 sequence and contained sites for the restriction enzymes NheI and KpnI (GG-TACC). The NheI site was added to the five prime upstream primer (SEQ ID NO:37) and the KpnI site was added to the three prime downstream primer; SEQ ID NO:38). The NheI and KpnI restriction enzymes were used for the digestion reaction. The reaction mixture for the digestion step consisted of 1 µg of DNA, 1× restriction buffer (provided with the enzyme), and 1 µL of each enzyme. Plasmid preparations were screened by digestion with NheI and KpnI. The digested plasmid DNA was electrophosesed on a TAE agarose gel and visualized by UV after staining with ethidium bromide. The resultant band sizes were predicted to be 1145 base pairs and 5782 base pairs. The positive plasmid clones were analyzed with automated sequencing. The resulting plasmid, a pCAL-c derivative that comprises an ORF encoding a rat Edg-3 protein operably linked to a T7 promoter and lac repressor binding sites, is designated "pEDG-3" herein.

Example 7

Cloning of a HIS-Tagged Rat Edg-3 into the pCAL-C Expression Vector

In order to detect expression of the rat Edg-3 protein in the minicell expression system, the rat Edg-3 coding sequence was manipulated so as to contain a 6×His tag at the carboxyl terminus of the protein. The cloning strategy used to create this construct was essentially the same as described above for the rEdg-3-pCAL-c (prEDG-3) construct cloning, with the upstream primer having the sequence of SEQ ID NO:37, with the exception that the three-prime downstream primer (SEQ ID NO:18) was designed to contain a 6×His coding sequence followed by a stop codon, which allowed for the incorporation of the 6×His amino acid sequence onto the carboxyl terminus of the Edg-3 receptor protein. Other cloning and screening steps were performed as described above. The resulting plasmid, a pCAL-c derivative that comprises an ORF encoding a carboxy-terminal His-tagged rat Edg-3 fusion protein operably linked to a T7 promoter and lac repressor binding sites, is designated "prEDG-3-6×His" herein.

Example 8

GFP Cloning into pCAL-C Expression Construct

Cloning of GFP-encoding nucleotide sequences into the pCAL-c vector was performed in order to produce an expression construct having a reporter gene that can be used to detect protein expression (GFP, green flourescent protein). The cloning strategy used was essentially the same as the cloning strategy described above with the following exceptions. The template used for PCR amplification was the peGFP plasmid "construct" (GFP construct sold by Clontech). The primers used for amplification were designed from the GFP coding sequence and contained sites for the restriction enzymes NcoI and BamHI. The NcoI site was added to the five prime upstream primer (SEQ ID NO:40) and the BamHI site was added to the three prime downstream primer; see SEQ ID NO:41) The NcoI and BamHI restriction enzymes were used for the digestion reaction. The reaction mixture for the digestion step consisted of 1 µg of DNA, 1× restriction buffer (provided with the enzyme), and 1 µL of each enzyme. The screening of the plasmid preparations was carried out using NcoI and BamHI. Digested plasmid preparations were electrophoresed and visualized on TAE agarose gels with UV after staining with ethidium bromide. Restriction products having the predicted sizes of 797 and 5782 base pairs were seen. Positive plasmid clones were sequenced using an automated sequencer. The resulting plasmid, a pCAL-c derivative that comprises an ORF encoding a rEdg-3-GFP fusion protein operably linked to a T7 promoter and lac repressor binding sites, is designated "prEDG-3-GFP" herein.

Example 9

Design Construction of Control Expression Elements

Control expression elements used to detect and quantify expression of proteins in minicells were preposed. These controls direct the expression of detectable proteins. An expression element used as positive control is pPTC12, which is supplied with the pCAL-c expression vector from Stratagene. This construct contains an ORF encoding a fusion protein comprising beta-galactosidase linked to CBP. Induction of expression of pTC12 should result in the production of a protein of about 120 kD, and this protein is detected via its enzymatic activity or by using antibodies directed to epitopes on the beta-galactosidase or CBP polypeptide.

A GFP fusion construct was created and used as a positive control for the CBP detection kit. This construct was a positive control for induction of protein expression in the minicell expression system. The cloning strategy used to create the construct was essentially the same as that used for the cloning of the GFP into the pCAL-c expression vector, with the exception that the three prime downstream primer did not contain a stop codon; this allowed for the in frame incorporation of the CBP fusion tag to the GFP protein. The upstream primer had the sequence of SEQ ID NO:42, and the downstream primer had the sequence SEQ ID NO:43. The nucleotide sequence of the expression element was confirmed using an automated sequencer. The resulting plasmid, a pCAL-c derivative that comprises an ORF encoding GFP operably linked to a T7 promoter and lac repressor binding sites, is designated "pGFP-CBP" herein.

Example 10

Introduction of pCAL-C Expression Constructs into the MC-T7 *Escherichia Coli* Strain The MC-T7 *E. coli* strain was made competent using the $CaCl_2$ technique. In brief, cells were grown in 40 mL LB medium to an $OD_{600}$ of 0.6 to 0.8, and then centrifuged at 8000 rpm (7,700 g) for 5 min at 4° C. The pellet was resuspended in 20 mL of cold $CaCl_2$ and left on ice for five minutes. The cells were then centrifuged at 8000 rpm (7,700 g) for 5 min at 4° C. The cell pellet was resuspended in 1 mL of cold $CaCl_2$ and incubated on ice for 30 min. Following this incubation 1 mL of 25% glycerol was added to the cells and they were distributed and frozen in 200 µL aliquots. Liquid nitrogen was used to freeze the cells. These cells subsequently then used for the transformation of expression constructs.

Example 11

Preparation of Minicells

To some degree, the preparation of minicells varied according to the type of expression approach that is used. In general, there are two such approaches, although it should be noted from the outset that these approaches are neither limiting nor mutually exclusive. One approach is designed to isolate minicells that already contain an expressed therapeutic protein or nucleic acid. Another approach is designed to isolate minicells that will express the protein or nucleic acid in the minicell following isolation.

*E. coli* are inoculated into bacterial growth media (e.g., Luria broth) and grown overnight. After this, the overall protocol varies with regards to methods of induction of expression. The minicell producing cultures used to express protein post isolation are diluted and grown to the desired $OD_{600}$ or OD450, typically in the log growth phase of bacterial cultures. The cultures are then induced with IPTG and then isolated. The IPTG concentration and exposure depended on which construct was being used, but was usually about 500 µM final for a short time, typically about 4 hours. This treatment results in the production of the T7 polymerase, which is under control of the LacUVR5 promoter, which is repressed by the LacI repressor protein. IPTG relieves the LacI repression and thus induces expression from the LacUVR5 promoter which controls expression of the T7 polymerase from the chromosome. This promoter is "leaky" that is, there is always a basal level of T7 polymerase which can be selected for or against so that the induction before isolation is not required. (This induction step is not required if a non-T7 expression system is used, as the reason for this step is to express the T7 RNA polymerase in the minicell-producing cells so that the polymerase and molecules segregate with the minicell.)

The E. coli cultures that produce minicells containing a therapeutic protein or nucleic acid have different induction protocols. The overnight cultures are diluted as described above; however, in the case of proteins that are not toxic to the parent cells, this time the media used for dilution already contains IPTG. The cultures are then grown to mid-log growth and minicells are isolated. These cultures produce the therapeutic protein or nucleic acid as they grow, and the minicells derived therefrom contain the therapeutic protein or nucleic acid.

Altenatively or additionally, IPTG is added and expression is induced after the isolation of minicells. In the case of non-toxic proteins or nucleic acids that are expressed from expression elements in minicells, this treatment enhances production of the eposimally encoded gene product. In the case of toxic gene products induction post-isolation is preferred.

Example 12

Minicell Isolation

Minicells were isolated from the minicell producing MC-T7 strain of E. coli using centrifugation techniques. The protocol that was used is essentially that of Jannatipour et al. (Translocation of Vibrio Harveyi N,N'-Diacetylchitobiase to the Outer Membrane of Escherichia Coli, J. Bacteriol. 169: 3785-3791, 1987) and Matsumura et al. (Synthesis of Mot and Che Products of Escherichia coli Programmed by Hybrid ColE1 Plasmids in Minicells, J. Bacteriol. 132:996-1002, 1977).

In brief, MC-T7 cells were grown overnight at 37° C. in 2 to 3 mL of LB media containing ampicillin (50 µg/mL), streptomycin (50 µg/mL), and tetracycline (50 µg/mL) (ampicillin was used only when growing MC-T7 cells containing a pCAL-c expression construct). The cells were diluted 1:100 in a total volume of 100 to 200 mL LB media with antibiotics, and grown at 37° C. until they reached an $OD_{600}$ of 0.4 to 0.6, which is roughly beginning of the log growth phase for the MC-T7 E. coli. During this incubation the remainder of the overnight culture was screened for the presence of the correct expression construct using the techniques described above. When the cultures reached the appropriate $OD_{600}$ they were transferred to 250 mL GS3 centrifuge bottles and centrifuged (Beckman centrifuge) at 4500 rpm (3,500 g) for 5 min. At this point the supernatant contains mostly minicells, although a few relatively small whole cells may be present.

The supernatant was transferred to a clean 250 mL GS3 centrifuge bottle and centrifuged at 8000 rpm (11,300 g) for 10 min. The pellet was resuspended in 2 mL of 1×BSG (10×BSG: 85 g NaCl, 3 g $KH_2PO_4$, 6 g $Na_2HPO_4$, and 1 g gelatin in 1 L $ddH_2O$) and layered onto a 32 mL 5 to 20% continuous sucrose gradient. The sucrose gradient was made with sucrose dissolved in 1×BSG.

The sucrose gradient was then loaded in a Beckman SW24 rotor and centrifuged in a Beckman Ultracentrifuge at 4500 rpm (9,000 g) for 14 min. Following ultracentrifugation a single diffuse band of minicells was present. The top two thirds of this band was aspirated using a 10 mL pipette and transferred to a 30 mL Oakridge tube containing 10 mL of 1×BSG. The sample was then centrifuged at 13,000 rpm (20,400 g) for 8 min. Following centrifugation, the pellet was resuspended in 2 mL 1×BSG, and the resuspended cells were loaded onto another 5 to 20% sucrose gradient. This sucrose gradient was centrifuged and the minicells were collected as described above. The sucrose gradient procedure was repeated a total of three times.

Following the final sucrose gradient step the entire minicell band was collected from the sucrose gradient and added to a 30 mL Oakridge tube that contained 10 mL of MMM buffer (200 mL 1×M9 salts, 2 mL 20% glucose, and 2.4 mL DIFCO Methionine Assay Medium). This minicell solution was centrifuged at 13,000 rpm (20,400 g) for 8 min. The pellet was resuspended in 1 mL of MMM Buffer.

The concentration of minicells was determined using a spectrophotometer. The $OD_{450}$ was obtained by reading a sample of minicells that was diluted 1:100.

Example 13

Other Methods to Prepare and Isolate Minicells

By way of non-limiting example, induction of E. coli parental cells to form minicells may occur by overexpression of the E. coli ftsZ gene. To accomplish this both plasmid-based and chromosomal overexpression constructs were created that place the ftsZ gene under the control of various regulatory elements (Table 6).

TABLE 6

REGULATORY CONSTRUCTS CONTROLLING FTSZ EXPRESSION.

| Regulatory region | inducer | [inducer] | SEQ ID NO.: |
|---|---|---|---|
| Para::ftsZ | Arabinose | 10 mM | 1, 3 |
| Prha::ftsZ | Rhamnose | 1 mM | 2, 4 |
| Ptac::ftsZ | IPTG | 30 µM | 5, Garrido et al.[a] |

[a]Garrido, T. et al. 1993. Transcription of ftsZ oscillates during the cell cycle of Escherichia coli.

Oligonucleotide names and PCR reactions use the following format:

"gene-1" is N-terminal, 100% homology oligo for chromosomal or cDNA amplification "gene-2" is C-terminal, 100% homology oligo for chromosomal or cDNA amplification "gene-1-RE site" is same sequence as gene-1 with additional residues for remainder of sequence, RE sites, and/or chimeric fusions.

"gene-2-RE site" is same sequence as gene-1 with additional residues for remainder of sequence, RE sites, and/or chimeric fusions.

Use "gene-1, 2" combo for chromosomal/cDNA amplification and "gene-1 RE site, gene-2-RE site" to amplify the mature sequence from the "gene-1, 2" gel-purified product.

TABLE 7

OLIGONUCLEOTIDE PRIMER SEQUENCES
FOR TABLE 6 CONSTRUCTS

| SEQ ID NO.: | Primer name | 5' to 3' sequence |
|---|---|---|
| 44 | FtsZ-1 | CCAATGGAACTTACCAATGACGCGGG |
| 45 | FtsZ-2 | CTTGCTTACGCAGGAATGCTGGG |
| 46 | FtsZ-1-PstI | CGCGGCTGCAGATGTTTGAACCAATG GAACTTACCAATGACGCGG |
| 47 | FtsZ-2-XbaI | GCGCCTCTAGATTATTAATCAGCTTG CTTACGCAGGAATGCTGGG |

Table 7 Oligonucleotide Sequences are for Use in Cloning ftsZ into SEQ ID NO.:1 and 2 (Insertions of ftsZ Behind the Arabinose Promotor (SEQ ID NO.: 1) and the Rhamnose Promotor (SEQ ID NO.: 2).

TABLE 8

OLIGONUCLEOTIDE PRIMER SEQUENCES FOR FTSZ
CHROMOSOMAL DUPLICATION CONSTRUCTS

| SEQ ID NO.: | Primer name | 5' to 3' sequence |
|---|---|---|
| 48 | Kan-1 | GCTAGACTGGGCGGTTTTATGGACAGCAAGC |
| 49 | Kan-2 | GCGTTAATAATTCAGAAGAACTCGTCAAGAA GGCG |
| 50 | Kan-1-X-frt | GCGCCTACTGACGTAGTTCGACCGTCGGACT AGCGAAGTTCCTATACTTTCTAGAGAATAGG AACTTCGCTAGACTGGGCGGTTTTATGGACA GCAAGC |
| 51 | Kan-2-intD-frt | CAAGATGCTTTGCCTTTGTCTGAGTTGATAC TGGCTTTGGGAAGTTCCTATTCTCTAGAAAG TATAGGAACTTCGCGTTAATAATTCAGAAGA ACTCGTCAAGAAGGCG |
| 52 | AraC-1 | CGTTACCAATTATGACAACTTGACGG |
| 53 | RhaR-1 | TTAATCTTTCTGCGAATTGAGATGACGCC |
| 54 | LacI$^q$-1 | GTGAGTCGATATTGTCTTTGTTGACCAG |
| 55 | Ara-1-intD | GCCTGCATTGCGGCGCTTCAGTCTCCGCTGC ATACTGTCCCGTTACCAATTATGACAACTTG ACGG |
| 56 | RhaR-1-intD | GCCTGCATTGCGGCGCTTCAGTCTCCGCTGC ATACTGTCCTTAATCTTTCTGCGAATTGAGA TGACGCC |
| 57 | LacI$^q$-1-intD | GCCTGCATTGCGGCGCTTCAGTCTCCGCTGC ATACTGTCCTTAATAAAGTGAGTCGATATTG TCTTTGTTGACCAG |
| 58 | FtsZ-1-X | GCCTGCATTGCGGCGCTTCAGTCTCCGCTGC ATACTGTCCCGTTACCAATTATGACAACTTG ACGG |

In like fashion, the ftsZ gene was amplified from SEQ ID NO.: 1, 2 and Ptac::ftsZ (Gamido, T. et al. 1993. Transcription of ftsZ oscillates during the cell cycle of *Escherichia coli*. EMBO J. 12:3957-3965) plasmid and chromosomal constructs, respectively using the following oligonucleotides:

For amplification of araC through ftsZ of SEQ ID NO.: 1 use oligonucleotides:
AraC-1
FtsZ-2

For amplification of rhaR through ftsZ of SEQ ID NO.: 2 use oligonucleotides:
RhaR-1
FtsZ-2

For amplification of lacIq through ftsZ of Ptac::ftsZ (Gamido, T., et al.) use oligonucleotides:
lacI$^q$-1
ftsZ-2

The above amplified DNA regions were gel-purified and used as template for the second round of PCR using oligonucleotides containing homology with the *E. coli* chromosomal gene intD and on the other end with random sequence termed "X". Oligonucleotides used in this round of PCR are shown below:

For amplification of araC through ftsZ from SEQ ID NO.: 1 to contain homology to intD and the random X use oligonucleotides:
AraC-1-intD
FtsZ-1-X For amplification of rhaR through ftsZ from SEQ ID NO.: 2 to contain homology to intD and the random X use oligonucleotides:
RhaR-1-intD
FtsZ-1-X For amplification of lacIq through ftsZ from Ptac::ftsZ to contain homology to intD and the random X use oligonucleotides: LacIq-1-intD
FtsZ-1-X The PCR products from these PCR reactions are as shown below:
intD-araC-Ara promotor-ftsZ-"X"
intD-rhaRS-Rha promotor-ftsZ-"X"
intD-lacI$^q$-Ptac promotor-ftsZ-"X"

To amplify the mature complexes, the following regions were mixed and amplified with the coupled oligonucleotide sequence primers:

SEQ ID NO.: 3 WAS PRODUCED USING:
intD-araC-Ara promotor-ftsZ-"X"
"X"-frt-Kan-frt-intD AraC-1-intD
Kan-2-intD-frt ↓ intD-araC-Ara promotor-ftsZ-"X"-frt-Kan-frt-intD

SEQ ID NO.: 4 WAS PRODUCED USING:
intD-rhaRS-Rha promotor-ftsZ-"X"
"X"-frt-Kan-frt-intD RhaR-1-intD
Kan-2-intD-frt ↓ intD-rhaRS-Ara promotor-ftsZ-"X"-frt-Kan-frt-intD

SEQ ID NO.: 5 WAS PRODUCED USING:
intD-lacI$^q$-Ptac promotor-ftsZ-"X"
"X"-frt-Kan-frt-intD lacI$^q$-1-intD
Kan-2-intD-frt ↓ intD-lacI$^q$-Ptac promotor-ftsZ-"X"-frt-Kan-frt-intD

These expression constructs may be expressed from the plasmid, placed in single copy, replacing the native ftsZ copy on the *E. coli* chromosome (Gamido, T., et al. 1993. Transcription of ftsZ oscillates during the cell cycle of *Escherichia coli*. EMBO J. 12:3957-3965), or in duplicate copy retaining the native ftsZ copy while inserting one of the expression constructs in Table 6 into the intD gene on the same chromosome. Chromosomal duplications were constructed using the RED recombinase system (Katsenko, K. A., and B. L. Wanner. One-Step Inactivation of Chromosomal Genes in *Escherichia coli* K-12 Using PCR Products. Proc. Natl. Acad. Sci. 97:6640-6645. 2000) and are shown in SEQ ID NO 3-5. The later constructs allow native replication during non-minicell producing conditions, thus avoiding selective pressure during strain construction and maintenance. Furthermore, these strains provide defined points of minicell induction that improve minicell purification while creating conditions that allow strain manipulation prior to, during, and following minicell production. By way of non-limiting example these manipulations may be protein production that the cytoplasmic redox state, modify plasmid copy number, and/or produce chaperone proteins.

For minicell production, a minicell producing strain described in the previous section is grown overnight in Luria broth (LB) supplemented with 0.1% dextrose, 100 µg/ml ampicillin, and when using the single-copy ftsZ construct, 15 µM IPTG. All incubations were performed at 37° C. For minicell induction only, overnight strains are subcultured 1/1000 into the same media. If minicell induction is to be coupled with co-expression of other proteins that are controlled by a catabolite repression-sensitive regulator, dextrose was excluded. Minicell induction is sensitive to aeration and mechanical forces. Therefore, flask size, media volume and shake speed is critical for optimal yields. Likewise, bioreactor conditions must be properly regulated to optimize these production conditions.

In shake-flask cultures, strains are grown to early exponential (log) phase as monitored by optical density (OD) at 600 nm ($OD_{600}$ 0.05-0.20). (Bioreactor conditions may differ significantly depending on the application and yield desired). For minicell induction alone, early log phase cultures are induced with the appropriate inducer concentration shown in Table 6. For coupled co-expression, these cultures are induced as shown in Table 6 for the appropriate minicell regulator, while the coupled protein(s) is induced with the inducer appropriate for the regulator controlling the synthesis of that protein. Cultures are grown under the appropriate conditions and harvested during late log($OD_{600}$ 0.8-1.2). Depending on the application, minicell induced cultures may be immediately chilled on ice prior to purification, or maintained at room temperature during the harvesting process.

To separate minicells from viable, parental cells, cultures are subjected to differential centrifugation (Voros, J., and R. N. Goodman. 1965. Filamentous forms of *Erwinia amylovora*. Phytopathol. 55:876-879). Briefly, cultures are centrifuged at 4,500 rpm in a GSA rotor for 5 min. Supernatants are removed to a fresh bottle and centrifuged at 8,000 rpm for an additional 10 min to pellet minicells. Pelleted minicells (containing contaminating parental cells) are resuspended in 2 ml LB, LBD (LB supplemented with 0.1% dextrose), Min (minimal M63 salt media) (Roozen, K. J., et al. 1971. Synthesis of ribonucleic acid and protein in plasmid-containing minicells of *Escherichia coli* K-12. J. Bacteriol. 107:21-23), supplemented with 0.5% casamino acids) or MDT (minimal M63 salt media, supplemented with 0.5% casamino acids, 0.1% dextrose, and thiamine). Resuspended minicells are next separated using linear density gradients. By way of non-limiting example, these gradients may contain sucrose (Cohen A., et al. 1968. The properties of DNA transferred to minicells during conjugation. Cold Spring Harb. Symp. Quant. Biol. 33:635-641), ficol, or glycerol. For example, linear sucrose gradients range from 5-20% and are poured in LB, LBD, Minor MDT. Using a SW28 swinging bucket rotor, gradients are centrifuged at 4,500 rpm for 14 min. Banded minicells are removed, mixed with LB, LBD, Minor MDT, and using a JA-20 rotor are centrifuged at 13,000 rpm for 12 min. Following centrifugation, pellets are resuspended in 2 ml LB, LBD, Minor MDT and subjected to a second density gradient. Following the second density separation, banded minicells are removed from the gradient, pelleted as described, and resuspended in LB, LBD, Minor MDT for use and/or storage.

Purified minicells are quantitated using an $OD_{600}$ measurement as compared to a standard curve incorporating LPS quantity, minicell size, and minicell volume. Quantitated minicells mixtures are analyzed for contaminating, viable parental cells by plating on the appropriate growth media (Table 9).

TABLE 9

MINICELL PURIFICATION AND PARENTAL CELL QUANTITATION

| Purification | Total cells | Total parental cells | MC/PC ratio | Fold-purification |
|---|---|---|---|---|
| Before | $4.76 \times 10^{11}$ | $3.14 \times 10^{11}$ | 0.25/1 | — |
| After | $1.49 \times 10^{11}$ | $6.01 \times 10^{4}$ | $2.48 \times 10^{6}/1$ | $5.23 \times 10^{6}$ |

Example 14

Protoplast Formation

In order to allow a membrane receptor to be presented to the outside environment (displayed), minicells are made into protoplasts. In order to make the integral membrane protein receptors in the inner membrane more accessible for ligand binding, the outer membrane and cell wall were removed. The removal of the outer membrane and cell wall from *E. coli* whole cells and minicells to produce protoplasts was performed essentially according to previously described protocols with a few modifications (Birdsell et al., Production and Ultrastructure of Lysozyme and Ethylenediaminetetraacetate-Lysozyme Spheroplasts of *Escherichia coli*, J. Bacteriol. 93:427-437, 1967; Weiss et al., Protoplast Formation in *Escherichia Coli*, J. Bacteriol. 128:668-670, 1976. Both minicells and whole cells were processed the same way.

In brief, the cells were grown to mid-log phase and pelleted at room temperature (minicells were isolated from cultures in mid-log phase). The pellet was washed twice with 10 mM Tris. Following the second wash protoplast production may be performed using two approaches. In the first approach, following the second wash, the cells were resuspended in 100 mM Tris (pH 8.0) that contained 6-20% sucrose and put in a 37° C. waterbath (the Tris/sucrose buffer was pre-warmed to 37° C.). The volume used to resuspend the cells was determined by the following equation: (volume of cells×$OD_{450}$)/10=resuspension volume. After a 1 minute incubation, 2 mg/mL lysozyme was added to a final concentration of 5-100 µg/mL. The samples were then incubated for 12 minutes at 37° C. while being gently mixed. Next, 100 mM EDTA (pH 7) was slowly added over a period of 2.5 minutes (amount of EDTA added=1/00-1/10 volume of cells) followed by a 10 min incubation at 37° C. The protoplasts are also diluted from 20% sucrose down to either 10% or 5% sucrose, which facilitates the complete removal of the outer membrane and cell wall. The protoplasts thus generated were separated from the outer membrane and cell wall using a sucrose step gradient. A sucrose step gradient does not have a gradual increase in sucrose percentage; rather, it goes directly from one percent to the other. For example, protoplasts generated from whole cells are loaded on a step gradient that is made from 5% and 15% sucrose. The protoplasts spin through the 15% sucrose but the debris generated when making the protoplasts does not spin through the 15% sucrose. The protoplasts are thus separated from the debris. The second method to prepare protoplasts, following the second wash, $1 \times 10^9$ cells were resuspended with 50 mM Tris, pH 8.0 containing 0.5-50 mM EDTA and 6-20% sucrose. This mixture was incubated at 37° C. for 10 min. Following incubation, the mixture was centrifuged at 13,200 RPM in a microcentrifuge for 2 min. After centrifugation, the pellet was resuspened in 50 mM Tris, pH 8.0 containing 5-100 µg/ml lysozyme and 6-20% sucrose. This mixture was incubated at 37° C. for 10 min. Following incubation, the mixture was centrifuged at 13,200 RPM in a microcentrifuge for 2 min, resuspended in 50 mM Tris pH 8.0 containing 6-20% sucrose for use.

An alternative method to remove contaminating LPS is to use affinity absorption with an anti-LPS antibody (Cortex). To accomplish this, the anti-LPS antibody was coated on either an activated agarose or sepharose matrix (Sigma) or epoxy-coated magnetic M-450 beads (Dynal). The spheroplast/protoplast mixture was subjected to the antibody coated matrix either in batch or using column chromatographic techniques to remove contaminating LPS. Following exposure, the unbound fraction(s) was collected and re-exposed to fresh matrix. To monitor the efficiency of the protoplasting reaction and LPS removal, three constructs were used (Table 10).

TABLE 10

PROTOPLAST MONITORING CONSTRUCTS

| Construct | SEQ ID NO | Plasmid | SEQ ID NO | Inducible protein | Inducer |
|---|---|---|---|---|---|
| PMPX-5 | 6 | pMPX-32 | 7 | ΔphoA | Rhamnose |
| PMPX-5 | 6 | pMPX-53 | 8 | phoA | Rhamnose |
| PMPX-5 | 6 | pMPX-33 | 9 | toxR-phoA | Rhamnose |

TABLE 11

OLIGONUCLEOTIDE PRIMER SEQUENCES FOR TABLE 10 CONSTRUCTS

| SEQ ID NO.: | Primer name | 5' to 3' sequence |
|---|---|---|
| 59 | ΔphoA-1 | GCCTGTTCTGGAAAACCGGGCTGCTCAGGG |
| 60 | ΔphoA-2 | GCGGCTTTCATGGTGTAGAAGAGATCGG |
| 61 | ΔphoA-1-PstI | CCGCGCTGCAGATGCCTGTTCTGGAAAACCGGGCTGCTCAGGG |
| 62 | ΔphoA-2-XbaI | GCGCCTCTAGATTATTATTTCAGCCCCAGAGCGGCTTTCATGGTGTAGAAGAGATCGG |
| 63 | PhoA-1 | GTCACGGCCGAGACTTATAGTCGC |
| 64 | PhoA-2 | GCGGCTTTCATGGTGTAGAAGAGATCGG |
| 65 | PhoA-1-PstI | CCGCGCTGCAGATGTCACGGCCGAGACTTATAGTCGC |
| 66 | PhoA-2-XbaI | GCGCCTCTAGATTATTATTTCAGCCCCAGAGCGGCTTTCATGGTGTAGAAGAGATCGG |
| 67 | T-phoA-1-PstI | CCGCGCTGCAGATGAACTTGGGGAATCGACTGTTTATTCTGATAGCGGTCTTACTTCCCCTCGCAGTATTAC |

TABLE 11-continued

OLIGONUCLEOTIDE PRIMER SEQUENCES FOR TABLE 10 CONSTRUCTS

| SEQ ID NO.: | Primer name | 5' to 3' sequence |
|---|---|---|
|  |  | TGCTCATGCCTGTTCTGGAAAACCGGGCTGCTCAGGG |
| 68 | T-phoA-2-XbaI | GCGCCTCTAGATTATTATTTCAGCCCCAGAGCGGCTTTCATGGTGTAGAAGAGATCGG |

Oligonucleotides SEQ ID NOS.:59, 60, 61 and 62 were used to amplify phoA lacking a leader sequence (ΔphoA) form the *E. coli* chromosome. Once amplified, this region was inserted into SEQ ID NO.: 6 using PstI and XbaI to create SEQ ID NO.: 7.

Oligonucleotides SEQ ID NOS.:63, 64, 65 and 66 were used to amplify phoA containing a leader sequence (phoA) form the *E. coli* chromosome. Once amplified, this region was inserted into SEQ ID NO.: 6 using PstI and XbaI to create SEQ ID NO.: 8.

Oligonucleotides SEQ ID NOS.:59, 60, 67 and 68 were used to amplify phoA lacking a leader sequence (ΔphoA) form the *E. coli* chromosome and form a translational fusion between the transmembrane domain of toxR from *Vibrio cholerae*. Once amplified, this region was inserted into SEQ ID NO.: 6 using PstI and XbaI to create SEQ ID NO.: 9.

By co-expression of minicells and protein, minicells were prepared that contained cytoplasmic PhoA (pMPX-32 expresses phoA lacking a leader sequence [ΔphoA]), periplasmic PhoA (pMPX-53 expresses native phoA that exports to the periplasmic space), or inner membrane-bound PhoA (pMPX-33 expresses phoA lacking a leader sequence fused to the transmembrane domain (TMD) of the toxR gene product from *Vibrio cholerae*). Using these expressed proteins, the efficiency of minicell protoplasting was monitored (Table 12).

TABLE 12

EFFICIENCY OF MINICELL PROTOPLAST PREPARATION AND PURIFICATION

| Step | Location [a] | ΔPhoA | PhoA | T-PhoA | LPS total [b] |
|---|---|---|---|---|---|
| Minicell | Pellet | 100 | 100 | 100 | 100 |
| EDTA/lysozyme | Whole | 100 | 100 | 100 | 100 |
| 1$^{st}$ Anti-LPS | Pellet | 80 | 0 | 80 | 30 |
| 2$^{nd}$ Anti-LPS | Pellet | 60 | 0 | 60 | 0 |

[a] Measuring the location of protein being measured using an anti-BAP antibody (Sigma). Pellet refers to the presence of the expressed protein in the low-speed centrifugation pellet. These pellets contain only intact cellular bodies. Whole refers to the reaction mixture prior to low-speed centifugation.
[b] Measured using a slot-blot apparatus (Bio-Rad) using the anti-LPS antibody (Cortex)

The data suggests that periplasmic PhoA is lost during the preparation, while both cytoplasmic and membrane-bound PhoA are retained in a cellular body that lacks LPS. However, during this process ~40% of the total minicell content is lost.

Example 15

T7-Dependent Induction of Expression

Expression from the pCAL-c expression vector is driven from a T7 bacteriophage promoter that is repressed by the LacI gene product. Transcription of the DNA into mRNA, and subsequent translation of mRNA into proteins, does not occur as long as the LacI repressor is bound to the T7 promoter.

However, in the presence of IPTG, the LacI repressor does not bind the T7 promoter. Thus, induction of expression from pCAL-c sequences is dependent on the presence of IPTG. Slightly different protocols were used for the induction of *Escherichia coli* whole and for the induction of minicells. Slight differences are also present in the protocols for induction of minicells for $^{35}$S-methionine labeling of proteins in contrast to those for the induction of minicells for Western blot analysis. These induction protocols are described bellow.

For expression in *E. coli* whole cells, the cells were first grown overnight in 3 mL of LB and antibiotics. The cultures were screened for the presence of the desired expression element as previously described. Cultures containing the desired expression elements were diluted 1:100 and grown to an $OD_{600}$ of between 0.4 to 0.6. The culture size varied depending on the intended use of the cells. IPTG was then added to a final concentration of 200 μg/mL, and the cells were shaken at 30° C. for 4 hours. Following the induction, cells were harvested for analysis.

The induction of minicells was carried out as follows. The minicells were diluted in MMM buffer to 1 mL total volume according to the concentration obtained from the isolation procedure ($OD_{450}$ of about 0.5). The cells were then treated with 50 μg/mL of cycloserine for 30 minutes at 37° C. to stop whole cell growth. Following the cycloserine treatment the cells were provided with an amino acid, methionine, which the MMM buffer does not contain. For $^{35}$S-labeled protein induction $^{35}$S-methionine was added to the minicell sample whereas, for unlabeled protein induction unlabeled methionine was added. Fifteen (15) μCi of $^{35}$S-methionine (Amersham Pharmacia Biotech, Piscataway, N.J.) was added to the samples for radiolabeling and 5 μmol of methionine was added to the non-labeled minicell samples. Two hundred (200) μg/mL IPTG was also added to the minicell samples, which were then shaken at 30° C. for about 4 hours. Following induction, the minicells were harvested for further preparation or analysis.

Example 16

Western Blot Analysis

The CBP detection kit was purchased from Stratagene. SDS running buffer, 10% Tris-HCl ready gels, Kaleidoscope Pre-stained Standards, and Laemmli Sample Buffer were purchased from BIO RAD (Hercules, Calif.). GFP (FL) HRP antibodies were purchased from Santa Cruz Biotechnology (Santa Cruz, Calif.). Edg-3CT antibody an antibody directed to the carboxy terminus of was purchased from Exalpha Biologicals (Boston, Mass.). Anti-6×His antibody, positrope, and the WesternBreeze Kit were purchased from Invitrogen (Carlsbad, Calif.). Protocols were carried out essentially according to the manufacturer's instructions unless otherwise indicated.

Three different Western blot protocols were used to detect protein expression in both a minicell expression system and in a whole cell expression system. For both systems, the SDS-PAGE gel and the transfer protocols were essentially as follows. The samples were denatured by diluting the samples 1:1 in Laemmli buffer (BIORAD) and then sonicated for 10 min. The denatured samples were loaded onto a 10% Tris-Glycine gel (BIORAD) and electrophoresed at 130 V for about 1.5 hours in 1×SDS running buffer (BIORAD). The electrophoresed proteins were electrotransferred to nitrocellulose membranes at 0.5 Amps for 1.5 hours in Transfer Buffer (5.8 g Tris, 2.9 g glycine, 200 mL methanol, and 3.7 mL of 10% SDS). The nitrocellulose membranes comprising the transferred proteins were used for Western bloting.

GFP Western blots were carried out as follows. The nitrocellulose membrane was blocked for 2 hours with 5% milk in PBST (PBS buffer with 0.05% Tween). Following the blocking step the nitrocellulose membrane was washed twice with PBST. For the detection of GFP protein, an anti-GFP-HRP conjugated antibody (Santa Cruz Biotechnology) was used at a dilution of 1:3000 in PBST (HRP, horse radish peroxidase). The nitrocellulose membrane was incubated in the anti-GFP-HRP antibody solution for one hour and then washed twice with PBST. GFP proteins on the nitrocellulose membrane were detected and visualized using the ECL system (Amersham).

The His-tagged Edg-1 and Edg-3 proteins were detected using a mouse anti-6×His antibody from Invitrogen and the WesternBreeze chemoluminecent Kit (Invitrogen). The antibody was diluted 1:4000 in buffers provided by the WesternBreeze Kit. The WesternBreeze immunoblot was carried out essentially according to the manufacturer's protocol. The Edg-1-CBP and GFP-CBP fusion proteins were detected using the CBP detection Kit (Stratagene). All antibodies and substrates were provided in the Kit. FIG. 3 is a photo of the Western hybridization results showing the presence of Edg-1-6×His and Edg-3-6×His in minicells and parent cells.

Example 17

Methods to Induce Expression

Expression in minicells may proceed following purification of minicells and/or minicell protoplasts from parental cells and LPS constituents, repectively. However, for some applications it is suitable to co-express proteins of interest with minicell induction. For these approaches, one may use the protocol described in EXAMPLE 13 for expression of the phoA constructs. By way of non-limiting example, either of these approaches may be accomplished using one or more of the following expression constructs (Table 13).

TABLE 13

EXPRESSION CONSTRUCTS

| Plasmid | Regulatory element(s) | inducer | Plasmid | SEQ ID NO.: |
|---|---|---|---|---|
| pMPX-5 | rhaRS | Rhamnose | pUC-18 | 6 |
| pMPX-7 | uidR | β-glucuronate | pUC-18 | 10 |
| pMPX-8 | melR | Melibiose | pUC-18 | 11 |
| pMPX-18 | araC | Arabinose | pUC-18 | 12 |
| pMPX-6 | araC | Arabinose | pUC-18 | 13 |

TABLE 14

OLIGONUCLEOTIDE PRIMER SEQUENCES FOR TABLE 13 CONSTRUCTS

| SEQ ID NO.: | Primer name | 5' to 3' sequence |
|---|---|---|
| 69 | Rha-1 | GCGAATTGAGATGACGCCACTGGC |
| 70 | Rha-2 | CCTGCTGAATTTCATTAACGACCAG |
| 71 | Rha-1-HindIII | CGGCGAAGCTTAATTAATCTTTCTGCG AATTGAGATGACGCCACTGGC |
| 72 | Rha-2-PstI | CGCCGTAATCGCCGCTGCAGAATGTGA TCCTGCTGAATTTCATTAACGACCAG |

TABLE 14-continued

OLIGONUCLEOTIDE PRIMER SEQUENCES FOR TABLE 13 CONSTRUCTS

| SEQ ID NO.: | Primer name | 5' to 3' sequence |
|---|---|---|
| 73 | Uid-1 | CGCAGCGCTGTTCCTTTGCTCG |
| 74 | Uid-2 | CCTCATTAAGATAATAATACTGG |
| 75 | Uid-1-HindIII | GCCGCAAGCTTCGCAGCGCTGTTCCTTTGCTCG |
| 76 | Uid-2-PstI | CCAATGCATTGGTTCTGCAGGACTCCTCATTAAGATAATAATACTGG |
| 77 | Mel-1 | CGTCTTTAGCCGGGAAACG |
| 78 | Mel-2 | GCAGATCTCCTGGCTTGC |
| 79 | Mel-1-HindIII | GCCGCAAGCTTCGTCTTTAGCCGGGAAACG |
| 80 | Mel-2-SalI | CGGTCGACGCAGATCTCCTGGCTTGC |
| 81 | Ara-1 | CAAGCCGTCAATTGTCTGATTCG |
| 82 | Ara-2 | GGTGAATTCCTCCTGCTAGCCC |
| 83 | Ara-1-HindIII | GCGCCAAGCTTCAAGCCGTCAATTGTCTGATTCG |
| 84 | Ara-2-PstI | CTGCAGGGTGAATTCCTCCTGCTAGCCC |
| 85 | Ara-1-XhoI | GCTTAACTCGAGCTTAATAACAAGCCGTCAATTGTCTGATTC |
| 86 | Ara-2-SstI | GCTTAACCGCGGGCCAAGCTTGCATGCCTGCTCC |

Oligonucleotides SEQ ID NOS.:69, 70, 71 and 72 were used to amplify the rhaRS genes and their divergent control region from the *E. coli* chromosome. Once amplified, this region was inserted into pUC18 using HindIII and PstI to create SEQ ID NO.: 6.

Oligonucleotides SEQ ID NOS.:73, 74, 75 and 76 were used to amplify the uidR control region, the uidR gene and the control region for expression from the *E. coli* chromosome. Once amplified, this region was inserted into pUC18 using HindIII and PstI to create SEQ ID NO.: 10.

Oligonucleotides SEQ ID NOS.:77, 78, 79 and 80 were used to amplify the melR gene and its divergent control region from the *E. coli* chromosome. Once amplified, this region was inserted into pUC18 using HindIII and SalI to create SEQ ID NO.: 11.

Oligonucleotides SEQ ID NOS.:81, 82, 83 and 84 were used to amplify the araC gene and its divergent control region from the *E. coli* chromosome. Once amplified, this region was inserted into pUC18 using HindIII and PstI to create SEQ ID NO.: 12.

Oligonucleotides SEQ ID NOS.:81, 82, 85 and 86 were used to amplify the araC gene and its divergent control region was PCR amplified from pBAD-24. Once amplified, this region was inserted into pEGFP (Clontech) using XhoI and SstI to create SEQ ID NO.: 13.

Except of pMPX-6, these expression constructs contain the same multiple cloning site. Therefore, any protein of interested may be inserted in each modular expression construct for simple expression screening and optimization.

By way of non-limiting example, other proteins that may be expressed are listed in Table 15.

TABLE 15

OTHER EXPRESSED PROTEINS

| Protein | Origin | Construct | Purpose | SEQ ID NO.: |
|---|---|---|---|---|
| Edg3 | Rat | native | GPCR | 14 |
| β2AR | Human | native | GPCR | 15 |
| TNFR-1a (human) | Human | residues 29-455 | Receptor | 18 |
| TNFR-1b (human) | Human | residues 41-455 | Receptor | 17 |
| TNF (human) | Human | native | Gene transfer | 19 |
| T-EGF | Human | chimera | Gene transfer | 20 |
| T-Invasin | *Y. pseudotuberculosis* | chimera | Gene transfer | 21 |

TABLE 16

OLIGONUCLEOTIDE PRIMER SEQUENCES FOR TABLE 15

| SEQ ID NO.: | Primer name | 5' to 3' sequence |
|---|---|---|
| 87 | Edg-1 | GGCAACCACGCACGCGCAGGGCCACC |
| 88 | Edg-2 | CAATGGTGATGGTGATGATGACCGG |
| 89 | Edg-1-SalI | CGCGGTCGACATGGCAACCACGCACGCGCAGGGCCACC |
| 90 | Edg-2-KpnI | GCGCCGGTACCTTATCAATGGTGATGGTGATGATGACCGG |
| 91 | β2AR-1 | GGGGCAACCCGGGAACGGCAGCGCC |
| 92 | β2AR-2 | GCAGTGAGTCATTTGTACTACAATTCCTCC |
| 93 | β2AR-1-SalI | CGCGGTCGACATGGGGCAACCCGGGAACGGCAGCGCC |
| 94 | β2AR-2-BamHI | GCGCCGGATCCTTATTATAGCAGTGAGTCATTTGTACTACAATTCCTCC |
| 95 | TNFR(29)-1 | GGACTGGTCCCTCACCTAGGGGACAGGG |
| 96 | TNFR(29)-2 | CTGAGAAGACTGGGCGCGGGCGGGAGG |
| 97 | TNFR(29)-1-SalI | CGCGGGTCGACATGGGACTGGTCCCTCACCTAGGGGACAGGG |
| 98 | TNFR(29)-2-KpnI | GCGCCGGTACCTTATTACTGAGAAGACTGGGCGCGGGCGGGAGG |
| 99 | TNFR(41)-1 | GATAGTGTGTGTCCCC |
| 100 | TNFR(41)-2 | CTGAGAAGACTGGGCGC |
| 101 | TNFR(41)-1-NcoI | GGGAGACCATGGATAGTGTGTGTCCCC |
| 102 | TNFR(41)-2-XbaI | GCCTCATCTAGATTACTGAGAAGACTGGGCGC |
| 103 | TNF-1 | GAGCACTGAAAGCATGATCCGGGACG |
| 104 | TNF-2 | CAGGGCAATGATCCCAAAGTAGACCTGC |
| 105 | TNF-1-EcoRI | CCGCGGAATTCATGAGCACTGAAAGCATGATCCGGGACG |
| 106 | TNF-2-HindIII | GGCGCAAGCTTATCACAGGGCAATGATCCCAAAGTAGACCTGC |
| 107 | T-EGF-1 | TCTGATAGCGGTCTTACTTCCCCTCGCAGTATTACTGCTCAATAGTGACTCTGAATGTCCCCTGTCCCACGATGGGTACTGCCTCCATGATGGTGTGTGCATGTATATTG |

TABLE 16-continued

OLIGONUCLEOTIDE PRIMER SEQUENCES FOR TABLE 15

| SEQ ID NO.: | Primer name | 5' to 3' sequence |
|---|---|---|
| 108 | T-EGF-2 | AGGTCTCGGTACTGACATCGCTCCCCGATG TAGCCAACAACACAGTTGCATGCATACTTG TCCAATGCTTCAATATACATGCACACACCA TCATGGAGGCA |
| 109 | T-EGF-3 | CCGCGGGTACCATGAACTTGGGGAATCGAC TGTTTATTCTGATAGCGGTCTTACTTCCCC TCG |
| 110 | T-EGF-4 | GCGCCAAGCTTATTAGCGCAGTTCCCACCA CTTCAGGTCTCGGTACTGACATCGCTCCCC G |
| 111 | Inv-1 | TCATTCACATTGAGCGTCACCG |
| 112 | Inv-2 | TTATATTGACAGCGCACAGAGCGG |
| 113 | Inv-1-ToxR-EcoRI | GCAAGAATTCACCATGAACTTGGGGAATCG ACTGTTTATTCTGATAGCGGTCTTACTTCC CCTCGCAGTATTACTGCTCTCATTCACATT GAGCGTCACCG |
| 114 | Inv-2-PstI | CGCGGTTACGTAAGCAACTGCAGTTATATT GACAGCGCACAGAGCGG |

Oligonucleotides SEQ ID NOS.:87, 88, 89 and 90 were used to amplify rat Edg3 from rat cDNA. Once amplified, this region was inserted into SEQ ID NO.: 6 (pMPX-5) using SalI and KpnI to create SEQ ID NO.:14.

Oligonucleotides SEQ ID NOS.:91, 92, 93 and 94 were used to amplify human β2 adrenergic receptor (β2AR) from human heart cDNA. Once amplified, this region was inserted into SEQ ID NO.: 6 (pMPX-5) using SalI and BamHI to create SEQ ID NO.:15.

Oligonucleotides SEQ ID NOS.:95, 96, 97 and 98 were used to amplify human tumor necrosis factor receptor (TNFR residues 29-455) from human Jurkat CL71 cDNA. Once amplified, this region was inserted into SEQ ID NO.: 12 (pMPX-18) using SalI and KpnI to create SEQ ID NO.:18.

Oligonucleotides SEQ ID NOS.:99, 100, 101 and 102 were used to amplify human tumor necrosis factor receptor (TNFR residues 41-455) from human Jurkat CL71 cDNA. Once amplified, this region was inserted into pBAD24 using NcoI and XbaI to create SEQ ID NO.:17.

Oligonucleotides SEQ ID NOS.:103, 104, 105 and 106 were used to amplify human tumor necrosis factor (TNF) from human Jurkat CL71 cDNA. Once amplified, this region was inserted into SEQ ID NO.: 13 (pMPX-6) using EcoRI and HindIII to create SEQ ID NO.:19.

TABLE 17

PROGRAM TO ANNEAL GRADIENT PCR WITH PFX POLYMERASE

| Step | Temp (° C.) | Time (min) |
|---|---|---|
| 1 | 95 | 2.0 |
| 2 | 95 | 0.5 |
| 3 | 64 | 0.5 |
| 4 | 68 | 2.5 |
| 5 | Goto 2, 2X | |
| 6 | 95 | 0.5 |
| 7 | 62 | 0.5 |
| 8 | 68 | 2.5 |
| 9 | Goto 6, 4X | |

TABLE 17-continued

PROGRAM TO ANNEAL GRADIENT PCR WITH PFX POLYMERASE

| Step | Temp (° C.) | Time (min) |
|---|---|---|
| 10 | 95 | 0.5 |
| 11 | 60 | 0.5 |
| 12 | 68 | 2.5 |
| 13 | Goto 10, 6X | |
| 14 | 95 | 0.5 |
| 15 | 58 | 0.5 |
| 16 | 68 | 2.5 |
| 17 | Goto 14, 24X | |
| 18 | 4 | hold |
| 19 | end | |

Oligonucleotides SEQ ID NOS.:107, 108, 109 and 110 were mixed and PCR amplified using anneal gradient PCR (Table 17) to form mature human epidermal growth factor (EGF) (residues 971-1023) translationally fused to the transmembrane domain of toxR from *Vibrio cholerae*. Once amplified, this region was inserted into SEQ ID NO.: 13 (pMPX-6) using KpnI and HindIII to create SEQ ID NO.:20.

Using PFX polymerase (Invitrogen) oligonucleotide SEQ ID NO.:111, 112, 113 and 114 were used to amplify invasin residues 490-986 (inv) from *Yersinia pseudotuberculosis* chromosomal DNA and form a translational fusion between the transmembrane domain of toxR from *Vibrio cholerae*. Once amplified, this region was inserted into SEQ ID NO.:13 (pMPX-6) using EcoRI and PstI to create SEQ ID NO.:21.

These proteins were proof-of-principle constructs used to evaluate the minicell platform. For purposes of this initial evaluation, all proteins except TNF, T-EGF and T-Invasin were cloned into pMPX-5, with these later proteins cloned into pMPX-6 for gene transfer experiments.

Whether the approach for protein expression is co-expression with minicell induction or expression following minicell and/or protoplast isolation, the procedure to transform the expression constructs is the same. To accomplish this, protein constructs were initially cloned into *E. coli* MG1655 and then into the minicell producing strain of interest. Transformation events were selected prior to minicell induction. For co-induction of protein and minicells, see the protocol for phoA expression above. For post-minicell and/or protoplast purification induction experiments, following minicell purification and/or protoplast preparation and purification, these cellular bodies were induced for protein production in either LBD or MDT at a minicell or protoplast/volume ratio of $1\times10^9$ minicells or protoplasts/1 ml media. Media was supplemented with the appropriate inducer concentration (see Table 6). Protein induction is sensitive to a variety of factors including, but not limited to aeration and temperature, thus reaction volume to surface area ratio is important, as is the method of shaking and temperature of induction. Therefore, each protein must be treated as required to optimize expression. In addition to expression parameters, protoplasted minicells are sensitive to osmotic and mechanical forces. Therefore, protoplast protein induction reactions must also contain 10% sucrose with greater volume to surface area ratios than required for intact minicells to achieve similar aeration at lower revolutions.

Using the T-PhoA as a non-limiting example, protein expression was performed during and following minicell isolation. To accomplish this task, t-phoA co-expressed with minicell induction was compared to t-phoA expressed after minicell isolation. In both cases, overnight minicell-producing parental strains containing pMPX-5::t-phoA were subcultured into LBD supplemented with the appropriate antibiotic. Cultures were grown to $OD_{600}$ 0.1 and induced for minicell production alone or for both minicell and protein production. Both cultures were harvested at $OD_{600}$ 1.0 and minicells produced were harvested as described above. Minicells to be induced for T-phoA production following purification were induced by introducing 1×10⁹ purified minicells into a 15 ml culture tube containing 1 ml MDT with 1 mM L-rhamnose. Minicell protein induction was allowed to proceed for up to 14 hours and compared to protein production obtained using the co-expression approach. For each approach, minicells were fractionated and analyzed for membrane association, total protein, and membrane association-dependent enzymatic activity. These observations were compared to post-induction, pre-isolation parental cell/minicell (PC/MC) mixtures from the co-expressed reactions. The first observation was that co-expression of minicell and protein induction was superior to post-minicell purification induction (Table 18). However, although the kinetics are slower for the post-minicell purification induction protocol, the end result is equivalent.

TABLE 18

COMPARATIVE EXPRESSION:
CO-EXPRESSION VERSUS POST MINICELL
PURIFICATION INDUCTION

| Time of induction | Purified minicell induction [a] | Co-expression induction [a] |
|---|---|---|
| 1.0 | 8.0 | — |
| 2.0 | — | 812.2 |
| 4.0 | 70.0 | — |
| 14.0 | 445.0 | — |

[a] Nanogram expressed T-PhoA per 1 × 10⁹ minicells.

Using the co-expression induction procedure, the amount of membrane-associated T-PhoA was measured and compared for both parental cells and minicells. Briefly, following co-expression induction of T-PhoA and minicells, minicells were purified and their membranes isolated. For membrane isolation, minicells containing expressed T-PhoA were subjected to three rounds of freeze-thaw lysis in the presence of 10 μg/ml lysozyme. Following freeze-thaw cycling, the reaction was subjected to sonication. Sonicated material was centrifuged at 6,000 rpm in a microcentrifuge for 5 min at room temperature. Supernatants were transferred to a fresh 1.5 ml Eppendorf tube and centrifuged at 70,000 rpm using a TLA-100 rotor. Following centrifugation, the pellet was resuspended in buffer and analyzed for total T-PhoA protein (Table 19) and T-PhoA enzyme activity (Table 20).

TABLE 19

MEMBRANE ASSOCIATED T-PHOA:
PARENTAL CELLS VERSUS MINICELLS

| Cell type [a] | Protein total [a] | T-PhoA total [b] | T-PhoA % total | Protein membrane associated [a] | T-PhoA membrane associated [b] | T-PhoA % membrane protein total |
|---|---|---|---|---|---|---|
| Parental cells | 107.5 | 5.3 | 4.9 | 10.7 | 3.1 | 29.0 |
| Minicells | 4.6 | 0.8 | 17.5 | 1.0 | 0.5 | 50.0 |
| Minicells EQ [b] | 25.2 | 4.4 | — | 5.5 | 2.7 | — |

[a] Total protein as determined by BCA assay (Pierce)
[b] Microgram expressed T-PhoA per 1 × 10⁹ minicells as determined via Western using an anti-PhoA antibody (Sigma) versus a PhoA standard curve (BCA determined).
[c] Equivalent membrane lipid to parental cell

TABLE 20

PHOA ENZYMATIC ACTIVITY[a] (RELATIVE UNITS):
PARENTAL CELLS VERSUS MINICELLS.

| Cell type [b] | Unlysed | Lysed, total | Lysed, membrane |
|---|---|---|---|
| Parent cell | — | 358 | 240 |
| Minicell | 275 | 265 | 211 |
| Minicell EQ [c] | 1,504 | 1,447 | 1,154 |

[a] Activity determined colorimetrically using PNPP measuring optical density at 405 nm
[b] Based on 1 × 10⁹ parental cells or minicells per reaction
[c] Equivalent membrane lipid to parental cell These results suggest that co-expression induction of T-PhoA and minicells together results in minicells containing an equivalent amount of T-PhoA produced in both parental cells and minicells. However, the percent of T-PhoA compared to total protein is 3.5× greater in minicells than in parental cells. Furthermore, of the protein made, T-PhoA constitutes 50% of the total membrane protein in minicells, whereas it is only 29% in parental cells. It should be noted that the T-PhoA protein associated with the membrane can be easily removed by treatment with mild, non-ionic detergent suggesting that the T-PhoA present in the membrane pellet is indeed associated with the membrane and not an insoluble, co-sedimenting precipitate (data not shown). Finally, PhoA is a periplasmic enzyme that requires export to the periplasmic space for proper folding and disulfide bond formation. Both of which are required for enzymatic activity. In the time course of this experiment, expression of ΔPhoA lacking a leader sequence does not demonstrate enzymatic activity. Furthermore, there is no difference between unlysed and lysed minicells containing expressed T-PhoA (Table 20) also demonstrating that the PhoA enzyme domain of the T-PhoA chimera must be present in the periplasmic space. Therefore, the T-PhoA construct must membrane associate and the PhoA domain must orient into the periplasmic space for enzymatic activity. Thus, when comparing equivalent amounts of membrane lipid between parental cells and minicells in Table 20, membrane association-dependent T-PhoA activity is almost 5× greater than in parental cells. Taking into account the data in Table 19 where 50% of T-PhoA is in the membrane compared to 29% in parental cells, the difference in T-PhoA membrane association is not sufficient to explain the almost 5× increase in minicell activity. These observations suggest that minicells contain a capacity to support more expressed membrane protein than parental cells and that the protein that associates with the membrane is more active. This activity may be simply result from minicells allowing greater efficiency of folding and disulfide bond formation for this particular protein. However, do to the fact that minicells do not contain chromosome, it is also possible that the overexpression of this protein is readily finding membrane-binding sites in the absence of chromosomally produced competitors present in parental cells. Furthermore, overexpression of proteins often leads to increased protease expression. Because minicells do not contain chromosome, these otherwise degraded surplus T-PhoA is allowed the continued opportunity to insert and properly fold in the membrane, an attribute that could lend favor to overexpression of more complex membrane proteins.

Example 18

Exemplary Methods to Induce and Study Complex Membrane Proteins

Expression of non-native (exogenous) complex membrane proteins in bacterial systems can be difficult. Using the minicell system, we are able to eliminate toxicity issues. However, issues still remain with proper translation, compartmentalization at the membrane, insertion in the membrane and proper folding for native activity. To account for these potential problems we have constructed a modular chimeric system that incorporates leader sequences and chaperone-recognized soluble domains that are native to our bacterial minicell system. In addition, we created modular constructs that overexpress the native chaperones groESL and trigger factor (tig). Finally, we have constructed minicell-producing strains that contain mutations that effect protein export and disulfide bond formation. For non-limiting examples of these constructs see Table 21.

TABLE 21

NON-LIMITING TOOLS FOR EXOGENOUS COMPLEX PROTEIN SYNTHESIS AND FUNCTION

| Tool | Reference | Residues of sequence | Purpose | SEQ ID NO |
|---|---|---|---|---|
| pMPX-5::phoA leader | — | 1-48 | Membrane targeting | 22 |
| pMPX-5::phoA leader | — | 1-494 | Membrane targeting | 23 |
| pMPX-5::malE leader | 1 | 1-28 | Membrane targeting | 24 |
| pMPX-5::malE leader | 1 | 1-370 | Membrane targeting | 25 |
| pMPX-17 (groESL, tig) | — | — | Chaperone | 26 |
| pMPX-5::trxA::FLAG | 2 | 2-109 [a] | Solubility | 27 |

[a] Residues do not include FLAG sequence.

References to Table 21
1. Grisshammer, R., et al. 1993. Expression of a rat neurotensin receptor in *Escherichia coli*. Biochem. J. 295:571-576.
2. Tucker, J., and R. Grisshammer. 1996. Purification of a rat neurotensin receptor expressed in *Escherichia coli*. Biochem. J. 317:891-899.

TABLE 22

OLIGONUCLEOTIDE PRIMER SEQUENCES FOR TABLE 21 CONSTRUCTS

| SEQ ID NO.: | Primer name | 5' to 3' sequence |
|---|---|---|
| 115 | PhoA lead-1 | GTCACGGCCGAGACTTATAGTCGC |
| 116 | PhoA lead-2 | GGTGTCCGGGCTTTTGTCACAGG |
| 117 | PhoA lead-1-PstI | CGCGGCTGCAGATGTCACGGCCGAGACTTATAGTCGC |
| 118 | PhoA lead-2-XbaI | CGCGGTCTAGATTCTGGTGTCCGGGCTTTTGTCACAGG |
| 119 | PhoA complete | CAGCCCCAGAGCGGCTTTCATGG |
| 120 | PhoA complete-2-XbaI | CGCGGTCTAGATTTCAGCCCCAGAGCGGCTTTCATGG |
| 121 | MalE lead-1 | CGCGGCTGCAGATGAAAATAAAAACAGGTGCACGCATCCTCGCATTATCCGCATTAACGACGATGATGTTTTCCGCCTCGGCTCTCGCCAAAATCTCTAGACGCGG |
| 122 | MalE lead-2 | CCGCGTCTAGAGATTTTGGCGAGAGCCGAGGCGGAAAACATCATCGTCGTTAATGCGGATAATGCGAGGATGCGTGCACCTGTTTTTATTTTCATCTGCAGCCGCG |
| 123 | MalE-1 | GGTGCACGCATCCTCGCATTATCCGC |
| 124 | MalE-2 | CGGCATACCAGAAAGCGGACATCTGC |
| 125 | MalE-1-PstI | CGCGGCTGCAGATGAAAATAAAAACAGGTGCACGCATCCTCGCATTATCCGC |
| 126 | MalE-2-XbaI | CGCGGTCTAGAACGCACGGCATACCAGAAAGCGGACATCTGC |
| 127 | Tig-1 | CGCGACAGCGCGCAATAACCGTTCTCG |
| 128 | Tig-2 | GCTGGTTCATCAGCTCGTTGAAAGTGG |
| 129 | Tig-1-NarI | GCGCCGGCGCCATACGCGACAGCGCGCAATAACCGTTCTCG |
| 130 | Tig-2-XbaI | GGCGCTCTAGATTATTATTACGCCTGCTGGTTCATCAGCTCGTTGAAAGTGG |
| 131 | Gro-1 | GGTAGCACAATCAGATTCGCTTATGACGG |
| 132 | Gro-2 | GCCGCCCATGCCACCCATGCCGCCC |
| 133 | Gro-1-XbaI | GCGTCTAGAGGTAGCACAATCAGATTCGCTTATGACGG |
| 134 | Gro-2-HindIII | GGCGCAAGCTTATTATTACATCATGCCGCCCATGCCACCCATGCCGCCC |
| 135 | TrxA-1 | GCGATAAAATTATTCACCTGACTGACG |
| 136 | TrxA-2 | GCGTCGAGGAACTCTTTCAACTGACC |
| 137 | TrxA-1-Fxa-PstI | CGCGGCTGCAGATGATCGAAGCCCGCTCTAGACTCGAGAGCGATAAAATTATTCACCTGACTGACG |
| 138 | TrxA-2-FLAG-BamHI | CCGCGGGATCCTTATTAATCATCATGATCTTTATAATCGCCATCATGATCTTTATAATCCTCGAGCGCCAGGTTAGCGTCGAGGAACTCTTTCAACTGACC |

Oligonucleotides SEQ ID NOS.:115, 116, 117 and 118 were used to amplify the phoA leader (residues 1-49) from *E. coli* chromosomal DNA. Once amplified, this region was inserted into SEQ ID NO.: 6 (pMPX-5) using PstI and XbaI to create SEQ ID NO.:22.

Oligonucleotides SEQ ID NOS.:115, 117, 119 and 120 were used to amplify the complete phoA gene from *E. coli* chromosomal DNA. Once amplified, this region was inserted into SEQ ID NO.: 6 (pMPX-5) using PstI and XbaI to create SEQ ID NO.23.

Oligonucleotides SEQ ID NOS.:121 and 122 were used to construct the malE leader (residues 1-28) sequence. Once annealed, this construct was inserted into SEQ ID NO.: 6 (pMPX-5) using PstI and XbaI to create SEQ ID NO.:24.

Oligonucleotides SEQ ID NOS.:123, 124, 125 and 126 were used to amplify the malE expanded leader (residues 1-370) from *E. coli* chromosomal DNA. Once amplified, this region was inserted into SEQ ID NO.: 6 (pMPX-5) using PstI and XbaI to create SEQ ID NO.:25.

Oligonucleotides SEQ ID NOS.:127, 128, 129 and 130 were used to amplify the tig control and gene region from *E. coli* chromosomal DNA. Once amplified, this region was ligated to the groESL amplified region below using XbaI prior to insertion into SEQ ID NO.: 6 (pMPX-5) using NarI (from the tig region) and HindIII (from the groESL region) to create SEQ ID NO.:26.

Oligonucleotides SEQ ID NOS.:131, 132, 133 and 134 were used to amplify the groESL control and gene region from *E. coli* chromosomal DNA. Once amplified, this region was ligated to the tig amplified region above using XbaI prior to insertion into SEQ ID NO.: 6 (pMPX-5) using NarI (from the tig region) and HindIII (from the groESL region) to create SEQ ID NO.:26.

Oligonucleotides SEQ ID NOS.:135, 136, 137 and 138 were used to amplify trxA (residues 2-109) from *E. coli* chromosomal DNA and insert FLAG and Factor Xa sequences. Once amplified, this region was inserted into SEQ ID NO.: 6 (pMPX-5) using PstI and BamHI to create SEQ ID NO.:27.

By way of non-limiting example, the pMPX-5::phoA leader (residues 1-48), pMPX-5::phoA leader (residues 1-494), pMPX-5::malE leader (residues 1-28), and pMPX-5::malE leader (residues 1-370) constructs are designed to direct expressed exogenous membrane proteins to the minicell cytoplasmic membrane. In addition to these constructs, By way of non-limiting example, mutations in *E. coli* genes secA and secY, specifically mutation prlA4 (Strader, J., et al. 1986. Kinetic analysis of lamB mutants suggests the signal sequence plays multiple roles in protein export. J. Biol. Chem. 261:15075-15080), permit promiscuous targeting to the membrane. These mutations, like the above constructs are integrated into the minicell expression system. To complement these mutations, the chaperone complex groESL and trigger factor have also been incorporated into the expression system. By way of non-limiting example, pMPX-5::trxA::FLAG will be used to create a carboxy-terminal fusion to the protein of interest to increase the membrane insertion efficiency of the membrane protein of interest (Tucker, J., and R. Grisshammer. 1996. Purification of a rat neurotensin receptor expressed in *Escherichia coli*. Biochem. J. 317:891-899). Also By way of non-limiting example, pMPX-5::FLAG::toxR and pMPX-5::FLAG::λcI constructs will be prepared to create a carboxy-terminal fusion to the protein of interest for use in a reporter-based assay for protein-protein interactions. By way of non-limiting example, the protein of interest for this system is a GPCR. Also By way of non-limiting example, this GPCR may be the neurotensin receptor from rat (Grisshammer, R., et al. 1993. Expression of a rat neurotensin receptor in *Escherichia coli*. Biochem. J. 295:571-576.), or the β2 adrenergic receptor from humans (Freissmuth, M., et al. 1991. Expression of two β-adrenergic receptors in *Escherichia coli*: functional interaction with two forms of the stimulatory G protein. Proc. Natl. Acad. Sci. 88:8548-8552). Insertion of a GPCR into one of these reporter constructs creates a carboxy-terminal fusion between the GPCR of interest and the DNA-binding regulatory domain of the ToxR positive activator, the λcI repressor, or the AraC positive activator. To complete this reporter system, By way of non-limiting example pMPX-5::(X)::toxR or pMPX-5::(X)::λcI will be used to create a carboxy-terminal fusion to the protein of interest for use in a reporter-based assay for protein-protein interactions, where (X) may be any protein or molecule involved in an intermolecular or intramolecular interaction. By way of non-limiting example, this molecule of interest may be a G-protein. This G-protein may be the $G\alpha_{i1}$-protein from rat (Grisshammer, R., and E. Hermans. 2001. Functional coupling with Gαq and Gαi1 protein subunits promotes high-affinity agonist binding to the neurotensin receptor NTS-1 expressed in *Escherichia coli*. FEBS Lett. 493:101-105), or the $G_{s\alpha}$-protein from human (Freissmuth, M., et al. 1991. Expression of two β-adrenergic receptors in *Escherichia coli*: functional interaction with two forms of the stimulatory G protein. Proc. Natl. Acad. Sci. 88:8548-8552). Like the GPCR, insertion of a G-protein into one of these reporter constructs creates a carboxy-terminal fusion between the G-protein of interest and the DNA-binding regulatory domain of the ToxR positive activator, the λcI repressor, or other regulatory protein. Finally, these plasmid constructs contain the DNA-binding domain of each regulator; the ctx regulatory region from *Vibrio cholerae* (Russ, W. P., and D. M. Engelman. 1999. TOXCAT: a measure of transmembrane helix association in a biological membrane. 96:863-868), or the $P_R1O_R1$ region of bacteriophage lambda (Hu, J. C., et al. 1990. Sequence requirements for coiled-coils: analysis with lambda repressor-GCN4 leucine zipper fusions. Science. 250:1400-1403), respectively. By way of non-limiting example, each binding domain is coupled to a reporter sequence encoding luciferase (Dunlap, P. V., and E. P. Greenberg. 1988. Control of *Vibrio fischeri* lux gene transcription by a cyclic AMP receptor protein-luxR protein regulatory circuit. J. Bacteriol. 170:4040-4046), green fluorescent protein (GFP) (Yang, T. T., et al. 1996. Dual color microscopic imagery of cells expressing the green fluorescent protein and a red-shifted variant. Gene. 173:19-23; Matthysse, A. G., et al. 1996. Construction of GFP vectors for use in gram-negative bacteria other than *Escherichia coli*. FEMS Microbiol. Lett. 145:87-94), or other reporter. Co-expression of these GPCR and G-protein chimeras will create a system measuring the interaction between a GPCR and G-protein within an intact minicell. This system is designed to be used as a positive or negative read-out assay and may be used to detect loss or gain of GPCR function. Although the GPCR-G-protein interaction is provided as an example, this modular system may be employed with any soluble or membrane protein system measuring protein-protein or other intermolecular interaction.

Example 19

Exemplary Methods for Gene Transfer Using Minicells or Minicell Protoplasts

Included in the design of the invention is the use of minicells to transfer genetic information to a recipient cell. By way of non-limiting example, this gene transfer may occur between a minicell and a mammalian cell in vitro, or in vivo, and this gene transfer may occur through cell-specific interactions, through general interactions, or a combination of each. To accomplish this task three basic constructs were created. Each of these constructs is created in pMPX-6 which contains a CMV promotor controlling the synthesis of GFP. The plasmid pMPX-6 was constructed by cloning the araC through the multiple cloning site of pBAD24 into pEGFP (Clontech). This construct provided a bacterial regulator as well as a method to monitor the success of gene transfer using GFP expression form the CMV promotor. In design, the protein expressed using the bacterial promotor will drive the cell-cell interaction, while the successful transfer of DNA from the minicell to the recipient cell will initiate the production of GFP. By way of non-limiting example, proteins that will drive the cell-cell interaction may be the invasin protein from *Yersinia pseudotuberculosis*, which stimulates β1 integrin-dependent endocytic events. To properly display the invasin protein on the surface of minicells, the domain of invasin that stimulates these events (residues 490-986) (Dersch, P., and R. R. Isberg. 1999. A region of the *Yersinia pseudotuberculosis* invasin protein enhances integrin-mediated uptake into mammalian cells and promotes self-association. EMBO J. 18:1199-1213) was fused to the transmembrane domain of ToxR. Expression of this construct from pMPX-6 will display T-Inv on the surface of the minicell and stimulate endocytosis with any cell displaying a β1 integrin. Thus, T-Inv display will provide a general mechanism of gene transfer from minicells. To provide specificity, By way of non-limiting example, the ligand portion of epidermal growth factor (EGF) may be fused to the transmembrane domain of ToxR, thus creating a protein that will interact with cells displaying the EGF receptor (EGFR). Likewise, tumor nucrosis factor (TNF) may also serve this purpose by stimulating cell-cell interactions between minicells displaying TNF and cells displaying TNF receptor (TNFR). Although EGF-EGFR and TNF-TNFR interactions may stimulate cell-cell fusion between minicells and recipient cells, or minicell uptake, this alone may not be sufficient to efficiently transfer genetic information from minicells. Therefore, a genetic approach to increasing the cell-cell genetic transfer may be the development of a genetic switch that senses the specificity interaction, e.g. EGF-EGFR interaction, and turns on the production of a second gene product, e.g. invasin, that stimulates the endocytic event. By way of non-limiting example, this genetic switch may be similar to the GPCR-G-protein interaction reporter system above, in that an extracellular event stimulates the dimerization of a transcriptional active regulator, thus turning on the production of invasin or invasin-like protein. In either approach, the display system to stimulate transfer of genetic information from minicells to recipient cells may also be applicable to the transfer of substances other than genetic information, e.g. pre-synthesized therapeutic drugs.

To test this targeting methodology, different pMPX-6 constructs containing each of these general or specific cell-cell interaction proteins will be transformed into a minicell producing strain and either by co-expression induction of minicells, by post-minicell purification induction, or by post-protoplasting induction, minicells displaying the targeting protein of interest will be produced. When using the co-expression induction and post-minicell purification induction of the targeting protein approaches, it is necessary to protoplast the purified minicells after protein induction. Once the targeting protein has been displayed on the surface of a minicell protoplast, these protoplasts are ready to be exposed to target cells. For preliminary experiments these interactions will be monitored using cell culture of Cos cells in comparison to lipofectamine (Invitrogen), electroporation, and other transfection techniques. Initial experiments will expose protoplasts displaying T-Inv to Cos cells and compare the transfection efficiency to protoplast containing pMPX-6::t-inv in the absence of t-inv expression, naked pMPX-6::t-inv alone, and naked pMPX-6::t-inv with lipofectamine. Each of these events will be monitored using fluorescent microscopy and/or flow cytometry. From these results the specific targeting apparatus proteins will be tested. Using A-431 (display EGFR) and K-562 (no EGFR) cell lines, the pMPX-6::t-egf constructs will be tested. Using the same approaches as for the t-inv study, the level of transfection between A-431 and K-562 cell lines will be measured and compared to those achieved using lipofectamine. Similarly, the ability of TNF to stimulate gene transfer will be studied using L-929 cells. In all cases, the ability of these general and specific targeting protein constructs will be compared to standard transfection techniques. Upon positive results, these methodologies will be tested on difficult to transfect cell lines, e.g. adult cardiomyocytes. The basis of these results will create a foundation for which applications into in vivo gene transfer may occur.

Example 20

Additional and Optimized Methods for Genetic Expression

Expression in minicells may occur following purification of minicells and/or minicell protoplasts from parental cells and LPS constituents, respectively. However, for some applications it is preferred to co-express proteins of interest with minicell induction. For these approaches, one may use the protocol described in Example 13 for expression of the phoA constructs. Either of these approaches may be accomplished using one or more of the following expression constructs (Table 23) and/or optimized expression constructs (Table 25).

Expression plasmid pCGV1 contains a temperature sensitive lambda cI repressor (cI857) and both lambda PR and PL promoters (Guzman, C. A., et al. 1994. A novel *Escherichia coli* expression-export vector containing alkaline phosphatase as an insertional inactivation screening system. Gene. 148:171-172) with an atpE initiation region (Schauder, B., et al. 1987. Inducible expression vectors incorporating the *Escherichia coli* atpE translational initiation region. Gene. 52:279-283). Included in the design of the invention is the modification of this expression vector to best align the required Shine-Delgarno ribosomal binding site with cloning sites. In addition, the pCGVI expression vector was modified to incorporate a stem-loop structure at the 3-prime end of the transcript in order to provide a strong transcriptional stop sequence (Table 23).

Expression plasmid pCL478 contains a temperature sensitive lambda cI repressor (cI857) and both lambda PR and PL promoters (Love, C. A., et al. 1996. Stable high-copy bacteriophage promoter vectors for overproduction of proteins in *Escherichia coli*. Gene. 176:49-53). Included in the design of the invention is the modification of this expression vector to best align the required Shine-Delgarno ribosomal binding site with cloning sites. In addition, the pCL478 expression vector was modified to incorporate a stem-loop structure at the 3-prime end of the transcript in order to provide a strong transcriptional stop sequence (Table 23).

TABLE 23

LAMBDA C1857 EXPRESSION VECTOR MODIFICATIONS

| New Plasmid | Parent plasmid | Region removed | Region added [a] | SEQ ID NO |
|---|---|---|---|---|
| pMPX-84 | pCGV1 | NdeI - BamHI | NdeI, SD - PstI, XbaI, KpnI, Stem-loop, BamHI | 139 |
| pMPX-85 | pCGV1 | NdeI - BamHI | NdeI, SD - SalI, XbaI, KpnI, Stem-loop, BamHI | 140 |
| pMPX-86 | pCL478 | BamHI - XhoI | BamHI, SD - PstI, XbaI, KpnI, Stem-loop, XhoI | 141 |
| pMPX-87 | pCL478 | BamHI - XhoI | BamHI, SD - SalI, XbaI, KpnI, Stem-loop, XhoI | 142 |

[a] "SD" refers to a Shine-Delgarno ribosome-binding sequence; "Stem-loop" refers to a stem-loop structure that functions as a transcriptional stop site.

TABLE 24

OLIGONUCLEOTIDE PRIMER SEQUENCES FOR TABLE 23

| SEQ ID NO.: | Primer name | 5' to 3' sequence |
|---|---|---|
| 143 | CGV1-1-SalI | TATGTAAGGAGGTTGTCGACCGGCTCAGTCTAGA GGTACCCGCCCTCATCCGAAAGGGCGTATTG |
| 144 | CGV1-2-SalI | GATCCAATACGCCCTTTCGGATGAGGGCGGGTAC CTCTAGACTGAGCCGGTCGACAACCTCCTTACA |

TABLE 24-continued

OLIGONUCLEOTIDE PRIMER SEQUENCES FOR TABLE 23

| SEQ ID NO.: | Primer name | 5' to 3' sequence |
|---|---|---|
| 145 | CGV1-1-PstI | TATGTAAGGAGGTTCTGCAGCGGCTCAGTCTAGA GGTACCCGCCCTCATCCGAAAGGGCGTATTG |
| 146 | CGV1-2-PstI | GATCCAATACGCCCTTTCGGATGAGGGCGGGTAC CTCTAGACTGAGCCGCTGCAGAACCTCCTTACA |
| 147 | CL478-1-SalI | GATCCTAAGGAGGTTGTCGACCGGCTCAGTCTAG AGGTACCCGCCCTCATCCGAAAGGGCGTATTC |
| 148 | CL478-2-SalI | TCGAGAATACGCCCTTTCGGATGAGGGCGGGTAC CTCTAGACTGAGCCGGTCGACAACCTCCTTAG |
| 149 | CL478-1-PstI | GATCCTAAGGAGGTTCTGCAGCGGCTCAGTCTAG AGGTACCCGCCCTCATCCGAAAGGGCGTATTC |
| 150 | CL478-2-PstI | TCGAGAATACGCCCTTTCGGATGAGGGCGGGTAC CTCTAGACTGAGCCGCTGCAGAACCTCCTTAG |

Oligonucleoides SEQ ID NOS.: 143 and 144 were annealed to each other to generate a DNA molecule with a 5' overhang at both ends. The overhangs are designed so that the DNA can be directly cloned into pCGVI cut with NdeI (5' overhang is TA) and BamHI (5' overhang is GATC). Insertion of the annealed DNA into pCGVI creates SEQ ID NO.: 139, pMPX-84.

Oligonucleoides SEQ ID NOS.: 145 and 146 were annealed to each other to generate a DNA molecule with a 5' overhang at both ends. The overhangs are designed so that the DNA can be directly cloned into pCGVI cut with NdeI (5' overhang is TA) and BamHI (5' overhang is GATC). Insertion of the annealed DNA into pCGVI creates SEQ ID NO.: 140, pMPX-85.

Oligonucleoides SEQ ID NOS.: 147 and 148 were annealed to each other to generate a DNA molecule with a 5' overhang at both ends. The overhangs are designed so that the DNA can be directly cloned into pCL478 cut with BamHI (5' overlap is GATC) and XhoI (overhang is TCGA). Insertion of the annealed DNA into pCL578 cut with BamHI and XhoI creates SEQ ID NO.: 141, pMPX-86.

Oligonucleoides SEQ ID NOS.: 149 and 150 were annealed to were annealed to each other to generate a DNA molecule with a 5' overhang at both ends. The overhangs are designed so that the DNA can be directly cloned into pCL578 cut with BamHI (5' overlap is GATC) and XhoI (overhang is TCGA). Insertion of the annealed DNA into pCL478 cut with BamHI and XhoI creates SEQ ID NO.: 142, pMPX-87.

The optimized expression constructs in Table 25 were created from SEQ ID NOS.: 6, 11, and 12 (see Table 13). Modifications were made to optimize the alignment of the SalI or PstI cloning sites with the Shine-Delgarno ribosome-binding site. In addition, stem-loop transcriptional termination sequences were added on the 3' end of the cloning region.

TABLE 25

EXPRESSION CONSTRUCTS

| Plasmid | Regulatory element(s) | inducer | Plasmid | SEQ ID NO.: |
|---|---|---|---|---|
| pMPX-67 | RhaRS | Rhamnose | PUC-18 | 151 |
| pMPX-72 | RhaRS | Rhamnose | PUC-18 | 152 |
| pMPX-66 | AraC | Arabinose | PUC-18 | 153 |
| pMPX-71 | AraC | Arabinose | PUC-18 | 154 |
| pMPX-68 | MelR | Melibiose | PUC-18 | 155 |

TABLE 26

OLIGONUCLEOTIDE PRIMER SEQUENCES FOR TABLE 25 CONSTRUCTS

| SEQ ID NO.: | Primer name | 5' to 3' sequence |
|---|---|---|
| 69 | Rha-1 | GCGAATTGAGATGACGCCACTGGC |
| 156 | Rha-SD | GCAGAACCTCCTGAATTTCATTACGACC |
| 71 | Rha-1-HindIII | CGGCGAAGCTTAATTAATCTTTCTGCGA ATTGAGATGACGCCACTGGC |
| 157 | Rha-SD SalI KpnI | CCGCGGGTACCAATACGCCCTTTCGGAT GAGGGCGCGGGGATCCTCTAGAGTCGAC GTCGACAACCTCCTGAATTTCATTACGA CC |
| 158 | Rha-SD KpnI KpnI | CCGCGGGTACCAATACGCCCTTTCGGAT GAGGGCGCGGGGATCCTCTAGAGTCGAC CTGCAGAACCTCCTGAATTTCATTACGA CC |
| 81 | Ara-1 | CAAGCCGTCAATTGTCTGATTCG |
| 159 | Ara-SD | CTGCAGGGCCTCCTGCTAGCCCAAAAAA ACGGGTATGG |
| 83 | Ara-1-HindIII | GCGCCAAGCTTCAAGCCGTCAATTGTCT GATTCG |
| 160 | Ara-SD SalI KpnI | CCGCGGGTACCAATACGCCCTTTCGGAT GAGGGCGCGGGGATCCTCTAGAGTCGAC GTCGACGCCTCCTGCTAGCCCAAAAAA ACGGGTATGG |
| 161 | Ara-SD PstI KpnI | CCGCGGGTACCAATACGCCCTTTCGGAT GAGGGCGCGGGGATCCTCTAGAGTCGAC CTGCAGGGCCTCCTGCTAGCCCAAAAAA ACGGGTATGG |
| 77 | Mel-1 | CGTCTTTAGCCGGGAAACG |
| 162 | Mel-SD | CCTCCTGGCTTGCTTGAATAACTTCATC ATGG |
| 79 | Mel-1-HindIII | GCCGCAAGCTTCGTCTTTAGCCGGGAAA CG |
| 163 | Mel-SD-SalI KpnI | CCGCGGGTACCAATACGCCCTTTCGGAT GAGGGCGCGGGGATCCTCTAGAGTCGAC CCCCTCCTGGCTTGCTTGAATAACTTCA TCATGGC |

Oligonucleotides SEQ ID NOS.: 69, 156, 72, and 157 were used to amplify the rhaRS genes and their divergent control region from the E. coli chromosome and insertion of an optimized SalI-Shine-Delgarno ribosome-binding alignment and a stem-loop transcriptional termination sequence. Once amplified, this region was inserted into pUC18 using HindIII and KpnI to create pMPX67, SEQ ID NO.: 151.

Oligonucleotides SEQ ID NOS.: 69, 156, 72, and 158 were used to amplify the rhaRS genes and their divergent control region from the E. coli chromosome and insertion of an optimized PstI-Shine-Delgarno ribosome-binding alignment and a stem-loop transcriptional termination sequence. Once amplified, this region was inserted into pUC18 using HindIII and KpnI to create, pMPX-72, SEQ ID NO.: 152.

Oligonucleotides SEQ ID NOS.: 81, 159, 81, 160 were used to amplify the araC genes and their divergent control region from the E. coli chromosome and insertion of an optimized SalI-Shine-Delgarno ribosome-binding alignment and a stem-loop transcriptional termination sequence. Once amplified, this region was inserted into pUC18 using HindIII and KpnI to create, pMPX-66, SEQ ID NO.: 153.

Oligonucleotides SEQ ID NOS.: 81, 159, 81, 161 were used to amplify the araC genes and their divergent control region from the E. coli chromosome and insertion of an optimized PstI-Shine-Delgarno ribosome-binding alignment and a stem-loop transcriptional termination sequence. Once amplified, this region was inserted into pUC18 using HindIII and KpnI to createm pMPX-71, SEQ ID NO.: 154.

Oligonucleotides SEQ ID NOS.: 77, 162, 79, 163 were used to amplify the melR genes and their divergent control region from the E. coli chromosome and insertion of an optimized SalI-Shine-Delgarno ribosome-binding alignment and a stem-loop transcriptional termination sequence. Once amplified, this region was inserted into pUC18 using HindIII and KpnI to create, pMPX-68, SEQ ID NO.: 155.

Example 21

Optimization of Rat Neurotensin Receptor (NTR) Expression

Expression of specific GPCR proteins in minicells may require chimeric domain fusions to stabilize the expressed protein and/or direct the synthesized protein to the membrane. The NTR protein from rat was cloned into several chimeric combinations to assist in NTR expression and membrane association (Grisshammer, R., et al. 1993. Expression of a rat neurotensin receptor in *Escherichia coli*. Biochem. J. 295:571-576; Tucker, J., and Grisshammer, R. 1996. Purification of a rat neurotensin receptor expressed in *Escherichia coli*. Biochem. J. 317:891-899). Methods for construction are shown the Tables below.

TABLE 27

NEUROTENSIN RECEPTOR EXPRESSION FACILITATING CONSTRUCTS

| Protein[a] | Construct[b] | SEQ ID NO |
|---|---|---|
| MalE(L) | SalI-MalE (1-370)-Factor Xa-NTR homology | 164 |
| NTR | Factor Xa-NTR (43-424)-NotI-FLAG-KpnI | 165 |
| MalE(L)-NTR | SalI-MalE(1-370)-Factor Xa-NTR(43-424)-NotI-FLAG-KpnI | 166 |
| MalE(S)-NTR | SalI-MalE(1-28)-Factor Xa-NTR(43-424)-NotI-FLAG-KpnI | 167 |
| TrxA | NotI-TrxA(2-109)-NotI | 168 |
| MalE(L)-NTR-TrxA | SalI-MalE(1-370)-Factor Xa-NTR(43-424)-NotI-TrxA(2-109)-FLAG-KpnI | 169 |
| MalE(S)-NTR-TrxA | SalI-MalE(1-28)-Factor Xa-NTR(43-424)-NotI-TrxA(2-109)-FLAG-KpnI | 170 |

[a] (L) refers to MalE residues 1-370, and (S) refers to MalE residues 1-28.
[b] All mature constructs were cloned into SalI and KpnI sites of SEQ ID NOS.: 140, 142, 151 and 153.

TABLE 28

OLIGONUCLEOTIDE PRIMER SEQUENCES FOR TABLE 27

| SEQ ID NO.: | Primer name | 5' to 3' sequence |
|---|---|---|
| 171 | MalE-1 | GGTGCACGCATCCTCGCATTATCCGC |
| 172 | MalE-2 | CGCACGGCATACCAGAAAGCGGACATCTGCG |
| 173 | MalE-1-SalI | CCGCGGTCGACATGAAAATAAAACAGGTGCACGCATCCTCGC |
| 174 | MalE-2-XaNTR | GCCGTGTCGGATTCCGAGGTGCGGCCTTCGATACGCACGGCATACCAAGAAAGCGGGATGTTCGGC |

TABLE 28-continued

OLIGONUCLEOTIDE PRIMER SEQUENCES FOR TABLE 27

| SEQ ID NO.: | Primer name | 5' to 3' sequence |
|---|---|---|
| 175 | NTR-1 | CCTCGGAATCCGACACGGCAGGGC |
| 176 | NTR-2 | GTACAGGGTCTCCCGGGTGGCGCTGG |
| 177 | NTR-1-Xa | CCGCGATCGAAGGCCGCACCTCGGAATCCGACACGGCAGGGCC |
| 178 | NTR-2-Flag | GGCGCGGTACCTTTGTCATCGTCATCTTTATAATCTGCGGCCGCGTACAGGGTCTCCCGGGTGGCGCTGGTGG |
| 179 | NTR-2-Stop KpnI | GCGGCGGTACCTTATTATTTGTCATCGTCATCTTTATAATCTGCGGCCGCG |
| 180 | NTR-1-Xa Lead | CCGCATTAACGACGATGATGTTTTCCGCCTCGGCTCTCGCCAAAATCATCGAAGGCCGCACCTCGGAATCCGACACGGC |
| 181 | NTR-2-Lead2 SalI | CCGCGGTCGACATGAAAATAAAAACAGGTGCACGCATCCTCGCATTATCCGCATTAACGACGATGATGTTTTCCGCCTCGGC |
| 182 | TrxA-1 | CCGCGAGCGATAAAATTATTCACCTGACTGACG |
| 183 | TrxA-2 | GCCCGCCAGGTTAGCGTCGAGGAACTCTTTCAACTGACC |
| 184 | TrxA-1-NotI | GCGGCCGCAAGCGATAAAATTATTCACCTGACTGACG |
| 185 | TrxA-2-NotI | GGCGCTGCGGCCGCATCATCATGATCTTTATAATCGCC |

Oligonucleotides SEQ ID NOS.: 171, 172, 173 and 174 were used to amplify malE residues 1-370 from the E. coli chromosome to create SEQ ID NO.: 164. Using overlap PCR with the extended NTR homology, a chimeric translational fusion was made between MalE (1-370) and NTR residues 43-424 (SEQ ID NO.: 165) to create a SEQ ID NO.: 166. SEQ ID NO.: 166 was cloned into plasmids pMPX-85, pMPX-87, pMPX-66 and pMPX-67 (respectively, SEQ ID NOS.: 140, 142, 151 and 153) using SalI and KpnI.

Three-step PCR with oligonucleotides, SEQ ID NOS.: 175 and 176 as primers was used to amplify NTR residues 43-424 from rat brain cDNA. SEQ ID NOS.: 177 and 178 were then used with the NTR (43-424) template to add factor Xa and FLAG sequence. Finally, SEQ ID NOS.: 177 and 179 were used to add a KpnI site to create SEQ ID NO.: 165. Using overlap PCR with malE (1-370) containing extended NTR homology, a chimeric translational fusion was made between NTR (43-424) and MalE (1-370) (SEQ ID NO.: 164) to create a SEQ ID NO.: 166. SEQ ID NO.: 166 was cloned into SEQ ID NOS.: 140, 142, 151 and 153 using SalI and KpnI.

Using three-step PCR oligonucleotides SEQ ID NOS.: 175 and 176 were first used to amplify NTR residues 43-424 from rat brain cDNA. SEQ ID NOS.: 178 and 180 were then used with the NTR (43-424) template to add factor Xa and FLAG sequence. Finally, SEQ ID NOS.: 179 and 181 were used to add KpnI to create SEQ ID NO.: 167. SEQ ID NO.: 167 was cloned into SEQ ID NOS.: 140, 142, 151 and 153 using SalI and KpnI.

Oligonucleotides SEQ ID NOS.: 182, 183, 184 and 185 were used to amplify TrxA residues 2-109 from the E. coli chromosome to create SEQ ID NO.: 168. Using NotI, TrxA residues 2-109 was cloned into SEQ ID NOS.: 166 and 167 to create SEQ ID NOS.: 169 and 170, respectively. SEQ ID NO.: 169 and 170 were cloned into SEQ ID NOS.: 140, 142, 151 and 153 using SalI and KpnI.

Example 22

Methods for Functional GPCR Assay

Functional G-protein-coupled receptor (GPCR) binding assays in minicells requires expression of a GPCR of interest into the minicell membrane bilayer and cytoplasmic expression of the required G-protein. For these purposes, constructs were created to co-express both a GPCR and a G-protein. To regulate the ratio of GPCR to G-protein, transcriptional fusions were created. In these constructs, the GPCR and G-protein are co-transcribed as a bi-cistronic mRNA. To measure the GPCR-G-protein interaction in the intact minicell, each protein was created as a chimera with a transactivation domain. For these studies the N-terminal DNA-binding, activation domain of the ToxR protein from *V. cholerae* was fused to the C-terminus of both the GPCR and G-protein. Finally, to measure the interaction GPCR-G-protein interaction, the ToxR-activated ctx promoter region was cloned in front of lacZ. Dimerization of the ToxR DNA-binding region will bind and activate the ctx promoter. In this construct, heterodimerization of the GPCR and G-protein will promote dimerization of ToxR that will be monitored by LacZ expression. Details of these constructs are shown in Table 29.

TABLE 29

FUNCTIONAL HUMAN GPCR CONSTRUCTS

| Protein [a,b] | Construct [a,b] | SEQ ID NO.: |
|---|---|---|
| β2AR | SalI-β2AR-PstI, XhoI | 186 |
| GS1α | XhoI-GS1α-XbaI | 187 |
| β2AR-GS1α fusion | SalI-β2AR-PstI, XhoI-GS1α-XbaI | 188 |
| β2AR-stop | SalI-β2AR-PstI-Stop-SD-XhoI | 189 |
| β2AR-stop-GS1α | SalI-β2AR-PstI-Stop-SD-XhoI-GS1α-XbaI | 190 |
| ToxR | ClaI-ToxR-XbaI | 191 |
| GS1α | XhoI-GS1α-ClaI | 192 |
| GS2α | XhoI-GS2α-ClaI | 193 |
| Gαq | XhoI-Gqα-ClaI | 194 |
| Giα | XhoI-Giα-ClaI | 195 |
| Gα12/13 | XhoI-Gα12/13-ClaI | 196 |
| GS1α-ToxR | XhoI-GS1α-ClaI-ToxR-XbaI | 197 |
| GS2α-ToxR | XhoI-GS2α-ClaI-ToxR-XbaI | 198 |
| Gαq-ToxR | XhoI-Gαq-ClaI-ToxR-XbaI | 199 |
| Giα-ToxR | XhoI-Giα-ClaI-ToxR-XbaI | 200 |
| Gα12/13-ToxR | XhoI-Gα12/13-ClaI-ToxR-XbaI | 201 |
| ToxR | PstI-ToxR-XhoI | 202 |
| β2AR | SalI-β2AR-PstI | 203 |
| β2AR-ToxR | SalI-β2AR-PstI-ToxR-Stop-SD-XhoI | 204 |
| β2AR-ToxR-stop-GS1α-ToxR | SalI-β2AR-PstI-ToxR-Stop-SD-XhoI-GS1α-ClaI-ToxR-XbaI | 205 |
| Pctx | XbaI-Pctx-lacZ homology | 206 |
| lacZ | Pctx homology-lacZ-XbaI | 207 |
| Pctx::lacZ | XbaI-Pctx-lacZ-XbaI | 208 |

[a] "SD" refers to the Shine-Delgarno ribosome-binding sequence and "ToxR" refers to the transactivation, DNA-binding domain of the ToxR protein (residues 5-141).
[b] All mature constructs were cloned into SalI and XbaI sites of SEQ ID NOS.: 140, 142, 151 and 153.

TABLE 30

OLIGONUCLEOTIDE PRIMER SEQUENCES FOR TABLE 29.

| SEQ ID NO.: | Primer name | 5' to 3' sequence |
|---|---|---|
| 209 | β2AR-1 | GGGGCAACCCGGGAACGGCAGCGCC |
| 210 | β2AR-2 | GCAGTGAGTCATTTGTACTACAATTCCTCC |
| 211 | β2AR-1-SalI | CGCGGTCGACATGGGGCAACCCGGGAACGGCAGCGCC |
| 212 | β2AR-2-Link-XhoI | GGCTCGAGCTGCAGGTTGGTGACCGTCTGGCCACGCTCTAGCAGTGAGTCATTTGTACTACAATTCC |
| 213 | GS1α-1 | GGGCTGCCTCGGGAACAGTAAGACCGAGG |
| 214 | GS1α-2 | GAGCAGCTCGTACTGACGAAGGTGCATGC |
| 215 | GS1α-1-XhoI | GGAGGCCCTCGAGATGGGCTGCCTCGGAACAGTAAGACCGAGG |
| 216 | GS1α-2-XbaI | CCTCTAGATTATTATCGATGAGCAGCTCGTACTGACGAAGGTGCATGC |
| 217 | GS1α-2-ClaI | CCATCGATGAGCAGCTCGTACTGACGAAGGTGCATGC |
| 218 | Gα12-1 | CCGGGGTGGTGCGGACCCTCAGCCGCC |
| 219 | Gα12-2 | TGCAGCATGATGTCCTTCAGGTTCTCC |
| 220 | Gα12-1-XhoI | GCGGGCTCGAGATGTCCGGGGTGGTGCGGACCCTCAGCCGC |
| 221 | Gα12-2-ClaI | GCGCCATCGATCTGCAGCATGATGTCCTTCAGGTTCTCC |
| 222 | Gαq-1 | GACTCTGGAGTCCATCATGGCGTGCTGC |
| 223 | Gαq-2 | CCAGATTGTACTCCTTCAGGTTCAACTGG |
| 224 | Gαq-1-XhoI | ATGACTCTGGAGTCCATCATGGCGTGCTGC |
| 225 | Gαq-2-ClaI | GCGCCATCGATGACCAGATTGTACTCCTTCAGGTTCAACTGG |
| 226 | Giα-1 | GGGCTGCACCGTGAGCGCCGAGGACAAGG |
| 227 | Giα-2 | CCTTCAGGTTGTTCTTGATGATGACATCGG |
| 228 | Giα-1-XhoI | ATGGGCTGCACCGTGAGCGCCGAGGACAAGG |
| 229 | Giα-2-ClaI | GCGCCATCGATGAAGAGGCCGCAGTCCTTCAGGTTGTTCTTGATGATGACATCGG |
| 230 | GS2α-1 | GGGCTGCCTCGGGAACAGTAAGACCGAGG |
| 231 | GS2α-2 | GAGCAGCTCGTACTGACGAAGGTGCATGC |
| 232 | GS2α-1-XhoI | ATGGGCTGCCTCGGGAACAGTAAGACCGAGG |
| 233 | GS2α-2-ClaI | GCGCCATCGATGAGCAGCTCGTACTGACGAAGGTGCATGC |

TABLE 30-continued

OLIGONUCLEOTIDE PRIMER SEQUENCES FOR TABLE 29.

| SEQ ID NO.: | Primer name | 5' to 3' sequence |
|---|---|---|
| 234 | β2AR-2-Link-Stop-XhoI | GGCTCGAGGGCCTCCTTGATTATTAC TCGAGGGCCTCCTTGATTATTACTGC AGGTTGGTGACCGTCTGGCCACGCTC TAGCAGTGAGTCATTTGTACTACAAT TCC |
| 235 | β2AR-2-Link | CCCTGCAGGTTGGTGACCGTCTGGCC ACGCTCTAGCAGTGAGTCATTTGTAC TACAATTCC |
| 236 | Tox (5-141)-1B | GGACACAACTCAAAAGAGATATCGAT GAGTCATATTGG |
| 237 | Tox (5-141)-2 | GAGATGTCATGAGCAGCTTCGTTTTC GCG |
| 238 | Tox (5-141)-1-Link | GCGTGGCCAGACGGTCACCAACCTGC AGGGACACAACTCAAAAGAGATATCG |
| 239 | Tox(5-141)-2-XhoI | CGGGGATCCTCTAGATTATTAAGAGA TGTCATGAGCAGCTTCGTTTTCGCG |
| 240 | Ctx-1 | GGCTGTGGGTAGAAGTGAAACGGGGT TTACCG |
| 241 | Ctx-2 | CTTTACCATATAATGCTCCCTTTGTT TAACAG |
| 242 | Ctx-2-XbaI | CGCGGTCTAGAGGCTGTGGGTAGAAG TGAAACGGGGTTTACCG |
| 243 | Ctx-2-LacZ | CGACGGCCAGTGAATCCGTAATCATG GTCTTTACCATATAATGCTCCCTTTG TTTAACAG |
| 244 | LacZ-1 | CCATGATTACGGATTCACTGGCCGTC G |
| 245 | LacZ-2 | CCAGACCAACTGGTAATGGTAGCGAC C |
| 246 | LacZ-1-Ctx | GGTAAAGACCATGATTACGGATTCAC TGGCCGTCG |
| 247 | LacZ-2-XbaI | GCGCCTCTAGAAATACGCCCTTTCGG ATGAGGGCGTTATTATTTTTGACACC AGACCAACTGGTAATGGTAGCGACC |

Oligonucleotides SEQ ID NOS.: 209, 210, 211 and 212 were used to amplify human β2AR from human cDNA to create SEQ ID NO.: 186. Using SalI and XhoI a translational fusion was made between β2AR and human GS1α (SEQ ID NO.: 187) to create a SEQ ID NO.: 188. SEQ ID NO.: 188 was cloned into SEQ ID NOS.: 140, 142, 151 and 153 using SalI and XbaI.

Oligonucleotides SEQ ID NOS.: 213, 214, 215 and 216 were used to amplify human GS1α from human cDNA to create SEQ ID NO.: 187. Using XhoI and XbaI a translational fusion was made between GS1α and human β2AR (SEQ ID NO.: 186) create SEQ ID NO.: 188. SEQ ID NO.: 188 was cloned into SEQ ID NOS.: 140, 142, 151 and 153 using SalI and XbaI.

Oligonucleotides SEQ ID NOS.: 213, 214, 215 and 217 were used to amplify human GS1α from human cDNA to create SEQ ID NO.: 192. Using XhoI and XbaI a translational fusion was made with ToxR residues 5-141 from *Vibrio cholerae* (SEQ ID NO.: 191) to create SEQ ID NO.: 197. To be used to create a transcriptional fusion with β2AR-ToxR chimeras as shown in SEQ ID NO.: 205 and future GPCR-ToxR chimeras.

Oligonucleotides SEQ ID NOS.: 218, 219, 220 and 221 were used to amplify human Gα12/13 from human cDNA to create SEQ ID NO.: 196. Using XhoI and XbaI a translational fusion was made with ToxR residues 5-141 from *Vibrio cholerae* (SEQ ID NO.: 191) to create SEQ ID NO.: 201. To be used to create future transcriptional fusions with GPCR-ToxR chimeras as shown in SEQ ID NO.: 205.

Oligonucleotides SEQ ID NOS.: 222, 223, 224 and 225 were used to amplify human Gαq from human cDNA to create SEQ ID NO.: 194. Using XhoI and XbaI a translational fusion was made with ToxR residues 5-141 from *Vibrio cholerae* (SEQ ID NO.: 191) to create SEQ ID NO.: 199. To be used to create future transcriptional fusions with GPCR-ToxR chimeras as shown in SEQ ID NO.: 205.

Oligonucleotides SEQ ID NOS.: 226, 227, 228 and 229 were used to amplify human Giα from human cDNA to create SEQ ID NO.: 195. Using XhoI and XbaI a translational fusion was made with ToxR residues 5-141 from *Vibrio cholerae* (SEQ ID NO.: 191) to create SEQ ID NO.: 200. To be used to create future transcriptional fusions with GPCR-ToxR chimeras as shown in SEQ ID NO.: 205.

Oligonucleotides SEQ ID NOS.: 230, 231, 232 and 233 were used to amplify human GS2α from human cDNA to create SEQ ID NO.: 193. Using XhoI and XbaI a translational fusion was made with ToxR residues 5-141 from *Vibrio cholerae* (SEQ ID NO.: 191) to create SEQ ID NO.: 198. To be used to create future transcriptional fusions with GPCR-ToxR chimeras as shown in SEQ ID NO.: 205.

Oligonucleotides SEQ ID NOS.: 209, 210, 211 and 234 were used to amplify human β2AR from human cDNA to create SEQ ID NO.: 189. Using SalI and XhoI a transcriptional fusion was made between β2AR and human GS1α (SEQ ID NO.: 187) to create a SEQ ID NO.: 190. SEQ ID NO.: 190 was cloned into SEQ ID NOS.: 140, 142, 151 and 153 using SalI and XbaI.

Oligonucleotides SEQ ID NOS.: 236, 237, 238 and 239 were used to amplify bases coinciding with ToxR residues 5-141 from *Vibrio Cholerae* to create SEQ ID NO.: 202. Using PstI and XhoI a translational fusion was made between ToxR and human β2AR (SEQ ID NO.: 203) to create SEQ ID NO.: 204.

Oligonucleotides SEQ ID NOS.: 209, 210, 211 and 235 were used to amplify human β2AR from human cDNA to create SEQ ID NO.: 203. Using SalI and PstI a translational fusion was made between β2AR and ToxR (SEQ ID NO.: 202) to create SEQ ID NO.: 204.

Using oligonucleotides SEQ ID NOS.: 197 and 204 transcriptional fusions were created between the β2AR-ToxR translational fusion (SEQ ID NO.: 204) and the GS1α-ToxR translational fusion (SEQ ID NO.: 197) to create SEQ ID NO.: 205.

Oligonucleotides SEQ ID NOS.: 240, 241, 242 and 243 were used to amplify the ctx promoter region (Pctx) from *Vibrio cholerae* to create SEQ ID NO.: 206. Combining this PCR product in combination with the SEQ ID NO.: 207 PCR product and amplifying in the presence of SEQ ID NOS.: 242, 247, SEQ ID NO.: 208 was created. Using XbaI, the SEQ ID NO.: 208 reporter construct was subsequently cloned into pACYC184 for co-transformation with the GPCR-G-protein fusions constructs above.

Oligonucleotides SEQ ID NOS.: 244, 245, 246 and 247 were used to amplify the lacZ from *E. coli* to create SEQ ID NO.: 207. Combining this PCR product in combination with the SEQ ID NO.: 206 PCR product and amplifying in the presence of SEQ ID NOS.: 242 and 247, SEQ ID NO.: 208 was created. Using XbaI, the 208 reporter construct was subsequently cloned into pACYC184 for co-transformation with the GPCR-G-protein fusions constructs above.

Example 23

Modular Membrane-Targeting and Solubilization Expression Constructs

To produce membrane proteins efficiently in minicells it may be necessary to create chimeric fusions with the membrane protein of interest. In this Example, various regions of the MalE protein have been cloned into a modular expression system designed to create chimeric fusions with direct difficult to target membrane proteins to produce leader domains that will direct the proteins to the cytoplasmic membrane (Miller, K., W., et al. 1998. Production of active chimeric pediocin AcH in *Escherichia coli* in the absence of processing and secretion genes from the *Pediococcus* pap operon. Appl. Environ. Microbiol. 64:14-20). Similarly, a modified version of the TrxA protein has also been cloned into this modular expression system to create chimeric fusions with proteins that are difficult to maintain in a soluble conformation (LaVallie, E. R., et al. 1993. A thioredoxin gene fusion expression system that circumvents inclusion body formation in the *E. coli* cytoplasm. Biotechnology (N.Y.) 11:187-193). Table 31 describes each of these modular constructs.

TABLE 31

MODULAR MEMBRANE-TARGETING AND SOLUBILIZATION EXPRESSION CONSTRUCTS

| Protein[a] | Construct[a] | SEQ ID NO |
|---|---|---|
| MalE (1-28) | NsiI-MalE(1-28)-Factor Xa-PstI, SalI, XbaI-FLAG, NheI | 248 |
| MalE (1-370, del 354-364) | NsiI-MalE(1-370, del 354-364)-Factor Xa-PstI, SalI, XbaI-FLAG, NheI | 249 |
| TrxA (2-109, del 103-107) | PstI, SalI, XbaI-TrxA(2-109, del 103-107)-FLAG-NheI | 250 |
| MalE (1-28)-TrxA (2-109, del 103-107) | NsiI-MalE(1-28)-Factor Xa-PstI, SalI, XbaI-TrxA (2-109 del 103-107)-FLAG, NheI | 251 |
| MalE (1-370, del 354-364)-TrxA (2-109, del 103-107) | NsiI-MalE(1-370, del 354-364)-Factor Xa-PstI, SalI, XbaI-TrxA (2-109 del 103-107)-FLAG, NheI | 252 |

[a] The term "del" refers to a deletion in which amino acid residues following the term "del" are removed from the sequence.

TABLE 32

OLIGONUCLEOTIDE PRIMER SEQUENCES FOR TABLE 31.

| SEQ ID NO.: | Primer name | 5' to 3' sequence |
|---|---|---|
| 253 | MalE-1-NsiI | CGCGGATGCATATGAAAATAAAAACAGGTGCACGC ATCCTCGCATTATCCGCATTAACGACGATGATGTT TTCCGCCTCGGCTCTCGCC |
| 254 | MalE-2-middle | CGTCGACCGAGGCCTGCAGGCGGGCTTCGATGATT TTGGCGAGAGCCGAGGCGGAAAACATCATCGTCG |
| 255 | MalE-3s-NheI | CGAAGCCCGCCTGCAGGCCTCGGTCGACGCCGAAT CTAGAGATTATAAAGATGACGATGACAAATAATAA GCTAGCGGCGC |
| 256 | MalE-4-NheI | GCGCCGCTAGCTTATTATTTGTCATCG |
| 257 | MalE-1a | GGTGCACGCATCCTCGCATTATCCGC |

TABLE 32-continued

OLIGONUCLEOTIDE PRIMER SEQUENCES FOR TABLE 31.

| SEQ ID NO.: | Primer name | 5' to 3' sequence |
|---|---|---|
| 258 | MalE-2a | GGCGTTTTCCATGGTGGCGGCAATACGTGG |
| 259 | MalE-1-NsiI | CGCGGATGCATATGAAAATAAAAACAGGTGCACGC ATCCTCGCATTATCCGC |
| 260 | MalE-2-NheI | CCGAGGCCTGCAGGCGGGCTTCGATACGCACGGCA TACCAGAAAGCGGACTGGGCGTTTTCCATGGTGGC GGCAATACGTGG |
| 261 | MalE-3L-NheI | GCGCCGCTAGCTTATTATTTGTCATCGTCATCTTT TATAATCTCAGATTCGGCGTCGACCGAGGCCTGCA GGCGGGCTTCGATACGC |
| 262 | TrxA-1a | CCTGACTGACGACAGTTTTGACACGG |
| 263 | TrxA-2a | CCTTTAGACAGTGCACCCACTTTGGTTGCCGC |
| 264 | TrxA-1a-PstI | CGCGGCTGCAGGCCTCGGTCGACGCCGAATCTAGA AGCGATAAAATTATTCACCTGACTGACGACAGTTT TGACACGG |
| 265 | TrxA-2-NheI | GCGCCGCTAGCTTATTATTTGTCATCGTCATCTTT ATAATCCGCCAGGTTCTCTTTCAACTGACCTTTAG ACAGTGCACCCACTTTGGTTGCCGC |

Oligonucleotides SEQ ID NOS.: 253, 254, 255 and 256 overlap with each other to form a scaffold template to PCR amplify malE (1-28) to create a SEQ ID NO.: 248. Following PCR amplification, SEQ ID NO.: 248 was digested with NsiI and NheI and cloned into SEQ ID NOS.: 152, 154, 139 and 141 digested with PstI and XbaI. The resultant products create SEQ ID NOS.: 266, 267, 268 and 269, respectively, that lose both the 5-prime PstI and 3-prime XbaI restriction site and retain the PstI, SalI, and XbaI restriction sites between MalE (1-28) and the FLAG sequence. Insertion of a protein in alignment with these sites results in a chimeric protein containing amino-terminal MalE (1-28) and carboxy-terminal FLAG.

Oligonucleotides SEQ ID NOS.: 257, 258, 259 and 260 were used to amplify malE (1-370 with a deletion removing residues 354-364) to create SEQ ID NO.: 249. Following PCR amplification, SEQ ID NO.: 249 was digested with NsiI and NheI and cloned into SEQ ID NOS.: 152, 154, 139 and 141 digested with PstI and XbaI. The resultant products create SEQ ID NOS.: 270, 271, 272 and 273, respectively, that lose both the 5-prime PstI and 3-prime XbaI restriction site and retain the PstI, SalI, and XbaI restriction sites between MalE (1-370, del 354-364) and the FLAG sequence. Insertion of a protein in alignment with these sites results in a chimeric protein containing amino-terminal MalE (1-370, del 354-364) and carboxy-terminal FLAG.

Oligonucleotides SEQ ID NOS.: 262, 263, 264 and 265 were used to amplify trxA (2-109 with a deletion removing residues 103-107) to create SEQ ID NO.: 250. Following PCR amplification, SEQ ID NO.: 250 was digested with PstI and NheI and cloned into SEQ ID NOS.: 152, 154, 139 and 141 digested with PstI and XbaI. to create SEQ ID NOS.: 274, 275, 276 and 277, respectively. Using these restriction digestion combinations results in loss of the XbaI SEQ ID NO.: 249 insertion site.

The resultant products create SEQ ID NOS.: 274, 275, 276 and 277, respectively, that lose the 3-prime XbaI restriction site and retain the PstI, SalI, and XbaI restriction sites on the 3-prime end of the TrxA (1-109, del 103-107) sequence.

Insertion of a protein in alignment with these sites results in a chimeric protein containing Carboxy-terminal TrxA (1-109, del 103-107)-FLAG.

SEQ ID NO.: 248 was digested with NsiI and XbaI and cloned into SEQ ID NOS.: 274, 275, 276 and 277 that were digested with PstI and XbaI. The resultant products create SEQ ID NOS.: 278, 279, 280 and 281, respectively, that lose the 5 prime PstI restriction site and retain the PstI, SalI, and XbaI restriction sites between MalE (1-28) and TrxA (1-109, del 103-107). Insertion of a protein in alignment with these sites results in a chimeric protein containing amino-terminal MalE (1-28) and carboxy-terminal TrxA (1-109, del 103-107)-FLAG.

SEQ ID NO.: 249 was digested with NsiI and XbaI and cloned into SEQ ID NOS.: 274, 275, 276 and 277 that were digested with PstI and XbaI. The resultant products create SEQ ID NOS.: 282, 283, 284 and 285, respectively, that lose the 5 prime PstI restriction site and retain the PstI, SalI, and XbaI restriction sites between MalE (1-370, del 354-364) and TrxA (1-109, del 103-107). Insertion of a protein in alignment with these sites results in a chimeric protein containing amino-terminal MalE (1-370, del 354-364) and carboxy-terminal TrxA (1-109, del 103-107)-FLAG.

Example 24

Poroplast™ Formation

Minicells are used to prepare Poroplasts in order to increase the accessibility of a membrane protein component and/or domain to the outside environment. Membrane proteins in the inner membrane are accessible for ligand binding and/or other interactions in poroplasts, due to the absence of an outer membrane. The removal of the outer membrane from *E. coli* whole cells and minicells to produce poroplasts was carried out using modifications of previously described protoplast and analysis protocols (Birdsell et al., Production and Ultrastructure of Lysozyme and Ethylenediaminetetraacetate-Lysozyme Spheroplasts of *Escherichia coli*, J. Bacteriol. 93:427-437, 1967; Weiss et al., Protoplast Formation in *Escherichia Coli*, J. Bacteriol. 128:668-670, 1976; Matsuyama, S-I., et al. SecD is involved in the release of translocated secretory proteins from the cytoplasmic membrane of *Escherichia coli*. 12:265-270, 1993).

In brief, cells were grown to late-log phase and pelleted at room temperature. Minicells were also isolated from cultures in late-log phase. The pellet was washed twice with 50 mM Tris, pH 8.0. Following the second wash, $1 \times 10^9$ cells were resuspended in 1 ml 50 mM Tris (pH 8.0) that contained 8% sucrose and 2 mM EDTA. Cell/EDTA/sucrose mixtures were incubated at 37° C. for 10 min, centrifuged, decanted, and poroplasted cells were resuspended in 50 mM Tris, pH 8.0 with 8% sucrose. Incubation with anti-LPS-coated magnetic beads, as described in Example 14, is used to enrich for poroplasts that lack LPS. Following incubation with the resuspended protoplasted cells, the anti-LPS magnetic beads were removed from suspension with a magnet.

To examine the range of molecular sizes that can pass through the cell wall, an IgG molecule was tested for its ability to pass the intact cell wall. Binding of an antibody to the ToxR-PhoA chimera expressed on the inner membrane minicell poroplasts was measured. Briefly, minicell poroplasts with and without inner membrane-bound ToxR-PhoA were incubated at 37° C. with anti-PhoA antibody in reaction buffer (50 mM Tris, pH 8.0, 8% sucrose, 1% BSA, and 0.01% Tween-20). Following incubation, poroplasts were centrifuged, washed 3 times with reaction buffer, and resuspended in 50 mM Tris, pH 8.0 with 8% sucrose. Following resuspension, bound proteins from $5 \times 10^7$ minicells or minicell poroplasts were separated using denaturing SDS-PAGE, transferred to nitrocellulose, and developed using with both anti-PhoA antibody and secondary antibody against both heavy and light chains of anti-PhoA IgG (Table 33).

TABLE 33

ANTI-PHOA ACCESSIBILITY TO POROPLAST INNER MEMBRANE-BOUND TOXR-PHOA

| | | | | |
|---|---|---|---|---|
| EDTA (mM) | 0 | 2 | 0 | 2 |
| Lysozyme (mg/ml) | 0 | 0 | 5 | 5 |
| | Poroplasts (ng antibody bound) | | Protoplasts (ng antibody bound) | |
| Minicells ToxR-PhoA | ND $^a$ | 0.6 | ND $^a$ | 12.8 |
| Minicells only | ND $^a$ | ND $^a$ | ND $^a$ | ND $^a$ |

$^a$ Non-detectable

These results demonstrate that the cell wall present on poroplasts is penetrable by an IgG molecule and that an IgG molecule is capable of passing the intact cell wall and binding to an inner membrane protein. From this data it appears that poroplast operate at ~10% the efficiency of protoplasts by allowing 0.6 ng of IgG to bind inner membrane-bound ToxR-PhoA compared to 12.8 ng. However, given the large size of IgG (~150,000 Daltons) it is expected that molecules having a smaller molecular weight will efficiently access inner membrane proteins in poroplasts.

Example 25

Production of Neurotensin Receptor (NTR)

Figure 2:
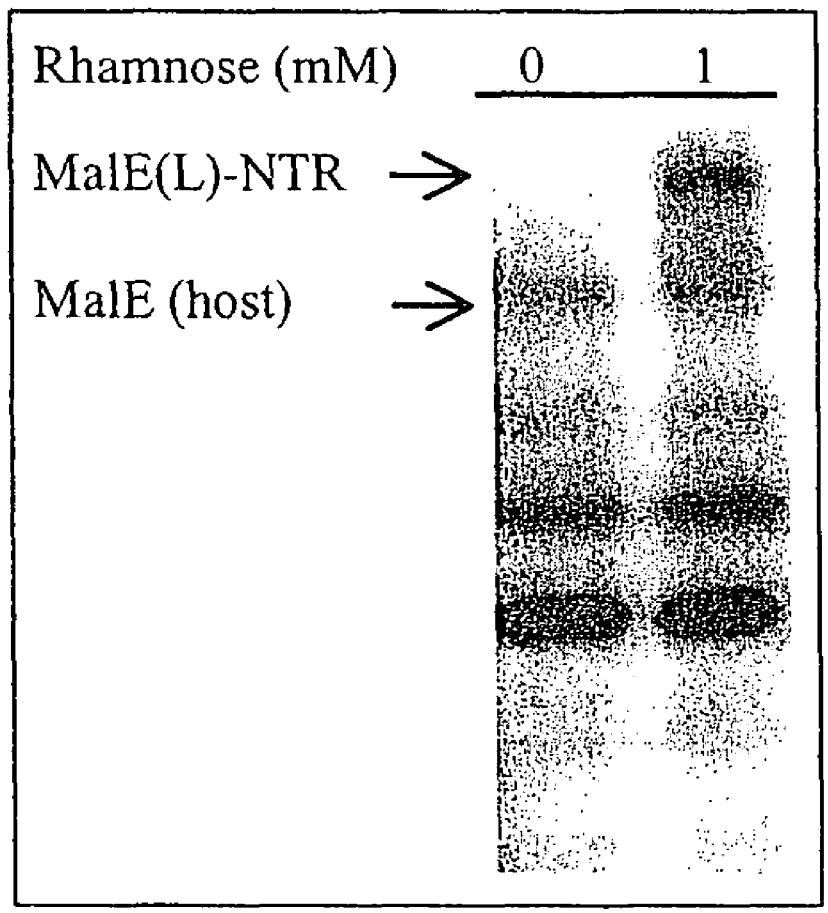
FIG. 2 shows induction of MalE(L)-NTR in isolated minicells.

To demonstrate expression of NTR in isolated minicells, MalE(L)-NTR (SEQ ID NO.: 166 was cloned into pMPX-67 (SEQ ID NO.: 151). Following minicell isolation, $1.5 \times 10^9$ minicells were induced with 1 mM Rhamnose for 2 hour at 37° C. Following induction, the protein produced was visualized via Western analysis using an anti-MalE antibody following separation on an SDS-PAGE. The results are shown in FIG. 2.

These data demonstrates that MalE(L)-NTR is induced 87-fold by addition of 1 mM rhamnose to the minicell induction mixture. Cross-reactive proteins are host MalE and non-specific binding by Goat-anti-mouse HRP secondary antibody.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

Additional Information Regarding Sequences
SEQ ID NO 1
pMPX-23 (completefisZ cloned into pMPX-18 using PCR-introduced PstI and XbaI)

```
                       Shine-Delgarno      PstI
1621 CCATACCCGTTTTTTTGGGCTAGCAGGAGGAATTCACCCTGCAGATGTTTGAACCAATGG
   1                                             M   F   E   P   M 1681 AACTTACCAATGACGCGGTGATTAAAGTCATCGGCGTCGGCGGCGGCGGTAATGCTG
   6  E   L   T   N   D   A   V   I   K   V   I   G   V   G   G   G   G   N   A 1741 TTGAACACATGGTGCGCGAGCGCATTGAAGGTGTTGAATTCTTCGCGGTAAATACCGATG
  26  V   E   H   M   V   R   E   R   I   E   G   V   E   F   F   A   V   N   T   D 1801 CACAAGCGCTGCGTAAAACAGCGGTTGGACAGACGATTCAAATCGGTAGCGGTATCACCA
  46  A   Q   A   L   R   K   T   A   V   G   Q   T   I   Q   I   G   S   G   I   T 1861 AAGGACTGGGCGCTGGCGCTAATCCAGAAGTTGGCCGCAATGCGGCTGATGAGGATCGCG
  66  K   G   L   G   A   G   A   N   P   E   V   G   R   N   A   A   D   E   D   R 1921 ATGCATTGCGTGCGGCGCTGGAAGGTGCAGACATGGTCTTTATTGCTGCGGGTATGGGTG
  86  D   A   L   R   A   A   L   E   G   A   D   M   V   F   I   A   A   G   M   G 1981 GTGGTACCGGTACAGGTGCAGCACCAGTCGTCGCTGAAGTGGCAAAAGATTTGGGTATCC
 106  G   G   T   G   T   G   A   A   P   V   V   A   E   V   A   K   D   L   G   I 2041 TGACCGTTGCTGTCGTCACTAAGCCTTTCAACTTTGAAGGCAAGAAGCGTATGGCATTCG
 126  L   T   V   A   V   V   T   K   P   F   N   F   E   G   K   K   R   M   A   F 2101 CGGAGCAGGGGATCACTGAACTGTCCAAGCATGTGGACTCTCTGATCACTATCCCGAACG
 146  A   E   Q   G   I   T   E   L   S   K   H   V   D   S   L   I   T   I   P   N 2161 ACAAACTGCTGAAAGTTCTGGGCCGCGGTATCTCCCTGCTGGATGCGTTTGGCGCAGCGA
 166  D   K   L   L   K   V   L   G   R   G   I   S   L   L   D   A   F   G   A   A 2221 ACGATGTACTGAAAGGCGCTGTGCAAGGTATCGCTGAACTGATTACTCGTCCGGGTTTGA
 186  N   D   V   L   K   G   A   V   Q   G   I   A   E   L   I   T   R   P   G   L 2281 TGAACGTGGACTTTGCAGACGTACGCACCGTAATGTCTGAGATGGGCTACGCAATGATGG
 206  M   N   V   D   F   A   D   V   R   T   V   M   S   E   M   G   Y   A   M   M 2341 GTTCTGGCGTGGCGAGCGGTGAAGACCGTGCGGAAGAAGCTGCTGAAATGGCTATCTCTT
 226  G   S   G   V   A   S   G   E   D   R   A   E   E   A   A   E   M   A   I   S 2401 CTCCGCTGCTGGAAGATATCGACCTGTCTGGCGCGCGCGGCGTGCTGGTTAACATCACGG
 246  S   P   L   L   E   D   I   D   L   S   G   A   R   G   V   L   V   N   I   T 2461 CGGGCTTCGACCTGCGTCTGGATGAGTTCGAAACGGTAGGTAACACCATCCGTGCATTTG
 266  A   G   F   D   L   R   L   D   E   F   E   T   V   G   N   T   I   R   A   F 2521 CTTCCGACAACGCGACTGTGGTTATCGGTACTTCTCTTGACCCGGATATGAATGACGAGC
 286  A   S   D   N   A   T   V   V   I   G   T   S   L   D   P   D   M   N   D   E 2581 TGCGCGTAACCGTTGTTGCGACAGGTATCGGCATGGACAAACGTCCTGAAATCACTCTGG
 306  L   R   V   T   V   V   A   T   G   I   G   M   D   K   R   P   E   I   T   L 2641 TGACCAATAAGCAGGTTCAGCAGCCAGTGATGGATCGCTACCAGCAGCATGGGATGGCTC
 326  V   T   N   K   Q   V   Q   Q   P   V   M   D   R   Y   Q   Q   H   G   M   A 2701 CGCTGACCCAGGAGCAGAAGCCGGTTGCTAAAGTCGTGAATGACAATGCGCCGCAAACTG
 346  P   L   T   Q   E   Q   K   P   V   A   K   V   V   N   D   N   A   P   Q   T 2761 CGAAAGAGCCGGATTATCTGGATATCCCAGCATTCCTGCGTAAGCAAGCTGATTAATAAT
 366  A   K   E   P   D   Y   L   D   I   P   A   F   L   R   K   Q   A   D XbaI
2821 CTAGAGGATCCCCGGGTACCGAGCTCGAATTCGTAATCATGGTCATAGCTGTTTCCTGTG
```

Sequence contains full-length ftsZ PCR amplified from *E. coli* MG1655 using oligos containing PstI and XbaI restriction sites.

SEQ ID NO 2
pMPX-47 (complete ftsZ cloned into pMPX-5 using PCR-introduced PstI and XbaI)

```
                                            Shine-Delgarno      PstI
2401 GAATTCAGGCGCTTTTTAGACTGGTCGTAATGAAATTCAGCAGGATCACATTCTGCAGAT
                                                                 M 2961 GTTTGAACCAATGGAACTTACCAATGACGCGGTGATTAAAGTCATCGGCGTCGGCGGCGG
   2  F   E   P   M   E   L   T   N   D   A   V   I   K   V   I   G   V   G   G 2521 CGGCGGTAATGCTGTTGAACACATGGTGCGCGAGCGCATTGAAGGTGTTGAATTCTTCGC
  22  G   G   N   A   V   E   H   M   V   R   E   R   I   E   G   V   E   F   F   A 2581 GGTAAATACCGATGCACAAGCGCTGCGTAAAACAGCGGTTGGACAGACGATTCAAATCGG
  42  V   N   T   D   A   Q   A   L   R   K   T   A   V   G   Q   T   I   Q   I   G 2691 TAGCGGTATCACCAAAGGACTGGGCGCTGGCGCTAATCCAGAAGTTGGCCGCAATGCGGC
  62  S   G   I   T   K   G   L   G   A   G   A   N   P   E   V   G   R   N   A   A 2701 TGATGAGGATCGCGATGCATTGCGTGCGGCGCTGGAAGGTGCAGACATGGTCTTTATTGC
  82  D   E   D   R   D   A   L   R   A   A   L   E   G   A   D   M   V   F   I   A 2761 TGCGGGTATGGGTGGTGGTACCGGTACAGGTGCAGCACCAGTCGTCGCTGAAGTGGCAAA
 102  A   G   M   G   G   G   T   G   T   G   A   A   P   V   V   A   E   V   A   K 2821 AGATTTGGGTATCCTGACCGTTGCTGTCGTCACTAAGCCTTTCAACTTTGAAGGCAAGAA
 122  D   L   G   I   L   T   V   A   V   V   T   K   P   F   N   F   E   G   K   K 2881 GCGTATGGCATTCGCGGAGCAGGGGATCACTGAACTGTCCAAGCATGTGGACTCTCTGAT
 192  R   M   A   F   A   E   Q   G   I   T   E   L   S   K   H   V   D   S   L   I 2991 CACTATCCCGAACGACAAACTGCTGAAAGTTCTGGGCCGCGGTATCTCCCTGCTGGATGC
 162  T   I   P   N   D   K   L   L   K   V   L   G   R   G   I   S   L   L   D   A 3001 GTTTGGCGCAGCGAACGATGTACTGAAAGGCGCTGTGCAAGGTATCGCTGAACTGATTAC
 182  F   G   A   A   N   D   V   L   K   G   A   V   Q   G   I   A   E   L   I   T 3061 TCGTCCGGGTTTGATGAACGTGGACTTTGCAGACGTACGCACCGTAATGTCTGAGATGGG
 202  R   P   G   L   M   N   V   D   F   A   D   V   R   T   V   M   S   E   M   G 3121 CTACGCAATGATGGGTTCTGGCGTGGCGAGCGGTGAAGACCGTGCGGAAGAAGCTGCTGA
 222  Y   A   M   M   G   S   G   V   A   S   G   E   D   R   A   E   E   A   A   E 3181 AATGGCTATCTCTTCTCCGCTGCTGGAAGATATCGACCTGTCTGGCGCGCGCGGCGTGCT
 242  M   A   I   S   S   P   L   L   E   D   I   D   L   S   G   A   R   G   V   L 3241 GGTTAACATCACGGCGGGCTTCGACCTGCGTCTGGATGAGTTCGAAACGGTAGGTAACAC
 262  V   N   I   T   A   G   F   D   L   R   L   D   E   F   E   T   V   G   N   T 3301 CATCCGTGCATTTGCTTCCGACAACGCGACTGTGGTTATCGGTACTTCTCTTGACCCGGA
 282  I   R   A   F   A   S   D   N   A   T   V   V   I   G   T   S   L   D   P   D 3361 TATGAATGACGAGCTGCGCGTAACCGTTGTTGCGACAGGTATCGGCATGGACAAACGTCC
 302  M   N   D   E   L   R   V   T   V   V   A   T   G   I   G   M   D   K   R   P 3421 TGAAATCACTCTGGTGACCAATAAGCAGGTTCAGCAGCCAGTGATGGATCGCTACCAGCA
 322  E   I   T   L   V   T   N   K   Q   V   Q   Q   P   V   M   D   R   Y   Q   Q 3481 GCATGGGATGGCTCCGCTGACCCAGGAGCAGAAGCCGGTTGCTAAAGTCGTGAATGACAA
 342  H   G   M   A   P   L   T   Q   E   Q   K   P   V   A   K   V   V   N   D   N 3541 TGCGCCGCAAACTGCGAAAGAGCCGGATTATCTGGATATCCCAGCATTCCTGCGTAAGCA
 362  A   P   Q   T   A   K   E   P   D   Y   L   D   I   P   A   F   L   R   K   Q XbaI
3601 AGCTGATTAATAATCTAGAGGATCCCCGGGTACCGAGCTCGAATTCGTAATCATGGTCAT
 382  A   D
```

Sequence contains full-length ftsZ PCR amplified from *E. coli* MG1655 using oligos containing PstI and XbaI restriction sites.

SEQ ID NO 3
araC::Para::ftsZ inserted by RED recombination into *E. coli* MG1655 intD

```
         intD homology for recombination              Stop araC
 181  AAGCCTGCAT TGCGGCGCTT CAGTCTCCGG TGCATACTGT CCCGTTACCA ATTATGACAA
 241  CTTGACGGCT ACATCATTCA CTTTTTCTTC ACAACCGGCA CGGAACTCGC TCGGGCTGGC
 301  CCCGGTGCAT TTTTTAAATA CCCGCGAGAA ATAGAGTTGA TCGTCAAAAC CAACATTGCG
 361  ACCGACGGTG GCGATAGGCA TCCGGGTGGT GCTCAAAAGC AGCTTCGCCT GGCTGATACG
 421  TTGGTCCTCG CGCCAGCTTA AGACGCTAAT CCCTAACTGC TGGCGGAAAA GATGTGACAG
 481  ACGCGACGGC GACAAGCAAA CATGCTGTGC GACGCTGGCG ATATCAAAAT TGCTGTCTGC
 541  CAGGTGATCG CTGATGTACT GACAAGCCTC GCGTACCCGA TTATCCATCG GTGGATGGAG
 601  CGACTCGTTA ATCGCTTCCA TGCGCCGCAG TAACAATTGC TCAAGCAGAT TTATCGCCAG
 661  CAGCTCCGAA TAGCGCCCTT CCCCTTGCCC GGCGTTAATG ATTTGCCCAA ACAGGTCGCT
 721  GAAATGCGGC TGGTGCGCTT CATCCGGGCG AAAGAACCCC GTATTGGCAA ATATTGACGG
 781  CCAGTTAAGC CATTCATGCC AGTAGGCGCG CGGACGAAAG TAAACCCACT GGTGATACCA
 841  TTCGCGAGCC TCCGGATGAC GACCGTAGTG ATGAATCTCT CCTGGCGGGA ACAGCAAAAT
 901  ATCACCCGGT CGGCAAACAA ATTCTCGTCC CTGATTTTTC ACCACCCCCT GACCGCGAAT
 961  GGTGAGATTG AGAATATAAC CTTTCATTCC CAGCGGTCGG TCGATAAAAA AATCGAGATA
1021  ACCGTTGGCC TCAATCGGCG TTAAACCCGC CACCAGATGG GCATTAAACG AGTATCCCGG
1081  CAGCAGGGGA TCATTTTGCG CTTCAGCCAT ACTTTTCATA CTCCCGCCAT TCAGAGAAGA
                                       Start araC
1141  AACCAATTGT CCATATTGCA TCAGACATTG CCGTCACTGC GTCTTTTACT GGCTCTTCTC
                              ←
1201  GCTAACCAAA CCGGTAACCC CGCTTATTAA AAGCATTCTG TAACAAAGCG GGACCAAAGC
1261  CATGACAAAA ACGCGTAACA AAAGTGTCTA TAATCACGGC AGAAAAGTCC ACATTGATTA
1321  TTTGCACGGC GTCACACTTT GCTATGCCAT AGCATTTTTA TCCATAAGAT TAGCGGATCC
1381  TACCTGACGC TTTTTATCGC AACTCTCTAC TGTTTCTCCA TACCCGTTTT TTTGGGCTAG
      Shine-Delgarno     Start ftsZ
1441  CAGGAGGAAT TCACCCTGCA GATGTTTGAA CCAATGGAAC TTACCAATGA CGCGGTGATT
                              →
1501  AAAGTCATCG GCGTCGGCGG CGGCGGCGGT AATGCTGTTG AACACATGGT GCGCGAGCGC
1561  ATTGAAGGTG TTGAATTCTT CGCGGTAAAT ACCGATGCAC AAGCGCTGCG TAAAACAGCG
1621  GTTGGACAGA CGATTCAAAT CGGTAGCGGT ATCACCAAAG GACTGGGCGC TGGCGCTAAT
1681  CCAGAAGTTG GCCGCAATGC GGCTGATGAG GATCGCGATG CATTGCGTGC GGCGCTGGAA
1741  GGTGCAGACA TGGTCTTTAT TGCTGCGGGT ATGGGTGGTG GTACCGGTAC AGGTGCAGCA
1801  CCAGTCGTCG CTGAAGTGGC AAAAGATTTG GGTATCCTGA CCGTTGCTGT CGTCACTAAG
1861  CCTTTCAACT TTGAAGGCAA GAAGCGTATG GCATTCGCGG AGCAGGGGAT CACTGAACTG
1921  TCCAAGCATG TGGACTCTCT GATCACTATC CCGAACGACA AACTGCTGAA AGTTCTGGGC
1981  CGCGGTATCT CCCTGCTGGA TGCGTTTGGC GCAGCGAACG ATGTACTGAA AGGCGCTGTG
2041  CAAGGTATCG CTGAACTGAT TACTCGTCCG GGTTTGATGA ACGTGGACTT TGCAGACGTA
2101  CGCACCGTAA TGTCTGAGAT GGGCTACGCA ATGATGGGTT CTGGCGTGGC GAGCGGTGAA
2161  GACCGTGCGG AAGAAGCTGC TGAAATGGCT ATCTCTTCTC CGCTGCTGGA AGATATCGAC
2221  CTGTCTGGCG CGCGCGGCGT GCTGGTTAAC ATCACGGCGG GCTTCGACCT GCGTCTGGAT
2281  GAGTTCGAAA CGGTAGGTAA CACCATCCGT GCATTTGCTT CCGACAACGC GACTGTGGTT
```

-continued

```
2341 ATCGGTACTT CTCTTGACCC GGATATGAAT GACGAGCTGC GCGTAACCGT TGTTGCGACA

2401 GGTATCGGCA TGGACAAACG TCCTGAAATC ACTCTGGTGA CCAATAAGCA GGTTCAGCAG

2461 CCAGTGATGG ATCGCTACCA GCAGCATGGG ATGGCTCCGC TGACCCAGGA GCAGAAGCCG

2521 GTTGCTAAAG TCGTGAATGA CAATGCGCCG CAAACTGCGA AGAGCCGGA TTATCTGGAT

Stop ftsZ
2581 ATCCCAGCAT TCCTGCGTAA GCAAGCTGAT TAATAATCTA GAGGCGTTAC CAATTATGAC FRT scar              intD homology
2641 AACTTGACGG GAAGTTCCTA TACTTTCTAG AGAATAGGAA CTTC CC AAAG CCAGTATCAA for recombination
3721  CTCAGACAAA GGCAAAGCAT CTTG
```

Bold, italicized represents homology between the PCR product shown below and intD.
  araC::Para::ftsZ::FRT::kan::Frt
Following RED recombination into intD, the kanamycin cassette was removed with flp recombinase resulting in a single FRT scar as depicted above. Bold alone represents FRT scar after the flp reaction.
SEQ ID NO 4
rhaRS::Prha::ftsZ inserted by RED recombination into E. coli MG1655 intD

```
    intD homology for recombination         Stop rhaR
181 AAGCCTGCAT TGCGGCGCTT CAGTCTCCGC TGCATACTGT CCTTAATCTT TCTGCGAATT

241 GAGATGACGC CACTGGCTGG GCGTCATCCC GGTTTCCCGG GTAAACACCA CCGAAAAATA

301 GTTACTATCT TCAAAGCCAC ATTCGGTCGA AATATCACTG ATTAACAGGC GGCTATGCTG

361 GAGAAGATAT TGCGCATGAC ACACTCTGAC CTGTCGCAGA TATTGATTGA TGGTCATTCC

421 AGTCTGCTGG CGAAATTGCT GACGCAAAAC GCGCTCACTG CACGATGCCT CATCACAAAA

481 TTTATCCAGC GCAAAGGGAC TTTTCAGGCT AGCCGCCAGC CGGGTAATCA GCTTATCCAG

541 CAACGTTTCG CTGGATGTTG GCGGCAACGA ATCACTGGTG TAACGATGGC GATTCAGCAA

601 CATCACCAAC TGCCCGAACA GCAACTCAGC CATTTCGTTA GCAAACGGCA CATGCTGACT

661 ACTTTCATGC TCAAGCTGAC CGATAACCTG CCGCGCCTGC GCCATCCCCA TGCTACCTAA

721 GCGCCAGTGT GGTTGCCCTG CGCTGGCGTT AAATCCCGGA ATCGCCCCCT GCCAGTCAAG

781 ATTCAGCTTC AGACGCTCCG GGCAATAAAT AATATTCTGC AAAACCAGAT CGTTAACGGA

841 AGCGTAGGAG TGTTTATCGT CAGCATGAAT GTAAAAGAGA TCGCCACGGG TAATGCGATA

901 AGGGCGATCG TTGAGTACAT GCAGGCCATT ACCGCGCCAG ACAATCACCA GCTCACAAAA

961 ATCATGTGTA TGTTCAGCAA AGACATCTTG CGGATAACGG TCAGCCACAG CGACTGCCTG

1021 CTGGTCGCTG GCAAAAAAAT CATCTTTGAG AAGTTTTAAC TGATGCGCCA CCGTGGCTAC

1081 CTCGGCCAGA GAACGAAGTT GATTATTCGC AATATGGCGT ACAAATACGT TGAGAAGATT

Stop rhaS        Start rhaR
1141 CGCGTTATTG CAGAAAGCCA TCCCGTCCCT GGCGAATATC ACGCGGTGAC CAGTTAAACT
                              ←

1201 CTCGGCCAGA AAGCGTCGAA AAGTGGTTAC TGTCGCTGAA TCCACAGCGA TAGGCGATGT

1261 CAGTAACGCT GGCCTCGCTG TGGCGTAGCA GATGTCGGGC TTTCATCAGT CGCAGGCGGT

1321 TCAGGTATCG CTGAGGCGTC AGTCCCGTTT GCTGCTTAAG CTGCCGATGT AGCGTACGCA

1381 GTGAAAGAGA AAATTGATCC GCCACGGCAT CCCAATTCAC CTCATCGGCA AAATGGTCCT

1441 CCAGCCAGGC CAGAAGCAAG TTGAGACGTG ATGCGCTGTT TTCCAGGTTC TCCTGCAAAC

1501 TGCTTTTACG CAGCAAGAGC AGTAATTGCA TAAACAAGAT CTCGCGACTG GCGGTCGAGG
```

-continued

```
1561 GTAAATCATT TTCCCCTTCC TGCTGTTCCA TCTGTGCAAC CAGCTGTCGC ACCTGCTGCA

1621 ATACGCTGTG GTTAACGCGC CAGTGAGACG GATACTGCCC ATCCAGCTCT TGTGGCAGCA

1681 ACTGATTCAG CCCGGCGAGA AACTGAAATC GATCCGGCGA GCGATACAGC ACATTGGTCA

1741 GACACAGATT ATCGGTATGT TCATACAGAT GCCGATCATG ATCGCGTACG AAACAGACCG

1801 TGCCACCGGT GATGGTATAG GGCTGCCCAT TAAACACATG AATACCCGTG CCATGTTCGA

1861 CAATCACAAT TTCATGAAAA TCATGATGAT GTTCAGGAAA ATCCGCCTGC GGGAGCCGGG
                                                               Start rhaS
1921 GTTCTATCGC CACGGACGCG TTACCAGACG GAAAAAAATC CACACTATGT AATACGGTCA
                                                                        ←

1981 TACTGGCCTC CTGATGTCGT CAACACGGCG AAATAGTAAT CACGAGGTCA GGTTCTTACC

2041 TTAAATTTTC GACGGAAAAC CACGTAAAAA ACGTCGATTT TTCAAGATAC AGCGTGAATT

2101 TTCAGGAAAT GCGGTGAGCA TCACATCACC ACAATTCAGC AAATTGTGAA CATCATCACG

2161 TTCATCTTTC CCTGGTTGCC AATGGCCCAT TTTCCTGTCA GTAACGAGAA GGTCGCGAAT
                                      Shine-Delgarno    Start ftsZ
2221 TCAGGCGCTT TTTAGACTGG TCGTAATGAA ATTC<u>AGCAGG</u> ATCACATATG TTTGAACCAA
                                                                  →

2581 TGGAACTTAC CAATGACGCG GTGATTAAAG TCATCGGCGT CGGCGGCGGC GGCGGTAATG

2641 CTGTTGAACA CATGGTGCGC GAGCGCATTG AAGGTGTTGA ATTCTTCGCG GTAAATACCG

2701 ATGCACAAGC GCTGCGTAAA ACAGCGGTTG GACAGACGAT TCAAATCGGT AGCGGTATCA

2761 CCAAAGGACT GGGCGCTGGC GCTAATCCAG AAGTTGGCCG CAATGCGGCT GATGAGGATC

2821 GCGATGCATT GCGTGCGGCG CTGGAAGGTG CAGACATGGT CTTTATTGCT GCGGGTATGG

2881 GTGGTGGTAC CGGTACAGGT GCAGCACCAG TCGTCGCTGA AGTGGCAAAA GATTTGGGTA

2941 TCCTGACCGT TGCTGTCGTC ACTAAGCCTT TCAACTTTGA AGGCAAGAAG CGTATGGCAT

3001 TCGCGGAGCA GGGGATCACT GAACTGTCCA AGCATGTGGA CTCTCTGATC ACTATCCCGA

3061 ACGACAAACT GCTGAAAGTT CTGGGCCGCG GTATCTCCCT GCTGGATGCG TTTGGCGCAG

3121 CGAACGATGT ACTGAAAGGC GCTGTGCAAG GTATCGCTGA ACTGATTACT CGTCCGGGTT

3181 TGATGAACGT GGACTTTGCA GACGTACGCA CCGTAATGTC TGAGATGGGC TACGCAATGA

3241 TGGGTTCTGG CGTGGCGAGC GGTGAAGACC GTGCGGAAGA AGCTGCTGAA ATGGCTATCT

3301 CTTCTCCGCT GCTGGAAGAT ATCGACCTGT CTGGCGCGCG CGGCGTGCTG GTTAACATCA

3361 CGGCGGGCTT CGACCTGCGT CTGGATGAGT TCGAAACGGT AGGTAACACC ATCCGTGCAT

3421 TTGCTTCCGA CAACGCGACT GTGGTTATCG GTACTTCTCT TGACCCGGAT ATGAATGACG

3481 AGCTGCGCGT AACCGTTGTT GCGACAGGTA TCGGCATGGA CAAACGTCCT GAAATCACTC

3541 TGGTGACCAA TAAGCAGGTT CAGCAGCCAG TGATGGATCG CTACCAGCAG CATGGGATGG

3601 CTCCGCTGAC CCAGGAGCAG AAGCCGGTTG CTAAAGTCGT GAATGACAAT GCGCCGCAAA
                                                                 Stop ftsZ
3661 CTGCGAAAGA GCCGGATTAT CTGGATATCC CAGCATTCCT GCGTAAGCAA GCTGATTAAT
                                                            FRT scar
3721 AATCTAGAGG CGTTACCAAT TATGACAACT TGACGGGAAG TTCCTATACT TTCTAGAGAA
          intD homology for recombination
3781 TAGGAACTTC *CCAAAGCCAG TATCAACTCA GACAAAGGCA AAGCATCTTG*
```

Bold, italicized represents homology between the PCR product shown below and intD.

rhaRS::Prha::ftsZ::FRT::kan::Frt

Following RED recombination into intD, the kanamycin cassette was removed with flp recombinase resulting in a single FRT scar as depicted above. Bold alone represents FRT scar after the flp reaction.

SEQ ID NO 5 lacI::Ptac::ftsZ inserted by RED recombination into *E. coli* MG1655 intD

```
         intD homology for recombination            Stop lacI
 181 AAGCCTGCAT TGCGGCGCTT CAGTCTCCGC TGCATACTGT CCTTAATAAA GTGAGTCGAT

241 ATTGTCTTTG TTGACCAGTA ATACCTTATG GAAACGGATA ATTCGCTTAT CCATATCTAC

301 GTCGGCCTTA CCCAGATTCT GCATTTCTAA TCCAGGCTTG ATCTCTTCAC CCTTCAGCAA

361 CGTGCTGGCG ACGGCTGCGA GTGCGTAACC TGCAGAGGCC GGATCGTAAG TAATCCCTTC

421 GGTGATATCA CCACTTTTAA TCAGTGATGC CGCCTGTGAA GGGATCATCA TGCCATAGAC

481 TGCGACTTTA TTTTTCGCCC GTTTCTCTTT CACCGCACGT CCCGCGCCAA TCGGACCGTT

541 TGAACCAAAG GAGACAACCG CTTTCAAGTC AGGATAGGTT TTCATCAGGT CCAGTGTAGT

601 ACGACGTGAG ACATCCACAC TCTCGGCAAC CGGCATGCGG CGGGTAACTT CATGCATATC

661 CGGGTAATGC TCTTTCTGGT ATTTCACCAG CAAGTCAGCC CATAAGTTAT GCTGCGGCAC

721 GGTCAAACTA CCCACGTAAA TCACATAGCC GCCCTTGCCA CCCATGCGTT TCGCCATATG

781 CTCAACATAT TCAGCGGCAA ATTTTTCGTT ATCAATGATT TCGATATCCC AGTTAGCACT

841 TGGCTGACCG GGGGATTCGT TGGTCAGAAC CACAATTCCG GCATCTCGCG CTTTTTTGAA

901 TACCGGTTCC AGCACGTTGG CATCGTTTGG CACGATAGTA ATTGCATTAA CCTTACGGGC

961 GATTAAATCC TCAATAATTT TAACTTGTTG CGGAGCATCA GTACTTGAAG GCCCCACCTG

1021 TGAGGCATTA ACACCAAAGG CTTTACCCGC CTCAACCACA CCTTCGCCCA TGCGATTAAA

1081 CCACGGCATA CCATCGACTT TAGAAATATT CACCACGACT TTTTCCGCTG CCTGGAGCGG

1141 CGCAGAAATT AGCGCAGCGC CTAATAACAG CGAAGACACC ATATTGATAA CAAAACGTTT

Start lacI                                      Start ftsZ
1201 ATTCATCAT     Ptac sequence (see reference below)    A TGGAACTTAC

12 CAATGACGCG GTGATTAAAG TCATCGGCGT CGGCGGCGGC GGCGGTAATG CTGTTGAACA

72 CATGGTGCGC GAGCGCATTG AAGGTGTTGA ATTCTTCGCG GTAAATACCG ATGCACAAGC

132 GCTGCGTAAA ACAGCGGTTG GACAGACGAT TCAAATCGGT AGCGGTATCA CCAAAGGACT

192 GGGCGCTGGC GCTAATCCAG AAGTTGGCCG CAATGCGGCT GATGAGGATC GCGATGCATT

252 GCGTGCGGCG CTGGAAGGTG CAGACATGGT CTTTATTGCT GCGGGTATGG GTGGTGGTAC

312 CGGTACAGGT GCAGCACCAG TCGTCGCTGA AGTGGCAAAA GATTTGGGTA TCCTGACCGT

372 TGCTGTCGTC ACTAAGCCTT TCAACTTTGA AGGCAAGAAG CGTATGGCAT TCGCGGAGCA

432 GGGGATCACT GAACTGTCCA AGCATGTGGA CTCTCTGATC ACTATCCCGA ACGACAAACT

492 GCTGAAAGTT CTGGGCCGCG GTATCTCCCT GCTGGATGCG TTTGGCGCAG CGAACGATGT

552 ACTGAAAGGC GCTGTGCAAG GTATCGCTGA ACTGATTACT CGTCCGGGTT TGATGAACGT

612 GGACTTTGCA GACGTACGCA CCGTAATGTC TGAGATGGGC TACGCAATGA TGGGTTCTGG

672 CGTGGCGAGC GGTGAAGACC GTGCGGAAGA AGCTGCTGAA ATGGCTATCT CTTCTCCGCT

732 GCTGGAAGAT ATCGACCTGT CTGGCGCGCG CGGCGTGCTG GTTAACATCA CGGCGGGCTT

792 CGACCTGCGT CTGGATGAGT TCGAAACGGT AGGTAACACC ATCCGTGCAT TTGCTTCCGA

852 CAACGCGACT GTGGTTATCG GTACTTCTCT TGACCCGGAT ATGAATGACG AGCTGCGCGT

912 AACCGTTGTT GCGACAGGTA TCGGCATGGA CAAACGTCCT GAAATCACTC TGGTGACCAA

972 TAAGCAGGTT CAGCAGCCAG TGATGGATCG CTACCAGCAG CATGGGATGG CTCCGCTGAC

1032 CCAGGAGCAG AAGCCGGTTG CTAAAGTCGT GAATGACAAT GCGCCGCAAA CTGCGAAAGA
```

-continued

```
1092 GCCGGATTAT CTGGATATCC CAGCATTCCT GCGTAAGCAA GCTGATTAAT AATCTAGAGG

1152 CGTTACCAAT TATGACAACT TGACGG***GAAG TTCCTATTCT CTAGAAAGTA TAGGAACTTC***

1212 *CCAAAGCCAG TATCAACTCA GACAAAGGCA AAGCATCTTG*
```

Bold, italicized represents homology between the PCR product shown below and intD.
  lacI::Ptac::ftsZ::FRT::kan::Frt
Following RED recombination into intD, the kanamycin cassette was removed with flp recombinase resulting in a single FRT scar as depicted above.
Gamido, T., et al. 1993. Transcription of ftsZ oscillates during the cell cycle of *Escherichia coli*. EMBO J. 12:3957-3965
SEQ ID NO 6
pMPX-5 expression vector

```
   1 TCGCGCGTTT CGGTGATGAC GGTGAAAACC TCTGACACAT GCAGCTCCCG GAGACGGTCA

61 CAGCTTGTCT GTAAGCGGAT GCCGGGAGCA GACAAGCCCG TCAGGGCGCG TCAGCGGGTG

121 TTGGCGGGTG TCGGGGCTGG CTTAACTATG CGGCATCAGA GCAGATTGTA CTGAGAGTGC

181 ACCATATGCG GTGTGAAATA CCGCACAGAT GCGTAAGGAG AAAATACCGC ATCAGGCGCC

241 ATTCGCCATT CAGGCTGCGC AACTGTTGGG AAGGGCGATC GGTGCGGGCC TCTTCGCTAT

301 TACGCCAGCT GGCGAAAGGG GGATGTGCTG CAAGGCGATT AAGTTGGGTA ACGCCAGGGT

Stop rhaR
 361 TTTCCCAGTC ACGACGTTGT AAAACGACGG CCAGTGCCAA GCTTAATTAA TCTTTCTGCG

421 AATTGAGATG ACGCCACTGG CTGGGCGTCA TCCCGGTTTC CCGGGTAAAC ACCACCGAAA

481 AATAGTTACT ATCTTCAAAG CCACATTCGG TCGAAATATC ACTGATTAAC AGGCGGCTAT

541 GCTGGAGAAG ATATTGCGCA TGACACACTC TGACCTGTCG CAGATATTGA TTGATGGTCA

601 TTCCAGTCTG CTGGCGAAAT TGCTGACGCA AAACGCGCTC ACTGCACGAT GCCTCATCAC

661 AAAATTTATC CAGCGCAAAG GGACTTTTCA GGCTAGCCGC CAGCCGGGTA ATCAGCTTAT

721 CCAGCAACGT TTCGCTGGAT GTTGGCGGCA ACGAATCACT GGTGTAACGA TGGCGATTCA

781 GCAACATCAC CAACTGCCCG AACAGCAACT CAGCCATTTC GTTAGCAAAC GGCACATGCT

841 GACTACTTTC ATGCTCAAGC TGACCGATAA CCTGCCGCGC CTGCGCCATC CCCATGCTAC

901 CTAAGCGCCA GTGTGGTTGC CCTGCGCTGG CGTTAAATCC CGGAATCGCC CCCTGCCAGT

961 CAAGATTCAG CTTCAGACGC TCCGGGCAAT AAATAATATT CTGCAAAACC AGATCGTTAA

1021 CGGAAGCGTA GGAGTGTTTA TCGTCAGCAT GAATGTAAAA GAGATCGCCA CGGGTAATGC

1081 GATAAGGGCG ATCGTTGAGT ACATGCAGGC CATTACCGCG CCAGACAATC ACCAGCTCAC

1141 AAAAATCATG TGTATGTTCA GCAAGACAT CTTGCGGATA ACGGTCAGCC ACAGCGACTG

1201 CCTGCTGGTC GCTGGCAAAA AAATCATCTT TGAGAAGTTT TAACTGATGC GCCACCGTGG

1261 CTACCTCGGC CAGAGAACGA AGTTGATTAT TCGCAATATG GCGTACAAAT ACGTTGAGAA

Stop rhaS    Start rhaR
1321 GATTCGCGTT ATTGCAGAAA GCCATCCCGT CCCTGGCGAA TATCACGCGG TGACCAGTTA
                           ←

1381 AACTCTCGGC GAAAAGCGT CGAAAAGTGG TTACTGTCGC TGAATCCACA GCGATAGGCG

1441 ATGTCAGTAA CGCTGGCCTC GCTGTGGCGT AGCAGATGTC GGGCTTTCAT CAGTCGCAGG

1501 CGGTTCAGGT ATCGCTGAGG CGTCAGTCCC GTTTGCTGCT TAAGCTGCCG ATGTAGCGTA

1561 CGCAGTGAAA GAGAAAATTG ATCCGCCACG GCATCCCAAT TCACCTCATC GGCAAAATGG

1621 TCCTCCAGCC AGGCCAGAAG CAAGTTGAGA CGTGATGCGC TGTTTTCCAG GTTCTCCTGC
```

```
1681 AAACTGCTTT TACGCAGCAA GAGCAGTAAT TGCATAAACA AGATCTCGCG ACTGGCGGTC

1741 GAGGGTAAAT CATTTTCCCC TTCCTGCTGT TCCATCTGTG CAACCAGCTG TCGCACCTGC

1801 TGCAATACGC TGTGGTTAAC GCGCCAGTGA GACGGATACT GCCCATCCAG CTCTTGTGGC

1861 AGCAACTGAT TCAGCCCGGC GAGAAACTGA AATCGATCCG CGAGCGATA CAGCACATTG

1921 GTCAGACACA GATTATCGGT ATGTTCATAC AGATGCCGAT CATGATCGCG TACGAAACAG

1981 ACCGTGCCAC CGGTGATGGT ATAGGGCTGC CATTAAACA CATGAATACC CGTGCCATGT

2041 TCGACAATCA CAATTTCATG AAAATCATGA TGATGTTCAG GAAAATCCGC CTGCGGGAGC

2101 CGGGGTTCTA TCGCCACGGA CGCGTTACCA GACGGAAAAA ATCCACACT ATGTAATACG

Start rhaS
2161 GT<b>CAT</b>ACTGG <i>CCTCCTGATG TCGTCAACAC GGCGAAATAG TAATCACGAG GTCAGGTTCT</i>
       ←

2221 <i>TACCTTAAAT TTTCGACGGA AAACCACGTA AAAAACGTCG ATTTTTCAAG ATACAGCGTG</i>

2281 <i>AATTTTCAGG AAATGCGGTG AGCATCACAT CACCACAATT CAGCAAATTG TGAACATCAT</i>

2341 <i>CACGTTCATC TTTCCCTGGT TGCCAATGGC CCATTTTCCT GTCAGTAACG AGAAGGTCGC</i>

A. _____ <u>Shine-Delgarno  PstI</u>
2401 <i>GAATTCAGGC GCTTTTTAGA CTGGTCGTAA TGAAATTC</i><b>AG CAGG</b>ATCACA TTCTGCAGGT
                                                   →

SalI XbaI   BamHI  KpnI
2461 CGACTCTAGA GGATCCCCGG GTACCGAGCT CGAATTCGTA ATCATGGTCA TAGCTGTTTC

2521 CTGTGTGAAA TTGTTATCCG CTCACAATTC CACACAACAT ACGAGCCGGA AGCATAAAGT

2581 GTAAAGCCTG GGGTGCCTAA TGAGTGAGCT AACTCACATT AATTGCGTTG CGCTCACTGC

2641 CCGCTTTCCA GTCGGGAAAC CTGTCGTGCC AGCTGCATTA ATGAATCGGC CAACGCGCGG

2701 GGAGAGGCGG TTTGCGTATT GGGCGCTCTT CCGCTTCCTC GCTCACTGAC TCGCTGCGCT

2761 CGGTCGTTCG GCTGCGGCGA GCGGTATCAG CTCACTCAAA GGCGGTAATA CGGTTATCCA

2821 CAGAATCAGG GGATAACGCA GGAAAGAACA TGTGAGCAAA AGGCCAGCAA AAGGCCAGGA

2881 ACCGTAAAAA GGCCGCGTTG CTGGCGTTTT TCCATAGGCT CCGCCCCCCT GACGAGCATC

2941 ACAAAAATCG ACGCTCAAGT CAGAGGTGGC GAAACCCGAC AGGACTATAA AGATACCAGG

3001 CGTTTCCCCC TGGAAGCTCC CTCGTGCGCT CTCCTGTTCC GACCCTGCCG CTTACCGGAT

3061 ACCTGTCCGC CTTTCTCCCT TCGGGAAGCG TGGCGCTTTC TCATAGCTCA CGCTGTAGGT

3121 ATCTCAGTTC GGTGTAGGTC GTTCGCTCCA AGCTGGGCTG TGTGCACGAA CCCCCCGTTC

3181 AGCCCGACCG CTGCGCCTTA TCCGGTAACT ATCGTCTTGA GTCCAACCCG GTAAGACACG

3241 ACTTATCGCC ACTGGCAGCA GCCACTGGTA ACAGGATTAG CAGAGCGAGG TATGTAGGCG

3301 GTGCTACAGA GTTCTTGAAG TGGTGGCCTA ACTACGGCTA CACTAGAAGG ACAGTATTTG

3361 GTATCTGCGC TCTGCTGAAG CCAGTTACCT TCGGAAAAAG AGTTGGTAGC TCTTGATCCG

3421 GCAAACAAAC CACCGCTGGT AGCGGTGGTT TTTTGTTTG CAAGCAGCAG ATTACGCGCA

3481 GAAAAAAGG ATCTCAAGAA GATCCTTTGA TCTTTTCTAC GGGGTCTGAC GCTCAGTGGA

3541 ACGAAAACTC ACGTTAAGGG ATTTTGGTCA TGAGATTATC AAAAGGATC TTCACCTAGA

3601 TCCTTTTAAA TTAAAAATGA AGTTTAAAT CAATCTAAAG TATATATGAG TAAACTTGGT

Stop bla
3661 CTGACAG<b>TTA</b> CCAATGCTTA ATCAGTGAGG CACCTATCTC AGCGATCTGT CTATTTCGTT

3721 CATCCATAGT TGCCTGACTC CCCGTCGTGT AGATAACTAC GATACGGGAG GGCTTACCAT

3781 CTGGCCCCAG TGCTGCAATG ATACCGCGAG ACCCACGCTC ACCGGCTCCA GATTTATCAG

3841 CAATAAACCA GCCAGCCGGA AGGGCCGAGC GCAGAAGTGG TCCTGCAACT TTATCCGCCT

3901 CCATCCAGTC TATTAATTGT TGCCGGGAAG CTAGAGTAAG TAGTTCGCCA GTTAATAGTT
```

```
                                            -continued
3961    TGCGCAACGT TGTTGCCATT GCTACAGGCA TCGTGGTGTC ACGCTCGTCG TTTGGTATGG

4021    CTTCATTCAG CTCCGGTTCC CAACGATCAA GGCGAGTTAC ATGATCCCCC ATGTTGTGCA

4081    AAAAAGCGGT TAGCTCCTTC GGTCCTCCGA TCGTTGTCAG AAGTAAGTTG GCCGCAGTGT

4141    TATCACTCAT GGTTATGGCA GCACTGCATA ATTCTCTTAC TGTCATGCCA TCCGTAAGAT

4201    GCTTTTCTGT GACTGGTGAG TACTCAACCA AGTCATTCTG AGAATAGTGT ATGCGGCGAC

4261    CGAGTTGCTC TTGCCCGGCG TCAATACGGG ATAATACCGC GCCACATAGC AGAACTTTAA

4321    AAGTGCTCAT CATTGGAAAA CGTTCTTCGG GGCGAAAACT CTCAAGGATC TTACCGCTGT

4381    TGAGATCCAG TTCGATGTAA CCCACTCGTG CACCCAACTG ATCTTCAGCA TCTTTTACTT

4441    TCACCAGCGT TTCTGGGTGA GCAAAAACAG GAAGGCAAAA TGCCGCAAAA AAGGGAATAA
                                            Start bla
4501    GGGCGACACG GAAATGTTGA ATACTCATAC TCTTCCTTTT TCAATATTAT TGAAGCATTT
                                            ←

4561    ATCAGGGTTA TTGTCTCATG AGCGGATACA TATTTGAATG TATTTAGAAA AATAAACAAA

4621    TAGGGGTTCC GCGCACATTT CCCCGAAAAG TGCCACCTGA CGTCTAAGAA ACCATTATTA

4681    TCATGACATT AACCTATAAA AATAGGCGTA TCACGAGGCC CTTTCGTC
```

The segment rhaR through the Prha control region was taken from the *E. coli* MG1655 chromosome using PCR-added HindIII and PstI restriciton sites. This fragment was cut with HindIII and PstI and cloned into pUC-18 cut with the same enzymes. Italicized sequence constitutes both rhaSR and protein to be expressed promotor region.

SEQ ID NO 7
pMPX-32 (ΔphoA cloned into pMPX-5 using PCR-introduced PstI and XbaI)

```
                                     Shine-Delgarno      PstI
2901    GAATTCAGGCGCTTTTTAGACTGGTCGTAATGAAATTCAGCAGGATCACATTCTGCAGAT
                                                                  M 2461    GCCTGTTCTGGAAAACCGGGCTGCTCAGGGCGATATTACTGCACCCGGCGGTGCTCGCCG
  2       P  V  L  E  N  R  A  A  Q  G  D  I  T  A  P  G  G  A  R  R 2521    TTTAACGGGTGATCAGACTGCCGCTCTGCGTGATTCTCTTAGCGATAAACCTGCAAAAAA
  22      L  T  G  D  Q  T  A  A  L  R  D  S  L  S  D  K  P  A  K  N 2581    TATTATTTTGCTGATTGGCGATGGGATGGGGGACTCGGAAATTACTGCCGCACGTAATTA
  42      I  I  L  L  I  G  D  G  M  G  D  S  E  I  T  A  A  R  N  Y 2641    TGCCGAAGGTGCGGGCGGCTTTTTTAAAGGTATAGATGCCTTACCGCTTACCGGGCAATA
  62      A  E  G  A  G  G  F  F  K  G  I  D  A  L  P  L  T  G  Q  Y 2701    CACTCACTATGCGCTGAATAAAAAAACCGGCAAACCGGACTACGTCACCGACTCGGCTGC
  82      T  H  Y  A  L  N  K  K  T  G  K  P  D  Y  V  T  D  S  A  A 2761    ATCAGCAACCGCCTGGTCAACCGGTGTCAAAACCTATAACGGCGCGCTGGGCGTCGATAT
 102      S  A  T  A  W  S  T  G  V  K  T  Y  N  G  A  L  G  V  D  I 2821    TCACGAAAAAGATCACCCAACGATTCTGGAAATGGCAAAAGCCGCAGGTCTGGCGACCGG
 122      H  E  K  D  H  P  T  I  L  E  M  A  K  A  A  G  L  A  T  G 2881    TAACGTTTCTACCGCAGAGTTGCAGGATGCCACGCCCGCTGCGCTGGTGGCACATGTGAC
 142      N  V  S  T  A  E  L  Q  D  A  T  P  A  A  L  V  A  H  V  T 2941    CTCGCGCAAATGCTACGGTCCGAGCGCGACCAGTGAAAAATGTCCGGGTAACGCTCTGGA
 162      S  R  K  C  Y  G  P  S  A  T  S  E  K  C  P  G  N  A  L  E 3001    AAAAGGCGGAAAAGGATCGATTACCGAACAGCTGCTTAACGCTCGTGCCGACGTTACGCT
 182      K  G  G  K  G  S  I  T  E  Q  L  L  N  A  R  A  D  V  T  L 3061    TGGCGGCGGCGCAAAAACCTTTGCTGAAACGGCAACCGCTGGTGAATGGCAGGGAAAAAC
 202      G  G  G  A  K  T  F  A  E  T  A  T  A  G  E  W  Q  G  K  T
```

```
                               -continued
3121  GCTGCGTGAACAGGCACAGGCGCGTGGTTATCAGTTGGTGAGCGATGCTGCCTCACTGAA
 222    L   R   E   Q   A   Q   A   R   G   Y   Q   L   V   S   D   A   A   S   L   N 3181  TTCGGTGACGGAAGCGAATCAGCAAAAACCCCTGCTTGGCCTGTTTGCTGACGGCAATAT
 242    S   V   T   E   A   N   Q   Q   K   P   L   L   G   L   F   A   D   G   N   M 3241  GCCAGTGCGCTGGCTAGGACCGAAAGCAACGTACCATGGCAATATCGATAAGCCCGCAGT
 262    P   V   R   W   L   G   P   K   A   T   Y   H   G   N   I   D   K   P   A   V 3301  CACCTGTACGCCAAATCCGCAACGTAATGACAGTGTACCAACCCTGGCGCAGATGACCGA
 282    T   C   T   P   N   P   Q   R   N   D   S   V   P   T   L   A   Q   M   T   D 3361  CAAAGCCATTGAATTGTTGAGTAAAAATGAGAAAGGCTTTTTCCTGCAAGTTGAAGGTGC
 302    K   A   I   E   L   L   S   K   N   E   K   G   F   F   L   Q   V   E   G   A 3421  GTCAATCGATAAACAGGATCATGCTGCGAATCCTTGTGGGCAAATTGGCGAGACGGTCGA
 322    S   I   D   K   Q   D   H   A   A   N   P   C   G   Q   I   G   E   T   V   D 3481  TCTCGATGAAGCCGTACAACGGGCGCTGGAATTCGCTAAAAAGGAGGGTAACACGCTGGT
 342    L   D   E   A   V   Q   R   A   L   E   F   A   K   K   E   G   N   T   L   V 3541  CATAGTCACCGCTGATCACGCCCACGCCAGCCAGATTGTTGCGCCGGATACCAAAGCTCC
 362    I   V   T   A   D   H   A   H   A   S   Q   I   V   A   P   D   T   K   A   P 3601  GGGCCTCACCCAGGCGCTAAATACCAAAGATGGCGCAGTGATGGTGATGAGTTACGGGAA
 382    G   L   T   Q   A   L   N   T   K   D   G   A   V   M   V   M   S   Y   G   N 3661  CTCCGAAGAGGATTCACAAGAACATACCGGCAGTCAGTTGCGTATTGCGGCGTATGGCCC
 402    S   E   E   D   S   Q   E   H   T   G   S   Q   L   R   I   A   A   Y   G   P 3721  GCATGCCGCCAATGTTGTTGGACTGACCGACCAGACCGATCTCTTCTACACCATGAAAGC
 422    H   A   A   N   V   V   G   L   T   D   Q   T   D   L   F   Y   T   M   K   A XbaI
3781  CGCTCTGGGGCTGAAATAATAATCTAGAGGATCCCCGGGTACCGAGCTCGAATTCGTAAT
 442    A   L   G   L   K
```

ΔphoA sequence constitutes phoA residues 49-453.
SEQ ID NO 8
pMPX-53 (phoA cloned into pMPX-5 using PCR-introduced PstI and XbaI)

```
                                     Shine-Delgarno      PstI
2401  GAATTCAGGCGCTTTTTAGACTGGTCGTAATGAAATTCAGCAGGATCACATTCTGCAGAT
                                                                    M 2461  GTCACGGCCGAGACTTATAGTCGCTTTGTTTTTATTTTTAATGTATTTGTACATGGAGA
   2    S   R   P   R   L   I   V   A   L   F   L   F   F   N   V   F   V   H   G   E 2521  AAATAAAGTGAAACAAAGCACTATTGCACTGGCACTCTTACCGTTACTGTTTACCCCTGT
  22    N   K   V   K   Q   S   T   I   A   L   A   L   L   P   L   L   F   T   P   V 2581  GACAAAAGCCCGGACACCAGAAATGCCTGTTCTGGAAAACCGGGCTGCTCAGGGCGATAT
  42    T   K   A   R   T   P   E   M   P   V   L   E   N   R   A   A   Q   G   D   I 2641  TACTGCACCCGGCGGTGCTCGCCGTTTAACGGGTGATCAGACTGCCGCTCTGCGTGATTC
  62    T   A   P   G   G   A   R   R   L   T   G   D   Q   T   A   A   L   R   D   S 2701  TCTTAGCGATAAACCTGCAAAAAATATTATTTTGCTGATTGGCGATGGGATGGGGGACTC
  82    L   S   D   K   P   A   K   N   I   I   L   L   I   G   D   G   M   G   D   S 2761  GGAAATTACTGCCGCACGTAATTATGCCGAAGGTGCGGGCGGCTTTTTTAAAGGTATAGA
 102    E   I   T   A   A   R   N   Y   A   E   G   A   G   G   F   F   K   G   I   D 2821  TGCCTTACCGCTTACCGGGCAATACACTCACTATGCGCTGAATAAAAAAACCGGCAAACC
 122    A   L   P   L   T   G   Q   Y   T   H   Y   A   L   N   K   K   T   G   K   P 2881  GGACTACGTCACCGACTCGGCTGCATCAGCAACCGCCTGGTCAACCGGTGTCAAAACCTA
 142    D   Y   V   T   D   S   A   A   S   A   T   A   W   S   T   G   V   K   T   Y 2941  TAACGGCGCGCTGGGCGTCGATATTCACGAAAAAGATCACCCAACGATTCTGGAAATGGC
 162    N   G   A   L   G   V   D   I   H   E   K   D   H   P   T   I   L   E   M   A 3001  AAAAGCCGCAGGTCTGGCGACCGGTAACGTTTCTACCGCAGAGTTGCAGGATGCCACGCC
 182    K   A   A   G   L   A   T   G   N   V   S   T   A   E   L   Q   D   A   T   P 3061  CGCTGCGCTGGTGGCACATGTGACCTCGCGCAAATGCTACGGTCCGAGCGCGACCAGTGA
 202    A   A   L   V   A   H   V   T   S   R   K   C   Y   G   P   S   A   T   S   E
```

```
3121 AAAATGTCCGGGTAACGCTCTGGAAAAAGGCGGAAAAGGATCGATTACCGAACAGCTGCT
 222   K  C  P  G  N  A  L  E  K  G  G  K  G  S  I  T  E  Q  L  L

3181 TAACGCTCGTGCCGACGTTACGCTTGGCGGCGGCGCAAAAACCTTTGCTGAAACGGCAAC
 242   N  A  R  A  D  V  T  L  G  G  G  A  K  T  F  A  E  T  A  T

3241 CGCTGGTGAATGGCAGGGAAAAACGCTGCGTGAACAGGCACAGGCGCGTGGTTATCAGTT
 262   A  G  E  W  Q  G  K  T  L  R  E  Q  A  Q  A  R  G  Y  Q  L

3301 GGTGAGCGATGCTGCCTCACTGAATTCGGTGACGGAAGCGAATCAGCAAAAACCCCTGCT
 282   V  S  D  A  A  S  L  N  S  V  T  E  A  N  Q  Q  K  P  L  L

3361 TGGCCTGTTTGCTGACGGCAATATGCCAGTGCGCTGGCTAGGACCGAAAGCAACGTACCA
 302   G  L  F  A  D  G  N  M  P  V  R  W  L  G  P  K  A  T  Y  H

3421 TGGCAATATCGATAAGCCCGCAGTCACCTGTACGCCAAATCCGCAACGTAATGACAGTGT
 322   G  N  I  D  K  P  A  V  T  C  T  P  N  P  Q  R  N  D  S  V

3481 ACCAACCCTGGCGCAGATGACCGACAAAGCCATTGAATTGTTGAGTAAAAATGAGAAAGG
 342   P  T  L  A  Q  M  T  D  K  A  I  E  L  L  S  K  N  E  K  G

3541 CTTTTTCCTGCAAGTTGAAGGTGCGTCAATCGATAAACAGGATCATGCTGCGAATCCTTG
 362   F  F  L  Q  V  E  G  A  S  I  D  K  Q  D  H  A  A  N  P  C

3601 TGGGCAAATTGGCGAGACGGTCGATCTCGATGAAGCCGTACAACGGGCGCTGGAATTCGC
 382   G  Q  I  G  E  T  V  D  L  D  E  A  V  Q  R  A  L  E  F  A

3661 TAAAAAGGAGGGTAACACGCTGGTCATAGTCACCGCTGATCACGCCCACGCCAGCCAGAT
 402   K  K  E  G  N  T  L  V  I  V  T  A  D  H  A  H  A  S  Q  I

3721 TGTTGCGCCGGATACCAAAGCTCCGGGCCTCACCCAGGCGCTAAATACCAAAGATGGCGC
 422   V  A  P  D  T  K  A  P  G  L  T  Q  A  L  N  T  K  D  G  A

3781 AGTGATGGTGATGAGTTACGGGAACTCCGAAGAGGATTCACAAGAACATACCGGCAGTCA
 442   V  M  V  M  S  Y  G  N  S  E  E  D  S  Q  E  H  T  G  S  Q

3841 GTTGCGTATTGCGGCGTATGGCCCGCATGCCGCCAATGTTGTTGGACTGACCGACCAGAC
 462   L  R  I  A  A  Y  G  P  H  A  A  N  V  V  G  L  T  D  Q  T

XbaI
3901 CGATCTCTTCTACACCATGAAAGCCGCTCTGGGGCTGAAATAATCTAGAGGATCCCCGGG
 482   D  L  F  Y  T  M  K  A  A  L  G  L  K
```

SEQ ID NO 9
pMPX-33 (toxR-ΔphoA cloned into pMPX-5 using PCR-introduced PstI and XbaI)

```
                                   Shine-Delgarno          PstI
2401 GAATTCAGGCGCTTTTTAGACTGGTCGTAATGAAATTCAGCAGGATCACATTCTGCAGAT
                                                                M 2461 GAACTTGGGGAATCGACTGTTTATTCTGATAGCGGTCTTACTTCCCCTCGCAGTATTACT
   2   N  L  G  N  R  L  F  I  L  I  A  V  L  L  P  L  A  V  L  L 2521 GCTCATGCCTGTTCTGGAAAACCGGGCTGCTCAGGGCGATATTACTGCACCCGGCGGTGC
  22   L  M  P  V  L  E  N  R  A  A  Q  G  D  I  T  A  P  G  G 2581 TCGCCGTTTAACGGGTGATCAGACTGCCGCTCTGCGTGATTCTCTTAGCGATAAACCTGC
  42   R  R  L  T  G  D  Q  T  A  A  L  R  D  S  L  S  D  K  P  A 2641 AAAAAATATTATTTTGCTGATTGGCGATGGGATGGGGGACTCGGAAATTACTGCCGCACG
  62   K  N  I  I  L  L  I  G  D  G  M  G  D  S  E  I  T  A  A  R 2701 TAATTATGCCGAAGGTGCGGGCGGCTTTTTTAAAGGTATAGATGCCTTACCGCTTACCGG
  82   N  Y  A  E  G  A  G  G  F  F  K  G  I  D  A  L  P  L  T  G 2761 GCAATACACTCACTATGCGCTGAATAAAAAAACCGGCAAACCGGACTACGTCACCGACTC
 102   Q  Y  T  H  Y  A  L  N  K  K  T  G  K  P  D  Y  V  T  D  S 2821 GGCTGCATCAGCAACCGCCTGGTCAACCGGTGTCAAAACCTATAACGGCGCGCTGGGCGT
 122   A  A  S  A  T  A  W  S  T  G  V  K  T  Y  N  G  A  L  G  V 2881 CGATATTCACGAAAAGATCACCCAACGATTCTGGAAATGGCAAAAGCCGCAGGTCTGGC
 142   D  I  H  E  K  D  H  P  T  I  L  E  M  A  K  A  A  G  L  A 2941 GACCGGTAACGTTTCTACCGCAGAGTTGCAGGATGCCACGCCCGCTGCGCTGGTGGCACA
 162   T  G  N  V  S  T  A  E  L  Q  D  A  T  P  A  A  L  V  A  H
```

```
3001 TGTGACCTCGCGCAAATGCTACGGTCCGAGCGCGACCAGTGAAAAATGTCCGGGTAACGC
 182    V  T  S  R  K  C  Y  G  P  S  A  T  S  E  K  C  P  G  N  A

3061 TCTGGAAAAAGGCGGAAAAGGATCGATTACCGAACAGCTGCTTAACGCTCGTGCCGACGT
 202    L  E  K  G  G  K  G  S  I  T  E  Q  L  L  N  A  R  A  D  V

3121 TACGCTTGGCGGCGGCGCAAAAACCTTTGCTGAAACGGCAACCGCTGGTGAATGGCAGGG
 222    T  L  G  G  G  A  K  T  F  A  E  T  A  T  A  G  E  W  Q  G

3181 AAAAACGCTGCGTGAACAGGCACAGGCGCGTGGTTATCAGTTGGTGAGCGATGCTGCCTC
 242    K  T  L  R  E  Q  A  Q  A  R  G  Y  Q  L  V  S  D  A  A  S

3241 ACTGAATTCGGTGACGGAAGCGAATCAGCAAAAACCCCTGCTTGGCCTGTTTGCTGACGG
 262    L  N  S  V  T  E  A  N  Q  Q  K  P  L  L  G  L  F  A  D  G

3301 CAATATGCCAGTGCGCTGGCTAGGACCGAAAGCAACGTACCATGGCAATATCGATAAGCC
 282    N  M  P  V  R  W  L  G  P  K  A  T  Y  H  G  N  I  D  K  P

3361 CGCAGTCACCTGTACGCCAAATCCGCAACGTAATGACAGTGTACCAACCCTGGCGCAGAT
 302    A  V  T  C  T  P  N  P  Q  R  N  D  S  V  P  T  L  A  Q  M

3421 GACCGACAAAGCCATTGAATTGTTGAGTAAAAATGAGAAAGGCTTTTTCCTGCAAGTTGA
 322    T  D  K  A  I  E  L  L  S  K  N  E  K  G  F  F  L  Q  V  E

3481 AGGTGCGTCAATCGATAAACAGGATCATGCTGCGAATCCTTGTGGGCAAATTGGCGAGAC
 342    G  A  S  I  D  K  Q  D  H  A  A  N  P  C  G  Q  I  G  E  T

3541 GGTCGATCTCGATGAAGCCGTACAACGGGCGCTGGAATTCGCTAAAAAGGAGGGTAACAC
 362    V  D  L  D  E  A  V  Q  R  A  L  E  F  A  K  K  E  G  N  T

3601 GCTGGTCATAGTCACCGCTGATCACGCCCACGCCAGCCAGATTGTTGCGCCGGATACCAA
 382    L  V  I  V  T  A  D  H  A  H  A  S  Q  I  V  A  P  D  T  K

3661 AGCTCCGGGCCTCACCCAGGCGCTAAATACCAAAGATGGCGCAGTGATGGTGATGAGTTA
 402    A  P  G  L  T  Q  A  L  N  T  K  D  G  A  V  M  V  M  S  Y

3721 CGGGAACTCCGAAGAGGATTCACAAGAACATACCGGCAGTCAGTTGCGTATTGCGGCGTA
 422    G  N  S  E  E  D  S  Q  E  H  T  G  S  Q  L  R  I  A  A  Y

3781 TGGCCCGCATGCCGCCAATGTTGTTGGACTGACCGACCAGACCGATCTCTTCTACACCAT
 442    G  P  H  A  A  N  V  V  G  L  T  D  Q  T  D  L  F  Y  T  M

XbaI
3841 GAAAGCCGCTCTGGGGCTGAAATAATAATCTAGAGGATCCCCGGGTACCGAGCTCGAATT
 462    K  A  A  L  G  L  K
```

Non-bold, underlined sequence is toxR transmembrane domain segment that constitutes toxR residues 178-198. The remaining sequence is from ΔphoA constituting phoA residues 49-453.

SEQ ID NO 10
pMPX-7 expression vector

```
  1    TCGCGCGTTT CGGTGATGAC GGTGAAAACC TCTGACACAT GCAGCTCCCG GAGACGGTCA

61    CAGCTTGTCT GTAAGCGGAT GCCGGGAGCA GACAAGCCCG TCAGGGCGCG TCAGCGGGTG

121    TTGGCGGGTG TCGGGGCTGG CTTAACTATG CGGCATCAGA GCAGATTGTA CTGAGAGTGC

181    ACCATATGCG GTGTGAAATA CCGCACAGAT GCGTAAGGAG AAAATACCGC ATCAGGCGCC

241    ATTCGCCATT CAGGCTGCGC AACTGTTGGG AAGGGCGATC GGTGCGGGCC TCTTCGCTAT

301    TACGCCAGCT GGCGAAAGGG GGATGTGCTG CAAGGCGATT AAGTTGGGTA ACGCCAGGGT

HindIII
361    TTTCCCAGTC ACGACGTTGT AAAACGACGG CCAGTGCCAA GCTTCGCAGC GCTGTTCCTT

421    TGCTCGCCTG CTGCGAGCTG GGTAAGCGGA CAAATTCTCA CCGTCTCCGG TGGTGGGGTA

481    CAGGAGCTCA ATTAATACAC TAACGGACCG GTAAACAACC GTGCGTGTTG TTTACCGGGA

541    TAAACTCATC AACGTCTCTG CTAAATAACT GGCAGCCAAA TCACGGCTAT TGGTTAACCA

601    ATTTCAGAGT GAAAAGTATA CGAATAGAGT GTGCCTTCGC ACTATTCAAC AGCAATGATA
```

```
                                                              Start uidR
 661  GGCGCTCACC TGACAACGCG GTAAACTAGT TATTCACGCT AACTATAATG GTTTAATGAT
                                                                  →

721  GGATAACATG CAGACTGAAG CACAACCGAC ACGGACCCGG ATCCTCAATG CTGCCAGAGA

781  GATTTTTTCA GAAAATGGAT TTCACAGTGC CTCGATGAAA GCCATCTGTA AATCTTGCGC

841  CATTAGTCCC GGGACGCTCT ATCACCATTT CATCTCCAAA GAAGCCTTGA TTCAGGCGAT

901  TATCTTACAG GACCAGGAGA GGGCGCTGGC CCGTTTCCGG AACCGATTG AAGGGATTCA

961  TTTCGTTGAC TATATGGTCG AGTCCATTGT CTCTCTCACC CATGAAGCCT TTGGACAACG

1021  GGCGCTGGTG GTTGAAATTA TGGCGGAAGG GATGCGTAAC CCACAGGTCG CCGCCATGCT

1081  TAAAAATAAG CATATGACGA TCACGGAATT TGTTGCCCAG CGGATGCGTG ATGCCCAGCA

1141  AAAAGGCGAG ATAAGCCCAG ACATCAACAC GGCAATGACT TCACGTTTAC TGCTGGATCT

1201  GACCTACGGT GTACTGGCCG ATATCGAAGC GGAAGACCTG GCGCGTGAAG CGTCGTTTGC
                                                           Stop uidR
1261  TCAGGGATTA CGCGCGATGA TTGGCGGTAT CTTAACCGCA TCCTGATTCT CTCTCTTTTT

1321  CGGCGGGCTG GTGATAACTG TGCCCGCGTT TCATATCGTA ATTTCTCTGT GCAAAAATTA

1381  TCCTTCCCGG CTTCGGAGAA TTCCCCCCAA AATATTCACT GTAGCCATAT GTCATGAGAG

1441  TTTATCGTTC CCAATACGCT CGAACGAACG TTCGGTTGCT TATTTTATGG CTTCTGTCAA

1501  CGCTGTTTTA AAGATTAATG CGATCTATAT CACGCTGTGG GTATTGCAGT TTTTGGTTTT

1561  TTGATCGCGG TGTCAGTTCT TTTTATTTCC ATTTCTCTTC CATGGGTTTC TCACAGATAA

1621  CTGTGTGCAA CACAGAATTG GTTAACTAAT CAGATTAAAG GTTGACCAGT ATTATTATCT

Shine-Delgarno  PstI    SalI    XbaI            KpnI
1681  TAATGAGGAG TCCTGCAGGT CGACTCTAGA GGATCCCCGG GTACCGAGCT CGAATTCGTA
           →

1741  ATCATGGTCA TAGCTGTTTC CTGTGTGAAA TTGTTATCCG CTCACAATTC CACACAACAT

1801  ACGAGCCGGA AGCATAAAGT GTAAAGCCTG GGGTGCCTAA TGAGTGAGCT AACTCACATT

1861  AATTGCGTTG CGCTCACTGC CCGCTTTCCA GTCGGGAAAC CTGTCGTGCC AGCTGCATTA

1921  ATGAATCGGC CAACGCGCGG GGAGAGGCGG TTTGCGTATT GGGCGCTCTT CCGCTTCCTC

1981  GCTCACTGAC TCGCTGCGCT CGGTCGTTCG GCTGCGGCGA GCGGTATCAG CTCACTCAAA

2041  GGCGGTAATA CGGTTATCCA CAGAATCAGG GGATAACGCA GGAAAGAACA TGTGAGCAAA

2101  AGGCCAGCAA AAGGCCAGGA ACCGTAAAAA GGCCGCGTTG CTGGCGTTTT TCCATAGGCT

2161  CCGCCCCCCT GACGAGCATC ACAAAAATCG ACGCTCAAGT CAGAGGTGGC GAAACCCGAC

2221  AGGACTATAA AGATACCAGG CGTTTCCCCC TGGAAGCTCC CTCGTGCGCT CTCCTGTTCC

2281  GACCCTGCCG CTTACCGGAT ACCTGTCCGC CTTTCTCCCT TCGGGAAGCG TGGCGCTTTC

2341  TCATAGCTCA CGCTGTAGGT ATCTCAGTTC GGTGTAGGTC GTTCGCTCCA AGCTGGGCTG

2401  TGTGCACGAA CCCCCCGTTC AGCCCGACCG CTGCGCCTTA TCCGGTAACT ATCGTCTTGA

2461  GTCCAACCCG GTAAGACACG ACTTATCGCC ACTGGCAGCA GCCACTGGTA ACAGGATTAG

2521  CAGAGCGAGG TATGTAGGCG GTGCTACAGA GTTCTTGAAG TGGTGGCCTA ACTACGGCTA

2581  CACTAGAAGG ACAGTATTTG GTATCTGCGC TCTGCTGAAG CCAGTTACCT TCGGAAAAAG

2641  AGTTGGTAGC TCTTGATCCG GCAAACAAAC CACCGCTGGT AGCGGTGGTT TTTTTGTTTG

2701  CAAGCAGCAG ATTACGCGCA GAAAAAAAGG ATCTCAAGAA GATCCTTTGA TCTTTTCTAC

2761  GGGGTCTGAC GCTCAGTGGA ACGAAAACTC ACGTTAAGGG ATTTTGGTCA TGAGATTATC

2821  AAAAAGGATC TTCACCTAGA TCCTTTTAAA TTAAAAATGA AGTTTTAAAT CAATCTAAAG
                                                Stop bla
2881  TATATATGAG TAAACTTGGT CTGACAGTTA CCAATGCTTA ATCAGTGAGG CACCTATCTC
```

```
                            -continued
2941    AGCGATCTGT CTATTTCGTT CATCCATAGT TGCCTGACTC CCCGTCGTGT AGATAACTAC

3001    GATACGGGAG GGCTTACCAT CTGGCCCCAG TGCTGCAATG ATACCGCGAG ACCCACGCTC

3061    ACCGGCTCCA GATTTATCAG CAATAAACCA GCCAGCCGGA AGGGCCGAGC GCAGAAGTGG

3121    TCCTGCAACT TTATCCGCCT CCATCCAGTC TATTAATTGT TGCCGGGAAG CTAGAGTAAG

3181    TAGTTCGCCA GTTAATAGTT TGCGCAACGT TGTTGCCATT GCTACAGGCA TCGTGGTGTC

3241    ACGCTCGTCG TTTGGTATGG CTTCATTCAG CTCCGGTTCC CAACGATCAA GGCGAGTTAC

3301    ATGATCCCCC ATGTTGTGCA AAAAGCGGT TAGCTCCTTC GGTCCTCCGA TCGTTGTCAG

3361    AAGTAAGTTG GCCGCAGTGT TATCACTCAT GGTTATGGCA GCACTGCATA ATTCTCTTAC

3421    TGTCATGCCA TCCGTAAGAT GCTTTTCTGT GACTGGTGAG TACTCAACCA AGTCATTCTG

3481    AGAATAGTGT ATGCGGCGAC CGAGTTGCTC TTGCCCGGCG TCAATACGGG ATAATACCGC

3541    GCCACATAGC AGAACTTTAA AAGTGCTCAT CATTGGAAAA CGTTCTTCGG GGCGAAAACT

3601    CTCAAGGATC TTACCGCTGT TGAGATCCAG TTCGATGTAA CCCACTCGTG CACCCAACTG

3661    ATCTTCAGCA TCTTTTACTT TCACCAGCGT TTCTGGGTGA GCAAAAACAG GAAGGCAAAA
                                                             Start bla
3721    TGCCGCAAAA AAGGGAATAA GGGCGACACG GAAATGTTGA ATACTCATAC TCTTCCTTTT
                                                             ←

3781    TCAATATTAT TGAAGCATTT ATCAGGGTTA TTGTCTCATG AGCGGATACA TATTTGAATG

3841    TATTTAGAAA AATAAACAAA TAGGGGTTCC GCGCACATTT CCCCGAAAAG TGCCACCTGA

3901    CGTCTAAGAA ACCATTATTA TCATGACATT AACCTATAAA AATAGGCGTA TCACGAGGCC

3961    CTTTCGTC
```

The segment uidR control region through the Puid promotor region was taken from the *E. coli* MG1655 chromosome using PCR-added HindIII and PstI restriciton sites. This fragment was cut with HindIII and PstI and cloned into pUC-18 cut with the same enzymes. Underlined sequence constitutes the uidR regulatory region while the italicized sequence constitutes the protein to be expressed promotor region under the control of uidR.

SEQ ID NO 11
pMPX-8 expression vector

```
  1    TCGCGCGTTT CGGTGATGAC GGTGAAAACC TCTGACACAT GCAGCTCCCG GAGACGGTCA

61    CAGCTTGTCT GTAAGCGGAT GCCGGGAGCA GACAAGCCCG TCAGGGCGCG TCAGCGGGTG

121    TTGGCGGGTG TCGGGCTGG CTTAACTATG CGGCATCAGA GCAGATTGTA CTGAGAGTGC

181    ACCATATGCG GTGTGAAATA CCGCACAGAT GCGTAAGGAG AAAATACCGC ATCAGGCGCC

241    ATTCGCCATT CAGGCTGCGC AACTGTTGGG AAGGGCGATC GGTGCGGGCC TCTTCGCTAT

301    TACGCCAGCT GGCGAAAGGG GGATGTGCTG CAAGGCGATT AAGTTGGGTA ACGCCAGGGT
                                                             Stop melR
361    TTTCCCAGTC ACGACGTTGT AAAACGACGG CCAGTGCCAA GCTTTTAGCC GGGAAACGTC

421    TGGCGGCGCT GTTGGCTAAG TTTGCGGTAT TGTTGCGGCG ACATGCCGAC ATATTTGCCG

481    AACGTGCTGT AAAAACGACT ACTTGAACGA AAGCCTGCCG TCAGGGCAAT ATCGAGAATA

541    CTTTTATCGG TATCGCTCAG TAACGCGCGA ACGTGGTTGA TGCGCATCGC GGTAATGTAC

601    TGTTTCATCG TCAATTGCAT GACCCGCTGG AATATCCCCA TTGCATAGTT GGCGTTAAGT

661    TTGACGTGCT CAGCCACATC GTTGATGGTC AGCGCCTGAT CATAGTTTTC GGCAATAAAG

721    CCCAGCATCT GGCTAACATA AAATTGCGCA TGGCGCGAGA CGCTGTTTTT GTGTGTGCGC

781    GAGGTTTTAT TGACCAGAAT CGGTTCCCAG CCAGAGAGGC TAAATCGCTT GAGCATCAGG

841    CCAATTTCAT CAATGGCGAG CTGGCGAATT TGCTCGTTCG GACTGTTTAA TTCCTGCTGC

901    CAGCGGCGCA CTTCAAACGG GCTAAGTTGC TGTGTGGCCA GTGATTTGAT CACCATGCCG

961    TGAGTGACGT GGTTAATCAG GTCTTTATCC AGCGGCCAGG AGAGAAACAG ATGCATCGGC
```

```
                                                  -continued
1021   AGATTAAAAA TCGCCATGCT CTGACAGGTT CCGGTATCTG TTAGTTGGTG CGGTGTACAG

1081   GCCCAGAACA GCGTGATATG ACCCTGATTG ATATTCACTT TTTCATTGTT GATCAGGTAT

1141   TCCACATCGC CATCGAAAGG CACATTCACT TCGACCTGAC CATGCCAGTG GCTGGTGGGC

1201   ATGATATGCG GTGCGCGAAA CTCAATCTCC ATCCGCTGGT ATTCCGAATA CAGCGACAGC

Start melR
1261   GGGCTGCGGG TCTGTTTTTC GTCGCTGCTG CACATAAACG TATCTGTATT CATGGATGGC
                                                                ←

1321   TCTCTTTCCT GGAATATCAG AATTATGGCA GGAGTGAGGG AGGATGACTG CGAGTGGGAG

1381   CACGGTTTTC ACCCTCTTCC CAGAGGGGCG AGGGGACTCT CCGAGTATCA TGAGGCCGAA

1441   AACTCTGCTT TTCAGGTAAT TTATTCCCAT AAACTCAGAT TTACTGCTGC TTCACGCAGG

Shine-Delgarno   PstI
1501   ATCTGAGTTT ATGGGAATGC TCAACCTGGA AGCCGGAGGT TTTCTGCAGA TTCGCCTGCC SalI   XbaI   BamHI
1561   ATGATGAAGT TATTCAAGCA AGCCAGGAGA TCTGGTACCC GGGTCGACTC TAGAGGATCC KpnI
1621   CCGGGTACCG AGCTCGAATT CGTAATCATG GTCATAGCTG TTTCCTGTGT GAAATTGTTA

1681   TCCGCTCACA ATTCCACACA ACATACGAGC CGGAAGCATA AAGTGTAAAG CCTGGGGTGC

1741   CTAATGAGTG AGCTAACTCA CATTAATTGC GTTGCGCTCA CTGCCCGCTT TCCAGTCGGG

1801   AAACCTGTCG TGCCAGCTGC ATTAATGAAT CGGCCAACGC GCGGGGAGAG GCGGTTTGCG

1861   TATTGGGCGC TCTTCCGCTT CCTCGCTCAC TGACTCGCTG CGCTCGGTCG TTCGGCTGCG

1921   GCGAGCGGTA TCAGCTCACT CAAAGGCGGT AATACGGTTA TCCACAGAAT CAGGGGATAA

1981   CGCAGGAAAG AACATGTGAG CAAAAGGCCA GCAAAAGGCC AGGAACCGTA AAAAGGCCGC

2041   GTTGCTGGCG TTTTTCCATA GGCTCCGCCC CCTGACGAG CATCACAAAA ATCGACGCTC

2101   AAGTCAGAGG TGGCGAAACC CGACAGGACT ATAAAGATAC CAGGCGTTTC CCCCTGGAAG

2161   CTCCCTCGTG CGCTCTCCTG TTCCGACCCT GCCGCTTACC GGATACCTGT CCGCCTTTCT

2221   CCCTTCGGGA AGCGTGGCGC TTTCTCATAG CTCACGCTGT AGGTATCTCA GTTCGGTGTA

2281   GGTCGTTCGC TCCAAGCTGG GCTGTGTGCA CGAACCCCCC GTTCAGCCCG ACCGCTGCGC

2341   CTTATCCGGT AACTATCGTC TTGAGTCCAA CCCGGTAAGA CACGACTTAT CGCCACTGGC

2401   AGCAGCCACT GGTAACAGGA TTAGCAGAGC GAGGTATGTA GGCGGTGCTA CAGAGTTCTT

2461   GAAGTGGTGG CCTAACTACG GCTACACTAG AAGGACAGTA TTTGGTATCT GCGCTCTGCT

2521   GAAGCCAGTT ACCTTCGGAA AAAGAGTTGG TAGCTCTTGA TCCGGCAAAC AAACCACCGC

2581   TGGTAGCGGT GGTTTTTTTG TTTGCAAGCA GCAGATTACG CGCAGAAAAA AAGGATCTCA

2641   AGAAGATCCT TTGATCTTTT CTACGGGGTC TGACGCTCAG TGGAACGAAA ACTCACGTTA

2701   AGGGATTTTG GTCATGAGAT TATCAAAAAG GATCTTCACC TAGATCCTTT TAAATTAAAA

Stop bla
2761   ATGAAGTTTT AAATCAATCT AAAGTATATA TGAGTAAACT TGGTCTGACA GTTACCAATG

2821   CTTAATCAGT GAGGCACCTA TCTCAGCGAT CTGTCTATTT CGTTCATCCA TAGTTGCCTG

2881   ACTCCCCGTC GTGTAGATAA CTACGATACG GGAGGGCTTA CCATCTGGCC CCAGTGCTGC

2941   AATGATACCG CGAGACCCAC GCTCACCGGC TCCAGATTTA TCAGCAATAA ACCAGCCAGC

3001   CGGAAGGGCC GAGCGCAGAA GTGGTCCTGC AACTTTATCC GCCTCCATCC AGTCTATTAA

3061   TTGTTGCCGG GAAGCTAGAG TAAGTAGTTC GCCAGTTAAT AGTTTGCGCA ACGTTGTTGC

3121   CATTGCTACA GGCATCGTGG TGTCACGCTC GTCGTTTGGT ATGGCTTCAT TCAGCTCCGG

3181   TTCCCAACGA TCAAGGCGAG TTACATGATC CCCCATGTTG TGCAAAAAAG CGGTTAGCTC
```

```
                           -continued
3241    CTTCGGTCCT CCGATCGTTG TCAGAAGTAA GTTGGCCGCA GTGTTATCAC TCATGGTTAT

3301    GGCAGCACTG CATAATTCTC TTACTGTCAT GCCATCCGTA AGATGCTTTT CTGTGACTGG

3361    TGAGTACTCA ACCAAGTCAT TCTGAGAATA GTGTATGCGG CGACCGAGTT GCTCTTGCCC

3421    GGCGTCAATA CGGGATAATA CCGCGCCACA TAGCAGAACT TTAAAAGTGC TCATCATTGG

3481    AAAACGTTCT TCGGGGCGAA AACTCTCAAG GATCTTACCG CTGTTGAGAT CCAGTTCGAT

3541    GTAACCCACT CGTGCACCCA ACTGATCTTC AGCATCTTTT ACTTTCACCA GCGTTTCTGG

3601    GTGAGCAAAA ACAGGAAGGC AAAATGCCGC AAAAAAGGGA ATAAGGGCGA CACGGAAATG

Start bla
3661    TTGAATACTC ATACTCTTCC TTTTTCAATA TTATTGAAGC ATTTATCAGG GTTATTGTCT
                  ←

3721    CATGAGCGGA TACATATTTG AATGTATTTA GAAAAATAAA CAAATAGGGG TTCCGCGCAC

3781    ATTTCCCCGA AAAGTGCCAC CTGACGTCTA AGAAACCATT ATTATCATGA CATTAACCTA

3841    TAAAAATAGG CGTATCACGA GGCCCTTTCG TC
```

The segment melR through the Pmel control region was taken from the *E. coli* MG1655 chromosome using PCR-added HindIII and PstI restriciton sites. This fragment was cut with HindIII and PstI and cloned into pUC-18 cut with the same enzymes. Italicized sequence constitutes both melR and protein to be expressed promotor region.
SEQ ID NO 12
pMPX-18 expression vector

```
   1    TCGCGCGTTT CGGTGATGAC GGTGAAAACC TCTGACACAT GCAGCTCCCG GAGACGGTCA

61    CAGCTTGTCT GTAAGCGGAT GCCGGGAGCA GACAAGCCCG TCAGGGCGCG TCAGCGGGTG

121    TTGGCGGGTG TCGGGCTGG CTTAACTATG CGGCATCAGA GCAGATTGTA CTGAGAGTGC

181    ACCATATGCG GTGTGAAATA CCGCACAGAT GCGTAAGGAG AAAATACCGC ATCAGGCGCC

241    ATTCGCCATT CAGGCTGCGC AACTGTTGGG AAGGGCGATC GGTGCGGGCC TCTTCGCTAT

301    TACGCCAGCT GGCGAAAGGG GGATGTGCTG CAAGGCGATT AAGTTGGGTA ACGCCAGGGT

HindIII
 361    TTTCCCAGTC ACGACGTTGT AAAACGACGG CCAGTGCCAA GCTTCAAGCC GTCAATTGTC Stop araC
 421    TGATTCGTTA CCAATTATGA CAACTTGACG GCTACATCAT TCACTTTTTC TTCACAACCG

481    GCACGGAACT CGCTCGGGCT GGCCCCGGTG CATTTTTTAA ATACCCGCGA GAAATAGAGT

541    TGATCGTCAA AACCAACATT GCGACCGACG GTGGCGATAG GCATCCGGGT GGTGCTCAAA

601    AGCAGCTTCG CCTGGCTGAT ACGTTGGTCC TCGCGCCAGC TTAAGACGCT AATCCCTAAC

661    TGCTGGCGGA AAAGATGTGA CAGACGCGAC GGCGACAAGC AAACATGCTG TGCGACGCTG

721    GCGATATCAA AATTGCTGTC TGCCAGGTGA TCGCTGATGT ACTGACAAGC CTCGCGTACC

781    CGATTATCCA TCGGTGGATG GAGCGACTCG TTAATCGCTT CCATGCGCCG CAGTAACAAT

841    TGCTCAAGCA GATTTATCGC CAGCAGCTCC GAATAGCGCC CTTCCCCTTG CCCGGCGTTA

901    ATGATTTGCC CAAACAGGTC GCTGAAATGC GGCTGGTGCG CTTCATCCGG GCGAAAGAAC

961    CCCGTATTGG CAAATATTGA CGGCCAGTTA AGCCATTCAT GCCAGTAGGC GCGCGGACGA

1021    AAGTAAACCC ACTGGTGATA CCATTCGCGA GCCTCCGGAT GACGACCGTA GTGATGAATC

1081    TCTCCTGGCG GGAACAGCAA AATATCACCC GGTCGGCAAA CAAATTCTCG TCCCTGATTT

1141    TTCACCACCC CCTGACCGCG AATGGTGAGA TTGAGAATAT AACCTTTCAT TCCCAGCGGT

1201    CGGTCGATAA AAAAATCGAG ATAACCGTTG GCCTCAATCG GCGTTAAACC CGCCACCAGA

1261    TGGGCATTAA ACGAGTATCC CGGCAGCAGG GGATCATTTT GCGCTTCAGC CATACTTTTC

Start araC
1321    ATACTCCCGC CATTCAGAGA AGAAACCAAT TGTCCATATT GCATCAGACA TTGCCGTCAC
                                                        ←
```

-continued

```
1381  TGCGTCTTTT ACTGGCTCTT CTCGCTAACC AAACCGGTAA CCCCGCTTAT TAAAAGCATT
1441  CTGTAACAAA GCGGGACCAA AGCCATGACA AAAACGCGTA ACAAAAGTGT CTATAATCAC
1501  GGCAGAAAAG TCCACATTGA TTATTTGCAC GGCGTCACAC TTTGCTATGC CATAGCATTT
1561  TTATCCATAA GATTAGCGGA TCCTACCTGA CGCTTTTTAT CGCAACTCTC TACTGTTTCT
                            Shine-Delgarno       PstI    SalI   XbaI
1621  CCATACCCGT TTTTTTGGGC TAGCAGGAGG AATTCACCCT GCAGGTCGAC TCTAGAGGAT
                                   →
      XmaI KpnI
1681  CCCCGGGTAC CGAGCTCGAA TTCGTAATCA TGGTCATAGC TGTTTCCTGT GTGAAATTGT
1741  TATCCGCTCA CAATTCCACA CAACATACGA GCCGGAAGCA TAAAGTGTAA AGCCTGGGGT
1801  GCCTAATGAG TGAGCTAACT CACATTAATT GCGTTGCGCT CACTGCCCGC TTTCCAGTCG
1861  GGAAACCTGT CGTGCCAGCT GCATTAATGA ATCGGCCAAC GCGCGGGGAG AGGCGGTTTG
1921  CGTATTGGGC GCTCTTCCGC TTCCTCGCTC ACTGACTCGC TGCGCTCGGT CGTTCGGCTG
1981  CGGCGAGCGG TATCAGCTCA CTCAAAGGCG GTAATACGGT TATCCACAGA ATCAGGGGAT
2041  AACGCAGGAA AGAACATGTG AGCAAAAGGC CAGCAAAAGG CCAGGAACCG TAAAAAGGCC
2101  GCGTTGCTGG CGTTTTTCCA TAGGCTCCGC CCCCCTGACG AGCATCACAA AAATCGACGC
2161  TCAAGTCAGA GGTGGCGAAA CCCGACAGGA CTATAAAGAT ACCAGGCGTT TCCCCCTGGA
2221  AGCTCCCTCG TGCGCTCTCC TGTTCCGACC CTGCCGCTTA CCGGATACCT GTCCGCCTTT
2281  CTCCCTTCGG GAAGCGTGGC GCTTTCTCAT AGCTCACGCT GTAGGTATCT CAGTTCGGTG
2341  TAGGTCGTTC GCTCCAAGCT GGGCTGTGTG CACGAACCCC CCGTTCAGCC CGACCGCTGC
2401  GCCTTATCCG GTAACTATCG TCTTGAGTCC AACCCGGTAA GACACGACTT ATCGCCACTG
2461  GCAGCAGCCA CTGGTAACAG GATTAGCAGA GCGAGGTATG TAGGCGGTGC TACAGAGTTC
2521  TTGAAGTGGT GGCCTAACTA CGGCTACACT AGAAGGACAG TATTTGGTAT CTGCGCTCTG
2581  CTGAAGCCAG TTACCTTCGG AAAAAGAGTT GGTAGCTCTT GATCCGGCAA ACAAACCACC
2641  GCTGGTAGCG GTGGTTTTTT TGTTTGCAAG CAGCAGATTA CGCGCAGAAA AAAGGATCT
2701  CAAGAAGATC CTTTGATCTT TTCTACGGGG TCTGACGCTC AGTGGAACGA AAACTCACGT
2761  TAAGGGATTT TGGTCATGAG ATTATCAAAA AGGATCTTCA CCTAGATCCT TTTAAATTAA
                                                                Start bla
2821  AAATGAAGTT TTAAATCAAT CTAAAGTATA TATGAGTAAA CTTGGTCTGA CAGTTACCAA
2881  TGCTTAATCA GTGAGGCACC TATCTCAGCG ATCTGTCTAT TTCGTTCATC CATAGTTGCC
2941  TGACTCCCCG TCGTGTAGAT AACTACGATA CGGGAGGGCT TACCATCTGG CCCCAGTGCT
3001  GCAATGATAC CGCGAGACCC ACGCTCACCG GCTCCAGATT TATCAGCAAT AAACCAGCCA
3061  GCCGGAAGGG CCGAGCGCAG AAGTGGTCCT GCAACTTTAT CCGCCTCCAT CCAGTCTATT
3121  AATTGTTGCC GGGAAGCTAG AGTAAGTAGT TCGCCAGTTA ATAGTTTGCG CAACGTTGTT
3181  GCCATTGCTA CAGGCATCGT GGTGTCACGC TCGTCGTTTG GTATGGCTTC ATTCAGCTCC
3241  GGTTCCCAAC GATCAAGGCG AGTTACATGA TCCCCCATGT TGTGCAAAAA AGCGGTTAGC
3301  TCCTTCGGTC TCCGATCGT TGTCAGAAGT AAGTTGGCCG CAGTGTTATC ACTCATGGTT
3361  ATGGCAGCAC TGCATAATTC TCTTACTGTC ATGCCATCCG TAAGATGCTT TTCTGTGACT
3421  GGTGAGTACT CAACCAAGTC ATTCTGAGAA TAGTGTATGC GGCGACCGAG TTGCTCTTGC
3481  CCGGCGTCAA TACGGGATAA TACCGCGCCA CATAGCAGAA CTTTAAAAGT GCTCATCATT
3541  GGAAAACGTT CTTCGGGGCG AAAACTCTCA AGGATCTTAC CGCTGTTGAG ATCCAGTTCG
3601  ATGTAACCCA CTCGTGCACC CAACTGATCT TCAGCATCTT TTACTTTCAC CAGCGTTTCT
```

```
                              -continued
3661   GGGTGAGCAA AAACAGGAAG GCAAAATGCC GCAAAAAAGG GAATAAGGGC GACACGGAAA Start bla
3721   TGTTGAATAC TCATACTCTT CCTTTTTCAA TATTATTGAA GCATTTATCA GGGTTATTGT
                  ←

3781   CTCATGAGCG GATACATATT TGAATGTATT TAGAAAAATA AACAAATAGG GGTTCCGCGC

3841   ACATTTCCCC GAAAAGTGCC ACCTGACGTC TAAGAAACCA TTATTATCAT GACATTAACC

3901   TATAAAAATA GGCGTATCAC GAGGCCCTTT CGTC
```

The segment araC through the Para control region was taken from pBAD24 using PCR-added HindIII and PstI restriciton sites. This fragment was cut with HindIII and PstI and cloned into pUC-18 cut with the same enzymes. Italicized sequence constitutes both araC and protein to be expressed promotor region.

SEQ ID NO 13
pMPX-6 expression vector

```
    1   *TAGTTATTAA TAGTAATCAA TTACGGGGTC ATTAGTTCAT AGCCCATATA TGGAGTTCCG*
   61   *CGTTACATAA CTTACGGTAA ATGGCCCGCC TGGCTGACCG CCCAACGACC CCCGCCCATT*
  121   *GACGTCAATA ATGACGTATG TTCCCATAGT AACGCCAATA GGGACTTTCC ATTGACGTCA*
  181   *ATGGGTGGAG TATTTACGGT AAACTGCCCA CTTGGCAGTA CATCAAGTGT ATCATATGCC*
  241   *AAGTACGCCC CCTATTGACG TCAATGACGG TAAATGGCCC GCCTGGCATT ATGCCCAGTA*
  301   *CATGACCTTA TGGGACTTTC CTACTTGGCA GTACATCTAC GTATTAGTCA TCGCTATTAC*
  361   *CATGGTGATG CGGTTTTGGC AGTACATCAA TGGGCGTGGA TAGCGGTTTG ACTCACGGGG*
  421   *ATTTCCAAGT CTCCACCCCA TTGACGTCAA TGGGAGTTTG TTTTGGCACC AAAATCAACG*
  481   *GGACTTTCCA AAATGTCGTA ACAACTCCGC CCCATTGACG CAAATGGGCG GTAGGCGTGT*
  541   *ACGGTGGGAG GTCTATATAA GCAGAGCTGG TTTAGTGAAC CGTCAGATCC* GCTAGCGCTA
                                    Start GFP
  601   CCGGTCGCCA CCATGGTGAG CAAGGGCGAG GAGCTGTTCA CCGGGGTGGT GCCCATCCTG
                        →
  661   GTCGAGCTGG ACGGCGACGT AAACGGCCAC AAGTTCAGCG TGTCCGGCGA GGGCGAGGGC
  721   GATGCCACCT ACGGCAAGCT GACCCTGAAG TTCATCTGCA CCACCGGCAA GCTGCCCGTG
  781   CCCTGGCCCA CCCTCGTGAC CACCCTGACC TACGGCGTGC AGTGCTTCAG CCGCTACCCC
  841   GACCACATGA AGCAGCACGA CTTCTTCAAG TCCGCCATGC CCGAAGGCTA CGTCCAGGAG
  901   CGCACCATCT TCTTCAAGGA CGACGGCAAC TACAAGACCC GCGCCGAGGT GAAGTTCGAG
  961   GGCGACACCC TGGTGAACCG CATCGAGCTG AAGGGCATCG ACTTCAAGGA GGACGGCAAC
 1021   ATCCTGGGGC ACAAGCTGGA GTACAACTAC AACAGCCACA ACGTCTATAT CATGGCCGAC
 1081   AAGCAGAAGA ACGGCATCAA GGTGAACTTC AAGATCCGCC ACAACATCGA GGACGGCAGC
 1141   GTGCAGCTCG CCGACCACTA CCAGCAGAAC ACCCCCATCG GCGACGGCCC CGTGCTGCTG
 1201   CCCGACAACC ACTACCTGAG CACCCAGTCC GCCCTGAGCA AAGACCCCAA CGAGAAGCGC
 1261   GATCACATGG TCCTGCTGGA GTTCGTGACC GCCGCCGGGA TCACTCTCGG CATGGACGAG
                                               XhoI   Stop GFP
 1321   CTGTACAAGT CCGGACTCAG ATCTCGAGCT TAATAACAAG CCGTCAATTG TCTGATTCGT
               Stop araC
 1381   TACCAATTAT GACAACTTGA CGGCTACATC ATTCACTTTT TCTTCACAAC CGGCACGGAA
 1441   CTCGCTCGGG CTGGCCCCGG TGCATTTTTT AAATACCCGC GAGAAATAGA GTTGATCGTC
 1501   AAAACCAACA TTGCGACCGA CGGTGGCGAT AGGCATCCGG GTGGTGCTCA AAAGCAGCTT
 1561   CGCCTGGCTG ATACGTTGGT CCTCGCGCCA GCTTAAGACG CTAATCCCTA ACTGCTGGCG
 1621   GAAAAGATGT GACAGACGCG ACGGCGACAA GCAAACATGC TGTGCGACGC TGGCGATATC
 1681   AAAATTGCTG TCTGCCAGGT GATCGCTGAT GTACTGACAA GCCTCGCGTA CCCGATTATC
```

-continued

```
1741  CATCGGTGGA TGGAGCGACT CGTTAATCGC TTCCATGCGC CGCAGTAACA ATTGCTCAAG
1801  CAGATTTATC GCCAGCAGCT CCGAATAGCG CCCTTCCCCT TGCCCGGCGT TAATGATTTG
1861  CCCAAACAGG TCGCTGAAAT GCGGCTGGTG CGCTTCATCC GGGCGAAAGA ACCCCGTATT
1921  GGCAAATATT GACGGCCAGT TAAGCCATTC ATGCCAGTAG GCGCGCGGAC GAAAGTAAAC
1981  CCACTGGTGA TACCATTCGC GAGCCTCCGG ATGACGACCG TAGTGATGAA TCTCTCCTGG
2041  CGGGAACAGC AAAATATCAC CCGGTCGGCA AACAAATTCT CGTCCCTGAT TTTTCACCAC
2101  CCCCTGACCG CGAATGGTGA GATTGAGAAT ATAACCTTTC ATTCCCAGCG GTCGGTCGAT
2161  AAAAAAATCG AGATAACCGT TGGCCTCAAT CGGCGTTAAA CCCGCCACCA GATGGGCATT
2221  AAACGAGTAT CCCGGCAGCA GGGGATCATT TTGCGCTTCA GCCATACTTT TCATACTCCC
                                                Start araC
2281  GCCATTCAGA GAAGAAACCA ATTGTCCATA TTGCATCAGA CATTGCCGTC ACTGCGTCTT
                                                   ←
2341  TTACTGGCTC TTCTCGCTAA CCAAACCGGT AACCCCGCTT ATTAAAAGCA TTCTGTAACA
2401  AAGCGGGACC AAAGCCATGA CAAAAACGCG TAACAAAAGT GTCTATAATC ACGGCAGAAA
2461  AGTCCACATT GATTATTTGC ACGGCGTCAC ACTTTGCTAT GCCATAGCAT TTTTATCCAT
2521  AAGATTAGCG GATCCTACCT GACGCTTTTT ATCGCAACTC TCTACTGTTT CTCCATACCC
             →         EcoRI        KpnI               SalI
2581  GTTTTTTTGG GCTAGCAGGA GGAATTCACC ATGGTACCCG GGATCCTCT AGAGTCGACC
              Shine-Delgarno
      PstI        HindIII    SstII
2641  TGCAGGCATG CAAGCTTGGC CCGCGGGCCC GGGATCCACC GGATCTAGAT AACTGATCAT
2701  AATCAGCCAT ACCACATTTG TAGAGGTTTT ACTTGCTTTA AAAAACCTCC CACACCTCCC
2761  CCTGAACCTG AAACATAAAA TGAATGCAAT TGTTGTTGTT AACTTGTTTA TTGCAGCTTA
2821  TAATGGTTAC AAATAAAGCA ATAGCATCAC AAATTTCACA AATAAAGCAT TTTTTTCACT
2881  GCATTCTAGT TGTGGTTTGT CCAAACTCAT CAATGTATCT TAACGCGTAA ATTGTAAGCG
2941  TTAATATTTT GTTAAAATTC GCGTTAAATT TTTGTTAAAT CAGCTCATTT TTTAACCAAT
3001  AGGCCGAAAT CGGCAAAATC CCTTATAAAT CAAAGAATA GACCGAGATA GGGTTGAGTG
3061  TTGTTCCAGT TTGGAACAAG AGTCCACTAT TAAAGAACGT GGACTCCAAC GTCAAAGGGC
3121  GAAAAACCGT CTATCAGGGC GATGGCCCAC TACGTGAACC ATCACCCTAA TCAAGTTTTT
3181  TGGGGTCGAG GTGCCGTAAA GCACTAAATC GGAACCCTAA AGGGAGCCCC CGATTTAGAG
3241  CTTGACGGGG AAAGCCGGCG AACGTGGCGA GAAAGGAAGG GAAGAAAGCG AAAGGAGCGG
3301  GCGCTAGGGC GCTGGCAAGT GTAGCGGTCA CGCTGCGCGT AACCACCACA CCCGCCGCGC
3361  TTAATGCGCC GCTACAGGGC GCGTCAGGTG GCACTTTTCG GGGAAATGTG CGCGGAACCC
3421  CTATTTGTTT ATTTTTCTAA ATACATTCAA ATATGTATCC GCTCATGAGA CAATAACCCT
3481  GATAAATGCT TCAATAATAT TGAAAAAGGA AGAGTCCTGA GGCGGAAAGA ACCAGCTGTG
3541  GAATGTGTGT CAGTTAGGGT GTGGAAAGTC CCCAGGCTCC CCAGCAGGCA GAAGTATGCA
3601  AAGCATGCAT CTCAATTAGT CAGCAACCAG GTGTGGAAAG TCCCCAGGCT CCCCAGCAGG
3661  CAGAAGTATG CAAAGCATGC ATCTCAATTA GTCAGCAACC ATAGTCCCGC CCCTAACTCC
3721  GCCCATCCCG CCCCTAACTC CGCCCAGTTC CGCCCATTCT CCGCCCCATG GCTGACTAAT
3781  TTTTTTTATT TATGCAGAGG CCGAGGCCGC CTCGGCCTCT GAGCTATTCC AGAAGTAGTG
3841  AGGAGGCTTT TTTGGAGGCC TAGGCTTTTG CAAAGATCGA TCAAGAGACA GGATGAGGAT
          Start Kan
3901  CGTTTCGCAT GATTGAACAA GATGGATTGC ACGCAGGTTC TCCGGCCGCT TGGGTGGAGA
             →
```

-continued

```
3961  GGCTATTCGG CTATGACTGG GCACAACAGA CAATCGGCTG CTCTGATGCC GCCGTGTTCC
4021  GGCTGTCAGC GCAGGGGCGC CCGGTTCTTT TTGTCAAGAC CGACCTGTCC GGTGCCCTGA
4081  ATGAACTGCA AGACGAGGCA GCGCGGCTAT CGTGGCTGGC CACGACGGGC GTTCCTTGCG
4141  CAGCTGTGCT CGACGTTGTC ACTGAAGCGG GAAGGGACTG GCTGCTATTG GGCGAAGTGC
4201  CGGGGCAGGA TCTCCTGTCA TCTCACCTTG CTCCTGCCGA GAAAGTATCC ATCATGGCTG
4261  ATGCAATGCG GCGGCTGCAT ACGCTTGATC CGGCTACCTG CCCATTCGAC CACCAAGCGA
4321  AACATCGCAT CGAGCGAGCA CGTACTCGGA TGGAAGCCGG TCTTGTCGAT CAGGATGATC
4381  TGGACGAAGA GCATCAGGGG CTCGCGCCAG CCGAACTGTT CGCCAGGCTC AAGGCGAGCA
4441  TGCCCGACGG CGAGGATCTC GTCGTGACCC ATGGCGATGC CTGCTTGCCG AATATCATGG
4501  TGGAAAATGG CCGCTTTTCT GGATTCATCG ACTGTGGCCG GCTGGGTGTG GCGGACCGCT
4561  ATCAGGACAT AGCGTTGGCT ACCCGTGATA TTGCTGAAGA GCTTGGCGGC GAATGGGCTG
4621  ACCGCTTCCT CGTGCTTTAC GGTATCGCCG CTCCCGATTC GCAGCGCATC GCCTTCTATC
4681  GCCTTCTTGA CGAGTTCTTC TGAGCGGGAC TCTGGGGTTC GAAATGACCG ACCAAGCGAC
4741  GCCCAACCTG CCATCACGAG ATTTCGATTC CACCGCCGCC TTCTATGAAA GGTTGGGCTT
4801  CGGAATCGTT TTCCGGGACG CCGGCTGGAT GATCCTCCAG CGCGGGATC TCATGCTGGA
4861  GTTCTTCGCC CACCCTAGGG GGAGGCTAAC TGAAACACGG AAGGAGACAA TACCGGAAGG
4921  AACCCGCGCT ATGACGGCAA TAAAAAGACA GAATAAAACG CACGGTGTTG GGTCGTTTGT
4981  TCATAAACGC GGGGTTCGGT CCCAGGGCTG GCACTCTGTC GATACCCCAC CGAGACCCCA
5041  TTGGGGCCAA TACGCCCGCG TTTCTTCCTT TTCCCCACCC CACCCCCCAA GTTCGGGTGA
5101  AGGCCCAGGG CTCGCAGCCA ACGTCGGGGC GGCAGGCCCT GCCATAGCCT CAGGTTACTC
5161  ATATATACTT TAGATTGATT TAAAACTTCA TTTTTAATTT AAAAGGATCT AGGTGAAGAT
5221  CCTTTTTGAT AATCTCATGA CCAAAATCCC TTAACGTGAG TTTTCGTTCC ACTGAGCGTC
5281  AGACCCCGTA GAAAAGATCA AAGGATCTTC TTGAGATCCT TTTTTTCTGC GCGTAATCTG
5341  CTGCTTGCAA ACAAAAAAAC CACCGCTACC AGCGGTGGTT TGTTTGCCGG ATCAAGAGCT
5401  ACCAACTCTT TTTCCGAAGG TAACTGGCTT CAGCAGAGCG CAGATACCAA ATACTGTCCT
5461  TCTAGTGTAG CCGTAGTTAG GCCACCACTT CAAGAACTCT GTAGCACCGC CTACATACCT
5521  CGCTCTGCTA ATCCTGTTAC CAGTGGCTGC TGCCAGTGGC GATAAGTCGT GTCTTACCGG
5581  GTTGGACTCA AGACGATAGT TACCGGATAA GGCGCAGCGG TCGGGCTGAA CGGGGGGTTC
5641  GTGCACACAG CCCAGCTTGG AGCGAACGAC CTACACCGAA CTGAGATACC TACAGCGTGA
5701  GCTATGAGAA AGCGCCACGC TTCCCGAAGG GAGAAAGGCG GACAGGTATC CGGTAAGCGG
5761  CAGGGTCGGA ACAGGAGAGC GCACGAGGGA GCTTCCAGGG GGAAACGCCT GGTATCTTTA
5821  TAGTCCTGTC GGGTTTCGCC ACCTCTGACT TGAGCGTCGA TTTTTGTGAT GCTCGTCAGG
5881  GGGGCGGAGC CTATGGAAAA ACGCCAGCAA CGCGGCCTTT TTACGGTTCC TGGCCTTTTG
5941  CTGGCCTTTT GCTCACATGT TCTTTCCTGC GTTATCCCCT GATTCTGTGG ATAACCGTAT
6001  TACCGCCATG CAT
```

Stop Kan

The segment araC through SstII following the Para control region was taken from pBAD24 using a PCR-added XhoI restriciton site. This fragment was cut with XhoI and SstII and cloned into pEGFP-C1 (Clontech) cut with the same enzymes. Italicized and underlined sequence constitutes the CMV promotor region while the italicized alone region constitutes both the araC and protein to be expressed promotor region.

SEQ ID NO 14
pMPX-56 (rat Edg3 cloned into pMPX-5 using PCR-introduced SalI and KpnI)

```
                              Shine-Delgarno
2401 GAATTCAGGCGCTTTTTAGACTGGTCGTAATGAAATTCAGCAGGATCACATTCTGCAGGT SalI
2461 CGACATGGCAACCACGCACGCGCAGGGCCACCCGCCAGTCTTGGGGAATGATACTCTCCG
   1     M  A  T  T  H  A  Q  G  H  P  P  V  L  G  N  D  T  L  R 2521 GGAACATTATGATTACGTGGGGAAGCTGGCAGGCAGGCTGCGGGATCCCCCTGAGGGTAG
  20   E  H  Y  D  Y  V  G  K  L  A  G  R  L  R  D  P  P  E  G  S 2581 CACCCTCATCACCACCATCCTCTTCTTGGTCACCTGTAGCTTCATCGTCTTGGAGAACCT
  40   T  L  I  T  T  I  L  F  L  V  T  C  S  F  I  V  L  E  N  L 2641 GATGGTTTTGATTGCCATCTGGAAAAACAATAAATTTCATAACCGCATGTACTTTTTCAT
  60   M  V  L  I  A  I  W  K  N  N  K  F  H  N  R  M  Y  F  F  I 2701 CGGCAACTTGGCTCTCTGCGACCTGCTGGCCGGCATAGCCTACAAGGTCAACATTCTGAT
  80   G  N  L  A  L  C  D  L  L  A  G  I  A  Y  K  V  N  I  L  M 2761 GTCCGGTAGGAAGACGTTCAGCCTGTCTCCAACAGTGTGGTTCCTCAGGGAGGGCAGTAT
 100   S  G  R  K  T  F  S  L  S  P  T  V  W  F  L  R  E  G  S  M 2821 GTTCGTAGCCCTGGGCGCATCCACATGCAGCTTATTGGCCATTGCCATTGAGCGGCACCT
 120   F  V  A  L  G  A  S  T  C  S  L  L  A  I  A  I  E  R  H  L 2881 GACCATGATCAAGATGAGGCCGTACGACGCCAACAAGAAGCACCGCGTGTTCCTTCTGAT
 140   T  M  I  K  M  R  P  Y  D  A  N  K  K  H  R  V  F  L  L  I 2941 TGGGATGTGCTGGCTAATTGCCTTCTCGCTGGGTGCCCTGCCCATCCTGGGCTGGAACTG
 160   G  M  C  W  L  I  A  F  S  L  G  A  L  P  I  L  G  W  N  C 3001 CCTGGAAAACTTTCCCGACTGCTCTACCATCTTGCCCCTCTACTCCAAGAAATACATTGC
 180   L  E  N  F  P  D  C  S  T  I  L  P  L  Y  S  K  K  Y  I  A 3061 CTTTCTCATCAGCATCTTCATAGCCATTCTGGTGACCATCGTCATCTTGTACGCGCGCAT
 200   F  L  I  S  I  F  I  A  I  L  V  T  I  V  I  L  Y  A  R  I 3121 CTACTTCCTGGTCAAGTCCAGCAGCCGCAGGGTGGCCAACCACAACTCCGAGAGATCCAT
 220   Y  F  L  V  K  S  S  S  R  R  V  A  N  H  N  S  E  R  S  M 3181 GGCCCTTCTGCGGACCGTAGTGATCGTGGTGAGCGTGTTCATCGCCTGTTGGTCCCCCCT
 240   A  L  L  R  T  V  V  I  V  V  S  V  F  I  A  C  W  S  P  L 3241 TTTCATCCTCTTCCTCATCGATGTGGCCTGCAGGGCGAAGGAGTGCTCCATCCTCTTCAA
 260   F  I  L  F  L  I  D  V  A  C  R  A  K  E  C  S  I  L  F  K 3301 GAGTCAGTGGTTCATCATGCTGGCTGTCCTCAACTCGGCCATGAACCCTGTCATCTACAC
 280   S  Q  W  F  I  M  L  A  V  L  N  S  A  M  N  P  V  I  Y  T 3361 GCTGGCCAGCAAAGAGATGCGGCGTGCTTTCTTCCGGTTGGTGTGCGGCTGTCTGGTCAA
 300   L  A  S  K  E  M  R  R  A  F  F  R  L  V  C  G  C  L  V  K 3421 GGGCAAGGGGACCCAGGCCTCCCCGATGCAGCCTGCTCTTGACCCGAGCAGAAGTAAATC
 320   G  K  G  T  Q  A  S  P  M  Q  P  A  L  D  P  S  R  S  K  S 3481 AAGCTCCAGTAACAACAGCAGCAGCCACTCTCCAAAGGTCAAGGAAGACCTGCCCCATGT
 340   S  S  S  N  N  S  S  S  H  S  P  K  V  K  E  D  L  P  H  V 3541 GGCTACCTCTTCCTGCGTTACTGACAAAACGAGGTCGCTTCAGAATGGGGTCCTCTGCAA
 360   A  T  S  S  C  V  T  D  K  T  R  S  L  Q  N  G  V  L  C  K 3601 GAAGGGCAATTCTGCAGATATCCAGCACAGTGGCGGCCGCTCGAGTCTAGAGGGCCCGCG
 380   K  G  N  S  A  D  I  Q  H  S  G  G  R  S  S  L  E  G  P  R 3661 GTTCGAAGGTAAGCCTATCCCTAACCCTCTCCTCGGTCTCGATTCTACGCGTACCGGTCA
 400   F  E  G  K  P  I  P  N  P  L  L  G  L  D  S  T  R  G  H KpnI
3721 TCATCACCATCACCATTGATAAGGTACCGAGCTCGAATTCGTAATCATGGTCATAGCTGT
 420   H  H  H  H  H
```

SEQ ID NO 15
pMPX-57 (β2 Adrenergic receptor (β2AR) cloned into
pMPX-5 using PCR-introduced SalI and BamHI)

```
                                            Shine-Delgarno
2401 GAATTCAGGCGCTTTTTAGACTGGTCGTAATGAAATTCAGCAGGATCACATTCTGCAGGT SalI
2461 CGACATGGGGCAACCCGGGAACGGCAGCGCCTTCTTGCTGGCACCCAATGGAAGCCATGC
  1     M  G  Q  P  G  N  G  S  A  F  L  L  A  P  N  G  S  H  A 2521 GCCGGACCACGACGTCACGCAGCAAAGGGACGAGGTGTGGGTGGTGGGCATGGGCATCGT
 20     P  D  H  D  V  T  Q  Q  R  D  E  V  W  V  V  G  M  G  I  V 2581 CATGTCTCTCATCGTCCTGGCCATCGTGTTTGGCAATGTGCTGGTCATCACAGCCATTGC
 40     M  S  L  I  V  L  A  I  V  F  G  N  V  L  V  I  T  A  I  A 2641 CAAGTTCGAGCGTCTGCAGACGGTCACCAACTACTTCATCACTTCACTGGCCTGTGCTGA
 60     K  F  E  R  L  Q  T  V  T  N  Y  F  I  T  S  L  A  C  A  D 2701 TCTGGTCATGGGCCTAGCAGTGGTGCCCTTTGGGGCCGCCCATATTCTTATGAAAATGTG
 80     L  V  M  G  L  A  V  V  P  F  G  A  A  H  I  L  M  K  M  W 2761 GACTTTTGGCAACTTCTGGTGCGAGTTTTGGACTTCCATTGATGTGCTGTGCGTCACGGC
100     T  F  G  N  F  W  C  E  F  W  T  S  I  D  V  L  C  V  T  A 2821 CAGCATTGAGACCCTGTGCGTGATCGCAGTGGATCGCTACTTTGCCATTACTTCACCTTT
120     S  I  E  T  L  C  V  I  A  V  D  R  Y  F  A  I  T  S  P  F 2881 CAAGTACCAGAGCCTGCTGACCAAGAATAAGGCCCGGGTGATCATTCTGATGGTGTGGAT
140     K  Y  Q  S  L  L  T  K  N  K  A  R  V  I  I  L  M  V  W  I 2941 TGTGTCAGGCCTTAYCTCCTTCTTGCCCATTCAGATGCACTGGTACAGGGCCACCCACCA
160     V  S  G  L  X  S  F  L  P  I  Q  M  H  W  Y  R  A  T  H  Q 3001 GGAAGCCATCAACTGCTATGCCAATGAGACCTGCTGTGACTTCTTCACGAACCAAGCCTA
180     E  A  I  N  C  Y  A  N  E  T  C  C  D  F  F  T  N  Q  A  Y 3061 TGCCATTGCCTCTTCCATCGTGTCCTTCTACGTTCCCCTGGTGATCATGGTCTTCGTCTA
200     A  I  A  S  S  I  V  S  F  Y  V  P  L  V  I  M  V  F  V  Y 3121 CTCCAGGGTCTTTCAGGAGGCCAAAAGGCAGCTCCAGAAGATTGACAAATCTGAGGGCCG
220     S  R  V  F  Q  E  A  K  R  Q  L  Q  K  I  D  K  S  E  G  R 3181 CTTCCATGTCCAGAACCTTAGCCAGGTGGAGCAGGATGGGCGGACGGGGCATGGACTCCG
240     F  H  V  Q  N  L  S  Q  V  E  Q  D  G  R  T  G  H  G  L  R 3241 CAGATCTTCCAAGTTCTGCTTGAAGGAGCACAAAGCCCTCAAGACGTTAGGCATCATCAT
260     R  S  S  K  F  C  L  K  E  H  K  A  L  K  T  L  G  I  I  M 3301 GGGCACTTTCACCCTCTGCTGGCTGCCCTTCTTCATCGTTAACATTGTGCATGTGATCCA
280     G  T  F  T  L  C  W  L  P  F  F  I  V  N  I  V  H  V  I  Q 3361 GGATAACCTCATCCGTAAGGAAGTTTACATCCTCCTAAATTGGATAGGCTATGTCAATTC
300     D  N  L  I  R  K  E  V  Y  I  L  L  N  W  I  G  Y  V  N  S 3921 TGGTTTCAATCCCCTTATCTACTGCCGGAGCCCAGATTTCAGGATTGCCTTCCAGGAGCT
320     G  F  N  P  L  I  Y  C  R  S  P  D  E  R  I  A  F  Q  E  L 3981 TCTGTGCCTGCGCAGGTCTTCTTTGAAGGCCTATGGCAATGGCTACTCCAGCAACGGCAA
340     L  C  L  R  R  S  S  L  K  A  Y  G  N  G  Y  S  S  N  G  N 3541 CACAGGGGAGCAGAGTGGATATCACGTGGAACAGGAGAAAGAAAATAAACTGCTGTGTGA
360     T  G  E  Q  S  G  Y  H  V  E  Q  E  K  E  N  K  L  L  C  E 3601 AGACCTCCCAGGCACGGAAGACTTTGTGGGCCATCAAGGTACTGTGCCTAGCGATAACAT
380     D  L  P  G  T  E  D  F  V  G  H  Q  G  T  V  P  S  D  N  I BamHI
3661 TGATTCACAAGGGAGGAATTGTAGTACAAATGACTCACTGCTATAATAAGGATCCCCGGG
400     D  S  Q  G  R  N  C  S  T  N  D  S  L  L
```

SEQ ID NO 16

```
AATTGGTACC TCAATGATGA TGATGATGAT GCTTGCAGAG
GACCCCATTC TG
```

SEQ ID NO 17 pMPX-1 (Human turner necrosis factor receptor (TNFR-1) residues 41-455 cloned into pBAD-24 using PCR-introduced NcoI and XbaI)

```
                                                      Shine-Delgarno
1261  TCGCAACTCTCTACTGTTTCTCCATACCCGTTTTTTTGGGCTAGCAGGAGGAATTCACCA NcoI
1321  TGGATAGTGTGTGTCCCCAAGGAAAATATATCCACCCTCAAAATAATTCGATTTGCTGTA
   1   M  D  S  V  C  P  Q  G  K  Y  I  H  P  Q  N  N  S  I  C  C 1381  CCAAGTGCCACAAAGGAACCTACTTGTACAATGACTGTCCAGGCCCGGGGCAGGATACGG
  21   T  K  C  H  K  G  T  Y  L  Y  N  D  C  P  G  P  G  Q  D  T 1441  ACTGCAGGGAGTGTGAGAGCGGCTCCTTCACCGCTTCAGAAAACCACCTCAGACACTGCC
  41   D  C  R  E  C  E  S  G  S  F  T  A  S  E  N  H  L  R  H  C 1501  TCAGCTGCTCCAAATGCCGAAAGGAAATGGGTCAGGTGGAGATCTCTTCTTGCACAGTGG
  61   L  S  C  S  K  C  R  K  E  M  G  Q  V  E  I  S  S  C  T  V 1561  ACCGGGACACCGTGTGTGGCTGCAGGAAGAACCAGTACCGGCATTATTGGAGTGAAAACC
  81   D  R  D  T  V  C  G  C  R  K  N  Q  Y  R  H  Y  W  S  E  N 1621  TTTTCCAGTGCTTCAATTGCAGCCTCTGCCTCAATGGGACCGTGCACCTCTCCTGCCAGG
 101   L  F  Q  C  F  N  C  S  L  C  L  N  G  T  V  H  L  S  C  Q 1681  AGAAACAGAACACCGTGTGCACCTGCCATGCAGGTTTCTTTCTAAGAGAAAACGAGTGTG
 121   E  K  Q  N  T  V  C  T  C  H  A  G  F  F  L  R  E  N  E  C 1741  TCTCCTGTAGTAACTGTAAGAAAAGCCTGGAGTGCACGAAGTTGTGCCTACCCCAGATTG
 141   V  S  C  S  N  C  K  K  S  L  E  C  T  K  L  C  L  P  Q  I 1801  AGAATGTTAAGGGCACTGAGGACTCAGGCACCACAGTGCTGTTGCCCCTGGTCATTTTCT
 161   E  N  V  K  G  T  E  D  S  G  T  T  V  L  L  P  L  V  I  F 1861  TTGGTCTTTGCCTTTTATCCCTCCTCTTCATTGGTTTAATGTATCGCTACCAACGGTGGA
 181   F  G  L  C  L  L  S  L  L  F  I  G  L  M  Y  R  Y  Q  R  W 1921  AGTCCAAGCTCTACTCCATTGTTTGTGGGAAATCGACACCTGAAAAAGAGGGGGAGCTTG
 201   K  S  K  L  Y  S  I  V  C  G  K  S  T  P  E  K  E  G  E  L 1981  AAGGAACTACTACTAAGCCCCTGGCCCCAAACCCAAGCTTCAGTCCCACTCCAGGCTTCA
 221   E  G  T  T  T  K  P  L  A  P  N  P  S  F  S  P  T  P  G  F 2041  CCCCCACCCTGGGCTTCAGTCCCGTGCCCAGTTCCACCTTCACCTCCAGCTCCACCTATA
 241   T  P  T  L  G  F  S  P  V  P  S  S  T  F  T  S  S  S  T  Y 2101  CCCCCGGTGACTGTCCCAACTTTGCGGCTCCCCGCAGAGAGGTGGCACCACCCTATCAGG
 261   T  P  G  D  C  P  N  F  A  A  P  R  R  E  V  A  P  P  Y  Q 2161  GGGCTGACCCCATCCTTGCGACAGCCCTCGCCTCCGACCCCATCCCCAACCCCCTTCAGA
 281   G  A  D  P  I  L  A  T  A  L  A  S  D  P  I  P  N  P  L  Q 2221  AGTGGGAGGACAGCGCCCACAAGCCACAGAGCCTAGACACTGATGACCCCGCGACGCTGT
 301   K  W  E  D  S  A  H  K  P  Q  S  L  D  T  D  D  P  A  T  L 2281  ACGCCGTGGTGGAGAACGTGCCCCCGTTGCGCTGGAAGGAATTCGTGCGGCGCCTAGGGC
 321   Y  A  V  V  E  N  V  P  P  L  R  W  K  E  F  V  R  R  L  G 2341  TGAGCGACCACGAGATCGATCGGCTGGAGCTGCAGAACGGGCGCTGCCTGCGCGAGGCGC
 341   L  S  D  H  E  I  D  R  L  E  L  Q  N  G  R  C  L  R  E  A 2401  AATACAGCATGCTGGCGACCTGGAGGCGGCGCACGCCGCGGCGCGAGGCCACGCTGGAGC
 361   Q  Y  S  M  L  A  T  W  R  R  R  T  P  R  R  E  A  T  L  E 2461  TGCTGGGACGCGTGCTCCGCGACATGGACCTGCTGGGCTGCCTGGAGGACATCGAGGAGG
 381   L  L  G  R  V  L  R  D  M  D  L  L  G  C  L  E  D  I  E  E XbaI
2521  CGCTTTGCGGCCCCGCCGCCCTCCCGCCCGCGCCCAGTCTTCTCAGATGATCTAGAGTCG
 401   A  L  C  G  P  A  A  L  P  P  A  P  S  L  L  R
```

SEQ ID NO 18
pMPX-22 (Human turner necrosis factor receptor (TNFR-1)
residues 29-455 cloned into pMPX-18 using PCR-introduced
SalI and KpnI)

```
                     Shine-Delgarno        SalI
1621 CCATACCCGTTTTTTTGGGCTAGCAGGAGGAATTCACCCTGCAGGTCGACATGGGACTGG
   1                                                         M G L 1681 TCCCTCACCTAGGGGACAGGGAGAAGAGAGATAGTGTGTGTCCCCAAGGAAAATATATCC
   9  V P H L G D R E K R D S V C P Q G K Y I 1791 ACCCTCAAAATAATTCGATTTGCTGTACCAAGTGCCACAAAGGAACCTACTTGTACAATG
  24  H P Q N N S I C C T K C H K G T Y L Y N 1801 ACTGTCCAGGCCCGGGGCAGGATACGGACTGCAGGGAGTGTGAGAGCGGCTCCTTCACCG
  44  D C P G P G Q D T D C R E C E S G S F T 1861 CTTCAGAAAACCACCTCAGACACTGCCTCAGCTGCTCCAAATGCCGAAAGGAAATGGGTC
  64  A S E N H L R H C L S C S K C R K E M G 1921 AGGTGGAGATCTCTTCTTGCACAGTGGACCGGGACACCGTGTGTGGCTGCAGGAAGAACC
  84  Q V E I S S C T V D R D T V C G C R K N 1981 AGTACCGGCATTATTGGAGTGAAAACCTTTTCCAGTGCTTCAATTGCAGCCTCTGCCTCA
 109  Q Y R H Y W S E N L F Q C F N C S L C L 2091 ATGGGACCGTGCACCTCTCCTGCCAGGAGAAACAGAACACCGTGTGCACCTGCCATGCAG
 129  N G T V H L S C Q E K Q N T V C T C H A 2101 GTTTCTTTCTAAGAGAAAACGAGTGTGTCTCCTGTAGTAACTGTAAGAAAAGCCTGGAGT
 144  G F E L R E N E C V S C S N C K K S L E 2161 GCACGAAGTTGTGCCTACCCCAGATTGAGAATGTTAAGGGCACTGAGGACTCAGGCACCA
 164  C T K L C L P Q I E N V K G T E D S G T 2221 CAGTGCTGTTGCCCCTGGTCATTTTCTTTGGTCTTTGCCTTTTATCCCTCCTCTTCATTG
 184  T V L L P L V I F F G L C L L S L L F I 2281 GTTTAATGTATCGCTACCAACGGTGGAAGTCCAAGCTCTACTCCATTGTTTGTGGGAAAT
 209  G L M Y R Y Q R W K S K L Y S I V C G K 2341 CGACACCTGAAAAAGAGGGGAGCTTGAAGGAACTACTACTAAGCCCCTGGCCCCAAACC
 229  S T P E K E G E L E G T T T K P L A P N 2401 CAAGCTTCAGTCCCACTCCAGGCTTCACCCCCACCCTGGGCTTCAGTCCCGTGCCCAGTT
 299  P S F S P T P G F T P T L G F S P V P S 2961 CCACCTTCACCTCCAGCTCCACCTATACCCCCGGTGACTGTCCCAACTTTGCGGCTCCCC
 269  S T F T S S S T Y T P G D C P N F A A P 2521 GCAGAGAGGTGGCACCACCCTATCAGGGGGCTGACCCCATCCTTGCGACAGCCCTCGCCT
 289  R R E V A P P Y Q G A D P I L A T A L A 2581 CCGACCCCATCCCCAACCCCCTTCAGAAGTGGGAGGACAGCGCCCACAAGCCACAGAGCC
 304  S D P I P N P L Q K W E D S A H K P Q S 2641 TAGACACTGATGACCCCGCGACGCTGTACGCCGTGGTGGAGAACGTGCCCCCGTTGCGCT
 324  L D T D D P A T L Y A V V E N V P P L R 2701 GGAAGGAATTCGTGCGGCGCCTAGGGCTGAGCGACCACGAGATCGATCGGCTGGAGCTGC
 344  W K E F V R R L G L S D H E I D R L E L 2761 AGAACGGGCGCTGCCTGCGCGAGGCGCAATACAGCATGCTGGCGACCTGGAGGCGGCGCA
 364  Q N G R C L R E A Q Y S M L A T W R R R 2821 CGCCGCGGCGCGAGGCCACGCTGGAGCTGCTGGGACGCGTGCTCCGCGACATGGACCTGC
 384  T P R R E A T L E L L G R V L R D M D L 2881 TGGGCTGCCTGGAGGACATCGAGGAGGCGCTTTGCGGCCCCGCCGCCCTCCCGCCCGCGC
 404  L G C L E D I E E A L C G P A A L P P A KpnI
2941 CCAGTCTTCTCAGATAATAAGGTACCGAGCTCGAATTCGTAATCATGGTCATAGCTGTTT
 424  P S L L R
```

SEQ ID NO 19
pMPX-40 (Human turner necrosis factor (TNF) cloned into
pMPX-6 using PCR-introduced EcoRI and HindIII)

```
                          EcoRI
              Shine-Delgarno
2581 GTTTTTTGGGCTAGCAGGAGGAATTCATGAGCACTGAAAGCATGATCCGGGACGTGGAG
   1                            M  S  T  E  S  M  I  R  D  V  E
2641 CTGGCCGAGGAGGCGCTCCCCAAGAAGACAGGGGGGCCCCAGGGCTCCAGGCGGTGCTTG
  12  L  A  E  E  A  L  P  K  K  T  G  G  P  Q  G  S  R  R  C  L 2701 TTCCTCAGCCTCTTCTCCTTCCTGATCGTGGCAGGCGCCACCACGCTCTTCTGCCTGCTG
  32  F  L  S  L  F  S  F  L  I  V  A  G  A  T  T  L  F  C  L  L 2761 CACTTTGGAGTGATCGGCCCCCAGAGGGAAGAGTTCCCCAGGGACCTCTCTCTAATCAGC
  52  H  F  G  V  I  G  P  Q  R  E  E  F  P  R  D  L  S  L  I  S 2821 CCTCTGGCCCAGGCAGTCAGATCATCTTCTCGAACCCCGAGTGACAAGCCTGTAGCCCAT
  72  P  L  A  Q  A  V  R  S  S  R  T  P  S  D  K  P  V  A  H 2881 GTTGTAGCAAACCCTCAAGCTGAGGGGCAGCTCCAGTGGCTGAACCGCCGGGCCAATGCC
  92  V  V  A  N  P  Q  A  E  G  Q  L  Q  W  L  N  R  R  A  N  A 2941 CTCCTGGCCAATGGCGTGGAGCTGAGAGATAACCAGCTGGTGGTGCCATCAGAGGGCCTG
 112  L  L  A  N  G  V  E  L  R  D  N  Q  L  V  V  P  S  E  G  L 3001 TACCTCATCTACTCCCAGGTCCTCTTCAAGGGCCAAGGCTGCCCCTCCACCCATGTGCTC
 132  Y  L  I  Y  S  Q  V  L  F  K  G  Q  G  C  P  S  T  H  V  L 3061 CTCACCCACACCATCAGCCGCATCGCCGTCTCCTACCAGACCAAGGTCAACCTCCTCTCT
 152  L  T  H  T  I  S  R  I  A  V  S  Y  Q  T  K  V  N  L  L  S 3121 GCCATCAAGAGCCCCTGCCAGAGGGAGACCCCAGAGGGGGCTGAGGCCAAGCCCTGGTAT
 172  A  I  K  S  P  C  Q  R  E  T  P  E  G  A  E  A  K  P  W  Y 3181 GAGCCCATCTATCTGGGAGGGGTCTTCCAGCTGGAGAAGGGTGACCGACTCAGCGCTGAG
 192  E  P  I  Y  L  G  G  V  F  Q  L  E  K  G  D  R  L  S  A  E 3241 ATCAATCGGCCCGACTATCTCGACTTTGCCGAGTCTGGGCAGGTCTACTTTGGGATCATT
 212  I  N  R  P  D  Y  L  D  F  A  E  S  G  Q  V  Y  F  G  I  I HindIII
3301 GCCCTGTGATAAGCTTGGCCCGCGGGCCCGGGATCCACCGGATCTAGATAACTGATCATA
 232  A  L
```

SEQ ID NO 20
pMPX-52 (toxR-EGF cloned into pMPX-6 using PCR-introduced KpnI and HindIII)

```
              Shine-Delgarno        KpnI
2581 GTTTTTTGGGCTAGCAGGAGGAATTCACCATGGTACCATGAACTTGGGGAATCGACTGT
   1                                   M  N  L  G  N  R  L 2641 TTATTCTGATAGCGGTCTTACTTCCCCTCGCAGTATTACTGCTCAATAGTGACTCTGAAT
   8  F  I  L  I  A  V  L  L  P  L  A  V  L  L  L  N  S  D  S  E 2701 GTCCCCTGTCCCACGATGGGTACTGCCTCCATGATGGTGTGTGCATGTATATTGAAGCAT
  28  C  P  L  S  H  D  G  Y  C  L  H  D  G  V  C  M  Y  I  E  A 2761 TGGACAAGTATGCATGCAACTGTGTTGTTGGCTACATCGGGGAGCGATGTCAGTACCGAG
  48  L  D  K  Y  A  C  N  C  V  V  G  Y  I  G  E  R  C  Q  Y  R HindIII
2821 ACCTGAAGTGGTGGGAACTGCGCTAATAAGCTTGGCCCGCGGGCCCGGGATCCACCGGAT
        68                D  L  K  W  W  E  L  R
```

Non-bold, underlined sequence is toxR transmembrane domain segment that constitutes toxR residues 178-198. The remaining sequence is from human EGF constituting EGF residues 971-1023.

SEQ ID NO 21
pMPX-27 (toxR-invasin cloned into pMPX-6 using PCR-introduced EcoRI and PstI)

```
                            EcoRI
              Shine-Delgarno
2581  GTTTTTTTGGGCTAGCAGGAGGAATTCACCATGAACTTGGGGAATCGACTGTTTATTCTG
   1                                   M   N   L   G   N   R   L   F   I   L 2641  ATAGCGGTCTTACTTCCCCTCGCAGTATTACTGCTCTCATTCACATTGAGCGTCACCGTT
  11   I   A   V   L   L   P   L   A   V   L   L   L   S   F   T   L   S   V   T   V 2701  CAGCAGCCTCAGTTGACATTAACGGCGGCCGTCATTGGTGATGGCGCACCGGCTAATGGG
  31   Q   Q   P   Q   L   T   L   T   A   A   V   I   G   D   G   A   P   A   N   G 2761  AAAACTGCAATCACCGTTGAGTTCACCGTTGCTGATTTTGAGGGGAAACCCTTAGCCGGG
  51   K   T   A   I   T   V   E   F   T   V   A   D   F   E   G   K   P   L   A   G 2821  CAGGAGGTGGTGATAACCACCAATAATGGTGCGCTACCGAATAAAATCACGGAAAAGACA
  71   Q   E   V   V   I   T   T   N   N   G   A   L   P   N   K   I   T   E   K   T 2881  GATGCAAATGGCGTCGCGCGCATTGCATTAACCAATACGACAGATGGCGTGACGGTAGTC
  91   D   A   N   G   V   A   R   I   A   L   T   N   T   T   D   G   V   T   V   V 2941  ACAGCAGAAGTGGAGGGGCAACGGCAAAGTGTTGATACCCACTTTGTTAAGGGTACTATC
 111   T   A   E   V   E   G   Q   R   Q   S   V   D   T   H   F   V   K   G   T   I 3001  GCGGCGGATAAATCCACTCTGGCTGCGGTACCGACATCTATCATCGCTGATGGTCTAATG
 131   A   A   D   K   S   T   L   A   A   V   P   T   S   I   I   A   D   G   L   M 3061  GCTTCAACCATCACGTTGGAGTTGAAGGATACCTATGGGGACCCGCAGGCTGGCGCGAAT
 151   A   S   T   I   T   L   E   L   K   D   T   Y   G   D   P   Q   A   G   A   N 3121  GTGGCTTTTGACACAACCTTAGGCAATATGGGCGTTATCACGGATCACAATGACGGCACT
 171   V   A   F   D   T   T   L   G   N   M   G   V   I   T   D   H   N   D   G   T 3181  TATAGCGCACCATTGACCAGTACCACGTTGGGGGTAGCAACAGTAACGGTGAAAGTGGAT
 191   Y   S   A   P   L   T   S   T   T   L   G   V   A   T   V   T   V   K   V   D 3241  GGGGCTGCGTTCAGTGTGCCGAGTGTGACGGTTAATTTCACGGCAGATCCTATTCCAGAT
 211   G   A   A   F   S   V   P   S   V   T   V   N   F   T   A   D   P   I   P   D 3301  GCTGGCCGCTCCAGTTTCACCGTCTCCACACCGGATATCTTGGCTGATGGCACGATGAGT
 231   A   G   R   S   S   F   T   V   S   T   P   D   I   L   A   D   G   T   M   S 3361  TCCACATTATCCTTTGTCCCTGTCGATAAGAATGGCCATTTTATCAGTGGGATGCAGGGC
 251   S   T   L   S   F   V   P   V   D   K   N   G   H   F   I   S   G   M   Q   G 3421  TTGAGTTTTACTCAAAACGGTGTGCCGGTGAGTATTAGCCCCATTACCGAGCAGCCAGAT
 271   L   S   F   T   Q   N   G   V   P   V   S   I   S   P   I   T   E   Q   P   D 3481  AGCTATACCGCGACGGTGGTTGGGAATAGTGTCGGTGATGTCACAATCACGCCGCAGGTT
 291   S   Y   T   A   T   V   V   G   N   S   V   G   D   V   T   I   T   P   Q   V 3541  GATACCCTGATACTGAGTACATTGCAGAAAAAAATATCCCTATTCCCGGTACCTACGCTG
 311   D   T   L   I   L   S   T   L   Q   K   K   I   S   L   F   P   V   P   T   L 3601  ACCGGTATTCTGGTTAACGGGCAAAATTTCGCTACGGATAAAGGGTTCCCGAAAACGATC
 331   T   G   I   L   V   N   G   Q   N   F   A   T   D   K   G   F   P   K   T   I 3661  TTTAAAAACGCCACATTCCAGTTACAGATGGATAACGATGTTGCTAATAATACTCAGTAT
 351   F   K   N   A   T   F   Q   L   Q   M   D   N   D   V   A   N   N   T   Q   Y 3721  GAGTGGTCGTCGTCATTCACACCCAATGTATCGGTTAACGATCAGGGTCAGGTGACGATT
 371   K   W   S   S   S   F   T   P   N   V   S   V   N   D   Q   G   Q   V   T   I 3781  ACCTACCAAACCTATAGCGAAGTGGCTGTGACGGCGAAAAGTAAAAAATTCCCAAGTTAT
 391   T   Y   Q   T   Y   S   E   V   A   V   T   A   K   S   K   K   F   P   S   Y 3841  TCGGTGAGTTATCGGTTCTACCCAAATCGGTGGATATACGATGGCGGCAGATCGCTGGTA
 411   S   V   S   Y   R   F   Y   P   N   R   W   I   Y   D   G   G   R   S   L   V 3901  TCCAGTCTCGAGGCCAGCAGACAATGCCAAGGTTCAGATATGTCTGCGGTTCTTGAATCC
 431   S   S   L   E   A   S   R   Q   C   Q   G   S   D   M   S   A   V   L   E   S 3961  TCACGTGCAACCAACGGAACGCGTGCGCCTGACGGGACATTGTGGGGCGAGTGGGGGAGC
 451   S   R   A   T   N   G   T   R   A   P   D   G   T   L   W   G   E   W   G   S 4021  TTGACCGCGTATAGTTCTGATTGGCAATCTGGTGAATATTGGGTCAAAAAGACCAGCACG
 471   L   T   A   Y   S   S   D   W   Q   S   G   E   Y   W   V   K   K   T   S   T
```

```
4081 GATTTTGAAACCATGAATATGGACACAGGCGCACTGCAACCAGGGCCTGCATACTTGGCG
 491    D  F  E  T  M  N  M  D  T  G  A  L  Q  P  G  P  A  Y  L  A

PstI
4141 TTCCCGCTCTGTGCGCTGTCAATATAACTGCAGGCATGCAAGCTTGGCCCGCGGGCCCGG
 511    F  P  L  C  A  L  S  I
```

Non-bold, underlined sequence is toxR transmembrane domain segment that constitutes toxR residues 178-198. The remaining sequence is from *Yersinia pseudotuberculosis* invasin constituting inv residues 490-986.
SEQ ID NO 22
pMPX-59 (phoA leader cloned into pMPX-5 using PCR-introduced PstI and XbaI)

```
                                                Shine-Delgarno     PstI
2401   GAATTCAGGCGCTTTTTAGACTGGTCGTAATGAAATTCAGCAGGATCACATTCTGCAGAT
                                                                    M 2461   GTCACGGCCGAGACTTATAGTCGCTTTGTTTTTATTTTTTAATGTATTTGTACATGGAGA
   2     S  R  P  R  L  I  V  A  L  F  L  F  F  N  V  F  V  H  G  E 2521   AAATAAAGTGAAACAAAGCACTATTGCACTGGCACTCTTACCGTTACTGTTTACCCCTGT
  22     N  K  V  K  Q  S  T  I  A  L  A  L  L  P  L  L  F  T  P  V XbaI
2581   GACAAAAGCCCGGACACCAGAATCTAGA
  42     T  K  A  R  T  P  E  S  R
```

PhoA leader (residues 1-48) from *E. coli* MG1655 cloned into pMPX-5. Create chimeric fusions with the phoA leader by cloning into XbaI and introducing a stop sequence.

SEQ ID NO 23 pMPX-60 (complete phoA cloned into pMPX-5 using PCR-introduced PstI and XbaI)

```
                                                Shine-Delgarno    PstI
2401 GAATTCAGGCGCTTTTTAGACTGGTCGTAATGAAATTCAGCAGGATCACATTCTGCAGAT
   1                                                              M
2461 GTCACGGCCGAGACTTATAGTCGCTTTGTTTTTATTTTTTAATGTATTTGTACATGGAGA
   2   S  R  P  R  L  I  V  A  L  F  L  F  F  N  V  F  V  H  G  E 2521 AAATAAAGTGAAACAAAGCACTATTGCACTGGCACTCTTACCGTTACTGTTTACCCCTGT
  22   N  K  V  K  Q  S  T  I  A  L  A  L  L  P  L  L  F  T  P  V 2581 GACAAAAGCCCGGACACCAGAAATGCCTGTTCTGGAAAACCGGGCTGCTCAGGGCGATAT
  42   T  K  A  R  T  P  E  M  P  V  L  E  N  R  A  A  Q  G  D  I 2641 TACTGCACCCGGCGGTGCTCGCCGTTTAACGGGTGATCAGACTGCCGCTCTGCGTGATTC
  62   T  A  P  G  G  A  R  R  L  T  G  D  Q  T  A  A  L  R  D  S 2701 TCTTAGCGATAAACCTGCAAAAAATATTATTTTGCTGATTGGCGATGGGATGGGGGACTC
  82   L  S  D  K  P  A  K  N  I  I  L  L  I  G  D  G  M  G  D  S 2761 GGAAATTACTGCCGCACGTAATTATGCCGAAGGTGCGGGCGGCTTTTTTAAAGGTATAGA
 102   E  I  T  A  A  R  N  Y  A  E  G  A  G  G  F  F  K  G  I  D 2821 TGCCTTACCGCTTACCGGGCAATACACTCACTATGCGCTGAATAAAAAAACCGGCAAACC
 122   A  L  P  L  T  G  Q  Y  T  H  Y  A  L  N  K  K  T  G  K  P 2881 GGACTACGTCACCGACTCGGCTGCATCAGCAACCGCCTGGTCAACCGGTGTCAAAACCTA
 142   D  Y  V  T  D  S  A  A  S  A  T  A  W  S  T  G  V  K  T  Y 2941 TAACGGCGCGCTGGGCGTCGATATTCACGAAAAAGATCACCCAACGATTCTGGAAATGGC
 162   N  G  A  L  G  V  D  I  H  E  K  D  H  P  T  I  L  E  M  A 3001 AAAAGCCGCAGGTCTGGCGACCGGTAACGTTTCTACCGCAGAGTTGCAGGATGCCACGCC
 182   K  A  A  G  L  A  T  G  N  V  S  T  A  E  L  Q  D  A  T  P 3061 CGCTGCGCTGGTGGCACATGTGACCTCGCGCAAATGCTACGGTCCGAGCGCGACCAGTGA
 202   A  A  L  V  A  H  V  T  S  R  K  C  Y  G  P  S  A  T  S  E
```

```
                                                      -continued
3121 AAAATGTCCGGGTAACGCTCTGGAAAAAGGCGGAAAAGGATCGATTACCGAACAGCTGCT
 222    K  C  P  G  N  A  L  E  K  G  G  K  G  S  I  T  E  Q  L  L 3181 TAACGCTCGTGCCGACGTTACGCTTGGCGGCGGCGCAAAAACCTTTGCTGAAACGGCAAC
 242    N  A  R  A  D  V  T  L  G  G  G  A  K  T  F  A  E  T  A  T 3241 CGCTGGTGAATGGCAGGGAAAAACGCTGCGTGAACAGGCACAGGCGCGTGGTTATCAGTT
 262    A  G  E  W  Q  G  K  T  L  R  E  Q  A  Q  A  R  G  Y  Q  L 3301 GGTGAGCGATGCTGCCTCACTGAATTCGGTGACGGAAGCGAATCAGCAAAAACCCCTGCT
 282    V  S  D  A  A  S  L  N  S  V  T  E  A  N  Q  Q  K  P  L  L 3361 TGGCCTGTTTGCTGACGGCAATATGCCAGTGCGCTGGCTAGGACCGAAAGCAACGTACCA
 302    G  L  F  A  D  G  N  M  P  V  R  W  L  G  P  K  A  T  Y  H 3421 TGGCAATATCGATAAGCCCGCAGTCACCTGTACGCCAAATCCGCAACGTAATGACAGTGT
 322    G  N  I  D  K  P  A  V  T  C  T  P  N  P  Q  R  N  D  S  V 3481 ACCAACCCTGGCGCAGATGACCGACAAAGCCATTGAATTGTTGAGTAAAAATGAGAAAGG
 342    P  T  L  A  Q  M  T  D  K  A  I  E  L  L  S  K  N  E  K  G 3541 CTTTTTCCTGCAAGTTGAAGGTGCGTCAATCGATAAACAGGATCATGCTGCGAATCCTTG
 362    F  F  L  Q  V  E  G  A  S  I  D  K  Q  D  H  A  A  N  P  C 3601 TGGGCAAATTGGCGAGACGGTCGATCTCGATGAAGCCGTACAACGGGCGCTGGAATTCGC
 382    G  Q  I  G  E  T  V  D  L  D  E  A  V  Q  R  A  L  E  F  A 3661 TAAAAAGGAGGGTAACACGCTGGTCATAGTCACCGCTGATCACGCCCACGCCAGCCAGAT
 402    K  K  E  G  N  T  L  V  I  V  T  A  D  H  A  H  A  S  Q  I 3721 TGTTGCGCCGGATACCAAAGCTCCGGGCCTCACCCAGGCGCTAAATACCAAAGATGGCGC
 422    V  A  P  D  T  K  A  P  G  L  T  Q  A  L  N  T  K  D  G  A 3781 AGTGATGGTGATGAGTTACGGGAACTCCGAAGAGGATTCACAAGAACATACCGGCAGTCA
 442    V  M  V  M  S  Y  G  N  S  E  E  D  S  Q  E  H  T  G  S  Q 3841 GTTGCGTATTGCGGCGTATGGCCCGCATGCCGCCAATGTTGTTGGACTGACCGACCAGAC
 462    L  R  I  A  A  Y  G  P  H  A  A  N  V  V  G  L  T  D  Q  T XbaI
3901 CGATCTCTTCTACACCATGAAAGCCGCTCTGGGGCTGAAATCTAGA
 482    D  L  F  Y  T  M  K  A  A  L  G  L  K  S  R
```

Complete PhoA from *E. coli* MG1655 cloned into pMPX-5. Create chimeric fusions with the phoA by cloning into XbaI and introducing a stop sequence.
SEQ ID NO 24
pMPX-62 (MalE residues 1-28 cloned into pMPX-5 using PCR-introduced PstI and XbaI)

```
                                    Shine-Delgarno      PstI
2401 GAATTCAGGCGCTTTTTAGACTGGTCGTAATGAAATTCAGCAGGATCACATTCTGCAGAT
   1                                                             M 2461 GAAAATAAAAACAGGTGCACGCATCCTCGCATTATCCGCATTAACGACGATGATGTTTTC
   2    K  I  K  T  G  A  R  I  L  A  L  S  A  L  T  T  M  M  F  S XbaI
2521 CGCCTCGGCTCTCGCCAAAATCTCTAGA
  22    A  S  A  L  A  K  I  S  R
```

MalE residues 1-28 from *E. coli* MG1655 cloned into pMPX-5. Create chimeric fusions with the malE by cloning into XbaI and introducing a stop sequence.
SEQ ID NO 25
pMPX-61 (MalE residues 1-370 cloned into pMPX-5 using PCR-introduced PstI and XbaI)

```
                                    Shine-Delgarno      PstI
2401 GAATTCAGGCGCTTTTTAGACTGGTCGTAATGAAATTCAGCAGGATCACATTCTGCAGAT
   1                                                             M 2461 GAAAATAAAAACAGGTGCACGCATCCTCGCATTATCCGCATTAACGACGATGATGTTTTC
   2    K  I  K  T  G  A  R  I  L  A  L  S  A  L  T  T  M  M  F  S
```

```
2521  CGCCTCGGCTCTCGCCAAATCGAAGAAGGTAAACTGGTAATCTGGATTAACGGCGATAA
  22    A   S   A   L   A   K   I   E   E   G   K   L   V   I   W   I   N   G   D   K

2581  AGGCTATAACGGTCTCGCTGAAGTCGGTAAGAAATTCGAGAAAGATACCGGAATTAAAGT
  42    G   Y   N   G   L   A   E   V   G   K   K   F   E   K   D   T   G   I   K   V

2691  CACCGTTGAGCATCCGGATAAACTGGAAGAGAAATTCCCACAGGTTGCGGCAACTGGCGA
  62    T   V   E   H   P   D   K   L   E   E   K   F   P   Q   V   A   A   T   G   D

2701  TGGCCCTGACATTATCTTCTGGGCACACGACCGCTTTGGTGGCTACGCTCAATCTGGCCT
  82    G   P   D   I   I   F   W   A   H   D   R   F   G   G   Y   A   Q   S   G   L

2761  GTTGGCTGAAATCACCCCGGACAAAGCGTTCCAGGACAAGCTGTATCCGTTTACCTGGGA
 102    L   A   E   I   T   P   D   K   A   F   Q   D   K   L   Y   P   F   T   W   D

2821  TGCCGTACGTTACAACGGCAAGCTGATTGCTTACCCGATCGCTGTTGAAGCGTTATCGCT
 122    A   V   R   Y   N   G   K   L   I   A   Y   P   I   A   V   E   A   L   S   L

2881  GATTTATAACAAAGATCTGCTGCCGAACCCGCCAAAAACCTGGGAAGAGATCCCGGCGCT
 142    I   Y   N   K   D   L   L   P   N   P   P   K   T   W   E   E   I   P   A   L

2941  GGATAAAGAACTGAAAGCGAAAGGTAAGAGCGCGCTGATGTTCAACCTGCAAGAACCGTA
 162    D   K   E   L   K   A   K   G   K   S   A   L   M   F   N   L   Q   E   P   Y

3001  CTTCACCTGGCCGCTGATTGCTGCTGACGGGGGTTATGCGTTCAAGTATGAAAACGGCAA
 182    F   T   W   P   L   I   A   A   D   G   G   Y   A   F   K   Y   E   N   G   K

3061  GTACGACATTAAAGACGTGGGCGTGGATAACGCTGGCGCGAAAGCGGGTCTGACCTTCCT
 202    Y   D   I   K   D   V   G   V   D   N   A   G   A   K   A   G   L   T   F   L

3121  GGTTGACCTGATTAAAAACAAACACATGAATGCAGACACCGATTACTCCATCGCAGAAGC
 222    V   D   L   I   K   N   K   H   M   N   A   D   T   D   I   S   I   A   E   A

3181  TGCCTTTAATAAAGGCGAAACAGCGATGACCATCAACGGCCCGTGGGCATGGTCCAACAT
 292    A   F   N   K   G   E   T   A   M   T   I   N   G   P   W   A   W   S   N   I

3291  CGACACCAGCAAAGTGAATTATGGTGTAACGGTACTGCCGACCTTCAAGGGTCAACCATC
 262    D   T   S   K   V   N   Y   G   V   T   V   L   P   T   F   K   G   Q   P   S

3301  CAAACCGTTCGTTGGCGTGCTGAGCGCAGGTATTAACGCCGCCAGTCCGAACAAAGAGCT
 282    K   P   F   V   G   V   L   S   A   G   I   N   A   A   S   P   N   K   E   L

3361  GGCGAAAGAGTTCCTCGAAAACTATCTGCTGACTGATGAAGGTCTGGAAGCGGTTAATAA
 302    A   K   E   F   L   E   N   Y   L   L   T   D   E   G   L   E   A   V   N   K

3421  AGACAAACCGCTGGGTGCCGTAGCGCTGAAGTCTTACGAGGAAGAGTTGGCGAAAGATCC
 322    D   K   P   L   G   A   V   A   L   K   S   Y   E   E   E   L   A   K   D   P

3481  ACGTATTGCCGCCACCATGGAAAACGCCCAGAAAGGTGAAATCATGCCGAACATCCCGCA
 342    R   I   A   A   T   M   E   N   A   Q   K   G   E   I   M   P   N   I   P   Q

XbaI
3541  GATGTCCGCTTTCTGGTATGCCGTGCGTTCTAGA
 362    M   S   A   F   W   Y   A   V   R   S   R
```

MalE residues 1-370 from *E. coli* MG1655 cloned into pMPX-5. Create chimeric fusions with the malE by cloning into XbaI and introducing a stop sequence.
SEQ ID NO 26
pMPX-17 (complete tig and groESL, both with complete native control region cloned into pMPX-5 using PCR-introduced NarI and HindIII. The tig and groESL regions are joined using XbaI). Construct to be used on same vector as protein to be expressed or as a template for insertion into pACYC184.

```
                                                                    NarI
 181  ACCATATGCG GTGTGAAATA CCGCACAGAT GCGTAAGGAG AAAATACCGC ATCAGGCGCC

241  *ATACGCGACA GCGCGCAATA ACCGTTCTCG ACTCATAAAA GTGATGCCGC TATAATGCCG*

301  *CGTCCTATTT GAATGCTTTC GGGATGATTC TGGTAACAGG GAATGTGATT GATTATAAGA*

361  *ACATCCCGGT TCCGCGAAGC CAACAACCTG TGCTTGCGGG GTAAGAGTTG ACCGAGCACT*

+1 tig
 421  *GTGATTTTTT GAGGTAACAA* GATGCAAGTT TCAGTTGAAA CCACTCAAGG CCTTGGCCGC
```

```
 481 CGTGTAACGA TTACTATCGC TGCTGACAGC ATCGAGACCG CTGTTAAAAG CGAGCTGGTC
 541 AACGTTGCGA AAAAGTACG TATTGACGGC TTCCGCAAAG GCAAAGTGCC AATGAATATC
 601 GTTGCTCAGC GTTATGGCGC GTCTGTACGC CAGGACGTTC TGGGTGACCT GATGAGCCGT
 661 AACTTCATTG ACGCCATCAT TAAAGAAAAA ATCAATCCGG CTGGCGCACC GACTTATGTT
 721 CCGGGCGAAT ACAAGCTGGG TGAAGACTTC ACTTACTCTG TAGAGTTTGA AGTTTATCCG
 781 GAAGTTGAAC TGCAGGGTCT GGAAGCGATC GAAGTTGAAA AACCGATCGT TGAAGTGACC
 841 GACGCTGACG TTGACGGCAT GCTGGATACT CTGCGTAAAC AGCAGGCGAC CTGGAAAGAA
 901 AAAGACGGCG CTGTTGAAGC AGAAGACCGC GTAACCATCG ACTTCACCGG TTCTGTAGAC
 961 GGCGAAGAGT TCGAAGGCGG TAAAGCGTCT GATTTCGTAC TGGCGATGGG CCAGGGTCGT
1021 ATGATCCCGG GCTTTGAAGA CGGTATCAAA GGCCACAAAG CTGGCGAAGA GTTCACCATC
1081 GACGTGACCT TCCCGGAAGA ATACCACGCA GAAAACCTGA AGGTAAAGC AGCGAAATTC
1141 GCTATCAACC TGAAGAAAGT TGAAGAGCGT GAACTGCCGG AACTGACTGC AGAATTCATC
1201 AAACGTTTCG GCGTTGAAGA TGGTTCCGTA GAAGGTCTGC GCGCTGAAGT GCGTAAAAAC
1261 ATGGAGCGCG AGCTGAAGAG CGCCATCCGT AACCGCGTTA AGTCTCAGGC GATCGAAGGT
1321 CTGGTAAAAG CTAACGACAT CGACGTACCG GCTGCGCTGA TCGACAGCGA AATCGACGTT
1381 CTGCGTCGCC AGGCTGCACA GCGTTTCGGT GGCAACGAAA ACAAGCTCT GGAACTGCCG
1441 CGCGAACTGT TCGAAGAACA GGCTAAACGC GCGTAGTTG TTGGCCTGCT GCTGGGCGAA
1501 GTTATCCGCA CCAACGAGCT GAAAGCTGAC GAAGAGCGCG TGAAAGGCCT GATCGAAGAG
1561 ATGGCTTCTG CGTACGAAGA TCCGAAAGAA GTTATCGAGT TCTACAGCAA AAACAAAGAA
1621 CTGATGGACA ACATGCGCAA TGTTGCTCTG GAAGAACAGG CTGTTAAGC TGTACTGGCG
                                                              Stop tig
1681 AAAGCGAAAG TGACTGAAAA AGAAACCACT TTCAACGAGC TGATGAACCA GCAGGCGTAA
1741 TAATAATCTA GAGGTAGCAC AATCAGATTC GCTTATGACG GCGATGAAGA AATTGCGATG
1801 AAATGTGAGG TGAATCAGGG TTTTCACCCG ATTTTGTGCT GATCAGAATT TTTTTTCTTT
1861 TTCCCCCTTG AAGGGGCGAA GCCTCATCCC CATTTCTCTG GTCACCAGCC GGGAAACCAC
                                                              +1 groES
1921 GTAAGCTCCG GCGTCACCCA TAACAGATAC GGACTTTCTC AAAGGAGAGT TATCAATGAA
1981 TATTCGTCCA TTGCATGATC GCGTGATCGT CAAGCGTAAA GAAGTTGAAA CTAAATCTGC
2041 TGGCGGCATC GTTCTGACCG GCTCTGCAGC GGCTAAATCC ACCCGCGGCG AAGTGCTGGC
2101 TGTCGGCAAT GGCCGTATCC TTGAAAATGG CGAAGTGAAG CCGCTGGATG TGAAAGTTGG
2161 CGACATCGTT ATTTTCAACG ATGGCTACGG TGTGAAATCT GAGAAGATCG ACAATGAAGA
                                                        Stop groES
2221 AGTGTTGATC ATGTCCGAAA GCGACATTCT GGCAATTGTT GAAGCGTAAT CCGCGCACGA
             +1 groEL
2281 CACTGAACAT ACGAATTTAA GGAATAAAGA TAATGGCAGC TAAAGACGTA AAATTCGGTA
2341 ACGACGCTCG TGTGAAAATG CTGCGCGGCG TAAACGTACT GGCAGATGCA GTGAAAGTTA
2401 CCCTCGGTCC AAAAGGCCGT AACGTAGTTC TGGATAAATC TTTCGGTGCA CCGACCATCA
2461 CCAAAGATGG TGTTTCCGTT GCTCGTGAAA TCGAACTGGA AGACAAGTTC GAAAATATGG
2521 GTGCGCAGAT GGTGAAAGAA GTTGCCTCTA AGCAAACGA CGCTGCAGGC GACGGTACCA
2581 CCACTGCAAC CGTACTGGCT CAGGCTATCA TCACTGAAGG TCTGAAAGCT GTTGCTGCGG
2641 GCATGAACCC GATGGACCTG AAACGTGGTA TCGACAAAGC GGTTACCGCT GCAGTTGAAG
```

-continued

```
2701 AACTGAAAGC GCTGTCCGTA CCATGCTCTG ACTCTAAAGC GATTGCTCAG GTTGGTACCA

2761 TCTCCGCTAA CTCCGACGAA ACCGTAGGTA AACTGATCGC TGAAGCGATG GACAAAGTCG

2821 GTAAAGAAGG CGTTATCACC GTTGAAGACG GTACCGGTCT GCAGGACGAA CTGGACGTGG

2881 TTGAAGGTAT GCAGTTCGAC CGTGGCTACC TGTCTCCTTA CTTCATCAAC AAGCCGGAAA

2941 CTGGCGCAGT AGAACTGGAA AGCCCGTTCA TCCTGCTGGC TGACAAGAAA ATCTCCAACA

3001 TCCGCGAAAT GCTGCCGGTT CTGGAAGCTG TTGCCAAAGC AGGCAAACCG CTGCTGATCA

3061 TCGCTGAAGA TGTAGAAGGC GAAGCGCTGG CAACTCTGGT TGTTAACACC ATGCGTGGCA

3121 TCGTGAAAGT CGCTGCCGTT AAAGCACCGG GCTTCGGCGA TCGTCGTAAA GCTATGCTGC

3181 AGGATATCGC AACCCTGACT GGCGGTACCG TGATCTCTGA AGAGATCGGT ATGGAGCTGG

3241 AAAAAGCAAC CCTGGAAGAC CTGGGTCAGG CTAAACGTGT TGTGATCAAC AAAGACACCA

3301 CCACTATCAT CGATGGCGTG GGTGAAGAAG CTGCAATCCA GGGCCGTGTT GCTCAGATCC

3361 GTCAGCAGAT TGAAGAAGCA ACTTCTGACT ACGACCGTGA AAAACTGCAG GAACGCGTAG

3421 CGAAACTGGC AGGCGGCGTT GCAGTTATCA AGTGGGTGC TGCTACCGAA GTTGAAATGA

3481 AAGAGAAAAA AGCACGCGTT GAAGATGCCC TGCACGCGAC CCGTGCTGCG GTAGAAGAAG

3541 GCGTGGTTGC TGGTGGTGGT GTTGCGCTGA TCCGCGTAGC GTCTAAACTG GCTGACCTGC

3601 GTGGTCAGAA CGAAGACCAG AACGTGGGTA TCAAAGTTGC ACTGCGTGCA ATGGAAGCTC

3661 CGCTGCGTCA GATCGTATTG AACTGCGGCG AAGAACCGTC TGTTGTTGCT AACACCGTTA

3721 AAGGCGGCGA CGGCAACTAC GGTTACAACG CAGCAACCGA AGAATACGGC AACATGATCG

3781 ACATGGGTAT CCTGGATCCA ACCAAAGTAA CTCGTTCTGC TCTGCAGTAC GCAGCTTCTG

3841 TGGCTGGCCT GATGATCACC ACCGAATGCA TGGTTACCGA CCTGCCGAAA AACGATGCAG

Stop groEL
3901 CTGACTTAGG CGCTGCTGGC GGTATGGGCG GCATGGGTGG CATGGGCGGC ATGATGTAAT HindIII
3961 AATAAGCTTG CATGCCTGCA GGTCGACTCT AGAGGATCCC CGGGTACCGA GCTCGAATTC
```

SEQ ID NO 27
pMPX-63 (C-terminal fusion with Factor Xa TrxA residues 2-109 FLAG cloned into pMPX-5 using PCR-introduced PstI and BamHI)

```
                              Shine-Delgarno      PstI
2401 GAATTCAGGCGCTTTTTAGACTGGTCGTAATGAAATTCAGCAGGATCACATTCTGCAGAT
   1                                                           M Factor Xa    XbaI  XhoI
2461 GATCGAAGCCCGCTCTAGACTCGAGAGCGATAAAATTATTCACCTGACTGACGACAGTTT
   2  I   E   A   R   S   R   L   E   S   D   K   I   I   H   L   T   D   D   S   F 2521 TGACACGGATGTACTCAAAGCGGACGGGGCGATCCTCGTCGATTTCTGGGCAGAGTGGTG
  22  D   T   D   V   L   K   A   D   G   A   I   L   V   D   F   W   A   E   W   C 2581 CGGTCCGTGCAAAATGATCGCCCCGATTCTGGATGAAATCGCTGACGAATATCAGGGCAA
  42  G   P   C   K   M   I   A   P   I   L   D   E   I   A   D   E   Y   Q   G   K 2641 ACTGACCGTTGCAAAACTGAACATCGATCAAAACCCTGGCACTGCGCCGAAATATGGCAT
  62  L   T   V   A   K   L   N   I   D   Q   N   P   G   T   A   P   K   Y   G   I 2701 CCGTGGTATCCCGACTCTGCTGCTGTTCAAAAACGGTGAAGTGGCGGCAACCAAAGTGGG
  82  R   G   I   P   T   L   L   L   F   K   N   G   E   V   A   A   T   K   V   G XhoI
2761 TGCACTGTCTAAAGGTCAGTTGAAAGAGTTCCTCGACGCTAACCTGGCGCTCGAGGATTA
 102  A   L   S   K   G   Q   L   K   E   F   L   D   A   N   L   A   L   E   D   Y BamHI
2821 TAAAGATCATGATGGCGATTATAAAGATCATGATGATTAATAAGGATCCCCGGGTACCGA
 122  K   D   H   D   G   D   Y   K   D   H   D   D
```

Gene trxA (2-109) from *E. coli* MG1655 cloned into pMPX-5. Create chimeric fusions with the trxA by cloning into PstI and XbaI. May remove trxA using XhoI. FLAG sequence shown in italics only.

SEQ ID NO:28

Rat Edg-3 nucleotide sequence

ATGGCAACCACGCACGCGCAGGGGCACCCGCCAGTCTTGG

GGAATGATACTCTCCGGGAACATTATGATTACGTGGGGAAGCTGGCAGG

CAGGCTGCGGGATCCCCCTGAGGGTAGCACCCTCATCACCACCATCCTC

TTCTTGGTCACCTGTAGCTTCATCGTCTTGGAGAACCTGATGGTTTTGA

TTGCCATCTGGAAAAACAATAAATTTCATAACCGCATGTACTTTTTCAT

CGGCAACTTGGCTCTCTGCGACCTGCTGGCCGGCATAGCCTACAAGGTC

AACATTCTGATGTCCGGTAGGAAGACGTTCAGCCTGTCTCCAACAGTGT

GGTTCCTCAGGGAGGGCAGTATGTTCGTAGCCCTGGGCGCATCCACATG

CAGCTTATTGGCCATTGCCATTGAGCGGCACCTGACCATGATCAAGATG

AGGCCGTACGACGCCAACAAGAAGCACCGCGTGTTCCTTCTGATTGGGA

TGTGCTGGCTAATTGCCTTCTCGCTGGGTGCCCTGCCCATCCTGGGCTG

GAACTGCCTGGAGAACTTTCCCGACTGCTCTACCATCTTGCCCCTCTAC

TCCAAGAAATACATTGCCTTTCTCATCAGCATCTTCACAGCCATTCTGG

TGACCATCGTCATCTTGTACGCGCATCTACTTCCTGGTCAAGTCCAG

CAGCCGCAGGGTGGCCAACCACAACTCCGAGAGATCCATGGCCCTTCTG

CGGACCGTAGTGATCGTGGTGAGCGTGTTCATCGCCTGTTGGTCCCCCC

TTTTCATCCTCTTCCTCATCGATGTGGCCTGCAGGGCGAAGGAGTGCTC

CATCCTCTTCAAGAGTCAGTGGTTCATCATGCTGGCTGTCCTCAACTCG

GCCATGAACCCTGTCATCTACACGCTGGCCAGCAAAGAGATGCGGCGTG

CTTTCTTCCGGTTGGTGTGCGGCTGTCTGGTCAAGGGCAAGGGGACCCA

GGCCTCCCCGATGCAGCCTGCTCTTGACCCGAGCAGAAGTAAATCAAGC

TCCAGTAACAACAGCAGCAGCCACTCTCCAAAGGTCAAGGAAGACCTGC

CCCATGTGGCTACCTCTTCCTGCGTCACTGACAAAACGAGGTCGCTTCA

GAATGGGGTCCTCTGCAAG<u>TGA</u> -1145

SEQ ID NO:29

Rat Edg-3 amino acid sequence

M A T T H A Q G H P P V L G N D T L R E H Y D Y V

G K L A G R L R D P P E G S T L I T T I L F L V T

C S F I V L E N L M V L I A I W K N N K F H N R M

Y F F I G N L A L C D L L A G I A Y K V N I L M S

G R K T F S L S P T V W F L R E G S M F V A L G A

S T C S L L A I A I E R H L T M I K M R P Y D A N

K K H R V F L L I G M C W L I A F S L G A L P I L

G W N C L E N F P D C S T I L P L Y S K K Y I A F

L I S I F T A I L V T I V I L Y A R I Y F L V K S

S S R R V A N H N S E R S M A L L R T V V I V V S

V F I A C W S P L F I L F L I D V A C R A K E C S

I L F K S Q W F I M L A V L N S A M N P V I Y T L

A S K E M R R A F F R L V C G C L V K G K G T Q A

S P M Q P A L D P S R S K S S S S N N S S S H S P

K V K E D L P H V A T S S C V T D K T R S L Q N G

V L C K

SEQ ID NO.: 153 pMPX-66 arabinose-inducible expression vector

```
  1  TCGCGCGTTT CGGTGATGAC GGTGAAAACC TCTGACACAT GCAGCTCCCG GAGACGGTCA
 61  CAGCTTGTCT GTAAGCGGAT GCCGGGAGCA GACAAGCCCG TCAGGGCGCG TCAGCGGGTG
121  TTGGCGGGTG TCGGGGCTGG CTTAACTATG CGGCATCAGA GCAGATTGTA CTGAGAGTGC
181  ACCATATGCG GTGTGAAATA CCGCACAGAT GCGTAAGGAG AAAATACCGC ATCAGGCGCC
241  ATTCGCCATT CAGGCTGCGC AACTGTTGGG AAGGGCGATC GGTGCGGGCC TCTTCGCTAT
301  TACGCCAGCT GGCGAAAGGG GGATGTGCTG CAAGGCGATT AAGTTGGGTA ACGCCAGGGT
                              HindIII
361  TTTCCCAGTC ACGACGTTGT AAAACGACGG CCAGTGCCAA GCTTCAAGCC GTCAATTGTC
           Stop araC
421  TGATTCGTTA CCAATTATGA CAACTTGACG GCTACATCAT TCACTTTTTC TTCACAACCG
481  GCACGGAACT CGCTCGGGCT GGCCCCGGTG CATTTTTTAA ATACCCGCGA GAAATAGAGT
541  TGATCGTCAA AACCAACATT GCGACCGACG GTGGCGATAG GCATCCGGGT GGTGCTCAAA
601  AGCAGCTTCG CCTGGCTGAT ACGTTGGTCC TCGCGCCAGC TTAAGACGCT AATCCCTAAC
661  TGCTGGCGGA AAAGATGTGA CAGACGCGAC GGCGACAAGC AAACATGCTG TGCGACGCTG
721  GCGATATCAA AATTGCTGTC TGCCAGGTGA TCGCTGATGT ACTGACAAGC CTCGCGTACC
781  CGATTATCCA TCGGTGGATG GAGCGACTCG TTAATCGCTT CCATGCGCCG CAGTAACAAT
```

-continued

```
 841  TGCTCAAGCA GATTTATCGC CAGCAGCTCC GAATAGCGCC CTTCCCCTTG CCCGGCGTTA
 901  ATGATTTGCC CAAACAGGTC GCTGAAATGC GGCTGGTGCG CTTCATCCGG GCGAAAGAAC
 961  CCCGTATTGG CAAATATTGA CGGCCAGTTA AGCCATTCAT GCCAGTAGGC GCGCGGACGA
1021  AAGTAAACCC ACTGGTGATA CCATTCGCGA GCCTCCGGAT GACGACCGTA GTGATGAATC
1081  TCTCCTGGCG GGAACAGCAA AATATCACCC GGTCGGCAAA CAAATTCTCG TCCCTGATTT
1141  TTCACCACCC CCTGACCGCG AATGGTGAGA TTGAGAATAT AACCTTTCAT TCCCAGCGGT
1201  CGGTCGATAA AAAAATCGAG ATAACCGTTG GCCTCAATCG GCGTTAAACC CGCCACCAGA
1261  TGGGCATTAA ACGAGTATCC CGGCAGCAGG GGATCATTTT GCGCTTCAGC CATACTTTTC
1321  ATACTCCCGC CATTCAGAGA AGAAACCAAT TGTCCATATT GCATCAGACA TTGCCGTCAC

1381  TGCGTCTTTT ACTGGCTCTT CTCGCTAACC AAACCGGTAA CCCCGCTTAT TAAAAGCATT
1441  CTGTAACAAA GCGGGACCAA AGCCATGACA AAAACGCGTA ACAAAAGTGT CTATAATCAC
1501  GGCAGAAAAG TCCACATTGA TTATTTGCAC GGCGTCACAC TTTGCTATGC CATAGCATTT
1561  TTATCCATAA GATTAGCGGA TCCTACCTGA CGCTTTTTAT CGCAACTCTC TACTGTTTCT
                 SD Sall XbaI
1621  CCATACCCGT TTTTTGGGC TAGCAGGAGG CCGTCGACTC TAGAGGATCC CCGCGCCCTC
      Stem-loopKpnI
1681  ATCCGAAAGG GCGTATTGGT ACCGAGCTCG AATTCGTAAT CATGGTCATA GCTGTTTCCT
1741  GTGTGAAATT GTTATCCGCT CACAATTCCA CACAACATAC GAGCCGGAAG CATAAAGTGT
1801  AAAGCCTGGG GTGCCTAATG AGTGAGCTAA CTCACATTAA TTGCGTTGCG CTCACTGCCC
1861  GCTTTCCAGT CGGGAAACCT GTCGTGCCAG CTGCATTAAT GAATCGGCCA ACGCGCGGGG
1921  AGAGGCGGTT TGCGTATTGG GCGCTCTTCC GCTTCCTCGC TCACTGACTC GCTGCGCTCG
1981  GTCGTTCGGC TGCGGCGAGC GGTATCAGCT CACTCAAAGG CGGTAATACG GTTATCCACA
2041  GAATCAGGGG ATAACGCAGG AAAGAACATG TGAGCAAAAG GCCAGCAAAA GGCCAGGAAC
2101  CGTAAAAAGG CCGCGTTGCT GGCGTTTTTC CATAGGCTCC GCCCCCCTGA CGAGCATCAC
2161  AAAAATCGAC GCTCAAGTCA GAGGTGGCGA AACCCGACAG GACTATAAAG ATACCAGGCG
2221  TTTCCCCCTG GAAGCTCCCT CGTGCGCTCT CCTGTTCCGA CCCTGCCGCT TACCGGATAC
2281  CTGTCCGCCT TTCTCCCTTC GGGAAGCGTG GCGCTTTCTC ATAGCTCACG CTGTAGGTAT
2341  CTCAGTTCGG TGTAGGTCGT TCGCTCCAAG CTGGGCTGTG TGCACGAACC CCCCGTTCAG
2401  CCCGACCGCT GCGCCTTATC CGGTAACTAT CGTCTTGAGT CCAACCCGGT AAGACACGAC
2461  TTATCGCCAC TGGCAGCAGC CACTGGTAAC AGGATTAGCA GAGCGAGGTA TGTAGGCGGT
2521  GCTACAGAGT TCTTGAAGTG GTGGCCTAAC TACGGCTACA CTAGAAGGAC AGTATTTGGT
2581  ATCTGCGCTC TGCTGAAGCC AGTTACCTTC GGAAAAAGAG TTGGTAGCTC TTGATCCGGC
2641  AAACAAACCA CCGCTGGTAG CGGTGGTTTT TTTGTTTGCA AGCAGCAGAT TACGCGCAGA
2701  AAAAAGGAT CTCAAGAAGA TCCTTTGATC TTTTCTACGG GGTCTGACGC TCAGTGGAAC
2761  GAAAACTCAC GTTAAGGGAT TTTGGTCATG AGATTATCAA AAAGGATCTT CACCTAGATC
2821  CTTTTAAATT AAAAATGAAG TTTTAAATCA ATCTAAAGTA TATATGAGTA AACTTGGTCT
2881  GACAGTTACC AATGCTTAAT CAGTGAGGCA CCTATCTCAG CGATCTGTCT ATTTCGTTCA
2941  TCCATAGTTG CCTGACTCCC CGTCGTGTAG ATAACTACGA TACGGGAGGG CTTACCATCT
3001  GGCCCCAGTG CTGCAATGAT ACCGCGAGAC CCACGCTCAC CGGCTCCAGA TTTATCAGCA
3061  ATAAACCAGC CAGCCGGAAG GGCCGAGCGC AGAAGTGGTC CTGCAACTTT ATCCGCCTCC
```

```
3121 ATCCAGTCTA TTAATTGTTG CCGGGAAGCT AGAGTAAGTA GTTCGCCAGT TAATAGTTTG
3181 CGCAACGTTG TTGCCATTGC TACAGGCATC GTGGTGTCAC GCTCGTCGTT TGGTATGGCT
3241 TCATTCAGCT CCGGTTCCCA ACGATCAAGG CGAGTTACAT GATCCCCCAT GTTGTGCAAA
3301 AAAGCGGTTA GCTCCTTCGG TCCTCCGATC GTTGTCAGAA GTAAGTTGGC CGCAGTGTTA
3361 TCACTCATGG TTATGGCAGC ACTGCATAAT TCTCTTACTG TCATGCCATC CGTAAGATGC
3421 TTTTCTGTGA CTGGTGAGTA CTCAACCAAG TCATTCTGAG AATAGTGTAT GCGGCGACCG
3481 AGTTGCTCTT GCCCGGCGTC AATACGGGAT AATACCGCGC CACATAGCAG AACTTTAAAA
3541 GTGCTCATCA TTGGAAAACG TTCTTCGGGG CGAAAACTCT CAAGGATCTT ACCGCTGTTG
3601 AGATCCAGTT CGATGTAACC CACTCGTGCA CCCAACTGAT CTTCAGCATC TTTTACTTTC
3661 ACCAGCGTTT CTGGGTGAGC AAAAACAGGA AGGCAAAATG CCGCAAAAAA GGGAATAAGG
3721 GCGACACGGA AATGTTGAAT ACTCATACTC TTCCTTTTTC AATATTATTG AAGCATTTAT
3781 CAGGGTTATT GTCTCATGAG CGGATACATA TTTGAATGTA TTTAGAAAAA TAAACAAATA
3841 GGGGTTCCGC GCACATTTCC CCGAAAAGTG CCACCTGACG TCTAAGAAAC CATTATTATC
3901 ATGACATTAA CCTATAAAAA TAGGCGTATC ACGAGGCCCT TTCGTC
```

Start araC

The segment araC through Para was taken from pBAD24 using PCR added HindIII and modified aligned Shine-Delgarno (SD) sequence with SalI followed by XbaI, a stem-loop transcriptional stop sequence, and KpnI. The PCR product was cloned into pUC18 using HindIII and KpnI.

SEQ ID NO.: 152 pMPX-72 rhamnose-inducible expression vector

```
   1 TCGCGCGTTT CGGTGATGAC GGTGAAAACC TCTGACACAT GCAGCTCCCG GAGACGGTCA
  61 CAGCTTGTCT GTAAGCGGAT GCCGGGAGCA GACAAGCCCG TCAGGGCGCG TCAGCGGGTG
 121 TTGGCGGGTG TCGGGCTGG CTTAACTATG CGGCATCAGA GCAGATTGTA CTGAGAGTGC
 181 ACCATATGCG GTGTGAAATA CCGCACAGAT GCGTAAGGAG AAAATACCGC ATCAGGCGCC
 241 ATTCGCCATT CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA ACGCCAGGGT
                                                         Stop rhaR
 361 TTTCCCAGTC ACGACGTTGT AAAACGACGG CCAGTGCCAA GCTTAATTAA TCTTTCTGCG
                                                HindIII
 421 AATTGAGATG ACGCCACTGG CTGGGCGTCA TCCCGGTTTC CCGGGTAAAC ACCACCGAAA
 481 AATAGTTACT ATCTTCAAAG CCACATTCGG TCGAAATATC ACTGATTAAC AGGCGGCTAT
 541 GCTGGAGAAG ATATTGCGCA TGACACACTC TGACCTGTCG CAGATATTGA TTGATGGTCA
 601 TTCCAGTCTG CTGGCGAAAT TGCTGACGCA AAACGCGCTC ACTGCACGAT GCCTCATCAC
 661 AAAATTTATC CAGCGCAAAG GGACTTTTCA GGCTAGCCGC CAGCCGGGTA ATCAGCTTAT
 721 CCAGCAACGT TTCGCTGGAT GTTGGCGGCA ACGAATCACT GGTGTAACGA TGGCGATTCA
 781 GCAACATCAC CAACTGCCCG AACAGCAACT CAGCCATTTC GTTAGCAAAC GGCACATGCT
 841 GACTACTTTC ATGCTCAAGC TGACCGATAA CCTGCCGCGC CTGCGCCATC CCCATGCTAC
 901 CTAAGCGCCA GTGTGGTTGC CCTGCGCTGG CGTTAAATCC CGGAATCGCC CCCTGCCAGT
 961 CAAGATTCAG CTTCAGACGC TCCGGGCAAT AAATAATATT CTGCAAAACC AGATCGTTAA
1021 CGGAAGCGTA GGAGTGTTTA TCGTCAGCAT GAATGTAAAA GAGATCGCCA CGGGTAATGC
1081 GATAAGGGCG ATCGTTGAGT ACATGCAGGC CATTACCGCG CCAGACAATC ACCAGCTCAC
1141 AAAAATCATG TGTATGTTCA GCAAAGACAT CTTGCGGATA ACGGTCAGCC ACAGCGACTG
```

```
                            -continued
1201  CCTGCTGGTC GCTGGCAAAA AAATCATCTT TGAGAAGTTT TAACTGATGC GCCACCGTGG

1261  CTACCTCGGC CAGAGAACGA AGTTGATTAT TCGCAATATG GCGTACAAAT ACGTTGAGAA

Stop rhaS Start rhaR
1321  GATTCGCGTT ATTGCAGAAA GCCATCCCGT CCCTGGCGAA TATCACGCGG TGACCAGTTA
                                <--

1381  AACTCTCGG CGAAAAAGCGT CGAAAAGTGG TTACTGTCGC TGAATCCACA GCGATAGGCG

1441  ATGTCAGTAA CGCTGGCCTC GCTGTGGCGT AGCAGATGTC GGGCTTTCAT CAGTCGCAGG

1501  CGGTTCAGGT ATCGCTGAGG CGTCAGTCCC GTTTGCTGCT TAAGCTGCCG ATGTAGCGTA

1561  CGCAGTGAAA GAGAAAATTG ATCCGCCACG GCATCCCAAT TCACCTCATC GGCAAAATGG

1621  TCCTCCAGCC AGGCCAGAAG CAAGTTGAGA CGTGATGCGC TGTTTTCCAG GTTCTCCTGC

1681  AAACTGCTTT TACGCAGCAA GAGCAGTAAT TGCATAAACA AGATCTCGCG ACTGGCGGTC

1741  GAGGGTAAAT CATTTTCCCC TTCCTGCTGT TCCATCTGTG CAACCAGCTG TCGCACCTGC

1801  TGCAATACGC TGTGGTTAAC GCGCCAGTGA GACGGATACT GCCCATCCAG CTCTTGTGGC

1861  AGCAACTGAT TCAGCCCGGC GAGAAACTGA ATCGATCCG GCGAGCGATA CAGCACATTG

1921  GTCAGACACA GATTATCGGT ATGTTCATAC AGATGCCGAT CATGATCGCG TACGAAACAG

1981  ACCGTGCCAC CGGTGATGGT ATAGGGCTGC CCATTAAACA CATGAATACC CGTGCCATGT

2041  TCGACAATCA CAATTTCATG AAAATCATGA TGATGTTCAG GAAAATCCGC CTGCGGGAGC

2101  CGGGGTTCTA TCGCCACGGA CGCGTTACCA GACGGAAAAA AATCCACACT ATGTAATACG

Start rhaS
2161  GTCATACTGG CCTCCTGATG TCGTCAACAC GGCGAAATAG TAATCACGAG GTCAGGTTCT

2221  TACCTTAAAT TTTCGACGGA AAACCACGTA AAAACGTCG ATTTTTCAAG ATACAGCGTG

2281  AATTTTCAGG AAATGCGGTG AGCATCACAT CACCACAATT CAGCAAATTG TGAACATCAT

2341  CACGTTCATC TTTCCCTGGT TGCCAATGGC CCATTTTCCT GTCAGTAACG AGAAGGTCGC

SD  PstI  SalI
2401  GAATTCAGGC GCTTTTTAGA CTGGTCGTAA TGAAATTCAG GAGGTTCTGC AGGTCGACTC

XbaI       Stem-loop   KpnI
2461  TAGAGGATCC CCGCGCCCTC ATCCGAAAGG GCGTATTGGT ACCGAGCTCG AATTCGTAAT

2521  CATGGTCATA GCTGTTTCCT GTGTGAAATT GTTATCCGCT CACAATTCCA CACAACATAC

2581  GAGCCGGAAG CATAAAGTGT AAAGCCTGGG GTGCCTAATG AGTGAGCTAA CTCACATTAA

2641  TTGCGTTGCG CTCACTGCCC GCTTTCCAGT CGGGAAACCT GTCGTGCCAG CTGCATTAAT

2701  GAATCGGCCA ACGCGCGGGG AGAGGCGGTT TGCGTATTGG GCGCTCTTCC GCTTCCTCGC

2761  TCACTGACTC GCTGCGCTCG GTCGTTCGGC TGCGGCGAGC GGTATCAGCT CACTCAAAGG

2821  CGGTAATACG GTTATCCACA GAATCAGGGG ATAACGCAGG AAAGAACATG TGAGCAAAAG

2881  GCCAGCAAAA GGCCAGGAAC CGTAAAAAGG CCGCGTTGCT GGCGTTTTTC CATAGGCTCC

2941  GCCCCCCTGA CGAGCATCAC AAAAATCGAC GCTCAAGTCA GAGGTGGCGA AACCCGACAG

3001  GACTATAAAG ATACCAGGCG TTTCCCCCTG GAAGCTCCCT CGTGCGCTCT CCTGTTCCGA

3061  CCCTGCCGCT TACCGGATAC CTGTCCGCCT TTCTCCCTTC GGGAAGCGTG GCGCTTTCTC

3121  ATAGCTCACG CTGTAGGTAT CTCAGTTCGG TGTAGGTCGT TCGCTCCAAG CTGGGCTGTG

3181  TGCACGAACC CCCCGTTCAG CCCGACCGCT GCGCCTTATC CGGTAACTAT CGTCTTGAGT

3241  CCAACCCGGT AAGACACGAC TTATCGCCAC TGGCAGCAGC CACTGGTAAC AGGATTAGCA

3301  GAGCGAGGTA TGTAGGCGGT GCTACAGAGT TCTTGAAGTG GTGGCCTAAC TACGGCTACA

3361  CTAGAAGGAC AGTATTTGGT ATCTGCGCTC TGCTGAAGCC AGTTACCTTC GGAAAAAGAG
```

```
3421  TTGGTAGCTC TTGATCCGGC AAACAAACCA CCGCTGGTAG CGGTGGTTTT TTTGTTTGCA
3481  AGCAGCAGAT TACGCGCAGA AAAAAAGGAT CTCAAGAAGA TCCTTTGATC TTTTCTACGG
3541  GGTCTGACGC TCAGTGGAAC GAAAACTCAC GTTAAGGGAT TTTGGTCATG AGATTATCAA
3601  AAAGGATCTT CACCTAGATC CTTTTAAATT AAAAATGAAG TTTTAAATCA ATCTAAAGTA
3661  TATATGAGTA AACTTGGTCT GACAGTTACC AATGCTTAAT CAGTGAGGCA CCTATCTCAG
3721  CGATCTGTCT ATTTCGTTCA TCCATAGTTG CCTGACTCCC CGTCGTGTAG ATAACTACGA
3781  TACGGGAGGG CTTACCATCT GGCCCCAGTG CTGCAATGAT ACCGCGAGAC CCACGCTCAC
3841  CGGCTCCAGA TTTATCAGCA ATAAACCAGC CAGCCGGAAG GGCCGAGCGC AGAAGTGGTC
3901  CTGCAACTIT ATCCGCCTCC ATCCAGTCTA TTAATTGTTG CCGGGAAGCT AGAGTAAGTA
3961  GTTCGCCAGT TAATAGTTTG CGCAACGTTG TTGCCATTGC TACAGGCATC GTGGTGTCAC
4021  GCTCGTCGTT TGGTATGGCT TCATTCAGCT CCGGTTCCCA ACGATCAAGG CGAGTTACAT
4081  GATCCCCCAT GTTGTGCAAA AAAGCGGTTA GCTCCTTCGG TCCTCCGATC GTTGTCAGAA
4141  GTAAGTTGGC CGCAGTGTTA TCACTCATGG TTATGGCAGC ACTGCATAAT TCTCTTACTG
4201  TCATGCCATC CGTAAGATGC TTTTCTGTGA CTGGTGAGTA CTCAACCAAG TCATTCTGAG
4261  AATAGTGTAT GCGGCGACCG AGTTGCTCTT GCCCGGCGTC AATACGGGAT AATACCGCGC
4321  CACATAGCAG AACTTTAAAA GTGCTCATCA TTGGAAAACG TTCTTCGGGG CGAAAACTCT
4381  CAAGGATCTT ACCGCTGTTG AGATCCAGTT CGATGTAACC CACTCGTGCA CCCAACTGAT
4441  CTTCAGCATC TTTTACTTTC ACCAGCGTTT CTGGGTGAGC AAAAACAGGA AGGCAAAATG
4501  CCGCAAAAAA GGGAATAAGG GCGACACGGA AATGTTGAAT ACTCATACTC TTCCTTTTTC
4561  AATATTATTG AAGCATTTAT CAGGGTTATT GTCTCATGAG CGGATACATA TTTGAATGTA
4621  TTTAGAAAAA TAAACAAATA GGGGTTCCGC GCACATTTCC CCGAAAAGTG CCACCTGACG
4681  TCTAAGAAAC CATTATTATC ATGACATTAA CCTATAAAAA TAGGCGTATC ACGAGGCCCT
4741  TTCGTC
```

The segment rhaR through Prha was taken from the *E. coli* chromosome using PCR added HindIII and modified aligned Shine-Delgarno (SD) sequence with PstI followed by SalI, XbaI, a stem-loop transcriptional stop sequence, and KpnI. The PCR product was cloned into pUC18 using HindIII and KpnI.

SEQ ID NO.: 151
pMPX-67 rhamnose-inducible expression vector

```
  1  TCGCGCGTT TCGGTGATGAC GGTGAAAACC TCTGACACAT GCAGCTCCCG GAGACGGTCA
 61  CAGCTTGTCT GTAAGCGGAT GCCGGGAGCA GACAAGCCCG TCAGGGCGCG TCAGCGGGTG
121  TTGGCGGGTG TCGGGCTGG CTTAACTATG CGGCATCAGA GCAGATTGTA CTGAGAGTGC
181  ACCATATGCG GTGTGAAATA CCGCACAGAT GCGTAAGGAG AAAATACCGC ATCAGGCGCC
241  ATTCGCCATT CAGGCTGCGC AACTGTTGGG AAGGGCGATC GGTGCGGGCC TCTTCGCTAT
301  TACGCCAGCT GGCGAAAGGG GGATGTGCTG CAAGGCGATT AAGTTGGGTA ACGCCAGGGT
                                                           Stop rhaR
361  TTTCCCAGTC ACGACGTTGT AAAACGACGG CCAGTGCCAA GCTTAATTAA TCTTTCTGCG
                                                HindIII
421  AATTGAGATG ACGCCACTGG CTGGGCGTCA TCCCGGTTTC CCGGGTAAAC ACCACCGAAA
481  AATAGTTACT ATCTTCAAAG CCACATTCGG TCGAAATATC ACTGATTAAC AGGCGGCTAT
541  GCTGGAGAAG ATATTGCGCA TGACACACTC TGACCTGTCG CAGATATTGA TTGATGGTCA
601  TTCCAGTCTG CTGGCGAAAT TGCTGACGCA AAACGCGCTC ACTGCACGAT GCCTCATCAC
```

```
                              -continued
 661  AAAATTTATC CAGCGCAAAG GGACTTTTCA GGCTAGCCGC CAGCCGGGTA ATCAGCTTAT

721  CCAGCAACGT TTCGCTGGAT GTTGGCGGCA ACGAATCACT GGTGTAACGA TGGCGATTCA

781  GCAACATCAC CAACTGCCCG AACAGCAACT CAGCCATTTC GTTAGCAAAC GGCACATGCT

841  GACTACTTTC ATGCTCAAGC TGACCGATAA CCTGCCGCGC CTGCGCCATC CCCATGCTAC

901  CTAAGCGCCA GTGTGGTTGC CCTGCGCTGG CGTTAAATCC CGGAATCGCC CCCTGCCAGT

961  CAAGATTCAG CTTCAGACGC TCCGGGCAAT AAATAATATT CTGCAAAACC AGATCGTTAA

1021  CGGAAGCGTA GGAGTGTTTA TCGTCAGCAT GAATGTAAAA GAGATCGCCA CGGGTAATGC

1081  GATAAGGGCG ATCGTTGAGT ACATGCAGGC CATTACCGCG CCAGACAATC ACCAGCTCAC

1141  AAAAATCATG TGTATGTTCA GCAAAGACAT CTTGCGGATA ACGGTCAGCC ACAGCGACTG

1201  CCTGCTGGTC GCTGGCAAAA AAATCATCTT TGAGAAGTTT TAACTGATGC GCCACCGTGG

1261  CTACCTCGGC CAGAGAACGA AGTTGATTAT TCGCAATATG GCGTACAAAT ACGTTGAGAA

Stop rhaS Start rhaR
1321  GATTCGCGTT ATTGCAGAAA GCCATCCCGT CCCTGGCGAA ATCACGCGG TGACCAGTTA
                       <--

1381  AACTCTCGGC GAAAAAGCGT CGAAAAGTGG TTACTGTCGC TGAATCCACA GCGATAGGCG

1441  ATGTCAGTAA CGCTGGCCTC GCTGTGGCGT AGCAGATGTC GGGCTTTCAT CAGTCGCAGG

1501  CGGTTCAGGT ATCGCTGAGG CGTCAGTCCC GTTTGCTGCT TAAGCTGCCA ATGTAGCGTA

1561  CGCAGTGAAA GAGAAAATTG ATCCGCCACG GCATCCCAAT TCACCTCATC GGCAAAATGG

1621  TCCTCCAGCC AGGCCAGAAG CAAGTTGAGA CGTGATGCGC TGTTTTCCAG GTTCTCCTGC

1681  AAACTGCTTT TACGCAGCAA GAGCAGTAAT TGCATAAACA AGATCTCGCG ACTGGCGGTC

1741  GAGGGTAAAT CATTTTCCCC TTCCTGCTGT TCCATCTGTG CAACCAGCTG TCGCACCTGC

1801  TGCAATACGC TGTGGTTAAC GCGCCAGTGA GACGGATACT GCCCATCCAG CTCTTGTGGC

1861  AGCAACTGAT TCAGCCCGGC GAGAAACTGA ATCGATCCG GCGAGCGATA CAGCACATTG

1921  GTCAGACACA GATTATCGGT ATGTTCATAC AGATGCCGAT CATGATCGCG TACGAAACAG

1981  ACCGTGCCAC CGGTGATGGT ATAGGGCTGC CCATTAAACA CATGAATACC CGTGCCATGT

2041  TCGACAATCA CAATTTCATG AAAATCATGA TGATGTTCAG GAAAATCCGC CTGCGGGAGC

2101  CGGGGTTCTA TCGCCACGGA CGCGTTACCA GACGGAAAAA AATCCACACT ATGTAATACG

Start rhaS
2161  GTCATACTGG CCTCCTGATG TCGTCAACAC GGCGAAATAG TAATCACGAG GTCAGGTTCT
                             <--

2221  TACCTTAAAT TTCGACGGA AAACCACGTA AAAACGTCG ATTTTTCAAG ATACAGCGTG

2281  AATTTTCAGG AAATGCGGTG AGCATCACAT CACCACAATT CAGCAAATTG TGAACATCAT

2341  CACGTTCATC TTTCCCTGGT TGCCAATGGC CCATTTTCCT GTCAGTAACG AGAAGGTCGC

SD   SalI XbaI
2401  GAATTCAGGC GCTTTTTAGA CTGGTCGTAA TGAAATTCAG GAGGTTGTCG ACTCTAGAGG

Stem-loop KpnI
2461  ATCCCCGCGC CCTCATCCGA AGGGCGTAT TGGTACCGAG CTCGAATTCG TAATCATGGT

2521  CATAGCTGTT TCCTGTGTGA AATTGTTATC CGCTCACAAT TCCACACAAC ATACGAGCCG

2581  GAAGCATAAA GTGTAAAGCC TGGGGTGCCT AATGAGTGAG CTAACTCACA TTAATTGCGT

2641  TGCGCTCACT GCCCGCTTTC CAGTCGGGAA ACCTGTCGTG CCAGCTGCAT TAATGAATCG

2701  GCCAACGCGC GGGGAGAGGC GGTTTGCGTA TTGGGCGCTC TTCCGCTTCC TCGCTCACTG

2761  ACTCGCTGCG CTCGGTCGTT CGGCTGCGGC GAGCGGTATC AGCTCACTCA AAGGCGGTAA

2821  TACGGTTATC CACAGAATCA GGGGATAACG CAGGAAAGAA CATGTGAGCA AAAGGCCAGC
```

```
2881  AAAAGGCCAG GAACCGTAAA AAGGCCGCGT TGCTGGCGTT TTTCCATAGG CTCCGCCCCC

2941  CTGACGAGCA TCACAAAAAT CGACGCTCAA GTCAGAGGTG GCGAAACCCG ACAGGACTAT

3001  AAAGATACCA GGCGTTTCCC CCTGGAAGCT CCCTCGTGCG CTCTCCTGTT CCGACCCTGC

3061  CGCTTACCGG ATACCTGTCC GCCTTTCTCC CTTCGGGAAG CGTGGCGCTT TCTCATAGCT

3121  CACGCTGTAG GTATCTCAGT TCGGTGTAGG TCGTTCGCTC CAAGCTGGGC TGTGTGCACG

3181  AACCCCCCGT TCAGCCCGAC CGCTGCGCCT TATCCGGTAA CTATCGTCTT GAGTCCAACC

3241  CGGTAAGACA CGACTTATCG CCACTGGCAG CAGCCACTGG TAACAGGATT AGCAGAGCGA

3301  GGTATGTAGG CGGTGCTACA GAGTTCTTGA AGTGGTGGCC TAACTACGGC TACACTAGAA

3361  GGACAGTATT TGGTATCTGC GCTCTGCTGA AGCCAGTTAC CTTCGGAAAA AGAGTTGGTA

3421  GCTCTTGATC CGGCAAACAA ACCACCGCTG GTAGCGGTGG TTTTTTTGTT TGCAAGCAGC

3481  AGATTACGCG CAGAAAAAAA GGATCTCAAG AAGATCCTTT GATCTTTTCT ACGGGGTCTG

3541  ACGCTCAGTG GAACGAAAAC TCACGTTAAG GGATTTTGGT CATGAGATTA TCAAAAAGGA

3601  TCTTCACCTA GATCCTTTTA AATTAAAAAT GAAGTTTTAA ATCAATCTAA AGTATATATG

3661  AGTAAACTTG GTCTGACAGT TACCAATGCT TAATCAGTGA GGCACCTATC TCAGCGATCT

3721  GTCTATTTCG TTCATCCATA GTTGCCTGAC TCCCCGTCGT GTAGATAACT ACGATACGGG

3781  AGGGCTTACC ATCTGGCCCC AGTGCTGCAA TGATACCGCG AGACCCACGC TCACCGGCTC

3841  CAGATTTATC AGCAATAAAC CAGCCAGCCG GAAGGGCCGA GCGCAGAAGT GGTCCTGCAA

3901  CTTTATCCGC CTCCATCCAG TCTATTAATT GTTGCCGGGA AGCTAGAGTA AGTAGTTCGC

3961  CAGTTAATAG TTTGCGCAAC GTTGTTGCCA TTGCTACAGG CATCGTGGTG TCACGCTCGT

4021  CGTTTGGTAT GGCTTCATTC AGCTCCGGTT CCCAACGATC AAGGCGAGTT ACATGATCCC

4081  CCATGTTGTG CAAAAAAGCG GTTAGCTCCT TCGGTCCTCC GATCGTTGTC AGAAGTAAGT

4141  TGGCCGCAGT GTTATCACTC ATGGTTATGG CAGCACTGCA TAATTCTCTT ACTGTCATGC

4201  CATCCGTAAG ATGCTTTTCT GTGACTGGTG AGTACTCAAC CAAGTCATTC TGAGAATAGT

4261  GTATGCGGCG ACCGAGTTGC TCTTGCCCGG CGTCAATACG GGATAATACC GCGCCACATA

4321  GCAGAACTTT AAAAGTGCTC ATCATTGGAA AACGTTCTTC GGGGCGAAAA CTCTCAAGGA

4381  TCTTACCGCT GTTGAGATCC AGTTCGATGT AACCCACTCG TGCACCCAAC TGATCTTCAG

4441  CATCTTTTAC TTTCACCAGC GTTTCTGGGT GAGCAAAAAC AGGAAGGCAA AATGCCGCAA

4501  AAAAGGGAAT AAGGGCGACA CGGAAATGTT GAATACTCAT ACTCTTCCTT TTTCAATATT

4561  ATTGAAGCAT TTATCAGGGT TATTGTCTCA TGAGCGGATA CATATTTGAA TGTATTTAGA

4621  AAAATAAACA AATAGGGGTT CCGCGCACAT TTCCCCGAAA AGTGCCACCT GACGTCTAAG

4681  AAACCATTAT TATCATGACA TTAACCTATA AAAATAGGCG TATCACGAGG CCCTTTCGTC
```

The segment rhaR through Prha was taken from the *E. coli* chromosome using PCR added HindIII and modified aligned Shine-Delgarno (SD) sequence with SalI followed by XbaI, a stem-loop transcriptional stop sequence, and KpnI. The PCR product was cloned into pUC18 using HindIII and KpnI.

SEQ ID NO.: 154
pMPX-71 arabinose-inducible expression vector

```
  1  TCGCGCGTTT CGGTGATGAC GGTGAAAACC TCTGACACAT GCAGCTCCCG GAGACGGTCA

61  CAGCTTGTCT GTAAGCGGAT GCCGGGAGCA GACAAGCCCG TCAGGGCGCG TCAGCGGGTG
```

-continued

```
 121 TTGGCGGGTG TCGGGGCTGG CTTAACTATG CGGCATCAGA GCAGATTGTA CTGAGAGTGC

181 ACCATATGCG GTGTGAAATA CCGCACAGAT GCGTAAGGAG AAAATACCGC ATCAGGCGCC

241 ATTCGCCATT CAGGCTGCGC AACTGTTGGG AAGGGCGATC GGTGCGGGCC TCTTCGCTAT

301 TACGCCAGCT GGCGAAAGGG GGATGTGCTG CAAGGCGATT AAGTTGGGTA ACGCCAGGGT
                              HindIII
 361 TTTCCCAGTC ACGACGTTGT AAAACGACGG CCAGTGCCAA GCTTCAAGCC GTCAATTGTC
          Stop araC
 421 TGATTCGTTA CCAATTATGA CAACTTGACG GCTACATCAT TCACTTTTTC TTCACAACCG

481 GCACGGAACT CGCTCGGGCT GGCCCCGGTG CATTTTTTAA ATACCCGCGA GAAATAGAGT

541 TGATCGTCAA AACCAACATT GCGACCGACG GTGGCGATAG GCATCCGGGT GGTGCTCAAA

601 AGCAGCTTCG CCTGGCTGAT ACGTTGGTCC TCGCGCCAGC TTAAGACGCT AATCCCTAAC

661 TGCTGGCGGA AAAGATGTGA CAGACGCGAC GGCGACAAGC AAACATGCTG TGCGACGCTG

721 GCGATATCAA AATTGCTGTC TGCCAGGTGA TCGCTGATGT ACTGACAAGC CTCGCGTACC

781 CGATTATCCA TCGGTGGATG GAGCGACTCG TTAATCGCTT CCATGCGCCG CAGTAACAAT

841 TGCTCAAGCA GATTTATCGC CAGCAGCTCC GAATAGCGCC CTTCCCCTTG CCCGGCGTTA

901 ATGATTTGCC CAAACAGGTC GCTGAAATGC GGCTGGTGCG CTTCATCCGG GCGAAAGAAC

961 CCCGTATTGG CAAATATTGA CGGCCAGTTA AGCCATTCAT GCCAGTAGGC GCGCGGACGA

1021 AAGTAAACCC ACTGGTGATA CCATTCGCGA GCCTCCGGAT GACGACCGTA GTGATGAATC

1081 TCTCCTGGCG GGAACAGCAA AATATCACCC GGTCGGCAAA CAAATTCTCG TCCCTGATTT

1141 TTCACCACCC CCTGACCGCG AATGGTGAGA TTGAGAATAT AACCTTTCAT TCCCAGCGGT

1201 CGGTCGATAA AAAAATCGAG ATAACCGTTG GCCTCAATCG GCGTTAAACC CGCCACCAGA

1261 TGGGCATTAA ACGAGTATCC CGGCAGCAGG GGATCATTTT GCGCTTCAGC CATACTTTTC
                                                Start araC
1321 ATACTCCCGC CATTCAGAGA AGAAACCAAT TGTCCATATT GCATCAGACA TTGCCGTCAC
                                                <--
1381 TGCGTCTTTT ACTGGCTCTT CTCGCTAACC AAACCGGTAA CCCCGCTTAT TAAAAGCATT

1441 CTGTAACAAA GCGGGACCAA AGCCATGACA AAAACGCGTA ACAAAAGTGT CTATAATCAC

1501 GGCAGAAAAG TCCACATTGA TTATTTGCAC GGCGTCACAC TTTGCTATGC CATAGCATTT

1561 TTATCCATAA GATTAGCGGA TCCTACCTGA CGCTTTTTAT CGCAACTCTC TACTGTTTCT
                                               SD PstI SalI XbaI
1621 CCATACCCGT TTTTTGGGC TAGCAGGAGG CCCTGCAGGT CGACTCTAGA GGATCCCCGC
          Stem-loop KpnI
1681 GCCCTCATCC GAAAGGGCGT ATTGGTACCG AGCTCGAATT CGTAATCATG GTCATAGCTG

1741 TTTCCTGTGT GAAATTGTTA TCCGCTCACA ATTCCACACA ACATACGAGC CGGAAGCATA

1801 AAGTGTAAAG CCTGGGGTGC CTAATGAGTG AGCTAACTCA CATTAATTGC GTTGCGCTCA

1861 CTGCCCGCTT TCCAGTCGGG AAACCTGTCG TGCCAGCTGC ATTAATGAAT CGGCCAACGC

1921 GCGGGGAGAG GCGGTTTGCG TAT-
TGGGCGC TCTTCCGCTT CCTCGCTCAC TGACTCGCTG

1981 CGCTCGGTCG TTCGGCTGCG GCGAGCGGTA TCAGCTCACT CAAAGGCGGT AATACGGTTA

2041 TCCACAGAAT CAGGGGATAA CGCAGGAAAG AACATGTGAG CAAAAGGCCA GCAAAAGGCC

2101 AGGAACCGTA AAAAGGCCGC GTTGCTGGCG TTTTTCCATA GGCTCCGCCC CCCTGACGAG

2161 CATCACAAAA ATCGACGCTC AAGTCAGAGG TGGCGAAACC CGACAGGACT ATAAAGATAC

2221 CAGGCGTTTC CCCCTGGAAG CTCCCTCGTG CGCTCTCCTG TTCCGACCCT GCCGCTTACC

2281 GGATACCTGT CCGCCTTTCT CCCTTCGGGA AGCGTGGCGC TTTCTCATAG CTCACGCTGT
```

```
2341  AGGTATCTCA GTTCGGTGTA GGTCGTTCGC TCCAAGCTGG GCTGTGTGCA CGAACCCCCC
2401  GTTCAGCCCG ACCGCTGCGC CTTATCCGGT AACTATCGTC TTGAGTCCAA CCCGGTAAGA
2461  CACGACTTAT CGCCACTGGC AGCAGCCACT GGTAACAGGA TTAGCAGAGC GAGGTATGTA
2521  GGCGGTGCTA CAGAGTTCTT GAAGTGGTGG CCTAACTACG GCTACACTAG AAGGACAGTA
2581  TTTGGTATCT GCGCTCTGCT GAAGCCAGTT ACCTTCGGAA AAAGAGTTGG TAGCTCTTGA
2641  TCCGGCAAAC AAACCACCGC TGGTAGCGGT GGTTTTTTTG TTTGCAAGCA GCAGATTACG
2701  CGCAGAAAAA AAGGATCTCA AGAAGATCCT TTGATCTTTT CTACGGGGTC TGACGCTCAG
2761  TGGAACGAAA ACTCACGTTA AGGGATTTTG GTCATGAGAT TATCAAAAAG GATCTTCACC
2821  TAGATCCTTT TAAATTAAAA ATGAAGTTTT AAATCAATCT AAAGTATATA TGAGTAAACT
2881  TGGTCTGACA GTTACCAATG CTTAATCAGT GAGGCACCTA TCTCAGCGAT CTGTCTATTT
2941  CGTTCATCCA TAGTTGCCTG ACTCCCCGTC GTGTAGATAA CTACGATACG GGAGGGCTTA
3001  CCATCTGGCC CCAGTGCTGC AATGATACCG CGAGACCCAC GCTCACCGGC TCCAGATTTA
3061  TCAGCAATAA ACCAGCCAGC CGGAAGGGCC GAGCGCAGAA GTGGTCCTGC AACTTTATCC
3121  GCCTCCATCC AGTCTATTAA TTGTTGCCGG GAAGCTAGAG TAAGTAGTTC GCCAGTTAAT
3181  AGTTTGCGCA ACGTTGTTGC CATTGCTACA GGCATCGTGG TGTCACGCTC GTCGTTTGGT
3241  ATGGCTTCAT TCAGCTCCGG TTCCCAACGA TCAAGGCGAG TTACATGATC CCCCATGTTG
3301  TGCAAAAAAG CGGTTAGCTC CTTCGGTCCT CCGATCGTTG TCAGAAGTAA GTTGGCCGCA
3361  GTGTTATCAC TCATGGTTAT GGCAGCACTG CATAATTCTC TTACTGTCAT GCCATCCGTA
3421  AGATGCTTTT CTGTGACTGG TGAGTACTCA ACCAAGTCAT TCTGAGAATA GTGTATGCGG
3481  CGACCGAGTT GCTCTTGCCC GGCGTCAATA CGGGATAATA CCGCGCCACA TAGCAGAACT
3541  TTAAAAGTGC TCATCATTGG AAAACGTTCT TCGGGCGAA AACTCTCAAG GATCTTACCG
3601  CTGTTGAGAT CCAGTTCGAT GTAACCCACT CGTGCACCCA ACTGATCTTC AGCATCTTTT
3661  ACTTTCACCA GCGTTTCTGG GTGAGCAAAA ACAGGAAGGC AAAATGCCGC AAAAAAGGGA
3721  ATAAGGGCGA CACGGAAATG TTGAATACTC ATACTCTTCC TTTTTCAATA TTATTGAAGC
3781  ATTTATCAGG GTTATTGTCT CATGAGCGGA TACATATTTG AATGTATTTA GAAAAATAAA
3841  CAAATAGGGG TTCCGCGCAC ATTTCCCCGA AAAGTGCCAC CTGACGTCTA AGAAACCATT
3901  ATTATCATGA CATTAACCTA TAAAAATAGG CGTATCACGA GGCCCTTTCG TC
```

The segment araC through Para was taken from pBAD24 using PCR added HindIII and modified aligned Shine-Delgarno (SD) sequence with PstI followed by SalI, XbaI, a stem-loop transcriptional stop sequence, and KpnI. The PCR product was cloned into pUC18 using HindIII and KpnI.

SEQ ID NO.: 155
pMPX-68 melibiose-inducible expression vector

```
  1  TCGCGCGTTT CGGTGATGAC GGTGAAAACC TCTGACACAT GCAGCTCCCG GAGACGGTCA
 61  CAGCTTGTCT GTAAGCGGAT GCCGGGAGCA GACAAGCCCG TCAGGGCGCG TCAGCGGGTG
121  TTGGCGGGTG TCGGGGCTGG CTTAACTATG CGGCATCAGA GCAGATTGTA CTGAGAGTGC
181  ACCATATGCG GTGTGAAATA CCGCACAGAT GCGTAAGGAG AAAATACCGC ATCAGGCGCC
241  ATTCGCCATT CAGGCTGCGC AACTGTTGGG AAGGGCGATC GGTGCGGGCC TCTTCGCTAT
301  TACGCCAGCT GGCGAAAGGG GGATGTGCTG CAAGGCGATT AAGTTGGGTA ACGCCAGGGT
```

```
                              HindIII
 361  TTTCCCAGTC ACGACGTTGT AAAACGACGG CCAGTGCCAA GCTTTTAGCC GGGAAACGTC Stop MelR
 421  TGGCGGCGCT GTTGGCTAAG TTTGCGGTAT TGTTGCGGCG ACATGCCGAC ATATTTGCCG

481  AACGTGCTGT AAAAACGACT ACTTGAACGA AAGCCTGCCG TCAGGGCAAT ATCGAGAATA

541  CTTTTATCGG TATCGCTCAG TAACGCGCGA ACGTGGTTGA TGCGCATCGC GGTAATGTAC

601  TGTTTCATCG TCAATTGCAT GACCCGCTGG AATATCCCCA TTGCATAGTT GGCGTTAAGT

661  TTGACGTGCT CAGCCACATC GTTGATGGTC AGCGCCTGAT CATAGTTTTC GGCAATAAAG

721  CCCAGCATCT GGCTAACATA AAATTGCGCA TGGCGCGAGA CGCTGTTTTT GTGTGTGCGC

781  GAGGTTTTAT TGACCAGAAT CGGTTCCCAG CCAGAGAGGC TAAATCGCTT GAGCATCAGG

841  CCAATTTCAT CAATGGCGAG CTGGCGAATT TGCTCGTTCG GACTGTTTAA TTCCTGCTGC

901  CAGCGGCGCA CTTCAAACGG GCTAAGTTGC TGTGTGGCCA GTGATTTGAT CACCATGCCG

961  TGAGTGACGT GGTTAATCAG GTCTTTATCC AGCGGCCAGG AGAGAAACAG ATGCATCGGC

1021  AGATTAAAAA TCGCCATGCT CTGACAGGTT CCGGTATCTG TTAGTTGGTG CGGTGTACAG

1081  GCCCAGAACA GCGTGATATG ACCCTGATTG ATATTCACTT TTTCATTGTT GATCAGGTAT

1141  TCCACATCGC CATCGAAAGG CACATTCACT TCGACCTGAC CATGCCAGTG GCTGGTGGGC

1201  ATGATATGCG GTGCGCGAAA CTCAATCTCC ATCCGCTGGT ATTCCGAATA CAGCGACAGC

+1 MelR
1261  GGGCTGCGGG TCTGTTTTTC GTCGCTGCTG CACATAAACG TATCTGTATT CATGGATGGC

1321  TCTCTTTCCT GGAATATCAG AATTATGGCA GGAGTGAGGG AGGATGACTG CGAGTGGGAG

1381  CACGGTTTTC ACCCTCTTCC CAGAGGGGCG AGGGGACTCT CCGAGTATCA TGAGGCCGAA

1441  AACTCTGCTT TTCAGGTAAT TTATTCCCAT AAACTCAGAT TTACTGCTGC TTCACGCAGG

1501  ATCTGAGTTT ATGGGAATGC TCAACCTGGA AGCCGGAGGT TTTCTGCAGA TTCGCCTGCC

SD        SalI XbaI
1561  ATGATGAAGT TATTCAAGCA AGCCAGGAGG TCGTCGACTC TAGAGGATCC CCGCGCCCTC

Stem-loop KpnI
1621  ATCCGAAAGG GCGTATTGGT ACCGAGCTCG AATTCGTAAT CATGGTCATA GCTGTTTCCT

1681  GTGTGAAATT GTTATCCGCT CACAATTCCA CACAACATAC GAGCCGGAAG CATAAAGTGT

1741  AAAGCCTGGG GTGCCTAATG AGTGAGCTAA CTCACATTAA TTGCGTTGCG CTCACTGCCC

1801  GCTTTCCAGT CGGGAAACCT GTCGTGCCAG CTGCATTAAT GAATCGGCCA ACGCGCGGGG

1861  AGAGGCGGTT TGCGTATTGG GCGCTCTTCC GCTTCCTCGC TCACTGACTC GCTGCGCTCG

1921  GTCGTTCGGC TGCGGCGAGC GGTATCAGCT CACTCAAAGG CGGTAATACG GTTATCCACA

1981  GAATCAGGGG ATAACGCAGG AAAGAACATG TGAGCAAAAG GCCAGCAAAA GGCCAGGAAC

2041  CGTAAAAAGG CCGCGTTGCT GGCGTTTTTC CATAGGCTCC GCCCCCCTGA CGAGCATCAC

2101  AAAAATCGAC GCTCAAGTCA GAGGTGGCGA AACCCGACAG GACTATAAAG ATACCAGGCG

2161  TTTCCCCCTG GAAGCTCCCT CGTGCGCTCT CCTGTTCCGA CCCTGCCGCT TACCGGATAC

2221  CTGTCCGCCT TTCTCCCTTC GGGAAGCGTG GCGCTTTCTC ATAGCTCACG CTGTAGGTAT

2281  CTCAGTTCGG TGTAGGTCGT TCGCTCCAAG CTGGGCTGTG TGCACGAACC CCCCGTTCAG

2341  CCCGACCGCT GCGCCTTATC CGGTAACTAT CGTCTTGAGT CCAACCCGGT AAGACACGAC

2401  TTATCGCCAC TGGCAGCAGC CACTGGTAAC AGGATTAGCA GAGCGAGGTA TGTAGGCGGT

2461  GCTACAGAGT TCTTGAAGTG GTGGCCTAAC TACGGCTACA CTAGAAGGAC AGTATTTGGT

2521  ATCTGCGCTC TGCTGAAGCC AGTTACCTTC GGAAAAAGAG TTGGTAGCTC TTGATCCGGC

2581  AAACAAACCA CCGCTGGTAG CGGTGGTTTT TTTGTTTGCA AGCAGCAGAT TACGCGCAGA
```

```
-continued
2641  AAAAAAGGAT CTCAAGAAGA TCCTTTGATC TTTTCTACGG GGTCTGACGC TCAGTGGAAC

2701  GAAAACTCAC GTTAAGGGAT TTTGGTCATG AGATTATCAA AAAGGATCTT CACCTAGATC

2761  CTTTTAAATT AAAAATGAAG TTTTAAATCA ATCTAAAGTA TATATGAGTA AACTTGGTCT

2821  GACAGTTACC AATGCTTAAT CAGTGAGGCA CCTATCTCAG CGATCTGTCT ATTTCGTTCA

2881  TCCATAGTTG CCTGACTCCC CGTCGTGTAG ATAACTACGA TACGGGAGGG CTTACCATCT

2941  GGCCCCAGTG CTGCAATGAT ACCGCGAGAC CCACGCTCAC CGGCTCCAGA TTTATCAGCA

3001  ATAAACCAGC CAGCCGGAAG GGCCGAGCGC AGAAGTGGTC CTGCAACTTT ATCCGCCTCC

3061  ATCCAGTCTA TTAATTGTTG CCGGGAAGCT AGAGTAAGTA GTTCGCCAGT TAATAGTTTG

3121  CGCAACGTTG TTGCCATTGC TACAGGCATC GTGGTGTCAC GCTCGTCGTT TGGTATGGCT

3181  TCATTCAGCT CCGGTTCCCA ACGATCAAGG CGAGTTACAT GATCCCCCAT GTTGTGCAAA

3241  AAAGCGGTTA GCTCCTTCGG TCCTCCGATC GTTGTCAGAA GTAAGTTGGC CGCAGTGTTA

3301  TCACTCATGG TTATGGCAGC ACTGCATAAT TCTCTTACTG TCATGCCATC CGTAAGATGC

3361  TTTTCTGTGA CTGGTGAGTA CTCAACCAAG TCATTCTGAG AATAGTGTAT GCGGCGACCG

3421  AGTTGCTCTT GCCCGGCGTC AATACGGGAT AATACCGCGC CACATAGCAG AACTTTAAAA

3481  GTGCTCATCA TTGGAAAACG TTCTTCGGGG CGAAAACTCT CAAGGATCTT ACCGCTGTTG

3541  AGATCCAGTT CGATGTAACC CACTCGTGCA CCCAACTGAT CTTCAGCATC TTTTACTTTC

3601  ACCAGCGTTT CTGGGTGAGC AAAAACAGGA AGGCAAAATG CCGCAAAAAA GGGAATAAGG

3661  GCGACACGGA AATGTTGAAT ACTCATACTC TTCCTTTTTC AATATTATTG AAGCATTTAT

3721  CAGGGTTATT GTCTCATGAG CGGATACATA TTTGAATGTA TTTAGAAAAA TAAACAAATA

3781  GGGGTTCCGC GCACATTTCC CCGAAAAGTG CCACCTGACG TCTAAGAAAC CATTATTATC

3841  ATGACATTAA CCTATAAAAA TAGGCGTATC ACGAGGCCCT TTCGTC
```

SEQ ID NO.: 166
MalE (1-370) Factor Xa NTR (43-424) FLAG
SalI+1 MalE (1-370)

```
  1  GTCGACATGAAAATAAAAACAGGTGCACGCATCCTCGCATTATCCGCATTAACGACGATGATGTTT

1  M  K  I  K  T  G  A  R  I  L  A  L  S  A  L  T  T  M  M  F

61  TCCGCCTCGGCTCTCGCCAAAATCGAAGAAGGTAAACTGGTAATCTGGATTAACGGCGAT

21  S  A  S  A  L  A  K  I  E  E  G  K  L  V  I  W  I  N  G  D

121  AAAGGCTATAACGGTCTCGCTGAAGTCGGTAAGAAATTCGAGAAAGATACCGGAATTAAA

41  K  G  Y  N  G  L  A  E  V  G  K  K  F  E  K  D  T  G  I  K

181  GTCACCGTTGAGCATCCGGATAAACTGGAAGAGAAATTCCCACAGGTTGCGGCAACTGGC

61  V  T  V  E  H  P  D  K  L  E  E  K  F  P  Q  V  A  A  T  G

241  GATGGCCCTGACATTATCTTCTGGGCACACGACCGCTTTGGTGGCTACGCTCAATCTGGC

81  D  G  P  D  I  I  F  W  A  H  D  R  F  G  G  Y  A  Q  S  G

301  CTGTTGGCTGAAATCACCCCGGACAAAGCGTTCCAGGACAAGCTGTATCCGTTTACCTGG

101  L  L  A  E  I  T  P  D  K  A  F  Q  D  K  L  Y  P  F  T  W

361  GATGCCGTACGTTACAACGGCAAGCTGATTGCTTACCCGATCGCTGTTGAAGCGTTATCG

121  D  A  V  R  Y  N  G  K  L  I  A  Y  P  I  A  V  E  A  L  S

421  CTGATTTATAACAAAGATCTGCTGCCGAACCCGCCAAAAACCTGGGAAGAGATCCCGGCG

141  L  I  Y  N  K  D  L  L  P  N  P  P  K  T  W  E  E  I  P  A
```

```
                                                     -continued
 481 CTGGATAAAGAACTGAAAGCGAAAGGTAAGAGCGCGCTGATGTTCAACCTGCAAGAACCG

161   L  D  K  E  L  A  K  G  K  S  A  L  M  F  N  L  Q  E  P

541 TACTTCACCTGGCCGCTGATTGCTGCTGACGGGGGTTATGCGTTCAAGTATGAAAACGGC

181   Y  F  T  W  P  L  I  A  A  D  G  G  Y  A  F  K  Y  E  N  G

601 AAGTACGACATTAAAGACGTGGGCGTGGATAACGCTGGCGCGAAAGCGGGTCTGACCTTC

201   K  Y  D  I  K  D  V  G  V  D  N  A  G  A  K  A  G  L  T  F

661 CTGGTTGACCTGATTAAAAACAAACACATGAATGCAGACACCGATTACTCCATCGCAGAA

221   L  V  D  L  I  K  N  K  H  M  N  A  D  T  D  Y  S  I  A  E

721 GCTGCCTTTAATAAAGGCGAAACAGCGATGACCATCAACGGCCCGTGGGCATGGTCCAAC

241   A  A  F  N  K  G  E  T  A  M  T  I  N  G  P  W  A  W  S  N

781 ATCGACACCAGCAAAGTGAATTATGGTGTAACGGTACTGCCGACCTTCAAGGGTCAACCA

261   I  D  T  S  K  V  N  Y  G  V  T  V  L  P  T  F  K  G  Q  P

841 TCCAAACCGTTCGTTGGCGTGCTGAGCGCAGGTATTAACGCCGCCAGTCCGAACAAAGAG

281   S  K  P  F  V  G  V  L  S  A  G  I  N  A  A  S  P  N  K  E

901 CTGGCGAAAGAGTTCCTCGAAAACTATCTGCTGACTGATGAAGGTCTGGAAGCGGTTAAT

301   L  A  K  E  F  L  E  N  Y  L  L  T  D  E  G  L  E  A  V  N

961 AAAGACAAACCGCTGGGTGCCGTAGCGCTGAAGTCTTACGAGGAAGAGTTGGCGAAAGAT

321   K  D  K  P  L  G  A  V  A  L  K  S  Y  E  E  E  L  A  K  D

1021 CCACGTATTGCCGCCACCATGGAAAACGCCCAGAAAGGTGAAATCATGCCGAACATCCCG

341   P  R  I  A  A  T  M  E  N  A  Q  K  G  E  I  M  P  N  I P
                                                    Factor Xa +43 NTR
1081 CAGATGTCCGCTTTCTGGTATGCCGTGCTGATCGAAGCCCGCACCTCGGAATCCGACACG

361   Q  M  S  A  F  W  Y  A  V  L  I  E  A  R  T  S  E  S  D  T

1141 GCAGGGCCCAACAGCGACCTGGACGTGAACACTGACATTTATTCCAAGGTGCTGGTGACT

381   A  G  P  N  S  D  L  D  V  N  T  D  I  Y  S  K  V  L  V  T

1201 GCTATATACCTGGCACTCTTCGTGGTGGGCACTGTGGGCAACTCCGTGACAGCCTTCACT

401   A  I  Y  L  A  L  F  V  V  G  T  V  G  N  S  V  T  A  F  T

1261 CTAGCGCGGAAGAAGTCACTGCAGAGCCTGCAGAGCACTGTGCATTACCACCTGGGCAGC

421   L  A  R  K  K  S  L  Q  S  L  Q  S  T  V  H  Y  H  L  G  S

1321 CTGGCACTGTCGGACCTGCTTATCCTTCTGCTGGCCATGCCCGTGGAGCTATACAACTTC

441   L  A  L  S  D  L  L  I  L  L  L  A  M  P  V  E  L  Y  N  F

1381 ATCTGGGTACACCATCCCTGGGCCTTTGGGGACGCTGGCTGCCGTGGCTACTATTTCCTG

461   I  W  V  H  H  P  W  A  F  G  D  A  G  C  R  G  Y  Y  F  L

1441 CGTGATGCCTGCACCTATGCCACAGCCCTCAATGTAGCCAGCCTGAGTGTGGAGCGCTAC

481   R  D  A  C  T  Y  A  T  A  L  N  V  A  S  L  S  V  E  R  Y

1501 TTGGCCATCTGCCATCCCTTCAAGGCCAAGACCCTCATGTCCCGCAGCCGCACCAAGAAA

501   L  A  I  C  H  P  F  K  A  K  T  L  M  S  R  S  R  T  K  K

1561 TTCATCAGTGCCATATGGCTAGCTTCGGCGCTGCTGGCTATACCCATGCTTTTCACCATG

521   F  I  S  A  I  W  L  A  S  A  L  L  A  I  P  M  L  F  T  M

1621 GGCCTGCAGAACCGCAGTGGTGACGGCACGCACCCTGGCGGCCTGGTGTGCACACCCATT

541   G  L  Q  N  R  S  G  D  G  T  H  P  G  G  L  V  C  T  P  I
```

```
1681  GTGGACACAGCCACTGTCAAGGTCGTCATCCAGGTTAACACCTTCATGTCCTTCCTGTTT

561  V  D  T  A  T  V  K  V  V  I  Q  V  N  T  F  M  S  F  L  F

1741  CCCATGTTGGTCATCTCCATCCTAAACACCGTGATTGCCAACAAACTGACAGTCATGGTG

581  P  M  L  V  I  S  I  L  N  T  V  I  A  N  K  L  T  V  M  V

1801  CACCAGGCCGCCGAGCAGGGCCGAGTGTGCACCGTGGGCACACACAACGGTTTAGAGCAC

601  H  Q  A  A  E  Q  G  R  V  C  T  V  G  T  H  N  G  L  E  H

1861  AGCACGTTCAACATGACCATCGAGCCGGGTCGTGTCCAGGCCCTGCGCCACGGAGTCCTC

621  S  T  F  N  M  T  I  E  P  G  R  V  Q  A  L  R  H  G  V  L

1921  GTCTTACGTGCTGTGGTCATTGCCTTTGTGGTCTGCTGGCTGCCCTACCACGTGCGACGC

641  V  L  R  A  V  V  I  A  F  V  V  C  W  L  P  Y  H  V  R  R

1981  CTGATGTTCTGCTATATCTCGGATGAACAGTGGACTACGTTCCTCTTCGATTTCTACCAC

661  L  M  F  C  Y  I  S  D  E  Q  W  T  T  F  L  F  D  F  Y  H

2041  TATTTCTACATGCTAACCAACGCTCTCTTCTACGTCAGCTCCGCCATCAATCCCATCCTC

681  Y  F  Y  M  L  T  N  A  L  F  Y  V  S  S  A  I  N  P  I  L

2101  TACAACCTGGTCTCCGCCAACTTCCGCCAGGTCTTTCTGTCCACGCTGGCCTGCCTTTGT

701  Y  N  L  V  S  A  N  F  R  Q  V  F  L  S  T  L  A  C  L  C

2161  CCTGGGTGGCGCCACCGCCGAAAGAAGAGGCCAACGTTCTCCAGGAAGCCCAACAGCATG

721  P  G  W  R  H  R  R  K  K  R  P  T  F  S  R  K  P  N  S  M

NotI
2221  TCCAGCAACCATGCCTTTTCCACCAGCGCCACCCGGGAGACCCTGTACgcggccgca

741  S  S  N  H  A  F  S  T  S  A  T  R  E  T  L  Y  A  A  A

Flag      stop  KpnI
      GATTATAAAGATGACGATGACAAATAATAAGGTACC

D  Y  K  D  D  D  D  K  *  *
```

SEQ ID NO.: 167
MalE (1-28) Factor Xa NTR (43-424) FLAG
SalI+1 MalE leader (1-28)

```
   1  gtcgacATGAAAATAAAAACAGGTGCACGCATCCTCGCATTATCCGCATTAACGACGATGATGTTT

1        M  K  I  K  T  G  A  R  I  L  A  L  S  A  L  T  T  M  M  F

Factor Xa +43 NTR
  61  TCCGCCTCGGCTCTCGCCAAAATCATCGAAGCCCGCACCTCGGAATCCGACACGGCAGGG

21  S  A  S  A  L  A  K  I  I  E  A  R  T  S  E  S  D  T  A  G

121  CCCAACAGCGACCTGGACGTGAACACTGACATTTATTCCAAGGTGCTGGTGACTGCTATA

41  P  N  S  D  L  D  V  N  T  D  I  Y  S  K  V  L  V  T  A  I

181  TACCTGGCACTCTTCGTGGTGGGCACTGTGGGCAACTCCGTGACAGCCTTCACTCTAGCG

61  Y  L  A  L  F  V  V  G  T  V  G  N  S  V  T  A  F  T  L  A

241  CGGAAGAAGTCACTGCAGAGCCTGCAGAGCACTGTGCATTACCACCTGGGCAGCCTGGCA

81  R  K  K  S  L  Q  S  L  Q  S  T  V  H  Y  H  L  G  S  L  A

301  CTGTCGGACCTGCTTATCCTTCTGCTGGCCATGCCCGTGGAGCTATACAACTTCATCTGG

101  L  S  D  L  L  I  L  L  L  A  M  P  V  E  L  Y  N  F  I  W

361  GTACACCATCCCTGGGCCTTTGGGGACGCTGGCTGCCGTGGCTACTATTTCCTGCGTGAT

121  V  H  H  P  W  A  F  G  D  A  G  C  R  G  Y  Y  F  L  R  D
```

```
 421  GCCTGCACCTATGCCACAGCCCTCAATGTAGCCAGCCTGAGTGTGGAGCGCTACTTGGCC
 141   A  C  T  Y  A  T  A  L  N  V  A  S  L  S  V  E  R  Y  L  A

481  ATCTGCCATCCCTTCAAGGCCAAGACCCTCATGTCCCGCAGCCGCACCAAGAAATTCATC
 161   I  C  H  P  F  K  A  K  T  L  M  S  R  S  R  T  K  K  F  I

541  AGTGCCATATGGCTAGCTTCGGCGCTGCTGGCTATACCCATGCTTTTCACCATGGGCCTG
 181   S  A  I  W  L  A  S  L  L  A  I  P  M  L  F  T  M  G  L

601  CAGAACCGCAGTGGTGACGGCACGCACCCTGGCGGCCTGGTGTGCACACCCATTGTGGAC
 201   Q  N  R  S  G  D  G  T  H  P  G  G  L  V  C  T  P  I  V  D

661  ACAGCCACTGTCAAGGTCGTCATCCAGGTTAACACCTTCATGTCCTTCCTGTTTCCCATG
 221   T  A  T  V  K  V  V  I  Q  V  N  T  F  M  S  F  L  F  P  M

721  TTGGTCATCTCCATCCTAAACACCGTGATTGCCAACAAACTGACAGTCATGGTGCACCAG
 241   L  V  I  S  I  L  N  T  V  I  A  N  K  L  T  V  M  V  H  Q

781  GCCGCCGAGCAGGGCCGAGTGTGCACCGTGGGCACACACAACGGTTTAGAGCACAGCACG
 261   A  A  E  Q  G  R  V  C  T  V  G  T  H  N  G  L  E  H  S  T

841  TTCAACATGACCATCGAGCCGGGTCGTGTCCAGGCCCTGCGCCACGGAGTCCTCGTCTTA
 281   F  N  M  T  I  E  P  G  R  V  Q  A  L  R  H  G  V  L  V  L

901  CGTGCTGTGGTCATTGCCTTTGTGGTCTGCTGGCTGCCCTACCACGTGCGACGCCTGATG
 301   R  A  V  V  I  A  F  V  V  C  W  L  P  Y  H  V  R  R  L  M

961  TTCTGCTATATCTCGGATGAACAGTGGACTACGTTCCTCTTCGATTTCTACCACTATTTC
 321   F  C  Y  I  S  D  E  Q  W  T  T  F  L  F  D  F  Y  H  Y  F

1021  TACATGCTAACCAACGCTCTCTTCTACGTCAGCTCCGCCATCAATCCCATCCTCTACAAC
 341   Y  M  L  T  N  A  L  F  Y  V  S  S  A  I  N  P  I  L  Y  N

1081  CTGGTCTCCGCCAACTTCCGCCAGGTCTTTCTGTCCACGCTGGCCTGCCTTTGTCCTGGG
 361   L  V  S  A  N  F  R  Q  V  F  L  S  T  L  A  C  L  C  P  G

1141  TGGCGCCACCGCCGAAAGAAGAGGCCAACGTTCTCCAGGAAGCCCAACAGCATGTCCAGC
 381   W  R  H  R  R  K  K  R  P  T  F  S  R  K  P  N  S  M  S  S
                                                         NotI    Flag
1201  AACCATGCCTTTTCCACCAGCGCCACCCGGGAGACCCTGTACgcggccgcaGATTATAAA
 401   N  H  A  F  S  T  S  A  T  R  E  T  L  Y  A  A  A  D  Y  K stop KpnI
      GATGACGATGACAAATAATAAGGTACC

D  D  D  D  K
```

SEQ ID NO.: 169
MalE (1-370) Factor Xa NTR (43-424) TrxA (2-109)
FLAG
SalI+1 MalE (1-370)

```
   1  GTCGACATGAAAATAAAAACAGGTGCACGCATCCTCGCATTATCCGCATTAACGACGATGATGTTT

1   M  K  I  K  T  G  A  R  I  L  A  L  S  A  L  T  T  M  M  F

61  TCCGCCTCGGCTCTCGCCAAAATCGAAGAAGGTAAACTGGTAATCTGGATTAACGGCGAT

21   S  A  S  A  L  A  K  I  E  E  G  K  L  V  I  W  I  N  G  D
```

```
 121 AAAGGCTATAACGGTCTCGCTGAAGTCGGTAAGAAATTCGAGAAAGATACCGGAATTAAA
  41  K  G  Y  N  G  L  A  E  V  G  K  K  F  E  K  D  T  G  I  K

181 GTCACCGTTGAGCATCCGGATAAACTGGAAGAGAAATTCCCACAGGTTGCGGCAACTGGC
  61  V  T  V  E  H  P  D  K  L  E  E  K  F  P  Q  V  A  A  T  G

241 GATGGCCCTGACATTATCTTCTGGGCACACGACCGCTTTGGTGGCTACGCTCAATCTGGC
  81  D  G  P  D  I  I  F  W  A  H  D  R  F  G  G  Y  A  Q  S  G

301 CTGTTGGCTGAAATCACCCCGGACAAAGCGTTCCAGGACAAGCTGTATCCGTTTACCTGG
 101  L  L  A  E  I  T  P  D  K  A  F  Q  D  K  L  Y  P  F  T  W

361 GATGCCGTACGTTACAACGGCAAGCTGATTGCTTACCCGATCGCTGTTGAAGCGTTATCG
 121  D  A  V  R  Y  N  G  K  L  I  A  Y  P  I  A  V  E  A  L  S

421 CTGATTTATAACAAAGATCTGCTGCCGAACCCGCCAAAAACCTGGGAAGAGATCCCGGCG
 141  L  I  Y  N  K  D  L  L  P  N  P  P  K  T  W  E  E  I  P  A

481 CTGGATAAAGAACTGAAAGCGAAAGGTAAGAGCGCGCTGATGTTCAACCTGCAAGAACCG
 161  L  D  K  E  L  K  A  K  G  K  S  A  L  M  F  N  L  Q  E  P

541 TACTTCACCTGGCCGCTGATTGCTGCTGACGGGGGTTATGCGTTCAAGTATGAAAACGGC
 181  Y  F  T  W  P  L  I  A  A  D  G  G  Y  A  F  K  Y  E  N  G

601 AAGTACGACATTAAAGACGTGGGCGTGGATAACGCTGGCGCGAAAGCGGGTCTGACCTTC
 201  K  Y  D  I  K  D  V  G  V  D  N  A  G  A  K  A  G  L  T  F

661 CTGGTTGACCTGATTAAAAACAAACACATGAATGCAGACACCGATTACTCCATCGCAGAA
 221  L  V  D  L  I  K  N  K  H  M  N  A  D  T  D  Y  S  I  A  E

721 GCTGCCTTTAATAAAGGCGAAACAGCGATGACCATCAACGGCCCGTGGGCATGGTCCAAC
 241  A  A  F  N  K  G  E  T  A  M  T  I  N  G  P  W  A  W  S  N

781 ATCGACACCAGCAAAGTGAATTATGGTGTAACGGTACTGCCGACCTTCAAGGGTCAACCA
 261  I  D  T  S  K  V  N  Y  G  V  T  V  L  P  T  F  K  G  Q  P

841 TCCAAACCGTTCGTTGGCGTGCTGAGCGCAGGTATTAACGCCGCCAGTCCGAACAAAGAG
 281  S  K  P  F  V  G  V  L  S  A  G  I  N  A  A  S  P  N  K  E

901 CTGGCGAAAGAGTTCCTCGAAAACTATCTGCTGACTGATGAAGGTCTGGAAGCGGTTAAT
 301  L  A  K  E  F  L  E  N  Y  L  L  T  D  E  G  L  E  A  V  N

961 AAAGACAAACCGCTGGGTGCCGTAGCGCTGAAGTCTTACGAGGAAGAGTTGGCGAAAGAT
 321  K  D  K  P  L  G  A  V  A  L  K  S  Y  E  E  E  L  A  K  D

1021 CCACGTATTGCCGCCACCATGGAAAACGCCCAGAAAGGTGAAATCATGCCGAACATCCCG
 341  P  R  I  A  A  T  M  E  N  A  Q  K  G  E  I  M  P  N  I  P
                                                 Factor Xa +43 NTR
1081 CAGATGTCCGCTTTCTGGTATGCCGTGCTGATCGAAGCCCGCACCTCGGAATCCGACACG
 361  Q  M  S  A     F  W  Y  A  V  L  I  E  A  R  T  S  E  S  D  T 1141 GCAGGGCCCAACAGCGACCTGGACGTGAACACTGACATTTATTCCAAGGTGCTGGTGACT
 381  A  G  P  N  S  D  L  D  V  N  T  D  I  Y  S  K  V  L  V  T 1201 GCTATATACCTGGCACTCTTCGTGGTGGGCACTGTGGGCAACTCCGTGACAGCCTTCACT
 401  A  I  Y  L  A  L  F  V  V  G  T  V  G  N  S  V  T  A  F  T 1261 CTAGCGCGGAAGAAGTCACTGCAGAGCCTGCAGAGCACTGTGCATTACCACCTGGGCAGC
 421  L  A  R  K  K  S  L  Q  S  L  Q  S  T  V  H  Y  H  L  G  S
```

-continued

```
1321 CTGGCACTGTCGGACCTGCTTATCCTTCTGCTGGCCATGCCCGTGGAGCTATACAACTTC
 441   L  A  L  S  D  L  L  I  L  L  L  A  M  P  V  E  L  Y  N  F

1381 ATCTGGGTACACCATCCCTGGGCCTTTGGGGACGCTGGCTGCCGTGGCTACTATTTCCTG
 461   I  W  V  H  H  P  W  A  F  G  D  A  G  C  R  G  Y  Y  F  L

1441 CGTGATGCCTGCACCTATGCCACAGCCCTCAATGTAGCCAGCCTGAGTGTGGAGCGCTAC
 481   R  D  A  C  T  Y  A  T  A  L  N  V  A  S  L  S  V  E  R  Y

1501 TTGGCCATCTGCCATCCCTTCAAGGCCAAGACCCTCATGTCCCGCAGCCGCACCAAGAAA
 501   L  A  I  C  H  P  F  K  A  K  T  L  M  S  R  S  R  T  K  K

1561 TTCATCAGTGCCATATGGCTAGCTTCGGCGCTGCTGGCTATACCCATGCTTTTCACCATG
 521   F  I  S  A  I  W  L  A  S  L  L  A  I  P  M  L  F  T  M

1621 GGCCTGCAGAACCGCAGTGGTGACGGCACGCACCCTGGCGGCCTGGTGTGCACACCCATT
 541   G  L  Q  N  R  S  G  D  G  T  H  P  G  G  L  V  C  T  P  I

1681 GTGGACACAGCCACTGTCAAGGTCGTCATCCAGGTTAACACCTTCATGTCCTTCCTGTTT
 561   V  D  T  A  T  V  K  V  V  I  Q  V  N  T  F  M  S  F  L  F

1741 CCCATGTTGGTCATCTCCATCCTAAACACCGTGATTGCCAACAAACTGACAGTCATGGTG
 581   P  M  L  V  I  S  I  L  N  T  V  I  A  N  K  L  T  V  M  V

1801 CACCAGGCCGCCGAGCAGGGCCGAGTGTGCACCGTGGGCACACACAACGGTTTAGAGCAC
 601   H  Q  A  A  E  Q  G  R  V  C  T  V  G  T  H  N  G  L  E  H

1861 AGCACGTTCAACATGACCATCGAGCCGGGTCGTGTCCAGGCCCTGCGCCACGGAGTCCTC
 621   S  T  F  N  M  T  I  E  P  G  R  V  Q  A  L  R  H  G  V  L

1921 GTCTTACGTGCTGTGGTCATTGCCTTTGTGGTCTGCTGGCTGCCCTACCACGTGCGACGC
 641   V  L  R  A  V  V  I  A  F  V  V  C  W  L  P  Y  H  V  R  R

1981 CTGATGTTCTGCTATATCTCGGATGAACAGTGGACTACGTTCCTCTTCGATTTCTACCAC
 661   L  M  F  C  Y  I  S  D  E  Q  W  T  T  F  L  F  D  F  Y  H

2041 TATTTCTACATGCTAACCAACGCTCTCTTCTACGTCAGCTCCGCCATCAATCCCATCCTC
 681   Y  F  Y  M  L  T  N  A  L  F  Y  V  S  S  A  I  N  P  I  L

2101 TACAACCTGGTCTCCGCCAACTTCCGCCAGGTCTTTCTGTCCACGCTGGCCTGCCTTTGT
 701   Y  N  L  V  S  A  N  F  R  Q  V  F  L  S  T  L  A  C  L  C

2161 CCTGGGTGGCGCCACCGCCGAAAGAAGAGGCCAACGTTCTCCAGGAAGCCCAACAGCATG
 721   P  G  W  R  H  R  R  K  K  R  P  T  F  S  R  K  P  N  S  M
                                  NotI +2 TrxA
2221 TCCAGCAACCATGCCTTTTCCACCAGCGCCACCCGGGAGACCCTGTACgcggccgcaAGC
 741   S  S  N  H  A  F  S  T  S  A  T  R  E  T  L  Y  A  A  A  S 2281 GATAAAATTATTCACCTGACTGACGACAGTTTTGACACGGATGTACTCAAAGCGGACGGG
 761   D  K  I  I  H  L  T  D  D  S  F  D  T  D  V  L  K  A  D  G 2341 GCGATCCTCGTCGATTTCTGGGCAGAGTGGTGCGGTCCGTGCAAAATGATCGCCCCGATT
 781   A  I  L  V  D  F  W  A  E  W  C  G  P  C  K  M  I  A  P  I 2401 CTGGATGAAATCGCTGACGAATATCAGGGCAAACTGACCGTTGCAAAACTGAACATCGAT
 801   L  D  E  I  A  D  E  Y  Q  G  K  L  T  V  A  K  L  N  I  D 2461 CAAAACCCTGGCACTGCGCCGAAATATGGCATCCGTGGTATCCCGACTCTGCTGCTGTTC
 821   Q  N  P  G  T  A  P  K  Y  G  I  R  G  I  P  T  L  L  L  F
```

```
                            -continued
2521  AAAAACGGTGAAGTGGCGGCAACCAAAGTGGGTGCACTGTCTAAAGGTCAGTTGAAAGAG

841  K  N  G  E  V  A  A  T  K  V  G  A  L  S  K  G  Q  L  K  E

NotI +2 Flag        stop
2581  TTCCTCGACGCTAACCTGGCGgcggccgcaGATTATAAAGATGACGATGACAAATAATAA

861  F  L  D  A  N  L  A  A  A  D  Y  K  D  D  D  K  *  *

KpnI
2641  GGTACC
```

SEQ ID NO.: 170
MalE (1-28) Factor Xa NTR (43-424) TrxA (2-109) FLAG
SalI+1 MalE leader (1-28)

```
   1  gtcgacATGAAAATAAAAACAGGTGCACGCATCCTCGCATTATCCGCATTAACGACGATGATGTTT

1  M  K  I  K  T  G  A  R  I  L  A  L  S  A  L  T  T  M  M  F

Factor Xa +43 NTR
  61  TCCGCCTCGGCTCTCGCCAAAATCATCGAAGCCCGCACCTCGGAATCCGACACGGCAGGG

21  S  A  S  A  L  A  K  I  I  E  A  R  T  S  E  S  D  T  A  G

121  CCCAACAGCGACCTGGACGTGAACACTGACATTTATTCCAAGGTGCTGGTGACTGCTATA

41  P  N  S  D  L  D  V  N  T  D  I  Y  S  K  V  L  V  T  A  I

181  TACCTGGCACTCTTCGTGGTGGGCACTGTGGGCAACTCCGTGACAGCCTTCACTCTAGCG

61  Y  L  A  L  F  V  V  G  T  V  G  N  S  V  T  A  F  T  L  A

241  CGGAAGAAGTCACTGCAGAGCCTGCAGAGCACTGTGCATTACCACCTGGGCAGCCTGGCA

81  R  K  K  S  L  Q  S  L  Q  S  T  V  H  Y  H  L  G  S  L  A

301  CTGTCGGACCTGCTTATCCTTCTGCTGGCCATGCCCGTGGAGCTATACAACTTCATCTGG

101  L  S  D  L  L  I  L  L  L  A  M  P  V  E  L  Y  N  F  I  W

361  GTACACCATCCCTGGGCCTTTGGGGACGCTGGCTGCCGTGGCTACTATTTCCTGCGTGAT

121  V  H  H  P  W  A  F  G  D  A  G  C  R  G  Y  Y  F  L  R  D

421  GCCTGCACCTATGCCACAGCCCTCAATGTAGCCAGCCTGAGTGTGGAGCGCTACTTGGCC

141  A  C  T  Y  A  T  A  L  N  V  A  S  L  S  V  E  R  Y  L  A

481  ATCTGCCATCCCTTCAAGGCCAAGACCCTCATGTCCCGCAGCCGCACCAAGAAATTCATC

161  I  C  H  P  F  K  A  K  T  L  M  S  R  S  R  T  K  K  F  I

541  AGTGCCATATGGCTAGCTTCGGCGCTGCTGGCTATACCCATGCTTTTCACCATGGGCCTG

181  S  A  I  W  L  A  S  A  L  L  A  I  P  M  L  F  T  M  G  L

601  CAGAACCGCAGTGGTGACGGCACGCACCCTGGCGGCCTGGTGTGCACACCCATTGTGGAC

201  Q  N  R  S  G  D  G  T  H  P  G  G  L  V  C  T  P  I  V  D

661  ACAGCCACTGTCAAGGTCGTCATCCAGGTTAACACCTTCATGTCCTTCCTGTTTCCCATG

221  T  A  T  V  K  V  V  I  Q  V  N  T  F  M  S  F  L  F  P  M

721  TTGGTCATCTCCATCCTAAACACCGTGATTGCCAACAAACTGACAGTCATGGTGCACCAG

241  L  V  I  S  I  L  N  T  V  I  A  N  K  L  T  V  M  V  H  Q

781  GCCGCCGAGCAGGGCCGAGTGTGCACCGTGGGCACACACAACGGTTTAGAGCACAGCACG

261  A  A  E  Q  G  R  V  C  T  V  G  T  H  N  G  L  E  H  S  T

841  TTCAACATGACCATCGAGCCGGGTCGTGTCCAGGCCCTGCGCCACGGAGTCCTCGTCTTA

281  F  N  M  T  I  E  P  G  R  V  Q  A  L  R  H  G  V  L  V  L

901  CGTGCTGTGGTCATTGCCTTTGTGGTCTGCTGGCTGCCCTACCACGTGCGACGCCTGATG
```

```
 301  R  A  V  V  I  A  F  V  V  C  W  L  P  Y  H  V  R  R  L  M

961  TTCTGCTATATCTCGGATGAACAGTGGACTACGTTCCTCTTCGATTTCTACCACTATTTC

321  F  C  Y  I  S  D  E  Q  W  T  T  F  L  F  D  F  Y  H  Y  F

1021  TACATGCTAACCAACGCTCTCTTCTACGTCAGCTCCGCCATCAATCCCATCCTCTACAAC

341  Y  M  L  T  N  A  L  F  Y  V  S  S  A  I  N  P  I  L  Y  N

1081  CTGGTCTCCGCCAACTTCCGCCAGGTCTTTCTGTCCACGCTGGCCTGCCTTTGTCCTGGG

361  L  V  S  A  N  F  R  Q  V  F  L  S  T  L  A  C  L  C  P  G

1141  TGGCGCCACCGCCGAAAGAAGAGGCCAACGTTCTCCAGGAAGCCCAACAGCATGTCCAGC

381  W  R  H  R  R  K  K  R  P  T  F  S  R  K  P  N  S  M  S  S

NotI +2 TrxA
1201  AACCATGCCTTTTCCACCAGCGCCACCCGGGAGACCCTGTACgcggccgcaAGCGATAAA

401  N  H  A  F  S  T  S  A  T  R  E  T  L  Y  A  A  A  S  D  K

1261  ATTATTCACCTGACTGACGACAGTTTTGACACGGATGTACTCAAAGCGGACGGGGCGATC

421  I  I  H  L  T  D  D  S  F  D  T  D  V  L  K  A  D  G  A  I

1321  CTCGTCGATTTCTGGGCAGAGTGGTGCGGTCCGTGCAAAATGATCGCCCCGATTCTGGAT

441  L  V  D  F  W  A  E  W  C  G  P  C  K  M  I  A  P  I  L  D

1381  GAAATCGCTGACGAATATCAGGGCAAACTGACCGTTGCAAAACTGAACATCGATCAAAAC

461  E  I  A  D  E  Y  Q  G  K  L  T  V  A  K  L  N  I  D  Q  N

1441  CCTGGCACTGCGCCGAAATATGGCATCCGTGGTATCCCGACTCTGCTGCTGTTCAAAAAC

481  P  G  T  A  P  K  Y  G  I  R  G  I  P  T  L  L  L  F  K  N

1501  GGTGAAGTGGCGGCAACCAAAGTGGGTGCACTGTCTAAAGGTCAGTTGAAAGAGTTCCTC

501  G  E  V  A  A  T  K  V  G  A  L  S  K  G  Q  L  K  E  F  L

NotI  Flag stop KpnI
1561  GACGCTAACCTGGCAgcggccgcaGATTATAAAGATGACGATGACAAATAATAAGGTACC

521  D  A  N  L  A  A  A  A  D  Y  K  D  D  D  D  K
```

SEQ ID NO.: 188
Human β2AR GS1a chimeric fusion
SalI+1 B2AR

```
   1  GTCGACATGG GGCAACCCGG GAACGGCAGC GCCTTCTTGC TGGCACCCAA TGGAAGCCAT
  61  GCGCCGGACC ACGACGTCAC GCAGCAAAGG GACGAGGTGT GGGTGGTGGG CATGGGCATC
 121  GTCATGTCTC TCATCGTCCT GGCCATCGTG TTTGGCAATG TGCTGGTCAT CACAGCCATT
 181  GCCAAGTTCG AGCGTCTGCA GACGGTCACC AACTACTTCA TCACTTCACT GGCCTGTGCT
 241  GATCTGGTCA TGGGCCTAGC AGTGGTGCCC TTTGGGGCCG CCCATATTCT TATGAAAATG
 301  TGGACTTTTG GCAACTTCTG GTGCGAGTTT TGGACTTCCA TTGATGTGCT GTGCGTCACG
 361  GCCAGCATTG AGACCCTGTG CGTGATCGCA GTGGATCGCT ACTTTGCCAT TACTTCACCT
 421  TTCAAGTACC AGAGCCTGCT GACCAAGAAT AAGGCCCGGG TGATCATTCT GATGGTGTGG
 481  ATTGTGTCAG GCCTTAYCTC CTTCTTGCCC ATTCAGATGC ACTGGTACAG GGCCACCCAC
 541  CAGGAAGCCA TCAACTGCTA TGCCAATGAG ACCTGCTGTG ACTTCTTCAC GAACCAAGCC
 601  TATGCCATTG CCTCTTCCAT CGTGTCCTTC TACGTTCCCC TGGTGATCAT GGTCTTCGTC
 661  TACTCCAGGG TCTTTCAGGA GGCCAAAAGG CAGCTCCAGA AGATTGACAA ATCTGAGGGC
 721  CGCTTCCATG TCCAGAACCT TAGCCAGGTG GAGCAGGATG GGCGGACGGG GCATGGACTC
```

```
-continued
 781   CGCAGATCTT CCAAGTTCTG CTTGAAGGAG CACAAAGCCC TCAAGACGTT AGGCATCATC

841   ATGGGCACTT TCACCCTCTG CTGGCTGCCC TTCTTCATCG TTAACATTGT GCATGTGATC

901   CAGGATAACC TCATCCGTAA GGAAGTTTAC ATCCTCCTAA ATTGGATAGG CTATGTCAAT

961   TCTGGTTTCA ATCCCCTTAT CTACTGCCGG AGCCCAGATT TCAGGATTGC CTTCCAGGAG

1021   CTTCTGTGCC TGCGCAGGTC TTCTTTGAAG GCCTATGGCA ATGGCTACTC CAGCAACGGC

1081   AACACAGGGG AGCAGAGTGG ATATCACGTG GAACAGGAGA AGAAAATAA ACTGCTGTGT

1141   GAAGACCTCC CAGGCACGGA AGACTTTGTG GGCCATCAAG GTACTGTGCC TAGCGATAAC
                                                           Last B2AR Linker sequence
1201   ATTGATTCAC AAGGGAGGAA TTGTAGTACA AATGACTCAC TGCTAGAGCG TGGCCAGACG
              PstI XhoI +2 GSI alpha
1261   GTCACCAACC TGCAGCTCGA GGGCTGCCTC GGGAACAGTA AGACCGAGGA CCAGCGCAAC

1321   GAGGAGAAGG CGCAGCGTGA GGCCAACAAA AAGATCGAGA AGCAGCTGCA GAAGGACAAG

1381   CAGGTCTACC GGGCCACGCA CCGCCTGCTG CTGCTGGGTG CTGGAGAATC TGGTAAAAGC

1441   ACCATTGTGA AGCAGATGAG GATCCTGCAT GTTAATGGGT TTAATGGAGA CAGTGAGAAG

1501   GCAACCAAAG TGCAGGACAT CAAAAACAAC CTGAAAGAGG CGATTGAAAC CATTGTGGCC

1561   GCCATGAGCA ACCTGGTGCC CCCCGTGGAG CTGGCCAACC CCGAGAACCA GTTCAGAGTG

1621   GACTACATCC TGAGTGTGAT GAACGTGCCT GACTTTGACT TCCCTCCCGA ATTCTATGAG

1681   CATGCCAAGG CTCTGTGGGA GGATGAAGGA GTGCGTGCCT GCTACGAACG CTCCAACGAG

1741   TACCAGCTGA TTGACTGTGC CCAGTACTTC CTGGACAAGA TCGACGTGAT CAAGCAGGCT

1801   GACTATGTGC CGAGCGATCA GGACCTGCTT CGCTGCCGTG TCCTGACTTC TGGAATCTTT

1861   GAGACCAAGT TCCAGGTGGA CAAAGTCAAC TTCCACATGT TTGACGTGGG TGGCCAGCGC

1921   GATGAACGCC GCAAGTGGAT CCAGTGCTTC AACGATGTGA CTGCCATCAT CTTCGTGGTG

1981   GCCAGCAGCA GCTACAACAT GGTCATCCGG GAGGACAACC AGACCAACCG CCTGCAGGAG

2041   GCTCTGAACC TCTTCAAGAG CATCTGGAAC AACAGATGGC TGCGCACCAT CTCTGTGATC

2101   CTGTTCCTCA ACAAGCAAGA TCTGCTCGCT GAGAAAGTCC TTGCTGGGAA ATCGAAGATT

2161   GAGGACTACT TTCCAGAATT TGCTCGCTAC ACTACTCCTG AGGATGCTAC TCCCGAGCCC

2221   GGAGAGGACC CACGCGTGAC CCGGGCCAAG TACTTCATTC GAGATGAGTT TCTGAGGATC

2281   AGCACTGCCA GTGGAGATGG GCGTCACTAC TGCTACCCTC ATTTCACCTG CGCTGTGGAC

2341   ACTGAGAACA TCCGCCGTGT GTTCAACGAC TGCCGTGACA TCATTCAGCG CATGCACCTT
                         ClaI Stop XbaI Stem-loop
2401   CGTCAGTACG AGCTGCTCAT CGATTAATAA TCTAGAGGAT CCCCGCGCCC TCATCCGAAA

2461   GGGCG
```

SEQ ID NO.: 190
Human β2AR stop GS1a transcriptional fusion
PstI+1 β2AR

```
   1   GTCGACATGG GGCAACCCGG GAACGGCAGC GCCTTCTTGC TGGCACCCAA TGGAAGCCAT

61   GCGCCGGACC ACGACGTCAC GCAGCAAAGG GACGAGGTGT GGGTGGTGGG CATGGGCATC

121   GTCATGTCTC TCATCGTCCT GGCCATCGTG TTTGGCAATG TGCTGGTCAT CACAGCCATT

181   GCCAAGTTCG AGCGTCTGCA GACGGTCACC AACTACTTCA TCACTTCACT GGCCTGTGCT

241   GATCTGGTCA TGGGCCTAGC AGTGGTGCCC TTTGGGGCCG CCCATATTCT TATGAAAATG

301   TGGACTTTTG GCAACTTCTG GTGCGAGTTT TGGACTTCCA TTGATGTGCT GTGCGTCACG
```

```
 361 GCCAGCATTG AGACCCTGTG CGTGATCGCA GTGGATCGCT ACTTTGCCAT TACTTCACCT

421 TTCAAGTACC AGAGCCTGCT GACCAAGAAT AAGGCCCGGG TGATCATTCT GATGGTGTGG

481 ATTGTGTCAG GCCTTAYCTC CTTCTTGCCC ATTCAGATGC ACTGGTACAG GGCCACCCAC

541 CAGGAAGCCA TCAACTGCTA TGCCAATGAG ACCTGCTGTG ACTTCTTCAC GAACCAAGCC

601 TATGCCATTG CCTCTTCCAT CGTGTCCTTC TACGTTCCCC TGGTGATCAT GGTCTTCGTC

661 TACTCCAGGG TCTTTCAGGA GGCCAAAAGG CAGCTCCAGA AGATTGACAA ATCTGAGGGC

721 CGCTTCCATG TCCAGAACCT TAGCCAGGTG GAGCAGGATG GGCGGACGGG GCATGGACTC

781 CGCAGATCTT CCAAGTTCTG CTTGAAGGAG CACAAAGCCC TCAAGACGTT AGGCATCATC

841 ATGGGCACTT TCACCCTCTG CTGGCTGCCC TTCTTCATCG TTAACATTGT GCATGTGATC

901 CAGGATAACC TCATCCGTAA GGAAGTTTAC ATCCTCCTAA ATTGGATAGG CTATGTCAAT

961 TCTGGTTTCA ATCCCCTTAT CTACTGCCGG AGCCCAGATT TCAGGATTGC CTTCCAGGAG

1021 CTTCTGTGCC TGCGCAGGTC TTCTTTGAAG GCCTATGGCA ATGGCTACTC CAGCAACGGC

1081 AACACAGGGG AGCAGAGTGG ATATCACGTG GAACAGGAGA AGAAAATAA ACTGCTGTGT

1141 GAAGACCTCC CAGGCACGGA AGACTTTGTG GGCCATCAAG GTACTGTGCC TAGCGATAAC
                                                      Last B2AR Linker sequence
1201 ATTGATTCAC AAGGGAGGAA TTGTAGTACA AATGACTCAC TGCTAGAGCG TGGCCAGACG PstI StopSD XhoI +2 GS1 alpha
1261 GTCACCAACC TGCAGTAATA ATCAAGGAGG CCCTCGAGAT GGGCTGCCTC GGGAACAGTA

1321 AGACCGAGGA CCAGCGCAAC GAGGAGAAGG CGCAGCGTGA GGCCAACAAA AGATCGAGA

1381 AGCAGCTGCA GAAGGACAAG CAGGTCTACC GGGCCACGCA CCGCCTGCTG CTGCTGGGTG

1441 CTGGAGAATC TGGTAAAAGC ACCATTGTGA AGCAGATGAG GATCCTGCAT GTTAATGGGT

1501 TTAATGGAGA CAGTGAGAAG GCAACCAAAG TGCAGGACAT CAAAAACAAC CTGAAAGAGG

1561 CGATTGAAAC CATTGTGGCC GCCATGAGCA ACCTGGTGCC CCCCGTGGAG CTGGCCAACC

1621 CCGAGAACCA GTTCAGAGTG GACTACATCC TGAGTGTGAT GAACGTGCCT GACTTTGACT

1681 TCCCTCCCGA ATTCTATGAG CATGCCAAGG CTCTGTGGGA GGATGAAGGA GTGCGTGCCT

1741 GCTACGAACG CTCCAACGAG TACCAGCTGA TTGACTGTGC CCAGTACTTC CTGGACAAGA

1801 TCGACGTGAT CAAGCAGGCT GACTATGTGC CGAGCGATCA GGACCTGCTT CGCTGCCGTG

1861 TCCTGACTTC TGGAATCTTT GAGACCAAGT TCCAGGTGGA CAAAGTCAAC TTCCACATGT

1921 TTGACGTGGG TGGCCAGCGC GATGAACGCC GCAAGTGGAT CCAGTGCTTC AACGATGTGA

1981 CTGCCATCAT CTTCGTGGTG GCCAGCAGCA GCTACAACAT GGTCATCCGG GAGGACAACC

2041 AGACCAACCG CCTGCAGGAG GCTCTGAACC TCTTCAAGAG CATCTGGAAC AACAGATGGC

2101 TGCGCACCAT CTCTGTGATC CTGTTCCTCA ACAAGCAAGA TCTGCTCGCT GAGAAAGTCC

2161 TTGCTGGGAA ATCGAAGATT GAGGACTACT TCCAGAATT TGCTCGCTAC ACTACTCCTG

2221 AGGATGCTAC TCCCGAGCCC GGAGAGGACC CACGCGTGAC CCGGGCCAAG TACTTCATTC

2281 GAGATGAGTT TCTGAGGATC AGCACTGCCA GTGGAGATGG GCGTCACTAC TGCTACCCTC

2341 ATTTCACCTG CGCTGTGGAC ACTGAGAACA TCCGCCGTGT GTTCAACGAC TGCCGTGACA
                                Clal Stop Xbal
2401 TCATTCAGCG CATGCACCTT CGTCAGTACG AGCTGCTCAT CGATTAATAA TCTAGAGGAT Stem-loop
2461 CCCCGCGCCC TCATCCGAAA GGGCG
```

SEQ ID NO.: 192
Human GS1a
XhoI

```
   1  CTCGAGATGGGCTGCCTCGGGAACAGTAAGACCGAGGACCAGCGCAACGAGGAGAAGGCGCAGCGT

1  M  G  C  L  G  N  S  K  T  E  D  Q  R  N  E  E  K  A  Q  R

61  GAGGCCAACAAAAAGATCGAGAAGCAGCTGCAGAAGGACAAGCAGGTCTACCGGGCCACG

21  E  A  N  K  K  I  E  K  Q  L  Q  K  D  K  Q  V  Y  R  A  T

121  CACCGCCTGCTGCTGCTGGGTGCTGGAGAATCTGGTAAAAGCACCATTGTGAAGCAGATG

41  H  R  L  L  L  L  G  A  G  E  S  G  K  S  T  I  V  K  Q  M

181  AGGATCCTGCATGTTAATGGGTTTAATGGAGACAGTGAGAAGGCAACCAAAGTGCAGGAC

61  R  I  L  H  V  N  G  F  N  G  D  S  E  K  A  T  K  V  Q  D

241  ATCAAAAACAACCTGAAAGAGGCGATTGAAACCATTGTGGCCGCCATGAGCAACCTGGTG

81  I  K  N  N  L  K  E  A  I  E  T  I  V  A  A  M  S  N  L  V

301  CCCCCCGTGGAGCTGGCCAACCCCGAGAACCAGTTCAGAGTGGACTACATCCTGAGTGTG

101  P  P  V  E  L  A  N  P  E  N  Q  F  R  V  D  Y  I  L  S  V

361  ATGAACGTGCCTGACTTTGACTTCCCTCCCGAATTCTATGAGCATGCCAAGGCTCTGTGG

121  M  N  V  P  D  F  D  F  P  P  E  F  Y  E  H  A  K  A  L  W

421  GAGGATGAAGGAGTGCGTGCCTGCTACGAACGCTCCAACGAGTACCAGCTGATTGACTGT

141  E  D  E  G  V  R  A  C  Y  E  R  S  N  E  Y  Q  L  I  D  C

481  GCCCAGTACTTCCTGGACAAGATCGACGTGATCAAGCAGGCTGACTATGTGCCGAGCGAT

161  A  Q  Y  F  L  D  K  I  D  V  I  K  Q  A  D  Y  V  P  S  D

541  CAGGACCTGCTTCGCTGCCGTGTCCTGACTTCTGGAATCTTTGAGACCAAGTTCCAGGTG

181  Q  D  L  L  R  C  R  V  L  T  S  G  I  F  E  T  K  F  Q  V

601  GACAAAGTCAACTTCCACATGTTTGACGTGGGTGGCCAGCGCGATGAACGCCGCAAGTGG

201  D  K  V  N  F  H  M  F  D  V  G  G  Q  R  D  E  R  R  K  W

661  ATCCAGTGCTTCAACGATGTGACTGCCATCATCTTCGTGGTGGCCAGCAGCAGCTACAAC

221  I  Q  C  F  N  D  V  T  A  I  I  F  V  V  A  S  S  S  Y  N

721  ATGGTCATCCGGGAGGACAACCAGACCAACCGCCTGCAGGAGGCTCTGAACCTCTTCAAG

241  M  V  I  R  E  D  N  Q  T  N  R  L  Q  E  A  L  N  L  F  K

781  AGCATCTGGAACAACAGATGGCTGCGCACCATCTCTGTGATCCTGTTCCTCAACAAGCAA

261  S  I  W  N  N  R  W  L  R  T  I  S  V  I  L  F  L  N  K  Q

841  GATCTGCTCGCTGAGAAAGTCCTTGCTGGGAAATCGAAGATTGAGGACTACTTTCCAGAA

281  D  L  L  A  E  K  V  L  A  G  K  S  K  I  E  D  Y  F  P  E

901  TTTGCTCGCTACACTACTCCTGAGGATGCTACTCCCGAGCCCGGAGAGGACCCACGCGTG

301  F  A  R  Y  T  T  P  E  D  A  T  P  E  P  G  E  D  P  R  V

961  ACCCGGGCCAAGTACTTCATTCGAGATGAGTTTCTGAGGATCAGCACTGCCAGTGGAGAT

321  T  R  A  K  Y  F  I  R  D  E  F  L  R  I  S  T  A  S  G  D

1021  GGGCGTCACTACTGCTACCCTCATTTCACCTGCGCTGTGGACACTGAGAACATCCGCCGT

341  G  R  H  Y  C  Y  P  H  F  T  C  A  V  D  T  E  N  I  R  R
```

```
1081  GTGTTCAACGACTGCCGTGACATCATTCAGCGCATGCACCTTCGTCAGTACGAGCTGCTC

361       V F N D C R D I I Q R M H L R Q Y E L L

ClaI
           ATCGAT
```

SEQ ID NO.: 193

Human GS2a

```
XhoI
1        CTCGAGATGGGCTGCCTCGGGAACAGTAAGACCGAGGAC
         CAGCGCAACGAGGAGAAGGCGCAGCGT

1         M G C L G N S K T E D Q R N E E K A Q R

61       GAGGCCAACAAAAAGATCGAGAAGCAGCTGCAGAAGGAC
         AAGCAGGTCTACCGGGCCACG

21         E A N K K I E K Q L Q K D Q V Y R A T

121      CACCGCCTGCTGCTGCTGGGTGCTGGAGAATCTGGTAAA
         AGCACCATTGTGAAGCAGATG

41         H R L L L L G A G E S G K S T I V K Q M

181      AGGATCCTGCATGTTAATGGGTTTAATGGAGAGGGCGGC
         GAAGAGGACCCGCAGGCTGCA

61         R I L H V N G F N G E G G E E D P Q A A

241      AGGAGCAACAGCGATGGTGAGAAGGCAACCAAAGTGCAG
         GACATCAAAAACAACCTGAAA

81         R S N S D G E K A T K V Q D I K N N L K

301      GAGGCGATTGAAACCATTGTGGCCGCCATGAGCAACCTG
         GTGCCCCCCGTGGAGCTGGCC

101         E A I E T I V A A M S N L V P P V E L A

361      AACCCCGAGAACCAGTTCAGAGTGGACTACATCCTGAGT
         GTGATGAACGTGCCTGACTTT

121         N P E N Q F R V D Y I L S V M N V P D F

421      GACTTCCCTCCCGAATTCTATGAGCATGCCAAGGCTCTG
         TGGGAGGATGAAGGAGTGCGT

141         D F P P E F Y E H A K A L W E D E G V R

481      GCCTGCTACGAACGCTCCAACGAGTACCAGCTGATTGAC
         TGTGCCCAGTACTTCCTGGAC

161         A C Y E R S N E Y Q L I D C A Q Y F L D

541      AAGATCGACGTGATCAAGCAGGCTGACTATGTGCCGAGC
         GATCAGGACCTGCTTCGCTGC

181         K I D V I K Q A D Y V P S D Q D L L R C

601      CGTGTCCTGACTTCTGGAATCTTTGAGACCAAGTTCCAG
         GTGGACAAAGTCAACTTCCAC

201         R V L T S G I F E T K F Q V D K V N F H

661      ATGTTTGACGTGGGTGGCCAGCGCGATGAACGCCGCAAG
         TGGATCCAGTGCTTCAACGAT

221         M F D V G G Q R D E R R K W I Q C F N D

721      GTGACTGCCATCATCTTCGTGGTGGCCAGCAGCAGCTAC
         AACATGGTCATCCGGGAGGAC

241         V T A I I F V V A S S S Y N M V I R E D

781      AACCAGACCAACCGCCTGCAGGAGGCTCTGAACCTCTTC
         AAGAGCATCTGGAACAACAGA

261         N Q T N R L Q E A L N L F K S I W N N R

841      TGGCTGCGCACCATCTCTGTGATCCTGTTCCTCAACAAG
         CAAGATCTGCTCGCTGAGAAA

281         W L R T I S V I L F L N K Q D L L A E K

901      GTCCTTGCTGGGAAATCGAAGATTGAGGACTACTTTCCA
         GAATTTGCTCGCTACACTACT

301         V L A G K S K I E D Y F P E F A R Y T T

961      CCTGAGGATGCTACTCCCGAGCCCGGAGAGGACCCACGC
         GTGACCCGGGCCAAGTACTTC

321         P E D A T P E P G E D P R V T R A K Y F

1021     ATTCGAGATGAGTTTCTGAGGATCAGCACTGCCAGTGGA
         GATGGGCGTCACTACTGCTAC

341         I R D E F L R I S T A S G D G R H Y C Y

1081     CCTCATTTCACCTGCGCTGTGGACACTGAGAACATCCGC
         CGTGTGTTCAACGACTGCCGT

361         P H F T C A V D T E N I R R V F N D C R

1141     GACATCATTCAGCGCATGCACCTTCGTCAGTACGAGCTG
            ClaI
            CTCATCGAT

381         D I I Q R M H L R Q Y E L L
```

SEQ ID NO.: 194

Human Gaq

```
XhoI
   1   CTCGAGATGACTCTGGAGTCCATCATGGCGTGCTGCCTGAGCGAGGAGGCCAAGGA
       AGCCCGGCGG
   1       M T L E S I M A C C L S E E A K E A R R

61   ATCAACGACGAGATCGAGCGGCAGCTCCGCAGGGACAAGCGGGACGCCCGCCGGG
       AGCTC
  21       I N D E I E R Q L R R D K R D A R R E L

121   AAGCTGCTGCTGCTCGGGACAGGAGAGAGTGGCAAGAGTACGTTTATCAAGCAGAT
       GAGA
  41       K L L L L G T G E S G K S T F I K Q M R
```

```
181 ATCATCCATGGGTCAGGATACTCTGATGAAGATAAAAGGGGCTTCACCAAGCTGGT
    GTAT
 61        I  I  H  G  S  G  Y  S  D  E  D  K  R  G  F  T  K  L  V  Y

241 CAGAACATCTTCACGGCCATGCAGGCCATGATCAGAGCCATGGACACACTCAAGAT
    CCCA
 81        Q  N  I  F  T  A  M  Q  A  M  I  R  A  M  D  T  L  K  I  P

301 TACAAGTATGAGCACAATAAGGCTCATGCACAATTAGTTCGAGAAGTTGATGTGGA
    GAAG
101        Y  K  Y  E  H  N  K  A  H  A  Q  L  V  R  E  V  D  V  E  K

361 GTGTCTGCTTTTGAGAATCCATATGTAGATGCAATAAAGAGTTTATGGAATGATCCT
    GGA
121        V  S  A  F  E  N  P  Y  V  D  A  I  K  S  L  W  N  D  P  G

421 ATCCAGGAATGCTATGATAGACGACGAGAATATCAATTATCTGACTCTACCAAATAC
    TAT
141        I  Q  E  C  Y  D  R  R  R  E  Y  Q  L  S  D  S  T  K  Y  Y

481 CTTAATGACTTGGACCGCGTAGCTGACCCTGCCTACCTGCCTACGCAACAAGATGTG
    CTT
161        L  N  D  L  D  R  V  A  D  P  A  Y  L  P  T  Q  Q  D  V  L

541 AGAGTTCGAGTCCCCACCACAGGGATCATCGAATACCCCTTTGACTTACAAAGTGTC
    ATT
181        R  V  R  V  P  T  T  G  I  I  E  Y  P  F  D  L  Q  S  V  I

601 TTCAGAATGGTCGATGTAGGGGGCCAAAGGTCAGAGAGAAGAAAATGGATACACTG
    CTTT
201        F  R  M  V  D  V  G  G  Q  R  S  E  R  R  K  W  I  H  C  F

661 GAAAATGTCACCTCTATCATGTTTCTAGTAGCGCTTAGTGAATATGATCAAGTTCTC
    GTG
221        E  N  V  T  S  I  M  F  L  V  A  L  S  E  Y  D  Q  V  L  V

721 GAGTCAGACAATGAGAACCGAATGGAGGAAAGCAAGGCTCTCTTTAGAACAATTAT
    CACA
241        E  S  D  N  E  N  R  M  E  E  S  K  A  L  F  R  T  I  I  T

781 TACCCCTGGTTCCAGAACTCCTCGGTTATTCTGTTCTTAAACAAGAAAGATCTTCTAG
    AG
261        Y  P  W  F  Q  N  S  S  V  I  L  F  L  N  K  K  D  L  L  E

841 GAGAAAATCATGTATTCCCATCTAGTCGACTACTTCCCAGAATATGATGGACCCCAG
    AGA
281        E  K  I  M  Y  S  H  L  V  D  Y  F  P  E  Y  D  G  P  Q  R

901 GATGCCCAGGCAGCCCGAGAATTCATTCTGAAGATGTTCGTGGACCTGAACCCAGA
    CAGT
301        D  A  Q  A  A  R  E  F  I  L  K  M  F  V  D  L  N  P  D  S

961 GACAAAATTATCTACTCCCACTTCACGTGCGCCACAGACACCGAGAATATCCGCTTT
    GTC
321        D  K  I  I  Y  S  H  F  T  C  A  T  D  T  E  N  I  R  F  V

ClaI
1021 TTTGCTGCCGTCAAGGACACCATCCTCCAGTTGAACCTGAAGGAGTACAATCTGGTC
     ATCGAT
341        F  A  A  V  K  D  T  I  L  Q  L  N  L  K  E  Y  N  L  V
```

SEQ ID NO.: 195
Human Giα
XhoI

SEQ ID NO.: 194

Human Gαq

XhoI

```
  1    CTCGAGATGGGCTGCACCGTGAGCGCCGAGGACAAGGCG
       GCGGCCGAGCGCTCTAAGATGATCGAC

1    M  G  C  T  V  S  A  E  D  K  A  A  A  E  R  S  K  M  I  D

61    AAGAACCTGCGGGAGGACGGAGAGAAGGCGGCGCGGGAG
       GTGAAGTTGCTGCTGTTGGGT

21    K  N  L  R  E  D  G  E  K  A  A  R  E  V  K  L  L  L  L  G

121    GCTGGGGAGTCAGGGAAGAGCACCATCGTCAAGCAGATG
       AAGATCATCCACGAGGATGGC

41    A  G  E  S  G  K  S  T  I  V  K  Q  M  K  I  I  H  E  D  G

181    TACTCCGAGGAGGAATGCCGGCAGTACCGGGCGGTTGTC
       TACAGCAACACCATCCAGTCC

61    Y  S  E  E  E  C  R  Q  Y  R  A  V  V  Y  S  N  T  I  Q  S

241    ATCATGGCCATTGTCAAAGCCATGGGAAACCTGCAGATC
       GACTTTGCCGACCCCTCCAGA

81    I  M  A  I  V  K  A  M  G  N  L  Q  I  D  F  A  D  P  S  R
```

```
301   GCGGACGACGCCAGGCAGCTATTTGCACTGTCCTGCACC
      GCCGAGGAGCAAGGCGTGCTC

101   A D D A R Q L F A L S C T A E E Q G V L

361   CCTGATGACCTGTCCGGCGTCATCCGGAGGCTCTGGGCT
      GACCATGGTGTGCAGGCCTGC

121   P D D L S G V I R R L W A D H G V Q A C

421   TTTGGCCGCTCAAGGGAATACCAGCTCAACGACTCAGCT
      GCCTACTACCTGAACGACCTG

141   F G R S R E Y Q L N D S A A Y Y L N D L

481   GAGCGTATTGCACAGAGTGACTACATCCCCACACAGCAA
      GATGTGCTACGGACCCGCGTA

161   E R I A Q S D Y I P T Q Q D V L R T R V

541   AAGACCACGGGGATCGTGGAGACACACTTCACCTTCAAG
      GACCTACACTTCAAGATGTTT

181   K T T G I V E T H F T F K D L H F K M F

601   GATGTGGGTGGTCAGCGGTCTGAGCGGAAGAAGTGGATC
      CACTGCTTTGAGGGCGTCACA

201   D V G G Q R S E R K K W I H C F E G V T

661   GCCATCATCTTCTGCGTAGCCTTGAGCGCCTATGACTTG
      GTGCTAGCTGAGGACGAGGAG

221   A I I F C V A L S A Y D L V L A E D E E

721   ATGAACCGCATGCATGAGAGCATGAAGCTATTCGATAGC
      ATCTGCAACAACAAGTGGTTC

241   M N R M H E S M K L F D S I C N N K W F

781   ACAGACACGTCCATCATCCTCTTCCTCAACAAGAAGGAC
      CTGTTTGAGGAGAAGATCACA

261   T D T S I I L F L N K K D L F E E K I T

841   CACAGTCCCCTGACCATCTGCTTCCCTGAGTACACAGGG
      GCCAACAAATATGATGAGGCA

281   H S P L T I C F P E Y T G A N K Y D E A

901   GCCAGCTACATCCAGAGTAAGTTTGAGGACCTGAATAAG
      CGCAAAGACACCAAGGAGATC

301   A S Y I Q S K F E D L N K R K D T K E I

961   TACACGCACTTCACGTGCGCCACCGACACCAAGAACGTG
      CAGTTCGTGTTTGACGCCGTC

321   Y T H F T C A T D T K N V Q F V F D A V

1021  ACCGATGTCATCATCAAGAACAACCTGAAGGACTGCGGC
      CTCTTCATGCAT

341   T D V I I K N N L K D C G L F

ClaI
SEQ ID NO.: 196
Human Ga 12/13
XhoI

SEQ ID NO.: 196

Human Ga 12/13

XhoI
1     CTCGAGATGTCCGGGGTGGTGCGGACCCTCAGCCGCTGC
      CTGCTGCCGGCCGAGGCCGGCGGGGCC

1     M S G V V R T L S R C L L P A E A G G A

61    CGCGAGCGCAGGGCGGGCAGCGGCGCGCGACGCGGAG
      CGCGAGGCCCGGAGGCGTAGC

21    R E R R A G S G A R D A E R E A R R S

121   CGCGACATCGACGCGCTGCTGGCCCGCGAGCGGCGCGCG
      GTCCGGCGCCTGGTGAAGATC

41    R D I D A L L A R E R R A V R R L V K I

181   CTGCTGCTGGGCGCGGGCGAGAGCGGCAAGTCCACGTTC
      CTCAAGCAGATGCGCATCATC

61    L L L G A G E S G K S T F L K Q M R I I

241   CACGGCCGCGAGTTCGACCAGAAGGCGCTGCTGGAGTTC
      CGCGACACCATCTTCGACAAC

81    H G R E F D Q K A L L E F R D T I F D N

301   ATCCTCAAGGGCTCAAGGGTTCTTGTTGATGCACGAGAT
      AAGCTTGGCATTCCTTGGCAG

101   I L K G S R V L V D A R D K L G I P W Q

361   TATTCTGAAAATGAGAAGCATGGGATGTTCCTGATGGCC
      TTCGAGAACAAGGCGGGGCTG

121   Y S E N E K H G M F L M A F E N K A G L

421   CCTGTGGAGCCGGCCACCTTCCAGCTGTACGTCCCGGCC
      CTGAGCGCACTCTGGAGGGAT

141   P V E P A T F Q L Y V P A L S A L W R D

481   TCTGGCATCAGGGAGGCTTTCAGCCGGAGAAGCGAGTTT
      CAGCTGGGGAGTCGGTGAAG

161   S G I R E A F S R R S E F Q L G E S V K

541   TACTTCCTGGACAACTTGGACCGGATCGGCCAGCTGAAT
      TACTTTCCTAGTAAGCAAGAT

181   Y F L D N L D R I G Q L N Y F P S K Q D

601   ATCCTGCTGGCTAGGAAAGCCACCAAGGGAATTGTGGAG
      CATGACTTCGTTATTAAGAAG

201   I L L A R K A T K G I V E H D F V K K

661   ATCCCCTTTAAGATGGTGGATGTGGGCGGCCAGCGGTCC
      CAGCGCCAGAAGTGGTTCCAG

221   I P F K M V D V G G Q R S Q R Q K W F Q

721   TGCTTCGACGGGATCACGTCCATCCTGTTCATGGTCTCC
      TCCAGCGAGTACGACCAGGTC

241   C F D G I T S I L F M V S S S E Y D Q V

781   CTCATGGAGGACAGGCGCACCAACCGGCTGGTGGAGTCC
      ATGAACATCTTCGAGACCATC

261   L M E D R R T N R L V E S M N I F E T I

841   GTCAACAACAAGCTCTTCTTCAACGTCTCCATCATTCTC
      TTCCTCAACAAGATGGACCTC

281   V N N K L F F N V S I I L F L N K M D L

901   CTGGTGGAGAAGGTGAAGACCGTGAGCATCAAGAAGCAC
      TTCCCGGACTTCAGGGGCGAC

301   L V E K V K T V S I K K H F P D F R G D

961   CCGCACCAGCTGGAGGACGTCCAGCGCTACCTGGTCCAG
      TGCTTCGACAGGAAGAGACGG

321   P H Q L E D V Q R Y L V Q C F D R K R R
```

```
1021 AACCGCAGCAAGCCACTCTTCCACCACTTCACCACCGCC
     ATCGACACCGAGAACGTCCGC

341  N R S K P L F H H F T T A I D T E N V R

1081 TTCGTGTTCCATGCTGTGAAAGACACCATCCTGCAGGAG
     AACCTGAAGGACATCATGCTG
```

```
361  F V F H A V K D T I L Q E N L K D I M L
                    ClaI
1141 CAGATCGAT

381  Q
```

SEQ ID NO.: 205
Human β2AR-ToxR (5-141) chimera stop GS1□-ToxR (5-141) chimera transcriptional fusion
SalI+1 B2AR

```
SEQ ID NO.: 205
Human  β2AR-ToxR (5-141)chimera stop GS1□-ToxR (5-141)
transcriptional fusion
SalI + B2AR
   1 GTCGACATGG GGCAACCCGG GAACGGCAGC GCCTTCTTGC TGGCACCCAA TGGAAGCCAT

61 GCGCCGGACC ACGACGTCAC GCAGCAAAGG GACGAGGTGT GGGTGGTGGG CATGGGCATC

121 GTCATGTCTC TCATCGTCCT GGCCATCGTG TTTGGCAATG TGCTGGTCAT CACAGCCATT

181 GCCAAGTTCG AGCGTCTGCA GACGGTCACC AACTACTTCA TCACTTCACT GGCCTGTGCT

241 GATCTGGTCA TGGGCCTAGC AGTGGTGCCC TTTGGGGCCG CCCATATTCT TATGAAAATG

301 TGGACTTTTG GCAACTTCTG GTGCGAGTTT TGGACTTCCA TTGATGTGCT GTGCGTCACG

361 GCCAGCATTG AGACCCTGTG CGTGATCGCA GTGGATCGCT ACTTTGCCAT TACTTCACCT

421 TTCAAGTACC AGAGCCTGCT GACCAAGAAT AAGGCCCGGG TGATCATTCT GATGGTGTGG

481 ATTGTGTCAG GCCTTAYCTC CTTCTTGCCC ATTCAGATGC ACTGGTACAG GGCCACCCAC

541 CAGGAAGCCA TCAACTGCTA TGCCAATGAG ACCTGCTGTG ACTTCTTCAC GAACCAAGCC

601 TATGCCATTG CCTCTTCCAT CGTGTCCTTC TACGTTCCCC TGGTGATCAT GGTCTTCGTC

661 TACTCCAGGG TCTTTCAGGA GGCCAAAAGG CAGCTCCAGA AGATTGACAA ATCTGAGGGC

721 CGCTTCCATG TCCAGAACCT TAGCCAGGTG GAGCAGGATG GGCGGACGGG CATGGACTC

781 CGCAGATCTT CCAAGTTCTG CTTGAAGGAG CACAAAGCCC TCAAGACGTT AGGCATCATC

841 ATGGGCACTT TCACCCTCTG CTGGCTGCCC TTCTTCATCG TTAACATTGT GCATGTGATC

901 CAGGATAACC TCATCCGTAA GGAAGTTTAC ATCCTCCTAA ATTGGATAGG CTATGTCAAT

961 TCTGGTTTCA ATCCCCTTAT CTACTGCCGG AGCCCAGATT TCAGGATTGC CTTCCAGGAG

1021 CTTCTGTGCC TGCGCAGGTC TTCTTTGAAG GCCTATGGCA ATGGCTACTC CAGCAACGGC

1081 AACACAGGGG AGCAGAGTGG ATATCACGTG AACAGGAGA AAGAAAATAA ACTGCTGTGT

1141 GAAGACCTCC CAGGCACGGA AGACTTTGTG GGCCATCAAG GTACTGTGCC TAGCGATAAC
                                    last B2AR linker sequence
1201 ATTGATTCAC AAGGGAGGAA TTGTAGTACA AATGACTCAC TGCTAGAGCG TGGCCAGACG
            PstI toxR (5-141)
1261 GTCACCAAC CTGCAGGGACA CAACTCAAAA GAGATATCGA TGAGTCATAT TGGTACTAAA

1321 TTCATTCTT GCTGAAAAATT TACCTTCGAT CCCCTAAGCA ATACTCTGAT TGACAAAGAA

1381 GATAGTGAA GAGATCATTCG ATTAGGCAGC AACGAAAGCC GAATTCTTTG GCTGCTGGCC

1441 CAACGTCCA AACGAGGTAAT TTCTCGCAAT GATTTGCATG ACTTTGTTTG GCGAGAGCAA

1501 GGTTTTGAA GTCGATGATTC CAGCTTAACC CAAGCCATTT CGACTCTGCG CAAAATGCTC

1561 AAAGATTCG ACAAAGTCCCC ACAATACGTC AAAACGGTTC CGAAGCGCGG TTACCAATTG

1621 ATCGCCCGA GTGGAAACGGT TGAAGAAGAG ATGGCTCGCG AAAACGAAGC TGCTCATGAC
             stop SD XhoI + GS1 alpha
1681 ATCTCTTAA TAATCAAGGAG GCCCTCGAGA TGGGCTGCCT CGGGAACAGT AAGACCGAGG

1741 ACCAGCGCA ACGAGGAGAAG GCGCAGCGTG AGGCCAACAA AAAGATCGAG AAGCAGCTGC
```

-continued

```
1801 AGAAGGACA AGCAGGTCTAC CGGGCCACGC ACCGCCTGCT GCTGCTGGGT GCTGGAGAAT

1861 CTGGTAAAA GCACCATTGTG AAGCAGATGA GGATCCTGCA TGTTAATGGG TTTAATGGAG

1921 ACAGTGAGA AGGCAACCAAA GTGCAGGACA TCAAAAACAA CCTGAAAGAG GCGATTGAAA

1981 CCATTGTGG CCGCCATGAGC AACCTGGTGC CCCCCGTGGA GCTGGCCAAC CCCGAGAACC

2041 AGTTCAGAG TGGACTACATC CTGAGTGTGA TGAACGTGCC TGACTTTGAC TTCCCTCCCG

2101 AATTCTATG AGCATGCCAAG GCTCTGTGGG AGGATGAAGG AGTGCGTGCC TGCTACGAAC

2161 GCTCCAACG AGTACCAGCTG ATTGACTGTG CCCAGTACTT CCTGGACAAG ATCGACGTGA

2221 TCAAGCAGG CTGACTATGTG CCGAGCGATC AGGACCTGCT TCGCTGCCGT GTCCTGACTT

2281 CTGGAATCT TTGAGACCAAG TTCCAGGTGG ACAAAGTCAA CTTCCACATG TTTGACGTGG

2341 GTGGCCAGC GCGATGAACGC CGCAAGTGGA TCCAGTGCTT CAACGATGTG ACTGCCATCA

2401 TCTTCGTGG TGGCCAGCAGC AGCTACAACA TGGTCATCCG GGAGGACAAC CAGACCAACC

2461 GCCTGCAGG AGGCTCTGAAC CTCTTCAAGA GCATCTGGAA CAACAGATGG CTGCGCACCA

2521 TCTCTGTGA TCCTGTTCCTC AACAAGCAAG ATCTGCTCGC TGAGAAAGTC CTTGCTGGGA

2581 AATCGAAGA TTGAGGACTAC TTTCCAGAAT TTGCTCGCTA CACTACTCCT GAGGATGCTA

2641 CTCCCGAGC CCGGAGAGGAC CCACGCGTGA CCCGGGCCAA GTACTTCATT CGAGATGAGT

2701 TTCTGAGGA TCAGCACTGCC AGTGGAGATG GGCGTCACTA CTGCTACCCT CATTTCACCT

2761 GCGCTGTGG ACACTGAGAAC ATCCGCCGTG TGTTCAACGA CTGCCGTGAC ATCATTCAGC

ClaI + 5 toxR (5-141)
2821 GCATGCACC TTCGTCAGTAC GAGCTGCTCA TCGATGGACA CAACTCAAAA GAGATATCGA

2881 TGAGTCATA TTGGTACTAAA TTCATTCTTG CTGAAAAATT TACCTTCGAT CCCCTAAGCA

2941 ATACTCTGA TTGACAAAGAA GATAGTGAAG AGATCATTCG ATTAGGCAGC AACGAAAGCC

3001 GAATTCTTT GGCTGCTGGCC CAACGTCCAA ACGAGGTAAT TTCTCGCAAT GATTTGCATG

3061 ACTTTGTTT GGCGAGAGCAA GGTTTTGAAG TCGATGATTC CAGCTTAACC CAAGCCATTT

3121 CGACTCTGC GCAAAATGCTC AAAGATTCGA CAAAGTCCCC ACAATACGTC AAAACGGTTC

3181 CGAAGCGCG GTTACCAATTG ATCGCCCGAG TGGAAACGGT TGAAGAAGAG ATGGCTCGCG

Stop XbaI         Stem-loop
3241 AAAACGAAG CTGCTCATGAC ATCTCTTAAT AATCTAGAGG ATCCCCGCGC CCTCATCCGA

3301 AAGGGCG
```

SEQ ID NO.: 208
*Vibrio cholerae* Pctx::lacZ reporter fusion constuct
XbaI

```
SEQ ID NO.: 208
Vibrio cholerate Pctx::lacZ reporter fusion constuct
XbaI
   1 TCTAGAGGCT GTGGGTAGAA GTGAAACGGG GTTTACCGAT AAAAACAGAA AATGATAAAA 3 ToxR binding repeats
  61 AAGGACTAAA TAGTATATTT TGATTTTTGA TTTTTGATTT CAAATAATAC AAATTTATTT +1
     lacZ
 121 ACTTATTTAA TTGTTTTGAT CAATTATTTT TCTGTTAAAC AAAGGGAGCA TTATATGGTA

181 AAGACCATGA TTACGGATTC ACTGGCCGTC GTTTTACAAC GTCGTGACTG GGAAAACCCT

241 GGCGTTACCC AACTTAATCG CCTTGCAGCA CATCCCCCTT TCGCCAGCTG GCGTAATAGC

301 GAAGAGGCCC GCACCGATCG CCCTTCCCAA CAGTTGCGCA GCCTGAATGG CGAATGGCGC

361 TTTGCCTGGT TTCCGGCACC AGAAGCGGTG CCGGAAAGCT GGCTGGAGTG CGATCTTCCT
```

-continued

```
 421 GAGGCCGATA CTGTCGTCGT CCCCTCAAAC TGGCAGATGC ACGGTTACGA TGCGCCCATC
 481 TACACCAACG TGACCTATCC CATTACGGTC AATCCGCCGT TTGTTCCCAC GGAGAATCCG
 541 ACGGGTTGTT ACTCGCTCAC ATTTAATGTT GATGAAAGCT GGCTACAGGA AGGCCAGACG
 601 CGAATTATTT TTGATGGCGT TAACTCGGCG TTTCATCTGT GGTGCAACGG GCGCTGGGTC
 661 GGTTACGGCC AGGACAGTCG TTTGCCGTCT GAATTTGACC TGAGCGCATT TTTACGCGCC
 721 GGAGAAAACC GCCTCGCGGT GATGGTGCTG CGCTGGAGTG ACGGCAGTTA TCTGGAAGAT
 781 CAGGATATGT GGCGGATGAG CGGCATTTTC CGTGACGTCT CGTTGCTGCA TAAACCGACT
 841 ACACAAATCA GCGATTTCCA TGTTGCCACT CGCTTTAATG ATGATTTCAG CCGCGCTGTA
 901 CTGGAGGCTG AAGTTCAGAT GTGCGGCGAG TTGCGTGACT ACCTACGGGT AACAGTTTCT
 961 TTATGGCAGG GTGAAACGCA GGTCGCCAGC GGCACCGCGC CTTTCGGCGG TGAAATTATC
1021 GATGAGCGTG GTGGTTATGC CGATCGCGTC ACACTACGTC TGAACGTCGA AAACCCGAAA
1081 CTGTGGAGCG CCGAAATCCC GAATCTCTAT CGTGCGGTGG TTGAACTGCA CACCGCCGAC
1141 GGCACGCTGA TTGAAGCAGA AGCCTGCGAT GTCGGTTTCC GCGAGGTGCG GATTGAAAAT
1201 GGTCTGCTGC TGCTGAACGG CAAGCCGTTG CTGATTCGAG GCGTTAACCG TCACGAGCAT
1261 CATCCTCTGC ATGGTCAGGT CATGGATGAG CAGACGATGG TGCAGGATAT CCTGCTGATG
1321 AAGCAGAACA ACTTTAACGC CGTGCGCTGT TCGCATTATC CGAACCATCC GCTGTGGTAC
1381 ACGCTGTGCG ACCGCTACGG CCTGTATGTG GTGGATGAAG CCAATATTGA AACCCACGGC
1441 ATGGTGCCAA TGAATCGTCT GACCGATGAT CCGCGCTGGC TACCGGCGAT GAGCGAACGC
1501 GTAACGCGAA TGGTGCAGCG CGATCGTAAT CACCCGAGTG TGATCATCTG GTCGCTGGGG
1561 AATGAATCAG GCCACGGCGC TAATCACGAC GCGCTGTATC GCTGGATCAA ATCTGTCGAT
1621 CCTTCCCGCC CGGTGCAGTA TGAAGGCGG GGAGCCGACA CCACGGCCAC CGATATTATT
1681 TGCCCGATGT ACGCGCGCGT GGATGAAGAC CAGCCCTTCC CGGCTGTGCC GAAATGGTCC
1741 ATCAAAAAAT GGCTTTCGCT ACCTGGAGAG ACGCGCCCGC TGATCCTTTG CGAATACGCC
1801 CACGCGATGG GTAACAGTCT TGGCGGTTTC GCTAAATACT GGCAGGCGTT TCGTCAGTAT
1861 CCCCGTTTAC AGGGCGGCTT CGTCTGGGAC TGGGTGGATC AGTCGCTGAT TAAATATGAT
1921 GAAAACGGCA ACCCGTGGTC GGCTTACGGC GGTGAITTTG GCGATACGCC GAACGATCGC
1981 CAGTTCTGTA TGAACGGTCT GGTCTTTGCC GACCGCACGC CGCATCCAGC GCTGACGGAA
2041 GCAAAACACC AGCAGCAGTT TTTCCAGTTC CGTTTATCCG GGCAAACCAT CGAAGTGACC
2101 AGCGAATACC TGTTCCGTCA TAGCGATAAC GAGCTCCTGC ACTGGATGGT GGCGCTGGAT
2161 GGTAAGCCGC TGGCAAGCGG TGAAGTGCCT CTGGATGTCG CTCCACAAGG TAAACAGTTG
2221 ATTGAACTGC TGAACTACC GCAGCCGGAG AGCGCCGGGC AACTCTGGCT CACAGTACGC
2281 GTAGTGCAAC CGAACGCGAC CGCATGGTCA GAAGCCGGGC ACATCAGCGC CTGGCAGCAG
2341 TGGCGTCTGG CGGAAAACCT CAGTGTGACG CTCCCCGCCG CGTCCACGC CATCCCGCAT
2401 CTGACCACCA GCGAAATGGA TTTTTGCATC GAGCTGGGTA ATAAGCGTTG GCAATTTAAC
2461 CGCCAGTCAG GCTTTCTTTC ACAGATGTGG ATTGGCGATA AAAACAACT GCTGACGCCG
2521 CTGCGCGATC AGTTCACCCG TGCACCGCTG GATAACGACA TTGGCGTAAG TGAAGCGACC
2581 CGCATTGACC CTAACGCCTG GGTCGAACGC TGGAAGGCGG CGGGCCATTA CCAGGCCGAA
2641 GCAGCGTTGT TGCAGTGCAC GGCAGATACA CTTGCTGATG CGGTGCTGAT TACGACCGCT
2701 CACGCGTGGC AGCATCAGGG GAAAACCTTA TTTATCAGCC GGAAAACCTA CCGGATTGAT
2761 GGTAGTGGTC AAATGGCGAT TACCGTTGAT GTTGAAGTGG CGAGCGATAC ACCGCATCCG
2821 GCGCGGATTG GCCTGAACTG CCAGCTGGCG CAGGTAGCAG AGCGGGTAAA CTGGCTCGGA
```

-continued

```
2881 TTAGGGCCGC AAGAAAACTA TCCCGACCGC CTTACTGCCG CCTGTTTTGA CCGCTGGGAT

2941 CTGCCATTGT CAGACATGTA TACCCCGTAC GTCTTCCCGA GCGAAAACGG TCTGCGCTGC

3001 GGGACGCGCG AATTGAATTA TGGCCCACAC CAGTGGCGCG GCGACTTCCA GTTCAACATC

3061 AGCCGCTACA GTCAACAGCA ACTGATGAA ACCAGCCATC GCCATCTGCT GCACGCGGAA

3121 GAAGGCACAT GGCTGAATAT CGACGGTTTC CATATGGGGA TTGGTGGCGA CGACTCCTGG

3181 AGCCCGTCAG TATCGGCGGA ATTCCAGCTG AGCGCCGGTC GCTACCATTA CCAGTTGGTC

Stop Stem-loop    XbaI
3241 TGGTGTCAAAAATAATAACGCCCTCATCCGAAAGGGCGTCTAGA
```

SEQ ID NO.: 266
pMPX-74 MalE (1-28) fusion vector
SD old PstI+1

```
     2401
GAATTCAGGCGCTTTTTAGACTGGTCGTAATGAAATTCAGGAGGTTCTGC
ATATGAAAAT
     1                                          M K I
     2461
AAAAACAGGTGCACGCATCCTCGCATTATCCGCATTAACGACGATGATGT
TTTCCGCCTC
     4    K T G A R I L A L S A L T T M M F S A S

Factor Xa  PstI    SalI  XbaI
     2521
GGCTCTCGCCAAAATCATCGAAGCCCGCCTGCAGGCCTCGGTCGACGCC
GAATCTAGAGA
     24    A L A K I I E A R L Q A S V D A E S R D FLAG             lost XbaI
     2581   TTATAAAGATGACGATGACAAATAATAAGCTAGAGG
(transcriptional stop)
     44     Y K D D D D K
``` pMPX-72::malE(1-28)::FXa::PstI, SalI, XbaI::FLAG
Rhamnose inducible, clone into PstI, SalI, XbaI
Made by cutting TOPO NsiI-malE (1-28)::FXa::PstI, SalI, XbaI::FLAG-NheI insertion with NsiI & NheI and cloning into pMPX-72 cut with PstI & XbaI.
SEQ ID NO.: 267
pMPX-75 MalE (1-28) fusion vector
SD old PstI+1

```
     1621
CCATACCCGTTTTTTTGGGCTAGCAGGAGGCCCTGCATATGAAAATAAAA
ACAGGTGCAC
     1                                  M K I K T G A

1681
GCATCCTCGCATTATCCGCATTAACGACGATGATGTTTTCCGCCTCGGCT
CTCGCCAAAA
     8   R I L A L S A L T T M M F S A S A L A K

Factor Xa  PstI    SalI     XbaI       FLAG
     1741
TCATCGAAGCCCGCCTGCAGGCCTCGGTCGACGCCGAATCTAGAGATTAT
AAAGATGACG Lost XbaI
     1801 ATGACAAATAATAAGCTAGAGG (Transcriptional
stop)
``` pMPX-71::malE(1-28)::FXa::PstI, SalI, XbaI::FLAG Arabinose inducible, clone into PstI, SalI, XbaI Made by cutting TOPO NsiI-malE (1-28)::FXa::PstI, SalI, XbaI::FLAG-NheI insertion with NsiI & NheI and cloning into pMPX-71 cut with PstI & XbaI.

SEQ ID NO.: 268
pMPX-88 MalE (1-28) fusion vector
SD old PstI+1

```
AGGAGGTTCTGCATATGAAAAT
1                   M K I

AAAAACAGGTGCACGCATCCTCGCATTATCCGCATTAACGACGATGATGT
TTTCCGCCTC
4    K T G A R I L A L S A L T T M M F S A S

Factor Xa  PstI   SalI  XbaI
GGCTCTCGCCAAAATCATCGAAGCCCGCCTGCAGGCCTCGGTCGACGCCG
AATCTAGAGA
24    A L A K I I E A R L Q A S V D A E S R D FLAG             lost XbaI
TTATAAAGATGACGATGACAAATAATAAGCTAGAGGTACC
(transcriptional stop)
44    Y K D D D D K
``` pMPX-84::malE(1-28)::FXa::PstI, SalI, XbaI::FLAG
Temperature inducible, clone into PstI, SalI, XbaI
Made by cutting TOPO NsiI-malE (1-28)::FXa::PstI, SalI, XbaI::FLAG-NheI insertion with NsiI & NheI and cloning into pMPX-84 cut with PstI & XbaI.
SEQ ID NO.: 269
pMPX-93 MalE (1-28) fusion vector
SD old PstI+1

```
AGGAGGTTCTGCATATGAAAAT
1                  M K I

AAAAACAGGTGCACGCATCCTCGCATTATCCGCATTAACGACGATGATGT
TTTCCGCCTC
4    K T G A R I L A L S A L T T M M F S A S

Factor Xa  PstI   SalI  XbaI
GGCTCTCGCCAAAATCATCGAAGCCCGCCTGCAGGCCTCGGTCGACGCCG
AATCTAGAGA
24    A L A K I I E A R L Q A S V D A E S R D FLAG             lost XbaI
TTATAAAGATGACGATGACAAATAATAAGCTAGAGGTACC
(transcriptional stop)
44    Y K D D D D K
``` pMPX-86::malE(1-28)::FXa::PstI, SalI, XbaI::FLAG
Temperature inducible, clone into PstI, SalI, XbaI
Made by cutting TOPO NsiI-malE (1-28)::FXa::PstI, SalI, XbaI::FLAG-NheI insertion with NsiI & NheI and cloning into pMPX-86 cut with PstI & XbaI.
SEQ ID NO.: 270
pMPX-77 MalE (1-370 del 354-364) fusion vector
SD old PstI+1

```
2401
GAATTCAGGCGCTTTTTAGACTGGTCGTAATGAAATTCAGGAGGTTCTGC
ATATGAAAAT
 1                                          M  K  I

2461
AAAAACAGGTGCACGCATCCTCGCATTATCCGCATTAACGACGATGATGT
TTTCCGCCTC
 4    K  T  G  A  R  I  L  A  L  S  A  L  T  T  M  M  F  S  A  S

2521
GGCTCTCGCCAAAATCGAAGAAGGTAAACTGGTAATCTGGATTAACGGCG
ATAAAGGCTA
 24   A  L  A  K  I  E  E  G  K  L  V  I  W  I  N  G  D  K  G  Y

2581
TAACGGTCTCGCTGAAGTCGGTAAGAAATTCGAGAAAGATACCGGAATTA
AAGTCACCGT
 44   N  G  L  A  E  V  G  K  K  F  E  K  D  T  G  I  K  V  T  V

2641
TGAGCATCCGGATAAACTGGAAGAGAAATTCCCACAGGTTGCGGCAACTG
GCGATGGCCC
 64   E  H  P  D  K  L  E  E  K  F  P  Q  V  A  A  T  G  D  G  P

2701
TGACATTATCTTCTGGGCACACGACCGCTTTGGTGGCTACGCTCAATCTG
GCCTGTTGGC
 84   D  I  I  F  W  A  H  D  R  F  G  G  Y  A  Q  S  G  L  L  A

2761
TGAAATCACCCCGGACAAAGCGTTCCAGGACAAGCTGTATCCGTTTACCT
GGGATGCCGT
 104  E  I  T  P  D  K  A  F  Q  D  K  L  Y  P  F  T  W  D  A  V

2821
ACGTTACAACGGCAAGCTGATTGCTTACCCGATCGCTGTTGAAGCGTTAT
CGCTGATTTA
 124  R  Y  N  G  K  L  I  A  Y  P  I  A  V  E  A  L  S  L  I  Y

2881
TAACAAAGATCTGCTGCCGAACCCGCCAAAAACCTGGGAAGAGATCCCGG
CGCTGGATAA
 144  N  K  D  L  L  P  N  P  P  K  T  W  E  E  I  P  A  L  D  K

2941
AGAACTGAAAGCGAAAGGTAAGAGCGCGCTGATGTTCAACCTGCAAGAAC
CGTACTTCAC
 164  E  L  K  A  K  G  K  S  A  L  M  F  N  L  Q  E  P  Y  F  T

3001
CTGGCCGCTGATTGCTGCTGACGGGGGTTATGCGTTCAAGTATGAAAACG
GCAAGTACGA
 184  W  P  L  I  A  A  D  G  G  Y  A  F  K  Y  E  N  G  K  Y  D

3061
CATTAAAGACGTGGGCGTGGATAACGCTGGCGCGAAAGCGGGTCTGACCT
TCCTGGTTGA
 204  I  K  D  V  G  V  D  N  A  G  A  K  A  G  L  T  F  L  V  D

3121
CCTGATTAAAAACAAACACATGAATGCAGACACCGATTACTCCATCGCAG
AAGCTGCCTT
 224  L  I  K  N  K  H  M  N  A  D  T  D  Y  S  I  A  E  A  A  F

3181
TAATAAAGGCGAAACAGCGATGACCATCAACGGCCCGTGGGCATGGTCCA
ACATCGACAC
 244  N  K  G  E  T  A  M  T  I  N  G  P  W  A  W  S  N  I  D  T

3241
CAGCAAAGTGAATTATGGTGTAACGGTACTGCCGACCTTCAAGGGTCAAC
CATCCAAACC
 264  S  K  V  N  Y  G  V  T  V  L  P  T  F  K  G  Q  P  S  K  P

3301
GTTCGTTGGCGTGCTGAGCGCAGGTATTAACGCCGCCAGTCCGAACAAAG
AGCTGGCGAA
 284  F  V  G  V  L  S  A  G  I  N  A  A  S  P  N  K  E  L  A  K

3361
AGAGTTCCTCGAAAACTATCTGCTGACTGATGAAGGTCTGGAAGCGGTTA
ATAAAGACAA
 304  E  F  L  E  N  Y  L  L  T  D  E  G  L  E  A  V  N  K  D  K

3421
ACCGCTGGGTGCCGTAGCGCTGAAGTCTTACGAGGAAGAGTTGGCGAAAG
ATCCACGTAT
 324  P  L  G  A  V  A  L  K  S  Y  E  E  E  L  A  K  D  P  R  I
``` pMPX-72::malE(1-370 del 354-364)::FXa::PstI, SalI, XbaI::FLAG

Rhamnose inducible, clone into PstI, SalI, XbaI

Made by cutting TOPO NsiI-malE (1-370 del 354-364)::FXa::PstI, SalI, XbaI::FLAG-NheI insertion with NsiI & NheI and cloning into pMPX-72 cut with PstI & XbaI.

SEQ ID NO.: 271 pMPX-76 MalE (1-370 del 354-364) fusion vector

SD old PstI+1

```
1621
CCATACCCGTTTTTTTGGGCTAGCAGGAGGCCCCTGCATATGAAAATAAAA
ACAGGTGCAC
 1                                    M  K  I  K  T  G  A

1681
GCATCCTCGCATTATCCGCATTAACGACGATGATGTTTTCCGCCTCGGCT
CTCGCCAAAA
 8    R  I  L  A  L  S  A  L  T  T  M  M  F  S  A  S  A  L  A  K

1741
TCGAAGAAGGTAAACTGGTAATCTGGATTAACGGCGATAAAGGCTATAAC
GGTCTCGCTG
 28   I  E  E  G  K  L  V  I  W  I  N  G  D  K  G  Y  N  G  L  A

1801
AAGTCGGTAAGAAATTCGAGAAAGATACCGGAATTAAAGTCACCGTTGAG
CATCCGGATA
 48   E  V  G  K  K  F  E  K  D  T  G  I  K  V  T  V  E  H  P  D

1861
AACTGGAAGAGAAATTCCCACAGGTTGCGGCAACTGGCGATGGCCCTGAC
ATTATCTTCT
 68   K  L  E  E  K  F  P  Q  V  A  A  T  G  D  G  P  D  I  I  F

1921
GGGCACACGACCGCTTTGGTGGCTACGCTCAATCTGGCCTGTTGGCTGAA
ATCACCCCGG
 88   W  A  H  D  R  F  G  G  Y  A  Q  S  G  L  L  A  E  I  T  P

1981
ACAAAGCGTTCCAGGACAAGCTGTATCCGTTTACCTGGGATGCCGTACGT
TACAACGGCA
 108  D  K  A  F  Q  D  K  L  Y  P  F  T  W  D  A  V  R  Y  N  G

2041
AGCTGATTGCTTACCCGATCGCTGTTGAAGCGTTATCGCTGATTTATAAC
AAAGATCTGC
 128  K  L  I  A  Y  P  I  A  V  E  A  L  S  L  I  Y  N  K  D  L

2101
TGCCGAACCCGCCAAAAACCTGGGAAGAGATCCCGGCGCTGGATAAAGAA
CTGAAAGCGA
 148  L  P  N  P  P  K  T  W  E  E  I  P  A  L  D  K  E  L  K  A

2161
AAGGTAAGAGCGCGCTGATGTTCAACCTGCAAGAACCGTACTTCACCTGG
CCGCTGATTG
 168  K  G  K  S  A  L  M  F  N  L  Q  E  P  Y  F  T  W  P  L  I

2221
CTGCTGACGGGGGTTATGCGTTCAAGTATGAAAACGGCAAGTACGACATT
AAAGACGTGG
 188  A  A  D  G  G  Y  A  F  K  Y  E  N  G  K  Y  D  I  K  D  V
```

```
                                      2281
GCGTGGATAACGCTGGCGCGAAAGCGGGTCTGACCTTCCTGGTTGACCTG
ATTAAAAACA
     208 G V D N A G A K A G L T F L V D L I K N

2341
AACACATGAATGCAGACACCGATTACTCCATCGCAGAAGCTGCCTTTAAT
AAAGGGCAAA
     228 K H M N A D T D Y S I A E A A F N K G E

2401
CAGCGATGACCATCAACGGCCCGTGGGCATGGTCCAACATCGACACCAGC
AAAGTGAATT
     248 T A M T I N G P W A W S N I D T S K V N

2461
ATGGTGTAACGGTACTGCCGACCTTCAAGGGTCAACCATCCAAACCGTTC
GTTGGCGTGC
     268 Y G V T V L P T F K G Q P S K P F V G V

2521
TGAGCGCAGGTATTAACGCCGCCAGTCCGAACAAAGAGCTGGCGAAAGAG
TTCCTCGAAA
     288 L S A G I N A A S P N K E L A K E F L E

2581
ACTATCTGCTGACTGATGAAGGTCTGGAAGCGGTTAATAAAGACAAACCG
CTGGGTGCCG
     308 N Y L L T D E G L E A V N K D K P L G A

2641
TAGCGCTGAAGTCTTACGAGGAAGAGTTGGCGAAAGATCCACGTATTGCC
GACCCCATGG
     328 V A L K S Y E E E L A K D P R I A A T M

Factor Xa  PstI
                                      2701
AAAACGCCCAGTCCGCTTTCTGGTATGCCGTGCGTATCGAAGCCCGCCTG
CAGGCCTCGG
     348 E N A Q S A F W Y A V R I E A R L Q A S SalI XbaI        FLAG                   Lost XbaI
                                      2761
TCGACGCCGAATCTAGAGATTATAAAGATGACGATGACAAATAATAAGCT
AGAGGA (trxn stop)
     368 V D A E S R D Y K D D D D K
``` pMPX-71::malE(1-370 del 354-364)::FXa::PstI, SalI, XbaI::FLAG

Arabinose inducible, clone into PstI, SalI, XbaI

Made by cutting TOPO NsiI-malE (1-370 del 354-364)::FXa::PstI, SalI, XbaI::FLAG-NheI insertion with NsiI & NheI and cloning into pMPX-71 cut with PstI & XbaI.

SEQ ID NO.: 272 pMPX-89 MalE (1-370 del 354-364) fusion vector

SD old PstI+1

```
AGGAGGTTCTGCATATGAAAATAAAAACAGGTGCAC
     1                      M K I K T G A

GCATCCTCGCATTATCCGCATTAACGACGATGATGTTTTCCGCCTCGGCT
CTCGCCAAAA
     8   R I L A L S A L T T M M F S A S A L A K

TCGAAGAAGGTAAACTGGTAATCTGGATTAACGGCGATAAAGGCTATAAC
GGTTCCGCTG
     28  I E E G K L V I W I N G D K G Y N G L A

AAGTCGGTAAGAAATTCGAGAAAGATACCGGAATTAAAGTCACCGTTGAG
CATCCGGATA
     48  E V G K K F E K D T G I K V T V E H P D

AACTGGAAGAGAAATTCCCACAGGTTGCGGCAACTGGCGATGGCCCTGAC
ATTATCTTCT
     68  K L E E K F P Q V A A T G D G P D I I F
```

```
GGGCACACGACCGCTTTGGTGGCTACGCTCAATCTGGCCTGTTGGCTGAA
ATCACCCCGG
     88  W A H D R F G G Y A Q S G L L A E I T P

ACAAAGCGTTCCAGGACAAGCTGTATCCGTTTACCTGGGATGCCGTACGT
TACAACGGCA
     108 D K A F Q D K L Y P F T W D A V R Y N G

AGCTGATTGCTTACCCGATCGCTGTTGAAGCGTTATCGCTGATTTATAAC
AAAGATCTGC
     128 K L I A Y P I A V E A L S L I Y N K D L

TGCCGAACCCGCCAAAAACCTGGGAAGAGATCCCGGCGCTGGATAAAGAA
CTGAAAGCGA
     148 L P N P P K T W E E I P A L D K E L K A

AAGGTAAGAGCGCGCTGATGTTCAACCTGCAAGAACCGTACTTCACCTGG
CCGCTGATTG
     168 K G K S A L M F N L Q E P Y F T W P L I

CTGCTGACGGGGGTTATGCGTTCAAGTATGAAAACGGCAAGTACGACATT
AAAGACGTGG
     188 A A D G G Y A F K Y E N G K Y D I K D V

GCGTGGATAACGCTGGCGCGAAAGCGGGTCTGACCTTCCTGGTTGACCTG
ATTAAAAACA
     208 G V D N A G A K A G L T F L V D L I K N

AACACATGAATGCAGACACCGATTACTCCATCGCAGAAGCTGCCTTTAAT
AAAGGGCAAA
     228 K H M N A D T D Y S I A E A A F N K G E

CAGCGATGACCATCAACGGCCCGTGGGCATGGTCCAACATCGACACCAGC
AAAGTGAATT
     248 T A M T I N G P W A W S N I D T S K V N

ATGGTGTAACGGTACTGCCGACCTTCAAGGGTCAACCATCCAAACCGTTC
GTTGGCGTGC
     268 Y G V T V L P T F K G Q P S K P F V G V

TGAGCGCAGGTATTAACGCCGCCAGTCCGAACAAAGAGCTGGCGAAAGAG
TTCCTCGAAA
     288 L S A G I N A A S P N K E L A K E F L E

ACTATCTGCTGACTGATGAAGGTCTGGAAGCGGTTAATAAAGACAAACCG
CTGGGTGCCG
     308 N Y L L T D E G L E A V N K D K P L G A

TAGCGCTGAAGTCTTACGAGGAAGAGTTGGCGAAAGATCCACGTATTGCC
GCCACCATGG
     328 V A L K S Y E E E L A K D P R I A A T M

Factor Xa  PstI
AAAACGCCCAGTCCGCTTTCTGGTATGCCGTGCGTATCGAAGCCCGCCTG
CAGGCCTCGG
     348 E N A Q S A F W Y A V R I E A R L Q A S SalI XbaI        FLAG                   Lost XbaI
TCGACGCCGAATCTAGAGATTATAAAGATGACGATGACAAATAATAAGCT
AGAGG (trxn stop)
     368 V D A E S R D Y K D D D D K
``` pMPX-84::malE(1-370 del 354-364)::FXa::PstI, SalI, XbaI::FLAG

Temperature inducible, clone into PstI, SalI, XbaI

Made by cutting TOPO NsiI-malE (1-370 del 354-364)::FXa::PstI, SalI, XbaI::FLAG-NheI insertion with NsiI & NheI and cloning into pMPX-84 cut with PstI & XbaI.

SEQ ID NO.: 273 pMPX-94 MalE (1-370 del 354-364) fusion vector

SD old PstI+1

```
AGGAGGTTCTGCATATGAAAATAAAAACAGGTGCAC
     1                      M K I K T G A

GCATCCTCGCATTATCCGCATTAACGACGATGATGTTTTCCGCCTCGGCT
CTCGCCAAAA
     8   R I L A L S A L T T M M F S A S A L A K
```

-continued

```
TCGAAGAAGGTAAACTGGTAATCTGGATTAACGGCGATAAAGGCTATAAC
GGTCTCGCTG
    28 I E E G K L V I W I N G D K G Y N G L A

AAGTCGGTAAGAAATTCGAGAAAGATACCGGAATTAAAGTCACCGTTGAG
CATCCGGATA
    48 E V G K K F E K D T G I K V T V E H P D

AACTGGAAGAGAAATTCCCACAGGTTGCGGCAACTGGCGATGGCCCTGAC
ATTATCTTCT
    68 K L E E K F P Q V A A T G D G P D I I F

GGGCACACGACCGCTTTGGTGGCTACGCTCAATCTGGCCTGTTGGCTGAA
ATCACCCCGG
    88 W A H D R F G G Y A Q S G L L A E I T P

ACAAAGCGTTCCAGGACAAGCTGTATCCGTTTACCTGGGATGCCGTACGT
TACAACGGCA
    108 D K A F Q D K L Y P F T W D A V R Y N G

AGCTGATTGCTTACCCGATCGCTGTTGAAGCGTTATCGCTGATTTATAAC
AAAGATCTGC
    128 K L I A Y P I A V E A L S L I Y N K D L

TGCCGAACCCGCCAAAAACCTGGGAAGAGATCCCGGCGCTGGATAAAGAA
CTGAAAGCGA
    148 L P N P P K T W E E I P A L D K E L K A

AAGGTAAGAGCGCGCTGATGTTCAACCTGCAAGAACCGTACTTCACCTGG
CCGCTGATTG
    168 K G K S A L M F N L Q E P Y F T W P L I

CTGCTGACGGGGGTTATGCGTTCAAGTATGAAAACGGCAAGTACGACATT
AAAGACGTGG
    188 A A D G G Y A F K Y E N G K Y D I K D V

GCGTGGATAACGCTGGCGCGAAAGCGGGTCTGACCTTCCTGGTTGACCTG
ATTAAAAACA
    208 G V D N A G A K A G L T F L V D L I K N

AACACATGAATGCAGACACCGATTACTCCATCGCAGAAGCTGCCTTTAAT
AAAGGCGAAA
    228 K H M N A D T D Y S I A E A A F N K G E

CAGCGATGACCATCAACGGCCCGTGGGCATGGTCCAACATCGACACCAGC
AAAGTGAATT
    248 T A M T I N G P W A W S N I D T S K V N

ATGGTGTAACGGTACTGCCGACCTTCAAGGGTCAACCATCCAAACCGTTC
GTTGGCGTGC
    268 Y G V T V L P T F K G Q P S K P F V G V

TGAGCGCAGGTATTAACGCCGCCAGTCCGAACAAAGAGCTGGCGAAAGAG
TTCCTCGAAA
    288 L S A G I N A A S P N K E L A K E F L E

ACTATCTGCTGACTGATGAAGGTCTGGAAGCGGTTAATAAAGACAAACCG
CTGGGTGCCG
    308 N Y L L T D E G L E A V N K D K P L G A

TAGCGCTGAAGTCTTACGAGGAAGAGTTGGCGAAAGATCCACGTATTGCC
GCCACCATGG
    328 V A L K S Y E E E L A K D P R I A A T M

Factor Xa PstI
AAAACGCCCAGTCCGCTTTCTGGTATGCCGTGCGTATCGAAGCCCGCCTG
CAGGCCTCGG
    348 E N A Q S A F W Y A V R I E A R L Q A S SalI XbaI      FLAG             Lost XbaI
TCGACGCCGAATCTAGAGATTATAAAGATGACGATGACAAATAATAAGCT
AGAGG (trxn stop)
    368 V D A E S R D Y K D D D D K
``` pMPX-86::malE(1-370 del 354-364)::FXa::PstI, SalI, XbaI::FLAG
  Temperature inducible, clone into PstI, SalI, XbaI
  Made by cutting TOPO NsiI-malE (1-370 del 354-364)::FXa::PstI, SalI, XbaI::FLAG-NheI insertion with NsiI & NheI and cloning into pMPX-86 cut with PstI & XbaI.

SEQ ID NO.: 274
pMPX-79 TrxA (2-109 del 103-107) fusion vector
SD PstI SalI XbaI+2 trxA(del 103-107)

```
    1
TAGCAGGAGGCCCTGCAGGCCTCGGTCGACGCCGAATCTAGAAGCGAT
AAAATTATT
    1              A S V D A E S R S D K I I

61
CACCTGACTGACGACAGTTTTGACACGGATGTACTCAAAGCGGACGGG
GCGATCCTCGTC
    17     H L T D D S F D T D V L K A D G A I L V

121
GATTTCTGGGCAGAGTGGTGCGGTCCGTGCAAAATGATCGCCCCGATT
CTGGATGAAATC
    37     D F W A E W C G P C K M I A P I L D E I

181
GCTGACGAATATCAGGGCAAACTGACCGTTGCAAAACTGAACATCGAT
CAAAACCCTGGC
    57     A D E Y Q G K L T V A K L N I D Q N P G

241
ACTGCGCCGAAATATGGCATCCGTGGTATCCCGACTCTGCTGCTGTTC
AAAAACGGTGAA
    77     T A P K Y G I R G I P T L L L F K N G E

301
GTGGCGGCAACCAAAGTGGGTGCACTGTCTAAAGGTCAGTTGAAAGAG
AACCTGGCGGAT
    97     V A A T K V G A L S K G Q L K E N L A D
```

FLAG Lost XbaI
```
    361      TATAAAGATGACGATGACAAATAATAAGCTAGAGG
(transcriptional stop)
    117    Y K D D D D K
``` pMPX-71::PstI, SalI, XbaI::trxA (2-109 del 103-107)::FLAG
  Arabinose inducible, clone into PstI, SalI, XbaI
  +1 Met required for protein to be fused
  Made by cutting TOPO PstI, SalI, XbaI::trxA (2-109 del 103-107)::FLAG-NheI insertion with PstI & NheI and cloning into pMPX-71 cut with PstI & XbaI.

SEQ ID NO.: 275
pMPX-78 TrxA (2-109 del 103-107) fusion vector
SD PstI

```
    1
GAATTCAGGCGCTTTTTAGACTGGTCGTAATGAAATTCAGGAGGTT
CTGCAGGCCTC
    1                        A S

SalI   XbaI +2 trxA(del 103-107)
    61
GGTCGACGCCGAATCTAGAAGCGATAAAATTATTCACCTGACTGAC
GACAGTTTTGACAC
    6       V D A E S R S D K I I H L T D D S F D T 121
GGATGTACTCAAAGCGGACGGGGCGATCCTCGTCGATTTCTGGGCAG
AGTGGTGCGGTCC
    26   D V L K A D G A I L V D F W A E W C G P
```

```
181
GTGCAAAATGATCGCCCCGATTCTGGATGAAATCGCTGACGAATATC
AGGGCAAACTGAC

46  C K M I A P I L D E I A D E Y Q G K L T

241
CGTTGCAAAACTGAACATCGATCAAAACCCTGGCACTGCGCCGAAAT
ATGGCATCCGTGG

66  V A K L N I D Q N P G T A P K Y G I R G

301
TATCCCGACTCTGCTGCTGTTCAAAAACGGTGAAGTGGCGGCAACCA
AAGTGGGTGCACT

86  I P T L L L F K N G E V A A T K V G A L
                                                     FLAG
361
GTCTAAAGGTCAGTTGAAAGAGAACCTGGCGGATTATAAAGATGACGA
TGACAAATAATAA

106  S K G Q L K E N L A D Y K D D D K
``` lost XbaI
GCTAGAGG (transcriptional stop)
pMPX-72::PstI, SalI, XbaI::trxA (2-109 del 103-107)::FLAG
  Rhamnose inducible, clone into PstI, SalI, XbaI
  +1 Met required for protein to be fused
  Made by cutting TOPO PstI, SalI, XbaI::trxA (2-109 del 103-107)::FLAG-NheI insertion with PstI & NheI and cloning into pMPX-72 cut with PstI & XbaI.
  SEQ ID NO.: 276
  pMPX-90 TrxA (2-109 del 103-107) fusion vector
  SD PstI SalI XbaI+2 trxA(del 103-107)

```
AGGAGGTTCTGCAGGCCTCGGTCGACGCCGAATCTAGAAGCGATAAA
ATTATT

1                A S V D A E S R S D K I I
CACCTGACTGACGACAGTTTTGACACGGATGTACTCAAAGCGGACGG
GGCGATCCTCGTC

17  H L T D D S F D T D V L K A D G A I L V

GATTTCTGGGCAGAGTGGTGCGGTCCGTGCAAAATGATCGCCCCGAT
TCTGGATGAAATC

37  D F W A E W C G P C K M I A P I L D E I

GCTGACGAATATCAGGGCAAACTGACCGTTGCAAAACTGAACATCGAT
CAAAACCCTGGC

57  A D E Y Q G K L T V A K L N I D Q N P G

ACTGCGCCGAAATATGGCATCCGTGGTATCCCGACTCTGCTGCTGTTC
AAAAACGGTGAA

77  T A P K Y G I R G I P T L L L F K N G E

GTGGCGGCAACCAAAGTGGGTGCACTGTCTAAAGGTCAGTTGAAAGAG
AACCTGGCGGAT

97  V A A T K V G A L S K G Q L K E N L A D
              FLAG                Lost XbaI
          TATAAAGATGACGATGACAAATAATAAGCTAGAGGTACC
(transcriptional stop)

117  Y K D D D D K
``` pMPX-84::PstI; SalI, XbaI::trxA (2-109 del 103-107)::FLAG
  Temperature inducible, clone into PstI, SalI, XbaI
  +1 Met required for protein to be fused
  Made by cutting TOPO PstI, SalI, XbaI::trxA (2-109 del 103-107)::FLAG-NheI insertion with PstI & NheI and cloning into pMPX-84 cut with PstI & XbaI.
  SEQ ID NO.: 277
  pMPX-95 TrxA (2-109 del 103-107) fusion vector
  SD PstI SalI XbaI+2 trxA(del 103-107)

```
AGGAGGTTCTGCAGGCCTCGGTCGACGCCGAATCTAGAAGCGATAAA
ATTATT

1                A S V D A E S R S D K I I

CACCTGACTGACGACAGTTTTGACACGGATGTACTCAAAGCGGACGG
GGCGATCCTCGTC

17  H L T D D S F D T D V L K A D G A I L V

GATTTCTGGGCAGAGTGGTGCGGTCCGTGCAAAATGATCGCCCCGAT
TCTGGATGAAATC

37  D F W A E W C G P C K M I A P I L D E I

GCTGACGAATATCAGGGCAAACTGACCGTTGCAAAACTGAACATCGAT
CAAAACCCTGGC

57  A D E Y Q G K L T V A K L N I D Q N P G

ACTGCGCCGAAATATGGCATCCGTGGTATCCCGACTCTGCTGCTGTTC
AAAAACGGTGAA

77  T A P K Y G I R G I P T L L L F K N G E

GTGGCGGCAACCAAAGTGGGTGCACTGTCTAAAGGTCAGTTGAAAGAG
AACCTGGCGGAT

97  V A A T K V G A L S K G Q L K E N L A D
              FLAG                Lost XbaI
          TATAAAGATGACGATGACAAATAATAAGCTAGAGGTACC
(transcriptional stop)

117  Y K D D D D K
``` pMPX-86::PstI, SalI, XbaI::trxA (2-109 del 103-107)::FLAG
  Temperature inducible, clone into PstI, SalI, XbaI
  +1 Met required for protein to be fused
  Made by cutting TOPO PstI, SalI, XbaI::trxA (2-109 del 103-107)::FLAG-NheI insertion with PstI & NheI and cloning into pMPX-86 cut with PstI & XbaI.
  SEQ ID NO.: 278
  pMPX-80 MalE (1-28) MCS TrxA (2-109 del 103-107) fusion vector
  SD Lost PstI+1 malE(1-28)

```
2401
GAATTCAGGCGCTTTTTAGACTGGTCGTAATGAAATTCAGGAGGTTC
TGCATATGAAAAT

1                                   M K I
2461
AAAAACAGGTGCACGCATCCTCGCATTATCCGCATTAACGACGATGA
TGTTTTCCGCCTC

4   K T G A R I L A L S A L T T M M F S A S
                            Factor Xa PstI SalI XbaI
2521
GGCTCTCGCCAAAATCATCGAAGCCCGCCTGCAGGCCTCGGTCGACG
CCGAATCTAGAAG
```

```
            24    A L A K I I E A R L Q A S V D A E S R S

+2 trxA (2-109 del 103-107)
            2581
            CGATAAAATTATTCACCTGACTGACGACAGTTTTGACACGGATGTAC
            TCAAAGCGGACGG

44    D K I I H L T D D S F D T D V L K A D G

2641
            GGCGATCCTCGTCGATTTCTGGGCAGAGTGGTGCGGTCCGTGCAAAA
            TGATCGCCCCGAT

64    A I L V D F W A E W C G P C K M I A P I

2701
            TCTGGATGAAATCGCTGACGAATATCAGGGCAAACTGACCGTTGCAA
            AACTGAACATCGA

84    L D E I A D E Y Q G K L T V A K L N I D

2761
            TCAAAACCCTGGCACTGCGCCGAAATATGGCATCCGTGGTATCCCGAC
            TCTGCTGCTGTT

104   Q N P G T A P K Y G I R G I P T L L L F

2821
            CAAAAACGGTGAAGTGGCGGCAACCAAAGTGGGTGCACTGTCTAAAGG
            TCAGTTGAAAGA

124   K N G E V A A T K V G A L S K G Q L K E

FLAG         Lost XbaI
            2881
            GAACCTGGCGGATTATAAAGATGACGATGACAAATAATAAGCTAGAGG
            (trxn stop)

144   N L A D Y K D D D D K pMPX-72::malE(1-28)::FXa::PstI, SalI,
            XbaI:TrxA(1-109 del 103-107)::FLAG
            Rhamnose inducible, clone into PstI, SalI,
            XbaI
```

Made by cutting TOPO NsiI-malE (1-28)::FXa::PstI, SalI, XbaI::FLAG-NheI insertion with NsiI & XbaI and cloning into pMPX-78 cut with PstI & XbaI.

SEQ ID NO.: 279

```
            pMPX-81 MalE (1-28) MCS TrxA (2-109 del
            103-107) fusion vector SD Lost PstI +1
                                        malE (1-28)
            1621
            CCATACCCGTTTTTTTGGGCTAGCAGGAGGCCCTGCATATGAAAATAA
            AAACAGGTGCAC

1                      M K I K T G A

1681
            GCATCCTCGCATTATCCGCATTAACGACGATGATGTTTTCCGCCTCGG
            CTCTCGCCAAAA

8     R I L A L S A L T T M M F S A S A L A K

+2 trxA(2-109 del    Factor Xa PstI SalI XbaI
            103-107)
            1741
            TCATCGAAGCCCGCCTGCAGGCCTCGGTCGACGCCGAATCTAGAAGCG
            ATAAAATTATTC
            28    I I E A R L Q A S V D A E S R S D K I I
```

```
            1801
            ACCTGACTGACGACAGTTTTGACACGGATGTACTCAAAGCGGACGGGG
            CGATCCTCGTCG

48    H L T D D S F D T D V L K A D G A I L V

1861
            ATTTCTGGGCAGAGTGGTGCGGTCCGTGCAAAATGATCGCCCCGATTC
            TGGATGAAATCG

68    D F W A E W C G P C K M I A P I L D E I

1921
            CTGACGAATATCAGGGCAAACTGACCGTTGCAAAACTGAACATCGATC
            AAAACCCTGGCA

88    A D E Y Q G K L T V A K L N I D Q N P G

1981
            CTGCGCCGAAATATGGCATCCGTGGTATCCCGACTCTGCTGCTGTTCA
            AAAACGGTGAAG

108   T A P K Y G I R G I P T L L L F K N G E

2041
            TGGCGGCAACCAAAGTGGGTGCACTGTCTAAAGGTCAGTTGAAAGAGA
            ACCTGGCGGATT

128   V A A T K V G A L S K G Q L K E N L A D

FLAG
            2101 ATAAAGATGACGATGACAAATAATAAGCTAGAGG
                        (transcriptional stop)

148   Y K D D D D K
``` pMPX-71::malE(1-28)::FXa::PstI, SalI, XbaI::TrxA(1-109 del 103-107)::FLAG

Arabinose inducible, clone into PstI, SalI, XbaI

Made by cutting TOPO NsiI-malE (1-28)::FXa::PstI, SalI, XbaI::FLAG-NheI insertion with NsiI & XbaI and cloning into pMPX-79 cut with PstI & XbaI.

SEQ ID NO.: 280 pMPX-91 MalE (1-28) MCS TrxA (2-109 del 103-107) fusion vector

SD Lost PstI+1 malE(1-28)

```
            AGGAGGTTCTGCATATGAAAAT

1                              M K I

AAAAACAGGTGCACGCATCCTCGCATTATCCGCATTAACGACGATGAT
            GTTTTCCGCCTC

4     K T G A R I L A L S A L T T M M F S A S

Factor Xa PstI SalI XbaI
            GGCTCTCGCCAAAATCATCGAAGCCCGCCTGCAGGCCTCGGTCGACGC
            CGAATCTAGAAG

24 A L A K I I E A R L Q A S V D A E S R S

+2 trxA (2-109 del 103-107)
            CGATAAAATTATTCACCTGACTGACGACAGTTTTGACACGGATGTACT
            CAAAGCGGACGG 44 D K I I H L T D D S F D T D V L K A D G
            GGCGATCCTCGTCGATTTCTGGGCAGAGTGGTGCGGTCCGTGCAAAAT
            GATCGCCCCGAT 64 A I L V D F W A E W C G P C K M I A P I
            TCTGGATGAAATCGCTGACGAATATCAGGGCAAACTGACCGTTGCAAA
            ACTGAACATCGA 84 L D E I A D E Y Q G K L T V A K L N I D
            TCAAAACCCTGGCACTGCGCCGAAATATGGCATCCGTGGTATCCCGAC
            TCTGCTGCTGTT
```

-continued

```
   104 Q N P G T A P K Y G I R G I P T L L L F
CAAAAACGGTGAAGTGGCGGCAACCAAAGTGGGTGCACTGTCTAAAGG
TCAGTTGAAAGA

124 K N G E V A A T K V G A L S K G Q L K E

FLAG       Lost XbaI
GAACCTGGCGGATTATAAAGATGACGATGACAAATAATAAGCTAGAGG
TACC  (trxn stop)

144 N L A D Y K D D D D K
``` pMPX-84::malE(1-28)::FXa::PstI, SalI, XbaI::
TrxA(1-109 del 103-107)::FLAG
Temperature inducible, clone into PstI,
SalI, XbaI
Made by cutting TOPO NsiI-malE (1-28)::FXa::
PstI, SalI, XbaI::FLAG-NheI insertion with
NsiI & XbaI and cloning into pMPX-90 cut
with PstI & XbaI.
SEQ ID NO.: 281
pMPX-96 MalE (1-28) MCS TrxA (2-109 del
103-107) fusion vector
                 SD Lost PstI +1 malE(1-28)

AGGAGGTTCTGCATATGAAAAT

```
   1                            M K I
AAAAACAGGTGCACGCATCCTCGCATTATCCGCATTAACGACGATGA
TGTTTTCCGCCTC

4     K T G A R I L A L S A L T T M M F S A S
                         Factor Xa PstI SalI XbaI
GGCTCTCGCCAAAATCATCGAAGCCCGCCTGCAGGCCTCGGTCGACG
CCGAATCTAGAAG 24   A L A K I I E A R L Q A S V D A E S R S
        +2 trxA (2-109 del 103-107)
CGATAAAATTATTCACCTGACTGACGACAGTTTTGACACGGATGTAC
TCAAAGCGGACGG 44   D K I I H L T D D S F D T D V L K A D G
GGCGATCCTCGTCGATTTCTGGGCAGAGTGGTGCGGTCCGTGCAAAA
TGATCGCCCCGAT 64   A I L V D F W A E W C G P C K M I A P I
TCTGGATGAAATCGCTGACGAATATCAGGGCAAACTGACCGTTGCAA
AACTGAACATCGA 84   L D E I A D E Y Q G K L T V A K L N I D
TCAAAACCCTGGCACTGCGCCGAAATATGGCATCCGTGGTATCCCGA
CTCTGCTGCTGTT 104 Q N P G T A P K Y G I R G I P T L L L F
CAAAAACGGTGAAGTGGCGGCAACCAAAGTGGGTGCACTGTCTAAAG
GTCAGTTGAAAGA

124 K N G E V A A T K V G A L S K G Q L K E

FLAG       Lost XbaI
GAACCTGGCGGATTATAAAGATGACGATGACAAATAATAAGCTAGAG
GTACC (trxn stop)

144 N L A D Y K D D D D K
``` pMPX-86::malE(1-28)::FXa::PstI, SalI, XbaI::TrxA(1-109 del 103-107)::FLAG
Temperature inducible, clone into PstI, SalI, XbaI
Made by cutting TOPO NsiI-malE (1-28)::FXa::PstI, SalI, XbaI::FLAG-NheI insertion with NsiI & XbaI and cloning into pMPX-95 cut with PstI & XbaI.
SEQ ID NO.: 282
pMPX-83 MalE (1-370 del 354-364) MCS TrxA (2-109 del 103-107) fusion vector
SD Lost PstI+1 malE(1-28)

```
   2401
GAATTCAGGCGCTTTTTAGACTGGTCGTAATGAAATTCAGGAGGTTC
TGCATATGAAAAT

1                            M K I
   2461
AAAAACAGGTGCACGCATCCTCGCATTATCCGCATTAACGACGATGA
TGTTTTCCGCCTC

4    K T G A R I L A L S A L T T M M F S A S
   2521
GGCTCTCGCCAAAATCGAAGAAGGTAAACTGGTAATCTGGATTAACG
GCGATAAAGGCTA

24   A L A K I E E G K L V I W I N G D K G Y
   2581
TAACGGTCTCGCTGAAGTCGGTAAGAAATTCGAGAAAGATACCGGAA
TTAAAGTCACCGT

44   N G L A E V G K K F E K D T G I K V T V
   2641
TGAGCATCCGGATAAACTGGAAGAGAAATTCCCACAGGTTGCGGCAA
CTGGCGATGGCCC

64   E H P D K L E E K F P Q V A A T G D G P
   2701
TGACATTATCTTCTGGGCACACGACCGCTTTGGTGGCTACGCTCAAT
CTGGCCTGTTGGC

84   D I I F W A H D R F G G Y A Q S G L L A
   2761
TGAAATCACCCCCGGACAAAGCGTTCCAGGACAAGCTGTATCCGTTTA
CCTGGGATGCCGT

104 E I T P D K A F Q D K L Y P F T W D A V
   2821
ACGTTACAACGGCAAGCTGATTGCTTACCCGATCGCTGTTGAAGCGT
TATCGCTGATTTA

124 R Y N G K L I A Y P I A V E A L S L I Y
   2881
TAACAAAGATCTGCTGCCGAACCCGCCAAAAACCTGGGAAGAGATCC
CGGCGCTGGATAA

144 N K D L L P N P P K T W E E I P A L D K
   2941
AGAACTGAAAGCGAAAGGTAAGAGCGCGCTGATGTTCAACCTGCAAG
AACCGTACTTCAC

164 E L K A K G K S A L M F N L Q E P Y F T
   3001
CTGGCCGCTGATTGCTGCTGACGGGGGTTATGCGTTCAAGTATGAAA
ACGGCAAGTACGA

184 W P L I A A D G G Y A F K Y E N G K Y D
   3061
CATTAAAGACGTGGGCGTGGATAACGCTGGCGCGAAAGCGGGTCTGA
CCTTCCTGGTTGA

204 I K D V G V D N A G A K A G L T F L V D
   3121
CCTGATTAAAAACAAACACATGAATGCAGACACCGATTACTCCATCG
CAGAAGCTGCCTT

224 L I K N K H M N A D T D Y S I A E A A F
```

```
3181
TAATAAAGGCGAAACAGCGATGACCATCAACGGCCCGTGGGCATGGT
CCAACATCGACAC

244  N K G E T A M T I N G P W A W S N I D T

3241
CAGCAAAGTGAATTATGGTGTAACGGTACTGCCGACCTTCAAGGGTC
AACCATCCAAACC

264  S K V N Y G V T V L P T F K G Q P S K P

3301
GTTCGTTGGCGTGCTGAGCGCAGGTATTAACGCCGCCAGTCCGAACA
AAGAGCTGGCGAA

284  F V G V L S A G I N A A S P N K E L A K

3361
AGAGTTCCTCGAAAACTATCTGCTGACTGATGAAGGTCTGGAAGCGG
TTAATAAAGACAA

304  E F L E N Y L L T D E G L E A V N K D K

3421
ACCGCTGGGTGCCGTAGCGCTGAAGTCTTACGAGGAAGAGTTGGCGA
AAGATCCACGTAT

324  P L G A V A L K S Y E E E L A K D P R I

Factor Xa
3481
TGCCGCCACCATGGAAAACGCCCAGTCCGCTTTCTGGTATGCCGTGC
GTATCGAAGCCCG

344  A A T M E N A Q S A F W Y A V R I E A R

PstI SalI XbaI +2 trxA (2-109 del 103-107)
3541
CCTGCAGGCCTCGGTCGACGCCGAATCTAGAAGCGATAAAATTATTC
ACCTGACTGACGA

364  L Q A S V D A E S R S D K I I H L T D D
```

```
3601
CAGTTTTGACACGGATGTACTCAAAGCGGACGGGGCGATCCTCGTCG
ATTTCTGGGCAGA

384  S F D T D V L K A D G A I L V D F W A E

3661
GTGGTGCGGTCCGTGCAAAATGATCGCCCCGATTCTGGATGAAATCG
CTGACGAATATCA

404  W C G P C K M I A P I L D E I A D E Y Q

3721
GGGCAAACTGACCGTTGCAAAACTGAACATCGATCAAAACCCTGGCA
CTGCGCCGAAATA

424  G K L T V A K L N I D Q N P G T A P K Y

3781
TGGCATCCGTGGTATCCCGACTCTGCTGCTGTTCAAAAACGGTGAAG
TGGCGGCAACCAA

444  G I R G I P T L L L F K N G E V A A T K

FLAG
3841
AGTGGGTGCACTGTCTAAAGGTCAGTTGAAAGAGAACCTGGCGGATT
ATAAAGATGACGA

464  V G A L S K G Q L K E N L A D Y K D D D

3901  TGACAAATAATAAGCTAGAGG (transcriptional
          stop)

484  D K
``` pMPX-72::malE(1-320 del 354-364)::FXa::PstI, SalI, XbaI::TrxA(1-109 del 103-107)::FLAG Rhamnose inducible, clone into PstI, SalI, XbaI Made by cutting TOPO NsiI-malE (1-370 del 354-364)::FXa::PstI, SalI, XbaI::FLAG-NheI insertion with NsiI & XbaI and cloning into pMPX-78 cut with PstI & XbaI.

SEQ ID NO.: 283 pMPX-82 MalE (1-370 del 354-364) MCS TrxA (2-109 del 103-107) fusion vector

SD Lost PstI+1 malE (1-370 del 352-362)

```
1621 CCATACCCGTTTTTTGGGCTAGCAGGAGGCCCTGCATATGAAAATAAAAACAGGTGCAC

1                   M K I K T G A

1681 GCATCCTCGCATTATCCGCATTAACGACGATGATGTTTTCCGCCTCGGCTCTCGCCAAAA

8 R I L A L S A L T T M M F S A S A L A K

1741 TCGAAGAAGGTAAACTGGTAATCTGGATTAACGGCGATAAAGGCTATAACGGTCTCGCTG

28 I E E G K L V I W I N G D K G Y N G L A

1801 AAGTCGGTAAGAAATTCGAGAAAGATACCGGAATTAAAGTCACCGTTGAGCATCCGGATA

48 E V G K K F E K D T G I K V T V E H P D

1861 AACTGGAAGAGAAATTCCCACAGGTTGCGGCAACTGGCGATGGCCCTGACATTATCTTCT

68 K L E E K F P Q V A A T G D G P D I I F

1921 GGGCACACGACCGCTTTGGTGGCTACGCTCAATCTGGCCTGTTGGCTGAAATCACCCCGG

88 W A H D R F G G Y A Q S G L L A E I T P

1981 ACAAAGCGTTCCAGGACAAGCTGTATCCGTTTACCTGGGATGCCGTACGTTACAACGGCA

108 D K A F Q D K L Y P F T W D A V R Y N G

2041 AGCTGATTGCTTACCCGATCGCTGTTGAAGCGTTATCGCTGATTTATAACAAAGATCTGC

128 K L I A Y P I A V E A L S L I Y N K D L
```

```
2101 TGCCGAACCCGCCAAAAACCTGGGAAGAGATCCCGGCGCTGGATAAAGAACTGAAAGCGA

148 L P N P P K T W E E I P A L D K E L K A

2161 AAGGTAAGAGCGCGCTGATGTTCAACCTGCAAGAACCGTACTTCACCTGGCCGCTGATTG

168 K G K S A L M F N L Q E P Y F T W P L I

2221 CTGCTGACGGGGGTTATGCGTTCAAGTATGAAAACGGCAAGTACGACATTAAAGACGTGG

188 A A D G G Y A F K Y E N G K Y D I K D V

2281 GCGTGGATAACGCTGGCGCGAAAGCGGGTCTGACCTTCCTGGTTGACCTGATTAAAAACA

208 G V D N A G A K A G L T F L V D L I K N

2341 AACACATGAATGCAGACACCGATTACTCCATCGCAGAAGCTGCCTTTAATAAAGGCGAAA

228 K H M N A D T D Y S I A E A A F N K G E

2401 CAGCGATGACCATCAACGGCCCGTGGGCATGGTCCAACATCGACACCAGCAAAGTGAATT

248 T A M T I N G P W A W S N I D T S K V N

2461 ATGGTGTAACGGTACTGCCGACCTTCAAGGGTCAACCATCCAAACCGTTCGTTGGCGTGC

268 Y G V T V L P T F K G Q P S K P F V G V

2521 TGAGCGCAGGTATTAACGCCGCCAGTCCGAACAAAGAGCTGGCGAAAGAGTTCCTCGAAA

288 L S A G I N A A S P N K E L A K E F L E

2581 ACTATCTGCTGACTGATGAAGGTCTGGAAGCGGTTAATAAAGACAAACCGCTGGGTGCCG

308 N Y L L T D E G L E A V N K D K P L G A

2641 TAGCGCTGAAGTCTTACGAGGAAGAGTTGGCGAAAGATCCACGTATTGCCGCCACCATGG

328 V A L K S Y E E E L A K D P R I A A T M

Factor Xa PstI
2701 AAAACGCCCAGTCCGCTTTCTGGTATGCCGTGCGTATCGAAGCCCGCCTGCAGGCCTCGG

348 E N A Q S A F W Y A V R I E A R L Q A S

SalI XbaI +2 trxA (2-109 del 103-107)
2761 TCGACGCCGAATCTAGAAGCGATAAAATTATTCACCTGACTGACGACAGTTTTGACACGG

368 V D A E S R S D K I I H L T D D S F D T

2821 ATGTACTCAAAGCGGACGGGGCGATCCTCGTCGATTTCTGGGCAGAGTGGTGCGGTCCGT

388 D V L K A D G A I L V D F W A E W C G P

2881 GCAAAATGATCGCCCCGATTCTGGATGAAATCGCTGACGAATATCAGGGCAAACTGACCG

408 C K M I A P I L D E I A D E Y Q G K L T

2941 TTGCAAAACTGAACATCGATCAAAACCCTGGCACTGCGCCGAAATATGGCATCCGTGGTA

428 V A K L N I D Q N P G T A P K Y G I R G

3001 TCCCGACTCTGCTGCTGTTCAAAAACGGTGAAGTGGCGGCAACCAAAGTGGGTGCACTGT

448 I P T L L L F K N G E V A A T K V G A L

FLAG
3061 CTAAAGGTCAGTTGAAAGAGAACCTGGCGGATTATAAAGATGACGATGACAAATAATAAG

468 S K G Q L K E N L A D Y K D D D D K

Lost XbaI
      CTAGAGG (transcriptional stop)
``` pMPX-71::malE(1-370 del 354-364)::FXa::PstI, SalI, XbaI::TrxA(1-109 del 103-107)::FLAG Arabinose inducible, clone into PstI, SalI, XbaI Made by cutting TOPO NsiI-malE (1-370 del 354-364)::FXa::PstI, SalI, XbaI:FLAG-NheI insertion with NsiI & XbaI and cloning into pMPX-79 cut with PstI & XbaI.

SEQ ID NO.: 284 pMPX-92 MalE (1-370 del 354-364) MCS TrxA (2-109 del 103-107) fusion vector

SD Lost PstI+1 malE (1-370 del 354-364)

```
         AGGAGGTTCTGCATATGAAAATAAAAACAGGTGCAC
   1                 M  K  I  K  T  G  A
         GCATCCTCGCATTATCCGCATTAACGACGATGATGTTTTCCGCCTCGGCTCTCGCCAAAA
   8      R  I  L  A  L  S  A  L  T  T  M  M  F  S  A  S  A  L  A  K
         TCGAAGAAGGTAAACTGGTAATCTGGATTAACGGCGATAAAGGCTATAACGGTCTCGCTG
  28      I  E  E  G  K  L  V  I  W  I  N  G  D  K  G  Y  N  G  L  A
         AAGTCGGTAAGAAATTCGAGAAAGATACCGGAATTAAAGTCACCGTTGAGCATCCGGATA
  48      E  V  G  K  K  F  E  K  D  T  G  I  K  V  T  V  E  H  P  D
         AACTGGAAGAGAAATTCCCACAGGTTGCGGCAACTGGCGATGGCCCTGACATTATCTTCT
  68      K  L  E  E  K  F  P  Q  V  A  A  T  G  D  G  P  D  I  I  F
         GGGCACACGACCGCTTTGGTGGCTACGCTCAATCTGGCCTGTTGGCTGAAATCACCCCGG
  88      W  A  H  D  R  F  G  G  Y  A  Q  S  G  L  L  A  E  I  T  P
         ACAAAGCGTTCCAGGACAAGCTGTATCCGTTTACCTGGGATGCCGTACGTTACAACGGCA
 108      D  K  A  F  Q  D  K  L  Y  P  F  T  W  D  A  V  R  Y  N  G
         AGCTGATTGCTTACCCGATCGCTGTTGAAGCGTTATCGCTGATTTATAACAAAGATCTGC
 128      K  L  I  A  Y  P  I  A  V  E  A  L  S  L  I  Y  N  K  D  L
         TGCCGAACCCGCCAAAAACCTGGGAAGAGATCCCGGCGCTGGATAAAGAACTGAAAGCGA
 148      L  P  N  P  P  K  T  W  E  E  I  P  A  L  D  K  E  L  K  A
         AAGGTAAGAGCGCGCTGATGTTCAACCTGCAAGAACCGTACTTCACCTGGCCGCTGATTG
 168      K  G  K  S  A  L  M  F  N  L  Q  E  P  Y  F  T  W  P  L  I
         CTGCTGACGGGGGTTATGCGTTCAAGTATGAAAACGGCAAGTACGACATTAAAGACGTGG
 188      A  A  D  G  G  Y  A  F  K  Y  E  N  G  K  Y  D  I  K  D  V
         GCGTGGATAACGCTGGCGCGAAAGCGGGTCTGACCTTCCTGGTTGACCTGATTAAAAACA
 208      G  V  D  N  A  G  A  K  A  G  L  T  F  L  V  D  L  I  K  N
2341     AACACATGAATGCAGACACCGATTACTCCATCGCAGAAGCTGCCTTTAATAAAGGCGAAA
 228      K  H  M  N  A  D  T  D  Y  S  I  A  E  A  A  F  N  K  G  E
2401     CAGCGATGACCATCAACGGCCCGTGGGCATGGTCCAACATCGACACCAGCAAAGTGAATT
 248      T  A  M  T  I  N  G  P  W  A  W  S  N  I  D  T  S  K  V  N
2461     ATGGTGTAACGGTACTGCCGACCTTCAAGGGTCAACCATCCAAACCGTTCGTTGGCGTGC
 268      Y  G  V  T  V  L  P  T  F  K  G  Q  P  S  K  P  F  V  G  V
2521     TGAGCGCAGGTATTAACGCCGCCAGTCCGAACAAAGAGCTGGCGAAAGAGTTCCTCGAAA
 288      L  S  A  G  I  N  A  A  S  P  N  K  E  L  A  K  E  F  L  E
2581     ACTATCTGCTGACTGATGAAGGTCTGGAAGCGGTTAATAAAGACAAACCGCTGGGTGCCG
 308      N  Y  L  L  T  D  E  G  L  E  A  V  N  K  D  K  P  L  G  A
2641     TAGCGCTGAAGTCTTACGAGGAAGAGTTGGCGAAAGATCCACGTATTGCCGCCACCATGG
 328      V  A  L  K  S  Y  E  E  E  L  A  K  D  P  R  I  A  A  T  M
                                                       Factor Xa PstI
```

```
2701 AAAACGCCCAGTCCGCTTTCTGGTATGCCGTGCGTATCGAAGCCCGCCTGCAGGCCTCGG

348    E  N  A  Q  S  A  F  W  Y  A  V  R  I  E  A  R  L  Q  A  S

SalI XbaI +2 trxA (2-109 del 103-107)
2761 TCGACGCCGAATCTAGAAGCGATAAAATTATTCACCTGACTGACGACAGTTTTGACACGG

368    V  D  A  E  S  R  S  D  K  I  I  H  L  T  D  D  S  F  D  T

2821 ATGTACTCAAAGCGGACGGGGCGATCCTCGTCGATTTCTGGGCAGAGTGGTGCGGTCCGT

388    D  V  L  K  A  D  G  A  I  L  V  D  F  W  A  E  W  C  G  P

2881 GCAAAATGATCGCCCCGATTCTGGATGAAATCGCTGACGAATATCAGGGCAAACTGACCG

408    C  K  M  I  A  P  I  L  D  E  I  A  D  E  Y  Q  G  K  L  T

2941 TTGCAAAACTGAACATCGATCAAAACCCTGGCACTGCGCCGAAATATGGCATCCGTGGTA

428    V  A  K  L  N  I  D  Q  N  P  G  T  A  P  K  Y  G  I  R  G

3001 TCCCGACTCTGCTGCTGTTCAAAAACGGTGAAGTGGCGGCAACCAAAGTGGGTGCACTGT

448    I  P  T  L  L  L  F  K  N  G  E  V  A  A  T  K  V  G  A  L
                                                              FLAG
3061 CTAAAGGTCAGTTGAAAGAGAACCTGGCGGATTATAAAGATGACGATGACAAATAATAAG

468    S  K  G  Q  L  K  E  N  L  A  D  Y  K  D  D  D  D  K

Lost XbaI
          CTAGAGGTACC (transcriptional stop)
``` pMPX-84::malE(1-370 del 354-364)::FXa::PstI, SalI, XbaI::TrxA(1-109 del 103-107)::FLAG Temperature inducible, clone into PstI, SalI, XbaI
Made by cutting TOPO NsiI-malE (1-370 del 354-364)::FXa::PstI, SalI, XbaI::FLAG-NheI insertion with NsiI & XbaI and cloning into pMPX-90 cut with PstI & XbaI .

SEQ ID NO.: 285 pMPX-97 MalE (1-370 del 354-364) MCS TrxA (2-109 del 103-107) fusion vector

SD Lost PstI+1 malE (1-370 del 354-364)

```
         AGGAGGTTCTGCATATGAAAATAAAAACAGGTGCAC
   1                  M  K  I  K  T  G  A

GCATCCTCGCATTATCCGCATTAACGACGATGATGTTTTCCGCCTCGGCTCTCGCCAAAA
   8     R  I  L  A  L  S  A  L  T  T  M  M  F  S  A  S  A  L  A  K

TCGAAGAAGGTAAACTGGTAATCTGGATTAACGGCGATAAAGGCTATAACGGTCTCGCTG
  28     I  E  E  G  K  L  V  I  W  I  N  G  D  K  G  Y  N  G  L  A

AAGTCGGTAAGAAATTCGAGAAAGATACCGGAATTAAAGTCACCGTTGAGCATCCGGATA
  48     E  V  G  K  K  F  E  K  D  T  G  I  K  V  T  V  E  H  P  D

AACTGGAAGAGAAATTCCCACAGGTTGCGGCAACTGGCGATGGCCCTGACATTATCTTCT
  68     K  L  E  E  K  F  P  Q  V  A  A  T  G  D  G  P  D  I  I  F

GGGCACACGACCGCTTTGGTGGCTACGCTCAATCTGGCCTGTTGGCTGAAATCACCCCGG
  88     W  A  H  D  R  F  G  G  Y  A  Q  S  G  L  L  A  E  I  T  P

ACAAAGCGTTCCAGGACAAGCTGTATCCGTTTACCTGGGATGCCGTACGTTACAACGGCA
 108     D  K  A  F  Q  D  K  L  Y  P  F  T  W  D  A  V  R  Y  N  G

AGCTGATTGCTTACCCGATCGCTGTTGAAGCGTTATCGCTGATTTATAACAAAGATCTGC
 128     K  L  I  A  Y  P  I  A  V  E  A  L  S  L  I  Y  N  K  D  L

TGCCGAACCCGCCAAAAACCTGGGAAGAGATCCCGGCGCTGGATAAAGAACTGAAAGCGA
 148     L  P  N  P  P  K  T  W  E  E  I  P  A  L  D  K  E  L  K  A

AAGGTAAGAGCGCGCTGATGTTCAACCTGCAAGAACCGTACTTCACCTGGCCGCTGATTG
```

```
                               -continued
168   K G K S A L M F N L Q E P Y F T W P L I

CTGCTGACGGGGGTTATGCGTTCAAGTATGAAAACGGCAAGTACGACATTAAAGACGTGG

188   A A D G G Y A F K Y E N G K Y D I K D V

GCGTGGATAACGCTGGCGCGAAAGCGGGTCTGACCTTCCTGGTTGACCTGATTAAAAACA

208   G V D N A G A K A G L T F L V D L I K N

2341  AACACATGAATGCAGACACCGATTACTCCATCGCAGAAGCTGCCTTTAATAAAGGCGAAA

228   K H M N A D T D Y S I A E A A F N K G E

2401  CAGCGATGACCATCAACGGCCCGTGGGCATGGTCCAACATCGACACCAGCAAAGTGAATT

248   T A M T I N G P W A W S N I D T S K V N

2461  ATGGTGTAACGGTACTGCCGACCTTCAAGGGTCAACCATCCAAACCGTTCGTTGGCGTGC

268   Y G V T V L P T F K G Q P S K P F V G V

2521  TGAGCGCAGGTATTAACGCCGCCAGTCCGAACAAAGAGCTGGCGAAAGAGTTCCTCGAAA

288   L S A G I N A A S P N K E L A K E F L E

2581  ACTATCTGCTGACTGATGAAGGTCTGGAAGCGGTTAATAAAGACAAACCGCTGGGTGCCG

308   N Y L L T D E G L E A V N K D K P L G A

2641  TAGCGCTGAAGTCTTACGAGGAAGAGTTGGCGAAAGATCCACGTATTGCCGCCACCATGG

328   V A L K S Y E E E L A K D P R I A A T M

Factor Xa    PstI
2701  AAAACGCCCAGTCCGCTTTCTGGTATGCCGTGCGTATCGAAGCCCGCCTGCAGGCCTCGG

348   E N A Q S A F W Y A V R I E A R L Q A S

SalI    XbaI  +2    trxA (2-109 del 103-107)
2761  TCGACGCCGAATCTAGAAGCGATAAAATTATTCACCTGACTGACGACAGTTTTGACACGG

368   V D A E S R S D K I I H L T D D S F D T

2821  ATGTACTCAAAGCGGACGGGGCGATCCTCGTCGATTTCTGGGCAGAGTGGTGCGGTCCGT

388   D V L K A D G A I L V D F W A E W C G P

2881  GCAAAATGATCGCCCCGATTCTGGATGAAATCGCTGACGAATATCAGGGCAAACTGACCG

408   C K M I A P I L D E I A D E Y Q G K L T

2941  TTGCAAAACTGAACATCGATCAAAACCCTGGCACTGCGCCGAAATATGGCATCCGTGGTA

428   V A K L N I D Q N P G T A P K Y G I R G

3001  TCCCGACTCTGCTGCTGTTCAAAAACGGTGAAGTGGCGGCAACCAAAGTGGGTGCACTGT

448   I P T L L L F K N G E V A A T K V G A L

FLAG
3061  CTAAAGGTCAGTTGAAAGAGAACCTGGCGGATTATAAAGATGACGATGACAAATAATAAG

468   S K G Q L K E N L A D Y K D D D D K

Lost XbaI
       CTAGAGGTACC (transcriptional stop)
``` pMPX-86::malE(1-370 del 354-364)::FXa::PstI, SalI, XbaI::TrxA(1-109 del 103-107)::FLAG Temperature inducible, clone into PstI, SalI, XbaI Made by cutting TOPO NsiI-malE (1-370 del 354-364)::FXa::PstI, SalI, XbaI::FLAG-NheI insertion with NsiI & XbaI and cloning into pMPX-95 cut with PstI & XbaI.

SEQ ID NO.: 151
pMPX-67 rhamnose-inducible expression vector

```
   1   TCGCGCGTTT CGGTGATGAC GGTGAAAACC TCTGACACAT GCAGCTCCCG GAGACGGTCA
  61   CAGCTTGTCT GTAAGCGGAT GCCGGGAGCA GACAAGCCCG TCAGGGCGCG TCAGCGGGTG
 121   TTGGCGGGTG TCGGGGCTGG CTTAACTATG CGGCATCAGA GCAGATTGTA CTGAGAGTGC
 181   ACCATATGCG GTGTGAAATA CCGCACAGAT GCGTAAGGAG AAAATACCGC ATCAGGCGCC
 241   ATTCGCCATT CAGGCTGCGC AACTGTTGGG AAGGGCGATC GGTGCGGGCC TCTTCGCTAT
 301   TACGCCAGCT GGCGAAAGGG GGATGTGCTG CAAGGCGATT AAGTTGGGTA ACGCCAGGGT
```

```
                                                                Stop rhaR
 361   TTTCCCAGTC ACGACGTTGT AAAACGACGG CCAGTGCCAA GCTTAATTAA TCTTTCTGCG
                                                           HindIII
```

```
 421   AATTGAGATG ACGCCACTGG CTGGGCGTCA TCCCGGTTTC CCGGGTAAAC ACCACCGAAA
 481   AATAGTTACT ATCTTCAAAG CCACATTCGG TCGAAATATC ACTGATTAAC AGGCGGCTAT
 541   GCTGGAGAAG ATATTGCGCA TGACACACTC TGACCTGTCG CAGATATTGA TTGATGGTCA
 601   TTCCAGTCTG CTGGCGAAAT TGCTGACGCA AAACGCGCTC ACTGCACGAT GCCTCATCAC
 661   AAAATTTATC CAGCGCAAAG GGACTTTTCA GGCTAGCCGC CAGCCGGGTA ATCAGCTTAT
 721   CCAGCAACGT TTCGCTGGAT GTTGGCGGCA ACGAATCACT GGTGTAACGA TGGCGATTCA
 781   GCAACATCAC CAACTGCCCG AACAGCAACT CAGCCATTTC GTTAGCAAAC GGCACATGCT
 841   GACTACTTTC ATGCTCAAGC TGACCGATAA CCTGCCGCGC TGCGCCATC CCCATGCTAC
 901   CTAAGCGCCA GTGTGGTTGC CCTGCGCTGG CGTTAAATCC CGGAATCGCC CCCTGCCAGT
 961   CAAGATTCAG CTTCAGACGC TCCGGGCAAT AAATAATATT CTGCAAAACC AGATCGTTAA
1021   CGGAAGCGTA GGAGTGTTTA TCGTCAGCAT GAATGTAAAA GAGATCGCCA CGGGTAATGC
1081   GATAAGGGCG ATCGTTGAGT ACATGCAGGC CATTACCGCG CCAGACAATC ACCAGCTCAC
1141   AAAAATCATG TGTATGTTCA GCAAAGACAT CTTGCGGATA ACGGTCAGCC ACAGCGACTG
1201   CCTGCTGGTC GCTGGCAAAA AAATCATCTT TGAGAAGTTT TAACTGATGC GCCACCGTGG
1261   CTACCTCGGC CAGAGAACGA AGTTGATTAT TCGCAATATG GCGTACAAAT ACGTTGAGAA
```

```
           Stop rhaS      Start rhaR
1321   GATTCGCGTT ATTGCAGAAA GCCATCCCGT CCCTGGCGAA TATCACGCGG TGACCAGTTA
                          <--
```

```
1381   AACTCTCGGC GAAAAAGCGT CGAAAAGTGG TTACTGTCGC TGAATCCACA GCGATAGGCG
1441   ATGTCAGTAA CGCTGGCCTC GCTGTGGCGT AGCAGATGTC GGGCTTTCAT CAGTCGCAGG
1501   CGGTTCAGGT ATCGCTGAGG CGTCAGTCCC GTTTGCTGCT TAAGCTGCCG ATGTAGCGTA
1561   CGCAGTGAAA GAGAAAATTG ATCCGCCACG GCATCCCAAT TCACCTCATC GGCAAAATGG
1621   TCCTCCAGCC AGGCCAGAAG CAAGTTGAGA CGTGATGCGC TGTTTTCCAG GTTCTCCTGC
1681   AAACTGCTTT TACGCAGCAA GAGCAGTAAT TGCATAAACA AGATCTCGCG ACTGGCGGTC
1741   GAGGGTAAAT CATTTTCCCC TTCCTGCTGT TCCATCTGTG CAACCAGCTG TCGCACCTGC
1801   TGCAATACGC TGTGGTTAAC GCGCCAGTGA GACGGATACT GCCCATCCAG CTCTTGTGGC
1861   AGCAACTGAT TCAGCCCGGC GAGAAACTGA ATCGATCCG GCGAGCGATA CAGCACATTG
1921   GTCAGACACA GATTATCGGT ATGTTCATAC AGATGCCGAT CATGATCGCG TACGAAACAG
1981   ACCGTGCCAC CGGTGATGGT ATAGGGCTGC CCATTAAACA CATGAATACC CGTGCCATGT
2041   TCGACAATCA CAATTTCATG AAAATCATGA TGATGTTCAG GAAATCCGC CTGCGGGAGC
2101   CGGGGTTCTA TCGCCACGGA CGCGTTACCA GACGGAAAAA AATCCACACT ATGTAATACG
```

```
       Start rhaS
```

```
2161 GTCATACTGG CCTCCTGATG TCGTCAACAC GGCGAAATAG TAATCACGAG GTCAGGTTCT
     <--
2221 TACCTTAAAT TTTCGACGGA AAACCACGTA AAAAACGTCG ATTTTTCAAG ATACAGCGTG
2281 AATTTTCAGG AAATGCGGTG AGCATCACAT CACCACAATT CAGCAAATTG TGAACATCAT
2341 CACGTTCATC TTTCCCTGGT TGCCAATGGC CCATTTTCCT GTCAGTAACG AGAAGGTCGC
                                                  SD         SalI       XbaI
2401 GAATTCAGGC GCTTTTTAGA CTGGTCGTAA TGAAATTCAG GAGGTTGTCG ACTCTAGAGG
     Stem-loop                      KpnI
2461 ATCCCCGCGC CCTCATCCGA AAGGGCGTAT TGGTACCGAG CTCGAATTCG TAATCATGGT
2521 CATAGCTGTT TCCTGTGTGA AATTGTTATC CGCTCACAAT TCCACACAAC ATACGAGCCG
2581 GAAGCATAAA GTGTAAAGCC TGGGGTGCCT AATGAGTGAG CTAACTCACA TTAATTGCGT
2641 TGCGCTCACT GCCCGCTTTC CAGTCGGGAA ACCTGTCGTG CCAGCTGCAT AATGAATCG
2701 GCCAACGCGC GGGGAGAGGC GGTTTGCGTA TTGGGCGCTC TTCCGCTTCC TCGCTCACTG
2761 ACTCGCTGCG CTCGGTCGTT CGGCTGCGGC GAGCGGTATC AGCTCACTCA AAGGCGGTAA
2821 TACGGTTATC CACAGAATCA GGGGATAACG CAGGAAAGAA CATGTGAGCA AAAGGCCAGC
2881 AAAAGGCCAG GAACCGTAAA AAGGCCGCGT TGCTGGCGTT TTTCCATAGG CTCCGCCCCC
2941 CTGACGAGCA TCACAAAAAT CGACGCTCAA GTCAGAGGTG GCGAAACCCG ACAGGACTAT
3001 AAAGATACCA GGCGTTTCCC CCTGGAAGCT CCCTCGTGCG CTCTCCTGTT CCGACCCTGC
3061 CGCTTACCGG ATACCTGTCC GCCTTTCTCC CTTCGGGAAG CGTGGCGCTT TCTCATAGCT
3121 CACGCTGTAG GTATCTCAGT TCGGTGTAGG TCGTTCGCTC CAAGCTGGGC TGTGTGCACG
3181 AACCCCCCGT TCAGCCCGAC CGCTGCGCCT TATCCGGTAA CTATCGTCTT GAGTCCAACC
3241 CGGTAAGACA CGACTTATCG CCACTGGCAG CAGCCACTGG TAACAGGATT AGCAGAGCGA
3301 GGTATGTAGG CGGTGCTACA GAGTTCTTGA AGTGGTGGCC TAACTACGGC TACACTAGAA
3361 GGACAGTATT TGGTATCTGC GCTCTGCTGA AGCCAGTTAC CTTCGGAAAA AGAGTTGGTA
3421 GCTCTTGATC CGGCAAACAA ACCACCGCTG GTAGCGGTGG TTTTTTTGTT TGCAAGCAGC
3481 AGATTACGCG CAGAAAAAAA GGATCTCAAG AAGATCCTTT GATCTTTTCT ACGGGGTCTG
3541 ACGCTCAGTG GAACGAAAAC TCACGTTAAG GGATTTTGGT CATGAGATTA TCAAAAAGGA
3601 TCTTCACCTA GATCCTTTTA AATTAAAAAT GAAGTTTTAA ATCAATCTAA AGTATATATG
3661 AGTAAACTTG GTCTGACAGT TACCAATGCT TAATCAGTGA GGCACCTATC TCAGCGATCT
3721 GTCTATTTCG TTCATCCATA GTTGCCTGAC TCCCCGTCGT GTAGATAACT ACGATACGGG
3781 AGGGCTTACC ATCTGGCCCC AGTGCTGCAA TGATACCGCG AGACCCACGC TCACCGGCTC
3841 CAGATTTATC AGCAATAAAC CAGCCAGCCG GAAGGGCCGA GCGCAGAAGT GGTCCTGCAA
3901 CTTTATCCGC CTCCATCCAG TCTATTAATT GTTGCCGGGA AGCTAGAGTA AGTAGTTCGC
3961 CAGTTAATAG TTTGCGCAAC GTTGTTGCCA TTGCTACAGG CATCGTGGTG TCACGCTCGT
4021 CGTTTGGTAT GGCTTCATTC AGCTCCGGTT CCCAACGATC AAGGCGAGTT ACATGATCCC
4081 CCATGTTGTG CAAAAAAGCG GTTAGCTCCT TCGGTCCTCC GATCGTTGTC AGAAGTAAGT
4141 TGGCCGCAGT GTTATCACTC ATGGTTATGG CAGCACTGCA TAATTCTCTT ACTGTCATGC
4201 CATCCGTAAG ATGCTTTTCT GTGACTGGTG AGTACTCAAC CAAGTCATTC TGAGAATAGT
4261 GTATGCGGCG ACCGAGTTGC TCTTGCCCGG CGTCAATACG GGATAATACC GCGCCACATA
4321 GCAGAACTTT AAAAGTGCTC ATCATTGGAA AACGTTCTTC GGGGCGAAAA CTCTCAAGGA
4381 TCTTACCGCT GTTGAGATCC AGTTCGATGT AACCCACTCG TGCACCCAAC TGATCTTCAG
4441 CATCTTTTAC TTTCACCAGC GTTTCTGGGT GAGCAAAAAC AGGAAGGCAA AATGCCGCAA
```

```
4501  AAAAGGGAAT AAGGGCGACA CGGAAATGTT GAATACTCAT ACTCTTCCTT TTTCAATATT

4561  ATTGAAGCAT TTATCAGGGT TATTGTCTCA TGAGCGGATA CATATTTGAA TGTATTTAGA

4621  AAAATAAACA AATAGGGGTT CCGCGCACAT TTCCCCGAAA AGTGCCACCT GACGTCTAAG

4681  AAACCATTAT TATCATGACA TTAACCTATA AAAATAGGCG TATCACGAGG CCCTTTCGTC
```

The segment rhaR through Prha was taken from the *E. coli* chromosome using PCR added HindIII and modified aligned 10 Shine-Delgarno (SD) sequence with SalI followed by XbaI, a stem-loop transcriptional stop sequence, and KpnI. The PCR product was cloned into pUC18 using HindIII and KpnI.
SEQ ID NO.: 152
pMPX-72 rhamnose-inducible expression vector

```
   1  TCGCGCGTTT CGGTGATGAC GGTGAAAACC TCTGACACAT GCAGCTCCCG GAGACGGTCA

61  CAGCTTGTCT GTAAGCGGAT GCCGGGAGCA GACAAGCCCG TCAGGGCGCG TCAGCGGGTG

121  TTGGCGGGTG TCGGGGCTGG CTTAACTATG CGGCATCAGA GCAGATTGTA CTGAGAGTGC

181  ACCATATGCG GTGTGAAATA CCGCACAGAT GCGTAAGGAG AAAATACCGC ATCAGGCGCC

241  ATTCGCCATT CAGGCTGCGC AACTGTTGGG AAGGGCGATC GGTGCGGGCC TCTTCGCTAT

301  TACGCCAGCT GGCGAAAGGG GGATGTGCTG CAAGGCGATT AAGTTGGGTA ACGCCAGGGT

Stop rhaR
 361  TTTCCCAGTC ACGACGTTGT AAAACGACGG CCAGTGCCAA GCTTAATTAA TCTTTCTGCG
                                                     HindIII

421  AATTGAGATG ACGCCACTGG CTGGGCGTCA TCCCGGTTTC CCGGGTAAAC ACCACCGAAA

481  AATAGTTACT ATCTTCAAAG CCACATTCGG TCGAAATATC ACTGATTAAC AGGCGGCTAT

541  GCTGGAGAAG ATATTGCGCA TGACACACTC TGACCTGTCG CAGATATTGA TTGATGGTCA

601  TTCCAGTCTG CTGGCGAAAT TGCTGACGCA AAACGCGCTC ACTGCACGAT GCCTCATCAC

661  AAAATTTATC CAGCGCAAAG GGACTTTTCA GGCTAGCCGC CAGCCGGGTA ATCAGCTTAT

721  CCAGCAACGT TTCGCTGGAT GTTGGCGGCA ACGAATCACT GGTGTAACGA TGGCGATTCA

781  GCAACATCAC CAACTGCCCG AACAGCAACT CAGCCATTTC GTTAGCAAAC GGCACATGCT

841  GACTACTTTC ATGCTCAAGC TGACCGATAA CCTGCCGCGC CTGCGCCATC CCATGCTAC

901  CTAAGCGCCA GTGTGGTTGC CCTGCGCTGG CGTTAAATCC CGGAATCGCC CCCTGCCAGT

961  CAAGATTCAG CTTCAGACGC TCCGGGCAAT AAATAATATT CTGCAAAACC AGATCGTTAA

1021  CGGAAGCGTA GGAGTGTTTA TCGTCAGCAT GAATGTAAAA GAGATCGCCA CGGGTAATGC

1081  GATAAGGGCG ATCGTTGAGT ACATGCAGGC CATTACCGCG CCAGACAATC ACCAGCTCAC

1141  AAAAATCATG TGTATGTTCA GCAAAGACAT CTTGCGGATA ACGGTCAGCC ACAGCGACTG

1201  CCTGCTGGTC GCTGGCAAAA AAATCATCTT TGAGAAGTTT TAACTGATGC GCCACCGTGG

1261  CTACCTCGGC CAGAGAACGA AGTTGATTAT TCGCAATATG GCGTACAAAT ACGTTGAGAA

Stop rhaS       Start rhaR
1321  GATTCGCGTT ATTGCAGAAA GCCATCCCGT CCCTGGCGAA TATCACGCGG TGACCAGTTA
                           <--

1381  AACTCTCGGC GAAAAAGCGT CGAAAAGTGG TTACTGTCGC TGAATCCACA GCGATAGGCG

1441  ATGTCAGTAA CGCTGGCCTC GCTGTGGCGT AGCAGATGTC GGGCTTTCAT CAGTCGCAGG

1501  CGGTTCAGGT ATCGCTGAGG CGTCAGTCCC GTTTGCTGCT TAAGCTGCCG ATGTAGCGTA

1561  CGCAGTGAAA GAGAAAATTG ATCCGCCACG GCATCCCAAT TCACCTCATC GGCAAAATGG

1621  TCCTCCAGCC AGGCCAGAAG CAAGTTGAGA CGTGATGCGC TGTTTTCCAG GTTCTCCTGC

1681  AAACTGCTTT TACGCAGCAA GAGCAGTAAT TGCATAAACA AGATCTCGCG ACTGGCGGTC
```

```
                                            -continued
1741    GAGGGTAAAT CATTTTCCCC TTCCTGCTGT TCCATCTGTG CAACCAGCTG TCGCACCTGC

1801    TGCAATACGC TGTGGTTAAC GCGCCAGTGA GACGGATACT GCCCATCCAG CTCTTGTGGC

1861    AGCAACTGAT TCAGCCCGGC GAGAAACTGA AATCGATCCG GCGAGCGATA CAGCACATTG

1921    GTCAGACACA GATTATCGGT ATGTTCATAC AGATGCCGAT CATGATCGCG TACGAAACAG

1981    ACCGTGCCAC CGGTGATGGT ATAGGGCTGC CCATTAAACA CATGAATACC CGTGCCATGT

2041    TCGACAATCA CAATTTCATG AAAATCATGA TGATGTTCAG GAAATCCGC CTGCGGGAGC

2101    CGGGGTTCTA TCGCCACGGA CGCGTTACCA GACGGAAAAA AATCCACACT ATGTAATACG

Start rhaS
2161    GTCATACTGG CCTCCTGATG TCGTCAACAC GGCGAAATAG TAATCACGAG GTCAGGTTCT
        <--

2221    TACCTTAAAT TTTCGACGGA AAACCACGTA AAAACGTCG ATTTTTCAAG ATACAGCGTG

2281    AATTTTCAGG AAATGCGGTG AGCATCACAT CACCACAATT CAGCAAATTG TGAACATCAT

2341    CACGTTCATC TTTCCCTGGT TGCCAATGGC CCATTTTCCT GTCAGTAACG AGAAGGTCGC

SD       PstI     SalI
2401    GAATTCAGGC GCTTTTTAGA CTGGTCGTAA TGAAATTCAG GAGGTTCTGC AGGTCGACTC

XbaI           Stem-loop              KpnI
2461    TAGAGGATCC CCGCGCCCTC ATCCGAAAGG GCGTATTGGT ACCGAGCTCG AATTCGTAAT

2521    CATGGTCATA GCTGTTTCCT GTGTGAAATT GTTATCCGCT CACAATTCCA CACAACATAC

2581    GAGCCGGAAG CATAAAGTGT AAAGCCTGGG GTGCCTAATG AGTGAGCTAA CTCACATTAA

2641    TTGCGTTGCG CTCACTGCCC GCTTTCCAGT CGGGAAACCT GTCGTGCCAG CTGCATTAAT

2701    GAATCGGCCA ACGCGCGGGG AGAGGCGGTT TGCGTATTGG GCGCTCTTCC GCTTCCTCGC

2761    TCACTGACTC GCTGCGCTCG GTCGTTCGGC TGCGGCGAGC GGTATCAGCT CACTCAAAGG

2821    CGGTAATACG GTTATCCACA GAATCAGGGG ATAACGCAGG AAAGAACATG TGAGCAAAAG

2881    GCCAGCAAAA GGCCAGGAAC CGTAAAAAGG CCGCGTTGCT GGCGTTTTTC CATAGGCTCC

2941    GCCCCCCTGA CGAGCATCAC AAAAATCGAC GCTCAAGTCA GAGGTGGCGA AACCCGACAG

3001    GACTATAAAG ATACCAGGCG TTTCCCCCTG GAAGCTCCCT CGTGCGCTCT CCTGTTCCGA

3061    CCCTGCCGCT TACCGGATAC CTGTCCGCCT TTCTCCCTTC GGGAAGCGTG GCGCTTTCTC

3121    ATAGCTCACG CTGTAGGTAT CTCAGTTCGG TGTAGGTCGT TCGCTCCAAG CTGGGCTGTG

3181    TGCACGAACC CCCCGTTCAG CCCGACCGCT GCGCCTTATC CGGTAACTAT CGTCTTGAGT

3241    CCAACCCGGT AAGACACGAC TTATCGCCAC TGGCAGCAGC CACTGGTAAC AGGATTAGCA

3301    GAGCGAGGTA TGTAGGCGGT GCTACAGAGT TCTTGAAGTG GTGGCCTAAC TACGGCTACA

3361    CTAGAAGGAC AGTATTTGGT ATCTGCGCTC TGCTGAAGCC AGTTACCTTC GGAAAAAGAG

3421    TTGGTAGCTC TTGATCCGGC AAACAAACCA CCGCTGGTAG CGGTGGTTTT TTTGTTTGCA

3481    AGCAGCAGAT TACGCGCAGA AAAAAGGAT CTCAAGAAGA TCCTTTGATC TTTTCTACGG

3541    GGTCTGACGC TCAGTGGAAC GAAAACTCAC GTTAAGGGAT TTTGGTCATG AGATTATCAA

3601    AAAGGATCTT CACCTAGATC CTTTTAAATT AAAAATGAAG TTTAAATCA ATCTAAAGTA

3661    TATATGAGTA AACTTGGTCT GACAGTTACC AATGCTTAAT CAGTGAGGCA CCTATCTCAG

3721    CGATCTGTCT ATTTCGTTCA TCCATAGTTG CCTGACTCCC CGTCGTGTAG ATAACTACGA

3781    TACGGGAGGG CTTACCATCT GGCCCCAGTG CTGCAATGAT ACCGCGAGAC CCACGCTCAC

3841    CGGCTCCAGA TTTATCAGCA ATAAACCAGC CAGCCGGAAG GGCCGAGCGC AGAAGTGGTC

3901    CTGCAACTTT ATCCGCCTCC ATCCAGTCTA TTAATTGTTG CCGGGAAGCT AGAGTAAGTA

3961    GTTCGCCAGT TAATAGTTTG CGCAACGTTG TTGCCATTGC TACAGGCATC GTGGTGTCAC
```

```
4021  GCTCGTCGTT TGGTATGGCT TCATTCAGCT CCGGTTCCCA ACGATCAAGG CGAGTTACAT

4081  GATCCCCCAT GTTGTGCAAA AAAGCGGTTA GCTCCTTCGG TCCTCCGATC GTTGTCAGAA

4141  GTAAGTTGGC CGCAGTGTTA TCACTCATGG TTATGGCAGC ACTGCATAAT TCTCTTACTG

4201  TCATGCCATC CGTAAGATGC TTTTCTGTGA CTGGTGAGTA CTCAACCAAG TCATTCTGAG

4261  AATAGTGTAT GCGGCGACCG AGTTGCTCTT GCCCGGCGTC AATACGGGAT AATACCGCGC

4321  CACATAGCAG AACTTTAAAA GTGCTCATCA TTGGAAAACG TTCTTCGGGG CGAAAACTCT

4381  CAAGGATCTT ACCGCTGTTG AGATCCAGTT CGATGTAACC CACTCGTGCA CCCAACTGAT

4441  CTTCAGCATC TTTTACTTTC ACCAGCGTTT CTGGGTGAGC AAAAACAGGA AGGCAAAATG

4501  CCGCAAAAAA GGGAATAAGG GCGACACGGA AATGTTGAAT ACTCATACTC TTCCTTTTTC

4561  AATATTATTG AAGCATTTAT CAGGGTTATT GTCTCATGAG CGGATACATA TTTGAATGTA

4621  TTTAGAAAAA TAAACAAATA GGGGTTCCGC GCACATTTCC CCGAAAAGTG CCACCTGACG

4681  TCTAAGAAAC CATTATTATC ATGACATTAA CCTATAAAAA TAGGCGTATC ACGAGGCCCT

4741  TTCGTC
```

The segment rhaR through Prha was taken from the *E. coli* chromosome using PCR added HindIII and modified aligned Shine-Delgarno (SD) sequence with PstI followed by SalI, XbaI, a stem-loop transcriptional stop sequence, and KpnI. The PCR product was cloned into pUC18 using HindIII and KpnI.

SEQ ID NO.: 153 pMPX-66 arabinose-inducible expression vector

```
    1  TCGCGCGTTT CGGTGATGAC GGTGAAAACC TCTGACACAT GCAGCTCCCG GAGACGGTCA

61  CAGCTTGTCT GTAAGCGGAT GCCGGGAGCA GACAAGCCCG TCAGGGCGCG TCAGCGGGTG

121  TTGGCGGGTG TCGGGCTGG CTTAACTATG CGGCATCAGA GCAGATTGTA CTGAGAGTGC

181  ACCATATGCG GTGTGAAATA CCGCACAGAT GCGTAAGGAG AAAATACCGC ATCAGGCGCC

241  ATTCGCCATT CAGGCTGCGC AACTGTTGGG AAGGGCGATC GGTGCGGGCC TCTTCGCTAT

301  TACGCCAGCT GGCGAAAGGG GGATGTGCTG CAAGGCGATT AAGTTGGGTA ACGCCAGGGT

HindIII
  361  TTTCCCAGTC ACGACGTTGT AAAACGACGG CCAGTGCCAA GCTTCAAGCC GTCAATTGTC Stop araC
  421  TGATTCGTTA CCAATTATGA CAACTTGACG GCTACATCAT TCACTTTTTC TTCACAACCG

481  GCACGGAACT CGCTCGGGCT GGCCCCGGTG CATTTTTTAA ATACCCGCGA GAAATAGAGT

541  TGATCGTCAA AACCAACATT GCGACCGACG GTGGCGATAG GCATCCGGGT GGTGCTCAAA

601  AGCAGCTTCG CCTGGCTGAT ACGTTGGTCC TCGCGCCAGC TTAAGACGCT AATCCCTAAC

661  TGCTGGCGGA AAAGATGTGA CAGACGCGAC GGCGACAAGC AAACATGCTG TGCGACGCTG

721  GCGATATCAA AATTGCTGTC TGCCAGGTGA TCGCTGATGT ACTGACAAGC CTCGCGTACC

781  CGATTATCCA TCGGTGGATG GAGCGACTCG TTAATCGCTT CCATGCGCCG CAGTAACAAT

841  TGCTCAAGCA GATTTATCGC CAGCAGCTCC GAATAGCGCC CTTCCCCTTG CCCGGCGTTA

901  ATGATTTGCC CAAACAGGTC GCTGAAATGC GGCTGGTGCG CTTCATCCGG GCGAAAGAAC

961  CCCGTATTGG CAAATATTGA CGGCCAGTTA AGCCATTCAT GCCAGTAGGC GCGCGGACGA

1021  AAGTAAACCC ACTGGTGATA CCATTCGCGA GCCTCCGGAT GACGACCGTA GTGATGAATC

1081  TCTCCTGGCG GGAACAGCAA AATATCACCC GGTCGGCAAA CAAATTCTCG TCCCTGATTT

1141  TTCACCACCC CCTGACCGCG AATGGTGAGA TTGAGAATAT AACCTTTCAT TCCCAGCGGT

1201  CGGTCGATAA AAAATCGAG ATAACCGTTG GCCTCAATCG GCGTTAAACC CGCCACCAGA

1261  TGGGCATTAA ACGAGTATCC CGGCAGCAGG GGATCATTTT GCGCTTCAGC CATACTTTTC

Start araC
```

```
                                            -continued
1321  ATACTCCCGC CATTCAGAGA AGAAACCAAT TGTCCATATT GCATCAGACA TTGCCGTCAC
                                                 <--

1381  TGCGTCTTTT ACTGGCTCTT CTCGCTAACC AAACCGGTAA CCCCGCTTAT TAAAAGCATT

1441  CTGTAACAAA GCGGGACCAA AGCCATGACA AAAACGCGTA ACAAAAGTGT CTATAATCAC

1501  GGCAGAAAAG TCCACATTGA TTATTTGCAC GGCGTCACAC TTTGCTATGC CATAGCATTT

1561  TTATCCATAA GATTAGCGGA TCCTACCTGA CGCTTTTTAT CGCAACTCTC TACTGTTTCT

SD         SalI    XbaI
1621  CCATACCCGT TTTTTGGGC TAGCAGGAGG CCGTCGACTC TAGAGGATCC CCGCGCCCTC

Stem-loop         KpnI
1681  ATCCGAAAGG GCGTATTGGT ACCGAGCTCG AATTCGTAAT CATGGTCATA GCTGTTTCCT

1741  GTGTGAAATT GTTATCCGCT CACAATTCCA CACAACATAC GAGCCGGAAG CATAAAGTGT

1801  AAAGCCTGGG GTGCCTAATG AGTGAGCTAA CTCACATTAA TTGCGTTGCG CTCACTGCCC

1861  GCTTTCCAGT CGGGAAACCT GTCGTGCCAG CTGCATTAAT GAATCGGCCA ACGCGCGGGG

1921  AGAGGCGGTT TGCGTATTGG GCGCTCTTCC GCTTCCTCGC TCACTGACTC GCTGCGCTCG

1981  GTCGTTCGGC TGCGGCGAGC GGTATCAGCT CACTCAAAGG CGGTAATACG GTTATCCACA

2041  GAATCAGGGG ATAACGCAGG AAAGAACATG TGAGCAAAAG GCCAGCAAAA GGCCAGGAAC

2101  CGTAAAAAGG CCGCGTTGCT GGCGTTTTTC CATAGGCTCC GCCCCCCTGA CGAGCATCAC

2161  AAAAATCGAC GCTCAAGTCA GAGGTGGCGA AACCCGACAG GACTATAAAG ATACCAGGCG

2221  TTTCCCCCTG GAAGCTCCCT CGTGCGCTCT CCTGTTCCGA CCCTGCCGCT TACCGGATAC

2281  CTGTCCGCCT TTCTCCCTTC GGGAAGCGTG GCGCTTTCTC ATAGCTCACG CTGTAGGTAT

2341  CTCAGTTCGG TGTAGGTCGT TCGCTCCAAG CTGGGCTGTG TGCACGAACC CCCCGTTCAG

2401  CCCGACCGCT GCGCCTTATC CGGTAACTAT CGTCTTGAGT CCAACCCGGT AAGACACGAC

2461  TTATCGCCAC TGGCAGCAGC CACTGGTAAC AGGATTAGCA GAGCGAGGTA TGTAGGCGGT

2521  GCTACAGAGT TCTTGAAGTG GTGGCCTAAC TACGGCTACA CTAGAAGGAC AGTATTTGGT

2581  ATCTGCGCTC TGCTGAAGCC AGTTACCTTC GGAAAAAGAG TTGGTAGCTC TTGATCCGGC

2641  AAACAAACCA CCGCTGGTAG CGGTGGTTTT TTTGTTTGCA AGCAGCAGAT TACGCGCAGA

2701  AAAAAAGGAT CTCAAGAAGA TCCTTTGATC TTTTCTACGG GGTCTGACGC TCAGTGGAAC

2761  GAAAACTCAC GTTAAGGGAT TTTGGTCATG AGATTATCAA AAAGGATCTT CACCTAGATC

2821  CTTTTAAATT AAAAATGAAG TTTTAAATCA ATCTAAAGTA TATATGAGTA AACTTGGTCT

2881  GACAGTTACC AATGCTTAAT CAGTGAGGCA CCTATCTCAG CGATCTGTCT ATTTCGTTCA

2941  TCCATAGTTG CCTGACTCCC CGTCGTGTAG ATAACTACGA TACGGGAGGG CTTACCATCT

3001  GGCCCCAGTG CTGCAATGAT ACCGCGAGAC CCACGCTCAC CGGCTCCAGA TTTATCAGCA

3061  ATAAACCAGC CAGCCGGAAG GGCCGAGCGC AGAAGTGGTC CTGCAACTTT ATCCGCCTCC

3121  ATCCAGTCTA TTAATTGTTG CCGGGAAGCT AGAGTAAGTA GTTCGCCAGT TAATAGTTTG

3181  CGCAACGTTG TTGCCATTGC TACAGGCATC GTGGTGTCAC GCTCGTCGTT TGGTATGGCT

3241  TCATTCAGCT CCGGTTCCCA ACGATCAAGG CGAGTTACAT GATCCCCCAT GTTGTGCAAA

3301  AAAGCGGTTA GCTCCTTCGG TCCTCCGATC GTTGTCAGAA GTAAGTTGGC CGCAGTGTTA

3361  TCACTCATGG TTATGGCAGC ACTGCATAAT TCTCTTACTG TCATGCCATC CGTAAGATGC

3421  TTTTCTGTGA CTGGTGAGTA CTCAACCAAG TCATTCTGAG AATAGTGTAT GCGGCGACCG

3481  AGTTGCTCTT GCCCGGCGTC AATACGGGAT AATACCGCGC CACATAGCAG AACTTTAAAA

3541  GTGCTCATCA TTGGAAAACG TTCTTCGGGG CGAAAACTCT CAAGGATCTT ACCGCTGTTG

3601  AGATCCAGTT CGATGTAACC CACTCGTGCA CCCAACTGAT CTTCAGCATC TTTTACTTTC
```

-continued

```
3661 ACCAGCGTTT CTGGGTGAGC AAAAACAGGA AGGCAAAATG CCGCAAAAAA GGGAATAAGG

3721 GCGACACGGA AATGTTGAAT ACTCATACTC TTCCTTTTTC AATATTATTG AAGCATTTAT

3781 CAGGGTTATT GTCTCATGAG CGGATACATA TTTGAATGTA TTTAGAAAAA TAAACAAATA

3841 GGGGTTCCGC GCACATTTCC CCGAAAAGTG CCACCTGACG TCTAAGAAAC CATTATTATC

3901 ATGACATTAA CCTATAAAAA TAGGCGTATC ACGAGGCCCT TTCGTC
```

The segment araC through Para was taken from pBAD24 using PCR added HindIII and modified aligned Shine-Delgarno (SD) sequence with SalI followed by XbaI, a stem-loop transcriptional stop sequence, and KpnI. The PCR product was cloned into pUC18 using HindIII and KpnI.
SEQ ID NO.: 154
pMPX-71 arabinose-inducible expression vector

```
   1 TCGCGCGTTT CGGTGATGAC GGTGAAAACC TCTGACACAT GCAGCTCCCG GAGACGGTCA

61 CAGCTTGTCT GTAAGCGGAT GCCGGGAGCA GACAAGCCCG TCAGGGCGCG TCAGCGGGTG

121 TTGGCGGGTG TCGGGCTGG CTTAACTATG CGGCATCAGA GCAGATTGTA CTGAGAGTGC

181 ACCATATGCG GTGTGAAATA CCGCACAGAT GCGTAAGGAG AAAATACCGC ATCAGGCGCC

241 ATTCGCCATT CAGGCTGCGC AACTGTTGGG AAGGGCGATC GGTGCGGGCC TCTTCGCTAT

301 TACGCCAGCT GGCGAAAGGG GGATGTGCTG CAAGGCGATT AAGTTGGGTA ACGCCAGGGT

HindIII
 361 TTTCCCAGTC ACGACGTTGT AAAACGACGG CCAGTGCCAA GCTTCAAGCC GTCAATTGTC Stop araC
 421 TGATTCGTTA CCAATTATGA CAACTTGACG GCTACATCAT TCACTTTTTC TTCACAACCG

481 GCACGGAACT CGCTCGGGCT GGCCCCGGTG CATTTTTTAA ATACCCGCGA GAAATAGAGT

541 TGATCGTCAA AACCAACATT GCGACCGACG GTGGCGATAG CATCCGGGT GGTGCTCAAA

601 AGCAGCTTCG CCTGGCTGAT ACGTTGGTCC TCGCGCCAGC TTAAGACGCT AATCCCTAAC

661 TGCTGGCGGA AAAGATGTGA CAGACGCGAC GGCGACAAGC AAACATGCTG TGCGACGCTG

721 GCGATATCAA AATTGCTGTC TGCCAGGTGA TCGCTGATGT ACTGACAAGC CTCGCGTACC

781 CGATTATCCA TCGGTGGATG GAGCGACTCG TTAATCGCTT CCATGCGCCG CAGTAACAAT

841 TGCTCAAGCA GATTTATCGC CAGCAGCTCC GAATAGCGCC CTTCCCCTTG CCCGGCGTTA

901 ATGATTTGCC CAAACAGGTC GCTGAAATGC GGCTGGTGCG CTTCATCCGG GCGAAAGAAC

961 CCCGTATTGG CAAATATTGA CGGCCAGTTA AGCCATTCAT GCCAGTAGGC GCGCGGACGA

1021 AAGTAAACCC ACTGGTGATA CCATTCGCGA GCCTCCGGAT GACGACCGTA GTGATGAATC

1081 TCTCCTGGCG GGAACAGCAA AATATCACCC GGTCGGCAAA CAAATTCTCG TCCCTGATTT

1141 TTCACCACCC CCTGACCGCG AATGGTGAGA TTGAGAATAT AACCTTTCAT TCCCAGCGGT

1201 CGGTCGATAA AAAAATCGAG ATAACCGTTG GCCTCAATCG GCGTTAAACC CGCCACCAGA

1261 TGGGCATTAA ACGAGTATCC CGGCAGCAGG GGATCATTTT GCGCTTCAGC CATACTTTTC

Start araC
1321 ATACTCCCGC CATTCAGAGA AGAAACCAAT TGTCCATATT GCATCAGACA TTGCCGTCAC
                                                      <--

1381 TGCGTCTTTT ACTGGCTCTT CTCGCTAACC AAACCGGTAA CCCCGCTTAT TAAAAGCATT

1441 CTGTAACAAA GCGGGACCAA AGCCATGACA AAAACGCGTA ACAAAAGTGT CTATAATCAC

1501 GGCAGAAAAG TCCACATTGA TTATTTGCAC GGCGTCACAC TTTGCTATGC CATAGCATTT

1561 TTATCCATAA GATTAGCGGA TCCTACCTGA CGCTTTTTAT CGCAACTCTC TACTGTTTCT

SD      PstI   SalI  XbaI
```

```
                                       -continued
1621 CCATACCCGT TTTTTTGGGC TAGCAGGAGG CCCTGCAGGT CGACTCTAGA GGATCCCCGC Stem-loop             KpnI
1681 GCCCTCATCC GAAAGGGCGT ATTGGTACCG AGCTCGAATT CGTAATCATG GTCATAGCTG

1741 TTTCCTGTGT GAAATTGTTA TCCGCTCACA ATTCCACACA ACATACGAGC CGGAAGCATA

1801 AAGTGTAAAG CCTGGGGTGC CTAATGAGTG AGCTAACTCA CATTAATTGC GTTGCGCTCA

1861 CTGCCCGCTT TCCAGTCGGG AAACCTGTCG TGCCAGCTGC ATTAATGAAT CGGCCAACGC

1921 GCGGGGAGAG GCGGTTTGCG TATTGGGCGC TCTTCCGCTT CCTCGCTCAC TGACTCGCTG

1981 CGCTCGGTCG TTCGGCTGCG GCGAGCGGTA TCAGCTCACT CAAAGGCGGT AATACGGTTA

2041 TCCACAGAAT CAGGGGATAA CGCAGGAAAG AACATGTGAG CAAAAGGCCA GCAAAAGGCC

2101 AGGAACCGTA AAAGGCCGCG TTGCTGGCG TTTTTCCATA GGCTCCGCCC CCTGACGAG

2161 CATCACAAAA ATCGACGCTC AAGTCAGAGG TGGCGAAACC CGACAGGACT ATAAAGATAC

2221 CAGGCGTTTC CCCCTGGAAG CTCCCTCGTG CGCTCTCCTG TTCCGACCCT GCCGCTTACC

2281 GGATACCTGT CCGCCTTTCT CCCTTCGGGA AGCGTGGCGC TTTCTCATAG CTCACGCTGT

2341 AGGTATCTCA GTTCGGTGTA GGTCGTTCGC TCCAAGCTGG GCTGTGTGCA CGAACCCCCC

2401 GTTCAGCCCG ACCGCTGCGC CTTATCCGGT AACTATCGTC TTGAGTCCAA CCCGGTAAGA

2461 CACGACTTAT CGCCACTGGC AGCAGCCACT GGTAACAGGA TTAGCAGAGC GAGGTATGTA

2521 GGCGGTGCTA CAGAGTTCTT GAAGTGGTGG CCTAACTACG GCTACACTAG AAGGACAGTA

2581 TTTGGTATCT GCGCTCTGCT GAAGCCAGTT ACCTTCGGAA AAAGAGTTGG TAGCTCTTGA

2641 TCCGGCAAAC AAACCACCGC TGGTAGCGGT GGTTTTTTTG TTTGCAAGCA GCAGATTACG

2701 CGCAGAAAAA AAGGATCTCA AGAAGATCCT TTGATCTTTT CTACGGGGTC TGACGCTCAG

2761 TGGAACGAAA ACTCACGTTA AGGGATTTTG GTCATGAGAT TATCAAAAAG GATCTTCACC

2821 TAGATCCTTT TAAATTAAAA ATGAAGTTTT AAATCAATCT AAAGTATATA TGAGTAAACT

2881 TGGTCTGACA GTTACCAATG CTTAATCAGT GAGGCACCTA TCTCAGCGAT CTGTCTATTT

2941 CGTTCATCCA TAGTTGCCTG ACTCCCCGTC GTGTAGATAA CTACGATACG GGAGGGCTTA

3001 CCATCTGGCC CCAGTGCTGC AATGATACCG CGAGACCCAC GCTCACCGGC TCCAGATTTA

3061 TCAGCAATAA ACCAGCCAGC CGGAAGGGCC GAGCGCAGAA GTGGTCCTGC AACTTTATCC

3121 GCCTCCATCC AGTCTATTAA TTGTTGCCGG GAAGCTAGAG TAAGTAGTTC GCCAGTTAAT

3181 AGTTTGCGCA ACGTTGTTGC CATTGCTACA GGCATCGTGG TGTCACGCTC GTCGTTTGGT

3241 ATGGCTTCAT TCAGCTCCGG TTCCCAACGA TCAAGGCGAG TTACATGATC CCCCATGTTG

3301 TGCAAAAAAG CGGTTAGCTC CTTCGGTCCT CCGATCGTTG TCAGAAGTAA GTTGGCCGCA

3361 GTGTTATCAC TCATGGTTAT GGCAGCACTG CATAATTCTC TTACTGTCAT GCCATCCGTA

3421 AGATGCTTTT CTGTGACTGG TGAGTACTCA ACCAAGTCAT TCTGAGAATA GTGTATGCGG

3481 CGACCGAGTT GCTCTTGCCC GGCGTCAATA CGGGATAATA CCGCGCCACA TAGCAGAACT

3541 TTAAAAGTGC TCATCATTGG AAAACGTTCT TCGGGGCGAA AACTCTCAAG GATCTTACCG

3601 CTGTTGAGAT CCAGTTCGAT GTAACCCACT CGTGCACCCA ACTGATCTTC AGCATCTTTT

3661 ACTTTCACCA GCGTTTCTGG GTGAGCAAAA ACAGGAAGGC AAAATGCCGC AAAAAAGGGA

3721 ATAAGGGCGA CACGGAAATG TTGAATACTC ATACTCTTCC TTTTTCAATA TTATTGAAGC

3781 ATTTATCAGG GTTATTGTCT CATGAGCGGA TACATATTTG AATGTATTTA GAAAAATAAA

3841 CAAATAGGGG TTCCGCGCAC ATTTCCCCGA AAAGTGCCAC CTGACGTCTA AGAAACCATT

3901 ATTATCATGA CATTAACCTA TAAAAATAGG CGTATCACGA GGCCCTTTCG TC
```

The segment araC through Para was taken from pBAD24 using PCR added HindIII and modified aligned Shine-Delgarno (SD) sequence with PstI followed by SalI, XbaI, a stem-loop transcriptional stop sequence, and KpnI. The PCR product was cloned into pUC18 using HindIII and KpnI.
SEQ ID NO.: 155
pMPX-68 melibiose-inducible expression vector

```
   1    TCGCGCGTTT CGGTGATGAC GGTGAAAACC TCTGACACAT GCAGCTCCCG GAGACGGTCA

61    CAGCTTGTCT GTAAGCGGAT GCCGGGAGCA GACAAGCCCG TCAGGGCGCG TCAGCGGGTG

121    TTGGCGGGTG TCGGGGCTGG CTTAACTATG CGGCATCAGA GCAGATTGTA CTGAGAGTGC

181    ACCATATGCG GTGTGAAATA CCGCACAGAT GCGTAAGGAG AAAATACCGC ATCAGGCGCC

241    ATTCGCCATT CAGGCTGCGC AACTGTTGGG AAGGGCGATC GGTGCGGGCC TCTTCGCTAT

301    TACGCCAGCT GGCGAAAGGG GGATGTGCTG CAAGGCGATT AAGTTGGGTA ACGCCAGGGT

HindIII
 361    TTTCCCAGTC ACGACGTTGT AAAACGACGG CCAGTGCCAA GCTTTTAGCC GGGAAACGTC
                                                           Stop MelR

421    TGGCGGCGCT GTTGGCTAAG TTTGCGGTAT TGTTGCGGCG ACATGCCGAC ATATTTGCCG

481    AACGTGCTGT AAAAACGACT ACTTGAACGA AAGCCTGCCG TCAGGGCAAT ATCGAGAATA

541    CTTTTATCGG TATCGCTCAG TAACGCGCGA ACGTGGTTGA TGCGCATCGC GGTAATGTAC

601    TGTTTCATCG TCAATTGCAT GACCCGCTGG AATATCCCCA TTGCATAGTT GGCGTTAAGT

661    TTGACGTGCT CAGCCACATC GTTGATGGTC AGCGCCTGAT CATAGTTTTC GGCAATAAAG

721    CCCAGCATCT GGCTAACATA AAATTGCGCA TGGCGCGAGA CGCTGTTTTT GTGTGTGCGC

781    GAGGTTTTAT TGACCAGAAT CGGTTCCCAG CCAGAGAGGC TAAATCGCTT GAGCATCAGG

841    CCAATTTCAT CAATGGCGAG CTGGCGAATT TGCTCGTTCG GACTGTTTAA TTCCTGCTGC

901    CAGCGGCGCA CTTCAAACGG GCTAAGTTGC TGTGTGGCCA GTGATTTGAT CACCATGCCG

961    TGAGTGACGT GGTTAATCAG GTCTTTATCC AGCGGCCAGG AGAGAAACAG ATGCATCGGC

1021    AGATTAAAAA TCGCCATGCT CTGACAGGTT CCGGTATCTG TTAGTTGGTG CGGTGTACAG

1081    GCCCAGAACA GCGTGATATG ACCCTGATTG ATATTCACTT TTTCATTGTT GATCAGGTAT

1141    TCCACATCGC CATCGAAAGG CACATTCACT TCGACCTGAC CATGCCAGTG GCTGGTGGGC

1201    ATGATATGCG GTGCGCGAAA CTCAATCTCC ATCCGCTGGT ATTCCGAATA CAGCGACAGC

+1 MelR
1261    GGGCTGCGGG TCTGTTTTTC GTCGCTGCTG CACATAAACG TATCTGTATT CATGGATGGC

1321    TCTCTTTCCT GGAATATCAG AATTATGGCA GGAGTGAGGG AGGATGACTG CGAGTGGGAG

1381    CACGGTTTTC ACCCTCTTCC CAGAGGGGCG AGGGGACTCT CCGAGTATCA TGAGGCCGAA

1441    AACTCTGCTT TTCAGGTAAT TTATTCCCAT AAACTCAGAT TTACTGCTGC TTCACGCAGG

1501    ATCTGAGTTT ATGGGAATGC TCAACCTGGA AGCCGGAGGT TTTCTGCAGA TTCGCCTGCC

SD            SalI      XbaI
1561    ATGATGAAGT TATTCAAGCA AGCCAGGAGG TCGTCGACTC TAGAGGATCC CCGCGCCCTC

Stem-loop           KpnI
1621    ATCCGAAAGG GCGTATTGGT ACCGAGCTCG AATTCGTAAT CATGGTCATA GCTGTTTCCT

1681    GTGTGAAATT GTTATCCGCT CACAATTCCA CACAACATAC GAGCCGGAAG CATAAAGTGT

1741    AAAGCCTGGG GTGCCTAATG AGTGAGCTAA CTCACATTAA TTGCGTTGCG CTCACTGCCC

1801    GCTTTCCAGT CGGGAAACCT GTCGTGCCAG CTGCATTAAT GAATCGGCCA ACGCGCGGGG

1861    AGAGGCGGTT TGCGTATTGG GCGCTCTTCC GCTTCCTCGC TCACTGACTC GCTGCGCTCG

1921    GTCGTTCGGC TGCGGCGAGC GGTATCAGCT CACTCAAAGG CGGTAATACG GTTATCCACA

1981    GAATCAGGGG ATAACGCAGG AAAGAACATG TGAGCAAAAG GCCAGCAAAA GGCCAGGAAC
```

-continued

```
2041  CGTAAAAAGG CCGCGTTGCT GGCGTTTTTC CATAGGCTCC GCCCCCCTGA CGAGCATCAC
2101  AAAAATCGAC GCTCAAGTCA GAGGTGGCGA AACCCGACAG GACTATAAAG ATACCAGGCG
2161  TTTCCCCCTG GAAGCTCCCT CGTGCGCTCT CCTGTTCCGA CCCTGCCGCT TACCGGATAC
2221  CTGTCCGCCT TTCTCCCTTC GGGAAGCGTG GCGCTTTCTC ATAGCTCACG CTGTAGGTAT
2281  CTCAGTTCGG TGTAGGTCGT TCGCTCCAAG CTGGGCTGTG TGCACGAACC CCCCGTTCAG
2341  CCCGACCGCT GCGCCTTATC CGGTAACTAT CGTCTTGAGT CCAACCCGGT AAGACACGAC
2401  TTATCGCCAC TGGCAGCAGC CACTGGTAAC AGGATTAGCA GAGCGAGGTA TGTAGGCGGT
2461  GCTACAGAGT TCTTGAAGTG GTGGCCTAAC TACGGCTACA CTAGAAGGAC AGTATTTGGT
2521  ATCTGCGCTC TGCTGAAGCC AGTTACCTTC GGAAAAAGAG TTGGTAGCTC TTGATCCGGC
2581  AAACAAACCA CCGCTGGTAG CGGTGGTTTT TTTGTTTGCA AGCAGCAGAT TACGCGCAGA
2641  AAAAAAGGAT CTCAAGAAGA TCCTTTGATC TTTTCTACGG GGTCTGACGC TCAGTGGAAC
2701  GAAAACTCAC GTTAAGGGAT TTTGGTCATG AGATTATCAA AAAGGATCTT CACCTAGATC
2761  CTTTTAAATT AAAAATGAAG TTTTAAATCA ATCTAAAGTA TATATGAGTA AACTTGGTCT
2821  GACAGTTACC AATGCTTAAT CAGTGAGGCA CCTATCTCAG CGATCTGTCT ATTTCGTTCA
2881  TCCATAGTTG CCTGACTCCC CGTCGTGTAG ATAACTACGA TACGGGAGGG CTTACCATCT
2941  GGCCCCAGTG CTGCAATGAT ACCGCGAGAC CCACGCTCAC CGGCTCCAGA TTTATCAGCA
3001  ATAAACCAGC CAGCCGGAAG GGCCGAGCGC AGAAGTGGTC CTGCAACTTT ATCCGCCTCC
3061  ATCCAGTCTA TTAATTGTTG CCGGGAAGCT AGAGTAAGTA GTTCGCCAGT TAATAGTTTG
3121  CGCAACGTTG TTGCCATTGC TACAGGCATC GTGGTGTCAC GCTCGTCGTT TGGTATGGCT
3181  TCATTCAGCT CCGGTTCCCA ACGATCAAGG CGAGTTACAT GATCCCCCAT GTTGTGCAAA
3241  AAAGCGGTTA GCTCCTTCGG TCCTCCGATC GTTGTCAGAA GTAAGTTGGC CGCAGTGTTA
3301  TCACTCATGG TTATGGCAGC ACTGCATAAT TCTCTTACTG TCATGCCATC CGTAAGATGC
3361  TTTTCTGTGA CTGGTGAGTA CTCAACCAAG TCATTCTGAG AATAGTGTAT GCGGCGACCG
3421  AGTTGCTCTT GCCCGGCGTC AATACGGGAT AATACCGCGC CACATAGCAG AACTTTAAAA
3481  GTGCTCATCA TTGGAAAACG TTCTTCGGGG CGAAAACTCT CAAGGATCTT ACCGCTGTTG
3541  AGATCCAGTT CGATGTAACC CACTCGTGCA CCCAACTGAT CTTCAGCATC TTTTACTTTC
3601  ACCAGCGTTT CTGGGTGAGC AAAAACAGGA AGGCAAAATG CCGCAAAAAA GGGAATAAGG
3661  GCGACACGGA AATGTTGAAT ACTCATACTC TTCCTTTTTC AATATTATTG AAGCATTTAT
3721  CAGGGTTATT GTCTCATGAG CGGATACATA TTTGAATGTA TTTAGAAAAA TAAACAAATA
3781  GGGGTTCCGC GCACATTTCC CCGAAAAGTG CCACCTGACG TCTAAGAAAC CATTATTATC
3841  ATGACATTAA CCTATAAAAA TAGGCGTATC ACGAGGCCCT TCGTC
```

SEQ ID NO.: 166
MalE (1-370) Factor Xa NTR (43-424) FLAG

```
         SalI +1  MalE (1-370)
   1  GTCGACATGAAAATAAAAACAGGTGCACGCATCCTCGCATTATCCGCATTAACGACGATGATGTTT
   1         M   K   I   K   T   G   A   R   I   L   A   L   S   A   L   T   T   M   M   F

61     TCCGCCTCGGCTCTCGCCAAAATCGAAGAAGGTAAACTGGTAATCTGGATTAACGGCGAT
  21      S   A   S   A   L   A   K   I   E   E   G   K   L   V   I   W   I   N   G   D

121     AAAGGCTATAACGGTCTCGCTGAAGTCGGTAAGAAATTCGAGAAAGATACCGGAATTAAA
  41      K   G   Y   N   G   L   A   E   V   G   K   K   F   E   K   D   T   G   I   K

181     GTCACCGTTGAGCATCCGGATAAACTGGAAGAGAAATTCCCACAGGTTGCGGCAACTGGC
  61      V   T   V   E   H   P   D   K   L   E   E   K   F   P   Q   V   A   A   T   G
```

```
 241   GATGGCCCTGACATTATCTTCTGGGCACACGACCGCTTTGGTGGCTACGCTCAATCTGGC
  81    D   G   P   D   I   I   F   W   A   H   D   R   F   G   G   Y   A   Q   S   G

301   CTGTTGGCTGAAATCACCCCGGACAAAGCGTTCCAGGACAAGCTGTATCCGTTTACCTGG
 101    L   L   A   E   I   T   P   D   K   A   F   Q   D   K   L   Y   P   F   T   W

361   GATGCCGTACGTTACAACGGCAAGCTGATTGCTTACCCGATCGCTGTTGAAGCGTTATCG
 121    D   A   V   R   Y   N   G   K   L   I   A   Y   P   I   A   V   E   A   L   S

421   CTGATTTATAACAAAGATCTGCTGCCGAACCCGCCAAAAACCTGGGAAGAGATCCCGGCG
 141    L   I   Y   N   K   D   L   L   P   N   P   P   K   T   W   E   E   I   P   A

481   CTGGATAAAGAACTGAAAGCGAAAGGTAAGAGCGCGCTGATGTTCAACCTGCAAGAACCG
 161    L   D   K   E   L   K   A   K   G   K   S   A   L   M   F   N   L   Q   E   P

541   TACTTCACCTGGCCGCTGATTGCTGCTGACGGGGGTTATGCGTTCAAGTATGAAAACGGC
 181    Y   F   T   W   P   L   I   A   A   D   G   G   Y   A   F   K   Y   E   N   G

601   AAGTACGACATTAAAGACGTGGGCGTGGATAACGCTGGCGCGAAAGCGGGTCTGACCTTC
 201    K   Y   D   I   K   D   V   G   V   D   N   A   G   A   K   A   G   L   T   F

661   CTGGTTGACCTGATTAAAAACAAACATGAATGCAGACACCGATTACTCCATCGCAGAA
 221    L   V   D   L   I   K   N   K   H   M   N   A   D   T   D   Y   S   I   A   E

721   GCTGCCTTTAATAAAGGCGAAACAGCGATGACCATCAACGGCCCGTGGGCATGGTCCAAC
 241    A   A   F   N   K   G   E   T   A   M   T   I   N   G   P   W   A   W   S   N

781   ATCGACACCAGCAAAGTGAATTATGGTGTAACGGTACTGCCGACCTTCAAGGGTCAACCA
 261    I   D   T   S   K   V   N   Y   G   V   T   V   L   P   T   F   K   G   Q   P

841   TCCAAACCGTTCGTTGGCGTGCTGAGCGCAGGTATTAACGCCGCCAGTCCGAACAAAGAG
 281    S   K   P   F   V   G   V   L   S   A   G   I   N   A   A   S   P   N   K   E

901   CTGGCGAAAGAGTTCCTCGAAAACTATCTGCTGACTGATGAAGGTCTGGAAGCGGTTAAT
 301    L   A   K   E   F   L   E   N   Y   L   L   T   D   E   G   L   E   A   V   N

961   AAAGACAAACCGCTGGGTGCCGTAGCGCTGAAGTCTTACGAGGAAGAGTTGGCGAAAGAT
 321    K   D   K   P   L   G   A   V   A   L   K   S   Y   E   E   L   A   K   D

1021   CCACGTATTGCCGCCACCATGGAAAACGCCCAGAAAGGTGAAATCATGCCGAACATCCCG
 341    P   R   I   A   A   T   M   E   N   A   Q   K   G   E   I   M   P   N   I   P

Factor Xa  +43 NTR
1081   CAGATGTCCGCTTTCTGGTATGCCGTGCTGATCGAAGCCCGCACCTCGGAATCCGACACG
 361    Q   M   S   A   F   W   Y   A   V   L   I   E   A   R   T   S   E   S   D   T 1141   GCAGGGCCCAACAGCGACCTGGACGTGAACACTGACATTTATTCCAAGGTGCTGGTGACT
 381    A   G   P   N   S   D   L   D   V   N   T   D   I   Y   S   K   V   L   V   T 1201   GCTATATACCTGGCACTCTTCGTGGTGGGCACTGTGGGCAACTCCGTGACAGCCTTCACT
 401    A   I   Y   L   A   L   F   V   V   G   T   V   G   N   S   V   T   A   F   T 1261   CTAGCGCGGAAGAAGTCACTGCAGAGCCTGCAGAGCACTGTGCATTACCACCTGGGCAGC
 421    L   A   R   K   K   S   L   Q   S   L   Q   S   T   V   H   Y   H   L   G   S 1321   CTGGCACTGTCGGACCTGCTTATCCTTCTGCTGGCCATGCCCGTGGAGCTATACAACTTC
 441    L   A   L   S   D   L   L   I   L   L   L   A   M   P   V   E   L   Y   N   F 1381   ATCTGGGTACACCATCCCTGGGCCTTTGGGGACGCTGGCTGCCGTGGCTACTATTTCCTG
 461    I   W   V   H   H   P   W   A   F   G   D   A   G   C   R   G   Y   Y   F   L 1441   CGTGATGCCTGCACCTATGCCACAGCCCTCAATGTAGCCAGCCTGAGTGTGGAGCGCTAC
 481    R   D   A   C   T   Y   A   T   A   L   N   V   A   S   L   S   V   E   R   Y 1501   TTGGCCATCTGCCATCCCTTCAAGGCCAAGACCCTCATGTCCCGCAGCCGCACCAAGAAA
 501    L   A   I   C   H   P   F   K   A   K   T   L   M   S   R   S   R   T   K   K 1561   TTCATCAGTGCCATATGGCTAGCTTCGGCGCTGCTGGCTATACCCATGCTTTTCACCATG
 521    F   I   S   A   I   W   L   A   S   A   L   L   A   I   P   M   L   F   T   M 1621   GGCCTGCAGAACCGCAGTGGTGACGGCACGCACCCTGGCGGCCTGGTGTGCACACCCATT
 541    G   L   Q   N   R   S   G   D   G   T   H   P   G   G   L   V   C   T   P   I 1681   GTGGACACAGCCACTGTCAAGGTCGTCATCCAGGTTAACACCTTCATGTCCTTCCTGTTT
 561    V   D   T   A   T   V   K   V   V   I   Q   V   N   T   F   M   S   F   L   F 1741   CCCATGTTGGTCATCTCCATCCTAAACACCGTGATTGCCAACAAACTGACAGTCATGGTG
 581    P   M   L   V   I   S   I   L   N   T   V   I   A   N   K   L   T   V   M   V

1801   CACCAGGCCGCCGAGCAGGGCCGAGTGTGCACCGTGGGCACACACAACGGTTTAGAGCAC
```

```
601         H  Q  A  A  E  Q  G  R  V  C  T  V  G  T  H  N  G  L  E  H

1861        AGCACGTTCAACATGACCATCGAGCCGGGTCGTGTCCAGGCCCTGCGCCACGGAGTCCTC
621         S  T  F  N  M  T  I  E  P  G  R  V  Q  A  L  R  H  G  V  L

1921        GTCTTACGTGCTGTGGTCATTGCCTTTGTGGTCTGCTGGCTGCCCTACCACGTGCGACGC
641         V  L  R  A  V  V  I  A  F  V  V  C  W  L  P  Y  H  V  R  R

1981        CTGATGTTCTGCTATATCTCGGATGAACAGTGGACTACGTTCCTCTTCGATTTCTACCAC
661         L  M  F  C  Y  I  S  D  E  Q  W  T  T  F  L  F  D  F  Y  H

2041        TATTTCTACATGCTAACCAACGCTCTCTTCTACGTCAGCTCCGCCATCAATCCCATCCTC
681         Y  F  Y  M  L  T  N  A  L  F  Y  V  S  S  A  I  N  P  I  L

2101        TACAACCTGGTCTCCGCCAACTTCCGCCAGGTCTTTCTGTCCACGCTGGCCTGCCTTTGT
701         Y  N  L  V  S  A  N  F  R  Q  V  F  L  S  T  L  A  C  L  C

2161        CCTGGGTGGCGCCACCGCCGAAAGAAGAGGCCAACGTTCTCCAGGAAGCCCAACAGCATG
721         P  G  W  R  H  R  R  K  K  R  P  T  F  S  R  K  P  N  S  M

Not I
2221        TCCAGCAACCATGCCTTTTCCACCAGCGCCACCCGGGAGACCCTGTACgcggccgca
741         S  S  N  H  A  F  S  T  S  A  T  R  E  T  L  Y  A  A  A Flag              stop   KpnI
            GATTATAAAGATGACGATGACAAATAATAAGGTACC
            D  Y  K  D  D  D  D  K  *  *
```

SEQ ID NO.: 167                          25
MalE (1-28) Factor Xa NTR (43-424) FLAG

```
            SalI   +1 MalE leader (1-28)
1           gtcgacATGAAAATAAAAACAGGTGCACGCATCCTCGCATTATCCGCATTAACGACGATGATGTTT
1                  M  K  I  K  T  G  A  R  I  L  A  L  S  A  L  T  T  M  M  F Factor Xa  +43 NTR
61          TCCGCCTCGGCTCTCGCCAAAATCATCGAAGCCCGCACCTCGGAATCCGACACGGCAGGG
21          S  A  S  A  L  A  K  I  I  E  A  R  T  S  E  S  D  T  A  G 121         CCCAACAGCGACCTGGACGTGAACACTGACATTTATTCCAAGGTGCTGGTGACTGCTATA
41          P  N  S  D  L  D  V  N  T  D  I  Y  S  K  V  L  V  T  A  I 181         TACCTGGCACTCTTCGTGGTGGGCACTGTGGGCAACTCCGTGACAGCCTTCACTCTAGCG
61          Y  L  A  L  F  V  V  G  T  V  G  N  S  V  T  A  F  T  L  A 241         CGGAAGAAGTCACTGCAGAGCCTGCAGAGCACTGTGCATTACCACCTGGGCAGCCTGGCA
81          R  K  K  S  L  Q  S  L  Q  S  T  V  H  Y  H  L  G  S  L  A 301         CTGTCGGACCTGCTTATCCTTCTGCTGGCCATGCCCGTGGAGCTATACAACTTCATCTGG
101         L  S  D  L  L  I  L  L  L  A  M  P  V  E  L  Y  N  F  I  W 361         GTACACCATCCCTGGGCCTTTGGGGACGCTGGCTGCCGTGGCTACTATTTCCTGCGTGAT
121         V  H  H  P  W  A  F  G  D  A  G  C  R  G  Y  Y  F  L  R  D 421         GCCTGCACCTATGCCACAGCCCTCAATGTAGCCAGCCTGAGTGTGGAGCGCTACTTGGCC
141         A  C  T  Y  A  T  A  L  N  V  A  S  L  S  V  E  R  Y  L  A 481         ATCTGCCATCCCTTCAAGGCCAAGACCCTCATGTCCCGCAGCCGCACCAAGAAATTCATC
161         I  C  H  P  F  K  A  K  T  L  M  S  R  S  R  T  K  K  F  I 541         AGTGCCATATGGCTAGCTTCGGCGCTGCTGGCTATACCCATGCTTTTCACCATGGGCCTG
181         S  A  I  W  L  A  S  A  L  L  A  I  P  M  L  F  T  M  G  L 601         CAGAACCGCAGTGGTGACGGCACGCACCCTGGCGGCCTGGTGTGCACACCCATTGTGGAC
201         Q  N  R  S  G  D  G  T  H  P  G  G  L  V  C  T  P  I  V  D 661         ACAGCCACTGTCAAGGTCGTCATCCAGGTTAACACCTTCATGTCCTTCCTGTTTCCCATG
221         T  A  T  V  K  V  V  I  Q  V  N  T  F  M  S  F  L  F  P  M 721         TTGGTCATCTCCATCCTAAACACCGTGATTGCCAACAAACTGACAGTCATGGTGCACCAG
241         L  V  I  S  I  L  N  T  V  I  A  N  K  L  T  V  M  V  H  Q 781         GCCGCCGAGCAGGGCCGAGTGTGCACCGTGGGCACACACAACGGTTTAGAGCACAGCACG
261         A  A  E  Q  G  R  V  C  T  V  G  T  H  N  G  L  E  H  S  T 841         TTCAACATGACCATCGAGCCGGGTCGTGTCCAGGCCCTGCGCCACGGAGTCCTCGTCTTA
281         F  N  M  T  I  E  P  G  R  V  Q  A  L  R  H  G  V  L  V  L
```

-continued

```
 901  CGTGCTGTGGTCATTGCCTTTGTGGTCTGCTGGCTGCCCTACCACGTGCGACGCCTGATG
 301   R  A  V  V  I  A  F  V  V  C  W  L  P  Y  H  V  R  R  L  M

961  TTCTGCTATATCTCGGATGAACAGTGGACTACGTTCCTCTTCGATTTCTACCACTATTTC
 321   F  C  Y  I  S  D  E  Q  W  T  T  F  L  F  D  F  Y  H  Y  F

1021  TACATGCTAACCAACGCTCTCTTCTACGTCAGCTCCGCCATCAATCCCATCCTCTACAAC
 341   Y  M  L  T  N  A  L  F  Y  V  S  S  A  I  N  P  I  L  Y  N

1081  CTGGTCTCCGCCAACTTCCGCCAGGTCTTTCTGTCCACGCTGGCCTGCCTTTGTCCTGGG
 361   L  V  S  A  N  F  R  Q  V  F  L  S  T  L  A  C  L  C  P  G

1141  TGGCGCCACCGCCGAAAGAAGAGGCCAACGTTCTCCAGGAAGCCCAACAGCATGTCCAGC
 381   W  R  H  R  R  K  K  R  P  T  F  S  R  K  P  N  S  M  S  S

NotI        Flag
1201  AACCATGCCTTTTCCACCAGCGCCACCCGGGAGACCCTGTACgcggccgcaGATTATAAA
 401   N  H  A  F  S  T  S  A  T  R  E  T  L  Y  A  A  A  D  Y  K stop  KpnI
      GATGACGATGACAAATAATAAGGTACC
       D  D  D  D  K
```

20

SEQ ID NO.: 169
MalE (1-370) Factor Xa NTR (43-424) TrxA (2-109) FLAG

```
      SalI +1 MalE (1-370)
   1  GTCGACATGAAAATAAAAACAGGTGCACGCATCCTCGCATTATCCGCATTAACGACGATGATGTTT
   1         M  K  I  K  T  G  A  R  I  L  A  L  S  A  L  T  T  M  M  F

61  TCCGCCTCGGCTCTCGCCAAAATCGAAGAAGGTAAACTGGTAATCTGGATTAACGGCGAT
  21   S  A  S  A  L  A  K  I  E  E  G  K  L  V  I  W  I  N  G  D

121  AAAGGCTATAACGGTCTCGCTGAAGTCGGTAAGAAATTCGAGAAAGATACCGGAATTAAA
  41   K  G  Y  N  G  L  A  E  V  G  K  K  F  E  K  D  T  G  I  K

181  GTCACCGTTGAGCATCCGGATAAACTGGAAGAGAAATTCCCACAGGTTGCGGCAACTGGC
  61   V  T  V  E  H  P  D  K  L  E  E  K  F  P  Q  V  A  A  T  G

241  GATGGCCCTGACATTATCTTCTGGGCACACGACCGCTTTGGTGGCTACGCTCAATCGGGC
  81   D  G  P  D  I  I  F  W  A  H  D  R  F  G  G  Y  A  Q  S  G

301  CTGTTGGCTGAAATCACCCCCGGACAAAGCGTTCCAGGACAAGCTGTATCCGTTTACCTGG
 101   L  L  A  E  I  T  P  D  K  A  F  Q  D  K  L  Y  P  F  T  W

361  GATGCCGTACGTTACAACGGCAAGCTGATTGCTTACCCGATCGCTGTTGAAGCGTTATCG
 121   D  A  V  R  Y  N  G  K  L  I  A  Y  P  I  A  V  E  A  L  S

421  CTGATTTATAACAAAGATCTGCTGCCGAACCCGCCAAAAACCTGGGAAGAGATCCCGGCG
 141   L  I  Y  N  K  D  L  L  P  N  P  P  K  T  W  E  E  I  P  A

481  CTGGATAAAGAACTGAAAGCGAAAGGTAAGAGCGCGCTGATGTTCAACCTGCAAGAACCG
 161   L  D  K  E  L  K  A  K  G  K  S  A  L  M  F  N  L  Q  E  P

541  TACTTCACCTGGCCGCTGATTGCTGCTGACGGGGGTTATGCGTTCAAGTATGAAAACGGC
 181   Y  F  T  W  P  L  I  A  A  D  G  G  Y  A  F  K  Y  E  N  G

601  AAGTACGACATTAAAGACGTGGGCGTGGATAACGCTGGCGCGAAAGCGGGTCTGACCTTC
 201   K  Y  D  I  K  D  V  G  V  D  N  A  G  A  K  A  G  L  T  F

661  CTGGTTGACCTGATTAAAAACAAACACATGAATGCAGACACCGATTACTCCATCGCAGAA
 221   L  V  D  L  I  K  N  K  H  M  N  A  D  T  D  Y  S  I  A  E

721  GCTGCCTTTAATAAAGGCGAAACAGCGATGACCATCAACGGCCCGTGGGCATGGTCCAAC
 241   A  A  F  N  K  G  E  T  A  M  T  I  N  G  P  W  A  W  S  N

781  ATCGACACCAGCAAAGTGAATTATGGTGTAACGGTACTGCCGACCTTCAAGGGTCAACCA
 261   I  D  T  S  K  V  N  Y  G  V  T  V  L  P  T  F  K  G  Q  P

841  TCCAAACCGTTCGTTGGCGTGCTGAGCGCAGGTATTAACGCCGCCAGTCCGAACAAAGAG
 281   S  K  P  F  V  G  V  L  S  A  G  I  N  A  A  S  P  N  K  E

901  CTGGCGAAAGAGTTCCTCGAAAACTATCTGCTGACTGATGAAGGTCTGGAAGCGGTTAAT
 301   L  A  K  E  F  L  E  N  Y  L  L  T  D  E  G  L  E  A  V  N

961  AAAGACAAACCGCTGGGTGCCGTAGCGCTGAAGTCTTACGAGGAAGAGTTGGCGAAAGAT
 321   K  D  K  P  L  G  A  V  A  L  K  S  Y  E  E  E  L  A  K  D
```

```
                                      -continued
1021  CCACGTATTGCCGCCACCATGGAAAACGCCCAGAAAGGTGAAATCATGCCGAACATCCCG
341      P   R   I   A   A   T   M   E   N   A   Q   K   G   E   I   M   P   N   I   P Factor Xa    +43 NTR
1081  CAGATGTCCGCTTTCTGGTATGCCGTGCTGATCGAAGCCCGCACCTCGGAATCCGACACG
361      Q   M   S   A   F   W   Y   A   V   L   T   E   A   R   T   S   E   S   D   T 1141  GCAGGGCCCAACAGCGACCTGGACGTGAACACTGACATTTATTCCAAGGTGCTGGTGACT
381      A   G   P   N   S   D   L   D   V   N   T   D   I   Y   S   K   V   L   V   T 1201  GCTATATACCTGGCACTCTTCGTGGTGGGCACTGTGGGCAACTCCGTGACAGCCTTCACT
401      A   I   Y   L   A   L   F   V   V   G   T   V   G   N   S   V   T   A   F   T 1261  CTAGCGCGGAAGAAGTCACTGCAGAGCCTGCAGAGCACTGTGCATTACCACCTGGGCAGC
421      L   A   R   K   K   S   L   Q   S   L   Q   S   T   V   H   Y   H   L   G   S 1321  CTGGCACTGTCGGACCTGCTTATCCTTCTGCTGGCCATGCCCGTGGAGCTATACAACTTC
441      L   A   L   S   D   L   L   I   L   L   L   A   M   P   V   E   L   Y   N   F 1381  ATCTGGGTACACCATCCCTGGGCCTTTGGGGACGCTGGCTGCCGTGGCTACTATTTCCTG
461      I   W   V   H   H   P   W   A   F   G   D   A   G   C   R   G   Y   Y   F   L 1441  CGTGATGCCTGCACCTATGCCACAGCCCTCAATGTAGCCAGCCTGAGTGTGGAGCGCTAC
481      R   D   A   C   T   Y   A   T   A   L   N   V   A   S   L   S   V   E   R   Y 1501  TTGGCCATCTGCCATCCCTTCAAGGCCAAGACCCTCATGTCCCGCAGCCGCACCAAGAAA
501      L   A   I   C   H   P   F   K   A   K   T   L   M   S   R   S   R   T   K   K 1561  TTCATCAGTGCCATATGGCTAGCTTCGGCGCTGCTGGCTATACCCATGCTTTTCACCATG
521      F   I   S   A   I   W   L   A   S   A   L   L   A   I   P   M   L   F   T   M 1621  GGCCTGCAGAACCGCAGTGGTGACGGCACGCACCCTGGCGGCCTGGTGTGCACACCCATT
541      G   L   Q   N   R   S   G   D   G   T   H   P   G   G   L   V   C   T   P   I 1681  GTGGACACAGCCACTGTCAAGGTCGTCATCCAGGTTAACACCTTCATGTCCTTCCTGTTT
561      V   D   T   A   T   V   K   V   V   I   Q   V   N   T   F   M   S   F   L   F 1741  CCCATGTTGGTCATCTCCATCCTAAACACCGTGATTGCCAACAAACTGACAGTCATGGTG
581      P   M   L   V   I   S   I   L   N   T   V   I   A   N   K   L   T   V   M   V 1801  CACCAGGCCGCCGAGCAGGGCCGAGTGTGCACCGTGGGCACACACAACGGTTTAGAGCAC
601      H   Q   A   A   E   Q   G   R   V   C   T   V   G   T   H   N   G   L   E   H 1861  AGCACGTTCAACATGACCATCGAGCCGGGTCGTGTCCAGGCCCTGCGCCACGGAGTCCTC
621      S   T   F   N   M   T   I   E   P   G   R   V   Q   A   L   R   H   G   V   L 1921  GTCTTACGTGCTGTGGTCATTGCCTTTGTGGTCTGCTGGCTGCCCTACCACGTGCGACGC
641      V   L   R   A   V   V   I   A   F   V   V   C   W   L   P   Y   H   V   R   R 1981  CTGATGTTCTGCTATATCTCGGATGAACAGTGGACTACGTTCCTCTTCGATTTCTACCAC
661      L   M   F   C   Y   I   S   D   E   Q   W   T   T   F   L   F   D   F   Y   H 2041  TATTTCTACATGCTAACCAACGCTCTCTTCTACGTCAGCTCCGCCATCAATCCCATCCTC
681      Y   F   Y   M   L   T   N   A   L   F   Y   V   S   S   A   I   N   P   I   L 2101  TACAACCTGGTCTCCGCCAACTTCCGCCAGGTCTTTCTGTCCACGCTGGCCTGCCTTTGT
701      Y   N   L   V   S   A   N   F   R   Q   V   F   L   S   T   L   A   C   L   C 2161  CCTGGGTGGCGCCACCGCCGAAAGAAGAGGCCAACGTTCTCCAGGAAGCCCAACAGCATG
721      P   G   W   R   H   R   R   K   K   R   P   T   F   S   R   K   P   N   S   M NotI    +2 TrxA
2221  TCCAGCAACCATGCCTTTTCCACCAGCGCCACCCGGGAGACCCTGTACgcggccgcaAGC
741      S   S   N   H   A   F   S   T   S   A   T   R   E   T   L   Y   A   A   A   S 2281  GATAAAATTATTCACCTGACTGACGACAGTTTTGACACGGATGTACTCAAAGCGGACGGG
761      D   K   I   I   H   L   T   D   D   S   F   D   T   D   V   L   K   A   D   G 2341  GCGATCCTCGTCGATTTCTGGGCAGAGTGGTGCGGTCCGTGCAAAATGATCGCCCCGATT
781      A   I   L   V   D   F   W   A   E   W   C   G   P   C   K   M   I   A   P   I 2401  CTGGATGAAATCGCTGACGAATATCAGGGCAAACTGACCGTTGCAAAACTGAACATCGAT
801      L   D   E   I   A   D   E   Y   Q   G   K   L   T   V   A   K   L   N   I   D 2461  CAAAACCCTGGCACTGCGCCGAAATATGGCATCCGTGGTATCCCGACTCTGCTGCTGTTC
821      Q   N   P   G   T   A   P   K   Y   G   I   R   G   I   P   T   L   L   L   F 2521  AAAAACGGTGAAGTGGCGGCAACCAAAGTGGGTGCACTGTCTAAAGGTCAGTTGAAAGAG
841      K   N   G   E   V   A   A   T   K   V   G   A   L   S   K   G   Q   L   K   E NotI   +2 Flag               stop
```

```
                                    -continued
2581    TTCCTCGACGCTAACCTGGCGgcggccgcaGATTATAAAGATGACGATGACAAATAATAA
 861     F   L   D   A   N   L   A   A   A   A   D   Y   K   D   D   D   D   K   *   *

KpnI
2641    GGTACC
```

SEQ ID NO.: 170
MalE (1-28) Factor Xa NTR (43-424) TrxA (2-109) FLAG

```
        SalI   +1 MalE leader (1-28)
   1    gtcgacATGAAAATAAAAACAGGTGCACGCATCCTCGCATTATCCGCATTAACGACGATGATGTTT
   1          M  K  I  K  T  G  A  R  I  L  A  L  S  A  L  T  T  M  M  F Factor Xa  +43 NTR
  61    TCCGCCTCGGCTCTCGCCAAAATCATCGAAGCCCGCACCTCGGAATCCGACACGGCAGGG
  21     S   A   S   A   L   A   K   I   I   E   A   R   T   S   E   S   D   T   A   G 121    CCCAACAGCGACCTGGACGTGAACACTGACATTTATTCCAAGGTGCTGGTGACTGCTATA
  41     P   N   S   D   L   D   V   N   T   D   I   Y   S   K   V   L   V   T   A   I 181    TACCTGGCACTCTTCGTGGTGGGCACTGTGGGCAACTCCGTGACAGCCTTCACTCTAGCG
  61     Y   L   A   L   F   V   V   G   T   V   G   N   S   V   T   A   F   T   L   A 241    CGGAAGAAGTCACTGCAGAGCCTGCAGAGCACTGTGCATTACCACCTGGGCAGCCTGGCA
  81     R   K   K   S   L   Q   S   L   Q   S   T   V   H   Y   H   L   G   S   L   A 301    CTGTCGGACCTGCTTATCCTTCTGCTGGCCATGCCCGTGGAGCTATACAACTTCATCTGG
 101     L   S   D   L   L   I   L   L   L   A   M   P   V   E   L   Y   N   F   I   W 361    GTACACCATCCCTGGGCCTTTGGGGACGCTGGCTGCCGTGGCTACTATTTCCTGCGTGAT
 121     V   H   H   P   W   A   F   G   D   A   G   C   R   G   Y   Y   F   L   R   D 421    GCCTGCACCTATGCCACAGCCCTCAATGTAGCCAGCCTGAGTGTGGAGCGCTACTTGGCC
 141     A   C   T   Y   A   T   A   L   N   V   A   S   L   S   V   E   R   Y   L   A 481    ATCTGCCATCCCTTCAAGGCCAAGACCCTCATGTCCCGCAGCCGCACCAAGAAATTCATC
 161     I   C   H   P   F   K   A   K   T   L   M   S   R   S   R   T   K   K   F   I 541    AGTGCCATATGGCTAGCTTCGGCGCTGCTGGCTATACCCATGCTTTTCACCATGGGCCTG
 181     S   A   I   W   L   A   S   A   L   L   A   I   P   M   L   F   T   M   G   L 601    CAGAACCGCAGTGGTGACGGCACGCACCCTGGCGGCCTGGTGTGCACACCCATTGTGGAC
 201     Q   N   R   S   G   D   G   T   H   P   G   G   L   V   C   T   P   I   V   D 661    ACAGCCACTGTCAAGGTCGTCATCCAGGTTAACACCTTCATGTCCTTCCTGTTTCCCATG
 221     T   A   T   V   K   V   V   I   Q   V   N   T   F   M   S   F   L   F   P   M 721    TTGGTCATCTCCATCCTAAACACCGTGATTGCCAACAAACTGACAGTCATGGTGCACCAG
 241     L   V   I   S   I   L   N   T   V   I   A   N   K   L   T   V   M   V   H   Q 781    GCCGCCGAGCAGGGCCGAGTGTGCACCGTGGGCACACACAACGGTTTAGAGCACAGCACG
 261     A   A   E   Q   G   R   V   C   T   V   G   T   H   N   G   L   E   H   S   T 841    TTCAACATGACCATCGAGCCGGGTCGTGTCCAGGCCCTGCGCCACGGAGTCCTCGTCTTA
 281     F   N   M   T   I   E   P   G   R   V   Q   A   L   R   H   G   V   L   V   L 901    CGTGCTGTGGTCATTGCCTTTGTGGTCTGCTGGCTGCCCTACCACGTGCGACGCCTGATG
 301     R   A   V   V   I   A   F   V   V   C   W   L   P   Y   H   V   R   R   L   M 961    TTCTGCTATATCTCGGATGAACAGTGGACTACGTTCCTCTTCGATTTCTACCACTATTTC
 321     F   C   Y   I   S   D   E   Q   W   T   T   F   L   F   D   F   Y   H   Y   F 1021    TACATGCTAACCAACGCTCTCTTCTACGTCAGCTCCGCCATCAATCCCATCCTCTACAAC
 341     Y   M   L   T   N   A   L   F   Y   V   S   S   A   I   N   P   Y   L   I   N 1081    CTGGTCTCCGCCAACTTCCGCCAGGTCTTTCTGTCCACGCTGGCCTGCCTTTGTCCTGGG
 361     L   V   S   A   N   F   R   Q   V   F   L   S   T   L   A   C   L   C   P   G 1141    TGGCGCCACCGCCGAAAGAAGAGGCCAACGTTCTCCAGGAAGCCCAACAGCATGTCCAGC
 381     W   R   H   R   R   K   K   R   P   T   F   S   R   K   P   N   S   M   S   S NotI  +2 TrxA
1201    AACCATGCCTTTTCCACCAGCGCCACCCGGGAGACCCTGTACgcggccgcaAGCGATAAA
 401     N   H   A   F   S   T   S   A   T   R   E   T   L   Y   A   A   A   S   D   K 1261    ATTATTCACCTGACTGACGACAGTTTTGACACGGATGTACTCAAAGCGGACGGGGCGATC
 421     I   I   H   L   T   D   D   S   F   D   T   D   V   L   K   A   D   G   A   I
```

```
                               -continued
1321 CTCGTCGATTTCTGGGCAGAGTGGTGCGGTCCGTGCAAAATGATCGCCCCGATTCTGGAT
 441  L   V   D   F   W   A   E   W   C   G   P   C   K   M   I   A   P   I   L   D 1381 GAAATCGCTGACGAATATCAGGGCAAACTGACCGTTGCAAAACTGAACATCGATCAAAAC
 461  E   I   A   D   E   Y   Q   G   K   L   T   V   A   K   L   N   I   D   Q   N 1441 CCTGGCACTGCGCCGAAATATGGCATCCGTGGTATCCCGACTCTGCTGCTGTTCAAAAAC
 481  P   G   T   A   P   K   Y   G   I   R   G   I   P   T   L   L   L   F   K   N 1501 GGTGAAGTGGCGGCAACCAAAGTGGGTGCACTGTCTAAAGGTCAGTTGAAAGAGTTCCTC
 501  G   E   V   A   A   T   K   V   G   A   L   S   K   G   Q   L   K   E   F   L NotI           Flag             stop  KpnI
1561 GACGCTAACCTGGCAgcggccgcaGATTATAAAGATGACGATGACAAATAATAAGGTACC
 521  D   A   N   L   A   A   A   A   D   Y   K   D   D   D   D   K
```

SEQ ID NO.: 188
Human β2AR GS1α chimeric fusion

```
        SalI  +1 B2AR
   1 GTCGACATGG GGCAACCCGG GAACGGCAGC GCCTTCTTGC TGGCACCCAA TGGAAGCCAT

61 GCGCCGGACC ACGACGTCAC GCAGCAAAGG GACGAGGTGT GGGTGGTGGG CATGGGCATC

121 GTCATGTCTC TCATCGTCCT GGCCATCGTG TTTGGCAATG TGCTGGTCAT CACAGCCATT

181 GCCAAGTTCG AGCGTCTGCA GACGGTCACC AACTACTTCA TCACTTCACT GGCCTGTGCT

241 GATCTGGTCA TGGGCCTAGC AGTGGTGCCC TTTGGGGCCG CCCATATTCT TATGAAAATG

301 TGGACTTTTG GCAACTTCTG GTGCGAGTTT TGGACTTCCA TTGATGTGCT GTGCGTCACG

361 GCCAGCATTG AGACCCTGTG CGTGATCGCA GTGGATCGCT ACTTTGCCAT TACTTCACCT

421 TTCAAGTACC AGAGCCTGCT GACCAAGAAT AAGGCCCGGG TGATCATTCT GATGGTGTGG

481 ATTGTGTCAG GCCTTAYCTC CTTCTTGCCC ATTCAGATGC ACTGGTACAG GGCCACCCAC

541 CAGGAAGCCA TCAACTGCTA TGCCAATGAG ACCTGCTGTG ACTTCTTCAC GAACCAAGCC

601 TATGCCATTG CCTCTTCCAT CGTGTCCTTC TACGTTCCCC TGGTGATCAT GGTCTTCGTC

661 TACTCCAGGG TCTTTCAGGA GGCCAAAAGG CAGCTCCAGA AGATTGACAA ATCTGAGGGC

721 CGCTTCCATG TCCAGAACCT TAGCCAGGTG GAGCAGGATG GGCGGACGGG GCATGGACTC

781 CGCAGATCTT CCAAGTTCTG CTTGAAGGAG CACAAAGCCC TCAAGACGTT AGGCATCATC

841 ATGGGCACTT TCACCCTCTG CTGGCTGCCC TTCTTCATCG TTAACATTGT GCATGTGATC

901 CAGGATAACC TCATCCGTAA GGAAGTTTAC ATCCTCCTAA ATTGGATAGG CTATGTCAAT

961 TCTGGTTTCA ATCCCCTTAT CTACTGCCGG AGCCCAGATT TCAGGATTGC CTTCCAGGAG

1021 CTTCTGTGCC TGCGCAGGTC TTCTTTGAAG GCCTATGGCA ATGGCTACTC CAGCAACGGC

1081 AACACAGGGG AGCAGAGTGG ATATCACGTG GAACAGGAGA AGAAAAATAA ACTGCTGTGT

1141 GAAGACCTCC CAGGCACGGA AGACTTTGTG GGCCATCAAG GTACTGTGCC TAGCGATAAC

Last B2AR    Linker sequence
1201 ATTGATTCAC AAGGGAGGAA TTGTAGTACA AATGACTCAC TGCTAGAGCG TGGCCAGACG PstI  XhoI  +2 GS1 alpha
1261 GTCACCAACC TGCAGCTCGA GGGCTGCCTC GGGAACAGTA AGACCGAGGA CCAGCGCAAC

1321 GAGGAGAAGG CGCAGCGTGA GGCCAACAAA AAGATCGAGA GCAGCTGCA GAAGGACAAG

1381 CAGGTCTACC GGGCCACGCA CCGCCTGCTG CTGCTGGGTG CTGGAGAATC TGGTAAAAGC

1441 ACCATTGTGA AGCAGATGAG GATCCTGCAT GTTAATGGGT TTAATGGAGA CAGTGAGAAG

1501 GCAACCAAAG TGCAGGACAT CAAAAACAAC CTGAAAGAGG CGATTGAAAC CATTGTGGCC

1561 GCCATGAGCA ACCTGGTGCC CCCCGTGGAG CTGGCCAACC CGAGAACCA GTTCAGAGTG

1621 GACTACATCC TGAGTGTGAT GAACGTGCCT GACTTTGACT TCCCTCCCGA ATTCTATGAG
```

```
1681 CATGCCAAGG CTCTGTGGGA GGATGAAGGA GTGCGTGCCT GCTACGAACG CTCCAACGAG

1741 TACCAGCTGA TTGACTGTGC CCAGTACTTC CTGGACAAGA TCGACGTGAT CAAGCAGGCT

1801 GACTATGTGC CGAGCGATCA GGACCTGCTT CGCTGCCGTG TCCTGACTTC TGGAATCTTT

1861 GAGACCAAGT TCCAGGTGGA CAAAGTCAAC TTCCACATGT TTGACGTGGG TGGCCAGCGC

1921 GATGAACGCC GCAAGTGGAT CCAGTGCTTC AACGATGTGA CTGCCATCAT CTTCGTGGTG

1981 GCCAGCAGCA GCTACAACAT GGTCATCCGG GAGGACAACC AGACCAACCG CCTGCAGGAG

2041 GCTCTGAACC TCTTCAAGAG CATCTGGAAC AACAGATGGC TGCGCACCAT CTCTGTGATC

2101 CTGTTCCTCA ACAAGCAAGA TCTGCTCGCT GAGAAAGTCC TTGCTGGGAA ATCGAAGATT

2161 GAGGACTACT TTCCAGAATT TGCTCGCTAC ACTACTCCTG AGGATGCTAC TCCCGAGCCC

2221 GGAGAGGACC CACGCGTGAC CCGGGCCAAG TACTTCATTC GAGATGAGTT TCTGAGGATC

2281 AGCACTGCCA GTGGAGATGG GCGTCACTAC TGCTACCCTC ATTTCACCTG CGCTGTGGAC

2341 ACTGAGAACA TCCGCCGTGT GTTCAACGAC TGCCGTGACA TCATTCAGCG CATGCACCTT

ClaI  Stop   XbaI              Stem-loop
2401 CGTCAGTACG AGCTGCTCAT CGATTAATAA TCTAGAGGAT CCCCGCGCCC TCATCCGAAA

2461 GGGCG
```

SEQ ID NO.: 190
Human β2AR stop GS1α transcriptional fusion

```
     PstI  +1 B2AR
   1 GTCGACATGG GGCAACCCGG GAACGGCAGC GCCTTCTTGC TGGCACCCAA TGGAAGCCAT

61 GCGCCGGACC ACGACGTCAC GCAGCAAAGG GACGAGGTGT GGGTGGTGGG CATGGGCATC

121 GTCATGTCTC TCATCGTCCT GGCCATCGTG TTTGGCAATG TGCTGGTCAT CACAGCCATT

181 GCCAAGTTCG AGCGTCTGCA GACGGTCACC AACTACTTCA TCACTTCACT GGCCTGTGCT

241 GATCTGGTCA TGGGCCTAGC AGTGGTGCCC TTTGGGGCCG CCCATATTCT TATGAAAATG

301 TGGACTTTTG GCAACTTCTG GTGCGAGTTT TGGACTTCCA TTGATGTGCT GTGCGTCACG

361 GCCAGCATTG AGACCCTGTG CGTGATCGCA GTGGATCGCT ACTTTGCCAT TACTTCACCT

421 TTCAAGTACC AGAGCCTGCT GACCAAGAAT AAGGCCCGGG TGATCATTCT GATGGTGTGG

481 ATTGTGTCAG GCCTTAYCTC CTTCTTGCCC ATTCAGATGC ACTGGTACAG GGCCACCCAC

541 CAGGAAGCCA TCAACTGCTA TGCCAATGAG ACCTGCTGTG ACTTCTTCAC GAACCAAGCC

601 TATGCCATTG CCTCTTCCAT CGTGTCCTTC TACGTTCCCC TGGTGATCAT GGTCTTCGTC

661 TACTCCAGGG TCTTTCAGGA GGCCAAAAGG CAGCTCCAGA AGATTGACAA ATCTGAGGGC

721 CGCTTCCATG TCCAGAACCT TAGCCAGGTG GAGCAGGATG GGCGGACGGG GCATGGACTC

781 CGCAGATCTT CCAAGTTCTG CTTGAAGGAG CACAAAGCCC TCAAGACGTT AGGCATCATC

841 ATGGGCACTT TCACCCTCTG CTGGCTGCCC TTCTTCATCG TTAACATTGT GCATGTGATC

901 CAGGATAACC TCATCCGTAA GGAAGTTTAC ATCCTCCTAA ATTGGATAGG CTATGTCAAT

961 TCTGGTTTCA ATCCCCTTAT CTACTGCCGG AGCCCAGATT TCAGGATTGC CTTCCAGGAG

1021 CTTCTGTGCC TGCGCAGGTC TTCTTTGAAG GCCTATGGCA ATGGCTACTC CAGCAACGGC

1081 AACACAGGGG AGCAGAGTGG ATATCACGTG GAACAGGAGA AGGAAAATAA ACTGCTGTGT

1141 GAAGACCTCC CAGGCACGGA AGACTTTGTG GGCCATCAAG GTACTGTGCC TAGCGATAAC

Last B2AR   Linker sequence
1201 ATTGATTCAC AAGGGAGGAA TTGTAGTACA AATGACTCAC TGCTAGAGCG TGGCCAGACG PstI      Stop      SD          XhoI  +2 GS1 alpha
1261 GTCACCAACC TGCAGTAATA ATCAAGGAGG CCCTCGAGAT GGGCTGCCTC GGGAACAGTA
```

-continued

```
1321 AGACCGAGGA CCAGCGCAAC GAGGAGAAGG CGCAGCGTGA GGCCAACAAA AAGATCGAGA

1381 AGCAGCTGCA GAAGGACAAG CAGGTCTACC GGGCCACGCA CCGCCTGCTG CTGCTGGGTG

1441 CTGGAGAATC TGGTAAAAGC ACCATTGTGA AGCAGATGAG GATCCTGCAT GTTAATGGGT

1501 TTAATGGAGA CAGTGAGAAG GCAACCAAAG TGCAGGACAT CAAAAACAAC CTGAAAGAGG

1561 CGATTGAAAC CATTGTGGCC GCCATGAGCA ACCTGGTGCC CCCCGTGGAG CTGGCCAACC

1621 CCGAGAACCA GTTCAGAGTG GACTACATCC TGAGTGTGAT GAACGTGCCT GACTTTGACT

1681 TCCCTCCCGA ATTCTATGAG CATGCCAAGG CTCTGTGGGA GGATGAAGGA GTGCGTGCCT

1741 GCTACGAACG CTCCAACGAG TACCAGCTGA TTGACTGTGC CCAGTACTTC CTGGACAAGA

1801 TCGACGTGAT CAAGCAGGCT GACTATGTGC CGAGCGATCA GGACCTGCTT CGCTGCCGTG

1861 TCCTGACTTC TGGAATCTTT GAGACCAAGT TCCAGGTGGA CAAAGTCAAC TTCCACATGT

1921 TTGACGTGGG TGGCCAGCGC GATGAACGCC GCAAGTGGAT CCAGTGCTTC AACGATGTGA

1981 CTGCCATCAT CTTCGTGGTG GCCAGCAGCA GCTACAACAT GGTCATCCGG GAGGACAACC

2041 AGACCAACCG CCTGCAGGAG GCTCTGAACC TCTTCAAGAG CATCTGGAAC AACAGATGGC

2101 TGCGCACCAT CTCTGTGATC CTGTTCCTCA ACAAGCAAGA TCTGCTCGCT GAGAAAGTCC

2161 TTGCTGGGAA ATCGAAGATT GAGGACTACT TTCCAGAATT TGCTCGCTAC ACTACTCCTG

2221 AGGATGCTAC TCCCGAGCCC GGAGAGGACC CACGCGTGAC CCGGGCCAAG TACTTCATTC

2281 GAGATGAGTT TCTGAGGATC AGCACTGCCA GTGGAGATGG GCGTCACTAC TGCTACCCTC

2341 ATTTCACCTG CGCTGTGGAC ACTGAGAACA TCCGCCGTGT GTTCAACGAC TGCCGTGACA

ClaI Stop  XbaI
2401 TCATTCAGCG CATGCACCTT CGTCAGTACG AGCTGCTCAT CGATTAATAA TCTAGAGGAT Stem-loop
2461 CCCCGCGCCC TCATCCGAAA GGGCG
```

SEQ ID NO.: 192
Human GS1α

```
    Xho I
  1 CTCGAGATGGGCTGCCTCGGGAACAGTAAGACCGAGGACCAGCGCAACGAGGAGAAGGCGCAGCGT
  1       M   G   C   L   G   N   S   K   T   E   D   Q   R   N   E   E   K   A   Q   R

61 GAGGCCAACAAAAAGATCGAGAAGCAGCTGCAGAAGGACAAGCAGGTCTACCGGGCCACG
 21       E   A   N   K   K   I   E   K   Q   L   Q   K   D   K   Q   V   Y   R   A   T

121 CACCGCCTGCTGCTGCTGGGTGCTGGAGAATCTGGTAAAAGCACCATTGTGAAGCAGATG
 41       H   R   L   L   L   L   G   A   G   E   S   G   K   S   T   I   V   K   Q   M

181 AGGATCCTGCATGTTAATGGGTTTAATGGAGACAGTGAGAAGGCAACCAAAGTGCAGGAC
 61       R   I   L   H   V   N   G   F   N   G   D   S   E   K   A   T   K   V   Q   D

241 ATCAAAAACAACCTGAAAGAGGCGATTGAAACCATTGTGGCCGCCATGAGCAACCTGGTG
 81       I   K   N   N   L   K   E   A   I   E   T   I   V   A   A   M   S   N   L   V

301 CCCCCCGTGGAGCTGGCCAACCCCGAGAACCAGTTCAGAGTGGACTACATCCTGAGTGTG
101       P   P   V   E   L   A   N   P   E   N   Q   F   R   V   D   Y   I   L   S   V

361 ATGAACGTGCCTGACTTTGACTTCCCTCCCGAATTCTATGAGCATGCCAAGGCTCTGTGG
121       M   N   V   P   D   F   D   F   P   P   E   F   Y   E   H   A   K   A   L   W

421 GAGGATGAAGGAGTGCGTGCCTGCTACGAACGCTCCAACGAGTACCAGCTGATTGACTGT
141       E   D   E   G   V   R   A   C   Y   E   R   S   N   E   Y   Q   L   I   D   C

481 GCCCAGTACTTCCTGGACAAGATCGACGTGATCAAGCAGGCTGACTATGTGCCGAGCGAT
161       A   Q   Y   F   L   D   K   I   D   V   I   K   Q   A   D   Y   V   P   S   D

541 CAGGACCTGCTTCGCTGCCGTGTCCTGACTTCTGGAATCTTTGAGACCAAGTTCCAGGTG
181       Q   D   L   L   R   C   R   V   L   T   S   G   I   F   E   T   K   F   Q   V

601 GACAAAGTCAACTTCCACATGTTTGACGTGGGTGGCCAGCGCGATGAACGCCGCAAGTGG
```

```
201       D   K   V   N   F   H   M   F   D   V   G   G   Q   R   D   E   R   R   K   W

661  ATCCAGTGCTTCAACGATGTGACTGCCATCATCTTCGTGGTGGCCAGCAGCAGCTACAAC
221       I   Q   C   F   N   D   V   T   A   I   I   F   V   V   A   S   S   S   Y   N

721  ATGGTCATCCGGGAGGACAACCAGACCAACCGCCTGCAGGAGGCTCTGAACCTCTTCAAG
241       M   V   I   R   E   D   N   Q   T   N   R   L   Q   E   A   L   N   L   F   K

781  AGCATCTGGAACAACAGATGGCTGCGCACCATCTCTGTGATCCTGTTCCTCAACAAGCAA
261       S   I   W   N   N   R   W   L   R   T   I   S   V   I   L   F   L   N   K   Q

841  GATCTGCTCGCTGAGAAAGTCCTTGCTGGGAAATCGAAGATTGAGGACTACTTTCCAGAA
281       D   L   L   A   E   K   V   L   A   G   K   S   K   I   E   D   Y   F   P   E

901  TTTGCTCGCTACACTACTCCTGAGGATGCTACTCCCGAGCCCGGAGAGGACCCACGCGTG
301       F   A   R   Y   T   T   P   E   D   A   T   P   E   P   G   E   D   P   R   V

961  ACCCGGGCCAAGTACTTCATTCGAGATGAGTTTCTGAGGATCAGCACTGCCAGTGGAGAT
321       T   R   A   K   Y   F   I   R   D   E   F   L   R   I   S   T   A   S   G   D

1021 GGGCGTCACTACTGCTACCCTCATTTCACCTGCGCTGTGGACACTGAGAACATCCGCCGT
391       G   R   H   Y   C   Y   P   H   F   T   C   A   V   D   T   E   N   I   R   R

1081 GTGTTCAACGACTGCCGTGACATCATTCAGCGCATGCACCTTCGTCAGTACGAGCTGCTC
361       V   F   N   D   C   R   D   I   I   Q   R   M   H   L   R   Q   Y   E   L   L

Cla I
     ATCGAT
```

SEQ ID NO.: 193
Human GS2α

```
     XhoI
  1  CTCGAGATGGGCTGCCTCGGGAACAGTAAGACCGAGGACCAGCGCAACGAGGAGAAGGCGCAGCGT
  1       M   G   C   L   G   N   S   K   T   E   D   Q   R   N   E   E   K   A   Q   R

61  GAGGCCAACAAAAAGATCGAGAAGCAGCTGCAGAAGGACAAGCAGGTCTACCGGGCCACG
 21       E   A   N   K   K   I   E   K   Q   L   Q   K   D   K   Q   V   Y   R   A   T

121  CACCGCCTGCTGCTGCTGGGTGCTGGAGAATCTGGTAAAAGCACCATTGTGAAGCAGATG
 41       H   R   L   L   L   L   G   A   G   E   S   G   K   S   T   I   V   K   Q   M

181  AGGATCCTGCATGTTAATGGGTTTAATGGAGAGGGCGGCGAAGAGGACCCGCAGGCTGCA
 61       R   I   L   H   V   N   G   F   N   G   E   G   G   E   E   D   P   Q   A   A

241  AGGAGCAACAGCGATGGTGAGAAGGCAACCAAAGTGCAGGACATCAAAAACAACCTGAAA
 81       R   S   N   S   D   G   E   K   A   T   K   V   Q   D   I   K   N   N   L   K

301  GAGGCGATTGAAACCATTGTGGCCGCCATGAGCAACCTGGTGCCCCCCGTGGAGCTGGCC
101       E   A   I   E   T   I   V   A   A   M   S   N   L   V   P   P   V   E   L   A

361  AACCCCGAGAACCAGTTCAGAGTGGACTACATCCTGAGTGTGATGAACGTGCCTGACTTT
121       N   P   E   N   Q   F   R   V   D   Y   I   L   S   V   M   N   V   P   D   F

421  GACTTCCCTCCCGAATTCTATGAGCATGCCAAGGCTCTGTGGGAGGATGAAGGAGTGCGT
141       D   F   P   P   E   F   Y   E   H   A   K   A   L   W   E   D   E   G   V   R

481  GCCTGCTACGAACGCTCCAACGAGTACCAGCTGATTGACTGTGCCCAGTACTTCCTGGAC
161       A   C   Y   E   R   S   N   E   Y   Q   L   I   D   C   A   Q   Y   F   L   D

541  AAGATCGACGTGATCAAGCAGGCTGACTATGTGCCGAGCGATCAGGACCTGCTTCGCTGC
181       K   I   D   V   I   K   Q   A   D   Y   V   P   S   D   Q   D   L   L   R   C

601  CGTGTCCTGACTTCTGGAATCTTTGAGACCAAGTTCCAGGTGGACAAAGTCAACTTCCAC
201       R   V   L   T   S   G   I   F   E   T   K   F   Q   V   D   K   V   N   F   H

661  ATGTTTGACGTGGGTGGCCAGCGCGATGAACGCCGCAAGTGGATCCAGTGCTTCAACGAT
221       M   F   D   V   G   G   Q   R   D   E   R   R   K   W   I   Q   C   F   N   D

721  GTGACTGCCATCATCTTCGTGGTGGCCAGCAGCAGCTACAACATGGTCATCCGGGAGGAC
241       V   T   A   I   I   F   V   V   A   S   S   S   Y   N   M   V   I   R   E   D

781  AACCAGACCAACCGCCTGCAGGAGGCTCTGAACCTCTTCAAGAGCATCTGGAACAACAGA
261       N   Q   T   N   R   L   Q   E   A   L   N   L   F   K   S   I   W   N   N   R

841  TGGCTGCGCACCATCTCTGTGATCCTGTTCCTCAACAAGCAAGATCTGCTCGCTGAGAAA
281       W   L   R   T   I   S   V   I   L   F   L   N   K   Q   D   L   L   A   E   K
```

```
                              -continued
 901   GTCCTTGCTGGGAAATCGAAGATTGAGGACTACTTTCCAGAATTTGCTCGCTACACTACT
 301    V  L  A  G  K  S  K  I  E  D  Y  F  P  E  F  A  R  Y  T  T 961   CCTGAGGATGCTACTCCCGAGCCCGGAGAGGACCCACGCGTGACCCGGGCCAAGTACTTC
 321    P  E  D  A  T  P  E  P  G  E  D  P  R  V  T  R  A  K  Y  F 1021   ATTCGAGATGAGTTTCTGAGGATCAGCACTGCCAGTGGAGATGGGCGTCACTACTGCTAC
 341    I  R  D  E  F  L  R  I  S  T  A  S  G  D  G  R  H  Y  C  Y 1081   CCTCATTTCACCTGCGCTGTGGACACTGAGAACATCCGCCGTGTGTTCAACGACTGCCGT
 361    P  H  F  T  C  A  V  D  T  E  N  I  R  R  V  F  N  D  C  R ClaI
1141   GACATCATTCAGCGCATGCACCTTCGTCAGTACGAGCTGCTCATCGAT
 381    D  I  I  Q  R  M  H  L  R  Q  Y  E  L  L
```

SEQ ID NO.: 194
Human Gαq

```
       XhoI
   1   CTCGAGATGACTCTGGAGTCCATCATGGCGTGCTGCCTGAGCGAGGAGGCCAAGGAAGCCCGGCGG
   1       M  T  L  E  S  I  M  A  C  C  L  S  E  E  A  K  E  A  R  R

61   ATCAACGACGAGATCGAGCGGCAGCTCCGCAGGGACAAGCGGGACGCCCGCCGGGAGCTC
  21    I  N  D  E  I  E  R  Q  L  R  R  D  K  R  D  A  R  R  E  L

121   AAGCTGCTGCTGCTCGGGACAGGAGAGAGTGGCAAGAGTACGTTTATCAAGCAGATGAGA
  41    K  L  L  L  L  G  T  G  E  S  G  K  S  T  F  I  K  Q  M  R

181   ATCATCCATGGGTCAGGATACTCTGATGAAGATAAAAGGGGCTTCACCAAGCTGGTGTAT
  61    I  I  H  G  S  G  Y  S  D  E  D  K  R  G  F  T  K  L  V  Y

241   CAGAACATCTTCACGGCCATGCAGGCCATGATCAGAGCCATGGACACACTCAAGATCCCA
  81    Q  N  I  F  T  A  M  Q  A  M  I  R  A  M  D  T  L  K  I  P

301   TACAAGTATGAGCACAATAAGGCTCATGCACAATTAGTTCGAGAAGTTGATGTGGAGAAG
 101    Y  K  Y  E  H  N  K  A  H  A  Q  L  V  R  E  V  D  V  E  K

361   GTGTCTGCTTTTGAGAATCCATATGTAGATGCAATAAAGAGTTTATGGAATGATCCTGGA
 121    V  S  A  F  E  N  P  Y  V  D  A  I  K  S  L  W  N  D  P  G

421   ATCCAGGAATGCTATGATAGACGACGAGAATATCAATTATCTGACTCTACCAAATACTAT
 141    I  Q  E  C  Y  D  R  R  R  E  Y  Q  L  S  D  S  T  K  Y  Y

481   CTTAATGACTTGGACCGCGTAGCTGACCCTGCCTACCTGCCTACGCAACAAGATGTGCTT
 161    L  N  D  L  D  R  V  A  D  P  A  Y  L  P  T  Q  Q  D  V  L

541   AGAGTTCGAGTCCCCACCACAGGGATCATCGAATACCCCTTTGACTTACAAAGTGTCATT
 181    R  V  R  V  P  T  T  G  I  I  E  Y  P  F  D  L  Q  S  V  I

601   TTCAGAATGGTCGATGTAGGGGGCCAAAGGTCAGAGAGAAGAAAATGGATACACTGCTTT
 201    F  R  M  V  D  V  G  G  Q  R  S  E  R  R  K  W  I  H  C  F

661   GAAAATGTCACCTCTATCATGTTTCTAGTAGCGCTTAGTGAATATGATCAAGTTCTCGTG
 221    E  N  V  T  S  I  M  F  L  V  A  L  S  E  Y  D  Q  V  L  V

721   GAGTCAGACAATGAGAACCGAATGGAGGAAAGCAAGGCTCTCTTTAGAACAATTATCACA
 241    E  S  D  N  E  N  R  M  E  E  S  K  A  L  F  R  T  I  I  T

781   TACCCCTGGTTCCAGAACTCCTCGGTTATTCTGTTCTTAAACAAGAAAGATCTTCTAGAG
 261    Y  P  W  F  Q  N  S  S  V  I  L  F  L  N  K  K  D  L  L  E

841   GAGAAAATCATGTATTCCCATCTAGTCGACTACTTCCCAGAATATGATGGACCCCAGAGA
 281    E  K  I  M  Y  S  H  L  V  D  Y  F  P  E  Y  D  G  P  Q  R

901   GATGCCCAGGCAGCCCGAGAATTCATTCTGAAGATGTTCGTGGACCTGAACCCAGACAGT
 301    D  A  Q  A  A  R  E  F  I  L  K  M  F  V  D  L  N  P  D  S

961   GACAAAATTATCTACTCCCACTTCACGTGCGCCACAGACACCGAGAATATCCGCTTTGTC
 321    D  K  I  I  Y  S  H  F  T  C  A  T  D  T  E  N  I  R  F  V

ClaI
1021   TTTGCTGCCGTCAAGGACACCATCCTCCAGTTGAACCTGAAGGAGTACAATCTGGTCATCGAT
 341    F  A  A  V  K  D  T  I  L  Q  L  N  L  K  E  Y  N  L  V
```

SEQ ID NO.: 195
Human Giα

```
       XhoI
   1 CTCGAGATGGGCTGCACCGTGAGCGCCGAGGACAAGGCGGCGGCCGAGCGCTCTAAGATGATCGAC
   1       M  G  C  T  V  S  A  E  D  K  A  A  A  E  R  S  K  M  I  D

61   AAGAACCTGCGGGAGGACGGAGAGAAGGCGGCGCGGGAGGTGAAGTTGCTGCTGTTGGGT
  21       K  N  L  R  E  D  G  E  K  A  A  R  E  V  K  L  L  L  L  G

121   GCTGGGGAGTCAGGGAAGAGCACCATCGTCAAGCAGATGAAGATCATCCACGAGGATGGC
  41       A  G  E  S  G  K  S  T  I  V  K  Q  M  K  I  I  H  E  D  G

181   TACTCCGAGGAGGAATGCCGGCAGTACCGGGCGGTTGTCTACAGCAACACCATCCAGTCC
  61       Y  S  E  E  E  C  R  Q  Y  R  A  V  V  Y  S  N  T  I  Q  S

241   ATCATGGCCATTGTCAAAGCCATGGGAAACCTGCAGATCGACTTTGCCGACCCCTCCAGA
  81       I  M  A  I  V  K  A  M  G  N  L  Q  I  D  F  A  D  P  S  R

301   GCGGACGACGCCAGGCAGCTATTTGCACTGTCCTGCACCGCCGAGGAGCAAGGCGTGCTC
 101       A  D  D  A  R  Q  L  F  A  L  S  C  T  A  E  E  Q  G  V  L

361   CCTGATGACCTGTCCGGCGTCATCCGGAGGCTCTGGGCTGACCATGGTGTGCAGGCCTGC
 121       P  D  D  L  S  G  V  I  R  R  L  W  A  D  H  G  V  Q  A  C

421   TTTGGCCGCTCAAGGGAATACCAGCTCAACGACTCAGCTGCCTACTACCTGAACGACCTG
 141       F  G  R  S  R  E  Y  Q  L  N  D  S  A  A  Y  Y  L  N  D  L

481   GAGCGTATTGCACAGAGTGACTACATCCCCACACAGCAAGATGTGCTACGGACCCGCGTA
 161       E  R  I  A  Q  S  D  Y  I  P  T  Q  Q  D  V  L  R  T  R  V

541   AAGACCACGGGGATCGTGGAGACACACTTCACCTTCAAGGACCTACACTTCAAGATGTTT
 181       K  T  T  G  I  V  E  T  H  F  T  F  K  D  L  H  F  K  M  F

601   GATGTGGGTGGTCAGCGGTCTGAGCGGAAGAAGTGGATCCACTGCTTTGAGGGCGTCACA
 201       D  V  G  G  Q  R  S  E  R  K  K  W  I  H  C  F  E  G  V  T

661   GCCATCATCTTCTGCGTAGCCTTGAGCGCCTATGACTTGGTGCTAGCTGAGGACGAGGAG
 221       A  I  I  F  C  V  A  L  S  A  Y  D  L  V  L  A  E  D  E  E

721   ATGAACCGCATGCATGAGAGCATGAAGCTATTCGATAGCATCTGCAACAACAAGTGGTTC
 241       M  N  R  M  H  E  S  M  K  L  F  D  S  I  C  N  N  K  W  F

781   ACAGACACGTCCATCATCCTCTTCCTCAACAAGAAGGACCTGTTTGAGGAGAAGATCACA
 261       T  D  T  S  I  I  L  F  L  N  K  K  D  L  F  E  E  K  I  T

841   CACAGTCCCCTGACCATCTGCTTCCCTGAGTACACAGGGGCCAACAAATATGATGAGGCA
 281       H  S  P  L  T  I  C  F  P  E  Y  T  G  A  N  K  Y  D  E  A

901   GCCAGCTACATCCAGAGTAAGTTTGAGGACCTGAATAAGCGCAAAGACACCAAGGAGATC
 301       A  S  Y  I  Q  S  K  F  E  D  L  N  K  R  K  D  T  K  E  I

961   TACACGCACTTCACGTGCGCCACCGACACCAAGAACGTGCAGTTCGTGTTTGACGCCGTC
 321       Y  T  H  F  T  C  A  T  D  T  K  N  V  Q  F  V  F  D  A  V

ClaI
1021   ACCGATGTCATCATCAAGAACAACCTGAAGGACTGCGGCCTCTTCATGCAT
 341       T  D  V  I  I  K  N  N  L  K  D  C  G  L  F
```

SEQ ID NO.: 196
Human Gα12/13

```
       Xho I
   1 CTCGAGATGTCCGGGGTGGTGCGGACCCTCAGCCGCTGCCTGCTGCCGGCCGAGGCCGGCGGGGCC
   1       M  S  G  V  V  R  T  L  S  R  C  L  L  P  A  E  A  G  G  A

61   CGCGAGCGCAGGGCGGGCAGCGGCGCGCGCGACGCGGGAGCGCGAGGCCCGGAGGCGTAGC
  21       R  E  R  R  A  G  S  G  A  R  D  A  E  R  E  A  R  R  R  S

121   CGCGACATCGACGCGCTGCTGGCCCGCGAGCGGCGCGCGGTCCGGCGCCTGGTGAAGATC
  41       R  D  I  D  A  L  L  A  R  E  R  R  A  V  R  R  L  V  K  I

181   CTGCTGCTGGGCGCGGGCGAGAGCGGCAAGTCCACGTTCCTCAAGCAGATGCGCATCATC
  61       L  L  L  G  A  G  E  S  G  K  S  T  F  L  K  Q  M  R  I  I

241   CACGGCCGCGAGTTCGACCAGAAGGCGCTGCTGGAGTTCCGCGACACCATCTTCGACAAC
  81       H  G  R  E  F  D  Q  K  A  L  L  E  F  R  D  T  I  F  D  N
```

```
                              -continued
 301      ATCCTCAAGGGCTCAAGGGTTCTTGTTGATGCACGAGATAAGCTTGGCATTCCTTGGCAG
 101        I  L  K  G  S  R  V  L  V  D  A  R  D  K  L  G  I  P  W  Q 361      TATTCTGAAAATGAGAAGCATGGGATGTTCCTGATGGCCTTCGAGAACAAGGCGGGGCTG
 121        Y  S  E  N  E  K  H  G  M  F  L  M  A  F  E  N  K  A  G  L 421      CCTGTGGAGCCGGCCACCTTCCAGCTGTACGTCCCGGCCCTGAGCGCACTCTGGAGGGAT
 141        P  V  E  P  A  T  F  Q  L  Y  V  P  A  L  S  A  L  W  R  D 481      TCTGGCATCAGGGAGGCTTTCAGCCGGAGAAGCGAGTTTCAGCTGGGGGAGTCGGTGAAG
 161        S  G  I  R  E  A  F  S  R  R  S  E  F  Q  L  G  E  S  V  K 541      TACTTCCTGGACAACTTGGACCGGATCGGCCAGCTGAATTACTTTCCTAGTAAGCAAGAT
 181        Y  F  L  D  N  L  D  R  I  G  Q  L  N  Y  F  P  S  K  Q  D 601      ATCCTGCTGGCTAGGAAAGCCACCAAGGGAATTGTGGAGCATGACTTCGTTATTAAGAAG
 201        I  L  L  A  R  K  A  T  K  G  I  V  E  H  D  F  V  I  K  K 661      ATCCCCTTTAAGATGGTGGATGTGGGCGGCCAGCGGTCCCAGCGCCAGAAGTGGTTCCAG
 221        I  P  F  K  M  V  D  V  G  G  Q  R  S  Q  R  Q  K  W  F  Q 721      TGCTTCGACGGGATCACGTCCATCCTGTTCATGGTCTCCTCCAGCGAGTACGACCAGGTC
 241        C  F  D  G  I  T  S  I  L  F  M  V  S  S  S  E  Y  D  Q  V 781      CTCATGGAGGACAGGCGCACCAACCGGCTGGTGGAGTCCATGAACATCTTCGAGACCATC
 261        L  M  E  D  R  R  T  N  R  L  V  E  S  M  N  I  F  E  T  I 841      GTCAACAACAAGCTCTTCTTCAACGTCTCCATCATTCTCTTCCTCAACAAGATGGACCTC
 281        V  N  N  K  L  F  F  N  V  S  I  I  L  F  L  N  K  M  D  L 901      CTGGTGGAGAAGGTGAAGACCGTGAGCATCAAGAAGCACTTCCCGGACTTCAGGGGCGAC
 301        L  V  E  K  V  K  T  V  S  I  K  K  H  F  P  D  F  R  G  D 961      CCGCACCAGCTGGAGGACGTCCAGCGCTACCTGGTCCAGTGCTTCGACAGGAAGAGACGG
 321        P  H  Q  L  E  D  V  Q  R  Y  L  V  Q  C  F  D  R  K  R  R 1021      AACCGCAGCAAGCCACTCTTCCACCACTTCACCACCGCCATCGACACCGAGAACGTCCGC
 341        N  R  S  K  P  L  F  H  H  F  T  T  A  I  D  T  E  N  V  R 1081      TTCGTGTTCCATGCTGTGAAAGACACCATCCTGCAGGAGAACCTGAAGGACATCATGCTG
 361        F  V  F  H  A  V  K  D  T  I  L  Q  E  N  L  K  D  I  M  L ClaI
1141      CAGATCGAT
 381        Q
```

SEQ ID NO.: 205
Human β2AR-ToxR (5-141) chimera stop GS1α-ToxR (5-141) chimera transcriptional fusion

```
      SalI  +1 B2AR
  1 GTCGACATGG GGCAACCCGG GAACGGCAGC GCCTTCTTGC TGGCACCCAA TGGAAGCCAT

61 GCGCCGGACC ACGACGTCAC GCAGCAAAGG GACGAGGTGT GGGTGGTGGG CATGGGCATC

121 GTCATGTCTC TCATCGTCCT GGCCATCGTG TTTGGCAATG TGCTGGTCAT CACAGCCATT

181 GCCAAGTTCG AGCGTCTGCA GACGGTCACC AACTACTTCA TCACTTCACT GGCCTGTGCT

241 GATCTGGTCA TGGGCCTAGC AGTGGTGCCC TTTGGGGCCG CCCATATTCT TATGAAAATG

301 TGGACTTTTG GCAACTTCTG GTGCGAGTTT TGGACTTCCA TTGATGTGCT GTGCGTCACG

361 GCCAGCATTG AGACCCTGTG CGTGATCGCA GTGGATCGCT ACTTTGCCAT TACTTCACCT

421 TTCAAGTACC AGAGCCTGCT GACCAAGAAT AAGGCCCGGG TGATCATTCT GATGGTGTGG

481 ATTGTGTCAG GCCTTAYCTC CTTCTTGCCC ATTCAGATGC ACTGGTACAG GGCCACCCAC

541 CAGGAAGCCA TCAACTGCTA TGCCAATGAG ACCTGCTGTG ACTTCTTCAC GAACCAAGCC

601 TATGCCATTG CCTCTTCCAT CGTGTCCTTC TACGTTCCCC TGGTGATCAT GGTCTTCGTC

661 TACTCCAGGG TCTTTCAGGA GGCCAAAAGG CAGCTCCAGA AGATTGACAA ATCTGAGGGC

721 CGCTTCCATG TCCAGAACCT TAGCCAGGTG GAGCAGGATG GCGGACGGGG CATGGACTC

781 CGCAGATCTT CCAAGTTCTG CTTGAAGGAG CACAAAGCCC TCAAGACGTT AGGCATCATC
```

-continued

```
 841 ATGGGCACTT TCACCCTCTG CTGGCTGCCC TTCTTCATCG TTAACATTGT GCATGTGATC

901 CAGGATAACC TCATCCGTAA GGAAGTTTAC ATCCTCCTAA ATTGGATAGG CTATGTCAAT

961 TCTGGTTTCA ATCCCCTTAT CTACTGCCGG AGCCCAGATT TCAGGATTGC CTTCCAGGAG

1021 CTTCTGTGCC TGCGCAGGTC TTCTTTGAAG GCCTATGGCA ATGGCTACTC CAGCAACGGC

1081 AACACAGGGG AGCAGAGTGG ATATCACGTG GAACAGGAGA AGAAAATAA ACTGCTGTGT

1141 GAAGACCTCC CAGGCACGGA AGACTTTGTG GGCCATCAAG GTACTGTGCC TAGCGATAAC last B2AR linker sequence
1201 ATTGATTCAC AAGGGAGGAA TTGTAGTACA AATGACTCAC TGCTAGAGCG TGGCCAGACG PstI   +5 toxR (5-141)
1261 GTCACCAACC TGCAGGGACA CAACTCAAAA GAGATATCGA TGAGTCATAT TGGTACTAAA

1321 TTCATTCTTG CTGAAAAATT TACCTTCGAT CCCCTAAGCA ATACTCTGAT TGACAAAGAA

1381 GATAGTGAAG AGATCATTCG ATTAGGCAGC AACGAAAGCC GAATTCTTTG GCTGCTGGCC

1441 CAACGTCCAA ACGAGGTAAT TTCTCGCAAT GATTTGCATG ACTTTGTTTG GCGAGAGCAA

1501 GGTTTTGAAG TCGATGATTC CAGCTTAACC CAAGCCATTT CGACTCTGCG CAAAATGCTC

1561 AAAGATTCGA CAAAGTCCCC ACAATACGTC AAAACGGTTC GAAGCGCGG TTACCAATTG

1621 ATCGCCCGAG TGGAAACGGT TGAAGAAGAG ATGGCTCGCG AAAACGAAGC TGCTCATGAC stop     SD       XhoI   +1 GS1 alpha
1681 ATCTCTTAAT AATCAAGGAG GCCCTCGAGA TGGGCTGCCT CGGGAACAGT AAGACCGAGG

1741 ACCAGCGCAA CGAGGAGAAG GCGCAGCGTG AGGCCAACAA AAAGATCGAG AAGCAGCTGC

1801 AGAAGGACAA GCAGGTCTAC CGGGCCACGC ACCGCCTGCT GCTGCTGGGT GCTGGAGAAT

1861 CTGGTAAAAG CACCATTGTG AAGCAGATGA GGATCCTGCA TGTTAATGGG TTTAATGGAG

1921 ACAGTGAGAA GGCAACCAAA GTGCAGGACA TCAAAAACAA CCTGAAAGAG GCGATTGAAA

1981 CCATTGTGGC CGCCATGAGC AACCTGGTGC CCCCCGTGGA GCTGGCCAAC CCCGAGAACC

2041 AGTTCAGAGT GGACTACATC CTGAGTGTGA TGAACGTGCC TGACTTTGAC TTCCCTCCCG

2101 AATTCTATGA GCATGCCAAG GCTCTGTGGG AGGATGAAGG AGTGCGTGCC TGCTACGAAC

2161 GCTCCAACGA GTACCAGCTG ATTGACTGTG CCCAGTACTT CCTGGACAAG ATCGACGTGA

2221 TCAAGCAGGC TGACTATGTG CCGAGCGATC AGGACCTGCT TCGCTGCCGT GTCCTGACTT

2281 CTGGAATCTT TGAGACCAAG TTCCAGGTGG ACAAAGTCAA CTTCCACATG TTTGACGTGG

2341 GTGGCCAGCG CGATGAACGC CGCAAGTGGA TCCAGTGCTT CAACGATGTG ACTGCCATCA

2401 TCTTCGTGGT GGCCAGCAGC AGCTACAACA TGGTCATCCG GGAGGACAAC CAGACCAACC

2461 GCCTGCAGGA GGCTCTGAAC CTCTTCAAGA GCATCTGGAA CAACAGATGG CTGCGCACCA

2521 TCTCTGTGAT CCTGTTCCTC AACAAGCAAG ATCTGCTCGC TGAGAAAGTC CTTGCTGGGA

2581 AATCGAAGAT TGAGGACTAC TTTCCAGAAT TTGCTCGCTA CACTACTCCT GAGGATGCTA

2641 CTCCCGAGCC CGGAGAGGAC CCACGCGTGA CCCGGGCCAA GTACTTCATT CGAGATGAGT

2701 TTCTGAGGAT CAGCACTGCC AGTGGAGATG GGCGTCACTA CTGCTACCCT CATTTCACCT

2761 GCGCTGTGGA CACTGAGAAC ATCCGCCGTG TGTTCAACGA CTGCCGTGAC ATCATTCAGC

ClaI   +5 toxR (5-141)
2821 GCATGCACCT TCGTCAGTAC GAGCTGCTCA TCGATGGACA CAACTCAAAA GAGATATCGA

2881 TGAGTCATAT TGGTACTAAA TTCATTCTTG CTGAAAAATT TACCTTCGAT CCCCTAAGCA

2941 ATACTCTGAT TGACAAAGAA GATAGTGAAG AGATCATTCG ATTAGGCAGC AACGAAAGCC

3001 GAATTCTTTG GCTGCTGGCC CAACGTCCAA ACGAGGTAAT TTCTCGCAAT GATTTGCATG

3061 ACTTTGTTTG GCGAGAGCAA GGTTTTGAAG TCGATGATTC CAGCTTAACC CAAGCCATTT
```

-continued

```
3121 CGACTCTGCG CAAAATGCTC AAAGATTCGA CAAAGTCCCC ACAATACGTC AAAACGGTTC

3181 CGAAGCGCGG TTACCAATTG ATCGCCCGAG TGGAAACGGT TGAAGAAGAG ATGGCTCGCG

Stop   XbaI                Stem-loop
3241 AAAACGAAGC TGCTCATGAC ATCTCTTAAT AATCTAGAGG ATCCCCGCGC CCTCATCCGA

3301 AAGGGCG
```

SEQ ID NO.: 208
*Vibrio cholerae* Pctx::lacZ reporter fusion constuct

```
     XbaI
   1 TCTAGAGGCT GTGGGTAGAA GTGAAACGGG GTTTACCGAT AAAAACAGAA AATGATAAAA

3 ToxR binding repeats
  61 AAGGACTAAA TAGTATATTT TGATTTTTGA TTTTTGATTT CAAATAATAC AAATTTATTT +1 lacZ
 121 ACTTATTTAA TTGTTTTGAT CAATTATTTT TCTGTTAAAC AAAGGGAGCA TTATATGGTA

181 AAGACCATGA TTACGGATTC ACTGGCCGTC GTTTTACAAC GTCGTGACTG GGAAAACCCT

241 GGCGTTACCC AACTTAATCG CCTTGCAGCA CATCCCCCTT TCGCCAGCTG GCGTAATAGC

301 GAAGAGGCCC GCACCGATCG CCCTTCCCAA CAGTTGCGCA GCCTGAATGG CGAATGGCGC

361 TTTGCCTGGT TTCCGGCACC AGAAGCGGTG CCGGAAAGCT GGCTGGAGTG CGATCTTCCT

421 GAGGCCGATA CTGTCGTCGT CCCCTCAAAC TGGCAGATGC ACGGTTACGA TGCGCCCATC

481 TACACCAACG TGACCTATCC CATTACGGTC AATCCGCCGT TTGTTCCCAC GGAGAATCCG

541 ACGGGTTGTT ACTCGCTCAC ATTTAATGTT GATGAAAGCT GGCTACAGGA AGGCCAGACG

601 CGAATTATTT TTGATGGCGT TAACTCGGCG TTTCATCTGT GGTGCAACGG GCGCTGGGTC

661 GGTTACGGCC AGGACAGTCG TTTGCCGTCT GAATTTGACC TGAGCGCATT TTTACGCGCC

721 GGAGAAAACC GCCTCGCGGT GATGGTGCTG CGCTGGAGTG ACGGCAGTTA TCTGGAAGAT

781 CAGGATATGT GGCGGATGAG CGGCATTTTC CGTGACGTCT CGTTGCTGCA TAAACCGACT

841 ACACAAATCA GCGATTTCCA TGTTGCCACT CGCTTTAATG ATGATTTCAG CCGCGCTGTA

901 CTGGAGGCTG AAGTTCAGAT GTGCGGCGAG TTGCGTGACT ACCTACGGGT AACAGTTTCT

961 TTATGGCAGG GTGAAACGCA GGTCGCCAGC GGCACCGCGC CTTTCGGCGG TGAAATTATC

1021 GATGAGCGTG GTGGTTATGC CGATCGCGTC ACACTACGTC TGAACGTCGA AAACCCGAAA

1081 CTGTGGAGCG CCGAAATCCC GAATCTCTAT CGTGCGGTGG TTGAACTGCA CACCGCCGAC

1141 GGCACGCTGA TTGAAGCAGA AGCCTGCGAT GTCGGTTTCC GCGAGGTGCG GATTGAAAAT

1201 GGTCTGCTGC TGCTGAACGG CAAGCCGTTG CTGATTCGAG GCGTTAACCG TCACGAGCAT

1261 CATCCTCTGC ATGGTCAGGT CATGGATGAG CAGACGATGG TGCAGGATAT CCTGCTGATG

1321 AAGCAGAACA ACTTTAACGC CGTGCGCTGT TCGCATTATC CGAACCATCC GCTGTGGTAC

1381 ACGCTGTGCG ACCGCTACGG CCTGTATGTG GTGGATGAAG CCAATATTGA AACCCACGGC

1441 ATGGTGCCAA TGAATCGTCT GACCGATGAT CCGCGCTGGC TACCGGCGAT GAGCGAACGC

1501 GTAACGCGAA TGGTGCAGCG CGATCGTAAT CACCCGAGTG TGATCATCTG GTCGCTGGGG

1561 AATGAATCAG GCCACGGCGC TAATCACGAC GCGCTGTATC GCTGGATCAA ATCTGTCGAT

1621 CCTTCCCGCC CGGTGCAGTA TGAAGGCGGC GGAGCCGACA CCACGGCCAC CGATATTATT

1681 TGCCCGATGT ACGCGCGCGT GGATGAAGAC CAGCCCTTCC CGGCTGTGCC GAAATGGTCC

1741 ATCAAAAAAT GGCTTTCGCT ACCTGGAGAG ACGCGCCCGC TGATCCTTTG CGAATACGCC

1801 CACGCGATGG GTAACAGTCT TGGCGGTTTC GCTAAATACT GGCAGGCGTT TCGTCAGTAT

1861 CCCCGTTTAC AGGGCGGCTT CGTCTGGGAC TGGGTGGATC AGTCGCTGAT TAAATATGAT
```

-continued

```
1921 GAAAACGGCA ACCCGTGGTC GGCTTACGGC GGTGATTTTG GCGATACGCC GAACGATCGC

1981 CAGTTCTGTA TGAACGGTCT GGTCTTTGCC GACCGCACGC CGCATCCAGC GCTGACGGAA

2041 GCAAAACACC AGCAGCAGTT TTTCCAGTTC CGTTTATCCG GCAAACCAT CGAAGTGACC

2101 AGCGAATACC TGTTCCGTCA TAGCGATAAC GAGCTCCTGC ACTGGATGGT GGCGCTGGAT

2161 GGTAAGCCGC TGGCAAGCGG TGAAGTGCCT CTGGATGTCG CTCCACAAGG TAAACAGTTG

2221 ATTGAACTGC CTGAACTACC GCAGCCGGAG AGCGCCGGGC AACTCTGGCT CACAGTACGC

2281 GTAGTGCAAC CGAACGCGAC CGCATGGTCA GAAGCCGGGC ACATCAGCGC CTGGCAGCAG

2341 TGGCGTCTGG CGGAAAACCT CAGTGTGACG CTCCCCGCCG CGTCCCACGC CATCCCGCAT

2401 CTGACCACCA GCGAAATGGA TTTTTGCATC GAGCTGGGTA ATAAGCGTTG CAATTTAAC

2461 CGCCAGTCAG GCTTTCTTTC ACAGATGTGG ATTGGCGATA AAAACAACT GCTGACGCCG

2521 CTGCGCGATC AGTTCACCCG TGCACCGCTG GATAACGACA TTGGCGTAAG TGAAGCGACC

2581 CGCATTGACC CTAACGCCTG GGTCGAACGC TGGAAGGCGG CGGGCCATTA CCAGGCCGAA

2641 GCAGCGTTGT TGCAGTGCAC GGCAGATACA CTTGCTGATG CGGTGCTGAT TACGACCGCT

2701 CACGCGTGGC AGCATCAGGG GAAAACCTTA TTTATCAGCC GGAAAACCTA CCGGATTGAT

2761 GGTAGTGGTC AAATGGCGAT TACCGTTGAT GTTGAAGTGG CGAGCGATAC ACCGCATCCG

2821 GCGCGGATTG CCTGAACTG CCAGCTGGCG CAGGTAGCAG AGCGGGTAAA CTGGCTCGGA

2881 TTAGGGCCGC AAGAAAACTA TCCCGACCGC CTTACTGCCG CCTGTTTTGA CCGCTGGGAT

2941 CTGCCATTGT CAGACATGTA TACCCCGTAC GTCTTCCCGA GCGAAAACGG TCTGCGCTGC

3001 GGGACGCGCG AATTGAATTA TGGCCCACAC CAGTGGCGCG CGACTTCCA GTTCAACATC

3061 AGCCGCTACA GTCAACAGCA ACTGATGGAA ACCAGCCATC GCCATCTGCT GCACGCGGAA

3121 GAAGGCACAT GGCTGAATAT CGACGGTTTC CATATGGGGA TTGGTGGCGA CGACTCCTGG

3181 AGCCCGTCAG TATCGGCGGA ATTCCAGCTG AGCGCCGGTC GCTACCATTA CCAGTTGGTC

Stop         Stem-loop        XbaI
3241 TGGTGTCAAA AA TAATAAC GCCCTCAT CCGAAAGGGC GTCTAGA
```

SEQ ID NO.: 266
pMPX-74 MalE (1-28) fusion vector

45

```
                                       SD      old PstI +1
2401 GAATTCAGGCGCTTTTTAGACTGGTCGTAATGAAATTC AGGAGGTT CTGCA TATGAAAAT
   1                                                       M  K  I 2461 AAAAACAGGTGCACGCATCCTCGCATTATCCGCATTAACGACGATGATGTTTTCCGCCTC
   4   K  T  G  A  R  I  L  A  L  S  A  L  T  T  M  M  F  S  A  S Factor Xa    PstI       SalI          XbaI
2521 GGCTCTCGCCAAAATC ATCGAAGCCCGC CTGCAG GCCTCG GTCGAC GCCGAA TCTAGA GA
  24   A  L  A  K  I  I  E  A  R  L  Q  A  S  V  D  A  E  S  R  D FLAG                 lost XbaI
2581 TTATAAAGATGACGATGACAAA TAATAA GCTAGA GG (transcriptional stop)
  44   Y  K  D  D  D  D  K
``` pMPX-72::malE(1-28)::FXa::PstI, SalI, XbaI::FLAG
Rhamnose inducible, clone into PstI, SalI, XbaI
Made by cutting TOPO NsiI-malE(1-28)::FXa::PstI, SalI, XbaI::FLAG-NheI
insertion with NsiI & NheI and cloning into pMPX-72 cut with PstI &
XbaI.

SEQ ID NO.: 267
pMPX-75 MalE (1-28) fusion vector

```
                          SD      old PstI +1
1621 CCATACCCGTTTTTTTGGGCTAGCAGGAGGCCCTGCATATGAAAATAAAAACAGGTGCAC
   1                                       M  K  I  K  T  G  A 1681 GCATCCTCGCATTATCCGCATTAACGACGATGATGTTTTCCGCCTCGGCTCTCGCCAAA
   8R  I  L  A  L  S  A  L  T  T  M  M  F  S  A  S  A  L  A  K Factor Xa   PstI        SalI        XbaI         FLAG
1741 TCATCGAAGCCCGCCTGCAGGCCTCGGTCGACGCCGAATCTAGAGATTATAAAGATGACG Lost XbaI
1801 ATGACAAATAATAAGCTAGAGG (Transcriptional stop)
``` pMPX-71::malE(1-28)::FXa::PstI, SalI, XbaI::FLAG
Arabinose inducible, clone into PstI, SalI, XbaI
Made by cutting TOPO NsiI-malE (1-28)::FXa::PstI, SalI,
XbaI::FLAG-NheI insertion with NsiI & NheI and cloning
into pMPX-71 cut with PstI & XbaI.
SEQ ID NO.: 268
pMPX-88 MalE (1-28) fusion vector

```
                                     SD     old PstI +1
                                     AGGAGGTTCTGCATATGAAAAT
   1                                                M  K  I AAAAACAGGTGCACGCATCCTCGCATTATCCGCATTAACGACGATGATGTTTTCCGCCTC
   4    K  T  G  A  R  I  L  A  L  S  A  L  T  T  M  M  F  S  A  S Factor Xa   PstI        SalI        XbaI
     GGCTCTCGCCAAAATCATCGAAGCCCGCCTGCAGGCCTCGGTCGACGCCGAATCTAGAGA
  24    A  L  A  K  I  I  E  A  R  L  Q  A  S  V  D  A  E  S  R  D FLAG              lost XbaI
     TTATAAAGATGACGATGACAAATAATAAGCTAGAGGTACC (transcriptional stop)
  44    Y  K  D  D  D  K
``` pMPX-84::malE(1-28)::FXa::PstI, SalI, XbaI::FLAG

Temperature inducible, clone into PstI, SalI, XbaI
Made by cutting TOPO NsiI-malE (1-28)::FXa::PstI, SalI,
XbaI::FLAG-NheI insertion with NsiI & NheI and cloning
into pMPX-84 cut with PstI & XbaI.
SEQ ID NO.: 269
pMPX-93 MalE (1-28) fusion vector

```
                                     SD     old PstI +1
                                     AGGAGGTTCTGCATATGAAAAT
   1                                                M  K  I AAAAACAGGTGCACGCATCCTCGCATTATCCGCATTAACGACGATGATGTTTTCCGCCTC
   4    K  T  G  A  R  I  L  A  L  S  A  L  T  T  M  M  F  S  A  S Factor Xa   PstI        SalI        XbaI
     GGCTCTCGCCAAAATCATCGAAGCCCGCCTGCAGGCCTCGGTCGACGCCGAATCTAGAGA
  24    A  L  A  K  I  I  E  A  R  L  Q  A  S  V  D  A  E  S  R  D FLAG              lost XbaI
     TTATAAAGATGACGATGACAAATAATAAGCTAGAGGTACC (transcriptional stop)
  44    Y  K  D  D  D  K
``` pMPX-86::malE(1-28)::FXa::PstI, SalI, XbaI::FLAG
Temperature inducible, clone into PstI, SalI, XbaI Made by cutting TOPO (1-28)::FXa::PstI, SalI, XbaI::FLAG-
NheI insertion with NsiI & NheI and cloning into pMPX-86
cut with PstI & XbaI.

SEQ ID NO.: 270
pMPX-77 MalE (1-370 del 354-364) fusion vector

```
                                          SD   old PstI  +1
2901 GAATTCAGGCGCTTTTTAGACTGGTCGTAATGAAATTCAGGAGGTTCTGCATATGAAAAT
   1                                                         M K I 2461 AAAAACAGGTGCACGCATCCTCGCATTATCCGCATTAACGACGATGATGTTTTCCGCCTC
   9  K  T  G  A  R  I  L  A  L  S  A  L  T  T  M  M  F  S  A  S 2521 GGCTCTCGCCAAAATCGAAGAAGGTAAACTGGTAATCTGGATTAACGGCGATAAAGGCTA
  29  A  L  A  K  I  E  E  G  K  L  V  I  W  I  N  G  D  K  G  Y 2581 TAACGGTCTCGCTGAAGTCGGTAAGAAATTCGAGAAAGATACCGGAATTAAAGTCACCGT
  44  N  G  L  A  E  V  G  K  K  F  E  K  D  T  G  I  K  V  T  V 2691 TGAGCATCCGGATAAACTGGAAGAGAAATTCCCACAGGTTGCGGCAACTGGCGATGGCCC
  64  E  H  P  D  K  L  E  E  K  F  P  Q  V  A  A  T  G  D  G  P 2701 TGACATTATCTTCTGGGCACACGACCGCTTTGGTGGCTACGCTCAATCTGGCCTGTTGGC
  84  D  I  I  F  W  A  H  D  R  F  G  G  Y  A  Q  S  G  L  L  A 2761 TGAAATCACCCCGGACAAAGCGTTCCAGGACAAGCTGTATCCGTTTACCTGGGATGCCGT
 104  E  I  T  P  D  K  A  F  Q  D  K  L  Y  P  F  T  W  D  A  V 2821 ACGTTACAACGGCAAGCTGATTGCTTACCCGATCGCTGTTGAAGCGTTATCGCTGATTTA
 124  R  Y  N  G  K  L  I  A  Y  P  I  A  V  E  A  L  S  L  I  Y 2881 TAACAAAGATCTGCTGCCGAACCCGCCAAAAACCTGGGAAGAGATCCCGGCGCTGGATAA
 144  N  K  D  L  L  P  N  P  P  K  T  W  E  E  I  P  A  L  D  K 2941 AGAACTGAAAGCGAAAGGTAAGAGCGCGCTGATGTTCAACCTGCAAGAACCGTACTTCAC
 164  E  L  K  A  K  G  K  S  A  L  M  F  N  L  Q  E  P  Y  F  T 3001 CTGGCCGCTGATTGCTGCTGACGGGGGTTATGCGTTCAAGTATGAAAACGGCAAGTACGA
 184  W  P  L  I  A  A  D  G  G  Y  A  F  K  Y  E  N  G  K  Y  D 3061 CATTAAAGACGTGGGCGTGGATAACGCTGGCGCGAAAGCGGGTCTGACCTTCCTGGTTGA
 204  I  K  D  V  G  V  D  N  A  G  A  K  A  G  L  T  F  L  V  D 3121 CCTGATTAAAAACAAACACATGAATGCAGACACCGATTACTCCATCGCAGAAGCTGCCTT
 224  L  I  K  N  K  H  M  N  A  D  T  D  Y  S  I  A  E  A  A  F 3181 TAATAAAGGCGAAACAGCGATGACCATCAACGGCCCGTGGGCATGGTCCAACATCGACAC
 244  N  K  G  E  T  A  M  T  I  N  G  P  W  A  W  S  N  I  D  T 3241 CAGCAAAGTGAATTATGGTGTAACGGTACTGCCGACCTTCAAGGGTCAACCATCCAAACC
 264  S  K  V  N  Y  G  V  T  V  L  P  T  F  K  G  Q  P  S  K  P 3301 GTTCGTTGGCGTGCTGAGCGCAGGTATTAACGCCGCCAGTCCGAACAAAGAGCTGGCGAA
 284  F  V  G  V  L  S  A  G  I  N  A  A  S  P  N  K  E  L  A  K 3361 AGAGTTCCTCGAAAACTATCTGCTGACTGATGAAGGTCTGGAAGCGGTTAATAAAGACAA
 304  E  F  L  E  N  Y  L  L  T  D  E  G  L  E  A  V  N  K  D  K 3421 ACCGCTGGGTGCCGTAGCGCTGAAGTCTTACGAGGAAGAGTTGGCGAAAGATCCACGTAT
 324  P  L  G  A  V  A  L  K  S  Y  E  E  L  A  K  D  P  R  I
``` pMPX-72::malE(1-370 del 354-364)::FXa::PstI, SalI, XbaI::FLAG
Rhamnose inducible, clone into PstI, SalI, XbaI
Made by cutting TOPO NsiI-malE (1-370 del 354-364)::FXa::PstI, SalI,
XbaI::FLAG-NheI insertion with NsiI & NheI and cloning into pMPX-72
cut with PstI & XbaI.

SEQ ID NO.: 271
pMPX-76 MalE (1-370 del 354-364) fusion vector

```
                           SD   old PstI  +1
1621 CCATACCCGTTTTTTTGGGCTAGCAGGAGGCCCTGCATATGAAAATAAAAACAGGTGCAC
   1                                       M  K  I  K  T  G  A 1681 GCATCCTCGCATTATCCGCATTAACGACGATGATGTTTTCCGCCTCGGCTCTCGCCAAAA
   8R  I  L  A  L  S  A  L  T  T  M  M  F  S  A  S  A  L  A  K 1741 TCGAAGAAGGTAAACTGGTAATCTGGATTAACGGCGATAAAGGCTATAACGGTCTCGCTG
  28I  E  E  G  K  L  V  I  W  I  N  G  D  K  G  Y  N  G  L  A
```

```
                                        -continued
1801 AAGTCGGTAAGAAATTCGAGAAAGATACCGGAATTAAAGTCACCGTTGAGCATCCGGATA
  48 E   V   G   K   K   F   E   K   D   T   G   I   K   V   T   E   H   P   D 1861 AACTGGAAGAGAAATTCCCACAGGTTGCGGCAACTGGCGATGGCCCTGACATTATCTTCT
  68 K   L   E   E   K   F   P   Q   V   A   A   T   G   D   G   P   D   I   I   F 1921 GGGCACACGACCGCTTTGGTGGCTACGCTCAATCTGGCCTGTTGGCTGAAATCACCCCGG
  88 W   A   H   D   R   F   G   G   Y   A   Q   S   G   L   L   A   E   I   T   P 1981 ACAAAGCGTTCCAGGACAAGCTGTATCCGTTTACCTGGGATGCCGTACGTTACAACGGCA
 108 D   K   A   F   Q   D   K   L   Y   P   F   T   W   D   A   V   R   Y   N   G 2041 AGCTGATTGCTTACCCGATCGCTGTTGAAGCGTTATCGCTGATTTATAACAAAGATCTGC
 128 K   L   I   A   Y   P   I   A   V   E   A   L   S   L   I   Y   N   K   D   L 2101 TGCCGAACCCGCCAAAAACCTGGGAAGAGATCCCGGCGCTGGATAAAGAACTGAAAGCGA
 148 L   P   N   P   P   K   T   W   E   E   I   P   A   L   D   K   E   L   K   A 2161 AAGGTAAGAGCGCGCTGATGTTCAACCTGCAAGAACCGTACTTCACCTGGCCGCTGATTG
 168 K   G   K   S   A   L   M   F   N   L   Q   E   P   Y   F   T   W   P   L   I 2221 CTGCTGACGGGGGTTATGCGTTCAAGTATGAAAACGGCAAGTACGACATTAAAGACGTGG
 188 A   A   D   G   G   Y   A   F   K   Y   E   N   G   K   Y   D   I   K   D   V 2281 GCGTGGATAACGCTGGCGCGAAAGCGGGTCTGACCTTCCTGGTTGACCTGATTAAAAACA
 208 G   V   D   N   A   G   A   K   A   G   L   T   F   L   V   D   L   I   K   N 2341 AACACATGAATGCAGACACCGATTACTCCATCGCAGAAGCTGCCTTTAATAAAGGCGAAA
 228 K   H   M   N   A   D   T   D   Y   S   I   A   E   A   A   F   N   K   G   E 2401 CAGCGATGACCATCAACGGCCCGTGGGCATGGTCCAACATCGACACCAGCAAAGTGAATT
 248 T   A   M   T   I   N   G   P   W   A   W   S   N   I   D   T   S   K   V   N 2461 ATGGTGTAACGGTACTGCCGACCTTCAAGGGTCAACCATCCAAACCGTTCGTTGGCGTGC
 268 Y   G   V   T   V   L   P   T   F   K   G   Q   P   S   K   P   F   V   G   V 2521 TGAGCGCAGGTATTAACGCCGCCAGTCCGAACAAAGAGCTGGCGAAAGAGTTCCTCGAAA
 288 L   S   A   G   I   N   A   A   S   P   N   K   E   L   A   K   E   F   L   E 2581 ACTATCTGCTGACTGATGAAGGTCTGGAAGCGGTTAATAAAGACAAACCGCTGGGTGCCG
 308 N   Y   L   L   T   D   E   G   L   E   A   V   N   K   D   K   P   L   G   A 2641 TAGCGCTGAAGTCTTACGAGGAAGAGTTGGCGAAAGATCCACGTATTGCCGCCACCATGG
 328 V   A   L   K   S   Y   E   E   E   L   A   K   D   P   R   I   A   A   T   M Factor Xa      PstI
2701 AAAACGCCCAGTCCGCTTTCTGGTATGCCGTGCGTATCGAAGCCCGCCTGCAGGCCTCGG
 348 E   N   A   Q   S   A   F   W   Y   A   V   R   I   E   A   R   L   Q   A   S SalI         XbaI              FLAG                      Lost XbaI
2761 TCGACGCCGAATCTAGAGATTATAAAGATGACGATGACAAATAATAAGCTAGAGGA(trxn stop)
 368 V   D   A   E   S   R   D   Y   K   D   D   D   D   K pMPX-71::malE(1-370 del 354-364)::FXa::PstI, SalI, XbaI::FLAG
Arabinose inducible, clone into PstI, SalI, XbaI
```

Made by cutting TOPO NsiI-malE (1-370 del 354-364)::
FXa::PstI, SalI, XbaI::FLAG-NheI insertion with NsiI &
NheI and cloning into pMPX-71 cut with PstI & XbaI.
SEQ ID NO.: 272
pMPX-89 MalE (1-370 del 354-364) fusion vector

```
              SD   old PstI  +1
           AGGAGGTTCTGCATATGAAAATAAAAACAGGTGCAC
  1                          M   K   I   K   T   G   A GCATCCTCGCATTATCCGCATTAACGACGATGATGTTTTCCGCCTCGGCTCTCGCCAAAA
   8 R   I   L   A   L   S   A   L   T   T   M   M   F   S   A   S   A   L   A   K TCGAAGAAGGTAAACTGGTAATCTGGATTAACGGCGATAAAGGCTATAACGGTCTCGCTG
  28 I   E   E   G   K   L   V   I   W   I   N   G   D   K   G   Y   N   G   L   A AAGTCGGTAAGAAATTCGAGAAAGATACCGGAATTAAAGTCACCGTTGAGCATCCGGATA
  48 E   V   G   K   K   F   E   K   D   T   G   I   K   V   T   E   H   P   D AACTGGAAGAGAAATTCCCACAGGTTGCGGCAACTGGCGATGGCCCTGACATTATCTTCT
  68 K   L   E   E   K   F   P   Q   V   A   A   T   G   D   G   P   D   I   I   F
```

```
                GGGCACACGACCGCTTTGGTGGCTACGCTCAATCTGGCCTGTTGGCTGAAATCACCCCGG
             88W  A  H  D  R  F  G  G  Y  A  Q  S  G  L  L  A  E  I  T  P

ACAAAGCGTTCCAGGACAAGCTGTATCCGTTTACCTGGGATGCCGTACGTTACAACGGCA
            108D  K  A  F  Q  D  K  L  Y  P  F  T  W  D  A  V  R  Y  N  G

AGCTGATTGCTTACCCGATCGCTGTTGAAGCGTTATCGCTGATTTATAACAAAGATCTGC
            128K  L  I  A  Y  P  I  A  V  E  A  L  S  L  I  Y  N  K  D  L

TGCCGAACCCGCCAAAAACCTGGGAAGAGATCCCGGCGCTGGATAAAGAACTGAAAGCGA
            148L  P  N  P  P  K  T  W  E  E  I  P  A  L  D  K  E  L  K  A

AAGGTAAGAGCGCGCTGATGTTCAACCTGCAAGAACCGTACTTCACCTGGCCGCTGATTG
            168K  G  K  S  A  L  M  F  N  L  Q  E  P  Y  F  T  W  P  L  I

CTGCTGACGGGGGTTATGCGTTCAAGTATGAAAACGGCAAGTACGACATTAAAGACGTGG
            188A  A  D  G  G  Y  A  F  K  Y  E  N  G  K  Y  D  I  K  D  V

GCGTGGATAACGCTGGCGCGAAAGCGGGTCTGACCTTCCTGGTTGACCTGATTAAAAACA
            208G  V  D  N  A  G  A  K  A  G  L  T  F  L  V  D  L  I  K  N

ACACATGAATGCAGACACCGATTACTCCATCGCAGAAGCTGCCTTTAATAAAGGCGAAA
            228K  H  M  N  A  D  T  D  Y  S  I  A  E  A  A  F  N  K  G  E

CAGCGATGACCATCAACGGCCCGTGGGCATGGTCCAACATCGACACCAGCAAAGTGAATT
            248T  A  M  T  I  N  G  P  W  A  W  S  N  I  D  T  S  K  V  N

ATGGTGTAACGGTACTGCCGACCTTCAAGGGTCAACCATCCAAACCGTTCGTTGGCGTGC
            268Y  G  V  T  V  L  P  T  F  K  G  Q  P  S  K  P  F  V  G  V

TGAGCGCAGGTATTAACGCCGCCAGTCCGAACAAAGAGCTGGCGAAAGAGTTCCTCGAAA
            288L  S  A  G  I  N  A  A  S  P  N  K  E  L  A  K  E  F  L  E

ACTATCTGCTGACTGATGAAGGTCTGGAAGCGGTTAATAAAGACAAACCGCTGGGTGCCG
            308N  Y  L  L  T  D  E  G  L  E  A  V  N  K  D  K  P  L  G  A

TAGCGCTGAAGTCTTACGAGGAAGAGTTGGCGAAAGATCCACGTATTGCCGCCACCATGG
            328V  A  L  K  S  Y  E  E  E  L  A  K  D  P  R  I  A  A  T  M

Factor Xa    PstI
                AAAACGCCCAGTCCGCTTTCTGGTATGCCGTGCGTATCGAAGCCCGCCTGCAGGCCTCGG
            348E  N  A  Q  S  A  F  W  Y  A  V  R  I  E  A  R  L  Q  A  S SalI      XbaI          FLAG            Lost XbaI
                TCGACGCCGAATCTAGAGATTATAAAGATGACGATGACAAATAATAAGCTAGAGG (trxn stop)
            368V  D  A  E  S  R  D  Y  K  D  D  D  D  K
``` pMPX-84::malE(1-370 del 354-364)::FXa::PstI, SalI, XbaI::FLAG
Temperature inducible, clone into PstI, SalI, XbaI
Made by cutting TOPO NsiI-malE (1-370 del 354-364)::FXa::PstI, SalI,
XbaI::FLAG-NheI insertion with NsiI & NheI and cloning into pMPX-84
cut with PstI & XbaI.

SEQ ID NO.: 273
pMPX-94 MalE (1-370 del 354-364) fusion vector

```
                       SD      old PstI +1
                   AGGAGGTTCTGCATATGAAAATAAAAACAGGTGCAC
              1                   M  K  I  K  T  G  A GCATCCTCGCATTATCCGCATTAACGACGATGATGTTTTCCGCCTCGGCTCTCGCCAAAA
              8R  I  L  A  L  S  A  L  T  T  M  M  F  S  A  S  A  L  A  K TCGAAGAAGGTAAACTGGTAATCTGGATTAACGGCGATAAAGGCTATAACGGTCTCGCTG
             28I  E  E  G  K  L  V  I  W  I  N  G  D  K  G  Y  N  G  L  A AAGTCGGTAAGAAATTCGAGAAAGATACCGGAATTAAAGTCACCGTTGAGCATCCGGATA
             48E  V  G  K  K  F  E  K  D  T  G  I  K  V  T  V  E  H  P  D AACTGGAAGAGAAATTCCCACAGGTTGCGGCAACTGGCGATGGCCCTGACATTATCTTCT
             68K  L  E  E  K  F  P  Q  V  A  A  T  G  D  G  P  D  I  I  F GGGCACACGACCGCTTTGGTGGCTACGCTCAATCTGGCCTGTTGGCTGAAATCACCCCGG
             88W  A  H  D  R  F  G  G  Y  A  Q  S  G  L  L  A  E  I  T  P ACAAAGCGTTCCAGGACAAGCTGTATCCGTTTACCTGGGATGCCGTACGTTACAACGGCA
            108D  K  A  F  Q  D  K  L  Y  P  F  T  W  D  A  V  R  Y  N  G
```

```
                                -continued
      AGCTGATTGCTTACCCGATCGCTGTTGAAGCGTTATCGCTGATTTATAACAAAGATCTGC
128K   L   I   A   Y   P   I   A   V   E   A   L   S   L   I   Y   N   K   D   L TGCCGAACCCGCCAAAAACCTGGGAAGAGATCCCGGCGCTGGATAAAGAACTGAAAGCGA
148L   P   N   P   P   K   T   W   E   E   I   P   A   L   D   K   E   L   K   A AAGGTAAGAGCGCGCTGATGTTCAACCTGCAAGAACCGTACTTCACCTGGCCGCTGATTG
168K   G   K   S   A   L   M   F   N   L   Q   E   P   Y   F   T   W   P   L   I CTGCTGACGGGGGTTATGCGTTCAAGTATGAAAACGGCAAGTACGACATTAAAGACGTGG
188A   A   D   G   G   Y   A   F   K   Y   E   N   G   K   Y   D   I   K   D   V GCGTGGATAACGCTGGCGCGAAAGCGGGTCTGACCTTCCTGGTTGACCTGATTAAAAACA
208G   V   D   N   A   G   A   K   A   G   L   T   F   L   V   D   L   I   K   N AACACATGAATGCAGACACCGATTACTCCATCGCAGAAGCTGCCTTTAATAAAGGCGAAA
228K   H   M   N   A   D   T   D   Y   S   I   A   E   A   A   F   N   K   G   E CAGCGATGACCATCAACGGCCCGTGGGCATGGTCCAACATCGACACCAGCAAAGTGAATT
248T   A   M   T   I   N   G   P   W   A   W   S   N   I   D   T   S   K   V   N ATGGTGTAACGGTACTGCCGACCTTCAAGGGTCAACCATCCAAACCGTTCGTTGGCGTGC
268Y   G   V   T   V   L   P   T   F   K   G   Q   P   S   K   P   F   V   G   V TGAGCGCAGGTATTAACGCCGCCAGTCCGAACAAAGAGCTGGCGAAAGAGTTCCTCGAAA
288L   S   A   G   I   N   A   A   S   P   N   K   E   L   A   K   E   F   L   E ACTATCTGCTGACTGATGAAGGTCTGGAAGCGGTTAATAAAGACAAACCGCTGGGTGCCG
308N   Y   L   L   T   D   E   G   L   E   A   V   N   K   D   K   P   L   G   A TAGCGCTGAAGTCTTACGAGGAAGAGTTGGCGAAAGATCCACGTATTGCCGCCACCATGG
328V   A   L   K   S   Y   E   E   E   L   A   K   D   P   R   I   A   A   T   M Factor Xa   PstI
      AAAACGCCCAGTCCGCTTTCTGGTATGCCGTGCGTATCGAAGCCCGCCTGCAGGCCTCGG
348E   N   A   Q   S   A   F   W   Y   A   V   R   I   E   A   R   L   Q   A   S SalI       XbaI             FLAG           Lost XbaI
      TCGACGCCGAATCTAGAGATTATAAAGATGACGATGACAAATAATAAGCTAGAGG (trxn stop)
368V   D   A   E   S   R   D   Y   K   D   D   D   D   K
``` pMPX-86::malE(1-370 del 354-364)::FXa::PstI, SalI, XbaI::FLAG
Temperature inducible, clone into PstI, SalI, XbaI
Made by cutting TOPO NsiI-malE (1-370 del 354-364)::FXa::PstI,SalI,
XbaI::FLAG-NheI insertion with NsiI & NheI and cloning into pMPX-86
cut with PstI & XbaI.

SEQ ID NO.: 274
pMPX-79 TrxA (2-109 del 103-107) fusion vector

```
         SD         PstI       SalI        XbaI  +2 trxA (del 103-107)
  1   TAGCAGGAGGCCCTGCAGGCCTCGGTCGACGCCGAATCTAGAAGCGATAAAATTATT
  1                             A   S   V   D   A   E   S   R   D   K   I   I 61 CACCTGACTGACGACAGTTTTGACACGGATGTACTCAAAGCGGACGGGGCGATCCTCGTC
 17 H   L   T   D   D   S   F   D   T   D   V   L   K   A   D   G   A   I   L   V 121 GATTTCTGGGCAGAGTGGTGCGGTCCGTGCAAAATGATCGCCCCGATTCTGGATGAAATC
 37 D   F   W   A   E   W   C   G   P   C   K   M   I   A   P   I   L   D   E   I 181 GCTGACGAATATCAGGGCAAACTGACCGTTGCAAAACTGAACATCGATCAAAACCCTGGC
 57 A   D   E   Y   Q   G   K   L   T   V   A   K   L   N   I   D   Q   N   P   G 241 ACTGCGCCGAAATATGGCATCCGTGGTATCCCGACTCTGCTGCTGTTCAAAAACGGTGAA
 77 T   A   P   K   Y   G   I   R   G   I   P   T   L   L   L   F   K   N   G   E 301 GTGGCGGCAACCAAAGTGGGTGCACTGTCTAAAGGTCAGTTGAAAGAGAACCTGGCGGAT
 97 V   A   A   T   K   V   G   A   L   S   K   G   Q   L   K   E   N   L   A   D FLAG                Lost XbaI
361 TATAAAGATGACGATGACAAATAATAAGCTAGAGG(transcriptional stop)
117 Y K D D D D K
``` pMPX-71::PstI, SalI, XbaI::trxA (2-109 del 103-107)::FLAG
Arabinose inducible, clone into PstI, SalI, XbaI
+1 Met required for protein to be fused Made by cutting TOPO PstI, SalI, XbaI::trxA (2-109 del 103-107)::FLAG-NheI insertion with PstI & NheI and cloning into pMPX-71 cut with PstI & XbaI.
SEQ ID NO.: 275
pMPX-78 TrxA (2-109 del 103-107) fusion vector

```
                                              SD        PstI
  1     GAATTCAGGCGCTTTTTAGACTGGTCGTAATGAAATTCAGGAGGTTCTGCAGGCCTC
  1                                                          A  S

SalI       XbaI     +2 trxA(del 103-107)
 61     GGTCGACGCCGAATCTAGAAGCGATAAAATTATTCACCTGACTGACGACAGTTTTGACAC
  6      V  D  A  E  S  R  S  D  K  I  I  H  L  T  D  D  S  F  D  T 121     GGATGTACTCAAAGCGGACGGGGCGATCCTCGTCGATTTCTGGGCAGAGTGGTGCGGTCC
 26      D  V  L  K  A  D  G  A  I  L  V  D  F  W  A  E  W  C  G  P 181     GTGCAAAATGATCGCCCCGATTCTGGATGAAATCGCTGACGAATATCAGGGCAAACTGAC
 46      C  K  M  I  A  P  I  L  D  E  I  A  D  E  Y  Q  G  K  L  T 241     CGTTGCAAAACTGAACATCGATCAAAACCCTGGCACTGCGCCGAAATATGGCATCCGTGG
 66      V  A  K  L  N  I  D  Q  N  P  G  T  A  P  K  Y  G  I  R  G 301     TATCCCGACTCTGCTGCTGTTCAAAAACGGTGAAGTGGCGGCAACCAAAGTGGGTGCACT
 86      I  P  T  L  L  L  F  K  N  G  E  V  A  A  T  K  V  G  A  L FLAG
361     GTCTAAAGGTCAGTTGAAAGAGAACCTGGCGGATTATAAAGATGACGATGACAAATAATAA
106      S  K  G  Q  L  K  E  N  L  A  D  Y  K  D  D  D  K lost XbaI
         GCTAGAGG (transcriptional stop)
``` pMPX-72::PstI,SalI, XbaI::trxA(2-109 del 103-107)::FLAG
Rhamnose inducible,clone into PstI, SalI, XbaI
+1 Met required for protein to be fused
Made by cutting TOPO PstI, SalI, XbaI::trxA (2-109 del 103-107)::FLAG-NheI insertion with PstI & NheI and cloning into pMPX-72 cut with PstI & XbaI.

SEQ ID NO.: 276
pMPX-90 TrxA (2-109 del 103-107) fusion vector

```
          SD        PstI        SalI         XbaI   +2 trxA(del 103-107)
         AGGAGGTTCTGCAGGCCTCGGTCGACGCCGAATCTAGAAGCGATAAAATTATT
  1                       A  S  V  D  A  E  S  R  S  D  K  I  I CACCTGACTGACGACAGTTTTGACACGGATGTACTCAAAGCGGACGGGGCGATCCTCGTC
 17      H  L  T  D  D  S  F  D  T  D  V  L  K  A  D  G  A  I  L  V GATTTCTGGGCAGAGTGGTGCGGTCCGTGCAAAATGATCGCCCCGATTCTGGATGAAATC
 37      D  F  W  A  E  W  C  G  P  C  K  M  I  A  P  I  L  D  E  I GCTGACGAATATCAGGGCAAACTGACCGTTGCAAAACTGAACATCGATCAAAACCCTGGC
 57      A  D  E  Y  Q  G  K  L  T  V  A  K  L  N  I  D  Q  N  P  G ACTGCGCCGAAATATGGCATCCGTGGTATCCCGACTCTGCTGCTGTTCAAAAACGGTGAA
 77      T  A  P  K  Y  G  I  R  G  I  P  T  L  L  L  F  K  N  G  E GTGGCGGCAACCAAAGTGGGTGCACTGTCTAAAGGTCAGTTGAAAGAGAACCTGGCGGAT
 97      V  A  A  T  K  V  G  A  L  S  K  G  Q  L  K  E  N  L  A  D FLAG                  Lost XbaI
         TATAAAGATGACGATGACAAATAATAAGCTAGAGGTACC (transcriptional stop)
117      Y  K  D  D  D  K
``` pMPX-84::PstI, SalI, XbaI::trxA (2-109 del 103-107)::FLAG
Temperature inducible, clone into PstI, SalI, XbaI
+1 Met required for protein to be fused
Made by cutting TOPO PstI, SalI, XbaI::trxA(2-109 del 103-107)::FLAG-NheI insertion with PstI & NheI and cloning into pMPX-84 cut with PstI & XbaI.

SEQ ID NO.: 277
pMPX-95 TrxA (2-109 del 103-107) fusion vector

```
        SD    PstI      SalI    XbaI+2 trxA(del 103-107)
        AGGAGGTTCTGCAGGCCTCGGTCGACGCCGAATCTAGAAGCGATAAAATTATT
  1                       A   S   V   D   A   E   S   R   S   D   K   I   I CACCTGACTGACGACAGTTTTGACACGGATGTACTCAAAGCGGACGGGGCGATCCTCGTC
 17   H   L   T   D   D   S   F   D   T   D   V   L   K   A   D   G   A   I   L   V GATTTCTGGGCAGAGTGGTGCGGTCCGTGCAAAATGATCGCCCCGATTCTGGATGAAATC
 37   D   F   W   A   E   W   C   G   P   C   K   M   I   A   P   I   L   D   E   I GCTGACGAATATCAGGGCAAACTGACCGTTGCAAAACTGAACATCGATCAAAACCCTGGC
 57   A   D   E   Y   Q   G   K   L   T   V   A   K   L   N   I   D   Q   N   P   G ACTGCGCCGAAATATGGCATCCGTGGTATCCCGACTCTGCTGCTGTTCAAAAACGGTGAA
 77   T   A   P   K   Y   G   I   R   G   I   P   T   L   L   L   F   K   N   G   E GTGGCGGCAACCAAAGTGGGTGCACTGTCTAAAGGTCAGTTGAAAGAGAACCTGGCGGAT
 97   V   A   A   T   K   V   G   A   L   S   K   G   Q   L   K   E   N   L   A   D FLAG                    Lost XbaI
     TATAAAGATGACGATGACAAATAATAAGCTAGAGGTACC (transcriptional stop)
117   Y   K   D   D   D   K
``` pMPX-86::PstI, SalI, XbaI::trxA (2-109 del 103-107)::FLAG
Temperature inducible, clone into PstI, SalI, XbaI
+1 Met required for protein to be fused
Made by cutting TOPO PstI, SalI, XbaI::trxA (2-109 del 103-107)::FLAG-NheI insertion with PstI & NheI and cloning into pMPX-86 cut with PstI & XbaI.

SEQ ID NO.: 278
pMPX-80 MalE (1-28) MCS TrxA (2-109 del 103-107) fusion vector

```
                                        SD    Lost PstI +1 malE(1-28)
2401 GAATTCAGGCGCTTTTTAGACTGGTCGTAATGAAATTCAGGAGGTTCTGCATATGAAAAT
   1                                                             M   K   I 2461 AAAAACAGGTGCACGCATCCTCGCATTATCCGCATTAACGACGATGATGTTTTCCGCCTC
   4    K   T   G   A   R   I   L   A   L   S   A   L   T   T   M   M   F   S   A   S Factor Xa          PstI          SalI        XbaI
2521 GGCTCTCGCCAAAATCATCGAAGCCCGCCTGCAGGCCTCGGTCGACGCCGAATCTAGAAG
  24    A   L   A   K   I   I   E   A   R   L   Q   A   S   V   D   A   E   S   R   S +2 trxA (2-109 del 103-107)
2581 CGATAAAATTATTCACCTGACTGACGACAGTTTTGACACGGATGTACTCAAAGCGGACGG
  44    D   K   I   I   H   L   T   D   D   S   F   D   T   D   V   L   K   A   D   G 2641 GGCGATCCTCGTCGATTTCTGGGCAGAGTGGTGCGGTCCGTGCAAAATGATCGCCCCGAT
  64    A   I   L   V   D   F   W   A   E   W   C   G   P   C   K   M   I   A   P   I 2701 TCTGGATGAAATCGCTGACGAATATCAGGGCAAACTGACCGTTGCAAAACTGAACATCGA
  84    L   D   E   I   A   D   E   Y   Q   G   K   L   T   V   A   K   L   N   I   D 2761 TCAAAACCCTGGCACTGCGCCGAAATATGGCATCCGTGGTATCCCGACTCTGCTGCTGTT
 104    Q   N   P   G   T   A   P   K   Y   G   I   R   G   I   P   T   L   L   L   F 2821 CAAAAACGGTGAAGTGGCGGCAACCAAAGTGGGTGCACTGTCTAAAGGTCAGTTGAAAGA
 124    K   N   G   E   V   A   A   T   K   V   G   A   L   S   K   G   Q   L   K   E FLAG              Lost XbaI
2881 GAACCTGGCGGATTATAAAGATGACGATGACAAATAATAAGCTAGAGG (trxn stop)
 144    N   L   A   D   Y   K   D   D   D   K
``` pMPX-72::malE(1-28)::FXa::PstI, SalI, XbaI::TrxA(1-109 del 103-107)::FLAG
Rhamnose inducible, clone into PstI, SalI, XbaI
Made by cutting TOPO NsiI-malE(1-28)::EXa::PstI, SalI, XbaI::FLAG-NheI insertion with NsiI & XbaI and cloning into pMPX-78 cut with PstI & XbaI.

SEQ ID NO.: 279
pMPX-81 MalE (1-28) MCS TrxA (2-109 del 103-107)
fusion vector

```
                              SD   Lost PstI  +1 malE (1-28)
1621 CCATACCCGTTTTTTTGGGCTAGCAGGAGGCCCTGCATATGAAAATAAAAACAGGTGCAC
   1                                            M  K  I  K  T  G  A 1681 GCATCCTCGCATTATCCGCATTAACGACGATGATGTTTTCCGCCTCGGCTCTCGCCAAAA
   8 R  I  L  A  L  S  A  L  T  T  M  M  F  S  A  S  A  L  A  K +2 trxA(2-109 del
       Factor Xa  PstI       SalI        XbaI            103-107)
1741 TCATCGAAGCCCGCCTGCAGGCCTCGGTCGACGCCGAATCTAGAAGCGATAAAATTATTC
  28 I  I  E  A  R  L  Q  A  S  V  D  A  E  S  R  S  D  K  I  I 1801 ACCTGACTGACGACAGTTTTGACACGGATGTACTCAAAGCGGACGGGGCGATCCTCGTCG
  48 H  L  T  D  D  S  F  D  T  D  V  L  K  A  D  G  A  I  L  V 1861 ATTTCTGGGCAGAGTGGTGCGGTCCGTGCAAAATGATCGCCCCGATTCTGGATGAAATCG
  68 D  F  W  A  E  W  C  G  P  C  K  M  I  A  P  I  L  D  E  I 1921 CTGACGAATATCAGGGCAAACTGACCGTTGCAAAACTGAACATCGATCAAAACCCTGGCA
  88 A  D  E  Y  Q  G  K  L  T  V  A  K  L  N  I  D  Q  N  P  G 1981 CTGCGCCGAAATATGGCATCCGTGGTATCCCGACTCTGCTGCTGTTCAAAAACGGTGAAG
 108 T  A  P  K  Y  G  I  R  G  I  P  T  L  L  L  F  K  N  G  E 2041 TGGCGGCAACCAAAGTGGGTGCACTGTCTAAAGGTCAGTTGAAAGAGAACCTGGCGGATT
 128 V  A  A  T  K  V  G  A  L  S  K  G  Q  L  K  E  N  L  A  D FLAG
2101 ATAAAGATGACGATGACAAATAATAAGCTAGAGG(transcriptional stop)
 148 Y  K  D  D  D  K
``` pMPX-71::malE(1-28)::FXa::PstI, SalI, XbaI::TrxA(1-109 del 103-107)::FLAG
*Arabinose* inducible, clone into PstI, SalI, XbaI
Made by cutting TOPO NsiI-malE (1-28)::FXa::PstI, SalI, XbaI::FLAG-NheI insertion with NsiI & XbaI and cloning into pMPX-79 cut with PstI & XbaI.

SEQ ID NO.: 280
pMPX-91 MalE (1-28) MCS TrxA (2-109 del 103-107)
fusion vector

```
                                       SD    Lost PstI +1 malE(1-
      28)
                                    AGGAGGTTCTGCATATGAAAAT
   1                                                 M  K  I AAAAACAGGTGCACGCATCCTCGCATTATCCGCATTAACGACGATGATGTTTTCCGCCTC
   4    K  T  G  A  R  I  L  A  L  S  A  L  T  T  M  M  F  S  A  S Factor Xa  PstI       SalI        XbaI
     GGCTCTCGCCAAAATCATCGAAGCCCGCCTGCAGGCCTCGGTCGACGCCGAATCTAGAAG
  24    A  L  A  K  I  I  E  A  R  L  Q  A  S  V  D  A  E  S  R  S +2 trxA (2-109 del 103-107)
     CGATAAAATTATTCACCTGACTGACGACAGTTTTGACACGGATGTACTCAAAGCGGACGG
  44    D  K  I  I  H  L  T  D  D  S  F  D  T  D  V  L  K  A  D  G GGCGATCCTCGTCGATTTCTGGGCAGAGTGGTGCGGTCCGTGCAAAATGATCGCCCCGAT
  64    A  I  L  V  D  F  W  A  E  W  C  G  P  C  K  M  I  A  P  I TCTGGATGAAATCGCTGACGAATATCAGGGCAAACTGACCGTTGCAAAACTGAACATCGA
  84    L  D  E  I  A  D  E  Y  Q  G  K  L  T  V  A  K  L  N  I  D TCAAAACCCTGGCACTGCGCCGAAATATGGCATCCGTGGTATCCCGACTCTGCTGCTGTT
 104    Q  N  P  G  T  A  P  K  Y  G  I  R  G  I  P  T  L  L  L  F CAAAAACGGTGAAGTGGCGGCAACCAAAGTGGGTGCACTGTCTAAAGGTCAGTTGAAAGA
 124    K  N  G  E  V  A  A  T  K  V  G  A  L  S  K  G  Q  L  K  E
```

```
                                FLAG                Lost XbaI
       GAACCTGGCGGATTATAAAGATGACGATGACAAATAATAAGCTAGAGGTACC (trxn stop)
   144  N  L  A  D  Y  K  D  D  D  D  K
``` pMPX-84::malE(1-28)::FXa::PstI, SalI, XbaI::TrxA(1-109 del 103-107)::FLAG
Temperature inducible, clone into PstI, SalI, XbaI
Made by cutting TOPO NsiI-malE(1-28)::FXa::PstI, SalI, XbaI::FLAG-NheI insertion with NsiI & XbaI and cloning into pMPX-90 cut with PstI & XbaI.

SEQ ID NO.: 281
pMPX-96 MalE (1-28) MCS TrxA (2-109 del 103-107) fusion vector

```
                                       SD    Lost PstI +1 malE(1-28)
                                      AGGAGGTTCTGCATATGAAAAT
   1                                                   M  K  I AAAAACAGGTGCACGCATCCTCGCATTATCCGCATTAACGACGATGATGTTTTCCGCCTC
   4   K  T  G  A  R  I  L  A  L  S  A  L  T  T  M  M  F  S  A  S Factor Xa       PstI        SalI        XbaI
       GGCTCTCGCCAAAATCATCGAAGCCCGCCTGCAGGCCTCGGTCGACGCCGAATCTAGAAG
   24  A  L  A  K  I  I  E  A  R  L  Q  A  S  V  D  A  E  S  R  S +2 trxA (2-109 del 103-107)
       CGATAAAATTATTCACCTGACTGACGACAGTTTTGACACGGATGTACTCAAAGCGGACGG
   44  D  K  I  I  H  L  T  D  D  S  F  D  T  D  V  L  K  A  D  G GGCGATCCTCGTCGATTTCTGGGCAGAGTGGTGCGGTCCGTGCAAAATGATCGCCCCGAT
   64  A  I  L  V  D  F  W  A  E  W  C  G  P  C  K  M  I  A  P  I TCTGGATGAAATCGCTGACGAATATCAGGGCAAACTGACCGTTGCAAAACTGAACATCGA
   84  L  D  E  I  A  D  E  Y  Q  G  K  L  T  V  A  K  L  N  I  D TCAAAACCCTGGCACTGCGCCGAAATATGGCATCCGTGGTATCCCGACTCTGCTGCTGTT
  104  Q  N  P  G  T  A  P  K  Y  G  I  R  G  I  P  T  L  L  L  F CAAAAACGGTGAAGTGGCGGCAACCAAAGTGGGTGCACTGTCTAAAGGTCAGTTGAAAGA
  124  K  N  G  E  V  A  A  T  K  V  G  A  L  S  K  G  Q  L  K  E FLAG                  Lost XbaI
       GAACCTGGCGGATTATAAAGATGACGATGACAAATAATAAGCTAGAGGTACC (trxn stop)
  144  N  L  A  D  Y  K  D  D  D  D  K
``` pMPX-86::malE(1-28)::FXa::PstI, SalI, XbaI::TrxA(1-109 del 103-107)::FLAG
Temperature inducible, clone into PstI, SalI, XbaI
Made by cutting TOPO NsiI-malE(1-28)::FXa::PstI, SalI, XbaI::FLAG-NheI insertion with NsiI & XbaI and cloning into pMPX-95 cut with PstI & XbaI.

SEQ ID NO.: 282
pMPX-83 MalE (1-370 del 354-364) MCS TrxA (2-109 del 103-107) fusion vector

```
                                            SD    Lost PstI +1 malE (1-28)
  2401 GAATTCAGGCGCTTTTTAGACTGGTCGTAATGAAATTCAGGAGGTTCTGCATATGAAAAT
   1                                                           M  K  I 2461 AAAAACAGGTGCACGCATCCTCGCATTATCCGCATTAACGACGATGATGTTTTCCGCCTC
   4   K  T  G  A  R  I  L  A  L  S  A  L  T  T  M  M  F  S  A  S 2521 GGCTCTCGCCAAAATCGAAGAAGGTAAACTGGTAATCTGGATTAACGGCGATAAAGGCTA
   24  A  L  A  K  I  E  E  G  K  L  V  I  W  I  N  G  D  K  G  Y 2581 TAACGGTCTCGCTGAAGTCGGTAAGAAATTCGAGAAAGATACCGGAATTAAAGTCACCGT
   44  N  G  L  A  E  V  G  K  K  F  E  K  D  T  G  I  K  V  T  V 2641 TGAGCATCCGGATAAACTGGAAGAGAAATTCCCACAGGTTGCGGCAACTGGCGATGGCCC
   64  E  H  P  D  K  L  E  E  K  F  P  Q  V  A  A  T  G  D  G  P
```

```
2701 TGACATTATCTTCTGGGCACACGACCGCTTTGGTGGCTACGCTCAATCTGGCCTGTTGGC
  84  D  I  I  F  W  A  H  D  R  F  G  G  Y  A  Q  S  G  L  L  A

2761 TGAAATCACCCCGGACAAAGCGTTCCAGGACAAGCTGTATCCGTTTACCTGGGATGCCGT
 104  E  I  T  P  D  K  A  F  Q  D  K  L  Y  P  F  T  W  D  A  V

2821 ACGTTACAACGGCAAGCTGATTGCTTACCCGATCGCTGTTGAAGCGTTATCGCTGATTTA
 124  R  Y  N  G  K  L  I  A  Y  P  I  A  V  E  A  L  S  L  I  Y

2881 TAACAAAGATCTGCTGCCGAACCCGCCAAAAACCTGGGAAGAGATCCCGGCGCTGGATAA
 144  N  K  D  L  L  P  N  P  P  K  T  W  E  E  I  P  A  L  D  K

2941 AGAACTGAAAGCGAAAGGTAAGAGCGCGCTGATGTTCAACCTGCAAGAACCGTACTTCAC
 164  E  L  K  A  K  G  K  S  A  L  M  F  N  L  Q  E  P  Y  F  T

3001 CTGGCCGCTGATTGCTGCTGACGGGGGTTATGCGTTCAAGTATGAAAACGGCAAGTACGA
 184  W  P  L  I  A  A  D  G  G  Y  A  F  K  Y  E  N  G  K  Y  D

3061 CATTAAAGACGTGGGCGTGGATAACGCTGGCGCGAAAGCGGGTCTGACCTTCCTGGTTGA
 204  I  K  D  V  G  V  D  N  A  G  A  K  A  G  L  T  F  L  V  D

3121 CCTGATTAAAAACAAACACATGAATGCAGACACCGATTACTCCATCGCAGAAGCTGCCTT
 224  L  I  K  N  K  H  M  N  A  D  T  D  Y  S  I  A  E  A  A  F

3181 TAATAAAGGCGAAACAGCGATGACCATCAACGGCCCGTGGGCATGGTCCAACATCGACAC
 244  N  K  G  E  T  A  M  T  I  N  G  P  W  A  W  S  N  I  D  T

3241 CAGCAAAGTGAATTATGGTGTAACGGTACTGCCGACCTTCAAGGGTCAACCATCCAAACC
 264  S  K  V  N  Y  G  V  T  V  L  P  T  F  K  G  Q  P  S  K  P

3301 GTTCGTTGGCGTGCTGAGCGCAGGTATTAACGCCGCCAGTCCGAACAAAGAGCTGGCGAA
 284  F  V  G  V  L  S  A  G  I  N  A  A  S  P  N  K  E  L  A  K

3361 AGAGTTCCTCGAAAACTATCTGCTGACTGATGAAGGTCTGGAAGCGGTTAATAAAGACAA
 304  E  F  L  E  N  Y  L  L  T  D  E  G  L  E  A  V  N  K  D  K

3421 ACCGCTGGGTGCCGTAGCGCTGAAGTCTTACGAGGAAGAGTTGGCGAAAGATCCACGTAT
 324  P  L  G  A  V  A  L  K  S  Y  E  E  E  L  A  K  D  P  R  I

Factor Xa
3481 TGCCGCCACCATGGAAAACGCCCAGTCCGCTTTCTGGTATGCCGTGCGTATCGAAGCCCG
 344  A  A  T  M  E  N  A  Q  S  A  F  W  Y  A  V  R  I  E  A  R PstI      SalI       XbaI   +2 trxA (2-109 del 103-107)
3541 CCTGCAGGCCTCGGTCGACGCCGAATCTAGAAGCGATAAAATTATTCACCTGACTGACGA
 364  L  Q  A  S  V  D  A  E  S  R  S  D  K  I  I  H  L  T  D  D 3601 CAGTTTTGACACGGATGTACTCAAAGCGGACGGGGCGATCCTCGTCGATTTCTGGGCAGA
 384  S  F  D  T  D  V  L  K  A  D  G  A  I  L  V  D  F  W  A  E 3661 GTGGTGCGGTCCGTGCAAAATGATCGCCCCGATTCTGGATGAAATCGCTGACGAATATCA
 404  W  C  G  P  C  K  M  I  A  P  I  L  D  E  I  A  D  E  Y  Q 3721 GGGCAAACTGACCGTTGCAAAACTGAACATCGATCAAAACCCTGGCACTGCGCCGAAATA
 424  G  K  L  T  V  A  K  L  N  I  D  Q  N  P  G  T  A  P  K  Y 3781 TGGCATCCGTGGTATCCCGACTCTGCTGCTGTTCAAAAACGGTGAAGTGGCGGCAACCAA
 444  G  I  R  G  I  P  T  L  L  L  F  K  N  G  E  V  A  A  T  K FLAG
3841 AGTGGGTGCACTGTCTAAAGGTCAGTTGAAAGAGAACCTGGCGGATTATAAAGATGACGA
 464  V  G  A  L  S  K  G  Q  L  K  E  N  L  A  D  Y  K  D  D  D 3901 TGACAAATAATAAGCTAGAGG (transcriptional stop)
 484  D  K pMPX-72::malE(1-320 del 354-364)::FXa::PstI, SalI, XbaI::TrxA(1-109
del 103-107)::FLAG
Rhamnose inducible, clone into PstI, SalI, XbaI
Made by cutting TOPO NsiI-malE (1-370 del 354-364)::FXa::PstI, SalI,
XbaI::FLAG-NheI insertion with NsiI & XbaI and cloning into pMPX-78
cut with PstI & XbaI.
```

SEQ ID NO.: 283
pMPX-82 MalE (1-370 del 354-364) MCS TrxA (2-109 del
103-107) fusion vector

```
                              SD    Lost PstI  +1 malE (1-370 del 352-362)
1621  CCATACCCGTTTTTTTGGGCTAGCAGGAGGCCCTGCATATGAAAATAAAAACAGGTGCAC
   1                                             M  K  I  K  T  G  A 1681  GCATCCTCGCATTATCCGCATTAACGACGATGATGTTTTCCGCCTCGGCTCTCGCCAAAA
   8   R  I  L  A  L  S  A  L  T  T  M  M  F  S  A  S  A  L  A  K 1741  TCGAAGAAGGTAAACTGGTAATCTGGATTAACGGCGATAAAGGCTATAACGGTCTCGCTG
  28   I  E  E  G  K  L  V  I  W  I  N  G  D  K  G  Y  N  G  L  A 1801  AAGTCGGTAAGAAATTCGAGAAAGATACCGGAATTAAAGTCACCGTTGAGCATCCGGATA
  48   E  V  G  K  K  F  E  K  D  T  G  I  K  V  T  V  E  H  P  D 1861  AACTGGAAGAGAAATTCCCACAGGTTGCGGCAACTGGCGATGGCCCTGACATTATCTTCT
  68   K  L  E  E  K  F  P  Q  V  A  A  T  G  D  G  P  D  I  I  F 1921  GGGCACACGACCGCTTTGGTGGCTACGCTCAATCTGGCCTGTTGGCTGAAATCACCCCGG
  88   G  A  H  D  R  F  G  G  Y  A  Q  S  G  L  L  A  E  I  T  P 1981  ACAAAGCGTTCCAGGACAAGCTGTATCCGTTTACCTGGGATGCCGTACGTTACAACGGCA
 108   D  K  A  F  Q  D  K  L  Y  P  F  T  W  D  A  V  R  Y  N  G 2041  AGCTGATTGCTTACCCGATCGCTGTTGAAGCGTTATCGCTGATTTATAACAAAGATCTGC
 128   K  L  I  A  Y  P  I  A  V  E  A  L  S  L  I  Y  N  K  D  L 2101  TGCCGAACCCGCCAAAAACCTGGGAAGAGATCCCGGCGCTGGATAAAGAACTGAAAGCGA
 148   L  P  N  P  P  K  T  W  E  E  I  P  A  L  D  K  E  L  K  A 2161  AAGGTAAGAGCGCGCTGATGTTCAACCTGCAAGAACCGTACTTCACCTGGCCGCTGATTG
 168   K  G  K  S  A  L  M  F  N  L  Q  E  P  Y  F  T  W  P  L  I 2221  CTGCTGACGGGGGTTATGCGTTCAAGTATGAAAACGGCAAGTACGACATTAAAGACGTGG
 188   A  A  D  G  G  Y  A  F  K  Y  E  N  G  K  Y  D  I  K  D  V 2281  GCGTGGATAACGCTGGCGCGAAAGCGGGTCTGACCTTCCTGGTTGACCTGATTAAAAACA
 208   G  V  D  N  A  G  A  K  A  G  L  T  F  L  V  D  L  I  K  N 2341  AACACATGAATGCAGACACCGATTACTCCATCGCAGAAGCTGCCTTTAATAAAGGCGAAA
 228   K  H  M  N  A  D  T  D  Y  S  I  A  E  A  A  F  N  K  G  E 2401  CAGCGATGACCATCAACGGCCCGTGGGCATGGTCCAACATCGACACCAGCAAAGTGAATT
 248   T  A  M  T  I  N  G  P  W  A  W  S  N  I  D  T  S  K  V  N 2461  ATGGTGTAACGGTACTGCCGACCTTCAAGGGTCAACCATCCAAACCGTTCGTTGGCGTGC
 268   Y  G  V  T  V  L  P  T  F  K  G  Q  P  S  K  P  F  V  G  V 2521  TGAGCGCAGGTATTAACGCCGCCAGTCCGAACAAAGAGCTGGCGAAAGAGTTCCTCGAAA
 288   L  S  A  G  I  N  A  A  S  P  N  K  E  L  A  K  E  F  L  E 2581  ACTATCTGCTGACTGATGAAGGTCTGGAAGCGGTTAATAAAGACAAACCGCTGGGTGCCG
 308   N  Y  L  L  T  D  E  G  L  E  A  V  N  K  D  K  P  L  G  A 2641  TAGCGCTGAAGTCTTACGAGGAAGAGTTGGCGAAAGATCCACGTATTGCCGCCACCATGG
 328   V  A  L  K  S  Y  E  E  L  A  K  D  P  R  I  A  A  T  M Factor Xa    PstI
2701  AAAACGCCCAGTCCGCTTTCTGGTATGCCGTGCGTATCGAAGCCCGCCTGCAGGCCTCGG
 348   E  N  A  Q  S  A  F  W  Y  A  V  R  I  E  A  R  L  Q  A  S SalI       XbaI    +2 trxA (2-109 del 103-107)
2761  TCGACGCCGAATCTAGAAGCGATAAAATTATTCACCTGACTGACAGTTTTGACACGG
 368   V  D  A  E  S  R  S  D  K  I  I  H  L  T  D  D  S  F  D  T 2821  ATGTACTCAAAGCGGACGGGGCGATCCTCGTCGATTTCTGGGCAGAGTGGTGCGGTCCGT
 388   D  V  L  K  A  D  G  A  I  L  V  D  F  W  A  E  W  C  G  P 2881  GCAAAATGATCGCCCCGATTCTGGATGAAATCGCTGACGAATATCAGGGCAAACTGACCG
 408   C  K  M  I  A  P  I  L  D  E  I  A  D  E  Y  Q  G  K  L  T 2941  TTGCAAAACTGAACATCGATCAAAACCCTGGCACTGCGCCGAAATATGGCATCCGTGGTA
 428   V  A  K  L  N  I  D  Q  N  P  G  T  A  P  K  Y  G  I  R  G
```

```
3001  TCCCGACTCTGCTGCTGTTCAAAAACGGTGAAGTGGCGGCAACCAAAGTGGGTGCACTGT
448    I  P  T  L  L  L  F  K  N  G  E  V  A  A  T  K  V  G  A  L

FLAG
3061  CTAAAGGTCAGTTGAAAGAGAACCTGGCGGATTATAAAGATGACGATGACAAATAATAAG
468    S  K  G  Q  L  K  E  N  L  A  D  Y  K  D  D  D  K

Lost XbaI
         CTAGAGG (transcriptional stop)

pMPX-71::malE(1-370 del 354-364)::FXa::PstI, SalI, XbaI::TrxA(1-109
del 103-107)::FLAG
Arabinose inducible, clone into PstI, SalI, XbaI
Made by cutting TOPO NsiI-malE (1-370 del 354-364)::FXa::PstI, SalI,
XbaI::FLAG-NheI insertion with NsiI & XbaI and cloning into pMPX-79
cut with PstI & XbaI.

SEQ ID NO.: 284
pMPX-92 MalE (1-370 del 354-364) MCS TrxA (2-109 del
103-107) fusion vector SD   Lost PstI +1 malE (1-370 del 354-364)
                 AGGAGGTTCTGCATATGAAAATAAAAACAGGTGCAC
1                                  M  K  I  K  T  G  A GCATCCTCGCATTATCCGCATTAACGACGATGATGTTTTCCGCCTCGGCTCTCGCCAAAA
8       R  I  L  A  L  S  A  L  T  T  M  M  F  S  A  S  A  L  A  K TCGAAGAAGGTAAACTGGTAATCTGGATTAACGGCGATAAAGGCTATAACGGTCTCGCTG
28      I  E  E  G  K  L  V  I  W  I  N  G  D  K  G  Y  N  G  L  A AAGTCGGTAAGAAATTCGAGAAAGATACCGGAATTAAAGTCACCGTTGAGCATCCGGATA
48      E  V  G  K  K  F  E  K  D  T  G  I  K  V  T  V  E  H  P  D AACTGGAAGAGAAATTCCCACAGGTTGCGGCAACTGGCGATGGCCCTGACATTATCTTCT
68      K  L  E  E  K  F  P  Q  V  A  A  T  G  D  G  P  D  I  I  F GGGCACACGACCGCTTTGGTGGCTACGCTCAATCTGGCCTGTTGGCTGAAATCACCCCGG
88      W  A  H  D  R  F  G  G  Y  A  Q  S  G  L  L  A  E  I  T  P ACAAAGCGTTCCAGGACAAGCTGTATCCGTTTACCTGGGATGCCGTACGTTACAACGGCA
108     D  K  A  F  Q  D  K  L  Y  P  F  T  W  D  A  V  R  Y  N  G AGCTGATTGCTTACCCGATCGCTGTTGAAGCGTTATCGCTGATTTATAACAAAGATCTGC
128     K  L  I  A  Y  P  I  A  V  E  A  L  S  L  I  Y  N  K  D  L TGCCGAACCCGCCAAAAACCTGGGAAGAGATCCCGGCGCTGGATAAAGAACTGAAAGCGA
148     L  P  N  P  P  K  T  W  E  E  I  P  A  L  D  K  E  L  K  A AAGGTAAGAGCGCGCTGATGTTCAACCTGCAAGAACCGTACTTCACCTGGCCGCTGATTG
168     K  G  K  S  A  L  M  F  N  L  Q  E  P  Y  F  T  W  P  L  I CTGCTGACGGGGGTTATGCGTTCAAGTATGAAAACGGCAAGTACGACATTAAAGACGTGG
188     A  A  D  G  G  Y  A  F  K  Y  E  N  G  K  Y  D  I  K  D  V GCGTGGATAACGCTGGCGCGAAAGCGGGTCTGACCTTCCTGGTTGACCTGATTAAAAACA
208     G  V  D  N  A  G  A  K  A  G  L  T  F  L  V  D  L  I  K  N 2341   AACACATGAATGCAGACACCGATTACTCCATCGCAGAAGCTGCCTTTAATAAAGGCGAAA
228     K  H  M  N  A  D  T  D  Y  S  I  A  E  A  A  F  N  K  G  E 2401   CAGCGATGACCATCAACGGCCCGTGGGCATGGTCCAACATCGACACCAGCAAAGTGAATT
248     T  A  M  T  I  N  G  P  W  A  W  S  N  I  D  T  S  K  V  N 2461   ATGGTGTAACGGTACTGCCGACCTTCAAGGGTCAACCATCCAAACCGTTCGTTGGCGTGC
268     Y  G  V  T  V  L  P  T  F  K  G  Q  P  S  K  P  F  V  G  V 2521   TGAGCGCAGGTATTAACGCCGCCAGTCCGAACAAAGAGCTGGCGAAAGAGTTCCTCGAAA
288     L  S  A  G  I  N  A  A  S  P  N  K  E  L  A  K  E  F  L  E 2581   ACTATCTGCTGACTGATGAAGGTCTGGAAGCGGTTAATAAAGACAAACCGCTGGGTGCCG
308     N  Y  L  L  T  D  E  G  L  E  A  V  N  K  D  K  P  L  G  A 2641   TAGCGCTGAAGTCTTACGAGGAAGAGTTGGCGAAAGATCCACGTATTGCCGCCACCATGG
328     V  A  L  K  S  Y  E  E  E  L  A  K  D  P  R  I  A  A  T  M
```

```
                         Factor Xa    PstI
2701  AAAACGCCCAGTCCGCTTTCTGGTATGCCGTGCGTATCGAAGCCCGCCTGCAGGCCTCGG
348    E   N   A   Q   S   A   F   W   Y   A   V   R   I   E   A   R   L   Q   A   S SalI         XbaI   +2 trxA (2-109 del 103-107)
2761  TCGACGCCGAATCTAGAAGCGATAAAATTATTCACCTGACTGACGACAGTTTTGACACGG
368    V   D   A   E   S   R   S   D   K   I   I   H   L   T   D   D   S   F   D   T 2821  ATGTACTCAAAGCGGACGGGGCGATCCTCGTCGATTTCTGGGCAGAGTGGTGCGGTCCGT
388    D   V   L   K   A   D   G   A   I   L   V   D   F   W   A   E   W   C   G   P 2881  GCAAAATGATCGCCCCGATTCTGGATGAAATCGCTGACGAATATCAGGGCAAACTGACCG
408    C   K   M   I   A   P   I   L   D   E   I   A   D   E   Y   Q   G   K   L   T 2941  TTGCAAAACTGAACATCGATCAAAACCCTGGCACTGCGCCGAAATATGGCATCCGTGGTA
428    V   A   K   L   N   I   D   Q   N   P   G   T   A   P   K   Y   G   I   R   G 3001  TCCCGACTCTGCTGCTGTTCAAAAACGGTGAAGTGGCGGCAACCAAAGTGGGTGCACTGT
448    I   P   T   L   L   L   F   K   N   G   E   V   A   A   T   K   V   G   A   L FLAG
3061  CTAAAGGTCAGTTGAAAGAGAACCTGGCGGATTATAAAGATGACGATGACAAATAATAAG
468    S   K   G   Q   L   K   E   N   L   A   D   Y   K   D   D   D   K Lost XbaI
      CTAGAGGTACC (transcriptional stop)

pMPX-84::malE(1-370 del 354-364)::FXa::PstI, SalI, XbaI::TrxA(1-109 del
103-107)::FLAG
Temperature inducible, clone into PstI, SalI, XbaI
Made by cutting TOPO NsiI-malE (1-370 del 354-364)::FXa::PstI, SalI,
XbaI::FLAG-NheI insertion with NsiI & XbaI and cloning into pMPX-90
cut with PstI & XbaI.
                                                                    30
SEQ ID NO.: 285
pMPX-97 MalE (1-370 del 354-364) MCS TrxA (2-109 del
103-107) fusion vector SD      Lost  PstI  +1 malE (1-370 del 354-364)
               AGGAGGTTCTGCATATGAAAATAAAAACAGGTGCAC
1                                    M   K   I   K   T   G   A GCATCCTCGCATTATCCGCATTAACGACGATGATGTTTTCCGCCTCGGCTCTCGCCAAAA
8      R   I   L   A   L   S   A   L   T   T   M   M   F   S   A   S   A   L   A   K TCGAAGAAGGTAAACTGGTAATCTGGATTAACGGCGATAAAGGCTATAACGGTCTCGCTG
28     I   E   E   G   K   L   V   I   W   I   N   G   D   K   G   Y   N   G   L   A AAGTCGGTAAGAAATTCGAGAAAGATACCGGAATTAAAGTCACCGTTGAGCATCCGGATA
48     E   V   G   K   K   F   E   K   D   T   G   I   K   V   T   V   E   H   P   D AACTGGAAGAGAAATTCCCACAGGTTGCGGCAACTGGCGATGGCCCTGACATTATCTTCT
68     K   L   E   E   K   F   P   Q   V   A   A   T   G   D   G   P   D   I   I   F GGGCACACGACCGCTTTGGTGGCTACGCTCAATCTGGCCTGTTGGCTGAAATCACCCCGG
88     W   A   H   D   R   F   G   G   Y   A   Q   S   G   L   L   A   E   I   T   P ACAAAGCGTTCCAGGACAAGCTGTATCCGTTTACCTGGGATGCCGTACGTTACAACGGCA
108    D   K   A   F   Q   D   K   L   Y   P   F   T   W   D   A   V   R   Y   N   G AGCTGATTGCTTACCCGATCGCTGTTGAAGCGTTATCGCTGATTTATAACAAAGATCTGC
128    K   L   I   A   Y   P   I   A   V   E   A   L   S   L   I   Y   N   K   D   L TGCCGAACCCGCCAAAAACCTGGGAAGAGATCCCGGCGCTGGATAAAGAACTGAAAGCGA
148    L   P   N   P   P   K   T   W   E   E   I   P   A   L   D   K   E   L   K   A AAGGTAAGAGCGCGCTGATGTTCAACCTGCAAGAACCGTACTTCACCTGGCCGCTGATTG
168    K   G   K   S   A   L   M   F   N   L   Q   E   P   Y   F   T   W   P   L   I CTGCTGACGGGGGTTATGCGTTCAAGTATGAAAACGGCAAGTACGACATTAAAGACGTGG
188    A   A   D   G   G   Y   A   F   K   Y   E   N   G   K   Y   D   I   K   D   V GCGTGGATAACGCTGGCGCGAAAGCGGGTCTGACCTTCCTGGTTGACCTGATTAAAAACA
208    G   V   D   N   A   G   A   K   A   G   L   T   F   L   V   D   L   I   K   N 2341  AACACATGAATGCAGACACCGATTACTCCATCGCAGAAGCTGCCTTTAATAAAGGCGAAA
228    K   H   M   N   A   D   T   D   Y   S   I   A   E   A   A   F   N   K   G   E
```

```
2401 CAGCGATGACCATCAACGGCCCGTGGGCATGGTCCAACATCGACACCAGCAAAGTGAATT
 248    T  A  M  T  I  N  G  P  W  A  W  S  N  I  D  T  S  K  V  N

2461 ATGGTGTAACGGTACTGCCGACCTTCAAGGGTCAACCATCCAAACCGTTCGTTGGCGTGC
 268    Y  G  V  T  V  L  P  T  F  K  G  Q  P  S  K  P  F  V  G  V

2521 TGAGCGCAGGTATTAACGCCGCCAGTCCGAACAAAGAGCTGGCGAAAGAGTTCCTCGAAA
 288    L  S  A  G  I  N  A  A  S  P  N  K  E  L  A  K  E  F  L  E

2581 ACTATCTGCTGACTGATGAAGGTCTGGAAGCGGTTAATAAAGACAAACCGCTGGGTGCCG
 308    N  Y  L  L  T  D  E  G  L  E  A  V  N  K  D  K  P  L  G  A

2641 TAGCGCTGAAGTCTTACGAGGAAGAGTTGGCGAAAGATCCACGTATTGCCGCCACCATGG
 328    V  A  L  K  S  Y  E  E  E  L  A  K  D  P  R  I  A  A  T  M

Factor Xa    Pst I
2701 AAAACGCCCAGTCCGCTTTCTGGTATGCCGTGCGTATCGAAGCCCGCCTGCAGGCCTCGG
 348    E  N  A  Q  S  A  F  W  Y  A  V  R  I  E  A  R  L  Q  A  S SalI        XbaI    +2 trxA (2-109 del 103-107)
2761 TCGACGCCGAATCTAGAAGCGATAAAATTATTCACCTGACTGACGACAGTTTTGACACGG
 368    V  D  A  E  S  R  S  D  K  I  I  H  L  T  D  D  S  F  D  T 2821 ATGTACTCAAAGCGGACGGGGCGATCCTCGTCGAT T TCTGGGCAGAGTGGTGCGGTCCGT
 388    D  V  L  K  A  D  G  A  I  L  V  D  F  W  A  E  W  C  G  P 2881 GCAAAATGATCGCCCCGATTCTGGATGAAATCGCTGACGAATATCAGGGCAAACTGACCG
 408    C  K  M  I  A  P  I  L  D  E  I  A  D  E  Y  Q  G  K  L  T 2941 TTGCAAAACTGAACATCGATCAAAACCCTGGCACTGCGCCGAAATATGGCATCCGTGGTA
 428    V  A  K  L  N  I  D  Q  N  P  G  T  A  P  K  Y  G  I  R  G 3001 TCCCGACTCTGCTGCTGTTCAAAAACGGTGAAGTGGCGGCAACCAAAGTGGGTGCACTGT
 448    I  P  T  L  L  L  F  K  N  G  E  V  A  A  T  K  V  G  A  L FLAG
3061 CTAAAGGTCAGTTGAAAGAGAACCTGGCGGATTATAAAGATGACGATGACAAATAATAAG
 468    S  K  G  Q  L  K  E  N  L  A  D  Y  K  D  D  D  D  K Lost XbaI
        CTAGAGGTACC (transcriptional stop)

pMPX-86::malE(1-370 del 354-364)::FXa::PstI, SalI, XbaI:TrxA(1-109 del
103-107)::FLAG
Temperature inducible, clone into PstI, SalI, XbaI
Made by cutting TOPO NsiI-malE (1-370 del 354-364)::FXa::PstI, SalI,
XbaI::FLAG-NheI insertion with NsiI & XbaI and cloning into pMPX-95
cut with PstI & XbaI.
```

---

What is claimed is:

1. A fully intact eubacterial minicell derived from a eubacterial parent cell, wherein the minicell comprises a biologically active compound and displays an antibody or antibody derivative, wherein the biologically active compound and antibody or antibody derivative are exogenous to the parent cell and distinct from each other.

2. The minicell of claim 1, wherein said antibody or antibody derivative is an antibody.

3. The minicell of claim 1, wherein said antibody or antibody derivative is an antibody derivative.

* * * * *

SEQUENCE LISTING

<160> NUMBER OF SEQ ID NOS: 370

<210> SEQ ID NO 1
<211> LENGTH: 1260
<212> TYPE: DNA
<213> ORGANISM: E. coli

<400> SEQUENCE: 1

```
ccatacccgt tttttgggc tagcaggagg aattcaccct gcagatgttt gaaccaatgg     60
aacttaccaa tgacgcggtg attaaagtca tcggcgtcgg cggcggcggc ggtaatgctg    120
ttgaacacat ggtgcgcgag cgcattgaag gtgttgaatt cttcgcggta ataccgatg     180 cacaagcgct gcgtaaaaca gcggttggac agacgattca aatcggtagc ggtatcacca    240
aaggactggg cgctggcgct aatccagaag ttggccgcaa tgcggctgat gaggatcgcg    300
atgcattgcg tgcggcgctg aaggtgcag acatggtctt tattgctgcg ggtatgggtg    360
gtggtaccgg tacaggtgca gcaccagtcg tcgctgaagt ggcaaaagat ttgggtatcc    420
tgaccgttgc tgtcgtcact aagcctttca actttgaagg caagaagcgt atggcattcg    480
```

```
cggagcaggg gatcactgaa ctgtccaagc atgtggactc tctgatcact atcccgaacg    540
acaaactgct gaaagttctg ggccgcggta tctccctgct ggatgcgttt ggcgcagcga    600
acgatgtact gaaaggcgct gtgcaaggta tcgctgaact gattactcgt ccgggtttga    660
tgaacgtgga ctttgcagac gtacgcaccg taatgtctga gatgggctac gcaatgatgg    720
gttctggcgt ggcgagcggt gaagaccgtg cggaagaagc tgctgaaatg gctatctctt    780
ctccgctgct ggaagatatc gacctgtctg gcgcgcgcgg cgtgctggtt aacatcacgg    840
cgggcttcga cctgcgtctg gatgagttcg aaacggtagg taacaccatc cgtgcatttg    900
cttccgacaa cgcgactgtg gttatcggta cttctcttga cccggatatg aatgacgagc    960
tgcgcgtaac cgttgttgcg acaggtatcg gcatggacaa acgtcctgaa atcactctgg   1020
tgaccaataa gcaggttcag cagccagtga tggatcgcta ccagcagcat gggatggctc   1080
cgctgaccca ggagcagaag ccggttgcta agtcgtgaa tgacaatgcg ccgcaaactg    1140
cgaaagagcc ggattatctg gatatcccag cattcctgcg taagcaagct gattaataat   1200
ctagaggatc cccgggtacc gagctcgaat tcgtaatcat ggtcatagct gtttcctgtg   1260

<210> SEQ ID NO 2
<211> LENGTH: 1260
<212> TYPE: DNA
<213> ORGANISM: E. coli

<400> SEQUENCE: 2
gaattcaggc gcttttttaga ctggtcgtaa tgaaattcag caggatcaca ttctgcagat     60 gtttgaaccca atggaactta ccaatgacgc ggtgattaaa gtcatcggcg tcggcggcgg    120
cggcggtaat gctgttgaac acatggtgcg cgagcgcatt gaaggtgttg aattcttcgc    180
ggtaaatacc gatgcacaag cgctgcgtaa acagcggtt ggacagacga ttcaaatcgg     240
tagcggtatc accaaaggac tgggcgctgg cgctaatcca gaagttggcc gcaatgcggc    300
tgatgaggat cgcgatgcat tgcgtgcggc gctggaaggt gcagacatgg tctttattgc    360
tgcgggtatg ggtggtggta ccggtacagg tgcagcacca gtcgtcgctg aagtggcaaa    420
agatttgggt atcctgaccg ttgctgtcgt cactaagcct ttcaactttg aaggcaagaa    480
gcgtatggca ttcgcggagc aggggatcac tgaactgtcc aagcatgtgg actctctgat    540
cactatcccg aacgacaaac tgctgaaagt tctgggccgc ggtatctccc tgctggatgc    600
gtttggcgca gcgaacgatg tactgaaagg cgctgtgcaa ggtatcgctg aactgattac    660
tcgtccgggt ttgatgaacg tggactttgc agacgtacgc accgtaatgt ctgagatggg    720
ctacgcaatg atgggttctg gcgtggcgag cggtgaagac cgtgcggaag aagctgctga    780
aatggctatc tcttctccgc tgctggaaga tatcgacctg tctggcgcgc gcggcgtgct    840
ggttaacatc acggcgggct tcgacctgcg tctggatgag ttcgaaacgg taggtaacac    900
catccgtgca tttgcttccg acaacgcgac tgtggttatc ggtacttctc ttgacccgga    960
tatgaatgac gagctgcgcg taaccgttgt tgcgacaggt atcggcatgg acaaacgtcc   1020
tgaaatcact ctggtgacca ataagcaggt tcagcagcca gtgatggatc gctaccagca   1080
gcatgggatg gctccgctga cccaggagca gaagccggtt gctaaagtcg tgaatgacaa   1140
tgcgccgcaa actgcgaaag agccggatta tctggatatc ccagcattcc tgcgtaagca   1200
agctgattaa taatctagag gatccccggg taccgagctc gaattcgtaa tcatggtcat   1260

<210> SEQ ID NO 3
<211> LENGTH: 2544
```

```
<212> TYPE: DNA
<213> ORGANISM: E. coli

<400> SEQUENCE: 3
aagcctgcat tgcggcgctt cagtctccgc tgcatactgt cccgttacca attatgacaa      60
cttgacggct acatcattca cttttcttc acaaccggca cggaactcgc tcgggctggc     120
cccggtgcat ttttaaata cccgcgagaa atagagttga tcgtcaaaac caacattgcg     180
accgacggtg gcgataggca tccggtggt gctcaaaagc agcttcgcct ggctgatacg     240
ttggtcctcg cgccagctta agacgctaat ccctaactgc tggcgaaaaa gatgtgacag     300
acgcgacggc gacaagcaaa catgctgtgc gacgctggcg atatcaaaat tgctgtctgc     360
caggtgatcg ctgatgtact gacaagcctc gcgtacccga ttatccatcg gtggatggag     420
cgactcgtta atcgcttcca tgcgccgcag taacaattgc tcaagcagat ttatcgccag     480
cagctccgaa tagcgccctt cccttgccc ggcgttaatg atttgcccaa acaggtcgct     540
gaaatgcggc tggtgcgctt catccggcg aaagaacccc gtattggcaa atattgacgg     600
ccagttaagc cattcatgcc agtaggcgcg cggacgaaag taaacccact ggtgatacca     660
ttcgcgagcc tccggatgac gaccgtagtg atgaatctct cctggcggga acagcaaaat     720
atcacccggt cggcaaacaa attctcgtcc ctgatttttc accacccct gaccgcgaat     780
ggtgagattg agaatataac ctttcattcc cagcggtcgg tcgataaaaa aatcgagata     840
accgttggcc tcaatcggcg ttaaacccgc caccagatgg gcattaaacg agtatcccgg     900
cagcagggga tcattttgcg cttcagccat acttttcata ctcccgccat tcagagaaga     960
aaccaattgt ccatattgca tcagacattg ccgtcactgc gtcttttact ggctcttctc    1020
gctaaccaaa ccggtaaccc cgcttattaa aagcattctg taacaaagcg ggaccaaagc    1080
catgacaaaa acgcgtaaca aaagtgtcta taatcacggc agaaaagtcc acattgatta    1140
tttgcacggc gtcacacttt gctatgccat agcatttta tccataagat tagcggatcc    1200
tacctgacgc tttttatcgc aactctctac tgtttctcca tacccgtttt tttgggctag    1260
caggaggaat tcaccctgca gatgtttgaa ccaatggaac ttaccaatga cgcggtgatt    1320
aaagtcatcg gcgtcggcgg cggcggcggt aatgctgttg aacacatggt gcgcgagcgc    1380
attgaaggtg ttgaattctt cgcggtaaat accgatgcac aagcgctgcg taaaacagcg    1440
gttggacaga cgattcaaat cggtagcggt atcaccaaag gactgggcgc tggcgctaat    1500
ccagaagttg gccgcaatgc ggctgatgag gatcgcgatg cattgcgtgc ggcgctggaa    1560
ggtgcagaca tggtctttat tgctgcgggt atgggtggtg gtaccggtac aggtgcagca    1620
ccagtcgtcg ctgaagtggc aaaagatttg ggtatcctga ccgttgctgt cgtcactaag    1680
cctttcaact ttgaaggcaa gaagcgtatg gcattcgcgg agcagggat cactgaactg    1740
tccaagcatg tggactctct gatcactatc ccgaacgaca aactgctgaa agttctgggc    1800
cgcggtatct ccctgctgga tgcgtttgc gcagcgaacg atgtactgaa aggcgctgtg    1860
caaggtatcg ctgaactgat tactcgtccg ggtttgatga cgtggactt tgcagacgta    1920
cgcaccgtaa tgtctgagat gggctacgca atgatgggtt ctggcgtggc gagcggtgaa    1980
gaccgtgcgg aagaagctgc tgaaatggct atctcttctc cgctgctgga agatatcgac    2040
ctgtctggcg cgcgcggcgt gctggttaac atcacgcgg gcttcgacct gcgtctggat    2100
gagttcgaaa cggtaggtaa caccatccgt gcatttgctt ccgacaacgc gactgtggtt    2160
atcggtactt ctcttgaccc ggatatgaat gacgagctgc gcgtaaccgt tgttgcgaca    2220
ggtatcggca tggacaaacg tcctgaaatc actctggtga ccaataagca ggttcagcag    2280
```

| | |
|---|---|
| ccagtgatgg atcgctacca gcagcatggg atggctccgc tgacccagga gcagaagccg | 2340 |
| gttgctaaag tcgtgaatga caatgcgccg caaactgcga aagagccgga ttatctggat | 2400 |
| atcccagcat tcctgcgtaa gcaagctgat taataatcta gaggcgttac caattatgac | 2460 |
| aacttgacgg gaagttccta tactttctag agaataggaa cttcccaaag ccagtatcaa | 2520 |
| ctcagacaaa ggcaaagcat cttg | 2544 |

<210> SEQ ID NO 4
<211> LENGTH: 3350
<212> TYPE: DNA
<213> ORGANISM: E. coli

<400> SEQUENCE: 4

| | |
|---|---|
| aagcctgcat tgcggcgctt cagtctccgc tgcatactgt ccttaatctt tctgcgaatt | 60 |
| gagatgacgc cactggctgg gcgtcatccc ggtttcccgg gtaaacacca ccgaaaaata | 120 |
| gttactatct tcaaagccac attcggtcga aatatcactg attaacaggc ggctatgctg | 180 |
| gagaagatat tgcgcatgac acactctgac ctgtcgcaga tattgattga tggtcattcc | 240 |
| agtctgctgg cgaaattgct gacgcaaaac gcgctcactg cacgatgcct catcacaaaa | 300 |
| tttatccagc gcaaagggac ttttcaggct agccgccagc cgggtaatca gcttatccag | 360 |
| caacgtttcg ctggatgttg gcggcaacga atcactggtg taacgatggc gattcagcaa | 420 |
| catcaccaac tgcccgaaca gcaactcagc catttcgtta gcaaacggca catgctgact | 480 |
| actttcatgc tcaagctgac cgataacctg ccgcgcctgc gccatcccca tgctacctaa | 540 |
| gcgccagtgt ggttgccctg cgctggcgtt aaatcccgga atcgccccct gccagtcaag | 600 |
| attcagcttc agacgctccg ggcaataaat aatattctgc aaaaccagat cgttaacgga | 660 |
| agcgtaggag tgtttatcgt cagcatgaat gtaaaagaga tcgccacggg taatgcgata | 720 |
| agggcgatcg ttgagtacat gcaggccatt accgcgccag acaatcacca gctcacaaaa | 780 |
| atcatgtgta tgttcagcaa agacatcttg cggataacgg tcagccacag cgactgcctg | 840 |
| ctggtcgctg gcaaaaaaat catctttgag aagttttaac tgatgcgcca ccgtggctac | 900 |
| ctcggccaga gaacgaagtt gattattcgc aatatggcgt acaaatacgt tgagaagatt | 960 |
| cgcgttattg cagaaagcca tcccgtccct ggcgaatatc acgcggtgac cagttaaact | 1020 |
| ctcggcgaaa aagcgtcgaa agtggttac tgtcgctgaa tccacagcga taggcgatgt | 1080 |
| cagtaacgct ggcctcgctg tggcgtagca gatgtcgggc tttcatcagt cgcaggcggt | 1140 |
| tcaggtatcg ctgaggcgtc agtcccgttt gctgcttaag ctgccgatgt agcgtacgca | 1200 |
| gtgaaagaga aaattgatcc gccacggcat cccaattcac ctcatcggca aaatggtcct | 1260 |
| ccagccaggc cagaagcaag ttgagacgtg atgcgctgtt ttccaggttc tcctgcaaac | 1320 |
| tgcttttacg cagcaagagc agtaattgca taaacaagat ctcgcgactg gcggtcgagg | 1380 |
| gtaaatcatt ttccccttcc tgctgttcca tctgtgcaac cagctgtcgc acctgctgca | 1440 |
| atacgctgtg gttaacgcgc cagtgagacg gatactgccc atccagctct tgtggcagca | 1500 |
| actgattcag cccggcgaga aactgaaatc gatccggcga gcgatacagc acattggtca | 1560 |
| gacacagatt atcggtatgt tcatacagat gccgatcatg atcgcgtacg aaacagaccg | 1620 |
| tgccaccggt gatggtatag gctgcccat taaacacatg aatacccgtg ccatgttcga | 1680 |
| caatcacaat ttcatgaaaa tcatgatgat gttcaggaaa atccgcctgc gggagccggg | 1740 |
| gttctatcgc cacggacgcg ttaccagacg gaaaaaaatc cacactatgt aatacggtca | 1800 |
| tactggcctc ctgatgtcgt caacacggcg aaatagtaat cacgaggtca ggttcttacc | 1860 |

-continued

```
ttaaattttc gacggaaaac cacgtaaaaa acgtcgattt ttcaagatac agcgtgaatt    1920
ttcaggaaat gcggtgagca tcacatcacc acaattcagc aaattgtgaa catcatcacg    1980
ttcatctttc cctggttgcc aatggcccat tttcctgtca gtaacgagaa ggtcgcgaat    2040
tcaggcgctt tttagactgg tcgtaatgaa attcagcagg atcacatatg tttgaaccaa    2100
tggaacttac caatgacgcg gtgattaaag tcatcggcgt cggcggcggc ggcggtaatg    2160
ctgttgaaca catggtgcgc gagcgcattg aaggtgttga attcttcgcg gtaaataccg    2220
atgcacaagc gctgcgtaaa acagcggttg acagacgat tcaaatcggt agcggtatca     2280
ccaaaggact gggcgctggc gctaatccag aagttggccg caatgcggct gatgaggatc    2340
gcgatgcatt gcgtgcggcg ctggaaggtg cagacatggt cttttattgct gcgggtatgg   2400 gtggtggtac cggtacaggt gcagcaccag tcgtcgctga gtggcaaaa gatttgggta    2460 tcctgaccgt tgctgtcgtc actaagcctt tcaactttga aggcaagaag cgtatggcat    2520
tcgcggagca gggatcact gaactgtcca agcatgtgga ctctctgatc actatcccga     2580
acgacaaact gctgaaagtt ctgggccgcg gtatctccct gctggatgcg tttggcgcag    2640
cgaacgatgt actgaaaggc gctgtgcaag gtatcgctga actgattact cgtccgggtt    2700
tgatgaacgt ggactttgca gacgtacgca ccgtaatgtc tgagatgggc tacgcaatga    2760
tgggttctgg cgtggcgagc ggtgaagacc gtgcggaaga agctgctgaa atggctatct    2820
cttctccgct gctggaagat atcgacctgt ctggcgcgcg cggcgtgctg gttaacatca    2880
cggcgggctt cgacctgcgt ctggatgagt tcgaaacggt aggtaacacc atccgtgcat    2940
ttgcttccga caacgcgact gtggttatcg gtacttctct tgacccggat atgaatgacg    3000
agctgcgcgt aaccgttgtt gcgacaggta tcggcatgga caaacgtcct gaaatcactc    3060
tggtgaccaa taagcaggtt cagcagccag tgatggatcg ctaccagcag catgggatgg    3120
ctccgctgac ccaggagcag aagccggttg ctaaagtcgt gaatgacaat gcgccgcaaa    3180
ctgcgaaaga gccggattat ctggatatcc cagcattcct gcgtaagcaa gctgattaat    3240
aatctagagg cgttaccaat tatgacaact tgacgggaag ttcctatact ttctagagaa    3300
taggaacttc ccaaagccag tatcaactca gacaaaggca aagcatcttg                3350
```

```
<210> SEQ ID NO 5
<211> LENGTH: 2280
<212> TYPE: DNA
<213> ORGANISM: E. coli

<400> SEQUENCE: 5
```

```
aagcctgcat tgcggcgctt cagtctccgc tgcatactgt ccttaataaa gtgagtcgat      60
attgtctttg ttgaccagta ataccttatg gaaacggata attcgcttat ccatatctac     120
gtcggcctta cccagattct gcatttctaa tccaggcttg atctcttcac ccttcagcaa     180
cgtgctggcg acggctgcga gtgcgtaacc tgcagaggcc ggatcgtaag taatcccttc     240
ggtgatatca ccacttttaa tcagtgatgc cgcctgtgaa gggatcatca tgccatagac     300
tgcgacttta ttttcgccc gtttctcttt caccgcacgt cccgcgccaa tcggaccgtt      360
tgaaccaaag gagacaaccg ctttcaagtc aggataggtt ttcatcaggt ccagtgtagt     420
acgacgtgag acatccacac tctcggcaac cggcatgcgg cgggtaactt catgcatatc    480
cgggtaatgc tctttctggt atttcaccag caagtcagcc ataagttat gctgcggcac     540 ggtcaaacta cccacgtaaa tcacatagcc gcccttgcca cccatgcgtt tcgccatatg    600
ctcaacatat tcagcggcaa attttttcgtt atcaatgatt tcgatatccc agttagcact    660
```

```
tggctgaccg ggggattcgt tggtcagaac cacaattccg gcatctcgcg cttttttgaa      720
taccggttcc agcacgttgg catcgttttgg cacgatagta attgcattaa ccttacgggc      780
gattaaatcc tcaataattt taacttgttg cggagcatca gtacttgaag gccccacctg      840
tgaggcatta acaccaaagg ctttacccgc ctcaaccaca ccttcgccca tgcgattaaa      900
ccacggcata ccatcgactt tagaaatatt caccacgact ttttccgctg cctggagcgg      960
cgcagaaatt agcgcagcgc ctaataacag cgaagacacc atattgataa caaaacgttt     1020
attcatcata tggaacttac caatgacgcg gtgattaaag tcatcggcgt cggcggcggc     1080
ggcggtaatg ctgttgaaca catggtgcgc gagcgcattg aaggtgttga attcttcgcg     1140
gtaaataccg atgcacaagc gctgcgtaaa acagcggttg gacagacgat tcaaatcggt     1200
agcggtatca ccaaaggact gggcgctggc gctaatccag aagttggccg caatgcggct     1260
gatgaggatc gcgatgcatt gcgtgcggcg ctggaaggtg cagacatggt ctttattgct     1320
gcgggtatgg gtggtggtac cggtacaggt gcagcaccag tcgtcgctga agtggcaaaa     1380
gatttgggta tcctgaccgt tgctgtcgtc actaagcctt tcaactttga aggcaagaag     1440
cgtatggcat tcgcggagca ggggatcact gaactgtcca agcatgtgga ctctctgatc     1500
actatcccga acgacaaact gctgaaagtt ctgggccgcg gtatctccct gctggatgcg     1560 tttgcgcag cgaacgatgt actgaaaggc gctgtgcaag gtatcgctga actgattact     1620
cgtccgggtt tgatgaacgt ggactttgca gacgtacgca ccgtaatgtc tgagatgggc     1680
tacgcaatga tggggttctgg cgtggcgagc ggtgaagacc gtgcggaaga agctgctgaa     1740
atggctatct cttctccgct gctggaagat atcgacctgt ctggcgcgcg cggcgtgctg     1800
gttaacatca cggcgggctt cgacctgcgt ctggatgagt tcgaaacggt aggtaacacc     1860
atccgtgcat ttgcttccga caacgcgact gtggttatcg gtacttctct tgacccggat     1920
atgaatgacg agctgcgcgt aaccgttgtt gcgacaggta tcggcatgga caaacgtcct     1980
gaaatcactc tggtgaccaa taagcaggtt cagcagccag tgatggatcg ctaccagcag     2040
catgggatgg ctccgctgac ccaggagcag aagccggttg ctaaagtcgt gaatgacaat     2100
gcgccgcaaa ctgcgaaaga gccggattat ctggatatcc cagcattcct gcgtaagcaa     2160
gctgattaat aatctagagg cgttaccaat tatgacaact tgacgggaag ttcctattct     2220
ctagaaagta taggaacttc ccaaagccag tatcaactca gacaaaggca aagcatcttg     2280

<210> SEQ ID NO 6
<211> LENGTH: 4728
<212> TYPE: DNA
<213> ORGANISM: E. coli

<400> SEQUENCE: 6
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgccaa gcttaattaa tctttctgcg      420
aattgagatg acgccactgg ctgggcgtca tcccggtttc ccgggtaaac accaccgaaa      480
aatagttact atcttcaaag ccacattcgg tcgaaatatc actgattaac aggcggctat      540
```

-continued

```
gctggagaag atattgcgca tgacacactc tgacctgtcg cagatattga ttgatggtca    600
ttccagtctg ctggcgaaat tgctgacgca aaacgcgctc actgcacgat gcctcatcac    660
aaaatttatc cagcgcaaag ggacttttca ggctagccgc cagccgggta atcagcttat    720
ccagcaacgt ttcgctggat gttggcggca acgaatcact ggtgtaacga tggcgattca    780
gcaacatcac caactgcccg aacagcaact cagccatttc gttagcaaac ggcacatgct    840
gactactttc atgctcaagc tgaccgataa cctgccgcgc ctgcgccatc ccatgctac     900 ctaagcgcca gtgtggttgc cctgcgctgg cgttaaatcc cggaatcgcc ccctgccagt    960
caagattcag cttcagacgc tccgggcaat aaataatatt ctgcaaaacc agatcgttaa   1020
cggaagcgta ggagtgttta tcgtcagcat gaatgtaaaa gagatcgcca cgggtaatgc   1080
gataagggcg atcgttgagt acatgcaggc cattaccgcg ccagacaatc accagctcac   1140
aaaaatcatg tgtatgttca gcaaagacat cttgcggata acggtcagcc acagcgactg   1200
cctgctggtc gctggcaaaa aaatcatctt tgagaagttt taactgatgc gccaccgtgg   1260
ctacctcggc cagagaacga agttgattat tcgcaatatg gcgtacaaat acgttgagaa   1320
gattcgcgtt attgcagaaa gccatcccgt ccctggcgaa tatcacgcgg tgaccagtta   1380
aactctcggc gaaaaagcgt cgaaagtgg ttactgtcgc tgaatccaca gcgataggcg    1440
atgtcagtaa cgctggcctc gctgtggcgt agcagatgtc gggctttcat cagtcgcagg   1500
cggttcaggt atcgctgagg cgtcagtccc gtttgctgct taagctgccg atgtagcgta   1560
cgcagtgaaa gagaaaattg atccgccacg gcatcccaat tcacctcatc ggcaaaatgg   1620
tcctccagcc aggccagaag caagttgaga cgtgatgcgc tgttttccag gttctcctgc   1680
aaactgcttt tacgcagcaa gagcagtaat tgcataaaca agatctcgcg actggcggtc   1740
gagggtaaat cattttcccc ttcctgctgt tccatctgtg caaccagctg tcgcacctgc   1800
tgcaatacgc tgtggttaac gcgccagtga acggatact gcccatccag ctcttgtggc    1860
agcaactgat tcagcccggc gagaaactga atcgatccg gcgagcgata cagcacattg    1920
gtcagacaca gattatcggt atgttcatac agatgccgat catgatcgcg tacgaaacag   1980
accgtgccac cggtgatggt atagggctgc ccattaaaca catgaatacc cgtgccatgt   2040
tcgacaatca caatttcatg aaaatcatga tgatgttcag gaaaatccgc ctgcgggagc   2100
cggggttcta tcgccacgga cgcgttacca gacggaaaaa aatccacact atgtaatacg   2160
gtcatactgg cctcctgatg tcgtcaacac ggcgaaatag taatcacgag gtcaggttct   2220
taccttaaat tttcgacgga aaaccacgta aaaaacgtcg attttttcaag atacagcgtg   2280 aattttcagg aaatgcggtg agcatcacat caccacaatt cagcaaattg tgaacatcat   2340
cacgttcatc tttccctggt tgccaatggc ccattttcct gtcagtaacg agaaggtcgc   2400
gaattcaggc gcttttttaga ctggtcgtaa tgaaattcag caggatcaca ttctgcaggt   2460
cgactctaga ggatccccgg gtaccgagct cgaattcgta atcatggtca tagctgtttc   2520
ctgtgtgaaa ttgttatccg ctcacaattc cacacaacat acgagccgga agcataaagt   2580
gtaaagcctg gggtgcctaa tgagtgagct aactcacatt aattgcgttg cgctcactgc   2640
ccgctttcca gtcgggaaac ctgtcgtgcc agctgcatta atgaatcggc caacgcgcgg   2700
ggagaggcgg tttgcgtatt gggcgctctt ccgcttcctc gctcactgac tcgctgcgct   2760
cggtcgttcg gctgcggcga gcggtatcag ctcactcaaa ggcggtaata cggttatcca   2820
cagaatcagg ggataacgca ggaaagaaca tgtgagcaaa aggccagcaa aaggccagga   2880
accgtaaaaa ggccgcgttg ctggcgtttt tccataggct ccgcccccct gacgagcatc   2940
```

```
acaaaaatcg acgctcaagt cagaggtggc gaaacccgac aggactataa agataccagg    3000
cgtttccccc tggaagctcc ctcgtgcgct ctcctgttcc gaccctgccg cttaccggat    3060
acctgtccgc ctttctccct tcgggaagcg tggcgctttc tcatagctca cgctgtaggt    3120
atctcagttc ggtgtaggtc gttcgctcca agctgggctg tgtgcacgaa ccccccgttc    3180
agcccgaccg ctgcgcctta tccggtaact atcgtcttga gtccaacccg gtaagacacg    3240
acttatcgcc actggcagca gccactggta acaggattag cagagcgagg tatgtaggcg    3300
gtgctacaga gttcttgaag tggtggccta actacggcta cactagaagg acagtatttg    3360
gtatctgcgc tctgctgaag ccagttacct tcggaaaaag agttggtagc tcttgatccg    3420
gcaaacaaac caccgctggt agcggtggtt ttttgtttg caagcagcag attacgcgca    3480
gaaaaaaagg atctcaagaa gatcctttga tcttttctac ggggtctgac gctcagtgga    3540
acgaaaactc acgttaaggg attttggtca tgagattatc aaaaggatc ttcacctaga    3600 tccttttaaa ttaaaaatga gttttaaat caatctaaag tatatatgag taaacttggt    3660
ctgacagtta ccaatgctta atcagtgagg cacctatctc agcgatctgt ctatttcgtt    3720
catccatagt tgcctgactc cccgtcgtgt agataactac gatacgggag ggcttaccat    3780
ctggccccag tgctgcaatg ataccgcgag acccacgctc accggctcca gatttatcag    3840
caataaacca gccagccgga agggccgagc gcagaagtgg tcctgcaact ttatccgcct    3900
ccatccagtc tattaattgt tgccgggaag ctagagtaag tagttcgcca gttaatagtt    3960
tgcgcaacgt tgttgccatt gctacaggca tcgtggtgtc acgctcgtcg tttggtatgg    4020
cttcattcag ctccggttcc caacgatcaa ggcgagttac atgatccccc atgttgtgca    4080
aaaaagcggt tagctccttc ggtcctccga tcgttgtcag aagtaagttg gccgcagtgt    4140
tatcactcat ggttatggca gcactgcata attctcttac tgtcatgcca tccgtaagat    4200
gcttttctgt gactggtgag tactcaacca agtcattctg agaatagtgt atgcggcgac    4260
cgagttgctc ttgcccggcg tcaatacggg ataataccgc gccacatagc agaactttaa    4320
aagtgctcat cattggaaaa cgttcttcgg ggcgaaaact ctcaaggatc ttaccgctgt    4380
tgagatccag ttcgatgtaa cccactcgtg cacccaactg atcttcagca tcttttactt    4440
tcaccagcgt ttctgggtga gcaaaaacag gaaggcaaaa tgccgcaaaa aagggaataa    4500
gggcgacacg gaaatgttga atactcatac tcttcctttt tcaatattat tgaagcattt    4560
atcagggtta ttgtctcatg agcggataca tatttgaatg tatttagaaa aataaacaaa    4620
taggggttcc gcgcacattt ccccgaaaag tgccacctga cgtctaagaa accattatta    4680
tcatgacatt aacctataaa aataggcgta tcacgaggcc ctttcgtc                4728
```

<210> SEQ ID NO 7
<211> LENGTH: 1440
<212> TYPE: DNA
<213> ORGANISM: E. coli

<400> SEQUENCE: 7

```
gaattcaggc gcttttttaga ctggtcgtaa tgaaattcag caggatcaca ttctgcagat      60
gcctgttctg gaaaaccggg ctgctcaggg cgatattact gcaccccggcg gtgctcgccg     120 tttaacgggt gatcagactg ccgctctgcg tgattctctt agcgataaac ctgcaaaaaa     180
tattattttg ctgattggcg atgggatggg ggactcggaa attactgccg cacgtaatta     240
tgccgaaggt gcgggcggct ttttaaagg tatagatgcc ttaccgctta ccgggcaata     300
cactcactat gcgctgaata aaaaaaccgg caaaccggac tacgtcaccg actcggctgc     360
```

-continued

```
atcagcaacc gcctggtcaa ccggtgtcaa aacctataac ggcgcgctgg gcgtcgatat      420
tcacgaaaaa gatcacccaa cgattctgga aatggcaaaa gccgcaggtc tggcgaccgg      480
taacgtttct accgcagagt tgcaggatgc cacgcccgct gcgctggtgg cacatgtgac      540
ctcgcgcaaa tgctacggtc cgagcgcgac cagtgaaaaa tgtccgggta acgctctgga      600
aaaaggcgga aaaggatcga ttaccgaaca gctgcttaac gctcgtgccg acgttacgct      660
tggcggcggc gcaaaaacct tgctgaaaac ggcaaccgct ggtgaatggc agggaaaaac      720
gctgcgtgaa caggcacagg cgcgtggtta tcagttggtg agcgatgctg cctcactgaa      780
ttcggtgacg gaagcgaatc agcaaaaacc cctgcttggc ctgtttgctg acggcaatat      840
gccagtgcgc tggctaggac cgaaagcaac gtaccatggc aatatcgata agcccgcagt      900
cacctgtacg ccaaatccgc aacgtaatga cagtgtacca cccctggcgc agatgaccga      960
caaagccatt gaattgttga gtaaaaatga gaaaggcttt ttcctgcaag ttgaaggtgc     1020
gtcaatcgat aaacaggatc atgctgcgaa tccttgtggg caaattggcg agacggtcga     1080
tctcgatgaa gccgtacaac gggcgctgga attcgctaaa aaggagggta acacgctggt     1140
catagtcacc gctgatcacg cccacgccag ccagattgtt gcgccggata ccaaagctcc     1200
gggcctcacc caggcgctaa ataccaaaga tggcgcagtg atggtgatga gttacgggaa     1260
ctccgaagag gattcacaag aacataccgg cagtcagttg cgtattgcgg cgtatggccc     1320
gcatgccgcc aatgttgttg gactgaccga ccagaccgat ctcttctaca ccatgaaagc     1380
cgctctgggg ctgaaataat aatctagagg atccccgggt accgagctcg aattcgtaat     1440
```

<210> SEQ ID NO 8
<211> LENGTH: 1560
<212> TYPE: DNA
<213> ORGANISM: E. coli

<400> SEQUENCE: 8

```
gaattcaggc gctttttaga ctggtcgtaa tgaaattcag caggatcaca ttctgcagat       60
gtcacggccg agacttatag tcgctttgtt tttattttt aatgtatttg tacatggaga      120
aaataaagtg aaacaaagca ctattgcact ggcactctta ccgttactgt ttacccctgt      180
gacaaaagcc cggacaccag aaatgcctgt tctggaaaac cgggctgctc agggcgatat      240
tactgcaccc ggcggtgctc gccgtttaac gggtgatcag actgccgctc tgcgtgattc      300
tcttagcgat aaacctgcaa aaatatat tttgctgatt ggcgatggga tgggggactc       360
ggaaattact gccgcacgta ttatgccga aggtgcgggc ggcttttta aaggtataga      420 tgccttaccg cttaccgggc aatacactca ctatgcgctg aataaaaaaa ccggcaaacc      480
ggactacgtc accgactcgg ctgcatcagc aaccgcctgg tcaaccggtg tcaaaaccta      540
taacggcgcg ctgggcgtcg atattcacga aaaagatcac ccaacgattc tggaaatggc      600
aaaagccgca ggtctggcga ccggtaacgt ttctaccgca gagttgcagg atgccacgcc      660
cgctgcgctg gtggcacatg tgacctcgcg caaatgctac ggtccgagcg cgaccagtga      720
aaaatgtccg ggtaacgctc tggaaaaagg cggaaaagga tcgattaccg aacagctgct     780
taacgctcgt gccgacgtta cgcttggcgg cggcgcaaaa acctttgctg aaacggcaac     840
cgctggtgaa tggcagggaa aaacgctgcg tgaacaggca caggcgcgtg gttatcagtt      900
ggtgagcgat gctgcctcac tgaattcggt gacggaagcg aatcagcaaa aacccctgct     960
tggcctgttt gctgacggca atatgccagt gcgctggcta ggaccgaaag caacgtacca    1020
tggcaatatc gataagcccg cagtcacctg tacgccaaat ccgcaacgta atgacagtgt    1080
```

```
accaaccctg gcgcagatga ccgacaaagc cattgaattg ttgagtaaaa atgagaaagg    1140 cttttcctg caagttgaag gtgcgtcaat cgataaacag gatcatgctg cgaatccttg    1200
tgggcaaatt ggcgagacgg tcgatctcga tgaagccgta caacgggcgc tggaattcgc    1260
taaaaaggag ggtaacacgc tggtcatagt caccgctgat cacgcccacg ccagccagat    1320
tgttgcgccg gataccaaag ctccgggcct cacccaggcg ctaaatacca agatggcgc     1380 agtgatggtg atgagttacg ggaactccga agaggattca agaacata ccggcagtca     1440 gttgcgtatt cgcgcgtatg ccccgcatgc cgccaatgtt gttggactga ccgaccagac    1500
cgatctcttc tacaccatga aagccgctct ggggctgaaa taatctagag gatccccggg    1560
```

<210> SEQ ID NO 9
<211> LENGTH: 1500
<212> TYPE: DNA
<213> ORGANISM: Synthetic chimeric nucleic acid sequence
<220> FEATURE:
<223> OTHER INFORMATION: Synthetic chimeric nucleic acid sequence

<400> SEQUENCE: 9

```
gaattcaggc gcttttaga ctggtcgtaa tgaaattcag caggatcaca ttctgcagat      60
gaacttgggg aatcgactgt ttattctgat agcggtctta cttcccctcg cagtattact    120
gctcatgcct gttctggaaa accgggctgc tcagggcgat attactgcac ccggcggtgc    180
tcgccgttta acgggtgatc agactgccgc tctgcgtgat tctcttagcg ataaacctgc    240 aaaaatatt attttgctga ttggcgatgg gatggggac tcggaaatta ctgccgcacg    300
taattatgcc gaaggtgcgg gcggctttt taaaggtata gatgccttac cgcttaccgg    360
gcaatacact cactatgcgc tgaataaaaa aaccggcaaa ccggactacg tcaccgactc    420
ggctgcatca gcaaccgcct ggtcaaccgg tgtcaaaacc tataacggcg cgctgggcgt    480
cgatattcac gaaaaagatc acccaacgat tctggaaatg gcaaaagccg caggtctggc    540
gaccggtaac gtttctaccg cagagttgca ggatgccacg cccgctgcgc tggtggcaca    600
tgtgacctcg cgcaaatgct acggtccgag cgcgaccagt gaaaaatgtc cgggtaacgc    660
tctggaaaaa ggcggaaaag gatcgattac cgaacagctg cttaacgctc gtgccgacgt    720
tacgcttggc ggcggcgcaa aaacctttgc tgaaacggca accgctggtg aatggcaggg    780
aaaaacgctg cgtgaacagg cacaggcgcg tggttatcag ttggtgagcg atgctgcctc    840
actgaattcg gtgacggaag cgaatcagca aaaccccctg cttggcctgt ttgctgacgg    900
caatatgcca gtgcgctggc taggaccgaa agcaacgtac catggcaata tcgataagcc    960
cgcagtcacc tgtacgccaa atccgcaacg taatgacagt gtaccaaccc tggcgcagat    1020
gaccgacaaa gccattgaat tgttgagtaa aatgagaaa ggctttttcc tgcaagttga    1080
aggtgcgtca atcgataaac aggatcatgc tgcgaatcct tgtgggcaaa ttggcgagac    1140
ggtcgatctc gatgaagccg tacaacggc gctggaattc gctaaaaagg agggtaacac    1200
gctggtcata gtcaccgctg atcacgccca cgccagccag attgttgcgc cggataccaa    1260
agctccgggc ctcacccagg cgctaaatac caaagatggc gcagtgatgg tgatgagtta    1320
cgggaactcc gaagaggatt cacaagaaca taccggcagt cagttgcgta ttgcggcgta    1380 tgcccccgcat gccgccaatg ttgttggact gaccgaccag accgatctct ctacaccat    1440 gaaagccgct ctggggctga ataataatc tagaggatcc ccgggtaccg agctcgaatt    1500
```

<210> SEQ ID NO 10
<211> LENGTH: 3968

<212> TYPE: DNA
<213> ORGANISM: E. coli

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttcgcagc gctgttcctt     420
tgctcgcctg ctgcgagctg gtaagcgga caaattctca ccgtctccgg tggtggggta     480
caggagctca attaatacac taacggaccg gtaaacaacc gtgcgtgttg tttaccggga     540
taaactcatc aacgtctctg ctaaataact ggcagccaaa tcacggctat tggttaacca     600
atttcagagt gaaaagtata cgaatagagt gtgccttcgc actattcaac agcaatgata     660
ggcgctcacc tgacaacgcg gtaaactagt tattcacgct aactataatg gtttaatgat     720
ggataacatg cagactgaag cacaaccgac acggacccgg atcctcaatg ctgccagaga     780
gattttttca gaaaatggat ttcacagtgc ctcgatgaaa gccatctgta aatcttgcgc     840
cattagtccc gggacgctct atcaccattt catctccaaa gaagccttga ttcaggcgat     900
tatcttacag gaccaggaga gggcgctggc ccgtttccgg gaaccgattg aagggattca     960
tttcgttgac tatatggtcg agtccattgt ctctctcacc catgaagcct tggacaacg    1020
ggcgctggtg gttgaaatta tggcggaagg gatgcgtaac ccacaggtcg ccgccatgct    1080
taaaaataag catatgacga tcacggaatt tgttgcccag cggatgcgtg atgcccagca    1140
aaaaggcgag ataagcccag acatcaacac ggcaatgact tcacgtttac tgctggatct    1200
gacctacggt gtactggccg atatcgaagc ggaagacctg gcgcgtgaag cgtcgtttgc    1260
tcagggatta cgcgcgatga ttggcggtat cttaaccgca tcctgattct ctctcttttt    1320
cggcgggctg gtgataactg tgcccgcgtt tcatatcgta atttctctgt gcaaaaatta    1380
tccttcccgg cttcggagaa ttccccccaa aatattcact gtagccatat gtcatgagag    1440
tttatcgttc ccaatacgct cgaacgaacg ttcggttgct tattttatgg cttctgtcaa    1500
cgctgtttta aagattaatg cgatctatat cacgctgtgg gtattgcagt ttttggtttt    1560
ttgatcgcgg tgtcagttct ttttatttcc atttctcttc catgggtttc tcacagataa    1620
ctgtgtgcaa cacagaattg gttaactaat cagattaaag gttgaccagt attattatct    1680
taatgaggag tcctgcaggt cgactctaga ggatccccgg gtaccgagct cgaattcgta    1740
atcatggtca tagctgtttc ctgtgtgaaa ttgttatccg ctcacaattc cacacaacat    1800
acgagccgga agcataaagt gtaaagcctg gggtgcctaa tgagtgagct aactcacatt    1860
aattgcgttg cgctcactgc ccgctttcca gtcgggaaac ctgtcgtgcc agctgcatta    1920
atgaatcggc caacgcgcgg ggagaggcgg tttgcgtatt gggcgctctt ccgcttcctc    1980
gctcactgac tcgctgcgct cggtcgttcg gctgcggcga gcggtatcag ctcactcaaa    2040
ggcggtaata cggttatcca cagaatcagg ggataacgca ggaaagaaca tgtgagcaaa    2100
aggccagcaa aaggccagga accgtaaaaa ggccgcgttg ctggcgtttt tccataggct    2160
ccgcccccct gacgagcatc acaaaaatcg acgctcaagt cagaggtggc gaaacccgac    2220
aggactataa agataccagg cgtttccccc tggaagctcc ctcgtgcgct ctcctgttcc    2280
```

```
gaccctgccg cttaccggat acctgtccgc ctttctccct tcgggaagcg tggcgctttc      2340
tcatagctca cgctgtaggt atctcagttc ggtgtaggtc gttcgctcca agctgggctg      2400
tgtgcacgaa ccccccgttc agcccgaccg ctgcgcctta tccggtaact atcgtcttga      2460
gtccaacccg gtaagacacg acttatcgcc actggcagca gccactggta acaggattag      2520
cagagcgagg tatgtaggcg gtgctacaga gttcttgaag tggtggccta actacggcta      2580
cactagaagg acagtatttg gtatctgcgc tctgctgaag ccagttacct tcggaaaaag      2640
agttggtagc tcttgatccg gcaaacaaac caccgctggt agcggtggtt ttttgtttg       2700 caagcagcag attacgcgca gaaaaaaagg atctcaagaa gatcctttga tcttttctac      2760
ggggtctgac gctcagtgga acgaaaactc acgttaaggg attttggtca tgagattatc      2820
aaaaaggatc ttcacctaga tccttttaaa ttaaaaatga agttttaaat caatctaaag      2880
tatatatgag taaacttggt ctgacagtta ccaatgctta atcagtgagg cacctatctc      2940
agcgatctgt ctatttcgtt catccatagt tgcctgactc cccgtcgtgt agataactac      3000
gatacgggag ggcttaccat ctggccccag tgctgcaatg ataccgcgag acccacgctc      3060
accggctcca gatttatcag caataaacca gccagccgga agggccgagc gcagaagtgg      3120
tcctgcaact ttatccgcct ccatccagtc tattaattgt tgccgggaag ctagagtaag      3180
tagttcgcca gttaatagtt tgcgcaacgt tgttgccatt gctacaggca tcgtggtgtc      3240
acgctcgtcg tttggtatgg cttcattcag ctccggttcc caacgatcaa ggcgagttac      3300
atgatccccc atgttgtgca aaaaagcggt tagctccttc ggtcctccga tcgttgtcag      3360
aagtaagttg gccgcagtgt tatcactcat ggttatggca gcactgcata attctcttac      3420
tgtcatgcca tccgtaagat gcttttctgt gactggtgag tactcaacca agtcattctg      3480
agaatagtgt atgcggcgac cgagttgctc ttgcccggcg tcaatacggg ataataccgc      3540
gccacatagc agaactttaa aagtgctcat cattggaaaa cgttcttcgg ggcgaaaact      3600
ctcaaggatc ttaccgctgt tgagatccag ttcgatgtaa cccactcgtg cacccaactg      3660
atcttcagca tcttttactt tcaccagcgt ttctgggtga gcaaaaacag gaaggcaaaa      3720
tgccgcaaaa aagggaataa gggcgacacg gaaatgttga atactcatac tcttcctttt      3780
tcaatattat tgaagcattt atcagggtta ttgtctcatg agcggataca tatttgaatg      3840
tatttagaaa aataaacaaa tagggggttcc gcgcacattt ccccgaaaag tgccacctga      3900
cgtctaagaa accattatta tcatgacatt aacctataaa aataggcgta tcacgaggcc      3960
ctttcgtc                                                              3968
```

<210> SEQ ID NO 11  
<211> LENGTH: 3872  
<212> TYPE: DNA  
<213> ORGANISM: E. coli

<400> SEQUENCE: 11

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgccaa gcttttagcc gggaaacgtc      420
```

-continued

```
tggcggcgct gttggctaag tttgcggtat tgttgcggcg acatgccgac atatttgccg     480
aacgtgctgt aaaaacgact acttgaacga aagcctgccg tcagggcaat atcgagaata     540
cttttatcgg tatcgctcag taacgcgcga acgtggttga tgcgcatcgc ggtaatgtac     600
tgtttcatcg tcaattgcat gacccgctgg aatatcccca ttgcatagtt ggcgttaagt     660
ttgacgtgct cagccacatc gttgatggtc agcgcctgat catagttttc ggcaataaag     720
cccagcatct ggctaacata aaattgcgca tggcgcgaga cgctgttttt gtgtgtgcgc     780
gaggttttat tgaccagaat cggttcccag ccagagaggc taaatcgctt gagcatcagg     840
ccaatttcat caatggcgag ctggcgaatt tgctcgttcg gactgtttaa ttcctgctgc     900
cagcggcgca cttcaaacgg gctaagttgc tgtgtggcca gtgatttgat caccatgccg     960
tgagtgacgt ggttaatcag gtctttatcc agcggccagg agagaaacag atgcatcggc    1020
agattaaaaa tcgccatgct ctgacaggtt ccggtatctg ttagttggtg cggtgtacag    1080
gcccagaaca gcgtgatatg accctgattg atattcactt tttcattgtt gatcaggtat    1140
tccacatcgc catcgaaagg cacattcact tcgacctgac catgccagtg gctggtgggc    1200
atgatatgcg gtgcgcgaaa ctcaatctcc atccgctggt attccgaata cagcgacagc    1260
gggctgcggg tctgtttttc gtcgctgctg cacataaacg tatctgtatt catggatggc    1320
tctctttcct ggaatatcag aattatgcag gagtgaggg aggatgactg cgagtgggag    1380
cacggttttc accctcttcc cagaggggcg aggggactct ccgagtatca tgaggccgaa    1440
aactctgctt tcaggtaat ttattcccat aaactcagat ttactgctgc ttcacgcagg    1500
atctgagttt atgggaatgc tcaacctgga agccggaggt tttctgcaga ttcgcctgcc    1560
atgatgaagt tattcaagca agccaggaga tctggtaccc gggtcgactc tagaggatcc    1620
ccgggtaccg agctcgaatt cgtaatcatg gtcatagctg tttcctgtgt gaaattgtta    1680
tccgctcaca attccacaca acatacgagc cggaagcata aagtgtaaag cctggggtgc    1740
ctaatgagtg agctaactca cattaattgc gttgcgctca ctgcccgctt tccagtcggg    1800
aaacctgtcg tgccagctgc attaatgaat cggccaacgc gcggggagag gcggtttgcg    1860
tattgggcgc tcttccgctt cctcgctcac tgactcgctg cgctcggtcg ttcggctgcg    1920
gcgagcggta tcagctcact caaaggcggt aatacggtta tccacagaat caggggataa    1980
cgcaggaaag aacatgtgag caaaaggcca gcaaaaggcc aggaaccgta aaaaggccgc    2040
gttgctggcg tttttccata ggctccgccc ccctgacgag catcacaaaa atcgacgctc    2100
aagtcagagg tggcgaaacc cgacaggact ataaagatac caggcgtttc ccctggaag    2160 ctccctcgtg cgctctcctg ttccgaccct gccgcttacc ggatacctgt ccgcctttct    2220
cccttcggga agcgtggcgc tttctcatag ctcacgctgt aggtatctca gttcggtgta    2280
ggtcgttcgc tccaagctgg gctgtgtgca cgaacccccc gttcagcccg accgctgcgc    2340
cttatccggt aactatcgtc ttgagtccaa cccggtaaga cacgacttat cgccactggc    2400
agcagccact ggtaacagga ttagcagagc gaggtatgta ggcggtgcta cagagttctt    2460
gaagtggtgg cctaactacg gctacactag aaggacagta tttggtatct gcgctctgct    2520
gaagccagtt accttcggaa aaagagttgg tagctcttga tccggcaaac aaaccaccgc    2580
tggtagcggt ggtttttttg tttgcaagca gcagattacg cgcagaaaaa aaggatctca    2640
agaagatcct ttgatctttt ctacggggtc tgacgctcag tggaacgaaa actcacgtta    2700
agggattttg gtcatgagat tatcaaaaag gatcttcacc tagatccttt taaattaaaa    2760
atgaagtttt aaatcaatct aaagtatata tgagtaaact tggtctgaca gttaccaatg    2820
```

```
cttaatcagt gaggcaccta tctcagcgat ctgtctattt cgttcatcca tagttgcctg    2880
actccccgtc gtgtagataa ctacgatacg ggagggctta ccatctggcc ccagtgctgc    2940
aatgataccg cgagacccac gctcaccggc tccagattta tcagcaataa accagccagc    3000
cggaagggcc gagcgcagaa gtggtcctgc aactttatcc gcctccatcc agtctattaa    3060
ttgttgccgg gaagctagag taagtagttc gccagttaat agtttgcgca acgttgttgc    3120
cattgctaca ggcatcgtgg tgtcacgctc gtcgtttggt atggcttcat tcagctccgg    3180
ttcccaacga tcaaggcgag ttacatgatc ccccatgttg tgcaaaaaag cggttagctc    3240
cttcggtcct ccgatcgttg tcagaagtaa gttggccgca gtgttatcac tcatggttat    3300
ggcagcactg cataattctc ttactgtcat gccatccgta agatgctttt ctgtgactgg    3360
tgagtactca accaagtcat tctgagaata gtgtatgcgg cgaccgagtt gctcttgccc    3420
ggcgtcaata cgggataata ccgcgccaca tagcagaact ttaaaagtgc tcatcattgg    3480
aaaacgttct cggggcgaaa actctcaag gatcttaccg ctgttgagat ccagttcgat    3540
gtaacccact cgtgcaccca actgatcttc agcatctttt actttcacca gcgtttctgg    3600
gtgagcaaaa acaggaaggc aaaatgccgc aaaaaaggga ataagggcga cacggaaatg    3660
ttgaatactc atactcttcc ttttttcaata ttattgaagc atttatcagg gttattgtct    3720
catgagcgga tacatatttg aatgtattta gaaaaataaa caaatagggg ttccgcgcac    3780
atttccccga aaagtgccac ctgacgtcta agaaaccatt attatcatga cattaaccta    3840
taaaaatagg cgtatcacga ggccctttcg tc                                  3872

<210> SEQ ID NO 12
<211> LENGTH: 3934
<212> TYPE: DNA
<213> ORGANISM: E. coli

<400> SEQUENCE: 12
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttcaagcc gtcaattgtc     420
tgattcgtta ccaattatga caacttgacg gctacatcat tcactttttc ttcacaaccg     480
gcacggaact cgctcgggct ggccccggtg cattttttaa atacccgcga gaaatagagt     540
tgatcgtcaa aaccaacatt gcgaccgacg gtggcgatag gcatccgggt ggtgctcaaa     600
agcagcttcg cctggctgat acgttggtcc tcgcgccagc ttaagacgct aatccctaac     660
tgctggcgga aaagatgtga cagacgcgac ggcgacaagc aaacatgctg tgcgacgctg     720
gcgatatcaa aattgctgtc tgccaggtga tcgctgatgt actgacaagc ctcgcgtacc     780
cgattatcca tcggtggatg gagcgactcg ttaatcgctt ccatgcgccg cagtaacaat     840
tgctcaagca gatttatcgc cagcagctcc gaatagcgcc cttccccttg cccggcgtta     900
atgatttgcc caaacaggtc gctgaaatgc ggctggtgcg cttcatccgg gcgaaagaac     960
cccgtattgg caaatattga cggccagtta agccattcat gccagtaggc gcgcggacga    1020
aagtaaaccc actggtgata ccattcgcga gcctccggat gacgaccgta gtgatgaatc    1080
```

```
tctcctggcg ggaacagcaa aatatcaccc ggtcggcaaa caaattctcg tccctgattt    1140
ttcaccaccc cctgaccgcg aatggtgaga ttgagaatat aacctttcat tcccagcggt    1200
cggtcgataa aaaaatcgag ataaccgttg gcctcaatcg gcgttaaacc cgccaccaga    1260
tgggcattaa acgagtatcc cggcagcagg ggatcatttt gcgcttcagc catactttc     1320 atactcccgc cattcagaga agaaaccaat tgtccatatt gcatcagaca ttgccgtcac    1380
tgcgtctttt actggctctt ctcgctaacc aaaccggtaa ccccgcttat taaaagcatt    1440
ctgtaacaaa gcgggaccaa agccatgaca aaaacgcgta acaaaagtgt ctataatcac    1500
ggcagaaaag tccacattga ttatttgcac ggcgtcacac tttgctatgc catagcattt    1560
ttatccataa gattagcgga tcctacctga cgctttttat cgcaactctc tactgtttct    1620
ccatacccgt ttttttgggc tagcaggagg aattcaccct gcaggtcgac tctagaggat    1680
ccccgggtac cgagctcgaa ttcgtaatca tggtcatagc tgtttcctgt gtgaaattgt    1740
tatccgctca caattccaca acatacga gccggaagca taaagtgtaa agcctggggt     1800
gcctaatgag tgagctaact cacattaatt gcgttgcgct cactgcccgc tttccagtcg    1860
ggaaacctgt cgtgccagct gcattaatga atcggccaac gcgcggggag aggcggtttg    1920
cgtattgggc gctcttccgc ttcctcgctc actgactcgc tgcgctcggt cgttcggctg    1980
cggcgagcgg tatcagctca ctcaaaggcg gtaatacggt tatccacaga atcaggggat    2040
aacgcaggaa agaacatgtg agcaaaaggc cagcaaaagg ccaggaaccg taaaaaggcc    2100
gcgttgctgg cgttttttcc ataggctccg cccccctgac gagcatcaca aaaatcgacg    2160
tcaagtcaga ggtggcgaaa cccgacagga ctataaagat accaggcgtt tccccctgga    2220
agctccctcg tgcgctctcc tgttccgacc ctgccgctta ccggatacct gtccgccttt    2280
ctcccttcgg gaagcgtggc gctttctcat agctcacgct gtaggtatct cagttcggtg    2340
taggtcgttc gctccaagct gggctgtgtg cacgaacccc ccgttcagcc cgaccgctgc    2400
gccttatccg gtaactatcg tcttgagtcc aacccggtaa gacacgactt atcgccactg    2460
gcagcagcca ctggtaacag gattagcaga gcgaggtatg taggcggtgc tacagagttc    2520
ttgaagtggt ggcctaacta cggctacact agaaggacag tatttggtat ctgcgctctg    2580
ctgaagccag ttaccttcgg aaaaagagtt ggtagctctt gatccggcaa acaaaccacc    2640
gctggtagcg gtggtttttt tgtttgcaag cagcagatta cgcgcagaaa aaaaggatct    2700
caagaagatc ctttgatctt ttctacgggg tctgacgctc agtggaacga aaactcacgt    2760
taagggattt tggtcatgag attatcaaaa aggatcttca cctagatcct ttaaattaa    2820 aaatgaagtt ttaaatcaat ctaaagtata tatgagtaaa cttggtctga cagttaccaa    2880
tgcttaatca gtgaggcacc tatctcagcg atctgtctat ttcgttcatc catagttgcc    2940
tgactccccg tcgtgtagat aactacgata cgggagggct taccatctgg ccccagtgct    3000
gcaatgatac cgcgagaccc acgctcaccg gctccagatt tatcagcaat aaaccagcca    3060
gccggaaggg ccgagcgcag aagtggtcct gcaactttat ccgcctccat ccagtctatt    3120
aattgttgcc gggaagctag agtaagtagt tcgccagtta atagtttgcg caacgttgtt    3180
gccattgcta caggcatcgt ggtgtcacgc tcgtcgtttg gtatggcttc attcagctcc    3240
ggttcccaac gatcaaggcg agttacatga tcccccatgt tgtgcaaaaa agcggttagc    3300
tccttcggtc ctccgatcgt tgtcagaagt aagttggccg cagtgttatc actcatggtt    3360
atggcagcac tgcataattc tcttactgtc atgccatccg taagatgctt ttctgtgact    3420
ggtgagtact caaccaagtc attctgagaa tagtgtatgc ggcgaccgag ttgctcttgc    3480
```

| | |
|---|---:|
| ccggcgtcaa tacgggataa taccgcgcca catagcagaa ctttaaaagt gctcatcatt | 3540 |
| ggaaaacgtt cttcggggcg aaaactctca aggatcttac cgctgttgag atccagttcg | 3600 |
| atgtaaccca ctcgtgcacc caactgatct tcagcatctt ttactttcac cagcgtttct | 3660 |
| gggtgagcaa aaacaggaag gcaaaatgcc gcaaaaaagg gaataagggc gacacggaaa | 3720 |
| tgttgaatac tcatactctt cctttttcaa tattattgaa gcatttatca gggttattgt | 3780 |
| ctcatgagcg gatacatatt tgaatgtatt tagaaaaata acaaataggg gttccgcgc | 3840 |
| acatttcccc gaaaagtgcc acctgacgtc taagaaacca ttattatcat gacattaacc | 3900 |
| tataaaaata ggcgtatcac gaggcccttt cgtc | 3934 |

<210> SEQ ID NO 13
<211> LENGTH: 6013
<212> TYPE: DNA
<213> ORGANISM: E. coli

<400> SEQUENCE: 13

| | |
|---|---:|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgc cccattgacg caaatgggcg gtaggcgtgt | 540 |
| acggtgggag gtctatataa gcagagctgg tttagtgaac cgtcagatcc gctagcgcta | 600 |
| ccggtcgcca ccatggtgag caagggcgag gagctgttca ccggggtggt gcccatcctg | 660 |
| gtcgagctgg acggcgacgt aaacggccac aagttcagcg tgtccggcga gggcgagggc | 720 |
| gatgccacct acggcaagct gaccctgaag ttcatctgca ccaccggcaa gctgcccgtg | 780 |
| ccctggccca ccctcgtgac caccctgacc tacggcgtgc agtgcttcag ccgctacccc | 840 |
| gaccacatga agcagcacga cttcttcaag tccgccatgc ccgaaggcta cgtccaggag | 900 |
| cgcaccatct tcttcaagga cgacggcaac tacaagaccc gcgccgaggt gaagttcgag | 960 |
| ggcgacaccc tggtgaaccg catcgagctg aagggcatcg acttcaagga ggacggcaac | 1020 |
| atcctggggc acaagctgga gtacaactac aacagccaca acgtctatat catggccgac | 1080 |
| aagcagaaga acggcatcaa ggtgaacttc aagatccgcc acaacatcga ggacggcagc | 1140 |
| gtgcagctcg ccgaccacta ccagcagaac acccccatcg gcgacggccc cgtgctgctg | 1200 |
| cccgacaacc actacctgag cacccagtcc gccctgagca agacccccaa cgagaagcgc | 1260 |
| gatcacatgg tcctgctgga gttcgtgacc gccgccggga tcactctcgg catggacgag | 1320 |
| ctgtacaagt ccggactcag atctcgagct taataacaag ccgtcaattg tctgattcgt | 1380 |
| taccaattat gacaacttga cggctacatc attcactttt tcttcacaac cggcacggaa | 1440 |
| ctcgctcggg ctggccccgg tgcattttt aaatacccgc gagaaataga gttgatcgtc | 1500 |
| aaaaccaaca ttgcgaccga cggtggcgat aggcatccgg gtggtgctca aaagcagctt | 1560 |
| cgcctggctg atacgttggt cctcgcgcca gcttaagacg ctaatcccta actgctggcg | 1620 |
| gaaaagatgt gacagacgcg acggcgacaa gcaaacatgc tgtgcgacgc tggcgatatc | 1680 |

```
aaaattgctg tctgccaggt gatcgctgat gtactgacaa gcctcgcgta cccgattatc    1740
catcggtgga tggagcgact cgttaatcgc ttccatgcgc cgcagtaaca attgctcaag    1800
cagatttatc gccagcagct ccgaatagcg cccttcccct tgcccggcgt taatgatttg    1860
cccaaacagg tcgctgaaat gcggctggtg cgcttcatcc gggcgaaaga accccgtatt    1920
ggcaaatatt gacggccagt taagccattc atgccagtag gcgcgcggac gaaagtaaac    1980
ccactggtga taccattcgc gagcctccgg atgacgaccg tagtgatgaa tctctcctgg    2040
cgggaacagc aaaatatcac ccggtcggca aacaaattct cgtccctgat ttttcaccac    2100
cccctgaccg cgaatggtga gattgagaat ataacctttc attcccagcg gtcggtcgat    2160
aaaaaaatcg ataaccgt tggcctcaat cggcgttaaa cccgccacca gatgggcatt     2220
aaacgagtat cccggcagca ggggatcatt ttgcgcttca gccatacttt tcatactccc    2280
gccattcaga gaagaaacca attgtccata ttgcatcaga cattgccgtc actgcgtctt    2340
ttactggctc ttctcgctaa ccaaaccggt aaccccgctt attaaaagca ttctgtaaca    2400
aagcgggacc aaagccatga caaaaacgcg taacaaaagt gtctataatc acggcagaaa    2460
agtccacatt gattatttgc acggcgtcac actttgctat gccatagcat ttttatccat    2520
aagattagcg gatcctacct gacgcttttt atcgcaactc tctactgttt ctccataccc    2580
gttttttggg gctagcagga ggaattcacc atggtacccg gggatcctct agagtcgacc    2640
tgcaggcatg caagcttggc ccgcgggccc gggatccacc ggatctagat aactgatcat    2700
aatcagccat accacatttg tagaggtttt acttgcttta aaaaacctcc cacacctccc    2760
cctgaacctg aaacataaaa tgaatgcaat tgttgttgtt aacttgttta ttgcagctta    2820
taatggttac aaataaagca atagcatcac aaatttcaca aataaagcat ttttttcact    2880
gcattctagt tgtggtttgt ccaaactcat caatgtatct taacgcgtaa attgtaagcg    2940
ttaatatttt gttaaaattc gcgttaaatt tttgttaaat cagctcattt tttaaccaat    3000
aggccgaaat cggcaaaatc ccttataaat caaaagaata gaccgagata gggttgagtg    3060
ttgttccagt ttggaacaag agtccactat taaagaacgt ggactccaac gtcaaagggc    3120
gaaaaaccgt ctatcagggc gatggcccac tacgtgaacc atcaccctaa tcaagttttt    3180
tggggtcgag gtgccgtaaa gcactaaatc ggaaccctaa agggagcccc cgatttagag    3240
cttgacgggg aaagccggcg aacgtggcga gaaaggaagg gaagaaagcg aaaggagcgg    3300
gcgctagggc gctggcaagt gtagcggtca cgctgcgcgt aaccaccaca cccgccgcgc    3360
ttaatgcgcc gctacagggc gcgtcaggtg gcacttttcg gggaaatgtg cgcggaaccc    3420
ctatttgttt atttttctaa atacattcaa atatgtatcc gctcatgaga caataaccct    3480
gataaatgct tcaataatat tgaaaaagga agagtcctga ggcggaaaga accagctgtg    3540
gaatgtgtgt cagttagggt gtggaaagtc cccaggctcc ccagcaggca gaagtatgca    3600
aagcatgcat ctcaattagt cagcaaccag gtgtggaaag tccccaggct ccccagcagg    3660
cagaagtatg caaagcatgc atctcaatta gtcagcaacc atagtcccgc ccctaactcc    3720
gcccatcccg cccctaactc cgcccagttc cgcccattct ccgccccatg ctgactaat    3780 tttttttatt tatgcagagg ccgaggccgc ctcggcctct gagctattcc agaagtagtg    3840
aggaggcttt tttggaggcc taggcttttg caaagatcga tcaagagaca ggatgaggat    3900
cgtttcgcat gattgaacaa gatggattgc acgcaggttc tccggccgct tgggtggaga    3960
ggctattcgg ctatgactgg gcacaacaga caatcggctg ctctgatgcc gccgtgttcc    4020
ggctgtcagc gcaggggcgc ccggttcttt ttgtcaagac cgacctgtcc ggtgccctga    4080
```

```
atgaactgca agacgaggca gcgcggctat cgtggctggc cacgacgggc gttccttgcg      4140
cagctgtgct cgacgttgtc actgaagcgg gaagggactg gctgctattg ggcgaagtgc      4200
cggggcagga tctcctgtca tctcaccttg ctcctgccga gaaagtatcc atcatggctg      4260
atgcaatgcg gcggctgcat acgcttgatc cggctaccty cccattcgac caccaagcga      4320
aacatcgcat cgagcgagca cgtactcgga tggaagccgg tcttgtcgat caggatgatc      4380
tggacgaaga gcatcagggg ctcgcgccag ccgaactgtt cgccaggctc aaggcgagca      4440
tgcccgacgg cgaggatctc gtcgtgaccc atggcgatgc ctgcttgccg aatatcatgg      4500
tggaaaatgg ccgcttttct ggattcatcg actgtggccg gctgggtgtg gcggaccgct      4560
atcaggacat agcgttggct acccgtgata ttgctgaaga gcttggcggc gaatgggctg      4620
accgcttcct cgtgctttac ggtatcgccg ctccgattc gcagcgcatc gccttctatc       4680
gccttcttga cgagttcttc tgagcggac tctggggtc gaaatgaccg accaagcgac        4740
gcccaacctg ccatcacgag atttcgattc caccgccgcc ttctatgaaa ggttgggctt      4800
cggaatcgtt ttccgggacg ccggctggat gatcctccag cgcggggatc tcatgctgga      4860
gttcttcgcc caccctaggg ggaggctaac tgaaacacgg aaggagacaa taccggaagg      4920
aacccgcgct atgacggcaa taaaaagaca gaataaaacg cacggtgttg ggtcgtttgt      4980
tcataaacgc ggggttcggt cccagggctg gcactctgtc gatacccac cgagacccca      5040 ttggggccaa tacgcccgcg tttcttcctt ttccccaccc cacccccaa gttcgggtga      5100 aggcccaggt ctcgcagcca acgtcggggc ggcaggccct gccatagcct caggttactc      5160
atatatactt tagattgatt taaaacttca ttttttaattt aaaaggatct aggtgaagat      5220 ccttttttgat aatctcatga ccaaaatccc ttaacgtgag ttttcgttcc actgagcgtc     5280
agaccccgta gaaaagatca aaggatcttc ttgagatcct ttttttctgc gcgtaatctg      5340
ctgcttgcaa acaaaaaaac caccgctacc agcggtggtt tgtttgccgg atcaagagct      5400
accaactctt tttccgaagg taactggctt cagcagagcg cagataccaa atactgtcct      5460
tctagtgtag ccgtagttag gccaccactt caagaactct gtagcaccgc ctacatacct      5520
cgctctgcta atcctgttac cagtggctgc tgccagtggc gataagtcgt gtcttaccgg      5580
gttggactca agacgatagt taccggataa ggcgcagcgg tcgggctgaa cggggggttc      5640
gtgcacacag cccagcttgg agcgaacgac ctacaccgaa ctgagatacc tacagcgtga      5700
gctatgagaa agcgccacgc ttcccgaagg gagaaaggcg gacaggtatc cggtaagcgg      5760
cagggtcgga acaggagagc gcacgaggga gcttccaggg gaaacgcct ggtatcttta       5820 tagtcctgtc gggtttcgcc acctctgact tgagcgtcga ttttttgtgat gctcgtcagg     5880 ggggcggagc ctatggaaaa acgccagcaa cgcggccttt ttacggttcc tggccttttg      5940
ctggcctttt gctcacatgt tctttcctgc gttatcccct gattctgtgg ataaccgtat      6000
taccgccatg cat                                                        6013
```

<210> SEQ ID NO 14
<211> LENGTH: 1380
<212> TYPE: DNA
<213> ORGANISM: Rattus norvegicus

<400> SEQUENCE: 14

```
gaattcaggc gcttttaga ctggtcgtaa tgaaattcag caggatcaca ttctgcaggt          60
cgacatggca accacgcacg cgcagggcca cccgccagtc ttggggaatg atactctccg        120
ggaacattat gattacgtgg ggaagctggc aggcaggctg cgggatcccc ctgagggtag       180
```

```
caccctcatc accaccatcc tcttcttggt cacctgtagc ttcatcgtct tggagaacct      240
gatggttttg attgccatct ggaaaaacaa taaatttcat aaccgcatgt acttttcat       300 cggcaacttg gctctctgcg acctgctggc cggcatagcc tacaaggtca acattctgat      360
gtccggtagg aagacgttca gcctgtctcc aacagtgtgg ttcctcaggg agggcagtat      420
gttcgtagcc ctgggcgcat ccacatgcag cttattggcc attgccattg agcggcacct      480
gaccatgatc aagatgaggc cgtacgacgc caacaagaag caccgcgtgt ccttctgat       540 tgggatgtgc tggctaattg ccttctcgct gggtgccctg cccatcctgg gctgaactg       600 cctggaaaac tttcccgact gctctaccat cttgcccctc tactccaaga aatacattgc      660
ctttctcatc agcatcttca tagccattct ggtgaccatc gtcatcttgt acgcgcgcat      720
ctacttcctg gtcaagtcca gcagccgcag ggtggccaac cacaactccg agagatccat      780
ggcccttctg cggaccgtag tgatcgtggt gagcgtgttc atcgcctgtt ggtcccccct      840
tttcatcctc ttcctcatcg atgtggcctg cagggcgaag gagtgctcca tcctcttcaa      900
gagtcagtgg ttcatcatgc tggctgtcct caactcggcc atgaaccctg tcatctacac      960
gctggccagc aaagagatgc ggcgtgcttt cttccggttg gtgtgcggct gtctggtcaa     1020
gggcaagggg acccaggcct ccccgatgca gcctgctctt gacccgagca gaagtaaatc     1080
aagctccagt aacaacagca gcagccactc tccaaaggtc aaggaagacc tgccccatgt     1140
ggctacctct tcctgcgtta ctgacaaaac gaggtcgctt cagaatgggg tcctctgcaa     1200
gaagggcaat tctgcagata tccagcacag tggcggccgc tcgagtctag agggcccgcg     1260
gttcgaaggt aagcctatcc ctaaccctct cctcggtctc gattctacgc gtaccggtca     1320
tcatcaccat caccattgat aaggtaccga gctcgaattc gtaatcatgg tcatagctgt     1380
```

<210> SEQ ID NO 15
<211> LENGTH: 1320
<212> TYPE: DNA
<213> ORGANISM: Homo sapiens

<400> SEQUENCE: 15

```
gaattcaggc gctttttaga ctggtcgtaa tgaaattcag caggatcaca ttctgcaggt       60
cgacatgggg caacccggga acggcagcgc cttcttgctg gcacccaatg gaagccatgc      120
gccggaccac gacgtcacgc agcaaaggga cgaggtgtgg gtggtgggca tgggcatcgt      180
catgtctctc atcgtcctgg ccatcgtgtt tggcaatgtg ctggtcatca cagccattgc      240
caagttcgag cgtctgcaga cggtcaccaa ctacttcatc acttcactgg cctgtgctga      300
tctggtcatg ggcctagcag tggtgccctt tggggccgcc catattctta tgaaaatgtg      360
gacttttggc aacttctggt gcgagttttg gacttccatt gatgtgctgt gcgtcacggc      420
cagcattgag accctgtgcg tgatcgcagt ggatcgctac tttgccatta cttcacctttt     480 caagtaccag agcctgctga ccaagaataa ggcccgggtg atcattctga tggtgtggat      540
tgtgtcaggc cttaycctcct tcttgcccat tcagatgcac tggtacaggg ccacccacca     600
ggaagccatc aactgctatg ccaatgagac ctgctgtgac ttcttcacga accaagccta      660
tgccattgcc tcttccatcg tgtccttcta cgttcccctg gtgatcatgg tcttcgtcta      720
ctccagggtc tttcaggagg ccaaaaggca gctccagaag attgacaaat ctgagggccg      780
cttccatgtc cagaacctta gccaggtgga gcaggatggg cggacggggc atggactccg      840
cagatcttcc aagttctgct tgaaggagca caaagccctc aagacgttag gcatcatcat      900
gggcactttc accctctgct ggctgccctt cttcatcgtt aacattgtgc atgtgatcca      960
```

```
ggataacctc atccgtaagg aagtttacat cctcctaaat tggataggct atgtcaattc    1020
tggtttcaat cccettatct actgccggag cccagatttc aggattgcct tccaggagct    1080
tctgtgcctg cgcaggtctt ctttgaaggc ctatggcaat ggctactcca gcaacggcaa    1140
cacaggggag cagagtggat atcacgtgga acaggagaaa gaaaataaac tgctgtgtga    1200
agacctccca ggcacggaag actttgtggg ccatcaaggt actgtgccta gcgataacat    1260
tgattcacaa gggaggaatt gtagtacaaa tgactcactg ctataataag gatccccggg    1320

<210> SEQ ID NO 16
<211> LENGTH: 52
<212> TYPE: DNA
<213> ORGANISM: Artificial Sequence
<220> FEATURE:
<223> OTHER INFORMATION: Synthetic oligonucleotide sequence

<400> SEQUENCE: 16
aattggtacc tcaatgatga tgatgatgat gcttgcagag gaccccattc tg            52

<210> SEQ ID NO 17
<211> LENGTH: 1320
<212> TYPE: DNA
<213> ORGANISM: Homo sapiens

<400> SEQUENCE: 17
tcgcaactct ctactgtttc tccatacccg ttttttgggg ctagcaggag gaattcacca     60
tggatagtgt gtgtcccaa ggaaaatata tccacctca aataattcg atttgctgta      120 ccaagtgcca caaggaacc tacttgtaca atgactgtcc aggcccgggg caggatacgg    180
actgcaggga gtgtgagagc ggctccttca ccgcttcaga aaaccacctc agacactgcc    240
tcagctgctc caaatgccga aggaaatgg gtcaggtgga gatctcttct tgcacagtgg    300
accgggacac cgtgtgtggc tgcaggaaga ccagtaccg gcattattgg agtgaaaacc    360 tttttccagtg cttcaattgc agcctctgcc tcaatgggac cgtgcacctc tcctgccagg    420
agaaacagaa caccgtgtgc acctgccatg caggtttctt tctaagagaa acgagtgtg    480 tctcctgtag taactgtaag aaaagcctgg agtgcacgaa gttgtgccta ccccagattg    540
agaatgttaa gggcactgag gactcaggca ccacagtgct gttgccctg gtcattttct    600 ttggtctttg cctttatcc ctcctcttca ttggtttaat gtatcgctac caacggtgga    660
agtccaagct ctactccatt gtttgtggga aatcgacacc tgaaaagag ggggagcttg    720 aaggaactac tactaagccc ctggccccaa acccaagctt cagtcccact ccaggcttca    780 cccccacct gggcttcagt cccgtgccca gttccacctt cacctccagc tccacctata    840
cccccggtga ctgtcccaac tttgcggctc cccgcagaga ggtggcacca ccctatcagg    900
gggctgaccc catccttgcg acagccctcg cctccgaccc catccccaac cccettcaga    960 agtgggagga cagcgcccac aagccacaga gcctagacac tgatgacccc gcgacgctgt    1020
acgccgtggt ggagaacgtg ccccgttgc gctggaagga attcgtgcgg cgcctagggc    1080
tgagcgacca cgagatcgat cggctggagc tgcaaacgg gcgctgcctg gcgaggcgc    1140 aatacagcat gctggcgacc tggaggcggc gcacgccgcg gcgcgaggcc acgctggagc    1200
tgctgggacg cgtgctccgc gacatggacc tgctgggctg cctggaggac atcgaggagg    1260
cgctttgcgg ccccgccgcc ctcccgcccg cgcccagtct tctcagatga tctagagtcg    1320

<210> SEQ ID NO 18
<211> LENGTH: 1380
```

<212> TYPE: DNA
<213> ORGANISM: Homo sapiens

<400> SEQUENCE: 18

```
ccatacccgt ttttttgggc tagcaggagg aattcaccct gcaggtcgac atgggactgg      60
tccctcacct aggggacagg gagaagagag atagtgtgtg tccccaagga aaatatatcc     120
accctcaaaa taattcgatt tgctgtacca agtgccacaa aggaacctac ttgtacaatg     180
actgtccagg cccggggcag gatacggact gcagggagtg tgagagcggc tccttcaccg     240
cttcagaaaa ccacctcaga cactgcctca gctgctccaa atgccgaaag gaaatgggtc     300
aggtggagat ctcttcttgc acagtggacc gggacaccgt gtgtggctgc aggaagaacc     360
agtaccggca ttattggagt gaaaaccttt ccagtgcttc caattgcagc ctctgcctca     420
atgggaccgt gcacctctcc tgccaggaga aacagaacac cgtgtgcacc tgccatgcag     480
gtttctttct aagagaaaac gagtgtgtct cctgtagtaa ctgtaagaaa agcctggagt     540
gcacgaagtt gtgcctaccc cagattgaga atgttaaggg cactgaggac tcaggcacca     600
cagtgctgtt gccctggtc attttctttg gtctttgcct tttatccctc ctcttcattg      660
gtttaatgta tcgctaccaa cggtggaagt ccaagctcta ctccattgtt tgtgggaaat     720
cgacacctga aaagagggg gagcttgaag gaactactac taagcccctg ccccaaacc      780
caagcttcag tcccactcca ggcttcaccc ccacccctggg cttcagtccc gtgcccagtt    840
ccaccttcac ctccagctcc acctataccc ccggtgactg tcccaacttt gcggctcccc    900
gcagagaggt ggcaccaccc tatcagggg ctgaccccat ccttgcgaca gccctcgcct     960
ccgacccat ccccaacccc cttcagaagt gggaggacag cgcccacaag ccacagagcc    1020
tagacactga tgaccccgcg acgctgtacg ccgtggtgga aacgtgccc ccgttgcgct     1080
ggaaggaatt cgtgcggcgc ctagggctga gcgaccacga gatcgatcgg ctggagctgc    1140
agaacgggcg ctgcctgcgc gaggcgcaat acagcatgct ggcgacctgg aggcggcgca    1200
cgccgcggcg cgaggccacg ctggagctgc tgggacgcgt gctccgcgac atggacctgc    1260
tgggctgcct ggaggacatc gaggaggcgc tttgcggccc cgccgccctc ccgcccgcgc    1320
ccagtcttct cagataataa ggtaccgagc tcgaattcgt aatcatggtc atagctgttt    1380
```

<210> SEQ ID NO 19
<211> LENGTH: 780
<212> TYPE: DNA
<213> ORGANISM: Homo sapiens

<400> SEQUENCE: 19

```
gttttttttgg gctagcagga ggaattcatg agcactgaaa gcatgatccg ggacgtggag      60
ctggccgagg aggcgctccc caagaagaca ggggggcccc agggctccag gcggtgcttg     120
ttcctcagcc tcttctcctt cctgatcgtg cagggcgcca ccacgctctt ctgcctgctg     180
cactttggag tgatcggccc ccagagggaa gagttcccca gggacctctc tctaatcagc     240
cctctggccc aggcagtcag atcatcttct cgaaccccga gtgacaagcc tgtagcccat     300
gttgtagcaa accctcaagc tgaggggcag ctccagtggc tgaaccgccg ggccaatgcc     360
ctcctggcca atggcgtgga gctgagagat aaccagctgg tggtgccatc agagggcctg     420
tacctcatct actcccaggt cctcttcaag gccaaggct gccctccac ccatgtgctc       480
ctcacccaca ccatcagccg catcgccgtc tcctaccaga ccaaggtcaa cctcctctct     540
gccatcaaga gccctgcca gagggagacc ccagaggggg ctgaggccaa gcctggtat      600
gagcccatct atctgggagg ggtcttccag ctggagaagg gtgaccgact cagcgctgag    660
```

| | |
|---|---:|
| atcaatcggc cgactatct cgactttgcc gagtctgggc aggtctactt tgggatcatt | 720 |
| gccctgtgat aagcttggcc cgcgggcccg ggatccaccg gatctagata actgatcata | 780 |

<210> SEQ ID NO 20
<211> LENGTH: 300
<212> TYPE: DNA
<213> ORGANISM: Artificial Sequence
<220> FEATURE:
<223> OTHER INFORMATION: Synthetic nucleic acid sequence

<400> SEQUENCE: 20

| | |
|---|---:|
| gtttttttgg gctagcagga ggaattcacc atggtaccat gaacttgggg aatcgactgt | 60 |
| ttattctgat agcggtctta cttcccctcg cagtattact gctcaatagt gactctgaat | 120 |
| gtcccctgtc ccacgatggg tactgcctcc atgatggtgt gtgcatgtat attgaagcat | 180 |
| tggacaagta tgcatgcaac tgtgttgttg gctacatcgg ggagcgatgt cagtaccgag | 240 |
| acctgaagtg tgggaactg cgctaataag cttggcccgc gggcccggga tccaccggat | 300 |

<210> SEQ ID NO 21
<211> LENGTH: 1620
<212> TYPE: DNA
<213> ORGANISM: Artificial Sequence
<220> FEATURE:
<223> OTHER INFORMATION: Synthetic nucleic acid sequence

<400> SEQUENCE: 21

| | |
|---|---:|
| gtttttttgg gctagcagga ggaattcacc atgaacttgg ggaatcgact gtttattctg | 60 |
| atagcggtct tacttcccct cgcagtatta ctgctctcat tcacattgag cgtcaccgtt | 120 |
| cagcagcctc agttgacatt aacggcggcc gtcattggtg atggcgcacc ggctaatggg | 180 |
| aaaactgcaa tcaccgttga gttcaccgtt gctgattttg aggggaaacc cttagccggg | 240 |
| caggaggtgg tgataaccac caataatggt gcgctaccga ataaaatcac ggaaaagaca | 300 |
| gatgcaaatg gcgtcgcgcg cattgcatta accaatacga cagatggcgt gacggtagtc | 360 |
| acagcagaag tggaggggca acggcaaagt gttgataccc actttgttaa gggtactatc | 420 |
| gcggcggata atccactct ggctgcggta ccgacatcta tcatcgctga tggtctaatg | 480 |
| gcttcaacca tcacgttgga gttgaaggat acctatgggg accgcaggc tggcgcgaat | 540 |
| gtggcttttg acacaacctt aggcaatatg ggcgttatca cggatcacaa tgacggcact | 600 |
| tatagcgcac cattgaccag taccacgttg ggggtagcaa cagtaacggt gaaagtggat | 660 |
| ggggctgcgt tcagtgtgcc gagtgtgacg gttaatttca cggcagatcc tattccagat | 720 |
| gctggccgct ccagtttcac cgtctccaca ccggatatct ggctgatgg cacgatgagt | 780 |
| tccacattat cctttgtccc tgtcgataag aatggccatt ttatcagtgg gatgcagggc | 840 |
| ttgagtttta ctcaaaacgg tgtgccggtg agtattagcc ccattaccga gcagccagat | 900 |
| agctataccg cgacggtggt tgggaatagt gtcggtgatg tcacaatcac gccgcaggtt | 960 |
| gataccctga tactgagtac attgcagaaa aaaatatccc tattcccggt acctacgctg | 1020 |
| accggtattc tggttaacgg gcaaaatttc gctacggata aagggttccc gaaaacgatc | 1080 |
| tttaaaaacg ccacattcca gttacagatg gataacgatg ttgctaataa tactcagtat | 1140 |
| gagtggtcgt cgtcattcac acccaatgta tcggttaacg atcagggtca ggtgacgatt | 1200 |
| acctaccaaa cctatagcga agtggctgtg acggcgaaaa gtaaaaaatt cccaagttat | 1260 |
| tcggtgagtt atcggttcta cccaaatcgg tggatatacg atggcggcag atcgctggta | 1320 |
| tccagtctcg aggccagcag acaatgccaa ggttcagata tgtctgcggt tcttgaatcc | 1380 |

```
tcacgtgcaa ccaacggaac gcgtgcgcct gacgggacat tgtggggcga gtgggggagc    1440
ttgaccgcgt atagttctga ttggcaatct ggtgaatatt gggtcaaaaa gaccagcacg    1500
gattttgaaa ccatgaatat ggacacaggc gcactgcaac cagggcctgc atacttggcg    1560
ttcccgctct gtgcgctgtc aatataactg caggcatgca agcttggccc gcgggcccgg    1620

<210> SEQ ID NO 22
<211> LENGTH: 208
<212> TYPE: DNA
<213> ORGANISM: E. coli

<400> SEQUENCE: 22
gaattcaggc gcttttagga ctggtcgtaa tgaaattcag caggatcaca ttctgcagat      60
gtcacggccg agacttatag tcgctttgtt tttattttt aatgtatttg tacatggaga     120
aaataaagtg aaacaaagca ctattgcact ggcactctta ccgttactgt ttacccctgt    180
gacaaaagcc cggacaccag aatctaga                                       208

<210> SEQ ID NO 23
<211> LENGTH: 1546
<212> TYPE: DNA
<213> ORGANISM: E. coli

<400> SEQUENCE: 23
gaattcaggc gcttttagga ctggtcgtaa tgaaattcag caggatcaca ttctgcagat      60
gtcacggccg agacttatag tcgctttgtt tttattttt aatgtatttg tacatggaga     120
aaataaagtg aaacaaagca ctattgcact ggcactctta ccgttactgt ttacccctgt    180
gacaaaagcc cggacaccag aaatgcctgt tctggaaaac cggctgctc agggcgatat    240 tactgcaccc ggcggtgctc gccgtttaac gggtgatcag actgccgctc tgcgtgattc    300
tcttagcgat aaacctgcaa aaatattat tttgctgatt ggcgatggga tggggactc     360 ggaaattact gccgcacgta attatgccga aggtgcgggc ggcttttta aaggtataga    420 tgccttaccg cttaccgggc aatacactca ctatgcgctg aataaaaaaa ccggcaaacc    480
ggactacgtc accgactcgg ctgcatcagc aaccgcctgg tcaaccggtg tcaaaaccta    540
taacggcgcg ctgggcgtcg atattcacga aaaagatcac ccaacgattc tggaaatggc    600
aaaagccgca ggtctggcga ccggtaacgt ttctaccgca gagttgcagg atgccacgcc    660
cgctgcgctg gtggcacatg tgacctcgcg caaatgctac ggtccgagcg cgaccagtga    720
aaaatgtccg ggtaacgctc tggaaaaagg cggaaaagga tcgattaccg aacagctgct    780
taacgctcgt gccgacgtta cgcttggcgg cggcgcaaaa acctttgctg aaacggcaac    840
cgctggtgaa tggcagggaa aaacgctgcg tgaacaggca caggcgcgtg ttatcagtt    900 ggtgagcgat gctgcctcac tgaattcggt gacggaagcg aatcagcaaa acccctgct    960 tggcctgttt gctgacggca atatgccagt gcgctggcta ggaccgaaag caacgtacca   1020
tggcaatatc gataagcccg cagtcacctg tacgccaaat ccgcaacgta atgcagtgt   1080 accaaccctg gcgcagatga ccgacaaagc cattgaattg ttgagtaaaa atgagaaagg   1140 cttttttcctg caagttgaag gtgcgtcaat cgataaacag gatcatgctg cgaatccttg   1200
tgggcaaatt ggcgagacgg tcgatctcga tgaagccgta caacgggcgc tggaattcgc   1260
taaaaaggag ggtaacacgc tggtcatagt caccgctgat cacgcccacg ccagccagat   1320
tgttgcgccg gataccaaag ctccgggcct cacccaggcg ctaaatacca agatggcgc    1380 agtgatggtg atgagttacg ggaactccga agaggattca caagaacata ccggcagtca   1440
```

```
gttgcgtatt cggcgtatg cccgcatgc cgccaatgtt gttggactga ccgaccagac    1500
cgatctcttc tacaccatga aagccgctct ggggctgaaa tctaga                1546

<210> SEQ ID NO 24
<211> LENGTH: 148
<212> TYPE: DNA
<213> ORGANISM: E. coli

<400> SEQUENCE: 24
gaattcaggc gcttttaga ctggtcgtaa tgaaattcag caggatcaca ttctgcagat     60
gaaaataaaa acaggtgcac gcatcctcgc attatccgca ttaacgacga tgatgttttc   120
cgcctcggct ctcgccaaaa tctctaga                                      148

<210> SEQ ID NO 25
<211> LENGTH: 1174
<212> TYPE: DNA
<213> ORGANISM: E. coli

<400> SEQUENCE: 25
gaattcaggc gcttttaga ctggtcgtaa tgaaattcag caggatcaca ttctgcagat     60
gaaaataaaa acaggtgcac gcatcctcgc attatccgca ttaacgacga tgatgttttc   120
cgcctcggct ctcgccaaaa tcgaagaagg taaactggta atctggatta acggcgataa   180
aggctataac ggtctcgctg aagtcggtaa gaaattcgag aaagataccg gaattaaagt   240
caccgttgag catccggata aactggaaga gaaattccca caggttgcgg caactggcga   300
tggccctgac attatcttct gggcacacga ccgctttggt ggctacgctc aatctggcct   360
gttggctgaa atcaccccgg acaaagcgtt ccaggacaag ctgtatccgt ttacctggga   420
tgccgtacgt tacaacggca agctgattgc ttacccgatc gctgttgaag cgttatcgct   480
gatttataac aaagatctgc tgccgaaccc gccaaaaacc tgggaagaga tcccggcgct   540
ggataaagaa ctgaaagcga aggtaagag cgcgctgatg ttcaacctgc aagaaccgta   600
cttcacctgg ccgctgattg ctgctgacgg gggttatgcg ttcaagtatg aaaacggcaa   660
gtacgacatt aaagacgtgg cgtggataa cgctggcgcg aaagcgggtc tgaccttcct   720
ggttgacctg attaaaaaca acacatgaa tgcagacacc gattactcca tcgcagaagc   780
tgcctttaat aaaggcgaaa cagcgatgac catcaacggc ccgtgggcat ggtccaacat   840
cgacaccagc aaagtgaatt atggtgtaac ggtactgccg accttcaagg gtcaaccatc   900
caaaccgttc gttggcgtgc tgagcgcagg tattaacgcc gccagtccga caaagagct   960 ggcgaaagag ttcctcgaaa actatctgct gactgatgaa ggtctggaag cggttaataa  1020
agacaaaccg ctgggtgccg tagcgctgaa gtcttacgag gaagagttgg cgaaagatcc  1080
acgtattgcc gccaccatgg aaaacgccca gaaggtgaa atcatgccga acatcccgca  1140
gatgtccgct ttctggtatg ccgtgcgttc taga                              1174

<210> SEQ ID NO 26
<211> LENGTH: 3840
<212> TYPE: DNA
<213> ORGANISM: Artificial Sequence
<220> FEATURE:
<223> OTHER INFORMATION: Synthetic nucleic acid sequence

<400> SEQUENCE: 26
accatatgcg gtgtgaaata ccgcacagat gcgtaaggag aaaataccgc atcaggcgcc     60
atacgcgaca gcgcgcaata accgttctcg actcataaaa gtgatgccgc tataatgccg    120
```

```
cgtcctattt gaatgctttc gggatgattc tggtaacagg gaatgtgatt gattataaga    180
acatcccggt tccgcgaagc caacaacctg tgcttgcggg gtaagagttg accgagcact    240 gtgattttt gaggtaacaa gatgcaagtt tcagttgaaa ccactcaagg ccttggccgc     300
cgtgtaacga ttactatcgc tgctgacagc atcgagaccg ctgttaaaag cgagctggtc    360
aacgttgcga aaaagtacg tattgacggc ttccgcaaag gcaaagtgcc aatgaatatc     420
gttgctcagc gttatggcgc gtctgtacgc caggacgttc tgggtgacct gatgagccgt    480
aacttcattg acgccatcat taaagaaaaa atcaatccgg ctggcgcacc gacttatgtt    540
ccgggcgaat acaagctggg tgaagacttc acttactctg tagagtttga agtttatccg    600
gaagttgaac tgcagggtct ggaagcgatc gaagttgaaa accgatcgt tgaagtgacc     660 gacgctgacg ttgacggcat gctggatact ctgcgtaaac agcaggcgac ctggaaagaa    720
aaagacggcg ctgttgaagc agaagaccgc gtaaccatcg acttcaccgg ttctgtagac    780
ggcgaagagt tcgaaggcgg taaagcgtct gatttcgtac tggcgatggg ccagggtcgt    840
atgatcccgg gctttgaaga cggtatcaaa ggccacaaag ctggcgaaga gttcaccatc    900
gacgtgacct cccggaaga ataccacgca gaaacctga aggtaaagc agcgaaattc       960 gctatcaacc tgaagaaagt tgaagagcgt gaactgccgg aactgactgc agaattcatc   1020
aaacgtttcg gcgttgaaga tggttccgta gaaggtctgc gcgctgaagt gcgtaaaaac   1080
atggagcgcg agctgaagag cgccatccgt aaccgcgtta agtctcaggc gatcgaaggt   1140
ctggtaaaag ctaacgacat cgacgtaccg gctgcgctga tcgacagcga aatcgacgtt   1200
ctgcgtcgcc aggctgcaca gcgtttcggt ggcaacgaaa acaagctct ggaactgccg    1260 cgcgaactgt tcgaagaaca ggctaaacgc gcgtagttg ttggcctgct gctgggcgaa    1320
gttatccgca ccaacgagct gaaagctgac gaagagcgcg tgaaaggcct gatcgaagag   1380
atggcttctg cgtacgaaga tccgaaagaa gttatcgagt tctacagcaa aaacaaagaa   1440
ctgatggaca acatgcgcaa tgttgctctg gaagaacagg ctgttgaagc tgtactggcg   1500
aaagcgaaag tgactgaaaa agaaaccact ttcaacgagc tgatgaacca gcaggcgtaa   1560
taataatcta gaggtagcac aatcagattc gcttatgacg gcgatgaaga aattgcgatg   1620
aaatgtgagg tgaatcaggg ttttcacccg atttttgtgct gatcagaatt ttttttcttt   1680 ttccccttg aagggggcgaa gcctcatccc catttctctg gtcaccagcc gggaaaccac    1740
gtaagctccg gcgtcaccca taacagatac ggactttctc aaaggagagt tatcaatgaa    1800
tattcgtcca ttgcatgatc gcgtgatcgt caagcgtaaa gaagttgaaa ctaaatctgc    1860
tggcggcatc gttctgaccg gctctgcagc ggctaaatcc acccgcggcg aagtgctggc    1920
tgtcggcaat ggccgtatcc ttgaaaatgg cgaagtgaag ccgctggatg tgaaagttgg    1980
cgacatcgtt attttcaacg atggctacgg tgtgaaatct gagaagatcg acaatgaaga    2040
agtgttgatc atgtccgaaa gcgacattct ggcaattgtt gaagcgtaat ccgcgcacga    2100
cactgaacat acgaatttaa ggaataaaga taatggcagc taaagacgta aaattcggta    2160
acgacgctcg tgtgaaaatg ctgcgcggcg taaacgtact ggcagatgca gtgaaagtta    2220
ccctcggtcc aaaaggccgt aacgtagttc tggataaatc tttcggtgca ccgaccatca    2280
ccaaagatgg tgtttccgtt gctcgtgaaa tcgaactgga agacaagttc gaaaatatgg    2340
gtgcgcagat ggtgaaagaa gttgcctcta agcaaacga cgctgcaggc gacggtacca    2400
ccactgcaac cgtactggct caggctatca tcactgaagg tctgaaagct gttgctgcgg    2460
gcatgaaccc gatggaccto aaacgtggta tcgacaaagc ggttaccgct gcagttgaag   2520
```

```
aactgaaagc gctgtccgta ccatgctctg actctaaagc gattgctcag gttggtacca    2580
tctccgctaa ctccgacgaa accgtaggta aactgatcgc tgaagcgatg gacaaagtcg    2640
gtaaagaagg cgttatcacc gttgaagacg gtaccggtct gcaggacgaa ctggacgtgg    2700
ttgaaggtat gcagttcgac cgtggctacc tgtctcctta cttcatcaac aagccggaaa    2760
ctggcgcagt agaactggaa agcccgttca tcctgctggc tgacaagaaa atctccaaca    2820
tccgcgaaat gctgccggtt ctggaagctg ttgccaaagc aggcaaaccg ctgctgatca    2880
tcgctgaaga tgtagaaggc gaagcgctgg caactctggt tgttaacacc atgcgtggca    2940
tcgtgaaagt cgctgcggtt aaagcaccgg gcttcggcga tcgtcgtaaa gctatgctgc    3000
aggatatcgc aaccctgact ggcggtaccg tgatctctga agatcggt atggagctgg       3060 aaaaagcaac cctggaagac ctgggtcagg ctaaacgtgt tgtgatcaac aaagacacca    3120
ccactatcat cgatggcgtg ggtgaagaag ctgcaatcca gggccgtgtt gctcagatcc    3180
gtcagcagat tgaagaagca acttctgact acgaccgtga aaaactgcag gaacgcgtag    3240
cgaaactggc aggcggcgtt gcagttatca agtgggtgc tgctaccgaa gttgaaatga     3300
aagagaaaaa agcacgcgtt gaagatgccc tgcacgcgac ccgtgctgcg gtagaagaag    3360
gcgtggttgc tggtggtggt gttgcgctga tccgcgtagc gtctaaactg gctgacctgc    3420
gtggtcagaa cgaagaccag aacgtgggta tcaaagttgc actgcgtgca atggaagctc    3480
cgctgcgtca gatcgtattg aactgcggcg aagaaccgtc tgttgttgct aacaccgtta    3540
aaggcggcga cggcaactac ggttacaacg cagcaaccga gaataccggc aacatgatcg    3600
acatgggtat cctggatcca accaaagtaa ctcgttctgc tctgcagtac gcagcttctg    3660
tggctggcct gatgatcacc accgaatgca tggttaccga cctgccgaaa aacgatgcag    3720
ctgacttagg cgctgctggc ggtatgggcg gcatgggtgg catgggcggc atgatgtaat    3780
aataagcttg catgcctgca ggtcgactct agaggatccc cgggtaccga gctcgaattc    3840

<210> SEQ ID NO 27
<211> LENGTH: 480
<212> TYPE: DNA
<213> ORGANISM: E. coli

<400> SEQUENCE: 27
gaattcaggc gctttttaga ctggtcgtaa tgaaattcag caggatcaca ttctgcagat     60
gatcgaagcc cgctctagac tcgagagcga taaaattatt cacctgactg acgacagttt    120
tgacacggat gtactcaaag cggacggggc gatcctcgtc gatttctggg cagagtggtg    180
cggtccgtgc aaaatgatcg ccccgattct ggatgaaatc gctgacgaat atcagggcaa    240
actgaccgtt gcaaaactga catcgatca aaaccctggc actgcgccga aatatggcat    300
ccgtggtatc ccgactctgc tgctgttcaa aaacggtgaa gtggcggcaa ccaaagtggg    360
tgcactgtct aaaggtcagt tgaaagagtt cctcgacgct aacctggcgc tcgaggatta    420
taaagatcat gatggcgatt ataaagatca tgatgattaa taaggatccc cgggtaccga    480

<210> SEQ ID NO 28
<211> LENGTH: 1140
<212> TYPE: DNA
<213> ORGANISM: Rattus norvegicus

<400> SEQUENCE: 28
atggcaacca cgcacgcgca ggggcacccg ccagtcttgg ggaatgatac tctccgggaa     60
cattatgatt acgtggggaa gctggcaggc aggctgcggg atccccctga gggtagcacc    120
```

```
ctcatcacca ccatcctctt cttggtcacc tgtagcttca tcgtcttgga gaacctgatg    180
gttttgattg ccatctggaa aaacaataaa tttcataacc gcatgtactt tttcatcggc    240
aacttggctc tctgcgacct gctggccggc atagcctaca aggtcaacat tctgatgtcc    300
ggtaggaaga cgttcagcct gtctccaaca gtgtggttcc tcaggagggg cagtatgttc    360
gtagccctgg gcgcatccac atgcagctta ttggccattg ccattgagcg gcacctgacc    420
atgatcaaga tgaggccgta cgacgccaac aagaagcacc gcgtgttcct tctgattggg    480
atgtgctggc taattgcctt ctcgctgggt gccctgccca tcctgggctg gaactgcctg    540
gagaactttc ccgactgctc taccatcttg cccctctact ccaagaaata cattgccttt    600
ctcatcagca tcttcacagc cattctggtg accatcgtca tcttgtacgc gcgcatctac    660
ttcctggtca agtccagcag ccgcagggtg gccaaccaca actccgagag atccatggcc    720
cttctgcgga ccgtagtgat cgtggtgagc gtgttcatcg cctgttggtc ccccctttc    780 atcctcttcc tcatcgatgt ggcctgcagg gcgaaggagt gctccatcct cttcaagagt    840
cagtggttca tcatgctggc tgtcctcaac tcggccatga ccctgtcat ctacacgctg    900 gccagcaaag gatgcggcg tgcttcttc cggttggtgt gcggctgtct ggtcaagggc    960 aagggacc aggcctcccc gatgcagcct gctcttgacc cgagcagaag taaatcaagc    1020
tccagtaaca acagcagcag ccactctcca aggtcaagg aagacctgcc ccatgtggct    1080
acctcttcct gcgtcactga caaaacgagg tcgcttcaga atggggtcct ctgcaagtga   1140

<210> SEQ ID NO 29
<211> LENGTH: 379
<212> TYPE: PRT
<213> ORGANISM: Rattus norvegicus

<400> SEQUENCE: 29

Met Ala Thr Thr His Ala Gln Gly His Pro Val Leu Gly Asn Asp
 1               5                  10                  15

Thr Leu Arg Glu His Tyr Asp Tyr Val Gly Lys Leu Ala Gly Arg Leu
                20                  25                  30

Arg Asp Pro Pro Glu Gly Ser Thr Leu Ile Thr Thr Ile Leu Phe Leu
            35                  40                  45

Val Thr Cys Ser Phe Ile Val Leu Glu Asn Leu Met Val Leu Ile Ala
        50                  55                  60

Ile Trp Lys Asn Asn Lys Phe His Asn Arg Met Tyr Phe Phe Ile Gly
65                  70                  75                  80

Asn Leu Ala Leu Cys Asp Leu Leu Ala Gly Ile Ala Tyr Lys Val Asn
                85                  90                  95

Ile Leu Met Ser Gly Arg Lys Thr Phe Ser Leu Ser Pro Thr Val Trp
            100                 105                 110

Phe Leu Arg Glu Gly Ser Met Phe Val Ala Leu Gly Ala Ser Thr Cys
        115                 120                 125

Ser Leu Leu Ala Ile Ala Ile Glu Arg His Leu Thr Met Ile Lys Met
    130                 135                 140

Arg Pro Tyr Asp Ala Asn Lys Lys His Arg Val Phe Leu Leu Ile Gly
145                 150                 155                 160

Met Cys Trp Leu Ile Ala Phe Ser Leu Gly Ala Leu Pro Ile Leu Gly
                165                 170                 175

Trp Asn Cys Leu Glu Asn Phe Pro Asp Cys Ser Thr Ile Leu Pro Leu
            180                 185                 190

Tyr Ser Lys Lys Tyr Ile Ala Phe Leu Ile Ser Ile Phe Thr Ala Ile
```

```
                195                 200                 205
Leu Val Thr Ile Val Ile Leu Tyr Ala Arg Ile Tyr Phe Leu Val Lys
    210                 215                 220

Ser Ser Ser Arg Arg Val Ala Asn His Asn Ser Glu Arg Ser Met Ala
225                 230                 235                 240

Leu Leu Arg Thr Val Val Ile Val Ser Val Phe Ile Ala Cys Trp
                245                 250                 255

Ser Pro Leu Phe Ile Leu Phe Leu Ile Asp Val Ala Cys Arg Ala Lys
            260                 265                 270

Glu Cys Ser Ile Leu Phe Lys Ser Gln Trp Phe Ile Met Leu Ala Val
            275                 280                 285

Leu Asn Ser Ala Met Asn Pro Val Ile Tyr Thr Leu Ala Ser Lys Glu
            290                 295                 300

Met Arg Arg Ala Phe Phe Arg Leu Val Cys Gly Cys Leu Val Lys Gly
305                 310                 315                 320

Lys Gly Thr Gln Ala Ser Pro Met Gln Pro Ala Leu Asp Pro Ser Arg
                325                 330                 335

Ser Lys Ser Ser Ser Asn Asn Ser Ser Ser His Ser Pro Lys Val
            340                 345                 350

Lys Glu Asp Leu Pro His Val Ala Thr Ser Ser Cys Val Thr Asp Lys
            355                 360                 365

Thr Arg Ser Leu Gln Asn Gly Val Leu Cys Lys
    370                 375

<210> SEQ ID NO 30

<400> SEQUENCE: 30

000

<210> SEQ ID NO 31
<211> LENGTH: 32
<212> TYPE: DNA
<213> ORGANISM: Artificial Sequence
<220> FEATURE:
<223> OTHER INFORMATION: Synthetic nucleic acid primer sequence

<400> SEQUENCE: 31
aattgctagc tccaccagca tcccagtggt ta                              32

<210> SEQ ID NO 32
<211> LENGTH: 32
<212> TYPE: DNA
<213> ORGANISM: Artificial Sequence
<220> FEATURE:
<223> OTHER INFORMATION: Synthetic nucleic acid primer sequence

<400> SEQUENCE: 32
aattggatcc ttaagaagaa gaattgacgt tt                              32

<210> SEQ ID NO 33
<211> LENGTH: 32
<212> TYPE: DNA
<213> ORGANISM: Artificial Sequence
<220> FEATURE:
<223> OTHER INFORMATION: Synthetic nucleic acid primer sequence

<400> SEQUENCE: 33
aattggatcc agaagaagaa ttgacgtttc ca                              32

<210> SEQ ID NO 34
```

```
<211> LENGTH: 52
<212> TYPE: DNA
<213> ORGANISM: Artificial Sequence
<220> FEATURE:
<223> OTHER INFORMATION: Synthetic nucleic acid primer sequence

<400> SEQUENCE: 34
aattggatcc ttaatgatga tgatgatgat gagaagaaga attgacgttt cc          52

<210> SEQ ID NO 35
<211> LENGTH: 24
<212> TYPE: DNA
<213> ORGANISM: Artificial Sequence
<220> FEATURE:
<223> OTHER INFORMATION: Synthetic nucleic acid primer sequence

<400> SEQUENCE: 35
ttatggcaac cacgcacgcg cagg                                         24

<210> SEQ ID NO 36
<211> LENGTH: 21
<212> TYPE: DNA
<213> ORGANISM: Artificial Sequence
<220> FEATURE:
<223> OTHER INFORMATION: Synthetic nucleic acid primer sequence

<400> SEQUENCE: 36
agaccgtcac ttgcagagga c                                            21

<210> SEQ ID NO 37
<211> LENGTH: 32
<212> TYPE: DNA
<213> ORGANISM: Artificial Sequence
<220> FEATURE:
<223> OTHER INFORMATION: Synthetic nucleic acid primer sequence

<400> SEQUENCE: 37
aattgctagc acgcacgcgc aggggcaccc gc                                32

<210> SEQ ID NO 38
<211> LENGTH: 34
<212> TYPE: DNA
<213> ORGANISM: Artificial Sequence
<220> FEATURE:
<223> OTHER INFORMATION: Synthetic nucleic acid primer sequence

<400> SEQUENCE: 38
aattggtacc tcacttgcag aggaccccat tctg                              34

<210> SEQ ID NO 39
<211> LENGTH: 32
<212> TYPE: DNA
<213> ORGANISM: Artificial Sequence
<220> FEATURE:
<223> OTHER INFORMATION: Synthetic nucleic acid primer sequence

<400> SEQUENCE: 39
aattgctagc acgcacgcgc aggggcaccc gc                                32

<210> SEQ ID NO 40
<211> LENGTH: 21
<212> TYPE: DNA
<213> ORGANISM: Artificial Sequence
<220> FEATURE:
<223> OTHER INFORMATION: Synthetic nucleic acid primer sequence

<400> SEQUENCE: 40
```

```
ggtcgccacc atggtgagca a                                           21

<210> SEQ ID NO 41
<211> LENGTH: 31
<212> TYPE: DNA
<213> ORGANISM: Artificial Sequence
<220> FEATURE:
<223> OTHER INFORMATION: Synthetic nucleic acid primer sequence

<400> SEQUENCE: 41
ttaaggatcc ttacttgtac agctcgtcca t                                31

<210> SEQ ID NO 42
<211> LENGTH: 21
<212> TYPE: DNA
<213> ORGANISM: Artificial Sequence
<220> FEATURE:
<223> OTHER INFORMATION: Synthetic nucleic acid primer sequence

<400> SEQUENCE: 42
ggtcgccacc atggtgagca a                                           21

<210> SEQ ID NO 43
<211> LENGTH: 31
<212> TYPE: DNA
<213> ORGANISM: Artificial Sequence
<220> FEATURE:
<223> OTHER INFORMATION: Synthetic nucleic acid primer sequence

<400> SEQUENCE: 43
ttaaggatcc cttgtacagc tcgtccatgc c                                31

<210> SEQ ID NO 44
<211> LENGTH: 25
<212> TYPE: DNA
<213> ORGANISM: Artificial Sequence
<220> FEATURE:
<223> OTHER INFORMATION: Synthetic oligonucleotide primer sequence

<400> SEQUENCE: 44
ccaatggaac ttaccaatga cgcgg                                       25

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide primer sequence

<400> SEQUENCE: 45
gcttgcttac gcaggaatgc tggg                                        24

<210> SEQ ID NO 46
<211> LENGTH: 45
<212> TYPE: DNA
<213> ORGANISM: Artificial Sequence
<220> FEATURE:
<223> OTHER INFORMATION: Synthetic oligonucleotide primer sequence

<400> SEQUENCE: 46
cgcggctgca gatgtttgaa ccaatggaac ttaccaatga cgcgg                 45

<210> SEQ ID NO 47
<211> LENGTH: 45
<212> TYPE: DNA
<213> ORGANISM: Artificial Sequence
<220> FEATURE:
```

```
<223> OTHER INFORMATION: Synthetic oligonucleotide primer sequence

<400> SEQUENCE: 47
gcgcctctag attattaatc agcttgctta cgcaggaatg ctggg                    45

<210> SEQ ID NO 48
<211> LENGTH: 31
<212> TYPE: DNA
<213> ORGANISM: Artificial Sequence
<220> FEATURE:
<223> OTHER INFORMATION: Synthetic oligonucleotide primer sequence

<400> SEQUENCE: 48
gctagactgg gcggttttat ggacagcaag c                                   31

<210> SEQ ID NO 49
<211> LENGTH: 35
<212> TYPE: DNA
<213> ORGANISM: Artificial Sequence
<220> FEATURE:
<223> OTHER INFORMATION: Synthetic oligonucleotide primer sequence

<400> SEQUENCE: 49
gcgttaataa ttcagaagaa ctcgtcaaga aggcg                               35

<210> SEQ ID NO 50
<211> LENGTH: 99
<212> TYPE: DNA
<213> ORGANISM: Artificial Sequence
<220> FEATURE:
<223> OTHER INFORMATION: Synthetic oligonucleotide primer sequence

<400> SEQUENCE: 50
gcgcctactg acgtagttcg accgtcggac tagcgaagtt cctatacttt ctagagaata    60
ggaacttcgc tagactgggc ggttttatgg acagcaagc                           99

<210> SEQ ID NO 51
<211> LENGTH: 109
<212> TYPE: DNA
<213> ORGANISM: Artificial Sequence
<220> FEATURE:
<223> OTHER INFORMATION: Synthetic oligonucleotide primer sequence

<400> SEQUENCE: 51
caagatgctt tgcctttgtc tgagttgata ctggctttgg gaagttccta ttctctagaa    60
agtataggaa cttcgcgtta ataattcaga agaactcgtc aagaaggcg                109

<210> SEQ ID NO 52
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 52
cgttaccaat tatgacaact tgacgg                                         26

<210> SEQ ID NO 53
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 53
```
ttaatctttc tgcgaattga gatgacgcc                                    29

<210> SEQ ID NO 54
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 54
gtgagtcgat attgtctttg ttgaccag                                     28

<210> SEQ ID NO 55
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 55
gcctgcattg cggcgcttca gtctccgctg catactgtcc cgttaccaat tatgacaact    60
tgacgg                                                             66

<210> SEQ ID NO 56
<211> LENGTH: 69
<212> TYPE: DNA
<213> ORGANISM: Artificial Sequence
<220> FEATURE:
<223> OTHER INFORMATION: Synthetic oligonucleotide primer sequence

<400> SEQUENCE: 56
gcctgcattg cggcgcttca gtctccgctg catactgtcc ttaatctttc tgcgaattga    60
gatgacgcc                                                          69

<210> SEQ ID NO 57
<211> LENGTH: 76
<212> TYPE: DNA
<213> ORGANISM: Artificial Sequence
<220> FEATURE:
<223> OTHER INFORMATION: Synthetic oligonucleotide primer sequence

<400> SEQUENCE: 57
gcctgcattg cggcgcttca gtctccgctg catactgtcc ttaataaagt gagtcgatat    60
tgtctttgtt gaccag                                                  76

<210> SEQ ID NO 58
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 58
gcctgcattg cggcgcttca gtctccgctg catactgtcc cgttaccaat tatgacaact    60
tgacgg                                                             66

<210> SEQ ID NO 59
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 59

```
gcctgttctg gaaaaccggg ctgctcaggg                                         30

<210> SEQ ID NO 60
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 60
gcggctttca tggtgtagaa gagatcgg                                           28

<210> SEQ ID NO 61
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 61
ccgcgctgca gatgcctgtt ctggaaaacc gggctgctca ggg                          43

<210> SEQ ID NO 62
<211> LENGTH: 58
<212> TYPE: DNA
<213> ORGANISM: Artificial Sequence
<220> FEATURE:
<223> OTHER INFORMATION: Synthetic oligonucleotide primer sequence

<400> SEQUENCE: 62
gcgcctctag attattattt cagccccaga gcggctttca tggtgtagaa gagatcgg         58

<210> SEQ ID NO 63
<211> LENGTH: 24
<212> TYPE: DNA
<213> ORGANISM: Artificial Sequence
<220> FEATURE:
<223> OTHER INFORMATION: Synthetic oligonucleotide primer sequence

<400> SEQUENCE: 63
gtcacggccg agacttatag tcgc                                               24

<210> SEQ ID NO 64
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 64
gcggctttca tggtgtagaa gagatcgg                                           28

<210> SEQ ID NO 65
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 65
ccgcgctgca gatgtcacgg ccgagactta tagtcgc                                 37

<210> SEQ ID NO 66
<211> LENGTH: 58
<212> TYPE: DNA
<213> ORGANISM: Artificial Sequence
<220> FEATURE:
```

```
<223> OTHER INFORMATION: Synthetic oligonucleotide primer sequence

<400> SEQUENCE: 66
gcgcctctag attattattt cagccccaga gcggctttca tggtgtagaa gagatcgg        58

<210> SEQ ID NO 67
<211> LENGTH: 109
<212> TYPE: DNA
<213> ORGANISM: Artificial Sequence
<220> FEATURE:
<223> OTHER INFORMATION: Synthetic oligonucleotide primer sequence

<400> SEQUENCE: 67
ccgcgctgca gatgaacttg gggaatcgac tgtttattct gatagcggtc ttacttcccc      60
tcgcagtatt actgctcatg cctgttctgg aaaaccgggc tgctcaggg                 109

<210> SEQ ID NO 68
<211> LENGTH: 58
<212> TYPE: DNA
<213> ORGANISM: Artificial Sequence
<220> FEATURE:
<223> OTHER INFORMATION: Synthetic oligonucleotide primer sequence

<400> SEQUENCE: 68
gcgcctctag attattattt cagccccaga gcggctttca tggtgtagaa gagatcgg        58

<210> SEQ ID NO 69
<211> LENGTH: 24
<212> TYPE: DNA
<213> ORGANISM: Artificial Sequence
<220> FEATURE:
<223> OTHER INFORMATION: Synthetic oligonucleotide primer sequence

<400> SEQUENCE: 69
gcgaattgag atgacgccac tggc                                             24

<210> SEQ ID NO 70
<211> LENGTH: 25
<212> TYPE: DNA
<213> ORGANISM: Artificial Sequence
<220> FEATURE:
<223> OTHER INFORMATION: Synthetic oligonucleotide primer sequence

<400> SEQUENCE: 70
cctgctgaat tcattaacg accag                                             25

<210> SEQ ID NO 71
<211> LENGTH: 48
<212> TYPE: DNA
<213> ORGANISM: Artificial Sequence
<220> FEATURE:
<223> OTHER INFORMATION: Synthetic oligonucleotide primer sequence

<400> SEQUENCE: 71
cggcgaagct taattaatct ttctgcgaat tgagatgacg ccactggc                   48

<210> SEQ ID NO 72
<211> LENGTH: 53
<212> TYPE: DNA
<213> ORGANISM: Artificial Sequence
<220> FEATURE:
<223> OTHER INFORMATION: Synthetic oligonucleotide primer sequence

<400> SEQUENCE: 72
cgccgtaatc gccgctgcag aatgtgatcc tgctgaattt cattaacgac cag             53
```

```
<210> SEQ ID NO 73
<211> LENGTH: 22
<212> TYPE: DNA
<213> ORGANISM: Artificial Sequence
<220> FEATURE:
<223> OTHER INFORMATION: Synthetic oligonucleotide primer sequence

<400> SEQUENCE: 73
cgcagcgctg ttcctttgct cg                                              22

<210> SEQ ID NO 74
<211> LENGTH: 23
<212> TYPE: DNA
<213> ORGANISM: Artificial Sequence
<220> FEATURE:
<223> OTHER INFORMATION: Synthetic oligonucleotide primer sequence

<400> SEQUENCE: 74
cctcattaag ataataatac tgg                                             23

<210> SEQ ID NO 75
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 75
gccgcaagct tcgcagcgct gttcctttgc tcg                                  33

<210> SEQ ID NO 76
<211> LENGTH: 47
<212> TYPE: DNA
<213> ORGANISM: Artificial Sequence
<220> FEATURE:
<223> OTHER INFORMATION: Synthetic oligonucleotide primer sequence

<400> SEQUENCE: 76
ccaatgcatt ggttctgcag gactcctcat taagataata atactgg                   47

<210> SEQ ID NO 77
<211> LENGTH: 19
<212> TYPE: DNA
<213> ORGANISM: Artificial Sequence
<220> FEATURE:
<223> OTHER INFORMATION: Synthetic oligonucleotide primer sequence

<400> SEQUENCE: 77
cgtctttagc cgggaaacg                                                  19

<210> SEQ ID NO 78
<211> LENGTH: 18
<212> TYPE: DNA
<213> ORGANISM: Artificial Sequence
<220> FEATURE:
<223> OTHER INFORMATION: Synthetic oligonucleotide primer sequence

<400> SEQUENCE: 78
gcagatctcc tggcttgc                                                   18

<210> SEQ ID NO 79
<211> LENGTH: 30
<212> TYPE: DNA
<213> ORGANISM: Artificial Sequence
<220> FEATURE:
<223> OTHER INFORMATION: Synthetic oligonucleotide primer sequence
```

```
<400> SEQUENCE: 79
gccgcaagct tcgtctttag ccgggaaacg                                     30

<210> SEQ ID NO 80
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 80
cggtcgacgc agatctcctg gcttgc                                         26

<210> SEQ ID NO 81
<211> LENGTH: 23
<212> TYPE: DNA
<213> ORGANISM: Artificial Sequence
<220> FEATURE:
<223> OTHER INFORMATION: Synthetic oligonucleotide primer sequence

<400> SEQUENCE: 81
caagccgtca attgtctgat tcg                                            23

<210> SEQ ID NO 82
<211> LENGTH: 22
<212> TYPE: DNA
<213> ORGANISM: Artificial Sequence
<220> FEATURE:
<223> OTHER INFORMATION: Synthetic oligonucleotide primer sequence

<400> SEQUENCE: 82
ggtgaattcc tcctgctagc cc                                             22

<210> SEQ ID NO 83
<211> LENGTH: 34
<212> TYPE: DNA
<213> ORGANISM: Artificial Sequence
<220> FEATURE:
<223> OTHER INFORMATION: Synthetic oligonucleotide primer sequence

<400> SEQUENCE: 83
gcgccaagct tcaagccgtc aattgtctga ttcg                                34

<210> SEQ ID NO 84
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 84
ctgcagggtg aattcctcct gctagccc                                       28

<210> SEQ ID NO 85
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 85
gcttaactcg agcttaataa caagccgtca attgtctgat tc                       42

<210> SEQ ID NO 86
<211> LENGTH: 34
<212> TYPE: DNA
```

```
<213> ORGANISM: Artificial Sequence
<220> FEATURE:
<223> OTHER INFORMATION: Synthetic oligonucleotide primer sequence

<400> SEQUENCE: 86
gcttaaccgc gggccaagct tgcatgcctg ctcc                               34

<210> SEQ ID NO 87
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 87
ggcaaccacg cacgcgcagg gccacc                                        26

<210> SEQ ID NO 88
<211> LENGTH: 25
<212> TYPE: DNA
<213> ORGANISM: Artificial Sequence
<220> FEATURE:
<223> OTHER INFORMATION: Synthetic oligonucleotide primer sequence

<400> SEQUENCE: 88
caatggtgat ggtgatgatg accgg                                         25

<210> SEQ ID NO 89
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 89
cgcggtcgac atggcaacca cgcacgcgca gggccacc                           38

<210> SEQ ID NO 90
<211> LENGTH: 40
<212> TYPE: DNA
<213> ORGANISM: Artificial Sequence
<220> FEATURE:
<223> OTHER INFORMATION: Synthetic oligonucleotide primer sequence

<400> SEQUENCE: 90
gcgccggtac cttatcaatg gtgatggtga tgatgaccgg                         40

<210> SEQ ID NO 91
<211> LENGTH: 25
<212> TYPE: DNA
<213> ORGANISM: Artificial Sequence
<220> FEATURE:
<223> OTHER INFORMATION: Synthetic oligonucleotide primer sequence

<400> SEQUENCE: 91
ggggcaaccc gggaacggca gcgcc                                         25

<210> SEQ ID NO 92
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 92
gcagtgagtc atttgtacta caattcctcc                                    30
```

```
<210> SEQ ID NO 93
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 93
cgcggtcgac atggggcaac ccgggaacgg cagcgcc                             37

<210> SEQ ID NO 94
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 94
gcgccggatc cttattatag cagtgagtca tttgtactac aattcctcc                49

<210> SEQ ID NO 95
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 95
ggactggtcc ctcacctagg ggacaggg                                       28

<210> SEQ ID NO 96
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 96
ctgagaagac tgggcgcggg cgggagg                                        27

<210> SEQ ID NO 97
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 97
cgcgggtcga catgggactg gtccctcacc taggggacag gg                       42

<210> SEQ ID NO 98
<211> LENGTH: 44
<212> TYPE: DNA
<213> ORGANISM: Artificial Sequence
<220> FEATURE:
<223> OTHER INFORMATION: Synthetic oligonucleotide primer sequence

<400> SEQUENCE: 98
gcgccggtac cttattactg agaagactgg gcgcgggcgg gagg                     44

<210> SEQ ID NO 99
<211> LENGTH: 16
<212> TYPE: DNA
<213> ORGANISM: Artificial Sequence
<220> FEATURE:
<223> OTHER INFORMATION: Synthetic oligonucleotide primer sequence
```

```
<400> SEQUENCE: 99
gatagtgtgt gtcccc                                                    16

<210> SEQ ID NO 100
<211> LENGTH: 17
<212> TYPE: DNA
<213> ORGANISM: Artificial Sequence
<220> FEATURE:
<223> OTHER INFORMATION: Synthetic oligonucleotide primer sequence

<400> SEQUENCE: 100
ctgagaagac tgggcgc                                                   17

<210> SEQ ID NO 101
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 101
gggagaccat ggatagtgtg tgtcccc                                        27

<210> SEQ ID NO 102
<211> LENGTH: 32
<212> TYPE: DNA
<213> ORGANISM: Artificial Sequence
<220> FEATURE:
<223> OTHER INFORMATION: Synthetic oligonucleotide primer sequence

<400> SEQUENCE: 102
gcctcatcta gattactgag aagactgggc gc                                  32

<210> SEQ ID NO 103
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 103
gagcactgaa agcatgatcc gggacg                                         26

<210> SEQ ID NO 104
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 104
cagggcaatg atcccaaagt agacctgc                                       28

<210> SEQ ID NO 105
<211> LENGTH: 39
<212> TYPE: DNA
<213> ORGANISM: Artificial Sequence
<220> FEATURE:
<223> OTHER INFORMATION: Synthetic oligonucleotide primer sequence

<400> SEQUENCE: 105
ccgcggaatt catgagcact gaaagcatga tccgggacg                           39

<210> SEQ ID NO 106
<211> LENGTH: 43
<212> TYPE: DNA
```

<213> ORGANISM: Artificial Sequence
<220> FEATURE:
<223> OTHER INFORMATION: Synthetic oligonucleotide primer sequence

<400> SEQUENCE: 106
ggcgcaagct tatcacaggg caatgatccc aaagtagacc tgc                43

<210> SEQ ID NO 107
<211> LENGTH: 110
<212> TYPE: DNA
<213> ORGANISM: Artificial Sequence
<220> FEATURE:
<223> OTHER INFORMATION: Synthetic oligonucleotide primer sequence

<400> SEQUENCE: 107
tctgatagcg gtcttacttc ccctcgcagt attactgctc aatagtgact ctgaatgtcc    60
cctgtcccac gatgggtact gcctccatga tggtgtgtgc atgtatattg              110

<210> SEQ ID NO 108
<211> LENGTH: 101
<212> TYPE: DNA
<213> ORGANISM: Artificial Sequence
<220> FEATURE:
<223> OTHER INFORMATION: Synthetic oligonucleotide primer sequence

<400> SEQUENCE: 108
aggtctcggt actgacatcg ctccccgatg tagccaacaa cacagttgca tgcatacttg    60
tccaatgctt caatatacat gcacacacca tcatggaggc a                      101

<210> SEQ ID NO 109
<211> LENGTH: 63
<212> TYPE: DNA
<213> ORGANISM: Artificial Sequence
<220> FEATURE:
<223> OTHER INFORMATION: Synthetic oligonucleotide primer sequence

<400> SEQUENCE: 109
ccgcgggtac catgaacttg gggaatcgac tgtttattct gatagcggtc ttacttcccc    60
tcg                                                                63

<210> SEQ ID NO 110
<211> LENGTH: 61
<212> TYPE: DNA
<213> ORGANISM: Artificial Sequence
<220> FEATURE:
<223> OTHER INFORMATION: Synthetic oligonucleotide primer sequence

<400> SEQUENCE: 110
gcgccaagct tattagcgca gttcccacca cttcaggtct cggtactgac atcgctcccc    60
g                                                                  61

<210> SEQ ID NO 111
<211> LENGTH: 22
<212> TYPE: DNA
<213> ORGANISM: Artificial Sequence
<220> FEATURE:
<223> OTHER INFORMATION: Synthetic oligonucleotide primer sequence

<400> SEQUENCE: 111
tcattcacat tgagcgtcac cg                                            22

<210> SEQ ID NO 112
<211> LENGTH: 24
<212> TYPE: DNA

```
<213> ORGANISM: Artificial Sequence
<220> FEATURE:
<223> OTHER INFORMATION: Synthetic oligonucleotide primer sequence

<400> SEQUENCE: 112
ttatattgac agcgcacaga gcgg                                            24

<210> SEQ ID NO 113
<211> LENGTH: 101
<212> TYPE: DNA
<213> ORGANISM: Artificial Sequence
<220> FEATURE:
<223> OTHER INFORMATION: Synthetic oligonucleotide primer sequence

<400> SEQUENCE: 113
gcaagaattc accatgaact tggggaatcg actgtttatt ctgatagcgg tcttacttcc     60
cctcgcagta ttactgctct cattcacatt gagcgtcacc g                        101

<210> SEQ ID NO 114
<211> LENGTH: 47
<212> TYPE: DNA
<213> ORGANISM: Artificial Sequence
<220> FEATURE:
<223> OTHER INFORMATION: Synthetic oligonucleotide primer sequence

<400> SEQUENCE: 114
cgcggttacg taagcaactg cagttatatt gacagcgcac agagcgg                   47

<210> SEQ ID NO 115
<211> LENGTH: 24
<212> TYPE: DNA
<213> ORGANISM: Artificial Sequence
<220> FEATURE:
<223> OTHER INFORMATION: Synthetic oligonucleotide primer sequence

<400> SEQUENCE: 115
gtcacggccg agacttatag tcgc                                            24

<210> SEQ ID NO 116

<400> SEQUENCE: 116

000

<210> SEQ ID NO 117
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 117
cgcggctgca gatgtcacgg ccgagactta tagtcgc                              37

<210> SEQ ID NO 118
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 118
cgcggtctag attctggtgt ccgggctttt gtcacagg                             38

<210> SEQ ID NO 119
<211> LENGTH: 23
```

```
<212> TYPE: DNA
<213> ORGANISM: Artificial Sequence
<220> FEATURE:
<223> OTHER INFORMATION: Synthetic oligonucleotide primer sequence

<400> SEQUENCE: 119
cagccccaga gcggctttca tgg                                            23

<210> SEQ ID NO 120
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 120
cgcggtctag atttcagccc cagagcggct ttcatgg                             37

<210> SEQ ID NO 121
<211> LENGTH: 106
<212> TYPE: DNA
<213> ORGANISM: Artificial Sequence
<220> FEATURE:
<223> OTHER INFORMATION: Synthetic oligonucleotide primer sequence

<400> SEQUENCE: 121
cgcggctgca gatgaaaata aaaacaggtg cacgcatcct cgcattatcc gcattaacga    60
cgatgatgtt ttccgcctcg gctctcgcca aaatctctag acgcgg                  106

<210> SEQ ID NO 122
<211> LENGTH: 106
<212> TYPE: DNA
<213> ORGANISM: Artificial Sequence
<220> FEATURE:
<223> OTHER INFORMATION: Synthetic oligonucleotide primer sequence

<400> SEQUENCE: 122
ccgcgtctag agattttggc gagagccgag gcggaaaaca tcatcgtcgt taatgcggat    60
aatgcgagga tgcgtgcacc tgtttttatt ttcatctgca gccgcg                  106

<210> SEQ ID NO 123
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 123
ggtgcacgca tcctcgcatt atccgc                                         26

<210> SEQ ID NO 124
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 124
cggcatacca gaaagcggac atctgc                                         26

<210> SEQ ID NO 125
<211> LENGTH: 52
<212> TYPE: DNA
<213> ORGANISM: Artificial Sequence
<220> FEATURE:
<223> OTHER INFORMATION: Synthetic oligonucleotide primer sequence
```

```
<400> SEQUENCE: 125
cgcggctgca gatgaaaata aaaacaggtg cacgcatcct cgcattatcc gc          52

<210> SEQ ID NO 126
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 126
cgcggtctag aacgcacggc ataccagaaa gcggacatct gc                    42

<210> SEQ ID NO 127
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 127
cgcgacagcg cgcaataacc gttctcg                                      27

<210> SEQ ID NO 128
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 128
gctggttcat cagctcgttg aaagtgg                                      27

<210> SEQ ID NO 129
<211> LENGTH: 41
<212> TYPE: DNA
<213> ORGANISM: Artificial Sequence
<220> FEATURE:
<223> OTHER INFORMATION: Synthetic oligonucleotide primer sequence

<400> SEQUENCE: 129
gcgccggcgc catacgcgac agcgcgcaat aaccgttctc g                     41

<210> SEQ ID NO 130
<211> LENGTH: 52
<212> TYPE: DNA
<213> ORGANISM: Artificial Sequence
<220> FEATURE:
<223> OTHER INFORMATION: Synthetic oligonucleotide primer sequence

<400> SEQUENCE: 130
ggcgctctag attattatta cgcctgctgg ttcatcagct cgttgaaagt gg         52

<210> SEQ ID NO 131
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 131
ggtagcacaa tcagattcgc ttatgacgg                                    29

<210> SEQ ID NO 132
<211> LENGTH: 25
```

```
<212> TYPE: DNA
<213> ORGANISM: Artificial Sequence
<220> FEATURE:
<223> OTHER INFORMATION: Synthetic oligonucleotide primer sequence

<400> SEQUENCE: 132
gccgcccatg ccacccatgc cgccc                                          25

<210> SEQ ID NO 133
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 133
gcgtctagag gtagcacaat cagattcgct tatgacgg                            38

<210> SEQ ID NO 134
<211> LENGTH: 49
<212> TYPE: DNA
<213> ORGANISM: Artificial Sequence
<220> FEATURE:
<223> OTHER INFORMATION: Synthetic oligonucleotide primer sequence

<400> SEQUENCE: 134
ggcgcaagct tattattaca tcatgccgcc catgccaccc atgccgccc                49

<210> SEQ ID NO 135
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 135
gcgataaaat tattcacctg actgacg                                        27

<210> SEQ ID NO 136
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 136
gcgtcgagga actctttcaa ctgacc                                         26

<210> SEQ ID NO 137
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 137
cgcggctgca gatgatcgaa gcccgctcta gactcgagag cgataaaatt attcacctga    60
ctgacg                                                               66

<210> SEQ ID NO 138
<211> LENGTH: 101
<212> TYPE: DNA
<213> ORGANISM: Artificial Sequence
<220> FEATURE:
<223> OTHER INFORMATION: Synthetic oligonucleotide primer sequence

<400> SEQUENCE: 138
```

```
ccgcgggatc cttattaatc atcatgatct ttataatcgc catcatgatc tttataatcc      60
tcgagcgcca ggttagcgtc gaggaactct ttcaactgac c                        101

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143
<211> LENGTH: 65
<212> TYPE: DNA
<213> ORGANISM: Artificial Sequence
<220> FEATURE:
<223> OTHER INFORMATION: Synthetic oligonucleotide primer sequence

<400> SEQUENCE: 143
tatgtaagga ggttgtcgac cggctcagtc tagaggtacc cgccctcatc cgaaagggcg      60
tattg                                                                 65

<210> SEQ ID NO 144
<211> LENGTH: 67
<212> TYPE: DNA
<213> ORGANISM: Artificial Sequence
<220> FEATURE:
<223> OTHER INFORMATION: Synthetic oligonucleotide primer sequence

<400> SEQUENCE: 144
gatccaatac gcccttcgg atgagggcgg gtacctctag actgagccgg tcgacaacct       60
ccttaca                                                               67

<210> SEQ ID NO 145
<211> LENGTH: 65
<212> TYPE: DNA
<213> ORGANISM: Artificial Sequence
<220> FEATURE:
<223> OTHER INFORMATION: Synthetic oligonucleotide primer sequence

<400> SEQUENCE: 145
tatgtaagga ggttctgcag cggctcagtc tagaggtacc cgccctcatc cgaaagggcg      60
tattg                                                                 65

<210> SEQ ID NO 146
<211> LENGTH: 67
<212> TYPE: DNA
<213> ORGANISM: Artificial Sequence
```

```
<220> FEATURE:
<223> OTHER INFORMATION: Synthetic oligonucleotide primer sequence

<400> SEQUENCE: 146
gatccaatac gcccttcgg atgagggcgg gtacctctag actgagccgc tgcagaacct    60
ccttaca                                                              67

<210> SEQ ID NO 147
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 147
gatcctaagg aggttgtcga ccggctcagt ctagaggtac ccgccctcat ccgaagggc     60 gtattc                                                               66

<210> SEQ ID NO 148
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 148
tcgagaatac gcccttcgg atgagggcgg gtacctctag actgagccgg tcgacaacct    60
ccttag                                                               66

<210> SEQ ID NO 149
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 149
gatcctaagg aggttctgca gcggctcagt ctagaggtac ccgccctcat ccgaagggc     60 gtattc                                                               66

<210> SEQ ID NO 150
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 150
tcgagaatac gcccttcgg atgagggcgg gtacctctag actgagccgc tgcagaacct    60
ccttag                                                               66

<210> SEQ ID NO 151
<211> LENGTH: 4740
<212> TYPE: DNA
<213> ORGANISM: E. coli

<400> SEQUENCE: 151
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120 ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
```

-continued

```
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttaattaa tctttctgcg    420
aattgagatg acgccactgg ctgggcgtca tcccggtttc ccgggtaaac accaccgaaa    480
aatagttact atcttcaaag ccacattcgg tcgaaatatc actgattaac aggcggctat    540
gctggagaag atattgcgca tgacacactc tgacctgtcg cagatattga ttgatggtca    600
ttccagtctg ctggcgaaat tgctgacgca aaacgcgctc actgcacgat gcctcatcac    660
aaaatttatc cagcgcaaag ggacttttca ggctagccgc cagccgggta atcagcttat    720
ccagcaacgt ttcgctggat gttggcggca acgaatcact ggtgtaacga tggcgattca    780
gcaacatcac caactgcccg aacagcaact cagccatttc gttagcaaac ggcacatgct    840
gactactttc atgctcaagc tgaccgataa cctgccgcgc ctgcgccatc ccatgctac     900 ctaagcgcca gtgtggttgc cctgcgctgg cgttaaatcc cggaatcgcc ccctgccagt    960
caagattcag cttcagacgc tccgggcaat aaataatatt ctgcaaaacc agatcgttaa   1020
cggaagcgta ggagtgttta tcgtcagcat gaatgtaaaa gagatcgcca cgggtaatgc   1080
gataagggcg atcgttgagt acatgcaggc cattaccgcg ccagacaatc accagctcac   1140
aaaaatcatg tgtatgttca gcaaagacat cttgcggata acggtcagcc acagcgactg   1200
cctgctggtc gctggcaaaa aaatcatctt tgagaagttt taactgatgc gccaccgtgg   1260
ctacctcggc cagagaacga agttgattat tcgcaatatg gcgtacaaat acgttgagaa   1320
gattcgcgtt attgcagaaa gccatcccgt ccctggcgaa tatcacgcgg tgaccagtta   1380
aactctcggc gaaaaagcgt cgaaaagtgg ttactgtcgc tgaatccaca gcgataggcg   1440
atgtcagtaa cgctggcctc gctgtggcgt agcagatgtc gggctttcat cagtcgcagg   1500
cggttcaggt atcgctgagg cgtcagtccc gtttgctgct taagctgccg atgtagcgta   1560
cgcagtgaaa gagaaaattg atccgccacg gcatcccaat tcacctcatc ggcaaaatgg   1620
tcctccagcc aggccagaag caagttgaga cgtgatgcgc tgttttccag gttctcctgc   1680
aaactgcttt tacgcagcaa gagcagtaat tgcataaaca agatctcgcg actggcggtc   1740
gagggtaaat catttccccc ttcctgctgt tccatctgtg caaccagctg tcgcacctgc   1800
tgcaatacgc tgtggttaac gcgccagtga gacggatact gcccatccag ctcttgtggc   1860
agcaactgat tcagcccggc gagaaactga aatcgatccg gcgagcgata cagcacattg   1920
gtcagacaca gattatcggt atgttcatac agatgccgat catgatcgcg tacgaaacag   1980
accgtgccac cggtgatggt ataggctgc ccattaaaca catgaatacc cgtgccatgt   2040
tcgacaatca caatttcatg aaaatcatga tgatgttcag gaaaatccgc ctgcgggagc   2100
cggggttcta tcgccacgga cgcgttacca gacggaaaaa aatccacact atgtaatacg   2160
gtcatactgg cctcctgatg tcgtcaacac ggcgaaatag taatcacgag gtcaggttct   2220
taccttaaat tttcgacgga aaaccacgta aaaaacgtcg attttcaag atacagcgtg     2280 aattttcagg aaatgcggtg agcatcacat caccacaatt cagcaaattg tgaacatcat   2340
cacgttcatc tttccctggt tgccaatggc ccattttcct gtcagtaacg agaaggtcgc   2400
gaattcaggc gcttttttaga ctggtcgtaa tgaaattcag gaggttgtcg actctagagg   2460
atccccgcgc cctcatccga aagggcgtat tggtaccgag ctcgaattcg taatcatggt   2520
catagctgtt tcctgtgtga aattgttatc cgctcacaat tccacacaac atacgagccg   2580
gaagcataaa gtgtaaagcc tggggtgcct aatgagtgag ctaactcaca ttaattgcgt   2640
```

-continued

```
tgcgctcact gcccgctttc cagtcgggaa acctgtcgtg ccagctgcat taatgaatcg    2700
gccaacgcgc ggggagaggc ggtttgcgta ttgggcgctc ttccgcttcc tcgctcactg    2760
actcgctgcg ctcggtcgtt cggctgcggc gagcggtatc agctcactca aaggcggtaa    2820
tacggttatc cacagaatca ggggataacg caggaaagaa catgtgagca aaaggccagc    2880
aaaaggccag gaaccgtaaa aaggccgcgt tgctggcgtt tttccatagg ctccgccccc    2940
ctgacgagca tcacaaaaat cgacgctcaa gtcagaggtg gcgaaacccg acaggactat    3000
aaagatacca ggcgtttccc cctggaagct ccctcgtgcg ctctcctgtt ccgaccctgc    3060
cgcttaccgg atacctgtcc gcctttctcc cttcgggaag cgtggcgctt tctcatagct    3120
cacgctgtag gtatctcagt tcggtgtagg tcgttcgctc caagctgggc tgtgtgcacg    3180
aaccccccgt tcagcccgac cgctgcgcct tatccggtaa ctatcgtctt gagtccaacc    3240
cggtaagaca cgacttatcg ccactggcag cagccactgg taacaggatt agcagagcga    3300
ggtatgtagg cggtgctaca gagttcttga agtggtggcc taactacggc tacactagaa    3360
ggacagtatt tggtatctgc gctctgctga agccagttac cttcggaaaa agagttggta    3420
gctcttgatc cggcaaacaa accaccgctg gtagcggtgg ttttttttgtt tgcaagcagc    3480 agattacgcg cagaaaaaaa ggatctcaag aagatccttt gatcttttct acggggtctg    3540
acgctcagtg gaacgaaaac tcacgttaag ggattttggt catgagatta tcaaaaagga    3600
tcttcaccta gatccttttta aattaaaaat gaagttttaa atcaatctaa agtatatatg    3660
agtaaacttg gtctgacagt taccaatgct taatcagtga ggcacctatc tcagcgatct    3720
gtctatttcg ttcatccata gttgcctgac tccccgtcgt gtagataact acgatacggg    3780
agggcttacc atctggcccc agtgctgcaa tgataccgcg agaccacgc tcaccggctc    3840 cagatttatc agcaataaac cagccagccg aagggccga gcgcagaagt ggtcctgcaa    3900
ctttatccgc ctccatccag tctattaatt gttgccggga agctagagta agtagttcgc    3960
cagttaatag tttgcgcaac gttgttgcca ttgctacagg catcgtggtg tcacgctcgt    4020
cgtttggtat ggcttcattc agctccggtt cccaacgatc aaggcgagtt acatgatccc    4080
ccatgttgtg caaaaaagcg gttagctcct tcggtcctcc gatcgttgtc agaagtaagt    4140
tggccgcagt gttatcactc atggttatgg cagcactgca taattctctt actgtcatgc    4200
catccgtaag atgcttttct gtgactggtg agtactcaac caagtcattc tgagaatagt    4260
gtatgcggcg accgagttgc tcttgcccgg cgtcaatacg ggataatacc gcgccacata    4320
gcagaacttt aaaagtgctc atcattggaa aacgttcttc ggggcgaaaa ctctcaagga    4380
tcttaccgct gttgagatcc agttcgatgt aacccactcg tgcacccaac tgatcttcag    4440
catcttttac tttcaccagc gtttctgggt gagcaaaaac aggaaggcaa aatgccgcaa    4500
aaaagggaat aagggcgaca cggaaatgtt gaatactcat actcttcctt tttcaatatt    4560
attgaagcat ttatcagggt tattgtctca tgagcggata catatttgaa tgtatttaga    4620
aaaataaaca ataggggtt ccgcgcacat ttccccgaaa agtgccacct gacgtctaag    4680
aaaccattat tatcatgaca ttaacctata aaaataggcg tatcacgagg ccctttcgtc    4740
```

<210> SEQ ID NO 152
<211> LENGTH: 4746
<212> TYPE: DNA
<213> ORGANISM: E. coli

<400> SEQUENCE: 152

```
tcgcgcgttt cggtgatgac ggtgaaaacc tctgacacat gcagctcccg gagacggtca      60
```

```
cagcttgtct gtaagcggat gccgggagca gacaagcccg tcaggcgcg tcagcgggtg      120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttaattaa tctttctgcg     420
aattgagatg acgccactgg ctgggcgtca tcccggtttc ccgggtaaac accaccgaaa     480
aatagttact atcttcaaag ccacattcgg tcgaaatatc actgattaac aggcggctat     540
gctggagaag atattgcgca tgacacactc tgacctgtcg cagatattga ttgatggtca     600
ttccagtctg ctggcgaaat tgctgacgca aaacgcgctc actgcacgat gcctcatcac     660
aaaatttatc cagcgcaaag ggacttttca ggctagccgc cagccgggta atcagcttat     720
ccagcaacgt ttcgctggat gttggcggca acgaatcact ggtgtaacga tggcgattca     780
gcaacatcac caactgcccg aacagcaact cagccatttc gttagcaaac ggcacatgct     840
gactactttc atgctcaagc tgaccgataa cctgccgcgc ctgcgccatc ccatgctac      900 ctaagcgcca gtgtggttgc cctgcgctgg cgttaaatcc cggaatcgcc cctgccagt      960 caagattcag cttcagacgc tccgggcaat aaataatatt ctgcaaaacc agatcgttaa    1020
cggaagcgta ggagtgttta tcgtcagcat gaatgtaaaa gagatcgcca cgggtaatgc    1080
gataagggcg atcgttgagt acatgcaggc cattaccgcg ccagacaatc accagctcac    1140
aaaaatcatg tgtatgttca gcaaagacat cttgcggata acggtcagcc acagcgactg    1200
cctgctggtc gctggcaaaa aaatcatctt tgagaagttt taactgatgc gccaccgtgg    1260
ctacctcggc cagagaacga agttgattat tcgcaatatg gcgtacaaat acgttgagaa    1320
gattcgcgtt attgcagaaa gccatcccgt ccctggcgaa tatcacgcgg tgaccagtta    1380
aactctcggc gaaaaagcgt cgaaaagtgg ttactgtcgc tgaatccaca gcgataggcg    1440
atgtcagtaa cgctggcctc gctgtggcgt agcagatgtc gggctttcat cagtcgcagg    1500
cggttcaggt atcgctgagg cgtcagtccc gtttgctgct taagctgccg atgtagcgta    1560
cgcagtgaaa gagaaaattg atccgccacg gcatcccaat tcacctcatc ggcaaaatgg    1620
tcctccagcc aggccagaag caagttgaga cgtgatgcgc tgttttccag gttctcctgc    1680
aaactgcttt tacgcagcaa gagcagtaat tgcataaaca agatctcgcg actggcggtc    1740
gagggtaaat cattttcccc ttcctgctgt tccatctgtg caaccagctg tcgcacctgc    1800
tgcaatacgc tgtggttaac gcgccagtga acggatact gcccatccag ctcttgtggc     1860
agcaactgat tcagcccggc gagaaactga atcgatccg gcgagcgata cagcacattg     1920
gtcagacaca gattatcggt atgttcatac agatgccgat catgatcgcg tacgaaacag    1980
accgtgccac cggtgatggt atagggctgc ccattaaaca catgaatacc cgtgccatgt    2040
tcgacaatca caatttcatg aaaatcatga tgatgttcag gaaaatccgc ctgcgggagc    2100
cggggttcta tcgccacgga cgcgttacca gacggaaaaa aatccacact atgtaatacg    2160
gtcatactgg cctcctgatg tcgtcaacac ggcgaaatag taatcacgag gtcaggttct    2220
taccttaaat tttcgacgga aaaccacgta aaaaacgtcg atttttcaag atacagcgtg    2280
aattttcagg aaatgcggtg agcatcacat caccacaatt cagcaaattg tgaacatcat    2340
cacgttcatc tttccctggt tgccaatggc ccatttcct gtcagtaacg agaaggtcgc     2400
gaattcaggc gcttttagaa ctggtcgtaa tgaaattcag gaggttctgc aggtcgactc    2460
```

```
tagaggatcc ccgcgccctc atccgaaagg gcgtattggt accgagctcg aattcgtaat   2520
catggtcata gctgtttcct gtgtgaaatt gttatccgct cacaattcca cacaacatac   2580
gagccggaag cataaagtgt aaagcctggg gtgcctaatg agtgagctaa ctcacattaa   2640
ttgcgttgcg ctcactgccc gctttccagt cgggaaacct gtcgtgccag ctgcattaat   2700
gaatcggcca acgcgcgggg agaggcggtt tgcgtattgg gcgctcttcc gcttcctcgc   2760
tcactgactc gctgcgctcg gtcgttcggc tgcggcgagc ggtatcagct cactcaaagg   2820
cggtaatacg gttatccaca gaatcagggg ataacgcagg aaagaacatg tgagcaaaag   2880
gccagcaaaa ggccaggaac cgtaaaaagg ccgcgttgct ggcgtttttc cataggctcc   2940
gcccccctga cgagcatcac aaaaatcgac gctcaagtca gaggtggcga aacccgacag   3000
gactataaag ataccaggcg tttccccctg gaagctccct cgtgcgctct cctgttccga   3060
ccctgccgct taccggatac ctgtccgcct ttctcccttc gggaagcgtg gcgctttctc   3120
atagctcacg ctgtaggtat ctcagttcgg tgtaggtcgt tcgctccaag ctgggctgtg   3180
tgcacgaacc ccccgttcag cccgaccgct gcgccttatc cggtaactat cgtcttgagt   3240
ccaacccggt aagacacgac ttatcgccac tggcagcagc cactggtaac aggattagca   3300
gagcgaggta tgtaggcggt gctacagagt tcttgaagtg gtggcctaac tacggctaca   3360
ctagaaggac agtatttggt atctgcgctc tgctgaagcc agttaccttc ggaaaaagag   3420
ttggtagctc ttgatccggc aaacaaacca ccgctggtag cggtggtttt tttgtttgca   3480
agcagcagat tacgcgcaga aaaaaggat ctcaagaaga tcctttgatc ttttctacgg   3540
ggtctgacgc tcagtggaac gaaaactcac gttaagggat tttggtcatg agattatcaa   3600
aaaggatctt cacctagatc cttttaaatt aaaaatgaag ttttaaatca atctaaagta   3660
tatatgagta aacttggtct gacagttacc aatgcttaat cagtgaggca cctatctcag   3720
cgatctgtct atttcgttca tccatagttg cctgactccc cgtcgtgtag ataactacga   3780
tacgggaggg cttaccatct ggccccagtg ctgcaatgat accgcgagac ccacgctcac   3840
cggctccaga tttatcagca ataaaccagc cagccggaag ggccgagcgc agaagtggtc   3900
ctgcaacttt atccgcctcc atccagtcta ttaattgttg ccgggaagct agagtaagta   3960
gttcgccagt taatagtttg cgcaacgttg ttgccattgc tacaggcatc gtggtgtcac   4020
gctcgtcgtt tggtatggct tcattcagct ccggttccca acgatcaagg cgagttacat   4080 gatccccat gttgtgcaaa aaagcggtta gctccttcgg tcctccgatc gttgtcagaa   4140
gtaagttggc cgcagtgtta tcactcatgg ttatggcagc actgcataat tctcttactg   4200
tcatgccatc cgtaagatgc ttttctgtga ctggtgagta ctcaaccaag tcattctgag   4260
aatagtgtat gcggcgaccg agttgctctt gcccggcgtc aatacgggat aataccgcgc   4320
cacatagcag aactttaaaa gtgctcatca ttggaaaacg ttcttcgggg cgaaaactct   4380
caaggatctt accgctgttg agatccagtt cgatgtaacc cactcgtgca cccaactgat   4440
cttcagcatc ttttactttc accagcgttt ctgggtgagc aaaaacagga aggcaaaatg   4500
ccgcaaaaaa gggaataagg gcgacacgga aatgttgaat actcatactc ttcctttttc   4560
aatattattg aagcatttat cagggttatt gtctcatgag cggatacata tttgaatgta   4620
tttagaaaaa taaacaaata ggggttccgc gcacatttcc ccgaaaagtg ccacctgacg   4680
tctaagaaac cattattatc atgacattaa cctataaaaa taggcgtatc acgaggccct   4740
ttcgtc                                                              4746
```

-continued

<210> SEQ ID NO 153
<211> LENGTH: 3946
<212> TYPE: DNA
<213> ORGANISM: E. coli

<400> SEQUENCE: 153

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccaa gcttcaagcc gtcaattgtc | 420 |
| tgattcgtta ccaattatga caacttgacg gctacatcat tcactttttc ttcacaaccg | 480 |
| gcacggaact cgctcgggct ggccccggtg cattttttaa atacccgcga gaatagagt | 540 |
| tgatcgtcaa accaacatt gcgaccgacg gtggcgatag catccgggt ggtgctcaaa | 600 |
| agcagcttcg cctggctgat acgttggtcc tcgcgccagc ttaagacgct aatccctaac | 660 |
| tgctggcgga aagatgtga cagacgcgac ggcgacaagc aaacatgctg tgcgacgctg | 720 |
| gcgatatcaa aattgctgtc tgccaggtga tcgctgatgt actgacaagc ctcgcgtacc | 780 |
| cgattatcca tcggtggatg gagcgactcg ttaatcgctt ccatgcgccg cagtaacaat | 840 |
| tgctcaagca gatttatcgc cagcagctcc gaatagcgcc cttccccttg cccggcgtta | 900 |
| atgatttgcc caaacaggtc gctgaaatgc ggctggtgcg cttcatccgg gcgaaagaac | 960 |
| cccgtattgg caaatattga cggccagtta agccattcat gccagtaggc gcgcggacga | 1020 |
| aagtaaaccc actggtgata ccattcgcga gcctccggat gacgaccgta gtgatgaatc | 1080 |
| tctcctggcg ggaacagcaa aatatcaccc ggtcggcaaa caattctcg tccctgattt | 1140 |
| ttcaccaccc cctgaccgcg aatggtgaga ttgagaatat aacctttcat tcccagcggt | 1200 |
| cggtcgataa aaaatcgag ataaccgttg gcctcaatcg gcgttaaacc cgccaccaga | 1260 |
| tgggcattaa acgagtatcc cggcagcagg ggatcatttt gcgcttcagc catacttttc | 1320 |
| atactcccgc cattcagaga agaaaccaat tgtccatatt gcatcagaca ttgccgtcac | 1380 |
| tgcgtctttt actggctctt ctcgctaacc aaaccggtaa ccccgcttat taaaagcatt | 1440 |
| ctgtaacaaa gcgggaccaa agccatgaca aaaacgcgta acaaaagtgt ctataatcac | 1500 |
| ggcagaaaag tccacattga ttatttgcac ggcgtcacac tttgctatgc catagcattt | 1560 |
| ttatccataa gattagcgga tcctacctga cgctttttat cgcaactctc tactgtttct | 1620 |
| ccatacccgt ttttttgggc tagcaggagg ccgtcgactc tagaggatcc ccgcgccctc | 1680 |
| atccgaaagg gcgtattggt accgagctcg aattcgtaat catggtcata gctgtttcct | 1740 |
| gtgtgaaatt gttatccgct cacaattcca cacaacatac gagccggaag cataaagtgt | 1800 |
| aaagcctggg gtgcctaatg agtgagctaa ctcacattaa ttgcgttgcg ctcactgccc | 1860 |
| gctttccagt cgggaaacct gtcgtgccag ctgcattaat gaatcggcca acgcgcgggg | 1920 |
| agaggcggtt tgcgtattgg gcgctcttcc gcttcctcgc tcactgactc gctgcgctcg | 1980 |
| gtcgttcggc tgcggcgagc ggtatcagct cactcaaagg cggtaatacg ttatccaca | 2040 |
| gaatcagggg ataacgcagg aaagaacatg tgagcaaaag gccagcaaaa ggccaggaac | 2100 |
| cgtaaaaagg ccgcgttgct ggcgtttttc cataggctcc gccccctga cgagcatcac | 2160 |
| aaaaatcgac gctcaagtca gaggtggcga aacccgacag gactataaag ataccaggcg | 2220 |

-continued

| | |
|---|---|
| tttccccctg gaagctccct cgtgcgctct cctgttccga ccctgccgct taccggatac | 2280 |
| ctgtccgcct ttctcccttc gggaagcgtg gcgctttctc atagctcacg ctgtaggtat | 2340 |
| ctcagttcgg tgtaggtcgt tcgctccaag ctgggctgtg tgcacgaacc ccccgttcag | 2400 |
| cccgaccgct gcgccttatc cggtaactat cgtcttgagt ccaacccggt aagacacgac | 2460 |
| ttatcgccac tggcagcagc cactggtaac aggattagca gagcgaggta tgtaggcggt | 2520 |
| gctacagagt tcttgaagtg gtggcctaac tacggctaca ctagaaggac agtatttggt | 2580 |
| atctgcgctc tgctgaagcc agttaccttc ggaaaaagag ttggtagctc ttgatccggc | 2640 |
| aaacaaacca ccgctggtag cggtggtttt tttgtttgca agcagcagat tacgcgcaga | 2700 |
| aaaaaaggat ctcaagaaga tcctttgatc ttttctacgg ggtctgacgc tcagtggaac | 2760 |
| gaaaactcac gttaagggat tttggtcatg agattatcaa aaaggatctt cacctagatc | 2820 |
| cttttaaatt aaaaatgaag ttttaaatca atctaaagta tatatgagta aacttggtct | 2880 |
| gacagttacc aatgcttaat cagtgaggca cctatctcag cgatctgtct atttcgttca | 2940 |
| tccatagttg cctgactccc cgtcgtgtag ataactacga tacgggaggg cttaccatct | 3000 |
| ggccccagtg ctgcaatgat accgcgagac ccacgctcac cggctccaga tttatcagca | 3060 |
| ataaaccagc cagccggaag ggccgagcgc agaagtggtc ctgcaacttt atccgcctcc | 3120 |
| atccagtcta ttaattgttg ccgggaagct agagtaagta gttcgccagt taatagtttg | 3180 |
| cgcaacgttg ttgccattgc tacaggcatc gtggtgtcac gctcgtcgtt tggtatggct | 3240 |
| tcattcagct ccggttccca acgatcaagg cgagttacat gatcccccat gttgtgcaaa | 3300 |
| aaagcggtta gctccttcgg tcctccgatc gttgtcagaa gtaagttggc cgcagtgtta | 3360 |
| tcactcatgg ttatggcagc actgcataat tctcttactg tcatgccatc cgtaagatgc | 3420 |
| ttttctgtga ctggtgagta ctcaaccaag tcattctgag aatagtgtat gcggcgaccg | 3480 |
| agttgctctt gcccggcgtc aatacggat aataccgcgc cacatagcag aactttaaaa | 3540 |
| gtgctcatca ttggaaaacg ttcttcgggg cgaaaactct caaggatctt accgctgttg | 3600 |
| agatccagtt cgatgtaacc cactcgtgca cccaactgat cttcagcatc ttttactttc | 3660 |
| accagcgttt ctgggtgagc aaaaacagga aggcaaaatg ccgcaaaaaa gggaataagg | 3720 |
| gcgacacgga aatgttgaat actcatactc ttcctttttc aatattattg aagcatttat | 3780 |
| cagggttatt gtctcatgag cggatacata tttgaatgta tttagaaaaa taaacaaata | 3840 |
| ggggttccgc gcacatttcc ccgaaaagtg ccacctgacg tctaagaaac cattattatc | 3900 |
| atgacattaa cctataaaaa taggcgtatc acgaggccct ttcgtc | 3946 |

<210> SEQ ID NO 154
<211> LENGTH: 3952
<212> TYPE: DNA
<213> ORGANISM: E. coli

<400> SEQUENCE: 154

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccaa gcttcaagcc gtcaattgtc | 420 |

-continued

```
tgattcgtta ccaattatga caacttgacg gctacatcat tcactttttc ttcacaaccg    480
gcacggaact cgctcgggct ggccccggtg catttttaa atacccgcga gaaatagagt    540
tgatcgtcaa aaccaacatt gcgaccgacg gtggcgatag gcatccgggt ggtgctcaaa    600
agcagcttcg cctggctgat acgttggtcc tcgcgccagc ttaagacgct aatccctaac    660
tgctggcgga aaagatgtga cagacgcgac ggcgacaagc aaacatgctg tgcgacgctg    720
gcgatatcaa aattgctgtc tgccaggtga tcgctgatgt actgacaagc ctcgcgtacc    780
cgattatcca tcggtggatg gagcgactcg ttaatcgctt ccatgcgccg cagtaacaat    840
tgctcaagca gatttatcgc cagcagctcc gaatagcgcc cttccccttg cccggcgtta    900
atgatttgcc caaacaggtc gctgaaatgc ggctggtgcg cttcatccgg gcgaaagaac    960
cccgtattgg caaatattga cggccagtta agccattcat gccagtaggc gcgcggacga   1020
aagtaaaccc actggtgata ccattcgcga gcctccggat gacgaccgta gtgatgaatc   1080
tctcctggcg ggaacagcaa aatatcaccc ggtcggcaaa caaattctcg tccctgattt   1140
ttcaccaccc cctgaccgcg aatggtgaga ttgagaatat aacctttcat tcccagcggt   1200
cggtcgataa aaaaatcgag ataaccgttg gcctcaatcg gcgttaaacc cgccaccaga   1260
tgggcattaa acgagtatcc cggcagcagg ggatcatttt gcgcttcagc catacttttc   1320
atactcccgc cattcagaga agaaaccaat tgtccatatt gcatcagaca ttgccgtcac   1380
tgcgtctttt actggctctt ctcgctaacc aaaccggtaa ccccgcttat taaaagcatt   1440
ctgtaacaaa gcgggaccaa agccatgaca aaaacgcgta acaaaagtgt ctataatcac   1500
ggcagaaaag tccacattga ttatttgcac ggcgtcacac tttgctatgc catagcattt   1560
ttatccataa gattagcgga tcctacctga cgcttttat cgcaactctc tactgtttct   1620
ccatacccgt ttttttgggc tagcaggagg ccctgcaggt cgactctaga ggatccccgc   1680
gccctcatcc gaaagggcgt attggtaccg agctcgaatt cgtaatcatg gtcatagctg   1740
tttcctgtgt gaaattgtta tccgctcaca attccacaca acatacgagc cggaagcata   1800
aagtgtaaag cctggggtgc ctaatgagtg agctaactca cattaattgc gttgcgctca   1860
ctgcccgctt tccagtcggg aaacctgtcg tgccagctgc attaatgaat cggccaacgc   1920
gcggggagag gcggtttgcg tattgggcgc tcttccgctt cctcgctcac tgactcgctg   1980
cgctcggtcg ttcggctgcg gcgagcggta tcagctcact caaaggcggt aatacggtta   2040
tccacagaat caggggataa cgcaggaaag aacatgtgag caaaaggcca gcaaaaggcc   2100
aggaaccgta aaaaggccgc gttgctggcg tttttccata ggctccgccc ccctgacgag   2160
catcacaaaa atcgacgctc aagtcagagg tggcgaaacc cgacaggact ataaagatac   2220
caggcgtttc cccctggaag ctccctcgtg cgctctcctg ttccgaccct gccgcttacc   2280
ggatacctgt ccgcctttct cccttcggga agcgtggcgc tttctcatag ctcacgctgt   2340
aggtatctca gttcggtgta ggtcgttcgc tccaagctgg gctgtgtgca cgaaccccc    2400 gttcagcccg accgctgcgc cttatccggt aactatcgtc ttgagtccaa cccggtaaga   2460
cacgacttat cgccactggc agcagccact ggtaacagga ttagcagagc gaggtatgta   2520
ggcggtgcta cagagttctt gaagtggtgg cctaactacg gctacactag aaggacagta   2580
tttggtatct gcgctctgct gaagccagtt accttcggaa aaagagttgg tagctcttga   2640
tccggcaaac aaaccaccgc tggtagcggt ggtttttttg tttgcaagca gcagattacg   2700
cgcagaaaaa aaggatctca agaagatcct ttgatctttt ctacgggtc tgacgctcag    2760 tggaacgaaa actcacgtta agggattttg gtcatgagat tatcaaaaag gatcttcacc   2820
```

-continued

```
tagatccttt taaattaaaa atgaagtttt aaatcaatct aaagtatata tgagtaaact    2880
tggtctgaca gttaccaatg cttaatcagt gaggcaccta tctcagcgat ctgtctattt    2940
cgttcatcca tagttgcctg actccccgtc gtgtagataa ctacgatacg ggagggctta    3000
ccatctggcc ccagtgctgc aatgataccg cgagacccac gctcaccggc tccagattta    3060
tcagcaataa accagccagc cggaagggcc gagcgcagaa gtggtcctgc aactttatcc    3120
gcctccatcc agtctattaa ttgttgccgg gaagctagag taagtagttc gccagttaat    3180
agtttgcgca acgttgttgc cattgctaca ggcatcgtgg tgtcacgctc gtcgtttggt    3240
atggcttcat tcagctccgg ttcccaacga tcaaggcgag ttacatgatc ccccatgttg    3300
tgcaaaaaag cggttagctc cttcggtcct ccgatcgttg tcagaagtaa gttggccgca    3360
gtgttatcac tcatggttat ggcagcactg cataattctc ttactgtcat gccatccgta    3420
agatgctttt ctgtgactgg tgagtactca accaagtcat tctgagaata gtgtatgcgg    3480
cgaccgagtt gctcttgccc ggcgtcaata cgggataata ccgcgccaca tagcagaact    3540
ttaaaagtgc tcatcattgg aaaacgttct cggggcgaaa actctcaag gatcttaccg    3600
ctgttgagat ccagttcgat gtaacccact cgtgcaccca actgatcttc agcatctttt    3660
actttcacca gcgtttctgg gtgagcaaaa acaggaaggc aaaatgccgc aaaaaaggga    3720
ataagggcga cacggaaatg ttgaatactc atactcttcc ttttcaata ttattgaagc    3780
atttatcagg gttattgtct catgagcgga tacatatttg aatgtattta gaaaaataaa    3840
caaatagggg ttccgcgcac atttccccga aaagtgccac ctgacgtcta agaaaccatt    3900
attatcatga cattaaccta taaaaatagg cgtatcacga ggccctttcg tc            3952
```

<210> SEQ ID NO 155
<211> LENGTH: 3886
<212> TYPE: DNA
<213> ORGANISM: E. coli

<400> SEQUENCE: 155

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttttagcc gggaaacgtc    420
tggcggcgct gttggctaag tttgcggtat tgttgcggcg acatgccgac atatttgccg    480
aacgtgctgt aaaaacgact acttgaacga aagcctgccg tcaggcaat atcgagaata    540
ctttatcgg tatcgctcag taacgcgcga acgtggttga tgcgcatcgc ggtaatgtac    600
tgtttcatcg tcaattgcat gacccgctgg aatatcccca ttgcatagtt ggcgttaagt    660
ttgacgtgct cagccacatc gttgatggtc agcgcctgat catagttttc ggcaataaag    720
cccagcatct ggctaacata aaattgcgca tggcgcgaga cgctgttttt gtgtgtgcgc    780
gaggttttat tgaccagaat cggttcccag ccagagaggc taaatcgctt gagcatcagg    840
ccaatttcat caatggcgag ctggcgaatt tgctcgttcg gactgtttaa ttcctgctgc    900
cagcggcgca cttcaaacgg gctaagttgc tgtgtggcca gtgatttgat caccatgccg    960
tgagtgacgt ggttaatcag gtctttatcc agcggccagg agagaaacag atgcatcggc   1020
```

-continued

```
agattaaaaa tcgccatgct ctgacaggtt ccggtatctg ttagttggtg cggtgtacag      1080
gcccagaaca gcgtgatatg accctgattg atattcactt tttcattgtt gatcaggtat      1140
tccacatcgc catcgaaagg cacattcact tcgacctgac catgccagtg gctggtgggc      1200
atgatatgcg gtgcgcgaaa ctcaatctcc atccgctggt attccgaata cagcgacagc      1260
gggctgcggg tctgttttc gtcgctgctg cacataaacg tatctgtatt catggatggc       1320
tctctttcct ggaatatcag aattatggca ggagtgaggg aggatgactg cgagtgggag      1380
cacggttttc accctcttcc cagaggggcg aggggactct ccgagtatca tgaggccgaa      1440
aactctgctt ttcaggtaat ttattcccat aaactcagat ttactgctgc ttcacgcagg      1500
atctgagttt atgggaatgc tcaacctgga agcggaggt tttctgcaga ttcgcctgcc       1560
atgatgaagt tattcaagca agccaggagg tcgtcgactc tagaggatcc ccgcgccctc      1620
atccgaaagg gcgtattggt accgagctcg aattcgtaat catggtcata gctgtttcct      1680
gtgtgaaatt gttatccgct cacaattcca cacaacatac gagccggaag cataaagtgt      1740
aaagcctggg gtgcctaatg agtgagctaa ctcacattaa ttgcgttgcg ctcactgccc      1800
gctttccagt cgggaaacct gtcgtgccag ctgcattaat gaatcggcca acgcgcgggg      1860
agaggcggtt tgcgtattgg gcgctcttcc gcttcctcgc tcactgactc gctgcgctcg      1920
gtcgttcggc tgcggcgagc ggtatcagct cactcaaagg cggtaatacg gttatccaca      1980
gaatcagggg ataacgcagg aaagaacatg tgagcaaaag gccagcaaaa ggccaggaac      2040
cgtaaaaagg ccgcgttgct ggcgtttttc cataggctcc gcccccctga cgagcatcac      2100
aaaaatcgac gctcaagtca gaggtggcga aacccgacag gactataaag ataccaggcg      2160
tttccccctg gaagctccct cgtgcgctct cctgttccga ccctgccgct taccggatac      2220
ctgtccgcct ttctcccttc gggaagcgtg gcgctttctc atagctcacg ctgtaggtat      2280
ctcagttcgg tgtaggtcgt tcgctccaag ctgggctgtg tgcacgaacc ccccgttcag      2340
cccgaccgct gcgccttatc cggtaactat cgtcttgagt ccaacccggt aagacacgac      2400
ttatcgccac tggcagcagc cactggtaac aggattagca gagcgaggta tgtaggcggt      2460
gctacagagt tcttgaagtg gtggcctaac tacggctaca ctagaaggac agtatttggt      2520
atctgcgctc tgctgaagcc agttaccttc ggaaaaagag ttggtagctc ttgatccggc      2580
aaacaaacca ccgctggtag cggtggtttt tttgtttgca agcagcagat tacgcgcaga      2640
aaaaaaggat ctcaagaaga tcctttgatc ttttctacgg ggtctgacgc tcagtggaac      2700
gaaaactcac gttaagggat tttggtcatg agattatcaa aaaggatctt cacctagatc      2760
cttttaaatt aaaaatgaag ttttaaatca atctaaagta tatatgagta aacttggtct      2820
gacagttacc aatgcttaat cagtgaggca cctatctcag cgatctgtct atttcgttca      2880
tccatagttg cctgactccc cgtcgtgtag ataactacga tacggagggc ttaccatct      2940 ggccccagtg ctgcaatgat accgcgagac ccacgctcac cggctccaga tttatcagca      3000
ataaaccagc cagccggaag ggccgagcgc agaagtggtc ctgcaacttt atccgcctcc      3060
atccagtcta ttaattgttg ccgggaagct agagtaagta gttcgccagt taatagtttg      3120
cgcaacgttg ttgccattgc tacaggcatc gtggtgtcac gctcgtcgtt tggtatggct      3180
tcattcagct ccggttccca acgatcaagg cgagttacat gatcccccat gttgtgcaaa      3240
aaagcggtta gctccttcgg tcctccgatc gttgtcagaa gtaagttggc cgcagtgtta      3300
tcactcatgg ttatggcagc actgcataat tctcttactg tcatgccatc cgtaagatgc      3360
ttttctgtga ctggtgagta ctcaaccaag tcattctgag aatagtgtat gcggcgaccg      3420
```

```
agttgctctt gcccggcgtc aatacgggat aataccgcgc cacatagcag aactttaaaa    3480
gtgctcatca ttggaaaacg ttcttcgggg cgaaaactct caaggatctt accgctgttg    3540
agatccagtt cgatgtaacc cactcgtgca cccaactgat cttcagcatc ttttactttc    3600
accagcgttt ctgggtgagc aaaaacagga aggcaaaatg ccgcaaaaaa gggaataagg    3660
gcgacacgga aatgttgaat actcatactc ttccttttc aatattattg aagcatttat    3720
cagggttatt gtctcatgag cggatacata tttgaatgta tttagaaaaa taaacaaata    3780
ggggttccgc gcacatttcc ccgaaaagtg ccacctgacg tctaagaaac cattattatc    3840
atgacattaa cctataaaaa taggcgtatc acgaggccct ttcgtc                   3886
```

<210> SEQ ID NO 156
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 156

```
gcagaacctc ctgaatttca ttacgacc                                          28
```

<210> SEQ ID NO 157
<211> LENGTH: 86
<212> TYPE: DNA
<213> ORGANISM: Artificial Sequence
<220> FEATURE:
<223> OTHER INFORMATION: Synthetic oligonucleotide primer sequence

<400> SEQUENCE: 157

```
ccgcgggtac caatacgccc tttcggatga gggcgcgggg atcctctaga gtcgacgtcg    60
acaacctcct gaatttcatt acgacc                                          86
```

<210> SEQ ID NO 158
<211> LENGTH: 86
<212> TYPE: DNA
<213> ORGANISM: Artificial Sequence
<220> FEATURE:
<223> OTHER INFORMATION: Synthetic oligonucleotide primer sequence

<400> SEQUENCE: 158

```
ccgcgggtac caatacgccc tttcggatga gggcgcgggg atcctctaga gtcgacctgc    60
agaacctcct gaatttcatt acgacc                                          86
```

<210> SEQ ID NO 159
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 159

```
ctgcagggcc tcctgctagc ccaaaaaaac gggtatgg                              38
```

<210> SEQ ID NO 160
<211> LENGTH: 94
<212> TYPE: DNA
<213> ORGANISM: Artificial Sequence
<220> FEATURE:
<223> OTHER INFORMATION: Synthetic oligonucleotide primer sequence

<400> SEQUENCE: 160

```
ccgcgggtac caatacgccc tttcggatga gggcgcgggg atcctctaga gtcgacgtcg    60
```
acggcctcct gctagcccaa aaaaacgggt atgg                                94

<210> SEQ ID NO 161
<211> LENGTH: 94
<212> TYPE: DNA
<213> ORGANISM: Artificial Sequence
<220> FEATURE:
<223> OTHER INFORMATION: Synthetic oligonucleotide primer sequence

<400> SEQUENCE: 161
ccgcgggtac caatacgccc tttcggatga gggcgcgggg atcctctaga gtcgacctgc    60
agggcctcct gctagcccaa aaaaacgggt atgg                                94

<210> SEQ ID NO 162
<211> LENGTH: 32
<212> TYPE: DNA
<213> ORGANISM: Artificial Sequence
<220> FEATURE:
<223> OTHER INFORMATION: Synthetic oligonucleotide primer sequence

<400> SEQUENCE: 162
cctcctggct tgcttgaata acttcatcat gg                                  32

<210> SEQ ID NO 163
<211> LENGTH: 91
<212> TYPE: DNA
<213> ORGANISM: Artificial Sequence
<220> FEATURE:
<223> OTHER INFORMATION: Synthetic oligonucleotide primer sequence

<400> SEQUENCE: 163
ccgcgggtac caatacgccc tttcggatga gggcgcgggg atcctctaga gtcgaccccc    60
tcctggcttg cttgaataac ttcatcatgg c                                   91

<210> SEQ ID NO 164

<400> SEQUENCE: 164

000

<210> SEQ ID NO 165

<400> SEQUENCE: 165

000

<210> SEQ ID NO 166
<211> LENGTH: 2319
<212> TYPE: DNA
<213> ORGANISM: Artificial Sequence
<220> FEATURE:
<223> OTHER INFORMATION: Synthetic nucleic acid sequence

<400> SEQUENCE: 166
gtcgacatga aaataaaaac aggtgcacgc atcctcgcat tatccgcatt aacgacgatg    60 atgtttccg cctcggctct cgccaaaatc gaagaaggta actggtaat ctggattaac     120 ggcgataaag gctataacgg tctcgctgaa gtcggtaaga aattcgagaa agataccgga   180
attaaagtca ccgttgagca tccgataaa ctggaagaga aattcccaca ggttgcggca    240
actggcgatg gccctgacat tatcttctgg gcacacgacc gctttggtgg ctacgctcaa   300
tctggcctgt tggctgaaat cacccccgac aaagcgttcc aggacaagct gtatccgttt   360
acctgggatg ccgtacgtta caacggcaag ctgattgctt acccgatcgc tgttgaagcg   420

```
ttatcgctga tttataacaa agatctgctg ccgaacccgc caaaaacctg ggaagagatc      480
ccggcgctgg ataaagaact gaaagcgaaa ggtaagagcg cgctgatgtt caacctgcaa      540
gaaccgtact tcacctggcc gctgattgct gctgacgggg gttatgcgtt caagtatgaa      600
aacggcaagt acgacattaa agacgtgggc gtggataacg ctggcgcgaa agcgggtctg      660
accttcctgg ttgacctgat taaaaacaaa cacatgaatg cagacaccga ttactccatc      720
gcagaagctg cctttaataa aggcgaaaca gcgatgacca tcaacggccc gtgggcatgg      780
tccaacatcg acaccagcaa agtgaattat ggtgtaacgg tactgccgac cttcaagggt      840
caaccatcca aaccgttcgt tggcgtgctg agcgcaggta ttaacgccgc cagtccgaac      900
aaagagctgg cgaaagagtt cctcgaaaac tatctgctga ctgatgaagg tctggaagcg      960
gttaataaag acaaaccgct gggtgccgta gcgctgaagt cttacgagga agagttggcg     1020
aaagatccac gtattgccgc caccatgaaa aacgcccaga aggtgaaat catgccgaac     1080 atcccgcaga tgtccgcttt ctggtatgcc gtgctgatcg aagcccgcac ctcggaatcc     1140
gacacggcag ggcccaacag cgacctggac gtgaacactg acatttattc caaggtgctg     1200
gtgactgcta tacctggc actcttcgt gtgggcactg tgggcaactc cgtgacagcc     1260
ttcactctag cgcggaagaa gtcactgcag agcctgcaga gcactgtgca ttaccacctg     1320
ggcagcctgg cactgtcgga cctgcttatc cttctgctgg ccatgcccgt ggagctatac     1380
aacttcatct gggtacacca tccctgggcc tttggggacg ctggctgccg tggctactat     1440
ttcctgcgtg atgcctgcac ctatgccaca gccctcaatg tagccagcct gagtgtggag     1500
cgctacttgg ccatctgcca tcccttcaag gccaagaccc tcatgtcccg cagccgcacc     1560
aagaaattca tcagtgccat atggctagct tcggcgctgc tggctatacc catgcttttc     1620
accatgggcc tgcagaaccg cagtggtgac ggcacgcacc ctggcggcct ggtgtgcaca     1680
cccattgtgg acacagccac tgtcaaggtc gtcatccagg ttaacaccttt catgtccttc     1740 ctgtttccca tgttggtcat ctccatccta aacaccgtga ttgccaacaa actgacagtc     1800
atggtgcacc aggccgccga gcagggccga gtgtgcaccg tgggcacaca caacggttta     1860
gagcacagca cgttcaacat gaccatcgag ccgggtcgtg tccaggccct gcgccacgga     1920
gtcctcgtct tacgtgctgt ggtcattgcc tttgtggtct gctggctgcc ctaccacgtg     1980
cgacgcctga tgttctgcta tatctcggat gaacagtgga ctacgttcct cttcgatttc     2040
taccactatt tctacatgct aaccaacgct ctcttctacg tcagctccgc catcaatccc     2100
atcctctaca acctggtctc cgccaacttc cgccaggtct ttctgtccac gctggcctgc     2160
ctttgtcctg ggtggcgcca ccgccgaaag aagaggccaa cgttctccag gaagcccaac     2220
agcatgtcca gcaaccatgc cttttccacc agcgccaccc gggagaccct gtacgcggcc     2280
gcagattata aagatgacga tgacaaataa taaggtacc                            2319

<210> SEQ ID NO 167
<211> LENGTH: 1293
<212> TYPE: DNA
<213> ORGANISM: Artificial Sequence
<220> FEATURE:
<223> OTHER INFORMATION: Synthetic nucleic acid sequence

<400> SEQUENCE: 167
gtcgacatga aaataaaaac aggtgcacgc atcctcgcat tatccgcatt aacgacgatg       60
atgttttccg cctcggctct cgccaaaatc atcgaagccc gcacctcgga atccgacacg      120
gcagggccca acagcgacct ggacgtgaac actgacattt attccaaggt gctggtgact      180
```

```
gctatatacc tggcactctt cgtggtgggc actgtgggca actccgtgac agccttcact    240
ctagcgcgga agaagtcact gcagagcctg cagagcactg tgcattacca cctgggcagc    300
ctggcactgt cggacctgct tatccttctg ctggccatgc ccgtggagct atacaacttc    360
atctgggtac accatccctg ggcctttggg gacgctggct gccgtggcta ctatttcctg    420
cgtgatgcct gcacctatgc cacagccctc aatgtagcca gcctgagtgt ggagcgctac    480
ttggccatct gccatccctt caaggccaag accctcatgt cccgcagccg caccaagaaa    540
ttcatcagtg ccatatggct agcttcggcg ctgctggcta tacccatgct ttttcaccatg   600 ggcctgcaga accgcagtgg tgacggcacg cacccctggcg gcctggtgtg cacacccatt   660
gtggacacag ccactgtcaa ggtcgtcatc caggttaaca ccttcatgtc cttcctgttt    720
cccatgttgg tcatctccat cctaaacacc gtgattgcca caaaactgac agtcatggtg    780
caccaggccg ccgagcaggg ccgagtgtgc accgtgggca cacaacgg tttagagcac      840 agcacgttca acatgaccat cgagccgggt cgtgtccagg ccctgcgcca cggagtcctc    900
gtcttacgtg ctgtggtcat tgcctttgtg gtctgctggc tgccctacca cgtgcgacgc    960
ctgatgttct gctatatctc ggatgaacag tggactacga tcctcttcga tttctaccac   1020
tatttctaca tgctaaccaa cgctctcttc tacgtcagct ccgccatcaa tcccatcctc   1080
tacaacctgg tctccgccaa cttccgccag gtctttctgt ccacgctggc ctgccttgt    1140 cctgggtggc gccaccgccg aaagaagagg ccaacgttct ccaggaagcc aacagcatg    1200 tccagcaacc atgccttttc caccagcgcc cccgggaga ccctgtacgc ggccgcagat    1260
tataaagatg acgatgacaa ataataaggt acc                                1293

<210> SEQ ID NO 168

<400> SEQUENCE: 168

000

<210> SEQ ID NO 169
<211> LENGTH: 2652
<212> TYPE: DNA
<213> ORGANISM: Artificial Sequence
<220> FEATURE:
<223> OTHER INFORMATION: Synthetic nucleic acid sequence

<400> SEQUENCE: 169
gtcgacatga aaataaaaac aggtgcacgc atcctcgcat tatccgcatt aacgacgatg     60
atgttttccg cctcggctct cgccaaaatc gaagaaggta aactggtaat ctggattaac    120
ggcgataaag gctataacgg tctcgctgaa gtcggtaaga attcgagaa agataccgga     180 attaaagtca ccgttgagca tccggataaa ctggaagaga attcccaca ggttgcggca    240 actggcgatg cccctgacat tatcttctgg gcacacgacc gctttggtgg ctacgctcaa    300
tctggcctgt tggctgaaat caccccggac aaagcgttcc aggacaagct gtatccgttt    360
acctgggatg ccgtacgtta caacggcaag ctgattgctt acccgatcgc tgttgaagcg    420
ttatcgctga tttataacaa agatctgctg ccgaacccgc caaaacctg ggaagagatc    480 ccggcgctgg ataaagaact gaaagcgaaa ggtaagagcg cgctgatgtt caacctgcaa    540
gaaccgtact tcacctggcc gctgattgct gctgacgggg gttatgcgtt caagtatgaa    600
aacggcaagt acgacattaa agacgtgggc gtggataacg ctggcgcgaa agcgggtctg    660
accttcctgg ttgacctgat taaaaacaaa cacatgaatg cagacaccga ttactccatc    720
```

```
gcagaagctg cctttaataa aggcgaaaca gcgatgacca tcaacggccc gtgggcatgg    780
tccaacatcg acaccagcaa agtgaattat ggtgtaacgg tactgccgac cttcaagggt    840
caaccatcca aaccgttcgt tggcgtgctg agcgcaggta ttaacgccgc cagtccgaac    900
aaagagctgg cgaaagagtt cctcgaaaac tatctgctga ctgatgaagg tctggaagcg    960
gttaataaag acaaaccgct gggtgccgta gcgctgaagt cttacgagga gagttggcg    1020 aaagatccac gtattgccgc caccatggaa acgcccagaa aggtgaaat catgccgaac    1080 atcccgcaga tgtccgcttt ctggtatgcc gtgctgatcg aagcccgcac ctcggaatcc   1140
gacacggcag ggcccaacag cgacctggac gtgaacactg acatttattc caaggtgctg   1200
gtgactgcta tacctggc actcttcgtg gtgggcactg tgggcaactc cgtgacagcc    1260
ttcactctag cgcggaagaa gtcactgcag agcctgcaga gcactgtgca ttaccacctg   1320
ggcagcctgg cactgtcgga cctgcttatc cttctgctgg ccatgcccgt ggagctatac   1380
aacttcatct gggtacacca tccctgggcc tttggggacg ctggctgccg tggctactat   1440
ttcctgcgtg atgcctgcac ctatgccaca gccctcaatg tagccagcct gagtgtggag   1500
cgctacttgg ccatctgcca tcccttcaag gccaagaccc tcatgtcccg cagccgcacc   1560
aagaaattca tcagtgccat atggctagct tcggcgctgc tggctatacc catgcttttc   1620
accatgggcc tgcagaaccg cagtggtgac ggcacgcacc ctggcggcct ggtgtgcaca   1680
cccattgtgg acacagccac tgtcaaggtc gtcatccagg ttaacacctt catgtccttc   1740
ctgtttccca tgttggtcat ctccatccta aacaccgtga ttgccaacaa actgacagtc   1800
atggtgcacc aggccgccga gcagggccga gtgtgcaccg tgggcacaca caacggttta   1860
gagcacagca cgttcaacat gaccatcgag ccgggtcgtg tccaggccct gcgccacgga   1920
gtcctcgtct tacgtgctgt ggtcattgcc tttgtggtct gctggctgcc ctaccacgtg   1980
cgacgcctga tgttctgcta tatctcggat gaacagtgga ctacgttcct cttcgatttc   2040
taccactatt tctacatgct aaccaacgct ctcttctacg tcagctccgc catcaatccc   2100
atcctctaca acctggtctc cgccaacttc gccaggtct ttctgtccac gctggcctgc   2160
ctttgtcctg ggtggcgcca ccgccgaaag aagaggccaa cgttctccag gaagcccaac   2220
agcatgtcca gcaaccatgc cttttccacc agcgccaccc gggagaccct gtacgcggcc   2280
gcaagcgata aaattattca cctgactgac gacagttttg acacggatgt actcaaagcg   2340
gacggggcga tcctcgtcga tttctgggca gagtggtgcg gtccgtgcaa aatgatcgcc   2400
ccgattctgg atgaaatcgc tgacgaatat cagggcaaac tgaccgttgc aaaactgaac   2460
atcgatcaaa accctggcac tgcgccgaaa tatggcatcc gtggtatccc gactctgctg   2520
ctgttcaaaa acggtgaagt ggcggcaacc aaagtgggtg cactgtctaa aggtcagttg   2580
aaagagttcc tcgacgctaa cctggcggcg ccgcagatt ataagatga cgatgacaaa   2640 taataaggta cc    2652
```

<210> SEQ ID NO 170
<211> LENGTH: 1626
<212> TYPE: DNA
<213> ORGANISM: Artificial Sequence
<220> FEATURE:
<223> OTHER INFORMATION: Synthetic nucleic acid sequence

<400> SEQUENCE: 170

```
gtcgacatga aaataaaaac aggtgcacgc atcctcgcat tatccgcatt aacgacgatg     60
atgttttccg cctcggctct cgccaaaatc atcgaagccc gcacctcgga atccgacacg    120
```

-continued

```
gcagggccca acagcgacct ggacgtgaac actgacattt attccaaggt gctggtgact   180
gctatatacc tggcactctt cgtggtgggc actgtgggca actccgtgac agccttcact   240
ctagcgcgga agaagtcact gcagagcctg cagagcactg tgcattacca cctgggcagc   300
ctggcactgt cggacctgct tatccttctg ctggccatgc ccgtggagct atacaacttc   360
atctgggtac accatccctg ggcctttggg gacgctggct gccgtggcta ctatttcctg   420
cgtgatgcct gcacctatgc cacagccctc aatgtagcca gcctgagtgt ggagcgctac   480
ttggccatct gccatccctt caaggccaag accctcatgt cccgcagccg caccaagaaa   540
ttcatcagtg ccatatggct agcttcggcg ctgctggcta tacccatgct tttcaccatg   600
ggcctgcaga accgcagtgg tgacggcacg caccctggcg gctggtgtg cacacccatt   660
gtggacacag ccactgtcaa ggtcgtcatc caggttaaca ccttcatgtc cttcctgttt   720
cccatgttgg tcatctccat cctaaacacc gtgattgcca caaaactgac agtcatggtg   780
caccaggccg ccgagcaggg ccgagtgtgc accgtgggca cacacaacgg tttagagcac   840
agcacgttca acatgaccat cgagccgggt cgtgtccagg ccctgcgcca cggagtcctc   900
gtcttacgtg ctgtggtcat tgcctttgtg gtctgctggc tgccctacca cgtgcgacgc   960
ctgatgttct gctatatctc ggatgaacag tggactacgt tcctcttcga tttctaccac  1020
tatttctaca tgctaaccaa cgctctcttc tacgtcagct ccgccatcaa tcccatcctc  1080
tacaacctgg tctccgccaa cttccgccag gtctttctgt ccacgctggc ctgcctttgt  1140
cctgggtggc gccaccgccg aaagaagagg ccaacgttct ccaggaagcc aacagcatg  1200
tccagcaacc atgccttttc caccagcgcc acccgggaga ccctgtacgc ggccgcaagc  1260
gataaaatta ttcacctgac tgacgacagt tttgacacgg atgtactcaa agcggacggg  1320
gcgatcctcg tcgatttctg ggcagagtgg tgcggtccgt gcaaaatgat cgcccccgatt  1380
ctggatgaaa tcgctgacga atatcagggc aaactgaccg ttgcaaaact gaacatcgat  1440
caaaaccctg gcactgcgcc gaaatatggc atccgtggta tcccgactct gctgctgttc  1500
aaaaacggtg aagtggcggc aaccaaagtg gtgcactgt ctaaaggtca gttgaaagag  1560
ttcctcgacg ctaacctggc agcggccgca gattataaag atgacgatga caataataa  1620
ggtacc                                                            1626
```

```
<210> SEQ ID NO 171
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 171
ggtgcacgca tcctcgcatt atccgc                                         26

<210> SEQ ID NO 172
<211> LENGTH: 31
<212> TYPE: DNA
<213> ORGANISM: Artificial Sequence
<220> FEATURE:
<223> OTHER INFORMATION: Synthetic oligonucleotide primer sequence

<400> SEQUENCE: 172
cgcacggcat accagaaagc ggacatctgc g                                   31

<210> SEQ ID NO 173
<211> LENGTH: 43
<212> TYPE: DNA
```

```
<213> ORGANISM: Artificial Sequence
<220> FEATURE:
<223> OTHER INFORMATION: Synthetic oligonucleotide primer sequence

<400> SEQUENCE: 173
ccgcggtcga catgaaaata aaaacaggtg cacgcatcct cgc                    43

<210> SEQ ID NO 174
<211> LENGTH: 66
<212> TYPE: DNA
<213> ORGANISM: Artificial Sequence
<220> FEATURE:
<223> OTHER INFORMATION: Synthetic oligonucleotide primer sequence

<400> SEQUENCE: 174
gccgtgtcgg attccgaggt gcggccttcg atacgcacgg cataccaaga aagcgggatg    60
ttcggc                                                              66

<210> SEQ ID NO 175
<211> LENGTH: 24
<212> TYPE: DNA
<213> ORGANISM: Artificial Sequence
<220> FEATURE:
<223> OTHER INFORMATION: Synthetic oligonucleotide primer sequence

<400> SEQUENCE: 175
cctcggaatc cgacacggca gggc                                          24

<210> SEQ ID NO 176
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 176
gtacagggtc tcccgggtgg cgctgg                                        26

<210> SEQ ID NO 177
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 177
ccgcgatcga aggccgcacc tcggaatccg acacggcagg gcc                     43

<210> SEQ ID NO 178
<211> LENGTH: 73
<212> TYPE: DNA
<213> ORGANISM: Artificial Sequence
<220> FEATURE:
<223> OTHER INFORMATION: Synthetic oligonucleotide primer sequence

<400> SEQUENCE: 178
ggcgcggtac ctttgtcatc gtcatcttta taatctgcgg ccgcgtacag ggtctcccgg    60
gtggcgctgg tgg                                                      73

<210> SEQ ID NO 179
<211> LENGTH: 51
<212> TYPE: DNA
<213> ORGANISM: Artificial Sequence
<220> FEATURE:
<223> OTHER INFORMATION: Synthetic oligonucleotide primer sequence
```

-continued

```
<400> SEQUENCE: 179
gcggcggtac cttattattt gtcatcgtca tctttataat ctgcggccgc g            51

<210> SEQ ID NO 180
<211> LENGTH: 79
<212> TYPE: DNA
<213> ORGANISM: Artificial Sequence
<220> FEATURE:
<223> OTHER INFORMATION: Synthetic oligonucleotide primer sequence

<400> SEQUENCE: 180
ccgcattaac gacgatgatg ttttccgcct cggctctcgc caaaatcatc gaaggccgca   60
cctcggaatc cgacacggc                                                79

<210> SEQ ID NO 181
<211> LENGTH: 82
<212> TYPE: DNA
<213> ORGANISM: Artificial Sequence
<220> FEATURE:
<223> OTHER INFORMATION: Synthetic oligonucleotide primer sequence

<400> SEQUENCE: 181
ccgcggtcga catgaaaata aaaacaggtg cacgcatcct cgcattatcc gcattaacga   60
cgatgatgtt ttccgcctcg gc                                            82

<210> SEQ ID NO 182
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 182
ccgcgagcga taaaattatt cacctgactg acg                                33

<210> SEQ ID NO 183
<211> LENGTH: 39
<212> TYPE: DNA
<213> ORGANISM: Artificial Sequence
<220> FEATURE:
<223> OTHER INFORMATION: Synthetic oligonucleotide primer sequence

<400> SEQUENCE: 183
gcccgccagg ttagcgtcga ggaactcttt caactgacc                          39

<210> SEQ ID NO 184
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 184
gcggccgcaa gcgataaaat tattcacctg actgacg                            37

<210> SEQ ID NO 185
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 185
ggcgctgcgg ccgcatcatc atgatcttta taatcgcc                           38
```

<210> SEQ ID NO 186

<400> SEQUENCE: 186

000

<210> SEQ ID NO 187

<400> SEQUENCE: 187

000

<210> SEQ ID NO 188
<211> LENGTH: 2465
<212> TYPE: DNA
<213> ORGANISM: Artificial Sequence
<220> FEATURE:
<223> OTHER INFORMATION: Synthetic nucleic acid sequence

<400> SEQUENCE: 188

```
gtcgacatgg ggcaacccgg gaacggcagc gccttcttgc tggcacccaa tggaagccat      60
gcgccggacc acgacgtcac gcagcaaagg gacgaggtgt gggtggtggg catgggcatc     120
gtcatgtctc tcatcgtcct ggccatcgtg tttggcaatg tgctggtcat cacagccatt    180
gccaagttcg agcgtctgca gacggtcacc aactacttca tcacttcact ggcctgtgct     240
gatctggtca tgggcctagc agtggtgccc tttggggccg cccatattct tatgaaaatg     300
tggacttttg gcaacttctg gtgcgagttt tggacttcca ttgatgtgct gtgcgtcacg     360
gccagcattg agaccctgtg cgtgatcgca gtggatcgct actttgccat tacttcacct     420
ttcaagtacc agagcctgct gaccaagaat aaggcccggg tgatcattct gatggtgtgg     480
attgtgtcag gccttayctc cttcttgccc attcagatgc actggtacag ggccacccac     540
caggaagcca tcaactgcta tgccaatgag acctgctgtg acttcttcac gaaccaagcc     600
tatgccattg cctcttccat cgtgtccttc tacgttcccc tggtgatcat ggtcttcgtc     660
tactccaggg tctttcagga ggccaaaagg cagctccaga agattgacaa atctgagggc     720
cgcttccatg tccagaacct tagccaggtg gagcaggatg gcggacggg gcatggactc    780
cgcagatctt ccaagttctg cttgaaggag cacaaagccc tcaagacgtt aggcatcatc     840
atgggcactt tcaccctctg ctggctgccc ttcttcatcg ttaacattgt gcatgtgatc     900
caggataacc tcatccgtaa ggaagtttac atcctcctaa attggatagg ctatgtcaat     960
tctggtttca atcccttat ctactgccgg agcccagatt tcaggattgc cttccaggag    1020
cttctgtgcc tgcgcaggtc ttcttttgaag gcctatggca atggctactc cagcaacggc    1080
aacacagggg agcagagtgg atatcacgtg aacaggaga agaaaatas actgctgtgt    1140
gaagacctcc caggcacgga agactttgtg ggccatcaag gtactgtgcc tagcgataac     1200
attgattcac aagggaggaa ttgtagtaca aatgactcac tgctagagcg tggccagacg     1260
gtcaccaacc tgcagctcga gggctgcctc gggaacagta agaccgagga ccagcgcaac     1320
gaggagaagg cgcagcgtga ggccaacaaa aagatcgaga agcagctgca gaaggacaag     1380
caggtctacc gggccacgca ccgcctgctg ctgctgggtg ctggagaatc tggtaaaagc     1440
accattgtga agcagatgag gatcctgcat gttaatgggt ttaatggaga cagtgagaag     1500
gcaaccaaag tgcaggacat caaaaacaac ctgaaagagg cgattgaaac cattgtggcc     1560
gccatgagca acctggtgcc ccccgtggag ctggccaacc ccgagaacca gttcagagtg     1620
gactacatcc tgagtgtgat gaacgtgcct gactttgact ccctcccga attctatgag    1680
```

```
catgccaagg ctctgtggga ggatgaagga gtgcgtgcct gctacgaacg ctccaacgag    1740
taccagctga ttgactgtgc ccagtacttc ctggacaaga tcgacgtgat caagcaggct    1800
gactatgtgc cgagcgatca ggacctgctt cgctgccgtg tcctgacttc tggaatcttt    1860
gagaccaagt tccaggtgga caaagtcaac ttccacatgt ttgacgtggg tggccagcgc    1920
gatgaacgcc gcaagtggat ccagtgcttc aacgatgtga ctgccatcat cttcgtggtg    1980
gccagcagca gctacaacat ggtcatccgg gaggacaacc agaccaaccg cctgcaggag    2040
gctctgaacc tcttcaagag catctggaac aacagatggc tgcgcaccat ctctgtgatc    2100
ctgttcctca acaagcaaga tctgctcgct gagaaagtcc ttgctgggaa atcgaagatt    2160
gaggactact ttccagaatt tgctcgctac actactcctg aggatgctac tcccgagccc    2220
ggagaggacc cacgcgtgac ccgggccaag tacttcattc gagatgagtt tctgaggatc    2280
agcactgcca gtggagatgg gcgtcactac tgctaccctc atttcacctg cgctgtggac    2340
actgagaaca tccgccgtgt gttcaacgac tgccgtgaca tcattcagcg catgcacctt    2400
cgtcagtacg agctgctcat cgattaataa tctagaggat ccccgcgccc tcatccgaaa    2460
gggcg                                                                 2465

<210> SEQ ID NO 189

<400> SEQUENCE: 189

000

<210> SEQ ID NO 190
<211> LENGTH: 2485
<212> TYPE: DNA
<213> ORGANISM: Artificial Sequence
<220> FEATURE:
<223> OTHER INFORMATION: Synthetic nucleic acid sequence

<400> SEQUENCE: 190
gtcgacatgg ggcaacccgg gaacggcagc gccttcttgc tggcacccaa tggaagccat      60
gcgccggacc acgacgtcac gcagcaaagg gacgaggtgt gggtggtggg catgggcatc     120
gtcatgtctc tcatcgtcct ggccatcgtg tttggcaatg tgctggtcat cacagccatt     180
gccaagttcg agcgtctgca gacggtcacc aactacttca tcacttcact ggcctgtgct     240
gatctggtca tgggcctagc agtggtgccc tttggggccg cccatattct tatgaaaatg     300 tggactttg gcaacttctg gtgcgagttt tggacttcca ttgatgtgct gtgcgtcacg     360
gccagcattg agaccctgtg cgtgatcgca gtggatcgct actttgccat tacttcacct     420
ttcaagtacc agagcctgct gaccaagaat aaggcccggg tgatcattct gatggtgtgg     480
attgtgtcag gccttayctc cttcttgccc attcagatgc actggtacag ggccacccac     540
caggaagcca tcaactgcta tgccaatgag acctgctgtg acttcttcac gaaccaagcc     600
tatgccattg cctcttccat cgtgtccttc tacgttcccc tggtgatcat ggtcttcgtc     660
tactccaggg tctttcagga ggccaaaagg cagctccaga agattgacaa atctgagggc     720
cgcttccatg tccagaacct tagccaggtg gagcaggatg gcggacgggg catggactc     780 cgcagatctt ccaagttctg cttgaaggag cacaaagccc tcaagacgtt aggcatcatc     840
atgggcactt tcaccctctg ctggctgccc ttcttcatcg ttaacattgt gcatgtgatc     900
caggataacc tcatccgtaa ggaagtttac atcctcctaa attggatagg ctatgtcaat     960
tctgggttca atcccctatt ctactgccgg agcccagatt tcaggattgc cttcaggag    1020 cttctgtgcc tgcgcaggtc ttctttgaag gcctatggca atggctactc cagcaacggc    1080
```

```
aacacagggg agcagagtgg atatcacgtg aacaggaga aagaaaataa actgctgtgt    1140
gaagacctcc caggcacgga agactttgtg ggccatcaag gtactgtgcc tagcgataac    1200
attgattcac aagggaggaa ttgtagtaca aatgactcac tgctagagcg tggccagacg    1260
gtcaccaacc tgcagtaata atcaaggagg ccctcgagat gggctgcctc gggaacagta    1320
agaccgagga ccagcgcaac gaggagaagg cgcagcgtga ggccaacaaa aagatcgaga    1380
agcagctgca gaaggacaag caggtctacc gggccacgca ccgcctgctg ctgctgggtg    1440
ctggagaatc tggtaaaagc accattgtga agcagatgag gatcctgcat gttaatgggt    1500
ttaatggaga cagtgagaag gcaaccaaag tgcaggacat caaaaacaac ctgaaagagg    1560
cgattgaaac cattgtggcc gccatgagca acctggtgcc ccccgtggag ctggccaacc    1620
ccgagaacca gttcagagtg gactacatcc tgagtgtgat gaacgtgcct gactttgact    1680
tccctcccga attctatgag catgccaagg ctctgtggga ggatgaagga gtgcgtgcct    1740
gctacgaacg ctccaacgag taccagctga ttgactgtgc ccagtacttc ctggacaaga    1800
tcgacgtgat caagcaggct gactatgtgc cgagcgatca ggacctgctt cgctgccgtg    1860
tcctgacttc tggaatcttt gagaccaagt tccaggtgga caaagtcaac ttccacatgt    1920
ttgacgtggg tggccagcgc gatgaacgcc gcaagtggat ccagtgcttc aacgatgtga    1980
ctgccatcat cttcgtggtg gccagcagca gctacaacat ggtcatccgg gaggacaacc    2040
agaccaaccg cctgcaggag gctctgaacc tcttcaagag catctggaac aacagatggc    2100
tgcgcaccat ctctgtgatc ctgttcctca acaagcaaga tctgctcgct gagaaagtcc    2160
ttgctgggaa atcgaagatt gaggactact ttccagaatt tgctcgctac actactcctg    2220
aggatgctac tcccgagccc ggagaggacc cacgcgtgac ccgggccaag tacttcattc    2280
gagatgagtt tctgaggatc agcactgcca gtggagatgg gcgtcactac tgctacccctc    2340 atttcacctg cgctgtggac actgagaaca tccgccgtgt gttcaacgac tgccgtgaca    2400
tcattcagcg catgcacctt cgtcagtacg agctgctcat cgattaataa tctagaggat    2460
ccccgcgccc tcatccgaaa gggcg                                          2485

<210> SEQ ID NO 191

<400> SEQUENCE: 191

000

<210> SEQ ID NO 192
<211> LENGTH: 1152
<212> TYPE: DNA
<213> ORGANISM: Homo sapiens

<400> SEQUENCE: 192
ctcgagatgg gctgcctcgg gaacagtaag accgaggacc agcgcaacga ggagaaggcg      60
cagcgtgagg ccaacaaaaa gatcgagaag cagctgcaga aggacaagca ggtctaccgg     120
gccacgcacc gcctgctgct gctgggtgct ggagaatctg gtaaaagcac cattgtgaag     180
cagatgagga tcctgcatgt taatgggttt aatggagaca gtgagaaggc aaccaaagtg     240
caggacatca aaaacaacct gaaagaggcg attgaaacca ttgtggccgc catgagcaac     300
ctggtgcccc ccgtggagct ggccaacccc gagaaccagt tcagagtgga ctacatcctg     360
agtgtgatga cgtgcctga ctttgacttc cctcccgaat tctatgagca tgccaaggct     420
ctgtgggagg atgaaggagt gcgtgcctgc tacgaacgct ccaacgagta ccagctgatt     480
```

| | | |
|---|---|---|
| gactgtgccc agtacttcct ggacaagatc gacgtgatca agcaggctga ctatgtgccg | 540 | |
| agcgatcagg acctgcttcg ctgccgtgtc ctgacttctg gaatctttga gaccaagttc | 600 | |
| caggtggaca aagtcaactt ccacatgttt gacgtgggtg gccagcgcga tgaacgccgc | 660 | |
| aagtggatcc agtgcttcaa cgatgtgact gccatcatct cgtggtggc cagcagcagc | 720 | |
| tacaacatgg tcatccggga ggacaaccag accaaccgcc tgcaggaggc tctgaacctc | 780 | |
| ttcaagagca tctggaacaa cagatggctg cgcaccatct ctgtgatcct gttcctcaac | 840 | |
| aagcaagatc tgctcgctga aaagtccttg ctgggaaat cgaagattga ggactacttt | 900 | |
| ccagaatttg ctcgctacac tactcctgag atgctactc ccgagcccgg agaggaccca | 960 | |
| cgcgtgaccc gggccaagta cttcattcga gatgagtttc tgaggatcag cactgccagt | 1020 | |
| ggagatgggc gtcactactg ctaccctcat ttcacctgcg ctgtggacac tgagaacatc | 1080 | |
| cgccgtgtgt tcaacgactg ccgtgacatc attcagcgca tgcaccttcg tcagtacgag | 1140 | |
| ctgctcatcg at | 1152 | |

<210> SEQ ID NO 193
<211> LENGTH: 1194
<212> TYPE: DNA
<213> ORGANISM: Homo sapiens

<400> SEQUENCE: 193

| | | |
|---|---|---|
| ctcgagatgg gctgcctcgg gaacagtaag accgaggacc agcgcaacga ggagaaggcg | 60 | |
| cagcgtgagg ccaacaaaaa gatcgagaag cagctgcaga aggacaagca ggtctaccgg | 120 | |
| gccacgcacc gcctgctgct gctgggtgct ggagaatctg gtaaaagcac cattgtgaag | 180 | |
| cagatgagga tcctgcatgt taatgggttt aatggagagg gcggcgaaga ggacccgcag | 240 | |
| gctgcaagga gcaacagcga tggtgagaag gcaaccaaag tgcaggacat caaaaacaac | 300 | |
| ctgaaagagg cgattgaaac cattgtggcc gccatgagca acctggtgcc ccccgtggag | 360 | |
| ctggccaacc ccgagaacca gttcagagtg gactacatcc tgagtgtgat gaacgtgcct | 420 | |
| gactttgact ccctcccga attctatgag catgccaagg ctctgtggga ggatgaagga | 480 | |
| gtgcgtgcct gctacgaacg ctccaacgag taccagctga ttgactgtgc ccagtacttc | 540 | |
| ctggacaaga tcgacgtgat caagcaggct gactatgtgc cgagcgatca ggacctgctt | 600 | |
| cgctgccgtg tcctgacttc tggaatcttt gagaccaagt tccaggtgga caaagtcaac | 660 | |
| ttccacatgt ttgacgtggg tggccagcgc gatgaacgcc gcaagtggat ccagtgcttc | 720 | |
| aacgatgtga ctgccatcat cttcgtggtg gccagcagca gctacaacat ggtcatccgg | 780 | |
| gaggacaacc agaccaaccg cctgcaggag gctctgaacc tcttcaagag catctggaac | 840 | |
| aacagatggc tgcgcaccat ctctgtgatc ctgttcctca acaagcaaga tctgctcgct | 900 | |
| gagaaagtcc ttgctgggaa atcgaagatt gaggactact ttccagaatt tgctcgctac | 960 | |
| actactcctg aggatgctac tcccgagccc ggagaggacc cacgcgtgac ccgggccaag | 1020 | |
| tacttcattc gagatgagtt tctgaggatc agcactgcca gtggagatgg gcgtcactac | 1080 | |
| tgctaccctc atttcacctg cgctgtggac actgagaaca tccgccgtgt gttcaacgac | 1140 | |
| tgccgtgaca tcattcagcg catgcacctt cgtcagtacg agctgctcat cgat | 1194 | |

<210> SEQ ID NO 194
<211> LENGTH: 1089
<212> TYPE: DNA
<213> ORGANISM: Homo sapiens

<400> SEQUENCE: 194

```
ctcgagatga ctctggagtc catcatggcg tgctgcctga gcgaggaggc caaggaagcc     60
cggcggatca acgacgagat cgagcggcag ctccgcaggg acaagcggga cgcccgccgg    120
gagctcaagc tgctgctgct cgggacagga gagagtggca agagtacgtt tatcaagcag    180
atgagaatca tccatgggtc aggatactct gatgaagata aaggggcttc accaagctg     240
gtgtatcaga acatcttcac ggccatgcag gccatgatca gagccatgga cacactcaag    300
atcccataca gtatgagcaa cataaggct catgcacaat tagttcgaga agttgatgtg     360
gagaaggtgt ctgcttttga gaatccatat gtagatgcaa taaagagttt atggaatgat    420
cctggaatcc aggaatgcta tgatagacga cgagaatatc aattatctga ctctaccaaa    480
tactatctta tgacttgga ccgcgtagct gaccctgcct acctgcctac gcaacaagat     540
gtgcttagag ttcgagtccc caccacaggg atcatcgaat accctttga cttacaaagt     600
gtcattttca gaatggtcga tgtagggggc caaaggtcag agagaagaaa atggatacac    660
tgcttgaaa atgtcacctc tatcatgttt ctagtagcgc ttagtgaata tgatcaagtt     720
ctcgtggagt cagacaatga gaaccgaatg gaggaaagca aggctctctt tagaacaatt    780
atcacatacc cctggttcca gaactcctcg gttattctgt tcttaaacaa gaaagatctt    840
ctagaggaga aaatcatgta ttcccatcta gtcgactact tcccagaata tgatggaccc    900
cagagagatg cccaggcagc ccgagaattc attctgaaga tgttcgtgga cctgaaccca    960
gacagtgaca aaattatcta ctcccacttc acgtgcgcca cagacaccga aatatccgc    1020
tttgtctttg ctgccgtcaa ggacaccatc ctccagttga acctgaagga gtacaatctg   1080
gtcatcgat                                                           1089

<210> SEQ ID NO 195
<211> LENGTH: 1077
<212> TYPE: DNA
<213> ORGANISM: Homo sapiens

<400> SEQUENCE: 195
ctcgagatgg gctgcaccgt gagcgccgag gacaaggcgg cggccgagcg ctctaagatg     60
atcgacaaga acctgcggga ggacggagag aaggcggcgc gggaggtgaa gttgctgctg    120
ttgggtgctg gggagtcagg gaagagcacc atcgtcaagc agatgaagat catccacgag    180
gatggctact ccgaggagga atgccggcag taccgggcgg ttgtctacag caacaccatc    240
cagtccatca tggccattgt caaagccatg ggaaacctgc agatcgactt tgccgacccc    300
tccagagcgg acgacgccag gcagctattt gcactgtcct gcaccgccga ggagcaaggc    360
gtgctccctg atgacctgtc cggcgtcatc cggaggctct gggctgacca tggtgtgcag    420
gcctgctttg gccgctcaag ggaataccag ctcaacgact cagctgccta ctacctgaac    480
gacctggagc gtattgcaca gagtgactac atccccacac agcaagatgt gctacggacc    540
cgcgtaaaga ccacggggat cgtggagaca cacttcacct tcaaggacct acacttcaag    600
atgtttgatg tgggtggtca gcggtctgag cggaagaagt ggatccactg ctttgagggc    660
gtcacagcca tcatcttctg cgtagccttg agcgcctatg acttggtgct agctgaggac    720
gaggagatga accgcatgca tgagagcatg aagctattcg atagcatctg caacaacaag    780
tggttcacag acacgtccat catcctcttc ctcaacaaga aggacctgtt tgaggagaag    840
atcacacaca gtccctgac catctgcttc cctgagtaca caggggccaa caaatatgat    900
gaggcagcca gctacatcca gagtaagttt gaggacctga ataagcgcaa agacaccaag    960
gagatctaca cgcacttcac gtgcgccacc gacaccaaga acgtgcagtt cgtgtttgac   1020
```

```
gccgtcaccg atgtcatcat caagaacaac ctgaaggact gcggcctctt catgcat      1077
```

<210> SEQ ID NO 196
<211> LENGTH: 1155
<212> TYPE: DNA
<213> ORGANISM: Homo sapiens

<400> SEQUENCE: 196

```
ctcgagatgt ccggggtggt gcggaccctc agccgctgcc tgctgccggc cgaggccggc    60
ggggcccgcg agcgcagggc gggcagcggc gcgcgcgacg cggagcgcga ggcccggagg   120
cgtagccgcg acatcgacgc gctgctggcc cgcgagcggc gcgcggtccg cgcctggtg    180
aagatcctgc tgctgggcgc gggcgagagc ggcaagtcca cgttcctcaa gcagatgcgc   240
atcatccacg gccgcgagtt cgaccagaag gcgctgctgg agttccgcga caccatcttc   300
gacaacatcc tcaagggctc aagggttctt gttgatgcac gagataagct tggcattcct   360
tggcagtatt ctgaaaatga gaagcatggg atgttcctga tggccttcga gaacaaggcg   420
gggctgcctg tggagccggc caccttccag ctgtacgtcc cggccctgag cgcactctgg   480
agggattctg gcatcaggga ggctttcagc cggagaagcg agtttcagct gggggagtcg   540
gtgaagtact tcctggacaa cttggaccgg atcggccagc tgaattactt tcctagtaag   600
caagatatcc tgctggctag gaaagccacc aagggaattg tggagcatga cttcgttatt   660
aagaagatcc cctttaagat ggtggatgtg ggcggccagc ggtcccagcg ccagaagtgg   720
ttccagtgct tcgacgggat cacgtccatc ctgttcatgg tctcctccag cgagtacgac   780
caggtcctca tggaggacag gcgcaccaac cggctggtgg agtccatgaa catcttcgag   840
accatcgtca caacaagct cttcttcaac gtctccatca ttctcttcct caacaagatg   900
gacctcctgg tggagaaggt gaagaccgtg agcatcaaga agcacttccc ggacttcagg   960
ggcgacccgc accagctgga ggacgttcag cgctacctgg tccagtgctt cgacaggaag  1020
agacggaacc gcagcaagcc actcttccac cacttcacca ccgccatcga caccgagaac  1080
gtccgcttcg tgttccatgc tgtgaaagac accatcctgc aggagaacct gaaggacatc  1140
atgctgcaga tcgat                                                   1155
```

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205
<211> LENGTH: 3307
<212> TYPE: DNA
<213> ORGANISM: Artificial Sequence
<220> FEATURE:
<223> OTHER INFORMATION: Synthetic nucleic acid sequence

<400> SEQUENCE: 205

```
gtcgacatgg ggcaacccgg gaacggcagc gccttcttgc tggcacccaa tggaagccat      60
gcgccggacc acgacgtcac gcagcaaagg gacgaggtgt gggtggtggg catgggcatc     120
gtcatgtctc tcatcgtcct ggccatcgtg tttggcaatg tgctggtcat cacagccatt     180
gccaagttcg agcgtctgca gacggtcacc aactacttca tcacttcact ggcctgtgct     240
gatctggtca tgggcctagc agtggtgccc tttggggccg cccatattct tatgaaaatg     300
tggacttttg gcaacttctg gtgcgagttt tggacttcca ttgatgtgct gtgcgtcacg     360
gccagcattg agaccctgtg cgtgatcgca gtggatcgct actttgccat tacttcacct     420
ttcaagtacc agagcctgct gaccaagaat aaggcccggg tgatcattct gatggtgtgg     480
attgtgtcag gccttayctc cttcttgccc attcagatgc actggtacag gccacccac     540 caggaagcca tcaactgcta tgccaatgag acctgctgtg acttcttcac gaaccaagcc     600
tatgccattg cctcttccat cgtgtccttc tacgttcccc tggtgatcat ggtcttcgtc     660
tactccaggg tctttcagga ggccaaaagg cagctccaga gattgacaa atctgagggc     720 cgcttccatg tccagaacct tagccaggtg gagcaggatg gcggacggg gcatggactc     780 cgcagatctt ccaagttctg cttgaaggag cacaaagccc tcaagacgtt aggcatcatc     840
atgggcactt tcaccctctg ctggctgccc ttcttcatcg ttaacattgt gcatgtgatc     900
caggataacc tcatccgtaa ggaagtttac atcctcctaa attggatagg ctatgtcaat     960
tctggtttca tcccccttat ctactgccgg agcccagatt tcaggattgc cttccaggag    1020
cttctgtgcc tgcgcaggtc ttcttgaag gcctatggca atggctactc cagcaacggc    1080
aacacagggg agcagagtgg atatcacgtg aacaggagaa agaaaataa actgctgtgt    1140 gaagacctcc caggcacgga agactttgtg ggccatcaag gtactgtgcc tagcgataac    1200
attgattcac aagggaggaa ttgtagtaca aatgactcac tgctagagcg tggccagacg    1260
gtcaccaacc tgcagggaca caactcaaaa gagatatcga tgagtcatat tggtactaaa    1320
```

```
ttcattcttg ctgaaaaatt taccttcgat cccctaagca atactctgat tgacaaagaa    1380
gatagtgaag agatcattcg attaggcagc aacgaaagcc gaattctttg gctgctggcc    1440
caacgtccaa acgaggtaat ttctcgcaat gatttgcatg actttgtttg gcgagagcaa    1500
ggttttgaag tcgatgattc cagcttaacc caagccattt cgactctgcg caaaatgctc    1560
aaagattcga caaagtcccc acaatacgtc aaaacggttc cgaagcgcgg ttaccaattg    1620
atcgcccgag tggaaacggt tgaagaagag atggctcgcg aaaacgaagc tgctcatgac    1680
atctcttaat aatcaaggag gccctcgaga tgggctgcct cgggaacagt aagaccgagg    1740
accagcgcaa cgaggagaag gcgcagcgtg aggccaacaa aaagatcgag aagcagctgc    1800
agaaggacaa gcaggtctac cgggccacgc accgcctgct gctgctgggt gctggagaat    1860
ctggtaaaag caccattgtg aagcagatga ggatcctgca tgttaatggg tttaatggag    1920
acagtgagaa ggcaaccaaa gtgcaggaca tcaaaaacaa cctgaaagag gcgattgaaa    1980
ccattgtggc cgccatgagc aacctggtgc ccccgtgga gctggccaac cccgagaacc    2040
agttcagagt ggactacatc ctgagtgtga tgaacgtgcc tgactttgac ttccctcccg    2100
aattctatga gcatgccaag gctctgtggg aggatgaagg agtgcgtgcc tgctacgaac    2160
gctccaacga gtaccagctg attgactgtg cccagtactt cctggacaag atcgacgtga    2220
tcaagcaggc tgactatgtg ccgagcgatc aggacctgct tcgctgccgt gtcctgactt    2280
ctggaatctt tgagaccaag ttccaggtgg acaaagtcaa cttccacatg tttgacgtgg    2340
gtggccagcg cgatgaacgc cgcaagtgga tccagtgctt caacgatgtg actgccatca    2400
tcttcgtggt ggccagcagc agctacaaca tggtcatccg ggaggacaac cagaccaacc    2460
gcctgcagga ggctctgaac ctcttcaaga gcatctggaa caacagatgg ctgcgcacca    2520
tctctgtgat cctgttcctc aacaagcaag atctgctcgc tgagaaagtc cttgctggga    2580
aatcgaagat tgaggactac tttccagaat ttgctcgcta cactactcct gaggatgcta    2640
ctcccgagcc cggagaggac ccacgcgtga cccgggccaa gtacttcatt cgagatgagt    2700
ttctgaggat cagcactgcc agtggagatg ggcgtcacta ctgctaccct catttcacct    2760
gcgctgtgga cactgagaac atccgccgtg tgttcaacga ctgccgtgac atcattcagc    2820
gcatgcacct tcgtcagtac gagctgctca tcgatggaca caactcaaaa gagatatcga    2880
tgagtcatat tggtactaaa ttcattcttg ctgaaaaatt taccttcgat cccctaagca    2940
atactctgat tgacaaagaa gatagtgaag agatcattcg attaggcagc aacgaaagcc    3000
gaattctttg gctgctggcc caacgtccaa acgaggtaat ttctcgcaat gatttgcatg    3060
actttgtttg gcgagagcaa ggttttgaag tcgatgattc cagcttaacc caagccattt    3120
cgactctgcg caaaatgctc aaagattcga caaagtcccc acaatacgtc aaaacggttc    3180
cgaagcgcgg ttaccaattg atcgcccgag tggaaacggt tgaagaagag atggctcgcg    3240
aaaacgaagc tgctcatgac atctcttaat aatctagagg atccccgcgc cctcatccga    3300
aagggcg                                                              3307
```

<210> SEQ ID NO 206

<400> SEQUENCE: 206

000

<210> SEQ ID NO 207

<400> SEQUENCE: 207

-continued

000

<210> SEQ ID NO 208
<211> LENGTH: 3284
<212> TYPE: DNA
<213> ORGANISM: Artificial Sequence
<220> FEATURE:
<223> OTHER INFORMATION: Synthetic nucleic acid sequence

<400> SEQUENCE: 208

```
tctagaggct gtgggtagaa gtgaaacggg gtttaccgat aaaaacagaa aatgataaaa      60
aaggactaaa tagtatattt tgattttga ttttgattt caaataatac aaatttattt      120
acttatttaa ttgttttgat caattatttt tctgttaaac aaagggagca ttatatggta     180
aagaccatga ttacggattc actggccgtc gttttacaac gtcgtgactg ggaaaaccct     240
ggcgttaccc aacttaatcg ccttgcagca catccccctt tcgccagctg gcgtaatagc     300
gaagaggccc gcaccgatcg cccttcccaa cagttgcgca gcctgaatgg cgaatggcgc     360
tttgcctggt ttccggcacc agaagcggtg ccggaaagct ggctggagtg cgatcttcct     420
gaggccgata ctgtcgtcgt cccctcaaac tggcagatgc acggttacga tgcgcccatc     480
tacaccaacg tgacctatcc cattacggtc aatccgccgt ttgttcccac ggagaatccg     540
acgggttgtt actcgctcac atttaatgtt gatgaaagct ggctacagga aggccagacg     600
cgaattattt ttgatggcgt taactcggcg tttcatctgt ggtgcaacgg gcgctgggtc     660
ggttacggcc aggacagtcg tttgccgtct gaatttgacc tgagcgcatt tttacgcgcc     720
ggagaaaacc gcctcgcggt gatggtgctg cgctggagtg acggcagtta tctggaagat     780
caggatatgt ggcggatgag cggcattttc cgtgacgtct cgttgctgca taaaccgact     840
acacaaatca gcgatttcca tgttgccact cgctttaatg atgatttcag ccgcgctgta     900
ctggaggctg aagttcagat gtgcggcgag ttgcgtgact acctacgggt aacagtttct     960
ttatggcagg gtgaaacgca ggtcgccagc ggcaccgcgc ctttcggcgg tgaaattatc    1020
gatgagcgtg gtggttatgc cgatcgcgtc acactacgtc tgaacgtcga aaacccgaaa    1080
ctgtggagcg ccgaaatccc gaatctctat cgtgcggtgg ttgaactgca caccgccgac    1140
ggcacgctga ttgaagcaga agcctgcgat gtcggtttcc gcgaggtgcg gattgaaaat    1200
ggtctgctgc tgctgaacgg caagccgttg ctgattcgag gcgttaaccg tcacgagcat    1260
catcctctgc atggtcaggt catggatgag cagacgatgg tgcaggatat cctgctgatg    1320
aagcagaaca actttaacgc cgtgcgctgt tcgcattatc cgaaccatcc gctgtggtac    1380
acgctgtgcg accgctacgg cctgtatgtg gtggatgaag ccaatattga aacccacggc    1440
atggtgccaa tgaatcgtct gaccgatgat ccgcgctggc taccggcgat gagcgaacgc    1500
gtaacgcgaa tggtgcagcg cgatcgtaat cacccgagtg tgatcatctg gtcgctgggg    1560
aatgaatcag gccacggcgc taatcacgac gcgctgtatc gctggatcaa atctgtcgat    1620
ccttcccgcc cggtgcagta tgaaggcggc ggagccgaca ccacggccac cgatattatt    1680
tgcccgatgt acgcgcgcgt ggatgaagac cagcccttcc cggctgtgcc gaaatggtcc    1740
atcaaaaaat ggcttctcgct acctggagag acgcgcccgc tgatcctttg cgaatacgcc    1800
cacgcgatgg gtaacagtct tggcggtttc gctaaatact ggcaggcgtt tcgtcagtat    1860
ccccgtttac agggcggctt cgtctgggac tgggtggatc agtcgctgat taaatatgat    1920
gaaaacggca accgtggtc ggcttacggc ggtgattttg gcgatacgcc gaacgatcgc    1980
cagttctgta tgaacggtct ggtctttgcc gaccgcacgc cgcatccagc gctgacggaa    2040
```

-continued

```
gcaaaacacc agcagcagtt tttccagttc cgtttatccg ggcaaaccat cgaagtgacc    2100
agcgaatacc tgttccgtca tagcgataac gagctcctgc actggatggt ggcgctggat    2160
ggtaagccgc tggcaagcgg tgaagtgcct ctggatgtcg ctccacaagg taaacagttg    2220
attgaactgc ctgaactacc gcagccggag agcgccgggc aactctggct cacagtacgc    2280
gtagtgcaac cgaacgcgac cgcatggtca gaagccgggc acatcagcgc ctggcagcag    2340
tggcgtctgg cggaaaacct cagtgtgacg ctccccgccg cgtcccacgc catcccgcat    2400
ctgaccacca gcgaaatgga tttttgcatc gagctgggta ataagcgttg gcaatttaac    2460
cgccagtcag gctttctttc acagatgtgg attggcgata aaaaacaact gctgacgccg    2520
ctgcgcgatc agttcacccg tgcaccgctg gataacgaca ttggcgtaag tgaagcgacc    2580
cgcattgacc ctaacgcctg ggtcgaacgc tggaaggcgg cgggccatta ccaggccgaa    2640
gcagcgttgt tgcagtgcac ggcagataca cttgctgatg cggtgctgat tacgaccgct    2700
cacgcgtggc agcatcaggg gaaaacctta tttatcagcc ggaaaaccta ccggattgat    2760
ggtagtggtc aaatggcgat taccgttgat gttgaagtgg cgagcgatac accgcatccg    2820
gcgcggattg gcctgaactg ccagctggcg caggtagcag agcgggtaaa ctggctcgga    2880
ttagggccgc aagaaaacta tcccgaccgc cttactgccg cctgttttga ccgctgggat    2940
ctgccattgt cagacatgta taccccgtac gtcttcccga gcgaaaacgg tctgcgctgc    3000
gggacgcgcg aattgaatta tggcccacac cagtggcgcg cgacttcca gttcaacatc    3060 agccgctaca gtcaacagca actgatgaa accagccatc gccatctgct gcacgcggaa    3120
gaaggcacat ggctgaatat cgacggtttc catatgggga ttggtggcga cgactcctgg    3180
agcccgtcag tatcggcgga attccagctg agcgccggtc gctaccatta ccagttggtc    3240
tggtgtcaaa aataataacg ccctcatccg aaagggcgtc taga                    3284
```

<210> SEQ ID NO 209
<211> LENGTH: 25
<212> TYPE: DNA
<213> ORGANISM: Artificial Sequence
<220> FEATURE:
<223> OTHER INFORMATION: Synthetic oligonucleotide primer sequence

<400> SEQUENCE: 209
ggggcaaccc gggaacggca gcgcc                                         25

<210> SEQ ID NO 210
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 210
gcagtgagtc atttgtacta caattcctcc                                    30

<210> SEQ ID NO 211
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 211
cgcggtcgac atggggcaac ccgggaacgg cagcgcc                             37

<210> SEQ ID NO 212

<211> LENGTH: 67
<212> TYPE: DNA
<213> ORGANISM: Artificial Sequence
<220> FEATURE:
<223> OTHER INFORMATION: Synthetic oligonucleotide primer sequence

<400> SEQUENCE: 212
ggctcgagct gcaggttggt gaccgtctgg ccacgctcta gcagtgagtc atttgtacta    60
caattcc    67

<210> SEQ ID NO 213
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 213
gggctgcctc gggaacagta agaccgagg    29

<210> SEQ ID NO 214
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 214
gagcagctcg tactgacgaa ggtgcatgc    29

<210> SEQ ID NO 215
<211> LENGTH: 44
<212> TYPE: DNA
<213> ORGANISM: Artificial Sequence
<220> FEATURE:
<223> OTHER INFORMATION: Synthetic oligonucleotide primer sequence

<400> SEQUENCE: 215
ggaggccctc gagatgggct gcctcgggaa cagtaagacc gagg    44

<210> SEQ ID NO 216
<211> LENGTH: 48
<212> TYPE: DNA
<213> ORGANISM: Artificial Sequence
<220> FEATURE:
<223> OTHER INFORMATION: Synthetic oligonucleotide primer sequence

<400> SEQUENCE: 216
cctctagatt attatcgatg agcagctcgt actgacgaag gtgcatgc    48

<210> SEQ ID NO 217
<211> LENGTH: 37
<212> TYPE: DNA
<213> ORGANISM: Artificial Sequence
<220> FEATURE:
<223> OTHER INFORMATION: Synthetic oligonucleotide primer sequence

<400> SEQUENCE: 217
ccatcgatga gcagctcgta ctgacgaagg tgcatgc    37

<210> SEQ ID NO 218
<211> LENGTH: 26
<212> TYPE: DNA
<213> ORGANISM: Artificial Sequence
<220> FEATURE:
<223> OTHER INFORMATION: Synthetic oligonucleotide primer sequence

```
<400> SEQUENCE: 218
ccggggtggt gcggaccctc agccgc                                    26

<210> SEQ ID NO 219
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 219
ctgcagcatg atgtccttca ggttctcc                                  28

<210> SEQ ID NO 220
<211> LENGTH: 41
<212> TYPE: DNA
<213> ORGANISM: Artificial Sequence
<220> FEATURE:
<223> OTHER INFORMATION: Synthetic oligonucleotide primer sequence

<400> SEQUENCE: 220
gcgggctcga gatgtccggg gtggtgcgga ccctcagccg c                   41

<210> SEQ ID NO 221
<211> LENGTH: 39
<212> TYPE: DNA
<213> ORGANISM: Artificial Sequence
<220> FEATURE:
<223> OTHER INFORMATION: Synthetic oligonucleotide primer sequence

<400> SEQUENCE: 221
gcgccatcga tctgcagcat gatgtccttc aggttctcc                      39

<210> SEQ ID NO 222
<211> LENGTH: 28
<212> TYPE: DNA
<213> ORGANISM: Artificial Sequence
<220> FEATURE:
<223> OTHER INFORMATION: Synthetic oligonucleotide primer sequence

<400> SEQUENCE: 222
gactctggag tccatcatgg cgtgctgc                                  28

<210> SEQ ID NO 223
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 223
ccagattgta ctccttcagg ttcaactgg                                 29

<210> SEQ ID NO 224
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 224
atgactctgg agtccatcat ggcgtgctgc                                30

<210> SEQ ID NO 225
<211> LENGTH: 42
<212> TYPE: DNA
```

```
<213> ORGANISM: Artificial Sequence
<220> FEATURE:
<223> OTHER INFORMATION: Synthetic oligonucleotide primer sequence

<400> SEQUENCE: 225
gcgccatcga tgaccagatt gtactccttc aggttcaact gg                    42

<210> SEQ ID NO 226
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 226
gggctgcacc gtgagcgccg aggacaagg                                   29

<210> SEQ ID NO 227
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 227
ccttcaggtt gttcttgatg atgacatcgg                                  30

<210> SEQ ID NO 228
<211> LENGTH: 31
<212> TYPE: DNA
<213> ORGANISM: Artificial Sequence
<220> FEATURE:
<223> OTHER INFORMATION: Synthetic oligonucleotide primer sequence

<400> SEQUENCE: 228
atgggctgca ccgtgagcgc cgaggacaag g                                31

<210> SEQ ID NO 229
<211> LENGTH: 55
<212> TYPE: DNA
<213> ORGANISM: Artificial Sequence
<220> FEATURE:
<223> OTHER INFORMATION: Synthetic oligonucleotide primer sequence

<400> SEQUENCE: 229
gcgccatcga tgaagaggcc gcagtccttc aggttgttct tgatgatgac atcgg      55

<210> SEQ ID NO 230
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 230
gggctgcctc gggaacagta agaccgagg                                   29

<210> SEQ ID NO 231
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 231
gagcagctcg tactgacgaa ggtgcatgc                                   29
```

```
<210> SEQ ID NO 232
<211> LENGTH: 31
<212> TYPE: DNA
<213> ORGANISM: Artificial Sequence
<220> FEATURE:
<223> OTHER INFORMATION: Synthetic oligonucleotide primer sequence

<400> SEQUENCE: 232
atgggctgcc tcgggaacag taagaccgag g                              31

<210> SEQ ID NO 233
<211> LENGTH: 40
<212> TYPE: DNA
<213> ORGANISM: Artificial Sequence
<220> FEATURE:
<223> OTHER INFORMATION: Synthetic oligonucleotide primer sequence

<400> SEQUENCE: 233
gcgccatcga tgagcagctc gtactgacga aggtgcatgc                     40

<210> SEQ ID NO 234
<211> LENGTH: 107
<212> TYPE: DNA
<213> ORGANISM: Artificial Sequence
<220> FEATURE:
<223> OTHER INFORMATION: Synthetic oligonucleotide primer sequence

<400> SEQUENCE: 234
ggctcgaggg cctccttgat tattactcga gggcctcctt gattattact gcaggttggt    60
gaccgtctgg ccacgctcta gcagtgagtc atttgtacta caattcc               107

<210> SEQ ID NO 235
<211> LENGTH: 61
<212> TYPE: DNA
<213> ORGANISM: Artificial Sequence
<220> FEATURE:
<223> OTHER INFORMATION: Synthetic oligonucleotide primer sequence

<400> SEQUENCE: 235
ccctgcaggt tggtgaccgt ctggccacgc tctagcagtg agtcatttgt actacaattc    60
c                                                                   61

<210> SEQ ID NO 236
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 236
ggacacaact caaaagagat atcgatgagt catattgg                       38

<210> SEQ ID NO 237
<211> LENGTH: 29
<212> TYPE: DNA
<213> ORGANISM: Artificial Sequence
<220> FEATURE:
<223> OTHER INFORMATION: Synthetic oligonucleotide primer sequence

<400> SEQUENCE: 237
gagatgtcat gagcagcttc gttttcgcg                                 29

<210> SEQ ID NO 238
<211> LENGTH: 52
<212> TYPE: DNA
```

```
<213> ORGANISM: Artificial Sequence
<220> FEATURE:
<223> OTHER INFORMATION: Synthetic oligonucleotide primer sequence

<400> SEQUENCE: 238
gcgtggccag acggtcacca acctgcaggg acacaactca aaagagatat cg         52

<210> SEQ ID NO 239
<211> LENGTH: 51
<212> TYPE: DNA
<213> ORGANISM: Artificial Sequence
<220> FEATURE:
<223> OTHER INFORMATION: Synthetic oligonucleotide primer sequence

<400> SEQUENCE: 239
cggggatcct ctagattatt aagagatgtc atgagcagct tcgttttcgc g          51

<210> SEQ ID NO 240
<211> LENGTH: 32
<212> TYPE: DNA
<213> ORGANISM: Artificial Sequence
<220> FEATURE:
<223> OTHER INFORMATION: Synthetic oligonucleotide primer sequence

<400> SEQUENCE: 240
ggctgtgggt agaagtgaaa cggggtttac cg                               32

<210> SEQ ID NO 241
<211> LENGTH: 32
<212> TYPE: DNA
<213> ORGANISM: Artificial Sequence
<220> FEATURE:
<223> OTHER INFORMATION: Synthetic oligonucleotide primer sequence

<400> SEQUENCE: 241
ctttaccata taatgctccc tttgtttaac ag                               32

<210> SEQ ID NO 242
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 242
cgcggtctag aggctgtggg tagaagtgaa acggggttta ccg                   43

<210> SEQ ID NO 243
<211> LENGTH: 60
<212> TYPE: DNA
<213> ORGANISM: Artificial Sequence
<220> FEATURE:
<223> OTHER INFORMATION: Synthetic oligonucleotide primer sequence

<400> SEQUENCE: 243
cgacggccag tgaatccgta atcatggtct ttaccatata atgctccctt tgtttaacag 60

<210> SEQ ID NO 244
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 244
ccatgattac ggattcactg gccgtcg                                     27
```

```
<210> SEQ ID NO 245
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 245
ccagaccaac tggtaatggt agcgacc                                          27

<210> SEQ ID NO 246
<211> LENGTH: 35
<212> TYPE: DNA
<213> ORGANISM: Artificial Sequence
<220> FEATURE:
<223> OTHER INFORMATION: Synthetic oligonucleotide primer sequence

<400> SEQUENCE: 246
ggtaaagacc atgattacgg attcactggc cgtcg                                 35

<210> SEQ ID NO 247
<211> LENGTH: 77
<212> TYPE: DNA
<213> ORGANISM: Artificial Sequence
<220> FEATURE:
<223> OTHER INFORMATION: Synthetic oligonucleotide primer sequence

<400> SEQUENCE: 247
gcgcctctag aaatacgccc tttcggatga gggcgttatt atttttgaca ccagaccaac      60
tggtaatggt agcgacc                                                    77

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253
<211> LENGTH: 89
<212> TYPE: DNA
<213> ORGANISM: Artificial Sequence
<220> FEATURE:
<223> OTHER INFORMATION: Synthetic oligonucleotide primer sequence
```

<400> SEQUENCE: 253
cgcggatgca tatgaaaata aaaacaggtg cacgcatcct cgcattatcc gcattaacga    60
cgatgatgtt ttccgcctcg gctctcgcc    89

<210> SEQ ID NO 254
<211> LENGTH: 69
<212> TYPE: DNA
<213> ORGANISM: Artificial Sequence
<220> FEATURE:
<223> OTHER INFORMATION: Synthetic oligonucleotide primer sequence

<400> SEQUENCE: 254
cgtcgaccga ggcctgcagg cgggcttcga tgattttggc gagagccgag gcggaaaaca    60
tcatcgtcg    69

<210> SEQ ID NO 255
<211> LENGTH: 81
<212> TYPE: DNA
<213> ORGANISM: Artificial Sequence
<220> FEATURE:
<223> OTHER INFORMATION: Synthetic oligonucleotide primer sequence

<400> SEQUENCE: 255
cgaagcccgc ctgcaggcct cggtcgacgc cgaatctaga gattataaag atgacgatga    60
caaataataa gctagcggcg c    81

<210> SEQ ID NO 256
<211> LENGTH: 27
<212> TYPE: DNA
<213> ORGANISM: Artificial Sequence
<220> FEATURE:
<223> OTHER INFORMATION: Synthetic oligonucleotide primer sequence

<400> SEQUENCE: 256
gcgccgctag cttattattt gtcatcg    27

<210> SEQ ID NO 257
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 257
ggtgcacgca tcctcgcatt atccgc    26

<210> SEQ ID NO 258
<211> LENGTH: 30
<212> TYPE: DNA
<213> ORGANISM: Artificial Sequence
<220> FEATURE:
<223> OTHER INFORMATION: Synthetic oligonucleotide primer sequence

<400> SEQUENCE: 258
ggcgttttcc atggtggcgg caatacgtgg    30

<210> SEQ ID NO 259
<211> LENGTH: 52
<212> TYPE: DNA
<213> ORGANISM: Artificial Sequence
<220> FEATURE:
<223> OTHER INFORMATION: Synthetic oligonucleotide primer sequence

<400> SEQUENCE: 259
cgcggatgca tatgaaaata aaaacaggtg cacgcatcct cgcattatcc gc                52

<210> SEQ ID NO 260
<211> LENGTH: 82
<212> TYPE: DNA
<213> ORGANISM: Artificial Sequence
<220> FEATURE:
<223> OTHER INFORMATION: Synthetic oligonucleotide primer sequence

<400> SEQUENCE: 260
ccgaggcctg caggcgggct tcgatacgca cggcatacca gaaagcggac tgggcgtttt    60
ccatggtggc ggcaatacgt gg                                              82

<210> SEQ ID NO 261
<211> LENGTH: 87
<212> TYPE: DNA
<213> ORGANISM: Artificial Sequence
<220> FEATURE:
<223> OTHER INFORMATION: Synthetic oligonucleotide primer sequence

<400> SEQUENCE: 261
gcgccgctag cttattattt gtcatcgtca tctttataat ctctagattc ggcgtcgacc    60
gaggcctgca ggcgggcttc gatacgc                                         87

<210> SEQ ID NO 262
<211> LENGTH: 26
<212> TYPE: DNA
<213> ORGANISM: Artificial Sequence
<220> FEATURE:
<223> OTHER INFORMATION: Synthetic oligonucleotide primer sequence

<400> SEQUENCE: 262
cctgactgac gacagttttg acacgg                                          26

<210> SEQ ID NO 263
<211> LENGTH: 32
<212> TYPE: DNA
<213> ORGANISM: Artificial Sequence
<220> FEATURE:
<223> OTHER INFORMATION: Synthetic oligonucleotide primer sequence

<400> SEQUENCE: 263
cctttagaca gtgcacccac tttggttgcc gc                                   32

<210> SEQ ID NO 264
<211> LENGTH: 78
<212> TYPE: DNA
<213> ORGANISM: Artificial Sequence
<220> FEATURE:
<223> OTHER INFORMATION: Synthetic oligonucleotide primer sequence

<400> SEQUENCE: 264
cgcggctgca ggcctcggtc gacgccgaat ctagaagcga taaaattatt cacctgactg    60
acgacagttt tgacacgg                                                   78

<210> SEQ ID NO 265
<211> LENGTH: 95
<212> TYPE: DNA
<213> ORGANISM: Artificial Sequence
<220> FEATURE:
<223> OTHER INFORMATION: Synthetic oligonucleotide primer sequence

<400> SEQUENCE: 265
gcgccgctag cttattattt gtcatcgtca tctttataat ccgccaggtt ctctttcaac    60

```
tgacctttag acagtgcacc cactttggtt gccgc                                95
```

<210> SEQ ID NO 266
<211> LENGTH: 216
<212> TYPE: DNA
<213> ORGANISM: Artificial Sequence
<220> FEATURE:
<223> OTHER INFORMATION: Synthetic nucleic acid sequence

<400> SEQUENCE: 266

```
gaattcaggc gcttttttaga ctggtcgtaa tgaaattcag gaggttctgc atatgaaaat    60
aaaaacaggt gcacgcatcc tcgcattatc cgcattaacg acgatgatgt tttccgcctc   120
ggctctcgcc aaaatcatcg aagcccgcct gcaggcctcg gtcgacgccg aatctagaga   180
ttataaagat gacgatgaca ataataagc tagagg                              216
```

<210> SEQ ID NO 267
<211> LENGTH: 202
<212> TYPE: DNA
<213> ORGANISM: Artificial Sequence
<220> FEATURE:
<223> OTHER INFORMATION: Synthetic nucleic acid sequence

<400> SEQUENCE: 267

```
ccatacccgt ttttttgggc tagcaggagg ccctgcatat gaaaataaaa acaggtgcac    60
gcatcctcgc attatccgca ttaacgacga tgatgttttc cgcctcggct ctcgccaaaa   120
tcatcgaagc ccgcctgcag gcctcggtcg acgccgaatc tagagattat aaagatgacg   180
atgacaaata taagctaga gg                                             202
```

<210> SEQ ID NO 268
<211> LENGTH: 182
<212> TYPE: DNA
<213> ORGANISM: Artificial Sequence
<220> FEATURE:
<223> OTHER INFORMATION: Synthetic nucleic acid sequence

<400> SEQUENCE: 268

```
aggaggttct gcatatgaaa ataaaaacag gtgcacgcat cctcgcatta tccgcattaa    60
cgacgatgat gttttccgcc tcggctctcg ccaaaatcat cgaagcccgc ctgcaggcct   120
cggtcgacgc cgaatctaga gattataaag atgacgatga caaataataa gctagaggta   180
cc                                                                  182
```

<210> SEQ ID NO 269
<211> LENGTH: 182
<212> TYPE: DNA
<213> ORGANISM: Artificial Sequence
<220> FEATURE:
<223> OTHER INFORMATION: Synthetic nucleic acid sequence

<400> SEQUENCE: 269

```
aggaggttct gcatatgaaa ataaaaacag gtgcacgcat cctcgcatta tccgcattaa    60
cgacgatgat gttttccgcc tcggctctcg ccaaaatcat cgaagcccgc ctgcaggcct   120
cggtcgacgc cgaatctaga gattataaag atgacgatga caaataataa gctagaggta   180
cc                                                                  182
```

<210> SEQ ID NO 270
<211> LENGTH: 1080
<212> TYPE: DNA
<213> ORGANISM: Artificial Sequence
<220> FEATURE:
<223> OTHER INFORMATION: Synthetic nucleic acid sequence

<400> SEQUENCE: 270

```
gaattcaggc gcttttttaga ctggtcgtaa tgaaattcag gaggttctgc atatgaaaat      60
aaaaacaggt gcacgcatcc tcgcattatc cgcattaacg acgatgatgt tttccgcctc     120
ggctctcgcc aaaatcgaag aaggtaaact ggtaatctgg attaacggcg ataaaggcta     180
taacggtctc gctgaagtcg gtaagaaatt cgagaaagat accggaatta aagtcaccgt     240
tgagcatccg gataaactgg aagagaaatt cccacaggtt gcggcaactg gcgatggccc     300
tgacattatc ttctgggcac acgaccgctt tggtggctac gctcaatctg gcctgttggc     360
tgaaatcacc ccggacaaag cgttccagga caagctgtat ccgtttacct gggatgccgt     420
acgttacaac ggcaagctga ttgcttaccc gatcgctgtt gaagcgttat cgctgattta     480
taacaaagat ctgctgccga acccgccaaa aacctgggaa gagatcccgg cgctggataa     540
agaactgaaa gcgaaaggta gagcgcgct gatgttcaac ctgcaagaac cgtacttcac     600
ctggccgctg attgctgctg acgggggtta tgcgttcaag tatgaaaacg gcaagtacga     660
cattaaagac gtgggcgtgg ataacgctgg cgcgaaagcg ggtctgacct tcctggttga     720
cctgattaaa aacaaacaca tgaatgcaga caccgattac tccatcgcag aagctgcctt     780
taataaaggc gaaacagcga tgaccatcaa cggcccgtgg gcatggtcca acatcgacac     840
cagcaaagtg aattatggtg taacggtact gccgaccttc aagggtcaac catccaaacc     900
gttcgttggc gtgctgagcg caggtattaa cgccgccagt ccgaacaaag agctggcgaa     960
agagttcctc gaaaactatc tgctgactga tgaaggtctg gaagcggtta taaagacaa    1020
accgctgggt gccgtagcgc tgaagtctta cgaggaagag ttggcgaaag atccacgtat    1080
```

<210> SEQ ID NO 271
<211> LENGTH: 1196
<212> TYPE: DNA
<213> ORGANISM: Artificial Sequence
<220> FEATURE:
<223> OTHER INFORMATION: Synthetic nucleic acid sequence

<400> SEQUENCE: 271

```
ccatacccgt ttttttgggc tagcaggagg ccctgcatat gaaaataaaa acaggtgcac      60
gcatcctcgc attatccgca ttaacgacga tgatgttttc cgcctcggct ctcgccaaaa     120
tcgaagaagg taaactggta atctggatta acggcgataa aggctataac ggtctcgctg     180
aagtcggtaa gaaattcgag aaagataccg gaattaaagt caccgttgag catccggata     240
aactggaaga gaaattccca caggttgcgg caactggcga tggccctgac attatcttct     300
gggcacacga ccgctttggt ggctacgctc aatctggcct gttggctgaa atcacccccgg     360
acaaagcgtt ccaggacaag ctgtatccgt ttacctggga tgccgtacgt tacaacggca     420
agctgattgc ttacccgatc gctgttgaag cgttatcgct gatttataac aaagatctgc     480
tgccgaaccc gccaaaaacc tgggaagaga tcccggcgct ggataaagaa ctgaaagcga     540
aaggtaagag cgcgctgatg ttcaacctgc aagaaccgta cttcacctgg ccgctgattg     600
ctgctgacgg gggttatgcg ttcaagtatg aaaacggcaa gtacgacatt aaagacgtgg     660
gcgtggataa cgctggcgcg aaagcgggtc tgaccttcct ggttgacctg attaaaaaca     720
aacacatgaa tgcagacacc gattactcca tcgcagaagc tgcctttaat aaaggcgaaa     780
cagcgatgac catcaacggc ccgtgggcat ggtccaacat cgacaccagc aaagtgaatt     840
atggtgtaac ggtactgccg accttcaagg gtcaaccatc caaaccgttc gttggcgtgc     900
```

| | | |
|---|---|---|
| tgagcgcagg tattaacgcc gccagtccga acaaagagct ggcgaaagag ttcctcgaaa | 960 | |
| actatctgct gactgatgaa ggtctggaag cggttaataa agacaaaccg ctgggtgccg | 1020 | |
| tagcgctgaa gtcttacgag gaagagttgg cgaaagatcc acgtattgcc gccaccatgg | 1080 | |
| aaaacgccca gtccgctttc tggtatgccg tgcgtatcga agcccgcctg caggcctcgg | 1140 | |
| tcgacgccga atctagagat tataaagatg acgatgacaa ataataagct agagga | 1196 | |

<210> SEQ ID NO 272
<211> LENGTH: 1171
<212> TYPE: DNA
<213> ORGANISM: Artificial Sequence
<220> FEATURE:
<223> OTHER INFORMATION: Synthetic nucleic acid sequence

<400> SEQUENCE: 272

| | | |
|---|---|---|
| aggaggttct gcatatgaaa ataaaaacag gtgcacgcat cctcgcatta tccgcattaa | 60 | |
| cgacgatgat gttttccgcc tcggctctcg ccaaaatcga agaaggtaaa ctggtaatct | 120 | |
| ggattaacgg cgataaaggc tataacggtc tcgctgaagt cggtaagaaa ttcgagaaag | 180 | |
| ataccggaat taaagtcacc gttgagcatc cggataaact ggaagagaaa ttcccacagg | 240 | |
| ttgcggcaac tggcgatggc cctgacatta tcttctgggc acacgaccgc tttggtggct | 300 | |
| acgctcaatc tggcctgttg gctgaaatca ccccggacaa agcgttccag gacaagctgt | 360 | |
| atccgtttac ctgggatgcc gtacgttaca acggcaagct gattgcttac ccgatcgctg | 420 | |
| ttgaagcgtt atcgctgatt tataacaaag atctgctgcc gaacccgcca aaaacctggg | 480 | |
| aagagatccc ggcgctggat aaagaactga agcgaaagg taagagcgcg ctgatgttca | 540 | |
| acctgcaaga accgtacttc acctggccgc tgattgctgc tgacgggggt tatgcgttca | 600 | |
| agtatgaaaa cggcaagtac gacattaaag acgtgggcgt ggataacgct ggcgcgaaag | 660 | |
| cgggtctgac cttcctggtt gacctgatta aaaacaaaca catgaatgca gacaccgatt | 720 | |
| actccatcgc agaagctgcc tttaataaag gcgaaacagc gatgaccatc aacggcccgt | 780 | |
| gggcatggtc caacatcgac accagcaaag tgaattatgg tgtaacggta ctgccgacct | 840 | |
| tcaagggtca accatccaaa ccgttcgttg gcgtgctgag cgcaggtatt aacgccgcca | 900 | |
| gtccgaacaa agagctggcg aaagagttcc tcgaaaacta tctgctgact gatgaaggtc | 960 | |
| tggaagcggt taataaagac aaaccgctgg gtgccgtagc gctgaagtct tacgaggaag | 1020 | |
| agttggcgaa agatccacgt attgccgcca ccatggaaaa cgcccagtcc gctttctggt | 1080 | |
| atgccgtgcg tatcgaagcc cgcctgcagg cctcggtcga cgccgaatct agagattata | 1140 | |
| aagatgacga tgacaaataa taagctagag g | 1171 | |

<210> SEQ ID NO 273
<211> LENGTH: 1171
<212> TYPE: DNA
<213> ORGANISM: Artificial Sequence
<220> FEATURE:
<223> OTHER INFORMATION: Synthetic nucleic acid sequence

<400> SEQUENCE: 273

| | | |
|---|---|---|
| aggaggttct gcatatgaaa ataaaaacag gtgcacgcat cctcgcatta tccgcattaa | 60 | |
| cgacgatgat gttttccgcc tcggctctcg ccaaaatcga agaaggtaaa ctggtaatct | 120 | |
| ggattaacgg cgataaaggc tataacggtc tcgctgaagt cggtaagaaa ttcgagaaag | 180 | |
| ataccggaat taaagtcacc gttgagcatc cggataaact ggaagagaaa ttcccacagg | 240 | |
| ttgcggcaac tggcgatggc cctgacatta tcttctgggc acacgaccgc tttggtggct | 300 | |

-continued

```
acgctcaatc tggcctgttg gctgaaatca ccccggacaa agcgttccag gacaagctgt      360
atccgtttac ctgggatgcc gtacgttaca acggcaagct gattgcttac ccgatcgctg      420
ttgaagcgtt atcgctgatt tataacaaag atctgctgcc gaacccgcca aaaacctggg      480
aagagatccc ggcgctggat aaagaactga agcgaaagg taagagcgcg ctgatgttca       540
acctgcaaga accgtacttc acctggccgc tgattgctgc tgacggggt tatgcgttca       600 agtatgaaaa cggcaagtac gacattaaag acgtgggcgt ggataacgct ggcgcgaaag      660
cgggtctgac cttcctggtt gacctgatta aaacaaaca catgaatgca gacaccgatt      720
actccatcgc agaagctgcc tttaataaag gcgaaacagc gatgaccatc aacggcccgt      780
gggcatggtc caacatcgac accagcaaag tgaattatgg tgtaacggta ctgccgacct      840
tcaagggtca accatccaaa ccgttcgttg gcgtgctgag cgcaggtatt aacgccgcca      900
gtccgaacaa agagctggcg aaagagttcc tcgaaaacta tctgctgact gatgaaggtc      960
tggaagcggt taataaagac aaaccgctgg gtgccgtagc gctgaagtct tacgaggaag     1020
agttggcgaa agatccacgt attgccgcca ccatggaaaa cgcccagtcc gctttctggt     1080
atgccgtgcg tatcgaagcc cgcctgcagg cctcggtcga cgccgaatct agagattata    1140
aagatgacga tgacaaataa taagctagag g                                   1171
```

<210> SEQ ID NO 274
<211> LENGTH: 392
<212> TYPE: DNA
<213> ORGANISM: Artificial Sequence
<220> FEATURE:
<223> OTHER INFORMATION: Synthetic nucleic acid sequence

<400> SEQUENCE: 274

```
tagcaggagg ccctgcaggc ctcggtcgac gccgaatcta aagcgataaa aattattcac       60
ctgactgacg acagttttga cacggatgta ctcaaagcgg acggggcgat cctcgtcgat      120
ttctgggcag agtggtgcgg tccgtgcaaa atgatcgccc cgattctgga tgaaatcgct      180
gacgaatatc agggcaaact gaccgttgca aaactgaaca tcgatcaaaa ccctggcact      240
gcgccgaaat atggcatccg tggtatcccg actctgctgc tgttcaaaaa cggtgaagtg      300
gcggcaacca agtgggtgc actgtctaaa ggtcagttga agagaacct ggcggattat       360 aaagatgacg atgacaaata taagctaga gg                                    392
```

<210> SEQ ID NO 275
<211> LENGTH: 426
<212> TYPE: DNA
<213> ORGANISM: Artificial Sequence
<220> FEATURE:
<223> OTHER INFORMATION: Synthetic nucleic acid sequence

<400> SEQUENCE: 275

```
gaattcaggc gcttttaga ctggtcgtaa tgaaattcag gaggttctgc aggcctcggt        60
cgacgccgaa tctagaagcg ataaaattat tcacctgact gacgacagtt ttgacacgga      120
tgtactcaaa gcggacgggg cgatcctcgt cgatttctgg gcagagtggt gcggtccgtg      180
caaaatgatc gccccgattc tggatgaaat cgctgacgaa tatcagggca aactgaccgt      240
tgcaaaactg aacatcgatc aaaaccctgg cactgcgccg aaatatggca tccgtggtat      300
cccgactctg ctgctgttca aaaacggtga agtggcggca accaaagtgg gtgcactgtc      360
taaaggtcag ttgaaagaga acctggcgga ttataaagat gacgatgaca aataataagc      420
tagagg                                                                 426
```

```
<210> SEQ ID NO 276
<211> LENGTH: 392
<212> TYPE: DNA
<213> ORGANISM: Artificial Sequence
<220> FEATURE:
<223> OTHER INFORMATION: Synthetic nucleic acid sequence

<400> SEQUENCE: 276
aggaggttct gcaggcctcg gtcgacgccg aatctagaag cgataaaatt attcacctga      60
ctgacgacag ttttgacacg gatgtactca aagcggacgg ggcgatcctc gtcgatttct    120
gggcagagtg gtgcggtccg tgcaaaatga tcgccccgat tctggatgaa atcgctgacg    180
aatatcaggg caaactgacc gttgcaaaac tgaacatcga tcaaaaccct ggcactgcgc    240
cgaaatatgg catccgtggt atcccgactc tgctgctgtt caaaaacggt gaagtggcgg    300
caaccaaagt gggtgcactg tctaaaggtc agttgaaaga gaacctggcg gattataaag    360
atgacgatga caaataataa gctagaggta cc                                   392

<210> SEQ ID NO 277
<211> LENGTH: 392
<212> TYPE: DNA
<213> ORGANISM: Artificial Sequence
<220> FEATURE:
<223> OTHER INFORMATION: Synthetic nucleic acid sequence

<400> SEQUENCE: 277
aggaggttct gcaggcctcg gtcgacgccg aatctagaag cgataaaatt attcacctga      60
ctgacgacag ttttgacacg gatgtactca aagcggacgg ggcgatcctc gtcgatttct    120
gggcagagtg gtgcggtccg tgcaaaatga tcgccccgat tctggatgaa atcgctgacg    180
aatatcaggg caaactgacc gttgcaaaac tgaacatcga tcaaaaccct ggcactgcgc    240
cgaaatatgg catccgtggt atcccgactc tgctgctgtt caaaaacggt gaagtggcgg    300
caaccaaagt gggtgcactg tctaaaggtc agttgaaaga gaacctggcg gattataaag    360
atgacgatga caaataataa gctagaggta cc                                   392

<210> SEQ ID NO 278
<211> LENGTH: 528
<212> TYPE: DNA
<213> ORGANISM: Artificial Sequence
<220> FEATURE:
<223> OTHER INFORMATION: Synthetic nucleic acid sequence

<400> SEQUENCE: 278
gaattcaggc gcttttttaga ctggtcgtaa tgaaattcag gaggttctgc atatgaaaat     60
aaaaacaggt gcacgcatcc tcgcattatc cgcattaacg acgatgatgt tttccgcctc    120
ggctctcgcc aaaatcatcg aagcccgcct gcaggcctcg gtcgacgccg aatctagaag    180
cgataaaatt attcacctga ctgacgacag ttttgacacg gatgtactca aagcggacgg    240
ggcgatcctc gtcgatttct gggcagagtg gtgcggtccg tgcaaaatga tcgccccgat    300
tctggatgaa atcgctgacg aatatcaggg caaactgacc gttgcaaaac tgaacatcga    360
tcaaaaccct ggcactgcgc cgaaatatgg catccgtggt atcccgactc tgctgctgtt    420
caaaaacggt gaagtggcgg caaccaaagt gggtgcactg tctaaaggtc agttgaaaga    480
gaacctggcg gattataaag atgacgatga caaataataa gctagagg                  528

<210> SEQ ID NO 279
<211> LENGTH: 514
```

```
<212> TYPE: DNA
<213> ORGANISM: Artificial Sequence
<220> FEATURE:
<223> OTHER INFORMATION: Synthetic nucleic acid sequence

<400> SEQUENCE: 279
ccatacccgt tttttgggc tagcaggagg ccctgcatat gaaaataaaa acaggtgcac      60
gcatcctcgc attatccgca ttaacgacga tgatgttttc cgcctcggct ctcgccaaaa     120
tcatcgaagc ccgcctgcag gcctcggtcg acgccgaatc tagaagcgat aaaattattc    180
acctgactga cgacagtttt gacacggatg tactcaaagc ggacggggcg atcctcgtcg    240
atttctgggc agagtggtgc ggtccgtgca aaatgatcgc cccgattctg atgaaatcg     300
ctgacgaata tcagggcaaa ctgaccgttg caaaactgaa catcgatcaa acccctggca    360
ctgcgccgaa atatggcatc cgtggtatcc cgactctgct gctgttcaaa aacggtgaag    420
tggcggcaac caaagtgggt gcactgtcta aggtcagtt gaaagagaac ctggcggatt    480
ataaagatga cgatgacaaa taataagcta gagg                                514

<210> SEQ ID NO 280
<211> LENGTH: 494
<212> TYPE: DNA
<213> ORGANISM: Artificial Sequence
<220> FEATURE:
<223> OTHER INFORMATION: Synthetic nucleic acid sequence

<400> SEQUENCE: 280
aggaggttct gcatatgaaa ataaaaacag gtgcacgcat cctcgcatta tccgcattaa     60
cgacgatgat gttttccgcc tcggctctcg ccaaaatcat cgaagcccgc ctgcaggcct    120
cggtcgacgc cgaatctaga agcgataaaa ttattcacct gactgacgac agttttgaca    180
cggatgtact caaagcggac ggggcgatcc tcgtcgattt ctgggcagag tggtgcggtc    240
cgtgcaaaat gatcgccccg attctggatg aaatcgctga cgaatatcag ggcaaactga    300
ccgttgcaaa actgaacatc gatcaaaacc ctggcactgc gccgaaatat ggcatccgtg    360
gtatcccgac tctgctgctg ttcaaaaacg gtgaagtggc ggcaaccaaa gtgggtgcac    420
tgtctaaagg tcagttgaaa gagaacctgg cggattataa agatgacgat gacaaataat    480
aagctagagg tacc                                                       494

<210> SEQ ID NO 281
<211> LENGTH: 494
<212> TYPE: DNA
<213> ORGANISM: Artificial Sequence
<220> FEATURE:
<223> OTHER INFORMATION: Synthetic nucleic acid sequence

<400> SEQUENCE: 281
aggaggttct gcatatgaaa ataaaaacag gtgcacgcat cctcgcatta tccgcattaa     60
cgacgatgat gttttccgcc tcggctctcg ccaaaatcat cgaagcccgc ctgcaggcct    120
cggtcgacgc cgaatctaga agcgataaaa ttattcacct gactgacgac agttttgaca    180
cggatgtact caaagcggac ggggcgatcc tcgtcgattt ctgggcagag tggtgcggtc    240
cgtgcaaaat gatcgccccg attctggatg aaatcgctga cgaatatcag ggcaaactga    300
ccgttgcaaa actgaacatc gatcaaaacc ctggcactgc gccgaaatat ggcatccgtg    360
gtatcccgac tctgctgctg ttcaaaaacg gtgaagtggc ggcaaccaaa gtgggtgcac    420
tgtctaaagg tcagttgaaa gagaacctgg cggattataa agatgacgat gacaaataat    480
aagctagagg tacc                                                       494
```

<210> SEQ ID NO 282
<211> LENGTH: 1521
<212> TYPE: DNA
<213> ORGANISM: Artificial Sequence
<220> FEATURE:
<223> OTHER INFORMATION: Synthetic nucleic acid sequence

<400> SEQUENCE: 282

```
gaattcaggc gcttttttaga ctggtcgtaa tgaaattcag gaggttctgc atatgaaaat        60
aaaaacaggt gcacgcatcc tcgcattatc cgcattaacg acgatgatgt tttccgcctc       120
ggctctcgcc aaaatcgaag aaggtaaact ggtaatctgg attaacggcg ataaaggcta       180
taacggtctc gctgaagtcg gtaagaaatt cgagaaagat accggaatta aagtcaccgt       240
tgagcatccg gataaactgg aagagaaatt cccacaggtt gcggcaactg gcgatggccc       300
tgacattatc ttctgggcac acgaccgctt tggtggctac gctcaatctg gcctgttggc       360
tgaaatcacc ccggacaaag cgttccagga caagctgtat ccgtttacct gggatgccgt       420
acgttacaac ggcaagctga ttgcttaccc gatcgctgtt gaagcgttat cgctgattta       480
taacaaagat ctgctgccga acccgccaaa aacctgggaa gagatcccgg cgctggataa       540
agaactgaaa gcgaaaggta gagcgcgct gatgttcaac ctgcaagaac cgtacttcac       600
ctggccgctg attgctgctg acgggggtta tgcgttcaag tatgaaaacg gcaagtacga       660
cattaaagac gtgggcgtgg ataacgctgg cgcgaaagcg gtctgaccct tcctggttga       720
cctgattaaa aacaaacaca tgaatgcaga caccgattac tccatcgcag aagctgcctt       780
taataaaggc gaaacagcga tgaccatcaa cggcccgtgg gcatggtcca acatcgacac       840
cagcaaagtg aattatggtg taacggtact gccgaccttc aagggtcaac catccaaacc       900
gttcgttggc gtgctgagcg caggtattaa cgccgccagt ccgaacaaag agctggcgaa       960
agagttcctc gaaaactatc tgctgactga tgaaggtctg gaagcggtta ataaagacaa      1020
accgctgggt gccgtagcgc tgaagtctta cgaggaagag ttggcgaaag atccacgtat      1080
tgccgccacc atggaaaacg cccagtccgc tttctggtat gccgtgcgta tcgaagcccg      1140
cctgcaggcc tcggtcgacg ccgaatctag aagcgataaa attattcacc tgactgacga      1200
cagttttgac acgatgtac tcaaagcgga cggggcgatc ctcgtcgatt tctgggcaga      1260
gtggtgcggt ccgtgcaaaa tgatcgcccc gattctggat gaaatcgctg acgaatatca      1320
gggcaaactg accgttgcaa aactgaacat cgatcaaaac cctggcactg cgccgaaata      1380
tggcatccgt ggtatcccga ctctgctgct gttcaaaaac ggtgaagtgg cggcaaccaa      1440
agtgggtgca ctgtctaaag gtcagttgaa agagaacctg gcggattata agatgacga       1500
tgacaaataa taagctagag g                                                1521
```

<210> SEQ ID NO 283
<211> LENGTH: 1507
<212> TYPE: DNA
<213> ORGANISM: Artificial Sequence
<220> FEATURE:
<223> OTHER INFORMATION: Synthetic nucleic acid sequence

<400> SEQUENCE: 283

```
ccatacccgt tttttgggc tagcaggagg ccctgcatat gaaaataaaa acaggtgcac        60
gcatcctcgc attatccgca ttaacgacga tgatgttttc cgcctcggct ctcgccaaaa       120
tcgaagaagg taaactggta atctggatta acggcgataa aggctataac ggtctcgctg       180
aagtcggtaa gaaattcgag aaagataccg gaattaaagt caccgttgag catccggata       240
```

```
aactggaaga gaaattccca caggttgcgg caactggcga tggccctgac attatcttct    300
gggcacacga ccgctttggt ggctacgctc aatctggcct gttggctgaa atcaccccgg    360
acaaagcgtt ccaggacaag ctgtatccgt ttacctggga tgccgtacgt tacaacggca    420
agctgattgc ttacccgatc gctgttgaag cgttatcgct gatttataac aaagatctgc    480
tgccgaaccc gccaaaaacc tgggaagaga tcccggcgct ggataaagaa ctgaaagcga    540 aggtaagag cgcgctgatg ttcaacctgc aagaaccgta cttcacctgg ccgctgattg     600
ctgctgacgg gggttatgcg ttcaagtatg aaaacggcaa gtacgacatt aaagacgtgg    660
gcgtggataa cgctggcgcg aaagcgggtc tgaccttcct ggttgacctg attaaaaaca    720
aacacatgaa tgcagacacc gattactcca tcgcagaagc tgcctttaat aaaggcgaaa    780
cagcgatgac catcaacggc ccgtgggcat ggtccaacat cgacaccagc aaagtgaatt    840
atggtgtaac ggtactgccg accttcaagg gtcaaccatc caaaccgttc gttggcgtgc    900
tgagcgcagg tattaacgcc gccagtccga caaagagct ggcgaaagag ttcctcgaaa     960
actatctgct gactgatgaa ggtctggaag cggttaataa agacaaaccg ctgggtgccg   1020
tagcgctgaa gtcttacgag gaagagttgg cgaaagatcc acgtattgcc gccaccatgg   1080
aaaacgccca gtccgctttc tggtatgccg tgcgtatcga agcccgcctg caggcctcgg   1140
tcgacgccga atctagaagc gataaaatta ttcacctgac tgacgacagt tttgacacgg   1200
atgtactcaa agcggacggg gcgatcctcg tcgatttctg ggcagagtgg tgcggtccgt   1260
gcaaaatgat cgccccgatt ctggatgaaa tcgctgacga atatcagggc aaactgaccg   1320
ttgcaaaact gaacatcgat caaaaccctg gcactgcgcc gaaatatggc atccgtggta   1380
tcccgactct gctgctgttc aaaaacggtg aagtggcggc aaccaaagtg ggtgcactgt   1440
ctaaaggtca gttgaaagag aacctggcgg attataaaga tgacgatgac aaataataag   1500
ctagagg                                                             1507
```

<210> SEQ ID NO 284
<211> LENGTH: 1476
<212> TYPE: DNA
<213> ORGANISM: Artificial Sequence
<220> FEATURE:
<223> OTHER INFORMATION: Synthetic nucleic acid sequence

<400> SEQUENCE: 284

```
aggaggttct gcatatgaaa ataaaaacag gtgcacgcat cctcgcatta tccgcattaa     60
cgacgatgat gttttccgcc tcggctctcg ccaaaatcga agaaggtaaa ctggtaatct    120
ggattaacgg cgataaaggc tataacggtc tcgctgaagt cggtaagaaa ttcgagaaag    180
ataccggaat taaagtcacc gttgagcatc cggataaact ggaagagaaa ttcccacagg    240
ttgcggcaac tggcgatggc cctgacatta tcttctgggc acacgaccgc tttggtggct    300
acgctcaatc tggcctgttg gctgaaatca ccccggacaa agcgttccag gacaagctgt    360
atccgtttac ctgggatgcc gtacgttaca cggcaagct gattgcttac ccgatcgctg    420
ttgaagcgtt atcgctgatt tataacaaag atctgctgcc gaacccgcca aaacctggg    480 aagagatccc ggcgctggat aaagaactga aagcgaaagg taagagcgcg ctgatgttca    540
acctgcaaga accgtacttc acctggccgc tgattgctgc tgacggggt tatgcgttca    600 agtatgaaaa cggcaagtac gacattaaag acgtgggcgt ggataacgct ggcgcgaaag    660
cgggtctgac cttcctggtt gacctgatta aaaacaaaca catgaatgca gacaccgatt    720
actccatcgc agaagctgcc tttaataaag gcgaaacagc gatgaccatc aacggcccgt    780
```

```
gggcatggtc caacatcgac accagcaaag tgaattatgg tgtaacggta ctgccgacct    840
tcaagggtca accatccaaa ccgttcgttg gcgtgctgag cgcaggtatt aacgccgcca    900
gtccgaacaa agagctggcg aaagagttcc tcgaaaacta tctgctgact gatgaaggtc    960
tggaagcggt taataaagac aaaccgctgg gtgccgtagc gctgaagtct tacgaggaag   1020
agttggcgaa agatccacgt attgccgcca ccatggaaaa cgcccagtcc gctttctggt   1080
atgccgtgcg tatcgaagcc cgcctgcagg cctcggtcga cgccgaatct agaagcgata   1140
aaattattca cctgactgac gacagttttg acacggatgt actcaaagcg gacggggcga   1200
tcctcgtcga tttctgggca gagtggtgcg gtccgtgcaa aatgatcgcc ccgattctgg   1260
atgaaatcgc tgacgaatat cagggcaaac tgaccgttgc aaaactgaac atcgatcaaa   1320
accctggcac tgcgccgaaa tatggcatcc gtggtatccc gactctgctg ctgttcaaaa   1380
acggtgaagt ggcggcaacc aaagtgggtg cactgtctaa aggtcagttg aaagagaacc   1440
tggcggatta taaagatgac gatgacaaat aataag                             1476
```

<210> SEQ ID NO 285
<211> LENGTH: 1476
<212> TYPE: DNA
<213> ORGANISM: Artificial Sequence
<220> FEATURE:
<223> OTHER INFORMATION: Synthetic nucleic acid sequence

<400> SEQUENCE: 285

```
aggaggttct gcatatgaaa ataaaaacag gtgcacgcat cctcgcatta tccgcattaa     60
cgacgatgat gttttccgcc tcggctctcg ccaaaatcga agaaggtaaa ctggtaatct    120
ggattaacgg cgataaaggc tataacggtc tcgctgaagt cggtaagaaa ttcgagaaag    180
ataccggaat taaagtcacc gttgagcatc cggataaact ggaagagaaa ttcccacagg    240
ttgcggcaac tggcgatggc cctgacatta tcttctgggc acacgaccgc tttggtggct    300
acgctcaatc tggcctgttg gctgaaatca ccccggacaa agcgttccag gacaagctgt    360
atccgtttac ctgggatgcc gtacgttaca acggcaagct gattgcttac ccgatcgctg    420
ttgaagcgtt atcgctgatt tataacaaag atctgctgcc gaacccgcca aaaacctggg    480
aagagatccc ggcgctggat aaagaactga aagcgaaagg taagagcgcg ctgatgttca    540
acctgcaaga accgtacttc acctggccgc tgattgctgc tgacggggt tatgcgttca    600 agtatgaaaa cggcaagtac gacattaaag acgtgggcgt ggataacgct ggcgcgaaag    660
cgggtctgac cttcctggtt gacctgatta aaaacaaaca catgaatgca gacaccgatt    720
actccatcgc agaagctgcc tttaataaag gcgaaacagc gatgaccatc aacggcccgt    780
gggcatggtc caacatcgac accagcaaag tgaattatgg tgtaacggta ctgccgacct    840
tcaagggtca accatccaaa ccgttcgttg gcgtgctgag cgcaggtatt aacgccgcca    900
gtccgaacaa agagctggcg aaagagttcc tcgaaaacta tctgctgact gatgaaggtc    960
tggaagcggt taataaagac aaaccgctgg gtgccgtagc gctgaagtct tacgaggaag   1020
agttggcgaa agatccacgt attgccgcca ccatggaaaa cgcccagtcc gctttctggt   1080
atgccgtgcg tatcgaagcc cgcctgcagg cctcggtcga cgccgaatct agaagcgata   1140
aaattattca cctgactgac gacagttttg acacggatgt actcaaagcg gacggggcga   1200
tcctcgtcga tttctgggca gagtggtgcg gtccgtgcaa aatgatcgcc ccgattctgg   1260
atgaaatcgc tgacgaatat cagggcaaac tgaccgttgc aaaactgaac atcgatcaaa   1320
accctggcac tgcgccgaaa tatggcatcc gtggtatccc gactctgctg ctgttcaaaa   1380
```

```
acggtgaagt ggcggcaacc aaagtgggtg cactgtctaa aggtcagttg aaagagaacc  1440
tggcggatta taaagatgac gatgacaaat aataag                             1476
```

<210> SEQ ID NO 286
<211> LENGTH: 383
<212> TYPE: PRT
<213> ORGANISM: Artificial Sequence
<220> FEATURE:
<223> OTHER INFORMATION: Synthetic amino acid sequence

<400> SEQUENCE: 286

```
Met Phe Glu Pro Met Glu Leu Thr Asn Asp Ala Val Ile Lys Val Ile
  1               5                  10                  15

Gly Val Gly Gly Gly Gly Gly Asn Ala Val Glu His Met Val Arg Glu
                 20                  25                  30

Arg Ile Glu Gly Val Glu Phe Phe Ala Val Asn Thr Asp Ala Gln Ala
             35                  40                  45

Leu Arg Lys Thr Ala Val Gly Gln Thr Ile Gln Ile Gly Ser Gly Ile
 50                  55                  60

Thr Lys Gly Leu Gly Ala Gly Ala Asn Pro Glu Val Gly Arg Asn Ala
 65                  70                  75                  80

Ala Asp Glu Asp Arg Asp Ala Leu Arg Ala Ala Leu Glu Gly Ala Asp
                 85                  90                  95

Met Val Phe Ile Ala Ala Gly Met Gly Gly Gly Thr Gly Thr Gly Ala
            100                 105                 110

Ala Pro Val Val Ala Glu Val Ala Lys Asp Leu Gly Ile Leu Thr Val
            115                 120                 125

Ala Val Val Thr Lys Pro Phe Asn Phe Glu Gly Lys Lys Arg Met Ala
130                 135                 140

Phe Ala Glu Gln Gly Ile Thr Glu Leu Ser Lys His Val Asp Ser Leu
145                 150                 155                 160

Ile Thr Ile Pro Asn Asp Lys Leu Leu Lys Val Leu Gly Arg Gly Ile
                165                 170                 175

Ser Leu Leu Asp Ala Phe Gly Ala Ala Asn Asp Val Leu Lys Gly Ala
            180                 185                 190

Val Gln Gly Ile Ala Glu Leu Ile Thr Arg Pro Gly Leu Met Asn Val
            195                 200                 205

Asp Phe Ala Asp Val Arg Thr Val Met Ser Glu Met Gly Tyr Ala Met
210                 215                 220

Met Gly Ser Gly Val Ala Ser Gly Glu Asp Arg Ala Glu Glu Ala Ala
225                 230                 235                 240

Glu Met Ala Ile Ser Ser Pro Leu Leu Glu Asp Ile Asp Leu Ser Gly
                245                 250                 255

Ala Arg Gly Val Leu Val Asn Ile Thr Ala Gly Phe Asp Leu Arg Leu
            260                 265                 270

Asp Glu Phe Glu Thr Val Gly Asn Thr Ile Arg Ala Phe Ala Ser Asp
            275                 280                 285

Asn Ala Thr Val Val Ile Gly Thr Ser Leu Asp Pro Asp Met Asn Asp
            290                 295                 300

Glu Leu Arg Val Thr Val Val Ala Thr Gly Ile Gly Met Asp Lys Arg
305                 310                 315                 320

Pro Glu Ile Thr Leu Val Thr Asn Lys Gln Val Gln Gln Pro Val Met
                325                 330                 335

Asp Arg Tyr Gln Gln His Gly Met Ala Pro Leu Thr Gln Glu Gln Lys
            340                 345                 350
```

Pro Val Ala Lys Val Val Asn Asp Asn Ala Pro Gln Thr Ala Lys Glu
          355                 360                 365

Pro Asp Tyr Leu Asp Ile Pro Ala Phe Leu Arg Lys Gln Ala Asp
          370                 375                 380

<210> SEQ ID NO 287
<211> LENGTH: 383
<212> TYPE: PRT
<213> ORGANISM: Artificial Sequence
<220> FEATURE:
<223> OTHER INFORMATION: Synthetic amino acid sequence

<400> SEQUENCE: 287

Met Phe Glu Pro Met Glu Leu Thr Asn Asp Ala Val Ile Lys Val Ile
 1               5                  10                  15

Gly Val Gly Gly Gly Gly Asn Ala Val Glu His Met Val Arg Glu
                20                  25                  30

Arg Ile Glu Gly Val Glu Phe Phe Ala Val Asn Thr Asp Ala Gln Ala
             35                  40                  45

Leu Arg Lys Thr Ala Val Gly Gln Thr Ile Gln Ile Gly Ser Gly Ile
 50                  55                  60

Thr Lys Gly Leu Gly Ala Gly Ala Asn Pro Glu Val Gly Arg Asn Ala
65                  70                  75                  80

Ala Asp Glu Asp Arg Asp Ala Leu Arg Ala Ala Leu Glu Gly Ala Asp
                 85                  90                  95

Met Val Phe Ile Ala Ala Met Gly Gly Gly Thr Gly Thr Gly Ala
                100                 105                 110

Ala Pro Val Val Ala Glu Val Ala Lys Asp Leu Gly Ile Leu Thr Val
            115                 120                 125

Ala Val Val Thr Lys Pro Phe Asn Phe Glu Gly Lys Lys Arg Met Ala
        130                 135                 140

Phe Ala Glu Gln Gly Ile Thr Glu Leu Ser Lys His Val Asp Ser Leu
145                 150                 155                 160

Ile Thr Ile Pro Asn Asp Lys Leu Leu Lys Val Leu Gly Arg Gly Ile
                165                 170                 175

Ser Leu Leu Asp Ala Phe Gly Ala Ala Asn Asp Val Leu Lys Gly Ala
            180                 185                 190

Val Gln Gly Ile Ala Glu Leu Ile Thr Arg Pro Gly Leu Met Asn Val
        195                 200                 205

Asp Phe Ala Asp Val Arg Thr Val Met Ser Glu Met Gly Tyr Ala Met
210                 215                 220

Met Gly Ser Gly Val Ala Ser Gly Glu Asp Arg Ala Glu Glu Ala Ala
225                 230                 235                 240

Glu Met Ala Ile Ser Ser Pro Leu Leu Glu Asp Ile Asp Leu Ser Gly
                245                 250                 255

Ala Arg Gly Val Leu Val Asn Ile Thr Ala Gly Phe Asp Leu Arg Leu
            260                 265                 270

Asp Glu Phe Glu Thr Val Gly Asn Thr Ile Arg Ala Phe Ala Ser Asp
        275                 280                 285

Asn Ala Thr Val Val Ile Gly Thr Ser Leu Asp Pro Asp Met Asn Asp
    290                 295                 300

Glu Leu Arg Val Thr Val Val Ala Thr Gly Ile Gly Met Asp Lys Arg
305                 310                 315                 320

Pro Glu Ile Thr Leu Val Thr Asn Lys Gln Val Gln Gln Pro Val Met
                325                 330                 335

-continued

```
Asp Arg Tyr Gln Gln His Gly Met Ala Pro Leu Thr Gln Glu Gln Lys
        340                 345                 350

Pro Val Ala Lys Val Val Asn Asp Asn Ala Pro Gln Thr Ala Lys Glu
        355                 360                 365

Pro Asp Tyr Leu Asp Ile Pro Ala Phe Leu Arg Lys Gln Ala Asp
        370                 375                 380

<210> SEQ ID NO 288
<211> LENGTH: 446
<212> TYPE: PRT
<213> ORGANISM: Artificial Sequence
<220> FEATURE:
<223> OTHER INFORMATION: Synthetic amino acid sequence

<400> SEQUENCE: 288

Met Pro Val Leu Glu Asn Arg Ala Ala Gln Gly Asp Ile Thr Ala Pro
  1               5                  10                  15

Gly Gly Ala Arg Arg Leu Thr Gly Asp Gln Thr Ala Ala Leu Arg Asp
             20                  25                  30

Ser Leu Ser Asp Lys Pro Ala Lys Asn Ile Ile Leu Leu Ile Gly Asp
         35                  40                  45

Gly Met Gly Asp Ser Glu Ile Thr Ala Ala Arg Asn Tyr Ala Glu Gly
     50                  55                  60

Ala Gly Gly Phe Phe Lys Gly Ile Asp Ala Leu Pro Leu Thr Gly Gln
 65                  70                  75                  80

Tyr Thr His Tyr Ala Leu Asn Lys Lys Thr Gly Lys Pro Asp Tyr Val
                 85                  90                  95

Thr Asp Ser Ala Ala Ser Ala Thr Ala Trp Ser Thr Gly Val Lys Thr
            100                 105                 110

Tyr Asn Gly Ala Leu Gly Val Asp Ile His Glu Lys Asp His Pro Thr
        115                 120                 125

Ile Leu Glu Met Ala Lys Ala Ala Gly Leu Ala Thr Gly Asn Val Ser
    130                 135                 140

Thr Ala Glu Leu Gln Asp Ala Thr Pro Ala Ala Leu Val Ala His Val
145                 150                 155                 160

Thr Ser Arg Lys Cys Tyr Gly Pro Ser Ala Thr Ser Glu Lys Cys Pro
                165                 170                 175

Gly Asn Ala Leu Glu Lys Gly Gly Lys Gly Ser Ile Thr Glu Gln Leu
            180                 185                 190

Leu Asn Ala Arg Ala Asp Val Thr Leu Gly Gly Gly Ala Lys Thr Phe
        195                 200                 205

Ala Glu Thr Ala Thr Ala Gly Glu Trp Gln Gly Lys Thr Leu Arg Glu
    210                 215                 220

Gln Ala Gln Ala Arg Gly Tyr Gln Leu Val Ser Asp Ala Ala Ser Leu
225                 230                 235                 240

Asn Ser Val Thr Glu Ala Asn Gln Gln Lys Pro Leu Leu Gly Leu Phe
                245                 250                 255

Ala Asp Gly Asn Met Pro Val Arg Trp Leu Gly Pro Lys Ala Thr Tyr
            260                 265                 270

His Gly Asn Ile Asp Lys Pro Ala Val Thr Cys Thr Pro Asn Pro Gln
        275                 280                 285

Arg Asn Asp Ser Val Pro Thr Leu Ala Gln Met Thr Asp Lys Ala Ile
    290                 295                 300

Glu Leu Leu Ser Lys Asn Glu Lys Gly Phe Phe Leu Gln Val Glu Gly
305                 310                 315                 320

Ala Ser Ile Asp Lys Gln Asp His Ala Ala Asn Pro Cys Gly Gln Ile
```

-continued

```
                325                 330                 335
Gly Glu Thr Val Asp Leu Asp Glu Ala Val Gln Arg Ala Leu Glu Phe
            340                 345                 350

Ala Lys Lys Glu Gly Asn Thr Leu Val Ile Val Thr Ala Asp His Ala
        355                 360                 365

His Ala Ser Gln Ile Val Ala Pro Asp Thr Lys Ala Pro Gly Leu Thr
    370                 375                 380

Gln Ala Leu Asn Thr Lys Asp Gly Ala Val Met Val Met Ser Tyr Gly
385                 390                 395                 400

Asn Ser Glu Glu Asp Ser Gln Glu His Thr Gly Ser Gln Leu Arg Ile
                405                 410                 415

Ala Ala Tyr Gly Pro His Ala Ala Asn Val Val Gly Leu Thr Asp Gln
            420                 425                 430

Thr Asp Leu Phe Tyr Thr Met Lys Ala Ala Leu Gly Leu Lys
        435                 440                 445

<210> SEQ ID NO 289
<211> LENGTH: 494
<212> TYPE: PRT
<213> ORGANISM: Artificial Sequence
<220> FEATURE:
<223> OTHER INFORMATION: Synthetic amino acid sequence

<400> SEQUENCE: 289

Met Ser Arg Pro Arg Leu Ile Val Ala Leu Phe Leu Phe Phe Asn Val
1               5                   10                  15

Phe Val His Gly Glu Asn Lys Val Lys Gln Ser Thr Ile Ala Leu Ala
            20                  25                  30

Leu Leu Pro Leu Leu Phe Thr Pro Val Thr Lys Ala Arg Thr Pro Glu
        35                  40                  45

Met Pro Val Leu Glu Asn Arg Ala Ala Gln Gly Asp Ile Thr Ala Pro
    50                  55                  60

Gly Gly Ala Arg Arg Leu Thr Gly Asp Gln Thr Ala Ala Leu Arg Asp
65                  70                  75                  80

Ser Leu Ser Asp Lys Pro Ala Lys Asn Ile Ile Leu Leu Ile Gly Asp
                85                  90                  95

Gly Met Gly Asp Ser Glu Ile Thr Ala Ala Arg Asn Tyr Ala Glu Gly
            100                 105                 110

Ala Gly Gly Phe Phe Lys Gly Ile Asp Ala Leu Pro Leu Thr Gly Gln
        115                 120                 125

Tyr Thr His Tyr Ala Leu Asn Lys Lys Thr Gly Lys Pro Asp Tyr Val
    130                 135                 140

Thr Asp Ser Ala Ala Ser Ala Thr Ala Trp Ser Thr Gly Val Lys Thr
145                 150                 155                 160

Tyr Asn Gly Ala Leu Gly Val Asp Ile His Glu Lys Asp His Pro Thr
                165                 170                 175

Ile Leu Glu Met Ala Lys Ala Ala Gly Leu Ala Thr Gly Asn Val Ser
            180                 185                 190

Thr Ala Glu Leu Gln Asp Ala Thr Pro Ala Ala Leu Val Ala His Val
        195                 200                 205

Thr Ser Arg Lys Cys Tyr Gly Pro Ser Ala Thr Ser Glu Lys Cys Pro
    210                 215                 220

Gly Asn Ala Leu Glu Lys Gly Gly Lys Gly Ser Ile Thr Glu Gln Leu
225                 230                 235                 240

Leu Asn Ala Arg Ala Asp Val Thr Leu Gly Gly Gly Ala Lys Thr Phe
                245                 250                 255
```

Ala Glu Thr Ala Thr Ala Gly Glu Trp Gln Gly Lys Thr Leu Arg Glu
            260                 265                 270

Gln Ala Gln Ala Arg Gly Tyr Gln Leu Val Ser Asp Ala Ala Ser Leu
        275                 280                 285

Asn Ser Val Thr Glu Ala Asn Gln Gln Lys Pro Leu Leu Gly Leu Phe
    290                 295                 300

Ala Asp Gly Asn Met Pro Val Arg Trp Leu Gly Pro Lys Ala Thr Tyr
305                 310                 315                 320

His Gly Asn Ile Asp Lys Pro Ala Val Thr Cys Thr Pro Asn Pro Gln
                325                 330                 335

Arg Asn Asp Ser Val Pro Thr Leu Ala Gln Met Thr Asp Lys Ala Ile
            340                 345                 350

Glu Leu Leu Ser Lys Asn Glu Lys Gly Phe Phe Leu Gln Val Glu Gly
        355                 360                 365

Ala Ser Ile Asp Lys Gln Asp His Ala Ala Asn Pro Cys Gly Gln Ile
    370                 375                 380

Gly Glu Thr Val Asp Leu Asp Glu Ala Val Gln Arg Ala Leu Glu Phe
385                 390                 395                 400

Ala Lys Lys Glu Gly Asn Thr Leu Val Ile Val Thr Ala Asp His Ala
                405                 410                 415

His Ala Ser Gln Ile Val Ala Pro Asp Thr Lys Ala Pro Gly Leu Thr
            420                 425                 430

Gln Ala Leu Asn Thr Lys Asp Gly Ala Val Met Val Met Ser Tyr Gly
        435                 440                 445

Asn Ser Glu Glu Asp Ser Gln Glu His Thr Gly Ser Gln Leu Arg Ile
    450                 455                 460

Ala Ala Tyr Gly Pro His Ala Ala Asn Val Val Gly Leu Thr Asp Gln
465                 470                 475                 480

Thr Asp Leu Phe Tyr Thr Met Lys Ala Ala Leu Gly Leu Lys
                485                 490

<210> SEQ ID NO 290
<211> LENGTH: 468
<212> TYPE: PRT
<213> ORGANISM: Artificial Sequence
<220> FEATURE:
<223> OTHER INFORMATION: Synthetic chimeric amino acid sequence

<400> SEQUENCE: 290

Met Asn Leu Gly Asn Arg Leu Phe Ile Leu Ile Ala Val Leu Leu Pro
1               5                   10                  15

Leu Ala Val Leu Leu Leu Met Pro Val Leu Glu Asn Arg Ala Ala Gln
            20                  25                  30

Gly Asp Ile Thr Ala Pro Gly Gly Ala Arg Arg Leu Thr Gly Asp Gln
        35                  40                  45

Thr Ala Ala Leu Arg Asp Ser Leu Ser Asp Lys Pro Ala Lys Asn Ile
    50                  55                  60

Ile Leu Leu Ile Gly Asp Gly Met Gly Asp Ser Glu Ile Thr Ala Ala
65                  70                  75                  80

Arg Asn Tyr Ala Glu Gly Ala Gly Gly Phe Phe Lys Gly Ile Asp Ala
                85                  90                  95

Leu Pro Leu Thr Gly Gln Tyr Thr His Tyr Ala Leu Asn Lys Lys Thr
            100                 105                 110

Gly Lys Pro Asp Tyr Val Thr Asp Ser Ala Ala Ser Ala Thr Ala Trp
        115                 120                 125

```
Ser Thr Gly Val Lys Thr Tyr Asn Gly Ala Leu Gly Val Asp Ile His
    130                 135                 140

Glu Lys Asp His Pro Thr Ile Leu Glu Met Ala Lys Ala Ala Gly Leu
145                 150                 155                 160

Ala Thr Gly Asn Val Ser Thr Ala Glu Leu Gln Asp Ala Thr Pro Ala
                165                 170                 175

Ala Leu Val Ala His Val Thr Ser Arg Lys Cys Tyr Gly Pro Ser Ala
            180                 185                 190

Thr Ser Glu Lys Cys Pro Gly Asn Ala Leu Glu Lys Gly Lys Gly
        195                 200                 205

Ser Ile Thr Glu Gln Leu Leu Asn Ala Arg Ala Asp Val Thr Leu Gly
    210                 215                 220

Gly Gly Ala Lys Thr Phe Ala Glu Thr Ala Thr Ala Gly Glu Trp Gln
225                 230                 235                 240

Gly Lys Thr Leu Arg Glu Gln Ala Gln Ala Arg Gly Tyr Gln Leu Val
                245                 250                 255

Ser Asp Ala Ala Ser Leu Asn Ser Val Thr Glu Ala Asn Gln Gln Lys
            260                 265                 270

Pro Leu Leu Gly Leu Phe Ala Asp Gly Asn Met Pro Val Arg Trp Leu
        275                 280                 285

Gly Pro Lys Ala Thr Tyr His Gly Asn Ile Asp Lys Pro Ala Val Thr
    290                 295                 300

Cys Thr Pro Asn Pro Gln Arg Asn Asp Ser Val Pro Thr Leu Ala Gln
305                 310                 315                 320

Met Thr Asp Lys Ala Ile Glu Leu Leu Ser Lys Asn Glu Lys Gly Phe
                325                 330                 335

Phe Leu Gln Val Glu Gly Ala Ser Ile Asp Lys Gln Asp His Ala Ala
            340                 345                 350

Asn Pro Cys Gly Gln Ile Gly Glu Thr Val Asp Leu Asp Glu Ala Val
        355                 360                 365

Gln Arg Ala Leu Glu Phe Ala Lys Lys Glu Gly Asn Thr Leu Val Ile
    370                 375                 380

Val Thr Ala Asp His Ala His Ala Ser Gln Ile Val Ala Pro Asp Thr
385                 390                 395                 400

Lys Ala Pro Gly Leu Thr Gln Ala Leu Asn Thr Lys Asp Gly Ala Val
                405                 410                 415

Met Val Met Ser Tyr Gly Asn Ser Glu Glu Asp Ser Gln Glu His Thr
            420                 425                 430

Gly Ser Gln Leu Arg Ile Ala Ala Tyr Gly Pro His Ala Ala Asn Val
        435                 440                 445

Val Gly Leu Thr Asp Gln Thr Asp Leu Phe Tyr Thr Met Lys Ala Ala
    450                 455                 460

Leu Gly Leu Lys
465

<210> SEQ ID NO 291
<211> LENGTH: 424
<212> TYPE: PRT
<213> ORGANISM: Artificial Sequence
<220> FEATURE:
<223> OTHER INFORMATION: Synthetic amino acid sequence

<400> SEQUENCE: 291

Met Ala Thr Thr His Ala Gln Gly His Pro Pro Val Leu Gly Asn Asp
1               5                   10                  15

Thr Leu Arg Glu His Tyr Asp Tyr Val Gly Lys Leu Ala Gly Arg Leu
```

-continued

```
                  20                  25                  30
Arg Asp Pro Pro Glu Gly Ser Thr Leu Ile Thr Ile Leu Phe Leu
            35                  40                  45
Val Thr Cys Ser Phe Ile Val Leu Glu Asn Leu Met Val Leu Ile Ala
        50                  55                  60
Ile Trp Lys Asn Asn Lys Phe His Asn Arg Met Tyr Phe Phe Ile Gly
65                  70                  75                  80
Asn Leu Ala Leu Cys Asp Leu Leu Ala Gly Ile Ala Tyr Lys Val Asn
                85                  90                  95
Ile Leu Met Ser Gly Arg Lys Thr Phe Ser Leu Ser Pro Thr Val Trp
            100                 105                 110
Phe Leu Arg Glu Gly Ser Met Phe Val Ala Leu Gly Ala Ser Thr Cys
        115                 120                 125
Ser Leu Leu Ala Ile Ala Ile Glu Arg His Leu Thr Met Ile Lys Met
    130                 135                 140
Arg Pro Tyr Asp Ala Asn Lys Lys His Arg Val Phe Leu Leu Ile Gly
145                 150                 155                 160
Met Cys Trp Leu Ile Ala Phe Ser Leu Gly Ala Leu Pro Ile Leu Gly
                165                 170                 175
Trp Asn Cys Leu Glu Asn Phe Pro Asp Cys Ser Thr Ile Leu Pro Leu
            180                 185                 190
Tyr Ser Lys Lys Tyr Ile Ala Phe Leu Ile Ser Ile Phe Ile Ala Ile
        195                 200                 205
Leu Val Thr Ile Val Ile Leu Tyr Ala Arg Ile Tyr Phe Leu Val Lys
    210                 215                 220
Ser Ser Ser Arg Arg Val Ala Asn His Asn Ser Glu Arg Ser Met Ala
225                 230                 235                 240
Leu Leu Arg Thr Val Val Ile Val Ser Val Phe Ile Ala Cys Trp
                245                 250                 255
Ser Pro Leu Phe Ile Leu Phe Leu Ile Asp Val Ala Cys Arg Ala Lys
            260                 265                 270
Glu Cys Ser Ile Leu Phe Lys Ser Gln Trp Phe Ile Met Leu Ala Val
        275                 280                 285
Leu Asn Ser Ala Met Asn Pro Val Ile Tyr Thr Leu Ala Ser Lys Glu
    290                 295                 300
Met Arg Arg Ala Phe Phe Arg Leu Val Cys Gly Cys Leu Val Lys Gly
305                 310                 315                 320
Lys Gly Thr Gln Ala Ser Pro Met Gln Pro Ala Leu Asp Pro Ser Arg
                325                 330                 335
Ser Lys Ser Ser Ser Asn Asn Ser Ser His Ser Pro Lys Val
            340                 345                 350
Lys Glu Asp Leu Pro His Val Ala Thr Ser Ser Cys Val Thr Asp Lys
        355                 360                 365
Thr Arg Ser Leu Gln Asn Gly Val Leu Cys Lys Lys Gly Asn Ser Ala
    370                 375                 380
Asp Ile Gln His Ser Gly Gly Arg Ser Ser Leu Glu Gly Pro Arg Phe
385                 390                 395                 400
Glu Gly Lys Pro Ile Pro Asn Pro Leu Leu Gly Leu Asp Ser Thr Arg
                405                 410                 415
Thr Gly His His His His His His
            420

<210> SEQ ID NO 292
<211> LENGTH: 413
```

```
<212> TYPE: PRT
<213> ORGANISM: Homo sapiens
<220> FEATURE:
<221> NAME/KEY: UNSURE
<222> LOCATION: 164
<223> OTHER INFORMATION: Xaa = unkown amino acid

<400> SEQUENCE: 292
```

| | | | | | | | | | | | | | | |
|---|---|---|---|---|---|---|---|---|---|---|---|---|---|---|
| Met | Gly | Gln | Pro | Gly | Asn | Gly | Ser | Ala | Phe | Leu | Leu | Ala | Pro | Asn | Gly |
| 1 | | | | 5 | | | | | 10 | | | | | 15 | |

| Ser | His | Ala | Pro | Asp | His | Asp | Val | Thr | Gln | Gln | Arg | Asp | Glu | Val | Trp |
|---|---|---|---|---|---|---|---|---|---|---|---|---|---|---|---|
| | | | 20 | | | | 25 | | | | | 30 | | | |

| Val | Val | Gly | Met | Gly | Ile | Val | Met | Ser | Leu | Ile | Val | Leu | Ala | Ile | Val |
|---|---|---|---|---|---|---|---|---|---|---|---|---|---|---|---|
| | | | 35 | | | | | 40 | | | | | 45 | | |

| Phe | Gly | Asn | Val | Leu | Val | Ile | Thr | Ala | Ile | Ala | Lys | Phe | Glu | Arg | Leu |
|---|---|---|---|---|---|---|---|---|---|---|---|---|---|---|---|
| | 50 | | | | | 55 | | | | | 60 | | | | |

| Gln | Thr | Val | Thr | Asn | Tyr | Phe | Ile | Thr | Ser | Leu | Ala | Cys | Ala | Asp | Leu |
|---|---|---|---|---|---|---|---|---|---|---|---|---|---|---|---|
| 65 | | | | | 70 | | | | | 75 | | | | | 80 |

| Val | Met | Gly | Leu | Ala | Val | Val | Pro | Phe | Gly | Ala | Ala | His | Ile | Leu | Met |
|---|---|---|---|---|---|---|---|---|---|---|---|---|---|---|---|
| | | | | 85 | | | | | 90 | | | | | 95 | |

| Lys | Met | Trp | Thr | Phe | Gly | Asn | Phe | Trp | Cys | Glu | Phe | Trp | Thr | Ser | Ile |
|---|---|---|---|---|---|---|---|---|---|---|---|---|---|---|---|
| | | | 100 | | | | | 105 | | | | | 110 | | |

| Asp | Val | Leu | Cys | Val | Thr | Ala | Ser | Ile | Glu | Thr | Leu | Cys | Val | Ile | Ala |
|---|---|---|---|---|---|---|---|---|---|---|---|---|---|---|---|
| | | 115 | | | | | 120 | | | | | 125 | | | |

| Val | Asp | Arg | Tyr | Phe | Ala | Ile | Thr | Ser | Pro | Phe | Lys | Tyr | Gln | Ser | Leu |
|---|---|---|---|---|---|---|---|---|---|---|---|---|---|---|---|
| 130 | | | | | 135 | | | | | 140 | | | | | |

| Leu | Thr | Lys | Asn | Lys | Ala | Arg | Val | Ile | Ile | Leu | Met | Val | Trp | Ile | Val |
|---|---|---|---|---|---|---|---|---|---|---|---|---|---|---|---|
| 145 | | | | | 150 | | | | | 155 | | | | | 160 |

| Ser | Gly | Leu | Xaa | Ser | Phe | Leu | Pro | Ile | Gln | Met | His | Trp | Tyr | Arg | Ala |
|---|---|---|---|---|---|---|---|---|---|---|---|---|---|---|---|
| | | | 165 | | | | | 170 | | | | | 175 | | |

| Thr | His | Gln | Glu | Ala | Ile | Asn | Cys | Tyr | Ala | Asn | Glu | Thr | Cys | Cys | Asp |
|---|---|---|---|---|---|---|---|---|---|---|---|---|---|---|---|
| | | | 180 | | | | | 185 | | | | | 190 | | |

| Phe | Phe | Thr | Asn | Gln | Ala | Tyr | Ala | Ile | Ala | Ser | Ser | Ile | Val | Ser | Phe |
|---|---|---|---|---|---|---|---|---|---|---|---|---|---|---|---|
| | | 195 | | | | | 200 | | | | | 205 | | | |

| Tyr | Val | Pro | Leu | Val | Ile | Met | Val | Phe | Val | Tyr | Ser | Arg | Val | Phe | Gln |
|---|---|---|---|---|---|---|---|---|---|---|---|---|---|---|---|
| 210 | | | | | 215 | | | | | 220 | | | | | |

| Glu | Ala | Lys | Arg | Gln | Leu | Gln | Lys | Ile | Asp | Lys | Ser | Glu | Gly | Arg | Phe |
|---|---|---|---|---|---|---|---|---|---|---|---|---|---|---|---|
| 225 | | | | | 230 | | | | | 235 | | | | | 240 |

| His | Val | Gln | Asn | Leu | Ser | Gln | Val | Glu | Gln | Asp | Gly | Arg | Thr | Gly | His |
|---|---|---|---|---|---|---|---|---|---|---|---|---|---|---|---|
| | | | 245 | | | | | 250 | | | | | 255 | | |

| Gly | Leu | Arg | Arg | Ser | Ser | Lys | Phe | Cys | Leu | Lys | Glu | His | Lys | Ala | Leu |
|---|---|---|---|---|---|---|---|---|---|---|---|---|---|---|---|
| | | | 260 | | | | | 265 | | | | | 270 | | |

| Lys | Thr | Leu | Gly | Ile | Ile | Met | Gly | Thr | Phe | Thr | Leu | Cys | Trp | Leu | Pro |
|---|---|---|---|---|---|---|---|---|---|---|---|---|---|---|---|
| | | 275 | | | | | 280 | | | | | 285 | | | |

| Phe | Phe | Ile | Val | Asn | Ile | Val | His | Val | Ile | Gln | Asp | Asn | Leu | Ile | Arg |
|---|---|---|---|---|---|---|---|---|---|---|---|---|---|---|---|
| | 290 | | | | | 295 | | | | | 300 | | | | |

| Lys | Glu | Val | Tyr | Ile | Leu | Leu | Asn | Trp | Ile | Gly | Tyr | Val | Asn | Ser | Gly |
|---|---|---|---|---|---|---|---|---|---|---|---|---|---|---|---|
| 305 | | | | | 310 | | | | | 315 | | | | | 320 |

| Phe | Asn | Pro | Leu | Ile | Tyr | Cys | Arg | Ser | Pro | Asp | Phe | Arg | Ile | Ala | Phe |
|---|---|---|---|---|---|---|---|---|---|---|---|---|---|---|---|
| | | | 325 | | | | | 330 | | | | | 335 | | |

| Gln | Glu | Leu | Leu | Cys | Leu | Arg | Arg | Ser | Ser | Leu | Lys | Ala | Tyr | Gly | Asn |
|---|---|---|---|---|---|---|---|---|---|---|---|---|---|---|---|
| | | | 340 | | | | | 345 | | | | | 350 | | |

| Gly | Tyr | Ser | Ser | Asn | Gly | Asn | Thr | Gly | Glu | Gln | Ser | Gly | Tyr | His | Val |
|---|---|---|---|---|---|---|---|---|---|---|---|---|---|---|---|
| | | 355 | | | | | 360 | | | | | 365 | | | |

| Glu | Gln | Glu | Lys | Glu | Asn | Lys | Leu | Leu | Cys | Glu | Asp | Leu | Pro | Gly | Thr |
|---|---|---|---|---|---|---|---|---|---|---|---|---|---|---|---|
| 370 | | | | | 375 | | | | | 380 | | | | | |

```
Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410
```

<210> SEQ ID NO 293
<211> LENGTH: 416
<212> TYPE: PRT
<213> ORGANISM: Artificial Sequence
<220> FEATURE:
<223> OTHER INFORMATION: Synthetic amino acid sequence

<400> SEQUENCE: 293

```
Met Asp Ser Val Cys Pro Gln Gly Lys Tyr Ile His Pro Gln Asn Asn
1               5                   10                  15

Ser Ile Cys Cys Thr Lys Cys His Lys Gly Thr Tyr Leu Tyr Asn Asp
                20                  25                  30

Cys Pro Gly Pro Gly Gln Asp Thr Asp Cys Arg Glu Cys Glu Ser Gly
            35                  40                  45

Ser Phe Thr Ala Ser Glu Asn His Leu Arg His Cys Leu Ser Cys Ser
50                  55                  60

Lys Cys Arg Lys Glu Met Gly Gln Val Glu Ile Ser Ser Cys Thr Val
65                  70                  75                  80

Asp Arg Asp Thr Val Cys Gly Cys Arg Lys Asn Gln Tyr Arg His Tyr
                85                  90                  95

Trp Ser Glu Asn Leu Phe Gln Cys Phe Asn Cys Ser Leu Cys Leu Asn
            100                 105                 110

Gly Thr Val His Leu Ser Cys Gln Glu Lys Gln Asn Thr Val Cys Thr
        115                 120                 125

Cys His Ala Gly Phe Phe Leu Arg Glu Asn Glu Cys Val Ser Cys Ser
130                 135                 140

Asn Cys Lys Lys Ser Leu Glu Cys Thr Lys Leu Cys Leu Pro Gln Ile
145                 150                 155                 160

Glu Asn Val Lys Gly Thr Glu Asp Ser Gly Thr Thr Val Leu Leu Pro
                165                 170                 175

Leu Val Ile Phe Phe Gly Leu Cys Leu Leu Ser Leu Leu Phe Ile Gly
            180                 185                 190

Leu Met Tyr Arg Tyr Gln Arg Trp Lys Ser Lys Leu Tyr Ser Ile Val
        195                 200                 205

Cys Gly Lys Ser Thr Pro Glu Lys Glu Gly Glu Leu Glu Gly Thr Thr
210                 215                 220

Thr Lys Pro Leu Ala Pro Asn Pro Ser Phe Ser Pro Thr Pro Gly Phe
225                 230                 235                 240

Thr Pro Thr Leu Gly Phe Ser Pro Val Pro Ser Ser Thr Phe Thr Ser
                245                 250                 255

Ser Ser Thr Tyr Thr Pro Gly Asp Cys Pro Asn Phe Ala Ala Pro Arg
            260                 265                 270

Arg Glu Val Ala Pro Pro Tyr Gln Gly Ala Asp Pro Ile Leu Ala Thr
        275                 280                 285

Ala Leu Ala Ser Asp Pro Ile Pro Asn Pro Leu Gln Lys Trp Glu Asp
290                 295                 300

Ser Ala His Lys Pro Gln Ser Leu Asp Thr Asp Asp Pro Ala Thr Leu
305                 310                 315                 320

Tyr Ala Val Val Glu Asn Val Pro Pro Leu Arg Trp Lys Glu Phe Val
                325                 330                 335
```

-continued

```
Arg Arg Leu Gly Leu Ser Asp His Glu Ile Asp Arg Leu Glu Leu Gln
            340                 345                 350

Asn Gly Arg Cys Leu Arg Glu Ala Gln Tyr Ser Met Leu Ala Thr Trp
        355                 360                 365

Arg Arg Arg Thr Pro Arg Glu Ala Thr Leu Glu Leu Leu Gly Arg
    370                 375                 380

Val Leu Arg Asp Met Asp Leu Leu Gly Cys Leu Glu Asp Ile Glu Glu
385                 390                 395                 400

Ala Leu Cys Gly Pro Ala Ala Leu Pro Pro Ala Pro Ser Leu Leu Arg
                405                 410                 415

<210> SEQ ID NO 294
<211> LENGTH: 428
<212> TYPE: PRT
<213> ORGANISM: Artificial Sequence
<220> FEATURE:
<223> OTHER INFORMATION: Synthetic amino acid sequence

<400> SEQUENCE: 294

Met Gly Leu Val Pro His Leu Gly Asp Arg Glu Lys Arg Asp Ser Val
1               5                   10                  15

Cys Pro Gln Gly Lys Tyr Ile His Pro Gln Asn Asn Ser Ile Cys Cys
            20                  25                  30

Thr Lys Cys His Lys Gly Thr Tyr Leu Tyr Asn Asp Cys Pro Gly Pro
        35                  40                  45

Gly Gln Asp Thr Asp Cys Arg Glu Cys Glu Ser Gly Ser Phe Thr Ala
    50                  55                  60

Ser Glu Asn His Leu Arg His Cys Leu Ser Cys Ser Lys Cys Arg Lys
65                  70                  75                  80

Glu Met Gly Gln Val Glu Ile Ser Ser Cys Thr Val Asp Arg Asp Thr
                85                  90                  95

Val Cys Gly Cys Arg Lys Asn Gln Tyr Arg His Tyr Trp Ser Glu Asn
            100                 105                 110

Leu Phe Gln Cys Phe Asn Cys Ser Leu Cys Leu Asn Gly Thr Val His
        115                 120                 125

Leu Ser Cys Gln Glu Lys Gln Asn Thr Val Cys Thr Cys His Ala Gly
    130                 135                 140

Phe Phe Leu Arg Glu Asn Glu Cys Val Ser Cys Ser Asn Cys Lys Lys
145                 150                 155                 160

Ser Leu Glu Cys Thr Lys Leu Cys Leu Pro Gln Ile Glu Asn Val Lys
                165                 170                 175

Gly Thr Glu Asp Ser Gly Thr Thr Val Leu Leu Pro Leu Val Ile Phe
            180                 185                 190

Phe Gly Leu Cys Leu Leu Ser Leu Leu Phe Ile Gly Leu Met Tyr Arg
        195                 200                 205

Tyr Gln Arg Trp Lys Ser Lys Leu Tyr Ser Ile Val Cys Gly Lys Ser
    210                 215                 220

Thr Pro Glu Lys Glu Gly Glu Leu Glu Gly Thr Thr Lys Pro Leu
225                 230                 235                 240

Ala Pro Asn Pro Ser Phe Ser Pro Thr Pro Gly Phe Thr Pro Thr Leu
                245                 250                 255

Gly Phe Ser Pro Val Pro Ser Ser Thr Phe Thr Ser Ser Ser Thr Tyr
            260                 265                 270

Thr Pro Gly Asp Cys Pro Asn Phe Ala Ala Pro Arg Arg Glu Val Ala
        275                 280                 285

Pro Pro Tyr Gln Gly Ala Asp Pro Ile Leu Ala Thr Ala Leu Ala Ser
```

```
                290                 295                 300
Asp Pro Ile Pro Asn Pro Leu Gln Lys Trp Glu Asp Ser Ala His Lys
305                 310                 315                 320

Pro Gln Ser Leu Asp Thr Asp Pro Ala Thr Leu Tyr Ala Val Val
            325                 330                 335

Glu Asn Val Pro Pro Leu Arg Trp Lys Glu Phe Val Arg Arg Leu Gly
            340                 345                 350

Leu Ser Asp His Glu Ile Asp Arg Leu Glu Leu Gln Asn Gly Arg Cys
            355                 360                 365

Leu Arg Glu Ala Gln Tyr Ser Met Leu Ala Thr Trp Arg Arg Arg Thr
    370                 375                 380

Pro Arg Arg Glu Ala Thr Leu Glu Leu Gly Arg Val Leu Arg Asp
385                 390                 395                 400

Met Asp Leu Leu Gly Cys Leu Glu Asp Ile Glu Glu Ala Leu Cys Gly
            405                 410                 415

Pro Ala Ala Leu Pro Ala Pro Ser Leu Leu Arg
            420                 425

<210> SEQ ID NO 295
<211> LENGTH: 233
<212> TYPE: PRT
<213> ORGANISM: Artificial Sequence
<220> FEATURE:
<223> OTHER INFORMATION: Synthetic amino acid sequence

<400> SEQUENCE: 295

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 296
<211> LENGTH: 75
<212> TYPE: PRT
<213> ORGANISM: Artificial Sequence
<220> FEATURE:
<223> OTHER INFORMATION: Synthetic amino acid sequence

<400> SEQUENCE: 296

```
Met Asn Leu Gly Asn Arg Leu Phe Ile Leu Ile Ala Val Leu Leu Pro
1               5                   10                  15

Leu Ala Val Leu Leu Asn Ser Asp Ser Glu Cys Pro Leu Ser His
            20                  25                  30

Asp Gly Tyr Cys Leu His Asp Gly Val Cys Met Tyr Ile Glu Ala Leu
        35                  40                  45

Asp Lys Tyr Ala Cys Asn Cys Val Val Gly Tyr Ile Gly Glu Arg Cys
    50                  55                  60

Gln Tyr Arg Asp Leu Lys Trp Trp Glu Leu Arg
65                  70                  75
```

<210> SEQ ID NO 297
<211> LENGTH: 518
<212> TYPE: PRT
<213> ORGANISM: Artificial Sequence
<220> FEATURE:
<223> OTHER INFORMATION: Synthetic amino acid sequence

<400> SEQUENCE: 297

```
Met Asn Leu Gly Asn Arg Leu Phe Ile Leu Ile Ala Val Leu Leu Pro
1               5                   10                  15

Leu Ala Val Leu Leu Ser Phe Thr Leu Ser Val Thr Val Gln Gln
            20                  25                  30

Pro Gln Leu Thr Leu Thr Ala Ala Val Ile Gly Asp Gly Ala Pro Ala
        35                  40                  45

Asn Gly Lys Thr Ala Ile Thr Val Glu Phe Thr Val Ala Asp Phe Glu
    50                  55                  60

Gly Lys Pro Leu Ala Gly Gln Glu Val Val Ile Thr Thr Asn Gly
65                  70                  75                  80

Ala Leu Pro Asn Lys Ile Thr Glu Lys Thr Asp Ala Asn Gly Val Ala
                85                  90                  95

Arg Ile Ala Leu Thr Asn Thr Asp Gly Val Thr Val Thr Ala
            100                 105                 110

Glu Val Glu Gly Gln Arg Gln Ser Val Asp Thr His Phe Val Lys Gly
                115                 120                 125

Thr Ile Ala Ala Asp Lys Ser Thr Leu Ala Ala Val Pro Thr Ser Ile
130                 135                 140

Ile Ala Asp Gly Leu Met Ala Ser Thr Ile Thr Leu Glu Leu Lys Asp
145                 150                 155                 160

Thr Tyr Gly Asp Pro Gln Ala Gly Ala Asn Val Ala Phe Asp Thr Thr
                165                 170                 175

Leu Gly Asn Met Gly Val Ile Thr Asp His Asn Asp Gly Thr Tyr Ser
            180                 185                 190

Ala Pro Leu Thr Ser Thr Thr Leu Gly Val Ala Thr Val Lys
        195                 200                 205

Val Asp Gly Ala Ala Phe Ser Val Pro Ser Val Thr Val Asn Phe Thr
    210                 215                 220

Ala Asp Pro Ile Pro Asp Ala Gly Arg Ser Ser Phe Thr Val Ser Thr
225                 230                 235                 240
```

Pro Asp Ile Leu Ala Asp Gly Thr Met Ser Ser Thr Leu Ser Phe Val
            245                 250                 255

Pro Val Asp Lys Asn Gly His Phe Ile Ser Gly Met Gln Gly Leu Ser
        260                 265                 270

Phe Thr Gln Asn Gly Val Pro Val Ser Ile Ser Pro Ile Thr Glu Gln
            275                 280                 285

Pro Asp Ser Tyr Thr Ala Thr Val Val Gly Asn Ser Val Gly Asp Val
    290                 295                 300

Thr Ile Thr Pro Gln Val Asp Thr Leu Ile Leu Ser Thr Leu Gln Lys
305                 310                 315                 320

Lys Ile Ser Leu Phe Pro Val Pro Thr Leu Thr Gly Ile Leu Val Asn
                325                 330                 335

Gly Gln Asn Phe Ala Thr Asp Lys Gly Phe Pro Lys Thr Ile Phe Lys
            340                 345                 350

Asn Ala Thr Phe Gln Leu Gln Met Asp Asn Asp Val Ala Asn Asn Thr
            355                 360                 365

Gln Tyr Glu Trp Ser Ser Ser Phe Thr Pro Asn Val Ser Val Asn Asp
    370                 375                 380

Gln Gly Gln Val Thr Ile Thr Tyr Gln Thr Tyr Ser Glu Val Ala Val
385                 390                 395                 400

Thr Ala Lys Ser Lys Lys Phe Pro Ser Tyr Ser Val Ser Tyr Arg Phe
                405                 410                 415

Tyr Pro Asn Arg Trp Ile Tyr Asp Gly Gly Arg Ser Leu Val Ser Ser
            420                 425                 430

Leu Glu Ala Ser Arg Gln Cys Gln Gly Ser Asp Met Ser Ala Val Leu
        435                 440                 445

Glu Ser Ser Arg Ala Thr Asn Gly Thr Arg Ala Pro Asp Gly Thr Leu
    450                 455                 460

Trp Gly Glu Trp Gly Ser Leu Thr Ala Tyr Ser Ser Asp Trp Gln Ser
465                 470                 475                 480

Gly Glu Tyr Trp Val Lys Lys Thr Ser Thr Asp Phe Glu Thr Met Asn
                485                 490                 495

Met Asp Thr Gly Ala Leu Gln Pro Gly Pro Ala Tyr Leu Ala Phe Pro
            500                 505                 510

Leu Cys Ala Leu Ser Ile
        515

<210> SEQ ID NO 298
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 298

Met Ser Arg Pro Arg Leu Ile Val Ala Leu Phe Leu Phe Phe Asn Val
 1               5                  10                  15

Phe Val His Gly Glu Asn Lys Val Lys Gln Ser Thr Ile Ala Leu Ala
            20                  25                  30

Leu Leu Pro Leu Leu Phe Thr Pro Val Thr Lys Ala Arg Thr Pro Glu
        35                  40                  45

Ser Arg
    50

<210> SEQ ID NO 299
<211> LENGTH: 496

```
<212> TYPE: PRT
<213> ORGANISM: Artificial Sequence
<220> FEATURE:
<223> OTHER INFORMATION: Synthetic amino acid sequence

<400> SEQUENCE: 299

Met Ser Arg Pro Arg Leu Ile Val Ala Leu Phe Leu Phe Phe Asn Val
 1               5                  10                  15

Phe Val His Gly Glu Asn Lys Val Lys Gln Ser Thr Ile Ala Leu Ala
                20                  25                  30

Leu Leu Pro Leu Leu Phe Thr Pro Val Thr Lys Ala Arg Thr Pro Glu
            35                  40                  45

Met Pro Val Leu Glu Asn Arg Ala Ala Gln Gly Asp Ile Thr Ala Pro
 50                  55                  60

Gly Gly Ala Arg Arg Leu Thr Gly Asp Gln Thr Ala Ala Leu Arg Asp
 65                  70                  75                  80

Ser Leu Ser Asp Lys Pro Ala Lys Asn Ile Ile Leu Leu Ile Gly Asp
                 85                  90                  95

Gly Met Gly Asp Ser Glu Ile Thr Ala Ala Arg Asn Tyr Ala Glu Gly
                100                 105                 110

Ala Gly Gly Phe Phe Lys Gly Ile Asp Ala Leu Pro Leu Thr Gly Gln
                115                 120                 125

Tyr Thr His Tyr Ala Leu Asn Lys Lys Thr Gly Lys Pro Asp Tyr Val
130                 135                 140

Thr Asp Ser Ala Ala Ser Ala Thr Ala Trp Ser Thr Gly Val Lys Thr
145                 150                 155                 160

Tyr Asn Gly Ala Leu Gly Val Asp Ile His Glu Lys Asp His Pro Thr
                165                 170                 175

Ile Leu Glu Met Ala Lys Ala Ala Gly Leu Ala Thr Gly Asn Val Ser
                180                 185                 190

Thr Ala Glu Leu Gln Asp Ala Thr Pro Ala Ala Leu Val Ala His Val
            195                 200                 205

Thr Ser Arg Lys Cys Tyr Gly Pro Ser Ala Thr Ser Glu Lys Cys Pro
210                 215                 220

Gly Asn Ala Leu Glu Lys Gly Gly Lys Gly Ser Ile Thr Glu Gln Leu
225                 230                 235                 240

Leu Asn Ala Arg Ala Asp Val Thr Leu Gly Gly Gly Ala Lys Thr Phe
                245                 250                 255

Ala Glu Thr Ala Thr Ala Gly Glu Trp Gln Gly Lys Thr Leu Arg Glu
            260                 265                 270

Gln Ala Gln Ala Arg Gly Tyr Gln Leu Val Ser Asp Ala Ala Ser Leu
        275                 280                 285

Asn Ser Val Thr Glu Ala Asn Gln Gln Lys Pro Leu Leu Gly Leu Phe
290                 295                 300

Ala Asp Gly Asn Met Pro Val Arg Trp Leu Gly Pro Lys Ala Thr Tyr
305                 310                 315                 320

His Gly Asn Ile Asp Lys Pro Ala Val Thr Cys Thr Pro Asn Pro Gln
                325                 330                 335

Arg Asn Asp Ser Val Pro Thr Leu Ala Gln Met Thr Asp Lys Ala Ile
            340                 345                 350

Glu Leu Leu Ser Lys Asn Glu Lys Gly Phe Phe Leu Gln Val Glu Gly
        355                 360                 365

Ala Ser Ile Asp Lys Gln Asp His Ala Ala Asn Pro Cys Gly Gln Ile
370                 375                 380

Gly Glu Thr Val Asp Leu Asp Glu Ala Val Gln Arg Ala Leu Glu Phe
```

```
                385                 390                 395                 400
Ala Lys Lys Glu Gly Asn Thr Leu Val Ile Val Thr Ala Asp His Ala
                    405                 410                 415

His Ala Ser Gln Ile Val Ala Pro Asp Thr Lys Ala Pro Gly Leu Thr
                420                 425                 430

Gln Ala Leu Asn Thr Lys Asp Gly Ala Val Met Val Met Ser Tyr Gly
            435                 440                 445

Asn Ser Glu Glu Asp Ser Gln Glu His Thr Gly Ser Gln Leu Arg Ile
        450                 455                 460

Ala Ala Tyr Gly Pro His Ala Ala Asn Val Val Gly Leu Thr Asp Gln
465                 470                 475                 480

Thr Asp Leu Phe Tyr Thr Met Lys Ala Ala Leu Gly Leu Lys Ser Arg
                485                 490                 495

<210> SEQ ID NO 300
<211> LENGTH: 30
<212> TYPE: PRT
<213> ORGANISM: Artificial Sequence
<220> FEATURE:
<223> OTHER INFORMATION: Synthetic amino acid sequence

<400> SEQUENCE: 300

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ser Arg
            20                  25                  30

<210> SEQ ID NO 301
<211> LENGTH: 372
<212> TYPE: PRT
<213> ORGANISM: Artificial Sequence
<220> FEATURE:
<223> OTHER INFORMATION: Synthetic amino acid sequence

<400> SEQUENCE: 301

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
```

```
                    180                 185                 190
Tyr Ala Phe Lys Tyr Glu Asn Gly Lys Tyr Asp Ile Lys Asp Val Gly
                195                 200                 205

Val Asp Asn Ala Gly Ala Lys Ala Gly Leu Thr Phe Leu Val Asp Leu
            210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Ser Arg
    370

<210> SEQ ID NO 302
<211> LENGTH: 133
<212> TYPE: PRT
<213> ORGANISM: Artificial Sequence
<220> FEATURE:
<223> OTHER INFORMATION: Synthetic amino acid sequence

<400> SEQUENCE: 302

Met Ile Glu Ala Arg Ser Arg Leu Glu Ser Asp Lys Ile Ile His Leu
 1               5                  10                  15

Thr Asp Asp Ser Phe Asp Thr Asp Val Leu Lys Ala Asp Gly Ala Ile
             20                  25                  30

Leu Val Asp Phe Trp Ala Glu Trp Cys Gly Pro Cys Lys Met Ile Ala
         35                  40                  45

Pro Ile Leu Asp Glu Ile Ala Asp Glu Tyr Gln Gly Lys Leu Thr Val
 50                  55                  60

Ala Lys Leu Asn Ile Asp Gln Asn Pro Gly Thr Ala Pro Lys Tyr Gly
65                  70                  75                  80

Ile Arg Gly Ile Pro Thr Leu Leu Leu Phe Lys Asn Gly Glu Val Ala
                 85                  90                  95

Ala Thr Lys Val Gly Ala Leu Ser Lys Gly Gln Leu Lys Glu Phe Leu
            100                 105                 110

Asp Ala Asn Leu Ala Leu Glu Asp Tyr Lys Asp His Asp Gly Asp Tyr
        115                 120                 125

Lys Asp His Asp Asp
    130

<210> SEQ ID NO 303
<211> LENGTH: 767
<212> TYPE: PRT
<213> ORGANISM: Artificial Sequence
```

-continued

```
<220> FEATURE:
<223> OTHER INFORMATION: Synthetic amino acid sequence

<400> SEQUENCE: 303

Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                    85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                    165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                    245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                    325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Leu Ile Glu Ala Arg Thr Ser Glu Ser Asp Thr Ala Gly Pro Asn
370                 375                 380

Ser Asp Leu Asp Val Asn Thr Asp Ile Tyr Ser Lys Val Leu Val Thr
385                 390                 395                 400
```

-continued

```
Ala Ile Tyr Leu Ala Leu Phe Val Val Gly Thr Val Gly Asn Ser Val
            405                 410                 415

Thr Ala Phe Thr Leu Ala Arg Lys Lys Ser Leu Gln Ser Leu Gln Ser
        420                 425                 430

Thr Val His Tyr His Leu Gly Ser Leu Ala Leu Ser Asp Leu Leu Ile
    435                 440                 445

Leu Leu Leu Ala Met Pro Val Glu Leu Tyr Asn Phe Ile Trp Val His
450                 455                 460

His Pro Trp Ala Phe Gly Asp Ala Gly Cys Arg Gly Tyr Tyr Phe Leu
465                 470                 475                 480

Arg Asp Ala Cys Thr Tyr Ala Thr Ala Leu Asn Val Ala Ser Leu Ser
                485                 490                 495

Val Glu Arg Tyr Leu Ala Ile Cys His Pro Phe Lys Ala Lys Thr Leu
            500                 505                 510

Met Ser Arg Ser Arg Thr Lys Lys Phe Ile Ser Ala Ile Trp Leu Ala
        515                 520                 525

Ser Ala Leu Leu Ala Ile Pro Met Leu Phe Thr Met Gly Leu Gln Asn
    530                 535                 540

Arg Ser Gly Asp Gly Thr His Pro Gly Gly Leu Val Cys Thr Pro Ile
545                 550                 555                 560

Val Asp Thr Ala Thr Val Lys Val Val Ile Gln Val Asn Thr Phe Met
                565                 570                 575

Ser Phe Leu Phe Pro Met Leu Val Ile Ser Ile Leu Asn Thr Val Ile
            580                 585                 590

Ala Asn Lys Leu Thr Val Met Val His Gln Ala Ala Glu Gln Gly Arg
        595                 600                 605

Val Cys Thr Val Gly Thr His Asn Gly Leu Glu His Ser Thr Phe Asn
    610                 615                 620

Met Thr Ile Glu Pro Gly Arg Val Gln Ala Leu Arg His Gly Val Leu
625                 630                 635                 640

Val Leu Arg Ala Val Val Ile Ala Phe Val Val Cys Trp Leu Pro Tyr
                645                 650                 655

His Val Arg Arg Leu Met Phe Cys Tyr Ile Ser Asp Glu Gln Trp Thr
            660                 665                 670

Thr Phe Leu Phe Asp Phe Tyr His Tyr Phe Tyr Met Leu Thr Asn Ala
        675                 680                 685

Leu Phe Tyr Val Ser Ser Ala Ile Asn Pro Ile Leu Tyr Asn Leu Val
    690                 695                 700

Ser Ala Asn Phe Arg Gln Val Phe Leu Ser Thr Leu Ala Cys Leu Cys
705                 710                 715                 720

Pro Gly Trp Arg His Arg Arg Lys Lys Arg Pro Thr Phe Ser Arg Lys
                725                 730                 735

Pro Asn Ser Met Ser Ser Asn His Ala Phe Ser Thr Ser Ala Thr Arg
            740                 745                 750

Glu Thr Leu Tyr Ala Ala Ala Asp Tyr Lys Asp Asp Asp Lys
        755                 760                 765

<210> SEQ ID NO 304
<211> LENGTH: 425
<212> TYPE: PRT
<213> ORGANISM: Artificial Sequence
<220> FEATURE:
<223> OTHER INFORMATION: Synthetic amino acid sequence

<400> SEQUENCE: 304

Met Lys Ile Lys Thr Gly Ala Arg Ile Leu Ala Leu Ser Ala Leu Thr
```

```
            1               5                  10                 15
Thr Met Met Phe Ser Ala Ser Ala Leu Ala Lys Ile Ile Glu Ala Arg
                20                  25                  30

Thr Ser Glu Ser Asp Thr Ala Gly Pro Asn Ser Asp Leu Asp Val Asn
                35                  40                  45

Thr Asp Ile Tyr Ser Lys Val Leu Val Thr Ala Ile Tyr Leu Ala Leu
                50                  55                  60

Phe Val Val Gly Thr Val Gly Asn Ser Val Thr Ala Phe Thr Leu Ala
65                  70                  75                  80

Arg Lys Lys Ser Leu Gln Ser Leu Gln Ser Thr Val His Tyr His Leu
                85                  90                  95

Gly Ser Leu Ala Leu Ser Asp Leu Leu Ile Leu Leu Leu Ala Met Pro
                100                 105                 110

Val Glu Leu Tyr Asn Phe Ile Trp Val His His Pro Trp Ala Phe Gly
                115                 120                 125

Asp Ala Gly Cys Arg Gly Tyr Tyr Phe Leu Arg Asp Ala Cys Thr Tyr
                130                 135                 140

Ala Thr Ala Leu Asn Val Ala Ser Leu Ser Val Glu Arg Tyr Leu Ala
145                 150                 155                 160

Ile Cys His Pro Phe Lys Ala Lys Thr Leu Met Ser Arg Ser Arg Thr
                165                 170                 175

Lys Lys Phe Ile Ser Ala Ile Trp Leu Ala Ser Ala Leu Leu Ala Ile
                180                 185                 190

Pro Met Leu Phe Thr Met Gly Leu Gln Asn Arg Ser Gly Asp Gly Thr
                195                 200                 205

His Pro Gly Gly Leu Val Cys Thr Pro Ile Val Asp Thr Ala Thr Val
                210                 215                 220

Lys Val Val Ile Gln Val Asn Thr Phe Met Ser Phe Leu Phe Pro Met
225                 230                 235                 240

Leu Val Ile Ser Ile Leu Asn Thr Val Ile Ala Asn Lys Leu Thr Val
                245                 250                 255

Met Val His Gln Ala Ala Glu Gln Gly Arg Val Cys Thr Val Gly Thr
                260                 265                 270

His Asn Gly Leu Glu His Ser Thr Phe Asn Met Thr Ile Glu Pro Gly
                275                 280                 285

Arg Val Gln Ala Leu Arg His Gly Val Leu Val Leu Arg Ala Val Val
                290                 295                 300

Ile Ala Phe Val Val Cys Trp Leu Pro Tyr His Val Arg Arg Leu Met
305                 310                 315                 320

Phe Cys Tyr Ile Ser Asp Glu Gln Trp Thr Thr Phe Leu Phe Asp Phe
                325                 330                 335

Tyr His Tyr Phe Tyr Met Leu Thr Asn Ala Leu Phe Tyr Val Ser Ser
                340                 345                 350

Ala Ile Asn Pro Ile Leu Tyr Asn Leu Val Ser Ala Asn Phe Arg Gln
                355                 360                 365

Val Phe Leu Ser Thr Leu Ala Cys Leu Cys Pro Gly Trp Arg His Arg
                370                 375                 380

Arg Lys Lys Arg Pro Thr Phe Ser Arg Lys Pro Asn Ser Met Ser Ser
385                 390                 395                 400

Asn His Ala Phe Ser Thr Ser Ala Thr Arg Glu Thr Leu Tyr Ala Ala
                405                 410                 415

Ala Asp Tyr Lys Asp Asp Asp Lys
                420                 425
```

<210> SEQ ID NO 305
<211> LENGTH: 878
<212> TYPE: PRT
<213> ORGANISM: Artificial Sequence
<220> FEATURE:
<223> OTHER INFORMATION: Synthetic amino acid sequence

<400> SEQUENCE: 305

```
Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Leu Ile Glu Ala Arg Thr Ser Glu Ser Asp Thr Ala Gly Pro Asn
```

```
                370             375             380
Ser Asp Leu Asp Val Asn Thr Asp Ile Tyr Ser Lys Val Leu Val Thr
385                 390                 395                 400

Ala Ile Tyr Leu Ala Leu Phe Val Val Gly Thr Val Gly Asn Ser Val
                405                 410                 415

Thr Ala Phe Thr Leu Ala Arg Lys Lys Ser Leu Gln Ser Leu Gln Ser
                420                 425                 430

Thr Val His Tyr His Leu Gly Ser Leu Ala Leu Ser Asp Leu Leu Ile
                435                 440                 445

Leu Leu Leu Ala Met Pro Val Glu Leu Tyr Asn Phe Ile Trp Val His
450                 455                 460

His Pro Trp Ala Phe Gly Asp Ala Gly Cys Arg Gly Tyr Tyr Phe Leu
465                 470                 475                 480

Arg Asp Ala Cys Thr Tyr Ala Thr Ala Leu Asn Val Ala Ser Leu Ser
                485                 490                 495

Val Glu Arg Tyr Leu Ala Ile Cys His Pro Phe Lys Ala Lys Thr Leu
                500                 505                 510

Met Ser Arg Ser Arg Thr Lys Lys Phe Ile Ser Ala Ile Trp Leu Ala
                515                 520                 525

Ser Ala Leu Leu Ala Ile Pro Met Leu Phe Thr Met Gly Leu Gln Asn
530                 535                 540

Arg Ser Gly Asp Gly Thr His Pro Gly Gly Leu Val Cys Thr Pro Ile
545                 550                 555                 560

Val Asp Thr Ala Thr Val Lys Val Val Ile Gln Val Asn Thr Phe Met
                565                 570                 575

Ser Phe Leu Phe Pro Met Leu Val Ile Ser Ile Leu Asn Thr Val Ile
                580                 585                 590

Ala Asn Lys Leu Thr Val Met Val His Gln Ala Ala Glu Gln Gly Arg
                595                 600                 605

Val Cys Thr Val Gly Thr His Asn Gly Leu Glu His Ser Thr Phe Asn
610                 615                 620

Met Thr Ile Glu Pro Gly Arg Val Gln Ala Leu Arg His Gly Val Leu
625                 630                 635                 640

Val Leu Arg Ala Val Val Ile Ala Phe Val Val Cys Trp Leu Pro Tyr
                645                 650                 655

His Val Arg Arg Leu Met Phe Cys Tyr Ile Ser Asp Glu Gln Trp Thr
                660                 665                 670

Thr Phe Leu Phe Asp Phe Tyr His Tyr Phe Tyr Met Leu Thr Asn Ala
                675                 680                 685

Leu Phe Tyr Val Ser Ser Ala Ile Asn Pro Ile Leu Tyr Asn Leu Val
                690                 695                 700

Ser Ala Asn Phe Arg Gln Val Phe Leu Ser Thr Leu Ala Cys Leu Cys
705                 710                 715                 720

Pro Gly Trp Arg His Arg Arg Lys Lys Arg Pro Thr Phe Ser Arg Lys
                725                 730                 735

Pro Asn Ser Met Ser Ser Asn His Ala Phe Ser Thr Ser Ala Thr Arg
                740                 745                 750

Glu Thr Leu Tyr Ala Ala Ala Ser Asp Lys Ile Ile His Leu Thr Asp
                755                 760                 765

Asp Ser Phe Asp Thr Asp Val Leu Lys Ala Asp Gly Ala Ile Leu Val
                770                 775                 780

Asp Phe Trp Ala Glu Trp Cys Gly Pro Cys Lys Met Ile Ala Pro Ile
785                 790                 795                 800
```

```
Leu Asp Glu Ile Ala Asp Glu Tyr Gln Gly Lys Leu Thr Val Ala Lys
            805                 810                 815

Leu Asn Ile Asp Gln Asn Pro Gly Thr Ala Pro Lys Tyr Gly Ile Arg
            820                 825                 830

Gly Ile Pro Thr Leu Leu Phe Lys Asn Gly Glu Val Ala Ala Thr
            835                 840                 845

Lys Val Gly Ala Leu Ser Lys Gly Gln Leu Lys Glu Phe Leu Asp Ala
            850                 855                 860

Asn Leu Ala Ala Ala Asp Tyr Lys Asp Asp Asp Lys
865             870                 875

<210> SEQ ID NO 306
<211> LENGTH: 536
<212> TYPE: PRT
<213> ORGANISM: Artificial Sequence
<220> FEATURE:
<223> OTHER INFORMATION: Synthetic amino acid sequence

<400> SEQUENCE: 306

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Thr Ser Glu Ser Asp Thr Ala Gly Pro Asn Ser Asp Leu Asp Val Asn
            35                  40                  45

Thr Asp Ile Tyr Ser Lys Val Leu Val Thr Ala Ile Tyr Leu Ala Leu
        50                  55                  60

Phe Val Val Gly Thr Val Gly Asn Ser Val Thr Ala Phe Thr Leu Ala
65              70                  75                  80

Arg Lys Lys Ser Leu Gln Ser Leu Gln Ser Thr Val His Tyr His Leu
                85                  90                  95

Gly Ser Leu Ala Leu Ser Asp Leu Leu Ile Leu Leu Leu Ala Met Pro
            100                 105                 110

Val Glu Leu Tyr Asn Phe Ile Trp Val His His Pro Trp Ala Phe Gly
            115                 120                 125

Asp Ala Gly Cys Arg Gly Tyr Tyr Phe Leu Arg Asp Ala Cys Thr Tyr
        130                 135                 140

Ala Thr Ala Leu Asn Val Ala Ser Leu Ser Val Glu Arg Tyr Leu Ala
145             150                 155                 160

Ile Cys His Pro Phe Lys Ala Lys Thr Leu Met Ser Arg Ser Arg Thr
                165                 170                 175

Lys Lys Phe Ile Ser Ala Ile Trp Leu Ala Ser Ala Leu Leu Ala Ile
            180                 185                 190

Pro Met Leu Phe Thr Met Gly Leu Gln Asn Arg Ser Gly Asp Gly Thr
        195                 200                 205

His Pro Gly Gly Leu Val Cys Thr Pro Ile Val Asp Thr Ala Thr Val
    210                 215                 220

Lys Val Val Ile Gln Val Asn Thr Phe Met Ser Phe Leu Phe Pro Met
225             230                 235                 240

Leu Val Ile Ser Ile Leu Asn Thr Val Ile Ala Asn Lys Leu Thr Val
                245                 250                 255

Met Val His Gln Ala Ala Glu Gln Gly Arg Val Cys Thr Val Gly Thr
            260                 265                 270

His Asn Gly Leu Glu His Ser Thr Phe Asn Met Thr Ile Glu Pro Gly
        275                 280                 285

Arg Val Gln Ala Leu Arg His Gly Val Leu Val Leu Arg Ala Val Val
```

```
                290                 295                 300
Ile Ala Phe Val Val Cys Trp Leu Pro Tyr His Val Arg Arg Leu Met
305                 310                 315                 320

Phe Cys Tyr Ile Ser Asp Glu Gln Trp Thr Thr Phe Leu Phe Asp Phe
                325                 330                 335

Tyr His Tyr Phe Tyr Met Leu Thr Asn Ala Leu Phe Tyr Val Ser Ser
                340                 345                 350

Ala Ile Asn Pro Ile Leu Tyr Asn Leu Val Ser Ala Asn Phe Arg Gln
                355                 360                 365

Val Phe Leu Ser Thr Leu Ala Cys Leu Cys Pro Gly Trp Arg His Arg
370                 375                 380

Arg Lys Lys Arg Pro Thr Phe Ser Arg Lys Pro Asn Ser Met Ser Ser
385                 390                 395                 400

Asn His Ala Phe Ser Thr Ser Ala Thr Arg Glu Thr Leu Tyr Ala Ala
                405                 410                 415

Ala Ser Asp Lys Ile Ile His Leu Thr Asp Asp Ser Phe Asp Thr Asp
                420                 425                 430

Val Leu Lys Ala Asp Gly Ala Ile Leu Val Asp Phe Trp Ala Glu Trp
                435                 440                 445

Cys Gly Pro Cys Lys Met Ile Ala Pro Ile Leu Asp Glu Ile Ala Asp
                450                 455                 460

Glu Tyr Gln Gly Lys Leu Thr Val Ala Lys Leu Asn Ile Asp Gln Asn
465                 470                 475                 480

Pro Gly Thr Ala Pro Lys Tyr Gly Ile Arg Gly Ile Pro Thr Leu Leu
                485                 490                 495

Leu Phe Lys Asn Gly Glu Val Ala Ala Thr Lys Val Gly Ala Leu Ser
                500                 505                 510

Lys Gly Gln Leu Lys Glu Phe Leu Asp Ala Asn Leu Ala Ala Ala Ala
                515                 520                 525

Asp Tyr Lys Asp Asp Asp Asp Lys
                530                 535

<210> SEQ ID NO 307
<211> LENGTH: 380
<212> TYPE: PRT
<213> ORGANISM: Artificial Sequence
<220> FEATURE:
<223> OTHER INFORMATION: Synthetic amino acid sequence

<400> SEQUENCE: 307

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
                35                  40                  45

Gly Glu Ser Gly Lys Ser Thr Ile Val Lys Gln Met Arg Ile Leu His
                50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
                100                 105                 110

Arg Val Asp Tyr Ile Leu Ser Val Met Asn Val Pro Asp Phe Asp Phe
                115                 120                 125
```

Pro Pro Glu Phe Tyr Glu His Ala Lys Ala Leu Trp Glu Asp Glu Gly
    130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
        195                 200                 205

Asp Val Gly Gly Gln Arg Asp Glu Arg Arg Lys Trp Ile Gln Cys Phe
    210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
        275                 280                 285

Ala Gly Lys Ser Lys Ile Glu Asp Tyr Phe Pro Glu Phe Ala Arg Tyr
    290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
                325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
        355                 360                 365

Ile Gln Arg Met His Leu Arg Gln Tyr Glu Leu Leu
    370                 375                 380

<210> SEQ ID NO 308
<211> LENGTH: 394
<212> TYPE: PRT
<213> ORGANISM: Artificial Sequence
<220> FEATURE:
<223> OTHER INFORMATION: Synthetic amino acid sequence

<400> SEQUENCE: 308

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

```
Leu Val Pro Val Glu Leu Ala Asn Pro Glu Asn Gln Phe Arg Val
        115                 120                 125

Asp Tyr Ile Leu Ser Val Met Asn Val Pro Asp Phe Asp Phe Pro Pro
130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Ile Ile Gln
370                 375                 380

Arg Met His Leu Arg Gln Tyr Glu Leu Leu
385                 390

<210> SEQ ID NO 309
<211> LENGTH: 359
<212> TYPE: PRT
<213> ORGANISM: Artificial Sequence
<220> FEATURE:
<223> OTHER INFORMATION: Synthetic amino acid sequence

<400> SEQUENCE: 309

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
```

```
                     85                  90                  95
Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 310
<211> LENGTH: 355
<212> TYPE: PRT
<213> ORGANISM: Artificial Sequence
<220> FEATURE:
<223> OTHER INFORMATION: Synthetic amino acid sequence

<400> SEQUENCE: 310

Met Gly Cys Thr Val Ser Ala Glu Asp Lys Ala Ala Ala Glu Arg Ser
1               5                   10                  15

Lys Met Ile Asp Lys Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Asp Gly Tyr Ser Glu Glu
    50                  55                  60

Glu Cys Arg Gln Tyr Arg Ala Val Val Tyr Ser Asn Thr Ile Gln Ser
65                  70                  75                  80

Ile Met Ala Ile Val Lys Ala Met Gly Asn Leu Gln Ile Asp Phe Ala
            85                  90                  95
```

```
Asp Pro Ser Arg Ala Asp Ala Arg Gln Leu Phe Ala Leu Ser Cys
            100                 105                 110

Thr Ala Glu Glu Gln Gly Val Leu Pro Asp Asp Leu Ser Gly Val Ile
        115                 120                 125

Arg Arg Leu Trp Ala Asp His Gly Val Gln Ala Cys Phe Gly Arg Ser
    130                 135                 140

Arg Glu Tyr Gln Leu Asn Asp Ser Ala Ala Tyr Tyr Leu Asn Asp Leu
145                 150                 155                 160

Glu Arg Ile Ala Gln Ser Asp Tyr Ile Pro Thr Gln Gln Asp Val Leu
                165                 170                 175

Arg Thr Arg Val Lys Thr Thr Gly Ile Val Glu Thr His Phe Thr Phe
            180                 185                 190

Lys Asp Leu His Phe Lys Met Phe Asp Val Gly Gly Gln Arg Ser Glu
        195                 200                 205

Arg Lys Lys Trp Ile His Cys Phe Glu Gly Val Thr Ala Ile Ile Phe
    210                 215                 220

Cys Val Ala Leu Ser Ala Tyr Asp Leu Val Leu Ala Glu Asp Glu Glu
225                 230                 235                 240

Met Asn Arg Met His Glu Ser Met Lys Leu Phe Asp Ser Ile Cys Asn
                245                 250                 255

Asn Lys Trp Phe Thr Asp Thr Ser Ile Ile Leu Phe Leu Asn Lys Lys
            260                 265                 270

Asp Leu Phe Glu Glu Lys Ile Thr His Ser Pro Leu Thr Ile Cys Phe
        275                 280                 285

Pro Glu Tyr Thr Gly Ala Asn Lys Tyr Asp Glu Ala Ala Ser Tyr Ile
    290                 295                 300

Gln Ser Lys Phe Glu Asp Leu Asn Lys Arg Lys Asp Thr Lys Glu Ile
305                 310                 315                 320

Tyr Thr His Phe Thr Cys Ala Thr Asp Thr Lys Asn Val Gln Phe Val
                325                 330                 335

Phe Asp Ala Val Thr Asp Val Ile Ile Lys Asn Asn Leu Lys Asp Cys
            340                 345                 350

Gly Leu Phe
        355

<210> SEQ ID NO 311
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 311

Met Ser Gly Val Val Arg Thr Leu Ser Arg Cys Leu Leu Pro Ala Glu
1               5                   10                  15

Ala Gly Gly Ala Arg Glu Arg Arg Ala Gly Ser Gly Ala Arg Asp Ala
            20                  25                  30

Glu Arg Glu Ala Arg Arg Ser Arg Asp Ile Asp Ala Leu Leu Ala
        35                  40                  45

Arg Glu Arg Arg Ala Val Arg Arg Leu Val Lys Ile Leu Leu Leu Gly
    50                  55                  60

Ala Gly Glu Ser Gly Lys Ser Thr Phe Leu Lys Gln Met Arg Ile Ile
65                  70                  75                  80

His Gly Arg Glu Phe Asp Gln Lys Ala Leu Leu Glu Phe Arg Asp Thr
                85                  90                  95
```

-continued

```
Ile Phe Asp Asn Ile Leu Lys Gly Ser Arg Val Leu Val Asp Ala Arg
            100                 105                 110

Asp Lys Leu Gly Ile Pro Trp Gln Tyr Ser Glu Asn Glu Lys His Gly
        115                 120                 125

Met Phe Leu Met Ala Phe Glu Asn Lys Ala Gly Leu Pro Val Glu Pro
    130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Arg Ser Glu Phe Gln Leu Gly
                165                 170                 175

Glu Ser Val Lys Tyr Phe Leu Asp Asn Leu Asp Arg Ile Gly Gln Leu
            180                 185                 190

Asn Tyr Phe Pro Ser Lys Gln Asp Ile Leu Leu Ala Arg Lys Ala Thr
        195                 200                 205

Lys Gly Ile Val Glu His Asp Phe Val Ile Lys Lys Ile Pro Phe Lys
    210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
                245                 250                 255

Tyr Asp Gln Val Leu Met Glu Asp Arg Arg Thr Asn Arg Leu Val Glu
            260                 265                 270

Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
    290                 295                 300

Val Lys Thr Val Ser Ile Lys Lys His Phe Pro Asp Phe Arg Gly Asp
305                 310                 315                 320

Pro His Gln Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
            340                 345                 350

Ala Ile Asp Thr Glu Asn Val Arg Phe Val Phe His Ala Val Lys Asp
        355                 360                 365

Thr Ile Leu Gln Glu Asn Leu Lys Asp Ile Met Leu Gln
    370                 375                 380

<210> SEQ ID NO 312
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 312

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Asp Tyr Lys Asp Asp Asp
        35                  40                  45

Asp Lys
    50

<210> SEQ ID NO 313
<211> LENGTH: 27
<212> TYPE: PRT
```

```
<213> ORGANISM: Artificial Sequence
<220> FEATURE:
<223> OTHER INFORMATION: Synthetic amino acid sequence

<400> SEQUENCE: 313

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys
            20                  25

<210> SEQ ID NO 314
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 314

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Asp Tyr Lys Asp Asp Asp
        35                  40                  45

Asp Lys
    50

<210> SEQ ID NO 315
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 315

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Asp Tyr Lys Asp Asp Asp
        35                  40                  45

Asp Lys
    50

<210> SEQ ID NO 316
<211> LENGTH: 343
<212> TYPE: PRT
<213> ORGANISM: Artificial Sequence
<220> FEATURE:
<223> OTHER INFORMATION: Synthetic amino acid sequence

<400> SEQUENCE: 316

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80
```

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
        180                 185                 190

Tyr Ala Phe Lys Tyr Glu Asn Gly Lys Tyr Asp Ile Lys Asp Val Gly
    195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
        260                 265                 270

Leu Pro Thr Phe Lys Gly Gln Pro Ser Lys Pro Phe Val Gly Val Leu
    275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile
            340

<210> SEQ ID NO 317
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 317

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
        355                 360                 365

Asp Ala Glu Ser Arg Asp Tyr Lys Asp Asp Asp Lys
    370                 375                 380

<210> SEQ ID NO 318
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 318

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr

```
                    85                  90                  95
Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
        355                 360                 365

Asp Ala Glu Ser Arg Asp Tyr Lys Asp Asp Asp Lys
    370                 375                 380

<210> SEQ ID NO 319
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 319

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80
```

-continued

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
        355                 360                 365

Asp Ala Glu Ser Arg Asp Tyr Lys Asp Asp Asp Lys
    370                 375                 380

<210> SEQ ID NO 320
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 320

Ala Ser Val Asp Ala Glu Ser Arg Ser Asp Lys Ile Ile His Leu Thr
1               5                   10                  15

Asp Asp Ser Phe Asp Thr Asp Val Leu Lys Ala Asp Gly Ala Ile Leu
            20                  25                  30

Val Asp Phe Trp Ala Glu Trp Cys Gly Pro Cys Lys Met Ile Ala Pro
        35                  40                  45

Ile Leu Asp Glu Ile Ala Asp Glu Tyr Gln Gly Lys Leu Thr Val Ala
    50                  55                  60

Lys Leu Asn Ile Asp Gln Asn Pro Gly Thr Ala Pro Lys Tyr Gly Ile
65                  70                  75                  80

Arg Gly Ile Pro Thr Leu Leu Leu Phe Lys Asn Gly Glu Val Ala Ala
                85                  90                  95

Thr Lys Val Gly Ala Leu Ser Lys Gly Gln Leu Lys Glu Asn Leu Ala
            100                 105                 110

Asp Tyr Lys Asp Asp Asp Asp Lys
        115                 120

<210> SEQ ID NO 321
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 321

Ala Ser Val Asp Ala Glu Ser Arg Ser Asp Lys Ile Ile His Leu Thr
1               5                   10                  15

Asp Asp Ser Phe Asp Thr Asp Val Leu Lys Ala Asp Gly Ala Ile Leu
                20                  25                  30

Val Asp Phe Trp Ala Glu Trp Cys Gly Pro Cys Lys Met Ile Ala Pro
            35                  40                  45

Ile Leu Asp Glu Ile Ala Asp Glu Tyr Gln Gly Lys Leu Thr Val Ala
        50                  55                  60

Lys Leu Asn Ile Asp Gln Asn Pro Gly Thr Ala Pro Lys Tyr Gly Ile
65                  70                  75                  80

Arg Gly Ile Pro Thr Leu Leu Leu Phe Lys Asn Gly Glu Val Ala Ala
                85                  90                  95

Thr Lys Val Gly Ala Leu Ser Lys Gly Gln Leu Lys Glu Asn Leu Ala
            100                 105                 110

Asp Tyr Lys Asp Asp Asp Asp Lys
        115                 120

<210> SEQ ID NO 322
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 322

Ala Ser Val Asp Ala Glu Ser Arg Ser Asp Lys Ile Ile His Leu Thr
1               5                   10                  15

Asp Asp Ser Phe Asp Thr Asp Val Leu Lys Ala Asp Gly Ala Ile Leu
                20                  25                  30

Val Asp Phe Trp Ala Glu Trp Cys Gly Pro Cys Lys Met Ile Ala Pro
            35                  40                  45

Ile Leu Asp Glu Ile Ala Asp Glu Tyr Gln Gly Lys Leu Thr Val Ala
        50                  55                  60

Lys Leu Asn Ile Asp Gln Asn Pro Gly Thr Ala Pro Lys Tyr Gly Ile
65                  70                  75                  80

Arg Gly Ile Pro Thr Leu Leu Leu Phe Lys Asn Gly Glu Val Ala Ala
                85                  90                  95

Thr Lys Val Gly Ala Leu Ser Lys Gly Gln Leu Lys Glu Asn Leu Ala
            100                 105                 110

Asp Tyr Lys Asp Asp Asp Asp Lys
        115                 120

-continued

<210> SEQ ID NO 323
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 323

Ala Ser Val Asp Ala Glu Ser Arg Ser Asp Lys Ile Ile His Leu Thr
1               5                   10                  15

Asp Asp Ser Phe Asp Thr Asp Val Leu Lys Ala Asp Gly Ala Ile Leu
            20                  25                  30

Val Asp Phe Trp Ala Glu Trp Cys Gly Pro Cys Lys Met Ile Ala Pro
        35                  40                  45

Ile Leu Asp Glu Ile Ala Asp Glu Tyr Gln Gly Lys Leu Thr Val Ala
    50                  55                  60

Lys Leu Asn Ile Asp Gln Asn Pro Gly Thr Ala Pro Lys Tyr Gly Ile
65                  70                  75                  80

Arg Gly Ile Pro Thr Leu Leu Leu Phe Lys Asn Gly Glu Val Ala Ala
                85                  90                  95

Thr Lys Val Gly Ala Leu Ser Lys Gly Gln Leu Lys Glu Asn Leu Ala
            100                 105                 110

Asp Tyr Lys Asp Asp Asp Asp Lys
        115                 120

<210> SEQ ID NO 324
<211> LENGTH: 154
<212> TYPE: PRT
<213> ORGANISM: Artificial Sequence
<220> FEATURE:
<223> OTHER INFORMATION: Synthetic amino acid sequence

<400> SEQUENCE: 324

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Ser Asp Lys Ile Ile His
        35                  40                  45

Leu Thr Asp Asp Ser Phe Asp Thr Asp Val Leu Lys Ala Asp Gly Ala
    50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
    130                 135                 140

Leu Ala Asp Tyr Lys Asp Asp Asp Asp Lys
145                 150

<210> SEQ ID NO 325
<211> LENGTH: 154
<212> TYPE: PRT
<213> ORGANISM: Artificial Sequence
<220> FEATURE:

<223> OTHER INFORMATION: Synthetic amino acid sequence

<400> SEQUENCE: 325

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
                20                  25                  30

Leu Gln Ala Ser Val Asp Ala Glu Ser Arg Ser Asp Lys Ile Ile His
            35                  40                  45

Leu Thr Asp Asp Ser Phe Asp Thr Asp Val Leu Lys Ala Asp Gly Ala
        50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
    130                 135                 140

Leu Ala Asp Tyr Lys Asp Asp Asp Lys
145                 150

<210> SEQ ID NO 326
<211> LENGTH: 154
<212> TYPE: PRT
<213> ORGANISM: Artificial Sequence
<220> FEATURE:
<223> OTHER INFORMATION: Synthetic amino acid sequence

<400> SEQUENCE: 326

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
                20                  25                  30

Leu Gln Ala Ser Val Asp Ala Glu Ser Arg Ser Asp Lys Ile Ile His
            35                  40                  45

Leu Thr Asp Asp Ser Phe Asp Thr Asp Val Leu Lys Ala Asp Gly Ala
        50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
    130                 135                 140

Leu Ala Asp Tyr Lys Asp Asp Asp Lys
145                 150

<210> SEQ ID NO 327
<211> LENGTH: 154
<212> TYPE: PRT
<213> ORGANISM: Artificial Sequence
<220> FEATURE:

<223> OTHER INFORMATION: Synthetic amino acid sequence

<400> SEQUENCE: 327

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
                20                  25                  30

Leu Gln Ala Ser Val Asp Ala Glu Ser Arg Ser Asp Lys Ile Ile His
            35                  40                  45

Leu Thr Asp Asp Ser Phe Asp Thr Asp Val Leu Lys Ala Asp Gly Ala
        50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
130                 135                 140

Leu Ala Asp Tyr Lys Asp Asp Asp Lys
145                 150

<210> SEQ ID NO 328
<211> LENGTH: 485
<212> TYPE: PRT
<213> ORGANISM: Artificial Sequence
<220> FEATURE:
<223> OTHER INFORMATION: Synthetic amino acid sequence

<400> SEQUENCE: 328

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

```
Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
            355                 360                 365

Asp Ala Glu Ser Arg Ser Asp Lys Ile Ile His Leu Thr Asp Asp Ser
370                 375                 380

Phe Asp Thr Asp Val Leu Lys Ala Asp Gly Ala Ile Leu Val Asp Phe
385                 390                 395                 400

Trp Ala Glu Trp Cys Gly Pro Cys Lys Met Ile Ala Pro Ile Leu Asp
            405                 410                 415

Glu Ile Ala Asp Glu Tyr Gln Gly Lys Leu Thr Val Ala Lys Leu Asn
            420                 425                 430

Ile Asp Gln Asn Pro Gly Thr Ala Pro Lys Tyr Gly Ile Arg Gly Ile
            435                 440                 445

Pro Thr Leu Leu Leu Phe Lys Asn Gly Glu Val Ala Ala Thr Lys Val
            450                 455                 460

Gly Ala Leu Ser Lys Gly Gln Leu Lys Glu Asn Leu Ala Asp Tyr Lys
465                 470                 475                 480

Asp Asp Asp Asp Lys
            485

<210> SEQ ID NO 329
<211> LENGTH: 485
<212> TYPE: PRT
<213> ORGANISM: Artificial Sequence
<220> FEATURE:
<223> OTHER INFORMATION: Synthetic amino acid sequence

<400> SEQUENCE: 329

Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
```

-continued

```
           65                   70                  75                  80
Asp Gly Pro Asp Ile Ile Phe Trp Ala His Asp Arg Phe Gly Gly Tyr
                    85                  90                  95
Ala Gln Ser Gly Leu Leu Ala Glu Ile Thr Pro Asp Lys Ala Phe Gln
                100                 105                 110
Asp Lys Leu Tyr Pro Phe Thr Trp Asp Ala Val Arg Tyr Asn Gly Lys
            115                 120                 125
Leu Ile Ala Tyr Pro Ile Ala Val Glu Ala Leu Ser Leu Ile Tyr Asn
            130                 135                 140
Lys Asp Leu Leu Pro Asn Pro Pro Lys Thr Trp Glu Glu Ile Pro Ala
145                 150                 155                 160
Leu Asp Lys Glu Leu Lys Ala Lys Gly Lys Ser Ala Leu Met Phe Asn
                165                 170                 175
Leu Gln Glu Pro Tyr Phe Thr Trp Pro Leu Ile Ala Ala Asp Gly Gly
                180                 185                 190
Tyr Ala Phe Lys Tyr Glu Asn Gly Lys Tyr Asp Ile Lys Asp Val Gly
            195                 200                 205
Val Asp Asn Ala Gly Ala Lys Ala Gly Leu Thr Phe Leu Val Asp Leu
            210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
                245                 250                 255
Ala Trp Ser Asn Ile Asp Thr Ser Lys Val Asn Tyr Gly Val Thr Val
                260                 265                 270
Leu Pro Thr Phe Lys Gly Gln Pro Ser Lys Pro Phe Val Gly Val Leu
                275                 280                 285
Ser Ala Gly Ile Asn Ala Ala Ser Pro Asn Lys Glu Leu Ala Lys Glu
            290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
                325                 330                 335
Leu Ala Lys Asp Pro Arg Ile Ala Ala Thr Met Glu Asn Ala Gln Ser
                340                 345                 350
Ala Phe Trp Tyr Ala Val Arg Ile Glu Ala Arg Leu Gln Ala Ser Val
            355                 360                 365
Asp Ala Glu Ser Arg Ser Asp Lys Ile Ile His Leu Thr Asp Asp Ser
            370                 375                 380
Phe Asp Thr Asp Val Leu Lys Ala Asp Gly Ala Ile Leu Val Asp Phe
385                 390                 395                 400
Trp Ala Glu Trp Cys Gly Pro Cys Lys Met Ile Ala Pro Ile Leu Asp
                405                 410                 415
Glu Ile Ala Asp Glu Tyr Gln Gly Lys Leu Thr Val Ala Lys Leu Asn
                420                 425                 430
Ile Asp Gln Asn Pro Gly Thr Ala Pro Lys Tyr Gly Ile Arg Gly Ile
            435                 440                 445
Pro Thr Leu Leu Leu Phe Lys Asn Gly Glu Val Ala Ala Thr Lys Val
            450                 455                 460
Gly Ala Leu Ser Lys Gly Gln Leu Lys Glu Asn Leu Ala Asp Tyr Lys
465                 470                 475                 480
Asp Asp Asp Asp Lys
                485
```

<210> SEQ ID NO 330
<211> LENGTH: 485
<212> TYPE: PRT
<213> ORGANISM: Artificial Sequence
<220> FEATURE:
<223> OTHER INFORMATION: Synthetic amino acid sequence

<400> SEQUENCE: 330

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
        355                 360                 365

Asp Ala Glu Ser Arg Ser Asp Lys Ile Ile His Leu Thr Asp Asp Ser

-continued

```
              370                 375                 380
Phe Asp Thr Asp Val Leu Lys Ala Asp Gly Ala Ile Leu Val Asp Phe
385                 390                 395                 400

Trp Ala Glu Trp Cys Gly Pro Cys Lys Met Ile Ala Pro Ile Leu Asp
                    405                 410                 415

Glu Ile Ala Asp Glu Tyr Gln Gly Lys Leu Thr Val Ala Lys Leu Asn
                420                 425                 430

Ile Asp Gln Asn Pro Gly Thr Ala Pro Lys Tyr Gly Ile Arg Gly Ile
                435                 440                 445

Pro Thr Leu Leu Leu Phe Lys Asn Gly Glu Val Ala Ala Thr Lys Val
            450                 455                 460

Gly Ala Leu Ser Lys Gly Gln Leu Lys Glu Asn Leu Ala Asp Tyr Lys
465                 470                 475                 480

Asp Asp Asp Asp Lys
                485

<210> SEQ ID NO 331
<211> LENGTH: 485
<212> TYPE: PRT
<213> ORGANISM: Artificial Sequence
<220> FEATURE:
<223> OTHER INFORMATION: Synthetic amino acid sequence

<400> SEQUENCE: 331

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
                35                  40                  45

Val Gly Lys Lys Phe Glu Lys Asp Thr Gly Ile Lys Val Thr Val Glu
            50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
130                 135                 140

Lys Asp Leu Leu Pro Asn Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255
```

```
Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
                340                 345                 350

Ala Phe Trp Tyr Ala Val Arg Ile Glu Ala Arg Leu Gln Ala Ser Val
                355                 360                 365

Asp Ala Glu Ser Arg Ser Asp Lys Ile Ile His Leu Thr Asp Asp Ser
            370                 375                 380

Phe Asp Thr Asp Val Leu Lys Ala Asp Gly Ala Ile Leu Val Asp Phe
385                 390                 395                 400

Trp Ala Glu Trp Cys Gly Pro Cys Lys Met Ile Ala Pro Ile Leu Asp
                405                 410                 415

Glu Ile Ala Asp Glu Tyr Gln Gly Lys Leu Thr Val Ala Lys Leu Asn
            420                 425                 430

Ile Asp Gln Asn Pro Gly Thr Ala Pro Lys Tyr Gly Ile Arg Gly Ile
            435                 440                 445

Pro Thr Leu Leu Leu Phe Lys Asn Gly Glu Val Ala Ala Thr Lys Val
            450                 455                 460

Gly Ala Leu Ser Lys Gly Gln Leu Lys Glu Asn Leu Ala Asp Tyr Lys
465                 470                 475                 480

Asp Asp Asp Asp Lys
                485

<210> SEQ ID NO 332
<211> LENGTH: 767
<212> TYPE: PRT
<213> ORGANISM: Artificial Sequence
<220> FEATURE:
<223> OTHER INFORMATION: Synthetic amino acid sequence

<400> SEQUENCE: 332

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125
```

```
Leu Ile Ala Tyr Pro Ile Ala Val Glu Ala Leu Ser Leu Ile Tyr Asn
    130                 135                 140
Lys Asp Leu Leu Pro Asn Pro Pro Lys Thr Trp Glu Glu Ile Pro Ala
145                 150                 155                 160
Leu Asp Lys Glu Leu Lys Ala Lys Gly Lys Ser Ala Leu Met Phe Asn
                165                 170                 175
Leu Gln Glu Pro Tyr Phe Thr Trp Pro Leu Ile Ala Ala Asp Gly Gly
            180                 185                 190
Tyr Ala Phe Lys Tyr Glu Asn Gly Lys Tyr Asp Ile Lys Asp Val Gly
        195                 200                 205
Val Asp Asn Ala Gly Ala Lys Ala Gly Leu Thr Phe Leu Val Asp Leu
    210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
                245                 250                 255
Ala Trp Ser Asn Ile Asp Thr Ser Lys Val Asn Tyr Gly Val Thr Val
            260                 265                 270
Leu Pro Thr Phe Lys Gly Gln Pro Ser Lys Pro Phe Val Gly Val Leu
        275                 280                 285
Ser Ala Gly Ile Asn Ala Ala Ser Pro Asn Lys Glu Leu Ala Lys Glu
    290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
                325                 330                 335
Leu Ala Lys Asp Pro Arg Ile Ala Ala Thr Met Glu Asn Ala Gln Lys
            340                 345                 350
Gly Glu Ile Met Pro Asn Ile Pro Gln Met Ser Ala Phe Trp Tyr Ala
        355                 360                 365
Val Leu Ile Glu Ala Arg Thr Ser Glu Ser Asp Thr Ala Gly Pro Asn
    370                 375                 380
Ser Asp Leu Asp Val Asn Thr Asp Ile Tyr Ser Lys Val Leu Val Thr
385                 390                 395                 400
Ala Ile Tyr Leu Ala Leu Phe Val Val Gly Thr Val Gly Asn Ser Val
                405                 410                 415
Thr Ala Phe Thr Leu Ala Arg Lys Lys Ser Leu Gln Ser Leu Gln Ser
            420                 425                 430
Thr Val His Tyr His Leu Gly Ser Leu Ala Leu Ser Asp Leu Leu Ile
        435                 440                 445
Leu Leu Leu Ala Met Pro Val Glu Leu Tyr Asn Phe Ile Trp Val His
    450                 455                 460
His Pro Trp Ala Phe Gly Asp Ala Gly Cys Arg Gly Tyr Tyr Phe Leu
465                 470                 475                 480
Arg Asp Ala Cys Thr Tyr Ala Thr Ala Leu Asn Val Ala Ser Leu Ser
                485                 490                 495
Val Glu Arg Tyr Leu Ala Ile Cys His Pro Phe Lys Ala Lys Thr Leu
            500                 505                 510
Met Ser Arg Ser Arg Thr Lys Lys Phe Ile Ser Ala Ile Trp Leu Ala
        515                 520                 525
Ser Ala Leu Leu Ala Ile Pro Met Leu Phe Thr Met Gly Leu Gln Asn
    530                 535                 540
Arg Ser Gly Asp Gly Thr His Pro Gly Gly Leu Val Cys Thr Pro Ile
545                 550                 555                 560
```

Val Asp Thr Ala Thr Val Lys Val Ile Gln Val Asn Thr Phe Met
                565                 570                 575

Ser Phe Leu Phe Pro Met Leu Val Ile Ser Ile Leu Asn Thr Val Ile
                580                 585                 590

Ala Asn Lys Leu Thr Val Met Val His Gln Ala Ala Glu Gln Gly Arg
                595                 600                 605

Val Cys Thr Val Gly Thr His Asn Gly Leu Glu His Ser Thr Phe Asn
610                 615                 620

Met Thr Ile Glu Pro Gly Arg Val Gln Ala Leu Arg His Gly Val Leu
625                 630                 635                 640

Val Leu Arg Ala Val Val Ile Ala Phe Val Val Cys Trp Leu Pro Tyr
                645                 650                 655

His Val Arg Arg Leu Met Phe Cys Tyr Ile Ser Asp Glu Gln Trp Thr
                660                 665                 670

Thr Phe Leu Phe Asp Phe Tyr His Tyr Phe Tyr Met Leu Thr Asn Ala
                675                 680                 685

Leu Phe Tyr Val Ser Ser Ala Ile Asn Pro Ile Leu Tyr Asn Leu Val
                690                 695                 700

Ser Ala Asn Phe Arg Gln Val Phe Leu Ser Thr Leu Ala Cys Leu Cys
705                 710                 715                 720

Pro Gly Trp Arg His Arg Arg Lys Lys Arg Pro Thr Phe Ser Arg Lys
                725                 730                 735

Pro Asn Ser Met Ser Ser Asn His Ala Phe Ser Thr Ser Ala Thr Arg
                740                 745                 750

Glu Thr Leu Tyr Ala Ala Ala Asp Tyr Lys Asp Asp Asp Asp Lys
                755                 760                 765

<210> SEQ ID NO 333
<211> LENGTH: 425
<212> TYPE: PRT
<213> ORGANISM: Artificial Sequence
<220> FEATURE:
<223> OTHER INFORMATION: Synthetic amino acid sequence

<400> SEQUENCE: 333

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
                20                  25                  30

Thr Ser Glu Ser Asp Thr Ala Gly Pro Asn Ser Asp Leu Asp Val Asn
                35                  40                  45

Thr Asp Ile Tyr Ser Lys Val Leu Val Thr Ala Ile Tyr Leu Ala Leu
50                  55                  60

Phe Val Val Gly Thr Val Gly Asn Ser Val Thr Ala Phe Thr Leu Ala
65                  70                  75                  80

Arg Lys Lys Ser Leu Gln Ser Leu Gln Ser Thr Val His Tyr His Leu
                85                  90                  95

Gly Ser Leu Ala Leu Ser Asp Leu Leu Ile Leu Leu Leu Ala Met Pro
                100                 105                 110

Val Glu Leu Tyr Asn Phe Ile Trp Val His His Pro Trp Ala Phe Gly
                115                 120                 125

Asp Ala Gly Cys Arg Gly Tyr Tyr Phe Leu Arg Asp Ala Cys Thr Tyr
                130                 135                 140

Ala Thr Ala Leu Asn Val Ala Ser Leu Ser Val Glu Arg Tyr Leu Ala
145                 150                 155                 160

```
Ile Cys His Pro Phe Lys Ala Lys Thr Leu Met Ser Arg Ser Arg Thr
                165                 170                 175

Lys Lys Phe Ile Ser Ala Ile Trp Leu Ala Ser Ala Leu Leu Ala Ile
            180                 185                 190

Pro Met Leu Phe Thr Met Gly Leu Gln Asn Arg Ser Gly Asp Gly Thr
        195                 200                 205

His Pro Gly Gly Leu Val Cys Thr Pro Ile Val Asp Thr Ala Thr Val
    210                 215                 220

Lys Val Val Ile Gln Val Asn Thr Phe Met Ser Phe Leu Phe Pro Met
225                 230                 235                 240

Leu Val Ile Ser Ile Leu Asn Thr Val Ile Ala Asn Lys Leu Thr Val
                245                 250                 255

Met Val His Gln Ala Ala Glu Gln Gly Arg Val Cys Thr Val Gly Thr
            260                 265                 270

His Asn Gly Leu Glu His Ser Thr Phe Asn Met Thr Ile Glu Pro Gly
        275                 280                 285

Arg Val Gln Ala Leu Arg His Gly Val Leu Val Leu Arg Ala Val Val
    290                 295                 300

Ile Ala Phe Val Val Cys Trp Leu Pro Tyr His Val Arg Arg Leu Met
305                 310                 315                 320

Phe Cys Tyr Ile Ser Asp Glu Gln Trp Thr Thr Phe Leu Phe Asp Phe
                325                 330                 335

Tyr His Tyr Phe Tyr Met Leu Thr Asn Ala Leu Phe Tyr Val Ser Ser
            340                 345                 350

Ala Ile Asn Pro Ile Leu Tyr Asn Leu Val Ser Ala Asn Phe Arg Gln
        355                 360                 365

Val Phe Leu Ser Thr Leu Ala Cys Leu Cys Pro Gly Trp Arg His Arg
    370                 375                 380

Arg Lys Lys Arg Pro Thr Phe Ser Arg Lys Pro Asn Ser Met Ser Ser
385                 390                 395                 400

Asn His Ala Phe Ser Thr Ser Ala Thr Arg Glu Thr Leu Tyr Ala Ala
                405                 410                 415

Ala Asp Tyr Lys Asp Asp Asp Lys
            420                 425

<210> SEQ ID NO 334
<211> LENGTH: 878
<212> TYPE: PRT
<213> ORGANISM: Artificial Sequence
<220> FEATURE:
<223> OTHER INFORMATION: Synthetic amino acid sequence

<400> SEQUENCE: 334

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
```

```
                 100                 105                 110
Asp Lys Leu Tyr Pro Phe Thr Trp Asp Ala Val Arg Tyr Asn Gly Lys
            115                 120                 125
Leu Ile Ala Tyr Pro Ile Ala Val Glu Ala Leu Ser Leu Ile Tyr Asn
        130                 135                 140
Lys Asp Leu Leu Pro Asn Pro Lys Thr Trp Glu Glu Ile Pro Ala
145                 150                 155                 160
Leu Asp Lys Glu Leu Lys Ala Lys Gly Lys Ser Ala Leu Met Phe Asn
            165                 170                 175
Leu Gln Glu Pro Tyr Phe Thr Trp Pro Leu Ile Ala Ala Asp Gly Gly
            180                 185                 190
Tyr Ala Phe Lys Tyr Glu Asn Gly Lys Tyr Asp Ile Lys Asp Val Gly
            195                 200                 205
Val Asp Asn Ala Gly Ala Lys Ala Gly Leu Thr Phe Leu Val Asp Leu
        210                 215                 220
Ile Lys Asn Lys His Met Asn Ala Asp Thr Asp Tyr Ser Ile Ala Glu
225                 230                 235                 240
Ala Ala Phe Asn Lys Gly Glu Thr Ala Met Thr Ile Asn Gly Pro Trp
            245                 250                 255
Ala Trp Ser Asn Ile Asp Thr Ser Lys Val Asn Tyr Gly Val Thr Val
            260                 265                 270
Leu Pro Thr Phe Lys Gly Gln Pro Ser Lys Pro Phe Val Gly Val Leu
            275                 280                 285
Ser Ala Gly Ile Asn Ala Ala Ser Pro Asn Lys Glu Leu Ala Lys Glu
        290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
            325                 330                 335
Leu Ala Lys Asp Pro Arg Ile Ala Ala Thr Met Glu Asn Ala Gln Lys
            340                 345                 350
Gly Glu Ile Met Pro Asn Ile Pro Gln Met Ser Ala Phe Trp Tyr Ala
            355                 360                 365
Val Leu Ile Glu Ala Arg Thr Ser Glu Ser Asp Thr Ala Gly Pro Asn
        370                 375                 380
Ser Asp Leu Asp Val Asn Thr Asp Ile Tyr Ser Lys Val Leu Val Thr
385                 390                 395                 400
Ala Ile Tyr Leu Ala Leu Phe Val Val Gly Thr Val Gly Asn Ser Val
            405                 410                 415
Thr Ala Phe Thr Leu Ala Arg Lys Lys Ser Leu Gln Ser Leu Gln Ser
            420                 425                 430
Thr Val His Tyr His Leu Gly Ser Leu Ala Leu Ser Asp Leu Leu Ile
        435                 440                 445
Leu Leu Leu Ala Met Pro Val Glu Leu Tyr Asn Phe Ile Trp Val His
        450                 455                 460
His Pro Trp Ala Phe Gly Asp Ala Gly Cys Arg Gly Tyr Tyr Phe Leu
465                 470                 475                 480
Arg Asp Ala Cys Thr Tyr Ala Thr Ala Leu Asn Val Ala Ser Leu Ser
            485                 490                 495
Val Glu Arg Tyr Leu Ala Ile Cys His Pro Phe Lys Ala Lys Thr Leu
            500                 505                 510
Met Ser Arg Ser Arg Thr Lys Lys Phe Ile Ser Ala Ile Trp Leu Ala
            515                 520                 525
```

-continued

```
Ser Ala Leu Leu Ala Ile Pro Met Leu Phe Thr Met Gly Leu Gln Asn
            530                 535                 540

Arg Ser Gly Asp Gly Thr His Pro Gly Gly Leu Val Cys Thr Pro Ile
545                 550                 555                 560

Val Asp Thr Ala Thr Val Lys Val Val Ile Gln Val Asn Thr Phe Met
                565                 570                 575

Ser Phe Leu Phe Pro Met Leu Val Ile Ser Ile Leu Asn Thr Val Ile
            580                 585                 590

Ala Asn Lys Leu Thr Val Met Val His Gln Ala Ala Glu Gln Gly Arg
            595                 600                 605

Val Cys Thr Val Gly Thr His Asn Gly Leu Glu His Ser Thr Phe Asn
610                 615                 620

Met Thr Ile Glu Pro Gly Arg Val Gln Ala Leu Arg His Gly Val Leu
625                 630                 635                 640

Val Leu Arg Ala Val Ile Ala Phe Val Val Cys Trp Leu Pro Tyr
                645                 650                 655

His Val Arg Arg Leu Met Phe Cys Tyr Ile Ser Asp Glu Gln Trp Thr
                660                 665                 670

Thr Phe Leu Phe Asp Phe Tyr His Tyr Phe Tyr Met Leu Thr Asn Ala
            675                 680                 685

Leu Phe Tyr Val Ser Ser Ala Ile Asn Pro Ile Leu Tyr Asn Leu Val
            690                 695                 700

Ser Ala Asn Phe Arg Gln Val Phe Leu Ser Thr Leu Ala Cys Leu Cys
705                 710                 715                 720

Pro Gly Trp Arg His Arg Arg Lys Lys Arg Pro Thr Phe Ser Arg Lys
                725                 730                 735

Pro Asn Ser Met Ser Ser Asn His Ala Phe Ser Thr Ser Ala Thr Arg
            740                 745                 750

Glu Thr Leu Tyr Ala Ala Ala Ser Asp Lys Ile Ile His Leu Thr Asp
            755                 760                 765

Asp Ser Phe Asp Thr Asp Val Leu Lys Ala Asp Gly Ala Ile Leu Val
770                 775                 780

Asp Phe Trp Ala Glu Trp Cys Gly Pro Cys Lys Met Ile Ala Pro Ile
785                 790                 795                 800

Leu Asp Glu Ile Ala Asp Glu Tyr Gln Gly Lys Leu Thr Val Ala Lys
                805                 810                 815

Leu Asn Ile Asp Gln Asn Pro Gly Thr Ala Pro Lys Tyr Gly Ile Arg
            820                 825                 830

Gly Ile Pro Thr Leu Leu Leu Phe Lys Asn Gly Glu Val Ala Ala Thr
            835                 840                 845

Lys Val Gly Ala Leu Ser Lys Gly Gln Leu Lys Glu Phe Leu Asp Ala
850                 855                 860

Asn Leu Ala Ala Ala Ala Asp Tyr Lys Asp Asp Asp Asp Lys
865                 870                 875

<210> SEQ ID NO 335
<211> LENGTH: 536
<212> TYPE: PRT
<213> ORGANISM: Artificial Sequence
<220> FEATURE:
<223> OTHER INFORMATION: Synthetic amino acid sequence

<400> SEQUENCE: 335

Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Ile Glu Ala Arg
```

-continued

```
                 20                  25                  30
Thr Ser Glu Ser Asp Thr Ala Gly Pro Asn Ser Asp Leu Asp Val Asn
             35                  40                  45

Thr Asp Ile Tyr Ser Lys Val Leu Val Thr Ala Ile Tyr Leu Ala Leu
         50                  55                  60

Phe Val Val Gly Thr Val Gly Asn Ser Val Thr Ala Phe Thr Leu Ala
65                  70                  75                  80

Arg Lys Lys Ser Leu Gln Ser Leu Gln Ser Thr Val His Tyr His Leu
                 85                  90                  95

Gly Ser Leu Ala Leu Ser Asp Leu Leu Ile Leu Leu Leu Ala Met Pro
            100                 105                 110

Val Glu Leu Tyr Asn Phe Ile Trp Val His His Pro Trp Ala Phe Gly
        115                 120                 125

Asp Ala Gly Cys Arg Gly Tyr Tyr Phe Leu Arg Asp Ala Cys Thr Tyr
    130                 135                 140

Ala Thr Ala Leu Asn Val Ala Ser Leu Ser Val Glu Arg Tyr Leu Ala
145                 150                 155                 160

Ile Cys His Pro Phe Lys Ala Lys Thr Leu Met Ser Arg Ser Arg Thr
                165                 170                 175

Lys Lys Phe Ile Ser Ala Ile Trp Leu Ala Ser Ala Leu Leu Ala Ile
            180                 185                 190

Pro Met Leu Phe Thr Met Gly Leu Gln Asn Arg Ser Gly Asp Gly Thr
        195                 200                 205

His Pro Gly Gly Leu Val Cys Thr Pro Ile Val Asp Thr Ala Thr Val
    210                 215                 220

Lys Val Val Ile Gln Val Asn Thr Phe Met Ser Phe Leu Phe Pro Met
225                 230                 235                 240

Leu Val Ile Ser Ile Leu Asn Thr Val Ile Ala Asn Lys Leu Thr Val
                245                 250                 255

Met Val His Gln Ala Ala Glu Gln Gly Arg Val Cys Thr Val Gly Thr
            260                 265                 270

His Asn Gly Leu Glu His Ser Thr Phe Asn Met Thr Ile Glu Pro Gly
        275                 280                 285

Arg Val Gln Ala Leu Arg His Gly Val Leu Val Leu Arg Ala Val Val
    290                 295                 300

Ile Ala Phe Val Val Cys Trp Leu Pro Tyr His Val Arg Arg Leu Met
305                 310                 315                 320

Phe Cys Tyr Ile Ser Asp Glu Gln Trp Thr Thr Phe Leu Phe Asp Phe
                325                 330                 335

Tyr His Tyr Phe Tyr Met Leu Thr Asn Ala Leu Phe Tyr Val Ser Ser
            340                 345                 350

Ala Ile Asn Pro Ile Leu Tyr Asn Leu Val Ser Ala Asn Phe Arg Gln
        355                 360                 365

Val Phe Leu Ser Thr Leu Ala Cys Leu Cys Pro Gly Trp Arg His Arg
    370                 375                 380

Arg Lys Lys Arg Pro Thr Phe Ser Arg Lys Pro Asn Ser Met Ser Ser
385                 390                 395                 400

Asn His Ala Phe Ser Thr Ser Ala Thr Arg Glu Thr Leu Tyr Ala Ala
                405                 410                 415

Ala Ser Asp Lys Ile Ile His Leu Thr Asp Asp Ser Phe Asp Thr Asp
            420                 425                 430

Val Leu Lys Ala Asp Gly Ala Ile Leu Val Asp Phe Trp Ala Glu Trp
        435                 440                 445
```

```
Cys Gly Pro Cys Lys Met Ile Ala Pro Ile Leu Asp Glu Ile Ala Asp
        450                 455                 460

Glu Tyr Gln Gly Lys Leu Thr Val Ala Lys Leu Asn Ile Asp Gln Asn
465                 470                 475                 480

Pro Gly Thr Ala Pro Lys Tyr Gly Ile Arg Gly Ile Pro Thr Leu Leu
                485                 490                 495

Leu Phe Lys Asn Gly Glu Val Ala Ala Thr Lys Val Gly Ala Leu Ser
            500                 505                 510

Lys Gly Gln Leu Lys Glu Phe Leu Asp Ala Asn Leu Ala Ala Ala Ala
        515                 520                 525

Asp Tyr Lys Asp Asp Asp Lys
530                 535

<210> SEQ ID NO 336
<211> LENGTH: 380
<212> TYPE: PRT
<213> ORGANISM: Artificial Sequence
<220> FEATURE:
<223> OTHER INFORMATION: Synthetic amino acid sequence

<400> SEQUENCE: 336

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
            100                 105                 110

Arg Val Asp Tyr Ile Leu Ser Val Met Asn Val Pro Asp Phe Asp Phe
        115                 120                 125

Pro Pro Glu Phe Tyr Glu His Ala Lys Ala Leu Trp Glu Asp Glu Gly
    130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
        195                 200                 205

Asp Val Gly Gly Gln Arg Asp Glu Arg Arg Lys Trp Ile Gln Cys Phe
    210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
```

```
                275                 280                 285
Ala Gly Lys Ser Lys Ile Glu Asp Tyr Phe Pro Glu Phe Ala Arg Tyr
290                 295                 300

Thr Thr Pro Glu Asp Ala Thr Pro Glu Pro Gly Glu Asp Pro Arg Val
305                 310                 315                 320

Thr Arg Ala Lys Tyr Phe Ile Arg Asp Glu Phe Leu Arg Ile Ser Thr
                325                 330                 335

Ala Ser Gly Asp Gly Arg His Tyr Cys Tyr Pro His Phe Thr Cys Ala
                340                 345                 350

Val Asp Thr Glu Asn Ile Arg Arg Val Phe Asn Asp Cys Arg Asp Ile
                355                 360                 365

Ile Gln Arg Met His Leu Arg Gln Tyr Glu Leu Leu
370                 375                 380

<210> SEQ ID NO 337
<211> LENGTH: 394
<212> TYPE: PRT
<213> ORGANISM: Artificial Sequence
<220> FEATURE:
<223> OTHER INFORMATION: Synthetic amino acid sequence

<400> SEQUENCE: 337

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
                35                  40                  45

Gly Glu Ser Gly Lys Ser Thr Ile Val Lys Gln Met Arg Ile Leu His
50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
                100                 105                 110

Leu Val Pro Pro Val Glu Leu Ala Asn Pro Glu Asn Gln Phe Arg Val
                115                 120                 125

Asp Tyr Ile Leu Ser Val Met Asn Val Pro Asp Phe Asp Phe Pro Pro
130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
                180                 185                 190

Ser Asp Gln Asp Leu Leu Arg Cys Arg Val Leu Thr Ser Gly Ile Phe
                195                 200                 205

Glu Thr Lys Phe Gln Val Asp Lys Val Asn Phe His Met Phe Asp Val
                210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Ser Tyr Asn Met Val
                245                 250                 255

Ile Arg Glu Asp Asn Gln Thr Asn Arg Leu Gln Glu Ala Leu Asn Leu
                260                 265                 270
```

```
Phe Lys Ser Ile Trp Asn Asn Arg Trp Leu Arg Thr Ile Ser Val Ile
            275                 280                 285

Leu Phe Leu Asn Lys Gln Asp Leu Leu Ala Glu Lys Val Leu Ala Gly
            290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
            355                 360                 365

Thr Glu Asn Ile Arg Arg Val Phe Asn Asp Cys Arg Asp Ile Ile Gln
            370                 375                 380

Arg Met His Leu Arg Gln Tyr Glu Leu Leu
385                 390

<210> SEQ ID NO 338
<211> LENGTH: 359
<212> TYPE: PRT
<213> ORGANISM: Artificial Sequence
<220> FEATURE:
<223> OTHER INFORMATION: Synthetic amino acid sequence

<400> SEQUENCE: 338

Met Thr Leu Glu Ser Ile Met Ala Cys Cys Leu Ser Glu Glu Ala Lys
  1               5                  10                  15

Glu Ala Arg Arg Ile Asn Asp Glu Ile Glu Arg Gln Leu Arg Arg Asp
             20                  25                  30

Lys Arg Asp Ala Arg Arg Glu Leu Lys Leu Leu Leu Leu Gly Thr Gly
         35                  40                  45

Glu Ser Gly Lys Ser Thr Phe Ile Lys Gln Met Arg Ile Ile His Gly
     50                  55                  60

Ser Gly Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240
```

```
Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 339
<211> LENGTH: 355
<212> TYPE: PRT
<213> ORGANISM: Artificial Sequence
<220> FEATURE:
<223> OTHER INFORMATION: Synthetic amino acid sequence

<400> SEQUENCE: 339

Met Gly Cys Thr Val Ser Ala Glu Asp Lys Ala Ala Ala Glu Arg Ser
1               5                   10                  15

Lys Met Ile Asp Lys Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Asp Gly Tyr Ser Glu Glu
    50                  55                  60

Glu Cys Arg Gln Tyr Arg Ala Val Val Tyr Ser Asn Thr Ile Gln Ser
65                  70                  75                  80

Ile Met Ala Ile Val Lys Ala Met Gly Asn Leu Gln Ile Asp Phe Ala
                85                  90                  95

Asp Pro Ser Arg Ala Asp Asp Ala Arg Gln Leu Phe Ala Leu Ser Cys
            100                 105                 110

Thr Ala Glu Glu Gln Gly Val Leu Pro Asp Asp Leu Ser Gly Val Ile
        115                 120                 125

Arg Arg Leu Trp Ala Asp His Gly Val Gln Ala Cys Phe Gly Arg Ser
    130                 135                 140

Arg Glu Tyr Gln Leu Asn Asp Ser Ala Ala Tyr Tyr Leu Asn Asp Leu
145                 150                 155                 160

Glu Arg Ile Ala Gln Ser Asp Tyr Ile Pro Thr Gln Gln Asp Val Leu
                165                 170                 175

Arg Thr Arg Val Lys Thr Thr Gly Ile Val Glu Thr His Phe Thr Phe
            180                 185                 190

Lys Asp Leu His Phe Lys Met Phe Asp Val Gly Gly Gln Arg Ser Glu
        195                 200                 205

Arg Lys Lys Trp Ile His Cys Phe Glu Gly Val Thr Ala Ile Ile Phe
    210                 215                 220

Cys Val Ala Leu Ser Ala Tyr Asp Leu Val Leu Ala Glu Asp Glu Glu
225                 230                 235                 240

Met Asn Arg Met His Glu Ser Met Lys Leu Phe Asp Ser Ile Cys Asn
```

```
                   245                 250                 255
Asn Lys Trp Phe Thr Asp Thr Ser Ile Ile Leu Phe Leu Asn Lys Lys
                260                 265                 270

Asp Leu Phe Glu Glu Lys Ile Thr His Ser Pro Leu Thr Ile Cys Phe
            275                 280                 285

Pro Glu Tyr Thr Gly Ala Asn Lys Tyr Asp Glu Ala Ala Ser Tyr Ile
        290                 295                 300

Gln Ser Lys Phe Glu Asp Leu Asn Lys Arg Lys Asp Thr Lys Glu Ile
305                 310                 315                 320

Tyr Thr His Phe Thr Cys Ala Thr Asp Thr Lys Asn Val Gln Phe Val
                325                 330                 335

Phe Asp Ala Val Thr Asp Val Ile Ile Lys Asn Asn Leu Lys Asp Cys
            340                 345                 350

Gly Leu Phe
        355

<210> SEQ ID NO 340
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 340

Met Ser Gly Val Val Arg Thr Leu Ser Arg Cys Leu Leu Pro Ala Glu
 1               5                  10                  15

Ala Gly Gly Ala Arg Glu Arg Arg Ala Gly Ser Gly Ala Arg Asp Ala
                20                  25                  30

Glu Arg Glu Ala Arg Arg Ser Arg Asp Ile Asp Ala Leu Leu Ala
            35                  40                  45

Arg Glu Arg Arg Ala Val Arg Arg Leu Val Lys Ile Leu Leu Leu Gly
        50                  55                  60

Ala Gly Glu Ser Gly Lys Ser Thr Phe Leu Lys Gln Met Arg Ile Ile
65                  70                  75                  80

His Gly Arg Glu Phe Asp Gln Lys Ala Leu Leu Glu Phe Arg Asp Thr
                85                  90                  95

Ile Phe Asp Asn Ile Leu Lys Gly Ser Arg Val Leu Val Asp Ala Arg
            100                 105                 110

Asp Lys Leu Gly Ile Pro Trp Gln Tyr Ser Glu Asn Glu Lys His Gly
        115                 120                 125

Met Phe Leu Met Ala Phe Glu Asn Lys Ala Gly Leu Pro Val Glu Pro
130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Ser Glu Phe Gln Leu Gly
            165                 170                 175

Glu Ser Val Lys Tyr Phe Leu Asp Asn Leu Asp Arg Ile Gly Gln Leu
        180                 185                 190

Asn Tyr Phe Pro Ser Lys Gln Asp Ile Leu Leu Ala Arg Lys Ala Thr
            195                 200                 205

Lys Gly Ile Val Glu His Asp Phe Val Ile Lys Lys Ile Pro Phe Lys
        210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
                245                 250                 255
```

```
Tyr Asp Gln Val Leu Met Glu Asp Arg Arg Thr Asn Arg Leu Val Glu
            260                 265                 270

Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
    290                 295                 300

Val Lys Thr Val Ser Ile Lys Lys His Phe Pro Asp Phe Arg Gly Asp
305                 310                 315                 320

Pro His Gln Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
            340                 345                 350

Ala Ile Asp Thr Glu Asn Val Arg Phe Val Phe His Ala Val Lys Asp
        355                 360                 365

Thr Ile Leu Gln Glu Asn Leu Lys Asp Ile Met Leu Gln
    370                 375                 380

<210> SEQ ID NO 341
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 341

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Asp Tyr Lys Asp Asp Asp
        35                  40                  45

Asp Lys
    50

<210> SEQ ID NO 342
<211> LENGTH: 27
<212> TYPE: PRT
<213> ORGANISM: Artificial Sequence
<220> FEATURE:
<223> OTHER INFORMATION: Synthetic amino acid sequence

<400> SEQUENCE: 342

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys
            20                  25

<210> SEQ ID NO 343
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 343

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Asp Tyr Lys Asp Asp Asp
```

-continued

```
             35                  40                  45

Asp Lys
    50

<210> SEQ ID NO 344
<211> LENGTH: 50
<212> TYPE: PRT
<213> ORGANISM: Artificial Sequence
<220> FEATURE:
<223> OTHER INFORMATION: Synthetic amino acid sequence

<400> SEQUENCE: 344

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Asp Tyr Lys Asp Asp Asp
        35                  40                  45

Asp Lys
    50

<210> SEQ ID NO 345
<211> LENGTH: 343
<212> TYPE: PRT
<213> ORGANISM: Artificial Sequence
<220> FEATURE:
<223> OTHER INFORMATION: Synthetic amino acid sequence

<400> SEQUENCE: 345

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
```

```
                        225                 230                 235                 240
Ala Ala Phe Asn Lys Gly Glu Thr Ala Met Thr Ile Asn Gly Pro Trp
                    245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
        290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile
                340

<210> SEQ ID NO 346
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 346

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255
```

```
Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
            355                 360                 365

Asp Ala Glu Ser Arg Asp Tyr Lys Asp Asp Asp Lys
            370                 375                 380

<210> SEQ ID NO 347
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 347

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240
```

```
Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
        355                 360                 365

Asp Ala Glu Ser Arg Asp Tyr Lys Asp Asp Asp Lys
    370                 375                 380

<210> SEQ ID NO 348
<211> LENGTH: 381
<212> TYPE: PRT
<213> ORGANISM: Artificial Sequence
<220> FEATURE:
<223> OTHER INFORMATION: Synthetic amino acid sequence

<400> SEQUENCE: 348

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
```

```
                225                 230                 235                 240
Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
                260                 265                 270

Leu Pro Thr Phe Lys Gly Gln Pro Ser Lys Pro Phe Val Gly Val Leu
                275                 280                 285

Ser Ala Gly Ile Asn Ala Ala Ser Pro Asn Lys Glu Leu Ala Lys Glu
                290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
                340                 345                 350

Ala Phe Trp Tyr Ala Val Arg Ile Glu Ala Arg Leu Gln Ala Ser Val
                355                 360                 365

Asp Ala Glu Ser Arg Asp Tyr Lys Asp Asp Asp Lys
370                 375                 380

<210> SEQ ID NO 349
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 349

Ala Ser Val Asp Ala Glu Ser Arg Ser Asp Lys Ile Ile His Leu Thr
1               5                   10                  15

Asp Asp Ser Phe Asp Thr Asp Val Leu Lys Ala Asp Gly Ala Ile Leu
                20                  25                  30

Val Asp Phe Trp Ala Glu Trp Cys Gly Pro Cys Lys Met Ile Ala Pro
            35                  40                  45

Ile Leu Asp Glu Ile Ala Asp Glu Tyr Gln Gly Lys Leu Thr Val Ala
        50                  55                  60

Lys Leu Asn Ile Asp Gln Asn Pro Gly Thr Ala Pro Lys Tyr Gly Ile
65                  70                  75                  80

Arg Gly Ile Pro Thr Leu Leu Leu Phe Lys Asn Gly Glu Val Ala Ala
                85                  90                  95

Thr Lys Val Gly Ala Leu Ser Lys Gly Gln Leu Lys Glu Asn Leu Ala
            100                 105                 110

Asp Tyr Lys Asp Asp Asp Asp Lys
        115                 120

<210> SEQ ID NO 350
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 350

Ala Ser Val Asp Ala Glu Ser Arg Ser Asp Lys Ile Ile His Leu Thr
1               5                   10                  15

Asp Asp Ser Phe Asp Thr Asp Val Leu Lys Ala Asp Gly Ala Ile Leu
                20                  25                  30

Val Asp Phe Trp Ala Glu Trp Cys Gly Pro Cys Lys Met Ile Ala Pro
```

```
                     35                  40                  45
Ile Leu Asp Glu Ile Ala Asp Glu Tyr Gln Gly Lys Leu Thr Val Ala
 50                  55                  60

Lys Leu Asn Ile Asp Gln Asn Pro Gly Thr Ala Pro Lys Tyr Gly Ile
 65                  70                  75                  80

Arg Gly Ile Pro Thr Leu Leu Leu Phe Lys Asn Gly Glu Val Ala Ala
                 85                  90                  95

Thr Lys Val Gly Ala Leu Ser Lys Gly Gln Leu Lys Glu Asn Leu Ala
                100                 105                 110

Asp Tyr Lys Asp Asp Asp Lys
            115                 120

<210> SEQ ID NO 351
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 351

Ala Ser Val Asp Ala Glu Ser Arg Ser Asp Lys Ile Ile His Leu Thr
  1               5                  10                  15

Asp Asp Ser Phe Asp Thr Asp Val Leu Lys Ala Asp Gly Ala Ile Leu
                 20                  25                  30

Val Asp Phe Trp Ala Glu Trp Cys Gly Pro Cys Lys Met Ile Ala Pro
             35                  40                  45

Ile Leu Asp Glu Ile Ala Asp Glu Tyr Gln Gly Lys Leu Thr Val Ala
 50                  55                  60

Lys Leu Asn Ile Asp Gln Asn Pro Gly Thr Ala Pro Lys Tyr Gly Ile
 65                  70                  75                  80

Arg Gly Ile Pro Thr Leu Leu Leu Phe Lys Asn Gly Glu Val Ala Ala
                 85                  90                  95

Thr Lys Val Gly Ala Leu Ser Lys Gly Gln Leu Lys Glu Asn Leu Ala
                100                 105                 110

Asp Tyr Lys Asp Asp Asp Lys
            115                 120

<210> SEQ ID NO 352
<211> LENGTH: 120
<212> TYPE: PRT
<213> ORGANISM: Artificial Sequence
<220> FEATURE:
<223> OTHER INFORMATION: Synthetic amino acid sequence

<400> SEQUENCE: 352

Ala Ser Val Asp Ala Glu Ser Arg Ser Asp Lys Ile Ile His Leu Thr
  1               5                  10                  15

Asp Asp Ser Phe Asp Thr Asp Val Leu Lys Ala Asp Gly Ala Ile Leu
                 20                  25                  30

Val Asp Phe Trp Ala Glu Trp Cys Gly Pro Cys Lys Met Ile Ala Pro
             35                  40                  45

Ile Leu Asp Glu Ile Ala Asp Glu Tyr Gln Gly Lys Leu Thr Val Ala
 50                  55                  60

Lys Leu Asn Ile Asp Gln Asn Pro Gly Thr Ala Pro Lys Tyr Gly Ile
 65                  70                  75                  80

Arg Gly Ile Pro Thr Leu Leu Leu Phe Lys Asn Gly Glu Val Ala Ala
                 85                  90                  95

Thr Lys Val Gly Ala Leu Ser Lys Gly Gln Leu Lys Glu Asn Leu Ala
```

```
                    100                 105                 110

Asp Tyr Lys Asp Asp Asp Lys
        115                 120

<210> SEQ ID NO 353
<211> LENGTH: 154
<212> TYPE: PRT
<213> ORGANISM: Artificial Sequence
<220> FEATURE:
<223> OTHER INFORMATION: Synthetic amino acid sequence

<400> SEQUENCE: 353

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Ser Asp Lys Ile Ile His
        35                  40                  45

Leu Thr Asp Asp Ser Phe Asp Thr Asp Val Leu Lys Ala Asp Gly Ala
    50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
    130                 135                 140

Leu Ala Asp Tyr Lys Asp Asp Asp Lys
145                 150

<210> SEQ ID NO 354
<211> LENGTH: 154
<212> TYPE: PRT
<213> ORGANISM: Artificial Sequence
<220> FEATURE:
<223> OTHER INFORMATION: Synthetic amino acid sequence

<400> SEQUENCE: 354

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
            20                  25                  30

Leu Gln Ala Ser Val Asp Ala Glu Ser Arg Ser Asp Lys Ile Ile His
        35                  40                  45

Leu Thr Asp Asp Ser Phe Asp Thr Asp Val Leu Lys Ala Asp Gly Ala
    50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
```

```
                130                 135                 140
Leu Ala Asp Tyr Lys Asp Asp Asp Lys
145                 150
```

<210> SEQ ID NO 355
<211> LENGTH: 154
<212> TYPE: PRT
<213> ORGANISM: Artificial Sequence
<220> FEATURE:
<223> OTHER INFORMATION: Synthetic amino acid sequence

<400> SEQUENCE: 355

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
                20                  25                  30

Leu Gln Ala Ser Val Asp Ala Glu Ser Arg Ser Asp Lys Ile Ile His
            35                  40                  45

Leu Thr Asp Asp Ser Phe Asp Thr Asp Val Leu Lys Ala Asp Gly Ala
        50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
    130                 135                 140

Leu Ala Asp Tyr Lys Asp Asp Asp Lys
145                 150
```

<210> SEQ ID NO 356
<211> LENGTH: 154
<212> TYPE: PRT
<213> ORGANISM: Artificial Sequence
<220> FEATURE:
<223> OTHER INFORMATION: Synthetic amino acid sequence

<400> SEQUENCE: 356

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Ile Glu Ala Arg
                20                  25                  30

Leu Gln Ala Ser Val Asp Ala Glu Ser Arg Ser Asp Lys Ile Ile His
            35                  40                  45

Leu Thr Asp Asp Ser Phe Asp Thr Asp Val Leu Lys Ala Asp Gly Ala
        50                  55                  60

Ile Leu Val Asp Phe Trp Ala Glu Trp Cys Gly Pro Cys Lys Met Ile
65                  70                  75                  80

Ala Pro Ile Leu Asp Glu Ile Ala Asp Glu Tyr Gln Gly Lys Leu Thr
                85                  90                  95

Val Ala Lys Leu Asn Ile Asp Gln Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Asn
```

```
                130               135               140
Leu Ala Asp Tyr Lys Asp Asp Asp Lys
145                 150
```

<210> SEQ ID NO 357
<211> LENGTH: 485
<212> TYPE: PRT
<213> ORGANISM: Artificial Sequence
<220> FEATURE:
<223> OTHER INFORMATION: Synthetic amino acid sequence

<400> SEQUENCE: 357

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
            340                 345                 350
```

Ala Phe Trp Tyr Ala Val Arg Ile Glu Ala Arg Leu Gln Ala Ser Val
            355                 360                 365

Asp Ala Glu Ser Arg Ser Asp Lys Ile Ile His Leu Thr Asp Asp Ser
    370                 375                 380

Phe Asp Thr Asp Val Leu Lys Ala Asp Gly Ala Ile Leu Val Asp Phe
385                 390                 395                 400

Trp Ala Glu Trp Cys Gly Pro Cys Lys Met Ile Ala Pro Ile Leu Asp
                405                 410                 415

Glu Ile Ala Asp Glu Tyr Gln Gly Lys Leu Thr Val Ala Lys Leu Asn
            420                 425                 430

Ile Asp Gln Asn Pro Gly Thr Ala Pro Lys Tyr Gly Ile Arg Gly Ile
        435                 440                 445

Pro Thr Leu Leu Leu Phe Lys Asn Gly Glu Val Ala Ala Thr Lys Val
    450                 455                 460

Gly Ala Leu Ser Lys Gly Gln Leu Lys Glu Asn Leu Ala Asp Tyr Lys
465                 470                 475                 480

Asp Asp Asp Asp Lys
                485

<210> SEQ ID NO 358
<211> LENGTH: 485
<212> TYPE: PRT
<213> ORGANISM: Artificial Sequence
<220> FEATURE:
<223> OTHER INFORMATION: Synthetic amino acid sequence

<400> SEQUENCE: 358

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

-continued

```
Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
        355                 360                 365

Asp Ala Glu Ser Arg Ser Asp Lys Ile Ile His Leu Thr Asp Ser
370                 375                 380

Phe Asp Thr Asp Val Leu Lys Ala Asp Gly Ala Ile Leu Val Asp Phe
385                 390                 395                 400

Trp Ala Glu Trp Cys Gly Pro Cys Lys Met Ile Ala Pro Ile Leu Asp
            405                 410                 415

Glu Ile Ala Asp Glu Tyr Gln Gly Lys Leu Thr Val Ala Lys Leu Asn
            420                 425                 430

Ile Asp Gln Asn Pro Gly Thr Ala Pro Lys Tyr Gly Ile Arg Gly Ile
        435                 440                 445

Pro Thr Leu Leu Leu Phe Lys Asn Gly Glu Val Ala Ala Thr Lys Val
450                 455                 460

Gly Ala Leu Ser Lys Gly Gln Leu Lys Glu Asn Leu Ala Asp Tyr Lys
465                 470                 475                 480

Asp Asp Asp Asp Lys
            485

<210> SEQ ID NO 359
<211> LENGTH: 485
<212> TYPE: PRT
<213> ORGANISM: Artificial Sequence
<220> FEATURE:
<223> OTHER INFORMATION: Synthetic amino acid sequence

<400> SEQUENCE: 359

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
```

```
                        100                 105                 110
Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
            355                 360                 365

Asp Ala Glu Ser Arg Ser Asp Lys Ile Ile His Leu Thr Asp Asp Ser
        370                 375                 380

Phe Asp Thr Asp Val Leu Lys Ala Asp Gly Ala Ile Leu Val Asp Phe
385                 390                 395                 400

Trp Ala Glu Trp Cys Gly Pro Cys Lys Met Ile Ala Pro Ile Leu Asp
            405                 410                 415

Glu Ile Ala Asp Glu Tyr Gln Gly Lys Leu Thr Val Ala Lys Leu Asn
            420                 425                 430

Ile Asp Gln Asn Pro Gly Thr Ala Pro Lys Tyr Gly Ile Arg Gly Ile
        435                 440                 445

Pro Thr Leu Leu Leu Phe Lys Asn Gly Glu Val Ala Ala Thr Lys Val
            450                 455                 460

Gly Ala Leu Ser Lys Gly Gln Leu Lys Glu Asn Leu Ala Asp Tyr Lys
465                 470                 475                 480

Asp Asp Asp Asp Lys
            485

<210> SEQ ID NO 360
<211> LENGTH: 485
<212> TYPE: PRT
<213> ORGANISM: Artificial Sequence
<220> FEATURE:
```

<223> OTHER INFORMATION: Synthetic amino acid sequence

<400> SEQUENCE: 360

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Ser
            340                 345                 350

Ala Phe Trp Tyr Ala Val Arg Ile Glu Ala Arg Leu Gln Ala Ser Val
        355                 360                 365

Asp Ala Glu Ser Arg Ser Asp Lys Ile Ile His Leu Thr Asp Ser
    370                 375                 380

Phe Asp Thr Asp Val Leu Lys Ala Asp Gly Ala Ile Leu Val Asp Phe
385                 390                 395                 400

Trp Ala Glu Trp Cys Gly Pro Cys Lys Met Ile Ala Pro Ile Leu Asp
```

-continued

```
                      405                 410                 415
Glu Ile Ala Asp Glu Tyr Gln Gly Lys Leu Thr Val Ala Lys Leu Asn
            420                 425                 430

Ile Asp Gln Asn Pro Gly Thr Ala Pro Lys Tyr Gly Ile Arg Gly Ile
        435                 440                 445

Pro Thr Leu Leu Leu Phe Lys Asn Gly Glu Val Ala Ala Thr Lys Val
    450                 455                 460

Gly Ala Leu Ser Lys Gly Gln Leu Lys Glu Asn Leu Ala Asp Tyr Lys
465                 470                 475                 480

Asp Asp Asp Asp Lys
            485

<210> SEQ ID NO 361
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 361
atgcctaaag ccgctccctc a                                          21

<210> SEQ ID NO 362
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 362
atgaagccgc tccct                                                 15

<210> SEQ ID NO 363
<211> LENGTH: 15
<212> TYPE: RNA
<213> ORGANISM: Artificial Sequence
<220> FEATURE:
<223> OTHER INFORMATION: Synthetic nucleic acid sequence

<400> SEQUENCE: 363
augaagccgc ucccu                                                 15

<210> SEQ ID NO 364
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 364

Met Pro Lys Ala Ala
 1               5

<210> SEQ ID NO 365
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 365
tgggttactc actca                                                 15

<210> SEQ ID NO 366
```

```
-continued

<211> LENGTH: 15
<212> TYPE: RNA
<213> ORGANISM: Artificial Sequence
<220> FEATURE:
<223> OTHER INFORMATION: Synthetic nucleic acid sequence

<400> SEQUENCE: 366
uggguuacuc acuca                                                    15

<210> SEQ ID NO 367
<211> LENGTH: 5
<212> TYPE: PRT
<213> ORGANISM: Artificial Sequence
<220> FEATURE:
<223> OTHER INFORMATION: Synthetic amino acid sequence

<400> SEQUENCE: 367

Trp Val Thr His Ser
 1               5

<210> SEQ ID NO 368
<211> LENGTH: 15
<212> TYPE: DNA
<213> ORGANISM: Artificial Sequence
<220> FEATURE:
<223> OTHER INFORMATION: Synthetic nucleic acid sequence

<400> SEQUENCE: 368
atgaagccgc actca                                                    15

<210> SEQ ID NO 369
<211> LENGTH: 15
<212> TYPE: DNA
<213> ORGANISM: Artificial Sequence
<220> FEATURE:
<223> OTHER INFORMATION: Synthetic amino acid sequence

<400> SEQUENCE: 369
augaagccgc acuca                                                    15

<210> SEQ ID NO 370
<211> LENGTH: 5
<212> TYPE: PRT
<213> ORGANISM: Artificial Sequence
<220> FEATURE:
<223> OTHER INFORMATION: Synthetic nucleic acid sequence

<400> SEQUENCE: 370

Met Pro Lys His Ser
 1               5
```